United States Patent
Burns et al.

(10) Patent No.: US 12,102,648 B2
(45) Date of Patent: *Oct. 1, 2024

(54) ORALLY-BIOAVAILABLE NUCLEOSIDE ANALOGS

(71) Applicant: Venatorx Pharmaceuticals, Inc., Malvern, PA (US)

(72) Inventors: Christopher J. Burns, Malvern, PA (US); Glen Coburn, Bethel, CT (US); Guo-Hua Chu, Exton, PA (US); Stephen M. Condon, Glenmoore, PA (US); Steven A. Boyd, Chester Springs, PA (US); Daniel C. Pevear, Downingtown, PA (US)

(73) Assignee: VENATORX PHARMACEUTICALS, INC., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/159,327

(22) Filed: Jan. 25, 2023

(65) Prior Publication Data

US 2023/0233593 A1 Jul. 27, 2023

Related U.S. Application Data

(63) Continuation of application No. 17/842,402, filed on Jun. 16, 2022, now Pat. No. 11,638,715, which is a continuation of application No. PCT/US2022/033196, filed on Jun. 13, 2022.

(60) Provisional application No. 63/328,106, filed on Apr. 6, 2022, provisional application No. 63/257,820, filed on Oct. 20, 2021, provisional application No. 63/210,385, filed on Jun. 14, 2021.

(51) Int. Cl.
| | |
|---|---|
| *A61K 31/7076* | (2006.01) |
| *A61K 9/00* | (2006.01) |
| *A61K 9/20* | (2006.01) |
| *A61K 9/48* | (2006.01) |
| *A61K 31/53* | (2006.01) |
| *A61K 31/675* | (2006.01) |
| *A61K 31/685* | (2006.01) |
| *A61K 31/7072* | (2006.01) |
| *C07D 487/04* | (2006.01) |
| *C07F 9/6561* | (2006.01) |
| *C07H 19/06* | (2006.01) |
| *C07H 19/10* | (2006.01) |
| *C07H 19/16* | (2006.01) |

(52) U.S. Cl.
CPC ........ *A61K 31/7076* (2013.01); *A61K 9/0053* (2013.01); *A61K 9/2018* (2013.01); *A61K 9/2054* (2013.01); *A61K 9/2059* (2013.01); *A61K 9/4858* (2013.01); *A61K 31/53* (2013.01); *A61K 31/675* (2013.01); *A61K 31/685* (2013.01); *A61K 31/7072* (2013.01); *C07D 487/04* (2013.01); *C07F 9/6561* (2013.01); *C07H 19/06* (2013.01); *C07H 19/10* (2013.01); *C07H 19/16* (2013.01)

(58) Field of Classification Search
None
See application file for complete search history.

(56) References Cited

U.S. PATENT DOCUMENTS

2023/0024722 A1   1/2023   Burns et al.

FOREIGN PATENT DOCUMENTS

| | | |
|---|---|---|
| CN | 111961057 A | 11/2020 |
| CN | 112778310 A | 5/2021 |
| CN | 113185519 A | 7/2021 |
| CN | 113735862 A | 12/2021 |
| WO | WO-02088159 A1 | 11/2002 |
| WO | WO-03045968 A1 | 6/2003 |
| WO | WO-2004041203 A2 | 5/2004 |
| WO | WO-2005121162 A1 | 12/2005 |
| WO | WO-2012158811 A2 | 11/2012 |
| WO | WO-2018067241 A1 | 4/2018 |
| WO | WO-2021154687 A1 | 8/2021 |
| WO | WO-2021213288 A1 | 10/2021 |
| WO | WO-2022046631 A1 | 3/2022 |
| WO | WO-2022047065 A2 | 3/2022 |
| WO | WO-2022089614 A1 | 5/2022 |
| WO | WO-2022119784 A1 | 6/2022 |
| WO | WO-2022265964 A1 | 12/2022 |
| WO | WO-2023196458 A1 | 10/2023 |

OTHER PUBLICATIONS

Cao et al. The adenosine analogue prodrug ATV006 is orally bioavailable and has potent preclinical efficacy against SARS-CoV-2 and its variants. bioRxiv (2021).

Grugier et al., Synthesis of 2-(N-Acetylamino)-2-deoxy-C-glucopyranosyl Nucleosides as Potential Inhibitors of Chitin Synthases. J. Org. Chem. 65(4):979-984 (2000).

Howard et al., Synthesis and Activity of 5'-Uridinyl Dipeptide Analogues Mimicking the Amino Terminal Peptide Chain of Nucleoside Antibiotic Mureidomycin A. Bioorg. Med. Chem. 11:3083-3099 (2003).

Kirschberg et al. Discovery of a 2'-fluoro-2'-C-methyl C-nucleotide HCV polymerase inhibitor and a phosphoramidate prodrug with favorable properties. Bioorg Med Chem Lett. 27(8):1840-1847 (2017).

Li et al., Tissue-Specific Proteomics Analysis of Anti-COVID-19 Nucleoside and Nucleotide Prodrug-Activating Enzymes Provides Insights into the Optimization of Prodrug Design and Pharmacotherapy Strategy. ACS Pharmacol. Transl. Sci. 4:870-887 (2021).

(Continued)

*Primary Examiner* — Patrick T Lewis
(74) *Attorney, Agent, or Firm* — WILSON SONSINI GOODRICH & ROSATI

(57) ABSTRACT

Described herein are orally-bioavailable nucleoside analogs and pharmaceutical compositions comprising said compounds. The subject compounds and compositions are useful for the treatment of coronavirus infections, including SARS-CoV-2 infection.

19 Claims, No Drawings

(56) References Cited

OTHER PUBLICATIONS

Montgomery et al. 9-(2-Deoxy-2-fluoro-beta-D-arabinofuranosyl)guanine: a metabolically stable cytotoxic analogue of 2'-deoxyguanosine. J Med Chem 29:2389-2392 (1986).
PCT/US2022/033196 International Search Report and Written Opinion dated Aug. 12, 2022.
Schooley et al. Rethinking Remdesivir: Synthesis of Lipid Prodrugs that Substantially Enhance Anti-Coronavirus Activity. bioRxiv (2020).
U.S. Appl. No. 17/842,402 Office Action dated Sep. 19, 2022.
Wang et al., A Search for Pyrophosphate Mimics for the Development of Substrates and Inhibitors of Glycosyltransferases. Bioorg. Med. Chem. Lett. 5(4):661-672 (1997).
Wang et al., Affinity chromatography using enzymatically synthesized nucleotide-containing DNA binding polymers. Biotechnol. Tech. 13(7):463-467 (1999).
Zemlicka et al., Aminoacyl derivatives of nucleosides, nucleotides, and polynucleotides. VIII. Preparation of 2'(3')-O-L-phenylalanyluridine, -cytidine, - adenosine, -inosine, -guanosine, and 2'-deoxy-3'-O-L-phenylalanyladenosine. Collection Czechoslov. Chem. Commun. 34(12):3755-3768 (1969).
PCT/US2023/017669 International Search Report and Written Opinion dated Jun. 23, 2023.

ORALLY-BIOAVAILABLE NUCLEOSIDE ANALOGS

CROSS-REFERENCE

This application is a continuation U.S. application Ser. No. 17/842,402 filed on Jun. 16, 2022, which is a continuation of International Application No. PCT/US2022/033196 filed Jun. 13, 2022, which claims the benefit of U.S. Provisional Application Ser. No. 63/210,385 filed Jun. 14, 2021, U.S. Provisional Application Ser. No. 63/257,820 filed Oct. 20, 2021, and U.S. Provisional Application Ser. No. 63/328, 106 filed Apr. 6, 2022, which are hereby incorporated by reference in their entirety.

BACKGROUND

Remdesivir is a parenterally administered prodrug that was previously developed for the treatment of Ebola virus disease and more recently received emergency use authorization for the treatment of severe acute respiratory syndrome-coronavirus 2 (SARS-CoV-2) infection (Eastman, R. T., Roth, J. S., Brimacombe, K. R., Simeonov, A., Shen, M., Patnaik, S., and Hall, M. D. (2020). Remdesivir: A Review of Its Discovery and Development Leading to Emergency Use Authorization for Treatment of COVID-19. *ACS Cent Sci* 6, 672-683). The parent compound is a 1'-cyano modified adenosine C-nucleoside analog (GS-441524) that is phosphorylated by intracellular nucleotide kinases to the active tri-phosphorylated form (GS-443902). GS-443902 inhibits viral replication by competing with endogenous nucleotides for incorporation into nascent RNA chains by viral RNA-dependent RNA polymerases leading to the production of non-functional viral genomes via lethal mutagenesis (Siegel, D., Hui, H. C., Doerffler, E., Clarke, M. O., Chun, K., Zhang, L., Neville, S., Carra, E., Lew, W., Ross, B., et al. (2017). Discovery and Synthesis of a Phosphoramidate Prodrug of a Pyrrolo[2,1-f][triazin-4-amino] Adenine C-Nucleoside (GS-5734) for the Treatment of Ebola and Emerging Viruses. *J Med Chem* 60, 1648-1661). Remdesivir (GS-5734) is a monophosphoramidate prodrug of GS-441524 and demonstrates broad spectrum antiviral activity against a wide range of different RNA virus families including: filoviruses (e.g. Ebola viruses, Marburg virus), paramyxoviruses (e.g. parainfluenza type II virus, Nipah virus, Hendra virus, measles morbillivirus, mumps virus), coronaviruses (e.g. SARS-CoV, SARS-CoV-2, MERS-CoV), and pneumoviruses (e.g. respiratory syncytial virus) (Cho, A., Saunders, O. L., Butler, T., Zhang, L., Xu, J., Vela, J. E., Feng, J. Y., Ray, A. S., and Kim, C. U. (2012). Synthesis and antiviral activity of a series of 1'-substituted 4-aza-7,9-dideazaadenosine C-nucleosides. *Bioorg Med Chem Lett* 22, 2705-2707).

Coronaviruses are a large family of viruses common in people and many different species of animals, including humans, camels, cattle, cats, and bats. Human coronaviruses infect people and can cause mild to moderate upper respiratory, lower respiratory and/or gastrointestinal tract illnesses. One example is "Middle East Respiratory Syndrome Coronavirus" (MERS-CoV or MERS) which was first reported in Saudi Arabia in 2012 and has spread to several countries. Another example is SARS-CoV, the coronavirus responsible for "Severe Acute Respiratory Syndrome" (SARS) was first identified in 2002 in China. Still another example is "Coronavirus Disease 2019" (COVID-19), also known as SARS-CoV-2, which can infect people and then spread between people. The SARS-CoV-2 virus is a beta-coronavirus, similar to MERS-CoV and SARS-CoV. Other human coronaviruses include 222E (alpha coronavirus), NL63 (alpha coronavirus), OC43 (beta coronavirus), and HKU1 (beta coronavirus).

SUMMARY

The present disclosure relates to small-molecule compounds that block coronavirus replication with the potential to be used as a monotherapy or in combination with additional antivirals and/or other agents that are useful for the treatment of coronavirus infection.

Disclosed herein is a compound of Formula (II), or a pharmaceutically acceptable salt, solvate, or stereoisomer thereof:

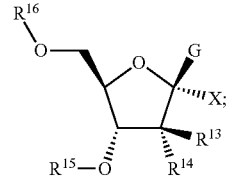

Formula (II)

wherein:
X is hydrogen or —CN;
G is

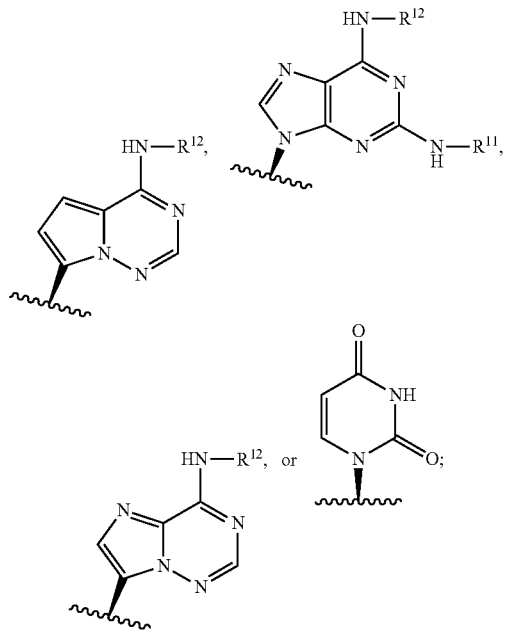

$R^{11}$ is hydrogen, —C(=O)$R^{21}$, —C(=O)O$R^{21}$, or $C_1$-$C_6$alkyl optionally substituted with one or more $R^{11a}$;

each $R^{11a}$ is independently halogen, —CN, —OH, —O$R^a$, —N$R^c R^d$, cycloalkyl, or heterocycloalkyl;

or two $R^{11a}$ on the same atom are taken together to form an oxo;

$R^{21}$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene (aryl), or $C_1$-$C_6$alkylene(heteroaryl); wherein the alkyl, alkylene, cycloalkyl, heterocycloalkyl, aryl, and heteroaryl is optionally and independently substituted with one or more $R^{21a}$;

each $R^{21a}$ is independently halogen, —CN, —NO$_2$, —OH, —OR$^a$, —OC(=O)R$^a$, —OC(=O)OR$^b$, —OC(=O)NR$^c$R$^d$, —S(=O)R$^a$, —S(=O)$_2$R$^a$, —S(=O)$_2$NR$^c$R$^d$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two $R^{21a}$ on the same atom are taken together to form an oxo;

or two $R^{21a}$ are taken together to form a cycloalkyl or heterocycloalkyl; each optionally and independently substituted with one or more R;

$R^{12}$ is hydrogen, —C(=O)R$^{22}$, —C(=O)OR$^{22}$, or $C_1$-$C_6$alkyl optionally substituted with one or more $R^{12a}$;

each $R^{12a}$ is independently halogen, —CN, —OH, —OR$^a$, —NR$^c$R$^d$, cycloalkyl, or heterocycloalkyl;

or two $R^{12a}$ on the same atom are taken together to form an oxo;

$R^{22}$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkyl, alkylene, cycloalkyl, heterocycloalkyl, aryl, and heteroaryl is optionally and independently substituted with one or more $R^{22a}$;

each $R^{22a}$ is independently halogen, —CN, —NO$_2$, —OH, —OR$^a$, —OC(=O)R$^a$, —OC(=O)OR$^b$, —OC(=O)NR$^c$R$^d$, —S(=O)R$^a$, —S(=O)$_2$R$^a$, —S(=O)$_2$NR$^c$R$^d$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two $R^{22a}$ on the same atom are taken together to form an oxo;

or two $R^{22a}$ are taken together to form a cycloalkyl or heterocycloalkyl; each optionally and independently substituted with one or more R;

$R^{13}$ is hydrogen or $C_1$-$C_6$alkyl;

$R^{14}$ is —OH or fluoro;

$R^{15}$ is hydrogen, —C(=O)R$^{25}$, —C(=O)OR$^{25}$, —CH$_2$—O—C(=O)R$^{25}$, —CH$_2$—O—C(=O)OR$^{25}$, or $C_1$-$C_6$alkyl optionally substituted with one or more $R^{15a}$;

each $R^{15a}$ is independently halogen, —CN, —OH, —OR$^a$, —NR$^c$R$^d$, cycloalkyl, or heterocycloalkyl;

or two $R^{15a}$ on the same atom are taken together to form an oxo;

$R^{25}$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkyl, alkylene, cycloalkyl, heterocycloalkyl, aryl, and heteroaryl is optionally and independently substituted with one or more $R^{25a}$;

each $R^{25a}$ is independently halogen, —CN, —NO$_2$, —OH, —OR$^a$, —OC(=O)R$^a$, —OC(=O)OR$^b$, —OC(=O)NR$^c$R$^d$, —S(=O)R$^a$, —S(=O)$_2$R$^a$, —S(=O)$_2$NR$^c$R$^d$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two $R^{25a}$ on the same atom are taken together to form an oxo;

or two $R^{25a}$ are taken together to form a cycloalkyl or heterocycloalkyl; each optionally and independently substituted with one or more R;

$R^{16}$ is —C(=O)R$^{26}$, —C(=O)OR$^{26}$, —CH$_2$—O—C(=O)R$^{26}$, or —CH$_2$—O—C(=O)OR$^{26}$, $R^{26}$ is $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkylene, cycloalkyl, heterocycloalkyl, aryl, and heteroaryl is optionally and independently substituted with one or more $R^{26a}$.

each $R^{26a}$ is independently halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{26a}$ on the same atom are taken together to form an oxo;

or two $R^{26a}$ on the same carbon are taken together to form a cycloalkyl or heterocycloalkyl; each optionally substituted with one or more R;

each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl), wherein the alkyl, alkenyl, alkynyl, cycloalkyl, heterocycloalkyl, aryl, and heteroaryl is independently optionally substituted with one or more R;

each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl), wherein the alkyl, alkenyl, alkynyl, cycloalkyl, heterocycloalkyl, aryl, and heteroaryl is independently optionally substituted with one or more R;

$R^c$ and $R^d$ are each independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl), wherein the alkyl, alkenyl, alkynyl, cycloalkyl, heterocycloalkyl, aryl, and heteroaryl is independently optionally substituted with one or more R;

or $R^c$ and $R^d$ are taken together with the atom to which they are attached to form a heterocycloalkyl optionally substituted with one or more R; and each R is independently halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$hydroxyalkyl, C$_1$-C$_6$aminoalkyl, and C$_1$-C$_6$heteroalkyl;

or two R on the same atom are taken together to form an oxo;

provided that when G is

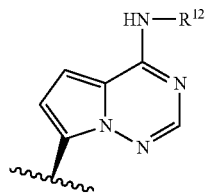

and X is —CN, or G is

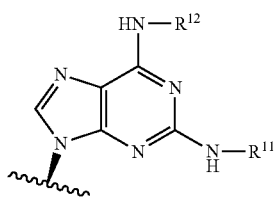

and X is hydrogen;

then at least one of $R^{11}$, $R^{12}$ or $R^{15}$ is not hydrogen.

Disclosed herein is a compound of Formula (III), or a pharmaceutically acceptable salt, solvate, or stereoisomer thereof:

Formula (III)

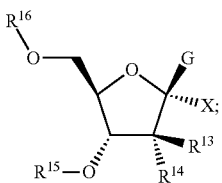

wherein:

X is hydrogen or —CN;

G is

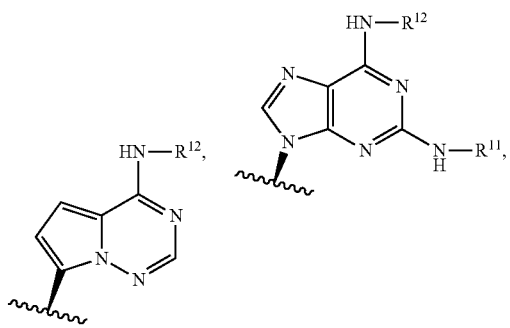

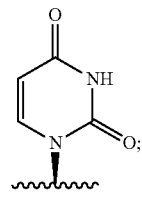

$R^{11}$ is hydrogen, —C(=O)R$^{21}$, —C(=O)OR$^{21}$, or C$_1$-C$_6$alkyl optionally substituted with one or more R$^{11a}$;

each R$^{11a}$ is independently halogen, —CN, —OH, —OR$^a$, —NR$^c$R$^d$, cycloalkyl, or heterocycloalkyl;

or two R$^{11a}$ on the same atom are taken together to form an oxo;

R$^{21}$ is C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein the alkyl, alkylene, cycloalkyl, heterocycloalkyl, aryl, and heteroaryl is optionally and independently substituted with one or more R$^{21a}$;

each R$^{21a}$ is independently halogen, —CN, —NO$_2$, —OH, —OR$^a$, —OC(=O)R$^a$, —OC(=O)OR$^b$, —OC(=O)NR$^c$R$^d$, —S(=O)R$^a$, —S(=O)$_2$R$^a$, —S(=O)$_2$NR$^c$R$^d$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two R$^{21a}$ on the same atom are taken together to form an oxo;

or two R$^{21a}$ are taken together to form a cycloalkyl or heterocycloalkyl; each optionally and independently substituted with one or more R;

R$^{12}$ is hydrogen, —C(=O)R$^{22}$, —C(=O)OR$^{22}$, or C$_1$-C$_6$alkyl optionally substituted with one or more R$^{12a}$;

each R$^{12a}$ is independently halogen, —CN, —OH, —OR$^a$, —NR$^c$R$^d$, cycloalkyl, or heterocycloalkyl;

or two R$^{12a}$ on the same atom are taken together to form an oxo;

R$^{22}$ is C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein the alkyl, alkylene, cycloalkyl, heterocycloalkyl, aryl, and heteroaryl is optionally and independently substituted with one or more R$^{22a}$;

each R$^{22a}$ is independently halogen, —CN, —NO$_2$, —OH, —OR$^a$, —OC(=O)R$^a$, —OC(=O)OR$^b$, —OC(=O)NR$^c$R$^d$, —S(=O)R$^a$, —S(=O)$_2$R$^a$, —S(=O)$_2$NR$^c$R$^d$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two $R^{22a}$ are taken together to form a cycloalkyl or heterocycloalkyl; each optionally and independently substituted with one or more R;

or two $R^{22a}$ on the same atom are taken together to form an oxo;

$R^{13}$ is hydrogen or $C_1$-$C_6$alkyl;

$R^{14}$ is —OH or fluoro;

$R^{15}$ is —C(=O)$R^{25}$, —C(=O)O$R^{25}$, —CH$_2$—O—C(=O)$R^{25}$, or —CH$_2$—O—C(=O)O$R^{25}$;

$R^{25}$ is $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkylene, cycloalkyl, heterocycloalkyl, aryl, and heteroaryl is optionally and independently substituted with one or more $R^{26a}$, each $R^{25a}$ is independently halogen, —CN, —NO$_2$, —OH, —OR$^a$, —OC(=O)$R^a$, —OC(=O)O$R^b$, —OC(=O)N$R^cR^d$, —SH, —S$R^a$, —S(=O)$R^a$, —S(=O)$_2R^a$, —S(=O)$_2$N$R^cR^d$, —N$R^cR^d$, —N$R^b$C(=O)N$R^cR^d$, —N$R^b$C(=O)$R^a$, —N$R^b$C(=O)O$R^b$, —N$R^b$S(=O)$_2R^a$, —C(=O)$R^a$, —C(=O)O$R^b$, —C(=O)N$R^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{25a}$ on the same atom are taken together to form an oxo;

or two $R^{25a}$ are taken together to form a cycloalkyl or heterocycloalkyl; each optionally and independently substituted with one or more R;

$R^{16}$ is hydrogen, —C(=O)$R^{26}$, —C(=O)O$R^{26}$, —CH$_2$—O—C(=O)$R^{26}$, —CH$_2$—O—C(=O)O$R^{26}$, or $C_1$-$C_6$alkyl optionally substituted with one or more $R^{16a}$;

each $R^{16a}$ is independently halogen, —CN, —OH, —OR$^a$, —N$R^cR^d$, cycloalkyl, or heterocycloalkyl;

or two $R^{16a}$ on the same atom are taken together to form an oxo;

$R^{26}$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkyl, alkylene, cycloalkyl, heterocycloalkyl, aryl, and heteroaryl is optionally and independently substituted with one or more $R^{26a}$, each $R^{26a}$ is independently halogen, —CN, —NO$_2$, —OH, —OR$^a$, —OC(=O)$R^a$, —OC(=O)O$R^b$, —OC(=O)N$R^cR^d$, —S(=O)$R^a$, —S(=O)$_2R^a$, —S(=O)$_2$N$R^cR^d$, —N$R^cR^d$, —C(=O)$R^a$, —C(=O)O$R^b$, —C(=O)N$R^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two $R^{26a}$ on the same atom are taken together to form an oxo;

or two $R^{26a}$ are taken together to form a cycloalkyl or heterocycloalkyl; each optionally and independently substituted with one or more R;

each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl), wherein the alkyl, alkenyl, alkynyl, cycloalkyl, heterocycloalkyl, aryl, and heteroaryl is independently optionally substituted with one or more R;

each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl), wherein the alkyl, alkenyl, alkynyl, cycloalkyl, heterocycloalkyl, aryl, and heteroaryl is independently optionally substituted with one or more R;

$R^c$ and $R^d$ are each independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl), wherein the alkyl, alkenyl, alkynyl, cycloalkyl, heterocycloalkyl, aryl, and heteroaryl is independently optionally substituted with one or more R;

or $R^c$ and $R^d$ are taken together with the atom to which they are attached to form a heterocycloalkyl optionally substituted with one or more R; and each R is independently halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$hydroxyalkyl, $C_1$-$C_6$aminoalkyl, and $C_1$-$C_6$heteroalkyl;

or two R on the same atom are taken together to form an oxo;

provided that when G is

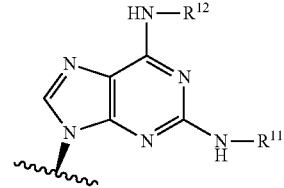

and X is hydrogen; then at least one of $R^{11}$, $R^{12}$, or $R^{16}$ is not hydrogen.

Also disclosed herein is a compound of Formula (IV), or a pharmaceutically acceptable salt, solvate, or stereoisomer thereof:

wherein:

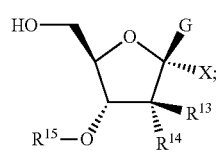

Formula (IV)

X is hydrogen or —CN;
G is

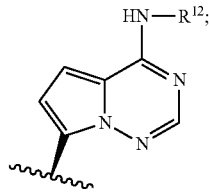

$R^{12}$ is —C(=O)$R^{22}$, —C(=O)O$R^{22}$, or $C_1$-$C_6$alkyl optionally substituted with one or more $R^{12a}$, each $R^{12a}$ is independently halogen, —CN, —OH, —O$R^a$, —N$R^cR^d$, cycloalkyl, or heterocycloalkyl;

or two $R^{12a}$ on the same atom are taken together to form an oxo;

$R^{22}$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkyl, alkylene, cycloalkyl, heterocycloalkyl, aryl, and heteroaryl is optionally and independently substituted with one or more $R^{22a}$;

each $R^{22a}$ is independently halogen, —CN, —NO$_2$, —OH, —O$R^a$, —OC(=O)$R^a$, —OC(=O)O$R^b$, —OC(=O)N$R^cR^d$, —S(=O)$R^a$, —S(=O)$_2R^a$, —S(=O)$_2$N$R^cR^d$, —N$R^cR^d$, —C(=O)$R^a$, —C(=O)O$R^b$, —C(=O)N$R^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two $R^{22a}$ on the same atom are taken together to form an oxo;

or two $R^{22a}$ are taken together to form a cycloalkyl or heterocycloalkyl; each optionally and independently substituted with one or more R;

$R^{13}$ is hydrogen or $C_1$-$C_6$alkyl;

$R^{14}$ is —OH or fluoro;

$R^{15}$ is —C(=O)$R^{25}$, —C(=O)O$R^{25}$, —CH$_2$—O—C(=O)$R^{25}$, or —CH$_2$—O—C(=O)O$R^{25}$;

$R^{25}$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkyl, alkylene, cycloalkyl, heterocycloalkyl, aryl, and heteroaryl is optionally and independently substituted with one or more $R^{25a}$;

each $R^{25a}$ is independently halogen, —CN, —NO$_2$, —OH, —O$R^a$, —OC(=O)$R^a$, —OC(=O)O$R^b$, —OC(=O)N$R^cR^d$, —S(=O)$R^a$, —S(=O)$_2R^a$, —S(=O)$_2$N$R^cR^d$, —N$R^cR^d$, —C(=O)$R^a$, —C(=O)O$R^b$, —C(=O)N$R^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two $R^{25a}$ on the same atom are taken together to form an oxo;

or two $R^{25a}$ are taken together to form a cycloalkyl or heterocycloalkyl; each optionally and independently substituted with one or more R;

each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl), wherein the alkyl, alkenyl, alkynyl, cycloalkyl, heterocycloalkyl, aryl, and heteroaryl is independently optionally substituted with one or more R;

each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl), wherein the alkyl, alkenyl, alkynyl, cycloalkyl, heterocycloalkyl, aryl, and heteroaryl is independently optionally substituted with one or more R;

$R^c$ and $R^d$ are each independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl), wherein the alkyl, alkenyl, alkynyl, cycloalkyl, heterocycloalkyl, aryl, and heteroaryl is independently optionally substituted with one or more R;

or $R^c$ and $R^d$ are taken together with the atom to which they are attached to form a heterocycloalkyl optionally substituted with one or more R; and each R is independently halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$hydroxyalkyl, $C_1$-$C_6$aminoalkyl, and $C_1$-$C_6$heteroalkyl;

or two R on the same atom are taken together to form an oxo.

Also disclosed herein is a compound of Formula (V), or a pharmaceutically acceptable salt, solvate, or stereoisomer thereof:

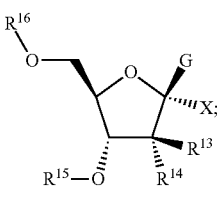

Formula (V)

wherein:

X is hydrogen or —CN;

G is

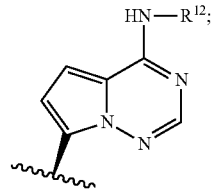

R$^{12}$ is —C(=O)R$^{22}$, —C(=O)OR$^{22}$, or C$_1$-C$_6$alkyl optionally substituted with one or more R$^{12a}$;

each R$^{12a}$ is independently halogen, —CN, —OH, —OR$^a$, —NR$^c$R$^d$, cycloalkyl, or heterocycloalkyl;

or two R$^{12a}$ on the same atom are taken together to form an oxo;

R$^{22}$ is C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein the alkyl, alkylene, cycloalkyl, heterocycloalkyl, aryl, and heteroaryl is optionally and independently substituted with one or more R$^{22a}$;

each R$^{22a}$ is independently halogen, —CN, —NO$_2$, —OH, —OR$^a$, —OC(=O)R$^a$, —OC(=O)OR$^b$, —OC(=O)NR$^c$R$^d$, —S(=O)R$^a$, —S(=O)$_2$R$^a$, —S(=O)$_2$NR$^c$R$^d$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two R$^{22a}$ on the same atom are taken together to form an oxo;

or two R$^{22a}$ are taken together to form a cycloalkyl or heterocycloalkyl; each optionally and independently substituted with one or more R;

R$^{13}$ is hydrogen or C$_1$-C$_6$alkyl;

R$^{14}$ is —OH or fluoro;

R$^{15}$ is hydrogen, —C(=O)R$^{25}$, —C(=O)OR$^{25}$, —CH$_2$—O—C(=O)R$^{25}$, or —CH$_2$—O—C(=O)OR$^{25}$;

R$^{25}$ is C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein the alkyl, alkylene, cycloalkyl, heterocycloalkyl, aryl, and heteroaryl is optionally and independently substituted with one or more R$^{25a}$;

each R$^{25a}$ is independently halogen, —CN, —NO$_2$, —OH, —OR$^a$, —OC(=O)R$^a$, —OC(=O)OR$^b$, —OC(=O)NR$^c$R$^d$, —S(=O)R$^a$, —S(=O)$_2$R$^a$, —S(=O)$_2$NR$^c$R$^d$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two R$^{25a}$ on the same atom are taken together to form an oxo;

or two R$^{25a}$ are taken together to form a cycloalkyl or heterocycloalkyl; each optionally and independently substituted with one or more R;

R$^{16}$ is —C(=O)R$^{26}$, —C(=O)OR$^{26}$, —CH$_2$—O—C(=O)R$^{26}$, —CH$_2$—O—C(=O)OR$^{26}$, or C$_1$-C$_6$alkyl optionally substituted with one or more R$^{16a}$;

each R$^{16a}$ is independently halogen, —CN, —OH, —OR$^a$, —NR$^c$R$^d$, cycloalkyl, or heterocycloalkyl;

or two R$^{16a}$ on the same atom are taken together to form an oxo;

R$^{26}$ is C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein the alkyl, alkylene, cycloalkyl, heterocycloalkyl, aryl, and heteroaryl is optionally and independently substituted with one or more R$^{26a}$, each R$^{26a}$ is independently halogen, —CN, —NO$_2$, —OH, —OR$^a$, —OC(=O)R$^a$, —OC(=O)OR$^b$, —OC(=O)NR$^c$R$^d$, —S(=O)R$^a$, —S(=O)$_2$R$^a$, —S(=O)$_2$NR$^c$R$^d$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two R$^{26a}$ on the same atom are taken together to form an oxo;

or two R$^{26a}$ are taken together to form a cycloalkyl or heterocycloalkyl; each optionally and independently substituted with one or more R;

each R$^a$ is independently C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl), wherein the alkyl, alkenyl, alkynyl, cycloalkyl, heterocycloalkyl, aryl, and heteroaryl is independently optionally substituted with one or more R;

each R$^b$ is independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl), wherein the alkyl, alkenyl, alkynyl, cycloalkyl, heterocycloalkyl, aryl, and heteroaryl is independently optionally substituted with one or more R;

R$^c$ and R$^d$ are each independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl), wherein the alkyl, alkenyl, alkynyl, cycloalkyl, heterocycloalkyl, aryl, and heteroaryl is independently optionally substituted with one or more R;

or $R^c$ and $R^d$ are taken together with the atom to which they are attached to form a heterocycloalkyl optionally substituted with one or more R; and each R is independently halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$hydroxyalkyl, C$_1$-C$_6$aminoalkyl, and C$_1$-C$_6$heteroalkyl;

or two R on the same atom are taken together to form an oxo.

Also disclosed herein is a compound of Formula (VIa), (VIb), or (VIc), or a pharmaceutically acceptable salt, solvate, or stereoisomer thereof:

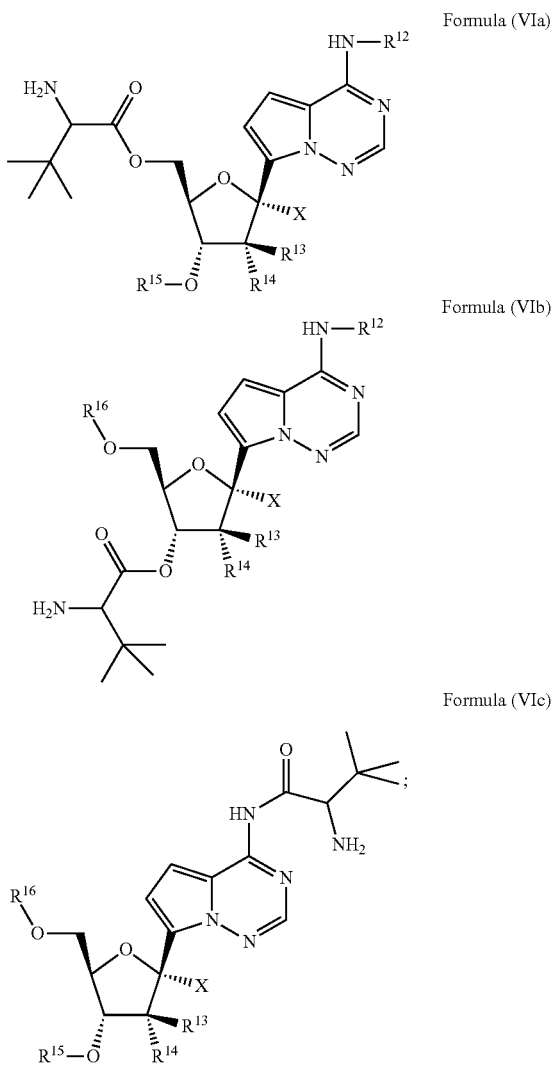

Formula (VIa)

Formula (VIb)

Formula (VIc)

wherein:

X is hydrogen or —CN;

$R^{12}$ is hydrogen, —C(=O)R$^{22}$, —C(=O)OR$^{22}$, or C$_1$-C$_6$alkyl optionally substituted with one or more $R^{12a}$;

each $R^{12a}$ is independently halogen, —CN, —OH, —OR$^a$, —NR$^c$R$^d$, cycloalkyl, or heterocycloalkyl;

or two $R^{12a}$ on the same atom are taken together to form an oxo;

$R^{22}$ is C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein the alkyl, alkylene, cycloalkyl, heterocycloalkyl, aryl, and heteroaryl is optionally and independently substituted with one or more $R^{22a}$;

each $R^{22a}$ is independently halogen, —CN, —NO$_2$, —OH, —OR$^a$, —OC(=O)R$^a$, —OC(=O)OR$^b$, —OC(=O)NR$^c$R$^d$, —S(=O)R$^a$, —S(=O)$_2$R$^a$, —S(=O)$_2$NR$^c$R$^d$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two $R^{22a}$ on the same atom are taken together to form an oxo;

or two $R^{22a}$ are taken together to form a cycloalkyl or heterocycloalkyl; each optionally and independently substituted with one or more R;

$R^{13}$ is hydrogen or C$_1$-C$_6$alkyl;

$R^{14}$ is —OH or fluoro;

$R^{15}$ is hydrogen, —C(=O)R$^{25}$, —C(=O)OR$^{25}$, —CH$_2$—O—C(=O)R$^{25}$, or —CH$_2$—O—C(=O)OR$^{25}$;

$R^{25}$ is C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein the alkyl, alkylene, cycloalkyl, heterocycloalkyl, aryl, and heteroaryl is optionally and independently substituted with one or more $R^{25a}$;

each $R^{25a}$ is independently halogen, —CN, —NO$_2$, —OH, —OR$^a$, —OC(=O)R$^a$, —OC(=O)OR$^b$, —OC(=O)NR$^c$R$^d$, —S(=O)R$^a$, —S(=O)$_2$R$^a$, —S(=O)$_2$NR$^c$R$^d$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two $R^{25a}$ on the same atom are taken together to form an oxo;

or two $R^{25a}$ are taken together to form a cycloalkyl or heterocycloalkyl; each optionally and independently substituted with one or more R;

$R^{16}$ is hydrogen, —C(=O)R$^{26}$, —C(=O)OR$^{26}$, —CH$_2$—O—C(=O)R$^{26}$, —CH$_2$—O—C(=O)OR$^{26}$, or C$_1$-C$_6$alkyl optionally substituted with one or more $R^{16a}$;

each $R^{16a}$ is independently halogen, —CN, —OH, —OR$^a$, —NR$^c$R$^d$, cycloalkyl, or heterocycloalkyl;

or two $R^{16a}$ on the same atom are taken together to form an oxo;

$R^{26}$ is C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein the alkyl, alkylene, cycloalkyl, heterocycloalkyl, aryl, and heteroaryl is optionally and independently substituted with one or more $R^{26a}$, each $R^{26a}$ is independently halogen, —CN, —NO$_2$, —OH, —OR$^a$, —OC(=O)R$^a$, —OC(=O)OR$^b$, —OC(=O)NR$^c$R$^d$, —S(=O)R$^a$, —S(=O)$_2$R$^a$, —S(=O)$_2$NR$^c$R$^d$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two $R^{26a}$ on the same atom are taken together to form an oxo;

or two $R^{26a}$ are taken together to form a cycloalkyl or heterocycloalkyl; each optionally and independently substituted with one or more R;

each $R^a$ is independently C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl), wherein the alkyl, alkenyl, alkynyl, cycloalkyl, heterocycloalkyl, aryl, and heteroaryl is independently optionally substituted with one or more R;

each $R^b$ is independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl), wherein the alkyl, alkenyl, alkynyl, cycloalkyl, heterocycloalkyl, aryl, and heteroaryl is independently optionally substituted with one or more R;

$R^c$ and $R^d$ are each independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl), wherein the alkyl, alkenyl, alkynyl, cycloalkyl, heterocycloalkyl, aryl, and heteroaryl is independently optionally substituted with one or more R;

or $R^c$ and $R^d$ are taken together with the atom to which they are attached to form a heterocycloalkyl optionally substituted with one or more R; and each R is independently halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$hydroxyalkyl, C$_1$-C$_6$aminoalkyl, and C$_1$-C$_6$heteroalkyl;

or two R on the same atom are taken together to form an oxo.

Disclosed herein are pharmaceutical compositions comprising the compound of any one of Formula (I), (Ia), (Ib), (Ic), (Id), (Ie), (If), (Ig), (II), (III), (IV), (V), (VIa), (VIb), and (VIc), or a pharmaceutically acceptable salt, solvate, or stereoisomer thereof, and at least one pharmaceutically acceptable carrier.

Disclosed herein methods of treating a viral infection, comprising administering to a subject in need thereof a therapeutically effective amount of the compound disclosed herein, or a pharmaceutically acceptable salt, solvate, or stereoisomer thereof, or the pharmaceutical composition disclosed herein and at least one pharmaceutically acceptable carrier.

In some embodiments, the method further comprises administering at least one antiviral agent in combination with the compound of disclosed herein, or a pharmaceutically acceptable salt, solvate, or stereoisomer thereof, or the pharmaceutical composition disclosed herein and at least one pharmaceutically acceptable carrier. In some embodiments, the compound, or a pharmaceutically acceptable salt, solvate, or stereoisomer thereof, or the pharmaceutical composition, and the at least one antiviral agent are administered simultaneously, approximately simultaneously, or sequentially, in any order. In some embodiments, the compound, or a pharmaceutically acceptable salt, solvate, or stereoisomer thereof, or the pharmaceutical composition, and the at least one antiviral agent are administered simultaneously or approximately simultaneously. In some embodiments, the compound, or a pharmaceutically acceptable salt, solvate, or stereoisomer thereof, or the pharmaceutical composition, and the at least one antiviral agent are administered sequentially. In some embodiments, the compound, or a pharmaceutically acceptable salt, solvate, or stereoisomer thereof, or the pharmaceutical composition, is administered before the at least one antiviral agent. In some embodiments, the compound, or a pharmaceutically acceptable salt, solvate, or stereoisomer thereof, or the pharmaceutical composition, is administered after the at least one antiviral agent.

In some embodiments, the viral infection is caused by a virus selected from the group consisting of coronavirus disease 2019 (SARS-CoV-2), YellowFever, Eastern Equine Encephalitis virus, Human Immunodeficiency virus (HIV), "African Swine Fever Viruses," Arbovirus, Adenoviridae, Arenaviridae, Arterivirus, Astroviridae, Baculoviridae, Bimaviridae, Bimaviridae, Bunyaviridae, Caliciviridae, Caulimoviridae, Circoviridae, Coronaviridae, Cystoviridae, Ebolavirus, Deltaviridae, Filviridae, Filoviridae, Flaviviridae, Iridoviridae, Mononegavirus, Myoviridae, Papiloma virus, Papovaviridae, Paramyxoviridae, Prions, Parvoviridae, Phycodnaviridae, Poxviridae, Potyviridae, Reoviridae, Retroviridae, Rhabdoviridae, Tectiviridae, Togaviridae, pox, papilloma, corona, influenza, sendai virus (SeV), sindbis virus (SINV), vaccinia viruses, West Nile, Hanta, viruses which cause the common cold, and any combination thereof. In some embodiments, the compound, or a pharmaceutically acceptable salt, solvate, or stereoisomer thereof, or the pharmaceutical composition is systemically administered intravenously, subcutaneously, intramuscularly, orally, or by inhalation.

In some embodiments, the at least one antiviral agent is remdesivir, ribavirin, favipiravir, T-705 monophosphate, T-705 diphosphate, T-705 triphosphate, ST-193, idoxuridine, edoxudine, trifluridine, vidarabine, brivudine, acyclovir, ganciclovir, valaciclovir, cidofovir, valganciclovir, penciclovir, famciclovir, zidovudine, didanosine, zalcitabine, stavudine, abacavir, lamivudine, emtricitabine, tenofovir disoproxil fumarate, tenofovir alafenamide fumarate, adefovir, entecavir, telbivudine, sofosbuvir, or a mixture thereof.

In some embodiments, the at least one antiviral agent is molnupiravir.

In some embodiments, the at least one antiviral agent is a ribonucleic acid (RNA)-dependent RNA polymerase inhibitor, a checkpoint inhibitor or PD-1/PD-L1 inhibitor, a therapeutic vaccine, an RNA interference (RNAi) therapeutic, an antisense-based therapeutic, an coronavirus entry inhibitor, a TLR agonist; an RIG-I agonist, or an interferon.

Also disclosed herein is a pharmaceutical composition comprising a compound disclosed herein, or a pharmaceutically acceptable salt, solvate, or stereoisomer thereof, and a pharmaceutically acceptable excipient.

Also disclosed herein is a method of treating an infection in a subject, comprising administering to the subject a compound disclosed herein, or a pharmaceutically acceptable salt, solvate, or stereoisomer thereof.

Also disclosed herein is a method of treating an infection in a subject, comprising administering to the subject a pharmaceutical composition disclosed herein.

In some embodiments, the infection is a viral infection.

In some embodiments, the infection is caused by the SARS-CoV or SARS-CoV-2 virus.

In some embodiments, the infection is COVID, or COVID-19.

In some embodiments, the method further comprises administering an additional therapeutic agent useful for treating a coronavirus infection.

In some embodiments, the additional therapeutic agent useful for treating a coronavirus infection is an RNA-dependent RNA polymerase inhibitor; a checkpoint inhibitor (PD-1/PD-L1 inhibitor); a therapeutic vaccine; an RNA interference (RNAi) therapeutic; an antisense-based therapeutic, an coronavirus entry inhibitor; a TLR agonist; an RIG-I agonist, or an interferon.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

The present disclosure provides a compound of Formula (I), (Ia), (Ib), (Ic), (Id), (Ie), (If), (Ig), (II), (III), (IV), (V), (VIa), (VIb), and (VIc), or a pharmaceutically acceptable salt, solvate, or stereoisomer thereof to treat viral infections. The disclosure provides a method of prevention, treatment and control of various viral infections caused by a virus selected from the group consisting of coronavirus disease 2019 (COVID-19), Zika, dengue, yellow fever, West Nile, Hendra, Newcastle, Venezuelan equine encephalitis, chikungunya, Semliki Forest, Sindbis, Avian influenza A, Porcine Reproductive and Respiratory Syndrome, Human immunodeficiency virus type 1, equine herpesvirus type 1, pseudorabies virus, BK polyomavirus, and porcine circovirus 2 using a compound of Formula (I), (Ia), (Ib), (Ic), (Id), (Ie), (If), (Ig), (II), (III), (IV), (V), (VIa), (VIb), and (VIc), or a pharmaceutically acceptable salt, solvate, or stereoisomer thereof, dosages, and treatment schedules. The disclosure also provides a method of prevention, treatment and control of various viral infections caused by a virus selected from the group consisting of coronavirus disease 2019 (COVID-19), Yellow Fever, Eastern Equine Encephalitis virus, Human Immunodeficiency virus (HIV), "African Swine Fever Viruses," Arbovirus, Adenoviridae, Arenaviridae, Arterivirus, Astroviridae, Baculoviridae, Bimaviridae, Bimaviridae, Bunyaviridae, Caliciviridae, Caulimoviridae, Circoviridae, Coronaviridae, Cystoviridae, Ebolavirus, Deltaviridae, Filviridae, Filoviridae, Flaviviridae, Iridoviridae, Mononegavirus, Myoviridae, Papiloma virus, Papovaviridae, Paramyxoviridae, Prions, Parvoviridae, Phycodnaviridae, Poxviridae, Potyviridae, Reoviridae, Retroviridae, Rhabdoviridae, Tectiviridae, Togaviridae, pox, papilloma, corona, influenza, sendai virus (SeV), sindbis virus (SINV), vaccinia viruses, West Nile, Hanta, viruses which cause the common cold, and any combination thereof, using a compound of Formula (I), (Ia), (Ib), (Ic), (Id), (Ie), (If), (Ig), (II), (III), (IV), (V), (VIa), (VIb), and (VIc), or a pharmaceutically acceptable salt, solvate, or stereoisomer thereof, dosages, and treatment schedules.

Remdesivir contains a monophosphoramidate substituent that is extensively metabolized via first pass metabolism and is prohibitive for oral delivery of the active metabolite (Siegel, D., Hui, H. C., Doerffler, E., Clarke, M. O., Chun, K., Zhang, L., Neville, S., Carra, E., Lew, W., Ross, B., et al. (2017). Discovery and Synthesis of a Phosphoramidate Prodrug of a Pyrrolo[2,1-f][triazin-4-amino] Adenine C-Nucleoside (GS-5734) for the Treatment of Ebola and Emerging Viruses. *J Med Chem* 60, 1648-1661). Following intravenous injection (IV), remdesivir is rapidly hydrolyzed by esterases ($T_{1/2}$ about 1 hr) to an alanine substituted metabolite GS-704277 prior to release of the active parent GS-441524. The parent compound, GS-441524, exhibits poor oral bioavailability in rats (% F=4.8%) and is expected to exhibit low oral bioavailability in humans (Li, Y., Cao, L., Li, G., Cong, F., Li, Y., Sun, J., Luo, Y., Chen, G., Li, G., Wang, P., et al. (2021). Remdesivir Metabolite GS-441524 Effectively Inhibits SARS-CoV-2 Infection in Mouse Models. *J Med Chem*, ASAP). The extended half-life of GS-441524 in plasma following IV administration (T½ about 24.5 hr) and its potent antiviral activity against SARS-CoV-2 both in vitro and in vivo suggests that optimization of the oral absorption properties of GS-441524 is an attractive strategy for developing a SARS-CoV-2 antiviral therapy (Jorgensen, S. C. J., Kebriaei, R., and Dresser, L. D. (2020). Remdesivir: Review of Pharmacology, Pre-clinical Data, and Emerging Clinical Experience for COVID-19. *Pharmacotherapy* 40, 659-671).

The need remains for new antiviral nucleoside with improved oral bioavailabilities for the treatment of coronavirus infections. An oral nucleoside analog for the treatment of SARS-CoV-2 infections (as well as other coronaviruses and emerging/re-emerging virus infections, including Ebolavirus infections) could play a critical role in facilitating post-exposure prophylaxis in non-vaccinated and immunosuppressed individuals. An oral SARS-CoV-2 antiviral would also have an important role in treating index cases during an earlier phase of infection prior to hospital admission.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "some embodiments" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

As used herein, the term "about" in the context of a given value or range refers to a value within 10% of the given value or range.

As used herein, the term "and/or" is to be taken as specific disclosure of each of the two specified features or components with or without the other. For example, "A and/or B" is to be taken as specific disclosure of each of (i) A, (ii) B and (iii) A and B, just as if each were set out individually herein.

As used herein, the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

"Oxo" refers to =O, an oxygen that is double bonded to an atom such as carbon.

"Alkyl" refers to a straight-chain, or branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_{1-10}$ alkyl. In some embodiments, the alkyl is a $C_{1-6}$ alkyl. In some embodiments, the alkyl is a $C_{1-5}$ alkyl. In some embodiments, the alkyl is a $C_{1-4}$ alkyl. In some embodiments, the alkyl is a $C_{1-3}$ alkyl. In some embodiments, the alkyl is a $C_{10-15}$ alkyl. In some embodiments, the alkyl is a $C_{16-20}$ alkyl. Unless stated otherwise specifically in the specification, an alkyl group may be optionally substituted, for example, with oxo, halogen, amino, nitrile, nitro, hydroxyl, haloalkyl, alkoxy, aryl, cycloalkyl, heterocycloalkyl, heteroaryl, carboxylic acid, ester, alkoxy, arylalkoxy, aryloxy, heteroarylalkoxy, cycloalkyloxy, or cycloalkylalkoxy. In some embodiments, the alkyl is optionally substituted with insertion of one or more —O— between two adjacent carbon atoms at one or more positions along the alkyl chain. In some embodiments, the alkyl is optionally substituted with oxo, halogen, —CN, —OH, —OMe, —NH$_2$, or —NO$_2$. In some embodiments, the alkyl is optionally substituted with halogen, —CN, —OH, or —OMe. In some embodiments, the alkyl is optionally substituted with halogen.

"Alkenyl" refers to a straight-chain, or branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (—CH=CH$_2$), 1-propenyl (—CH$_2$CH=CH$_2$), isopropenyl [—C(CH$_3$)=CH$_2$], butenyl, 1,3-butadienyl and the like. Whenever it appears herein, a numerical range such as "$C_2$-$C_6$ alkenyl" or "$C_{2-6}$alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. Unless stated otherwise specifically in the specification, an alkenyl group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, the alkenyl is optionally substituted with oxo, halogen, —CN, —OH, —OMe, —NH$_2$, or —NO$_2$. In some embodiments, the alkenyl is optionally substituted with halogen, —CN, —OH, or —OMe. In some embodiments, the alkenyl is optionally substituted with halogen.

"Alkynyl" refers to a straight-chain or branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. Unless stated otherwise specifically in the specification, an alkynyl group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, the alkynyl is optionally substituted with oxo, halogen, —CN, —OH, —OMe, —NH$_2$, or —NO$_2$. In some embodiments, the alkynyl is optionally substituted with halogen, —CN, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, the alkylene is optionally substituted with oxo, halogen, —CN, —OH, —OMe, —NH$_2$, or —NO$_2$. In some embodiments, the alkylene is optionally substituted with halogen, —CN, —OH, or —OMe. In some embodiments, the alkylene is optionally substituted with halogen.

"Alkoxy" refers to a radical of the formula —OR$_a$ where R$_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, the alkoxy is optionally substituted with halogen, —CN, —OH, —OMe, —NH$_2$, or —NO$_2$. In some embodiments, the alkoxy is optionally substituted with halogen, —CN, —OH, or —OMe. In some embodiments, the alkoxy is optionally substituted with halogen.

"Aryl" refers to a radical derived from a hydrocarbon ring system comprising 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl (phenyl). Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl may be optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, the aryl is optionally substituted with halogen, methyl, ethyl, —CN, —CF$_3$, —OH, —OMe, —NH$_2$, or —NO$_2$. In some embodiments, the aryl is optionally substituted with halogen, methyl, ethyl, —CN, —CF$_3$, —OH, or —OMe. In some embodiments, the aryl is optionally substituted with halogen.

"Cycloalkyl" refers to a partially or fully saturated, monocyclic or polycyclic carbocyclic ring, which may include fused (when fused with an aryl or a heteroaryl ring, the cycloalkyl is bonded through a non-aromatic ring atom) or bridged ring systems. In some embodiments, the cycloalkyl is fully saturated. Representative cycloalkyls include, but are not limited to, cycloalkyls having from three to fifteen carbon atoms (C$_3$-C$_{15}$ cycloalkyl), from three to ten carbon atoms (C$_3$-C$_{10}$ cycloalkyl), from three to eight carbon atoms (C$_3$-C$_8$ cycloalkyl), from three to six carbon atoms (C$_3$-C$_6$ cycloalkyl), from three to five carbon atoms (C$_3$-C$_5$ cycloalkyl), or three to four carbon atoms (C$_3$-C$_4$ cycloalkyl). In some embodiments, the cycloalkyl is a 3- to 10-membered cycloalkyl. In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a cycloalkyl is optionally substituted with oxo, halogen, methyl, ethyl, —CN, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Heteroatom" or "ring heteroatom" refers to oxygen (O), nitrogen (N), sulfur (S), phosphorus (P), and silicon (Si).

"Heterocycloalkyl" refers to a 3- to 24-membered partially or fully saturated ring radical comprising 2 to 23 carbon atoms and from one to 8 heteroatoms selected from the group consisting of nitrogen, oxygen, phosphorous and sulfur. In some embodiments, the heterocycloalkyl is fully saturated. In some embodiments, the heterocycloalkyl comprises one to three heteroatoms selected from the group consisting of nitrogen, oxygen, and sulfur. In some embodiments, the heterocycloalkyl comprises one to three heteroatoms selected from the group consisting of nitrogen and oxygen. In some embodiments, the heterocycloalkyl comprises one to three nitrogens. In some embodiments, the heterocycloalkyl comprises one or two nitrogens. In some embodiments, the heterocycloalkyl comprises one nitrogen. In some embodiments, the heterocycloalkyl comprises one nitrogen and one oxygen. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon, or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms (C$_2$-C$_{15}$ heterocycloalkyl), from two to ten carbon atoms (C$_2$-C$_{10}$ heterocycloalkyl), from two to eight carbon atoms (C$_2$-C$_8$ heterocycloalkyl), from two to seven carbon atoms (C$_2$-C$_7$ heterocycloalkyl), from two to six carbon atoms (C$_2$-C$_6$ heterocycloalkyl), from two to five carbon atoms (C$_2$-C$_5$ heterocycloalkyl), or two to four carbon atoms (C$_2$-C$_4$ heterocycloalkyl). Examples of such heterocycloalkyl radicals include, but are not limited to, aziridinyl, azetidinyl, oxetanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). In some embodiments, the heterocycloalkyl is a 3- to 8-membered heterocycloalkyl. In some embodiments, the heterocycloalkyl is a 3- to 7-membered heterocycloalkyl. In some embodiments, the heterocycloalkyl is a 3- to 6-membered heterocycloalkyl. In some embodiments, the heterocycloalkyl is a 4- to 6-membered heterocycloalkyl. In some embodiments, the heterocycloalkyl is a 5- to 6-membered heterocycloalkyl. Unless stated otherwise specifically in the specification, a heterocycloalkyl may be optionally substituted as described below, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, the heterocycloalkyl is optionally substituted with oxo, halogen, methyl, ethyl, —CN, —CF$_3$, —OH, —OMe, —NH$_2$, or —NO$_2$. In some embodiments, the heterocycloalkyl is optionally substituted with halogen, methyl, ethyl, —CN, —CF$_3$, —OH, or —OMe. In some embodiments, the heterocycloalkyl is optionally substituted with halogen.

"Heteroaryl" refers to a 5- to 14-membered ring system radical comprising one to thirteen carbon atoms, one to six heteroatoms selected from the group consisting of nitrogen, oxygen, phosphorous, and sulfur, and at least one aromatic ring. In some embodiments, the heteroaryl comprises one to three heteroatoms selected from the group consisting of nitrogen, oxygen, and sulfur. In some embodiments, the heteroaryl comprises one to three heteroatoms selected from the group consisting of nitrogen and oxygen. In some embodiments, the heteroaryl comprises one to three nitrogens. In some embodiments, the heteroaryl comprises one or two nitrogens. In some embodiments, the heteroaryl comprises one nitrogen. The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. In some embodiments, the heteroaryl is a 6-membered heteroaryl. In some embodiments, the heteroaryl is a 5-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl may be optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, the heteroaryl is optionally substituted with halogen, methyl, ethyl, —CN, —CF$_3$, —OH, —OMe, —NH$_2$, or —NO$_2$. In some embodiments, the heteroaryl is optionally substituted with halogen, methyl, ethyl, —CN, —CF$_3$, —OH, or —OMe. In some embodiments, the heteroaryl is optionally substituted with halogen.

The term "alkylarylene" refers to an arylene moiety covalently bonded to an alkylene moiety (also referred to herein as an alkylene linker). In some embodiments, the alkylarylene group has the formula:

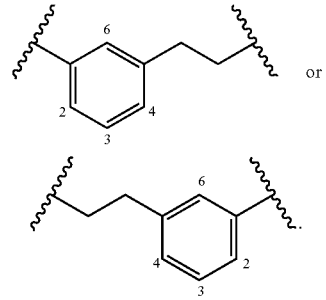

An alkylarylene moiety may be substituted (e.g., with a substituent group) on the alkylene moiety or the arylene linker (e.g., at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$— SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In some embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C(O)NR"NR'''R'''', —CN, —NO$_2$, —NR'SO$_2$R", —NR'C(O)R", —NR'C(O)—OR", —NR'OR", in a number ranging from zero to (2 m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B— wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

The term "amino acid" refers to a molecule containing both an amino group and a carboxyl group. Suitable amino acids include, without limitation, both the D- and L-isomers of the naturally-occurring amino acids, as well as non-naturally-occurring amino acids prepared by organic synthesis or other metabolic routes. The term amino acid, as used herein, includes, without limitation, α-amino acids, natural amino acids, non-natural amino acids, and amino acid analogues.

The term "α-amino acid" refers to a molecule containing both an amino group and a carboxyl group bound to a carbon which is designated the α-carbon.

The term "β-amino acid" refers to a molecule containing both an amino group and a carboxyl group in a β configuration.

The term "naturally-occurring amino acid" refers to any one of the twenty amino acids commonly found in peptides synthesized in nature, and known by the one letter abbreviations A, R, N, C, D, Q, E, G, H, I, L, K, M, F, P, S, T, W, Y and V.

The following table shows a summary of the properties of natural amino acids:

| Amino Acid | 3-Letter Code | 1-Letter Code | Side-chain Polarity | Side-chain charge (pH 7.4) | Hydropathy Index |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | polar | neutral | 2.5 |
| Glutamc acid | Glu | E | polar | negative | −3.5 |

-continued

| Amino Acid | 3-Letter Code | 1-Letter Code | Side-chain Polarity | Side-chain charge (pH 7.4) | Hydropathy Index |
|---|---|---|---|---|---|
| Glutamine | Gln | Q | polar | neutral | −3.5 |
| Glycine | Gly | G | nonpolar | neutral | −0.4 |
| Histidine | His | H | polar | Positive (10%) Neutral (90%) | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

"Hydrophobic amino acids" include small hydrophobic amino acids and large hydrophobic amino acids. "Small hydrophobic amino acids" are glycine, alanine, proline, and analogues thereof. "Large hydrophobic amino acids" are valine, leucine, isoleucine, phenylalanine, methionine, tryptophan, and analogues thereof. "Polar amino acids" are serine, threonine, asparagine, glutamine, cysteine, tyrosine, and analogues thereof. "Charged amino acids" are lysine, arginine, histidine, aspartate, glutamate, and analogues thereof.

The term "amino acid analogue" refers to a molecule which is structurally similar to an amino acid and which can be substituted for an amino acid in the formation of a peptidomimetic macrocycle. Amino acid analogues include, without limitation, O-amino acids and amino acids wherein the amino or carboxy group is substituted by a similarly reactive group (e.g., substitution of the primary amine with a secondary or tertiary amine, or substitution of the carboxy group with an ester).

The term "non-natural amino acid" refers to an amino acid which is not one of the twenty amino acids commonly found in peptides synthesized in nature, and known by the one letter abbreviations A, R, N, C, D, Q, E, G, H, I, L, K, M, F, P, S, T, W, Y and V. Non-natural amino acids or amino acid analogues include, without limitation, structures according to the following:

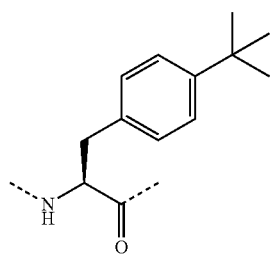

4-t-butylphenylalanine (F4tBu)

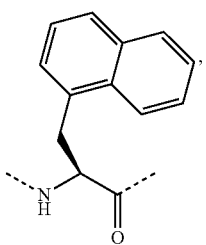

1-Naphthylalanine (1Nal)

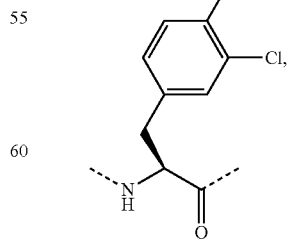

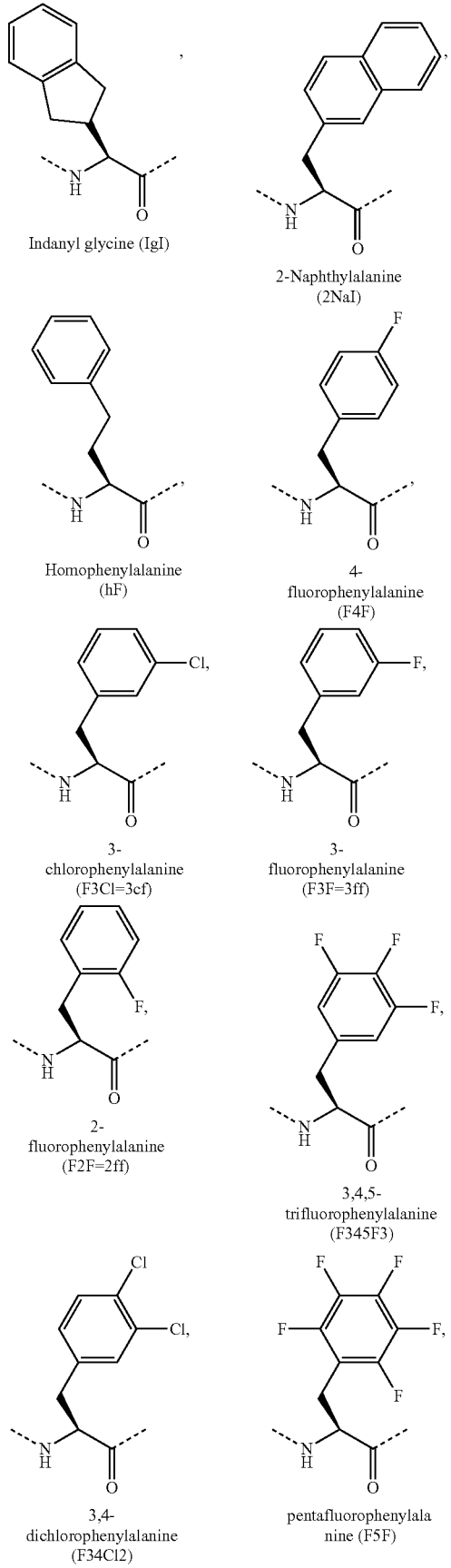

-continued

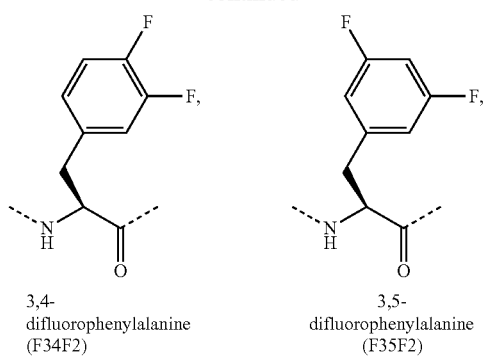

3,4-difluorophenylalanine (F34F2)

3,5-difluorophenylalanine (F35F2)

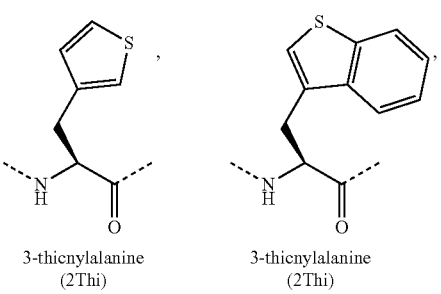

3-thienylalanine (2Thi)

3-thienylalanine (2Thi)

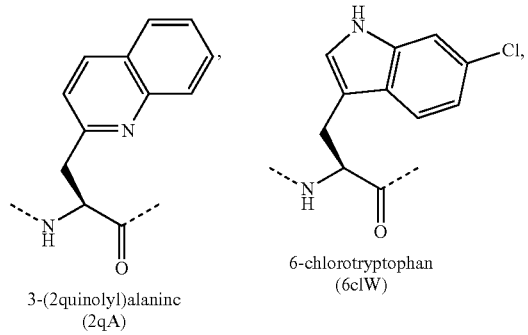

3-(2quinolyl)alanine (2qA)

6-chlorotryptophan (6clW)

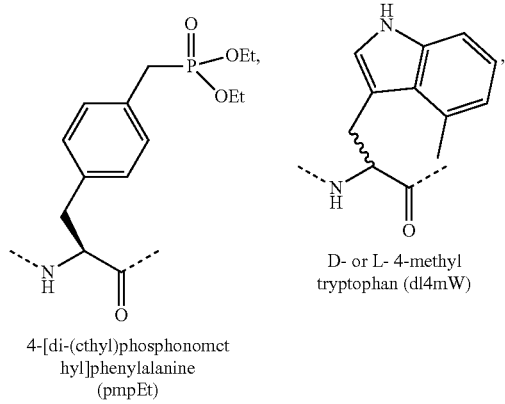

4-[di-(ethyl)phosphonomethyl]phenylalanine (pmpEt)

D- or L- 4-methyl tryptophan (dl4mW)

-continued

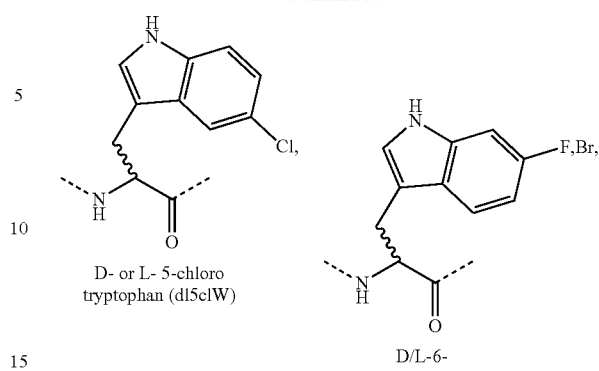

D- or L- 5-chloro tryptophan (dl5clW)

D/L-6-fluorotryptophan & D/L -6-bromotryptophan (ddl6fW & dl6brW)

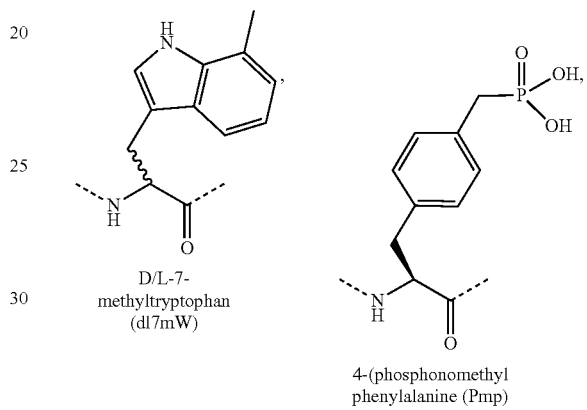

D/L-7-methyltryptophan (dl7mW)

4-(phosphonomethyl phenylalanine (Pmp)

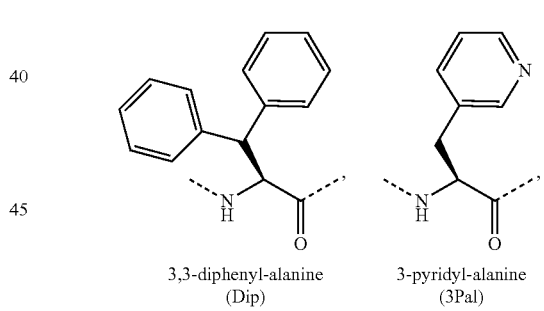

3,3-diphenyl-alanine (Dip)

3-pyridyl-alanine (3Pal)

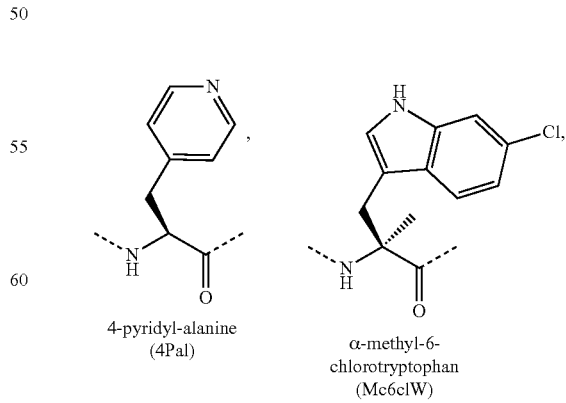

4-pyridyl-alanine (4Pal)

α-methyl-6-chlorotryptophan (Mc6clW)

-continued

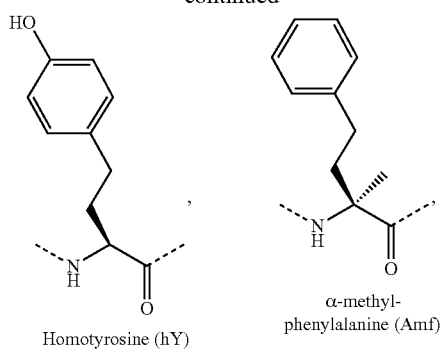

Homotyrosine (hY), α-methyl-phenylalanine (Amf),

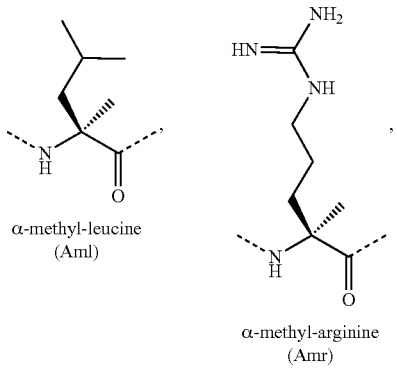

α-methyl-leucine (Aml), α-methyl-arginine (Amr),

α-methyl-serine (Ams), α-methyl-tryptophan (Amw)

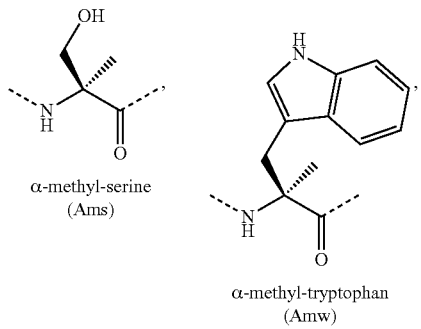

1-amino-cyclopropane-1-carboxylic acid (Ac3c), 1-amino-cyclopentane-1-carboxylic acid (Ac5c), 1-amino-cyclohexane-1-carboxylic acid (Ac6c)

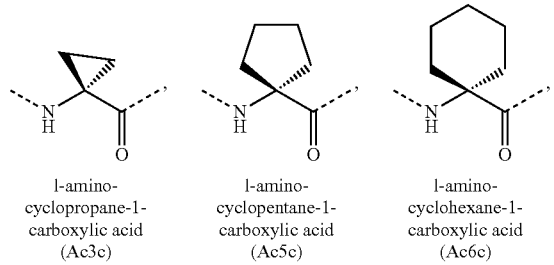

α-amino isobutyric acid (Aib), Norleucine (Nle), Homoleucine (hL)

-continued

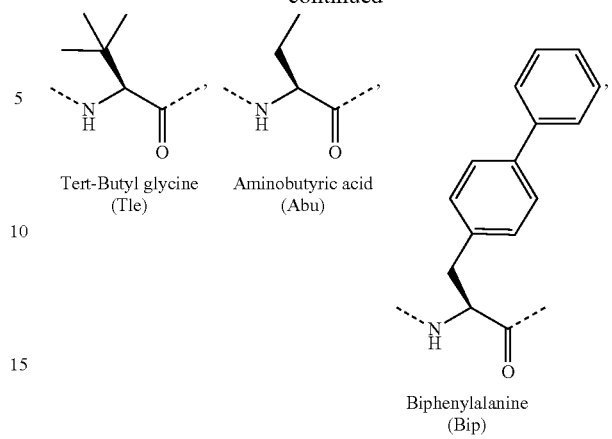

Tert-Butyl glycine (Tle), Aminobutyric acid (Abu), Biphenylalanine (Bip)

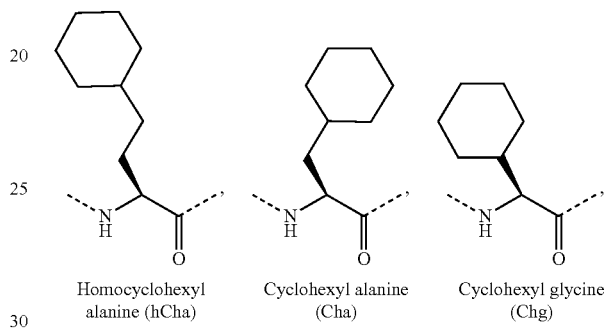

Homocyclohexyl alanine (hCha), Cyclohexyl alanine (Cha), Cyclohexyl glycine (Chg)

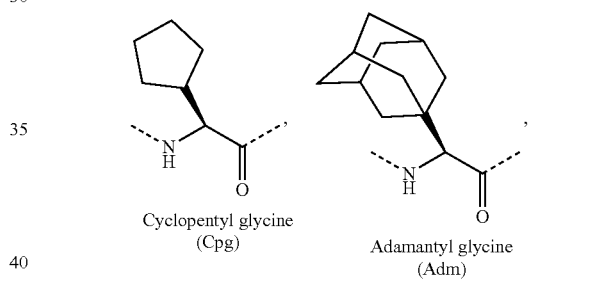

Cyclopentyl glycine (Cpg), Adamantyl glycine (Adm)

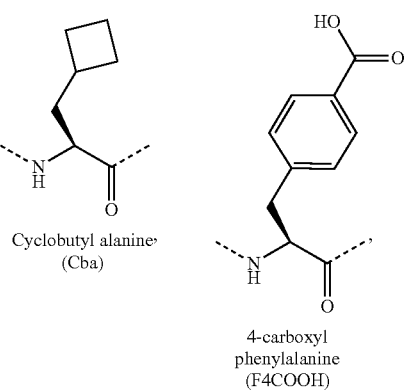

Cyclobutyl alanine (Cba), 4-carboxyl phenylalanine (F4COOH)

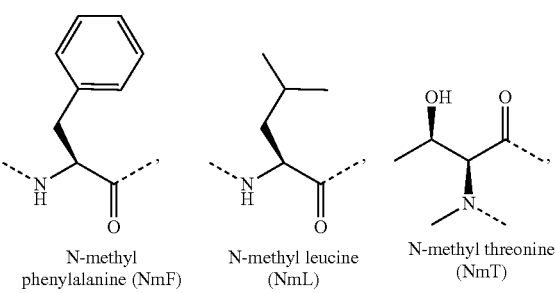

N-methyl phenylalanine (NmF), N-methyl leucine (NmL), N-methyl threonine (NmT)

-continued

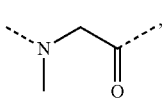

Sarcosine (Sar)

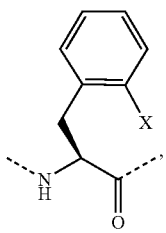

2-chlorophenylalanine
(X = Cl)
2-bromophenylalanine
(X = Br)
2-trimethyl phenylalanine
(X = CF3)
2-cyanophenylalanine
(X = CN)
2-methylphenylalanine
(X = Me)
2-nitrophenylalanine
(X = NO2)
(F2X, X = Cl, Br, CF3, CN, Me, NO2)

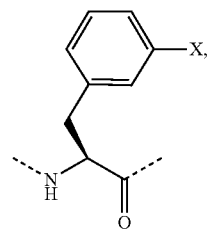

3-chlorophenylalanine
(X = Cl)
3-bromophenylalanine
(X = Br)
3-trimethyl phenylalanine
(X = CF3)
3-cyanophenylalanine
(X = CN)
3-methylphenylalanine
(X = Me)
3-nitrophenylalanine
(X = NO2)
(F3X, X = Cl, Br, CF3, CN, Me, NO2)

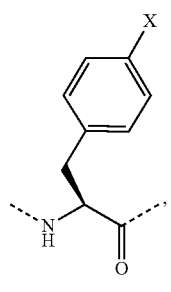

4-chlorophenylalanine
(X = Cl)
4-bromophenylalanine
(X = Br)
4-trimethyl phenylalanine
(X = CF3)
4-cyanophenylalanine
(X = CN)
4-methylphenylalanine
(X = Me)
4-nitrophenylalanine
(X = NO2)
(F3X, X = Cl, Br, CF3, CN, Me, NO2)

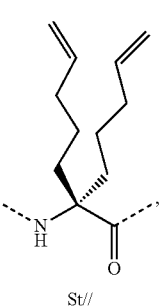

S5///

-continued

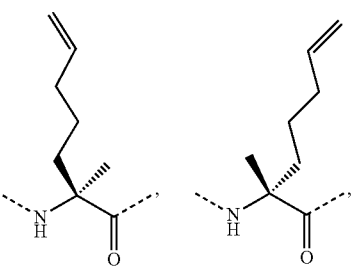

$/          $/r5

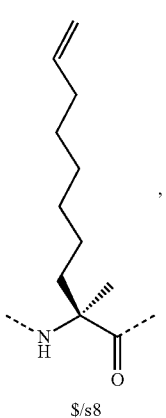

$/s8

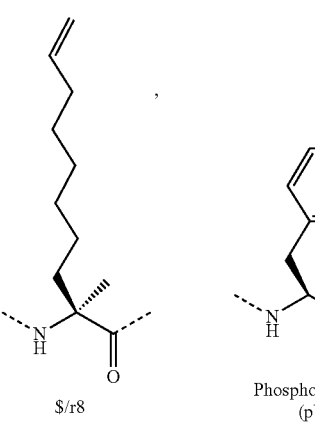

$/r8

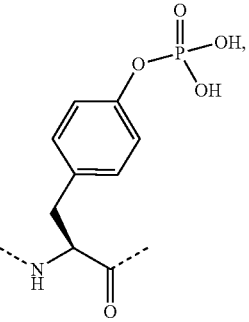

Phosphotyrosine
(pY)

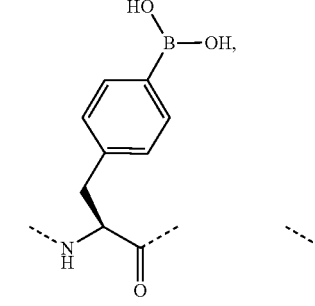

4-borono-phenylalanine
(F4bOH2)

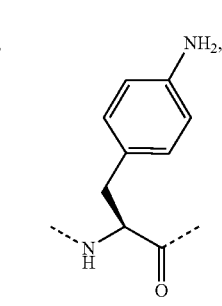

4-aminophenylalanine
(F4NH2)

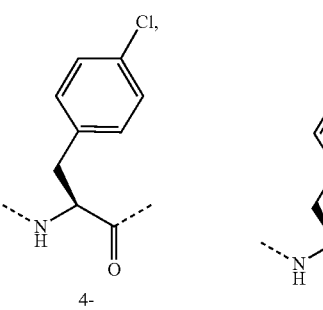

4-chlorophenylalanine
(F4Cl)

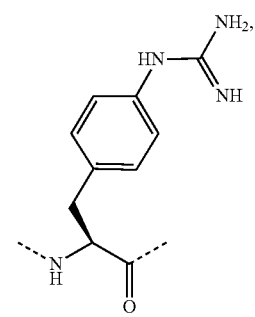

4-guanido phenylalanine (F4g)

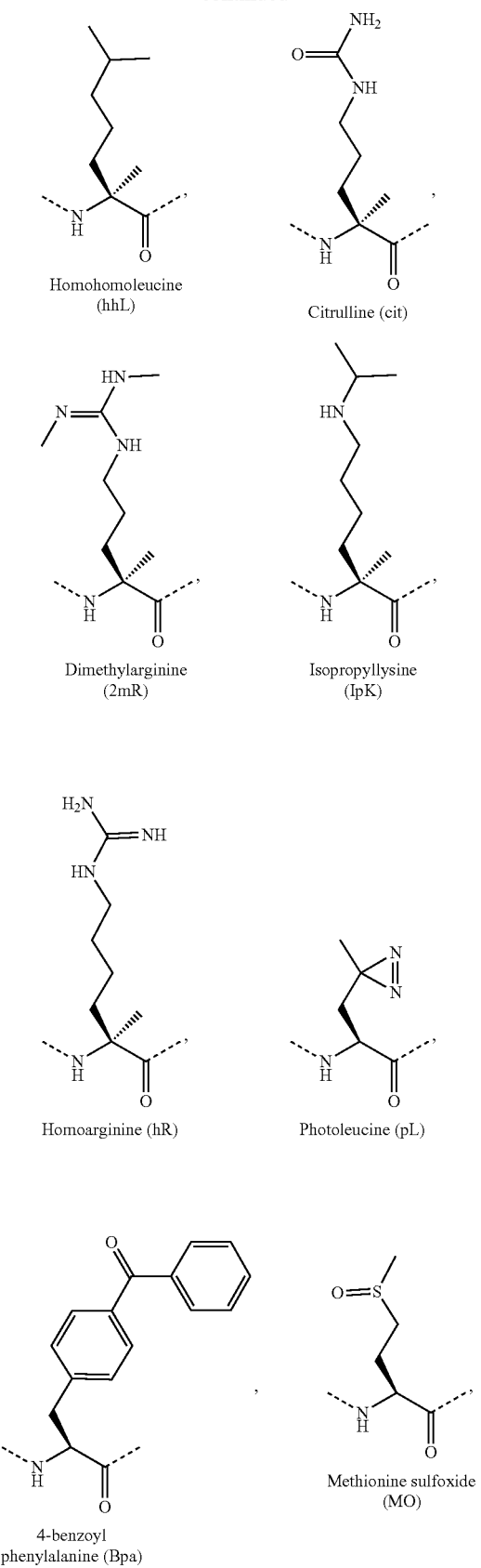
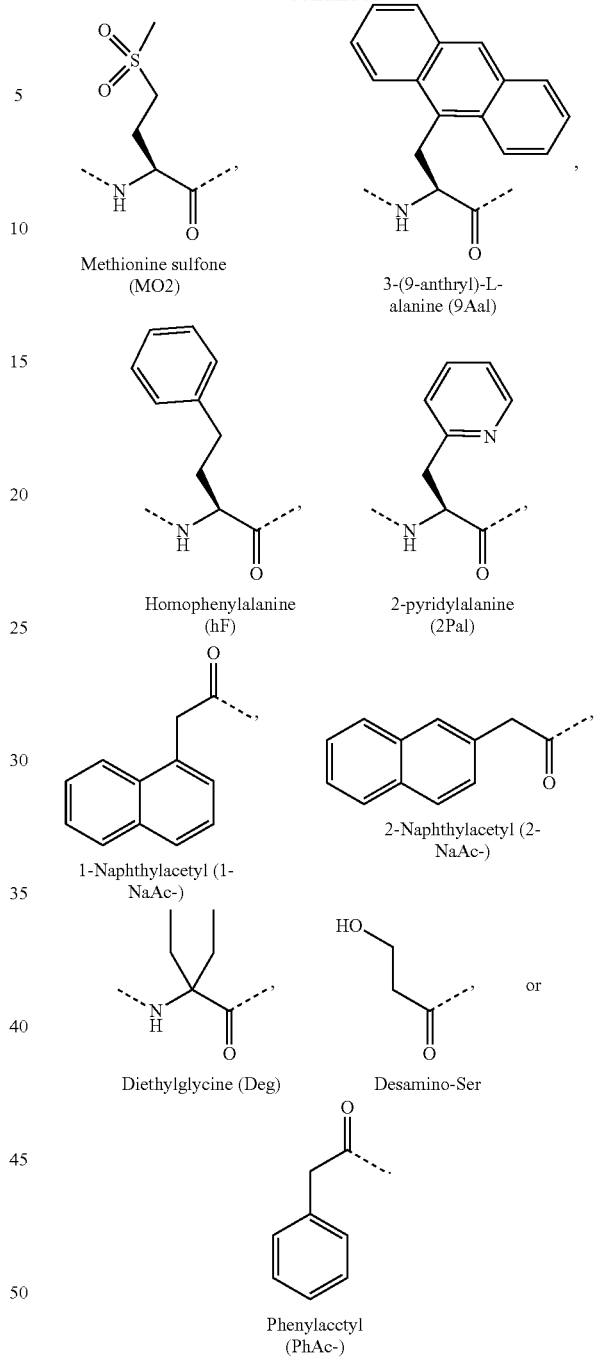

Amino acid analogues include β-amino acid analogues. Examples of β-amino acid analogues include, but are not limited to, the following: cyclic β-amino acid analogues; β-alanine; (R)-β-phenylalanine; (R)-1,2,3,4-tetrahydro-isoquinoline-3-acetic acid; (R)-3-amino-4-(1-naphthyl)-butyric acid; (R)-3-amino-4-(2,4-dichlorophenyl)butyric acid; (R)-3-amino-4-(2-chlorophenyl)-butyric acid; (R)-3-amino-4-(2-cyanophenyl)-butyric acid; (R)-3-amino-4-(2-fluorophenyl)-butyric acid; (R)-3-amino-4-(2-furyl)-butyric acid; (R)-3-amino-4-(2-methylphenyl)-butyric acid; (R)-3-amino-4-(2-naphthyl)-butyric acid; (R)-3-amino-4-(2-thienyl)-butyric acid; (R)-3-amino-4-(2-trifluoromethylphenyl)-butyric acid; (R)-3-amino-4-(3,4-dichlorophenyl)butyric acid; (R)-3-amino-4-(3,4-difluorophenyl)butyric acid; (R)-3-amino-4-(3-benzothienyl)-butyric acid; (R)-3-amino-4-(3-chlorophenyl)-butyric acid; (R)-3-amino-4-(3-cyanophenyl)-butyric acid; (R)-3-amino-4-(3-fluorophenyl)-butyric acid; (R)-3-amino-4-(3-methylphenyl)-butyric acid; (R)-3-amino-4-(3-pyridyl)-butyric acid; (R)-3-amino-4-(3-thienyl)-butyric acid; (R)-3-amino-4-(3-trifluoromethylphenyl)-butyric acid; (R)-3-amino-4-(4-bromophenyl)-butyric acid; (R)-3-amino-4-(4-chlorophenyl)-butyric acid; (R)-3-amino-4-(4-cyanophenyl)-butyric acid; (R)-3-amino-4-(4-fluorophenyl)-butyric acid; (R)-3-amino-4-(4-iodophenyl)-butyric acid; (R)-3-amino-4-(4-methylphenyl)-butyric acid; (R)-3-amino-4-(4-nitrophenyl)-butyric acid; (R)-3-amino-4-(4-pyridyl)-butyric acid; (R)-3-amino-4-(4-trifluoromethylphenyl)-butyric acid; (R)-3-amino-4-pentafluoro-phenylbutyric acid; (R)-3-amino-5-hexenoic acid; (R)-3-amino-5-hexynoic acid; (R)-3-amino-5-phenylpentanoic acid; (R)-3-amino-6-phenyl-5-hexenoic acid; (S)-1,2,3,4-tetrahydroisoquinoline-3-acetic acid; (S)-3-amino-4-(1-naphthyl)-butyric acid; (S)-3-amino-4-(2,4-dichlorophenyl)butyric acid; (S)-3-amino-4-(2-chlorophenyl)-butyric acid; (S)-3-amino-4-(2-cyanophenyl)-butyric acid; (S)-3-amino-4-(2-fluorophenyl)-butyric acid; (S)-3-amino-4-(2-furyl)-butyric acid; (S)-3-amino-4-(2-methylphenyl)-butyric acid; (S)-3-amino-4-(2-naphthyl)-butyric acid; (S)-3-amino-4-(2-thienyl)-butyric acid; (S)-3-amino-4-(2-trifluoromethylphenyl)-butyric acid; (S)-3-amino-4-(3,4-dichlorophenyl)butyric acid; (S)-3-amino-4-(3,4-difluorophenyl)butyric acid; (S)-3-amino-4-(3-benzothienyl)-butyric acid; (S)-3-amino-4-(3-chlorophenyl)-butyric acid; (S)-3-amino-4-(3-cyanophenyl)-butyric acid; (S)-3-amino-4-(3-fluorophenyl)-butyric acid; (S)-3-amino-4-(3-methylphenyl)-butyric acid; (S)-3-amino-4-(3-pyridyl)-butyric acid; (S)-3-amino-4-(3-thienyl)-butyric acid; (S)-3-amino-4-(3-trifluoromethylphenyl)-butyric acid; (S)-3-amino-4-(4-bromophenyl)-butyric acid; (S)-3-amino-4-(4-chlorophenyl)-butyric acid; (S)-3-amino-4-(4-cyanophenyl)-butyric acid; (S)-3-amino-4-(4-fluorophenyl)-butyric acid; (S)-3-amino-4-(4-iodophenyl)-butyric acid; (S)-3-amino-4-(4-methylphenyl)-butyric acid; (S)-3-amino-4-(4-nitrophenyl)-butyric acid; (S)-3-amino-4-(4-pyridyl)-butyric acid; (S)-3-amino-4-(4-trifluoromethylphenyl)-butyric acid; (S)-3-amino-4-pentafluoro-phenylbutyric acid; (S)-3-amino-5-hexenoic acid; (S)-3-amino-5-hexynoic acid; (S)-3-amino-5-phenylpentanoic acid; (S)-3-amino-6-phenyl-5-hexenoic acid; 1,2,5,6-tetrahydropyridine-3-carboxylic acid; 1,2,5,6-tetrahydropyridine-4-carboxylic acid; 3-amino-3-(2-chlorophenyl)-propionic acid; 3-amino-3-(2-thienyl)-propionic acid; 3-amino-β-(3-bromophenyl)-propionic acid; 3-amino-3-(4-chlorophenyl)-propionic acid; 3-amino-3-(4-methoxyphenyl)-propionic acid; 3-amino-4,4,4-trifluoro-butyric acid; 3-aminoadipic acid; D-β-phenylalanine; β-leucine; L-β-homoalanine; L-β-homoaspartic acid γ-benzyl ester; L-β-homoglutamic acid δ-benzyl ester; L-β-homoisoleucine; L-β-homoleucine; L-β-homomethionine; L-β-homophenylalanine; L-β-homoproline; L-0-homotryptophan; L-β-homovaline; L-Nω-benzyloxycarbonyl-β-homolysine; Nω-L-β-homoarginine; O-benzyl-L-β-homohydroxyproline; O-benzyl-L-β-homoserine; O-benzyl-L-β-homothreonine; O-benzyl-L-β-homotyrosine; γ-trityl-L-β-homoasparagine; (R)-β-phenylalanine; L-β-homoaspartic acid γ-t-butyl ester; L-β-homoglutamic acid δ-t-butyl ester; L-Nω-β-homolysine; Nδ-trityl-L-β-homoglutamine; Nω-2,2,4,6,7-pentamethyl-dihydrobenzofuran-5-sulfonyl-L-β-homoarginine; O-t-butyl-L-β-homohydroxyproline; O-t-butyl-L-β-homoserine; O-t-butyl-L-β-homothreonine; O-t-butyl-L-β-homotyrosine; 2-aminocyclopentane carboxylic acid; and 2-aminocyclohexane carboxylic acid.

Amino acid analogues include analogues of alanine, valine, glycine or leucine. Examples of amino acid analogues of alanine, valine, glycine, and leucine include, but are not limited to, the following: α-methoxyglycine; α-allyl-L-alanine; α-aminoisobutyric acid; α-methyl-leucine; β-(1-naphthyl)-D-alanine; β-(1-naphthyl)-L-alanine; β-(2-naphthyl)-D-alanine; β-(2-naphthyl)-L-alanine; β-(2-pyridyl)-D-alanine; β-(2-pyridyl)-L-alanine; β-(2-thienyl)-D-alanine; β-(2-thienyl)-L-alanine; β-(3-benzothienyl)-D-alanine; β-(3-benzothienyl)-L-alanine; β-(3-pyridyl)-D-alanine; β-(3-pyridyl)-L-alanine; β-(4-pyridyl)-D-alanine; β-(4-pyridyl)-L-alanine; β-chloro-L-alanine; O-cyano-L-alanine; β-cyclohexyl-D-alanine; β-cyclohexyl-L-alanine; β-cyclopenten-1-yl-alanine; β-cyclopentyl-alanine; β-cyclopropyl-L-Ala-OH·dicyclohexylammonium salt; β-t-butyl-D-alanine; β-t-butyl-L-alanine; γ-aminobutyric acid; L-α,β-diaminopropionic acid; 2,4-dinitro-phenylglycine; 2,5-dihydro-D-phenylglycine; 2-amino-4,4,4-trifluorobutyric acid; 2-fluoro-phenylglycine; 3-amino-4,4,4-trifluoro-butyric acid; 3-fluoro-valine; 4,4,4-trifluoro-valine; 4,5-dehydro-L-leu-OH·dicyclohexylammonium salt; 4-fluoro-D-phenylglycine; 4-fluoro-L-phenylglycine; 4-hydroxy-D-phenylglycine; 5,5,5-trifluoro-leucine; 6-aminohexanoic acid; cyclopentyl-D-Gly-OH·dicyclohexylammonium salt; cyclopentyl-Gly-OH·dicyclohexylammonium salt; D-α,β-diaminopropionic acid; D-α-aminobutyric acid; D-α-t-butylglycine; D-(2-thienyl)glycine; D-(3-thienyl)glycine; D-2-aminocaproic acid; D-2-indanylglycine; D-allylglycine·dicyclohexylammonium salt; D-cyclohexylglycine; D-norvaline; D-phenylglycine; β-aminobutyric acid; β-aminoisobutyric acid; (2-bromophenyl)glycine; (2-methoxyphenyl)glycine; (2-methylphenyl)glycine; (2-thiazoyl)glycine; (2-thienyl)glycine; 2-amino-3-(dimethylamino)-propionic acid; L-α,β-diaminopropionic acid; L-α-aminobutyric acid; L-α-t-butylglycine; L-(3-thienyl)glycine; L-2-amino-3-(dimethylamino)-propionic acid; L-2-aminocaproic acid dicyclohexyl-ammonium salt; L-2-indanylglycine; L-allylglycine·dicyclohexyl ammonium salt; L-cyclohexylglycine; L-phenylglycine; L-propargylglycine; L-norvaline; N-α-aminomethyl-L-alanine; D-α,γ-diaminobutyric acid; L-α,γ-diaminobutyric acid; O-cyclopropyl-L-alanine; (N-β-(2,4-dinitrophenyl))-L-α,β-diaminopropionic acid; (N-β-1-(4,4-dimethyl-2,6-dioxocyclohex-1-ylidene)ethyl)-D-α,β-diaminopropionic acid; (N-β-1-(4,4-dimethyl-2,6-dioxocyclohex-1-ylidene)ethyl)-L-α,β-diaminopropionic acid; (N-β-4-methyltrityl)-L-α,β-diaminopropionic acid; (N-β-allyloxycarbonyl)-L-α,β-diaminopropionic acid; (N-γ-1-(4,4-dimethyl-2,6-dioxocyclohex-1-ylidene)ethyl)-D-α,γ-diaminobutyric acid; (N-γ-1-(4,4-dimethyl-2,6-dioxocyclohex-1-ylidene)ethyl)-L-α,γ-diaminobutyric acid; (N-γ4-methyltrityl)-D-α,γ-diaminobutyric acid; (N-γ-4-methyltrityl)-L-α,γ-diaminobutyric acid; (N-γ-allyloxycarbonyl)-L-α,γ-diaminobutyric acid; D-α,γ-diaminobutyric acid; 4,5-dehydro-L-leucine; cyclopentyl-D-Gly-OH; cyclopentyl-Gly-OH; D-allylglycine; D-homocyclohexylalanine; L-1-pyrenylalanine; L-2-aminocaproic acid; L-allylglycine; L-homocyclohexylalanine; and N-(2-hydroxy-4-methoxy-Bzl)-Gly-OH.

Amino acid analogues include analogues of arginine or lysine. Examples of amino acid analogues of arginine and lysine include, but are not limited to, the following: citrulline; L-2-amino-3-guanidinopropionic acid; L-2-amino-3-ureidopropionic acid; L-citrulline; Lys(Me)₂-OH; Lys(N₃)—OH; Nδ-benzyloxycarbonyl-L-ornithine; Nω-nitro-D-arginine; Nω-nitro-L-arginine; α-methyl-ornithine; 2,6-diaminoheptanedioic acid; L-ornithine; (Nδ-1-(4,4-dimethyl-2,6-dioxo-cyclohex-1-ylidene)ethyl)-D-ornithine;

(Nδ-1-(4,4-dimethyl-2,6-dioxo-cyclohex-1-ylidene)ethyl)-L-ornithine; (Nδ-4-methyltrityl)-D-ornithine; (Nδ-4-methyltrityl)-L-ornithine; D-ornithine; L-ornithine; Arg(Me) (Pbf)-OH; Arg(Me)$_2$-OH (asymmetrical); Arg(Me)$_2$-OH (symmetrical); Lys(ivDde)-OH; Lys(Me)$_2$-OH·HCl; Lys(Me$_3$)-OH chloride; Nω-nitro-D-arginine; and Nω-nitro-L-arginine.

Amino acid analogues include analogues of aspartic or glutamic acids. Examples of amino acid analogues of aspartic and glutamic acids include, but are not limited to, the following: α-methyl-D-aspartic acid; α-methyl-glutamic acid; α-methyl-L-aspartic acid; γ-methylene-glutamic acid; (N-γ-ethyl)-L-glutamine; [N-α-(4-aminobenzoyl)]-L-glutamic acid; 2,6-diaminopimelic acid; L-α-aminosuberic acid; D-2-aminoadipic acid; D-α-aminosuberic acid; α-aminopimelic acid; iminodiacetic acid; L-2-aminoadipic acid; threo-β-methyl-aspartic acid; γ-carboxy-D-glutamic acid γ,γ-di-t-butyl ester; γ-carboxy-L-glutamic acid γ,γ-di-t-butyl ester; Glu(OAll)-OH; L-Asu(OtBu)-OH; and pyroglutamic acid.

Amino acid analogues include analogues of cysteine and methionine. Examples of amino acid analogues of cysteine and methionine include, but are not limited to, Cys(farnesyl)-OH, Cys(farnesyl)-OMe, α-methyl-methionine, Cys(2-hydroxyethyl)-OH, Cys(3-aminopropyl)-OH, 2-amino-4-(ethylthio)butyric acid, buthionine, buthioninesulfoximine, ethionine, methionine methylsulfonium chloride, selenomethionine, cysteic acid, [2-(4-pyridyl)ethyl]-DL-penicillamine, [2-(4-pyridyl)ethyl]-L-cysteine, 4-methoxybenzyl-D-penicillamine, 4-methoxybenzyl-L-penicillamine, 4-methylbenzyl-D-penicillamine, 4-methylbenzyl-L-penicillamine, benzyl-D-cysteine, benzyl-L-cysteine, benzyl-DL-homocysteine, carbamoyl-L-cysteine, carboxyethyl-L-cysteine, carboxymethyl-L-cysteine, diphenylmethyl-L-cysteine, ethyl-L-cysteine, methyl-L-cysteine, t-butyl-D-cysteine, trityl-L-homocysteine, trityl-D-penicillamine, cystathionine, homocystine, L-homocystine, (2-aminoethyl)-L-cysteine, seleno-L-cystine, cystathionine, Cys(StBu)-OH, and acetamidomethyl-D-penicillamine.

Amino acid analogues include analogues of phenylalanine and tyrosine. Examples of amino acid analogues of phenylalanine and tyrosine include β-methyl-phenylalanine, β-hydroxyphenylalanine, α-methyl-3-methoxy-DL-phenylalanine, α-methyl-D-phenylalanine, α-methyl-L-phenylalanine, 1,2,3,4-tetrahydroisoquinoline-3-carboxylic acid, 2,4-dichloro-phenylalanine, 2-(trifluoromethyl)-D-phenylalanine, 2-(trifluoromethyl)-L-phenylalanine, 2-bromo-D-phenylalanine, 2-bromo-L-phenylalanine, 2-chloro-D-phenylalanine, 2-chloro-L-phenylalanine, 2-cyano-D-phenylalanine, 2-cyano-L-phenylalanine, 2-fluoro-D-phenylalanine, 2-fluoro-L-phenylalanine, 2-methyl-D-phenylalanine, 2-methyl-L-phenylalanine, 2-nitro-D-phenylalanine, 2-nitro-L-phenylalanine, 2;4;5-trihydroxy-phenylalanine, 3,4,5-trifluoro-D-phenylalanine, 3,4,5-trifluoro-L-phenylalanine, 3,4-dichloro-D-phenylalanine, 3,4-dichloro-L-phenylalanine, 3,4-difluoro-D-phenylalanine, 3,4-difluoro-L-phenylalanine, 3,4-dihydroxy-L-phenylalanine, 3,4-dimethoxy-L-phenylalanine, 3,5,3'-triiodo-L-thyronine, 3,5-diiodo-D-tyrosine, 3,5-diiodo-L-tyrosine, 3,5-diiodo-L-thyronine, 3-(trifluoromethyl)-D-phenylalanine, 3-(trifluoromethyl)-L-phenylalanine, 3-amino-L-tyrosine, 3-bromo-D-phenylalanine, 3-bromo-L-phenylalanine, 3-chloro-D-phenylalanine, 3-chloro-L-phenylalanine, 3-chloro-L-tyrosine, 3-cyano-D-phenylalanine, 3-cyano-L-phenylalanine, 3-fluoro-D-phenylalanine, 3-fluoro-L-phenylalanine, 3-fluoro-tyrosine, 3-iodo-D-phenylalanine, 3-iodo-L-phenylalanine, 3-iodo-L-tyrosine, 3-methoxy-L-tyrosine, 3-methyl-D-phenylalanine, 3-methyl-L-phenylalanine, 3-nitro-D-phenylalanine, 3-nitro-L-phenylalanine, 3-nitro-L-tyrosine, 4-(trifluoromethyl)-D-phenylalanine, 4-(trifluoromethyl)-L-phenylalanine, 4-amino-D-phenylalanine, 4-amino-L-phenylalanine, 4-benzoyl-D-phenylalanine, 4-benzoyl-L-phenylalanine, 4-bis(2-chloroethyl)amino-L-phenylalanine, 4-bromo-D-phenylalanine, 4-bromo-L-phenylalanine, 4-chloro-D-phenylalanine, 4-chloro-L-phenylalanine, 4-cyano-D-phenylalanine, 4-cyano-L-phenylalanine, 4-fluoro-D-phenylalanine, 4-fluoro-L-phenylalanine, 4-iodo-D-phenylalanine, 4-iodo-L-phenylalanine, homophenylalanine, thyroxine, 3,3-diphenylalanine, thyronine, ethyl-tyrosine, and methyl-tyrosine.

Amino acid analogues include analogues of proline. Examples of amino acid analogues of proline include, but are not limited to, 3,4-dehydro-proline, 4-fluoro-proline, cis-4-hydroxy-proline, thiazolidine-2-carboxylic acid, and trans-4-fluoro-proline.

Amino acid analogues include analogues of serine and threonine. Examples of amino acid analogues of serine and threonine include, but are not limited to, 3-amino-2-hydroxy-5-methylhexanoic acid, 2-amino-3-hydroxy-4-methylpentanoic acid, 2-amino-3-ethoxybutanoic acid, 2-amino-3-methoxybutanoic acid, 4-amino-3-hydroxy-6-methylheptanoic acid, 2-amino-3-benzyloxypropionic acid, 2-amino-3-benzyloxypropionic acid, 2-amino-3-ethoxypropionic acid, 4-amino-3-hydroxybutanoic acid, and α-methylserine.

Amino acid analogues include analogues of tryptophan. Examples of amino acid analogues of tryptophan include, but are not limited to, the following: α-methyl-tryptophan; β-(3-benzothienyl)-D-alanine; β-(3-benzothienyl)-L-alanine; 1-methyl-tryptophan; 4-methyl-tryptophan; 5-benzyloxy-tryptophan; 5-bromo-tryptophan; 5-chloro-tryptophan; 5-fluoro-tryptophan; 5-hydroxy-tryptophan; 5-hydroxy-L-tryptophan; 5-methoxy-tryptophan; 5-methoxy-L-tryptophan; 5-methyl-tryptophan; 6-bromo-tryptophan; 6-chloro-D-tryptophan; 6-chloro-tryptophan; 6-fluoro-tryptophan; 6-methyl-tryptophan; 7-benzyloxy-tryptophan; 7-bromo-tryptophan; 7-methyl-tryptophan; D-1,2,3,4-tetrahydro-norharman-3-carboxylic acid; 6-methoxy-1,2,3,4-tetrahydronorharman-1-carboxylic acid; 7-azatryptophan; L-1,2,3,4-tetrahydro-norharman-3-carboxylic acid; 5-methoxy-2-methyl-tryptophan; and 6-chloro-L-tryptophan.

In some embodiments, amino acid analogues are racemic. In some embodiments, the D isomer of the amino acid analogue is used. In some embodiments, the L isomer of the amino acid analogue is used. In other embodiments, the amino acid analogue comprises chiral centers that are in the R or S configuration. In still other embodiments, the amino group(s) of a β-amino acid analogue is substituted with a protecting group, e.g., tert-butyloxycarbonyl (BOC group), 9-fluorenylmethyloxycarbonyl (FMOC), tosyl, and the like. In yet other embodiments, the carboxylic acid functional group of a β-amino acid analogue is protected, e.g., as its ester derivative. In some embodiments the salt of the amino acid analogue is used.

The term "amino acid side chain" refers to a moiety attached to the α-carbon (or another backbone atom) in an amino acid. For example, the amino acid side chain for alanine is methyl, the amino acid side chain for phenylalanine is phenylmethyl, the amino acid side chain for cysteine is thiomethyl, the amino acid side chain for aspartate is carboxymethyl, the amino acid side chain for tyrosine is 4-hydroxyphenylmethyl, etc. Other non-naturally-occurring amino acid side chains are also included, for example, those that occur in nature (e.g., an amino acid metabolite) or those that are made synthetically (e.g., an α,α di-substituted amino acid).

Certain compounds of this disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein without clear indication of stereochemistry are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen with a deuterium or tritium, or the replacement of a carbon with $^{13}$C- or $^{14}$C- enriched carbon are within the scope of this invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., $-CH_2CH_3$), fully substituted (e.g., $-CF_2CF_3$), mono-substituted (e.g., $-CH_2CH_2F$) or substituted at a level anywhere in-between fully substituted and mono-substituted (e.g., $-CH_2CHF_2$, $-CH_2CF_3$, $-CF_2CH_3$, $-CFHCHF_2$, etc.). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

"Derivative" refers to a compound that retains the biological activity of the parent compound from which it is derived, or is a prodrug for the parent compound. Derivatives may include esters, amides, ethers of the parent compound, obtained by chemically modifying a moiety of the parent compound. For example, a derivative can be a compound in which a hydrogen atom or a certain atomic group is replaced with another atom or atomic group.

As used herein, the recitation of a numerical range for a variable is intended to convey that the variable is equal to any of the values within that range. Thus, for a variable which is inherently discrete, the variable is equal to any integer value within the numerical range, including the end-points of the range. Similarly, for a variable which is inherently continuous, the variable is equal to any real value within the numerical range, including the end-points of the range. As an example, and without limitation, a variable which is described as having values between 0 and 2 takes the values 0, 1 or 2 if the variable is inherently discrete, and takes the values 0.0, 0.1, 0.01, 0.001, or any other real values ≥0 and ≤2 if the variable is inherently continuous.

As used herein, unless specifically indicated otherwise, the word "or" is used in the inclusive sense of "and/or" and not the exclusive sense of "either/or."

An "effective amount" or "therapeutically effective amount" refers to an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An example of an "effective amount" is an amount sufficient accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). Another example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and Remington: *The Science and Practice of Pharmacy*, 20th Edition, 2003, Gennaro, Ed., Lippincott, Williams & Wilkins). The therapeutically effective amount can be ascertained by measuring relevant physiological effects, and it can be adjusted in connection with the dosing regimen and diagnostic analysis of the subject's condition, and the like. By way of example, measurement of the serum level of a CCR4 inhibitor (or, e.g., a metabolite thereof) at a particular time post-administration may be indicative of whether a therapeutically effective amount has been administered.

For any compound described herein, the therapeutically effective amount can be initially determined from cell culture assays. Target concentrations will be those concentrations of active compound(s) that are capable of achieving the methods described herein, as measured using the methods described herein or known in the art.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control. Therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan. Adjusting the dose to achieve maximal therapeutic window efficacy or toxicity in humans based on the methods described above and other methods is well within the capabilities of the ordinarily skilled artisan.

"Pharmaceutically acceptable salt" refers to those salts which are suitable for pharmaceutical use, such as, for example, for use in humans and lower animals without undue irritation, allergic response and the like. Pharmaceutically acceptable salts of amines, carboxylic acids, and other types of compounds, are well known in the art. For example, S. M. Berge, et al., describe pharmaceutically acceptable salts in detail in J Pharmaceutical Sciences, 66: 1-19 (1977), incorporated herein by reference. The salts can be prepared in situ during the final isolation and purification of the compound disclosed herein, or separately by reacting a free base or free acid function with a suitable reagent, as described generally below. For example, a free base function can be reacted with a suitable acid. Suitable pharmaceutically acceptable salts can, include metal salts such as alkali metal salts, e.g. sodium, potassium, and lithium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, hydroiodic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzoate, bisulfate, borate, butyrate, camphorate, camphorsulfonate, citrate, cyclopentanepropionate, digluconate, dodecylsulfate, formate, fumarate, glucoheptonate, glycerophosphate, gluconate, hernisulfate, heptanoate, hexanoate, hydroiodide, 2-hydroxy-ethanesulfonate, lactobionate, lactate, laurate, lauryl sulfate, malate, maleate, malonate, methanesulfonate, nicotinate, nitrate, oleate, oxalate, palmitate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition. In some embodiments, treatment also includes prophylactic treatment (e.g., administration of a composition described herein when an individual is suspected to be suffering from a viral infection, e.g., coronavirus). The terms "treating", "treat", "treatment" also refer to reducing, relieving, ameliorating, or alleviating at least one of the symptoms of the disease or disorder. The terms "treating", "treat", and "treatment" cover the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting relieving, or slowing progression of one or more symptoms of the disease or disorder. Treatment and treating refers to the intentional act of physiological intervention that is intended to cure, retard, or ameliorate one or more symptoms associated with a disease.

"Coronavirus infection" refers to any and all conditions deriving from infection with coronaviruses, including but not limited to SARS-CoV, SARS-CoV-2, and MERS, preferably SARS-CoV-2.

Compounds

Described herein are compounds of Formula (I), (Ia), (Ib), (Ic), (Id), (Ie), (If), (Ig), (II), (III), (IV), (V), (VIa), (VIb), and (VIc), or a pharmaceutically acceptable salt, solvate, or stereoisomer thereof useful in the treatment of viral infections. In some embodiments, the viral infection is a coronavirus infection.

Described herein are compounds of Formula (I), or a pharmaceutically acceptable salt, solvate, or stereoisomer thereof:

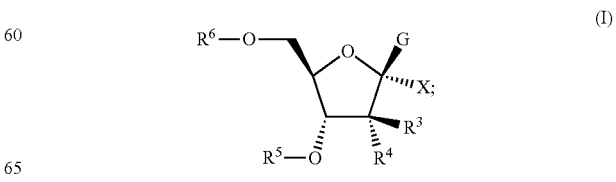

wherein:
X is H or CN;
G is

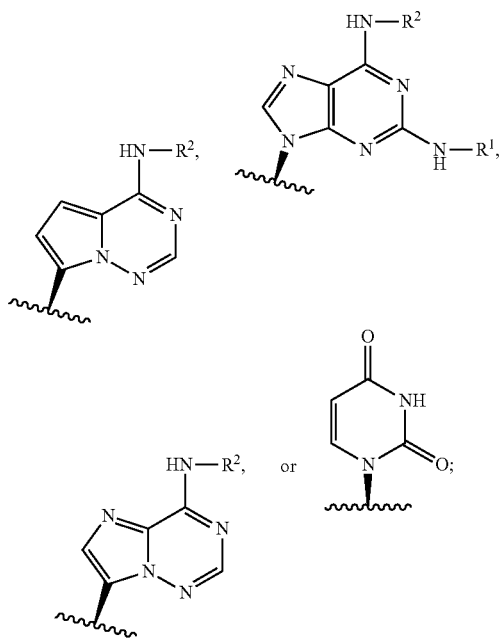

$R^1$ is hydrogen, substituted or unsubstituted alkyl, —C(O)$R^{1A}$, or —C(O)O$R^{1B}$;
$R^2$ is hydrogen, substituted or unsubstituted alkyl,

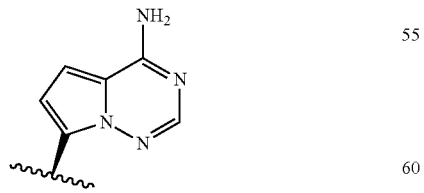

—C(O)$R^{2A}$, or —C(O)O$R^{2B}$;
$R^3$ is hydrogen or methyl;
$R^4$ is OH or F;
$R^5$ is hydrogen, —C(O)$R^{5A}$, —C(O)O$R^{5B}$, or —CH$_2$—O—C(O)$R^{5C}$.
$R^6$ is hydrogen, —C(O)$R^{6A}$, —C(O)O$R^{6B}$, —CH$_2$—O—C(O)$R^{6C}$, or —P(O)(O$R^{6D}$)(O$R^{6E}$), with the proviso (1) that when G is and X is CN, $R^6$ is not —P(O)(O$R^{6D}$)(O$R^{6E}$), and (2) that at least one of $R^5$ and $R^6$ is not hydrogen;
$R^{1A}$, $R^{1B}$, $R^{2A}$, $R^{2B}$, $R^{5A}$, $R^{5B}$, $R^{5C}$, $R^{6A}$, $R^{6B}$, $R^{6C}$, $R^{6D}$, and $R^{6E}$ are independently hydrogen, substituted or unsubstituted alkyl, substituted or unsubstituted heteroalkyl, substituted or unsubstituted arylalkyl, substituted or unsubstituted heteroarylalkyl, substituted or unsubstituted cycloalkyl, substituted or unsubstituted heterocycloalkyl, substituted or unsubstituted aryl, or substituted or unsubstituted heteroaryl; or (HO)C(O)$R^{5A}$ is a natural or unnatural amino acid; or (HO)C(O)$R^{6A}$ is a natural or unnatural amino acid; or $R^{6D}$ and $R^{6E}$ together with the oxygen atoms they are attached, respectively, form a substituted or unsubstituted heterocycle, or $R^{6E}$ comprises alkylene, alkenylene, cycloalkylene with a 3-7 membered ring, alkynylene, arylene, heteroarylene, heterocyclene with a 5-12 membered ring comprising 1-3 atoms of N, O or S, —O—, —NH—, —S—, —N(C$_{1-6}$ alkyl)-, —C(=O)—, —C(=O)NH—, or combinations thereof, and $R^{6E}$ is 10-40 atoms in length.

In some embodiments, the compound is Formula (Ia):

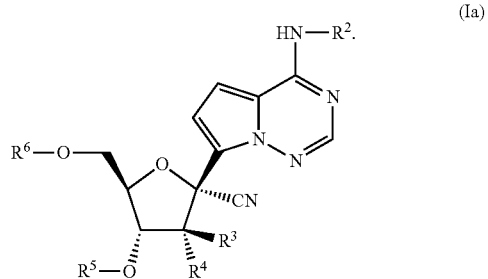

(Ia)

In some embodiments, the compound is Formula (Ib):

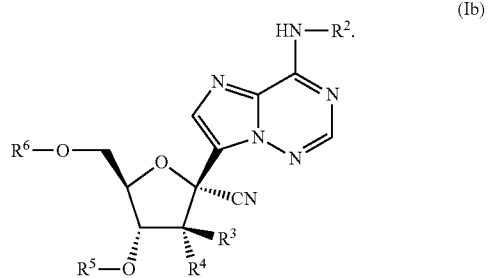

(Ib)

In some embodiments, the compound is Formula (Ic):

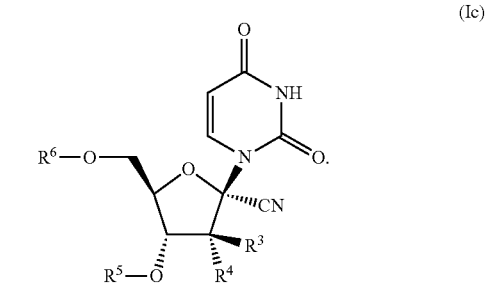

(Ic)

In some embodiments, the compound is Formula (Id):

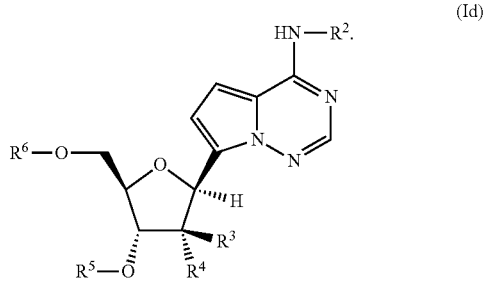

(Id)

In some embodiments, the compound is Formula (Ie):

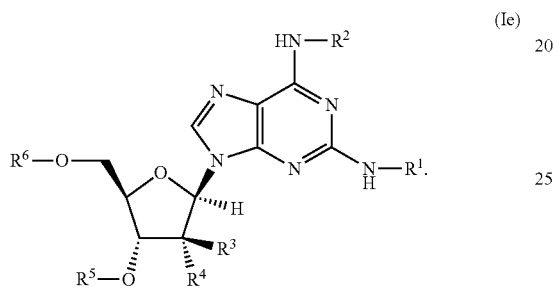

(Ie)

In some embodiments, the compound is Formula (If):

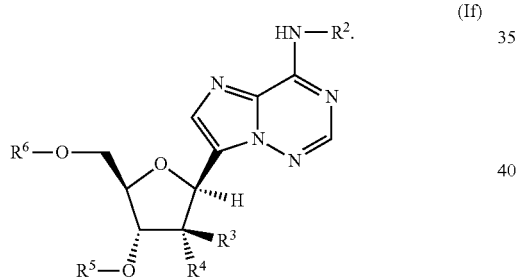

(If)

In some embodiments, the compound is Formula (Ig):

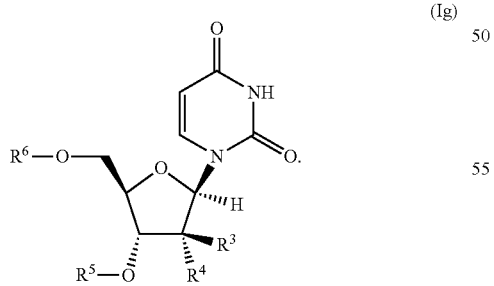

(Ig)

In some embodiments, $R^3$ is hydrogen, and $R^4$ is OH. In some embodiments, $R^3$ is methyl, and $R^4$ is F. In some embodiments, $R^{6D}$ is hydrogen. In some embodiments, $R^{6E}$ is substituted or unsubstituted alkyl, or $R^{6E}$ comprises alkylene, alkenylene, cycloalkylene with a 3-7 membered ring, alkynylene, arylene, heteroarylene, heterocyclene with a 5-12 membered ring comprising 1-3 atoms of N, O or S, —O—, —NH—, —S—, —N($C_{1-6}$ alkyl)-, —C(=O)—, —C(=O)NH—, or combinations thereof, and $R^{6E}$ is 10-40 atoms in length. In some embodiments, $R^{1A}$, $R^{2A}$, $R^{5A}$, and $R^{6A}$ are independently substituted or unsubstituted alkyl, substituted or unsubstituted cycloalkyl, or substituted or unsubstituted aryl. In some embodiments, $R^{1B}$, $R^{2B}$, $R^{5B}$, and $R^{6B}$ are independently substituted or unsubstituted alkyl, substituted or unsubstituted cycloalkyl, or substituted or unsubstituted aryl. In some embodiments, $R^{5C}$, and $R^{6C}$ are independently substituted or unsubstituted alkyl.

In some embodiments, for compounds of formulas (Ia) and (Id):

(1) $R^2$ is hydrogen, $R^5$ is hydrogen, and $R^6$ is —C(O)$R^{6A}$, —C(O)O$R^{6B}$, —CH$_2$—O—C(O)$R^{6C}$, or —P(O)(O$R^{6D}$)(O$R^{6E}$), or (2) $R^2$ is hydrogen, $R^5$ is —C(O)$R^{5A}$, —C(O)O$R^{5B}$, or —CH$_2$—O—C(O)$R^{5C}$, and $R^6$ is hydrogen, or (3) $R^2$ is substituted or unsubstituted alkyl,

[dioxolone-methyl ester structure]

—C(O)$R^{2A}$, or —C(O)O$R^{2B}$, $R^5$ is hydrogen, and $R^6$ is hydrogen, or (4) $R^2$ is hydrogen, $R^5$ is —C(O)$R^{5A}$, —C(O)O$R^{5B}$, or —CH$_2$—O—C(O)$R^{5C}$, and $R^6$ is —C(O)$R^{6A}$, —C(O)O$R^{6B}$, —CH$_2$—O—C(O)$R^{6C}$, or —P(O)(O$R^{6D}$)(O$R^{6E}$), or (5) $R^2$ is substituted or unsubstituted alkyl,

[dioxolone-methyl ester structure]

—C(O)$R^{2A}$, or —C(O)O$R^{2B}$, $R^5$ is hydrogen, and $R^6$ is —C(O)$R^{6A}$, —C(O)O$R^{6B}$, —CH$_2$—O—C(O)$R^{6C}$, or —P(O)(O$R^{6D}$)(O$R^{6E}$), or (6) $R^2$ is substituted or unsubstituted alkyl,

[dioxolone-methyl ester structure]

—C(O)$R^{2A}$, or —C(O)O$R^{2B}$, $R^5$ is —C(O)$R^{5A}$, —C(O)O$R^{5B}$, or —CH$_2$—O—C(O)$R^{5C}$, and $R^6$ is —C(O)$R^{6A}$, —C(O)O$R^{6B}$, —CH$_2$—O—C(O)$R^{6C}$, or —P(O)(O$R^{6D}$)(O$R^{6E}$).

In some embodiments, for compounds of formula (Ie):

(1) $R^1$ is hydrogen, $R^2$ is hydrogen, $R^5$ is hydrogen, and $R^6$ is —C(O)$R^{6A}$, —C(O)O$R^{6B}$, —CH$_2$—O—C(O)$R^{6C}$, or —P(O)(O$R^{6D}$)(O$R^{6E}$), or (2) $R^1$ is hydrogen, $R^2$ is hydrogen, $R^5$ is —C(O)$R^{5A}$, —C(O)O$R^{5B}$, or —CH$_2$—O—C(O)$R^{5C}$, and $R^6$ is hydrogen, or
(3) $R^1$ is hydrogen, $R^2$ is substituted or unsubstituted alkyl,

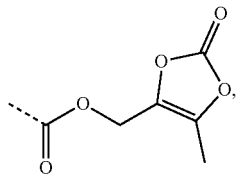

—C(O)$R^{2A}$ or —C(O)O$R^{2B}$, $R^5$ is hydrogen, and $R^6$ is hydrogen, or
(4) $R^1$ is substituted or unsubstituted alkyl, —C(O)$R^{1A}$, or —C(O)O$R^{1B}$, $R^2$ is hydrogen, $R^5$ is hydrogen, and $R^6$ is hydrogen,
(5) $R^1$ is hydrogen, $R^2$ is hydrogen, $R^5$ is —C(O)$R^{5A}$, —C(O)O$R^{5B}$, or —CH$_2$—O—C(O)$R^{5C}$, and $R^6$ is —C(O)$R^{6A}$, —C(O)O$R^{6B}$, —CH$_2$—O—C(O)$R^{6C}$, or —P(O)(O$R^{6D}$)(O$R^{6E}$), or
(6) $R^1$ is hydrogen, $R^2$ is substituted or unsubstituted alkyl,

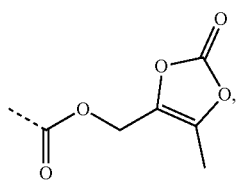

—C(O)$R^{2A}$, or C(O)O$R^{2B}$, $R^5$ is hydrogen, and $R^6$ is hydrogen, or
(7) $R^1$ is substituted or unsubstituted alkyl, —C(O)$R^{1A}$, or —C(O)O$R^{1B}$, $R^2$ is hydrogen, $R^5$ is hydrogen, and $R^6$ is hydrogen, or
(8) $R^1$ is hydrogen, $R^2$ is substituted or unsubstituted alkyl,

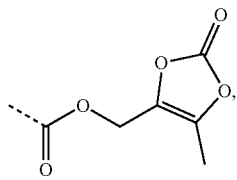

—C(O)$R^{2A}$, or C(O)O$R^{2B}$, $R^5$ is —C(O)$R^{5A}$, —C(O)O$R^{5B}$, or —CH$_2$—O—C(O)$R^{5C}$, and $R^6$ is hydrogen, or,
(9) $R^1$ is substituted or unsubstituted alkyl, —C(O)$R^{1A}$, or —C(O)O$R^{1B}$, $R^2$ is hydrogen, $R^5$ is —C(O)$R^{5A}$, —C(O)O$R^{5B}$, or —CH$_2$—O—C(O)$R^{5C}$, and $R^6$ is hydrogen, or
(10) $R^1$ is substituted or unsubstituted alkyl, —C(O)$R^{1A}$, or —C(O)O$R^{1B}$, $R^2$ is substituted or unsubstituted alkyl,

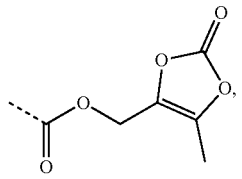

—C(O)$R^{2A}$, or —C(O)O$R^{2B}$, $R^5$ is hydrogen, and $R^6$ is hydrogen, or
(11) $R^1$ is hydrogen, $R^2$ is substituted or unsubstituted alkyl,

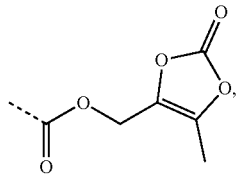

—C(O)$R^{2A}$, or —C(O)O$R^{2B}$, $R^5$ is —C(O)$R^{5A}$, —C(O)O$R^{5B}$, or —CH$_2$—O—C(O)$R^{5C}$, and $R^6$ is —C(O)$R^{6A}$, —C(O)O$R^{6B}$, —CH$_2$—O—C(O)$R^{6C}$, or —P(O)(OR©)(O$R^{6E}$), or
(12) $R^1$ is substituted or unsubstituted alkyl, —C(O)$R^{1A}$, or —C(O)O$R^{1B}$, $R^2$ is hydrogen, $R^5$ is —C(O)$R^{5A}$, —C(O)O$R^{5B}$, or —CH$_2$—O—C(O)$R^{5C}$, and $R^6$ is —C(O)$R^{6A}$, —C(O)O$R^{6B}$, —CH$_2$—O—C(O)$R^{6C}$, or —P(O)(O$R^{6D}$)(O$R^{6E}$), or
(13) $R^1$ is substituted or unsubstituted alkyl, —C(O)$R^{1A}$, or —C(O)O$R^{1B}$, $R^2$ is substituted or unsubstituted alkyl,

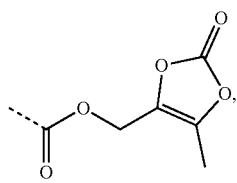

—C(O)$R^{2A}$, or —C(O)O$R^{2B}$, $R^5$ is hydrogen, and $R^6$ is —C(O)$R^{6A}$, —C(O)O$R^{6B}$, —CH$_2$—O—C(O)$R^{6C}$, or —P(O)(O$R^{6D}$)(O$R^{6E}$), or
(14) $R^1$ is substituted or unsubstituted alkyl, —C(O)$R^{1A}$, or —C(O)O$R^{1B}$, $R^2$ is substituted or unsubstituted alkyl,

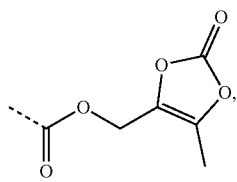

—C(O)$R^{2A}$, or —C(O)O$R^{2B}$, $R^5$ is —C(O)$R^{5A}$, —C(O)O$R^{5B}$ or —CH$_2$—O—C(O)$R^{5C}$, and $R^6$ is hydrogen, or
(15) $R^1$ is substituted or unsubstituted alkyl, —C(O)$R^{1A}$, or —C(O)O$R^{1B}$, $R^2$ is substituted or unsubstituted alkyl,

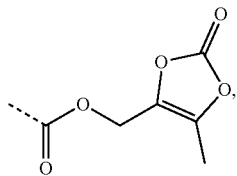

—C(O)R$^{2A}$, or —C(O)OR$^{2B}$, R$^5$ is —C(O)R$^{5A}$, —C(O)OR$^{5B}$, or —CH$_2$—O—C(O)R$^{5C}$, and R$^6$ is —C(O)R$^{6A}$, —C(O)OR$^{6B}$, —CH$_2$—O—C(O)R$^{6C}$, or —P(O)(OR$^{6D}$)(OR$^{6E}$).

In some embodiments, for compounds of formulas (Ib) and (If):

(1) R$^2$ is hydrogen, R$^5$ is hydrogen, and R$^6$ is —C(O)R$^{6A}$, —C(O)OR$^{6B}$, —CH$_2$—O—C(O)R$^{6C}$, or —P(O)(OR$^{6D}$)(OR$^{6E}$), or (2) R$^2$ is hydrogen, R$^5$ is —C(O)R$^{5A}$, —C(O)OR$^{5B}$, or —CH$_2$—O—C(O)R$^{5C}$, and R$^6$ is hydrogen, or (3) R$^2$ is substituted or unsubstituted alkyl,

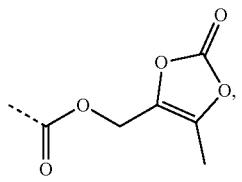

—C(O)R$^{2A}$, or —C(O)OR$^{2B}$, R$^5$ is hydrogen, and R$^6$ is hydrogen, or (4) R$^2$ is hydrogen, R$^5$ is —C(O)R$^{5A}$, —C(O)OR$^{5B}$, or —CH$_2$—O—C(O)R$^{5C}$, and R$^6$ is —C(O)R$^{6A}$, —C(O)OR$^{6B}$, —CH$_2$—O—C(O)R$^{6C}$, or —P(O)(OR$^{6D}$)(OR$^{6E}$), or (5) R$^2$ is substituted or unsubstituted alkyl,

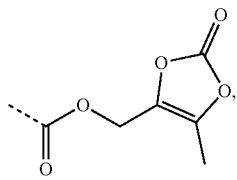

—C(O)R$^{2A}$, or —C(O)OR$^{2B}$, R$^5$ is hydrogen, and R$^6$ is —C(O)R$^{6A}$, —C(O)OR$^{6B}$, —CH$_2$—O—C(O)R$^{6C}$, or —P(O)(OR$^{6D}$)(OR$^{6E}$), or (6) R$^2$ is substituted or unsubstituted alkyl,

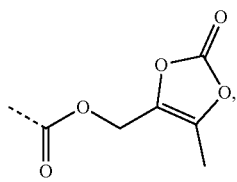

—C(O)R$^{2A}$, or —C(O)OR$^{2B}$, R$^5$ is —C(O)R$^{5A}$, —C(O)OR$^{5B}$, or —CH$_2$—O—C(O)R$^{5C}$, and R$^6$ is —C(O)R$^{6A}$, —C(O)OR$^{6B}$, —CH$_2$—O—C(O)R$^{6C}$, or —P(O)(OR$^{6D}$)(OR$^{6E}$).

In some embodiments, for compounds of formulas (Ic) and (Ig):

(1) R$^5$ is hydrogen, and R$^6$ is —C(O)R$^{6A}$, —C(O)OR$^{6B}$, —CH$_2$—O—C(O)R$^{6C}$, or —P(O)(OR$^{6D}$)(OR$^{6E}$), or (2) R$^5$ is —C(O)R$^{5A}$, —C(O)OR$^{5B}$, or —CH$_2$—O—C(O)R$^{5C}$, and R$^6$ is hydrogen, or (3) R$^5$ is —C(O)R$^{5A}$, —C(O)OR$^{5B}$, or —CH$_2$—O—C(O)R$^{5C}$, and R$^6$ is —C(O)R$^{6A}$, —C(O)OR$^{6B}$, —CH$_2$—O—C(O)R$^{6C}$, or —P(O)(OR$^{6D}$)(OR$^{6E}$).

In some embodiments, R$^3$ is hydrogen, and R$^4$ is OH. In some embodiments, R$^3$ is methyl, and R$^4$ is F. In some embodiments, R$^6$ is hydrogen. In some embodiments, R$^6$ is —C(O)R$^{6A}$, and wherein (HO)C(O)R$^{6A}$ is a natural amino acid. In some embodiments, R$^6$ is —C(O)R$^{6A}$, and wherein R$^{6A}$ is substituted or unsubstituted alkyl, substituted or unsubstituted heteroalkyl, substituted or unsubstituted arylalkyl, substituted or unsubstituted heteroarylalkyl, substituted or unsubstituted cycloalkyl, substituted or unsubstituted heterocycloalkyl, substituted or unsubstituted aryl, or substituted or unsubstituted heteroaryl. In some embodiments, R$^6$ is —C(O)OR$^{6B}$, and wherein R$^{6B}$ is substituted or unsubstituted alkyl, substituted or unsubstituted heteroalkyl, substituted or unsubstituted arylalkyl, substituted or unsubstituted heteroarylalkyl, substituted or unsubstituted cycloalkyl, substituted or unsubstituted heterocycloalkyl, substituted or unsubstituted aryl, or substituted or unsubstituted heteroaryl. In some embodiments, R$^6$ is —CH$_2$—O—C(O)R$^{6C}$, and wherein R$^{6C}$ is substituted or unsubstituted alkyl, substituted or unsubstituted heteroalkyl, substituted or unsubstituted arylalkyl, substituted or unsubstituted heteroarylalkyl, substituted or unsubstituted cycloalkyl, substituted or unsubstituted heterocycloalkyl, substituted or unsubstituted aryl, or substituted or unsubstituted heteroaryl. In some embodiments, R$^6$ is —P(O)(OR$^{6D}$)(OR$^{6E}$). In some embodiments, R$^{6D}$ is hydrogen, and R$^{6E}$ is substituted or unsubstituted alkyl, or R$^{6E}$ comprises alkylene, alkenylene, cycloalkylene with a 3-7 membered ring, alkynylene, arylene, heteroarylene, heterocyclene with a 5-12 membered ring comprising 1-3 atoms of N, O or S, —O—, —NH—, —S—, —N(C$_{1-6}$ alkyl)-, —C(=O)—, —C(=O)NH—, or combinations thereof, and R$^{6E}$ is 10-40, 15-40, or 20-40 atoms in length. In some embodiments, R$^5$ is hydrogen. In some embodiments, R$^5$ is —C(O)R$^{5A}$, and wherein (HO)C(O)R$^{5A}$ is a natural amino acid.

In some embodiments, R$^5$ is —C(O)R$^{5A}$, and R$^{5A}$ is substituted or unsubstituted alkyl, substituted or unsubstituted heteroalkyl, substituted or unsubstituted arylalkyl, substituted or unsubstituted heteroarylalkyl, substituted or unsubstituted cycloalkyl, substituted or unsubstituted heterocycloalkyl, substituted or unsubstituted aryl, or substituted or unsubstituted heteroaryl. In some embodiments, R$^5$ is —C(O)OR$^{5B}$, and R$^{5B}$ is substituted or unsubstituted alkyl, substituted or unsubstituted heteroalkyl, substituted or unsubstituted arylalkyl, substituted or unsubstituted heteroarylalkyl, substituted or unsubstituted cycloalkyl, substituted or unsubstituted heterocycloalkyl, substituted or unsubstituted aryl, or substituted or unsubstituted heteroaryl. In some embodiments, R$^5$ is —CH$_2$—O—C(O)R$^{5C}$, and wherein R$^{5C}$ is substituted or unsubstituted alkyl, substituted or unsubstituted heteroalkyl, substituted or unsubstituted arylalkyl, substituted or unsubstituted heteroarylalkyl, substituted or unsubstituted cycloalkyl, substituted or unsubstituted heterocycloalkyl, substituted or unsubstituted aryl, or substituted or unsubstituted heteroaryl.

In some embodiments, R$^2$ is hydrogen. In some embodiments, R$^2$ is substituted or unsubstituted alkyl. In some embodiments, R$^2$ is

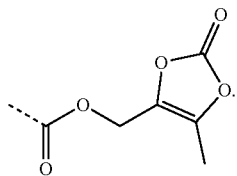

In some embodiments, $R^2$ is —C(O)$R^{2A}$, and wherein $R^{2A}$ is substituted or unsubstituted alkyl, substituted or unsubstituted heteroalkyl, substituted or unsubstituted arylalkyl, substituted or unsubstituted heteroarylalkyl, substituted or unsubstituted cycloalkyl, substituted or unsubstituted heterocycloalkyl, substituted or unsubstituted aryl, or substituted or unsubstituted heteroaryl. In some embodiments, $R^2$ is —C(O)O$R^{2B}$, and wherein $R^{2B}$ is substituted or unsubstituted alkyl, substituted or unsubstituted heteroalkyl, substituted or unsubstituted arylalkyl, substituted or unsubstituted heteroarylalkyl, substituted or unsubstituted cycloalkyl, substituted or unsubstituted heterocycloalkyl, substituted or unsubstituted aryl, or substituted or unsubstituted heteroaryl.

In some embodiments, $R^1$ is hydrogen. In some embodiments, $R^1$ is substituted or unsubstituted alkyl. In some embodiments, $R^1$ is —C(O)$R^{1A}$, and wherein $R^{1A}$ is substituted or unsubstituted alkyl, substituted or unsubstituted heteroalkyl, substituted or unsubstituted arylalkyl, substituted or unsubstituted heteroarylalkyl, substituted or unsubstituted cycloalkyl, substituted or unsubstituted heterocycloalkyl, substituted or unsubstituted aryl, or substituted or unsubstituted heteroaryl. In some embodiments, $R^1$ is —C(O)O$R^{1B}$, and wherein $R^{1B}$ is substituted or unsubstituted alkyl, substituted or unsubstituted heteroalkyl, substituted or unsubstituted arylalkyl, substituted or unsubstituted heteroarylalkyl, substituted or unsubstituted cycloalkyl, substituted or unsubstituted heterocycloalkyl, substituted or unsubstituted aryl, or substituted or unsubstituted heteroaryl.

Also disclosed herein is a compound of Formula (II), or a pharmaceutically acceptable salt, solvate, or stereoisomer thereof:

Formula (II)

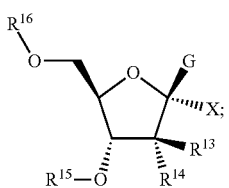

wherein:
X is hydrogen or —CN;
G is

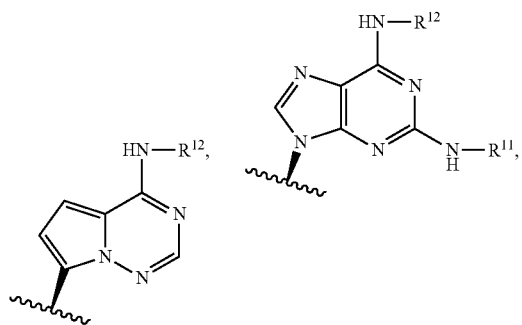

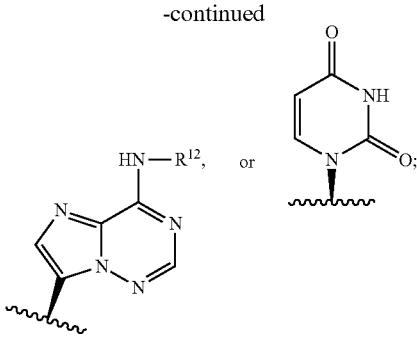

$R^{11}$ is hydrogen, —C(=O)$R^{21}$, —C(=O)O$R^{21}$, or $C_1$-$C_6$alkyl optionally substituted with one or more $R^{11a}$;

each $R^{11a}$ is independently halogen, —CN, —OH, —OR$^a$, —NR$^c$R$^d$, cycloalkyl, or heterocycloalkyl;

or two $R^{11a}$ on the same atom are taken together to form an oxo;

$R^{21}$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkyl, alkylene, cycloalkyl, heterocycloalkyl, aryl, and heteroaryl is optionally and independently substituted with one or more $R^{21a}$;

each $R^{21a}$ is independently halogen, —CN, —NO$_2$, —OH, —OR$^a$, —OC(=O)R$^a$, —OC(=O)OR$^b$, —OC(=O)NR$^c$R$^d$, —S(=O)R$^a$, —S(=O)$_2$R$^a$, —S(=O)$_2$NR$^c$R$^d$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two $R^{21a}$ on the same atom are taken together to form an oxo;

or two $R^{21a}$ are taken together to form a cycloalkyl or heterocycloalkyl; each optionally and independently substituted with one or more R;

$R^{12}$ is hydrogen, —C(=O)$R^{22}$, —C(=O)O$R^{22}$, or $C_1$-$C_6$alkyl optionally substituted with one or more $R^{12a}$;

each $R^{12a}$ is independently halogen, —CN, —OH, —OR$^a$, —NR$^c$R$^d$, cycloalkyl, or heterocycloalkyl;

or two $R^{12a}$ on the same atom are taken together to form an oxo;

$R^{22}$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkyl, alkylene, cycloalkyl, heterocycloalkyl, aryl, and heteroaryl is optionally and independently substituted with one or more $R^{22a}$;

each $R^{22a}$ is independently halogen, —CN, —NO$_2$, —OH, —OR$^a$, —OC(=O)R$^a$, —OC(=O)OR$^b$, —OC(=O)NR$^c$R$^d$, —S(=O)R$^a$, —S(=O)$_2$R$^a$, —S(=O)$_2$NR$^c$R$^d$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two R$^{22a}$ on the same atom are taken together to form an oxo;

or two R$^{22a}$ are taken together to form a cycloalkyl or heterocycloalkyl; each optionally and independently substituted with one or more R;

R$^{13}$ is hydrogen or C$_1$-C$_6$alkyl;

R$^{14}$ is —OH or fluoro;

R$^{15}$ is hydrogen, —C(=O)R$^{25}$, —C(=O)OR$^{25}$, —CH$_2$—O—C(=O)R$^{25}$, —CH$_2$—O—C(=O)OR$^{25}$, or C$_1$-C$_6$alkyl optionally substituted with one or more R$^{15a}$;

each R$^{15a}$ is independently halogen, —CN, —OH, —OR$^a$, —NR$^c$R$^d$, cycloalkyl, or heterocycloalkyl;

or two R$^{15a}$ on the same atom are taken together to form an oxo;

R$^{25}$ is C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein the alkyl, alkylene, cycloalkyl, heterocycloalkyl, aryl, and heteroaryl is optionally and independently substituted with one or more R$^{25a}$;

each R$^{25a}$ is independently halogen, —CN, —NO$_2$, —OH, —OR$^a$, —OC(=O)R$^a$, —OC(=O)OR$^b$, —OC(=O)NR$^c$R$^d$, —S(=O)R$^a$, —S(=O)$_2$R$^a$, —S(=O)$_2$NR$^c$R$^d$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two R$^{25a}$ on the same atom are taken together to form an oxo;

or two R$^{25a}$ are taken together to form a cycloalkyl or heterocycloalkyl; each optionally and independently substituted with one or more R;

R$^{16}$ is —C(=O)R$^{26}$, —C(=O)OR$^{26}$, —CH$_2$—O—C(=O)R$^{26}$, or —CH$_2$—O—C(=O)OR$^{26}$;

R$^{26}$ is C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein the alkylene, cycloalkyl, heterocycloalkyl, aryl, and heteroaryl is optionally and independently substituted with one or more R$^{26a}$, each R$^{26a}$ is independently halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;

or two R$^{26a}$ on the same atom are taken together to form an oxo;

or two R$^{26a}$ on the same carbon are taken together to form a cycloalkyl or heterocycloalkyl; each optionally substituted with one or more R;

each R$^a$ is independently C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl), wherein the alkyl, alkenyl, alkynyl, cycloalkyl, heterocycloalkyl, aryl, and heteroaryl is independently optionally substituted with one or more R;

each R$^b$ is independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl), wherein the alkyl, alkenyl, alkynyl, cycloalkyl, heterocycloalkyl, aryl, and heteroaryl is independently optionally substituted with one or more R;

R$^c$ and R$^d$ are each independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl), wherein the alkyl, alkenyl, alkynyl, cycloalkyl, heterocycloalkyl, aryl, and heteroaryl is independently optionally substituted with one or more R;

or R$^c$ and R$^d$ are taken together with the atom to which they are attached to form a heterocycloalkyl optionally substituted with one or more R; and each R is independently halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$hydroxyalkyl, C$_1$-C$_6$aminoalkyl, and C$_1$-C$_6$heteroalkyl;

or two R on the same atom are taken together to form an oxo;

provided that when G is

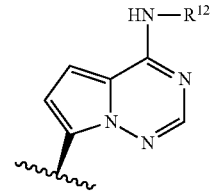

and X is —CN, or G is

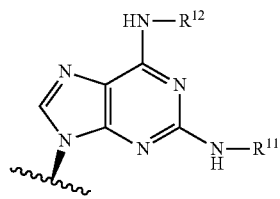

and X is hydrogen;

then at least one of R$^{11}$, R$^{12}$ or R$^{15}$ is not hydrogen.

In some embodiments of a compound of Formula (II), X is hydrogen. In some embodiments of a compound of Formula (II), X is —CN.

In some embodiments of a compound of Formula (II), $R^{13}$ is hydrogen. In some embodiments of a compound of Formula (II), $R^{13}$ is $C_1$-$C_6$alkyl.

In some embodiments of a compound of Formula (II), $R^{14}$ is —OH. In some embodiments of a compound of Formula (II), $R^{14}$ is fluoro.

In some embodiments of a compound of Formula (II), G is

[Structure: pyrrolo[2,1-f][1,2,4]triazine with HN—$R^{12}$ substituent]

In some embodiments of a compound of Formula (II), G is

[Structure: purine with HN—$R^{12}$ and N—$R^{11}$ substituents]

In some embodiments of a compound of Formula (II), G is

[Structure: imidazo[2,1-f][1,2,4]triazine with HN—$R^{12}$ substituent]

In some embodiments of a compound of Formula (II), G is

[Structure: uracil attached via N]

In some embodiments of a compound of Formula (II):
$R^{11}$ is hydrogen, —C(=O)$R^{21}$, —C(=O)O$R^{21}$, or $C_1$-$C_6$alkyl optionally substituted with one or more $R^{11a}$;
$R^{12}$ is hydrogen, —C(=O)$R^{22}$, —C(=O)O$R^{22}$, or $C_1$-$C_6$alkyl optionally substituted with one or more $R^{12a}$;
$R^{15}$ is —C(=O)$R^{25}$, —C(=O)O$R^{25}$, —CH$_2$—O—C(=O)$R^{25}$, —CH$_2$—O—C(=O)O$R^{25}$, or $C_1$-$C_6$alkyl optionally substituted with one or more $R^{15a}$; and
$R^{16}$ is —C(=O)$R^{26}$, —C(=O)O$R^{26}$, —CH$_2$—O—C(=O)$R^{26}$, or —CH$_2$—O—C(=O)O$R^2$.

In some embodiments of a compound of Formula (II),
$R^{11}$ is hydrogen, —C(=O)$R^{21}$, —C(=O)O$R^{21}$, or $C_1$-$C_6$alkyl optionally substituted with one or more $R^{11a}$;
$R^{12}$ is —C(=O)$R^{22}$, —C(=O)O$R^{22}$, or $C_1$-$C_6$alkyl optionally substituted with one or more $R^{12a}$;
$R^{15}$ is hydrogen, —C(=O)$R^{25}$, —C(=O)O$R^{25}$, —CH$_2$—O—C(=O)$R^{25}$, —CH$_2$—O—C(=O)O$R^{25}$, or $C_1$-$C_6$alkyl optionally substituted with one or more $R^{15a}$; and
$R^{16}$ is —C(=O)$R^{26}$, —C(=O)O$R^{26}$, —CH$_2$—O—C(=O)$R^{26}$, or —CH$_2$—O—C(=O)O$R^2$.

In some embodiments of a compound of Formula (II),
$R^{11}$ is —C(=O)$R^{21}$, —C(=O)O$R^{21}$, or $C_1$-$C_6$alkyl optionally substituted with one or more $R^{11a}$;
$R^{12}$ is hydrogen, —C(=O)$R^{22}$, —C(=O)O$R^{22}$, or $C_1$-$C_6$alkyl optionally substituted with one or more $R^{12a}$;
$R^{15}$ is hydrogen, —C(=O)$R^{25}$, —C(=O)O$R^{25}$, —CH$_2$—O—C(=O)$R^{25}$, —CH$_2$—O—C(=O)O$R^{25}$, or $C_1$-$C_6$alkyl optionally substituted with one or more $R^{15a}$; and
$R^{16}$ is —C(=O)$R^{26}$, —C(=O)O$R^{26}$, —CH$_2$—O—C(=O)$R^{26}$, or —CH$_2$—O—C(=O)O$R^2$.

In some embodiments of a compound of Formula (II),
$R^{11}$ is hydrogen, —C(=O)$R^{21}$, —C(=O)O$R^{21}$, or $C_1$-$C_6$alkyl optionally substituted with one or more $R^{11a}$;
$R^{12}$ is —C(=O)$R^{22}$, —C(=O)O$R^{22}$, or $C_1$-$C_6$alkyl optionally substituted with one or more $R^{12a}$;
$R^{15}$ is —C(=O)$R^{25}$, —C(=O)O$R^{25}$, —CH$_2$—O—C(=O)$R^{25}$, —CH$_2$—O—C(=O)O$R^{25}$, or $C_1$-$C_6$alkyl optionally substituted with one or more $R^{15a}$; and
$R^{16}$ is —C(=O)$R^{26}$, —C(=O)O$R^{26}$, —CH$_2$—O—C(=O)$R^{26}$, or —CH$_2$—O—C(=O)O$R^2$.

In some embodiments of a compound of Formula (II),
$R^{11}$ is —C(=O)$R^{21}$, —C(=O)O$R^{21}$, or $C_1$-$C_6$alkyl optionally substituted with one or more $R^{11a}$;
$R^{12}$ is —C(=O)$R^{22}$, —C(=O)O$R^{22}$, or $C_1$-$C_6$alkyl optionally substituted with one or more $R^{12a}$;
$R^{15}$ is hydrogen, —C(=O)$R^{25}$, —C(=O)O$R^{25}$, —CH$_2$—O—C(=O)$R^{25}$, —CH$_2$—O—C(=O)O$R^{25}$, or $C_1$-$C_6$alkyl optionally substituted with one or more $R^{15a}$; and
$R^{16}$ is —C(=O)$R^{26}$, —C(=O)O$R^{26}$, —CH$_2$—O—C(=O)$R^{26}$, or —CH$_2$—O—C(=O)O$R^2$.

In some embodiments of a compound of Formula (II),
$R^{11}$ is —C(=O)$R^{21}$, —C(=O)O$R^{21}$, or $C_1$-$C_6$alkyl optionally substituted with one or more $R^{11a}$;
$R^{12}$ is —C(=O)$R^{22}$, —C(=O)O$R^{22}$, or $C_1$-$C_6$alkyl optionally substituted with one or more $R^{12a}$;
$R^{15}$ is —C(=O)$R^{25}$, —C(=O)O$R^{25}$, —CH$_2$—O—C(=O)$R^{25}$, —CH$_2$—O—C(=O)O$R^{25}$, or $C_1$-$C_6$alkyl optionally substituted with one or more $R^{15a}$; and
$R^{16}$ is —C(=O)$R^{26}$, —C(=O)O$R^{26}$, —CH$_2$—O—C(=O)$R^{26}$, or —CH$_2$—O—C(=O)O$R^2$.

In some embodiments of a compound of Formula (II), $R^{11}$ is hydrogen, —C(=O)$R^{21}$, or $C_1$-$C_6$alkyl optionally substituted with one or more $R^1La$. In some embodiments of a compound of Formula (II), $R^{11}$ is hydrogen or —C(=O)$R^{21}$. In some embodiments of a compound of Formula (II), $R^{11}$ is hydrogen. In some embodiments of a compound of Formula (II), $R^{11}$ is —C(=O)$R^{21}$.

In some embodiments of a compound of Formula (II), each $R^{11a}$ is independently halogen, —CN, —OH, —O$R^a$, or —N$R^cR^d$. In some embodiments of a compound of Formula (II), each $R^1La$ is independently halogen.

In some embodiments of a compound of Formula (II), $R^{21}$ is $C_1$-$C_6$alkyl, $C_1$-$C_6$haloalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkyl, alkylene, cycloalkyl, heterocycloalkyl, aryl, and heteroaryl is optionally and independently substituted with one or more $R^{21a}$. In some embodiments of a compound of Formula (II), $R^{21}$ is $C_1$-$C_6$alkyl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl). In some embodiments of a compound of Formula (II), $R^{21}$ is $C_1$-$C_6$alkyl, $C_1$-$C_6$alkylene(cycloalkyl), or $C_1$-$C_6$alkylene(aryl).

In some embodiments of a compound of Formula (II), each $R^{21a}$ is independently halogen, —CN, —OH, —O$R^a$, —N$R^cR^d$, —C(=O)$R^a$, —C(=O)O$R^b$, —C(O)N$R^cR^d$, $C_1$-$C_6$alkyl, or $C_1$-$C_6$haloalkyl. In some embodiments of a compound of Formula (II), each $R^{21a}$ is independently halogen, —OH, —O$R^a$, —N$R^cR^d$, $C_1$-$C_6$alkyl, or $C_1$-$C_6$haloalkyl.

In some embodiments of a compound of Formula (II), $R^{12}$ is hydrogen, —C(=O)$R^{22}$, —C(=O)O$R^{22}$, or $C_1$-$C_6$alkyl. In some embodiments of a compound of Formula (II), $R^{12}$ is —C(=O)$R^{22}$, —C(=O)O$R^{22}$, or $C_1$-$C_6$alkyl. In some embodiments of a compound of Formula (II), $R^{12}$ is hydrogen or —C(=O)$R^{22}$. In some embodiments of a compound of Formula (II), $R^{12}$ is hydrogen, or —C(=O)O$R^{22}$. In some embodiments of a compound of Formula (II), $R^{12}$ is hydrogen or $C_1$-$C_6$alkyl.

In some embodiments of a compound of Formula (II), each $R^{12a}$ is independently halogen, —CN, —OH, —O$R^a$, or —N$R^cR^d$. In some embodiments of a compound of Formula (II), each $R^{12a}$ is independently halogen.

In some embodiments of a compound of Formula (II), $R^{22}$ is $C_1$-$C_6$alkyl, $C_1$-$C_6$aminoalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkyl, alkylene, cycloalkyl, heterocycloalkyl, aryl, and heteroaryl is optionally and independently substituted with one or more $R^{22a}$. In some embodiments of a compound of Formula (II), $R^{22}$ is $C_1$-$C_6$alkyl, $C_1$-$C_6$aminoalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl). In some embodiments of a compound of Formula (II), $R^{22}$ is $C_1$-$C_6$alkyl, $C_1$-$C_6$aminoalkyl, aryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl). In some embodiments of a compound of Formula (II), $R^{22}$ is $C_1$-$C_6$alkyl, $C_1$-$C_6$aminoalkyl, aryl, $C_1$-$C_6$alkylene(cycloalkyl), or $C_1$-$C_6$alkylene(aryl).

In some embodiments of a compound of Formula (II), $R^{22}$ is $C_1$-$C_6$alkyl or $C_1$-$C_6$alkylene(aryl); wherein the alkyl, alkylene, and aryl is optionally and independently substituted with one or more $R^{22a}$. In some embodiments of a compound of Formula (II), $R^{22}$ is $C_1$-$C_6$alkyl optionally and independently substituted with one or more $R^{22a}$.

In some embodiments of a compound of Formula (II), each $R^{22a}$ is independently halogen, —CN, —OH, —O$R^a$, —OC(=O)$R^a$, —OC(=O)O$R^b$, —OC(=O)N$R^cR^d$, —N$R^cR^d$, —C(=O)$R^a$, —C(=O)O$R^b$, —C(=O)N$R^cR^d$, $C_1$-$C_6$alkyl, or $C_1$-$C_6$haloalkyl.

In some embodiments of a compound of Formula (II), each $R^{22a}$ is independently halogen, —CN, —OH, —O$R^a$, —N$R^cR^d$, —C(=O)$R^a$, —C(=O)O$R^b$, —C(O)N$R^cR^d$, $C_1$-$C_6$alkyl, or $C_1$-$C_6$haloalkyl. In some embodiments of a compound of Formula (II), each $R^{22a}$ is independently halogen, —OH, —O$R^a$, —N$R^cR^d$, $C_1$-$C_6$alkyl, or $C_1$-$C_6$haloalkyl. In some embodiments of a compound of Formula (II), each $R^{22a}$ is independently halogen, —OC(=O)$R^a$, or —N$R^cR^d$. In some embodiments of a compound of Formula (II), each $R^{22a}$ is independently —OC(=O)$R^a$ or —N$R^cR^d$. In some embodiments of a compound of Formula (II), each $R^{22a}$ is independently —OC(=O)$R^a$.

In some embodiments of a compound of Formula (II), $R^{15}$ is hydrogen, —C(=O)$R^{25}$, or —CH$_2$—O—C(=O)$R^{25}$. In some embodiments of a compound of Formula (II), $R^{15}$ is hydrogen or —C(=O)$R^{25}$. In some embodiments of a compound of Formula (II), $R^{15}$ is —C(=O)$R^{25}$. In some embodiments of a compound of Formula (II), $R^{15}$ is hydrogen.

In some embodiments of a compound of Formula (II), each $R^{15a}$ is independently halogen, —CN, —OH, —O$R^a$, or —N$R^cR^d$. In some embodiments of a compound of Formula (II), each $R^{15a}$ is independently halogen.

In some embodiments of a compound of Formula (II), $R^{25}$ is $C_1$-$C_6$alkyl, $C_1$-$C_6$aminoalkyl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkyl, alkylene, cycloalkyl, heterocycloalkyl, aryl, and heteroaryl is optionally and independently substituted with one or more $R^{25a}$. In some embodiments of a compound of Formula (II), $R^{25}$ is $C_1$-$C_6$alkyl, $C_1$-$C_6$aminoalkyl, $C_1$-$C_6$alkylene(cycloalkyl), or $C_1$-$C_6$alkylene(aryl); wherein the alkyl, alkylene, cycloalkyl, and aryl, is optionally and independently substituted with one or more $R^{25a}$. In some embodiments of a compound of Formula (II), $R^{25}$ is $C_1$-$C_6$alkylene(cycloalkyl) or $C_1$-$C_6$alkylene(aryl); wherein the alkylene, cycloalkyl, and aryl, is optionally and independently substituted with one or more $R^{25a}$.

In some embodiments of a compound of Formula (II), each $R^{25a}$ is independently halogen, —CN, —OH, —O$R^a$, —N$R^cR^d$, —C(=O)$R^a$, —C(=O)O$R^b$, —C(O)N$R^cR^d$, $C_1$-$C_6$alkyl, or $C_1$-$C_6$haloalkyl. In some embodiments of a compound of Formula (II), each $R^{25a}$ is independently halogen, —OH, —O$R^a$, —N$R^cR^d$, $C_1$-$C_6$alkyl, or $C_1$-$C_6$haloalkyl.

In some embodiments of a compound of Formula (II), $R^{16}$ is —C(=O)$R^{26}$. In some embodiments of a compound of Formula (II), $R^{16}$ is —C(=O)O$R^{26}$. In some embodiments of a compound of Formula (II), $R^{16}$ is —CH$_2$—O—C(=O)$R^{26}$.

In some embodiments of a compound of Formula (II), $R^{26}$ is $C_1$-$C_6$alkylene(cycloalkyl) or $C_1$-$C_6$alkylene(aryl); wherein the alkylene, cycloalkyl, and aryl is optionally and independently substituted with one or more $R^{26a}$. In some embodiments of a compound of Formula (II), $R^{26}$ is $C_1$-$C_6$alkylene(cycloalkyl); wherein the alkylene and cycloalkyl is optionally and independently substituted with one or more $R^{26a}$. In some embodiments of a compound of Formula (II), $R^{26}$ is $C_1$-$C_6$alkylene(aryl); wherein the alkylene, and aryl is optionally and independently substituted with one or more $R^{26a}$.

In some embodiments of a compound of Formula (II), each $R^{26a}$ is independently halogen, —CN, —OH, —OR$^a$, —NR$^c$R$^d$, —C(=O)R$^a$, —C(=O)OR$^b$, —C(O)NR$^c$R$^d$, $C_1$-$C_6$alkyl, or $C_1$-$C_6$haloalkyl. In some embodiments of a compound of Formula (II), each $R^{26a}$ is independently halogen, —OH, —OR$^a$, —NR$^c$R$^d$, $C_1$-$C_6$alkyl, or $C_1$-$C_6$haloalkyl.

Also disclosed herein is a compound of Formula (III), or a pharmaceutically acceptable salt, solvate, or stereoisomer thereof:

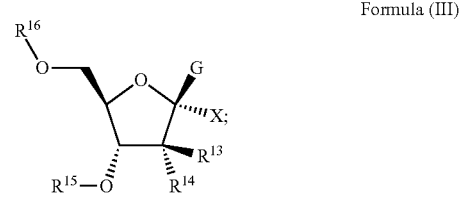

Formula (III)

wherein:
X is hydrogen or —CN;
G is

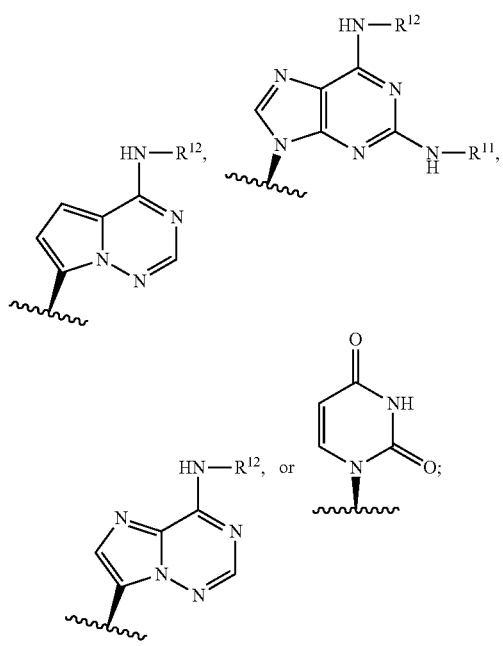

$R^{11}$ is hydrogen, —C(=O)R$^{21}$, —C(=O)OR$^{21}$, or $C_1$-$C_6$alkyl optionally substituted with one or more $R^{11a}$;

each $R^{11a}$ is independently halogen, —CN, —OH, —OR$^a$, —NR$^c$R$^d$, cycloalkyl, or heterocycloalkyl;

or two $R^{11a}$ on the same atom are taken together to form an oxo;

$R^{21}$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkyl, alkylene, cycloalkyl, heterocycloalkyl, aryl, and heteroaryl is optionally and independently substituted with one or more $R^{21a}$;

each $R^{21a}$ is independently halogen, —CN, —NO$_2$, —OH, —OR$^a$, —OC(=O)R$^a$, —OC(=O)OR$^b$, —OC(=O)NR$^c$R$^d$, —S(=O)R$^a$, —S(=O)$_2$R$^a$, —S(=O)$_2$NR$^c$R$^d$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two $R^{21a}$ on the same atom are taken together to form an oxo;

or two $R^{21a}$ are taken together to form a cycloalkyl or heterocycloalkyl; each optionally and independently substituted with one or more R;

$R^{12}$ is hydrogen, —C(=O)R$^{22}$, —C(=O)OR$^{22}$, or $C_1$-$C_6$alkyl optionally substituted with one or more $R^{12a}$;

each $R^{12a}$ is independently halogen, —CN, —OH, —OR$^a$, —NR$^c$R$^d$, cycloalkyl, or heterocycloalkyl;

or two $R^{12a}$ on the same atom are taken together to form an oxo;

$R^{22}$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkyl, alkylene, cycloalkyl, heterocycloalkyl, aryl, and heteroaryl is optionally and independently substituted with one or more $R^{22a}$;

each $R^{22a}$ is independently halogen, —CN, —NO$_2$, —OH, —OR$^a$, —OC(=O)R$^a$, —OC(=O)OR$^b$, —OC(=O)NR$^c$R$^d$, —S(=O)R$^a$, —S(=O)$_2$R$^a$, —S(=O)$_2$NR$^c$R$^d$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two $R^{22a}$ are taken together to form a cycloalkyl or heterocycloalkyl; each optionally and independently substituted with one or more R;

or two $R^{22a}$ on the same atom are taken together to form an oxo;

$R^{13}$ is hydrogen or $C_1$-$C_6$alkyl;
$R^{14}$ is —OH or fluoro;
$R^{15}$ is —C(=O)R$^{25}$, —C(=O)OR$^{25}$, —CH$_2$—O—C(=O)R$^{25}$, or —CH$_2$—O—C(=O)OR$^{25}$;

$R^{25}$ is $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkylene, cycloalkyl, heterocycloalkyl, aryl, and heteroaryl is optionally and independently substituted with one or more $R^{26a}$, each $R^{25a}$ is independently halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{25a}$ on the same atom are taken together to form an oxo;

or two $R^{25a}$ are taken together to form a cycloalkyl or heterocycloalkyl; each optionally and independently substituted with one or more R;

$R^{16}$ is hydrogen, —C(=O)$R^{26}$, —C(=O)O$R^{26}$, —CH$_2$—O—C(=O)$R^{26}$, —CH$_2$—O—C(=O)O$R^{26}$, or $C_1$-$C_6$alkyl optionally substituted with one or more $R^{16a}$;

each $R^{16a}$ is independently halogen, —CN, —OH, —O$R^a$, —N$R^cR^d$, cycloalkyl, or heterocycloalkyl;

or two $R^{16a}$ on the same atom are taken together to form an oxo;

$R^{26}$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkyl, alkylene, cycloalkyl, heterocycloalkyl, aryl, and heteroaryl is optionally and independently substituted with one or more $R^{26a}$, each $R^{26a}$ is independently halogen, —CN, —NO$_2$, —OH, —O$R^a$, —OC(=O)$R^a$, —OC(=O)O$R^b$, —OC(=O)N$R^cR^d$, —S(=O)$R^a$, —S(=O)$_2R^a$, —S(=O)$_2$N$R^cR^d$, —N$R^cR^d$, —C(=O)$R^a$, —C(=O)O$R^b$, —C(=O)N$R^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two $R^{26a}$ on the same atom are taken together to form an oxo;

or two $R^{26a}$ are taken together to form a cycloalkyl or heterocycloalkyl; each optionally and independently substituted with one or more R;

each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl), wherein the alkyl, alkenyl, alkynyl, cycloalkyl, heterocycloalkyl, aryl, and heteroaryl is independently optionally substituted with one or more R;

each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl), wherein the alkyl, alkenyl, alkynyl, cycloalkyl, heterocycloalkyl, aryl, and heteroaryl is independently optionally substituted with one or more R;

$R^c$ and $R^d$ are each independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl), wherein the alkyl, alkenyl, alkynyl, cycloalkyl, heterocycloalkyl, aryl, and heteroaryl is independently optionally substituted with one or more R;

or $R^c$ and $R^d$ are taken together with the atom to which they are attached to form a heterocycloalkyl optionally substituted with one or more R; and each R is independently halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$hydroxyalkyl, $C_1$-$C_6$aminoalkyl, and $C_1$-$C_6$heteroalkyl;

or two R on the same atom are taken together to form an oxo;

provided that when G is

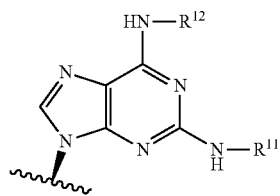

and X is hydrogen; then at least one of $R^{11}$, $R^{12}$, or $R^{16}$ is not hydrogen.

In some embodiments of a compound of Formula (III), X is hydrogen. In some embodiments of a compound of Formula (III), X is —CN.

In some embodiments of a compound of Formula (III), $R^{13}$ is hydrogen. In some embodiments of a compound of Formula (III), $R^{13}$ is $C_1$-$C_6$alkyl.

In some embodiments of a compound of Formula (III), $R^{14}$ is —OH. In some embodiments of a compound of Formula (III), $R^{14}$ is fluoro.

In some embodiments of a compound of Formula (III), G is

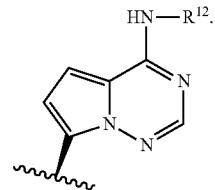

In some embodiments of a compound of Formula (III), G is

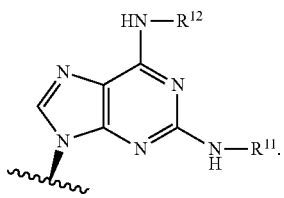

In some embodiments of a compound of Formula (III), G is

[Chemical structure: imidazo-triazine with HN—R$^{12}$ substituent]

In some embodiments of a compound of Formula (III), G is

[Chemical structure: uracil/pyrimidine-2,4-dione ring]

In some embodiments of a compound of Formula (III), R$^{11}$ is hydrogen, —C(=O)R$^{21}$, —C(=O)OR$^{21}$, or C$_1$-C$_6$alkyl optionally substituted with one or more R$^{11a}$;
R$^{12}$ is hydrogen, —C(=O)R$^{22}$, —C(=O)OR$^{22}$, or C$_1$-C$_6$alkyl optionally substituted with one or more R$^{12a}$;
R$^{15}$ is —C(=O)R$^{25}$, —C(=O)OR$^{25}$, —CH$_2$—O—C(=O)R$^{25}$, or —CH$_2$—O—C(=O)OR$^{25}$; and
R$^{16}$ is —C(=O)R$^{26}$, —C(=O)OR$^{26}$, —CH$_2$—O—C(=O)R$^{26}$, —CH$_2$—O—C(=O)OR$^{26}$, or C$_1$-C$_6$alkyl optionally substituted with one or more R$^{16a}$.

In some embodiments of a compound of Formula (III), R$^{11}$ is —C(=O)R$^{21}$, —C(=O)OR$^{21}$, or C$_1$-C$_6$alkyl optionally substituted with one or more R$^{11a}$;
R$^{12}$ is hydrogen, —C(=O)R$^{22}$, —C(=O)OR$^{22}$, or C$_1$-C$_6$alkyl optionally substituted with one or more R$^{12a}$;
R$^{15}$ is —C(=O)R$^{25}$, —C(=O)OR$^{25}$, —CH$_2$—O—C(=O)R$^{25}$, or —CH$_2$—O—C(=O)OR$^{25}$; and
R$^{16}$ is hydrogen, —C(=O)R$^{26}$, —C(=O)OR$^{26}$, —CH$_2$—O—C(=O)R$^{26}$, —CH$_2$—O—C(=O)OR$^{26}$, or C$_1$-C$_6$alkyl optionally substituted with one or more R$^{16a}$.

In some embodiments of a compound of Formula (III), R$^{11}$ is hydrogen, —C(=O)R$^{21}$, —C(=O)OR$^{21}$, or C$_1$-C$_6$alkyl optionally substituted with one or more R$^{11a}$;
R$^{12}$ is —C(=O)R$^{22}$, —C(=O)OR$^{22}$, or C$_1$-C$_6$alkyl optionally substituted with one or more R$^{12a}$;
R$^{15}$ is —C(=O)R$^{25}$, —C(=O)OR$^{25}$, —CH$_2$—O—C(=O)R$^{25}$, or —CH$_2$—O—C(=O)OR$^{25}$; and
R$^{16}$ is hydrogen, —C(=O)R$^{26}$, —C(=O)OR$^{26}$, —CH$_2$—O—C(=O)R$^{26}$, —CH$_2$—O—C(=O)OR$^{26}$, or C$_1$-C$_6$alkyl optionally substituted with one or more R$^{16a}$.

In some embodiments of a compound of Formula (III), R$^{11}$ is hydrogen, —C(=O)R$^{21}$, —C(=O)OR$^{21}$, or C$_1$-C$_6$alkyl optionally substituted with one or more R$^{11a}$;
R$^{12}$ is —C(=O)R$^{22}$, —C(=O)OR$^{22}$, or C$_1$-C$_6$alkyl optionally substituted with one or more R$^{12a}$;
R$^{15}$ is —C(=O)R$^{25}$, —C(=O)OR$^{25}$, —CH$_2$—O—C(=O)R$^{25}$, or —CH$_2$—O—C(=O)OR$^{25}$; and
R$^{16}$ is —C(=O)R$^{26}$, —C(=O)OR$^{26}$, —CH$_2$—O—C(=O)R$^{26}$, —CH$_2$—O—C(=O)OR$^{26}$, or C$_1$-C$_6$alkyl optionally substituted with one or more R$^{16a}$.

In some embodiments of a compound of Formula (III), R$^{11}$ is —C(=O)R$^{21}$, —C(=O)OR$^{21}$, or C$_1$-C$_6$alkyl optionally substituted with one or more R$^{11a}$;
R$^{12}$ is —C(=O)R$^{22}$, —C(=O)OR$^{22}$, or C$_1$-C$_6$alkyl optionally substituted with one or more R$^{12a}$;
R$^{15}$ is —C(=O)R$^{25}$, —C(=O)OR$^{25}$, —CH$_2$—O—C(=O)R$^{25}$, or —CH$_2$—O—C(=O)OR$^{25}$; and
R$^{16}$ is hydrogen, —C(=O)R$^{26}$, —C(=O)OR$^{26}$, —CH$_2$—O—C(=O)R$^{26}$, —CH$_2$—O—C(=O)OR$^{26}$, or C$_1$-C$_6$alkyl optionally substituted with one or more R$^{16a}$.

In some embodiments of a compound of Formula (III), R$^{11}$ is —C(=O)R$^{21}$, —C(=O)OR$^{21}$, or C$_1$-C$_6$alkyl optionally substituted with one or more R$^{11a}$;
R$^{12}$ is —C(=O)R$^{22}$, —C(=O)OR$^{22}$, or C$_1$-C$_6$alkyl optionally substituted with one or more R$^{12a}$;
R$^{15}$ is —C(=O)R$^{25}$, —C(=O)OR$^{25}$, —CH$_2$—O—C(=O)R$^{25}$, or —CH$_2$—O—C(=O)OR$^{25}$; and
R$^{16}$ is —C(=O)R$^{26}$, —C(=O)OR$^{26}$, —CH$_2$—O—C(=O)R$^{26}$, —CH$_2$—O—C(=O)OR$^{26}$, or C$_1$-C$_6$alkyl optionally substituted with one or more R$^{16a}$.

In some embodiments of a compound of Formula (III), R$^{11}$ is hydrogen, —C(=O)R$^{21}$, or C$_1$-C$_6$alkyl optionally substituted with one or more R$^{11a}$. In some embodiments of a compound of Formula (III), R$^{11}$ is hydrogen or —C(=O)R$^{21}$. In some embodiments of a compound of Formula (III), R$^1$ is hydrogen. In some embodiments of a compound of Formula (III), R$^{11}$ is —C(=O)R$^{21}$.

In some embodiments of a compound of Formula (III), each R$^{11a}$ is independently halogen, —CN, —OH, —OR$^a$, or —NR$^c$R$^d$. In some embodiments of a compound of Formula (III), each R$^{11a}$ is independently halogen.

In some embodiments of a compound of Formula (III), R$^{21}$ is C$_1$-C$_6$alkyl, C$_1$-C$_6$haloalkyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein the alkyl, alkylene, cycloalkyl, heterocycloalkyl, aryl, and heteroaryl is optionally and independently substituted with one or more R$^{21a}$. In some embodiments of a compound of Formula (III), R$^{21}$ is C$_1$-C$_6$alkyl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl). In some embodiments of a compound of Formula (III), R$^{21}$ is C$_1$-C$_6$alkyl, C$_1$-C$_6$alkylene(cycloalkyl), or C$_1$-C$_6$alkylene(aryl).

In some embodiments of a compound of Formula (III), each R$^{21a}$ is independently halogen, —CN, —OH, —OR$^a$, —NR$^c$R$^d$, —C(=O)R$^a$, —C(=O)OR$^b$, —C(O)NR$^c$R$^d$, C$_1$-C$_6$alkyl, or C$_1$-C$_6$haloalkyl. In some embodiments of a compound of Formula (III), each $R^{21a}$ is independently halogen, —OH, —OR$^a$, —NR$^c$R$^d$, C$_1$-C$_6$alkyl, or C$_1$-C$_6$haloalkyl.

In some embodiments of a compound of Formula (III), $R^{12}$ is hydrogen, —C(=O)R$^{22}$, —C(=O)OR$^{22}$, or C$_1$-C$_6$alkyl. In some embodiments of a compound of Formula (III), $R^{12}$ is —C(=O)R$^{22}$, —C(=O)OR$^{22}$, or C$_1$-C$_6$alkyl. In some embodiments of a compound of Formula (III), $R^{12}$ is hydrogen or —C(=O)R$^{22}$. In some embodiments of a compound of Formula (III), $R^{12}$ is hydrogen, or —C(=O)OR$^{22}$. In some embodiments of a compound of Formula (III), $R^{12}$ is hydrogen or C$_1$-C$_6$alkyl. In some embodiments of a compound of Formula (III), $R^{12}$ is —C(=O)OR$^{22}$.

In some embodiments of a compound of Formula (III), each $R^{12a}$ is independently halogen, —CN, —OH, —OR$^a$, or —NR$^c$R$^d$. In some embodiments of a compound of Formula (III), each $R^{12a}$ is independently halogen.

In some embodiments of a compound of Formula (III), $R^{22}$ is C$_1$-C$_6$alkyl, C$_1$-C$_6$aminoalkyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein the alkyl, alkylene, cycloalkyl, heterocycloalkyl, aryl, and heteroaryl is optionally and independently substituted with one or more $R^{22a}$. In some embodiments of a compound of Formula (III), $R^{22}$ is C$_1$-C$_6$alkyl, C$_1$-C$_6$aminoalkyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl). In some embodiments of a compound of Formula (III), $R^{22}$ is C$_1$-C$_6$alkyl, C$_1$-C$_6$aminoalkyl, aryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl). In some embodiments of a compound of Formula (III), $R^{22}$ is C$_1$-C$_6$alkyl, C$_1$-C$_6$aminoalkyl, aryl, C$_1$-C$_6$alkylene(cycloalkyl), or C$_1$-C$_6$alkylene(aryl).

In some embodiments of a compound of Formula (III), $R^{22}$ is C$_1$-C$_6$alkyl or C$_1$-C$_6$alkylene(aryl); wherein the alkyl, alkylene, and aryl is optionally and independently substituted with one or more $R^{22a}$. In some embodiments of a compound of Formula (III), $R^{22}$ is C$_1$-C$_6$alkyl optionally and independently substituted with one or more $R^{22a}$.

In some embodiments of a compound of Formula (III), each $R^{22a}$ is independently halogen, —CN, —OH, —OR$^a$, —OC(=O)R$^a$, —OC(=O)OR$^b$, —OC(=O)NR$^c$R$^d$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl.

In some embodiments of a compound of Formula (III), each $R^{22a}$ is independently halogen, —CN, —OH, —OR$^a$, —NR$^c$R$^d$, —C(=O)R$^a$, —C(=O)OR$^b$, —C(O)NR$^c$R$^d$, C$_1$-C$_6$alkyl, or C$_1$-C$_6$haloalkyl. In some embodiments of a compound of Formula (III), each $R^{22a}$ is independently halogen, —OH, —OR$^a$, —NR$^c$R$^d$, C$_1$-C$_6$alkyl, or C$_1$-C$_6$haloalkyl. In some embodiments of a compound of Formula (III), each $R^{22a}$ is independently halogen, —OC(=O)R$^a$, or —NR$^c$R$^d$. In some embodiments of a compound of Formula (III), each $R^{22a}$ is independently —OC(=O)R$^a$ or —NR$^c$R$^d$. In some embodiments of a compound of Formula (V), each $R^{22a}$ is independently —OC(=O)R$^a$.

In some embodiments of a compound of Formula (III), $R^{15}$ is —C(=O)R$^{25}$. In some embodiments of a compound of Formula (III), $R^{15}$ is —C(=O)OR$^{25}$. In some embodiments of a compound of Formula (III), $R^{15}$ is —CH$_2$—O—C(=O)R$^{25}$.

In some embodiments of a compound of Formula (III), $R^{25}$ is C$_1$-C$_6$alkylene(cycloalkyl) or C$_1$-C$_6$alkylene(aryl); wherein the alkylene, cycloalkyl, and aryl is optionally and independently substituted with one or more $R^{25a}$. In some embodiments of a compound of Formula (III), $R^{25}$ is C$_1$-C$_6$alkylene(cycloalkyl); wherein the alkylene and cycloalkyl is optionally and independently substituted with one or more $R^{25a}$. In some embodiments of a compound of Formula (III), $R^{25}$ is C$_1$-C$_6$alkylene(aryl); wherein the alkylene, and aryl is optionally and independently substituted with one or more $R^{25a}$.

In some embodiments of a compound of Formula (III), each $R^{25a}$ is independently halogen, —CN, —OH, —OR$^a$, —NR$^c$R$^d$, —C(=O)R$^a$, —C(=O)OR$^b$, —C(O)NR$^c$R$^d$, C$_1$-C$_6$alkyl, or C$_1$-C$_6$haloalkyl. In some embodiments of a compound of Formula (III), each $R^{25a}$ is independently halogen, —OH, —OR$^a$, —NR$^c$R$^d$, C$_1$-C$_6$alkyl, or C$_1$-C$_6$haloalkyl.

In some embodiments of a compound of Formula (III), $R^{16}$ is hydrogen, —C(=O)R$^{26}$, or —CH$_2$—O—C(=O)R$^{26}$. In some embodiments of a compound of Formula (III), $R^{16}$ is hydrogen or —C(=O)R$^{26}$. In some embodiments of a compound of Formula (III), $R^{16}$ is —C(=O)R$^{26}$. In some embodiments of a compound of Formula (III), $R^{16}$ is hydrogen. In some embodiments of a compound of Formula (III), $R^{16}$ is —CH$_2$—O—C(=O)R$^6$.

In some embodiments of a compound of Formula (III), each $R^{16a}$ is independently halogen, —CN, —OH, —OR$^a$, or —NR$^c$R$^d$. In some embodiments of a compound of Formula (III), each $R^{16a}$ is independently halogen.

In some embodiments of a compound of Formula (III), $R^{26}$ is C$_1$-C$_6$alkyl, C$_1$-C$_6$aminoalkyl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein the alkyl, alkylene, cycloalkyl, heterocycloalkyl, aryl, and heteroaryl is optionally and independently substituted with one or more $R^{26a}$. In some embodiments of a compound of Formula (III), $R^{26}$ is C$_1$-C$_6$alkyl, C$_1$-C$_6$aminoalkyl, C$_1$-C$_6$alkylene(cycloalkyl), or C$_1$-C$_6$alkylene(aryl); wherein the alkyl, alkylene, cycloalkyl, and aryl, is optionally and independently substituted with one or more $R^{26a}$. In some embodiments of a compound of Formula (III), $R^{26}$ is C$_1$-C$_6$alkylene(cycloalkyl) or C$_1$-C$_6$alkylene(aryl); wherein the alkylene, cycloalkyl, and aryl, is optionally and independently substituted with one or more $R^{26a}$.

In some embodiments of a compound of Formula (III), each $R^{26a}$ is independently halogen, —CN, —OH, —OR$^a$, —NR$^c$R$^d$, —C(=O)R$^a$, —C(=O)OR$^b$, —C(O)NR$^c$R$^d$, C$_1$-C$_6$alkyl, or C$_1$-C$_6$haloalkyl. In some embodiments of a compound of Formula (III), each $R^{26a}$ is independently halogen, —OH, —OR$^a$, —NR$^c$R$^d$, C$_1$-C$_6$alkyl, or C$_1$-C$_6$haloalkyl.

Also disclosed herein is a compound of Formula (IV), or a pharmaceutically acceptable salt, solvate, or stereoisomer thereof:

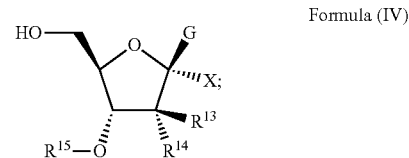

Formula (IV)

wherein:
X is hydrogen or —CN;
G is

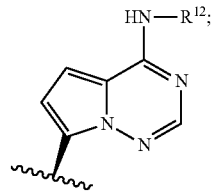

$R^{12}$ is —C(=O)$R^{22}$, —C(=O)O$R^{22}$, or $C_1$-$C_6$alkyl optionally substituted with one or more $R^{12a}$;
each $R^{12a}$ is independently halogen, —CN, —OH, —O$R^a$, —N$R^c R^d$, cycloalkyl, or heterocycloalkyl;
or two $R^{12a}$ on the same atom are taken together to form an oxo;
$R^{22}$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkyl, alkylene, cycloalkyl, heterocycloalkyl, aryl, and heteroaryl is optionally and independently substituted with one or more $R^{22a}$;
each $R^{22a}$ is independently halogen, —CN, —NO$_2$, —OH, —O$R^a$, —OC(=O)$R^a$, —OC(=O)O$R^b$, —OC(=O)N$R^c R^d$, —S(=O)$R^a$, —S(=O)$_2R^a$, —S(=O)$_2$N$R^c R^d$, —N$R^c R^d$, —C(=O)$R^a$, —C(=O)O$R^b$, —C(=O)N$R^c R^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;
or two $R^{22a}$ on the same atom are taken together to form an oxo;
or two $R^{22a}$ are taken together to form a cycloalkyl or heterocycloalkyl; each optionally and independently substituted with one or more R;
$R^{13}$ is hydrogen or $C_1$-$C_6$alkyl;
$R^{14}$ is —OH or fluoro;
$R^{15}$ is —C(=O)$R^{25}$, —C(=O)O$R^{25}$, —CH$_2$—O—C(=O)$R^{25}$, or —CH$_2$—O—C(=O)O$R^{25}$;
$R^{25}$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkyl, alkylene, cycloalkyl, heterocycloalkyl, aryl, and heteroaryl is optionally and independently substituted with one or more $R^{25a}$;
each $R^{25a}$ is independently halogen, —CN, —NO$_2$, —OH, —O$R^a$, —OC(=O)$R^a$, —OC(=O)O$R^b$, —OC(=O)N$R^c R^d$, —S(=O)$R^a$, —S(=O)$_2R^a$, —S(=O)$_2$N$R^c R^d$, —N$R^c R^d$, —C(=O)$R^a$, —C(=O)O$R^b$, —C(=O)N$R^c R^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two $R^{21a}$ on the same atom are taken together to form an oxo;
or two $R^{25a}$ are taken together to form a cycloalkyl or heterocycloalkyl; each optionally and independently substituted with one or more R;
each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl), wherein the alkyl, alkenyl, alkynyl, cycloalkyl, heterocycloalkyl, aryl, and heteroaryl is independently optionally substituted with one or more R;
each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl), wherein the alkyl, alkenyl, alkynyl, cycloalkyl, heterocycloalkyl, aryl, and heteroaryl is independently optionally substituted with one or more R;
$R^c$ and $R^d$ are each independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl), wherein the alkyl, alkenyl, alkynyl, cycloalkyl, heterocycloalkyl, aryl, and heteroaryl is independently optionally substituted with one or more R;
or $R^c$ and $R^d$ are taken together with the atom to which they are attached to form a heterocycloalkyl optionally substituted with one or more R; and
each R is independently halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$hydroxyalkyl, $C_1$-$C_6$aminoalkyl, and $C_1$-$C_6$heteroalkyl;
or two R on the same atom are taken together to form an oxo.

In some embodiments of a compound of Formula (IV), X is hydrogen. In some embodiments of a compound of Formula (IV), X is —CN. In some embodiments of a compound of Formula (IV), $R^{13}$ is hydrogen. In some embodiments of a compound of Formula (IV), $R^{13}$ is $C_1$-$C_6$alkyl.

In some embodiments of a compound of Formula (IV), $R^{14}$ is —OH. In some embodiments of a compound of Formula (IV), $R^{14}$ is fluoro.

In some embodiments of a compound of Formula (IV), $R^{12}$ is —C(=O)$R^{22}$, —C(=O)O$R^{22}$, or $C_1$-$C_6$alkyl. In some embodiments of a compound of Formula (IV), $R^{12}$ is —C(=O)$R^{22}$. In some embodiments of a compound of Formula (IV), $R^{12}$ is —C(=O)O$R^{22}$. In some embodiments of a compound of Formula (IV), $R^{12}$ is $C_1$-$C_6$alkyl.

In some embodiments of a compound of Formula (IV), each $R^{12a}$ is independently halogen, —CN, —OH, —O$R^a$, or —N$R^c R^d$. In some embodiments of a compound of Formula (IV), each $R^{12a}$ is independently halogen.

In some embodiments of a compound of Formula (IV), $R^{22}$ is $C_1$-$C_6$alkyl, $C_1$-$C_6$aminoalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkyl, alkylene, cycloalkyl, heterocycloalkyl, aryl, and heteroaryl is optionally and independently substituted with one or more $R^{22a}$.

In some embodiments of a compound of Formula (IV), $R^{22}$ is $C_1$-$C_6$alkyl, $C_1$-$C_6$aminoalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl). In some embodiments of a compound of Formula (IV), $R^{22}$ is $C_1$-$C_6$alkyl, $C_1$-$C_6$aminoalkyl, aryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl). In some embodiments of a compound of Formula (IV), $R^{22}$ is $C_1$-$C_6$alkyl, $C_1$-$C_6$aminoalkyl, aryl, $C_1$-$C_6$alkylene(cycloalkyl), or $C_1$-$C_6$alkylene(aryl).

In some embodiments of a compound of Formula (IV), $R^{22}$ is $C_1$-$C_6$alkyl or $C_1$-$C_6$alkylene(aryl); wherein the alkyl, alkylene, and aryl is optionally and independently substituted with one or more $R^{22a}$. In some embodiments of a compound of Formula (IV), $R^{22}$ is $C_1$-$C_6$alkyl optionally and independently substituted with one or more $R^{22a}$.

In some embodiments of a compound of Formula (IV), each $R^{22a}$ is independently halogen, —CN, —OH, —OR$^a$, —OC(=O)R$^a$, —OC(=O)OR$^b$, —OC(=O)NR$^c$R$^d$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (IV), each $R^{22a}$ is independently halogen, —CN, —OH, —OR$^a$, —NR$^c$R$^d$, —C(=O)R$^a$, —C(=O)OR$^b$, —C(O)NR$^c$R$^d$, $C_1$-$C_6$alkyl, or $C_1$-$C_6$haloalkyl. In some embodiments of a compound of Formula (IV), each $R^{22a}$ is independently halogen, —OH, —OR$^a$, —NR$^c$R$^d$, $C_1$-$C_6$alkyl, or $C_1$-$C_6$haloalkyl. In some embodiments of a compound of Formula (IV), each $R^{22a}$ is independently halogen, —OC(=O)R$^a$, or —NR$^c$R$^d$. In some embodiments of a compound of Formula (IV), each $R^{22a}$ is independently —OC(=O)R$^a$ or —NR$^c$R$^d$. In some embodiments of a compound of Formula (IV), each $R^{22a}$ is independently —OC(=O)R$^a$.

In some embodiments of a compound of Formula (IV), $R^{15}$ is —C(=O)R$^{25}$. In some embodiments of a compound of Formula (IV), $R^{15}$ is —C(=O)OR$^{25}$. In some embodiments of a compound of Formula (IV), $R^{15}$ is —CH$_2$—O—C(=O)R$^{25}$. In some embodiments of a compound of Formula (IV), $R^{25}$ is $C_1$-$C_6$alkylene(cycloalkyl) or $C_1$-$C_6$alkylene(aryl); wherein the alkylene, cycloalkyl, and aryl is optionally and independently substituted with one or more $R^{25a}$. In some embodiments of a compound of Formula (IV), $R^{25}$ is $C_1$-$C_6$alkylene(cycloalkyl); wherein the alkylene and cycloalkyl is optionally and independently substituted with one or more $R^{25a}$. In some embodiments of a compound of Formula (IV), $R^{25}$ is $C_1$-$C_6$alkylene(aryl); wherein the alkylene, and aryl is optionally and independently substituted with one or more $R^{25a}$.

In some embodiments of a compound of Formula (IV), each $R^{25a}$ is independently halogen, —CN, —OH, —OR$^a$, —NR$^c$R$^d$, —C(=O)R$^a$, —C(=O)OR$^b$, —C(O)NR$^c$R$^d$, $C_1$-$C_6$alkyl, or $C_1$-$C_6$haloalkyl. In some embodiments of a compound of Formula (IV), each $R^{25a}$ is independently halogen, —OH, —OR$^a$, —NR$^c$R$^d$, $C_1$-$C_6$alkyl, or $C_1$-$C_6$haloalkyl.

Also disclosed herein is a compound of Formula (V), or a pharmaceutically acceptable salt, solvate, or stereoisomer thereof:

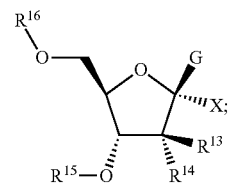

Formula (V)

wherein:
X is hydrogen or —CN;
G is

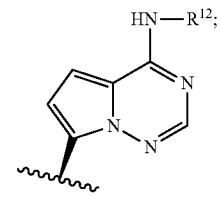

$R^{12}$ is —C(=O)R$^{22}$, —C(=O)OR$^{22}$, or $C_1$-$C_6$alkyl optionally substituted with one or more $R^{12a}$;

each $R^{12a}$ is independently halogen, —CN, —OH, —OR$^a$, —NR$^c$R$^d$, cycloalkyl, or heterocycloalkyl;

or two $R^{12a}$ on the same atom are taken together to form an oxo;

$R^{22}$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkyl, alkylene, cycloalkyl, heterocycloalkyl, aryl, and heteroaryl is optionally and independently substituted with one or more $R^{22a}$;

each $R^{22a}$ is independently halogen, —CN, —NO$_2$, —OH, —OR$^a$, —OC(=O)R$^a$, —OC(=O)OR$^b$, —OC(=O)NR$^c$R$^d$, —S(=O)R$^a$, —S(=O)$_2$R$^a$, —S(=O)$_2$NR$^c$R$^d$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two $R^{22a}$ on the same atom are taken together to form an oxo;

or two $R^{22a}$ are taken together to form a cycloalkyl or heterocycloalkyl; each optionally and independently substituted with one or more R;

$R^{13}$ is hydrogen or $C_1$-$C_6$alkyl;

$R^{14}$ is —OH or fluoro;

$R^{15}$ is hydrogen, —C(=O)R$^{25}$, —C(=O)OR$^{25}$, —CH$_2$—O—C(=O)R$^{25}$, or —CH$_2$—O—C(=O)OR$^{25}$;

$R^{25}$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkyl, alkylene, cycloalkyl, heterocycloalkyl, aryl, and heteroaryl is optionally and independently substituted with one or more $R^{25a}$;

each $R^{25a}$ is independently halogen, —CN, —NO$_2$, —OH, —OR$^a$, —OC(=O)R$^a$, —OC(=O)OR$^b$, —OC(=O)NR$^c$R$^d$, —S(=O)R$^a$, —S(=O)$_2$R$^a$, —S(=O)$_2$NR$^c$R$^d$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two $R^{25a}$ on the same atom are taken together to form an oxo;

or two $R^{25a}$ are taken together to form a cycloalkyl or heterocycloalkyl; each optionally and independently substituted with one or more R;

$R^{16}$ is —C(=O)R$^{26}$, —C(=O)OR$^{26}$, —CH$_2$—O—C(=O)R$^{26}$, —CH$_2$—O—C(=O)OR$^{26}$, or C$_1$-C$_6$alkyl optionally substituted with one or more $R^{16a}$;

each $R^{16a}$ is independently halogen, —CN, —OH, —OR$^a$, —NR$^c$R$^d$, cycloalkyl, or heterocycloalkyl;

or two $R^{16a}$ on the same atom are taken together to form an oxo;

$R^{26}$ is C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein the alkyl, alkylene, cycloalkyl, heterocycloalkyl, aryl, and heteroaryl is optionally and independently substituted with one or more $R^{26a}$, each $R^{26a}$ is independently halogen, —CN, —NO$_2$, —OH, —OR$^a$, —OC(=O)R$^a$, —OC(=O)OR$^b$, —OC(=O)NR$^c$R$^d$, —S(=O)R$^a$, —S(=O)$_2$R$^a$, —S(=O)$_2$NR$^c$R$^d$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two $R^{26a}$ on the same atom are taken together to form an oxo;

or two $R^{26a}$ are taken together to form a cycloalkyl or heterocycloalkyl; each optionally and independently substituted with one or more R;

each $R^a$ is independently C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl), wherein the alkyl, alkenyl, alkynyl, cycloalkyl, heterocycloalkyl, aryl, and heteroaryl is independently optionally substituted with one or more R;

each $R^b$ is independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl), wherein the alkyl, alkenyl, alkynyl, cycloalkyl, heterocycloalkyl, aryl, and heteroaryl is independently optionally substituted with one or more R;

$R^c$ and $R^d$ are each independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl), wherein the alkyl, alkenyl, alkynyl, cycloalkyl, heterocycloalkyl, aryl, and heteroaryl is independently optionally substituted with one or more R;

or $R^c$ and $R^d$ are taken together with the atom to which they are attached to form a heterocycloalkyl optionally substituted with one or more R; and each R is independently halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$hydroxyalkyl, C$_1$-C$_6$aminoalkyl, and C$_1$-C$_6$heteroalkyl;

or two R on the same atom are taken together to form an oxo.

In some embodiments of a compound of Formula (V), X is hydrogen. In some embodiments of a compound of Formula (V), X is —CN.

In some embodiments of a compound of Formula (V), $R^{13}$ is hydrogen. In some embodiments of a compound of Formula (V), $R^{13}$ is C$_1$-C$_6$alkyl.

In some embodiments of a compound of Formula (V), $R^{14}$ is —OH. In some embodiments of a compound of Formula (V), $R^{14}$ is fluoro.

In some embodiments of a compound of Formula (V), $R^{12}$ is —C(=O)R$^{22}$, —C(=O)OR$^{22}$, or C$_1$-C$_6$alkyl. In some embodiments of a compound of Formula (V), $R^{12}$ is —C(=O)R$^{22}$. In some embodiments of a compound of Formula (V), $R^{12}$ is —C(=O)OR$^{22}$. In some embodiments of a compound of Formula (V), $R^{12}$ is C$_1$-C$_6$alkyl.

In some embodiments of a compound of Formula (V), $R^{22}$ is C$_1$-C$_6$alkyl, C$_1$-C$_6$aminoalkyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein the alkyl, alkylene, cycloalkyl, heterocycloalkyl, aryl, and heteroaryl is optionally and independently substituted with one or more $R^{22a}$.

In some embodiments of a compound of Formula (V), $R^{22}$ is C$_1$-C$_6$alkyl, C$_1$-C$_6$aminoalkyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl).

In some embodiments of a compound of Formula (V), $R^{22}$ is C$_1$-C$_6$alkyl, C$_1$-C$_6$aminoalkyl, aryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl).

In some embodiments of a compound of Formula (V), $R^{22}$ is C$_1$-C$_6$alkyl, C$_1$-C$_6$aminoalkyl, aryl, C$_1$-C$_6$alkylene(cycloalkyl), or C$_1$-C$_6$alkylene(aryl).

In some embodiments of a compound of Formula (V), $R^{22}$ is C$_1$-C$_6$alkyl or C$_1$-C$_6$alkylene(aryl); wherein the alkyl, alkylene, and aryl is optionally and independently substituted with one or more $R^{22a}$.

In some embodiments of a compound of Formula (V), $R^{22}$ is C$_1$-C$_6$alkyl optionally and independently substituted with one or more $R^{22a}$.

In some embodiments of a compound of Formula (V), each $R^{22a}$ is independently halogen, —CN, —OH, —OR$^a$, —OC(=O)R$^a$, —OC(=O)OR$^b$, —OC(=O)NR$^c$R$^d$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl.

In some embodiments of a compound of Formula (V), each $R^{22a}$ is independently halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl.

In some embodiments of a compound of Formula (V), each R$^{22a}$ is independently halogen, —OH, —OR$^a$, —NR$^c$R$^d$, C$_1$-C$_6$alkyl, or C$_1$-C$_6$haloalkyl.

In some embodiments of a compound of Formula (V), each R$^{22a}$ is independently halogen, —OC(=O)R$^a$, or —NR$^c$R$^d$. In some embodiments of a compound of Formula (V), each R$^{22a}$ is independently —OC(=O)R$^a$ or —NR$^c$R$^d$. In some embodiments of a compound of Formula (V), each R$^{22a}$ is independently —OC(=O)R$^a$.

In some embodiments of a compound of Formula (V), R$^{15}$ is hydrogen.

In some embodiments of a compound of Formula (V), R$^{15}$ is —C(=O)R$^{25}$.

In some embodiments of a compound of Formula (V), R$^{15}$ is —C(=O)OR$^{25}$.

In some embodiments of a compound of Formula (V), R$^{25}$ is C$_1$-C$_6$alkylene(cycloalkyl) or C$_1$-C$_6$alkylene(aryl); wherein the alkylene, cycloalkyl, and aryl is optionally and independently substituted with one or more R$^{25a}$.

In some embodiments of a compound of Formula (V), R$^{25}$ is C$_1$-C$_6$alkylene(cycloalkyl); wherein the alkylene and cycloalkyl is optionally and independently substituted with one or more R$^{25a}$.

In some embodiments of a compound of Formula (V), R$^{25}$ is C$_1$-C$_6$alkylene(aryl); wherein the alkylene, and aryl is optionally and independently substituted with one or more R$^{25a}$.

In some embodiments of a compound of Formula (V), each R$^{25a}$ is independently halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl.

In some embodiments of a compound of Formula (V), each R$^{25a}$ is independently halogen, —OH, —OR$^a$, —NR$^c$R$^d$, C$_1$-C$_6$alkyl, or C$_1$-C$_6$haloalkyl.

In some embodiments of a compound of Formula (V), R$^{16}$ is —C(=O)R$^{26}$.

In some embodiments of a compound of Formula (V), R$^{16}$ is —C(=O)OR$^{26}$.

In some embodiments of a compound of Formula (V), R$^{26}$ is C$_1$-C$_6$alkyl, C$_1$-C$_6$aminoalkyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein the alkyl, alkylene, cycloalkyl, heterocycloalkyl, aryl, and heteroaryl is optionally and independently substituted with one or more R$^{26a}$.

In some embodiments of a compound of Formula (V), R$^{26}$ is C$_1$-C$_6$alkyl, C$_1$-C$_6$aminoalkyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl).

In some embodiments of a compound of Formula (V), R$^{26}$ is C$_1$-C$_6$alkyl, C$_1$-C$_6$aminoalkyl, aryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl).

In some embodiments of a compound of Formula (V), R$^{26}$ is C$_1$-C$_6$alkyl, C$_1$-C$_6$aminoalkyl, aryl, C$_1$-C$_6$alkylene(cycloalkyl), or C$_1$-C$_6$alkylene(aryl).

In some embodiments of a compound of Formula (V), R$^{26}$ is C$_1$-C$_6$alkyl or C$_1$-C$_6$aminoalkyl.

In some embodiments of a compound of Formula (V), each R$^{26a}$ is independently halogen, —CN, —OH, —OR$^a$, —OC(=O)R$^a$, —OC(=O)OR$^b$, —OC(=O)NR$^c$R$^d$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl.

In some embodiments of a compound of Formula (V), each R$^{26a}$ is independently halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl.

In some embodiments of a compound of Formula (V), each R$^{26a}$ is independently halogen, —OH, —OR$^a$, —NR$^c$R$^d$, C$_1$-C$_6$alkyl, or C$_1$-C$_6$haloalkyl.

In some embodiments of a compound of Formula (V), each R$^{26a}$ is independently —OC(=O)R$^a$, or —NR$^c$R$^d$.

Also disclosed herein is a compound of Formula (VIa), (VIb), or (VIc), or a pharmaceutically acceptable salt, solvate, or stereoisomer thereof:

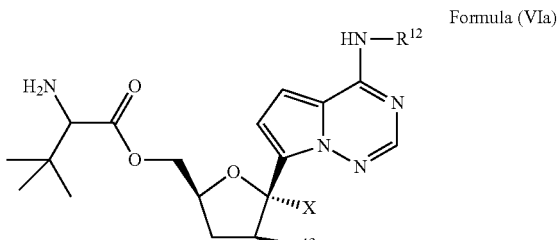

Formula (VIa)

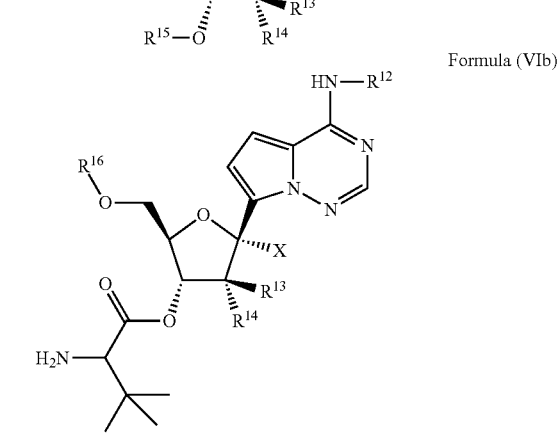

Formula (VIb)

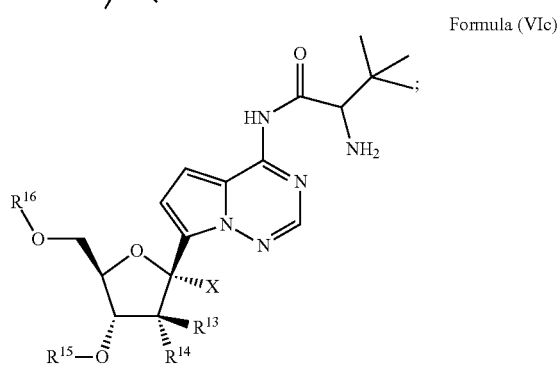

Formula (VIc)

wherein:

X is hydrogen or —CN;

R$^{12}$ is hydrogen, —C(=O)R$^{22}$, —C(=O)OR$^{22}$, or C$_1$-C$_6$alkyl optionally substituted with one or more R$^{12a}$;

each R$^{12a}$ is independently halogen, —CN, —OH, —OR$^a$, —NR$^c$R$^d$, cycloalkyl, or heterocycloalkyl;

or two R$^{12a}$ on the same atom are taken together to form an oxo;

R$^{22}$ is C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, heterocycloalkyl, aryl, heteroaryl, C$_1$-C$_6$alkylene(cycloalkyl), $C_1$-$C_6$alkylene(heterocycloalkyl), $C_1$-$C_6$alkylene (aryl), or $C_1$-$C_6$alkylene(heteroaryl); wherein the alkyl, alkylene, cycloalkyl, heterocycloalkyl, aryl, and heteroaryl is optionally and independently substituted with one or more $R^{22a}$;

each $R^{22a}$ is independently halogen, —CN, —$NO_2$, —OH, —$OR^a$, —OC(=O)$R^a$, —OC(=O)$OR^b$, —OC(=O)$NR^cR^d$, —S(=O)$R^a$, —S(=O)$_2R^a$, —S(=O)$_2NR^cR^d$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two $R^{22a}$ on the same atom are taken together to form an oxo;

or two $R^{22a}$ are taken together to form a cycloalkyl or heterocycloalkyl; each optionally and independently substituted with one or more R;

$R^{13}$ is hydrogen or $C_1$-$C_6$alkyl;

$R^{14}$ is —OH or fluoro;

$R^{15}$ is hydrogen, —C(=O)$R^{25}$, —C(=O)$OR^{25}$, —$CH_2$—O—C(=O)$R^{25}$, or —$CH_2$—O—C(=O)$OR^{25}$;

$R^{25}$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene (aryl), or $C_1$-$C_6$alkylene(heteroaryl); wherein the alkyl, alkylene, cycloalkyl, heterocycloalkyl, aryl, and heteroaryl is optionally and independently substituted with one or more $R^{25a}$;

each $R^{25a}$ is independently halogen, —CN, —$NO_2$, —OH, —$OR^a$, —OC(=O)$R^a$, —OC(=O)$OR^b$, —OC(=O)$NR^cR^d$, —S(=O)$R^a$, —S(=O)$_2R^a$, —S(=O)$_2NR^cR^d$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two $R^{25a}$ on the same atom are taken together to form an oxo;

or two $R^{25a}$ are taken together to form a cycloalkyl or heterocycloalkyl; each optionally and independently substituted with one or more R;

$R^{16}$ is hydrogen, —C(=O)$R^{26}$, —C(=O)$OR^{26}$, —$CH_2$—O—C(=O)$R^{26}$, —$CH_2$—O—C(=O)$OR^{26}$, or $C_1$-$C_6$alkyl optionally substituted with one or more $R^{16a}$;

each $R^{16a}$ is independently halogen, —CN, —OH, —$OR^a$, —$NR^cR^d$, cycloalkyl, or heterocycloalkyl;

or two $R^{16a}$ on the same atom are taken together to form an oxo;

$R^{26}$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene (aryl), or $C_1$-$C_6$alkylene(heteroaryl); wherein the alkyl, alkylene, cycloalkyl, heterocycloalkyl, aryl, and heteroaryl is optionally and independently substituted with one or more $R^{26a}$, each $R^{26a}$ is independently halogen, —CN, —$NO_2$, —OH, —$OR^a$, —OC(=O)$R^a$, —OC(=O)$OR^b$, —OC(=O)$NR^cR^d$, —S(=O)$R^a$, —S(=O)$_2R^a$, —S(=O)$_2NR^cR^d$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two $R^{26a}$ on the same atom are taken together to form an oxo;

or two $R^{26a}$ are taken together to form a cycloalkyl or heterocycloalkyl; each optionally and independently substituted with one or more R;

each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl), wherein the alkyl, alkenyl, alkynyl, cycloalkyl, heterocycloalkyl, aryl, and heteroaryl is independently optionally substituted with one or more R;

each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl), wherein the alkyl, alkenyl, alkynyl, cycloalkyl, heterocycloalkyl, aryl, and heteroaryl is independently optionally substituted with one or more R;

$R^c$ and $R^d$ are each independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl), wherein the alkyl, alkenyl, alkynyl, cycloalkyl, heterocycloalkyl, aryl, and heteroaryl is independently optionally substituted with one or more R;

or $R^c$ and $R^d$ are taken together with the atom to which they are attached to form a heterocycloalkyl optionally substituted with one or more R; and each R is independently halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$hydroxyalkyl, $C_1$-$C_6$aminoalkyl, and $C_1$-$C_6$heteroalkyl;

or two R on the same atom are taken together to form an oxo.

In some embodiments, the compound is a compound of Formula (VIa):

Formula (VIa)

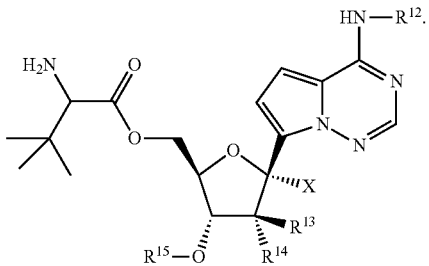

In some embodiments, the compound is a compound of Formula (VIb):

Formula (VIb)

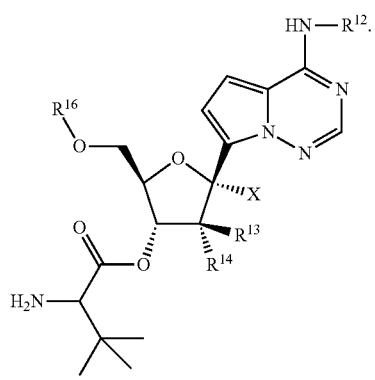

In some embodiments, the compound is a compound of Formula (VIc):

Formula (VIc)

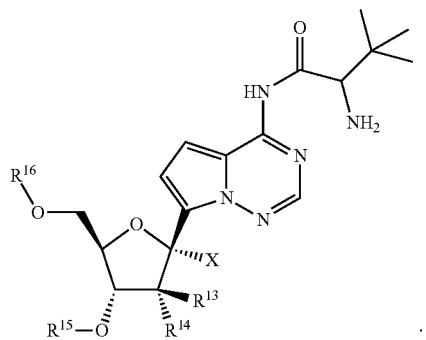

In some embodiments of a compound of Formula (VIa), (VIb), or (VIc), X is hydrogen. In some embodiments of a compound of Formula (VIa), (VIb), or (VIc), X is —CN.

In some embodiments of a compound of Formula (VIa), (VIb), or (VIc), $R^{13}$ is hydrogen. In some embodiments of a compound of Formula (VIa), (VIb), or (VIc), $R^{13}$ is $C_1$-$C_6$alkyl.

In some embodiments of a compound of Formula (VIa), (VIb), or (VIc), $R^{14}$ is —OH. In some embodiments of a compound of Formula (VIa), (VIb), or (VIc), $R^{14}$ is fluoro.

In some embodiments of a compound of Formula (VIa) or (VIb), $R^{12}$ is hydrogen, —C(=O)$R^{22}$, —C(=O)O$R^{22}$, or $C_1$-$C_6$alkyl. In some embodiments of a compound of Formula (VIa) or (VIb), $R^{12}$ is —C(=O)$R^{22}$, —C(=O)O$R^{22}$, or $C_1$-$C_6$alkyl. In some embodiments of a compound of Formula (VIa) or (VIb), $R^{12}$ is —C(=O)$R^{22}$. In some embodiments of a compound of Formula (VIa) or (VIb), $R^{12}$ is —C(=O)O$R^{22}$. In some embodiments of a compound of Formula (VIa) or (VIb), $R^{12}$ is $C_1$-$C_6$alkyl. In some embodiments of a compound of Formula (VIa) or (VIb), $R^{12}$ is hydrogen.

In some embodiments of a compound of Formula (VIa) or (VIb), $R^{22}$ is $C_1$-$C_6$alkyl, $C_1$-$C_6$aminoalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkyl, alkylene, cycloalkyl, heterocycloalkyl, aryl, and heteroaryl is optionally and independently substituted with one or more $R^{22a}$.

In some embodiments of a compound of Formula (VIa) or (VIb), $R^{22}$ is $C_1$-$C_6$alkyl, $C_1$-$C_6$aminoalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl).

In some embodiments of a compound of Formula (VIa) or (VIb), $R^{22}$ is $C_1$-$C_6$alkyl, $C_1$-$C_6$aminoalkyl, aryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl).

In some embodiments of a compound of Formula (VIa) or (VIb), $R^{22}$ is $C_1$-$C_6$alkyl, $C_1$-$C_6$aminoalkyl, aryl, $C_1$-$C_6$alkylene(cycloalkyl), or $C_1$-$C_6$alkylene(aryl).

In some embodiments of a compound of Formula (VIa) or (VIb), $R^{22}$ is $C_1$-$C_6$alkyl or $C_1$-$C_6$alkylene(aryl); wherein the alkyl, alkylene, and aryl is optionally and independently substituted with one or more $R^{22a}$.

In some embodiments of a compound of Formula (VIa) or (VIb), $R^{22}$ is $C_1$-$C_6$alkyl optionally and independently substituted with one or more $R^{22a}$.

In some embodiments of a compound of Formula (VIa) or (VIb), each $R^{22a}$ is independently halogen, —CN, —OH, —OR$^a$, —OC(=O)R$^a$, —OC(=O)OR$^b$, —OC(=O)NR$^c$R$^d$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (VIa) or (VIb), each $R^{22a}$ is independently halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (VIa) or (VIb), each $R^{22a}$ is independently halogen, —OH, —OR$^a$, —NR$^c$R$^d$, $C_1$-$C_6$alkyl, or $C_1$-$C_6$haloalkyl.

In some embodiments of a compound of Formula (VIa) or (VIb), each $R^{22a}$ is independently halogen, —OC(=O)R$^a$, or —NR$^c$R$^d$. In some embodiments of a compound of Formula (VIa) or (VIb), each $R^{22a}$ is independently —OC(=O)R$^a$ or —NR$^c$R$^d$. In some embodiments of a compound of Formula (VIa) or (VIb), each $R^{22a}$ is independently —OC(=O)R$^a$.

In some embodiments of a compound of Formula (VIa) or (VIc), $R^{15}$ is —C(=O)R$^{25}$ or —C(=O)OR$^{25}$, or —CH$_2$—O—C(=O)R$^{25}$.

In some embodiments of a compound of Formula (VIa) or (VIc), $R^{15}$ is hydrogen.

In some embodiments of a compound of Formula (VIa) or (VIc), $R^{15}$ is —C(=O)R$^{25}$.

In some embodiments of a compound of Formula (VIa) or (VIc), $R^{15}$ is —C(=O)OR$^{25}$.

In some embodiments of a compound of Formula (VIa) or (VIc), $R^{25}$ is $C_1$-$C_6$alkylene(cycloalkyl) or $C_1$-$C_6$alkylene(aryl); wherein the alkylene, cycloalkyl, and aryl is optionally and independently substituted with one or more $R^{25a}$.

In some embodiments of a compound of Formula (VIa) or (VIc), $R^{25}$ is $C_1$-$C_6$alkylene(cycloalkyl); wherein the alkylene and cycloalkyl is optionally and independently substituted with one or more $R^{25a}$.

In some embodiments of a compound of Formula (VIa) or (VIc), $R^{25}$ is $C_1$-$C_6$alkylene(aryl); wherein the alkylene, and aryl is optionally and independently substituted with one or more $R^{25a}$.

In some embodiments of a compound of Formula (VIa) or (VIc), each $R^{25a}$ is independently halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (VIa) or (VIc), each $R^{25a}$ is independently halogen, —OH, —OR$^a$, —NR$^c$R$^d$, $C_1$-$C_6$alkyl, or $C_1$-$C_6$haloalkyl.

In some embodiments of a compound of Formula (VIb) or (VIc), $R^{16}$ is hydrogen, —C(=O)R$^{26}$, —C(=O)OR$^{26}$, or $C_1$-$C_6$alkyl optionally substituted with one or more $R^{16a}$. In some embodiments of a compound of Formula (VIb) or (VIc), $R^{16}$ is hydrogen, —C(=O)R$^{26}$, or —C(=O)OR$^{26}$. In some embodiments of a compound of Formula (VIb) or (VIc), $R^{16}$ is —C(=O)R$^{26}$ or —C(=O)OR$^{26}$. In some embodiments of a compound of Formula (VIb) or (VIc), $R^{16}$ is hydrogen. In some embodiments of a compound of Formula (VIb) or (VIc), $R^{16}$ is —C(=O)R$^{26}$. In some embodiments of a compound of Formula (VIb) or (VIc), $R^{16}$ is —C(=O)OR$^{26}$.

In some embodiments of a compound of Formula (VIb) or (VIc), $R^{26}$ is $C_1$-$C_6$alkyl, $C_1$-$C_6$aminoalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkyl, alkylene, cycloalkyl, heterocycloalkyl, aryl, and heteroaryl is optionally and independently substituted with one or more $R^{26a}$.

In some embodiments of a compound of Formula (VIb) or (VIc), $R^{26}$ is $C_1$-$C_6$alkyl, $C_1$-$C_6$aminoalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl).

In some embodiments of a compound of Formula (VIb) or (VIc), $R^{26}$ is $C_1$-$C_6$alkyl, $C_1$-$C_6$aminoalkyl, aryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl).

In some embodiments of a compound of Formula (VIb) or (VIc), $R^{26}$ is $C_1$-$C_6$alkyl, $C_1$-$C_6$aminoalkyl, aryl, $C_1$-$C_6$alkylene(cycloalkyl), or $C_1$-$C_6$alkylene(aryl). In some embodiments of a compound of Formula (VIb) or (VIc), $R^{26}$ is $C_1$-$C_6$alkylene(cycloalkyl) or $C_1$-$C_6$alkylene(aryl).

In some embodiments of a compound of Formula (VIb) or (VIc), $R^{26}$ is $C_1$-$C_6$alkyl or $C_1$-$C_6$aminoalkyl.

In some embodiments of a compound of Formula (VIb) or (VIc), each $R^{26a}$ is independently halogen, —CN, —OH, —OR$^a$, —OC(=O)R$^a$, —OC(=O)OR$^b$, —OC(=O)NR$^c$R$^d$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (VIb) or (VIc), each $R^{26a}$ is independently halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (VIb) or (VIc), each $R^{26a}$ is independently halogen, —OH, —OR$^a$, —NR$^c$R$^d$, $C_1$-$C_6$alkyl, or $C_1$-$C_6$haloalkyl.

In some embodiments of a compound of Formula (VIb) or (VIc), each $R^{26a}$ is independently —OC(=O)R$^a$, or —NR$^c$R$^d$.

In some embodiments of a compound disclosed herein, or a pharmaceutically acceptable salt, solvate, or stereoisomer thereof, each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkyl(cycloalkyl), $C_1$-$C_6$alkylene(heterocycloalkyl), $C_1$-$C_6$alkyl(aryl), or $C_1$-$C_6$alkyl(heteroaryl); wherein each alkyl, cycloalkyl, heterocycloalkyl, aryl, and heteroaryl is independently optionally substituted with one or more R. In some embodiments of a compound disclosed herein, or a pharmaceutically acceptable salt, solvate, or stereoisomer thereof, each $R^a$ is independently $C_1$-$C_6$alkyl, $C_1$-$C_6$haloalkyl, or cycloalkyl, heterocycloalkyl; wherein each alkyl, cycloalkyl, and heterocycloalkyl is independently optionally substituted with one or more R. In some embodiments of a compound disclosed herein, or a pharmaceutically acceptable salt, solvate, or stereoisomer thereof, each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl). In some embodiments of a compound disclosed herein, or a pharmaceutically acceptable salt, solvate, or stereoisomer thereof, each $R^a$ is independently $C_1$-$C_6$alkyl, $C_1$-$C_6$haloalkyl, or cycloalkyl, heterocycloalkyl. In some embodiments of a compound disclosed herein, or a pharmaceutically acceptable salt, solvate, or stereoisomer thereof, each $R^a$ is independently $C_1$-$C_6$alkyl or $C_1$-$C_6$haloalkyl. In some embodiments of a compound disclosed herein, or a pharmaceutically acceptable salt, solvate, or stereoisomer thereof, each $R^a$ is independently $C_1$-$C_6$alkyl.

In some embodiments of a compound disclosed herein, or a pharmaceutically acceptable salt, solvate, or stereoisomer thereof, each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, cycloalkyl, heterocycloalkyl, aryl, and heteroaryl is independently optionally substituted with one or more R. In some embodiments of a compound disclosed herein, or a pharmaceutically acceptable salt, solvate, or stereoisomer thereof, each $R^b$ is independently hydrogen, $C_1$-$C_6$alkyl, $C_1$-$C_6$haloalkyl, or cycloalkyl, heterocycloalkyl; wherein each alkyl, cycloalkyl, and heterocycloalkyl is independently optionally substituted with one or more R. In some embodiments of a compound disclosed herein, or a pharmaceutically acceptable salt, solvate, or stereoisomer thereof, each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl). In some embodiments of a compound disclosed herein, or a pharmaceutically acceptable salt, solvate, or stereoisomer thereof, each $R^b$ is independently hydrogen, $C_1$-$C_6$alkyl, $C_1$-$C_6$haloalkyl, or cycloalkyl, heterocycloalkyl. In some embodiments of a compound disclosed herein, or a pharmaceutically acceptable salt, solvate, or stereoisomer thereof, each $R^b$ is independently hydrogen, $C_1$-$C_6$alkyl or $C_1$-$C_6$haloalkyl. In some embodiments of a compound disclosed herein, or a pharmaceutically acceptable salt, solvate, or stereoisomer thereof, each $R^b$ is independently hydrogen or $C_1$-$C_6$alkyl. In some embodiments of a compound disclosed herein, or a pharmaceutically acceptable salt, solvate, or stereoisomer thereof, each $R^b$ is hydrogen. In some embodiments of a compound disclosed herein, or a pharmaceutically acceptable salt, solvate, or stereoisomer thereof, each $R^b$ is independently $C_1$-$C_6$alkyl.

In some embodiments of a compound disclosed herein, or a pharmaceutically acceptable salt, solvate, or stereoisomer thereof, each $R^c$ and $R^d$ are independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, cycloalkyl, heterocycloalkyl, aryl, and heteroaryl is independently optionally substituted with one or more R. In some embodiments of a compound disclosed herein, or a pharmaceutically acceptable salt, solvate, or stereoisomer thereof, each $R^c$ and $R^d$ are independently hydrogen, $C_1$-$C_6$alkyl, $C_1$-$C_6$haloalkyl, or cycloalkyl, heterocycloalkyl; wherein each alkyl, cycloalkyl, and heterocycloalkyl is independently optionally substituted with one or more R. In some embodiments of a compound disclosed herein, or a pharmaceutically acceptable salt, solvate, or stereoisomer thereof, each $R^c$ and $R^d$ are independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkyl(heteroaryl). In some embodiments of a compound disclosed herein, or a pharmaceutically acceptable salt, solvate, or stereoisomer thereof, each $R^c$ and $R^d$ are independently hydrogen, $C_1$-$C_6$alkyl, $C_1$-$C_6$haloalkyl, or cycloalkyl, heterocycloalkyl. In some embodiments of a compound disclosed herein, or a pharmaceutically acceptable salt, solvate, or stereoisomer thereof, each $R^c$ and $R^d$ are independently hydrogen, $C_1$-$C_6$alkyl or $C_1$-$C_6$haloalkyl. In some embodiments of a compound disclosed herein, or a pharmaceutically acceptable salt, solvate, or stereoisomer thereof, each $R^c$ and $R^d$ are independently hydrogen or $C_1$-$C_6$alkyl. In some embodiments of a compound disclosed herein, or a pharmaceutically acceptable salt, solvate, or stereoisomer thereof, each $R^c$ and $R^d$ are hydrogen. In some embodiments of a compound disclosed herein, or a pharmaceutically acceptable salt, solvate, or stereoisomer thereof, each $R^c$ and $R^d$ are independently $C_1$-$C_6$alkyl.

In some embodiments of a compound disclosed herein, or a pharmaceutically acceptable salt, solvate, or stereoisomer thereof, $R^c$ and $R^d$ are taken together with the atom to which they are attached to form a heterocycloalkyl optionally substituted with one or more R.

In some embodiments of a compound disclosed herein, or a pharmaceutically acceptable salt, solvate, or stereoisomer thereof, each R is independently halogen, —CN, —OH, —OC$_1$-C$_6$alkyl, —NH$_2$, —NHC$_1$-C$_6$alkyl, —N(C$_1$-C$_6$alkyl)$_2$, —NHC(=O)OC$_1$-C$_6$alkyl, —C(=O)C$_1$-C$_6$alkyl, —C(=O)OH, —C(=O)OC$_1$-C$_6$alkyl, —C(=O)NH$_2$, —C(=O)N(C$_1$-C$_6$alkyl)$_2$, —C(=O)NHC$_1$-C$_6$alkyl, $C_1$-$C_6$alkyl, or $C_1$-$C_6$haloalkyl. In some embodiments of a compound disclosed herein, or a pharmaceutically acceptable salt, solvate, or stereoisomer thereof, each R is independently halogen, —CN, —OH, —OC$_1$-C$_6$alkyl, —NH$_2$, —C(=O)C$_1$-C$_6$alkyl, —C(=O)OH, —C(=O)OC$_1$-C$_6$alkyl, —C(=O)NH$_2$, $C_1$-$C_6$alkyl, or $C_1$-$C_6$haloalkyl. In some embodiments of a compound disclosed herein, or a pharmaceutically acceptable salt, solvate, or stereoisomer thereof, each R is independently halogen, —CN, —OH, —OC$_1$-C$_6$alkyl, —NH$_2$, $C_1$-$C_6$alkyl, or $C_1$-$C_6$haloalkyl.

In some embodiments of a compound disclosed herein, each $R^{11}$, $R^{21}$, $R^{21a}$, $R^{12}$, $R^{22}$, $R^{22a}$, $R^{15}$, $R^{25}$, $R^{25a}$, $R^{16}$, $R^{26}$, $R^{26a}$, $R^a$, $R^b$, $R^c$, $R^d$, the cycloalkyl and heterocycloalkyl formed when two $R^{25a}$ are taken together, the cycloalkyl and heterocycloalkyl formed when two $R^{26a}$ are taken together, and the heterocycloalkyl formed when $R^c$ and $R^d$ are taken together, is optionally and independently substituted with one, two, three, or four substituents as defined herein.

In some embodiments of a compound disclosed herein, each $R^{11}$, $R^{21}$, $R^{21a}$, $R^{12}$, $R^{22}$, $R^{22a}$, $R^{15}$, $R^{25}$, $R^{25a}$, $R^{16}$, $R^{26}$, $R^{26a}$, $R^a$, $R^b$, $R^c$, $R^d$, the cycloalkyl and heterocycloalkyl formed when two $R^{25a}$ are taken together, the cycloalkyl and heterocycloalkyl formed when two $R^{26a}$ are taken together, and the heterocycloalkyl formed when $R^c$ and $R^d$ are taken together, is optionally and independently substituted with one, two, or three substituents as defined herein.

In some embodiments of a compound disclosed herein, each $R^{11}$, $R^{21}$, $R^{21a}$, $R^{12}$, $R^{22}$, $R^{22a}$, $R^{15}$, $R^{25}$, $R^{25a}$, $R^{16}$, $R^{26}$, $R^{26a}$, $R^a$, $R^b$, $R^c$, $R^d$, the cycloalkyl and heterocycloalkyl formed when two $R^{25a}$ are taken together, the cycloalkyl and heterocycloalkyl formed when two $R^{26a}$ are taken together, and the heterocycloalkyl formed when $R^c$ and $R^d$ are taken together, is optionally and independently substituted with one or two substituents as defined herein.

Any combination of the groups described above for the various variables is contemplated herein. Throughout the specification, groups and substituents thereof are chosen by one skilled in the field to provide stable moieties and compounds.

Described herein is a compound of Formula (I), (Ia), (Ib), (Ic), (Id), (Ie), (If), (Ig), (II), (III), (IV), (V), (VIa), (VIb), and (VIc), or a pharmaceutically acceptable salt, solvate, or stereoisomer thereof, selected from a compound in Table 1.

TABLE 1

Exemplary compounds

| Cpd. No. | Structure | Chemical Name | ESI-MS (M + H)+ (m/z) |
|---|---|---|---|
| 1 | 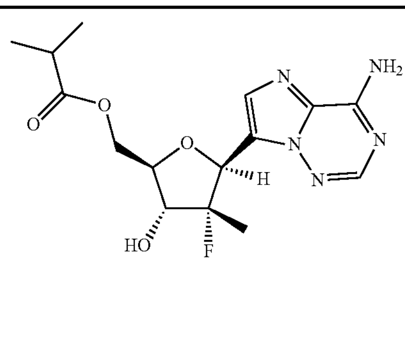 | ((2R,3R,4R,5S)-5-(4-aminoimidazo[2,1-f][1,2,4]triazin-7-yl)-4-fluoro-3-hydroxy-4-methyltetrahydrofuran-2-yl)methyl isobutyrate | 354.3 |

TABLE 1-continued

Exemplary compounds

| Cpd. No. | Structure | Chemical Name | ESI-MS (M + H)+ (m/z) |
|---|---|---|---|
| 2 | 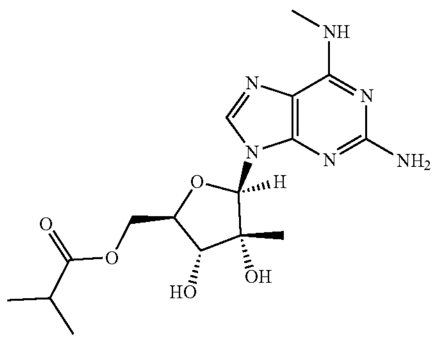 [SMILES: CNc1nc(N)nc2c1ncn2[C@@H]1O[C@H](COC(=O)C(C)C)[C@@H](O)[C@@]1(C)O] | ((2R,3R,4R,5R)-5-(2-amino-6-(methylamino)-9H-purin-9-yl)-3,4-dihydroxy-4-methyltetrahydrofuran-2-yl)methyl isobutyrate | 381.1 |
| 3 | 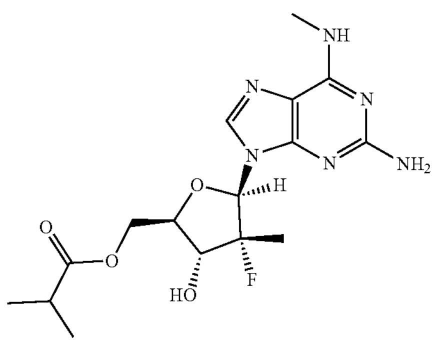 [SMILES: CNc1nc(N)nc2c1ncn2[C@@H]1O[C@H](COC(=O)C(C)C)[C@@H](O)[C@@]1(C)F] | ((2R,3R,4R,5R)-5-(2-amino-6-(methylamino)-9H-purin-9-yl)-4-fluoro-3-hydroxy-4-methyltetrahydrofuran-2-yl)methyl isobutyrate | 383.3 |
| 4 | 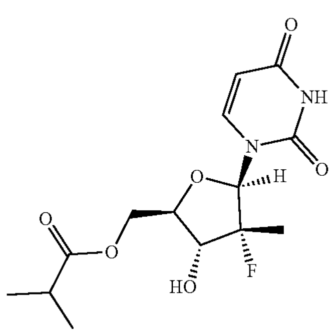 [SMILES: CC(C)C(=O)OC[C@H]1O[C@@H](n2ccc(=O)[nH]c2=O)[C@](C)(F)[C@@H]1O] | ((2R,3R,4R,5R)-5-(2,4-dioxo-3,4-dihydropyrimidin-1(2H)-yl)-4-fluoro-3-hydroxy-4-methyltetrahydrofuran-2-yl)methyl isobutyrate | 331.0 |
| 5 | 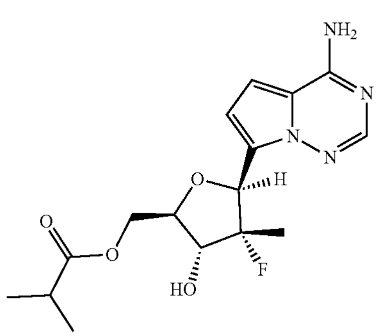 [SMILES: CC(C)C(=O)OC[C@H]1O[C@@H](c2ccc3c(N)ncnn23)[C@](C)(F)[C@@H]1O] | ((2R,3R,4R,5S)-5-(4-aminopyrrolo[2,1-f][1,2,4]triazin-7-yl)-4-fluoro-3-hydroxy-4-methyltetrahydrofuran-2-yl)methyl isobutyrate | 354 |

TABLE 1-continued

Exemplary compounds

| Cpd. No. | Structure | Chemical Name | ESI-MS (M + H)+ (m/z) |
|---|---|---|---|
| 6 | 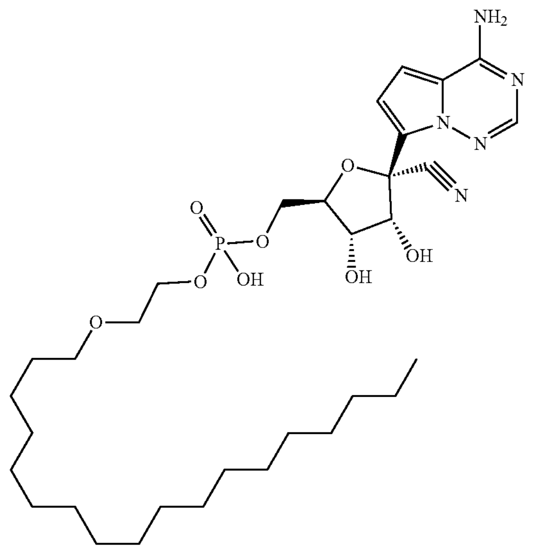 [SMILES: CCCCCCCCCCCCCCCCCCOCCOP(=O)(O)OC[C@H]1O[C@@](C#N)(c2ccc3c(N)ncnn23)[C@H](O)[C@@H]1O] | ((2R,3S,4R,5R)-5-(4-aminopyrrolo[2,1-f][1,2,4]triazin-7-yl)-5-cyano-3,4-dihydroxytetrahydrofuran-2-yl)methyl(2-(octadecyloxy)ethyl) hydrogen phosphate | 666.4 [M − H]− |
| 7 | 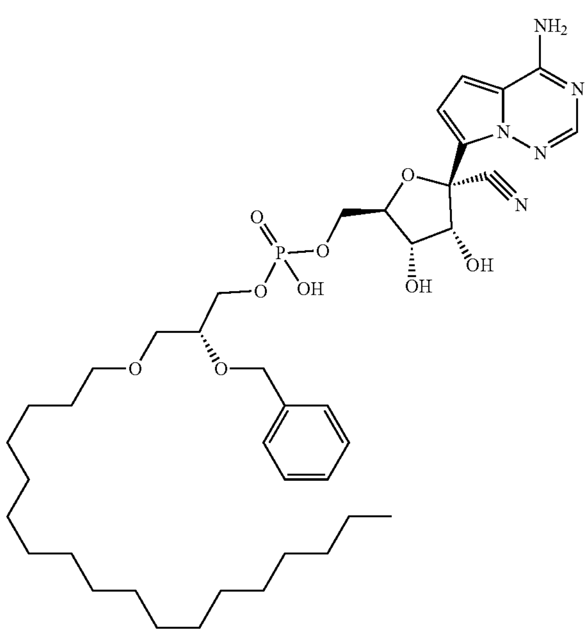 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)OCc1ccccc1] | ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(benzyloxy)-3-(octadecyloxy)propyl) hydrogen phosphate | 786 [M − H]− |

TABLE 1-continued

Exemplary compounds

| Cpd. No. | Structure | Chemical Name | ESI-MS (M + H)+ (m/z) |
|---|---|---|---|
| 8 | 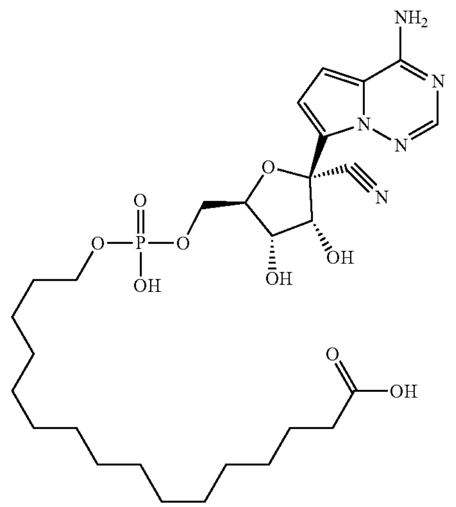 [SMILES: N#C[C@@]1(c2ccc3c(N)ncnn23)O[C@H](COP(=O)(O)OCCCCCCCCCCCCCCCC(=O)O)[C@@H](O)[C@H]1O] | 16-(((((2R,3S,4R,5R)-5-(4-aminopyrrolo[2,1-f][1,2,4]triazin-7-yl)-5-cyano-3,4-dihydroxytetrahydrofuran-2-yl)methoxy)(hydroxy)phosphoryl)oxy) hexadecanoic acid | 624.3 [M − H]− |
| 9 | 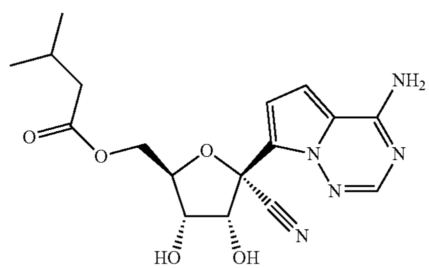 [SMILES: CC(C)CC(=O)OC[C@H]1O[C@@](C#N)(c2ccc3c(N)ncnn23)[C@H](O)[C@@H]1O] | ((2R,3S,4R,5R)-5-(4-aminopyrrolo[2,1-f][1,2,4]triazin-7-yl)-5-cyano-3,4-dihydroxytetrahydrofuran-2-yl)methyl 3-methylbutanoate | 376.1 |
| 10 | 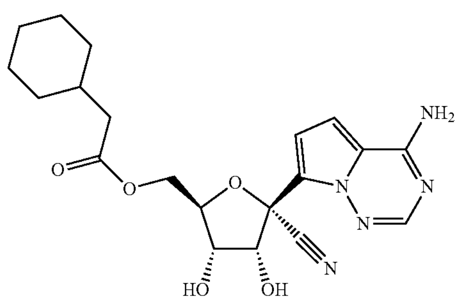 [SMILES: N#C[C@@]1(c2ccc3c(N)ncnn23)O[C@H](COC(=O)CC2CCCCC2)[C@@H](O)[C@H]1O] | ((2R,3S,4R,5R)-5-(4-aminopyrrolo[2,1-f][1,2,4]triazin-7-yl)-5-cyano-3,4-dihydroxytetrahydrofuran-2-yl)methyl 2-cyclohexylacetate | 416.2 |
| 11 | 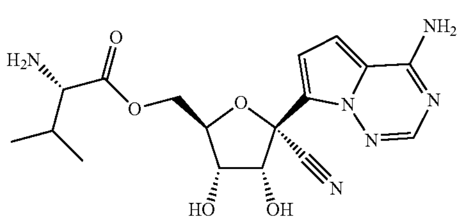 [SMILES: CC(C)[C@H](N)C(=O)OC[C@H]1O[C@@](C#N)(c2ccc3c(N)ncnn23)[C@H](O)[C@@H]1O] | ((2R,3S,4R,5R)-5-(4-aminopyrrolo[2,1-f][1,2,4]triazin-7-yl)-5-cyano-3,4-dihydroxytetrahydrofuran-2-yl)methyl L-valinate | 391.1 |

TABLE 1-continued

Exemplary compounds

| Cpd. No. | Structure | Chemical Name | ESI-MS (M + H)+ (m/z) |
|---|---|---|---|
| 12 | 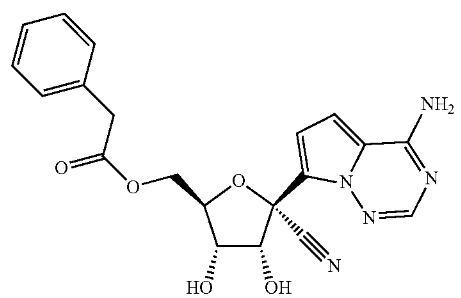 [SMILES: N#C[C@@]1(c2ccc3c(N)ncnn23)O[C@H](COC(=O)Cc2ccccc2)[C@@H](O)[C@H]1O] | ((2R,3S,4R,5R)-5-(4-aminopyrrolo[2,1-f][1,2,4]triazin-7-yl)-5-cyano-3,4-dihydroxytetrahydrofuran-2-yl)methyl 2-phenylacetate | 410.1 |
| 13 | 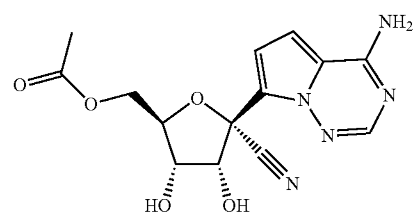 [SMILES: CC(=O)OC[C@H]1O[C@@](C#N)(c2ccc3c(N)ncnn23)[C@H](O)[C@@H]1O] | ((2R,3S,4R,5R)-5-(4-aminopyrrolo[2,1-f][1,2,4]triazin-7-yl)-5-cyano-3,4-dihydroxytetrahydrofuran-2-yl)methyl acetate | 334.2 |
| 14 | 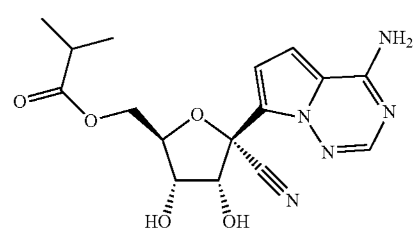 [SMILES: CC(C)C(=O)OC[C@H]1O[C@@](C#N)(c2ccc3c(N)ncnn23)[C@H](O)[C@@H]1O] | ((2R,3S,4R,5R)-5-(4-aminopyrrolo[2,1-f][1,2,4]triazin-7-yl)-5-cyano-3,4-dihydroxytetrahydrofuran-2-yl)methyl isobutyrate | 362.1 |
| 15 | 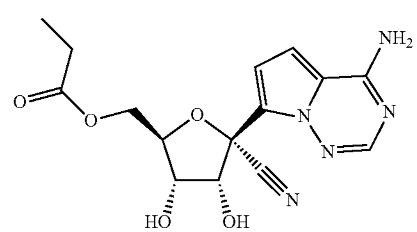 [SMILES: CCC(=O)OC[C@H]1O[C@@](C#N)(c2ccc3c(N)ncnn23)[C@H](O)[C@@H]1O] | ((2R,3S,4R,5R)-5-(4-aminopyrrolo[2,1-f][1,2,4]triazin-7-yl)-5-cyano-3,4-dihydroxytetrahydrofuran-2-yl)methyl propionate | 347.9 |
| 16 | 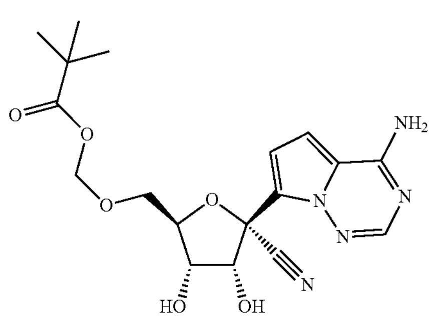 [SMILES: CC(C)(C)C(=O)OCOC[C@H]1O[C@@](C#N)(c2ccc3c(N)ncnn23)[C@H](O)[C@@H]1O] | (((2R,3S,4R,5R)-5-(4-aminopyrrolo[2,1-f][1,2,4]triazin-7-yl)-5-cyano-3,4-dihydroxytetrahydrofuran-2-yl)methoxy)methyl pivalate | |

TABLE 1-continued

Exemplary compounds

| Cpd. No. | Structure | Chemical Name | ESI-MS (M + H)+ (m/z) |
|---|---|---|---|
| 17 | 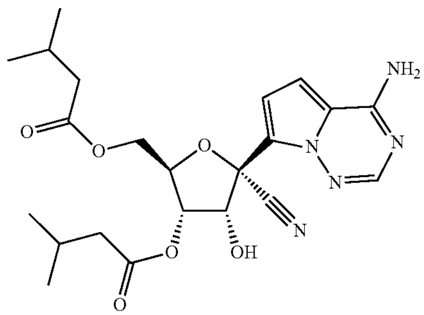 [SMILES: CC(C)CC(=O)OC[C@H]1O[C@@](C#N)(c2ccc3c(N)ncnn23)[C@H](O)[C@@H]1OC(=O)CC(C)C] | (2R,3S,4R,5R)-5-(4-aminopyrrolo[2,1-f][1,2,4]triazin-7-yl)-5-cyano-4-hydroxy-2-(((3-methylbutanoyl)oxy)methyl)tetrahydrofuran-3-yl 3-methylbutanoate | 460.1 |
| 18 | 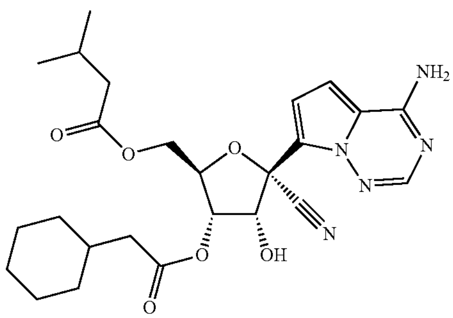 [SMILES: CC(C)CC(=O)OC[C@H]1O[C@@](C#N)(c2ccc3c(N)ncnn23)[C@H](O)[C@@H]1OC(=O)CC1CCCCC1] | ((2R,3S,4R,5R)-5-(4-aminopyrrolo[2,1-f][1,2,4]triazin-7-yl)-5-cyano-3-(2-cyclohexylacetoxy)-4-hydroxytetrahydrofuran-2-yl)methyl 3-methylbutanoate | 500.4 |
| 19 | 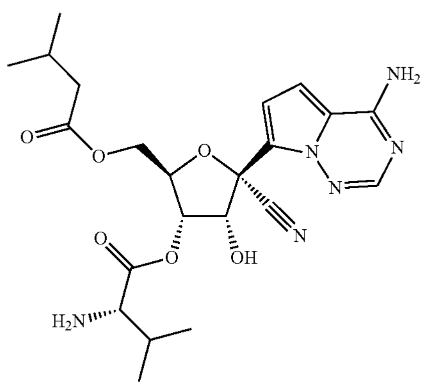 [SMILES: CC(C)CC(=O)OC[C@H]1O[C@@](C#N)(c2ccc3c(N)ncnn23)[C@H](O)[C@@H]1OC(=O)[C@@H](N)C(C)C] | (2R,3S,4R,5R)-5-(4-aminopyrrolo[2,1-f][1,2,4]triazin-7-yl)-5-cyano-4-hydroxy-2-(((3-methylbutanoyl)oxy)methyl)tetrahydrofuran-3-yl L-valinate | 475.3 |
| 20 | 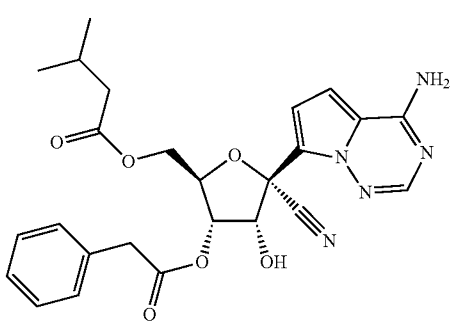 [SMILES: CC(C)CC(=O)OC[C@H]1O[C@@](C#N)(c2ccc3c(N)ncnn23)[C@H](O)[C@@H]1OC(=O)Cc1ccccc1] | ((2R,3S,4R,5R)-5-(4-aminopyrrolo[2,1-f][1,2,4]triazin-7-yl)-5-cyano-4-hydroxy-3-(2-phenylacetoxy)tetrahydrofuran-2-yl)methyl 3-methylbutanoate | 494.4 |

TABLE 1-continued

Exemplary compounds

| Cpd. No. | Structure | Chemical Name | ESI-MS (M + H)+ (m/z) |
|---|---|---|---|
| 21 | 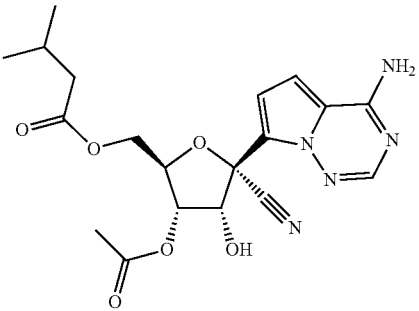 [SMILES: CC(=O)O[C@H]1[C@@H](O)[C@](C#N)(c2ccc3c(N)ncnn23)O[C@@H]1COC(=O)CC(C)C] | ((2R,3S,4R,5R)-3-acetoxy-5-(4-aminopyrrolo[2,1-f][1,2,4]triazin-7-y)-5-cyano-4-hydroxytetrahydrofuran-2-yl)methyl 3-methylbutanoate | 418.2 |
| 22 | 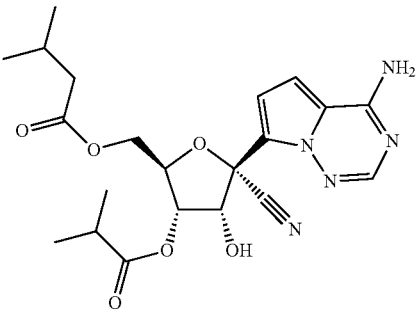 [SMILES: CC(C)CC(=O)OC[C@H]1O[C@@](C#N)(c2ccc3c(N)ncnn23)[C@H](O)[C@@H]1OC(=O)C(C)C] | ((2R,3S,4R,5R)-5-(4-aminopyrrolo[2,1-f][1,2,4]triazin-7-yl)-5-cyano-4-hydroxy-3-(isobutyryloxy)tetrahydrofuran-2-yl)methyl 3-methylbutanoate | 446.1 |
| 23 | 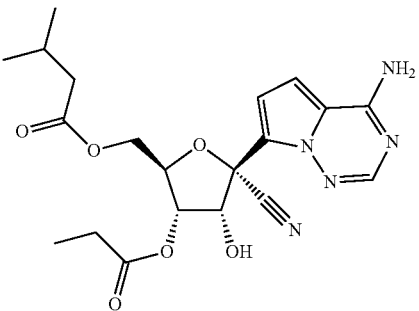 [SMILES: CCC(=O)O[C@H]1[C@@H](O)[C@](C#N)(c2ccc3c(N)ncnn23)O[C@@H]1COC(=O)CC(C)C] | ((2R,3S,4R,5R)-5-(4-aminopyrrolo[2,1-f][1,2,4]triazin-7-yl)-5-cyano-4-hydroxy-3-(propionyloxy)tetrahydrofuran-2-yl)methyl 3-methylbutanoate | 432.1 |
| 24 | 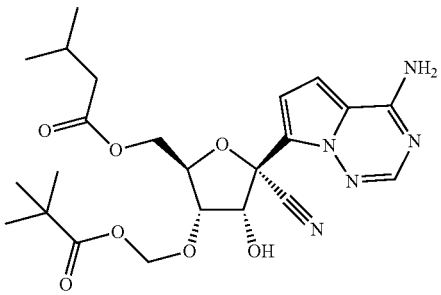 [SMILES: CC(C)CC(=O)OC[C@H]1O[C@@](C#N)(c2ccc3c(N)ncnn23)[C@H](O)[C@@H]1OCOC(=O)C(C)(C)C] | ((2R,3S,4R,5R)-5-(4-aminopyrrolo[2,1-f][1,2,4]triazin-7-yl)-5-cyano-4-hydroxy-3-((pivaloyloxy)methoxy)tetrahydrofuran-2-yl)methyl 3-methylbutanoate | 490.2 |

TABLE 1-continued

Exemplary compounds

| Cpd. No. | Structure | Chemical Name | ESI-MS (M + H)+ (m/z) |
|---|---|---|---|
| 25 | 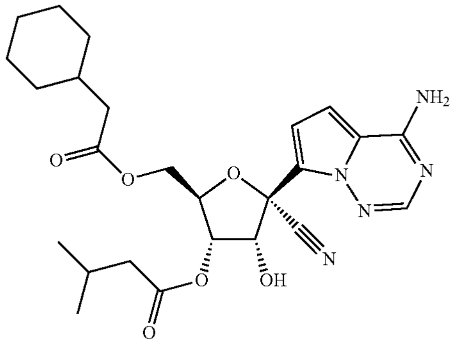 [SMILES: CC(C)CC(=O)O[C@H]1[C@@H](O)[C@](C#N)(c2ccc3c(N)ncnn23)O[C@@H]1COC(=O)CC1CCCCC1] | (2R,3S,4R,5R)-5-(4-aminopyrrolo[2,1-f][1,2,4]triazin-7-yl)-5-cyano-2-((2-cyclohexylacetoxy)methyl)-4-hydroxytetrahydrofuran-3-yl 3-methylbutanoate | 500.2 |
| 26 | 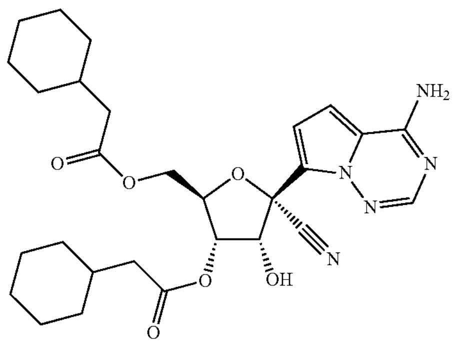 [SMILES: N#C[C@@]1(c2ccc3c(N)ncnn23)O[C@H](COC(=O)CC2CCCCC2)[C@@H](OC(=O)CC2CCCCC2)[C@H]1O] | (2R,3S,4R,5R)-5-(4-aminopyrrolo[2,1-f][1,2,4]triazin-7-yl)-5-cyano-2-((2-cyclohexylacetoxy)methyl)-4-hydroxytetrahydrofuran-3-yl 2-cyclohexylacetate | 540.2 |
| 27 | 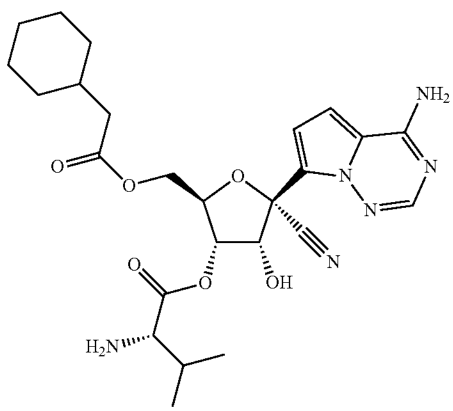 [SMILES: CC(C)[C@H](N)C(=O)O[C@H]1[C@@H](O)[C@](C#N)(c2ccc3c(N)ncnn23)O[C@@H]1COC(=O)CC1CCCCC1] | (2R,3S,4R,5R)-5-(4-aminopyrrolo[2,1-f][1,2,4]triazin-7-yl)-5-cyano-2-((2-cyclohexylacetoxy)methyl)-4-hydroxytetrahydrofuran-3-yl L-valinate | 515.4 |
| 28 | 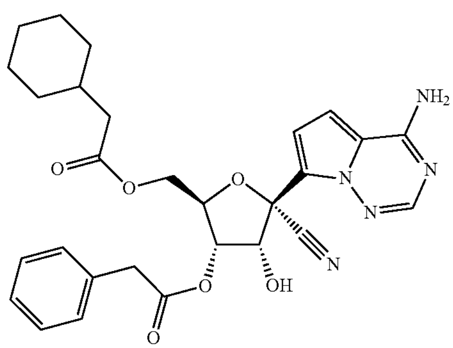 [SMILES: N#C[C@@]1(c2ccc3c(N)ncnn23)O[C@H](COC(=O)CC2CCCCC2)[C@@H](OC(=O)Cc2ccccc2)[C@H]1O] | (2R,3S,4R,5R)-5-(4-aminopyrrolo[2,1-f][1,2,4]triazin-7-yl)-5-cyano-2-((2-cyclohexylacetoxy)methyl)-4-hydroxytetrahydrofuran-3-yl 2-phenylacetate | 534.2 |

TABLE 1-continued

Exemplary compounds

| Cpd. No. | Structure | Chemical Name | ESI-MS (M + H)+ (m/z) |
|---|---|---|---|
| 29 | 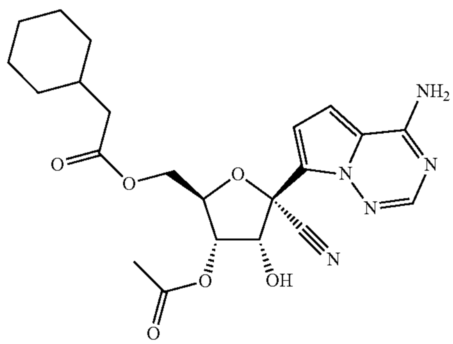 [SMILES: CC(=O)O[C@H]1[C@@H](O)[C@](C#N)(c2ccc3c(N)ncnn23)O[C@@H]1COC(=O)CC1CCCCC1] | ((2R,3S,4R,5R)-3-acetoxy-5-(4-aminopyrrolo[2,1-f][1,2,4]triazin-7-yl)-5-cyano-4-hydroxytetrahydrofuran-2-yl)methyl 2-cyclohexylacetate | 458.1 |
| 30 | 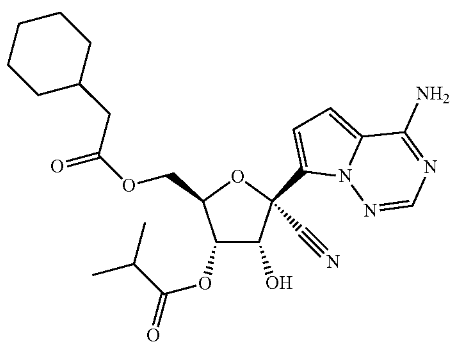 [SMILES: CC(C)C(=O)O[C@H]1[C@@H](O)[C@](C#N)(c2ccc3c(N)ncnn23)O[C@@H]1COC(=O)CC1CCCCC1] | (2R,3S,4R,5R)-5-(4-aminopyrrolo[2,1-f][1,2,4]triazin-7-yl)-5-cyano-2-((2-cyclohexylacetoxy)methyl)-4-hydroxytetrahydrofuran-3-yl isobutyrate | 486.2 |
| 31 | 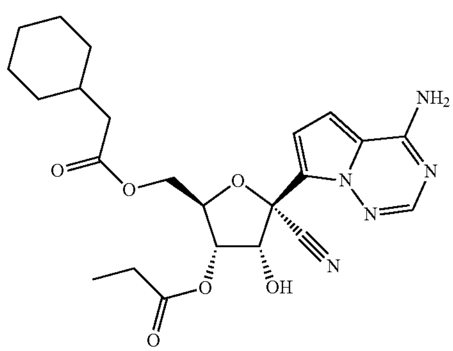 [SMILES: CCC(=O)O[C@H]1[C@@H](O)[C@](C#N)(c2ccc3c(N)ncnn23)O[C@@H]1COC(=O)CC1CCCCC1] | (2R,3S,4R,5R)-5-(4-aminopyrrolo[2,1-f][1,2,4]triazin-7-yl)-5-cyano-2-((2-cyclohexylacetoxy)methyl)-4-hydroxytetrahydrofuran-3-yl propionate | 472.1 |
| 32 | 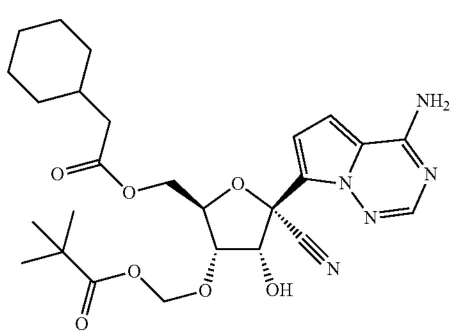 [SMILES: CC(C)(C)C(=O)OCO[C@H]1[C@@H](O)[C@](C#N)(c2ccc3c(N)ncnn23)O[C@@H]1COC(=O)CC1CCCCC1] | (((2R,3S,4R,5R)-5-(4-aminopyrrolo[2,1-f][1,2,4]triazin-7-yl)-5-cyano-2-((2-cyclohexylacetoxy)methyl)-4-hydroxytetrahydrofuran-3-yl)oxy)methyl pivalate | 530.4 |

TABLE 1-continued

Exemplary compounds

| Cpd. No. | Structure | Chemical Name | ESI-MS (M + H)+ (m/z) |
|---|---|---|---|
| 33 | 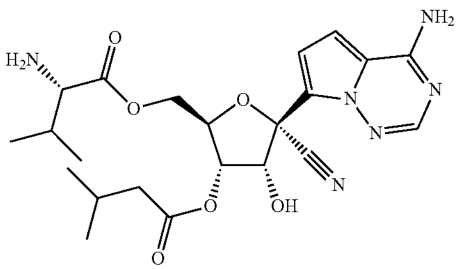 [SMILES: CC(C)CC(=O)O[C@H]1[C@@H](O)[C@](C#N)(c2ccc3c(N)ncnn23)O[C@@H]1COC(=O)[C@@H](N)C(C)C] | ((2R,3S,4R,5R)-5-(4-aminopyrrolo[2,1-f][1,2,4]triazin-7-yl)-5-cyano-4-hydroxy-3-((3-methylbutanoyl)oxy)tetrahydrofuran-2-yl)methyl L-valinate | 475.1 |
| 34 | 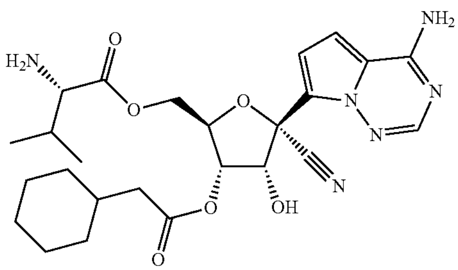 [SMILES: CC(C)[C@H](N)C(=O)OC[C@H]1O[C@@](C#N)(c2ccc3c(N)ncnn23)[C@H](O)[C@@H]1OC(=O)CC1CCCCC1] | ((2R,3S,4R,5R)-5-(4-aminopyrrolo[2,1-f][1,2,4]triazin-7-yl)-5-cyano-3-(2-cyclohexylacetoxy)-4-hydroxytetrahydrofuran-2-yl)methyl L-valinate | 515.2 |
| 35 | 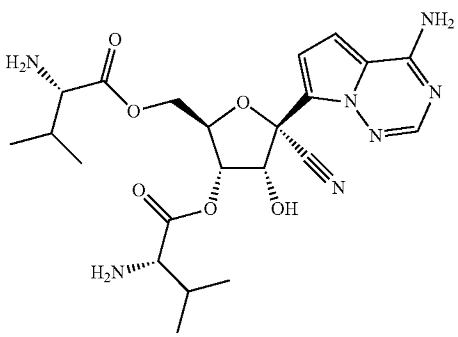 [SMILES: CC(C)[C@H](N)C(=O)OC[C@H]1O[C@@](C#N)(c2ccc3c(N)ncnn23)[C@H](O)[C@@H]1OC(=O)[C@@H](N)C(C)C] | ((2R,3S,4R,5R)-3-((L-valyl)oxy)-5-(4-aminopyrrolo[2,1-f][1,2,4]triazin-7-yl)-5-cyano-4-hydroxytetrahydrofuran-2-yl)methyl L-valinate | |
| 36 | 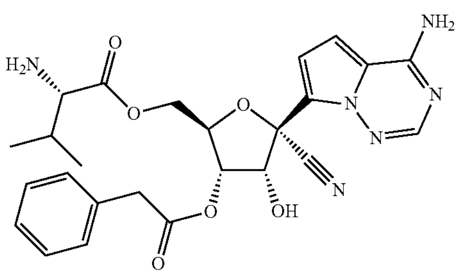 [SMILES: CC(C)[C@H](N)C(=O)OC[C@H]1O[C@@](C#N)(c2ccc3c(N)ncnn23)[C@H](O)[C@@H]1OC(=O)Cc1ccccc1] | ((2R,3S,4R,5R)-5-(4-aminopyrrolo[2,1-f][1,2,4]triazin-7-yl)-5-cyano-4-hydroxy-3-(2-phenylacetoxy)tetrahydrofuran-2-yl)methyl L-valinate | 509.3 |
| 37 | 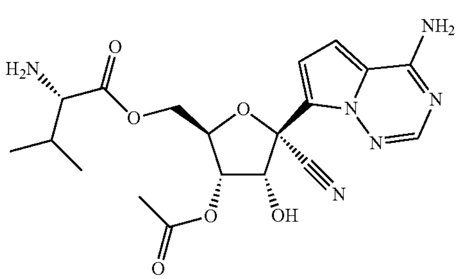 [SMILES: CC(=O)O[C@H]1[C@@H](O)[C@](C#N)(c2ccc3c(N)ncnn23)O[C@@H]1COC(=O)[C@@H](N)C(C)C] | ((2R,3S,4R,5R)-3-acetoxy-5-(4-aminopyrrolo[2,1-f][1,2,4]triazin-7-yl)-5-cyano-4-hydroxytetrahydrofuran-2-yl)methyl L-valinate | 433.1 |

TABLE 1-continued

Exemplary compounds

| Cpd. No. | Structure | Chemical Name | ESI-MS (M + H)+ (m/z) |
|---|---|---|---|
| 38 | 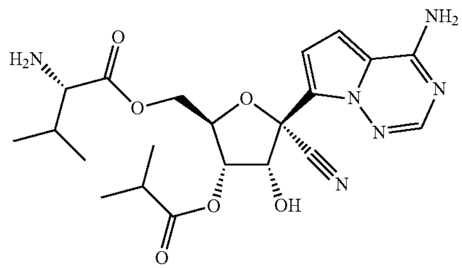 [SMILES: CC(C)C(=O)O[C@H]1[C@@H](O)[C@](C#N)(c2ccc3c(N)ncnn23)O[C@@H]1COC(=O)[C@@H](N)C(C)C] | ((2R,3S,4R,5R)-5-(4-aminopyrrolo[2,1-f][1,2,4]triazin-7-yl)-5-cyano-4-hydroxy-3-(isobutyryloxy)tetrahydrofuran-2-yl)methyl L-valinate | 461.1 |
| 39 | 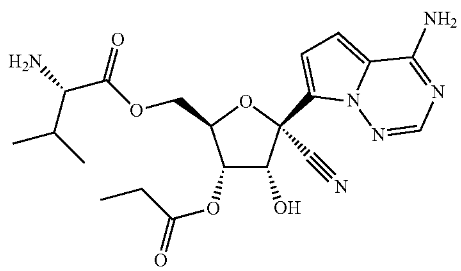 [SMILES: CCC(=O)O[C@H]1[C@@H](O)[C@](C#N)(c2ccc3c(N)ncnn23)O[C@@H]1COC(=O)[C@@H](N)C(C)C] | ((2R,3S,4R,5R)-5-(4-aminopyrrolo[2,1-f][1,2,4]triazin-7-yl)-5-cyano-4-hydroxy-3-(propionyloxy)tetrahydrofuran-2-yl)methyl L-valinate | 447.3 |
| 40 | 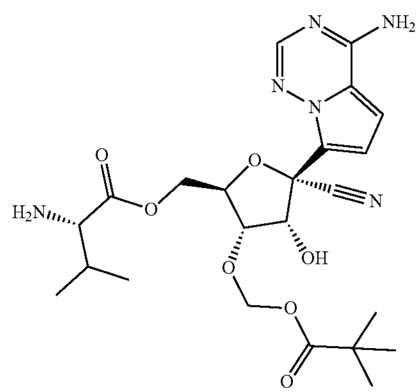 [SMILES: CC(C)[C@H](N)C(=O)OC[C@H]1O[C@@](C#N)(c2ccc3c(N)ncnn23)[C@H](O)[C@@H]1OCOC(=O)C(C)(C)C] | ((2R,3S,4R,5R)-5-(4-aminopyrrolo[2,1-f][1,2,4]triazin-7-yl)-5-cyano-4-hydroxy-3-((pivaloyloxy)methoxy)tetrahydrofuran-2-yl)methyl L-valinate | |
| 41 | 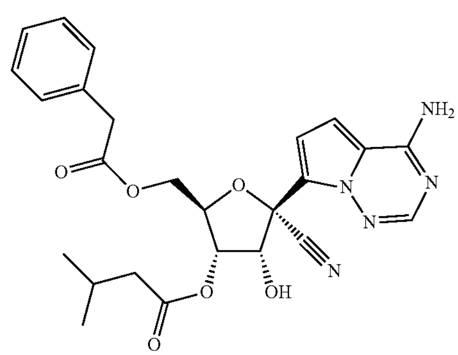 [SMILES: CC(C)CC(=O)O[C@H]1[C@@H](O)[C@](C#N)(c2ccc3c(N)ncnn23)O[C@@H]1COC(=O)Cc1ccccc1] | (2R,3S,4R,5R)-5-(4-aminopyrrolo[2,1-f][1,2,4]triazin-7-yl)-5-cyano-4-hydroxy-2-((2-phenylacetoxy)methyl)tetrahydrofuran-3-yl 3-methylbutanoate | 494.2 |

TABLE 1-continued

Exemplary compounds

| Cpd. No. | Structure | Chemical Name | ESI-MS (M + H)+ (m/z) |
|---|---|---|---|
| 42 | 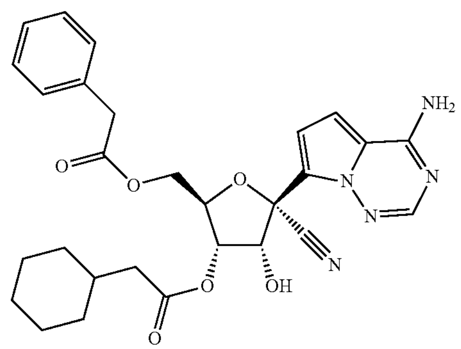 [SMILES: N#C[C@@]1(c2ccc3c(N)ncnn23)O[C@H](COC(=O)Cc2ccccc2)[C@@H](OC(=O)CC2CCCCC2)[C@H]1O] | ((2R,3S,4R,5R)-5-(4-aminopyrrolo[2,1-f][1,2,4]triazin-7-yl)-5-cyano-3-(2-cyclohexylacetoxy)-4-hydroxytetrahydrofuran-2-yl)methyl 2-phenylacetate | 534.3 |
| 43 | 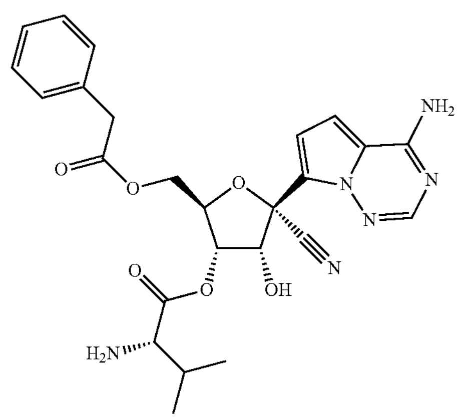 [SMILES: CC(C)[C@H](N)C(=O)O[C@H]1[C@@H](O)[C@](C#N)(c2ccc3c(N)ncnn23)O[C@@H]1COC(=O)Cc1ccccc1] | (2R,3S,4R,5R)-5-(4-aminopyrrolo[2,1-f][1,2,4]triazin-7-yl)-5-cyano-4-hydroxy-2-((2-phenylacetoxy)methyl)tetrahydrofuran-3-yl L-valinate | 509.1 |
| 44 | 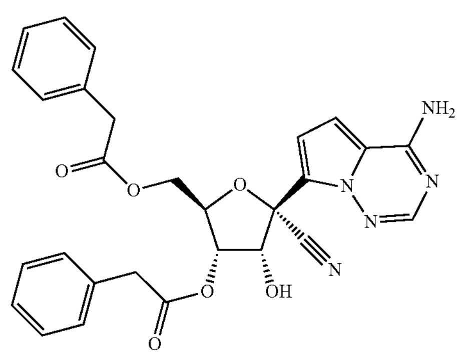 [SMILES: N#C[C@@]1(c2ccc3c(N)ncnn23)O[C@H](COC(=O)Cc2ccccc2)[C@@H](OC(=O)Cc2ccccc2)[C@H]1O] | (2R,3S,4R,5R)-5-(4-aminopyrrolo[2,1-f][1,2,4]triazin-7-yl)-5-cyano-4-hydroxy-2-((2-phenylacetoxy)methyl)tetrahydrofuran-3-yl 2-phenylacetate | 528.2 |
| 45 | 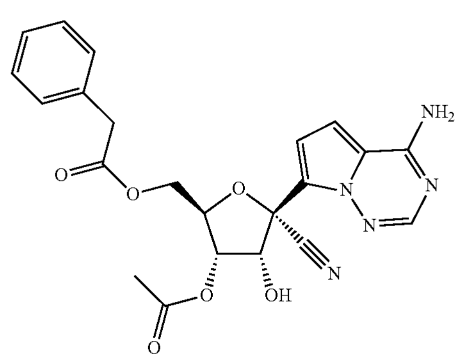 [SMILES: CC(=O)O[C@H]1[C@@H](O)[C@](C#N)(c2ccc3c(N)ncnn23)O[C@@H]1COC(=O)Cc1ccccc1] | ((2R,3S,4R,5R)-3-acetoxy-5-(4-aminopyrrolo[2,1-f][1,2,4]triazin-7-yl)-5-cyano-4-hydroxytetrahydrofuran-2-yl)methyl 2-phenylacetate | 452.0 |

TABLE 1-continued

Exemplary compounds

| Cpd. No. | Structure | Chemical Name | ESI-MS (M + H)+ (m/z) |
|---|---|---|---|
| 46 | 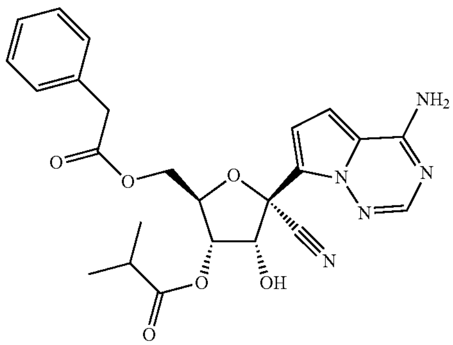 [SMILES: CC(C)C(=O)O[C@H]1[C@@H](O)[C@](C#N)(c2ccc3c(N)ncnn23)O[C@@H]1COC(=O)Cc1ccccc1] | (2R,3S,4R,5R)-5-(4-aminopyrrolo[2,1-f][1,2,4]triazin-7-yl)-5-cyano-4-hydroxy-2-((2-phenylacetoxy)methyl)tetrahydrofuran-3-yl isobutyrate | 480.1 |
| 47 | 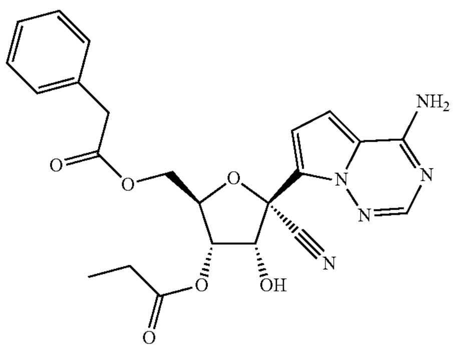 [SMILES: CCC(=O)O[C@H]1[C@@H](O)[C@](C#N)(c2ccc3c(N)ncnn23)O[C@@H]1COC(=O)Cc1ccccc1] | (2R,3S,4R,5R)-5-(4-aminopyrrolo[2,1-f][1,2,4]triazin-7-yl)-5-cyano-4-hydroxy-2-((2-phenylacetoxy)methyl)tetrahydrofuran-3-yl propionate | 466.2 |
| 48 | 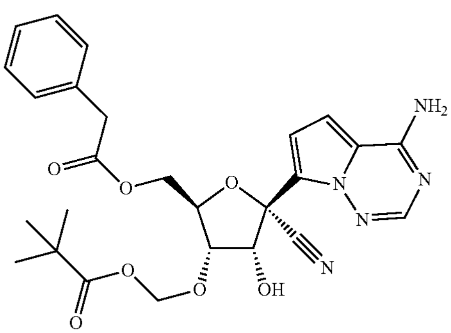 [SMILES: CC(C)(C)C(=O)OCO[C@H]1[C@@H](O)[C@](C#N)(c2ccc3c(N)ncnn23)O[C@@H]1COC(=O)Cc1ccccc1] | (((2R,3S,4R,5R)-5-(4-aminopyrrolo[2,1-f][1,2,4]triazin-7-yl)-5-cyano-4-hydroxy-2-((2-phenylacetoxy)methyl)tetrahydrofuran-3-yl)oxy)methyl pivalate | 524.1 |
| 49 | 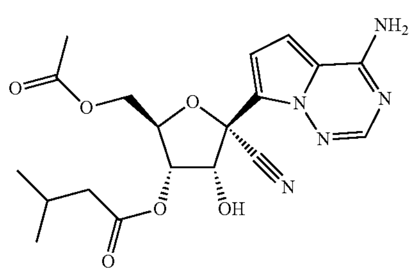 [SMILES: CC(=O)OC[C@H]1O[C@@](C#N)(c2ccc3c(N)ncnn23)[C@H](O)[C@@H]1OC(=O)CC(C)C] | (2R,3S,4R,5R)-2-(acetoxymethyl)-5-(4-aminopyrrolo[2,1-f][1,2,4]triazin-7-yl)-5-cyano-4-hydroxytetrahydrofuran-3-yl 3-methylbutanoate | 418.1 |

TABLE 1-continued

Exemplary compounds

| Cpd. No. | Structure | Chemical Name | ESI-MS (M + H)+ (m/z) |
|---|---|---|---|
| 50 | 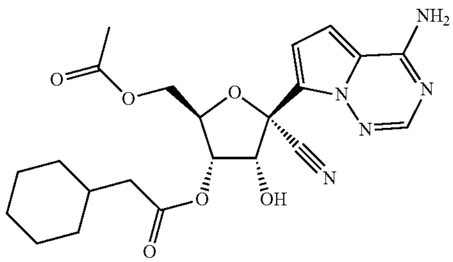 [SMILES: CC(=O)OC[C@H]1O[C@@](C#N)(c2ccc3c(N)ncnn23)[C@H](O)[C@@H]1OC(=O)CC1CCCCC1] | (2R,3S,4R,5R)-2-(acetoxymethyl)-5-(4-aminopyrrolo[2,1-f][1,2,4]triazin-7-yl)-5-cyano-4-hydroxytetrahydrofuran-3-yl 2-cyclohexylacetate | 458.1 |
| 51 | 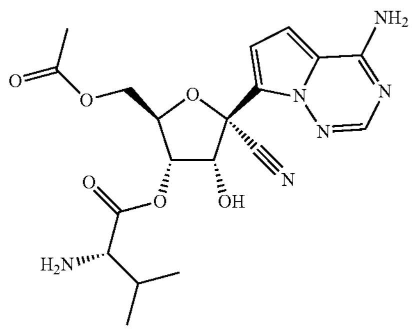 [SMILES: CC(=O)OC[C@H]1O[C@@](C#N)(c2ccc3c(N)ncnn23)[C@H](O)[C@@H]1OC(=O)[C@@H](N)C(C)C] | (2R,3S,4R,5R)-2-(acetoxymethyl)-5-(4-aminopyrrolo[2,1-f][1,2,4]triazin-7-yl)-5-cyano-4-hydroxytetrahydrofuran-3-yl L-valinate | 433.3 |
| 52 | 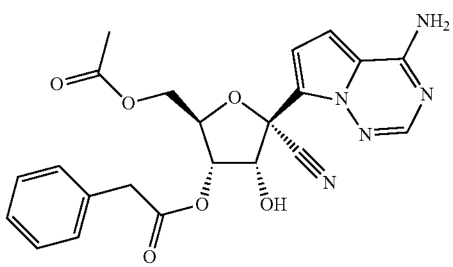 [SMILES: CC(=O)OC[C@H]1O[C@@](C#N)(c2ccc3c(N)ncnn23)[C@H](O)[C@@H]1OC(=O)Cc1ccccc1] | (2R,3S,4R,5R)-2-(acetoxymethyl)-5-(4-aminopyrrolo[2,1-f][1,2,4]triazin-7-yl)-5-cyano-4-hydroxytetrahydrofuran-3-yl 2-phenylacetate | 452.2 |
| 53 | 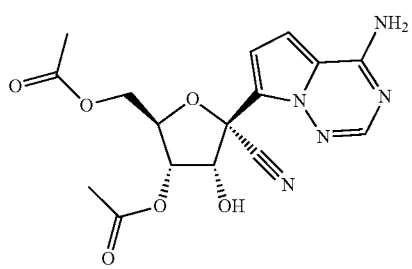 [SMILES: CC(=O)OC[C@H]1O[C@@](C#N)(c2ccc3c(N)ncnn23)[C@H](O)[C@@H]1OC(C)=O] | ((2R,3S,4R,5R)-3-acetoxy-5-(4-aminopyrrolo[2,1-f][1,2,4]triazin-7-yl)-5-cyano-4-hydroxytetrahydrofuran-2-yl)methyl acetate | 376.0 |
| 54 | 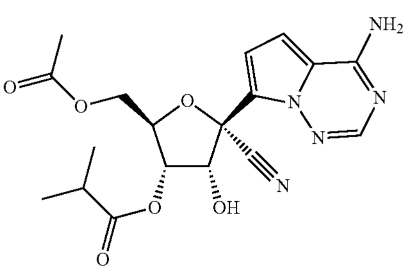 [SMILES: CC(=O)OC[C@H]1O[C@@](C#N)(c2ccc3c(N)ncnn23)[C@H](O)[C@@H]1OC(=O)C(C)C] | (2R,3S,4R,5R)-2-(acetoxymethyl)-5-(4-aminopyrrolo[2,1-f][1,2,4]triazin-7-yl)-5-cyano-4-hydroxytetrahydrofuran-3-yl isobutyrate | 404.2 |

TABLE 1-continued

Exemplary compounds

| Cpd. No. | Structure | Chemical Name | ESI-MS (M + H)+ (m/z) |
|---|---|---|---|
| 55 | 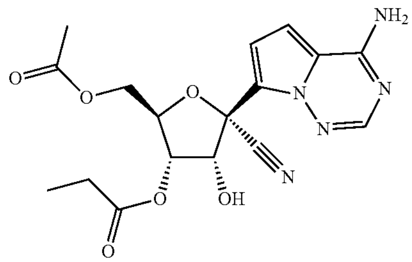 [SMILES: CCC(=O)O[C@H]1[C@@H](O)[C@](C#N)(c2ccc3c(N)ncnn23)O[C@@H]1COC(C)=O] | (2R,3S,4R,5R)-2-(acetoxymethyl)-5-(4-aminopyrrolo[2,1-f][1,2,4]triazin-7-yl)-5-cyano-4-hydroxytetrahydrofuran-3-yl propionate | 390.1 |
| 56 | 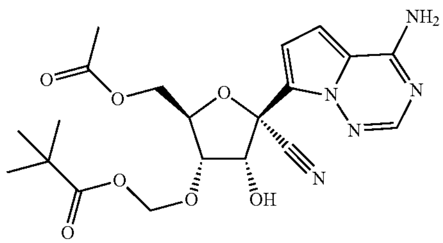 [SMILES: CC(=O)OC[C@H]1O[C@@](C#N)(c2ccc3c(N)ncnn23)[C@H](O)[C@@H]1OCOC(=O)C(C)(C)C] | (((2R,3S,4R,5R)-2-(acetoxymethyl)-5-(4-aminopyrrolo[2,1-f][1,2,4]triazin-7-yl)-5-cyano-4-hydroxytetrahydrofuran-3-yl)oxy)methyl pivalate | 448.1 |
| 57 | 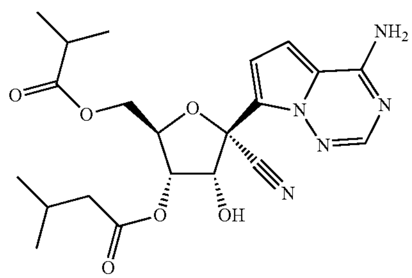 [SMILES: CC(C)CC(=O)O[C@H]1[C@@H](O)[C@](C#N)(c2ccc3c(N)ncnn23)O[C@@H]1COC(=O)C(C)C] | (2R,3S,4R,5R)-5-(4-aminopyrrolo[2,1-f][1,2,4]triazin-7-yl)-5-cyano-4-hydroxy-2-((isobutyryloxy)methyl)tetrahydrofuran-3-yl 3-methylbutanoate | 446.2 |
| 58 | 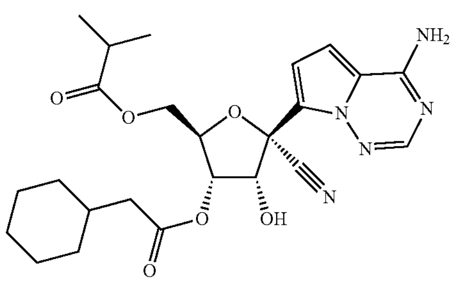 [SMILES: CC(C)C(=O)OC[C@H]1O[C@@](C#N)(c2ccc3c(N)ncnn23)[C@H](O)[C@@H]1OC(=O)CC1CCCCC1] | ((2R,3S,4R,5R)-5-(4-aminopyrrolo[2,1-f][1,2,4]triazin-7-yl)-5-cyano-3-(2-cyclohexylacetoxy)-4-hydroxytetrahydrofuran-2-yl)methyl isobutyrate | 486.2 |
| 59 | 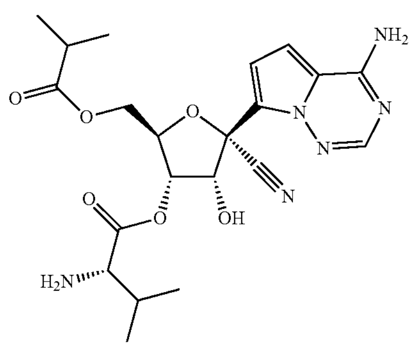 [SMILES: CC(C)C(=O)OC[C@H]1O[C@@](C#N)(c2ccc3c(N)ncnn23)[C@H](O)[C@@H]1OC(=O)[C@@H](N)C(C)C] | (2R,3S,4R,5R)-5-(4-aminopyrrolo[2,1-f][1,2,4]triazin-7-yl)-5-cyano-4-hydroxy-2-((isobutyryloxy)methyl)tetrahydrofuran-3-yl L-valinate | 461.3 |

TABLE 1-continued

Exemplary compounds

| Cpd. No. | Structure | Chemical Name | ESI-MS (M + H)+ (m/z) |
|---|---|---|---|
| 60 | 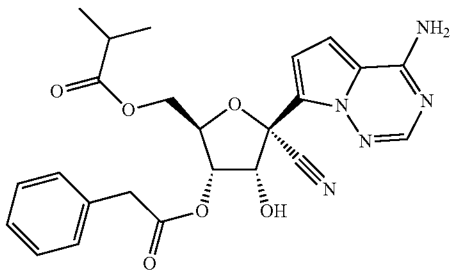 [SMILES: CC(C)C(=O)OC[C@H]1O[C@@](C#N)(c2ccc3c(N)ncnn23)[C@H](O)[C@@H]1OC(=O)Cc1ccccc1] | ((2R,3S,4R,5R)-5-(4-aminopyrrolo[2,1-f][1,2,4]triazin-7-yl)-5-cyano-4-hydroxy-3-(2-phenylacetoxy)tetrahydrofuran-2-yl)methyl isobutyrate | 480.1 |
| 61 | 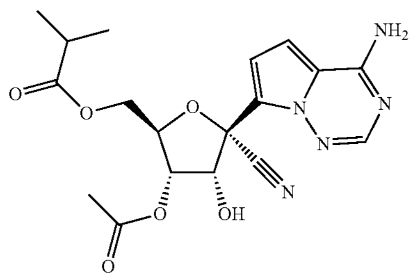 [SMILES: CC(=O)O[C@H]1[C@@H](O)[C@](C#N)(c2ccc3c(N)ncnn23)O[C@@H]1COC(=O)C(C)C] | ((2R,3S,4R,5R)-3-acetoxy-5-(4-aminopyrrolo[2,1-f][1,2,4]triazin-7-yl)-5-cyano-4-hydroxytetrahydrofuran-2-yl)methyl isobutyrate | 404.0 |
| 62 | 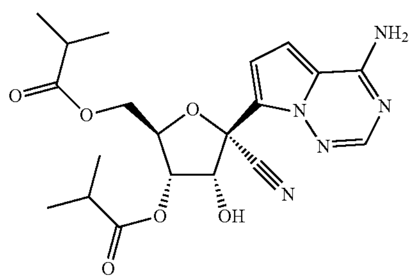 [SMILES: CC(C)C(=O)OC[C@H]1O[C@@](C#N)(c2ccc3c(N)ncnn23)[C@H](O)[C@@H]1OC(=O)C(C)C] | (2R,3S,4R,5R)-5-(4-aminopyrrolo[2,1-f][1,2,4]triazin-7-yl)-5-cyano-4-hydroxy-2-((isobutyryloxy)methyl)tetrahydrofuran-3-yl isobutyrate | 432.1 |
| 63 | 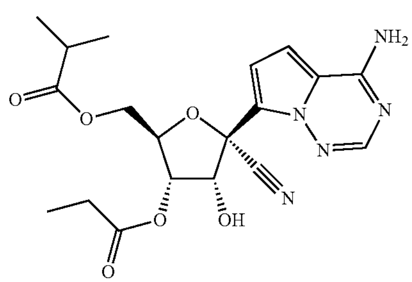 [SMILES: CCC(=O)O[C@H]1[C@@H](O)[C@](C#N)(c2ccc3c(N)ncnn23)O[C@@H]1COC(=O)C(C)C] | ((2R,3S,4R,5R)-5-(4-aminopyrrolo[2,1-f][1,2,4]triazin-7-yl)-5-cyano-4-hydroxy-3-(propionyloxy)tetrahydrofuran-2-yl)methyl isobutyrate | 418.1 |
| 64 | 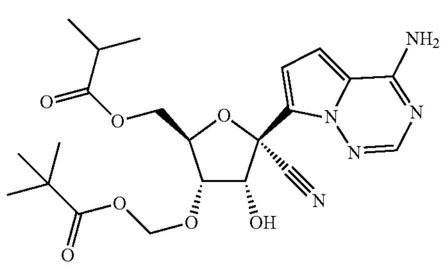 [SMILES: CC(C)C(=O)OC[C@H]1O[C@@](C#N)(c2ccc3c(N)ncnn23)[C@H](O)[C@@H]1OCOC(=O)C(C)(C)C] | (((2R,3S,4R,5R)-5-(4-aminopyrrolo[2,1-f][1,2,4]triazin-7-yl)-5-cyano-4-hydroxy-2-((isobutyryloxy)methyl)tetrahydrofuran-3-yl)oxy)methyl pivalate | 476.3 |

TABLE 1-continued

Exemplary compounds

| Cpd. No. | Structure | Chemical Name | ESI-MS (M + H)+ (m/z) |
|---|---|---|---|
| 65 | 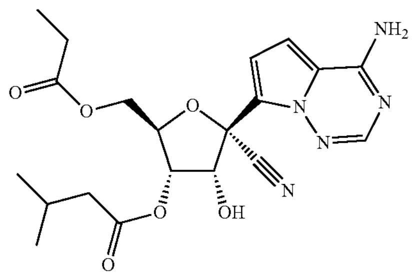 [SMILES: CCC(=O)OC[C@H]1O[C@@](C#N)(c2ccc3c(N)ncnn23)[C@H](O)[C@@H]1OC(=O)CC(C)C] | (2R,3S,4R,5R)-5-(4-aminopyrrolo[2,1-f][1,2,4]triazin-7-yl)-5-cyano-4-hydroxy-2-((propionyloxy)methyl)tetrahydrofuran-3-yl 3-methylbutanoate | 432.1 |
| 66 | 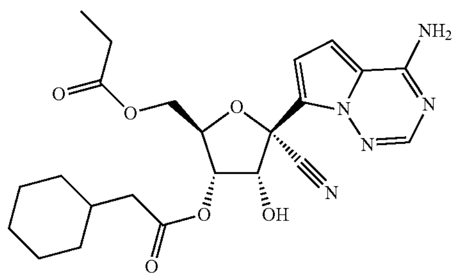 [SMILES: CCC(=O)OC[C@H]1O[C@@](C#N)(c2ccc3c(N)ncnn23)[C@H](O)[C@@H]1OC(=O)CC1CCCCC1] | ((2R,3S,4R,5R)-5-(4-aminopyrrolo[2,1-f][1,2,4]triazin-7-yl)-5-cyano-3-(2-cyclohexylacetoxy)-4-hydroxytetrahydrofuran-2-yl)methyl propionate | 472.2 |
| 67 | 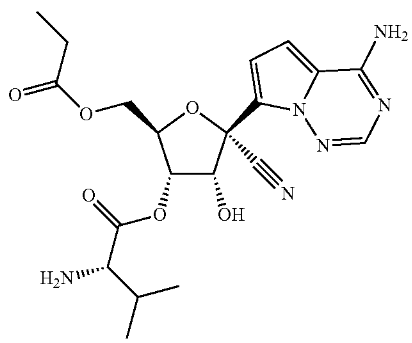 [SMILES: CCC(=O)OC[C@H]1O[C@@](C#N)(c2ccc3c(N)ncnn23)[C@H](O)[C@@H]1OC(=O)[C@@H](N)C(C)C] | (2R,3S,4R,5R)-5-(4-aminopyrrolo[2,1-f][1,2,4]triazin-7-yl)-5-cyano-4-hydroxy-2-((propionyloxy)methyl)tetrahydrofuran-3-yl L-valinate | 447.3 |
| 68 | 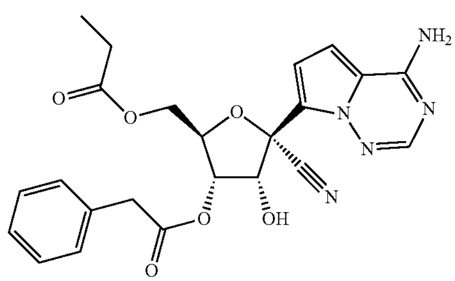 [SMILES: CCC(=O)OC[C@H]1O[C@@](C#N)(c2ccc3c(N)ncnn23)[C@H](O)[C@@H]1OC(=O)Cc1ccccc1] | ((2R,3S,4R,5R)-5-(4-aminopyrrolo[2,1-f][1,2,4]triazin-7-yl)-5-cyano-4-hydroxy-3-(2-phenylacetoxy)tetrahydrofuran-2-yl)methyl propionate | 466.1 |
| 69 | 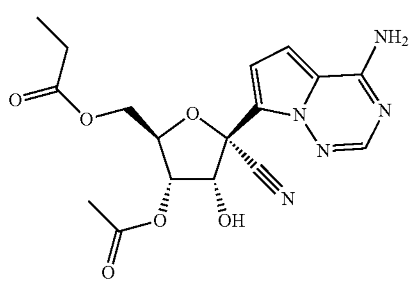 [SMILES: CCC(=O)OC[C@H]1O[C@@](C#N)(c2ccc3c(N)ncnn23)[C@H](O)[C@@H]1OC(C)=O] | ((2R,3S,4R,5R)-3-acetoxy-5-(4-aminopyrrolo[2,1-f][1,2,4]triazin-7-yl)-5-cyano-4-hydroxytetrahydrofuran-2-yl)methyl propionate | 390.1 |

TABLE 1-continued

Exemplary compounds

| Cpd. No. | Structure | Chemical Name | ESI-MS (M + H)+ (m/z) |
|---|---|---|---|
| 70 | 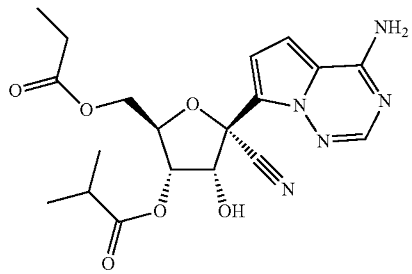 [SMILES: CCC(=O)OC[C@H]1O[C@@](C#N)(c2ccc3c(N)ncnn23)[C@H](O)[C@@H]1OC(=O)C(C)C] | (2R,3S,4R,5R)-5-(4-aminopyrrolo[2,1-f][1,2,4]triazin-7-yl)-5-cyano-4-hydroxy-2-((propionyloxy)methyl)tetrahydrofuran-3-yl isobutyrate | 418.1 |
| 71 | 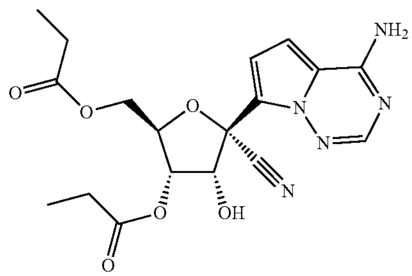 [SMILES: CCC(=O)OC[C@H]1O[C@@](C#N)(c2ccc3c(N)ncnn23)[C@H](O)[C@@H]1OC(=O)CC] | (2R,3S,4R,5R)-5-(4-aminopyrrolo[2,1-f][1,2,4]triazin-7-yl)-5-cyano-4-hydroxy-2-((propionyloxy)methyl)tetrahydrofuran-3-yl propionate | 404.0 |
| 72 | 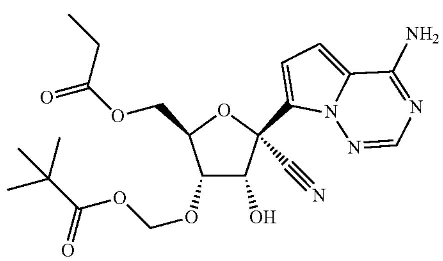 [SMILES: CCC(=O)OC[C@H]1O[C@@](C#N)(c2ccc3c(N)ncnn23)[C@H](O)[C@@H]1OCOC(=O)C(C)(C)C] | (((2R,3S,4R,5R)-5-(4-aminopyrrolo[2,1-f][1,2,4]triazin-7-yl)-5-cyano-4-hydroxy-2-((propionyloxy)methyl)tetrahydrofuran-3-yl)oxy)methyl pivalate | 462.1 |
| 73 | 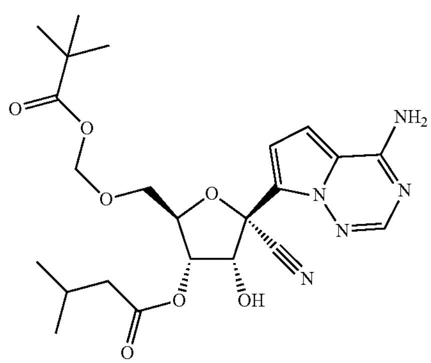 [SMILES: CC(C)CC(=O)O[C@H]1[C@@H](O)[C@](C#N)(c2ccc3c(N)ncnn23)O[C@@H]1COCOC(=O)C(C)(C)C] | (2R,3S,4R,5R)-5-(4-aminopyrrolo[2,1-f][1,2,4]triazin-7-yl)-5-cyano-4-hydroxy-2-(((pivaloyloxy)methoxy)methyl)tetrahydrofuran-3-yl 3-methylbutanoate | |
| 74 | 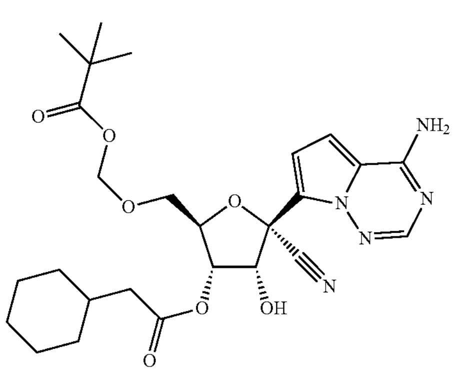 [SMILES: CC(C)(C)C(=O)OCOC[C@H]1O[C@@](C#N)(c2ccc3c(N)ncnn23)[C@H](O)[C@@H]1OC(=O)CC1CCCCC1] | (((2R,3S,4R,5R)-5-(4-aminopyrrolo[2,1-f][1,2,4]triazin-7-yl)-5-cyano-3-(2-cyclohexylacetoxy)-4-hydroxytetrahydrofuran-2-yl)methoxy)methyl pivalate | |

TABLE 1-continued

Exemplary compounds

| Cpd. No. | Structure | Chemical Name | ESI-MS (M + H)+ (m/z) |
|---|---|---|---|
| 75 | 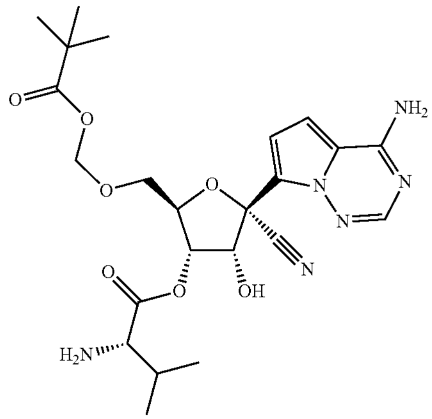 [SMILES: CC(C)[C@H](N)C(=O)O[C@H]1[C@@H](O)[C@](C#N)(c2ccc3c(N)ncnn23)O[C@@H]1COCOC(=O)C(C)(C)C] | (2R,3S,4R,5R)-5-(4-aminopyrrolo[2,1-f][1,2,4]triazin-7-yl)-5-cyano-4-hydroxy-2-(((pivaloyloxy)methoxy)methyl)tetrahydrofuran-3-yl L-valinate | |
| 76 | 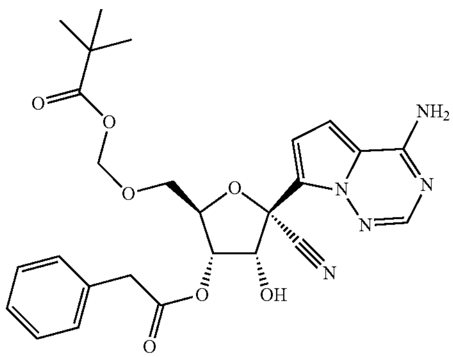 [SMILES: CC(C)(C)C(=O)OCOC[C@H]1O[C@@](C#N)(c2ccc3c(N)ncnn23)[C@H](O)[C@@H]1OC(=O)Cc1ccccc1] | (((2R,3S,4R,5R)-5-(4-aminopyrrolo[2,1-f][1,2,4]triazin-7-yl)-5-cyano-4-hydroxy-3-(2-phenylacetoxy)tetrahydrofuran-2-yl)methoxy)methyl pivalate | |
| 77 | 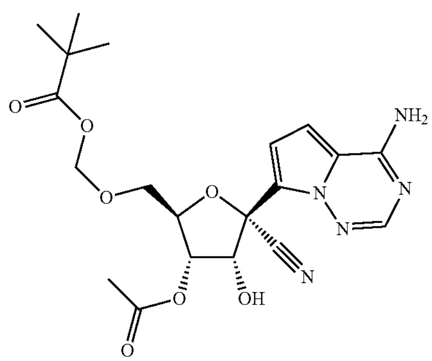 [SMILES: CC(=O)O[C@H]1[C@@H](O)[C@](C#N)(c2ccc3c(N)ncnn23)O[C@@H]1COCOC(=O)C(C)(C)C] | (((2R,3S,4R,5R)-3-acetoxy-5-(4-aminopyrrolo[2,1-f][1,2,4]triazin-7-yl)-5-cyano-4-hydroxytetrahydrofuran-2-yl)methoxy)methyl pivalate | |
| 78 | 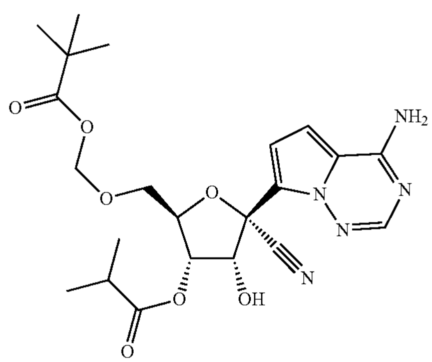 [SMILES: CC(C)C(=O)O[C@H]1[C@@H](O)[C@](C#N)(c2ccc3c(N)ncnn23)O[C@@H]1COCOC(=O)C(C)(C)C] | (((2R,3S,4R,5R)-5-(4-aminopyrrolo[2,1-f][1,2,4]triazin-7-yl)-5-cyano-4-hydroxy-3-(isobutyryloxy)tetrahydrofuran-2-yl)methoxy)methyl pivalate | |

TABLE 1-continued

Exemplary compounds

| Cpd. No. | Structure | Chemical Name | ESI-MS (M + H)+ (m/z) |
|---|---|---|---|
| 79 | 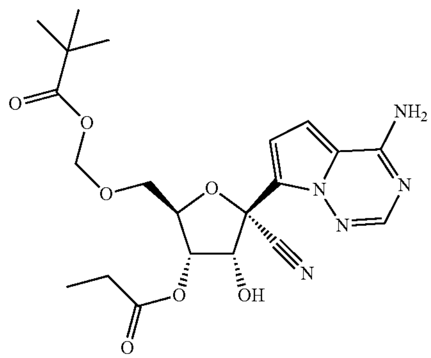 [SMILES: CCC(=O)O[C@H]1[C@@H](O)[C@](C#N)(c2ccc3c(N)ncnn23)O[C@@H]1COCOC(=O)C(C)(C)C] | (((2R,3S,4R,5R)-5-(4-aminopyrrolo[2,1-f][1,2,4]triazin-7-yl)-5-cyano-4-hydroxy-3-(propionyloxy)tetrahydrofuran-2-yl)methoxy)methyl pivalate | |
| 80 | 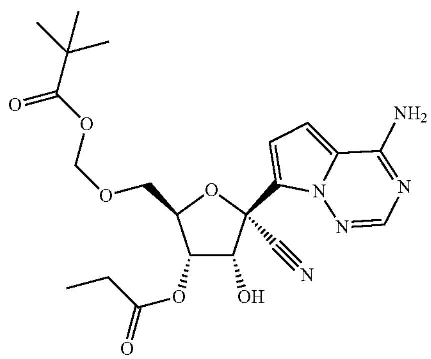 [SMILES: CCC(=O)O[C@H]1[C@@H](O)[C@](C#N)(c2ccc3c(N)ncnn23)O[C@@H]1COCOC(=O)C(C)(C)C] | (((2R,3S,4R,5R)-5-(4-aminopyrrolo[2,1-f][1,2,4]triazin-7-yl)-5-cyano-4-hydroxy-2-(((pivaloyloxy)methoxy)methyl)tetrahydrofuran-3-yl)oxy)methyl pivalate | |
| 81 | 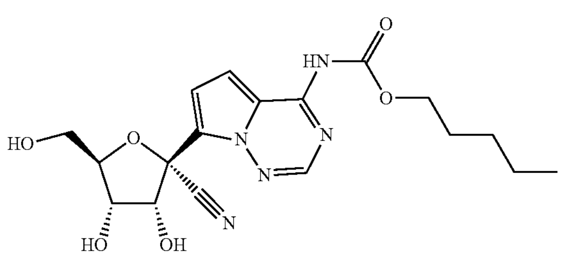 [SMILES: CCCCCOC(=O)Nc1ncnn2c([C@]3(C#N)O[C@H](CO)[C@@H](O)[C@H]3O)ccc12] | pentyl (7-((2R,3R,4S,5R)-2-cyano-3,4-dihydroxy-5-(hydroxymethyl)tetrahydrofuran-2-yl)pyrrolo[2,1-f][1,2,4]triazin-4-yl)carbamate | 406.0 |
| 82 | 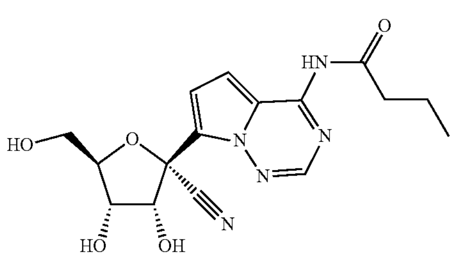 [SMILES: CCCC(=O)Nc1ncnn2c([C@]3(C#N)O[C@H](CO)[C@@H](O)[C@H]3O)ccc12] | N-(7-((2R,3R,4S,5R)-2-cyano-3,4-dihydroxy-5-(hydroxymethyl)tetrahydrofuran-2-yl)pyrrolo[2,1-f][1,2,4]triazin-4-yl)butyramide | |
| 83 | 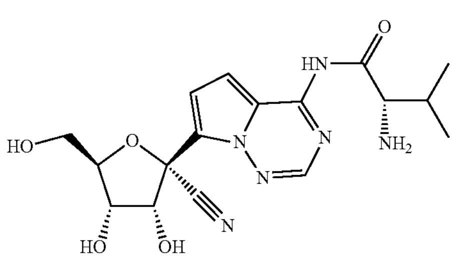 [SMILES: CC(C)[C@H](N)C(=O)Nc1ncnn2c([C@]3(C#N)O[C@H](CO)[C@@H](O)[C@H]3O)ccc12] | (S)-2-amino-N-(7-((2R,3R,4S,5R)-2-cyano-3,4-dihydroxy-5-(hydroxymethyl)tetrahydrofuran-2-yl)pyrrolo[2,1-f][1,2,4]triazin-4-yl)-3-methylbutanamide | 391.2 |

TABLE 1-continued

Exemplary compounds

| Cpd. No. | Structure | Chemical Name | ESI-MS (M + H)+ (m/z) |
|---|---|---|---|
| 84 | 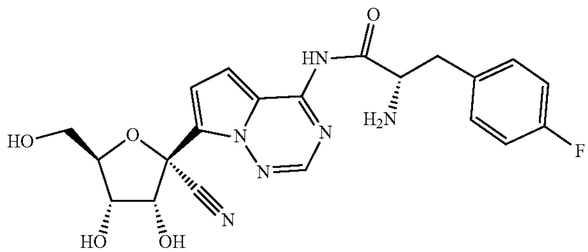 [SMILES: N#C[C@@]1(c2ccc3c(NC(=O)[C@@H](N)Cc4ccc(F)cc4)ncnn23)O[C@H](CO)[C@@H](O)[C@H]1O] | (S)-2-amino-N-(7-((2R,3R,4S,5R)-2-cyano-3,4-dihydroxy-5-(hydroxymethyl)tetrahydrofuran-2-yl)pyrrolo[2,1-f][1,2,4]triazin-4-yl)-3-(4-fluorophenyl)propanamide | 457.1 |
| 85 | 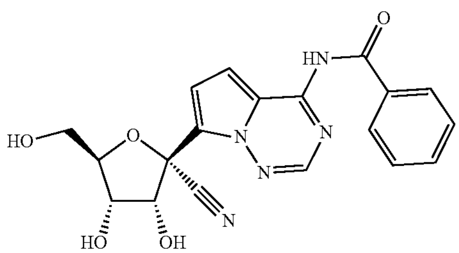 [SMILES: N#C[C@@]1(c2ccc3c(NC(=O)c4ccccc4)ncnn23)O[C@H](CO)[C@@H](O)[C@H]1O] | N-(7-((2R,3R,4S,5R)-2-cyano-3,4-dihydroxy-5-(hydroxymethyl)tetrahydrofuran-2-yl)pyrrolo[2,1-f][1,2,4]triazin-4-yl)benzamide | 396.0 |
| 86 | 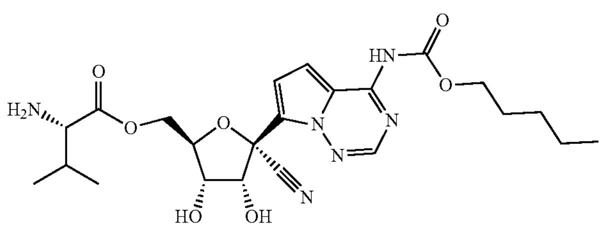 [SMILES: CCCCCOC(=O)Nc1ncnn2c([C@]3(C#N)O[C@H](COC(=O)[C@@H](N)C(C)C)[C@@H](O)[C@H]3O)ccc12] | ((2R,3S,4R,5R)-5-cyano-3,4-dihydroxy-5-(4-(((pentyloxy)carbonyl)amino)pyrrolo[2,1-f][1,2,4]triazin-7-yl)tetrahydrofuran-2-yl)methyl L-valinate | 505.2 |
| 87 | 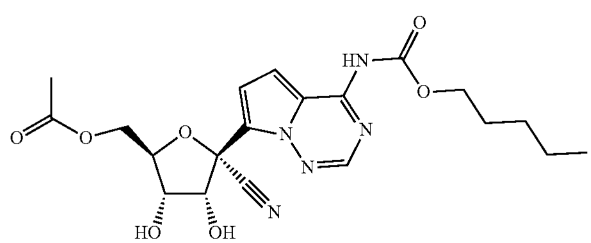 [SMILES: CCCCCOC(=O)Nc1ncnn2c([C@]3(C#N)O[C@H](COC(C)=O)[C@@H](O)[C@H]3O)ccc12] | ((2R,3S,4R,5R)-5-cyano-3,4-dihydroxy-5-(4-(((pentyloxy)carbonyl)amino)pyrrolo[2,1-f][1,2,4]triazin-7-yl)tetrahydrofuran-2-yl)methylacetate | 448.3 |
| 88 | 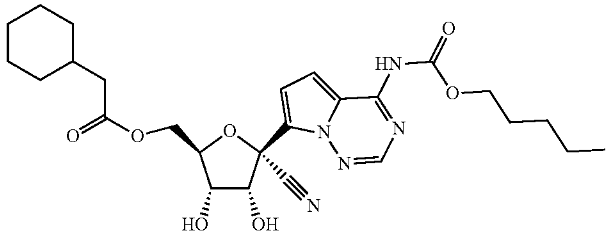 [SMILES: CCCCCOC(=O)Nc1ncnn2c([C@]3(C#N)O[C@H](COC(=O)CC4CCCCC4)[C@@H](O)[C@H]3O)ccc12] | ((2R,3S,4R,5R)-5-cyano-3,4-dihydroxy-5-(4-(((pentyloxy)carbonyl)amino)pyrrolo[2,1-f][1,2,4]triazin-7-yl)tetrahydrofuran-2-yl)methyl 2-cyclohexylacetate | 530.2 |
| 89 | 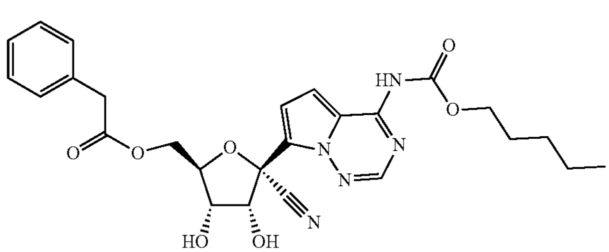 [SMILES: CCCCCOC(=O)Nc1ncnn2c([C@]3(C#N)O[C@H](COC(=O)Cc4ccccc4)[C@@H](O)[C@H]3O)ccc12] | ((2R,3S,4R,5R)-5-cyano-3,4-dihydroxy-5-(4-(((pentyloxy)carbonyl)amino)pyrrolo[2,1-f][1,2,4]triazin-7-yl)tetrahydrofuran-2-yl)methyl 2-phenylacetate | 524.2 |

TABLE 1-continued

Exemplary compounds

| Cpd. No. | Structure | Chemical Name | ESI-MS (M + H)+ (m/z) |
|---|---|---|---|
| 90 | 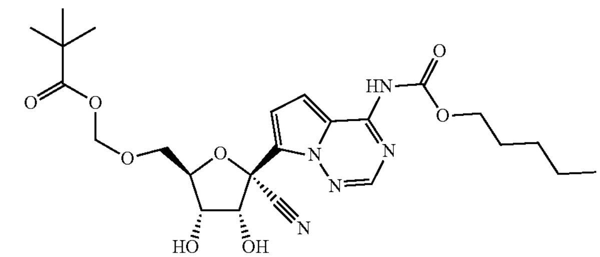 [SMILES: CCCCCOC(=O)Nc1ncnn2c([C@]3(C#N)O[C@H](COCOC(=O)C(C)(C)C)[C@@H](O)[C@H]3O)ccc12] | (((2R,3S,4R,5R)-5-cyano-3,4-dihydroxy-5-(4-(((pentyloxy)carbonyl)amino)pyrrolo[2,1-f][1,2,4]triazin-7-yl)tetrahydrofuran-2-yl)methoxy)methyl pivalate | |
| 91 | 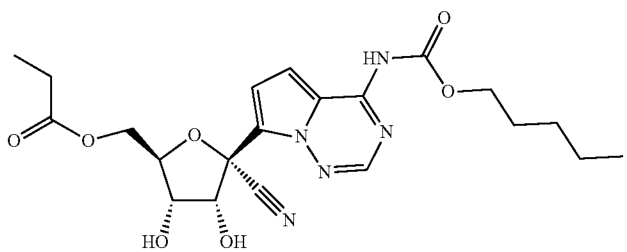 [SMILES: CCCCCOC(=O)Nc1ncnn2c([C@]3(C#N)O[C@H](COC(=O)CC)[C@@H](O)[C@H]3O)ccc12] | ((2R,3S,4R,5R)-5-cyano-3,4-dihydroxy-5-(4-(((pentyloxy)carbonyl)amino)pyrrolo[2,1-f][1,2,4]triazin-7-yl)tetrahydrofuran-2-yl)methyl propionate | 462.2 |
| 92 | 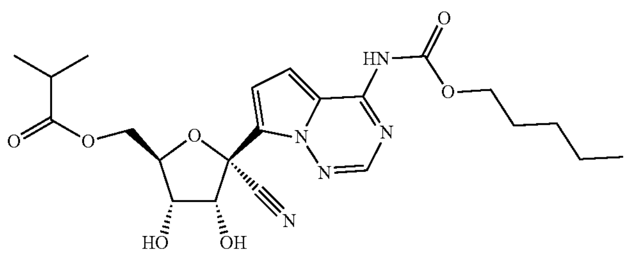 [SMILES: CCCCCOC(=O)Nc1ncnn2c([C@]3(C#N)O[C@H](COC(=O)C(C)C)[C@@H](O)[C@H]3O)ccc12] | ((2R,3S,4R,5R)-5-cyano-3,4-dihydroxy-5-(4-(((pentyloxy)carbonyl)amino)pyrrolo[2,1-f][1,2,4]triazin-7-yl)tetrahydrofuran-2-yl)methyl isobutyrate | 476.1 |
| 93 | 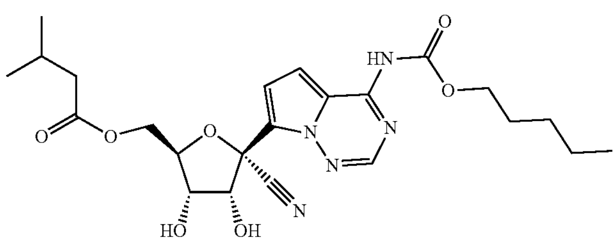 [SMILES: CCCCCOC(=O)Nc1ncnn2c([C@]3(C#N)O[C@H](COC(=O)CC(C)C)[C@@H](O)[C@H]3O)ccc12] | ((2R,3S,4R,5R)-5-cyano-3,4-dihydroxy-5-(4-(((pentyloxy)carbonyl)amino)pyrrolo[2,1-f][1,2,4]triazin-7-yl)tetrahydrofuran-2-yl)methyl 3-methylbutanoate | 490.3 |
| 94 | 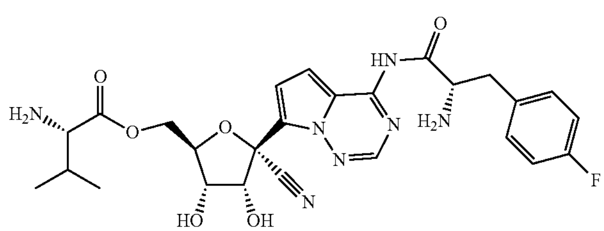 [SMILES: CC(C)[C@H](N)C(=O)OC[C@H]1O[C@@](C#N)(c2ccc3c(NC(=O)[C@@H](N)Cc4ccc(F)cc4)ncnn23)[C@H](O)[C@@H]1O] | ((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methyl L-valinate | 578.2 (M + Na)+ |
| 95 | 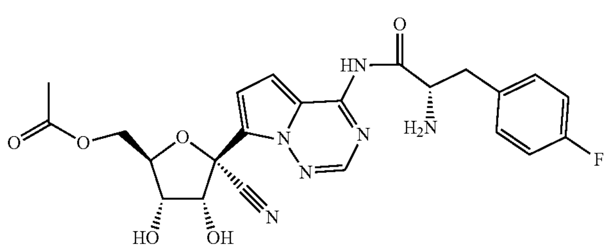 [SMILES: CC(=O)OC[C@H]1O[C@@](C#N)(c2ccc3c(NC(=O)[C@@H](N)Cc4ccc(F)cc4)ncnn23)[C@H](O)[C@@H]1O] | ((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methyl acetate | 499.1 |

TABLE 1-continued

Exemplary compounds

| Cpd. No. | Structure | Chemical Name | ESI-MS (M + H)+ (m/z) |
|---|---|---|---|
| 96 | 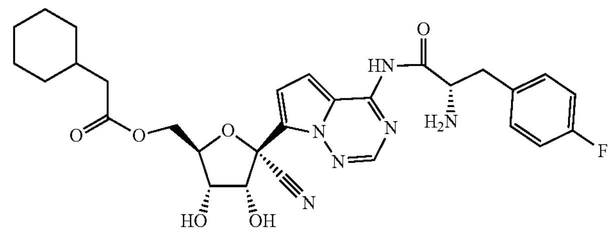 [SMILES: N#C[C@@]1(c2ccc3c(NC(=O)[C@@H](N)Cc4ccc(F)cc4)ncnn23)O[C@H](COC(=O)CC2CCCCC2)[C@@H](O)[C@H]1O] | ((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methyl 2-cyclohexylacetate | 581.2 |
| 97 | 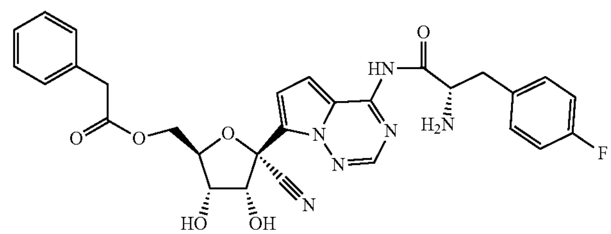 [SMILES: N#C[C@@]1(c2ccc3c(NC(=O)[C@@H](N)Cc4ccc(F)cc4)ncnn23)O[C@H](COC(=O)Cc2ccccc2)[C@@H](O)[C@H]1O] | ((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methyl 2-phenylacetate | 575.1 |
| 98 | 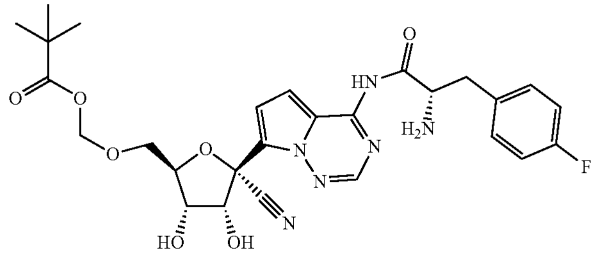 [SMILES: CC(C)(C)C(=O)OCOC[C@H]1O[C@@](C#N)(c2ccc3c(NC(=O)[C@@H](N)Cc4ccc(F)cc4)ncnn23)[C@H](O)[C@@H]1O] | (((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methoxy)methyl pivalate | |
| 99 | 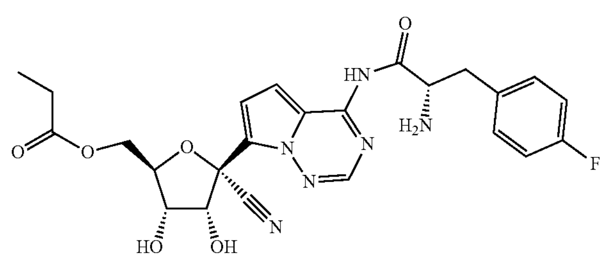 [SMILES: CCC(=O)OC[C@H]1O[C@@](C#N)(c2ccc3c(NC(=O)[C@@H](N)Cc4ccc(F)cc4)ncnn23)[C@H](O)[C@@H]1O] | ((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methyl propionate | 513.1 |
| 100 | 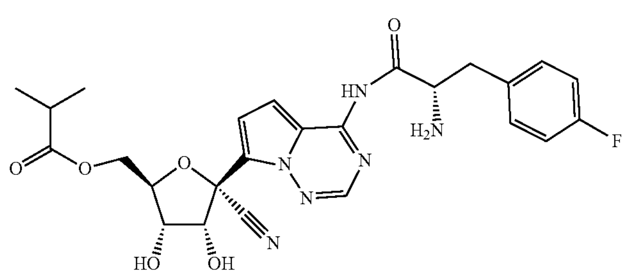 [SMILES: CC(C)C(=O)OC[C@H]1O[C@@](C#N)(c2ccc3c(NC(=O)[C@@H](N)Cc4ccc(F)cc4)ncnn23)[C@H](O)[C@@H]1O] | ((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methyl isobutyrate | 527.1 |
| 101 | 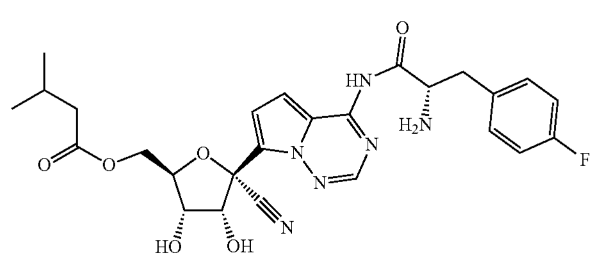 [SMILES: CC(C)CC(=O)OC[C@H]1O[C@@](C#N)(c2ccc3c(NC(=O)[C@@H](N)Cc4ccc(F)cc4)ncnn23)[C@H](O)[C@@H]1O] | ((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methyl 3-methylbutanoate | 541.1 |

TABLE 1-continued

Exemplary compounds

| Cpd. No. | Structure | Chemical Name | ESI-MS (M + H)+ (m/z) |
|---|---|---|---|
| 102 | 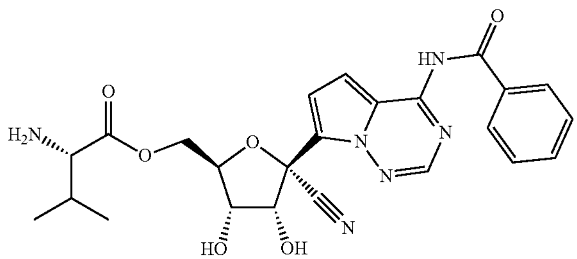 [SMILES: CC(C)[C@H](N)C(=O)OC[C@H]1O[C@@](C#N)(c2ccc3c(NC(=O)c4ccccc4)ncnn23)[C@H](O)[C@@H]1O] | ((2R,3S,4R,5R)-5-(4-benzamidopyrrolo[2,1-f][1,2,4]triazin-7-yl)-5-cyano-3,4-dihydroxytetrahydrofuran-2-yl)methyl L-valinate | 495.1 |
| 103 | 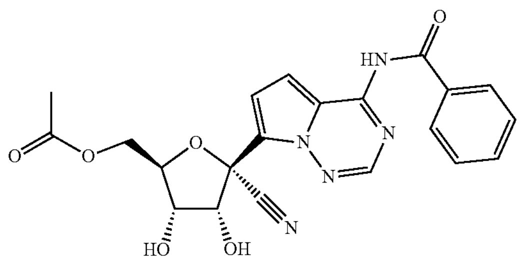 [SMILES: CC(=O)OC[C@H]1O[C@@](C#N)(c2ccc3c(NC(=O)c4ccccc4)ncnn23)[C@H](O)[C@@H]1O] | ((2R,3S,4R,5R)-5-(4-benzamidopyrrolo[2,1-f][1,2,4]triazin-7-yl)-5-cyano-3,4-dihydroxytetrahydrofuran-2-yl)methyl acetate | 438.2 |
| 104 | 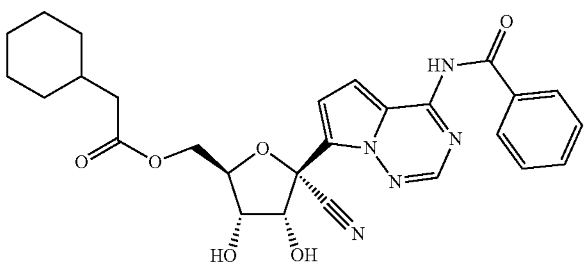 [SMILES: N#C[C@@]1(c2ccc3c(NC(=O)c4ccccc4)ncnn23)O[C@H](COC(=O)CC2CCCCC2)[C@@H](O)[C@H]1O] | ((2R,3S,4R,5R)-5-(4-benzamidopyrrolo[2,1-f][1,2,4]triazin-7-yl)-5-cyano-3,4-dihydroxytetrahydrofuran-2-yl)methyl 2-cyclohexylacetate | |
| 105 | 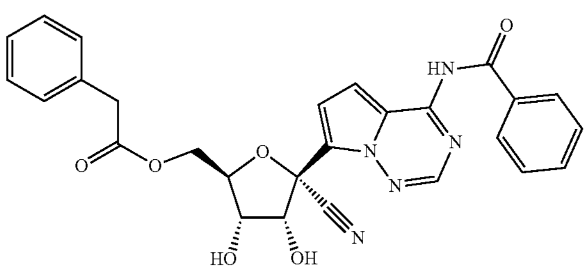 [SMILES: N#C[C@@]1(c2ccc3c(NC(=O)c4ccccc4)ncnn23)O[C@H](COC(=O)Cc2ccccc2)[C@@H](O)[C@H]1O] | ((2R,3S,4R,5R)-5-(4-benzamidopyrrolo[2,1-f][1,2,4]triazin-7-yl)-5-cyano-3,4-dihydroxytetrahydrofuran-2-yl)methyl 2-phenylacetate | 514.2 |
| 106 | 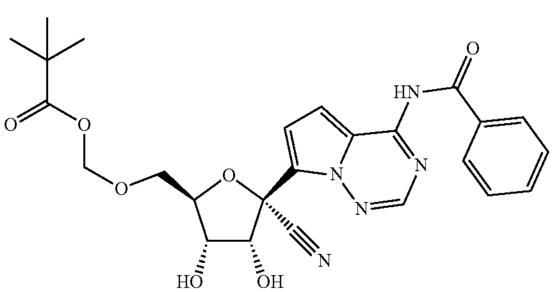 [SMILES: CC(C)(C)C(=O)OCOC[C@H]1O[C@@](C#N)(c2ccc3c(NC(=O)c4ccccc4)ncnn23)[C@H](O)[C@@H]1O] | (((2R,3S,4R,5R)-5-(4-benzamidopyrrolo[2,1-f][1,2,4]triazin-7-yl)-5-cyano-3,4-dihydroxytetrahydrofuran-2-yl)methoxy)methyl pivalate | |

TABLE 1-continued

Exemplary compounds

| Cpd. No. | Structure | Chemical Name | ESI-MS (M + H)+ (m/z) |
|---|---|---|---|
| 107 | 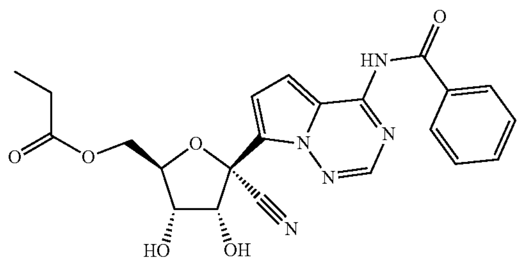 [SMILES: CCC(=O)OC[C@H]1O[C@@](C#N)(c2ccc3c(NC(=O)c4ccccc4)ncnn23)[C@H](O)[C@@H]1O] | ((2R,3S,4R,5R)-5-(4-benzamidopyrrolo[2,1-f][1,2,4]triazin-7-yl)-5-cyano-3,4-dihydroxytetrahydrofuran-2-yl)methyl propionate | 452.0 |
| 108 | 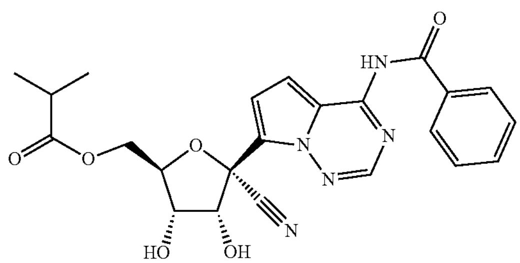 [SMILES: CC(C)C(=O)OC[C@H]1O[C@@](C#N)(c2ccc3c(NC(=O)c4ccccc4)ncnn23)[C@H](O)[C@@H]1O] | ((2R,3S,4R,5R)-5-(4-benzamidopyrrolo[2,1-f][1,2,4]triazin-7-yl)-5-cyano-3,4-dihydroxytetrahydrofuran-2-yl)methyl isobutyrate | 466.1 |
| 109 | 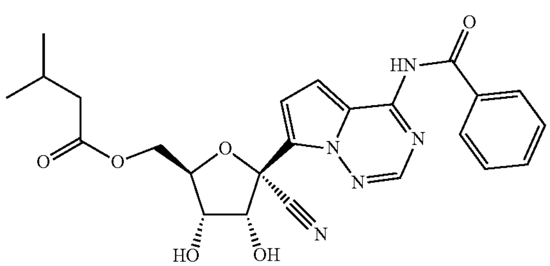 [SMILES: CC(C)CC(=O)OC[C@H]1O[C@@](C#N)(c2ccc3c(NC(=O)c4ccccc4)ncnn23)[C@H](O)[C@@H]1O] | ((2R,3S,4R,5R)-5-(4-benzamidopyrrolo[2,1-f][1,2,4]triazin-7-yl)-5-cyano-3,4-dihydroxytetrahydrofuran-2-yl)methyl 3-methylbutanoate | 480.1 |
| 110 | 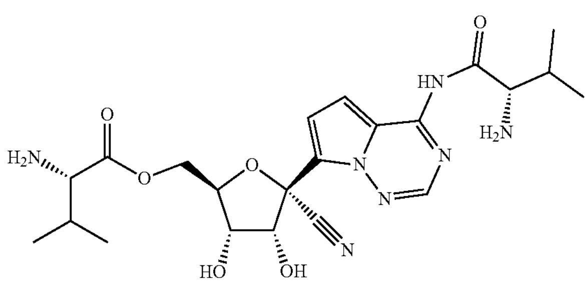 [SMILES: CC(C)[C@H](N)C(=O)Nc1ncnn2c([C@]3(C#N)O[C@H](COC(=O)[C@@H](N)C(C)C)[C@@H](O)[C@H]3O)ccc12] | ((2R,3S,4R,5R)-5-(4-((S)-2-amino-3-methylbutanamido)pyrrolo[2,1-f][1,2,4]triazin-7-yl)-5-cyano-3,4-dihydroxytetrahydrofuran-2-yl)methyl L-valinate | 490.2 |
| 111 | 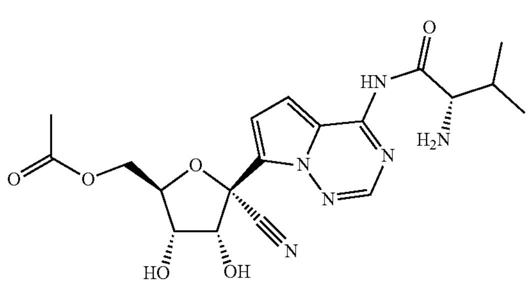 [SMILES: CC(=O)OC[C@H]1O[C@@](C#N)(c2ccc3c(NC(=O)[C@@H](N)C(C)C)ncnn23)[C@H](O)[C@@H]1O] | ((2R,3S,4R,5R)-5-(4-((S)-2-amino-3-methylbutanamido)pyrrolo[2,1-f][1,2,4]triazin-7-yl)-5-cyano-3,4-dihydroxytetrahydrofuran-2-yl)methyl acetate | |

TABLE 1-continued

Exemplary compounds

| Cpd. No. | Structure | Chemical Name | ESI-MS (M + H)+ (m/z) |
|---|---|---|---|
| 112 | 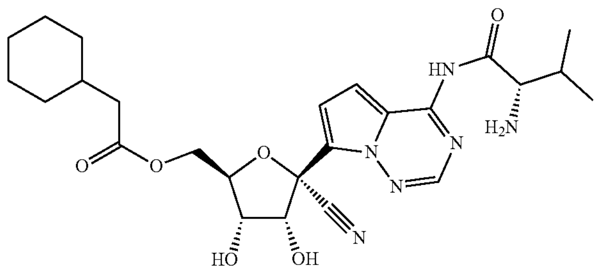 [SMILES: CC(C)[C@H](N)C(=O)Nc1ncnn2c([C@]3(C#N)O[C@H](COC(=O)CC4CCCCC4)[C@@H](O)[C@H]3O)ccc12] | ((2R,3S,4R,5R)-5-(4-((S)-2-amino-3-methylbutanamido)pyrrolo[2,1-f][1,2,4]triazin-7-yl)-5-cyano-3,4-dihydroxytetrahydrofuran-2-yl)methyl 2-cyclohexylacetate | 515.2 |
| 113 | 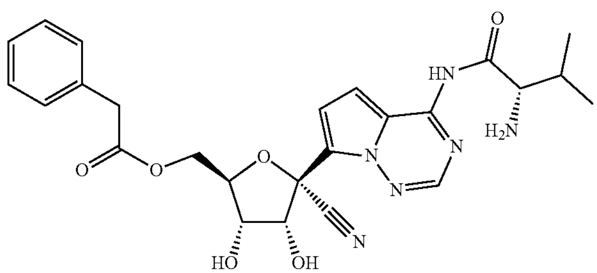 [SMILES: CC(C)[C@H](N)C(=O)Nc1ncnn2c([C@]3(C#N)O[C@H](COC(=O)Cc4ccccc4)[C@@H](O)[C@H]3O)ccc12] | ((2R,3S,4R,5R)-5-(4-((S)-2-amino-3-methylbutanamido)pyrrolo[2,1-f][1,2,4]triazin-7-yl)-5-cyano-3,4-dihydroxytetrahydrofuran-2-yl)methyl 2-phenylacetate | 509.1 |
| 114 | 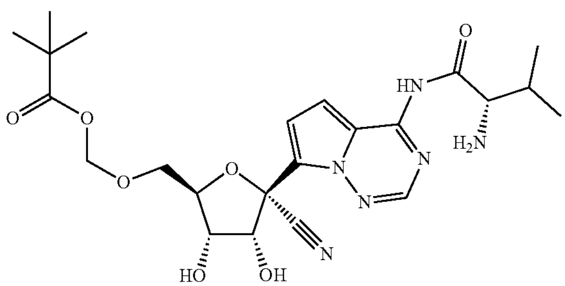 [SMILES: CC(C)[C@H](N)C(=O)Nc1ncnn2c([C@]3(C#N)O[C@H](COCOC(=O)C(C)(C)C)[C@@H](O)[C@H]3O)ccc12] | (((2R,3S,4R,5R)-5-(4-((S)-2-amino-3-methylbutanamido)pyrrolo[2,1-f][1,2,4]triazin-7-yl)-5-cyano-3,4-dihydroxytetrahydrofuran-2-yl)methoxy)methyl pivalate | |
| 115 | 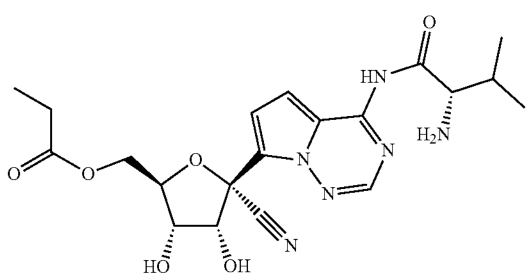 [SMILES: CCC(=O)OC[C@H]1O[C@@](C#N)(c2ccc3c(NC(=O)[C@@H](N)C(C)C)ncnn23)[C@H](O)[C@@H]1O] | ((2R,3S,4R,5R)-5-(4-((S)-2-amino-3-methylbutanamido)pyrrolo[2,1-f][1,2,4]triazin-7-yl)-5-cyano-3,4-dihydroxytetrahydrofuran-2-yl)methyl propionate | 447.1 |
| 116 | 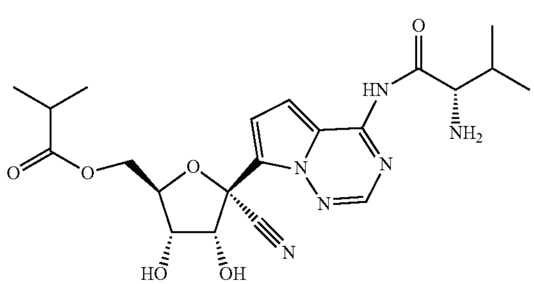 [SMILES: CC(C)C(=O)OC[C@H]1O[C@@](C#N)(c2ccc3c(NC(=O)[C@@H](N)C(C)C)ncnn23)[C@H](O)[C@@H]1O] | ((2R,3S,4R,5R)-5-(4-((S)-2-amino-3-methylbutanamido)pyrrolo[2,1-f][1,2,4]triazin-7-yl)-5-cyano-3,4-dihydroxytetrahydrofuran-2-yl)methyl isobutyrate | 461.3 |

TABLE 1-continued

Exemplary compounds

| Cpd. No. | Structure | Chemical Name | ESI-MS (M + H)+ (m/z) |
|---|---|---|---|
| 117 | 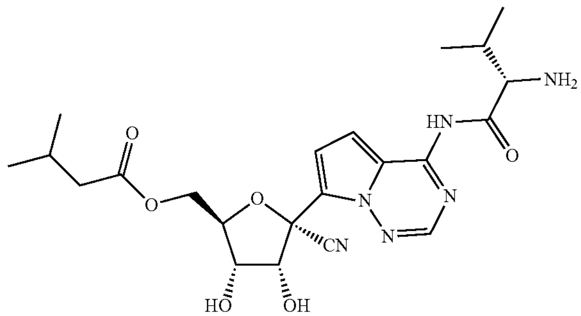 [SMILES: CC(C)CC(=O)OC[C@H]1O[C@@](C#N)(c2ccc3c(NC(=O)[C@@H](N)C(C)C)ncnn23)[C@H](O)[C@@H]1O] | ((2R,3S,4R,5R)-5-(4-((S)-2-amino-3-methylbutanamido)pyrrolo[2,1-f][1,2,4]triazin-7-yl)-5-cyano-3,4-dihydroxytetrahydrofuran-2-yl)methyl 3-methylbutanoate | 475.1 |
| 118 | 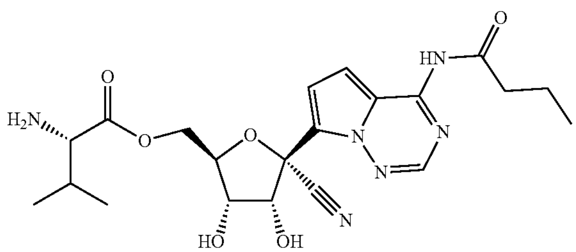 [SMILES: CCCC(=O)Nc1ncnn2c([C@]3(C#N)O[C@H](COC(=O)[C@@H](N)C(C)C)[C@@H](O)[C@H]3O)ccc12] | ((2R,3S,4R,5R)-5-(4-butyramidopyrrolo[2,1-f][1,2,4]triazin-7-yl)-5-cyano-3,4-dihydroxytetrahydrofuran-2-yl)methyl L-valinate | |
| 119 | 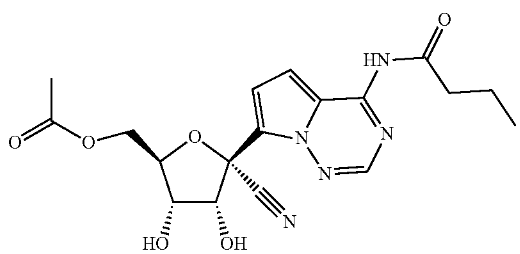 [SMILES: CCCC(=O)Nc1ncnn2c([C@]3(C#N)O[C@H](COC(C)=O)[C@@H](O)[C@H]3O)ccc12] | ((2R,3S,4R,5R)-5-(4-butyramidopyrrolo[2,1-f][1,2,4]triazin-7-yl)-5-cyano-3,4-dihydroxytetrahydrofuran-2-yl)methyl acetate | |
| 120 | 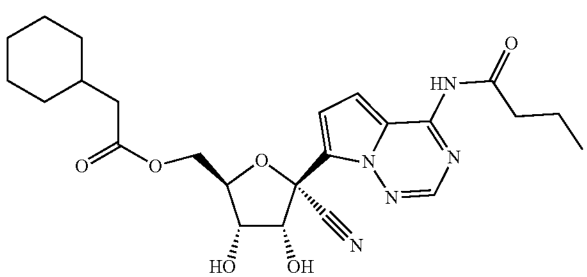 [SMILES: CCCC(=O)Nc1ncnn2c([C@]3(C#N)O[C@H](COC(=O)CC4CCCCC4)[C@@H](O)[C@H]3O)ccc12] | ((2R,3S,4R,5R)-5-(4-butyramidopyrrolo[2,1-f][1,2,4]triazin-7-yl)-5-cyano-3,4-dihydroxytetrahydrofuran-2-yl)methyl 2-cyclohexylacetate | |
| 121 | 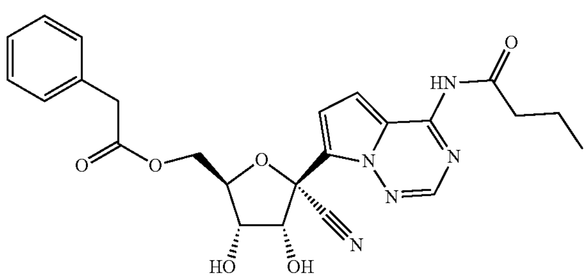 [SMILES: CCCC(=O)Nc1ncnn2c([C@]3(C#N)O[C@H](COC(=O)Cc4ccccc4)[C@@H](O)[C@H]3O)ccc12] | ((2R,3S,4R,5R)-5-(4-butyramidopyrrolo[2,1-f][1,2,4]triazin-7-yl)-5-cyano-3,4-dihydroxytetrahydrofuran-2-yl)methyl 2-phenylacetate | |

TABLE 1-continued

Exemplary compounds

| Cpd. No. | Structure | Chemical Name | ESI-MS (M + H)+ (m/z) |
|---|---|---|---|
| 122 | 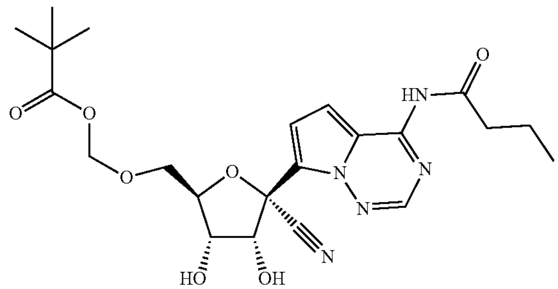 [SMILES: CCCC(=O)Nc1ncnn2c([C@]3(C#N)O[C@H](COCOC(=O)C(C)(C)C)[C@@H](O)[C@H]3O)ccc12] | (((2R,3S,4R,5R)-5-(4-butyramidopyrrolo[2,1-f][1,2,4]triazin-7-yl)-5-cyano-3,4-dihydroxytetrahydrofuran-2-yl)methoxy)methyl pivalate | |
| 123 | 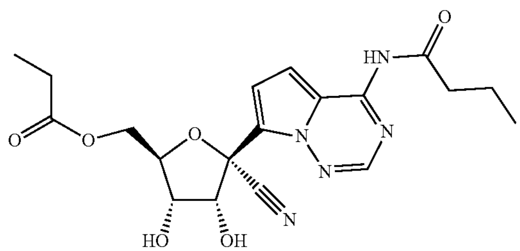 [SMILES: CCCC(=O)Nc1ncnn2c([C@]3(C#N)O[C@H](COC(=O)CC)[C@@H](O)[C@H]3O)ccc12] | ((2R,3S,4R,5R)-5-(4-butyramidopyrrolo[2,1-f][1,2,4]triazin-7-yl)-5-cyano-3,4-dihydroxytetrahydrofuran-2-yl)methyl propionate | |
| 124 | 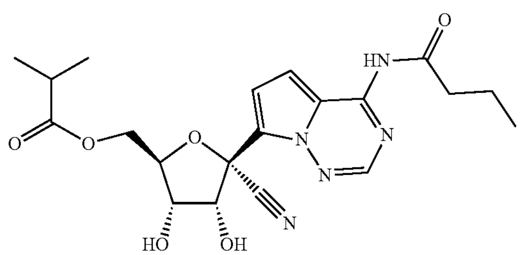 [SMILES: CCCC(=O)Nc1ncnn2c([C@]3(C#N)O[C@H](COC(=O)C(C)C)[C@@H](O)[C@H]3O)ccc12] | ((2R,3S,4R,5R)-5-(4-butyramidopyrrolo[2,1-f][1,2,4]triazin-7-yl)-5-cyano-3,4-dihydroxytetrahydrofuran-2-yl)methyl isobutyrate | |
| 125 | 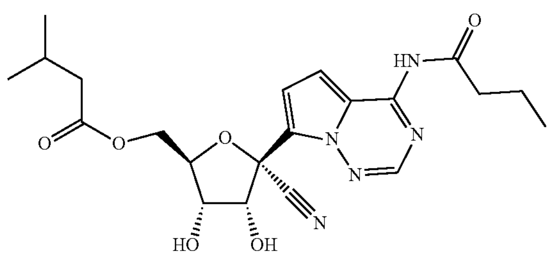 [SMILES: CCCC(=O)Nc1ncnn2c([C@]3(C#N)O[C@H](COC(=O)CC(C)C)[C@@H](O)[C@H]3O)ccc12] | ((2R,3S,4R,5R)-5-(4-butyramidopyrrolo[2,1-f][1,2,4]triazin-7-yl)-5-cyano-3,4-dihydroxytetrahydrofuran-2-yl)methyl 3-methylbutanoate | |
| 126 | 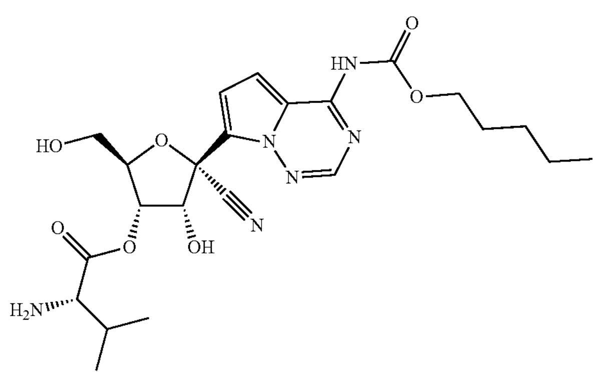 [SMILES: CCCCCOC(=O)Nc1ncnn2c([C@]3(C#N)O[C@H](CO)[C@@H](OC(=O)[C@@H](N)C(C)C)[C@H]3O)ccc12] | (2R,3S,4R,5R)-5-cyano-4-hydroxy-2-(hydroxymethyl)-5-(4-(((pentyloxy)carbonyl)amino)pyrrolo[2,1-f][1,2,4]triazin-7-yl)tetrahydrofuran-3-yl L-valinate | |

TABLE 1-continued

Exemplary compounds

| Cpd. No. | Structure | Chemical Name | ESI-MS (M + H)+ (m/z) |
|---|---|---|---|
| 127 | 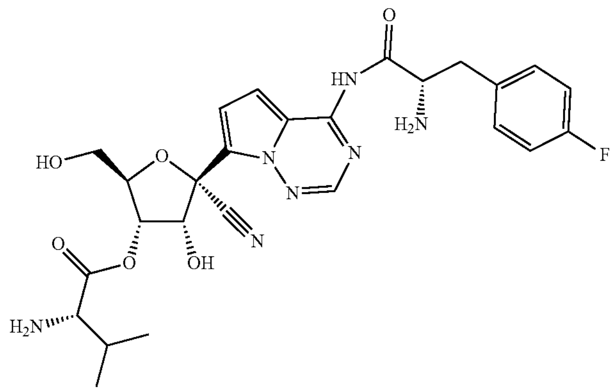 [SMILES: CC(C)[C@H](N)C(=O)O[C@H]1[C@@H](O)[C@](C#N)(c2ccc3c(NC(=O)[C@@H](N)Cc4ccc(F)cc4)ncnn23)O[C@@H]1CO] | (2R,3S,4R,5R)-5-(4-((S)-2-amino-3-(4-fluorophenyl)propanamido)pyrrolo[2,1-f][1,2,4]triazin-7-yl)-5-cyano-4-hydroxy-2-(hydroxymethyl)tetrahydrofuran-3-yl L-valinate | |
| 128 | 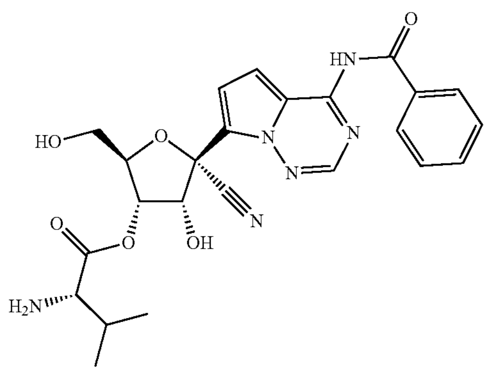 [SMILES: CC(C)[C@H](N)C(=O)O[C@H]1[C@@H](O)[C@](C#N)(c2ccc3c(NC(=O)c4ccccc4)ncnn23)O[C@@H]1CO] | (2R,3S,4R,5R)-5-(4-benzamidopyrrolo[2,1-f][1,2,4]triazin-7-yl)-5-cyano-4-hydroxy-2-(hydroxymethyl)tetrahydrofuran-3-yl L-valinate | 495.1 |
| 129 | 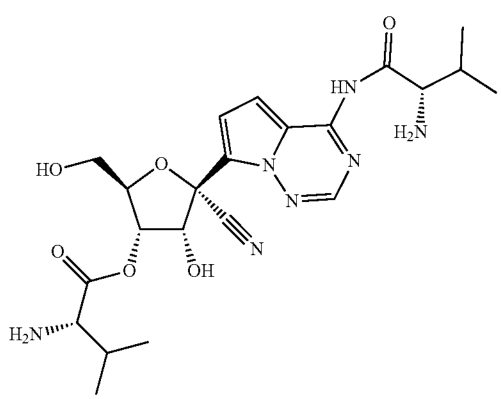 [SMILES: CC(C)[C@H](N)C(=O)Nc1ncnn2c([C@]3(C#N)O[C@H](CO)[C@@H](OC(=O)[C@@H](N)C(C)C)[C@H]3O)ccc12] | (2R,3S,4R,5R)-5-(4-((S)-2-amino-3-methylbutanamido)pyrrolo[2,1-f][1,2,4]triazin-7-yl)-5-cyano-4-hydroxy-2-(hydroxymethyl)tetrahydrofuran-3-yl L-valinate | 490.3 |
| 130 | 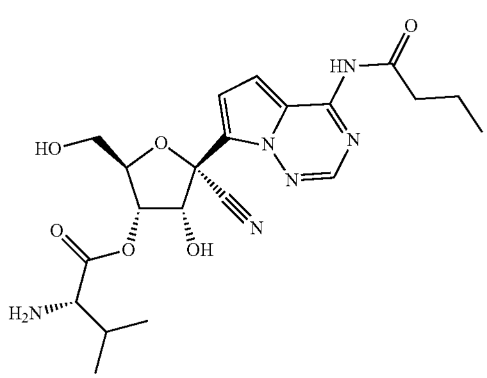 [SMILES: CCCC(=O)Nc1ncnn2c([C@]3(C#N)O[C@H](CO)[C@@H](OC(=O)[C@@H](N)C(C)C)[C@H]3O)ccc12] | (2R,3S,4R,5R)-5-(4-butyramidopyrrolo[2,1-f][1,2,4]triazin-7-yl)-5-cyano-4-hydroxy-2-(hydroxymethyl)tetrahydrofuran-3-yl L-valinate | |

TABLE 1-continued

Exemplary compounds

| Cpd. No. | Structure | Chemical Name | ESI-MS (M + H)+ (m/z) |
|---|---|---|---|
| 131 | 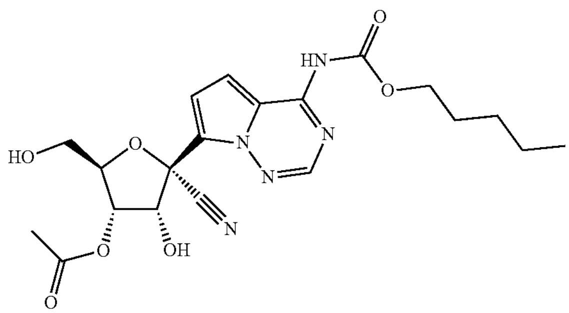 [SMILES: CCCCCOC(=O)Nc1ncnn2c([C@]3(C#N)O[C@H](CO)[C@@H](OC(C)=O)[C@H]3O)ccc12] | (2R,3S,4R,5R)-5-cyano-4-hydroxy-2-(hydroxymethyl)-5-(4-(((pentyloxy)carbonyl)amino)pyrrolo[2,1-f][1,2,4]triazin-7-yl)tetrahydrofuran-3-yl acetate | |
| 132 | 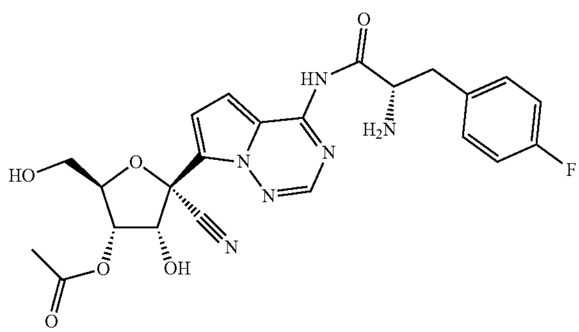 [SMILES: CC(=O)O[C@H]1[C@@H](O)[C@](C#N)(c2ccc3c(NC(=O)[C@@H](N)Cc4ccc(F)cc4)ncnn23)O[C@@H]1CO] | (2R,3S,4R,5R)-5-(4-((S)-2-amino-3-(4-fluorophenyl)propanamido)pyrrolo[2,1-f][1,2,4]triazin-7-yl)-5-cyano-4-hydroxy-2-(hydroxymethyl)tetrahydrofuran-3-yl acetate | |
| 133 | 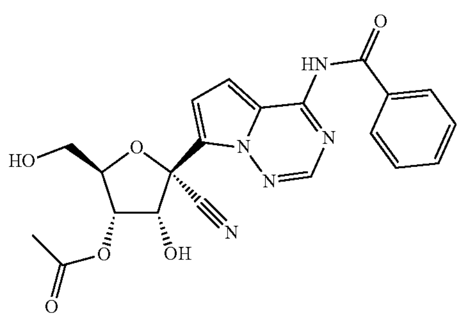 [SMILES: CC(=O)O[C@H]1[C@@H](O)[C@](C#N)(c2ccc3c(NC(=O)c4ccccc4)ncnn23)O[C@@H]1CO] | (2R,3S,4R,5R)-5-(4-benzamidopyrrolo[2,1-f][1,2,4]triazin-7-yl)-5-cyano-4-hydroxy-2-(hydroxymethyl)tetrahydrofuran-3-yl acetate | |
| 134 | 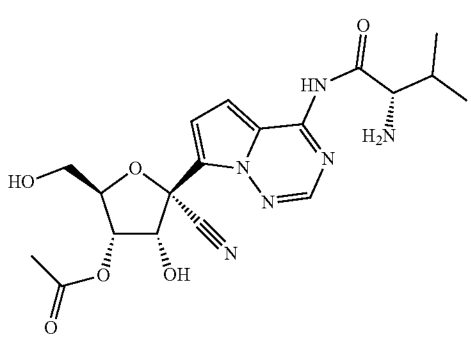 [SMILES: CC(=O)O[C@H]1[C@@H](O)[C@](C#N)(c2ccc3c(NC(=O)[C@@H](N)C(C)C)ncnn23)O[C@@H]1CO] | (2R,3S,4R,5R)-5-(4-((S)-2-amino-3-methylbutanamido)pyrrolo[2,1-f][1,2,4]triazin-7-yl)-5-cyano-4-hydroxy-2-(hydroxymethyl)tetrahydrofuran-3-yl acetate | |

TABLE 1-continued

Exemplary compounds

| Cpd. No. | Structure | Chemical Name | ESI-MS (M + H)+ (m/z) |
|---|---|---|---|
| 135 | 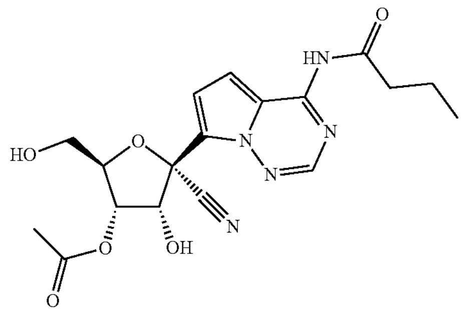 [SMILES: CCCC(=O)Nc1ncnn2c([C@]3(C#N)O[C@H](CO)[C@@H](OC(C)=O)[C@H]3O)ccc12] | (2R,3S,4R,5R)-5-(4-butyramidopyrrolo[2,1-f][1,2,4]triazin-7-yl)-5-cyano-4-hydroxy-2-(hydroxymethyl)tetrahydrofuran-3-yl acetate | |
| 136 | 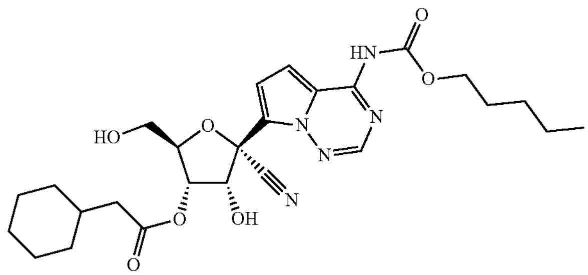 [SMILES: CCCCCOC(=O)Nc1ncnn2c([C@]3(C#N)O[C@H](CO)[C@@H](OC(=O)CC4CCCCC4)[C@H]3O)ccc12] | (2R,3S,4R,5R)-5-cyano-4-hydroxy-2-(hydroxymethyl)-5-(4-(((pentyloxy)carbonyl)amino)pyrrolo[2,1-f][1,2,4]triazin-7-yl)tetrahydrofuran-3-yl 2-cyclohexylacetate | |
| 137 | 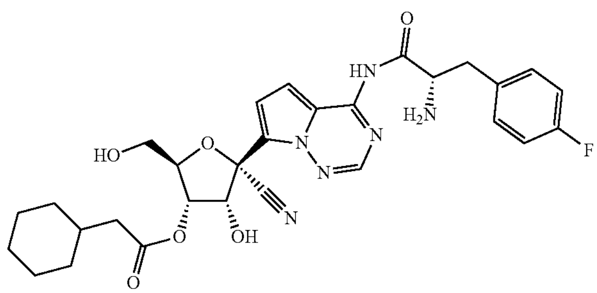 [SMILES: N#C[C@@]1(c2ccc3c(NC(=O)[C@@H](N)Cc4ccc(F)cc4)ncnn23)O[C@H](CO)[C@@H](OC(=O)CC2CCCCC2)[C@H]1O] | (2R,3S,4R,5R)-5-(4-((S)-2-amino-3-(4-fluorophenyl)propanamido)pyrrolo[2,1-f][1,2,4]triazin-7-yl)-5-cyano-4-hydroxy-2-(hydroxymethyl)tetrahydrofuran-3-yl 2-cyclohexylacetate | 581.2 |
| 138 | 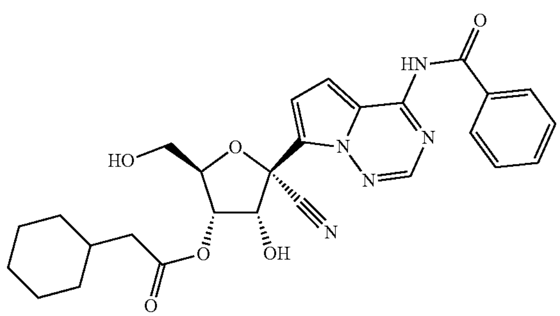 [SMILES: N#C[C@@]1(c2ccc3c(NC(=O)c4ccccc4)ncnn23)O[C@H](CO)[C@@H](OC(=O)CC2CCCCC2)[C@H]1O] | (2R,3S,4R,5R)-5-(4-benzamidopyrrolo[2,1-f][1,2,4]triazin-7-yl)-5-cyano-4-hydroxy-2-(hydroxymethyl)tetrahydrofuran-3-yl 2-cyclohexylacetate | |
| 139 | 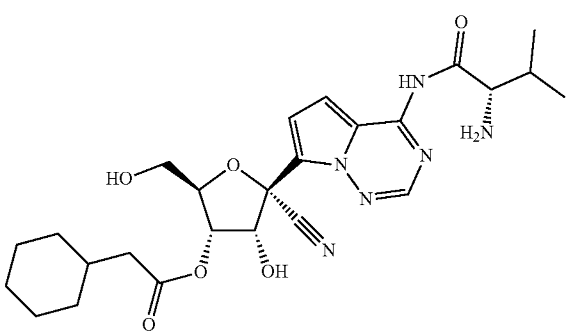 [SMILES: CC(C)[C@H](N)C(=O)Nc1ncnn2c([C@]3(C#N)O[C@H](CO)[C@@H](OC(=O)CC4CCCCC4)[C@H]3O)ccc12] | (2R,3S,4R,5R)-5-(4-((S)-2-amino-3-methylbutanamido)pyrrolo[2,1-f][1,2,4]triazin-7-yl)-5-cyano-4-hydroxy-2-(hydroxymethyl)tetrahydrofuran-3-yl 2-cyclohexylacetate | 515.2 |

TABLE 1-continued

Exemplary compounds

| Cpd. No. | Structure | Chemical Name | ESI-MS (M + H)+ (m/z) |
| --- | --- | --- | --- |
| 140 | 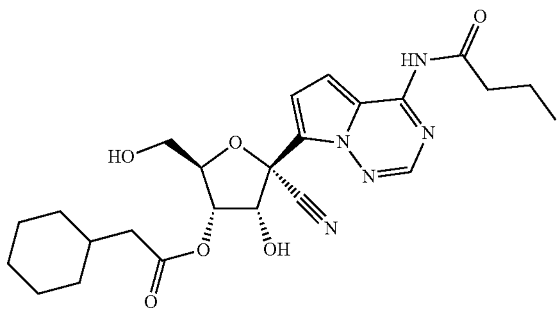 [SMILES: CCCC(=O)Nc1ncnn2c([C@]3(C#N)O[C@H](CO)[C@@H](OC(=O)CC4CCCCC4)[C@H]3O)ccc12] | (2R,3S,4R,5R)-5-(4-butyramidopyrrolo[2,1-f][1,2,4]triazin-7-yl)-5-cyano-4-hydroxy-2-(hydroxymethyl)tetrahydrofuran-3-yl 2-cyclohexylacetate | |
| 141 | 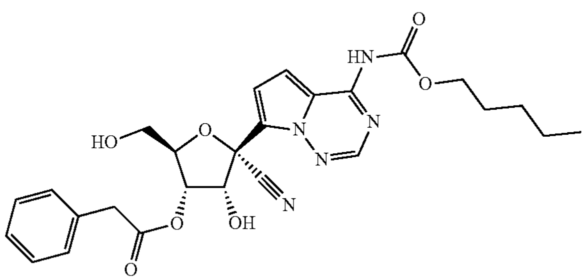 [SMILES: CCCCCOC(=O)Nc1ncnn2c([C@]3(C#N)O[C@H](CO)[C@@H](OC(=O)Cc4ccccc4)[C@H]3O)ccc12] | (2R,3S,4R,5R)-5-cyano-4-hydroxy-2-(hydroxymethyl)-5-(4-(((pentyloxy)carbonyl)amino)pyrrolo[2,1-f][1,2,4]triazin-7-yl)tetrahydrofuran-3-yl 2-phenylacetate | 524.2 |
| 142 | 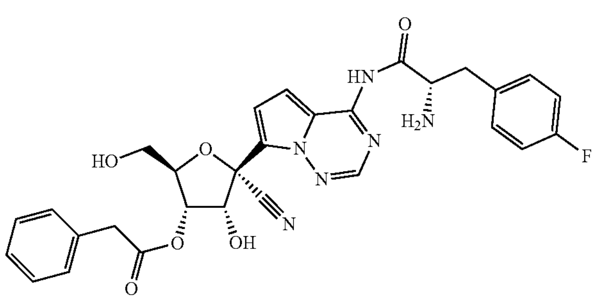 [SMILES: N#C[C@@]1(c2ccc3c(NC(=O)[C@@H](N)Cc4ccc(F)cc4)ncnn23)O[C@H](CO)[C@@H](OC(=O)Cc2ccccc2)[C@H]1O] | (2R,3S,4R,5R)-5-(4-((S)-2-amino-3-(4-fluorophenyl)propanamido)pyrrolo[2,1-f][1,2,4]triazin-7-yl)-5-cyano-4-hydroxy-2-(hydroxymethyl)tetrahydrofuran-3-yl 2-phenylacetate | |
| 143 | 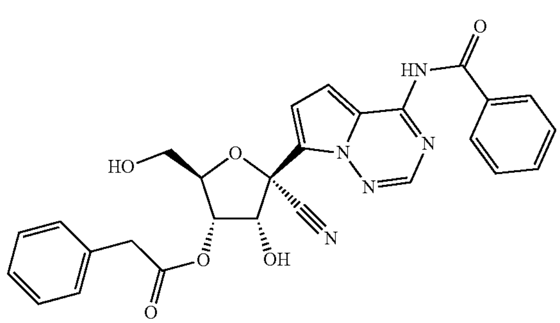 [SMILES: N#C[C@@]1(c2ccc3c(NC(=O)c4ccccc4)ncnn23)O[C@H](CO)[C@@H](OC(=O)Cc2ccccc2)[C@H]1O] | (2R,3S,4R,5R)-5-(4-benzamidopyrrolo[2,1-f][1,2,4]triazin-7-yl)-5-cyano-4-hydroxy-2-(hydroxymethyl)tetrahydrofuran-3-yl 2-phenylacetate | 514.2 |

TABLE 1-continued

Exemplary compounds

| Cpd. No. | Structure | Chemical Name | ESI-MS (M + H)+ (m/z) |
|---|---|---|---|
| 144 | 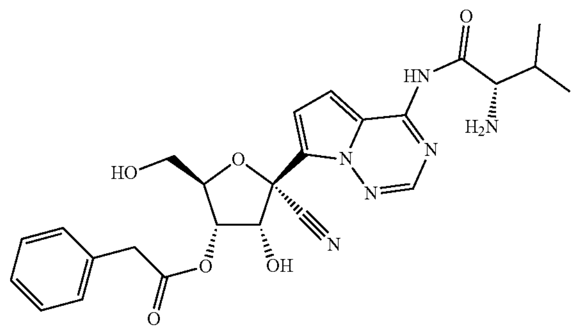 [SMILES: CC(C)[C@H](N)C(=O)Nc1ncnn2c([C@]3(C#N)O[C@H](CO)[C@@H](OC(=O)Cc4ccccc4)[C@H]3O)ccc12] | (2R,3S,4R,5R)-5-(4-((S)-2-amino-3-methylbutanamido)pyrrolo[2,1-f][1,2,4]triazin-7-yl)-5-cyano-4-hydroxy-2-(hydroxymethyl)tetrahydrofuran-3-yl 2-phenylacetate | 509.2 |
| 145 | 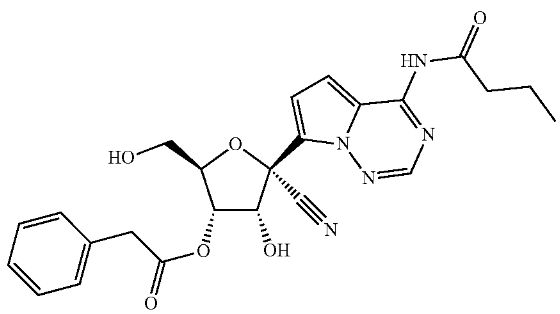 [SMILES: CCCC(=O)Nc1ncnn2c([C@]3(C#N)O[C@H](CO)[C@@H](OC(=O)Cc4ccccc4)[C@H]3O)ccc12] | (2R,3S,4R,5R)-5-(4-butyramidopyrrolo[2,1-f][1,2,4]triazin-7-yl)-5-cyano-4-hydroxy-2-(hydroxymethyl)tetrahydrofuran-3-yl 2-phenylacetate | |
| 146 | 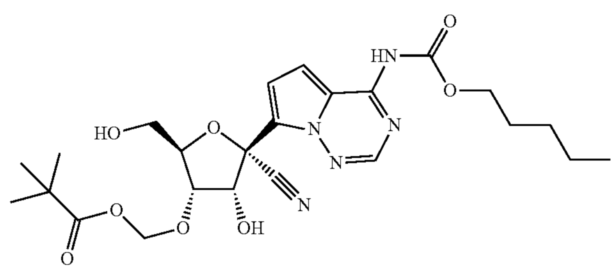 [SMILES: CCCCCOC(=O)Nc1ncnn2c([C@]3(C#N)O[C@H](CO)[C@@H](OCOC(=O)C(C)(C)C)[C@H]3O)ccc12] | (((2R,3S,4R,5R)-5-cyano-4-hydroxy-2-(hydroxymethyl)-5-(4-(((pentyloxy)carbonyl)amino)pyrrolo[2,1-f][1,2,4]triazin-7-yl)tetrahydrofuran-3-yl)oxy)methyl pivalate | |
| 147 | 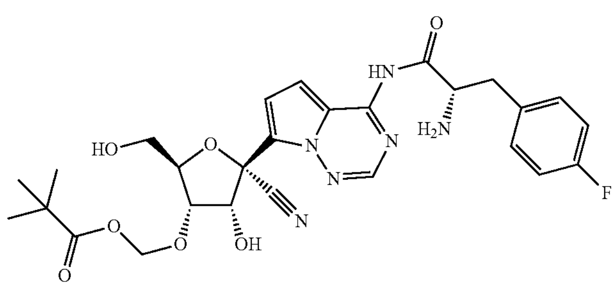 [SMILES: CC(C)(C)C(=O)OCO[C@H]1[C@@H](O)[C@](C#N)(c2ccc3c(NC(=O)[C@@H](N)Cc4ccc(F)cc4)ncnn23)O[C@@H]1CO] | (((2R,3S,4R,5R)-5-(4-((S)-2-amino-3-(4-fluorophenyl)propanamido)pyrrolo [2,1-f][1,2,4]triazin-7-yl)-5-cyano-4-hydroxy-2-(hydroxymethyl)tetrahydrofuran-3-yl)oxy)methylpivalate | |
| 148 | 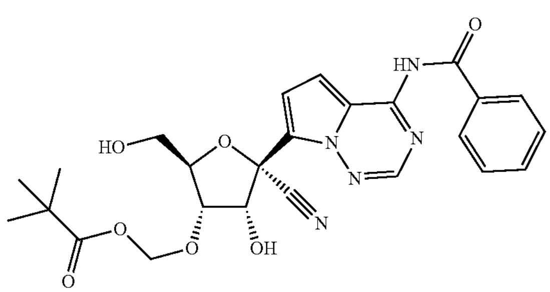 [SMILES: CC(C)(C)C(=O)OCO[C@H]1[C@@H](O)[C@](C#N)(c2ccc3c(NC(=O)c4ccccc4)ncnn23)O[C@@H]1CO] | (((2R,3S,4R,5R)-5-(4-benzamidopyrrolo[2,1-f][1,2,4]triazin-7-yl)-5-cyano-4-hydroxy-2-(hydroxymethyl)tetrahydrofuran-3-yl)oxy)methyl pivalate | |

TABLE 1-continued

Exemplary compounds

| Cpd. No. | Structure | Chemical Name | ESI-MS (M + H)+ (m/z) |
|---|---|---|---|
| 149 | 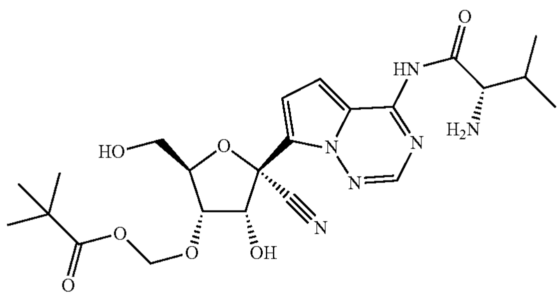 [SMILES: CC(C)[C@H](N)C(=O)Nc1ncnn2c([C@]3(C#N)O[C@H](CO)[C@@H](OCOC(=O)C(C)(C)C)[C@H]3O)ccc12] | (((2R,3S,4R,5R)-5-(4-((S)-2-amino-3-methylbutanamido)pyrrolo[2,1-f][1,2,4]triazin-7-yl)-5-cyano-4-hydroxy-2-(hydroxymethyl)tetrahydrofuran-3-yl)oxy)methyl pivalate | |
| 150 | 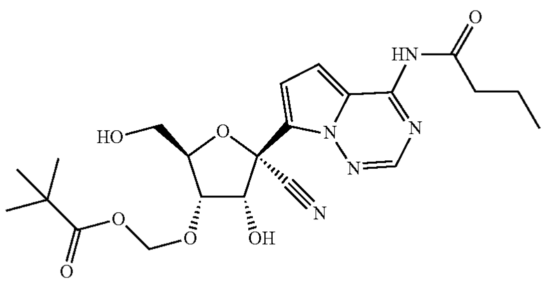 [SMILES: CCCC(=O)Nc1ncnn2c([C@]3(C#N)O[C@H](CO)[C@@H](OCOC(=O)C(C)(C)C)[C@H]3O)ccc12] | (((2R,3S,4R,5R)-5-(4-butyramidopyrrolo[2,1-f][1,2,4]triazin-7-yl)-5-cyano-4-hydroxy-2-(hydroxymethyl)tetrahydrofuran-3-yl)oxy)methyl pivalate | |
| 151 | 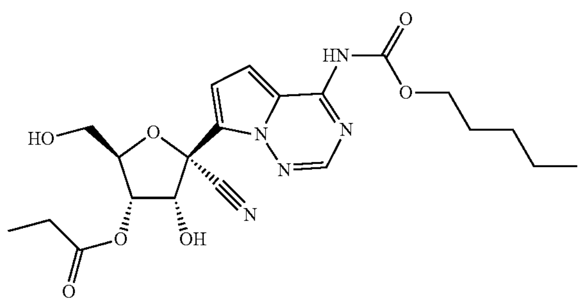 [SMILES: CCCCCOC(=O)Nc1ncnn2c([C@]3(C#N)O[C@H](CO)[C@@H](OC(=O)CC)[C@H]3O)ccc12] | (2R,3S,4R,5R)-5-cyano-4-hydroxy-2-(hydroxymethyl)-5-(4-(((pentyloxy)carbonyl)amino)pyrrolo[2,1-f][1,2,4]triazin-7-yl)tetrahydrofuran-3-yl propionate | |
| 152 | 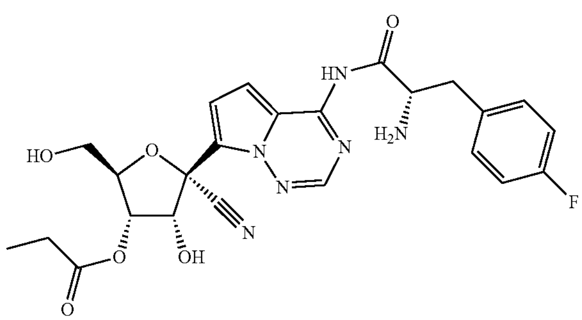 [SMILES: CCC(=O)O[C@H]1[C@@H](O)[C@](C#N)(c2ccc3c(NC(=O)[C@@H](N)Cc4ccc(F)cc4)ncnn23)O[C@@H]1CO] | (2R,3S,4R,5R)-5-(4-((S)-2-amino-3-(4-fluorophenyl)propanamido)pyrrolo[2,1-f][1,2,4]triazin-7-yl)-5-cyano-4-hydroxy-2-(hydroxymethyl)tetrahydrofuran-3-yl propionate | |
| 153 | 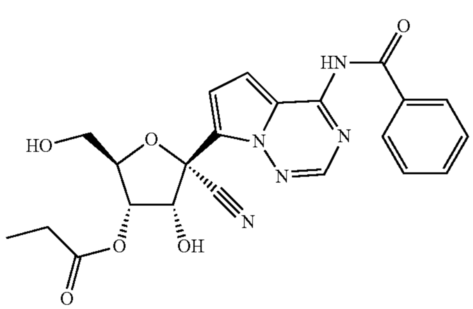 [SMILES: CCC(=O)O[C@H]1[C@@H](O)[C@](C#N)(c2ccc3c(NC(=O)c4ccccc4)ncnn23)O[C@@H]1CO] | (2R,3S,4R,5R)-5-(4-benzamidopyrrolo[2,1-f][1,2,4]triazin-7-yl)-5-cyano-4-hydroxy-2-(hydroxymethyl)tetrahydrofuran-3-yl propionate | |

TABLE 1-continued

Exemplary compounds

| Cpd. No. | Structure | Chemical Name | ESI-MS (M + H)+ (m/z) |
|---|---|---|---|
| 154 | 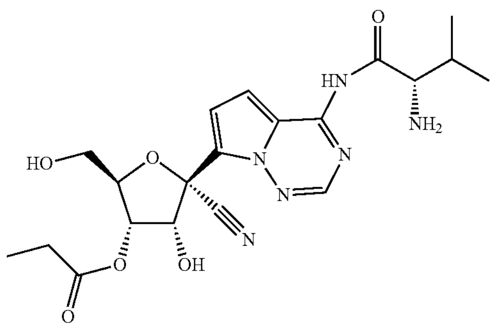 [SMILES: CCC(=O)O[C@H]1[C@@H](O)[C@](C#N)(c2ccc3c(NC(=O)[C@@H](N)C(C)C)ncnn23)O[C@@H]1CO] | (2R,3S,4R,5R)-5-(4-((S)-2-amino-3-methylbutanamido)pyrrolo[2,1-f][1,2,4]triazin-7-yl)-5-cyano-4-hydroxy-2-(hydroxymethyl)tetrahydrofuran-3-yl propionate | |
| 155 | 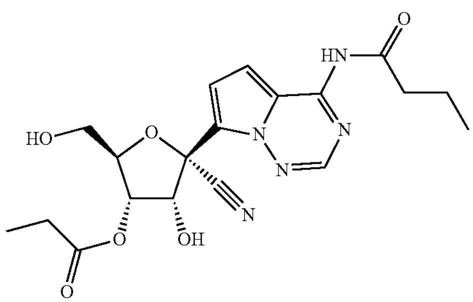 [SMILES: CCCC(=O)Nc1ncnn2c([C@]3(C#N)O[C@H](CO)[C@@H](OC(=O)CC)[C@H]3O)ccc12] | (2R,3S,4R,5R)-5-(4-butyramidopyrrolo[2,1-f][1,2,4]triazin-7-yl)-5-cyano-4-hydroxy-2-(hydroxymethyl)tetrahydrofuran-3-yl propionate | |
| 156 | 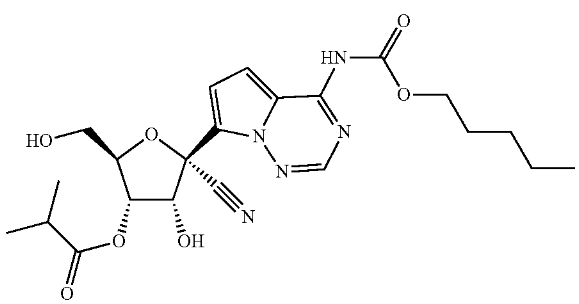 [SMILES: CCCCCOC(=O)Nc1ncnn2c([C@]3(C#N)O[C@H](CO)[C@@H](OC(=O)C(C)C)[C@H]3O)ccc12] | (2R,3S,4R,5R)-5-cyano-4-hydroxy-2-(hydroxymethyl)-5-(4-(((pentyloxy)carbonyl)amino)pyrrolo[2,1-f][1,2,4]triazin-7-yl)tetrahydrofuran-3-yl isobutyrate | |
| 157 | 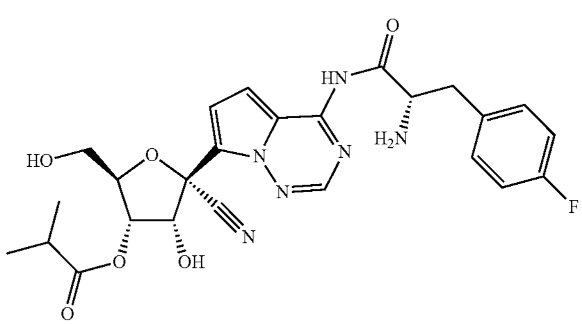 [SMILES: CC(C)C(=O)O[C@H]1[C@@H](O)[C@](C#N)(c2ccc3c(NC(=O)[C@@H](N)Cc4ccc(F)cc4)ncnn23)O[C@@H]1CO] | (2R,3S,4R,5R)-5-(4-((S)-2-amino-3-(4-fluorophenyl)propanamido)pyrrolo[2,1-f][1,2,4]triazin-7-yl)-5-cyano-4-hydroxy-2-(hydroxymethyl)tetrahydrofuran-3-yl isobutyrate | |

TABLE 1-continued

Exemplary compounds

| Cpd. No. | Structure | Chemical Name | ESI-MS (M + H)+ (m/z) |
|---|---|---|---|
| 158 | 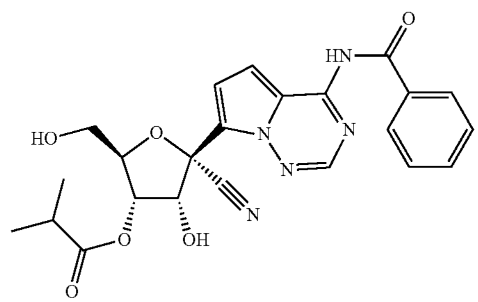 [SMILES: CC(C)C(=O)O[C@H]1[C@@H](O)[C@](C#N)(c2ccc3c(NC(=O)c4ccccc4)ncnn23)O[C@@H]1CO] | (2R,3S,4R,5R)-5-(4-benzamidopyrrolo[2,1-f][1,2,4]triazin-7-yl)-5-cyano-4-hydroxy-2-(hydroxymethyl)tetrahydrofuran-3-yl isobutyrate | |
| 159 | 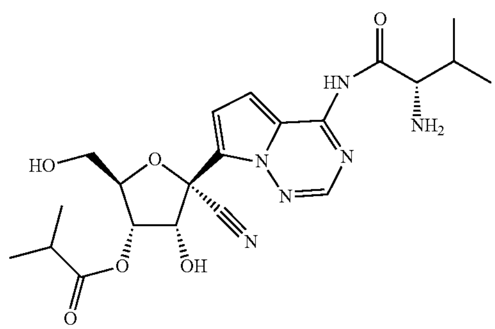 [SMILES: CC(C)C(=O)O[C@H]1[C@@H](O)[C@](C#N)(c2ccc3c(NC(=O)[C@@H](N)C(C)C)ncnn23)O[C@@H]1CO] | (2R,3S,4R,5R)-5-(4-((S)-2-amino-3-methylbutanamido)pyrrolo[2,1-f][1,2,4]triazin-7-yl)-5-cyano-4-hydroxy-2-(hydroxymethyl)tetrahydrofuran-3-yl isobutyrate | |
| 160 | 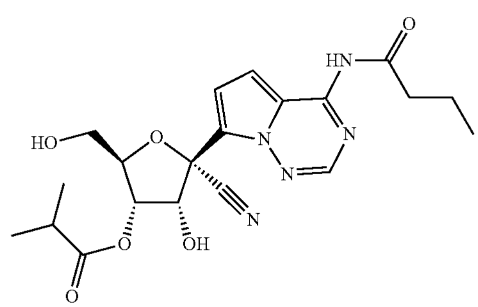 [SMILES: CCCC(=O)Nc1ncnn2c([C@]3(C#N)O[C@H](CO)[C@@H](OC(=O)C(C)C)[C@H]3O)ccc12] | (2R,3S,4R,5R)-5-(4-butyramidopyrrolo[2,1-f][1,2,4]triazin-7-yl)-5-cyano-4-hydroxy-2-(hydroxymethyl)tetrahydrofuran-3-yl isobutyrate | |
| 161 | 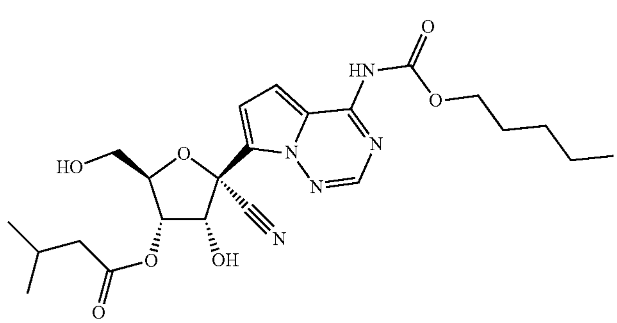 [SMILES: CCCCCOC(=O)Nc1ncnn2c([C@]3(C#N)O[C@H](CO)[C@@H](OC(=O)CC(C)C)[C@H]3O)ccc12] | (2R,3S,4R,5R)-5-cyano-4-hydroxy-2-(hydroxymethyl)-5-(4-(((pentyloxy)carbonyl)amino)pyrrolo[2,1-f][1,2,4]triazin-7-yl)tetrahydrofuran-3-yl 3-methylbutanoate | |

TABLE 1-continued

Exemplary compounds

| Cpd. No. | Structure | Chemical Name | ESI-MS (M + H)+ (m/z) |
|---|---|---|---|
| 162 | 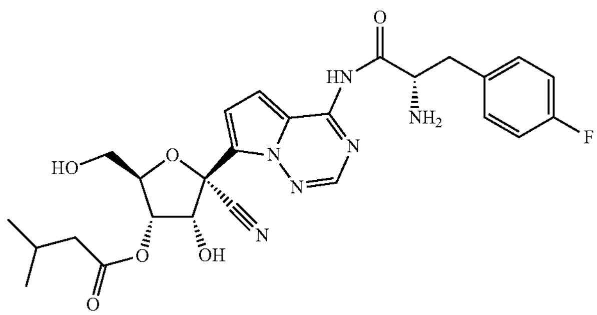 [SMILES: CC(C)CC(=O)O[C@H]1[C@@H](O)[C@](C#N)(c2ccc3c(NC(=O)[C@@H](N)Cc4ccc(F)cc4)ncnn23)O[C@@H]1CO] | (2R,3S,4R,5R)-5-(4-((S)-2-amino-3-(4-fluorophenyl)propanamido)pyrrolo[2,1-f][1,2,4]triazin-7-yl)-5-cyano-4-hydroxy-2-(hydroxymethyl)tetrahydrofuran-3-yl 3-methylbutanoate | |
| 163 | 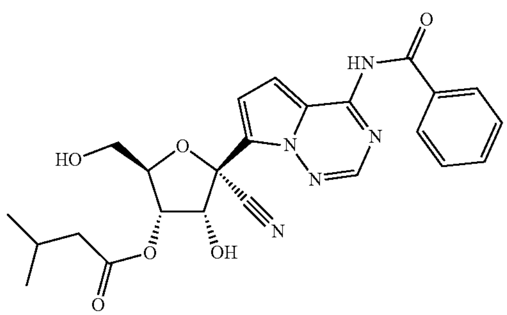 [SMILES: CC(C)CC(=O)O[C@H]1[C@@H](O)[C@](C#N)(c2ccc3c(NC(=O)c4ccccc4)ncnn23)O[C@@H]1CO] | (2R,3S,4R,5R)-5-(4-benzamidopyrrolo[2,1-f][1,2,4]triazin-7-yl)-5-cyano-4-hydroxy-2-(hydroxymethyl)tetrahydrofuran-3-yl 3-methylbutanoate | |
| 164 | 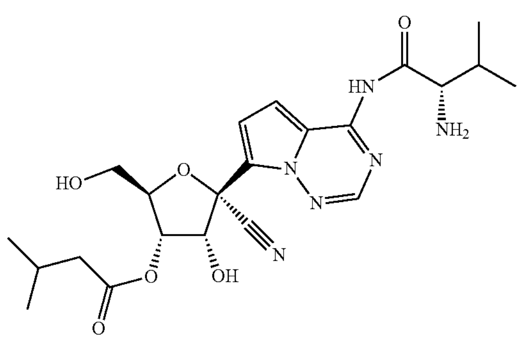 [SMILES: CC(C)CC(=O)O[C@H]1[C@@H](O)[C@](C#N)(c2ccc3c(NC(=O)[C@@H](N)C(C)C)ncnn23)O[C@@H]1CO] | (2R,3S,4R,5R)-5-(4-((S)-2-amino-3-methylbutanamido)pyrrolo[2,1-f][1,2,4]triazin-7-yl)-5-cyano-4-hydroxy-2-(hydroxymethyl)tetrahydrofuran-3-yl 3-methylbutanoate | |
| 165 | 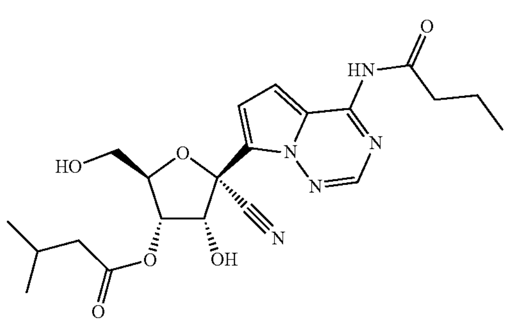 [SMILES: CCCC(=O)Nc1ncnn2c([C@]3(C#N)O[C@H](CO)[C@@H](OC(=O)CC(C)C)[C@H]3O)ccc12] | (2R,3S,4R,5R)-5-(4-butyramidopyrrolo[2,1-f][1,2,4]triazin-7-yl)-5-cyano-4-hydroxy-2-(hydroxymethyl)tetrahydrofuran-3-yl 3-methylbutanoate | |

TABLE 1-continued

Exemplary compounds

| Cpd. No. | Structure | Chemical Name | ESI-MS (M + H)+ (m/z) |
|---|---|---|---|
| 166 | 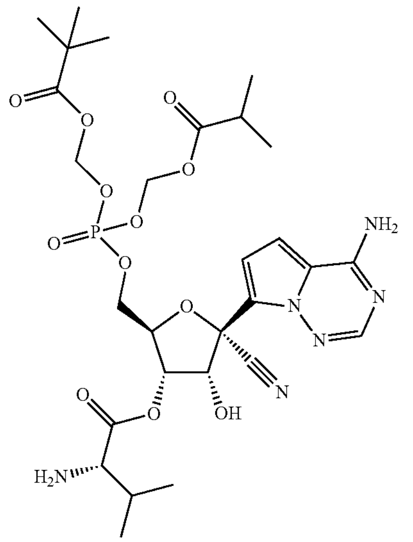 [SMILES: CC(C)C(=O)OCOP(=O)(OCOC(=O)C(C)(C)C)OC[C@H]1O[C@@](C#N)(c2ccc3c(N)ncnn23)[C@H](O)[C@@H]1OC(=O)[C@@H](N)C(C)C] | (2R,3S,4R,5R)-5-(4-aminopyrrolo[2,1-f][1,2,4]triazin-7-yl)-5-cyano-4-hydroxy-2-(((((isobutyryloxy)methoxy)((pivaloyloxy)methoxy)phosphoryl)oxy)methyl)tetrahydrofuran-3-yl L-valinate | |
| 167 | 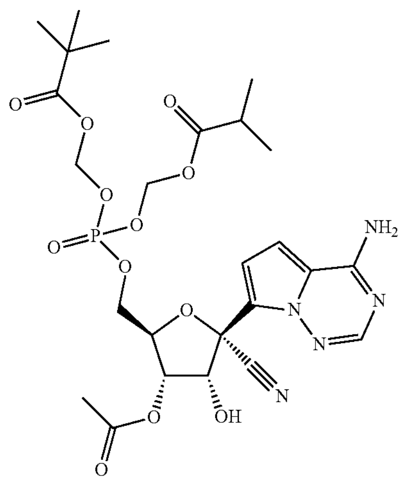 [SMILES: CC(=O)O[C@H]1[C@@H](O)[C@](C#N)(c2ccc3c(N)ncnn23)O[C@@H]1COP(=O)(OCOC(=O)C(C)C)OCOC(=O)C(C)(C)C] | (((((2R,3S,4R,5R)-3-acetoxy-5-(4-aminopyrrolo[2,1-f][1,2,4]triazin-7-yl)-5-cyano-4-hydroxytetrahydrofuran-2-yl)methoxy)((isobutyryloxy)methoxy)phosphoryl)oxy)methyl pivalate | |
| 168 | 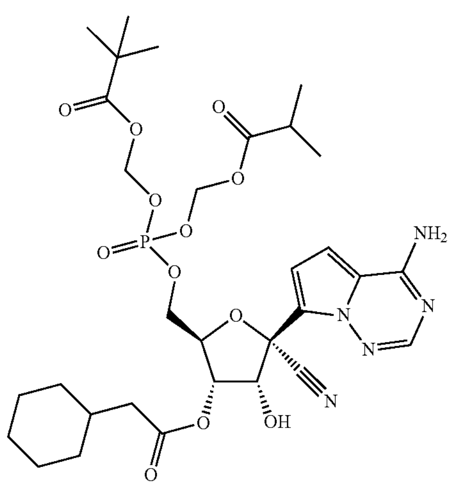 [SMILES: CC(C)C(=O)OCOP(=O)(OCOC(=O)C(C)(C)C)OC[C@H]1O[C@@](C#N)(c2ccc3c(N)ncnn23)[C@H](O)[C@@H]1OC(=O)CC1CCCCC1] | (((((2R,3S,4R,5R)-5-(4-aminopyrrolo[2,1-f][1,2,4]triazin-7-yl)-5-cyano-3-(2-cyclohexylacetoxy)-4-hydroxytetrahydrofuran-2-yl)methoxy)((isobutyryloxy)methoxy)phosphoryl)oxy)methyl pivalate | |

TABLE 1-continued

Exemplary compounds

| Cpd. No. | Structure | Chemical Name | ESI-MS (M + H)+ (m/z) |
|---|---|---|---|
| 169 | 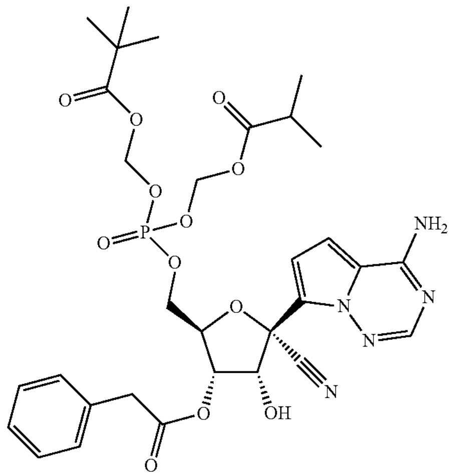 [SMILES: CC(C)C(=O)OCOP(=O)(OCOC(=O)C(C)(C)C)OC[C@H]1O[C@@](C#N)(c2ccc3c(N)ncnn23)[C@H](O)[C@@H]1OC(=O)Cc1ccccc1] | (((((2R,3S,4R,5R)-5-(4-aminopyrrolo[2,1-f][1,2,4]triazin-7-yl)-5-cyano-4-hydroxy-3-(2-phenylacetoxy)tetrahydrofuran-2-yl)methoxy)((isobutyryloxy)methoxy) phosphoryl)oxy)methyl pivalate | |
| 170 | 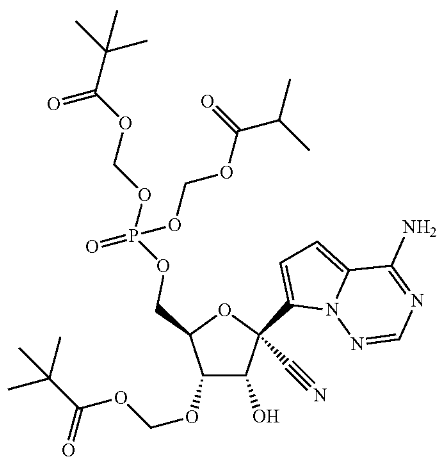 [SMILES: CC(C)C(=O)OCOP(=O)(OCOC(=O)C(C)(C)C)OC[C@H]1O[C@@](C#N)(c2ccc3c(N)ncnn23)[C@H](O)[C@@H]1OCOC(=O)C(C)(C)C] | (((2R,3S,4R,5R)-5-(4-aminopyrrolo[2,1-f][1,2,4]triazin-7-yl)-5-cyano-4-hydroxy-2-(((((isobutyryloxy)methoxy) ((pivaloyloxy)methoxy) phosphoryl)oxy)methyl) tetrahydrofuran-3-yl)oxy)methyl pivalate | |
| 171 | 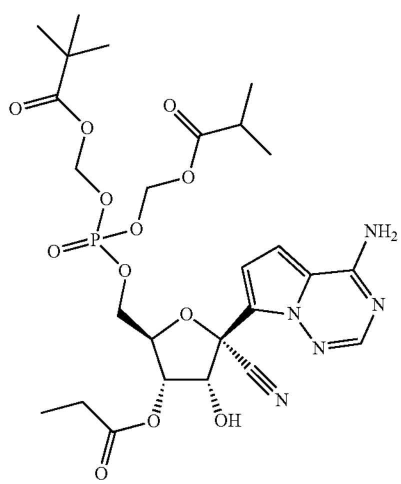 [SMILES: CCC(=O)O[C@H]1[C@@H](O)[C@](C#N)(c2ccc3c(N)ncnn23)O[C@@H]1COP(=O)(OCOC(=O)C(C)C)OCOC(=O)C(C)(C)C] | (((((2R,3S,4R,5R)-5-(4-aminopyrrolo[2,1-f][1,2,4]triazin-7-yl)-5-cyano-4-hydroxy-3-(propionyloxy)tetrahydrofuran-2-yl)methoxy)((isobutyryloxy)methoxy) phosphoryl)oxy)methyl pivalate | |

TABLE 1-continued

Exemplary compounds

| Cpd. No. | Structure | Chemical Name | ESI-MS (M + H)+ (m/z) |
|---|---|---|---|
| 172 | 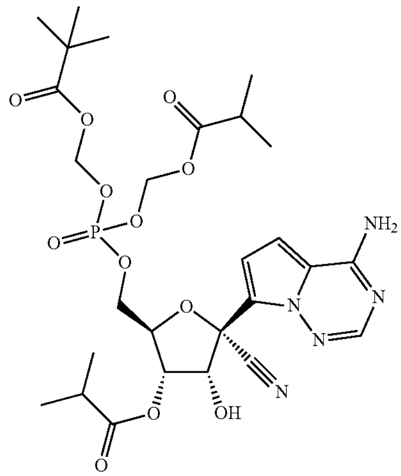 [SMILES: CC(C)C(=O)OCOP(=O)(OCOC(=O)C(C)(C)C)OC[C@H]1O[C@@](C#N)(c2ccc3c(N)ncnn23)[C@H](O)[C@@H]1OC(=O)C(C)C] | (((((2R,3S,4R,5R)-5-(4-aminopyrrolo[2,1-f][1,2,4]triazin-7-yl)-5-cyano-4-hydroxy-3-(isobutyryloxy)tetrahydrofuran-2-yl)methoxy)((isobutyryloxy)methoxy)phosphoryl)oxy)methyl pivalate | |
| 173 | 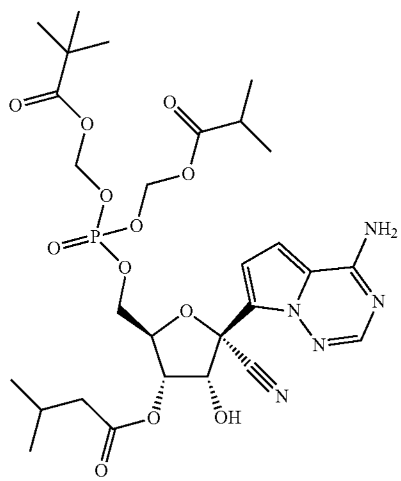 [SMILES: CC(C)CC(=O)O[C@H]1[C@@H](O)[C@](C#N)(c2ccc3c(N)ncnn23)O[C@@H]1COP(=O)(OCOC(=O)C(C)C)OCOC(=O)C(C)(C)C] | (2R,3S,4R,5R)-5-(4-aminopyrrolo[2,1-f][1,2,4]triazin-7-yl)-5-cyano-4-hydroxy-2-(((((isobutyryloxy)methoxy)((pivaloyloxy)methoxy)phosphoryl)oxy)methyl)tetrahydrofuran-3-yl 3-methylbutanoate | |
| 174 | 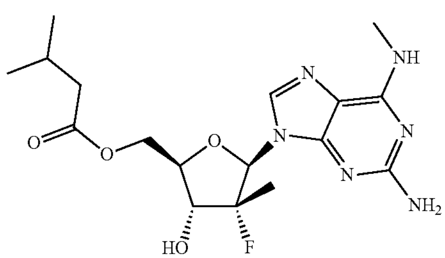 [SMILES: CNc1nc(N)nc2c1ncn2[C@@H]1O[C@H](COC(=O)CC(C)C)[C@@H](O)[C@@]1(C)F] | ((2R,3R,4R,5R)-5-(2-amino-6-(methylamino)-9H-purin-9-yl)-4-fluoro-3-hydroxy-4-methyltetrahydrofuran-2-yl)methyl 3-methylbutanoate | 397.2 |
| 175 | 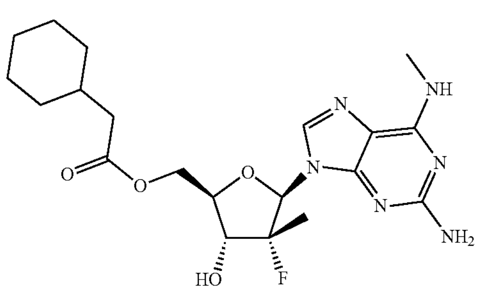 [SMILES: CNc1nc(N)nc2c1ncn2[C@@H]1O[C@H](COC(=O)CC2CCCCC2)[C@@H](O)[C@@]1(C)F] | ((2R,3R,4R,5R)-5-(2-amino-6-(methylamino)-9H-purin-9-yl)-4-fluoro-3-hydroxy-4-methyltetrahydrofuran-2-yl)methyl 2-cyclohexylacetate | 437 |

TABLE 1-continued

Exemplary compounds

| Cpd. No. | Structure | Chemical Name | ESI-MS (M + H)+ (m/z) |
|---|---|---|---|
| 176 | 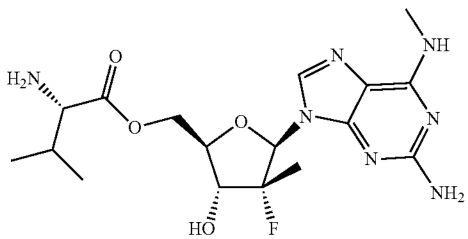 [SMILES: CNc1nc(N)nc2c1ncn2[C@@H]1O[C@H](COC(=O)[C@@H](N)C(C)C)[C@@H](O)[C@@]1(C)F] | ((2R,3R,4R,5R)-5-(2-amino-6-(methylamino)-9H-purin-9-yl)-4-fluoro-3-hydroxy-4-methyltetrahydrofuran-2-yl)methyl L-valinate | 412.1 |
| 177 | 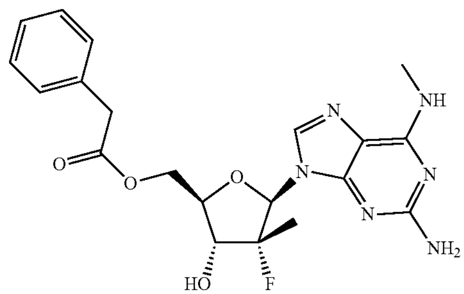 [SMILES: CNc1nc(N)nc2c1ncn2[C@@H]1O[C@H](COC(=O)Cc2ccccc2)[C@@H](O)[C@@]1(C)F] | ((2R,3R,4R,5R)-5-(2-amino-6-(methylamino)-9H-purin-9-yl)-4-fluoro-3-hydroxy-4-methyltetrahydrofuran-2-yl)methyl 2-phenylacetate | 431.1 |
| 178 | 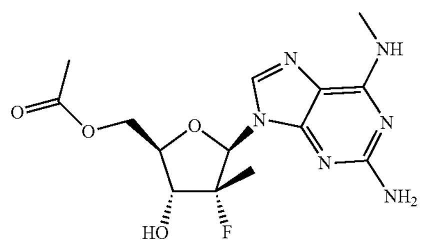 [SMILES: CNc1nc(N)nc2c1ncn2[C@@H]1O[C@H](COC(C)=O)[C@@H](O)[C@@]1(C)F] | ((2R,3R,4R,5R)-5-(2-amino-6-(methylamino)-9H-purin-9-yl)-4-fluoro-3-hydroxy-4-methyltetrahydrofuran-2-yl)methyl acetate | 355.0 |
| 179 | 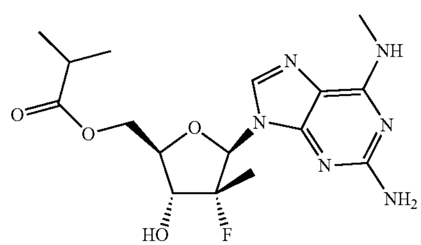 [SMILES: CNc1nc(N)nc2c1ncn2[C@@H]1O[C@H](COC(=O)C(C)C)[C@@H](O)[C@@]1(C)F] | ((2R,3R,4R,5R)-5-(2-amino-6-(methylamino)-9H-purin-9-yl)-4-fluoro-3-hydroxy-4-methyltetrahydrofuran-2-yl)methyl isobutyrate | |
| 180 | 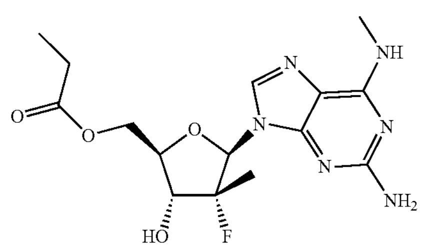 [SMILES: CCC(=O)OC[C@H]1O[C@@H](n2cnc3c(NC)nc(N)nc32)[C@](C)(F)[C@@H]1O] | ((2R,3R,4R,5R)-5-(2-amino-6-(methylamino)-9H-purin-9-yl)-4-fluoro-3-hydroxy-4-methyltetrahydrofuran-2-yl)methyl propionate | 369.2 |
| 181 | 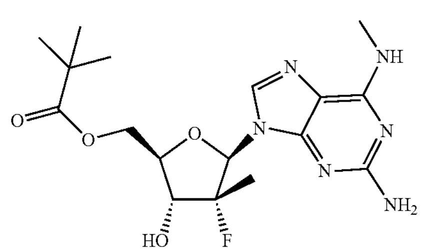 [SMILES: CNc1nc(N)nc2c1ncn2[C@@H]1O[C@H](COC(=O)C(C)(C)C)[C@@H](O)[C@@]1(C)F] | (((2R,3R,4R,5R)-5-(2-amino-6-(methylamino)-9H-purin-9-yl)-4-fluoro-3-hydroxy-4-methyltetrahydrofuran-2-yl)methoxy)methyl pivalate | |

TABLE 1-continued

Exemplary compounds

| Cpd. No. | Structure | Chemical Name | ESI-MS (M + H)+ (m/z) |
|---|---|---|---|
| 182 | 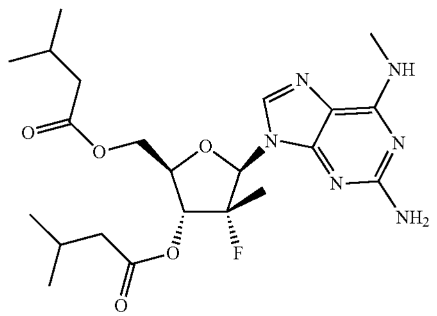 [SMILES: CNc1nc(N)nc2c1ncn2[C@@H]1O[C@H](COC(=O)CC(C)C)[C@@H](OC(=O)CC(C)C)[C@@]1(C)F] | (2R,3R,4R,5R)-5-(2-amino-6-(methylamino)-9H-purin-9-yl)-4-fluoro-4-methyl-2-(((3-methylbutanoyl)oxy)methyl)tetrahydrofuran-3-yl 3-methylbutanoate | |
| 183 | 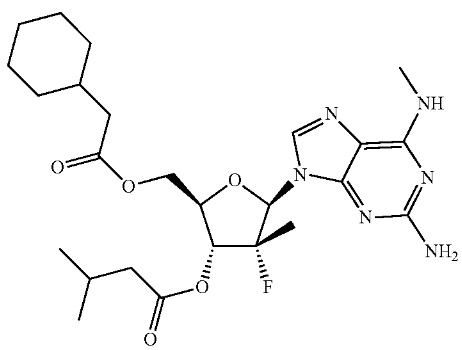 [SMILES: CNc1nc(N)nc2c1ncn2[C@@H]1O[C@H](COC(=O)CC2CCCCC2)[C@@H](OC(=O)CC(C)C)[C@@]1(C)F] | (2R,3R,4R,5R)-5-(2-amino-6-(methylamino)-9H-purin-9-yl)-2-((2-cyclohexylacetoxy)methyl)-4-fluoro-4-methyltetrahydrofuran-3-yl 3-methylbutanoate | 521.2 |
| 184 | 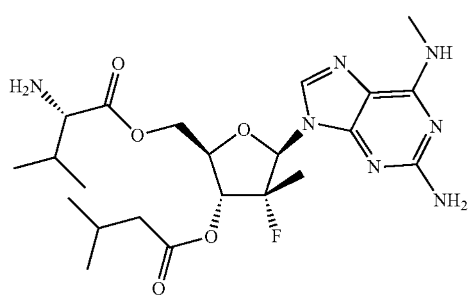 [SMILES: CNc1nc(N)nc2c1ncn2[C@@H]1O[C@H](COC(=O)[C@@H](N)C(C)C)[C@@H](OC(=O)CC(C)C)[C@@]1(C)F] | ((2R,3R,4R,5R)-5-(2-amino-6-(methylamino)-9H-purin-9-yl)-4-fluoro-4-methyl-3-((3-methylbutanoyl)oxy)tetrahydrofuran-2-yl)methyl L-valinate | |
| 185 | 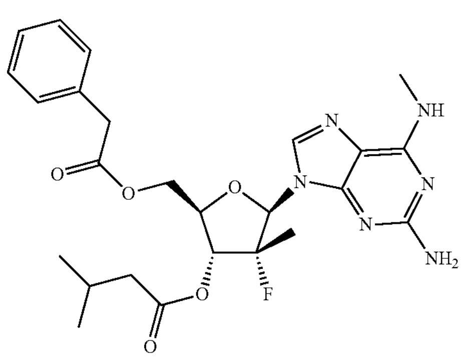 [SMILES: CNc1nc(N)nc2c1ncn2[C@@H]1O[C@H](COC(=O)Cc2ccccc2)[C@@H](OC(=O)CC(C)C)[C@@]1(C)F] | (2R,3R,4R,5R)-5-(2-amino-6-(methylamino)-9H-purin-9-yl)-4-fluoro-4-methyl-2-((2-phenylacetoxy)methyl)tetrahydrofuran-3-yl 3-methylbutanoate | 515.2 |

TABLE 1-continued

Exemplary compounds

| Cpd. No. | Structure | Chemical Name | ESI-MS (M + H)+ (m/z) |
|---|---|---|---|
| 186 | 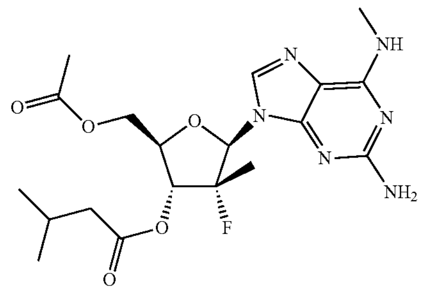 [SMILES: CNc1nc(N)nc2c1ncn2[C@@H]1O[C@H](COC(C)=O)[C@@H](OC(=O)CC(C)C)[C@@]1(C)F] | (2R,3R,4R,5R)-2-(acetoxymethyl)-5-(2-amino-6-(methylamino)-9H-purin-9-yl)-4-fluoro-4-methyltetrahydrofuran-3-yl 3-methylbutanoate | 439.1 |
| 187 | 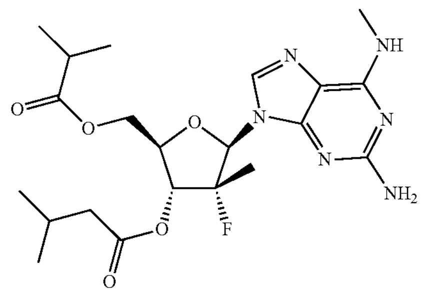 [SMILES: CNc1nc(N)nc2c1ncn2[C@@H]1O[C@H](COC(=O)C(C)C)[C@@H](OC(=O)CC(C)C)[C@@]1(C)F] | (2R,3R,4R,5R)-5-(2-amino-6-(methylamino)-9H-purin-9-yl)-4-fluoro-2-((isobutyryloxy)methyl)-4-methyltetrahydrofuran-3-yl 3-methylbutanoate | 467.2 |
| 188 | 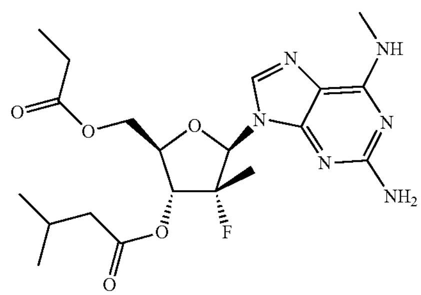 [SMILES: CCC(=O)OC[C@H]1O[C@@H](n2cnc3c(NC)nc(N)nc32)[C@](C)(F)[C@@H]1OC(=O)CC(C)C] | (2R,3R,4R,5R)-5-(2-amino-6-(methylamino)-9H-purin-9-yl)-4-fluoro-4-methyl-2-((propionyloxy)methyl)tetrahydrofuran-3-yl 3-methylbutanoate | 453.1 |
| 189 | 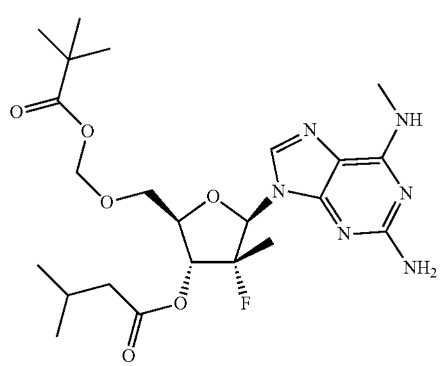 [SMILES: CNc1nc(N)nc2c1ncn2[C@@H]1O[C@H](COCOC(=O)C(C)(C)C)[C@@H](OC(=O)CC(C)C)[C@@]1(C)F] | (2R,3R,4R,5R)-5-(2-amino-6-(methylamino)-9H-purin-9-yl)-4-fluoro-4-methyl-2-(((pivaloyloxy)methoxy)methyl)tetrahydrofuran-3-yl 3-methylbutanoate | |

TABLE 1-continued

Exemplary compounds

| Cpd. No. | Structure | Chemical Name | ESI-MS (M + H)+ (m/z) |
|---|---|---|---|
| 190 | 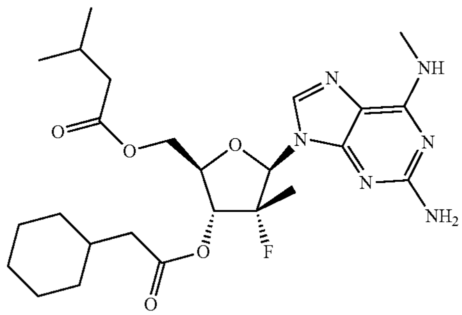 [SMILES: CNc1nc(N)nc2c1ncn2[C@@H]1O[C@H](COC(=O)CC(C)C)[C@@H](OC(=O)CC2CCCCC2)[C@@]1(C)F] | ((2R,3R,4R,5R)-5-(2-amino-6-(methylamino)-9H-purin-9-yl)-3-(2-cyclohexylacetoxy)-4-fluoro-4-methyltetrahydrofuran-2-yl)methyl 3-methylbutanoate | 521.3 |
| 191 | 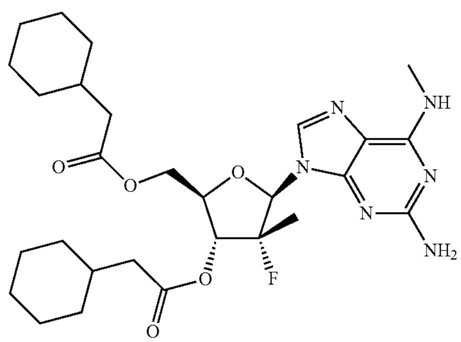 [SMILES: CNc1nc(N)nc2c1ncn2[C@@H]1O[C@H](COC(=O)CC2CCCCC2)[C@@H](OC(=O)CC2CCCCC2)[C@@]1(C)F] | (2R,3R,4R,5R)-5-(2-amino-6-(methylamino)-9H-purin-9-yl)-2-((2-cyclohexylacetoxy)methyl)-4-fluoro-4-methyltetrahydrofuran-3-yl 2-cyclohexylacetate | 561.3 |
| 192 | 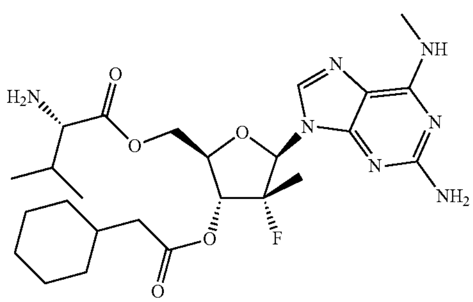 [SMILES: CNc1nc(N)nc2c1ncn2[C@@H]1O[C@H](COC(=O)[C@@H](N)C(C)C)[C@@H](OC(=O)CC2CCCCC2)[C@@]1(C)F] | ((2R,3R,4R,5R)-5-(2-amino-6-(methylamino)-9H-purin-9-yl)-3-(2-cyclohexylacetoxy)-4-fluoro-4-methyltetrahydrofuran-2-yl)methyl L-valinate | |
| 193 | 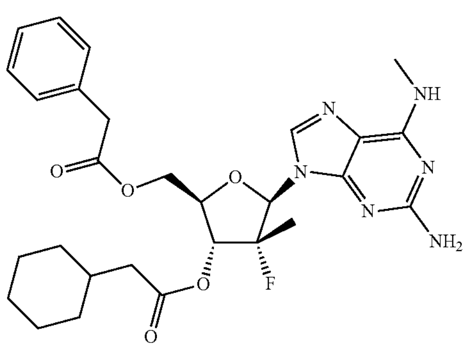 [SMILES: CNc1nc(N)nc2c1ncn2[C@@H]1O[C@H](COC(=O)Cc2ccccc2)[C@@H](OC(=O)CC2CCCCC2)[C@@]1(C)F] | ((2R,3R,4R,5R)-5-(2-amino-6-(methylamino)-9H-purin-9-yl)-3-(2-cyclohexylacetoxy)-4-fluoro-4-methyltetrahydrofuran-2-yl)methyl 2-phenylacetate | 555.2 |

TABLE 1-continued

Exemplary compounds

| Cpd. No. | Structure | Chemical Name | ESI-MS (M + H)+ (m/z) |
|---|---|---|---|
| 194 | 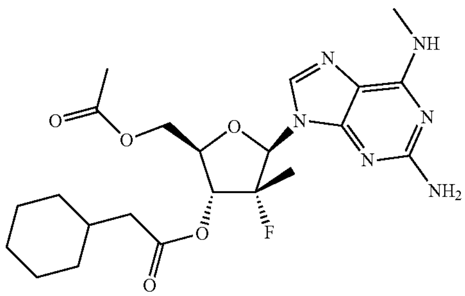 [SMILES: CNc1nc(N)nc2c1ncn2[C@@H]1O[C@H](COC(C)=O)[C@@H](OC(=O)CC2CCCCC2)[C@@]1(C)F] | (2R,3R,4R,5R)-2-(acetoxymethyl)-5-(2-amino-6-(methylamino)-9H-purin-9-yl)-4-fluoro-4-methyltetrahydrofuran-3-yl 2-cyclohexylacetate | 479.2 |
| 195 | 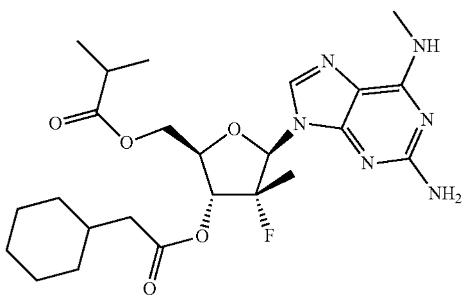 [SMILES: CNc1nc(N)nc2c1ncn2[C@@H]1O[C@H](COC(=O)C(C)C)[C@@H](OC(=O)CC2CCCCC2)[C@@]1(C)F] | ((2R,3R,4R,5R)-5-(2-amino-6-(methylamino)-9H-purin-9-yl)-3-(2-cyclohexylacetoxy)-4-fluoro-4-methyltetrahydrofuran-2-yl)methyl isobutyrate | 507.3 |
| 196 | 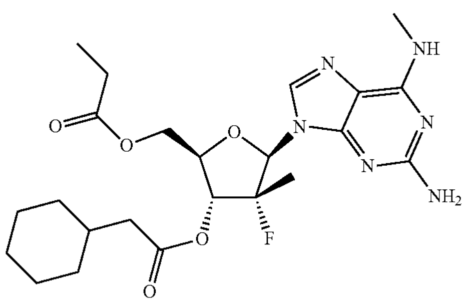 [SMILES: CCC(=O)OC[C@H]1O[C@@H](n2cnc3c(NC)nc(N)nc32)[C@](C)(F)[C@@H]1OC(=O)CC1CCCCC1] | ((2R,3R,4R,5R)-5-(2-amino-6-(methylamino)-9H-purin-9-yl)-3-(2-cyclohexylacetoxy)-4-fluoro-4-methyltetrahydrofuran-2-yl)methyl propionate | 493.2 |
| 197 | 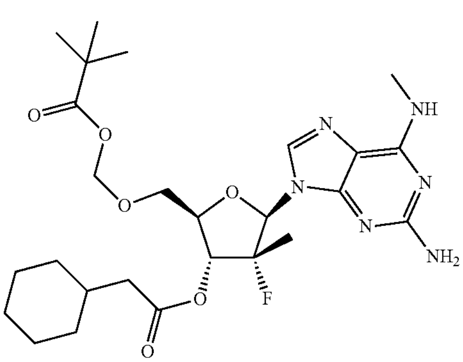 [SMILES: CNc1nc(N)nc2c1ncn2[C@@H]1O[C@H](COCOC(=O)C(C)(C)C)[C@@H](OC(=O)CC2CCCCC2)[C@@]1(C)F] | (((2R,3R,4R,5R)-5-(2-amino-6-(methylamino)-9H-purin-9-yl)-3-(2-cyclohexylacetoxy)-4-fluoro-4-methyltetrahydrofuran-2-yl)methoxy)methyl pivalate | |

TABLE 1-continued

Exemplary compounds

| Cpd. No. | Structure | Chemical Name | ESI-MS (M + H)+ (m/z) |
|---|---|---|---|
| 198 | 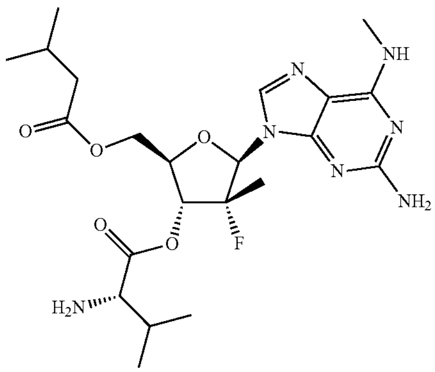 [SMILES: CNc1nc(N)nc2c1ncn2[C@@H]1O[C@H](COC(=O)CC(C)C)[C@@H](OC(=O)[C@@H](N)C(C)C)[C@@]1(C)F] | (2R,3R,4R,5R)-5-(2-amino-6-(methylamino)-9H-purin-9-yl)-4-fluoro-4-methyl-2-(((3-methylbutanoyl)oxy)methyl)tetrahydrofuran-3-yl L-valinate | |
| 199 | 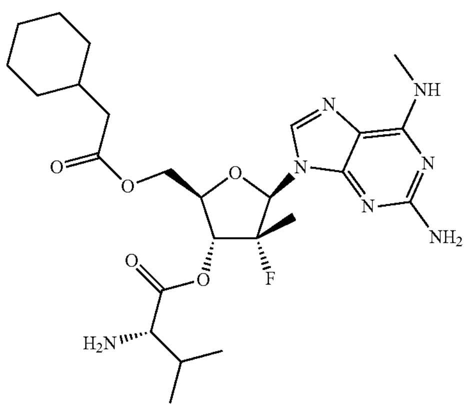 [SMILES: CNc1nc(N)nc2c1ncn2[C@@H]1O[C@H](COC(=O)CC2CCCCC2)[C@@H](OC(=O)[C@@H](N)C(C)C)[C@@]1(C)F] | (2R,3R,4R,5R)-5-(2-amino-6-(methylamino)-9H-purin-9-yl)-2-((2-cyclohexylacetoxy)methyl)-4-fluoro-4-methyltetrahydrofuran-3-yl L-valinate | |
| 200 | 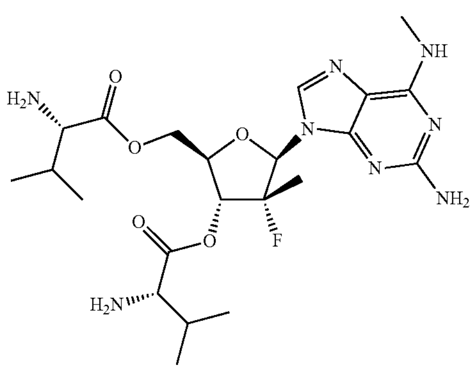 [SMILES: CNc1nc(N)nc2c1ncn2[C@@H]1O[C@H](COC(=O)[C@@H](N)C(C)C)[C@@H](OC(=O)[C@@H](N)C(C)C)[C@@]1(C)F] | ((2R,3R,4R,5R)-3-((L-valyl)oxy)-5-(2-amino-6-(methylamino)-9H-purin-9-yl)-4-fluoro-4-methyltetrahydrofuran-2-yl)methyl L-valinate | |

TABLE 1-continued

Exemplary compounds

| Cpd. No. | Structure | Chemical Name | ESI-MS (M + H)+ (m/z) |
|---|---|---|---|
| 201 | 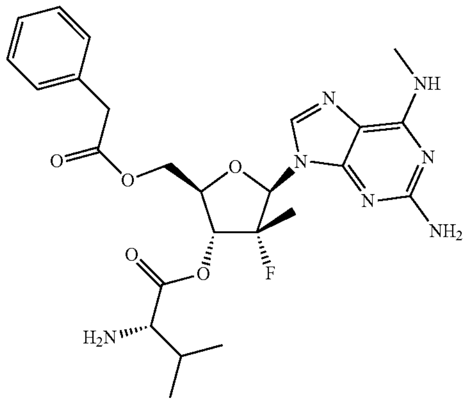 [SMILES: CNc1nc(N)nc2c1ncn2[C@@H]1O[C@H](COC(=O)Cc2ccccc2)[C@@H](OC(=O)[C@@H](N)C(C)C)[C@@]1(C)F] | (2R,3R,4R,5R)-5-(2-amino-6-(methylamino)-9H-purin-9-yl)-4-fluoro-4-methyl-2-((2-phenylacetoxy)methyl)tetrahydrofuran-3-yl L-valinate | |
| 202 | 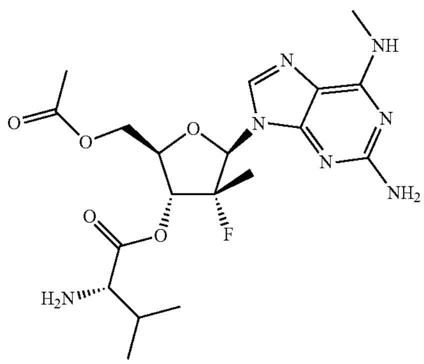 [SMILES: CNc1nc(N)nc2c1ncn2[C@@H]1O[C@H](COC(C)=O)[C@@H](OC(=O)[C@@H](N)C(C)C)[C@@]1(C)F] | (2R,3R,4R,5R)-2-(acetoxymethyl)-5-(2-amino-6-(methylamino)-9H-purin-9-yl)-4-fluoro-4-methyltetrahydrofuran-3-yl L-valinate | |
| 203 | 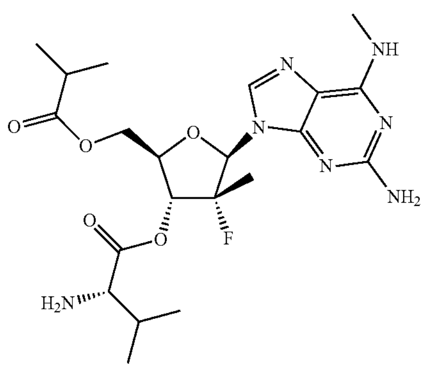 [SMILES: CNc1nc(N)nc2c1ncn2[C@@H]1O[C@H](COC(=O)C(C)C)[C@@H](OC(=O)[C@@H](N)C(C)C)[C@@]1(C)F] | (2R,3R,4R,5R)-5-(2-amino-6-(methylamino)-9H-purin-9-yl)-4-fluoro-2-((isobutyryloxy)methyl)-4-methyltetrahydrofuran-3-yl L-valinate | |
| 204 | 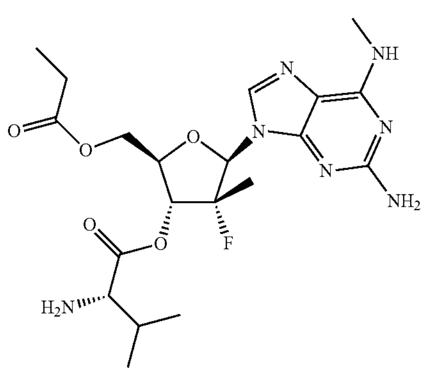 [SMILES: CCC(=O)OC[C@H]1O[C@@H](n2cnc3c(NC)nc(N)nc32)[C@](C)(F)[C@@H]1OC(=O)[C@@H](N)C(C)C] | (2R,3R,4R,5R)-5-(2-amino-6-(methylamino)-9H-purin-9-yl)-4-fluoro-4-methyl-2-((propionyloxy)methyl)tetrahydrofuran-3-yl L-valinate | |

TABLE 1-continued

Exemplary compounds

| Cpd. No. | Structure | Chemical Name | ESI-MS (M + H)+ (m/z) |
|---|---|---|---|
| 205 | 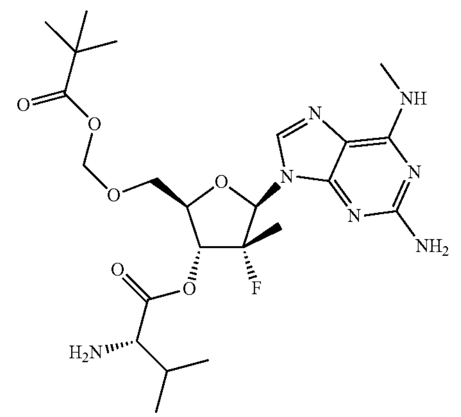 [SMILES: CNc1nc(N)nc2c1ncn2[C@@H]1O[C@H](COCOC(=O)C(C)(C)C)[C@@H](OC(=O)[C@@H](N)C(C)C)[C@@]1(C)F] | (2R,3R,4R,5R)-5-(2-amino-6-(methylamino)-9H-purin-9-yl)-4-fluoro-4-methyl-2-(((pivaloyloxy)methoxy)methyl)tetrahydrofuran-3-yl L-valinate | |
| 206 | 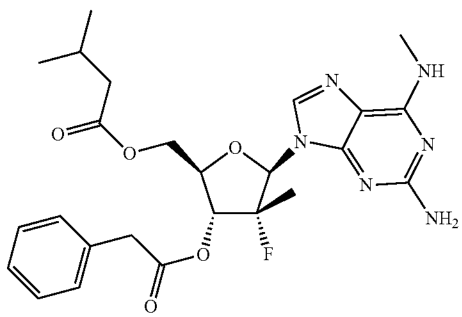 [SMILES: CNc1nc(N)nc2c1ncn2[C@@H]1O[C@H](COC(=O)CC(C)C)[C@@H](OC(=O)Cc2ccccc2)[C@@]1(C)F] | ((2R,3R,4R,5R)-5-(2-amino-6-(methylamino)-9H-purin-9-yl)-4-fluoro-4-methyl-3-(2-phenylacetoxy)tetrahydrofuran-2-yl)methyl 3-methylbutanoate | 515.2 |
| 207 | 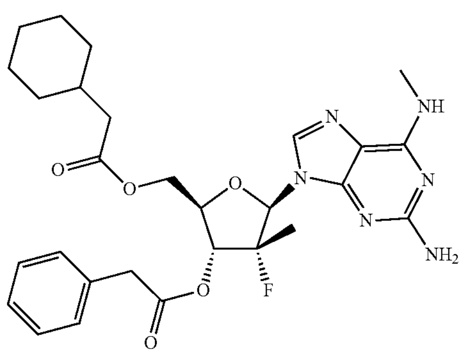 [SMILES: CNc1nc(N)nc2c1ncn2[C@@H]1O[C@H](COC(=O)CC2CCCCC2)[C@@H](OC(=O)Cc2ccccc2)[C@@]1(C)F] | (2R,3R,4R,5R)-5-(2-amino-6-(methylamino)-9H-purin-9-yl)-2-((2-cyclohexylacetoxy)methyl)-4-fluoro-4-methyltetrahydrofuran-3-yl 2-phenylacetate | 555.2 |
| 208 | 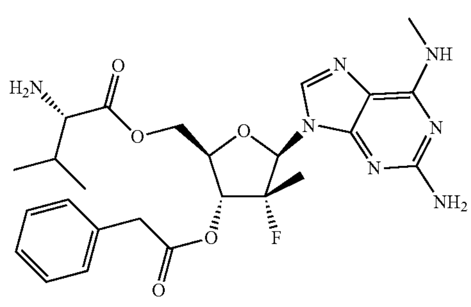 [SMILES: CNc1nc(N)nc2c1ncn2[C@@H]1O[C@H](COC(=O)[C@@H](N)C(C)C)[C@@H](OC(=O)Cc2ccccc2)[C@@]1(C)F] | ((2R,3R,4R,5R)-5-(2-amino-6-(methylamino)-9H-purin-9-yl)-4-fluoro-4-methyl-3-(2-phenylacetoxy)tetrahydrofuran-2-yl)methyl L-valinate | |

TABLE 1-continued

Exemplary compounds

| Cpd. No. | Structure | Chemical Name | ESI-MS (M + H)+ (m/z) |
|---|---|---|---|
| 209 | 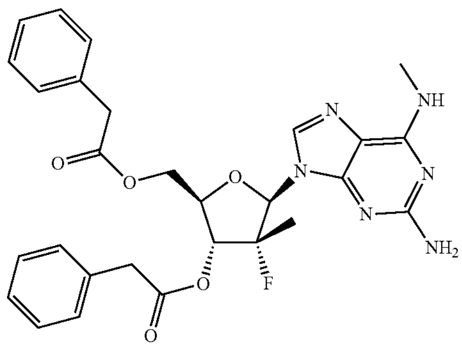 [SMILES: CNc1nc(N)nc2c1ncn2[C@@H]1O[C@H](COC(=O)Cc2ccccc2)[C@@H](OC(=O)Cc2ccccc2)[C@@]1(C)F] | (2R,3R,4R,5R)-5-(2-amino-6-(methylamino)-9H-purin-9-yl)-4-fluoro-4-methyl-2-((2-phenylacetoxy)methyl)tetrahydrofuran-3-yl 2-phenylacetate | 549.1 |
| 210 | 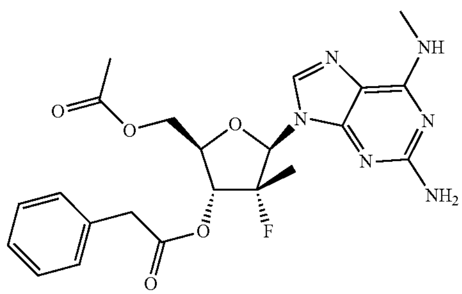 [SMILES: CNc1nc(N)nc2c1ncn2[C@@H]1O[C@H](COC(C)=O)[C@@H](OC(=O)Cc2ccccc2)[C@@]1(C)F] | (2R,3R,4R,5R)-2-(acetoxymethyl)-5-(2-amino-6-(methylamino)-9H-purin-9-yl)-4-fluoro-4-methyltetrahydrofuran-3-yl 2-phenylacetate | 473.1 |
| 211 | 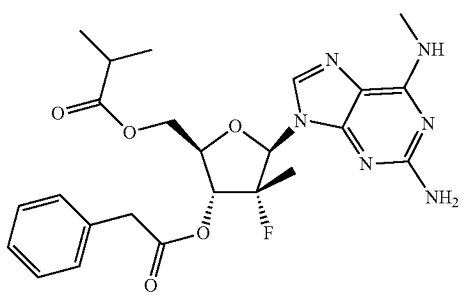 [SMILES: CNc1nc(N)nc2c1ncn2[C@@H]1O[C@H](COC(=O)C(C)C)[C@@H](OC(=O)Cc2ccccc2)[C@@]1(C)F] | ((2R,3R,4R,5R)-5-(2-amino-6-(methylamino)-9H-purin-9-yl)-4-fluoro-4-methyl-3-(2-phenylacetoxy)tetrahydrofuran-2-yl)methyl isobutyrate | 501.2 |
| 212 | 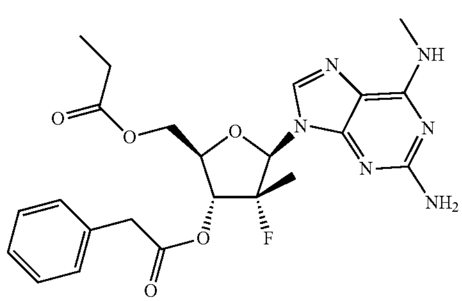 [SMILES: CCC(=O)OC[C@H]1O[C@@H](n2cnc3c(NC)nc(N)nc32)[C@](C)(F)[C@@H]1OC(=O)Cc1ccccc1] | ((2R,3R,4R,5R)-5-(2-amino-6-(methylamino)-9H-purin-9-yl)-4-fluoro-4-methyl-3-(2-phenylacetoxy)tetrahydrofuran-2-yl)methyl propionate | 487.2 |

TABLE 1-continued

Exemplary compounds

| Cpd. No. | Structure | Chemical Name | ESI-MS (M + H)+ (m/z) |
|---|---|---|---|
| 213 | 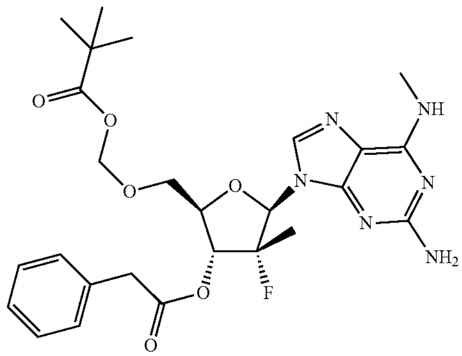 [SMILES: CNc1nc(N)nc2c1ncn2[C@@H]1O[C@H](COCOC(=O)C(C)(C)C)[C@@H](OC(=O)Cc2ccccc2)[C@@]1(C)F] | (((2R,3R,4R,5R)-5-(2-amino-6-(methylamino)-9H-purin-9-yl)-4-fluoro-4-methyl-3-(2-phenylacetoxy)tetrahydrofuran-2-yl)methoxy)methyl pivalate | |
| 214 | 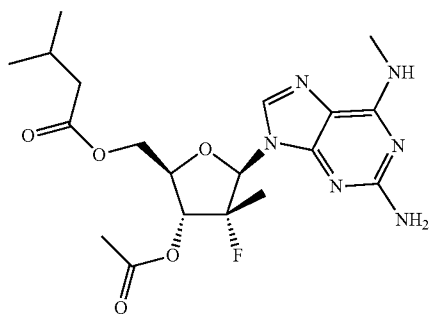 [SMILES: CNc1nc(N)nc2c1ncn2[C@@H]1O[C@H](COC(=O)CC(C)C)[C@@H](OC(C)=O)[C@@]1(C)F] | ((2R,3R,4R,5R)-3-acetoxy-5-(2-amino-6-(methylamino)-9H-purin-9-yl)-4-fluoro-4-methyltetrahydrofuran-2-yl)methyl 3-methylbutanoate | 439.2 |
| 215 | 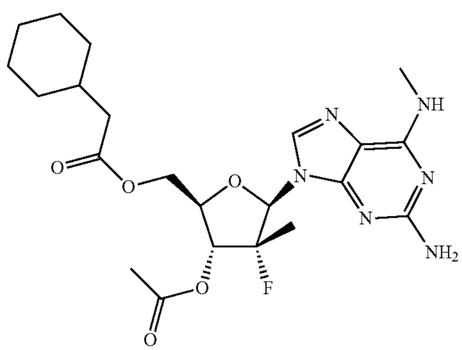 [SMILES: CNc1nc(N)nc2c1ncn2[C@@H]1O[C@H](COC(=O)CC2CCCCC2)[C@@H](OC(C)=O)[C@@]1(C)F] | ((2R,3R,4R,5R)-3-acetoxy-5-(2-amino-6-(methylamino)-9H-purin-9-yl)-4-fluoro-4-methyltetrahydrofuran-2-yl)methyl 2-cyclohexylacetate | 479.2 |
| 216 | 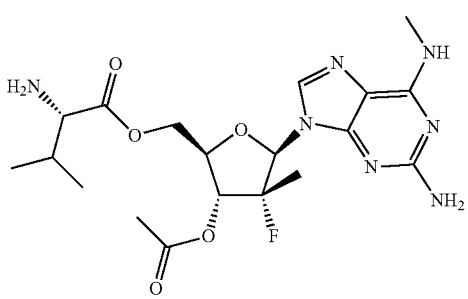 [SMILES: CNc1nc(N)nc2c1ncn2[C@@H]1O[C@H](COC(=O)[C@@H](N)C(C)C)[C@@H](OC(C)=O)[C@@]1(C)F] | ((2R,3R,4R,5R)-3-acetoxy-5-(2-amino-6-(methylamino)-9H-purin-9-yl)-4-fluoro-4-methyltetrahydrofuran-2-yl)methyl L-valinate | |

TABLE 1-continued

Exemplary compounds

| Cpd. No. | Structure | Chemical Name | ESI-MS (M + H)+ (m/z) |
|---|---|---|---|
| 217 | 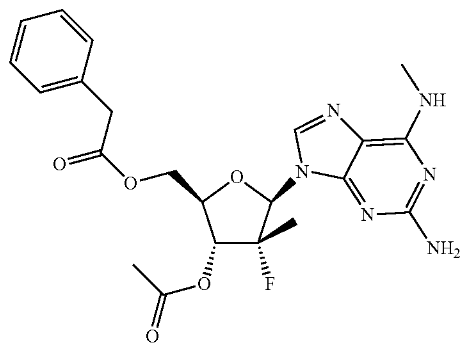 [SMILES: CNc1nc(N)nc2c1ncn2[C@@H]1O[C@H](COC(=O)Cc2ccccc2)[C@@H](OC(C)=O)[C@@]1(C)F] | ((2R,3R,4R,5R)-3-acetoxy-5-(2-amino-6-(methylamino)-9H-purin-9-yl)-4-fluoro-4-methyltetrahydrofuran-2-yl)methyl 2-phenylacetate | 473.1 |
| 218 | 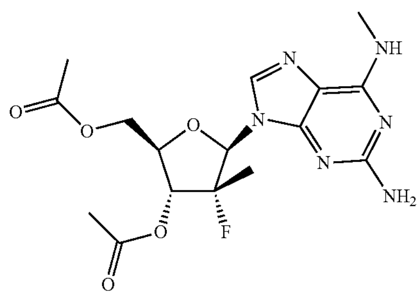 [SMILES: CNc1nc(N)nc2c1ncn2[C@@H]1O[C@H](COC(C)=O)[C@@H](OC(C)=O)[C@@]1(C)F] | ((2R,3R,4R,5R)-3-acetoxy-5-(2-amino-6-(methylamino)-9H-purin-9-yl)-4-fluoro-4-methyltetrahydrofuran-2-yl)methyl acetate | 397.0 |
| 219 | 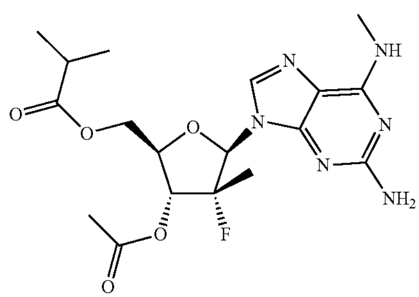 [SMILES: CNc1nc(N)nc2c1ncn2[C@@H]1O[C@H](COC(=O)C(C)C)[C@@H](OC(C)=O)[C@@]1(C)F] | ((2R,3R,4R,5R)-3-acetoxy-5-(2-amino-6-(methylamino)-9H-purin-9-yl)-4-fluoro-4-methyltetrahydrofuran-2-yl)methyl isobutyrate | 425.1 |
| 220 | 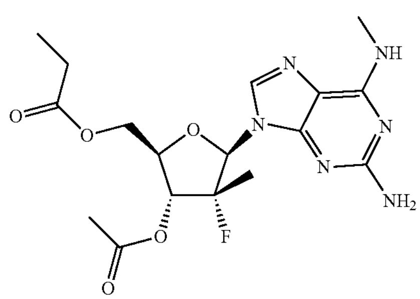 [SMILES: CCC(=O)OC[C@H]1O[C@@H](n2cnc3c(NC)nc(N)nc32)[C@](C)(F)[C@@H]1OC(C)=O] | ((2R,3R,4R,5R)-3-acetoxy-5-(2-amino-6-(methylamino)-9H-purin-9-yl)-4-fluoro-4-methyltetrahydrofuran-2-yl)methyl propionate | 411.1 |

TABLE 1-continued

Exemplary compounds

| Cpd. No. | Structure | Chemical Name | ESI-MS (M + H)+ (m/z) |
|---|---|---|---|
| 221 | 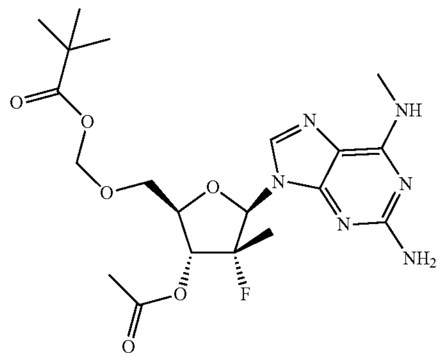 [SMILES: CNc1nc(N)nc2c1ncn2[C@@H]1O[C@H](COCOC(=O)C(C)(C)C)[C@@H](OC(C)=O)[C@@]1(C)F] | (((2R,3R,4R,5R)-3-acetoxy-5-(2-amino-6-(methylamino)-9H-purin-9-yl)-4-fluoro-4-methyltetrahydrofuran-2-yl)methoxy)methyl pivalate | |
| 222 | 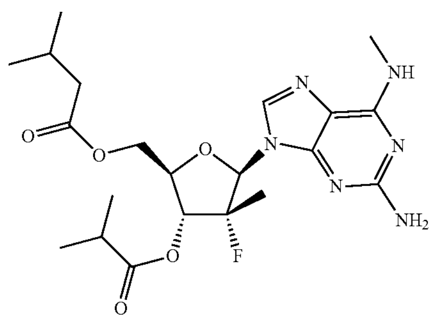 [SMILES: CNc1nc(N)nc2c1ncn2[C@@H]1O[C@H](COC(=O)CC(C)C)[C@@H](OC(=O)C(C)C)[C@@]1(C)F] | ((2R,3R,4R,5R)-5-(2-amino-6-(methylamino)-9H-purin-9-yl)-4-fluoro-3-(isobutyryloxy)-4-methyltetrahydrofuran-2-yl)methyl 3-methylbutanoate | 467.2 |
| 223 | 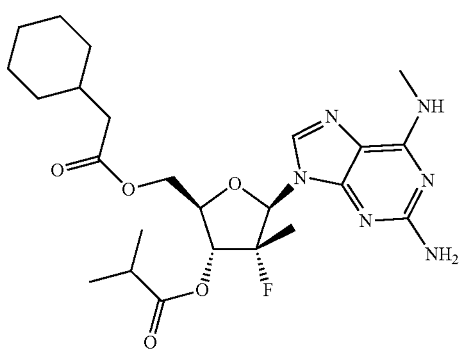 [SMILES: CNc1nc(N)nc2c1ncn2[C@@H]1O[C@H](COC(=O)CC2CCCCC2)[C@@H](OC(=O)C(C)C)[C@@]1(C)F] | (2R,3R,4R,5R)-5-(2-amino-6-(methylamino)-9H-purin-9-yl)-2-((2-cyclohexylacetoxy)methyl)-4-fluoro-4-methyltetrahydrofuran-3-yl isobutyrate | 507.2 |
| 224 | 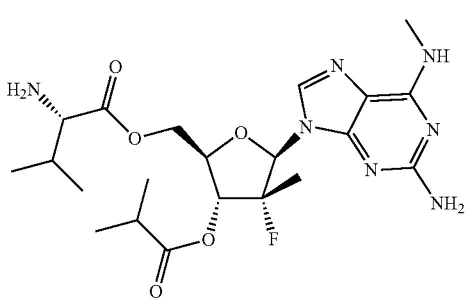 [SMILES: CNc1nc(N)nc2c1ncn2[C@@H]1O[C@H](COC(=O)[C@@H](N)C(C)C)[C@@H](OC(=O)C(C)C)[C@@]1(C)F] | ((2R,3R,4R,5R)-5-(2-amino-6-(methylamino)-9H-purin-9-yl)-4-fluoro-3-(isobutyryloxy)-4-methyltetrahydrofuran-2-yl)methyl L-valinate | |

TABLE 1-continued

Exemplary compounds

| Cpd. No. | Structure | Chemical Name | ESI-MS (M + H)+ (m/z) |
|---|---|---|---|
| 225 | 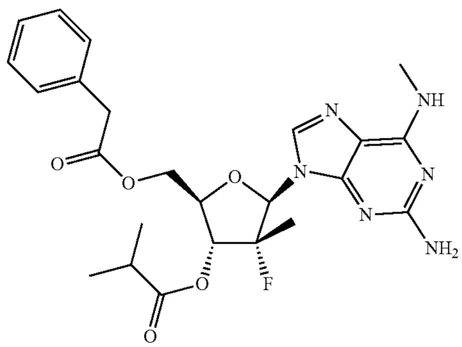 [SMILES: CNc1nc(N)nc2c1ncn2[C@@H]1O[C@H](COC(=O)Cc2ccccc2)[C@@H](OC(=O)C(C)C)[C@@]1(C)F] | (2R,3R,4R,5R)-5-(2-amino-6-(methylamino)-9H-purin-9-yl)-4-fluoro-4-methyl-2-((2-phenylacetoxy)methyl)tetrahydrofuran-3-yl isobutyrate | 501.2 |
| 226 | 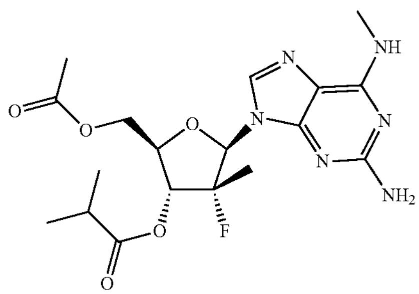 [SMILES: CNc1nc(N)nc2c1ncn2[C@@H]1O[C@H](COC(C)=O)[C@@H](OC(=O)C(C)C)[C@@]1(C)F] | (2R,3R,4R,5R)-2-(acetoxymethyl)-5-(2-amino-6-(methylamino)-9H-purin-9-yl)-4-fluoro-4-methyltetrahydrofuran-3-yl isobutyrate | 425.1 |
| 227 | 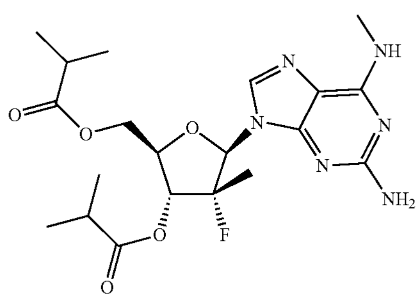 [SMILES: CNc1nc(N)nc2c1ncn2[C@@H]1O[C@H](COC(=O)C(C)C)[C@@H](OC(=O)C(C)C)[C@@]1(C)F] | (2R,3R,4R,5R)-5-(2-amino-6-(methylamino)-9H-purin-9-yl)-4-fluoro-2-((isobutyryloxy)methyl)-4-methyltetrahydrofuran-3-yl isobutyrate | 453.1 |
| 228 | 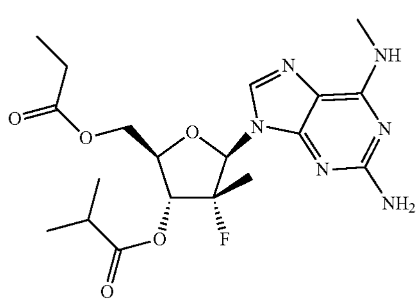 [SMILES: CCC(=O)OC[C@H]1O[C@@H](n2cnc3c(NC)nc(N)nc32)[C@](C)(F)[C@@H]1OC(=O)C(C)C] | (2R,3R,4R,5R)-5-(2-amino-6-(methylamino)-9H-purin-9-yl)-4-fluoro-4-methyl-2-((propionyloxy)methyl)tetrahydrofuran-3-yl isobutyrate | 439.2 |

TABLE 1-continued

Exemplary compounds

| Cpd. No. | Structure | Chemical Name | ESI-MS (M + H)+ (m/z) |
|---|---|---|---|
| 229 | 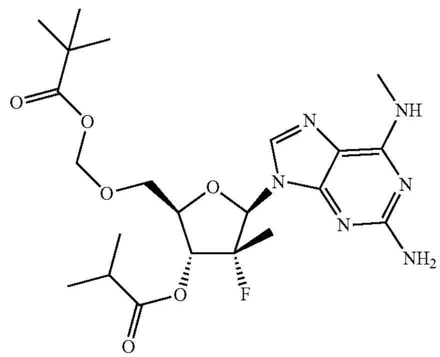 [SMILES: CNc1nc(N)nc2c1ncn2[C@@H]1O[C@H](COCOC(=O)C(C)(C)C)[C@@H](OC(=O)C(C)C)[C@@]1(C)F] | (((2R,3R,4R,5R)-5-(2-amino-6-(methylamino)-9H-purin-9-yl)-4-fluoro-3-(isobutyryloxy)-4-methyltetrahydrofuran-2-yl)methoxy)methyl pivalate | |
| 230 | 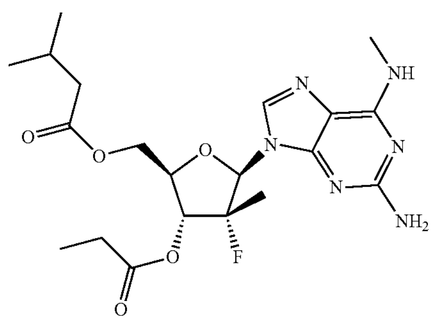 [SMILES: CCC(=O)O[C@@H]1[C@@H](COC(=O)CC(C)C)O[C@@H](n2cnc3c(NC)nc(N)nc32)[C@]1(C)F] | ((2R,3R,4R,5R)-5-(2-amino-6-(methylamino)-9H-purin-9-yl)-4-fluoro-4-methyl-3-(propionyloxy)tetrahydrofuran-2-yl)methyl 3-methylbutanoate | 453.2 |
| 231 | 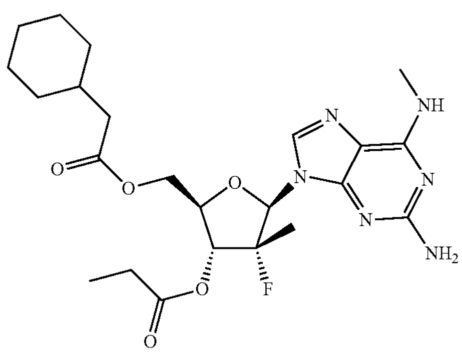 [SMILES: CCC(=O)O[C@@H]1[C@@H](COC(=O)CC2CCCCC2)O[C@@H](n2cnc3c(NC)nc(N)nc32)[C@]1(C)F] | (2R,3R,4R,5R)-5-(2-amino-6-(methylamino)-9H-purin-9-yl)-2-((2-cyclohexylacetoxy)methyl)-4-fluoro-4-methyltetrahydrofuran-3-yl propionate | 493.2 |
| 232 | 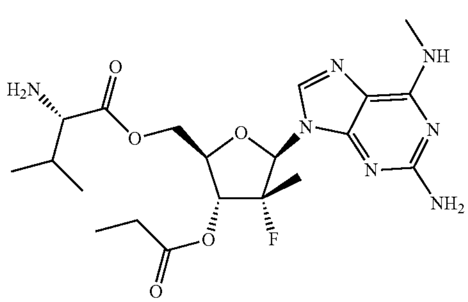 [SMILES: CCC(=O)O[C@@H]1[C@@H](COC(=O)[C@@H](N)C(C)C)O[C@@H](n2cnc3c(NC)nc(N)nc32)[C@]1(C)F] | ((2R,3R,4R,5R)-5-(2-amino-6-(methylamino)-9H-purin-9-yl)-4-fluoro-4-methyl-3-(propionyloxy)tetrahydrofuran-2-yl)methyl L-valinate | |

TABLE 1-continued

Exemplary compounds

| Cpd. No. | Structure | Chemical Name | ESI-MS (M + H)+ (m/z) |
|---|---|---|---|
| 233 | 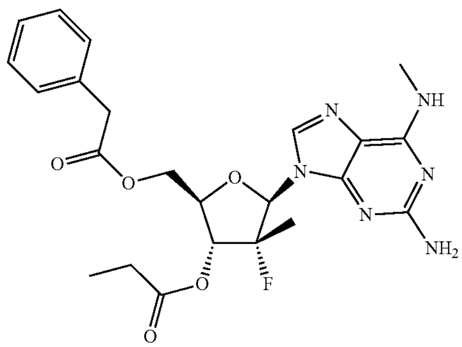 [SMILES: CCC(=O)O[C@@H]1[C@@H](COC(=O)Cc2ccccc2)O[C@@H](n2cnc3c(NC)nc(N)nc32)[C@]1(C)F] | (2R,3R,4R,5R)-5-(2-amino-6-(methylamino)-9H-purin-9-yl)-4-fluoro-4-methyl-2-((2-phenylacetoxy)methyl)tetrahydrofuran-3-yl propionate | 487.2 |
| 234 | 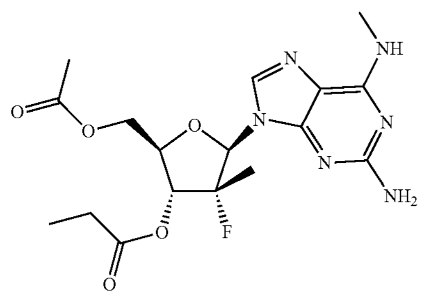 | (2R,3R,4R,5R)-2-(acetoxymethyl)-5-(2-amino-6-(methylamino)-9H-purin-9-yl)-4-fluoro-4-methyltetrahydrofuran-3-yl propionate | |
| 235 | 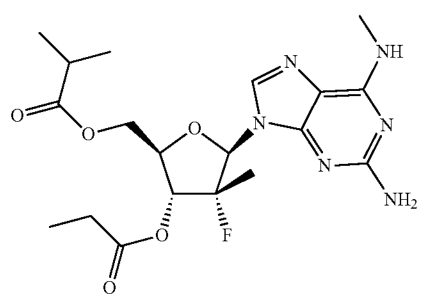 [SMILES: CCC(=O)O[C@@H]1[C@@H](COC(=O)C(C)C)O[C@@H](n2cnc3c(NC)nc(N)nc32)[C@]1(C)F] | ((2R,3R,4R,5R)-5-(2-amino-6-(methylamino)-9H-purin-9-yl)-4-fluoro-4-methyl-3-(propionyloxy)tetrahydrofuran-2-yl)methyl isobutyrate | 439.2 |
| 236 | 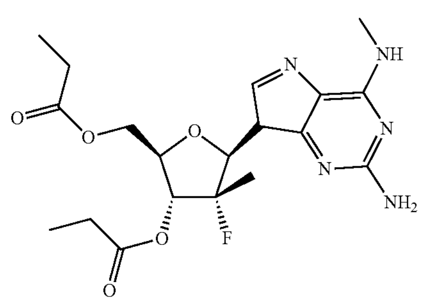 [SMILES: CCC(=O)OC[C@H]1O[C@@H](C2C=Nc3c(NC)nc(N)nc32)[C@](C)(F)[C@@H]1OC(=O)CC] | (2R,3R,4R,5R)-5-(2-amino-6-(methylamino)-9H-purin-9-yl)-4-fluoro-4-methyl-2-((propionyloxy)methyl)tetrahydrofuran-3-yl propionate | 425.1 |

TABLE 1-continued

Exemplary compounds

| Cpd. No. | Structure | Chemical Name | ESI-MS (M + H)+ (m/z) |
|---|---|---|---|
| 237 | 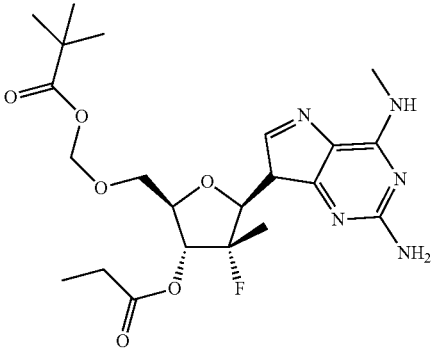 [SMILES: CCC(=O)O[C@@H]1[C@@H](COCOC(=O)C(C)(C)C)O[C@@H](C2C=Nc3c(NC)nc(N)nc32)[C@]1(C)F] | (((2R,3R,4R,5R)-5-(2-amino-6-(methylamino)-9H-purin-9-yl)-4-fluoro-4-methyl-3-(propionyloxy)tetrahydrofuran-2-yl)methoxy)methyl pivalate | |
| 238 | 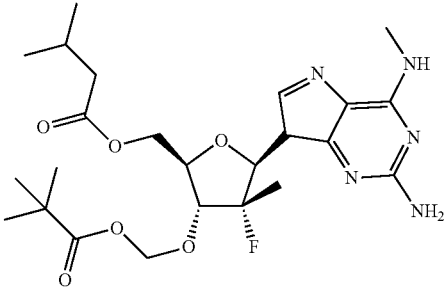 [SMILES: CNc1nc(N)nc2c1N=CC2[C@@H]1O[C@H](COC(=O)CC(C)C)[C@@H](OCOC(=O)C(C)(C)C)[C@@]1(C)F] | ((2R,3R,4R,5R)-5-(2-amino-6-(methylamino)-9H-purin-9-yl)-4-fluoro-4-methyl-3-((pivaloyloxy)methoxy)tetrahydrofuran-2-yl)methyl 3-methylbutanoate | |
| 239 | 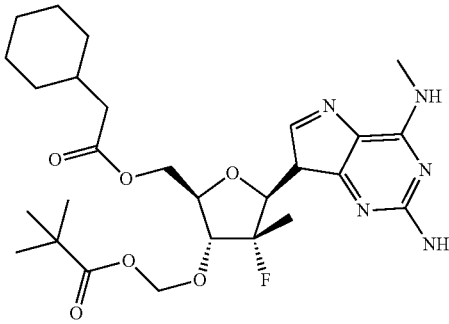 | (((2R,3R,4R,5R)-5-(2-amino-6-(methylamino)-9H-purin-9-yl)-2-((2-cyclohexylacetoxy)methyl)-4-fluoro-4-methyltetrahydrofuran-3-yl)oxy)methyl pivalate | |
| 240 | 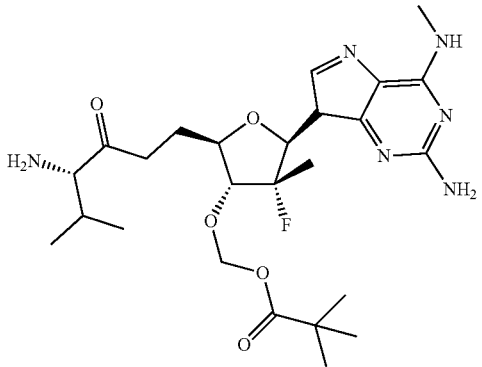 [SMILES: CNc1nc(N)nc2c1N=CC2[C@@H]1O[C@H](CCC(=O)[C@@H](N)C(C)C)[C@@H](OCOC(=O)C(C)(C)C)[C@@]1(C)F] | ((2R,3R,4R,5R)-5-(2-amino-6-(methylamino)-9H-purin-9-yl)-4-fluoro-4-methyl-3-((pivaloyloxy)methoxy)tetrahydrofuran-2-yl)methyl L-valinate | |

TABLE 1-continued

Exemplary compounds

| Cpd. No. | Structure | Chemical Name | ESI-MS (M + H)+ (m/z) |
|---|---|---|---|
| 241 | 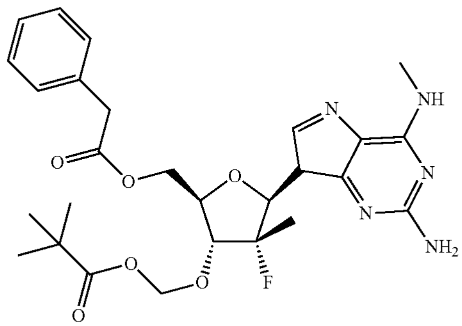 [SMILES: CNc1nc(N)nc2c1N=CC2[C@@H]1O[C@H](COC(=O)Cc2ccccc2)[C@@H](OCOC(=O)C(C)(C)C)[C@@]1(C)F] | (((2R,3R,4R,5R)-5-(2-amino-6-(methylamino)-9H-purin-9-yl)-4-fluoro-4-methyl-2-((2-phenylacetoxy)methyl)tetrahydrofuran-3-yl)oxy)methyl pivalate | |
| 242 | 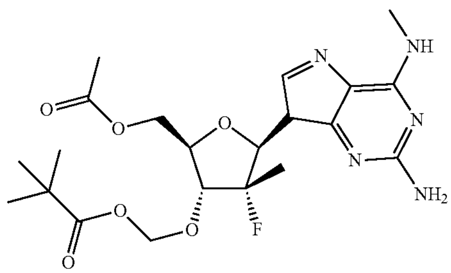 [SMILES: CNc1nc(N)nc2c1N=CC2[C@@H]1O[C@H](COC(C)=O)[C@@H](OCOC(=O)C(C)(C)C)[C@@]1(C)F] | (((2R,3R,4R,5R)-2-(acetoxymethyl)-5-(2-amino-6-(methylamino)-9H-purin-9-yl)-4-fluoro-4-methyltetrahydrofuran-3-yl)oxy)methyl pivalate | |
| 243 | 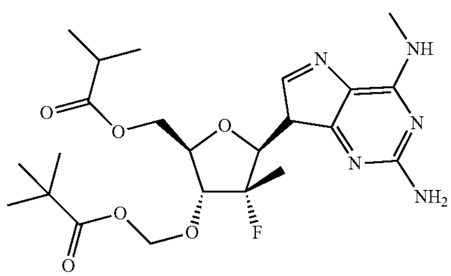 [SMILES: CNc1nc(N)nc2c1N=CC2[C@@H]1O[C@H](COC(=O)C(C)C)[C@@H](OCOC(=O)C(C)(C)C)[C@@]1(C)F] | (((2R,3R,4R,5R)-5-(2-amino-6-(methylamino)-9H-purin-9-yl)-4-fluoro-2-((isobutyryloxy)methyl)-4-methyltetrahydrofuran-3-yl)oxy) methyl pivalate | |
| 244 | 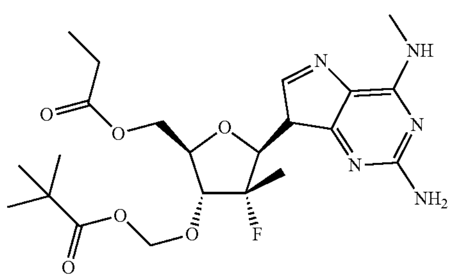 [SMILES: CCC(=O)OC[C@H]1O[C@@H](C2C=Nc3c(NC)nc(N)nc32)[C@](C)(F)[C@@H]1OCOC(=O)C(C)(C)C] | (((2R,3R,4R,5R)-5-(2-amino-6-(methylamino)-9H-purin-9-yl)-4-fluoro-4-methyl-2-((propionyloxy)methyl)tetrahydrofuran-3-yl)oxy) methyl pivalate | |
| 245 | 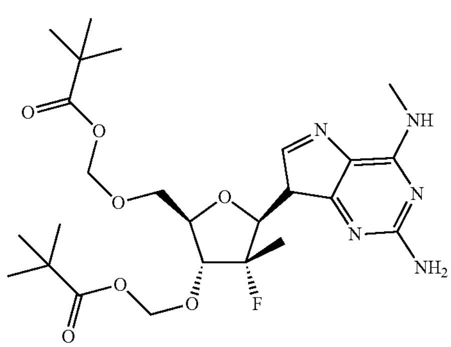 [SMILES: CNc1nc(N)nc2c1N=CC2[C@@H]1O[C@H](COCOC(=O)C(C)(C)C)[C@@H](OCOC(=O)C(C)(C)C)[C@@]1(C)F] | (((2R,3R,4R,5R)-5-(2-amino-6-(methylamino)-9H-purin-9-yl)-4-fluoro-4-methyl-2-(((pivaloyloxy)methoxy)methyl)tetrahydrofuran-3-yl)oxy) methyl pivalate | |

TABLE 1-continued

Exemplary compounds

| Cpd. No. | Structure | Chemical Name | ESI-MS (M + H)+ (m/z) |
|---|---|---|---|
| 246 | 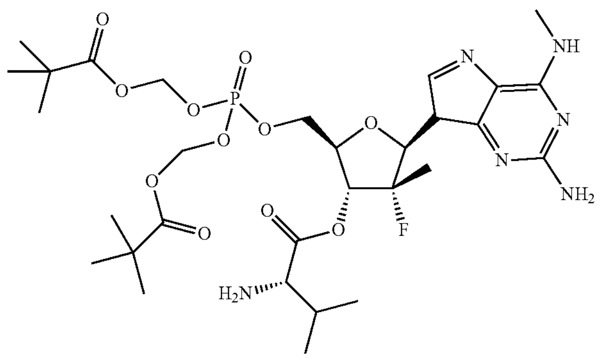 [SMILES: CNc1nc(N)nc2c1N=CC2[C@@H]1O[C@H](COP(=O)(OCOC(=O)C(C)(C)C)OCOC(=O)C(C)(C)C)[C@@H](OC(=O)[C@@H](N)C(C)C)[C@@]1(C)F] | ((2R,3R,4R,5R)-5-(2-amino-6-(methylamino)-9H-purin-9-yl)-3,4-dihydroxy-4-methyltetrahydrofuran-2-yl)methyl isobutyrate | |
| 247 | 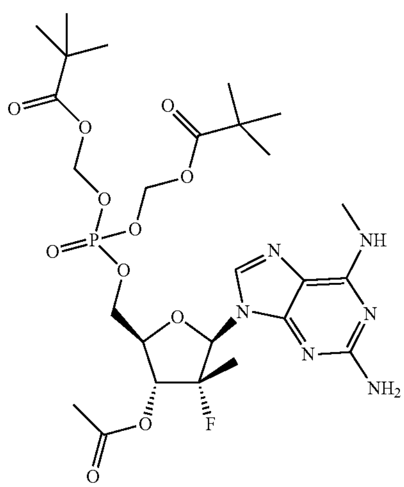 [SMILES: CNc1nc(N)nc2c1ncn2[C@@H]1O[C@H](COP(=O)(OCOC(=O)C(C)(C)C)OCOC(=O)C(C)(C)C)[C@@H](OC(C)=O)[C@@]1(C)F] | (2R,3R,4R,5R)-5-(2-amino-6-(methylamino)-9H-purin-9-yl)-4-fluoro-2-(((bis-((pivaloyloxy)methoxy)phosphoryl)oxy)methyl)-4-methyltetrahydrofuran-3-yl 3-acetate | |
| 248 | 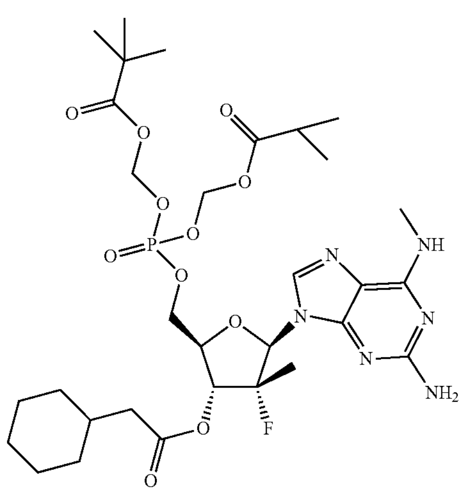 [SMILES: CNc1nc(N)nc2c1ncn2[C@@H]1O[C@H](COP(=O)(OCOC(=O)C(C)C)OCOC(=O)C(C)(C)C)[C@@H](OC(=O)CC2CCCCC2)[C@@]1(C)F] | (2R,3R,4R,5R)-5-(2-amino-6-(methylamino)-9H-purin-9-yl)-4-fluoro-2-(((bis-((pivaloyloxy)methoxy)phosphoryl)oxy)methyl)-4-methyltetrahydrofuran-3-yl cyclohexylacetate | |

TABLE 1-continued

Exemplary compounds

| Cpd. No. | Structure | Chemical Name | ESI-MS (M + H)+ (m/z) |
|---|---|---|---|
| 249 | 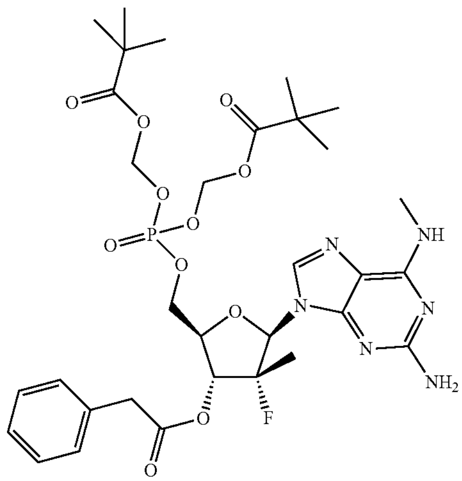 [SMILES: CNc1nc(N)nc2c1ncn2[C@@H]1O[C@H](COP(=O)(OCOC(=O)C(C)(C)C)OCOC(=O)C(C)(C)C)[C@@H](OC(=O)Cc2ccccc2)[C@@]1(C)F] | (2R,3R,4R,5R)-5-(2-amino-6-(methylamino)-9H-purin-9-yl)-4-fluoro-2-(((bis-((pivaloyloxy)methoxy)phosphoryl)oxy)methyl)-4-methyltetrahydrofuran-3-yl phenylacetate | |
| 250 | 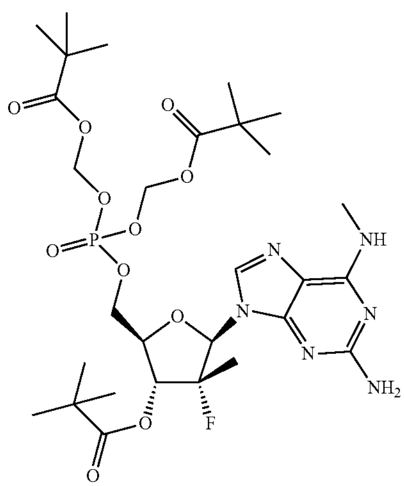 [SMILES: CNc1nc(N)nc2c1ncn2[C@@H]1O[C@H](COP(=O)(OCOC(=O)C(C)(C)C)OCOC(=O)C(C)(C)C)[C@@H](OC(=O)C(C)(C)C)[C@@]1(C)F] | (((2R,3R,4R,5R)-5-(2-amino-6-(methylamino)-9H-purin-9-yl)-4-fluoro-2-((((bis-((pivaloyloxy)methoxy)phosphoryl)oxy)methyl)-4-methyltetrahydrofuran-3-yl)oxy)methyl pivalate | |
| 251 | 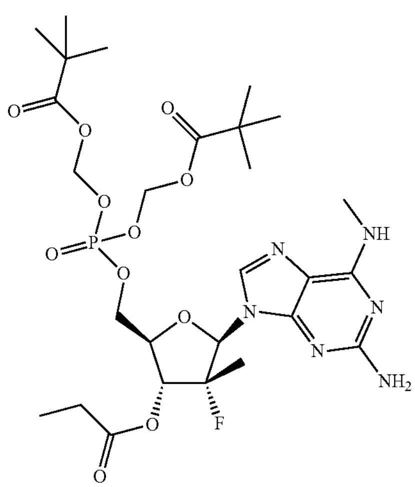 [SMILES: CCC(=O)O[C@@H]1[C@@H](COP(=O)(OCOC(=O)C(C)(C)C)OCOC(=O)C(C)(C)C)O[C@@H](n2cnc3c(NC)nc(N)nc32)[C@]1(C)F] | (2R,3R,4R,5R)-5-(2-amino-6-(methylamino)-9H-purin-9-yl)-4-fluoro-2-(((bis-((pivaloyloxy)methoxy)phosphoryl)oxy)methyl)-4-methyltetrahydrofuran-3-yl propanoate | |

TABLE 1-continued

Exemplary compounds

| Cpd. No. | Structure | Chemical Name | ESI-MS (M + H)+ (m/z) |
|---|---|---|---|
| 252 | 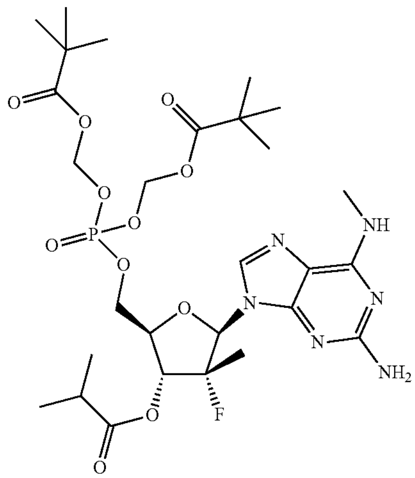 [SMILES: CNc1nc(N)nc2c1ncn2[C@@H]1O[C@H](COP(=O)(OCOC(=O)C(C)(C)C)OCOC(=O)C(C)(C)C)[C@@H](OC(=O)C(C)C)[C@@]1(C)F] | (2R,3R,4R,5R)-5-(2-amino-6-(methylamino)-9H-purin-9-yl)-4-fluoro-2-(((bis-((pivaloyloxy)methoxy)phosphoryl)oxy)methyl)-4-methyltetrahydrofuran-3-yl isobutanoate | |
| 253 | 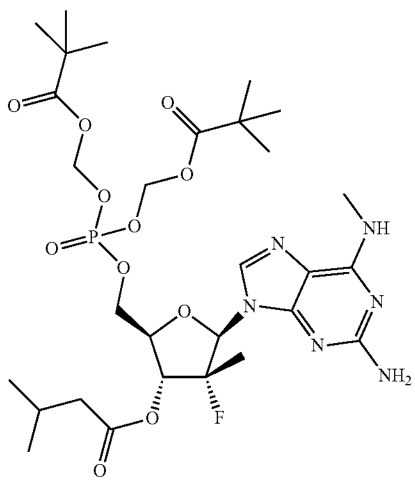 [SMILES: CNc1nc(N)nc2c1ncn2[C@@H]1O[C@H](COP(=O)(OCOC(=O)C(C)(C)C)OCOC(=O)C(C)(C)C)[C@@H](OC(=O)CC(C)C)[C@@]1(C)F] | (2R,3R,4R,5R)-5-(2-amino-6-(methylamino)-9H-purin-9-yl)-4-fluoro-2-(((bis-((pivaloyloxy)methoxy)phosphoryl)oxy)methyl)-4-methyltetrahydrofuran-3-yl 3-methylbutanoate | |
| 254 | 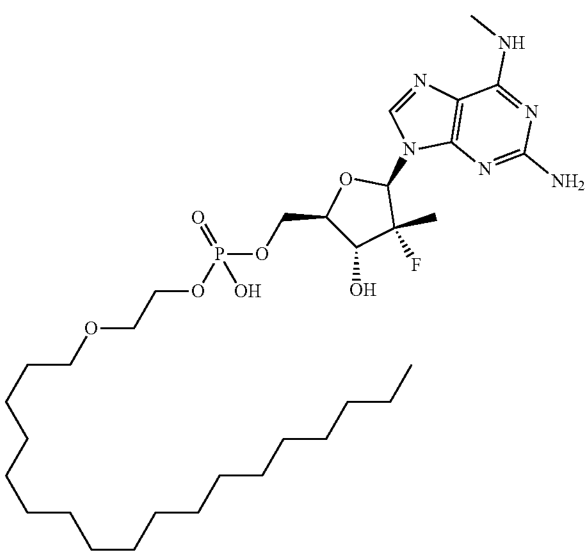 [SMILES: CCCCCCCCCCCCCCCCCCOCCOP(=O)(O)OC[C@H]1O[C@@H](n2cnc3c(NC)nc(N)nc32)[C@](C)(F)[C@@H]1O] | ((2R,3R,4R,5R)-5-(2-amino-6-(methylamino)-9H-purin-9-yl)-4-fluoro-3-hydroxy-4-methyltetrahydrofuran-2-yl)methyl (2-(octadecyloxy)ethyl) hydrogen phosphate | 687.4 [M − H]− |

TABLE 1-continued

Exemplary compounds

| Cpd. No. | Structure | Chemical Name | ESI-MS (M + H)+ (m/z) |
|---|---|---|---|
| 255 | 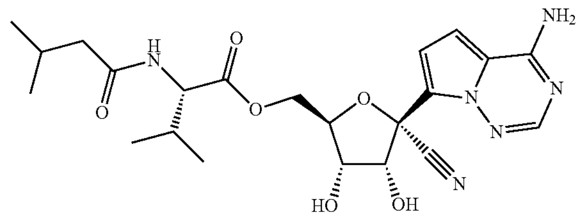 [SMILES: CC(C)CC(=O)N[C@H](C(=O)OC[C@H]1O[C@@](C#N)(c2ccc3c(N)ncnn23)[C@H](O)[C@@H]1O)C(C)C] | ((2R,3S,4R,5R)-5-(4-aminopyrrolo[2,1-f][1,2,4]triazin-7-yl)-5-cyano-3,4-dihydroxytetrahydrofuran-2-yl)methyl (3-methylbutanoyl)-L-valinate | 475.2 |
| 256 | 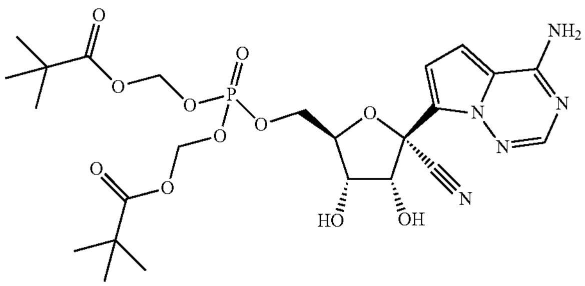 [SMILES: CC(C)(C)C(=O)OCOP(=O)(OCOC(=O)C(C)(C)C)OC[C@H]1O[C@@](C#N)(c2ccc3c(N)ncnn23)[C@H](O)[C@@H]1O] | | 600.2 |
| 257 | 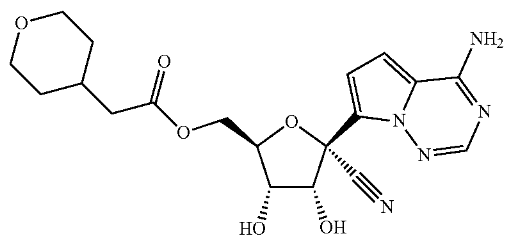 [SMILES: N#C[C@@]1(c2ccc3c(N)ncnn23)O[C@H](COC(=O)CC2CCOCC2)[C@@H](O)[C@H]1O] | ((2R,3S,4R,5R)-5-(4-aminopyrrolo[2,1-f][1,2,4]triazin-7-yl)-5-cyano-3,4-dihydroxytetrahydrofuran-2-yl)methyl 2-(tetrahydro-2H-pyran-4-yl)acetate | 418.0 |
| 258 | 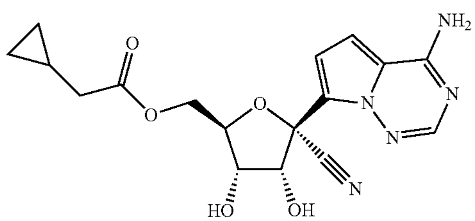 [SMILES: N#C[C@@]1(c2ccc3c(N)ncnn23)O[C@H](COC(=O)CC2CC2)[C@@H](O)[C@H]1O] | ((2R,3S,4R,5R)-5-(4-aminopyrrolo[2,1-f][1,2,4]triazin-7-yl)-5-cyano-3,4-dihydroxytetrahydrofuran-2-yl)methyl 2-cyclopropylacetate | 374.2 |
| 259 | 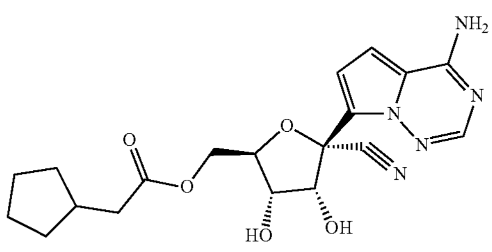 [SMILES: N#C[C@@]1(c2ccc3c(N)ncnn23)O[C@H](COC(=O)CC2CCCC2)[C@@H](O)[C@H]1O] | ((2R,3S,4R,5R)-5-(4-aminopyrrolo[2,1-f][1,2,4]triazin-7-yl)-5-cyano-3,4-dihydroxytetrahydrofuran-2-yl)methyl 2-cyclopentylacetate | 402.0 |
| 260 | 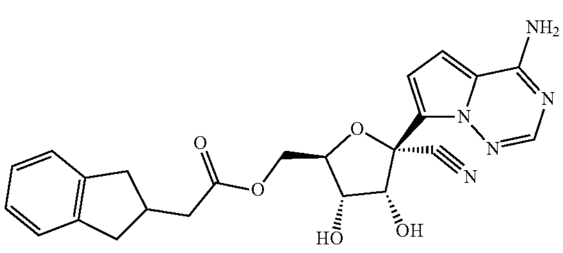 [SMILES: N#C[C@@]1(c2ccc3c(N)ncnn23)O[C@H](COC(=O)CC2Cc3ccccc3C2)[C@@H](O)[C@H]1O] | ((2R,3S,4R,5R)-5-(4-aminopyrrolo[2,1-f][1,2,4]triazin-7-yl)-5-cyano-3,4-dihydroxytetrahydrofuran-2-yl)methyl 2-(2,3-dihydro-1H-inden-2-yl)acetate | 450.0 |

TABLE 1-continued

Exemplary compounds

| Cpd. No. | Structure | Chemical Name | ESI-MS (M + H)+ (m/z) |
|---|---|---|---|
| 261 | 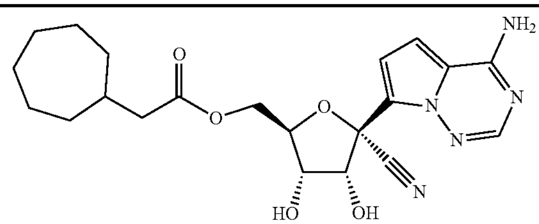 | ((2R,3S,4R,5R)-5-(4-aminopyrrolo[2,1-f][1,2,4]triazin-7-yl)-5-cyano-3,4-dihydroxytetrahydrofuran-2-yl)methyl 2-cycloheptylacetate | 430.3 |
| 262 | 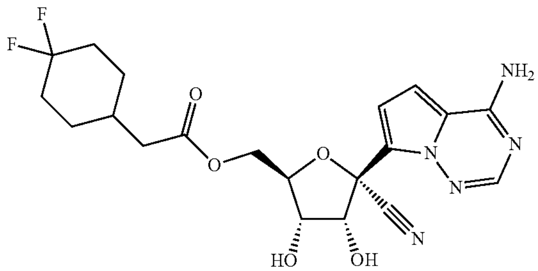 [SMILES: N#C[C@@]1(c2ccc3c(N)ncnn23)O[C@H](COC(=O)CC2CCC(F)(F)CC2)[C@@H](O)[C@H]1O] | ((2R,3S,4R,5R)-5-(4-aminopyrrolo[2,1-f][1,2,4]triazin-7-yl)-5-cyano-3,4-dihydroxytetrahydrofuran-2-yl)methyl 2-(4,4-difluorocyclohexyl)acetate | 452.1 |
| 263 | 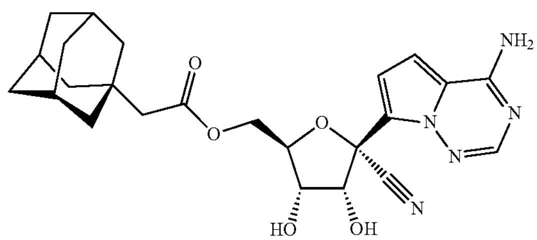 | ((2R,3S,4R,5R)-5-(4-aminopyrrolo[2,1-f][1,2,4]triazin-7-yl)-5-cyano-3,4-dihydroxytetrahydrofuran-2-yl)methyl 2-((3R,5R,7R)-adamantan-1-yl)acetate | 468.1 |
| 264 | 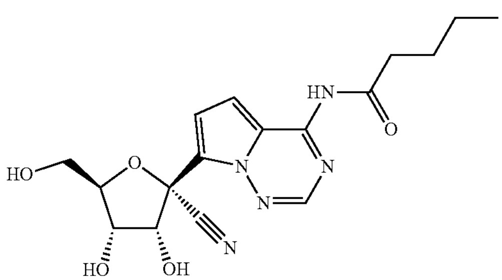 [SMILES: CCCCC(=O)Nc1ncnn2c([C@]3(C#N)O[C@H](CO)[C@@H](O)[C@H]3O)ccc12] | N-(7-((2R,3R,4S,5R)-2-cyano-3,4-dihydroxy-5-(hydroxymethyl)tetrahydrofuran-2-yl)pyrrolo[2,1-f][1,2,4]triazin-4-yl)pentanamide | 376.2 |
| 265 | 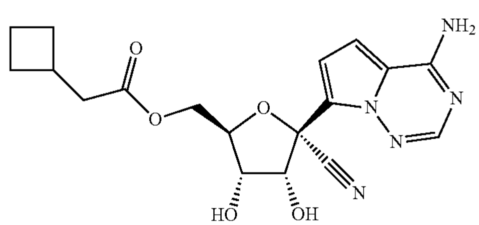 [SMILES: N#C[C@@]1(c2ccc3c(N)ncnn23)O[C@H](COC(=O)CC2CCC2)[C@@H](O)[C@H]1O] | ((2R,3S,4R,5R)-5-(4-aminopyrrolo[2,1-f][1,2,4]triazin-7-yl)-5-cyano-3,4-dihydroxytetrahydrofuran-2-yl)methyl 2-cyclobutylacetate | 388.1 |
| 266 | 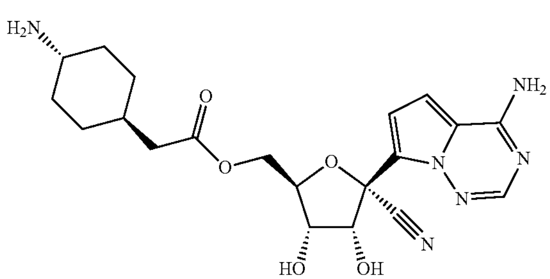 [SMILES: N#C[C@@]1(c2ccc3c(N)ncnn23)O[C@H](COC(=O)C[C@H]2CC[C@H](N)CC2)[C@@H](O)[C@H]1O] | ((2R,3S,4R,5R)-5-(4-aminopyrrolo[2,1-f][1,2,4]triazin-7-yl)-5-cyano-3,4-dihydroxytetrahydrofuran-2-yl)methyl 2-((1r,4R)-4-aminocyclohexyl)acetate | 431.1 |

TABLE 1-continued

Exemplary compounds

| Cpd. No. | Structure | Chemical Name | ESI-MS (M + H)+ (m/z) |
|---|---|---|---|
| 267 | 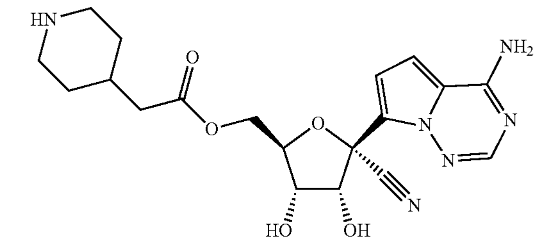 [SMILES: N#C[C@@]1(c2ccc3c(N)ncnn23)O[C@H](COC(=O)CC2CCNCC2)[C@@H](O)[C@H]1O] | ((2R,3S,4R,5R)-5-(4-aminopyrrolo[2,1-f][1,2,4]triazin-7-yl)-5-cyano-3,4-dihydroxytetrahydrofuran-2-yl)methyl 2-(piperidin-4-yl)acetate | 417.2 |
| 268 | 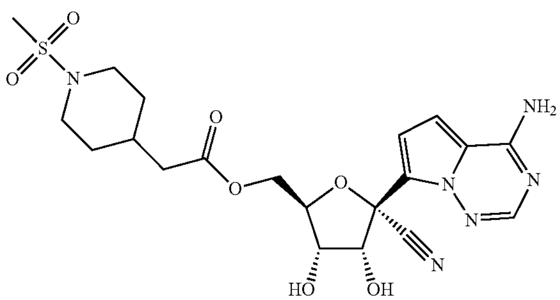 [SMILES: CS(=O)(=O)N1CCC(CC(=O)OC[C@H]2O[C@@](C#N)(c3ccc4c(N)ncnn34)[C@H](O)[C@@H]2O)CC1] | ((2R,3S,4R,5R)-5-(4-aminopyrrolo[2,1-f][1,2,4]triazin-7-yl)-5-cyano-3,4-dihydroxytetrahydrofuran-2-yl)methyl 2-(1-(methylsulfonyl)piperidin-4-yl)acetate | 495.2 |
| 269 | 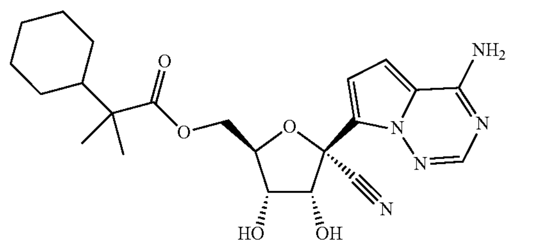 [SMILES: CC(C)(C(=O)OC[C@H]1O[C@@](C#N)(c2ccc3c(N)ncnn23)[C@H](O)[C@@H]1O)C1CCCCC1] | ((2R,3S,4R,5R)-5-(4-aminopyrrolo[2,1-f][1,2,4]triazin-7-yl)-5-cyano-3,4-dihydroxytetrahydrofuran-2-yl)methyl 2-cyclohexyl-2-methylpropanoate | 444.1 |
| 270 | 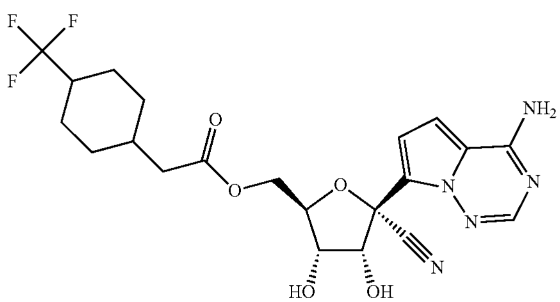 [SMILES: N#C[C@@]1(c2ccc3c(N)ncnn23)O[C@H](COC(=O)CC2CCC(C(F)(F)F)CC2)[C@@H](O)[C@H]1O] | ((2R,3S,4R,5R)-5-(4-aminopyrrolo[2,1-f][1,2,4]triazin-7-yl)-5-cyano-3,4-dihydroxytetrahydrofuran-2-yl)methyl 2-(4-(trifluoromethyl)cyclohexyl)acetate | 484.3 |
| 271 | 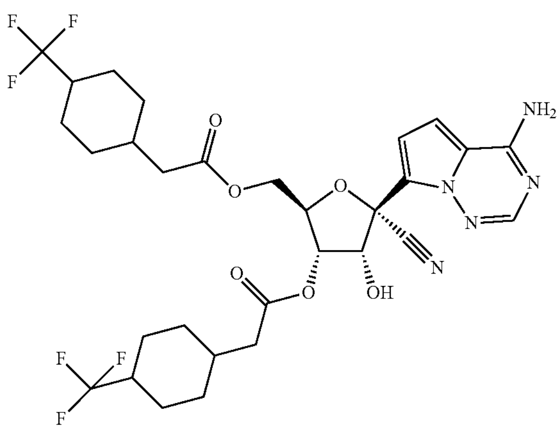 [SMILES: N#C[C@@]1(c2ccc3c(N)ncnn23)O[C@H](COC(=O)CC2CCC(C(F)(F)F)CC2)[C@@H](OC(=O)CC2CCC(C(F)(F)F)CC2)[C@H]1O] | (2R,3S,4R,5R)-5-(4-aminopyrrolo[2,1-f][1,2,4]triazin-7-yl)-5-cyano-4-hydroxy-2-((2-(4-(trifluoromethyl)cyclohexyl)acetoxy)methyl)tetrahydrofuran-3-yl 2-(4-(trifluoromethyl)cyclohexyl)acetate | 676.2 |

TABLE 1-continued

Exemplary compounds

| Cpd. No. | Structure | Chemical Name | ESI-MS (M + H)+ (m/z) |
|---|---|---|---|
| 272 | 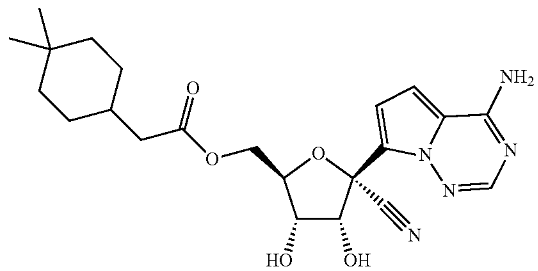 [SMILES: CC1(C)CCC(CC(=O)OC[C@H]2O[C@@](C#N)(c3ccc4c(N)ncnn34)[C@H](O)[C@@H]2O)CC1] | ((2R,3S,4R,5R)-5-(4-aminopyrrolo[2,1-f][1,2,4]triazin-7-yl)-5-cyano-3,4-dihydroxytetrahydrofuran-2-yl)methyl 2-(4,4-dimethylcyclohexyl)acetate | 444.3 |
| 273 | 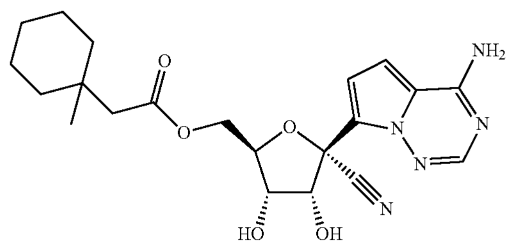 [SMILES: CC1(CC(=O)OC[C@H]2O[C@@](C#N)(c3ccc4c(N)ncnn34)[C@H](O)[C@@H]2O)CCCCC1] | ((2R,3S,4R,5R)-5-(4-aminopyrrolo[2,1-f][1,2,4]triazin-7-yl)-5-cyano-3,4-dihydroxytetrahydrofuran-2-yl)methyl 2-(1-methylcyclohexyl)acetate | 430.1 |
| 274 | 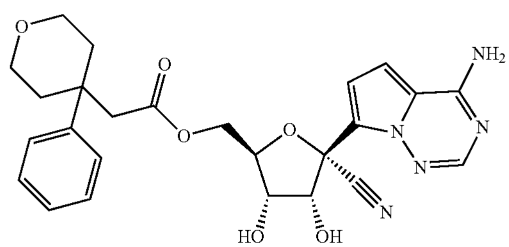 [SMILES: N#C[C@@]1(c2ccc3c(N)ncnn23)O[C@H](COC(=O)CC2(c3ccccc3)CCOCC2)[C@@H](O)[C@H]1O] | ((2R,3S,4R,5R)-5-(4-aminopyrrolo[2,1-f][1,2,4]triazin-7-yl)-5-cyano-3,4-dihydroxytetrahydrofuran-2-yl)methyl 2-(4-phenyltetrahydro-2H-pyran-4-yl)acetate | 494.3 |
| 275 | 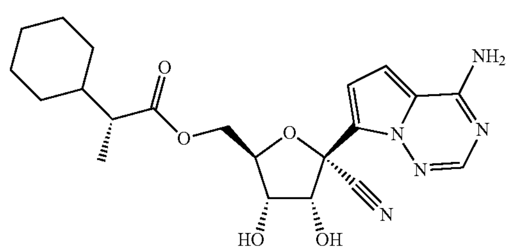 [SMILES: C[C@@H](C(=O)OC[C@H]1O[C@@](C#N)(c2ccc3c(N)ncnn23)[C@H](O)[C@@H]1O)C1CCCCC1] | ((2R,3S,4R,5R)-5-(4-aminopyrrolo[2,1-f][1,2,4]triazin-7-yl)-5-cyano-3,4-dihydroxytetrahydrofuran-2-yl)methyl (R)-2-cyclohexylpropanoate | 430.1 |
| 276 | 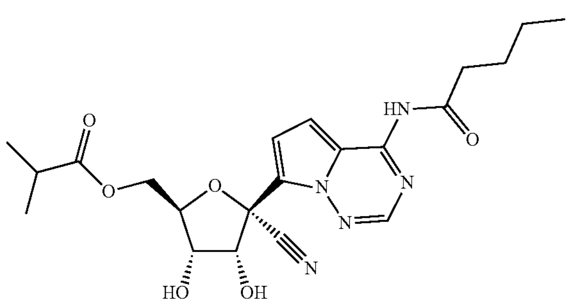 [SMILES: CCCCC(=O)Nc1ncnn2c([C@]3(C#N)O[C@H](COC(=O)C(C)C)[C@@H](O)[C@H]3O)ccc12] | ((2R,3S,4R,5R)-5-cyano-3,4-dihydroxy-5-(4-pentanamidopyrrolo[2,1-f][1,2,4]triazin-7-yl)tetrahydrofuran-2-yl)methyl isobutyrate | 446.1 |

TABLE 1-continued

Exemplary compounds

| Cpd. No. | Structure | Chemical Name | ESI-MS (M + H)+ (m/z) |
| --- | --- | --- | --- |
| 277 | 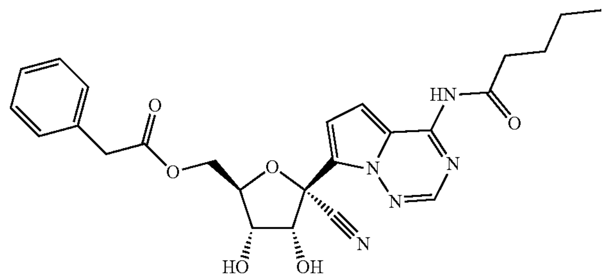 [SMILES: CCCCC(=O)Nc1ncnn2c([C@]3(C#N)O[C@H](COC(=O)Cc4ccccc4)[C@@H](O)[C@H]3O)ccc12] | ((2R,3S,4R,5R)-5-cyano-3,4-dihydroxy-5-(4-pentanamidopyrrolo[2,1-f][1,2,4]triazin-7-yl)tetrahydrofuran-2-yl)methyl 2-phenylacetate | 494.1 |
| 278 | 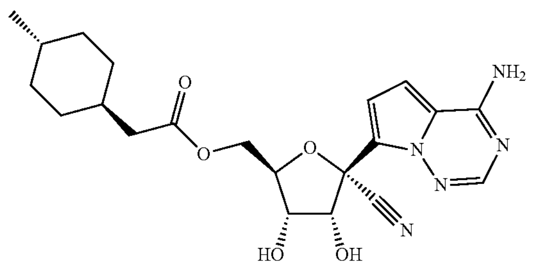 [SMILES: C[C@H]1CC[C@H](CC(=O)OC[C@H]2O[C@@](C#N)(c3ccc4c(N)ncnn34)[C@H](O)[C@@H]2O)CC1] | ((2R,3S,4R,5R)-5-(4-aminopyrrolo[2,1-f][1,2,4]triazin-7-yl)-5-cyano-3,4-dihydroxytetrahydrofuran-2-yl)methyl 2-((1r,4R)-4-methylcyclohexyl)acetate | 430.2 |
| 279 | 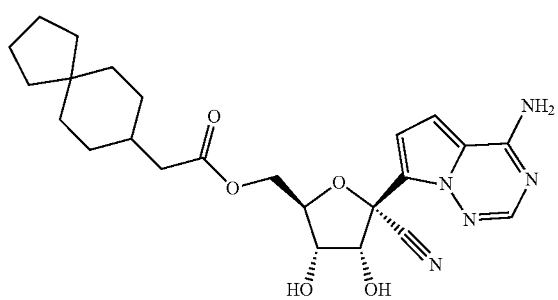 [SMILES: N#C[C@@]1(c2ccc3c(N)ncnn23)O[C@H](COC(=O)CC2CCC3(CCCC3)CC2)[C@@H](O)[C@H]1O] | ((2R,3S,4R,5R)-5-(4-aminopyrrolo[2,1-f][1,2,4]triazin-7-yl)-5-cyano-3,4-dihydroxytetrahydrofuran-2-yl)methyl 2-(spiro[4.5]decan-8-yl)acetate | 470.3 |
| 280 | 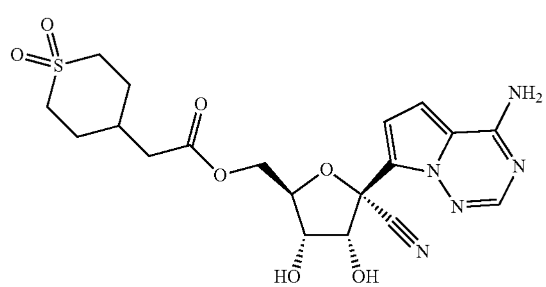 [SMILES: N#C[C@@]1(c2ccc3c(N)ncnn23)O[C@H](COC(=O)CC2CCS(=O)(=O)CC2)[C@@H](O)[C@H]1O] | ((2R,3S,4R,5R)-5-(4-aminopyrrolo[2,1-f][1,2,4]triazin-7-yl)-5-cyano-3,4-dihydroxytetrahydrofuran-2-yl)methyl 2-(1,1-dioxidotetrahydro-2H-thiopyran-4-yl)acetate | 466.2 |
| 281 | 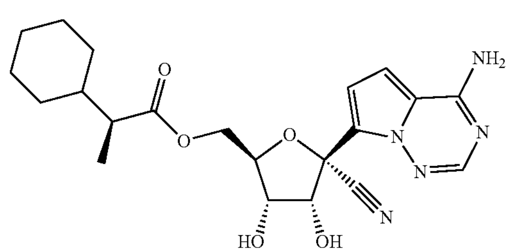 [SMILES: C[C@H](C(=O)OC[C@H]1O[C@@](C#N)(c2ccc3c(N)ncnn23)[C@H](O)[C@@H]1O)C1CCCCC1] | ((2R,3S,4R,5R)-5-(4-aminopyrrolo[2,1-f][1,2,4]triazin-7-yl)-5-cyano-3,4-dihydroxytetrahydrofuran-2-yl)methyl (S)-2-cyclohexylpropanoate | 430.2 |

TABLE 1-continued

Exemplary compounds

| Cpd. No. | Structure | Chemical Name | ESI-MS (M + H)+ (m/z) |
|---|---|---|---|
| 282 | 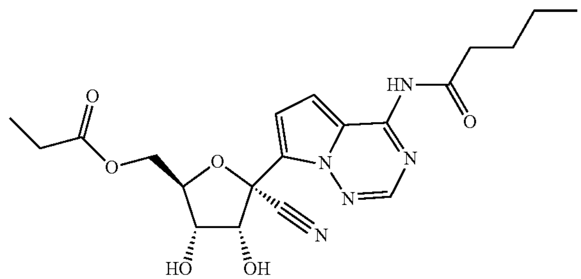 [SMILES: CCCCC(=O)Nc1ncnn2c([C@]3(C#N)O[C@H](COC(=O)CC)[C@@H](O)[C@H]3O)ccc12] | ((2R,3S,4R,5R)-5-cyano-3,4-dihydroxy-5-(4-pentanamidopyrrolo[2,1-f][1,2,4]triazin-7-yl)tetrahydrofuran-2-yl)methyl propionate | 432.2 |
| 283 | 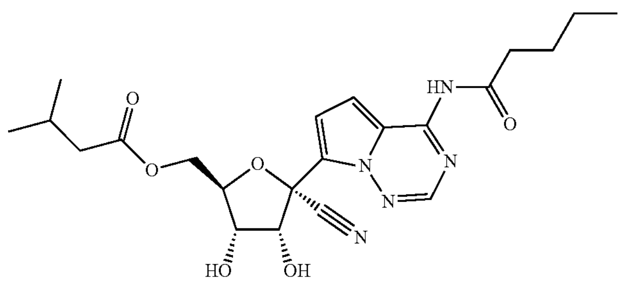 [SMILES: CCCCC(=O)Nc1ncnn2c([C@]3(C#N)O[C@H](COC(=O)CC(C)C)[C@@H](O)[C@H]3O)ccc12] | ((2R,3S,4R,5R)-5-cyano-3,4-dihydroxy-5-(4-pentanamidopyrrolo[2,1-f][1,2,4]triazin-7-yl)tetrahydrofuran-2-yl)methyl 3-methylbutanoate | 460.3 |
| 284 | 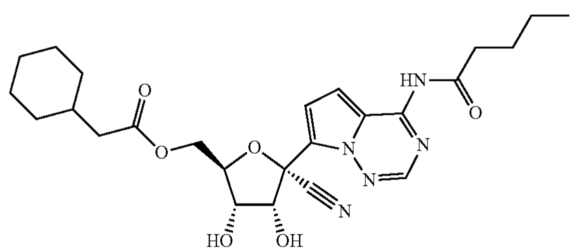 [SMILES: CCCCC(=O)Nc1ncnn2c([C@]3(C#N)O[C@H](COC(=O)CC4CCCCC4)[C@@H](O)[C@H]3O)ccc12] | ((2R,3S,4R,5R)-5-cyano-3,4-dihydroxy-5-(4-pentanamidopyrrolo[2,1-f][1,2,4]triazin-7-yl)tetrahydrofuran-2-yl)methyl 2-cyclohexylacetate | 500.1 |
| 285 | 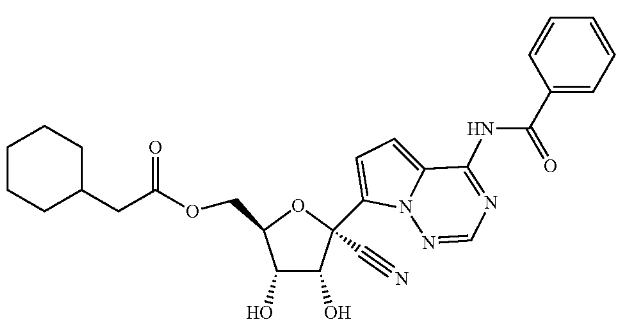 [SMILES: N#C[C@@]1(c2ccc3c(NC(=O)c4ccccc4)ncnn23)O[C@H](COC(=O)CC2CCCCC2)[C@@H](O)[C@H]1O] | ((2R,3S,4R,5R)-5-(4-benzamidopyrrolo[2,1-f][1,2,4]triazin-7-yl)-5-cyano-3,4-dihydroxytetrahydrofuran-2-yl)methyl 2-cyclohexylacetate | 520.1 |
| 286 | 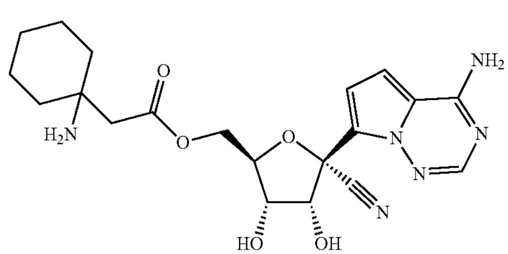 [SMILES: N#C[C@@]1(c2ccc3c(N)ncnn23)O[C@H](COC(=O)CC2(N)CCCCC2)[C@@H](O)[C@H]1O] | ((2R,3S,4R,5R)-5-(4-aminopyrrolo[2,1-f][1,2,4]triazin-7-yl)-5-cyano-3,4-dihydroxytetrahydrofuran-2-yl)methyl 2-(1-aminocyclohexyl)acetate | 431.1 |

TABLE 1-continued

Exemplary compounds

| Cpd. No. | Structure | Chemical Name | ESI-MS (M + H)+ (m/z) |
|---|---|---|---|
| 287 | 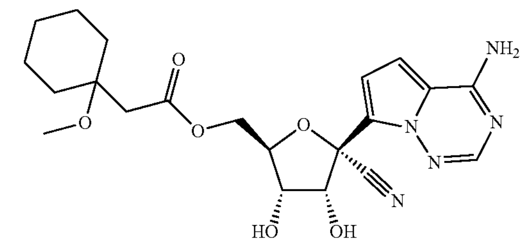 [SMILES: COC1(CC(=O)OC[C@H]2O[C@@](C#N)(c3ccc4c(N)ncnn34)[C@H](O)[C@@H]2O)CCCCC1] | ((2R,3S,4R,5R)-5-(4-aminopyrrolo[2,1-f][1,2,4]triazin-7-yl)-5-cyano-3,4-dihydroxytetrahydrofuran-2-yl)methyl 2-(1-methoxycyclohexyl)acetate | 446.3 |
| 288 | 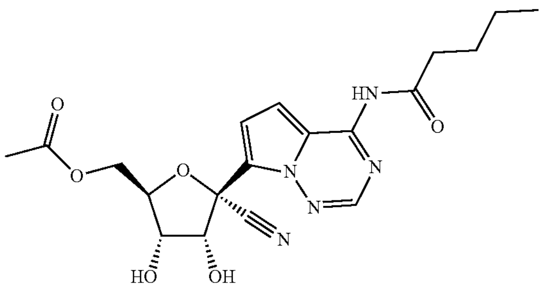 [SMILES: CCCCC(=O)Nc1ncnn2c([C@]3(C#N)O[C@H](COC(C)=O)[C@@H](O)[C@H]3O)ccc12] | ((2R,3S,4R,5R)-5-cyano-3,4-dihydroxy-5-(4-pentanamidopyrrolo[2,1-f][1,2,4]triazin-7-yl)tetrahydrofuran-2-yl)methyl acetate | 418.1 |
| 289 | 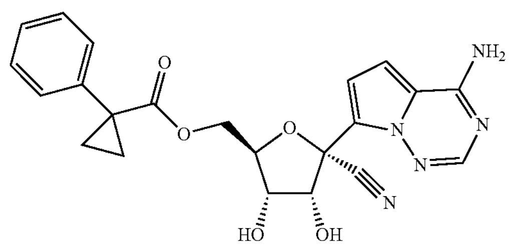 [SMILES: N#C[C@@]1(c2ccc3c(N)ncnn23)O[C@H](COC(=O)C2(c3ccccc3)CC2)[C@@H](O)[C@H]1O] | ((2R,3S,4R,5R)-5-(4-aminopyrrolo[2,1-f][1,2,4]triazin-7-yl)-5-cyano-3,4-dihydroxytetrahydrofuran-2-yl)methyl 1-phenylcyclopropane-1-carboxylate | 436.0 |
| 290 | 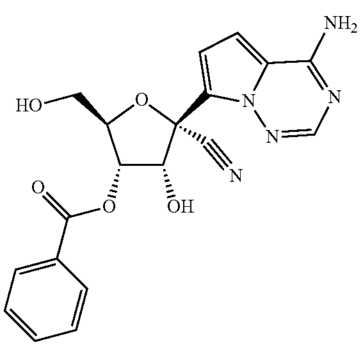 [SMILES: N#C[C@@]1(c2ccc3c(N)ncnn23)O[C@H](CO)[C@@H](OC(=O)c2ccccc2)[C@H]1O] | (2R,3S,4R,5R)-5-(4-aminopyrrolo[2,1-f][1,2,4]triazin-7-yl)-5-cyano-4-hydroxy-2-(hydroxymethyl)tetrahydrofuran-3-yl benzoate | 396.0 |
| 291 | 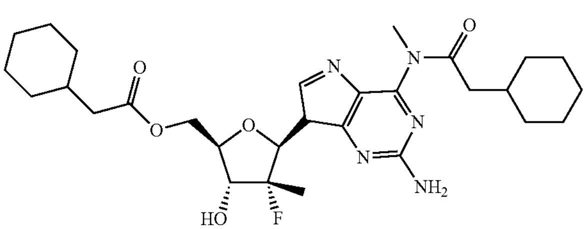 [SMILES: CN(C(=O)CC1CCCCC1)c1nc(N)nc2c1N=CC2[C@@H]1O[C@H](COC(=O)CC2CCCCC2)[C@@H](O)[C@@]1(C)F] | ((2R,3R,4R,5R)-5-(2-amino-6-(2-cyclohexyl-N-methylacetamido)-9H-purin-9-yl)-4-fluoro-3-hydroxy-4-methyltetrahydrofuran-2-yl)methyl 2-cyclohexylacetate | 561.3 |

TABLE 1-continued

Exemplary compounds

| Cpd. No. | Structure | Chemical Name | ESI-MS (M + H)+ (m/z) |
|---|---|---|---|
| 292 | 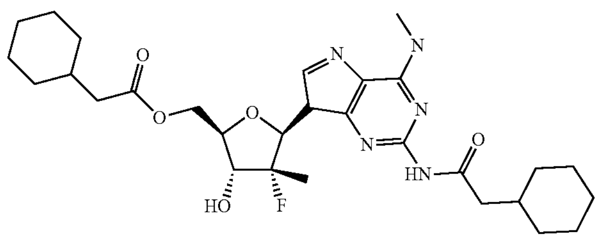 [SMILES: CNc1nc(NC(=O)CC2CCCCC2)nc2c1N=CC2[C@@H]1O[C@H](COC(=O)CC2CCCCC2)[C@@H](O)[C@@]1(C)F] | ((2R,3R,4R,5R)-5-(2-(2-cyclohexylacetamido)-6-(methylamino)-9H-purin-9-yl)-4-fluoro-3-hydroxy-4-methyltetrahydrofuran-2-yl)methyl 2-cyclohexylacetate | 561.3 |
| 293 | 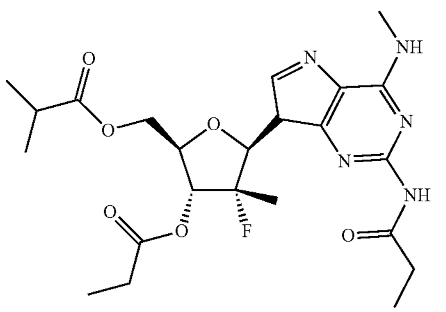 [SMILES: CCC(=O)Nc1nc(NC)c2c(n1)C([C@@H]1O[C@H](COC(=O)C(C)C)[C@@H](OC(=O)CC)[C@@]1(C)F)C=N2] | ((2R,3R,4R,5R)-4-fluoro-4-methyl-5-(6-(methylamino)-2-propionamido-9H-purin-9-yl)-3-(propionyloxy)tetrahydrofuran-2-yl)methyl isobutyrate | 495.2 |
| 294 | 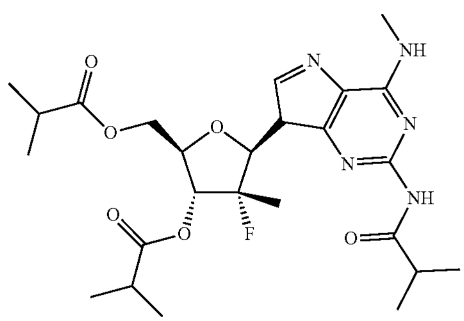 [SMILES: CNc1nc(NC(=O)C(C)C)nc2c1N=CC2[C@@H]1O[C@H](COC(=O)C(C)C)[C@@H](OC(=O)C(C)C)[C@@]1(C)F] | (2R,3R,4R,5R)-4-fluoro-5-(2-isobutyramido-6-(methylamino)-9H-purin-9-yl)-2-((isobutyryloxy)methyl)-4-methyltetrahydrofuran-3-yl isobutyrate | 523.3 |
| 295 | 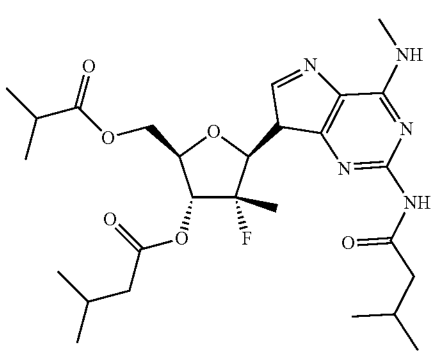 [SMILES: CNc1nc(NC(=O)CC(C)C)nc2c1N=CC2[C@@H]1O[C@H](COC(=O)C(C)C)[C@@H](OC(=O)CC(C)C)[C@@]1(C)F] | (2R,3R,4R,5R)-4-fluoro-2-((isobutyryloxy)methyl)-4-methyl-5-(6-(methylamino)-2-(3-methylbutanamido)-9H-purin-9-yl)tetrahydrofuran-3-yl 3-methylbutanoate | 551.3 |

TABLE 1-continued

Exemplary compounds

| Cpd. No. | Structure | Chemical Name | ESI-MS (M + H)+ (m/z) |
|---|---|---|---|
| 296 | 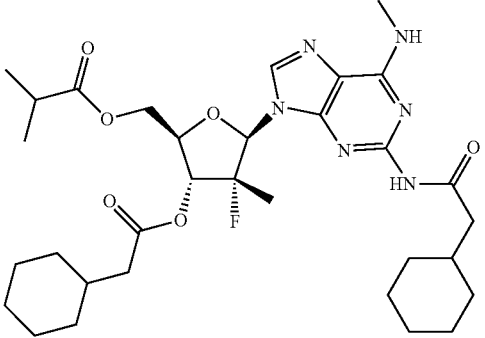 [SMILES: CNc1nc(NC(=O)CC2CCCCC2)nc2c1ncn2[C@@H]1O[C@H](COC(=O)C(C)C)[C@@H](OC(=O)CC2CCCCC2)[C@@]1(C)F] | ((2R,3R,4R,5R)-5-(2-(2-cyclohexylacetamido)-6-(methylamino)-9H-purin-9-yl)-3-(2-cyclohexylacetoxy)-4-fluoro-4-methyltetrahydrofuran-2-yl)methyl isobutyrate | 631.4 |
| 297 | 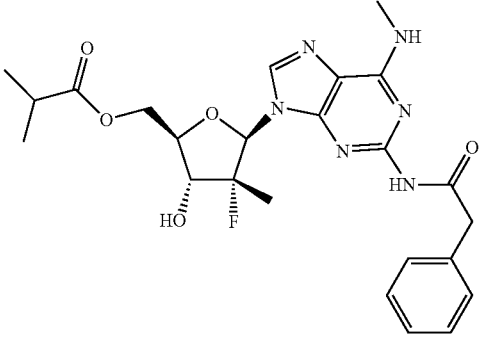 [SMILES: CNc1nc(NC(=O)Cc2ccccc2)nc2c1ncn2[C@@H]1O[C@H](COC(=O)C(C)C)[C@@H](O)[C@@]1(C)F] | ((2R,3R,4R,5R)-4-fluoro-3-hydroxy-4-methyl-5-(6-(methylamino)-2-(2-phenylacetamido)-9H-purin-9-yl)tetrahydrofuran-2-yl)methyl isobutyrate | 501.3 |
| 298 | 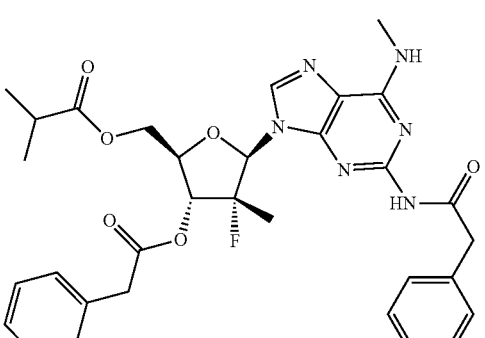 | ((2R,3R,4R,5R)-4-fluoro-4-methyl-5-(6-(methylamino)-2-(2-phenylacetamido)-9H-purin-9-yl)-3-(2-phenylacetoxy)tetrahydrofuran-2-yl)methyl isobutyrate | 619.2 |
| 299 | 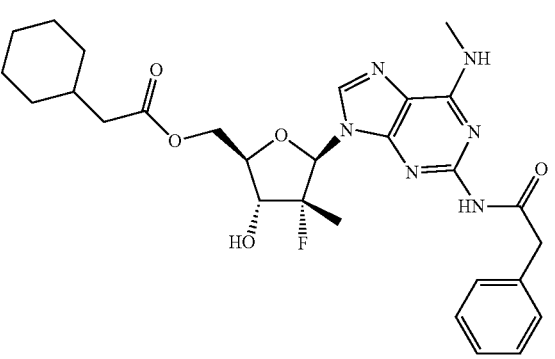 [SMILES: CNc1nc(NC(=O)Cc2ccccc2)nc2c1ncn2[C@@H]1O[C@H](COC(=O)CC2CCCCC2)[C@@H](O)[C@@]1(C)F] | ((2R,3R,4R,5R)-4-fluoro-3-hydroxy-4-methyl-5-(6-(methylamino)-2-(2-phenylacetamido)-9H-purin-9-yl)tetrahydrofuran-2-yl)methyl 2-cyclohexylacetate | 555.2 |

TABLE 1-continued

Exemplary compounds

| Cpd. No. | Structure | Chemical Name | ESI-MS (M + H)+ (m/z) |
| --- | --- | --- | --- |
| 300 | 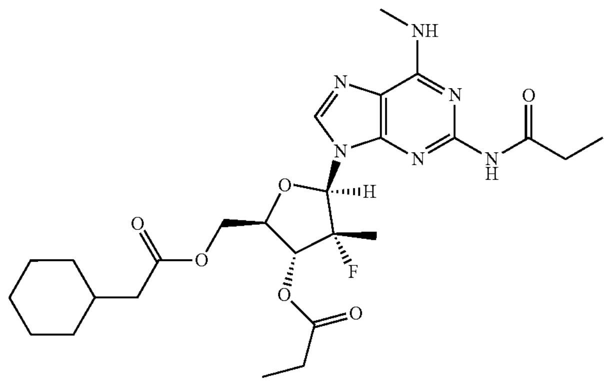 [SMILES: CCC(=O)Nc1nc(NC)c2ncn([C@@H]3O[C@H](COC(=O)CC4CCCCC4)[C@@H](OC(=O)CC)[C@@]3(C)F)c2n1] | (2R,3R,4R,5R)-2-((2-cyclohexylacetoxy)methyl)-4-fluoro-4-methyl-5-(6-(methylamino)-2-propionamido-9H-purin-9-yl)tetrahydrofuran-3-yl propionate | 549.4 |
| 301 | 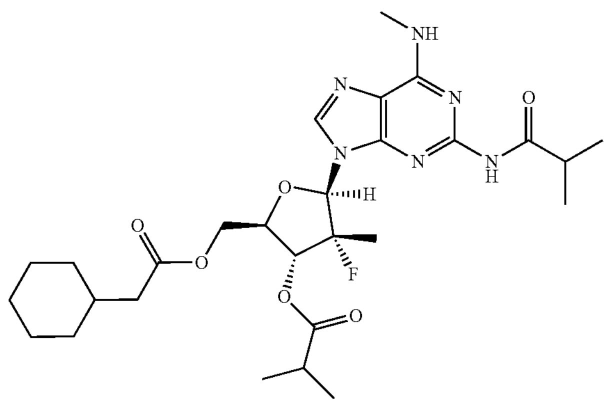 [SMILES: CNc1nc(NC(=O)C(C)C)nc2c1ncn2[C@@H]1O[C@H](COC(=O)CC2CCCCC2)[C@@H](OC(=O)C(C)C)[C@@]1(C)F] | (2R,3R,4R,5R)-2-((2-cyclohexylacetoxy)methyl)-4-fluoro-5-(2-isobutyramido-6-(methylamino)-9H-purin-9-yl)-4-methyltetrahydrofuran-3-yl isobutyrate | 577.3 |
| 302 | 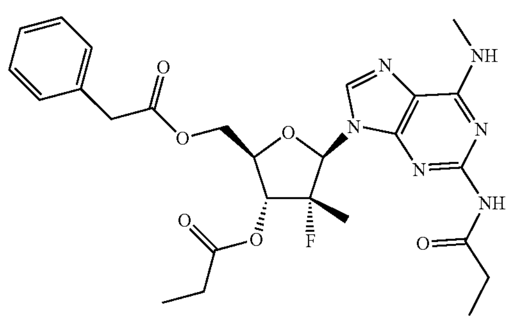 [SMILES: CCC(=O)Nc1nc(NC)c2ncn([C@@H]3O[C@H](COC(=O)Cc4ccccc4)[C@@H](OC(=O)CC)[C@@]3(C)F)c2n1] | (2R,3R,4R,5R)-4-fluoro-4-methyl-5-(6-(methylamino)-2-propionamido-9H-purin-9-yl)-2-((2-phenylacetoxy)methyl)tetrahydrofuran-3-yl propionate | 543.2 |
| 303 | 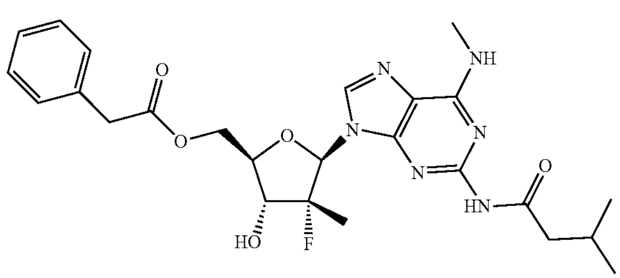 [SMILES: CNc1nc(NC(=O)CC(C)C)nc2c1ncn2[C@@H]1O[C@H](COC(=O)Cc2ccccc2)[C@@H](O)[C@@]1(C)F] | ((2R,3R,4R,5R)-4-fluoro-3-hydroxy-4-methyl-5-(6-(methylamino)-2-(3-methylbutanamido)-9H-purin-9-yl)tetrahydrofuran-2-yl)methyl 2-phenylacetate | 515.2 |

TABLE 1-continued

Exemplary compounds

| Cpd. No. | Structure | Chemical Name | ESI-MS (M + H)+ (m/z) |
|---|---|---|---|
| 304 | 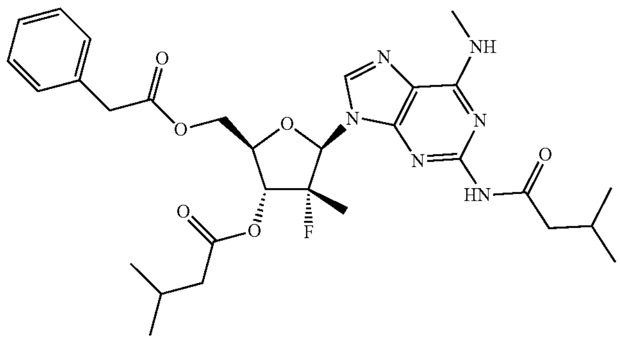 [SMILES: CNc1nc(NC(=O)CC(C)C)nc2c1ncn2[C@@H]1O[C@H](COC(=O)Cc2ccccc2)[C@@H](OC(=O)CC(C)C)[C@@]1(C)F] | (2R,3R,4R,5R)-4-fluoro-4-methyl-5-(6-(methylamino)-2-(3-methylbutanamido)-9H-purin-9-yl)-2-((2-phenylacetoxy)methyl)tetrahydrofuran-3-yl 3-methylbutanoate | 599.3 |
| 305 | 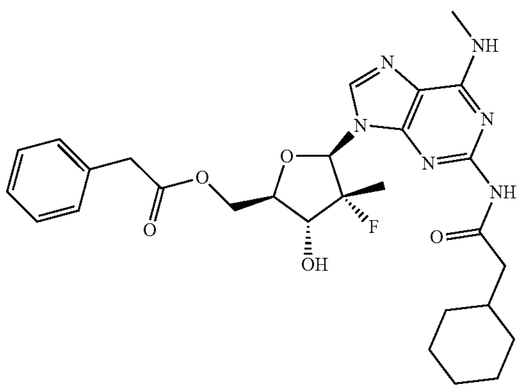 [SMILES: CNc1nc(NC(=O)CC2CCCCC2)nc2c1ncn2[C@@H]1O[C@H](COC(=O)Cc2ccccc2)[C@@H](O)[C@@]1(C)F] | ((2R,3R,4R,5R)-5-(2-(2-cyclohexylacetamido)-6-(methylamino)-9H-purin-9-yl)-4-fluoro-3-hydroxy-4-methyltetrahydrofuran-2-yl)methyl 2-phenylacetate | 555.3 |
| 306 | 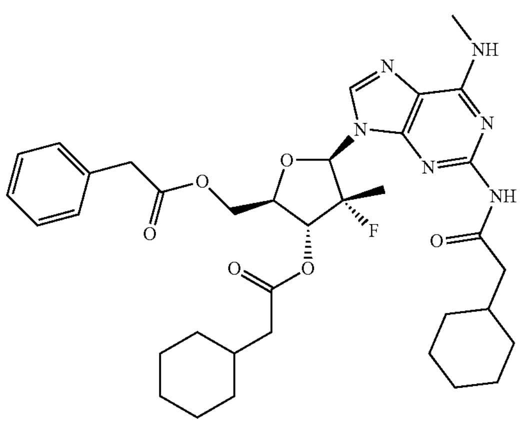 [SMILES: CNc1nc(NC(=O)CC2CCCCC2)nc2c1ncn2[C@@H]1O[C@H](COC(=O)Cc2ccccc2)[C@@H](OC(=O)CC2CCCCC2)[C@@]1(C)F] | ((2R,3R,4R,5R)-5-(2-(2-cyclohexylacetamido)-6-(methylamino)-9H-purin-9-yl)-3-(2-cyclohexylacetoxy)-4-fluoro-4-methyltetrahydrofuran-2-yl)methyl 2-phenylacetate | 679.4 |
| 307 | 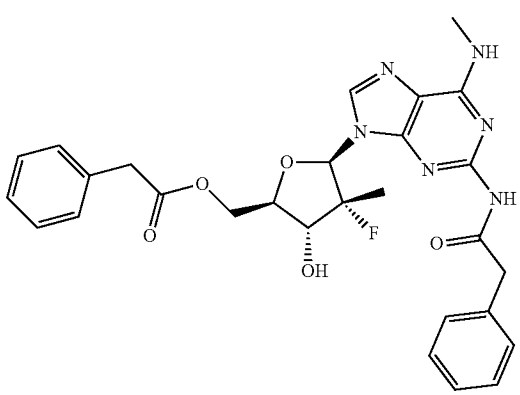 [SMILES: CNc1nc(NC(=O)Cc2ccccc2)nc2c1ncn2[C@@H]1O[C@H](COC(=O)Cc2ccccc2)[C@@H](O)[C@@]1(C)F] | ((2R,3R,4R,5R)-4-fluoro-3-hydroxy-4-methyl-5-(6-(methylamino)-2-(2-phenylacetamido)-9H-purin-9-yl)tetrahydrofuran-2-yl)methyl 2-phenylacetate | 549.1 |

TABLE 1-continued

Exemplary compounds

| Cpd. No. | Structure | Chemical Name | ESI-MS (M + H)+ (m/z) |
|---|---|---|---|
| 308 | 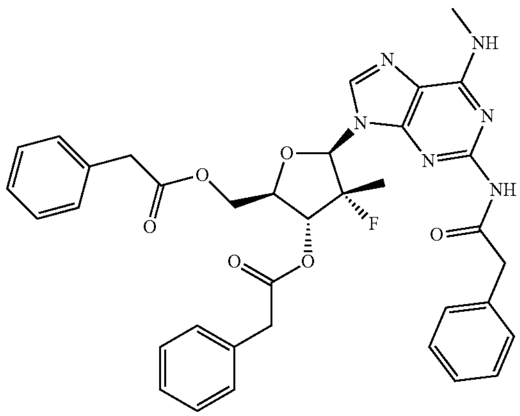 [SMILES: CNc1nc(NC(=O)Cc2ccccc2)nc2c1ncn2[C@@H]1O[C@H](COC(=O)Cc2ccccc2)[C@@H](OC(=O)Cc2ccccc2)[C@@]1(C)F] | (2R,3R,4R,5R)-4-fluoro-4-methyl-5-(6-(methylamino)-2-(2-phenylacetamido)-9H-purin-9-yl)-2-((2-phenylacetoxy)methyl)tetrahydrofuran-3-yl 2-phenylacetate | 667.2 |
| 309 | 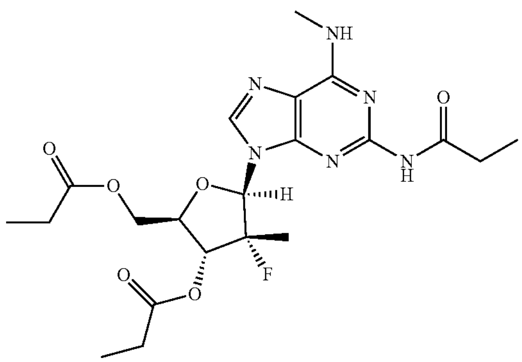 [SMILES: CCC(=O)Nc1nc(NC)c2ncn([C@@H]3O[C@H](COC(=O)CC)[C@@H](OC(=O)CC)[C@@]3(C)F)c2n1] | (2R,3R,4R,5R)-4-fluoro-4-methyl-5-(6-(methylamino)-2-propionamido-9H-purin-9-yl)-2-((propionyloxy)methyl)tetrahydrofuran-3-yl propionate | 481.1 |
| 310 | 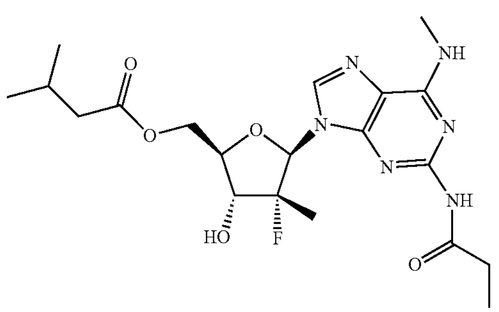 [SMILES: CCC(=O)Nc1nc(NC)c2ncn([C@@H]3O[C@H](COC(=O)CC(C)C)[C@@H](O)[C@@]3(C)F)c2n1] | ((2R,3R,4R,5R)-4-fluoro-3-hydroxy-4-methyl-5-(6-(methylamino)-2-propionamido-9H-purin-9-yl)tetrahydrofuran-2-yl)methyl 3-methylbutanoate | 453.2 |
| 311 | 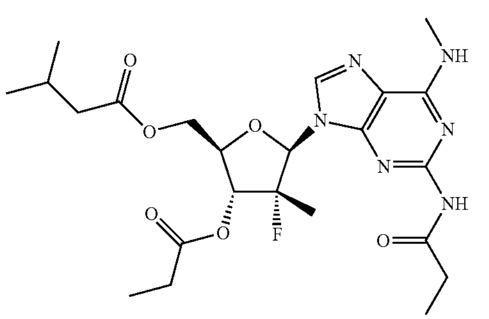 [SMILES: CCC(=O)Nc1nc(NC)c2ncn([C@@H]3O[C@H](COC(=O)CC(C)C)[C@@H](OC(=O)CC)[C@@]3(C)F)c2n1] | ((2R,3R,4R,5R)-4-fluoro-4-methyl-5-(6-(methylamino)-2-propionamido-9H-purin-9-yl)-3-(propionyloxy)tetrahydrofuran-2-yl)methyl 3-methylbutanoate | 509.2 |

TABLE 1-continued

Exemplary compounds

| Cpd. No. | Structure | Chemical Name | ESI-MS (M + H)+ (m/z) |
|---|---|---|---|
| 312 | 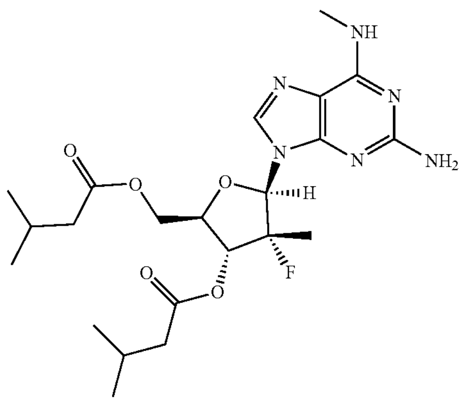 [SMILES: CNc1nc(N)nc2c1ncn2[C@@H]1O[C@H](COC(=O)CC(C)C)[C@@H](OC(=O)CC(C)C)[C@@]1(C)F] | (2R,3R,4R,5R)-5-(2-amino-6-(methylamino)-9H-purin-9-yl)-4-fluoro-4-methyl-2-(((3-methylbutanoyl)oxy)methyl)tetrahydrofuran-3-yl 3-methylbutanoate | 481.3 |
| 313 | 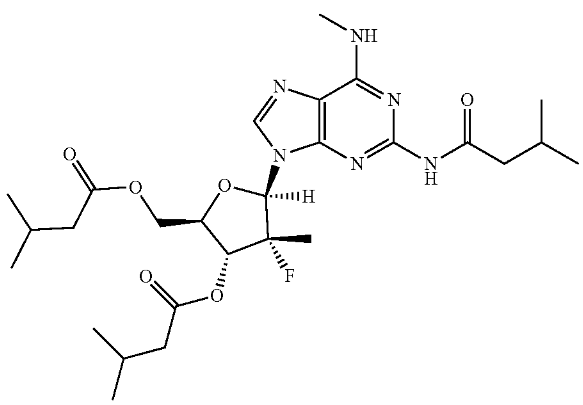 [SMILES: CNc1nc(NC(=O)CC(C)C)nc2c1ncn2[C@@H]1O[C@H](COC(=O)CC(C)C)[C@@H](OC(=O)CC(C)C)[C@@]1(C)F] | (2R,3R,4R,5R)-4-fluoro-4-methyl-5-(6-(methylamino)-2-(3-methylbutanamido)-9H-purin-9-yl)-2-(((3-methylbutanoyl)oxy)methyl)tetrahydrofuran-3-yl 3-methylbutanoate | 565.4 |
| 314 | 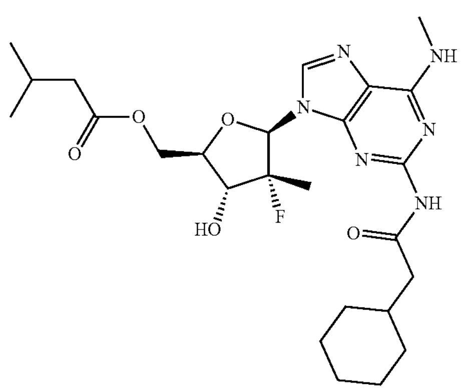 [SMILES: CNc1nc(NC(=O)CC2CCCCC2)nc2c1ncn2[C@@H]1O[C@H](COC(=O)CC(C)C)[C@@H](O)[C@@]1(C)F] | ((2R,3R,4R,5R)-5-(2-(2-cyclohexylacetamido)-6-(methylamino)-9H-purin-9-yl)-4-fluoro-3-hydroxy-4-methyltetrahydrofuran-2-yl)methyl 3-methylbutanoate | 521.3 |

TABLE 1-continued

Exemplary compounds

| Cpd. No. | Structure | Chemical Name | ESI-MS (M + H)+ (m/z) |
|---|---|---|---|
| 315 | 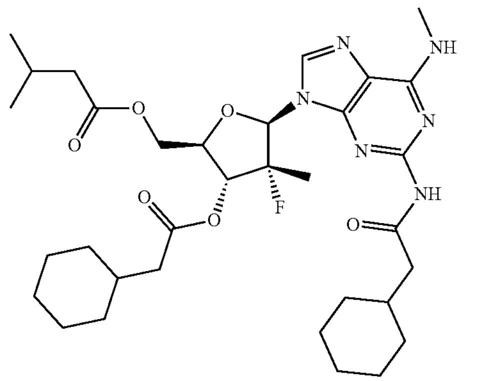 [SMILES: CNc1nc(NC(=O)CC2CCCCC2)nc2c1ncn2[C@@H]1O[C@H](COC(=O)CC(C)C)[C@@H](OC(=O)CC2CCCCC2)[C@@]1(C)F] | ((2R,3R,4R,5R)-5-(2-(2-cyclohexylacetamido)-6-(methylamino)-9H-purin-9-yl)-3-(2-cyclohexylacetoxy)-4-fluoro-4-methyltetrahydrofuran-2-yl)methyl 3-methylbutanoate | 645.4 |
| 316 | 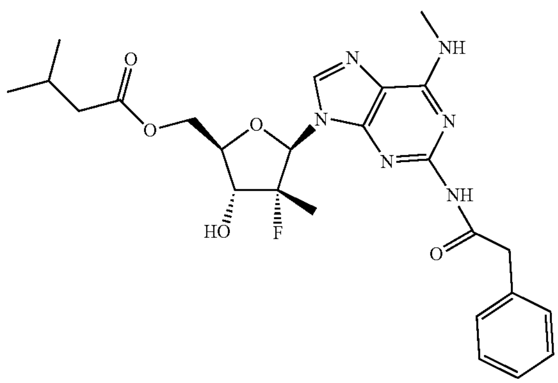 [SMILES: CNc1nc(NC(=O)Cc2ccccc2)nc2c1ncn2[C@@H]1O[C@H](COC(=O)CC(C)C)[C@@H](O)[C@@]1(C)F] | ((2R,3R,4R,5R)-4-fluoro-3-hydroxy-4-methyl-5-(6-(methylamino)-2-(2-phenylacetamido)-9H-purin-9-yl)tetrahydrofuran-2-yl)methyl 3-methylbutanoate | 515.2 |
| 317 | 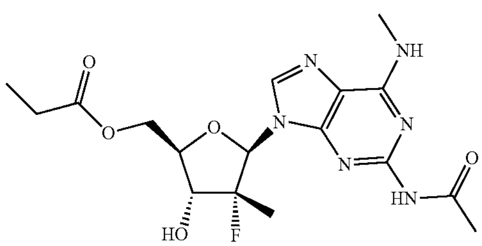 [SMILES: CCC(=O)OC[C@H]1O[C@@H](n2cnc3c(NC)nc(NC(C)=O)nc32)[C@](C)(F)[C@@H]1O] | ((2R,3R,4R,5R)-5-(2-acetamido-6-(methylamino)-9H-purin-9-yl)-4-fluoro-3-hydroxy-4-methyltetrahydrofuran-2-yl)methyl propionate | 411.1 |
| 318 | 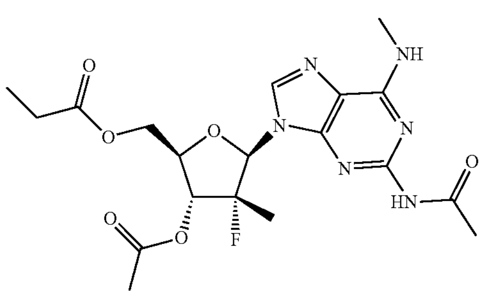 [SMILES: CCC(=O)OC[C@H]1O[C@@H](n2cnc3c(NC)nc(NC(C)=O)nc32)[C@](C)(F)[C@@H]1OC(C)=O] | ((2R,3R,4R,5R)-5-(2-acetamido-6-(methylamino)-9H-purin-9-yl)-3-acetoxy-4-fluoro-4-methyltetrahydrofuran-2-yl)methyl propionate | 453.1 |

TABLE 1-continued

Exemplary compounds

| Cpd. No. | Structure | Chemical Name | ESI-MS (M + H)+ (m/z) |
| --- | --- | --- | --- |
| 319 | 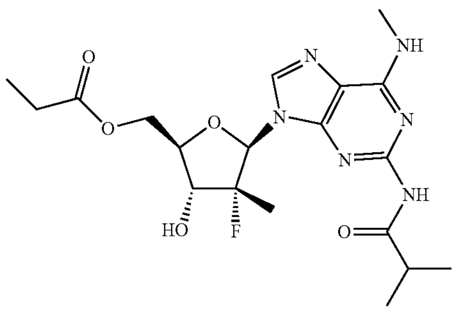 [SMILES: CCC(=O)OC[C@H]1O[C@@H](n2cnc3c(NC)nc(NC(=O)C(C)C)nc32)[C@](C)(F)[C@@H]1O] | ((2R,3R,4R,5R)-4-fluoro-3-hydroxy-5-(2-isobutyramido-6-(methylamino)-9H-purin-9-yl)-4-methyltetrahydrofuran-2-yl)methyl propionate | 439.2 |
| 320 | 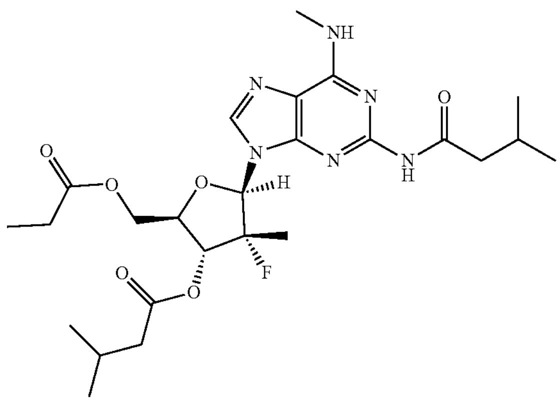 [SMILES: CCC(=O)OC[C@H]1O[C@@H](n2cnc3c(NC)nc(NC(=O)CC(C)C)nc32)[C@](C)(F)[C@@H]1OC(=O)CC(C)C] | (2R,3R,4R,5R)-4-fluoro-4-methyl-5-(6-(methylamino)-2-(3-methylbutanamido)-9H-purin-9-yl)-2-((propionyloxy)methyl)tetrahydrofuran-3-yl 3-methylbutanoate | 537.2 |
| 321 | 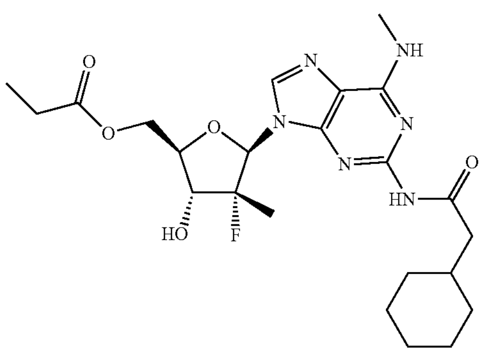 [SMILES: CCC(=O)OC[C@H]1O[C@@H](n2cnc3c(NC)nc(NC(=O)CC4CCCCC4)nc32)[C@](C)(F)[C@@H]1O] | ((2R,3R,4R,5R)-5-(2-(2-cyclohexylacetamido)-6-(methylamino)-9H-purin-9-yl)-4-fluoro-3-hydroxy-4-methyltetrahydrofuran-2-yl)methyl propionate | 493.2 |
| 322 | 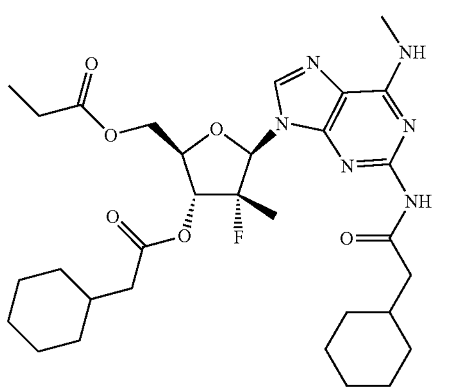 [SMILES: CCC(=O)OC[C@H]1O[C@@H](n2cnc3c(NC)nc(NC(=O)CC4CCCCC4)nc32)[C@](C)(F)[C@@H]1OC(=O)CC1CCCCC1] | ((2R,3R,4R,5R)-5-(2-(2-cyclohexylacetamido)-6-(methylamino)-9H-purin-9-yl)-3-(2-cyclohexylacetoxy)-4-fluoro-4-methyltetrahydrofuran-2-yl)methyl propionate | 617.3 |

TABLE 1-continued

Exemplary compounds

| Cpd. No. | Structure | Chemical Name | ESI-MS (M + H)+ (m/z) |
|---|---|---|---|
| 323 | 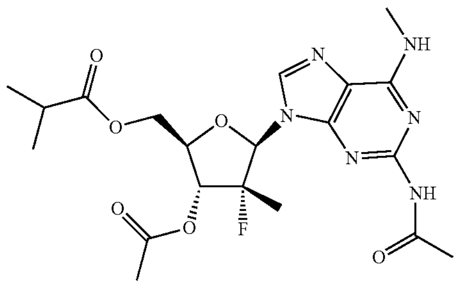 [SMILES: CNc1nc(NC(C)=O)nc2c1ncn2[C@@H]1O[C@H](COC(=O)C(C)C)[C@@H](OC(C)=O)[C@@]1(C)F] | ((2R,3R,4R,5R)-5-(2-acetamido-6-(methylamino)-9H-purin-9-yl)-3-acetoxy-4-fluoro-4-methyltetrahydrofuran-2-yl)methyl isobutyrate | 467.1 |
| 324 | 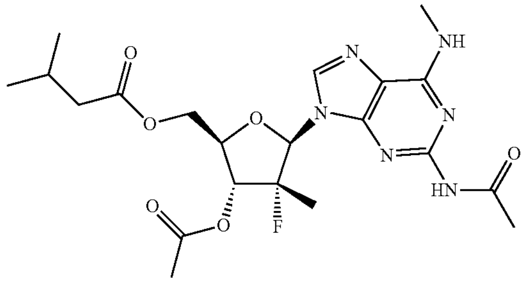 [SMILES: CNc1nc(NC(C)=O)nc2c1ncn2[C@@H]1O[C@H](COC(=O)CC(C)C)[C@@H](OC(C)=O)[C@@]1(C)F] | ((2R,3R,4R,5R)-5-(2-acetamido-6-(methylamino)-9H-purin-9-yl)-3-acetoxy-4-fluoro-4-methyltetrahydrofuran-2-yl)methyl 3-methylbutanoate | 481.2 |
| 325 | 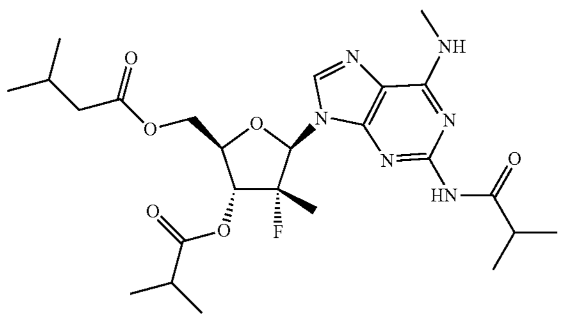 [SMILES: CNc1nc(NC(=O)C(C)C)nc2c1ncn2[C@@H]1O[C@H](COC(=O)CC(C)C)[C@@H](OC(=O)C(C)C)[C@@]1(C)F] | ((2R,3R,4R,5R)-4-fluoro-5-(2-isobutyramido-6-(methylamino)-9H-purin-9-yl)-3-(isobutyryloxy)-4-methyltetrahydrofuran-2-yl)methyl 3-methylbutanoate | 537.3 |
| 326 | 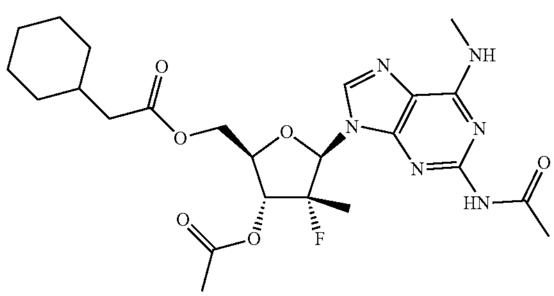 [SMILES: CNc1nc(NC(C)=O)nc2c1ncn2[C@@H]1O[C@H](COC(=O)CC2CCCCC2)[C@@H](OC(C)=O)[C@@]1(C)F] | ((2R,3R,4R,5R)-5-(2-acetamido-6-(methylamino)-9H-purin-9-yl)-3-acetoxy-4-fluoro-4-methyltetrahydrofuran-2-yl)methyl 2-cyclohexylacetate | 521.2 |
| 327 | 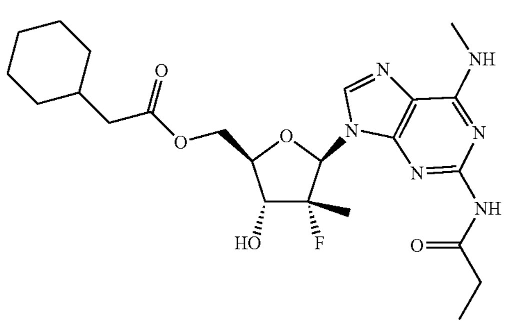 [SMILES: CCC(=O)Nc1nc(NC)c2ncn([C@@H]3O[C@H](COC(=O)CC4CCCCC4)[C@@H](O)[C@@]3(C)F)c2n1] | ((2R,3R,4R,5R)-4-fluoro-3-hydroxy-4-methyl-5-(6-(methylamino)-2-propionamido-9H-purin-9-yl)tetrahydrofuran-2-yl)methyl 2-cyclohexylacetate | 493.2 |

TABLE 1-continued

Exemplary compounds

| Cpd. No. | Structure | Chemical Name | ESI-MS (M + H)+ (m/z) |
|---|---|---|---|
| 328 | 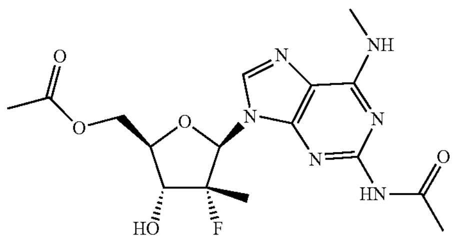 [SMILES: CNc1nc(NC(C)=O)nc2c1ncn2[C@@H]1O[C@H](COC(C)=O)[C@@H](O)[C@@]1(C)F] | ((2R,3R,4R,5R)-5-(2-acetamido-6-(methylamino)-9H-purin-9-yl)-4-fluoro-3-hydroxy-4-methyltetrahydrofuran-2-yl)methyl acetate | 397.1 |
| 329 | 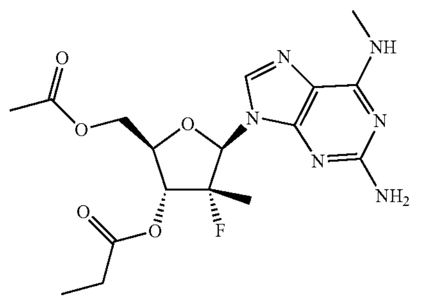 [SMILES: CCC(=O)O[C@@H]1[C@@H](COC(C)=O)O[C@@H](n2cnc3c(NC)nc(N)nc32)[C@]1(C)F] | (2R,3R,4R,5R)-2-(acetoxymethyl)-5-(2-amino-6-(methylamino)-9H-purin-9-yl)-4-fluoro-4-methyltetrahydrofuran-3-yl propionate | 411.1 |
| 330 | 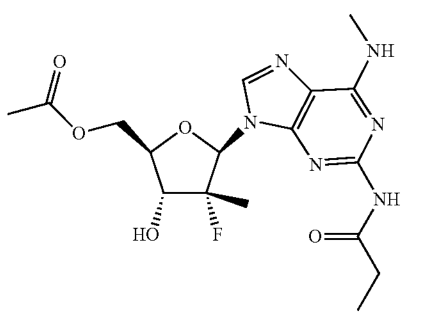 [SMILES: CCC(=O)Nc1nc(NC)c2ncn([C@@H]3O[C@H](COC(C)=O)[C@@H](O)[C@@]3(C)F)c2n1] | ((2R,3R,4R,5R)-4-fluoro-3-hydroxy-4-methyl-5-(6-(methylamino)-2-propionamido-9H-purin-9-yl)tetrahydrofuran-2-yl)methyl acetate | 411.1 |
| 331 | 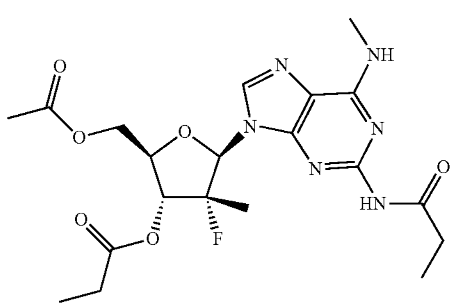 [SMILES: CCC(=O)Nc1nc(NC)c2ncn([C@@H]3O[C@H](COC(C)=O)[C@@H](OC(=O)CC)[C@@]3(C)F)c2n1] | (2R,3R,4R,5R)-2-(acetoxymethyl)-4-fluoro-4-methyl-5-(6-(methylamino)-2-propionamido-9H-purin-9-yl)tetrahydrofuran-3-yl propionate | 467.1 |

TABLE 1-continued

Exemplary compounds

| Cpd. No. | Structure | Chemical Name | ESI-MS (M + H)+ (m/z) |
|---|---|---|---|
| 332 | 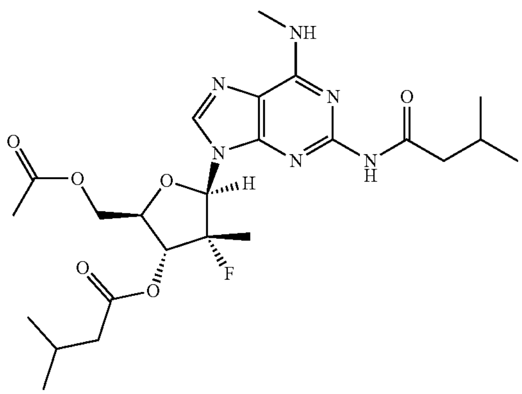 [SMILES: CNc1nc(NC(=O)CC(C)C)nc2c1ncn2[C@@H]1O[C@H](COC(C)=O)[C@@H](OC(=O)CC(C)C)[C@@]1(C)F] | (2R,3R,4R,5R)-2-(acetoxymethyl)-4-fluoro-4-methyl-5-(6-(methylamino)-2-(3-methylbutanamido)-9H-purin-9-yl)tetrahydrofuran-3-yl 3-methylbutanoate | 523.2 |
| 333 | 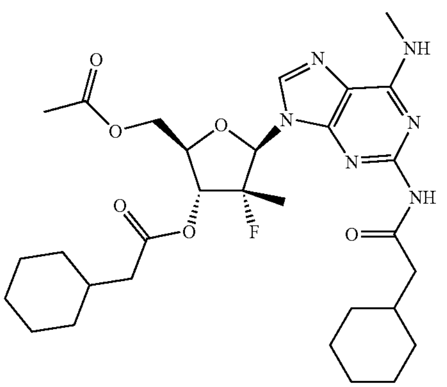 [SMILES: CNc1nc(NC(=O)CC2CCCCC2)nc2c1ncn2[C@@H]1O[C@H](COC(C)=O)[C@@H](OC(=O)CC2CCCCC2)[C@@]1(C)F] | (2R,3R,4R,5R)-2-(acetoxymethyl)-5-(2-(2-cyclohexylacetamido)-6-(methylamino)-9H-purin-9-yl)-4-fluoro-4-methyltetrahydrofuran-3-yl 2-cyclohexylacetate | 603.4 |
| 334 | 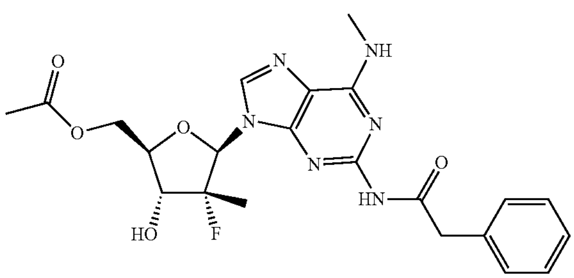 [SMILES: CNc1nc(NC(=O)Cc2ccccc2)nc2c1ncn2[C@@H]1O[C@H](COC(C)=O)[C@@H](O)[C@@]1(C)F] | ((2R,3R,4R,5R)-4-fluoro-3-hydroxy-4-methyl-5-(6-(methylamino)-2-(2-phenylacetamido)-9H-purin-9-yl)tetrahydrofuran-2-yl)methyl acetate | 473.1 |
| 335 | 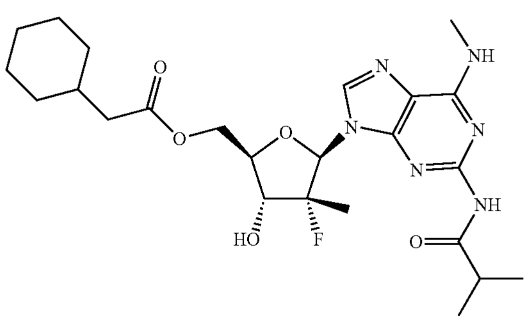 [SMILES: CNc1nc(NC(=O)C(C)C)nc2c1ncn2[C@@H]1O[C@H](COC(=O)CC2CCCCC2)[C@@H](O)[C@@]1(C)F] | ((2R,3R,4R,5R)-4-fluoro-3-hydroxy-5-(2-isobutyramido-6-(methylamino)-9H-purin-9-yl)-4-methyltetrahydrofuran-2-yl)methyl 2-cyclohexylacetate | 507.2 |

TABLE 1-continued

Exemplary compounds

| Cpd. No. | Structure | Chemical Name | ESI-MS (M + H)+ (m/z) |
|---|---|---|---|
| 336 | 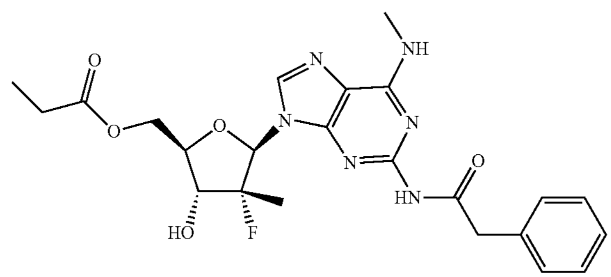 [SMILES: CCC(=O)OC[C@H]1O[C@@H](n2cnc3c(NC)nc(NC(=O)Cc4ccccc4)nc32)[C@](C)(F)[C@@H]1O] | ((2R,3R,4R,5R)-4-fluoro-3-hydroxy-4-methyl-5-(6-(methylamino)-2-(2-phenylacetamido)-9H-purin-9-yl)tetrahydrofuran-2-yl)methyl propionate | 487.2 |
| 337 | 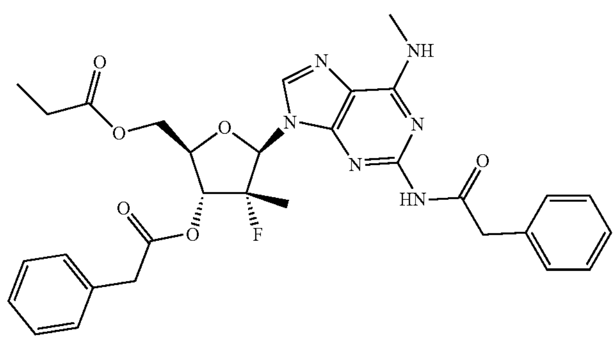 [SMILES: CCC(=O)OC[C@H]1O[C@@H](n2cnc3c(NC)nc(NC(=O)Cc4ccccc4)nc32)[C@](C)(F)[C@@H]1OC(=O)Cc1ccccc1] | ((2R,3R,4R,5R)-4-fluoro-4-methyl-5-(6-(methylamino)-2-(2-phenylacetamido)-9H-purin-9-yl)-3-(2-phenylacetoxy)tetrahydrofuran-2-yl)methyl propionate | 605.2 |
| 338 | 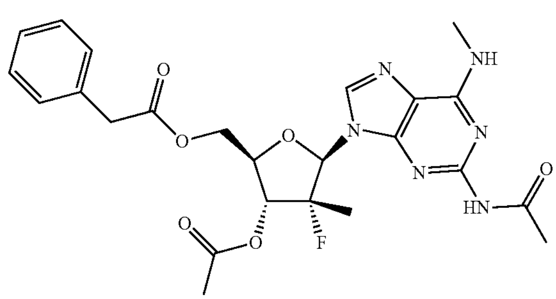 [SMILES: CNc1nc(NC(C)=O)nc2c1ncn2[C@@H]1O[C@H](COC(=O)Cc2ccccc2)[C@@H](OC(C)=O)[C@@]1(C)F] | ((2R,3R,4R,5R)-5-(2-acetamido-6-(methylamino)-9H-purin-9-yl)-3-acetoxy-4-fluoro-4-methyltetrahydrofuran-2-yl)methyl 2-phenylacetate | 515.1 |
| 339 | 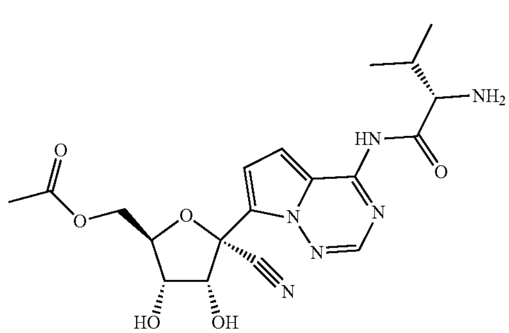 [SMILES: CC(=O)OC[C@H]1O[C@@](C#N)(c2ccc3c(NC(=O)[C@@H](N)C(C)C)ncnn23)[C@H](O)[C@@H]1O] | ((2R,3S,4R,5R)-5-(4-((S)-2-amino-3-methylbutanamido)pyrrolo[2,1-f][1,2,4]triazin-7-yl)-5-cyano-3,4-dihydroxytetrahydrofuran-2-yl)methyl acetate | 433.1 |

TABLE 1-continued

Exemplary compounds

| Cpd. No. | Structure | Chemical Name | ESI-MS (M + H)+ (m/z) |
|---|---|---|---|
| 340 | 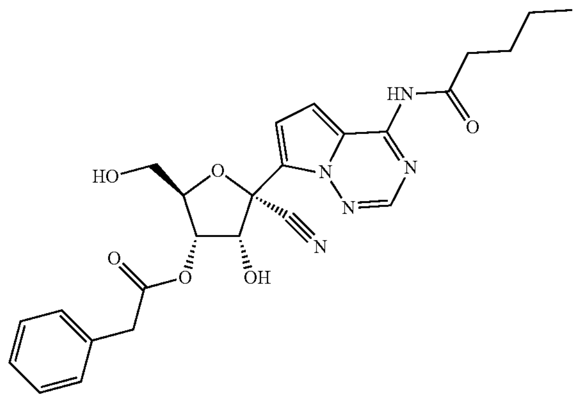 [SMILES: CCCCC(=O)Nc1ncnn2c([C@]3(C#N)O[C@H](CO)[C@@H](OC(=O)Cc4ccccc4)[C@H]3O)ccc12] | (2R,3S,4R,5R)-5-cyano-4-hydroxy-2-(hydroxymethyl)-5-(4-pentanamidopyrrolo[2,1-f][1,2,4]triazin-7-yl)tetrahydrofuran-3-yl 2-phenylacetate | 494.1 |
| 341 | 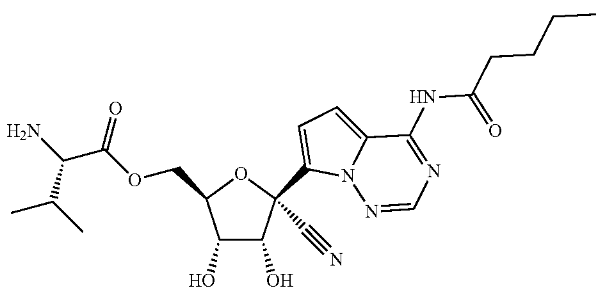 [SMILES: CCCCC(=O)Nc1ncnn2c([C@]3(C#N)O[C@H](COC(=O)[C@@H](N)C(C)C)[C@@H](O)[C@H]3O)ccc12] | ((2R,3S,4R,5R)-5-cyano-3,4-dihydroxy-5-(4-pentanamidopyrrolo[2,1-f][1,2,4]triazin-7-yl)tetrahydrofuran-2-yl)methyl L-valinate | 475.2 |
| 342 | 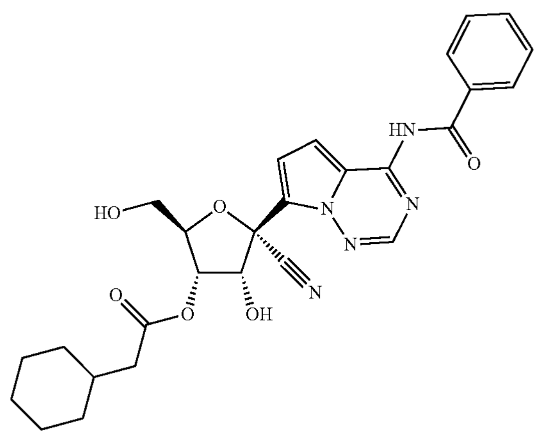 [SMILES: N#C[C@@]1(c2ccc3c(NC(=O)c4ccccc4)ncnn23)O[C@H](CO)[C@@H](OC(=O)CC2CCCCC2)[C@H]1O] | (2R,3S,4R,5R)-5-(4-benzamidopyrrolo[2,1-f][1,2,4]triazin-7-yl)-5-cyano-4-hydroxy-2-(hydroxymethyl)tetrahydrofuran-3-yl 2-cyclohexylacetate | 520.2 |
| 343 | 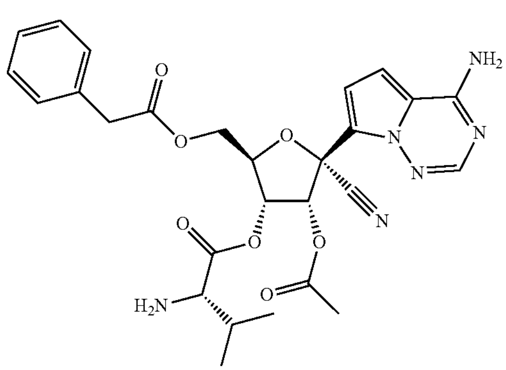 [SMILES: CC(=O)O[C@@H]1[C@H](OC(=O)[C@@H](N)C(C)C)[C@@H](COC(=O)Cc2ccccc2)O[C@@]1(C#N)c1ccc2c(N)ncnn12] | (2R,3R,4R,5R)-4-acetoxy-5-(4-aminopyrrolo[2,1-f][1,2,4]triazin-7-yl)-5-cyano-2-((2-phenylacetoxy)methyl)tetrahydrofuran-3-yl L-valinate | 551.2 |

TABLE 1-continued

Exemplary compounds

| Cpd. No. | Structure | Chemical Name | ESI-MS (M + H)+ (m/z) |
|---|---|---|---|
| 344 | 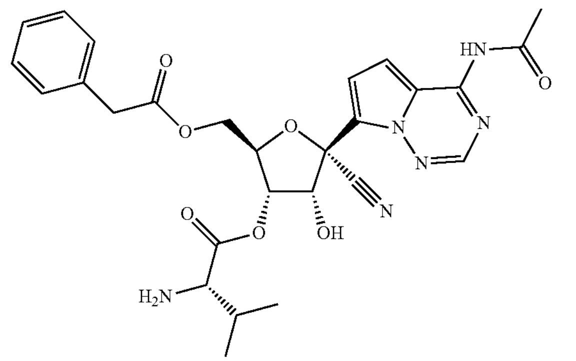 [SMILES: CC(=O)Nc1ncnn2c([C@]3(C#N)O[C@H](COC(=O)Cc4ccccc4)[C@@H](OC(=O)[C@@H](N)C(C)C)[C@H]3O)ccc12] | (2R,3S,4R,5R)-5-(4-acetamidopyrrolo[2,1-f][1,2,4]triazin-7-yl)-5-cyano-4-hydroxy-2-((2-phenylacetoxy)methyl)tetrahydrofuran-3-yl L-valinate | 551.2 |
| 345 | 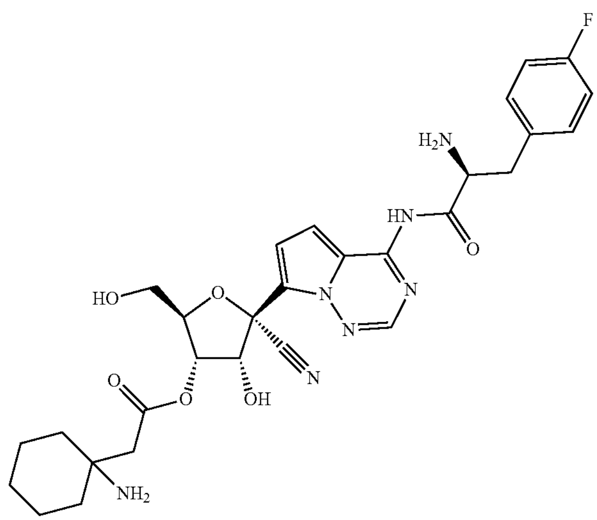 [SMILES: N#C[C@@]1(c2ccc3c(NC(=O)[C@@H](N)Cc4ccc(F)cc4)ncnn23)O[C@H](CO)[C@@H](OC(=O)CC2(N)CCCCC2)[C@H]1O] | (2R,3S,4R,5R)-5-(4-((S)-2-amino-3-(4-fluorophenyl)propanamido)pyrrolo[2,1-f][1,2,4]triazin-7-yl)-5-cyano-4-hydroxy-2-(hydroxymethyl)tetrahydrofuran-3-yl 2-(1-aminocyclohexyl)acetate | 596.2 |
| 346 | 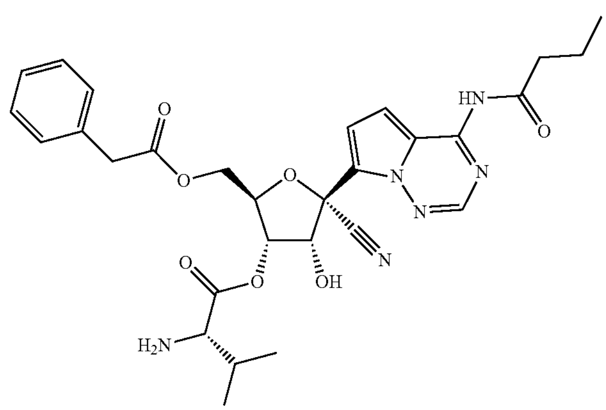 [SMILES: CCCC(=O)Nc1ncnn2c([C@]3(C#N)O[C@H](COC(=O)Cc4ccccc4)[C@@H](OC(=O)[C@@H](N)C(C)C)[C@H]3O)ccc12] | (2R,3S,4R,5R)-5-(4-butyramidopyrrolo[2,1-f][1,2,4]triazin-7-yl)-5-cyano-4-hydroxy-2-((2-phenylacetoxy)methyl)tetrahydrofuran-3-yl L-valinate | 579.3 |

TABLE 1-continued

Exemplary compounds

| Cpd. No. | Structure | Chemical Name | ESI-MS (M + H)+ (m/z) |
|---|---|---|---|
| 347 | 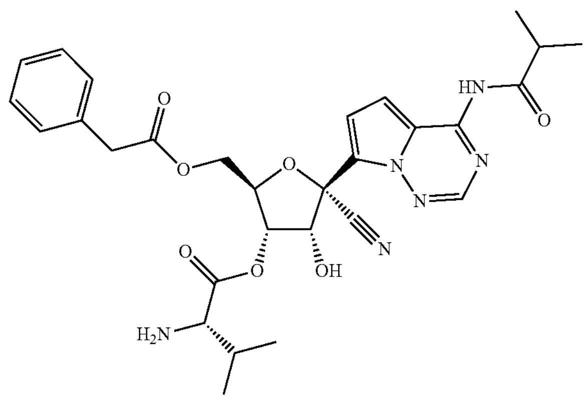 [SMILES: CC(C)C(=O)Nc1ncnn2c([C@]3(C#N)O[C@H](COC(=O)Cc4ccccc4)[C@@H](OC(=O)[C@@H](N)C(C)C)[C@H]3O)ccc12] | (2R,3S,4R,5R)-5-cyano-4-hydroxy-5-(4-isobutyramidopyrrolo[2,1-f][1,2,4]triazin-7-yl)-2-((2-phenylacetoxy)methyl)tetrahydrofuran-3-yl L-valinate | 579.2 |
| 348 | 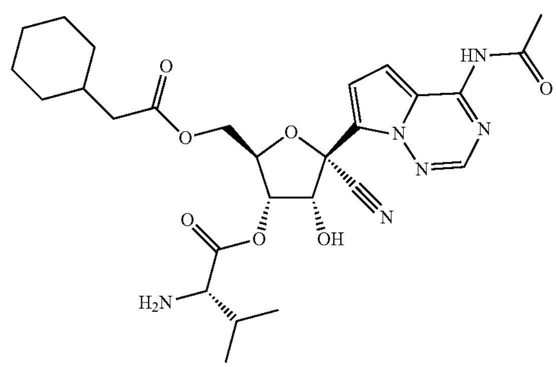 [SMILES: CC(=O)Nc1ncnn2c([C@]3(C#N)O[C@H](COC(=O)CC4CCCCC4)[C@@H](OC(=O)[C@@H](N)C(C)C)[C@H]3O)ccc12] | (2R,3S,4R,5R)-5-(4-acetamidopyrrolo[2,1-f][1,2,4]triazin-7-yl)-5-cyano-2-((2-cyclohexylacetoxy)methyl)-4-hydroxytetrahydrofuran-3-yl L-valinate | 557.3 |
| 349 | 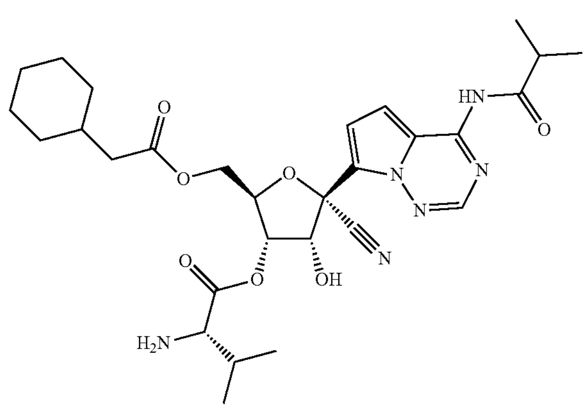 [SMILES: CC(C)C(=O)Nc1ncnn2c([C@]3(C#N)O[C@H](COC(=O)CC4CCCCC4)[C@@H](OC(=O)[C@@H](N)C(C)C)[C@H]3O)ccc12] | (2R,3S,4R,5R)-5-cyano-2-((2-cyclohexylacetoxy)methyl)-4-hydroxy-5-(4-isobutyramidopyrrolo[2,1-f][1,2,4]triazin-7-yl)tetrahydrofuran-3-yl L-valinate | 585.3 |

TABLE 1-continued

Exemplary compounds

| Cpd. No. | Structure | Chemical Name | ESI-MS (M + H)+ (m/z) |
|---|---|---|---|
| 350 | 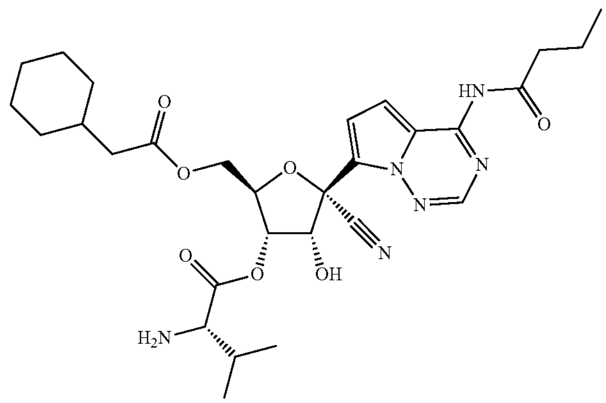 [SMILES: CCCC(=O)Nc1ncnn2c([C@]3(C#N)O[C@H](COC(=O)CC4CCCCC4)[C@@H](OC(=O)[C@@H](N)C(C)C)[C@H]3O)ccc12] | (2R,3S,4R,5R)-5-(4-butyramidopyrrolo[2,1-f][1,2,4]triazin-7-yl)-5-cyano-2-((2-cyclohexylacetoxy)methyl)-4-hydroxytetrahydrofuran-3-yl L-valinate | 585.2 |
| 351 | 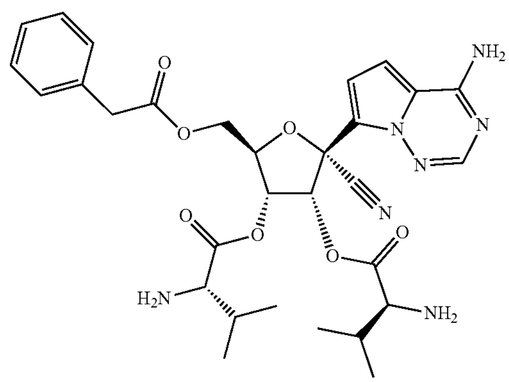 [SMILES: CC(C)[C@H](N)C(=O)O[C@H]1[C@@H](OC(=O)[C@@H](N)C(C)C)[C@](C#N)(c2ccc3c(N)ncnn23)O[C@@H]1COC(=O)Cc1ccccc1] | (2R,3R,4R,5R)-2-(4-aminopyrrolo[2,1-f][1,2,4]triazin-7-yl)-2-cyano-5-((2-phenylacetoxy)methyl)tetrahydrofuran-3,4-diyl (2S,2'S)-bis(2-amino-3-methylbutanoate) | 608.2 |
| 352 | 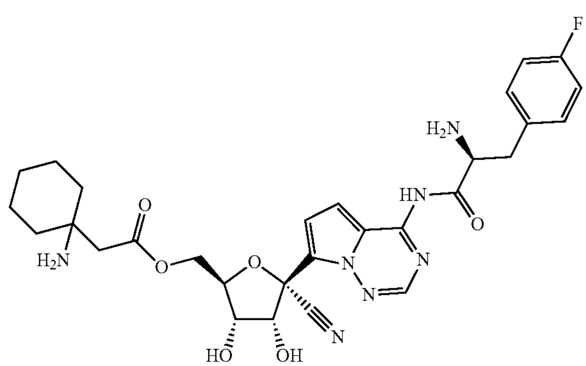 [SMILES: N#C[C@@]1(c2ccc3c(NC(=O)[C@@H](N)Cc4ccc(F)cc4)ncnn23)O[C@H](COC(=O)CC2(N)CCCCC2)[C@@H](O)[C@H]1O] | ((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methyl 2-(1-aminocyclohexyl)acetate | 596.3 |
| 353 | 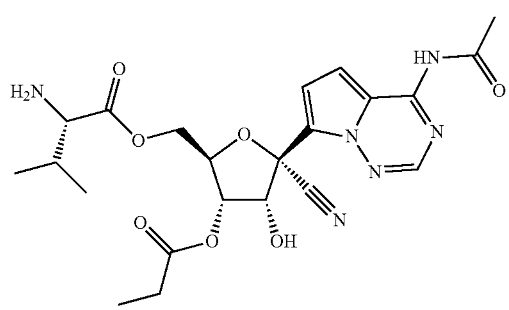 [SMILES: CCC(=O)O[C@H]1[C@@H](O)[C@](C#N)(c2ccc3c(NC(C)=O)ncnn23)O[C@@H]1COC(=O)[C@@H](N)C(C)C] | ((2R,3S,4R,5R)-5-(4-acetamidopyrrolo[2,1-f][1,2,4]triazin-7-yl)-5-cyano-4-hydroxy-3-(propionyloxy)tetrahydrofuran-2-yl)methyl L-valinate | 489.1 |

TABLE 1-continued

Exemplary compounds

| Cpd. No. | Structure | Chemical Name | ESI-MS (M + H)+ (m/z) |
|---|---|---|---|
| 354 | 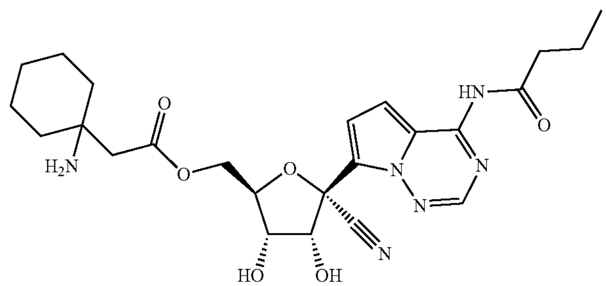 [SMILES: CCCC(=O)Nc1ncnn2c([C@]3(C#N)O[C@H](COC(=O)CC4(N)CCCCC4)[C@@H](O)[C@H]3O)ccc12] | ((2R,3S,4R,5R)-5-(4-butyramidopyrrolo[2,1-f][1,2,4]triazin-7-yl)-5-cyano-3,4-dihydroxytetrahydrofuran-2-yl)methyl 2-(1-aminocyclohexyl)acetate | 501.1 |
| 355 | 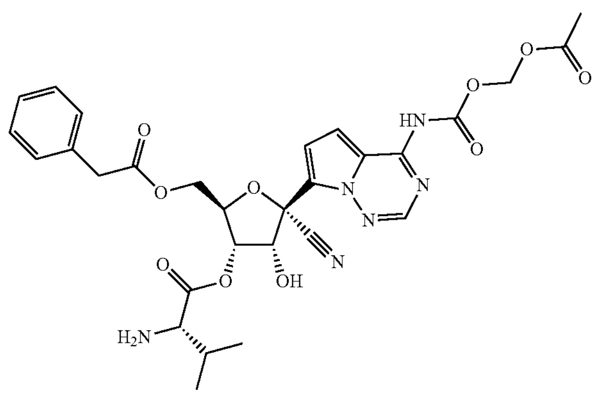 [SMILES: CC(=O)OCOC(=O)Nc1ncnn2c([C@]3(C#N)O[C@H](COC(=O)Cc4ccccc4)[C@@H](OC(=O)[C@@H](N)C(C)C)[C@H]3O)ccc12] | (2R,3S,4R,5R)-5-(4-(((acetoxymethoxy)carbonyl)amino)pyrrolo[2,1-f][1,2,4]triazin-7-yl)-5-cyano-4-hydroxy-2-((2-phenylacetoxy)methyl)tetrahydrofuran-3-yl L-valinate | 625.1 |
| 356 | 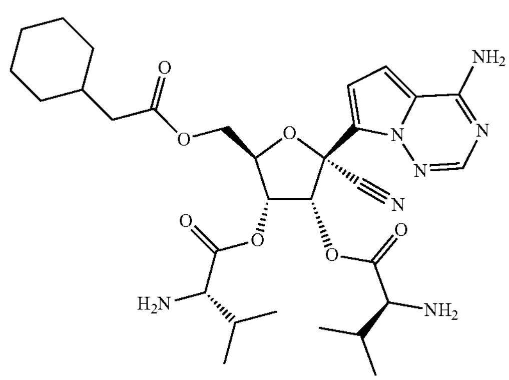 [SMILES: CC(C)[C@H](N)C(=O)O[C@H]1[C@@H](OC(=O)[C@@H](N)C(C)C)[C@](C#N)(c2ccc3c(N)ncnn23)O[C@@H]1COC(=O)CC1CCCCC1] | (2R,3R,4R,5R)-2-(4-aminopyrrolo[2,1-f][1,2,4]triazin-7-yl)-2-cyano-5-((2-cyclohexylacetoxy)methyl)tetrahydrofuran-3,4-diyl (2S,2'S)-bis(2-amino-3-methylbutanoate) | 614.3 |
| 357 | 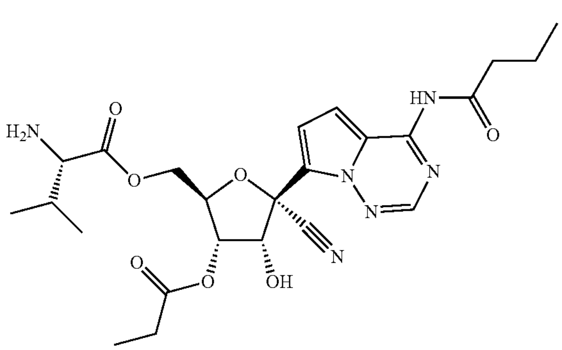 [SMILES: CCCC(=O)Nc1ncnn2c([C@]3(C#N)O[C@H](COC(=O)[C@@H](N)C(C)C)[C@@H](OC(=O)CC)[C@H]3O)ccc12] | ((2R,3S,4R,5R)-5-(4-butyramidopyrrolo[2,1-f][1,2,4]triazin-7-yl)-5-cyano-4-hydroxy-3-(propionyloxy)tetrahydrofuran-2-yl)methyl L-valinate | 517.2 |

TABLE 1-continued

Exemplary compounds

| Cpd. No. | Structure | Chemical Name | ESI-MS (M + H)+ (m/z) |
|---|---|---|---|
| 358 | 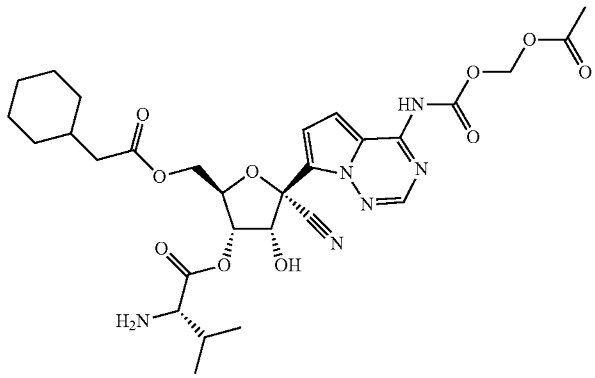 [SMILES: CC(=O)OCOC(=O)Nc1ncnn2c([C@]3(C#N)O[C@H](COC(=O)CC4CCCCC4)[C@@H](OC(=O)[C@@H](N)C(C)C)[C@H]3O)ccc12] | (2R,3S,4R,5R)-5-(4-((((acetoxymethoxy)carbonyl)amino)pyrrolo[2,1-f][1,2,4]triazin-7-yl)-5-cyano-2-((2-cyclohexylacetoxy)methyl)-4-hydroxytetrahydrofuran-3-yl L-valinate | 631.2 |
| 359 | 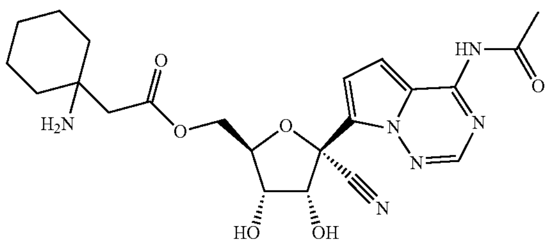 [SMILES: CC(=O)Nc1ncnn2c([C@]3(C#N)O[C@H](COC(=O)CC4(N)CCCCC4)[C@@H](O)[C@H]3O)ccc12] | ((2R,3S,4R,5R)-5-(4-acetamidopyrrolo[2,1-f][1,2,4]triazin-7-yl)-5-cyano-3,4-dihydroxytetrahydrofuran-2-yl)methyl 2-(1-aminocyclohexyl)acetate | 473.1 |
| 360 | 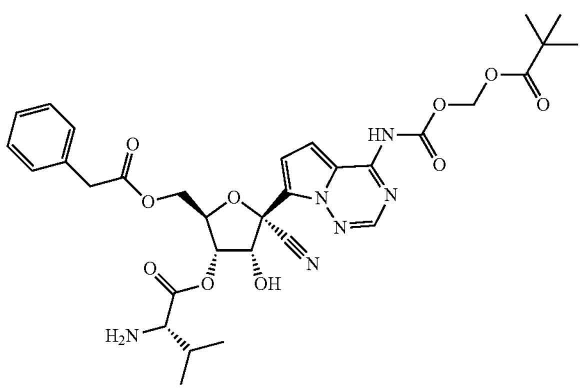 [SMILES: CC(C)[C@H](N)C(=O)O[C@H]1[C@@H](O)[C@](C#N)(c2ccc3c(NC(=O)OCOC(=O)C(C)(C)C)ncnn23)O[C@@H]1COC(=O)Cc1ccccc1] | (2R,3S,4R,5R)-5-cyano-4-hydroxy-2-((2-phenylacetoxy)methyl)-5-(4-(((((pivaloyloxy)methoxy)carbonyl)amino)pyrrolo[2,1-f][1,2,4]triazin-7-yl)tetrahydrofuran-3-yl L-valinate | 667.2 |
| 361 | 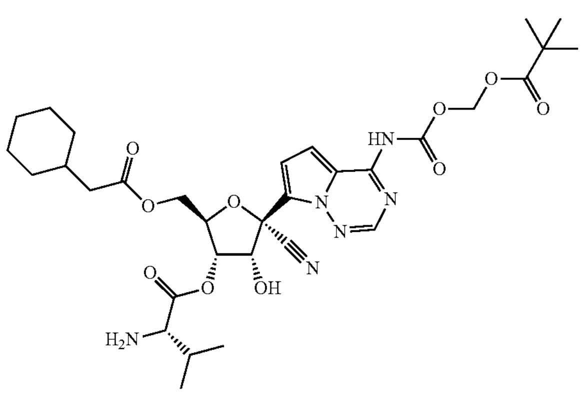 [SMILES: CC(C)[C@H](N)C(=O)O[C@H]1[C@@H](O)[C@](C#N)(c2ccc3c(NC(=O)OCOC(=O)C(C)(C)C)ncnn23)O[C@@H]1COC(=O)CC1CCCCC1] | (2R,3S,4R,5R)-5-cyano-2-((2-cyclohexylacetoxy)methyl)-4-hydroxy-5-(4-(((((pivaloyloxy)methoxy)carbonyl)amino)pyrrolo[2,1-f][1,2,4]triazin-7-yl)tetrahydrofuran-3-yl L-valinate | 673.2 |

TABLE 1-continued

Exemplary compounds

| Cpd. No. | Structure | Chemical Name | ESI-MS (M + H)+ (m/z) |
|---|---|---|---|
| 362 | 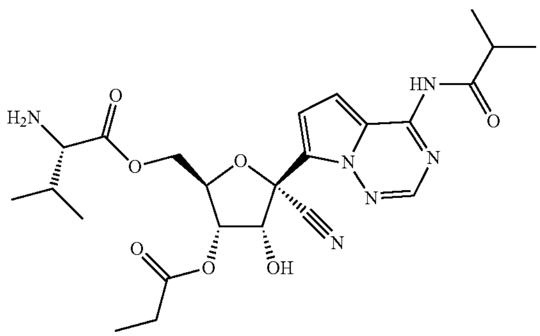 [SMILES: CCC(=O)O[C@H]1[C@@H](O)[C@](C#N)(c2ccc3c(NC(=O)C(C)C)ncnn23)O[C@@H]1COC(=O)[C@@H](N)C(C)C] | ((2R,3S,4R,5R)-5-cyano-4-hydroxy-5-(4-isobutyramidopyrrolo[2,1-f][1,2,4]triazin-7-yl)-3-(propionyloxy)tetrahydrofuran-2-yl)methyl L-valinate | 517.1 |
| 363 | 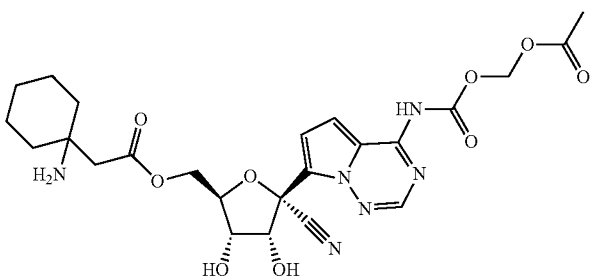 [SMILES: CC(=O)OCOC(=O)Nc1ncnn2c([C@]3(C#N)O[C@H](COC(=O)CC4(N)CCCCC4)[C@@H](O)[C@H]3O)ccc12] | ((2R,3S,4R,5R)-5-(4-(((acetoxymethoxy)carbonyl)amino)pyrrolo[2,1-f][1,2,4]triazin-7-yl)-5-cyano-3,4-dihydroxytetrahydrofuran-2-yl)methyl 2-(1-aminocyclohexyl)acetate | 547.1 |
| 364 | 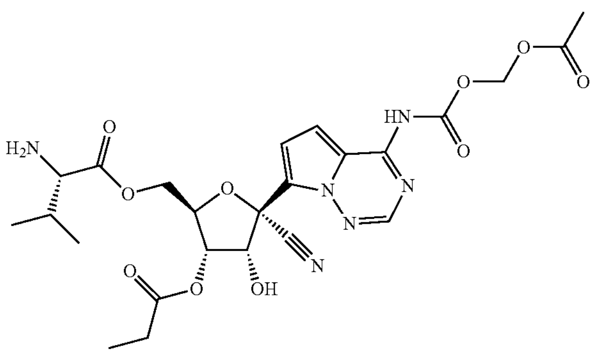 [SMILES: CCC(=O)O[C@H]1[C@@H](O)[C@](C#N)(c2ccc3c(NC(=O)OCOC(C)=O)ncnn23)O[C@@H]1COC(=O)[C@@H](N)C(C)C] | ((2R,3S,4R,5R)-5-(4-(((acetoxymethoxy)carbonyl)amino)pyrrolo[2,1-f][1,2,4]triazin-7-yl)-5-cyano-4-hydroxy-3-(propionyloxy)tetrahydrofuran-2-yl)methyl L-valinate | 563.2 |
| 365 | 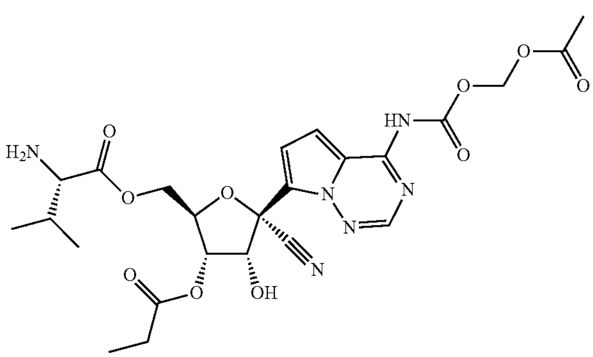 [SMILES: CCC(=O)O[C@H]1[C@@H](O)[C@](C#N)(c2ccc3c(NC(=O)OCOC(C)=O)ncnn23)O[C@@H]1COC(=O)[C@@H](N)C(C)C] | ((2R,3S,4R-5R)-5-cyano-4-hydroxy-5-(4-(((((pivaloyloxy)methoxy)carbonyl)amino)pyrrolo[2,1-f][1,2,4]triazin-7-yl)-3-(propionyloxy)tetrahydrofuran-2-yl)methyl L-valinate | 605.2 |

TABLE 1-continued

Exemplary compounds

| Cpd. No. | Structure | Chemical Name | ESI-MS (M + H)+ (m/z) |
|---|---|---|---|
| 366 | 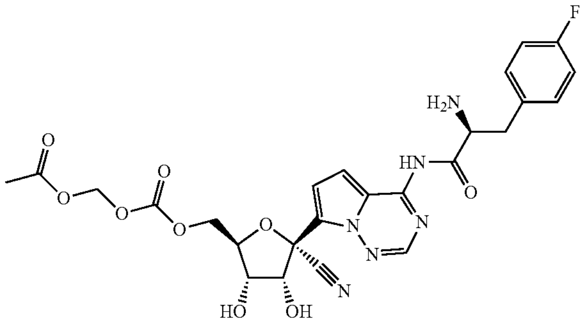 [SMILES: CC(=O)OCOC(=O)OC[C@H]1O[C@@](C#N)(c2ccc3c(NC(=O)[C@@H](N)Cc4ccc(F)cc4)ncnn23)[C@H](O)[C@@H]1O] | (((((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methoxy)carbonyl)oxy)methyl acetate | 573.2 |
| 367 | 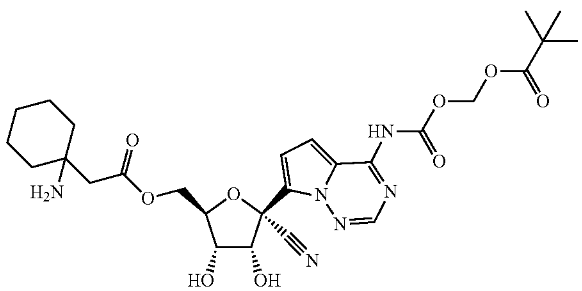 [SMILES: CC(C)(C)C(=O)OCOC(=O)Nc1ncnn2c([C@]3(C#N)O[C@H](COC(=O)CC4(N)CCCCC4)[C@@H](O)[C@H]3O)ccc12] | (((7-((2R,3R,4S,5R)-5-((2-(1-aminocyclohexyl)acetoxy)methyl)-2-cyano-3,4-dihydroxytetrahydrofuran-2-yl)pyrrolo[2,1-f][1,2,4]triazin-4-yl)carbamoyl)oxy)methyl pivalate | 589.2 |
| 368 | 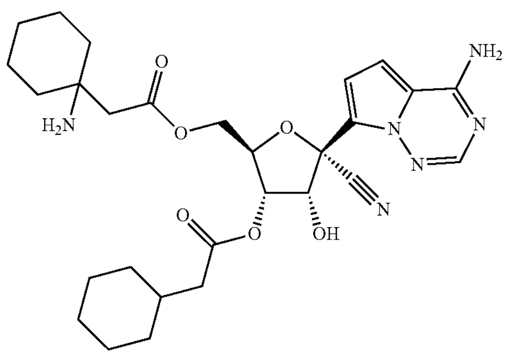 [SMILES: N#C[C@@]1(c2ccc3c(N)ncnn23)O[C@H](COC(=O)CC2(N)CCCCC2)[C@@H](OC(=O)CC2CCCCC2)[C@H]1O] | (2R,3S,4R,5R)-2-((2-(1-aminocyclohexyl)acetoxy)methyl)-5-(4-aminopyrrolo[2,1-f][1,2,4]triazin-7-yl)-5-cyano-4-hydroxytetrahydrofuran-3-yl 2-cyclohexylacetate | 555.3 |
| 369 | 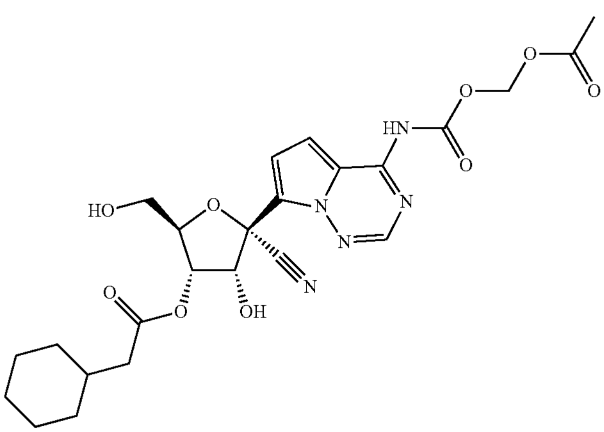 [SMILES: CC(=O)OCOC(=O)Nc1ncnn2c([C@]3(C#N)O[C@H](CO)[C@@H](OC(=O)CC4CCCCC4)[C@H]3O)ccc12] | (2R,3S,4R,5R)-5-(4-(((acetoxymethoxy)carbonyl)amino)pyrrolo[2,1-f][1,2,4]triazin-7-yl)-5-cyano-4-hydroxy-2-(hydroxymethyl)tetrahydrofuran-3-yl 2-cyclohexylacetate | 532.2 |

TABLE 1-continued

Exemplary compounds

| Cpd. No. | Structure | Chemical Name | ESI-MS (M + H)+ (m/z) |
|---|---|---|---|
| 370 | 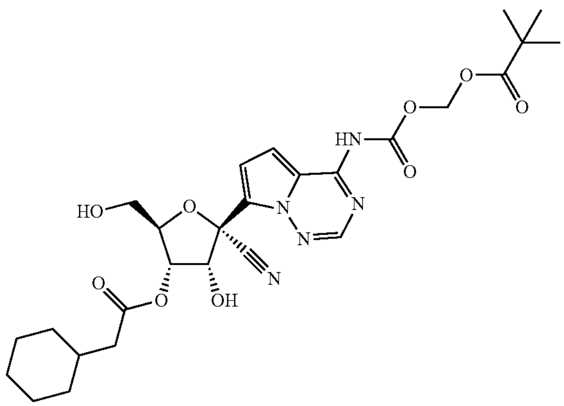 [SMILES: CC(C)(C)C(=O)OCOC(=O)Nc1ncnn2c([C@]3(C#N)O[C@H](CO)[C@@H](OC(=O)CC4CCCCC4)[C@H]3O)ccc12] | (((7-((2R,3R,4S,5R)-2-cyano-4-(2-cyclohexylacetoxy)-3-hydroxy-5-(hydroxymethyl)tetrahydrofuran-2-yl)pyrrolo[2,1-f][1,2,4]triazin-4-yl)carbamoyl)oxy)methyl pivalate | 574.3 |
| 371 | 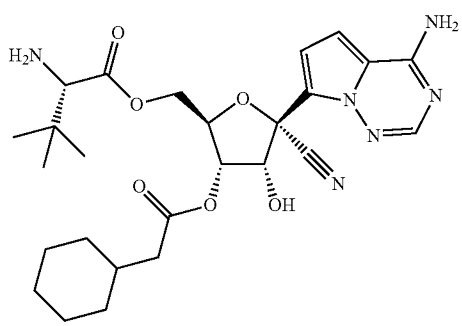 [SMILES: CC(C)(C)[C@H](N)C(=O)OC[C@H]1O[C@@](C#N)(c2ccc3c(N)ncnn23)[C@H](O)[C@@H]1OC(=O)CC1CCCCC1] | ((2R,3S,4R,5R)-5-(4-aminopyrrolo[2,1-f][1,2,4]triazin-7-yl)-5-cyano-3-(2-cyclohexylacetoxy)-4-hydroxytetrahydrofuran-2-yl)methyl (S)-2-amino-3,3-dimethylbutanoate | 529.3 |
| 372 | 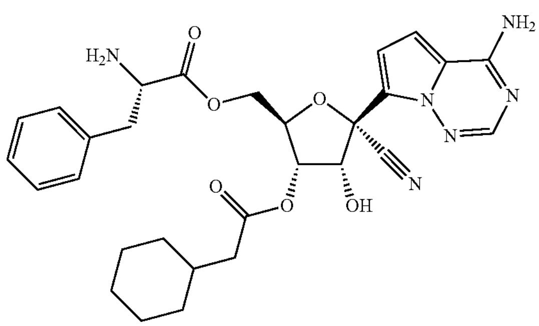 [SMILES: N#C[C@@]1(c2ccc3c(N)ncnn23)O[C@H](COC(=O)[C@@H](N)Cc2ccccc2)[C@@H](OC(=O)CC2CCCCC2)[C@H]1O] | ((2R,3S,4R,5R)-5-(4-aminopyrrolo[2,1-f][1,2,4]triazin-7-yl)-5-cyano-3-(2-cyclohexylacetoxy)-4-hydroxytetrahydrofuran-2-yl)methyl L-phenylalaninate | 563.2 |
| 373 | 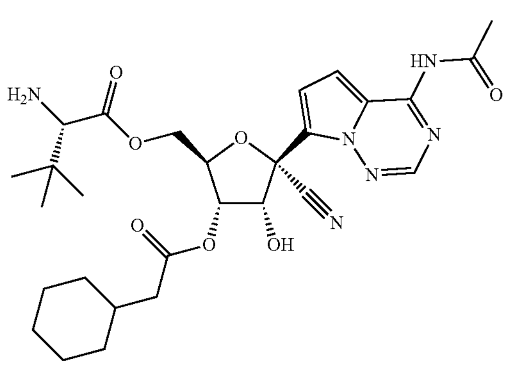 [SMILES: CC(=O)Nc1ncnn2c([C@]3(C#N)O[C@H](COC(=O)[C@@H](N)C(C)(C)C)[C@@H](OC(=O)CC4CCCCC4)[C@H]3O)ccc12] | ((2R,3S,4R,5R)-5-(4-acetamidopyrrolo[2,1-f][1,2,4]triazin-7-yl)-5-cyano-3-(2-cyclohexylacetoxy)-4-hydroxytetrahydrofuran-2-yl)methyl (S)-2-amino-3,3-dimethylbutanoate | 571.4 |

TABLE 1-continued

Exemplary compounds

| Cpd. No. | Structure | Chemical Name | ESI-MS (M + H)+ (m/z) |
| --- | --- | --- | --- |
| 374 | 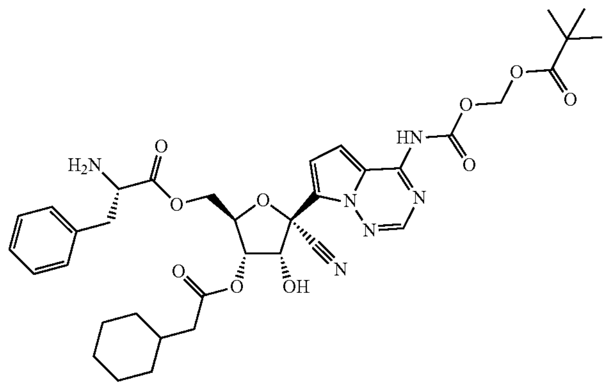 [SMILES: CC(C)(C)C(=O)OCOC(=O)Nc1ncnn2c([C@]3(C#N)O[C@H](COC(=O)[C@@H](N)Cc4ccccc4)[C@@H](OC(=O)CC4CCCCC4)[C@H]3O)ccc12] | (((7-((2R,3R,4S,5R)-5-(((L-phenylalanyl)oxy)methyl)-2-cyano-4-(2-cyclohexylacetoxy)-3-hydroxytetrahydrofuran-2-yl)pyrrolo[2,1-f][1,2,4]triazin-4-yl)carbamoyl)oxy)methyl pivalate | 721.3 |
| 375 | 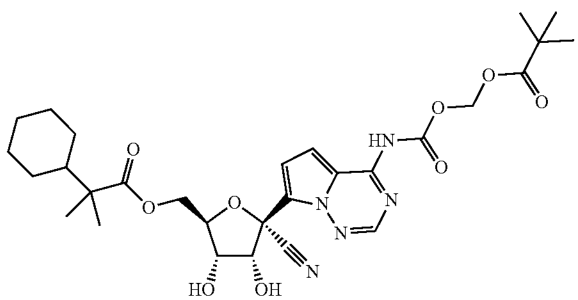 [SMILES: CC(C)(C)C(=O)OCOC(=O)Nc1ncnn2c([C@]3(C#N)O[C@H](COC(=O)C(C)(C)C4CCCCC4)[C@@H](O)[C@H]3O)ccc12] | ((2R,3S,4R,5R)-5-cyano-3,4-dihydroxy-5-(4-(((((pivaloyloxy)methoxy)carbonyl)amino)pyrrolo[2,1-f][1,2,4]triazin-7-yl)tetrahydrofuran-2-yl)methyl 2-cyclohexyl-2-methylpropanoate | 602.3 |
| 376 | 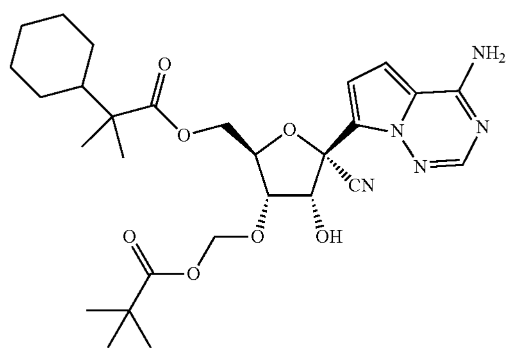 [SMILES: CC(C)(C)C(=O)OCO[C@H]1[C@@H](O)[C@](C#N)(c2ccc3c(N)ncnn23)O[C@@H]1COC(=O)C(C)(C)C1CCCCC1] | (((2R,3S,4R,5R)-5-(4-aminopyrrolo[2,1-f][1,2,4]triazin-7-yl)-5-cyano-2-(((2-cyclohexyl-2-methylpropanoyl)oxy)methyl)-4-hydroxytetrahydrofuran-3-yl)oxy)methyl pivalate | |
| 377 | 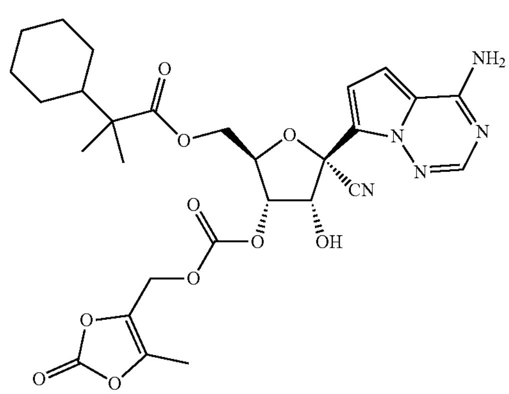 [SMILES: Cc1oc(=O)oc1COC(=O)O[C@H]1[C@@H](O)[C@](C#N)(c2ccc3c(N)ncnn23)O[C@@H]1COC(=O)C(C)(C)C1CCCCC1] | ((2R,3S,4R,5R)-5-(4-aminopyrrolo[2,1-f][1,2,4]triazin-7-yl)-5-cyano-4-hydroxy-3-(((((5-methyl-2-oxo-1,3-dioxol-4-yl)methoxy)carbonyl)oxy)tetrahydrofuran-2-yl) methyl 2-cyclohexyl-2-methylpropanoate | |

TABLE 1-continued

Exemplary compounds

| Cpd. No. | Structure | Chemical Name | ESI-MS (M + H)+ (m/z) |
|---|---|---|---|
| 378 | 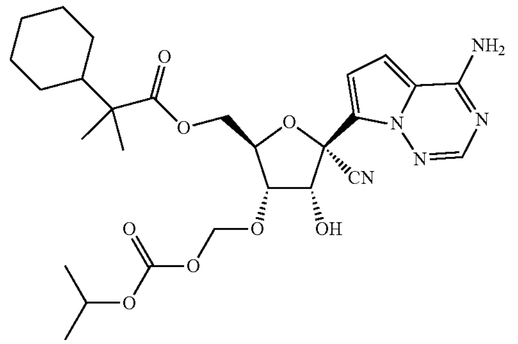 [SMILES: CC(C)OC(=O)OCO[C@H]1[C@@H](O)[C@](C#N)(c2ccc3c(N)ncnn23)O[C@@H]1COC(=O)C(C)(C)C1CCCCC1] | ((2R,3S,4R,5R)-5-(4-aminopyrrolo[2,1-f][1,2,4]triazin-7-yl)-5-cyano-4-hydroxy-3-(((isopropoxycarbonyl)oxy)methoxy)tetrahydrofuran-2-yl)methyl 2-cyclohexyl-2-methylpropanoate | |
| 379 | 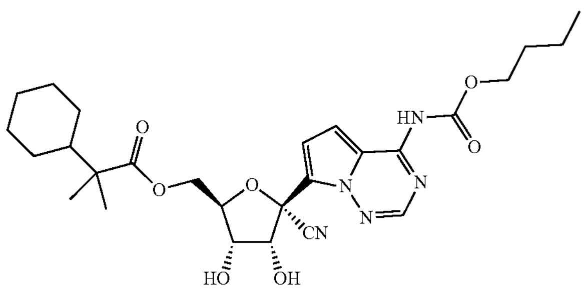 [SMILES: CCCCOC(=O)Nc1ncnn2c([C@]3(C#N)O[C@H](COC(=O)C(C)(C)C4CCCCC4)[C@@H](O)[C@H]3O)ccc12] | ((2R,3S,4R,5R)-5-(4-((butoxycarbonyl)amino)pyrrolo[2,1-f][1,2,4]triazin-7-yl)-5-cyano-3,4-dihydroxytetrahydrofuran-2-yl)methyl 2-cyclohexyl-2-methylpropanoate | 544.2 |
| 380 | 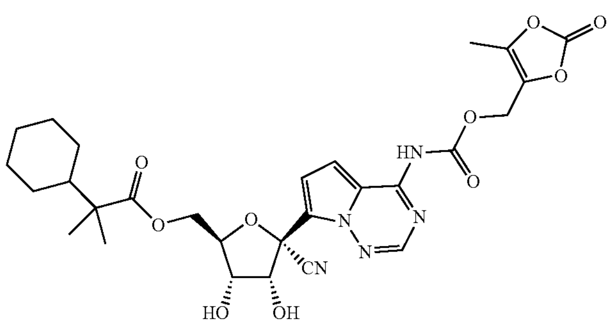 [SMILES: Cc1oc(=O)oc1COC(=O)Nc1ncnn2c([C@]3(C#N)O[C@H](COC(=O)C(C)(C)C4CCCCC4)[C@@H](O)[C@H]3O)ccc12] | ((2R,3S,4R,5R)-5-cyano-3,4-dihydroxy-5-(4-((((5-methyl-2-oxo-1,3-dioxol-4-yl)methoxy)carbonyl)amino)pyrrolo[2,1-f][1,2,4]triazin-7-yl)tetrahydrofuran-2-yl)methyl 2-cyclohexyl-2-methylpropanoate | |
| 381 | 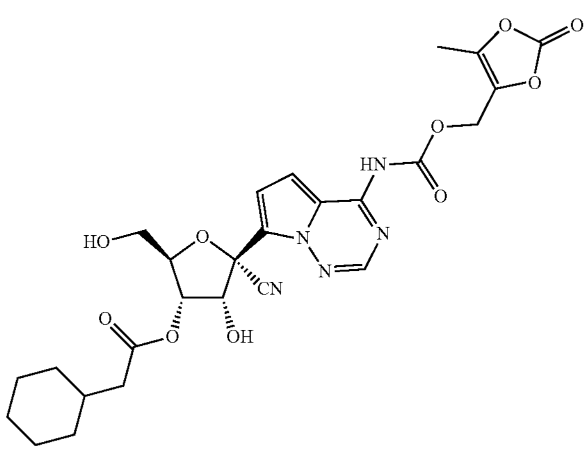 [SMILES: Cc1oc(=O)oc1COC(=O)Nc1ncnn2c([C@]3(C#N)O[C@H](CO)[C@@H](OC(=O)CC4CCCCC4)[C@H]3O)ccc12] | (2R,3S,4R,5R)-5-cyano-4-hydroxy-2-(hydroxymethyl)-5-(4-((((5-methyl-2-oxo-1,3-dioxol-4-yl)methoxy)carbonyl)amino)pyrrolo[2,1-f][1,2,4]triazin-7-yl)tetrahydrofuran-3-yl 2-cyclohexylacetate | |

TABLE 1-continued

Exemplary compounds

| Cpd. No. | Structure | Chemical Name | ESI-MS (M + H)+ (m/z) |
|---|---|---|---|
| 382 | 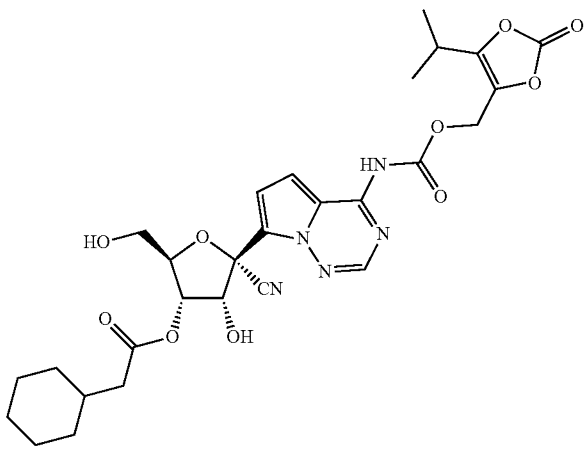 [SMILES: CC(C)c1oc(=O)oc1COC(=O)Nc1ncnn2c([C@]3(C#N)O[C@H](CO)[C@@H](OC(=O)CC4CCCCC4)[C@H]3O)ccc12] | (2R,3S,4R,5R)-5-cyano-4-hydroxy-2-(hydroxymethyl)-5-(4-((((5-isopropyl-2-oxo-1,3-dioxol-4-yl)methoxy)carbonyl)amino)pyrrolo[2,1-f][1,2,4]triazin-7-yl)tetrahydrofuran-3-yl 2-cyclohexylacetate | |
| 383 | 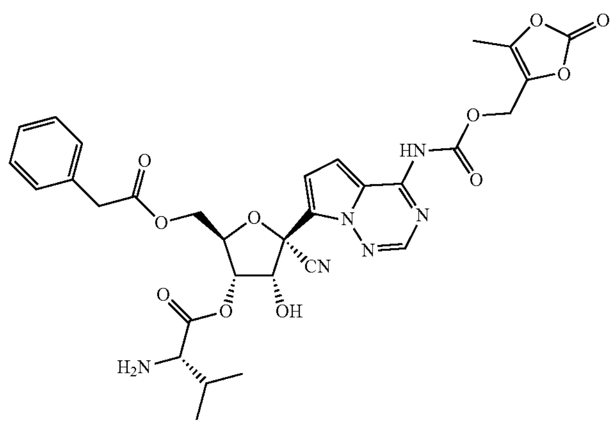 [SMILES: Cc1oc(=O)oc1COC(=O)Nc1ncnn2c([C@]3(C#N)O[C@H](COC(=O)Cc4ccccc4)[C@@H](OC(=O)[C@@H](N)C(C)C)[C@H]3O)ccc12] | (2R,3S,4R,5R)-5-cyano-4-hydroxy-5-(4-((((5-methyl-2-oxo-1,3-dioxol-4-yl)methoxy)carbonyl)amino)pyrrolo[2,1-f][1,2,4]triazin-7-yl)-2-((2-phenylacetoxy)methyl)tetrahydrofuran-3-yl L-valinate | 665.2 |
| 384 | 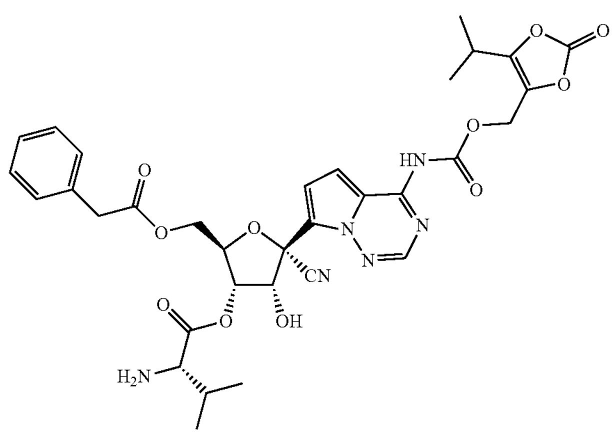 [SMILES: CC(C)c1oc(=O)oc1COC(=O)Nc1ncnn2c([C@]3(C#N)O[C@H](COC(=O)Cc4ccccc4)[C@@H](OC(=O)[C@@H](N)C(C)C)[C@H]3O)ccc12] | (2R,3S,4R,5R)-5-cyano-4-hydroxy-5-(4-((((5-isopropyl-2-oxo-1,3-dioxol-4-yl)methoxy)carbonyl)amino)pyrrolo[2,1-f][1,2,4]triazin-7-yl)-2-((2-phenylacetoxy)methyl)tetrahydrofuran-3-yl L-valinate | |

TABLE 1-continued

Exemplary compounds

| Cpd. No. | Structure | Chemical Name | ESI-MS (M + H)+ (m/z) |
|---|---|---|---|
| 385 | 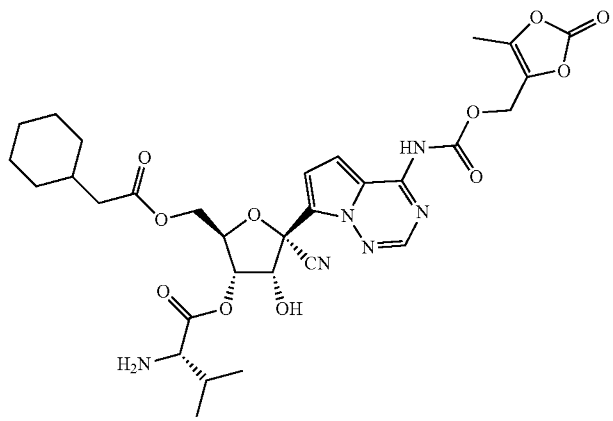 [SMILES: Cc1oc(=O)oc1COC(=O)Nc1ncnn2c([C@]3(C#N)O[C@H](COC(=O)CC4CCCCC4)[C@@H](OC(=O)[C@@H](N)C(C)C)[C@H]3O)ccc12] | (2R,3S,4R,5R)-5-cyano-2-((2-cyclohexylacetoxy)methyl)-4-hydroxy-5-(4-((((5-methyl-2-oxo-1,3-dioxol-4-yl)methoxy)carbonyl)amino)pyrrolo[2,1-f][1,2,4]triazin-7-yl)tetrahydrofuran-3-yl L-valinate | 671.2 |
| 386 | 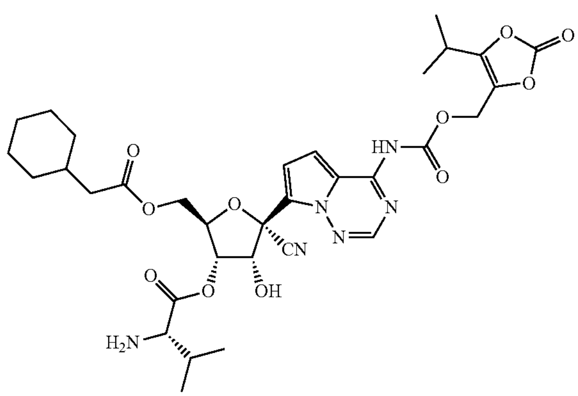 [SMILES: CC(C)c1oc(=O)oc1COC(=O)Nc1ncnn2c([C@]3(C#N)O[C@H](COC(=O)CC4CCCCC4)[C@@H](OC(=O)[C@@H](N)C(C)C)[C@H]3O)ccc12] | (2R,3S,4R,5R)-5-cyano-2-((2-cyclohexylacetoxy)methyl)-4-hydroxy-5-(4-((((5-isopropyl-2-oxo-1,3-dioxol-4-yl)methoxy)carbonyl)amino)pyrrolo[2,1-f][1,2,4]triazin-7-yl)tetrahydrofuran-3-yl L-valinate | |
| 387 | 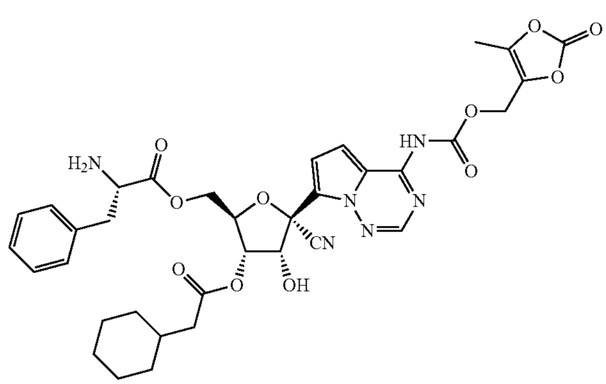 [SMILES: Cc1oc(=O)oc1COC(=O)Nc1ncnn2c([C@]3(C#N)O[C@H](COC(=O)[C@@H](N)Cc4ccccc4)[C@@H](OC(=O)CC4CCCCC4)[C@H]3O)ccc12] | ((2R,3S,4R,5R)-5-cyano-3-(2-cyclohexylacetoxy)-4-hydroxy-5-(4-((((5-methyl-2-oxo-1,3-dioxol-4-yl)methoxy)carbonyl)amino)pyrrolo[2,1-f][1,2,4]triazin-7-yl)tetrahydrofuran-2-yl)methyl L-phenylalaninate | |

TABLE 1-continued

Exemplary compounds

| Cpd. No. | Structure | Chemical Name | ESI-MS (M + H)+ (m/z) |
|---|---|---|---|
| 388 | 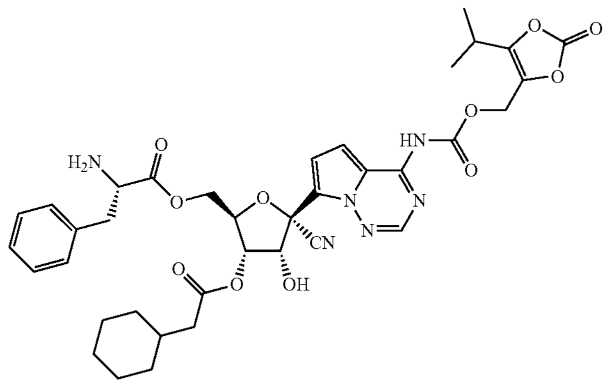 [SMILES: CC(C)c1oc(=O)oc1COC(=O)Nc1ncnn2c([C@]3(C#N)O[C@H](COC(=O)[C@@H](N)Cc4ccccc4)[C@@H](OC(=O)CC4CCCCC4)[C@H]3O)ccc12] | ((2R,3S,4R,5R)-5-cyano-3-(2-cyclohexylacetoxy)-4-hydroxy-5-(4-((((5-isopropyl-2-oxo-1,3-dioxol-4-yl)methoxy)carbonyl)amino)pyrrolo[2,1-f][1,2,4]triazin-7-yl)tetrahydrofuran-2-yl)methyl L-phenylalaninate | |
| 389 | 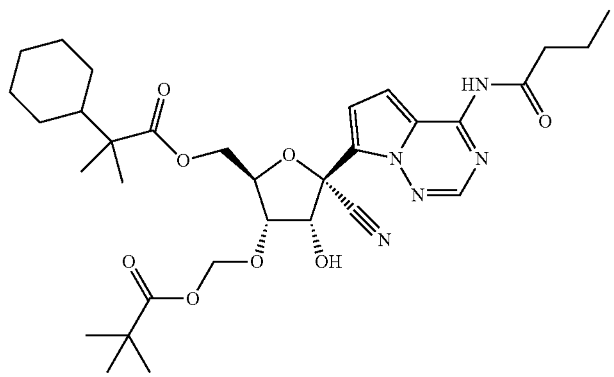 [SMILES: CCCC(=O)Nc1ncnn2c([C@]3(C#N)O[C@H](COC(=O)C(C)(C)C4CCCCC4)[C@@H](OCOC(=O)C(C)(C)C)[C@H]3O)ccc12] | (((2R,3S,4R,5R)-5-(4-butyramidopyrrolo[2,1-f][1,2,4]triazin-7-yl)-5-cyano-2-(((2-cyclohexyl-2-methylpropanoyl)oxy)methyl)-4-hydroxytetrahydrofuran-3-yl)oxy)methyl pivalate | |
| 390 | 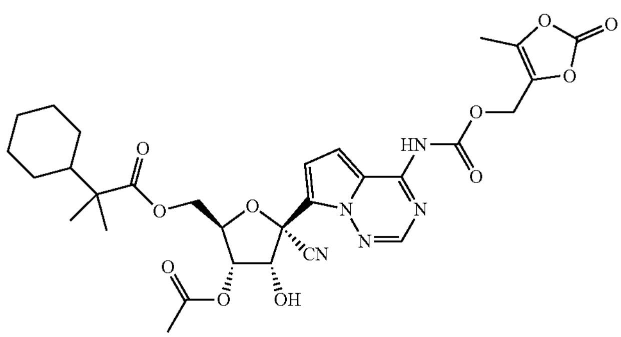 [SMILES: CC(=O)O[C@H]1[C@@H](O)[C@](C#N)(c2ccc3c(NC(=O)OCc4oc(=O)oc4C)ncnn23)O[C@@H]1COC(=O)C(C)(C)C1CCCCC1] | ((2R,3S,4R,5R)-3-acetoxy-5-cyano-4-hydroxy-5-(4-((((5-methyl-2-oxo-1,3-dioxol-4-yl)methoxy)carbonyl)amino)pyrrolo[2,1-f][1,2,4]triazin-7-yl)tetrahydrofuran-2-yl)methyl 2-cyclohexyl-2-methylpropanoate | |
| 391 | 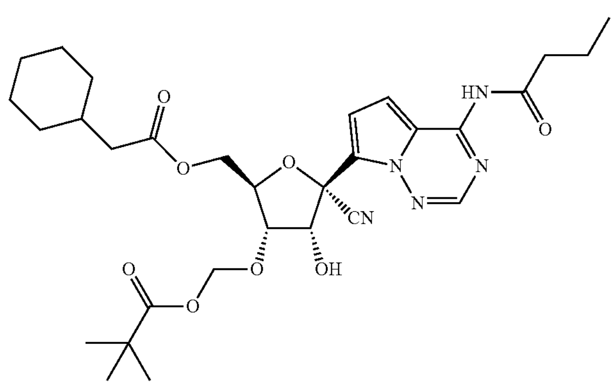 [SMILES: CCCC(=O)Nc1ncnn2c([C@]3(C#N)O[C@H](COC(=O)CC4CCCCC4)[C@@H](OCOC(=O)C(C)(C)C)[C@H]3O)ccc12] | (((2R,3S,4R,5R)-5-(4-butyramidopyrrolo[2,1-f][1,2,4]triazin-7-yl)-5-cyano-2-((2-cyclohexylacetoxy)methyl)-4-hydroxytetrahydrofuran-3-yl)oxy)methyl pivalate | 600.3 |

TABLE 1-continued

Exemplary compounds

| Cpd. No. | Structure | Chemical Name | ESI-MS (M + H)+ (m/z) |
|---|---|---|---|
| 392 | 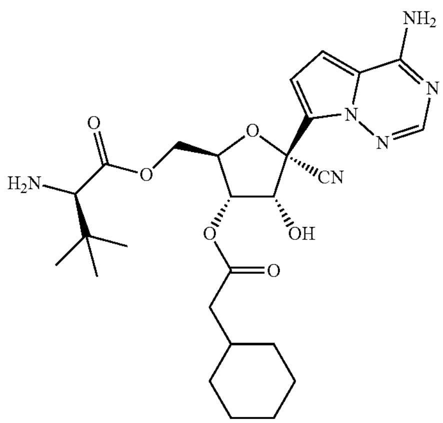 [SMILES: CC(C)(C)[C@@H](N)C(=O)OC[C@H]1O[C@@](C#N)(c2ccc3c(N)ncnn23)[C@H](O)[C@@H]1OC(=O)CC1CCCCC1] | ((2R,3S,4R,5R)-5-(4-aminopyrrolo[2,1-f][1,2,4]triazin-7-yl)-5-cyano-3-(2-cyclohexylacetoxy)-4-hydroxytetrahydrofuran-2-yl)methyl (R)-2-amino-3,3-dimethylbutanoate | 529.3 |
| 393 | 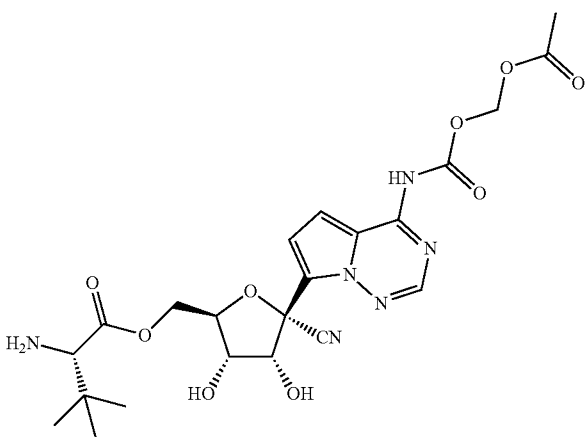 [SMILES: CC(=O)OCOC(=O)Nc1ncnn2c([C@]3(C#N)O[C@H](COC(=O)[C@@H](N)C(C)(C)C)[C@@H](O)[C@H]3O)ccc12] | ((2R,3S,4R,5R)-5-(4-(((acetoxymethoxy)carbonyl)amino)pyrrolo[2,1-f][1,2,4]triazin-7-yl)-5-cyano-3,4-dihydroxytetrahydrofuran-2-yl)methyl(S)-2-amino-3,3-dimethylbutanoate | |
| 394 | 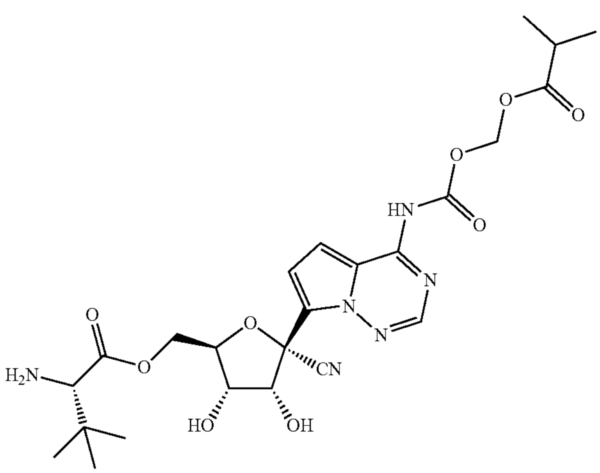 [SMILES: CC(C)C(=O)OCOC(=O)Nc1ncnn2c([C@]3(C#N)O[C@H](COC(=O)[C@@H](N)C(C)(C)C)[C@@H](O)[C@H]3O)ccc12] | ((2R,3S,4R,5R)-5-cyano-3,4-dihydroxy-5-(4-(((((isobutyryloxy)methoxy)carbonyl)amino)pyrrolo[2,1-f][1,2,4]triazin-7-yl)tetrahydrofuran-2-yl)methyl (S)-2-amino-3,3-dimethylbutanoate | |

TABLE 1-continued

Exemplary compounds

| Cpd. No. | Structure | Chemical Name | ESI-MS (M + H)+ (m/z) |
|---|---|---|---|
| 395 | 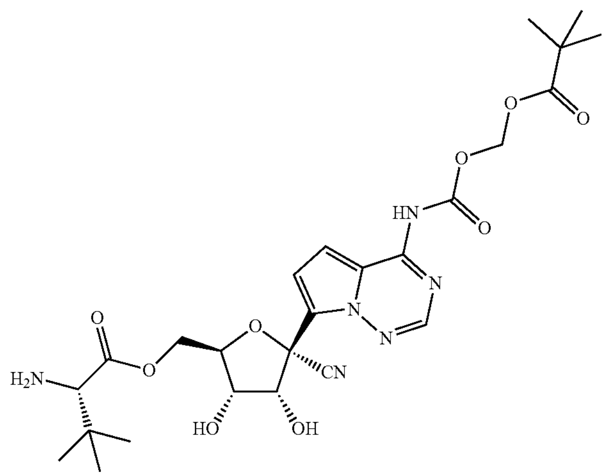 [SMILES: CC(C)(C)C(=O)OCOC(=O)Nc1ncnn2c([C@]3(C#N)O[C@H](COC(=O)[C@@H](N)C(C)(C)C)[C@@H](O)[C@H]3O)ccc12] | ((2R,3S,4R,5R)-5-cyano-3,4-dihydroxy-5-(4-(((((pivaloyloxy)methoxy)carbonyl)amino)pyrrolo[2,1-f][1,2,4]triazin-7-yl)tetrahydrofuran-2-yl)methyl (S)-2-amino-3,3-dimethylbutanoate | 563.2 |
| 396 | 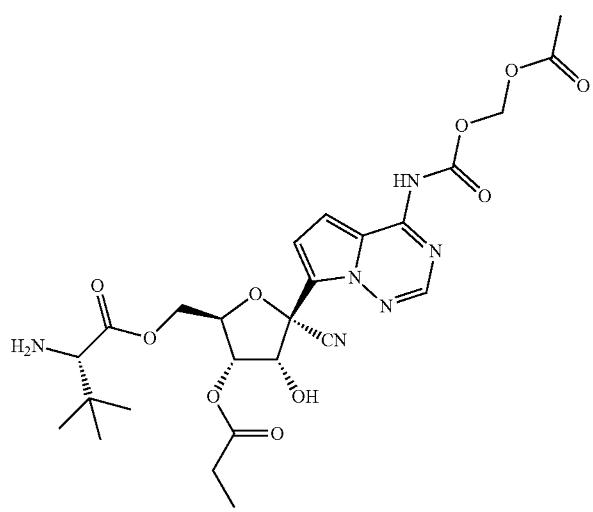 [SMILES: CCC(=O)O[C@H]1[C@@H](O)[C@](C#N)(c2ccc3c(NC(=O)OCOC(C)=O)ncnn23)O[C@@H]1COC(=O)[C@@H](N)C(C)(C)C] | ((2R,3S,4R,5R)-5-(4-(((acetoxymethoxy)carbonyl)amino)pyrrolo[2,1-f][1,2,4]triazin-7-yl)-5-cyano-4-hydroxy-3-(propionyloxy)tetrahydrofuran-2-yl)methyl (S)-2-amino-3,3-dimethylbutanoate | |
| 397 | 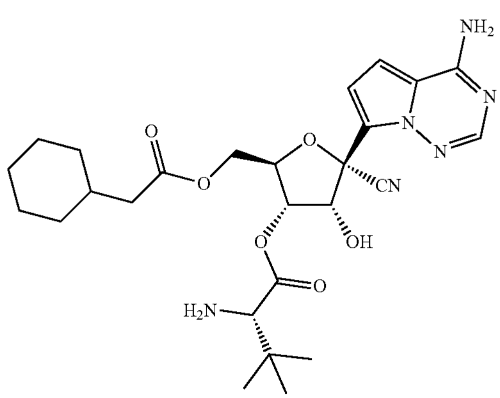 [SMILES: CC(C)(C)[C@H](N)C(=O)O[C@H]1[C@@H](O)[C@](C#N)(c2ccc3c(N)ncnn23)O[C@@H]1COC(=O)CC1CCCCC1] | (2R,3S,4R,5R)-5-(4-aminopyrrolo[2,1-f][1,2,4]triazin-7-yl)-5-cyano-2-((2-cyclohexylacetoxy)methyl)-4-hydroxytetrahydrofuran-3-yl (S)-2-amino-3,3-dimethylbutanoate | 529.2 |

TABLE 1-continued

Exemplary compounds

| Cpd. No. | Structure | Chemical Name | ESI-MS (M + H)+ (m/z) |
|---|---|---|---|
| 398 | 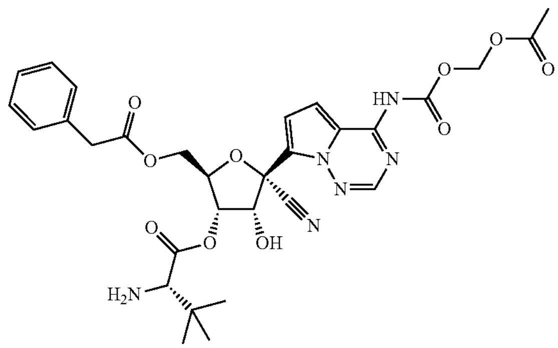 [SMILES: CC(=O)OCOC(=O)Nc1ncnn2c([C@]3(C#N)O[C@H](COC(=O)Cc4ccccc4)[C@@H](OC(=O)[C@@H](N)C(C)(C)C)[C@H]3O)ccc12] | (2R,3S,4R,5R)-5-(4-(((acetoxymethoxy)carbonyl)amino)pyrrolo[2,1-f][1,2,4]triazin-7-yl)-5-cyano-4-hydroxy-2-((2-phenylacetoxy)methyl)tetrahydrofuran-3-yl (S)-2-amino-3,3-dimethylbutanoate | |
| 399 | 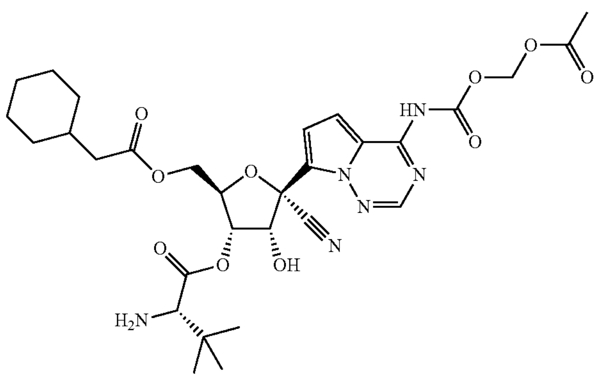 [SMILES: CC(=O)OCOC(=O)Nc1ncnn2c([C@]3(C#N)O[C@H](COC(=O)CC4CCCCC4)[C@@H](OC(=O)[C@@H](N)C(C)(C)C)[C@H]3O)ccc12] | (2R,3S,4R,5R)-5-(4-(((acetoxymethoxy)carbonyl)amino)pyrrolo[2,1-f][1,2,4]triazin-7-yl)-5-cyano-2-((2-cyclohexylacetoxy)methyl)-4-hydroxytetrahydrofuran-3-yl (S)-2-amino-3,3-dimethylbutanoate | 639.3 |
| 400 | 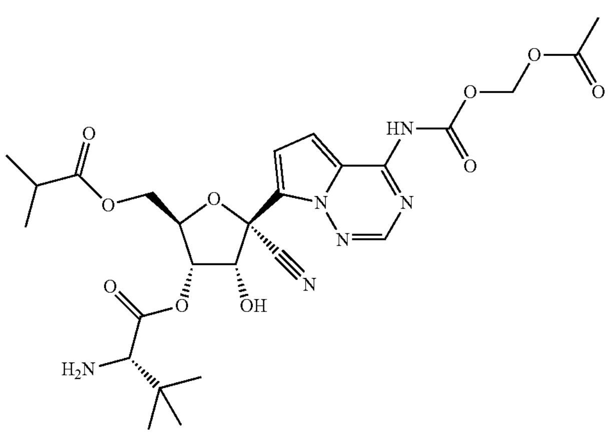 [SMILES: CC(=O)OCOC(=O)Nc1ncnn2c([C@]3(C#N)O[C@H](COC(=O)C(C)C)[C@@H](OC(=O)[C@@H](N)C(C)(C)C)[C@H]3O)ccc12] | (2R,3S,4R,5R)-5-(4-(((acetoxymethoxy)carbonyl)amino)pyrrolo[2,1-f][1,2,4]triazin-7-yl)-5-cyano-4-hydroxy-2-((isobutyryloxy)methyl)tetrahydrofuran-3-yl (S)-2-amino-3,3-dimethylbutanoate | |

TABLE 1-continued

Exemplary compounds

| Cpd. No. | Structure | Chemical Name | ESI-MS (M + H)+ (m/z) |
|---|---|---|---|
| 401 | 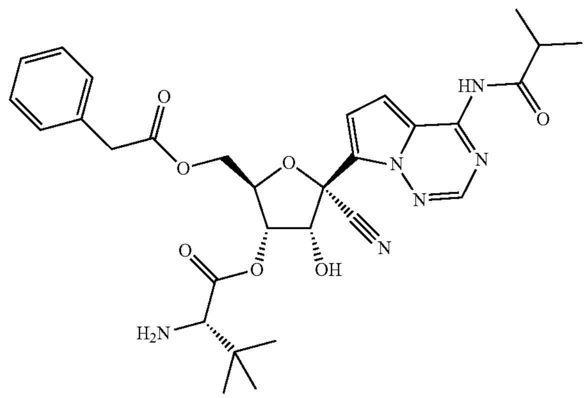 [SMILES: CC(C)C(=O)Nc1ncnn2c([C@]3(C#N)O[C@H](COC(=O)Cc4ccccc4)[C@@H](OC(=O)[C@@H](N)C(C)(C)C)[C@H]3O)ccc12] | (2R,3S,4R,5R)-5-cyano-4-hydroxy-5-(4-isobutyramidopyrrolo[2,1-f][1,2,4]triazin-7-yl)-2-((2-phenylacetoxy)methyl)tetrahydrofuran-3-yl (S)-2-amino-3,3-dimethylbutanoate | 593.3 |
| 402 | 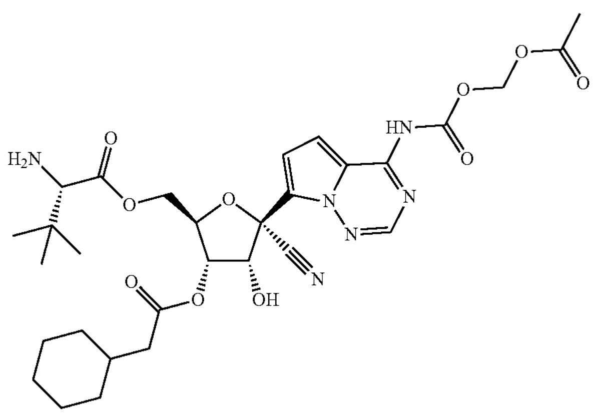 [SMILES: CC(=O)OCOC(=O)Nc1ncnn2c([C@]3(C#N)O[C@H](COC(=O)[C@@H](N)C(C)(C)C)[C@@H](OC(=O)CC4CCCCC4)[C@H]3O)ccc12] | ((2R,3S,4R,5R)-5-(4-(((acetoxymethoxy)carbonyl)amino)pyrrolo[2,1-f][1,2,4]triazin-7-yl)-5-cyano-3-(2-cyclohexylacetoxy)-4-hydroxytetrahydrofuran-2-yl)methyl (S)-2-amino-3,3-dimethylbutanoate | 645.3 |
| 403 | 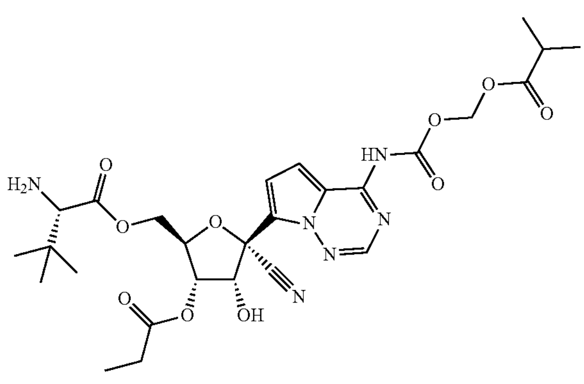 [SMILES: CCC(=O)O[C@H]1[C@@H](O)[C@](C#N)(c2ccc3c(NC(=O)OCOC(=O)C(C)C)ncnn23)O[C@@H]1COC(=O)[C@@H](N)C(C)(C)C] | ((2R,3S,4R,5R)-5-cyano-4-hydroxy-5-(4-(((((isobutyryloxy)methoxy)carbonyl)amino)pyrrolo[2,1-f][1,2,4]triazin-7-yl)-3-(propionyloxy)tetrahydrofuran-2-yl)methyl (S)-2-amino-3,3-dimethylbutanoate | |

TABLE 1-continued

Exemplary compounds

| Cpd. No. | Structure | Chemical Name | ESI-MS (M + H)+ (m/z) |
|---|---|---|---|
| 404 | 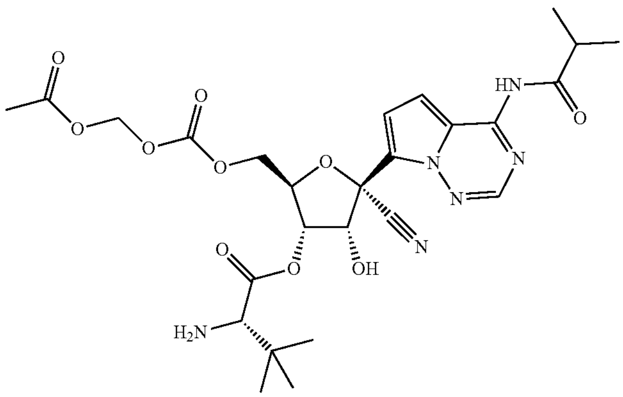 [SMILES: CC(=O)OCOC(=O)OC[C@H]1O[C@@](C#N)(c2ccc3c(NC(=O)C(C)C)ncnn23)[C@H](O)[C@@H]1OC(=O)[C@@H](N)C(C)(C)C] | (2R,3S,4R,5R)-2-(((((acetoxymethoxy)carbonyl)oxy)methyl)-5-cyano-4-hydroxy-5-(4-isobutyramidopyrrolo[2,1-f][1,2,4]triazin-7-yl)tetrahydrofuran-3-yl (S)-2-amino-3,3-dimethylbutanoate | |
| 405 | 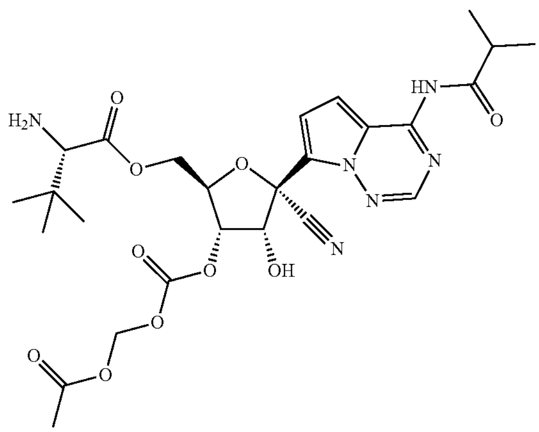 [SMILES: CC(=O)OCOC(=O)O[C@H]1[C@@H](O)[C@](C#N)(c2ccc3c(NC(=O)C(C)C)ncnn23)O[C@@H]1COC(=O)[C@@H](N)C(C)(C)C] | ((2R,3S,4R,5R)-3-(((acetoxymethoxy)carbonyl)oxy)-5-cyano-4-hydroxy-5-(4-isobutyramidopyrrolo[2,1-f][1,2,4]triazin-7-yl)tetrahydrofuran-2-yl)methyl (S)-2-amino-3,3-dimethylbutanoate | |
| 406 | 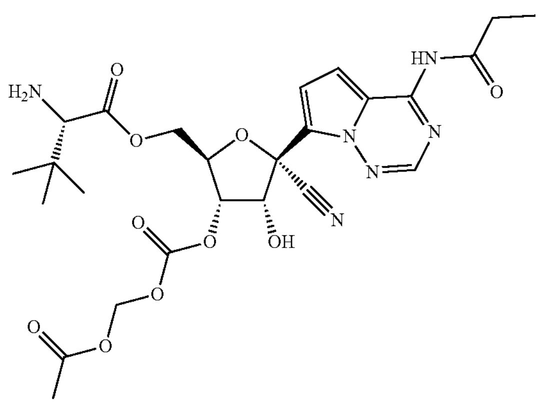 [SMILES: CCC(=O)Nc1ncnn2c([C@]3(C#N)O[C@H](COC(=O)[C@@H](N)C(C)(C)C)[C@@H](OC(=O)OCOC(C)=O)[C@H]3O)ccc12] | ((2R,3S,4R,5R)-3-(((acetoxymethoxy)carbonyl)oxy)-5-(4-butyramidopyrrolo[2,1-f][1,2,4]triazin-7-yl)-5-cyano-4-hydroxytetrahydrofuran-2-yl)methyl (S)-2-amino-3,3-dimethylbutanoate | |
| 407 | 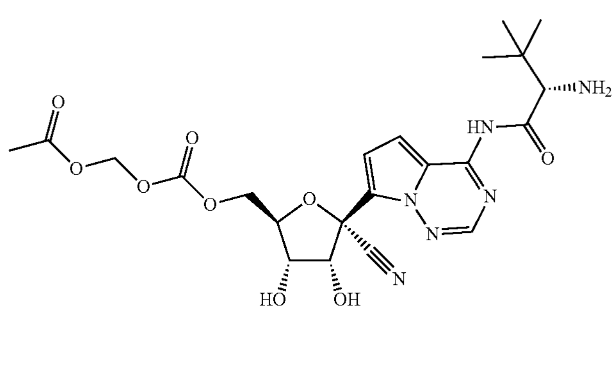 [SMILES: CC(=O)OCOC(=O)OC[C@H]1O[C@@](C#N)(c2ccc3c(NC(=O)[C@@H](N)C(C)(C)C)ncnn23)[C@H](O)[C@@H]1O] | (((((2R,3S,4R,5R)-5-(4-((S)-2-amino-3,3-dimethylbutanamido)pyrrolo[2,1-f][1,2,4]triazin-7-yl)-5-cyano-3,4-dihydroxytetrahydrofuran-2-yl)methoxy)carbonyl)oxy)methyl acetate | |

TABLE 1-continued

Exemplary compounds

| Cpd. No. | Structure | Chemical Name | ESI-MS (M + H)+ (m/z) |
|---|---|---|---|
| 408 | 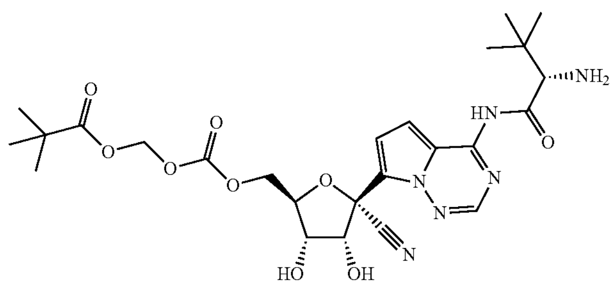 [SMILES: CC(C)(C)C(=O)OCOC(=O)OC[C@H]1O[C@@](C#N)(c2ccc3c(NC(=O)[C@@H](N)C(C)(C)C)ncnn23)[C@H](O)[C@@H]1O] | (((((2R,3S,4R,5R)-5-(4-((S)-2-amino-3,3-dimethylbutanamido)pyrrolo[2,1-f][1,2,4]triazin-7-yl)-5-cyano-3,4-dihydroxytetrahydrofuran-2-yl)methoxy)carbonyl)oxy)methyl pivalate | |
| 409 | 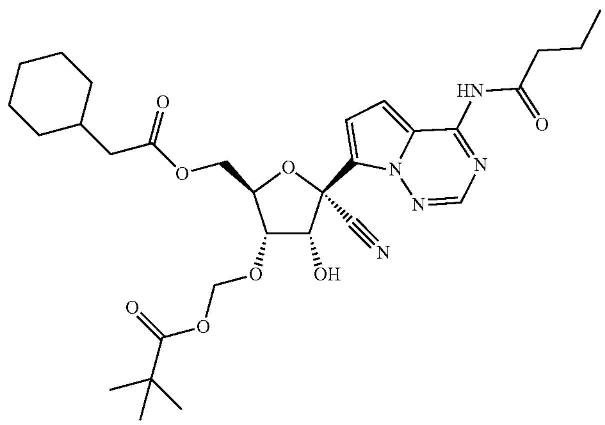 [SMILES: CCCC(=O)Nc1ncnn2c([C@]3(C#N)O[C@H](COC(=O)CC4CCCCC4)[C@@H](OCOC(=O)C(C)(C)C)[C@H]3O)ccc12] | (((2R,3S,4R,5R)-5-(4-butyramidopyrrolo[2,1-f][1,2,4]triazin-7-yl)-5-cyano-2-((2-cyclohexylacetoxy)methyl)-4-hydroxytetrahydrofuran-3-yl)oxy)methyl pivalate | 600.3 |
| 410 | 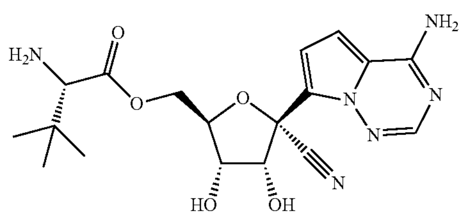 [SMILES: CC(C)(C)[C@H](N)C(=O)OC[C@H]1O[C@@](C#N)(c2ccc3c(N)ncnn23)[C@H](O)[C@@H]1O] | ((2R,3S,4R,5R)-5-(4-aminopyrrolo[2,1-f][1,2,4]triazin-7-yl)-5-cyano-3,4-dihydroxytetrahydrofuran-2-yl)methyl (S)-2-amino-3,3-dimethylbutanoate | 405.2 |
| 411 | 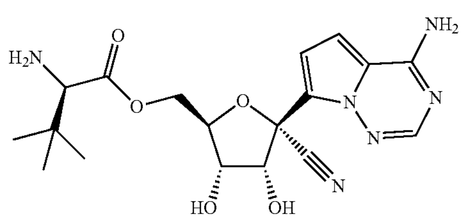 [SMILES: CC(C)(C)[C@@H](N)C(=O)OC[C@H]1O[C@@](C#N)(c2ccc3c(N)ncnn23)[C@H](O)[C@@H]1O] | ((2R,3S,4R,5R)-5-(4-aminopyrrolo[2,1-f][1,2,4]triazin-7-yl)-5-cyano-3,4-dihydroxytetrahydrofuran-2-yl)methyl (R)-2-amino-3,3-dimethylbutanoate | 405.2 |
| 412 | 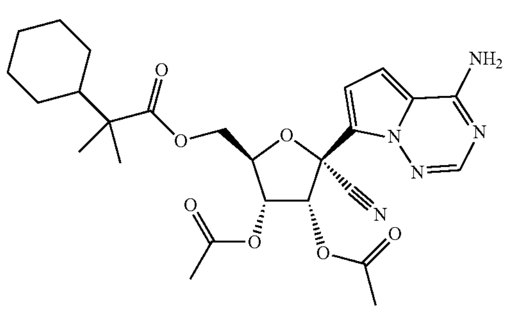 [SMILES: CC(=O)O[C@H]1[C@@H](OC(C)=O)[C@](C#N)(c2ccc3c(N)ncnn23)O[C@@H]1COC(=O)C(C)(C)C1CCCCC1] | (2R,3R,4R,5R)-2-(4-aminopyrrolo[2,1-f][1,2,4]triazin-7-yl)-2-cyano-5-(((2-cyclohexyl-2-methylpropanoyl)oxy)methyl)tetrahydrofuran-3,4-diyl diacetate | 428.2 |

TABLE 1-continued

Exemplary compounds

| Cpd. No. | Structure | Chemical Name | ESI-MS (M + H)+ (m/z) |
|---|---|---|---|
| 413 | 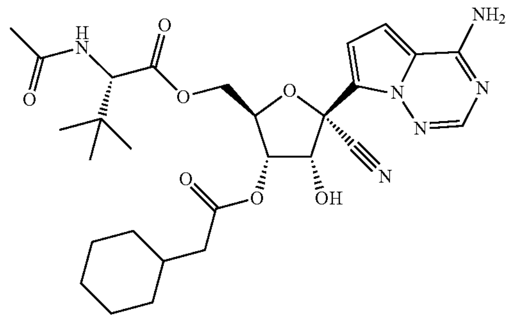 [SMILES: CC(=O)N[C@H](C(=O)OC[C@H]1O[C@@](C#N)(c2ccc3c(N)ncnn23)[C@H](O)[C@@H]1OC(=O)CC1CCCCC1)C(C)(C)C] | ((2R,3S,4R,5R)-5-(4-aminopyrrolo[2,1-f][1,2,4]triazin-7-yl)-5-cyano-3-(2-cyclohexylacetoxy)-4-hydroxytetrahydrofuran-2-yl)methyl (S)-2-acetamido-3,3-dimethylbutanoate | 571.2 |
| 414 | 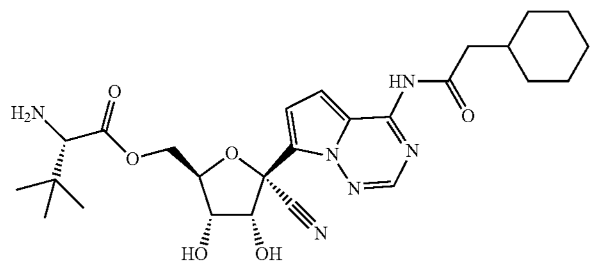 [SMILES: CC(C)(C)[C@H](N)C(=O)OC[C@H]1O[C@@](C#N)(c2ccc3c(NC(=O)CC4CCCCC4)ncnn23)[C@H](O)[C@@H]1O] | ((2R,3S,4R,5R)-5-cyano-5-(4-(2-cyclohexylacetamido)pyrrolo[2,1-f][1,2,4]triazin-7-yl)-3,4-dihydroxytetrahydrofuran-2-yl)methyl (S)-2-amino-3,3-dimethylbutanoate | 529.2 |
| 415 | 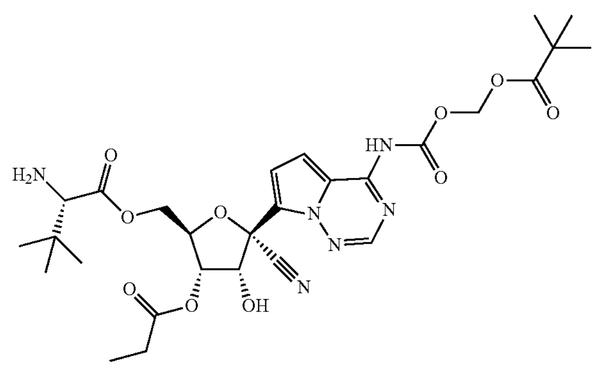 [SMILES: CCC(=O)O[C@H]1[C@@H](O)[C@](C#N)(c2ccc3c(NC(=O)OCOC(=O)C(C)(C)C)ncnn23)O[C@@H]1COC(=O)[C@@H](N)C(C)(C)C] | ((2R,3S,4R,5R)-5-cyano-4-hydroxy-5-(4-((((pivaloyloxy)methoxy)carbonyl)amino)pyrrolo[2,1-f][1,2,4]triazin-7-yl)-3-(propionyloxy)tetrahydrofuran-2-yl)methyl (S)-2-amino-3,3-dimethylbutanoate | 619.3 |

Further Forms of Compounds Disclosed Herein

Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds disclosed herein include isotopes of hydrogen, carbon, nitrogen, oxygen, phosphorous, sulfur, fluorine and chloride, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds described herein, and the pharmaceutically acceptable salts, solvates, or stereoisomers thereof which contain the aforementioned isotopes and/or other isotopes of other atoms are within the scope of this invention. Certain isotopically-labeled compounds, for example those into which radioactive isotopes such as $^3$H and $^{14}$C are incorporated, are useful in drug and/or substrate tissue distribution assays. Tritiated, i.e., $^3$H and carbon-14, i.e., $^{14}$C, isotopes are particularly preferred for their ease of preparation and detectability. Further, substitution with heavy isotopes such as deuterium, i.e., $^2$H, produces certain therapeutic advantages resulting from greater metabolic stability, for example increased in vivo half-life or reduced dosage requirements.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds disclosed herein, or a solvate, or stereoisomer thereof, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds disclosed herein, solvate, or stereoisomer thereof and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, N$^+$(C$_{1-4}$ alkyl)$_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Prodrugs

"Prodrug" is meant to indicate a compound that is, in some embodiments, converted under physiological conditions or by solvolysis to a biologically active compound described herein. Thus, the term "prodrug" refers to a precursor of a biologically active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). Prodrugs are delivered through any known methods described herein, including but not limited to orally, intravenously, intraperitoneal, or other method of administration known by those skilled in the art.

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. In some embodiments, prodrugs include any group bound to a heteroatom, such as the nitrogen of a pyridine which is cleaved in vivo to form the active compound or metabolite thereof. Examples of prodrugs include, but are not limited to, acetate, formate phosphate, and benzoate derivatives of alcohol or amine functional groups in the active compounds and the like.

In some embodiments, a prodrug is a salt. In some embodiments, a prodrug is a phosphate salt. In some embodiments, a prodrug is an alkyl phosphate salt. In some embodiments, a prodrug is an alkylated heteroaromatic salt. In some embodiments, a prodrug is a pyridinium salt. In some embodiments, a prodrug is a pyridinium alkylphosphate salt. In some embodiments, a prodrug is a pyridinium methylphosphate salt. In some embodiments, a prodrug comprises an alkyl phosphate bound to a heteroatom. In some embodiments, a prodrug comprises an alkyl phosphate bound to a heteroatom of a heterocycle.

In some embodiments, a prodrug is any compound that when administered to a biological system generates a biologically active compound as a result of spontaneous chemical reaction(s), enzyme catalyzed chemical reaction(s), and/or metabolic chemical reaction(s), or a combination of each. In other embodiments, prodrugs are formed using groups attached to functionality, e.g., HO—, HS—, HOOC—, NHR—, associated with the drug or active compounds, that cleave in vivo. In some embodiments, prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated above are exemplary, not exhaustive, and other varieties of prodrugs are possible. Such prodrugs of disclosed compounds fall within this scope. In some embodiments, the compounds of the present application are prodrugs themselves and are converted into other forms, including the biologically active compound forms, when administered to a biological system.

In some embodiments, prodrugs undergo some form of a chemical transformation to produce the compound that is biologically active or is a precursor of the biologically active compound. In some cases, the prodrug is biologically active, more or less than the intended active drug itself, and serves to improve drug efficacy or safety through improved oral bioavailability, and/or pharmacodynamic half-life, etc. Prodrug forms of compounds are utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Prodrugs are described in The Organic Chemistry of Drug Design and Drug Action, by Richard B. Silverman, Academic Press, San Diego, 1992, Chapter 8: "Prodrugs and Drug delivery Systems" pp. 352-401; Design of Prodrugs, edited by H. Bundgaard, Elsevier Science, Amsterdam, 1985; Design of Biopharmaceutical Properties through Prodrugs and Analogs, Ed. by E. B. Roche, American Pharmaceutical Association, Washington, 1977; and Drug Delivery Systems, ed. by R. L. Juliano, Oxford Univ. Press, Oxford, 1980.

In some embodiments, prodrugs comprise phosphorus moieties including phosphates or derivatives thereof. One such class of prodrugs is the aryl amidate (McGuigan) type. One report disclosed pharmacokinetic evaluation in the cynomolgus monkey of an aryl amidate prodrug of abacavir. (C. McGuigan et al., "Application of phosphoramidate pronucleotide technology to abacavir leads to a significant enhancement of antiviral potency," J. Med. Chem. 2005, 48, 3504-3515).

In some embodiments, the compounds of the present application comprise a prodrug moiety that is carbamate, thiocarbamate or urea to mask an amino group on the active compound. In some embodiments, the prodrug moiety of carbamate, thiocarbamate or urea is metabolized in vivo to afford the free amino moiety on the active compound.

Method of Treatment

In one aspect, the disclosure provides a method of treating, preventing and/or reducing the severity or extent of viral infections by administering to a subject in need thereof a therapeutically effective amount of a compound of Formula (I), (Ia), (Ib), (Ic), (Id), (Ie), (If), (Ig), (II), (III), (IV), (V), (VIa), (VIb), and (VIc), or a pharmaceutically acceptable salt, solvate, or stereoisomer thereof, or a pharmaceutical composition comprising the compound.

The compounds described herein find use in a variety of applications for human and animal health. In some embodiments, the compounds described herein are inhibitors of coronavirus.

In some embodiments, the efficacy of treatment is determined using quantification of viral load or other evidence of infection.

In some embodiments, the compounds described herein reduce viral load in an individual suffering from an coronavirus infection.

As used herein, the term "administering" or "administration" refers to any route of introducing or delivering the composition or formulation to perform the intended function or treatment. Administration can be carried out by any route suitable for the delivery of composition or formulation. Thus, delivery routes can include intravenous, intramuscular, intraperitoneal, or subcutaneous delivery. Administration includes self-administration and the administration by another.

As used herein, the terms "patient" "subject" "individual" and the like are used interchangeably, and refer to any animal, or cells thereof whether in vitro or in situ, amenable to the methods described herein. In certain non-limiting embodiments, the patient, subject or individual is a human.

As used herein, the terms "prevent" and "prevention" refer to acting prior to overt disease or disorder onset, to prevent the disease or disorder from developing, or to minimize the extent of the disease or disorder, or to slow its course of development.

As used herein, the term "cure" refers to heal, to make well, or to restore to good health or to allow a time without recurrence of disease so that the risk of recurrence is small.

The subjects receiving the therapy described herein (e.g. a therapeutically effective amount of a compound of Formula (I), (Ia), (Ib), (Ic), (Id), (Ie), (If), (Ig), (II), (III), (IV), (V), (VIa), (VIb), and (VIc), or a pharmaceutically acceptable salt, solvate, or stereoisomer thereof, or a pharmaceutical composition comprising the compound) may experience as a result of the therapy a reduction of virus count or improvement of at least one symptom associated with the virus infection, including, for example, fever, coughing, fatigue, pain, etc.

In one aspect, the disclosure provides a method for treating, preventing and/or reducing the severity or extent of viral infection, including, for example, a single-stranded positive sense RNA virus, coronavirus, severe acute respiratory syndrome coronavirus (SARS-CoV), Zika, dengue, yellow fever, West Nile, Hendra, Newcastle, Venezuelan equine encephalitis, chikungunya, Semliki Forest, Sindbis, Avian influenza A, Porcine Reproductive and Respiratory Syndrome, and Human immunodeficiency virus type 1. In another aspect, the disclosure provides a method for treating, preventing and/or reducing the severity or extent of viral infection, including, for example, a DNA virus, equine herpesvirus type 1, pseudorabies virus, BK polyomavirus, and porcine circovirus 2. COVID-19 pandemic, SARS-CoV-2, is a single stranded positive sense RNA virus that is closely related to severe acute respiratory syndrome coronavirus (SARS-CoV).

Also disclosed herein is a method of treating an infection in a subject, comprising administering to the subject a compound disclosed herein, or a pharmaceutically acceptable salt, solvate, or stereoisomer thereof.

Also disclosed herein is a method of treating an infection in a subject, comprising administering to the subject a pharmaceutical composition disclosed herein.

In some embodiments, the infection is a viral infection. In some embodiments, the infection is caused by the SARS-CoV or SARS-CoV-2 virus. In some embodiments, the infection is COVID, or COVID-19.

In some embodiments, the viral infection is caused by a virus selected from the group consisting of coronavirus disease 2019 (SARS-CoV-2), YellowFever, Eastern Equine Encephalitis virus, Human Immunodeficiency virus (HIV), "African Swine Fever Viruses," Arbovirus, Adenoviridae, Arenaviridae, Arterivirus, Astroviridae, Baculoviridae, Bimaviridae, Bimaviridae, Bunyaviridae, Caliciviridae, Caulimoviridae, Circoviridae, Coronaviridae, Cystoviridae, Ebolavirus, Deltaviridae, Filviridae, Filoviridae, Flaviviridae, Iridoviridae, Mononegavirus, Myoviridae, Papiloma virus, Papovaviridae, Paramyxoviridae, Prions, Parvoviridae, Phycodnaviridae, Poxviridae, Potyviridae, Reoviridae, Retroviridae, Rhabdoviridae, Tectiviridae, Togaviridae, pox, papilloma, corona, influenza, sendai virus (SeV), sindbis virus (SINV), vaccinia viruses, West Nile, Hanta, viruses which cause the common cold, and any combination thereof.

Zaire ebolavirus, more commonly known as Ebola virus, is one of six known species within the genus Ebolavirus. Four of the six known ebolaviruses, including EBOV, cause a severe and often fatal hemorrhagic fever in humans and other mammals, known as Ebola virus disease (EVD). In some embodiments the viral infection is caused by one ebolavirus. In some embodiments the viral infection is caused by the Ebola virus.

Compositions/Formulations

The compounds described herein are administered to a subject in need thereof, either alone or in combination with pharmaceutically acceptable carriers, excipients or diluents, in a pharmaceutical composition, according to standard pharmaceutical practice. In one embodiment, the compounds of this invention may be administered to animals. The compounds can be administered orally or parenterally, including the intravenous, intramuscular, intraperitoneal, subcutaneous, rectal and topical routes of administration.

In another aspect, provided herein are pharmaceutical compositions comprising a compound describe herein, or a pharmaceutically acceptable salt, solvate, or stereoisomer thereof, and at least one pharmaceutically acceptable excipient. Pharmaceutical compositions are formulated in a conventional manner using one or more pharmaceutically acceptable excipients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the pharmaceutically acceptable excipient is selected from carriers, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, and any combinations thereof.

The pharmaceutical compositions described herein are administered to a subject by appropriate administration routes, including, but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including compounds described herein, or a pharmaceutically acceptable salt, solvate, or stereoisomer thereof are manufactured in a conventional manner, such as, by way of example only, by means of conventional mixing, dissolving, granulating, dragee-making, levigating, emulsifying, encapsulating, entrapping, or compression processes.

Pharmaceutical compositions for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical compositions that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

Pharmaceutical compositions for parental use are formulated as infusions or injections. In some embodiments, the pharmaceutical composition suitable for injection or infusion includes sterile aqueous solutions, or dispersions, or sterile powders comprising a compound described herein, or a pharmaceutically acceptable salt, solvate, or stereoisomer thereof. In some embodiments, the pharmaceutical composition comprises a liquid carrier. In some embodiments, the liquid carrier is a solvent or liquid dispersion medium comprising, for example, water, saline, ethanol, a polyol (for example, glycerol, propylene glycol, liquid polyethylene glycols, and the like), vegetable oils, nontoxic glyceryl esters, and any combinations thereof. In some embodiments, the pharmaceutical compositions further comprise a preservative to prevent growth of microorganisms.

As used herein, the term "composition" or "pharmaceutical composition" refers to a composition comprising a therapeutically effective compound and a pharmaceutically acceptable carrier and optionally, other materials, e.g., one or more inert components (for example, a detectable agent or label) or one or more active components. The pharmaceutical composition facilitates administration of the therapeutically effective compound to a subject.

As used herein, the term "carrier" refers to a diluent, adjuvant, excipient, or vehicle in which the pharmaceutical composition is administered. Pharmaceutically acceptable carriers may include one or more solvents, dispersion media, coatings, isotonic and absorption delaying agents, and the like that are physiologically compatible. Compositions can include components such as diluents, binders, stabilizers, buffers, salts, lipophilic solvents, preservatives, or mixtures thereof. Examples of pharmaceutically acceptable carriers include but are not limited to water, saline, phosphate buffered saline, aqueous dextrose solutions, glycerol solutions. Suitable pharmaceutical excipients include starch, glucose, lactose, sucrose, dextrose, gelatin, mannitol, cellulose malt, rice, flour, chalk, silica gel, sodium stearate, glycerol monostearate, talc, sodium chloride, milk powder, glycerol, propylene, glycol, water, ethanol and the like.

Carriers may also encompass a buffer or pH adjusting agent such as a salt prepared from an organic acid or base optionally mixed with a nontoxic surfactant. Examples of buffers include but are not limited to organic acid salts such as salts of citric acid, ascorbic acid, gluconic acid, carbonic acid, tartaric acid, succinic acid, acetic acid, or phthalic acid, Tris, tromethamine hydrochloride, and phosphate buffers. Additional carriers may include polymeric excipients or additives such as polyvinylpyrrolidones, ficolls (a polymeric sugar), dextrates (e.g., cyclodextrins, such as 2-hydroxypropyl-.quadrature.-cyclodextrin), polyethylene glycols, flavoring agents such as cherry or wintergreen flavor, antimicrobial agents, sweeteners, antioxidants, antistatic agents. The compositions may include a pharmaceutical carrier or excipient and a compound of Formula (I), (Ia), (Ib), (Ic), (Id), (Ie), (If), (Ig), (II), (III), (IV), (V), (VIa), (VIb), and (VIc), and, in addition, may include other medicinal agents, pharmaceutical agents, carriers, adjuvants, binding agents etc. A pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

The compositions can take the form of solid, semi-solid, lyophilized powder, or liquid dosage forms, such as for example, solutions, suspensions, emulsion, aerosols, gels, implants, microneedles, tablets, pills, capsules, soft elastic or hard gelatin capsules, dermal patch, gummy bears, powders, suspensions, extended-release formulations and the like, for example, in unit dosage forms suitable for simple administration of precise dosages. In one embodiment the composition takes the forms of tablets, capsules, liquid caps, sublingual dissolving tablets, sublingual spray, nasal spray, gummy bear and/or dermal patch.

In one aspect, the composition is a liquid-based formulation including but not limited to an emulsion, suspension, solution, elixirs, or syrup in which the disclosed compound is dissolved and/or suspended, or in the form of a liquid-containing capsule in which the disclosed compound is dissolved and/or suspended in the liquid portion of the capsule core. The composition may be a capsule filled with an effective therapeutic amount of the liquid pharmaceutical formulation.

Combination

Disclosed herein are methods of treating coronavirus infection using a compound disclosed herein in combination with additional therapeutic agents useful for treating coronavirus infection.

In some embodiments, the compound disclosed herein in combination with additional therapeutic agents useful for treating a coronavirus infection are administered simultaneously. In some embodiments, the compound disclosed herein in combination with additional therapeutic agents useful for treating a coronavirus infection are administered sequentially.

For the treatment of Arenaviridae virus infections or coronavirus infection, preferably, the other active therapeutic agent is active against Arenaviridae virus infections, particularly Lassa virus, coronavirus infection and Junin virus infections. Non-limiting examples of these other active therapeutic agents are ribavirin, favipiravir (also known as T-705 or Avigan), T-705 monophosphate, T-705 diphosphate, T-705 triphosphate, ST-193, and mixtures thereof. The compounds and compositions of the present disclosure are also intended for use with general care provided to patients with Arenaviridae viral infections, including parenteral fluids (including dextrose saline and Ringer's lactate) and nutrition, antibiotic (including metronidazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K and zinc sulfate), anti-inflammatory agents (such as ibuprofen), pain medications, and medications for other common diseases in the patient population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis.

It is also possible to combine any compound of the disclosure with one or more additional active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the disclosure with one or more other active therapeutic agents generally refers to simultaneous or sequential administration of a compound of the disclosure and one or more other active therapeutic agents, such that therapeutically effective amounts of the compound of the disclosure and one or more other active therapeutic agents are both present in the body of the patient.

Co-administration includes administration of unit dosages of the compounds of the disclosure before or after administration of unit dosages of one or more other active therapeutic agents, for example, administration of the compounds of the disclosure within seconds, minutes, or hours of the administration of one or more other active therapeutic agents. For example, a unit dose of a compound of the disclosure can be administered first, followed within seconds or minutes by administration of a unit dose of one or more other active therapeutic agents. Alternatively, a unit dose of one or more other therapeutic agents can be administered first, followed by administration of a unit dose of a compound of the disclosure within seconds or minutes. In some cases, it may be desirable to administer a unit dose of a compound of the disclosure first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the disclosure.

The combination therapy may provide "synergy" and "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic anti-viral effect denotes an antiviral effect which is greater than the predicted purely additive effects of the individual compounds of the combination.

Additional non-limiting examples of additional therapeutic agents useful for treating coronavirus infections include:
TLR Agonists In some embodiments, the compound described herein is used in combination with a TLR agonist (TLR7, 8 and/or 9). In some embodiments, the TLR agonist is RG7795, GS-9620, SM360320, or AZD 8848.
RIG-I Agonists In some embodiments, the compound described herein is used in combination with a RIG-I agonist. In some embodiments, the RIG-I agonist is inarigivir.
Interferons In some embodiments, the compound described herein is used in combination with an interferon. In some embodiments, the interferon is interferon alpha (IFN-α), interferon alpha-2a, recombinant interferon alpha-2a, peginterferon alpha-2a, interferon alpha-2b, recombinant interferon alpha-2b, interferon alpha-2b XL, peginterferon alpha-2b, glycosylated interferon alpha-2b, interferon alpha-2c, recombinant interferon alpha-2c, interferon beta, interferon beta-1a, peginterferon beta-1a, interferon delta, interferon lambda (IFN-1), peginterferon lambda-1, interferon omega, interferon tau, interferon gamma (IFN-g), interferon alfacon-1, interferon alpha-n1, interferon alpha-n3, albinterferon alpha-2b, BLX-883, DA-3021, PI 101 (also known as AOP2014), PEG-infergen, belerofon, INTEFEN-IFN, albumin/interferon alpha 2a fusion protein, rHSA-IFN alpha2a, rHSA-IFN alpha 2b, PEG-IFN-SA, interferon alpha biobetter; in particular, peginterferon alpha-2a, peginterferon alpha-2b, glycosylated interferon alpha-2b, peginterferon beta-1a, or peginterferon lambda-1.

Preparation of Compounds

The size and scale of the synthetic methods will vary depending on the desired amount of end product. It is understood that while specific reactants and amounts are provided in the Examples, one of skill in the art knows other alternative and equally feasible sets of reactants that will also yield the same compounds. Thus, where general oxidizers, reducers, solvents of various nature (aprotic, apolar, polar, etc.) are utilized, equivalents will be known in the art and are herein contemplated for use in the present methods.

For instance, in all instances, where a drying agent is used, contemplated drying agents include all those reported in the literature and known to one of skill, such as, but not limited to, magnesium sulfate, sodium sulfate, calcium sulfate, calcium chloride, potassium chloride, potassium hydroxide, sulfuric acid, quicklime, phosphorous pentoxide, potassium carbonate, sodium, silica gel, aluminum oxide, calcium hydride, lithium aluminum hydride (LAH), potassium hydroxide, and the like. (See, Burfield et al., "Dessicant Efficiency in Solvent Drying. A Reappraisal by Application of a Novel Method for Solvent Water Assay," *J. Org. Chem.*, 42(18):3060-3065, 1977). The amount of drying agent to add in each work up may be optimized by one of skill in the art and is not particularly limited. Further, although general guidance is provided for work-up of the intermediates in each step, it is generally understood by one of skill that other optional solvents and reagents may be equally substituted during the work-up steps. However, in some exceptional instances, it was found the very specific work-up conditions are required to maintain an unstable intermediate. Those instances are indicated below in the steps in which they occur.

Many of the steps below indicate various work-ups following termination of the reaction. A work-up involves generally quenching of a reaction to terminate any remaining catalytic activity and starting reagents. This is generally followed by addition of an organic solvent and separation of the aqueous layer from the organic layer. The product is typically obtained from the organic layer and unused reactants and other spurious side products and unwanted chemicals are generally trapped in the aqueous layer and discarded. The work-up in standard organic synthetic procedures found throughout the literature is generally followed by drying the product by exposure to a drying agent to remove any excess water or aqueous byproducts remaining partially dissolved in the organic layer and concentration of the remaining organic layer. Concentration of product dissolved in solvent may be achieved by any known means, such as evaporation under pressure, evaporation under increased temperature and pressure, and the like. Such concentrating may be achieved by use of standard laboratory equipment such as rotary-evaporator distillation, and the like. This is optionally followed by one or more purification steps which may include, but is not limited to, flash column chromatography, filtration through various media and/or other preparative methods known in the art. (See, for instance, Addison Ault, "Techniques and Experiments for Organic Chemistry," 6$^{th}$ Ed., University Science Books, Sausalito, Calif., 1998, Ann B. McGuire, Ed., pp. 45-59). Though certain organic co-solvents and quenching agents may be indicated in the steps described below, other equivalent organic solvents and quenching agents known to one of skill may be employed equally as well and are fully contemplated herein. Further, most of the work-ups in most steps may be further altered according to preference and desired end use or end product. Drying and evaporation, routine steps at the organic synthetic chemist bench, need not be employed and may be considered in all steps to be optional. The number of extractions with organic solvent may be as many as one, two, three, four, five, or ten or more, depending on the desired result and scale of reaction. Except where specifically noted, the volume, amount of quenching agent, and volume of organic solvents used in the work-up may be varied depending on specific reaction conditions and optimized to yield the best results.

Additionally, where inert gas or noble gas is indicated, any inert gas commonly used in the art may be substituted for the indicated inert gas, such as argon, nitrogen, helium, neon, etc.

EXAMPLES

Examples below are intended to illustrate the general procedures used for preparing the compounds of the present invention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 1: Synthesis of ((2R,3R,4R,5S)-5-(4-aminoimidazo[2,1-f][1,2,4]triazin-7-yl)-4-fluoro-3-hydroxy-4-methyltetrahydrofuran-2-yl)methyl isobutyrate (Compound 1)

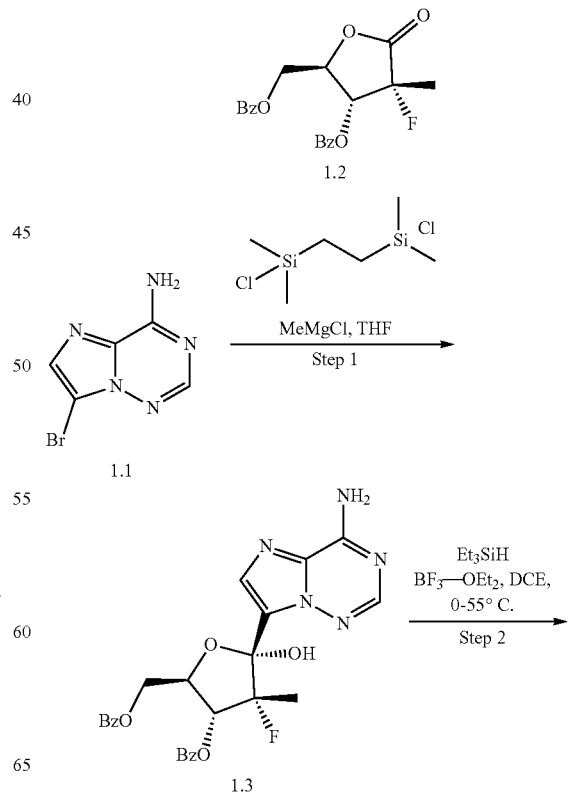

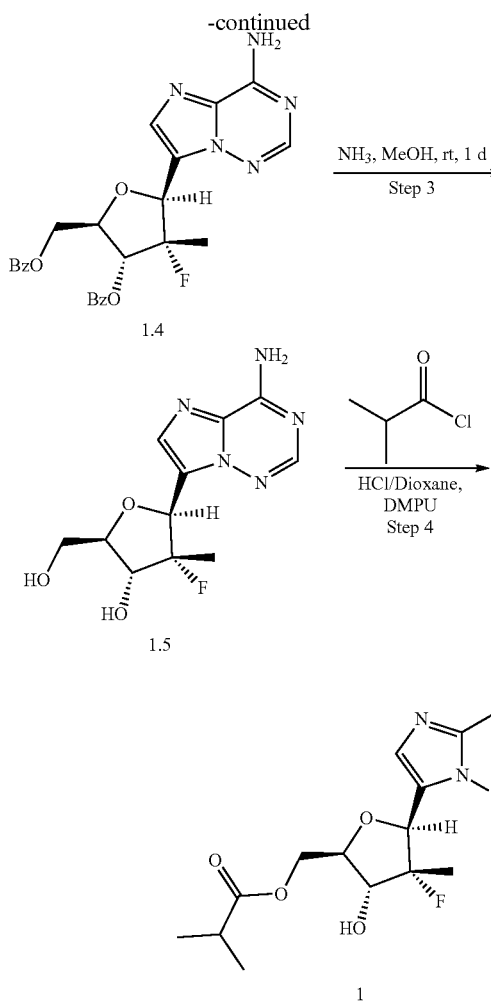

Step 1: Synthesis of (2R,3R,4R,5S)-5-(4-aminoimidazo[2,1-f][1,2,4]triazin-7-yl)-2-((benzoyloxy)methyl)-4-fluoro-5-hydroxy-4-methyltetrahydrofuran-3-yl benzoate (1.3)

To a suspension of 7-bromoimidazo[2,1-f][1,2,4]triazin-4-amine (1.1, 1 g, 4.7 mmol) in anhydrous THF (25 ml) was added MeMgCl (3 N, 1.6 mL, 4.7 mmol) dropwise at 0° C., followed by addition of 1,2-bis(chlorodimethylsilyl)ethane (1.0 g, 4.7 mmol) in THF (5 mL) in one portion. Then a second portion of MeMgCl (3 N, 1.6 mL, 4.7 mmol) was added. The temperature was controlled below 10° C. and $^i$PrMgCl·LiCl (1.3 N, 4 mL, 5.2 mmol) was added dropwise. Then the mixture was stirred at RT for 2 h. ((2R,3R,4R)-3-(Benzoyloxy)-4-fluoro-4-methyl-5-oxotetrahydrofuran-2-yl)methyl benzoate (1.2, 3.5 g, 9.4 mmol) in THF (20 mL) was added dropwise at 0° C. The mixture was stirred at RT for another 5 hours. The reaction was quenched by NH$_4$Cl (sat. aqueous, 20 mL) and extracted with EtOAc (30 mL×3). The combined organics were dried over sodium sulfate and concentrated in vacuo. The residue was purified by flash column chromatography (MeOH/DCM from 2% to 10%) to obtain 1.3 as a white solid (1.3 g, 51% yield). MS (ESI): mass calcd. for $C_{25}H_{22}FN_5O_6$, 507.16, m/z found 508 [M+H]$^+$.

Step 2: Synthesis of (2R,3R,4S,5S)-5-(4-aminoimidazo[2,1-f][1,2,4]triazin-7-yl)-2-((benzoyloxy)methyl)-4-fluoro-4-methyltetrahydrofuran-3-yl benzoate (1.4)

To a solution of 1.3 (300 mg, 0.5912 mmol) in DCE (30 mL) were added triethylsilane (550 mg, 4.73 mmol, 0.76 mL) and BF$_3$—OEt$_2$ (1.4 g, 4.73 mmol, 1.27 mL) at 0° C. The solution was stirred at 55° C. for 5 hours, then another portion of triethylsilane (550 mg, 4.73 mmol, 0.76 mL) and BF$_3$—OEt$_2$ (1.4 g, 4.73 mmol, 1.27 mL) were added at 0° C. The mixture was stirred 55° C. for 16 hours. The reaction was quenched by NaHCO$_3$ (sat. aqueous, 20 mL) and extracted with DCM (30 mL×3). The combined organics were dried over sodium sulfate and concentrated. The residue was purified by flash column chromatography (MeOH/DCM from 2% to 10%) to obtain 5 as a white solid (550 mg, 44% yield). MS (ESI): mass calcd. for $C_{25}H_{22}FN_5O_5$, 491.16, m/z found 492 [M+H]$^+$.

Step 3: Synthesis of (2R,3R,4R,5S)-5-(4-aminoimidazo[2,1-f][1,2,4]triazin-7-yl)-4-fluoro-2-(hydroxymethyl)-4-methyltetrahydrofuran-3-ol (1.5)

(2R,3R,4S,5S)-5-(4-aminoimidazo[2,1-f][1,2,4]triazin-7-yl)-2-((benzoyloxy)methyl)-4-fluoro-4-methyltetrahydrofuran-3-yl benzoate (1.4, 550 mg, 1.12 mmol) was dissolved in a solution of NH$_3$ in MeOH (7 N, 15 mL). The mixture was stirred at 25° C. for 24 h and concentrated in vacuo. The residue was washed with DCM (5 mL×2) and dried in vacuum. The crude product was purified by prep-HPLC (ACN in 0.1% FA/H$_2$O=5~30%) to afford 1.5 (90 mg, 28.4% yield) as a white solid. MS (ESI): m/z calcd. for $C_{11}H_{14}FN_5O_3$ 283.11, found 284.0 [M+H]$^+$. $^1$H NMR (400 MHz, MeOD) δ 8.09 (s, 1H), 7.75 (s, 1H), 5.65 (d, J=24.7 Hz, 1H), 4.18-4.10 (m, 1H), 4.03-3.96 (m, 2H), 3.85-3.82 (m, 1H), 1.20 (d, J=22.0 Hz, 3H). $^{19}$F NMR (400 MHz, MeOD) δ −156.26.

Step 4: Synthesis of ((2R,3R,4R,5S)-5-(4-aminoimidazo[2,1-f][1,2,4]triazin-7-yl)-4-fluoro-3-hydroxy-4-methyltetrahydrofuran-2-yl)methyl isobutyrate To a solution of (2R,3R,4R,5S)-5-(4-aminoimidazo[2,1-f][1,2,4]triazin-7-yl)-4-fluoro-2-(hydroxymethyl)-4-methyltetrahydrofuran-3-ol (1.5) (80 mg, 0.28 mmol) in DMPU (2 mL) was added HCl in dioxane (4 M, 0.1 mL). The mixture solution was stirred at 25° C. for 15 min. Then isobutyryl chloride (90 mg, 0.84 mmol) was added at 0° C., and the resulting mixture was stirred at 0° C. for another 3 h. The reaction was quenched by MeOH (2 mL) and purified by prep-HPLC to afford the title compound (12.18 mg, 12% yield) as a white solid. MS (ESI): m/z calcd. for $C_{15}H_{20}FN_5O_4$ 353.35, found 354.0.35 [M+H]$^+$. $^1$H NMR (400 MHz, MeOD) δ 8.10 (s, 1H), 7.64 (s, 1H), 5.65 (d, J=8.0 Hz, 1H), 4.51-4.48 (m, 1H), 4.18-4.10 (m, 2H), 4.21-4.09 (m, 1H), 3.91-3.97 (m, 1H), 2.68-2. (m, 1H), 1.25 (d, J=20.0 Hz, 3H), 1.21 (d, J=8.0 Hz, 6H). $^{19}$F NMR (376 MHz, CD$_3$OD) δ −155.75.

Example 2. Synthesis of ((2R,3R,4R,5R)-5-(2-amino-6-(methylamino)-9H-purin-9-yl)-3,4-dihydroxy-4-methyltetrahydrofuran-2-yl)methyl isobutyrate (Compound 2)

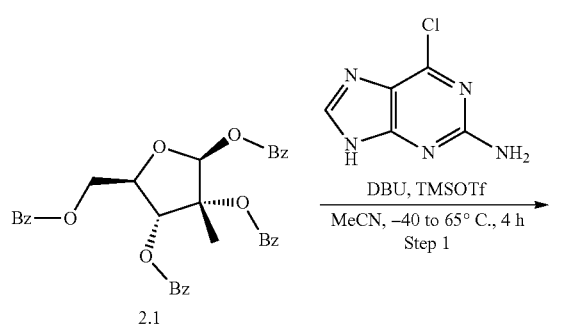

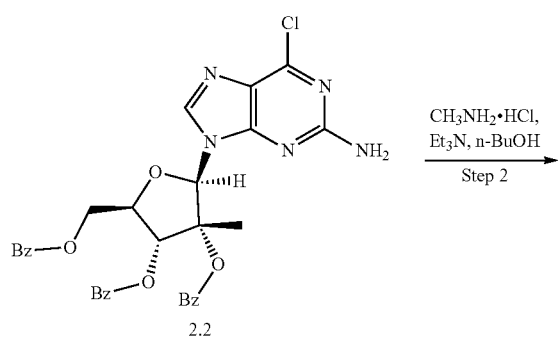

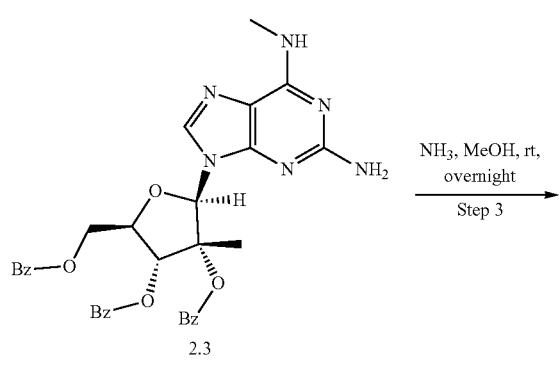

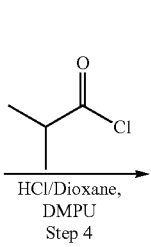

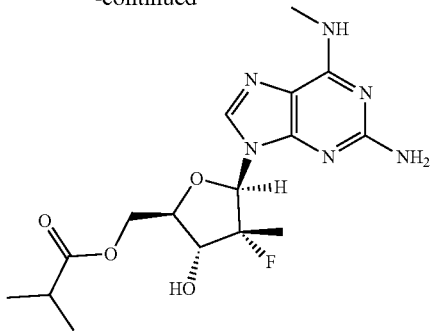

Step 1: Synthesis of (2R,3R,4R,5R)-2-(2-amino-6-chloro-9H-purin-9-yl)-5-((benzoyloxy)methyl)-3-methyltetrahydrofuran-3,4-diyl dibenzoate (2.2)

To a suspension of (2S,3R,4R,5R)-5-((benzoyloxy)methyl)-3-methyltetrahydrofuran-2,3,4-triyl tribenzoate (2.1, 1.22 g, 2.10 mmol) and 6-chloro-9H-purin-2-amine (0.39 g, 2.30 mmol) in dry acetonitrile (25 ml) was added DBU (0.96 g, 6.30 mmol) dropwise and TMSOTf (1.87 g, 8.40 mmol) at −40° C. under $N_2$. The mixture was stirred at −40° C. for 20 min, then warmed up to RT. After 30 min, the mixture was heated and stirred at 65° C. for another 5 h. The reaction was quenched by $NaHCO_3$ (sat. aqueous, 120 mL) and extracted with DCM (40 mL×3). The combined organics were dried over sodium sulfate and concentrated. The residue was purified by flash column chromatography (EA/PE from 0% to 40%) to obtain 2.2 as a yellow solid (800 mg, 52.4% yield). MS (ESI): mass calcd. for $C_{32}H_{26}ClN_5O_7$, 627.15, m/z found 628 $[M+H]^+$.

Step 2: Synthesis of (2R,3R,4R,5R)-2-(2-amino-6-(methylamino)-9H-purin-9-yl)-5-((benzoyloxy)methyl)-3-methyltetrahydrofuran-3,4-diyl dibenzoate (2.3)

To a solution of 3 (600 mg, 0.96 mmol) in n-BuOH (30 mL) was added $CH_3NH_2·HCl$ (0.60 g, 8.89 mmol) and triethylamine (0.42 g, 4.16 mmol). The mixture solution was stirred at 90° C. for 4 h, then the mixture was concentrated in vacuo. The obtained crude product was extracted with DCM (60 mL×3). The combined organics were dried in vacuo to afford 2.3 (600 mg, 93.8%) as a white solid. MS (ESI): m/z calcd. for $C_{33}H_{30}N_6O_7$, 622.24, found 623 $[M+H]^+$.

Step 3: Synthesis of (2R,3R,4R,5R)-2-(2-amino-6-(methylamino)-9H-purin-9-yl)-5-(hydroxymethyl)-3-methyltetrahydrofuran-3,4-diol (2.4)

(2R,3R,4R,5R)-2-(2-amino-6-(methylamino)-9H-purin-9-yl)-5-((benzoyloxy)methyl)-3-methyltetrahydrofuran-3,4-diyl dibenzoate (2.3, 0.60 g, 0.96 mmol) was dissolved into a solution of $NH_3$ in MeOH (7 M, 60 mL). The mixture was stirred at 30° C. for 72 h and concentrated in vacuo. The residue was washed with DCM (40 mL×3) and dried in vacuo to afford 2.4 (120 mg, 45.9%) as a white solid. MS (ESI): m/z calcd. for $C_{12}H_{18}N_6O_4$, 310.31, found 311.2 $[M+H]^+$. $^1H$ NMR (400 MHz, $CD_3OD$) δ 8.07 (s, 1H), 5.91 (s, 1H), 4.24 (d, J=8.7 Hz, 1H), 4.02 (d, J=10.2 Hz, 2H), 3.85 (dd, J=3.2 Hz, 3.2 Hz, 1H), 3.04 (s, 3H), 0.93 (s, 3H).

Step 4: Synthesis of ((2R,3R,4R,5R)-5-(2-amino-6-(methylamino)-9H-purin-9-yl)-3,4-dihydroxy-4-methyltetrahydrofuran-2-yl)methyl isobutyrate To a solution of 2.4 (100 mg, 0.32 mmol) in DMPU (1 mL) was added HCl in dioxane (4 M, 0.1 mL). The mixture solution was stirred at 0° C. for 15 min. Then isobutyryl chloride (53 mg, 0.50 mmol) was added to above solution at 0° C., the resulting mixture was stirred at 0° C. for another 2 h. The mixture was purified by prep-HPLC to afford the title compound (55 mg, 43.97% yield) as a white solid. MS (ESI): m/z calcd. for $C_{16}H_{24}N_6O_5$ 380.18, found 381.1 [M+H]$^+$. $^1$H NMR (400 MHz, MeOD) δ 7.84 (s, 1H), 5.92 (s, 1H), 4.51 (dd, J=2.3 Hz, 2.3 Hz, 1H), 4.43 (dd, J=4.8 Hz, 4.8 Hz, 1H), 4.22-4.14 (m, 2H), 3.05 (s, 3H), 2.67 (m, 1H), 1.20 (dd, J=7.0 Hz, 4.2 Hz, 7H), 0.97 (s, 3H).

Example 3. Synthesis of ((2R,3R,4R,5R)-5-(2-amino-6-(methylamino)-9H-purin-9-yl)-4-fluoro-3-hydroxy-4-methyltetrahydrofuran-2-yl)methyl isobutyrate (Compound 3)

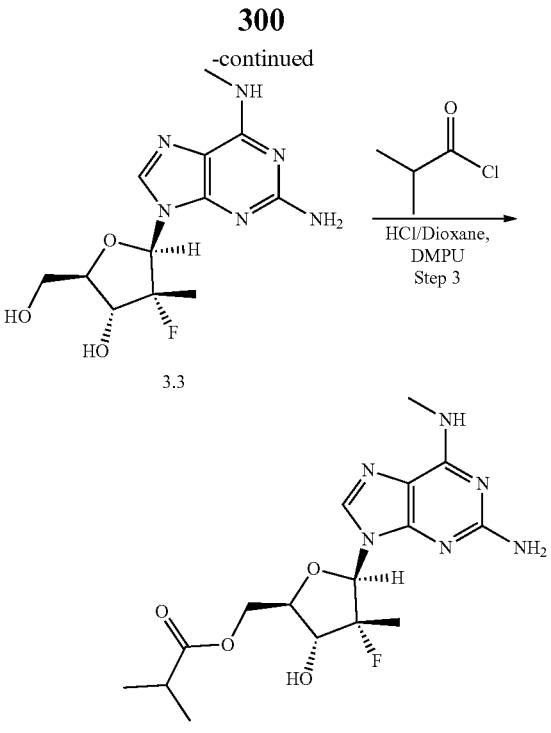

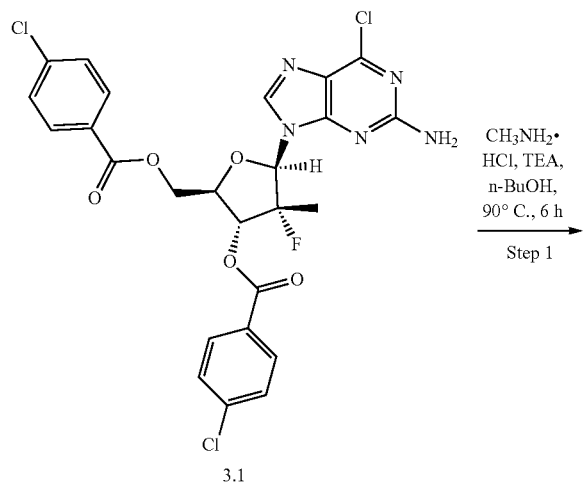

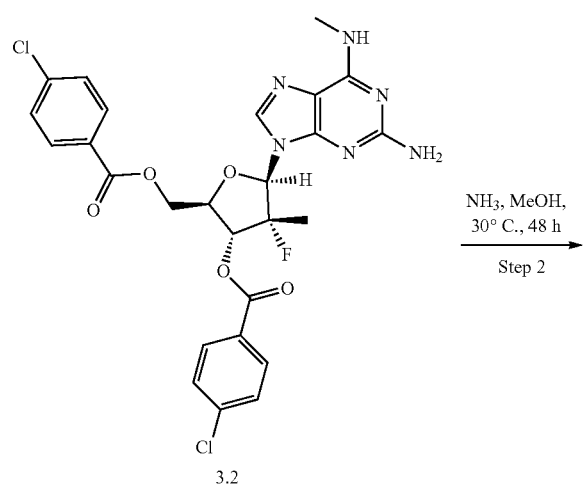

Step 1. Synthesis of (2R,3R,4R,5R)-5-(2-amino-6-(methylamino)-9H-purin-9-yl)-2-(((4-chlorobenzoyl)oxy)methyl)-4-fluoro-4-methyltetrahydrofuran-3-yl 4-chlorobenzoate (3.2)

To a solution of (2R,3R,4R,5R)-5-(2-amino-6-chloro-9H-purin-9-yl)-2-(((4-chlorobenzoyl)oxy)methyl)-4-fluoro-4-methyltetrahydrofuran-3-yl 4-chlorobenzoate (3.1, 200 mg, 0.34 mmol) in n-BuOH (20 mL) was added $CH_3NH_2 \cdot HCl$ (200 mg, 2.96 mmol) and triethylamine (141 mg, 1.40 mmol). The mixture solution was stirred at 90° C. for 4 h. Then the mixture was concentrated in vacuo to afford 3.1 (300 mg, crude) as a white solid. MS (ESI): m/z calcd. for $C_{26}H_{23}Cl_2FN_6O_5$, 588.11, found 589.3 [M+H]$^+$.

Step 2: Synthesis of (2R,3R,4R,5R)-5-(2-amino-6-(methylamino)-9H-purin-9-yl)-4-fluoro-2-(hydroxymethyl)-4-methyltetrahydrofuran-3-ol (3.3)

(2R,3R,4R,5R)-5-(2-amino-6-(methylamino)-9H-purin-9-yl)-2-(((4-chlorobenzoyl)oxy)methyl)-4-fluoro-4-methyltetrahydrofuran-3-yl 4-chlorobenzoate (3.2, 200 mg, 0.34 mmol) was dissolved into a solution of $NH_3$ in MeOH (7 N, 40 mL). The mixture was stirred at 30° C. for 36 h and concentrated in vacuo. The mixture was purified by prep-HPLC to afford 3.3 (55 mg, 50.3% yield) as a white solid. MS (ESI): m/z calcd. for $C_{12}H_{17}FN_6O_3$ 312.13, found 313.2 [M+H]$^+$. $^1$H NMR (400 MHz, MeOD) δ 7.97 (s, 1H), 6.01 (d, J=18.1 Hz, 1H), 4.30 (dd, J=9.1 Hz, 9.1 Hz, 1H), 3.96-3.91 (m, 2H), 3.76 (dd, J=3.3 Hz, 3.3 Hz, 1H), 2.94 (s, 3H), 1.06 (d, J=22.2 Hz, 3H).

Step 3: Synthesis of ((2R,3R,4R,5R)-5-(2-amino-6-(methylamino)-9H-purin-9-yl)-4-fluoro-3-hydroxy-4-methyltetrahydrofuran-2-yl)methyl isobutyrate To a solution of (2R,3R,4R,5R)-5-(2-amino-6-(methylamino)-9H-purin-9-yl)-4-fluoro-2-(hydroxymethyl)-4- methyltetrahydrofuran-3-ol (3.3, 90 mg, 0.288 mmol) in DMPU (1 mL) was added HCl in dioxane (4 M, 0.1 mL), The solution was stirred at 0° C. for 15 min. Then isobutyryl chloride (0.1 mL, 0.967 mmol) was added at 0° C., the resulting mixture was stirred at 0° C. for another 2 h. The mixture was purified by prep-HPLC to afford the title compound (50 mg, 44.5% yield) as a white solid. MS (ESI): m/z calcd. for $C_{16}H_{23}FN_6O_4$ 382.18, found 383.3 $[M+H]^+$. $^1$H NMR (400 MHz, MeOD) δ 7.82 (s, 1H), 6.10 (d, J=18.8 Hz, 1H), 4.58 (dd, J=12.4, 2.8 Hz, 1H), 4.48-4.39 (m, 2H), 4.21-4.19 (m, 1H), 3.04 (s, 3H), 2.70-2.63 (m, 1H), 1.21 (m, 9H). $^{19}$F NMR (377 MHz, MeOD) δ −163.12.

Example 4. Synthesis of ((2R,3R,4R,5R)-5-(2,4-dioxo-3,4-dihydropyrimidin-1 (2H)-yl)-4-fluoro-3-hydroxy-4-methyltetrahydrofuran-2-yl)methyl isobutyrate (Compound 4)

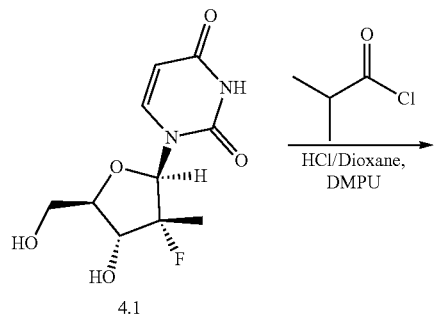

4

To a solution of 4.1 (100 mg, 0.38 mmol, obtained commercially) in DMPU (3 mL) was added HCl in dioxane (4 M, 0.1 mL). The mixture solution was stirred at 25° C. for 15 minutes. Then isobutyryl chloride (205 mg, 1.92 mmol) was added at 0° C., the resulting mixture was stirred at 0° C. for another 3 hours. The reaction was quenched by MeOH (2 mL) and purified by prep-HPLC to afford the title compound (60.32 mg, 47% yield) as a white solid. MS (ESI): m/z calcd. for $C_{14}H_{19}FN_2O_6$ 330.31, found 331.0 $[M+H]^+$. $^1$H NMR (400 MHz, MeOD) δ 7.66 (d, J=8.0 Hz, 1H), 6.12 (d, J=20.0 Hz, 1H), 5.75 (d, J=8.0 Hz, 1H), 4.49 (dd, J=2.4 Hz, 2.4 Hz, 1H), 4.42 (d, J=6.4 Hz, 1H), 4.21-4.09 (m, 1H), 3.91-3.97 (m, 1H), 2.74-2.58 (m, 1H), 1.39 (d, J=22.4 Hz, 3H), 1.21 (dd, J=8.0 Hz, 1.6 Hz, 6H). $^{19}$F NMR (376 MHz, CD$_3$OD) δ −162.131.

Example 5. Synthesis of ((2R,3R,4R,5S)-5-(4-aminopyrrolo[2,1-f][1,2,4]triazin-7-yl)-4-fluoro-3-hydroxy-4-methyltetrahydrofuran-2-yl)methyl isobutyrate (Compound 5)

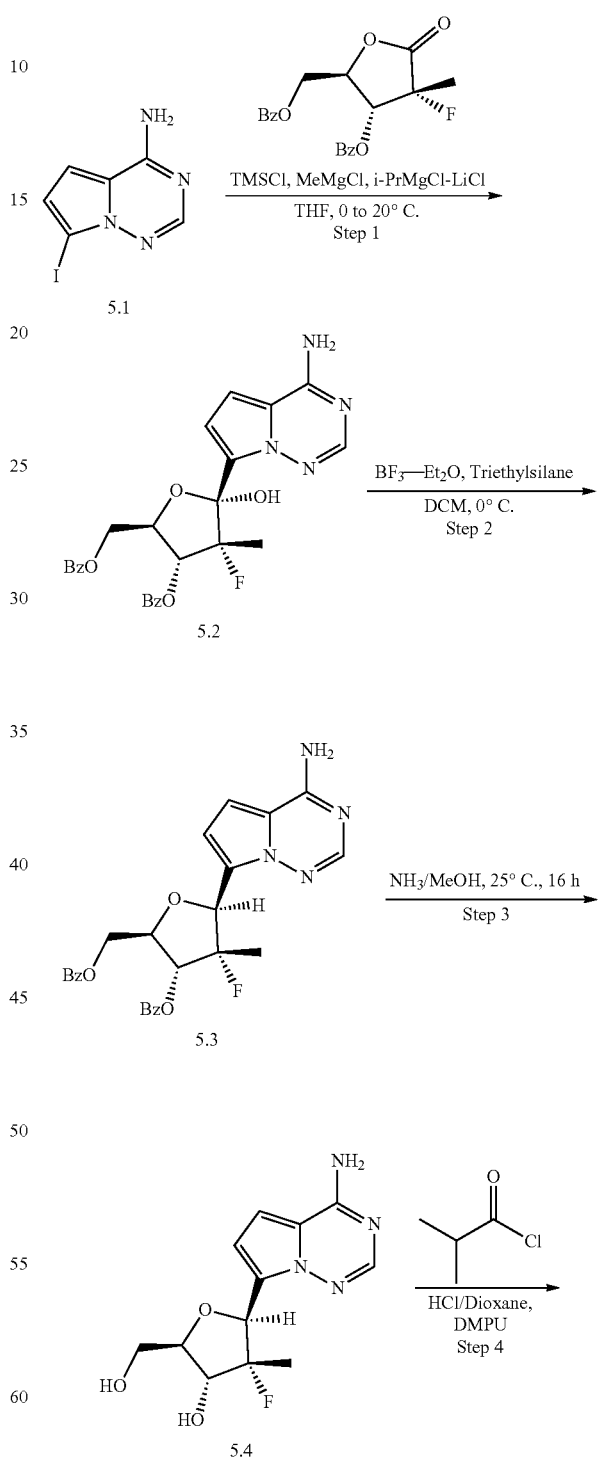

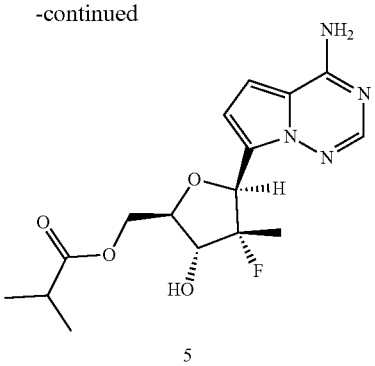

5

Step 1. Synthesis of (2R,3R,4R,5S)-5-(4-aminopyrrolo[2,1-f][1,2,4]triazin-7-yl)-2-((benzoyloxy)methyl)-4-fluoro-5-hydroxy-4-methyltetrahydrofuran-3-yl benzoate (5.2)

To a solution of 7-iodopyrrolo[2,1-f][1,2,4]triazin-4-amine (1.5 g, 5.8 mmol) in dry THF (21 mL) was added TMSCl (1.3 g, 12 mmol) dropwise at 25° C. under nitrogen. The reaction mixture was turned turbid and stirred for 15 min. Then the reaction mixture was cooled to 0° C. and MeMgCl (3.8 mL, 3 M, 12 mmol) was added dropwise. The reaction mixture turned to clear. After stirring for 15 min, i-PrMgCl—LiCl (4.4 mL, 1.3 M, 5.8 mmol) was added dropwise. The reaction mixture was stirred for another 15 min. The reaction mixture was cooled to −20° C. and a solution of ((2R,3R,4R)-3-(benzoyloxy)-4-fluoro-4-methyl-5-oxotetrahydrofuran-2-yl)methyl benzoate (2.1 g, 5.8 mmol) in dry THF (4 mL) was added into the flask vessel dropwise. The reaction mixture was stirred for 1 h at −20° C. under nitrogen. The reaction was quenched with saturated aqueous NH$_4$Cl (15 mL), and extracted with ethyl acetate (10 mL×3). The combined organic phase was washed with brine (10 mL), dried over anhydrous Na$_2$SO$_4$, then filtered and the filtrate was concentrated in vacuo. The residue was purified by flash column chromatography (EtOAc/petroleum ether, from 0% to 10%) to give 5.2 (1.4 g, 75% purity, 36% yield) as a yellow oil. MS (ESI): mass calcd. for C$_{26}$H$_{23}$FN$_4$O$_6$, 506.16, m/z found 507 [M+H]$^+$.

Step 2. Synthesis of (2R,3R,4S,5S)-5-(4-aminopyrrolo[2,1-f][1,2,4]triazin-7-yl)-2-((benzoyloxy)methyl)-4-fluoro-4-methyltetrahydrofuran-3-yl benzoate (5.3)

To a solution of 5.2 (0.70 g, 1.4 mmol) and triethylsilane (0.48 g, 4.1 mmol) in dry DCM (30 mL) was added boron trifluoride etherate (1.2 g, 4.1 mmol) dropwise at 0° C. under nitrogen. The reaction mixture was stirred for 2 h at 0° C. The reaction mixture was diluted with DCM (30 mL) and washed with saturated aqueous NaHCO$_3$ (15 mL×2), followed by brine (15 mL), then the organic phase was dried over anhydrous Na$_2$SO$_4$, filtered, and the filtrate was concentrated in vacuo. The residue was purified by flash column chromatography (EtOAc/petroleum ether, from 0% to 10%) to give 5.3 (0.49 g, 36% yield) as a white solid. MS (ESI): mass calcd. for C$_{26}$H$_{23}$FN$_4$O$_5$, 490.17, m/z found 491 [M+H]$^+$.

Step 3. Synthesis of (2R,3R,4R,5S)-5-(4-aminopyrrolo[2,1-f][1,2,4]triazin-7-yl)-4-fluoro-2-(hydroxymethyl)-4-methyltetrahydrofuran-3-ol (5.4)

A solution of 5.3 (0.49 g, 0.99 mmol) in NH$_3$/MeOH (10 mL) was stirred for 16 hours at 25° C. The reaction mixture was concentrated to dryness. The residue was purified by Prep-HPLC [Gradient: 5-30% ACN in water (0.1% FA)] to give 5.4 (0.20 g, 71% yield) as a white solid. MS (ESI): mass calcd. for C$_{12}$H$_{15}$FN$_4$O$_3$, 282.11, m/z found 283 [M+H]$^+$. $^1$H NMR (400 MHz, MeOD) δ 7.82 (s, 1H), 6.86 (dd, J=29.6, 4.5 Hz, 2H), 5.76 (d, J=25.2 Hz, 1H), 4.13-3.95 (m, 3H), 3.83 (dd, J=12.4, 4.4 Hz, 1H), 1.11 (d, J=22.0 Hz, 3H).

Step 4. Synthesis of ((2R,3R,4R,5S)-5-(4-aminopyrrolo[2,1-f][1,2,4]triazin-7-yl)-4-fluoro-3-hydroxy-4-methyltetrahydrofuran-2-yl)methyl isobutyrate (5)

To a solution of 5.4 (70 mg, 0.25 mmol) in DMPU (1.0 mL) was added HCl/1,4-dioxane (0.1 mL) at 0° C. The mixture solution was stirred for 10 min, and isobutyryl chloride (0.13 g, 1.2 mmol) was added into the flask vessel dropwise. The reaction mixture was stirred for 1 h at 0° C. under nitrogen and purified by prep-HPLC to give the title compound (26 mg, 30% yield) as a white solid. MS (ESI): mass calcd. for C$_{16}$H$_{21}$FN$_4$O$_4$, 352.15, m/z found 353 [M+H]$^+$. $^1$H NMR (400 MHz, MeOD) δ 7.83 (s, 1H), 6.90 (d, J=4.6 Hz, 1H), 6.71 (d, J=4.4 Hz, 1H), 5.76 (d, J=25.6 Hz, 1H), 4.53 (d, J=12.2 Hz, 1H), 4.36 (dd, J=12.3 Hz, 5.2 Hz, 1H), 4.17-4.11 (m, 1H), 4.10-4.00 (m, 1H), 2.73-2.64 (m, 1H), 1.23 (d, J=6.8 Hz, 6H), 1.14 (d, J=22.0 Hz, 3H).

Example 6. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl (2-(octadecyloxy)ethyl) hydrogen phosphate (Compound 6)

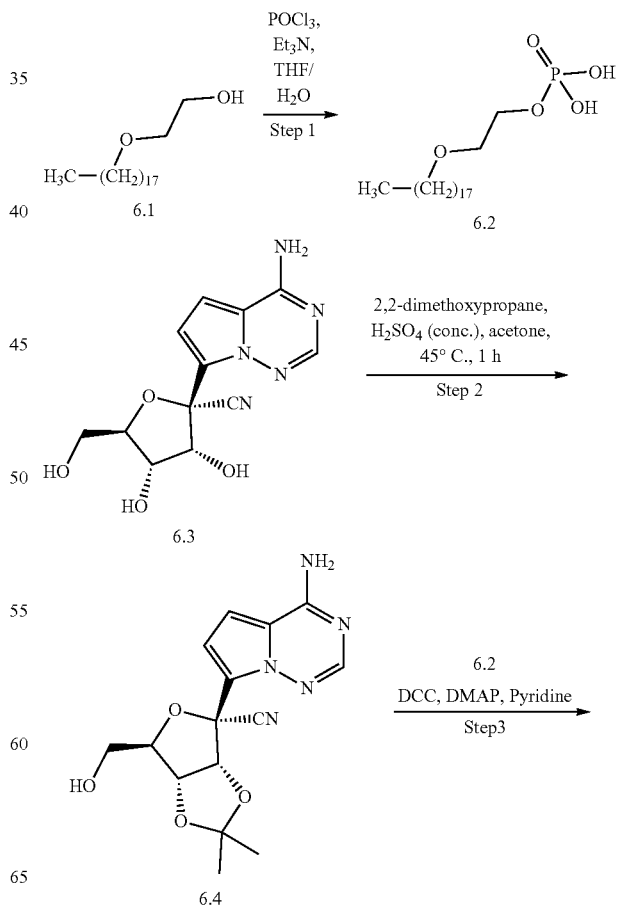

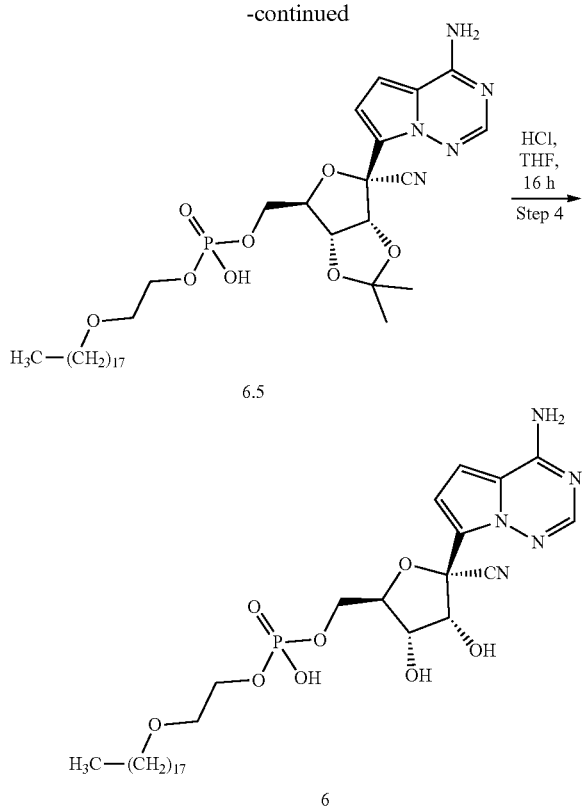

Step 1. Synthesis of 2-(octadecyloxy)ethyl dihydrogen phosphate (6.2)

To a solution of (R)-oxiran-2-ylmethyl 4-methylbenzenesulfonate (100 mg, 0.317 mmol) in THF (3 mL) and triethylamine (64 mg, 0.635 mmol) was added phosphoryl trichloride (97 mg, 0.635 mmol) in THF (1 mL), the solution was stirred at 0° C. for 1 h, then water was added and the resulting mixture was stirred at 25° C. for 16 h. The reaction mixture was extracted with ethyl ether (5 mL×3). The combined organic phase was dried over sodium sulfate and filtered. The filtrate was concentrated under reduced pressure to obtain 6.2 (80 mg, 57% yield) as a yellow solid. MS (ESI): m/z calcd. for $C_{20}H_{43}O_5P$ 394.53, found 393.0 [M−H]−. 1H NMR (400 MHz, CDK3) δ 7.80 (d, J=8.3 Hz, 2H), 7.35 (d, J=6.4 Hz, 2H), 4.11-3.96 (m, 3H), 3.48-3.37 (m, 4H), 2.45 (s, 3H), 1.51 (quint, J=6.4 Hz, 2H), 1.29-1.24 (m, 30H), 0.88 (t, J=6.8 Hz, 3H).

Step 2. Synthesis of (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile (6.4)

To a solution of 6.3 (prepared according to Siegel, D., et al., *J. Med. Chem.* 2017, 60, 1648-1661, 2 g, 0.006 mol) and 2,2-dimethoxypropane (3.45 g, 0.033 mol) in acetone (50 mL) was added sulfuric acid (0.90 g, 98%) dropwise at 25° C. for 0.5 h, then heated to 45° C. for 0.5 h. The reaction mixture was quenched by NaHCO3 (sat. aqueous, 10 mL) and extracted with EtOAc (15 mL×3). The combined organic phase was dried over sodium sulfate and filtered. The filtrate was concentrated under reduced pressure. The residue was purified by flash column chromatography (MeOH/DCM from 0% to 5%) to obtain 6.4 (2.3 g, 96% yield) as a white solid. MS (ESI): m/z calcd. for $C_{15}H_{17}N_5O_4$ 331.33, found 332.0 [M+H]+.

Step 3. Synthesis of ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl (2-(octadecyloxy)ethyl) hydrogen phosphate (6.5)

To a solution of 6.4 (262 mg, 0.663 mmol), 6.2 (200 mg, 0.603 mmol) and 4-dimethylaminopyridine (66 mg, 0.543 mmol) in pyridine (10 mL) was added DCC (249 mg, 1.207 mmol), the resulting mixture was stirred at 90° C. for 16 h. The solution was concentrated under reduced pressure to obtain the crude product, which was purified by prep-HPLC to afford 6.5 (150 mg, 33% yield) as a white solid. MS (ESI): m/z calcd. for $C_{35}H_{58}N_5O_8P$ 707.85, found 706.3 [M−H]−.

Step 3. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl (2-(octadecyloxy)ethyl) hydrogen phosphate (6)

To a solution of 6.5 (150 mg, 0.211 mmol) in THF (5 mL) was added HCl (0.3 mL, 12 M aqueous) dropwise at 0° C., the mixture was stirred at 25° C. for 16 h. The reaction was quenched by NaHCO3 (sat. aqueous, 5 mL), concentrated under reduced pressure and purified by prep-HPLC to afford the title compound (120.88 mg, 84% yield) as a white solid. MS (ESI): m/z calcd. for $C_{32}H_{54}N_5O_8P$ 667.78, found 666.4 [M−H]−. 1H NMR (400 MHz, MeOD) δ 7.91 (s, 1H), 7.03 (d, J=5.2 Hz, 1H), 6.95 (d, J=5.2 Hz, 1H), 4.85 (d, J=5.2 Hz, 1H), 4.36-4.32 (m, 1H), 4.27 (t, J=5.2 Hz, 1H), 4.16-4.04 (m, 2H), 3.90-3.81 (m, 2H), 3.48-3.45 (m, 2H), 3.40-3.35 (m, 2H), 1.55-1.48 (m, 2H), 1.29-2.25 (m, 30H), 0.92 (t, J=6.4 Hz, 3H). 31P NMR (162 MHz, CD3OD) δ 0.36.

Example 7. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(benzyloxy)-3-(octadecyloxy)propyl) hydrogen phosphate (Compound 7)

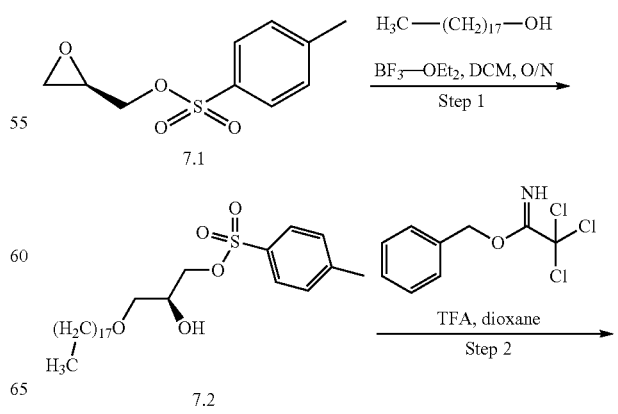

-continued

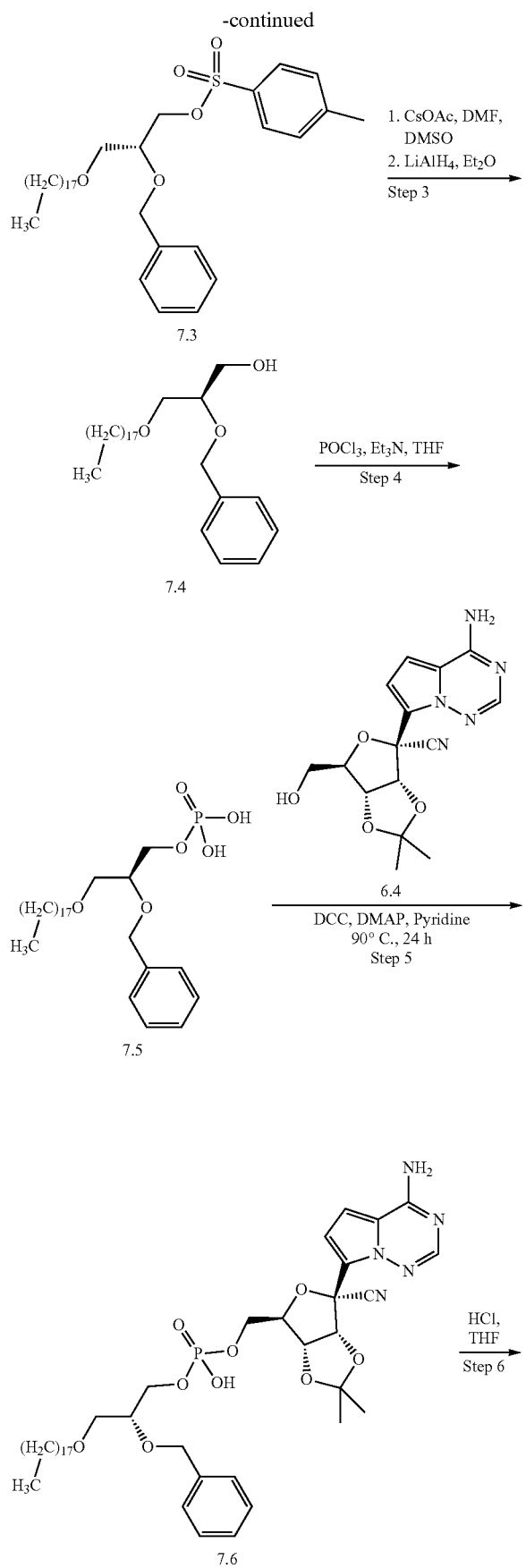

7.3

7.4

7.5

7.6

1. CsOAc, DMF, DMSO
2. LiAlH₄, Et₂O
Step 3

POCl₃, Et₃N, THF
Step 4

DCC, DMAP, Pyridine
90° C., 24 h
Step 5

HCl, THF
Step 6

-continued

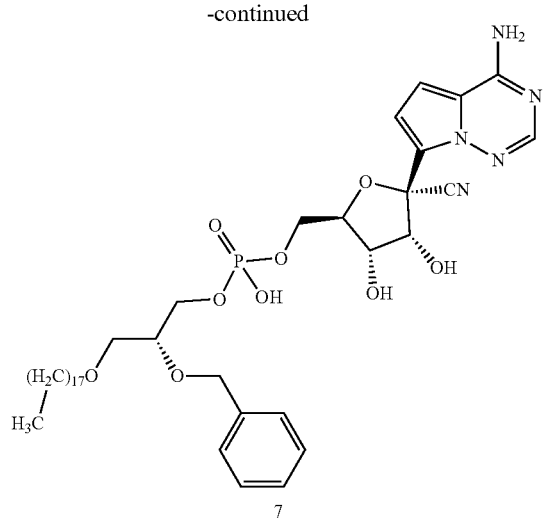

7

Step 1. Synthesis of (S)-2-hydroxy-3-(octadecyloxy)propyl 4-methylbenzenesulfonate (7.2)

To a solution of (R)-oxiran-2-ylmethyl 4-methylbenzenesulfonate (7.1, 1.0 g, 4.39 mmol) and octadecan-1-ol (1.7 g, 6.1 mmol) in dry DCM (20 mL) was added boron trifluoride etherate (8 drops) dropwise at 25° C. under $N_2$. The reaction mixture was stirred at 25° C. for 16 h, then the solution was concentrated to dryness. The residue was purified by flash column chromatography (EtOAc/petroleum ether, from 0% to 20%) to give 7.2 (1.4 g, 63% yield) as a white solid. MS (ESI): mass calcd. for $C_{28}H_{50}O_5S$, 498.34, m/z found 499 $[M+H]^+$.

Step 2. Synthesis of (R)-2-(benzyloxy)-3-(octadecyloxy)propyl 4-methylbenzenesulfonate (7.3)

To a solution of 7.2 (1.0 g, 2.01 mmol) in 1,4-dioxane (20 mL) was added benzyl 2,2,2-trichloroacetimidate (1.0 g, 3.98 mmol) under $N_2$, followed by trifluoromethanesulfonic acid (9 drops). The reaction mixture was stirred at 25° C. for 1 h. TLC showed complete consumption of 7.2. The reaction mixture was diluted with DCM (60 mL) and washed with saturated aqueous $NaHCO_3$ (20 mL×2), followed by water (20 mL), then the organic phase was dried over anhydrous $Na_2SO_4$, filtered and the filtrate was concentrated to dryness. The residue was purified by flash column chromatography (EtOAc/petroleum ether, from 0% to 20%) to give 7.3 (0.85 g, 80% purity, 60% yield) as a colorless oil, and used directly in the next step.

Step 3. Synthesis of (R)-2-(benzyloxy)-3-(octadecyloxy)propan-1-ol (7.4)

To a solution of 7.3 (0.70 g, 1.19 mmol) in dry DMF (2.5 mL) and dry DMSO (10 mL) was added cesium acetate (0.48 g, 2.50 mmol) under $N_2$. The reaction mixture was stirred at 60° C. for 16 h. TLC showed complete consumption of starting material 7.3. The reaction mixture was quenched with water (15 mL) and extracted with ether (10 mL×3). The organic phase was separated and washed with water (12 mL×3), dried over anhydrous $Na_2SO_4$, filtered, and the filtrate was concentrated to dryness, re-evaporated with toluene. The residue was dissolved with ether (10 mL)

and LiAlH₄ (90 mg, 2.4 mmol) was added at 0° C. The reaction mixture was stirred for 30 min at 0° C. and 3 h at 25° C. TLC showed complete consumption of intermediate. The reaction mixture was quenched by very slow addition of water (5.0 mL). The mixture was filtered through celite. The mixture was separated and the aqueous phase was extracted with DCM (3.0 mL×2). The combined organic phase was dried over anhydrous Na₂SO₄, filtered, and the filtrate was concentrated to dryness. The residue was purified by flash column chromatography (EtOAc/petroleum ether, from 0% to 20%) to give 7.4 (0.34 g, 52% yield) as a milk white oil. ¹H NMR (400 MHz, CDCl₃) δ 7.38-7.27 (m, 5H), 4.73-4.61 (dd, J=36.0, 11.6 Hz, 2H), 3.78-3.52 (m, 5H), 3.44 (td, J=6.8, 1.6 Hz, 2H), 1.57 (quint, J=7.2 Hz, 2H), 1.33-1.24 (m, 30H), 0.88 (t, J=7.2 Hz, 3H).

Step 4. Synthesis of (S)-2-(benzyloxy)-3-(octadecyloxy)propyl dihydrogen phosphate (7.5)

To a solution of 7.4 (0.34 g, 0.77 mmol) in dry THF (8.0 mL) was added a solution of triethylamine (78 mg, 0.77 mmol) and pyridine (61 mg, 0.77 mmol) in dry THF (1.0 mL) under N₂ at 0° C. The reaction mixture was stirred for 5 min, and phosphoryl trichloride (0.24 g, 1.5 mmol) was added into the flask vessel dropwise at 0° C. The reaction mixture was stirred for 4 h at 0° C. Then water (5.0 mL) was added very slowly into the flask vessel. The reaction mixture was stirred for 16 h at 25° C. The reaction mixture was extracted with ether (10 mL×3). The organic phase was dried over anhydrous Na₂SO₄ and concentrated to dryness to give 7.5 (0.40 g, crude) as a milk white oil. MS (ESI): mass calcd for $C_{28}H_{51}O_6P$, 514.34, m/z found 513 [M−H]⁻. ¹H NMR (400 MHz, CDCl₃) δ 7.35-7.26 (m, 5H), 6.18 (br, 5H), 4.67 (dd, J=25.7, 11.8 Hz, 2H), 4.20-3.99 (m, 2H), 3.79 (quint, J=4.8 Hz, 1H), 3.58-3.51 (m, 2H), 3.42 (td, J=6.8, 1.9 Hz, 2H), 1.53 (quint, J=6.4 Hz, 2H), 1.30-1.24 (m, 30H), 0.88 (t, J=7.2 Hz, 3H).

Step 5. Synthesis of ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl ((R)-2-(benzyloxy)-3-(octadecyloxy)propyl) hydrogen phosphate (7.6)

To a solution of 7.5 (0.40 g, 0.77 mmol), (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile, 6.4 (0.23 g, 0.69 mmol), and DMAP (94 mg, 0.77 mmol) in pyridine (40 mL) was added DCC (0.24 mg, 1.2 mmol). The reaction mixture was stirred for 24 h at 90° C. under N₂. The reaction mixture was concentrated to dryness and the residue was purified by Prep-HPLC [Gradient: 50-95% MeOH in water (0.1% NH₃·H₂O)] to give 7.6 (0.28 g, 43% yield) as a white solid. MS (ESI): mass calcd. for $C_{43}H_{66}N_5O_9P$, 827.46, m/z found 826 [M−H]⁻. ¹H NMR (400 MHz, MeOD) δ 8.02 (s, 1H), 7.40-7.12 (m, 6H), 7.08 (d, J=4.7 Hz, 1H), 5.31 (d, J=6.3 Hz, 1H), 5.07 (dd, J=6.3, 2.5 Hz, 1H), 4.68-4.58 (m, 3H), 4.06 (t, J=4.7 Hz, 2H), 3.97-3.86 (m, 2H), 3.74 (quint J=5.2 Hz, 1H), 3.58-3.48 (m, 2H), 3.43 (t, J=6.8 Hz, 2H), 1.73 (s, 3H), 1.55 (quint, J=6.8 Hz, 2H), 1.42 (s, 3H), 1.38-1.26 (m, 30H), 0.92 (t, J=6.7 Hz, 3H).

Step 6. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl (2-(octadecyloxy)ethyl) hydrogen phosphate (7)

To a solution of 7.6 (0.10 g, 0.12 mmol) in dry THF (5.0 mL) was added a solution of conc. aqueous HCl (0.05 mL) in dry THF (0.5 mL). The reaction mixture was stirred for 16 h at 25° C. The reaction mixture was evaporated to dryness with a stream of nitrogen. The residue was purified by prep-HPLC [Gradient: 50%-95% MeOH in water (0.1% NH₃·H₂O)] to give the title compound (74% yield) as a white solid. MS (ESI): mass calcd. for $C_{40}H_{62}N_5O_9P$, 787.43, m/z found 786 [M−H]⁻. ¹H NMR (400 MHz, MeOD) δ 7.96 (s, 1H), 7.36-7.20 (m, 5H), 7.10 (d, J=4.7 Hz, 2H), 4.79 (d, J=5.2 Hz, 1H), 4.63 (q, J=11.9 Hz, 2H), 4.37-4.33 (m, 1H), 4.26 (t, J=5.4 Hz, 1H), 4.19-4.03 (m, 2H), 3.91 (tq, J=10.9, 5.4 Hz, 2H), 3.73 (quint, J=4.8 Hz, 1H), 3.57-3.45 (m, 2H), 3.41 (t, J=6.0 Hz, 2H), 1.53 (quint, J=6.8 Hz, 2H), 1.37-1.27 (m, 30H), 0.92 (t, J=6.7 Hz, 3H).

Example 8. Synthesis of 16-(((((2R,3S,4R,5R)-5-(4-aminopyrrolo[2,1-f][1,2,4]triazin-7-yl)-5-cyano-3,4-dihydroxytetrahydrofuran-2-yl)methoxy)(hydroxy)phosphoryl)oxy)hexadecanoic acid (Compound 8)

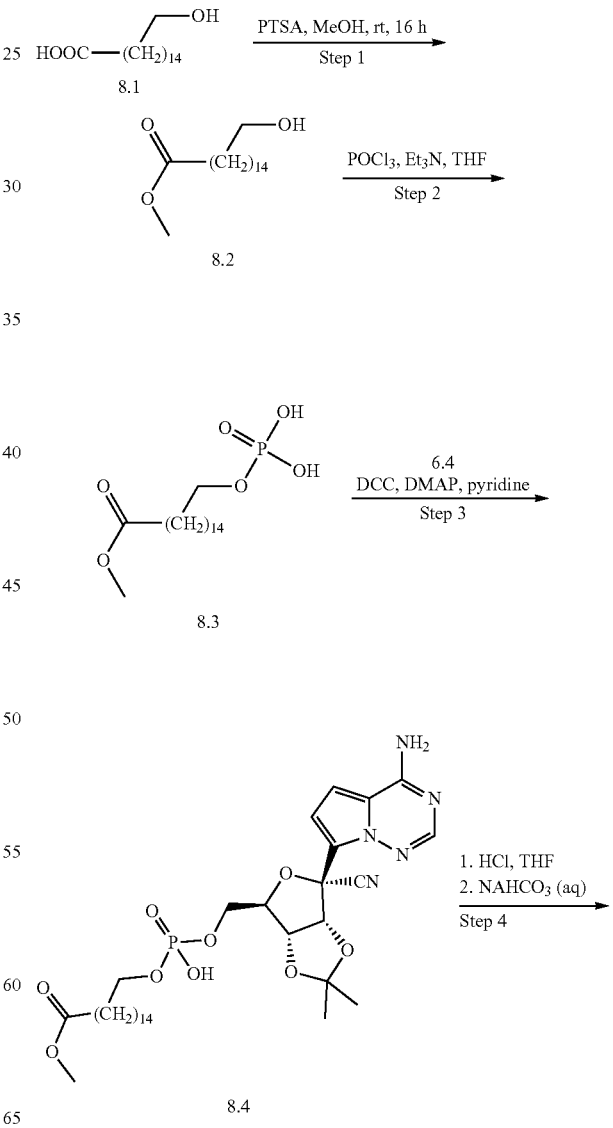

-continued

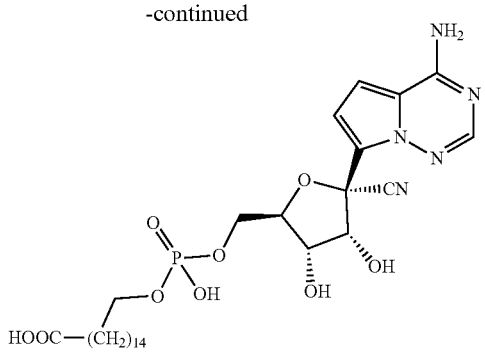

8

Step 1. Synthesis of Methyl 16-hydroxyhexadecanoate (8.2)

To a solution of 16-hydroxyhexadecanoic acid (8.1, 50 mg, 0.183 mmol) in MeOH (4 mL) was added p-TSA (13 mg, 0.073 mmol), then the mixture was stirred at 25° C. for 16 h. The reaction was quenched by NaHCO$_3$ (50 mg) and concentrated under reduced pressure to obtain the crude product. The crude product was purified by flash column chromatography (EtOAc/petroleum ether, from 0% to 30%) to obtain 8.2 (40 mg, 76% yield) as a white solid. MS (ESI): m/z calcd. for $C_{17}H_{34}O_3$ 286.25, found 285.0 [M–H]$^-$.

Step 2. Synthesis of Methyl 16-(phosphonooxy)hexadecanoate (8.3)

To a solution of 8.2 (50 mg, 0.174 mmol) in THF (3 mL) and triethylamine (35 mg, 0.349 mmol) was added a solution of phosphoryl trichloride (54 mg, 0.349 mmol) in THF (1 mL) dropwise, the solution was stirred at 0° C. for 1 h, then water was added and the resulting mixture was stirred at 25° C. for 16 h. The solution was extracted with ethyl ether (5 mL×3). The combined organic phase was dried over sodium sulfate and filtered, and the filtrate was concentrated under reduced pressure to obtain 8.3 (50 mg, 70% yield) as a white solid. MS (ESI): m/z calcd. for $C_{17}H_{35}O_6P$ 366.43, found 365.0 [M–H]$^-$.

Step 3. Synthesis of Methyl 16-(((((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methoxy)(hydroxy)phosphoryl)oxy)hexadecanoate (8.4)

To a solution of 8.3 (50 mg, 0.136 mmol), 4 (50 mg, 0.15 mmol) and 4-dimethylaminopyridine (15 mg, 0.122 mmol) in pyridine (5 mL) was added DCC (59 mg, 0.286 mmol), the resulting mixture was stirred at 90° C. for 16 h. The solution was concentrated under reduced pressure to a residue, which was purified by prep-HPLC to afford 8.4 (150 mg, 33% yield) as a white solid. MS (ESI): m/z calcd. for $C_{32}H_{50}N_5O_9P$ 679.75, found 678.0 [M–H]$^-$.

Step 4. Synthesis of 16-(((((2R,3S,4R,5R)-5-(4-aminopyrrolo[2,1-f][1,2,4]triazin-7-yl)-5-cyano-3,4-dihydroxytetrahydrofuran-2-yl)methoxy)(hydroxy)phosphoryl)oxy)hexadecanoic acid To a solution of 8.4 (400 mg, 0.588 mmol) in THF (5 mL) was added HCl (5 mL, 12 M) dropwise at 0° C., the mixture was stirred at 25° C. for 16 h. The reaction was quenched by NaHCO$_3$ (sat. aqueous, 10 mL) and concentrated under reduced pressure to get the crude product. The residue was redispersed in MeOH (5 mL) and purified by prep-HPLC to afford the title compound (85.0 mg, 23% yield) as a white solid. MS (ESI): m/z calcd. for $C_{28}H_{44}N_5O_9P$ 625.66, found 624.3 [M–H]$^-$. $^1$H NMR (400 MHz, MeOD) δ 7.78 (s, 1H), 6.89 (d, J=5.2 Hz, 1H), 6.80 (d, J=5.2 Hz, 1H), 4.75 (d, J=5.2 Hz, 1H), 4.25-4.20 (m, 1H), 4.16 (t, J=5.2 Hz, 1H), 3.94-3.90 (m, 2H), 3.60-3.58 (m, 2H), 2.19 (t, J=7.2 Hz, 2H), 1.51-1.48 (m, 2H), 1.38-1.35 (m, 2H), 1.25-1.12 (m, 22H). $^{31}$P NMR (162 MHz, CD$_3$OD) δ 0.54.

Example 9. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 3-methylbutanoate (Compound 9)

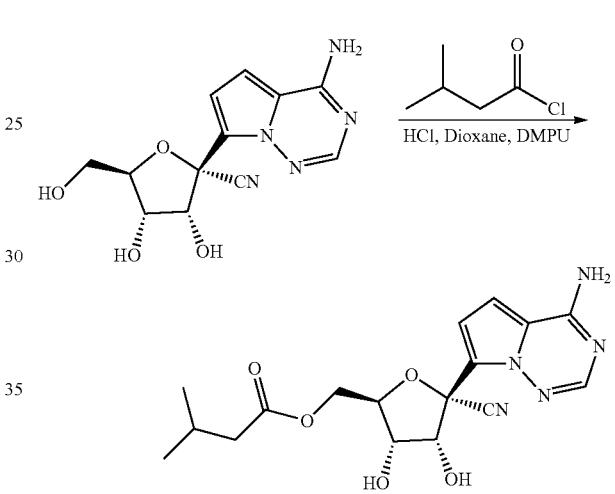

The title compound was prepared according to the procedure of Example 5, Step 4, using 6.3 and 3-methylbutyryl chloride. MS (ESI): mass calcd. for $C_{17}H_{21}N_5O_5$, 375.15, m/z found 376.1 [M+H]$^+$. $^1$H NMR (400 MHz, DMSO-d$_6$) δ 7.92 (br s, 3H), 6.90 (d, J=4.4 Hz, 1H), 6.80 (d, J=4.4 Hz, 1H), 6.32 (d, J=6 Hz, 1H), 5.37 (d, J=6 Hz, 1H), 4.68 (d, J=5.2 Hz, 1H), 4.3 (d, J=6 Hz, 1H), 4.1-4.2 (m, 2H), 3.91 (m, 1H), 2.15 (m, 2H), 1.92 (m, 1H), 0.86 (m, 6H).

Example 10. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-cyclohexylacetate (Compound 10)

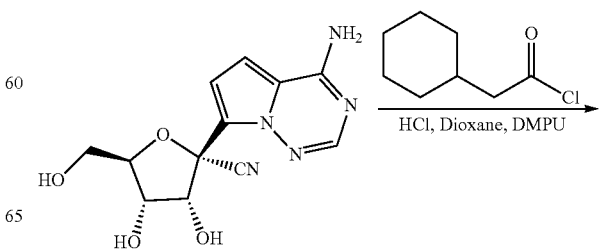

-continued

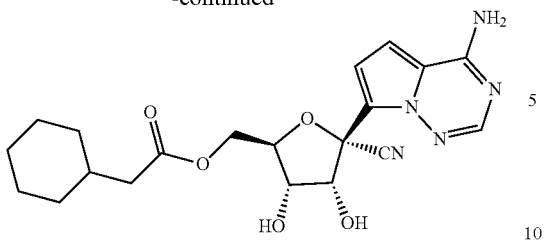

The title compound was prepared according to the procedure of Example 5, Step 4, using 6.3 and cyclohexylacetyl chloride. MS (ESI): mass calcd. for $C_{20}H_{25}N_5O_5$, 415.19, m/z found 416.2 [M+H]$^+$. $^1$H NMR (400 MHz, DMSO-d$_6$) δ 7.92 (br s, 3H), 6.91 (d, J=4.4 Hz, 1H), 6.80 (d, J=4.4 Hz, 1H), 6.31 (d, J=6 Hz, 1H), 5.37 (d, J=6 Hz, 1H), 4.68 (d, J=5.2 Hz, 1H), 4.22 (d, J=6 Hz, 1H), 3.9-4.15 (m, 2H), 3.92 (m, 1H), 2.07 (m, 2H), 1.5 (br m, 6H), 1.0-1.2 (m, 3H), 0.86-1.1 (m, 2H).

Example 11. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-phenylacetate (Compound 12)

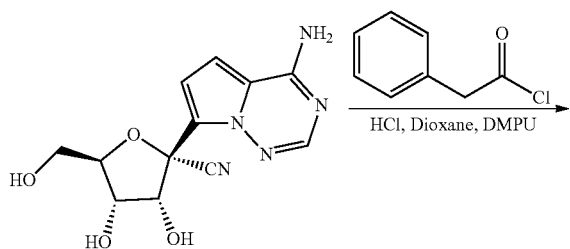

The title compound was prepared according to the procedure of Example 5, Step 4, using 6.3 and phenylacetyl chloride. MS (ESI): mass calcd. for $C_{20}H_{19}N_5O_5$, 409.14, m/z found 410.0 [M+H]$^+$. $^1$H NMR (400 MHz, DMSO-d$_6$) δ 8.13 (br s, 2H), 7.95 (s, 1H), 7.21-7.28 (m, 5H), 6.91 (d, J=4.4 Hz, 1H), 6.79 (d, J=4.4 Hz, 1H), 6.3 (br s, 1H), 5.39 (br s, 1H), 4.65 (d, J=4.8 Hz, 1H), 4.35 (m, 1H), 3.9-4.2 (m, 2H), 3.67 (m, 2H).

Example 12. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl isobutyrate (Compound 14)

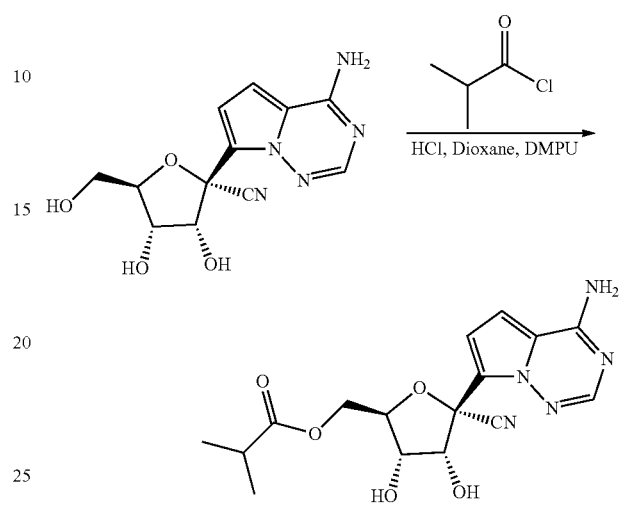

The title compound was prepared according to the procedure of Example 5, Step 4, using 6.3 and isobutyryl chloride. MS (ESI): mass calcd. for $C_{16}H_{19}N_5O_5$, 361.1, m/z found 362.1 [M+H]$^+$. $^1$H NMR (400 MHz, DMSO-d$_6$) δ 7.92 (br s, 3H), 6.90 (d, J=4.8 Hz, 1H), 6.80 (d, J=4.8 Hz, 1H), 6.31 (d, J=6 Hz, 1H), 5.37 (d, J=6 Hz, 1H), 4.68 (d, J=5.2 Hz, 1H), 4.1-4.3 (m, 3H), 3.93 (m, 1H), 2.53 (m, 1H), 1.05 (m, 6H).

Example 13. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl propionate (Compound 15)

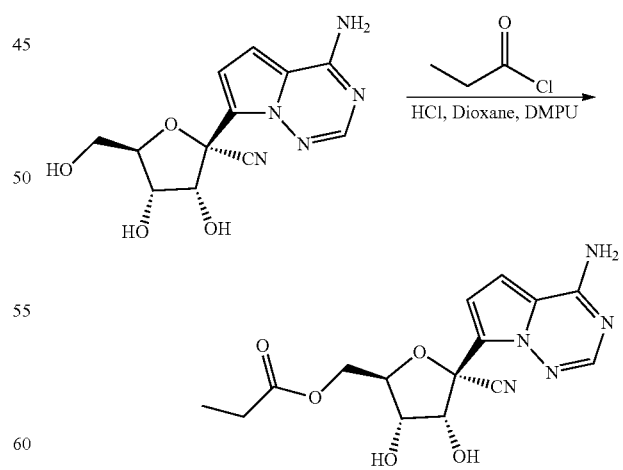

The title compound was prepared according to the procedure of Example 5, Step 4, using 6.3 and propanoyl chloride. MS (ESI): mass calcd. for $C_{15}H_{17}N_5O_5$, 347.1, m/z found 347.9 [M+H]$^+$. $^1$H NMR (400 MHz, DMSO-d$_6$) δ 7.92 (br s, 3H), 6.91 (d, J=4.4 Hz, 1H), 6.80 (d, J=4.4 Hz, 1H), 6.31 (d, J=6 Hz, 1H), 5.37 (d, J=6 Hz, 1H), 4.68 (d, J=5.2 Hz, 1H), 4.34 (d, J=6 Hz, 1H), 3.9-4.2 (m, 2H), 3.91 (m, 1H), 2.3 (q, J=7.6 Hz, 2H), 1.0 (t J=7.6 Hz, 3H).

Example 14. Synthesis of (2R,3S,4R,5R)-5-{4-aminopyrrolo[2,1-f][1,2,4]triazin-7-yl}-5-cyano-4-hydroxy-2-{[(3-methylbutanoyl)oxy]methyl}oxolan-3-yl (2S)-2-amino-3-methylbutanoate (Compound 19)

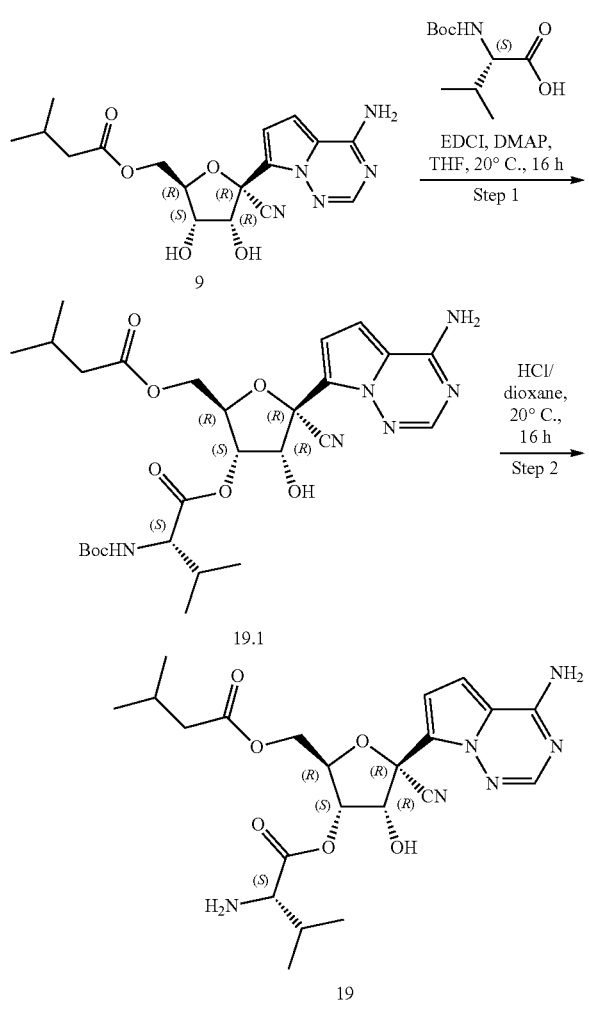

Step 1. Synthesis of [(2R,3S,4R,5R)-5-{4-aminopyrrolo[2,1-f][1,2,4]triazin-7-yl}-3-{[(2S)-2-{[(tert-butoxy)carbonyl]amino}-3-methylbutanoyl]oxy}-5-cyano-4-hydroxyoxolan-2-yl]methyl 3-methylbutanoate (19.1)

To a solution of [(2R,3S,4R,5R)-5-{4-aminopyrrolo[2,1-f][1,2,4]triazin-7-yl}-5-cyano-3,4-dihydroxyoxolan-2-yl]methyl 3-methylbutanoate (9, 300 mg, 0.799 mmol) in THF (15 mL) was added (2S)-2-{[(tert-butoxy)carbonyl]amino}-3-methylbutanoic acid (173.43 mg, 0.799 mmol), EDCI (459.62 mg, 2.397 mmol) and DMAP (292.91 mg, 2.397 mmol), the mixture was stirred at 25° C. for 16 h. The reaction was washed with EtOAc (5 mL×3). The combined organics were dried over sodium sulfate and concentrated in vacuo. The crude product was purified by prep-HPLC to afford 19.1 (70 mg, 14% yield) as a white solid. MS (ESI): m/z calcd. for $C_{27}H_{38}N_6O_8$ 574.28, found 575.2 [M+H]$^+$.

Step 2. Synthesis of Synthesis of (2R,3S,4R,5R)-5-{4-aminopyrrolo[2,1-f][1,2,4]triazin-7-yl}-5-cyano-4-hydroxy-2-{[(3-methylbutanoyl)oxy]methyl}oxolan-3-yl (2S)-2-amino-3-methylbutanoate (19)

To a solution of [(2R,3S,4R,5R)-5-{4-aminopyrrolo[2,1-f][1,2,4]triazin-7-yl}-3-{[(2S)-2-{[(tert-butoxy)carbonyl]amino}-3-methylbutanoyl]oxy}-5-cyano-4-hydroxyoxolan-2-yl]methyl 3-methylbutanoate (19.1, 100 mg, 0.174 mmol) in THF (5 mL) was added HCl in dioxane (4M, 3 mL), the mixture was stirred at 25° C. for 4 h. the mixture was stirred at 25° C. for 16 h. The reaction was concentrated in vacuo and purified by prep-HPLC to afford 19 (35.89 mg, 39% yield) as a white solid. MS (ESI): m/z calcd. for $C_{22}H_{30}N_6O_6$ 474.22, found 475.3 [M+H]$^+$. $^1$H NMR (400 MHz, DMSO) δ 7.93-7.90 (br, s, 3H), 6.93 (d, J=4.8 Hz, 1H), 6.87 (d, J=4.8 Hz, 1H), 6.62-6.60 (m, 1H), 5.12-5.10 (m, 2H), 4.45-4.43 (m, 1H), 4.27 (dd, J=12.0, 4.4 Hz, 1H), 4.24 (dd, J=12.0, 4.8 Hz, 1H), 3.23 (d, J=5.2 Hz, 1H), 2.16-2.15 (m, 2H), 1.99-1.97 (m, 1H), 1.93-1.91 (m, 1H), 0.93-0.83 (m, 12H).

Example 15. Synthesis of ((2R,3S,4R,5R)-5-(4-aminopyrrolo[2,1-f][1,2,4]triazin-7-yl)-5-cyano-4-hydroxy-3-((pivaloyloxy)methoxy)tetrahydrofuran-2-yl)methyl 3-methylbutanoate (Compound 24)

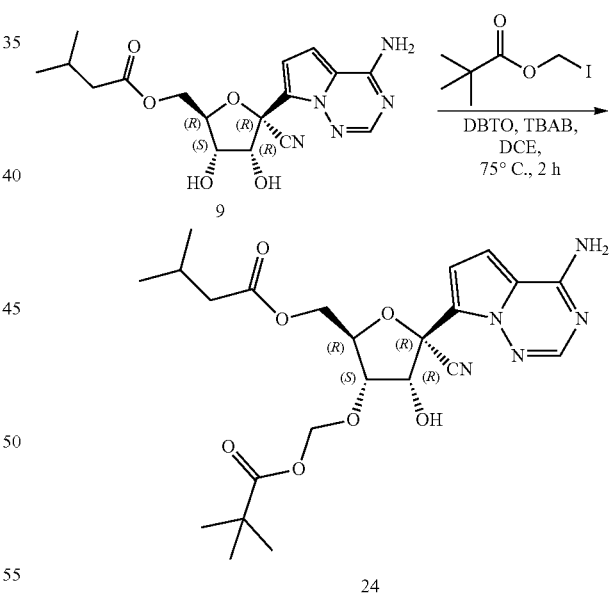

To a suspension of 9 (100 mg, 0.266 mmol), dibutyltin oxide (86.2 mg, 0.346 mmol) and tetrabutylammonium bromide (112 mg, 0.346 mmol) in DCE (1.0 mL) was added iodomethyl pivalate (161 mg, 0.666 mmol). The reaction mixture was stirred at 75° C. for 2 h under nitrogen. The reaction mixture was diluted with EA (5.0 mL) and washed with Sat. aq. $Na_2S_2O_3$ (3.0 mL×2), followed by water (3.0 mL×2), brine (3.0 mL). The organic phase was dried over anhydrous $Na_2SO_4$, filtered. The filtrate was concentrated to dryness. The residue was purified by Prep-HPLC to give 24

(22.09 mg, 16% yield) as a white solid. MS (ESI): m/z calcd. for $C_{23}H_{31}N_5O_7$ 489.22, found 490.2 [M+H]$^+$. $^1$H NMR (400 MHz, DMSO) δ 7.92 (br s, 3H), 6.92 (d, J=4.4 Hz, 1H), 6.83 (d, J=4.8 Hz, 1H), 6.50 (d, J=6.0 Hz, 1H), 5.32 (dd, J=23.2, 6.4 Hz, 2H), 5.00-4.95 (dd, J=6.0, 4.8 Hz, 1H), 4.37-4.28 (m, 2H), 4.18-4.09 (m, 2H), 2.14 (d, J=7.2 Hz, 2H), 1.97-1.86 (m, 1H), 1.11 (s, 9H), 0.86 (dd, J=6.8, 4.0 Hz, 6H).

Example 16. Synthesis of (2R,3S,4R,5R)-5-{4-aminopyrrolo[2,1-f][1,2,4]triazin-7-yl}-5-cyano-2-{[(2-cyclohexylacetyl)oxy]methyl}-4-hydroxyoxolan-3-yl (2S)-2-amino-3-methylbutanoate (Compound 27)

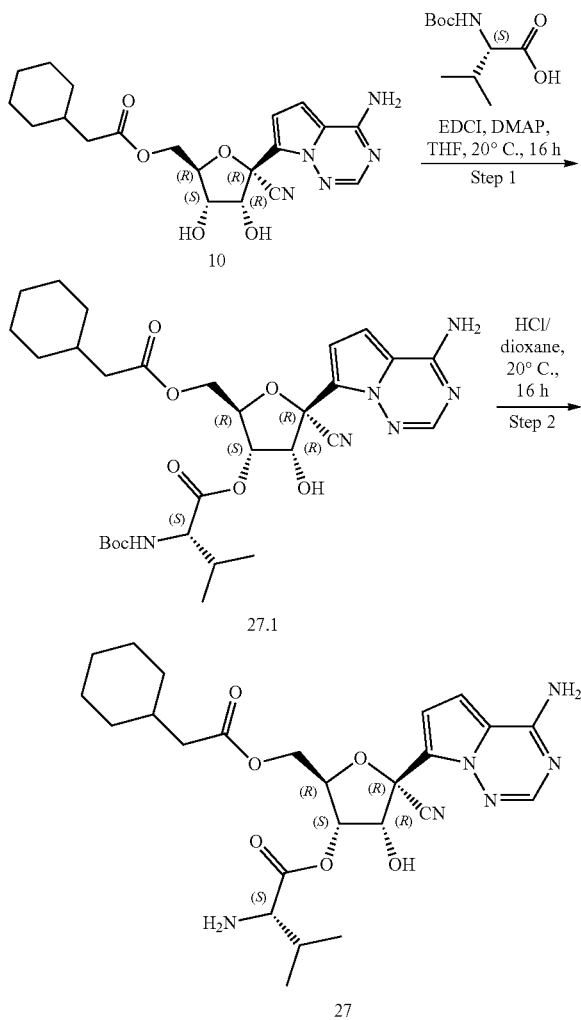

Step 1. Synthesis of (2R,3S,4R,5R)-5-{4-aminopyrrolo[2,1-f][1,2,4]triazin-7-yl}-5-cyano-2-{[(2-cyclohexylacetyl)oxy]methyl}-4-hydroxyoxolan-3-yl (2S)-2-amino-3-methylbutanoate (27.1)

The compound 27.1 was prepared according to the procedure of Example 19, Step 1, using 10 and (2S)-2-{[(tert-butoxy)carbonyl]amino}-3-methylbutanoic acid. MS (ESI): mass calcd. for $C_{30}H_{42}N_6O_8$, 614.31, m/z found 615.3 [M+H]+.

Step 2. Synthesis of (2R,3S,4R,5R)-5-{4-aminopyrrolo[2,1-f][1,2,4]triazin-7-yl}-5-cyano-2-{[(2-cyclohexylacetyl)oxy]methyl}-4-hydroxyoxolan-3-yl (2S)-2-amino-3-methylbutanoate (27)

The title compound 27 was prepared according to the procedure of Example 19, Step 2, using 27.1. MS (ESI): mass calcd. for $C_{25}H_{34}N_6O_6$, 514.25, m/z found 515.4 [M+H]$^+$. $^1$H NMR (400 MHz, DMSO) δ 7.92-7.90 (br, s, 3H), 6.93 (d, J=4.8 Hz, 1H), 6.82 (d, J=4.4 Hz, 1H), 6.60 (d, J=2.8 Hz, 1H), 5.12-5.09 (m, 2H), 4.44-4.40 (m, 1H), 4.29 (dd, J=12.0, 3.6 Hz, 1H), 4.22 (dd, J=12.0, 4.8 Hz, 1H), 3.23 (d, J=5.2 Hz, 1H), 2.19-2.12 (m, 2H), 2.03-1.96 (m, 1H), 1.57-1.50 (m, 6H), 1.15-1.05 (m, 3H), 0.94-0.85 (m, 8H).

Example 17. Synthesis of ((2R,3S,4R,5R)-5-(4-aminopyrrolo[2,1-f][1,2,4]triazin-7-yl)-5-cyano-4-hydroxy-3-((3-methylbutanoyl)oxy)tetrahydrofuran-2-yl)methyl L-valinate (Compound 33)

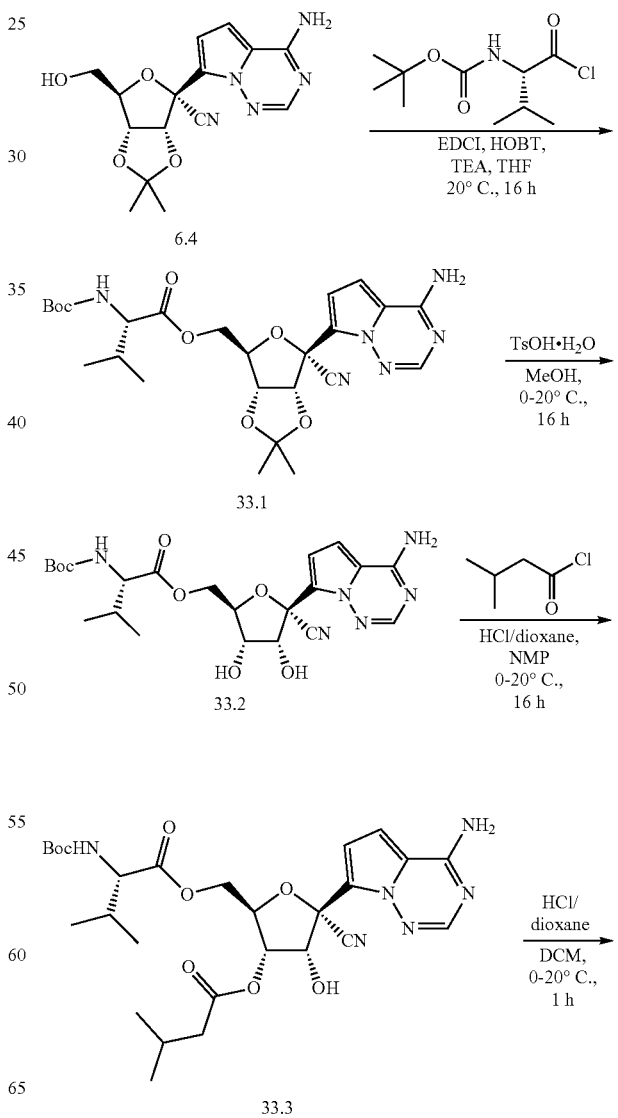

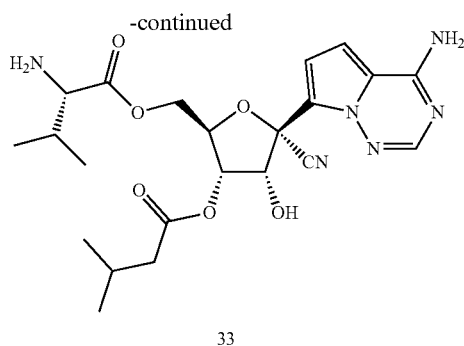

33

Step 1. Synthesis of ((3aR,4R,6R,6aR)-6-(4-amino-pyrrolo[2,1-f][1,2,4]triazin-7-yl)-6-cyano-2,2-dimethyltetrahydrofuro[3,4-d][1,3]dioxol-4-yl)methyl (tert-butoxycarbonyl)-L-valinate (33.1)

The title compound was prepared according to Example 16, Step 1, using intermediate acetonide 6.4.

Step 2. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl (tert-butoxycarbonyl)-L-valinate (33.2)

To a solution of 33.1 (3.50 g, 6.6 mmol) in MeOH (70 mL) was added TsOH·H$_2$O (2.51 g, 13.2 mmol) at 0° C. The mixture was stirred at 0° C. for 30 minutes and then warmed up to 20° C. and stirred for 16 h. After completion, the mixture was concentrated in vacuo to afford a residue, the residue was purified by Prep-HPLC [Gradient: 40-60% ACN in water (0.1% FA)] to give 33.2 (1.25 g, 2.5 mmol, 37.8% yield) as a white solid. MS (ESI): m/z calcd. for C$_{22}$H$_{30}$N$_6$O$_7$, 490.22, found 491.10 [M+H]$^+$. $^1$H NMR (400 MHz, DMSO) δ 8.05 (d, J=70.8 Hz, 3H), 7.17-7.09 (m, 1H), 6.97 (d, J=4.4 Hz, 1H), 6.84 (d, J=4.4 Hz, 1H), 6.34 (s, 1H), 5.40 (s, 1H), 4.68 (d, J=4.8 Hz, 1H), 4.38-4.18 (m, 3H), 3.98-3.83 (m, 2H), 1.96 (d, J=6.8 Hz, 1H), 1.34 (d, J=32.4 Hz, 9H), 0.82 (t, J=6.0 Hz, 6H).

Step 2. Synthesis of ((2R,3S,4R,5R)-5-(4-aminopyrrolo[2,1-f][1,2,4]triazin-7-yl)-5-cyano-4-hydroxy-3-((3-methylbutanoyl)oxy)tetrahydrofuran-2-yl)methyl (tert-butoxycarbonyl)-L-valinate (33.3)

To a solution of 33.2 (200 mg, 0.40 mmol) in NMP (1 mL) was added HCl in dioxane (4 M, 0.5 mL), the solution was stirred at 20° C. for 15 minutes. The reaction mixture was cooled at 0° C. and 3-methylbutanoyl chloride (0.25 mL, 2.0 mmol) was added at once. The reaction was stirred at 20° C. for 16 hours. The reaction was diluted with ACN (2 mL) and purified by prep-HPLC to obtain 33.3 (90 mg, 37.3% yield) as a white solid. MS (ESI): m/z calcd. for C$_{27}$H$_{38}$N$_6$O$_8$, 574.28, found 575.2 [M+H]$^+$. $^1$H NMR (400 MHz, DMSO-d$_6$) δ 7.93 (br s, 3H), 7.16 (d, J=8.2 Hz, 1H), 6.93 (d, J=4.8 Hz, 1H), 6.87 (d, J=4.8 Hz, 1H), 6.63 (d, J=6.0 Hz, 1H), 5.17-4.99 (m, 2H), 4.49-4.44 (m, 1H), 4.31 (t, J=7.2 Hz, 2H), 3.80 (dd, J=44.0, 37.6 Hz, 1H), 2.26 (d, J=7.2 Hz, 2H), 2.10-2.02 (m, 1H), 1.99-1.88 (m, 1H), 1.30 (d, J=52.8 Hz, 9H), 0.93 (d, J=6.8 Hz, 6H), 0.86 (d, J=26.4 Hz, 1H), 0.78 (t, J=6.8 Hz, 5H).

Step 3. Synthesis of ((2R,3S,4R,5R)-5-(4-aminopyrrolo[2,1-f][1,2,4]triazin-7-yl)-5-cyano-4-hydroxy-3-((3-methylbutanoyl)oxy)tetrahydrofuran-2-yl)methyl L-valinate (33)

To a solution of 33.3 (60 mg, 0.104 mmol) in DCM (0.5 mL) was added HCl in 1,4-dioxane (0.5 mL, 4M) at 0° C., then the reaction was stirred at 20° C. for 1 hour. The reaction was diluted with ACN (2 mL) and purified by prep-HPLC to obtain 33 (37.6 mg, 71.1% yield) as a white solid. MS (ESI): m/z calcd. for C$_{22}$H$_{30}$N$_6$O$_6$, 474.22, found 475.1 [M+H]$^+$. $^1$H NMR (400 MHz, DMSO-d$_6$) δ 7.93 (br s, 3H), 6.93 (d, J=4.8 Hz, 1H), 6.87 (d, J=4.8 Hz, 1H), 6.64 (s, 1H), 5.15-5.07 (m, 2H), 4.47 (q, J=4.4 Hz, 1H), 4.37-4.24 (m, 2H), 3.14 (d, J=5.2 Hz, 1H), 2.26 (d, J=7.2 Hz, 2H), 2.15-2.01 (m, 1H), 1.85-1.75 (m, 1H), 0.95-0.91 (m, 6H), 0.84-0.68 (m, 6H).

Example 18. Synthesis of ((2R,3S,4R,5R)-5-(4-aminopyrrolo[2,1-f][1,2,4]triazin-7-yl)-5-cyano-3-(2-cyclohexylacetoxy)-4-hydroxytetrahydrofuran-2-yl)methyl L-valinate (Compound 34)

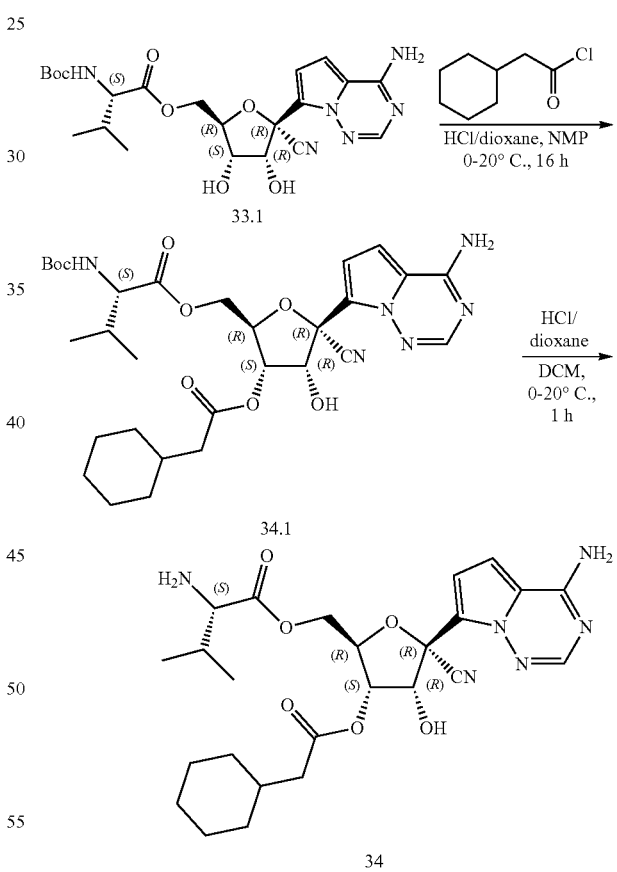

Step 1. Synthesis of ((2R,3S,4R,5R)-5-(4-aminopyrrolo[2,1-f][1,2,4]triazin-7-yl)-5-cyano-3-(2-cyclohexylacetoxy)-4-hydroxytetrahydrofuran-2-yl) methyl (tert-butoxycarbonyl)-L-valinate (34.1)

The title compound was prepared according to the procedure of Example 33, Step 2, using 33.2 and 2-cyclohexylacetyl chloride. MS (ESI): m/z calcd. for C$_{30}$H$_{42}$N$_6$O$_8$, 614.31, found 615.2 [M+H]$^+$. $^1$H NMR (400 MHz, DMSO) δ 7.93 (br s, 3H), 8.10-7.80 (m, 3H), 7.17 (d, J=8.0 Hz, 1H), 6.93 (d, J=4.4 Hz, 2H), 6.87 (d, J=4.4 Hz, 1H), 6.64 (d, J=5.6 Hz, 1H), 5.08 (s, 2H), 4.45 (d, J=3.2 Hz, 1H), 4.30 (s, 2H), 3.84 (t, J=7.2 Hz, 1H), 2.25 (d, J=6.8 Hz, 2H), 1.93 (dd, J=13.2, 6.8 Hz, 1H), 1.75-1.55 (m, 6H), 1.37 (s, 7H), 1.25-1.11 (m 4H), 0.94 (d, J=12.0 Hz, 2H), 0.77 (t, J=7.2 Hz, 6H).

Step 2. Synthesis of ((2R,3S,4R,5R)-5-(4-aminopyrrolo[2,1-f][1,2,4]triazin-7-yl)-5-cyano-3-(2-cyclohexylacetoxy)-4-hydroxytetrahydrofuran-2-yl) methyl L-valinate (34)

The title compound was prepared according to the procedure of Example 33, Step 3, using 34.1. MS (ESI): m/z calcd. for C$_{25}$H$_{34}$N$_6$O$_6$, 514.25, found 515.2 [M+H]$^+$. $^1$H NMR (400 MHz, DMSO) δ 7.92 (br s, 3H), 6.93 (d, J=4.8 Hz, 1H), 6.86 (d, J=4.8 Hz, 1H), 6.63 (s, 1H), 5.16-5.04 (m, 2H), 4.47 (q, J=4.4 Hz, 1H), 4.33-4.24 (m, 2H), 3.12 (d, J=5.2 Hz, 1H), 2.26 (d, J=6.8 Hz, 2H), 1.80-1.57 (m, 7H), 1.27-1.06 (m, 3H), 1.00-0.89 (m, 2H), 0.84-0.73 (m, 6H).

Example 19. Synthesis of ((2R,3S,4R,5R)-5-(4-aminopyrrolo[2,1-f][1,2,4]triazin-7-yl)-5-cyano-4-hydroxy-3-(2-phenylacetoxy)tetrahydrofuran-2-yl) methyl L-valinate (Compound 36)

Step 1. Synthesis of ((2R,3S,4R,5R)-5-(4-aminopyrrolo[2,1-f][1,2,4]triazin-7-yl)-5-cyano-4-hydroxy-3-(2-phenylacetoxy)tetrahydrofuran-2-yl)methyl (tert-butoxycarbonyl)-L-valinate (36.1)

The title compound was prepared according to the procedure of Example 33, Step 2, using 33.2 and 2-phenylacetyl chloride. MS (ESI): m/z calcd. for C$_{30}$H$_{36}$N$_6$O$_8$, 608.26, found 609.15 [M+H]$^+$. $^1$H NMR (400 MHz, DMSO) δ 7.92 (s, 3H), 7.32 (d, J=4.4 Hz, 4H), 7.28-7.23 (m, 1H), 7.15 (d, J=8.0 Hz, 1H), 6.93 (d, J=4.4 Hz, 1H), 6.87 (d, J=4.4 Hz, 1H), 6.69 (d, J=6.0 Hz, 1H), 5.11 (t, J=5.2 Hz, 2H), 4.48 (d, J=4.0 Hz, 1H), 4.33-4.24 (m, 2H), 3.88-3.66 (m, 3H), 1.91 (dt, J=13.2, 6.8 Hz, 1H), 1.40-1.20 (m, 9H), 0.75 (dd, J=8.8, 7.2 Hz, 6H).

Step 2. Synthesis of ((2R,3S,4R,5R)-5-(4-aminopyrrolo[2,1-f][1,2,4]triazin-7-yl)-5-cyano-4-hydroxy-3-(2-phenylacetoxy)tetrahydrofuran-2-yl)methyl L-valinate (36)

The title compound was prepared according to the procedure of Example 33, Step 3, using 36.1. MS (ESI): m/z calcd. for C$_{25}$H$_{28}$N$_6$O$_6$, 508.21, found 509.25 [M+H]$^+$. $^1$H NMR (400 MHz, DMSO) δ 7.92 (s, 3H), 7.32 (d, J=4.0 Hz, 4H), 7.30-7.23 (m, 1H), 6.93 (d, J=4.8 Hz, 1H), 6.87 (d, J=4.8 Hz, 1H), 6.69 (d, J=6.4 Hz, 1H), 5.18-5.08 (m, 2H), 4.49 (q, J=4.4 Hz, 1H), 4.28 (d, J=4.4 Hz, 2H), 3.76 (q, J=16.0 Hz, 2H), 3.10 (d, J=5.2 Hz, 1H), 1.82-1.70 (m, 1H), 0.78 (d, J=6.8 Hz, 3H), 0.72 (d, J=6.8 Hz, 3H).

Example 20. Synthesis of ((2R,3S,4R,5R)-3-acetoxy-5-(4-aminopyrrolo[2,1-f][1,2,4]triazin-7-yl)-5-cyano-4-hydroxytetrahydrofuran-2-yl)methyl L-valinate (Compound 37)

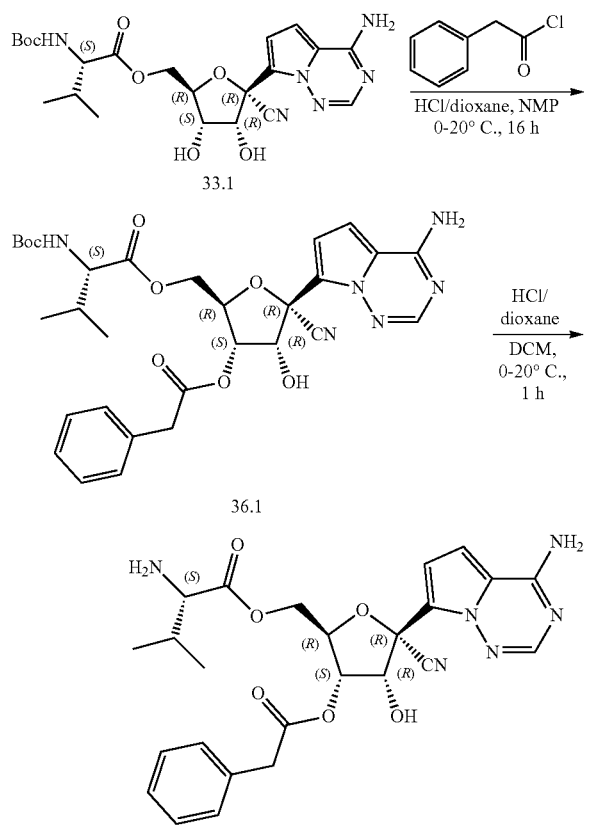

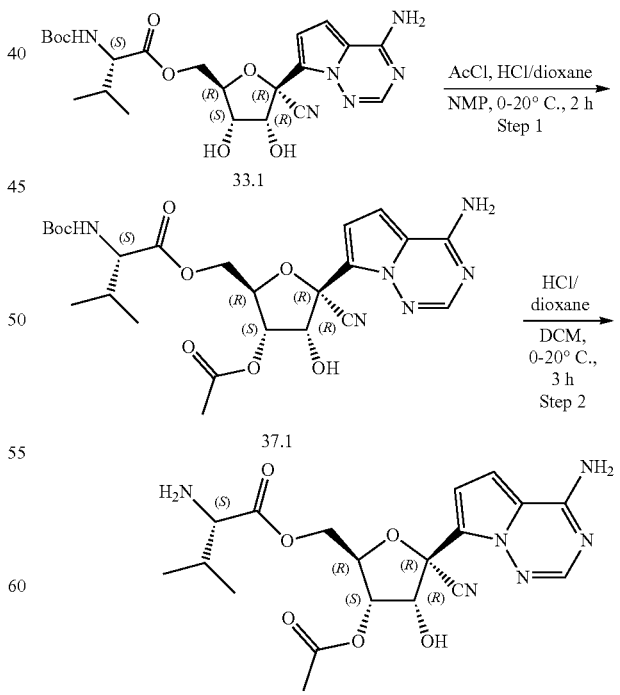

Step 1. Synthesis of ((2R,3S,4R,5R)-3-acetoxy-5-(4-aminopyrrolo[2,1-f][1,2,4]triazin-7-yl)-5-cyano-4-hydroxytetrahydrofuran-2-yl)methyl (tert-butoxycarbonyl)-L-valinate (37.1)

The title compound was prepared according to the procedure of Example 33, Step 2, using 33.2 and acetyl chloride. $^1$H NMR (400 MHz, DMSO) δ 7.93 (br s, 3H), 7.15 (d, J=8.0 Hz, 1H), 6.93 (d, J=4.8 Hz, 1H), 6.86 (d, J=4.8 Hz, 1H), 6.63 (d, J=6.0 Hz, 1H), 5.13-5.00 (m, 2H), 4.51-4.44 (m, 1H), 4.35-4.23 (m, 2H), 3.89-3.81 (m, 1H), 2.08 (s, 3H), 1.98-1.85 (m, 2H), 1.37 (s, 9H), 0.78 (t J=6.8 Hz, 6H).

Step 2. Synthesis ((2R,3S,4R,5R)-3-acetoxy-5-(4-aminopyrrolo[2,1-f][1,2,4]triazin-7-yl)-5-cyano-4-hydroxytetrahydrofuran-2-yl)methyl L-valinate (37)

The title compound was prepared according to the procedure of Example 33, Step 3, using 37.1. MS (ESI): m/z calcd. for $C_{19}H_{24}N_6O_6$ 432.18, found 433.1 [M+H]$^+$. $^1$H NMR (400 MHz, DMSO) δ 7.93 (br s, 3H), 6.93 (d, J=4.4 Hz, 1H), 6.86 (d, J=4.8 Hz, 1H), 6.63 (d, J=4.4 Hz, 1H), 5.16-4.99 (m, 2H), 4.52-4.46 (q, J=4.4 Hz, 1H), 4.35-4.24 (m, 2H), 3.18-3.12 (m, 1H), 2.09 (s, 3H), 1.84-1.74 (m, 1H), 0.81 (d, J=6.8 Hz, 3H), 0.76 (d, J=6.8 Hz, 3H).

Example 21. Synthesis of ((2R,3S,4R,5R)-5-(4-aminopyrrolo[2,1-f][1,2,4]triazin-7-yl)-5-cyano-4-hydroxy-3-(isobutyryloxy)tetrahydrofuran-2-yl)methyl L-valinate (Compound 38)

Step 1. Synthesis of ((2R,3S,4R,5R)-5-(4-aminopyrrolo[2,1-f][1,2,4]triazin-7-yl)-5-cyano-4-hydroxy-3-(isobutyryloxy)tetrahydrofuran-2-yl)methyl (tert-butoxycarbonyl)-L-valinate (38.1)

The title compound was prepared according to the procedure of Example 33, Step 2, using 33.2 and 2-methylpropanoyl chloride. MS (ESI): m/z calcd. for $C_{26}H_{36}N_6O_8$ 560.26, found 561.3 [M+H]+. $^1$H NMR (400 MHz, DMSO) δ 7.92 (br s, 3H), 7.16 (d, J=8.4 Hz, 1H), 6.92 (d, J=4.8 Hz, 1H), 6.87 (d, J=4.4 Hz, 1H), 6.58 (d, J=6.0 Hz, 1H), 5.17-5.07 (m, 2H), 4.46 (dd, J=8.4, 4.8 Hz, 1H), 4.34-4.24 (m, 2H), 3.88-3.82 (m, 1H), 2.65-2.57 (m, 1H), 1.98-1.86 (m, 1H), 1.42-1.20 (m, 9H), 1.14 (t J=7.2 Hz, 6H), 0.77 (t, J=7.2 Hz, 6H).

Step 2. Synthesis of ((2R,3S,4R,5R)-5-(4-aminopyrrolo[2,1-f][1,2,4]triazin-7-yl)-5-cyano-4-hydroxy-3-(isobutyryloxy)tetrahydrofuran-2-yl)methyl L-valinate (38)

The title compound was prepared according to the procedure of Example 33, Step 3, using 38.1. MS (ESI): m/z calcd. for $C_{21}H_2N_{66}$ 460.21, found 461.1 [M+H]$^+$. $^1$H NMR (400 MHz, DMSO) δ 7.92 (br s, 3H), 6.93 (d, J=4.8 Hz, 1H), 6.86 (d, J=4.4 Hz, 1H), 6.57 (d, J=6.0 Hz, 1H), 5.18-5.08 (m, 2H), 4.50-4.43 (m, 1H), 4.37-4.23 (m, 2H), 3.12 (d, J=4.0 Hz, 1H), 2.66-2.56 (m, 1H), 1.83-1.72 (m, 1H), 1.15 (t, J=7.2 Hz, 6H), 0.77 (dd, J=22.8, 6.8 Hz, 6H).

Example 22. Synthesis of ((2R,3S,4R,5R)-5-(4-aminopyrrolo[2,1-f][1,2,4]triazin-7-yl)-5-cyano-4-hydroxy-3-(propionyloxy)tetrahydrofuran-2-yl)methyl L-valinate (Compound 39)

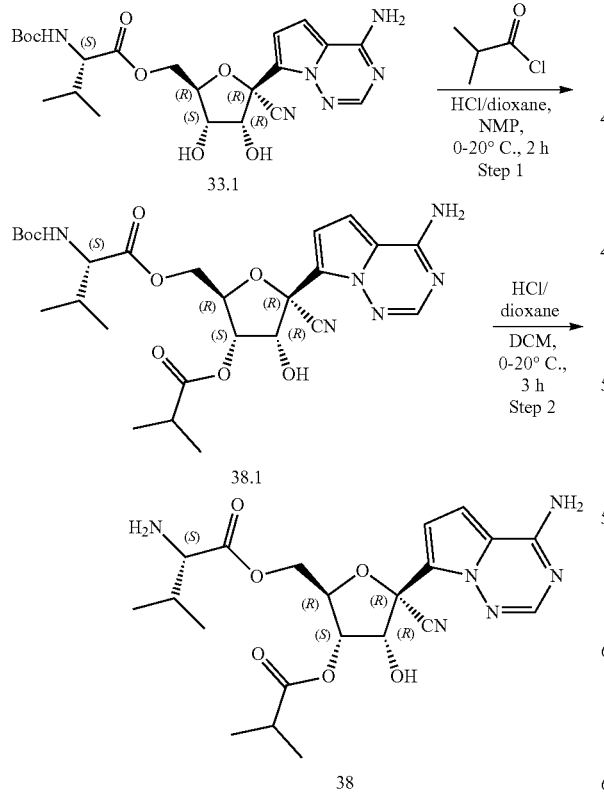

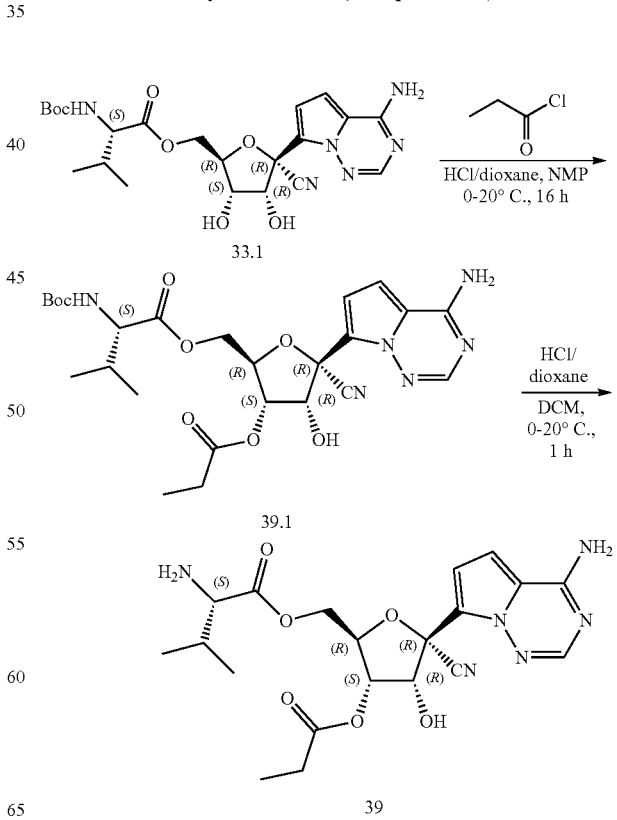

Step 1. Synthesis of ((2R,3S,4R,5R)-5-(4-aminopyrrolo[2,1-f][1,2,4]triazin-7-yl)-5-cyano-4-hydroxy-3-(propionyloxy)tetrahydrofuran-2-yl)methyl (tert-butoxycarbonyl)-L-valinate (39.1)

The title compound was prepared according to the procedure of Example 33, Step 2, using 33.2 and propionyl chloride. MS (ESI): m/z calcd. for $C_{25}H_{34}N_6O_8$, 546.24, found 547.30 [M+H]+. 1H NMR (400 MHz, DMSO) δ 7.93 (s, 3H), 7.16 (d, J=8.0 Hz, 1H), 6.93 (d, J=4.4 Hz, 1H), 6.86 (d, J=4.4 Hz, 1H), 6.60 (d, J=6.0 Hz, 1H), 5.17-5.03 (m, 2H), 4.47 (d, J=4.4 Hz, 1H), 4.30 (d, J=4.4 Hz, 2H), 3.80 (dd, J=44.4, 37.6 Hz, 1H), 2.40 (q, J=7.6 Hz, 2H), 1.93 (dt J=13.2, 6.4 Hz, 1H), 1.37 (s, 9H), 1.07 (t, J=7.6 Hz, 3H), 0.78 (t J=6.8 Hz, 6H).

Step 2. Synthesis of ((2R,3S,4R,5R)-5-(4-aminopyrrolo[2,1-f][1,2,4]triazin-7-yl)-5-cyano-4-hydroxy-3-(propionyloxy)tetrahydrofuran-2-yl)methyl L-valinate (39)

The title compound was prepared according to the procedure of Example 33, Step 3, using 39.1. MS (ESI): m/z calcd. for $C_{20}H_{26}N_6O_6$, 446.19, found 447.25 [M+H]+. 1H NMR (400 MHz, DMSO) δ 7.92 (s, 3H), 6.93 (d, J=4.8 Hz, 1H), 6.84 (d, J=4.4 Hz, 1H), 6.61 (d, J=5.6 Hz, 1H), 5.18-5.05 (m, 2H), 4.49 (q, J=4.4 Hz, 1H), 4.42-4.24 (m, 3H), 3.32 (d, J=5.2 Hz, 1H), 2.40 (q, J=7.6 Hz, 2H), 1.92-1.81 (m, 1H), 1.08 (t, J=7.6 Hz, 3H), 0.86-0.75 (m, 6H).

Example 23. Synthesis of (2R,3S,4R,5R)-5-{4-aminopyrrolo[2,1-f][1,2,4]triazin-7-yl}-5-cyano-4-hydroxy-2-{[(2-phenylacetyl)oxy]methyl}oxolan-3-yl (2S)-2-amino-3-methylbutanoate (Compound 43)

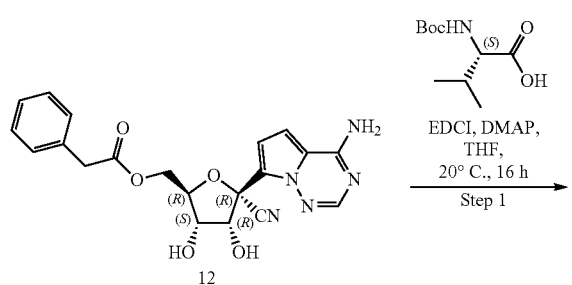

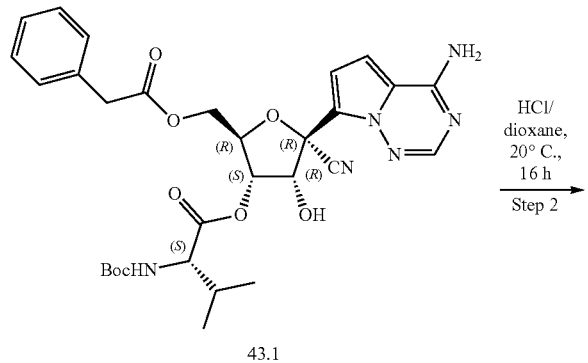

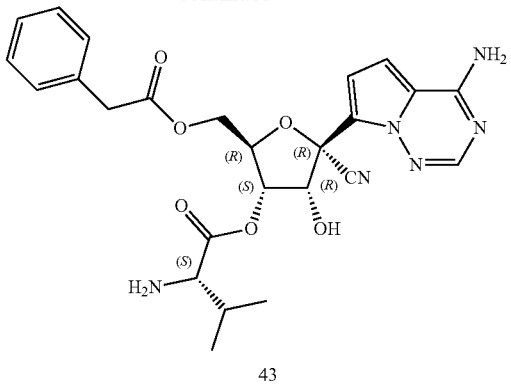

43

Step 1. Synthesis of (2R,3S,4R,5R)-5-{4-aminopyrrolo[2,1-f][1,2,4]triazin-7-yl}-5-cyano-4-hydroxy-2-{[(2-phenylacetyl)oxy]methyl}oxolan-3-yl (2S)-2-{[(tert-butoxy)carbonyl]amino}-3-methylbutanoate (43.1)

The compound 43.1 was prepared according to the procedure of Example 19, Step 1, using 12 and (2S)-2-{[(tert-butoxy) carbonyl]amino}-3-methylbutanoic acid. MS (ESI): mass calcd. for $C_{30}H_{36}N_6O_8$, 608.26, m/z found 608.3 [M+H]+.

Step 2. Synthesis of (2R,3S,4R,5R)-5-{4-aminopyrrolo[2,1-f][1,2,4]triazin-7-yl}-5-cyano-4-hydroxy-2-{[(2-phenylacetyl)oxy]methyl}oxolan-3-yl (2S)-2-amino-3-methylbutanoate (43)

The title compound 27 was prepared according to the procedure of Example 19, Step 2, using 43.1. MS (ESI): mass calcd. for $C_{25}H_{28}N_6O_6$, 508.21, m/z found 509.1 [M+H]+. 1H NMR (400 MHz, DMSO) δ 7.93 (br, s, 3H), 7.30-7.17 (m, 5H), 6.94 (d, J=4.8 Hz, 1H), 6.84 (d, J=4.8 Hz, 1H), 6.58 (d, J=5.6 Hz, 1H), 5.17-5.11 (m, 1H), 5.08-5.07 (m, 1H), 4.46-4.44 (m, 1H), 4.34 (dd, J=12.0, 3.6 Hz, 1H), 4.25 (dd, J=12.4, 5.2 Hz, 1H), 3.66 (s, 2H), 3.24 (d, J=5.2 Hz, 1H), 2.00-1.97 (m, 1H), 0.92 (d, J=6.8 Hz, 3H), 0.88 (d, J=6.8 Hz, 3H).

Example 24. Synthesis of {[(2R,3S,4R,5R)-5-{4-aminopyrrolo[2,1-f][1,2,4]triazin-7-yl}-5-cyano-4-hydroxy-2-{[(2-phenylacetyl)oxy]methyl}oxolan-3-yl]oxy}methyl 2,2-dimethylpropanoate (Compound 48)

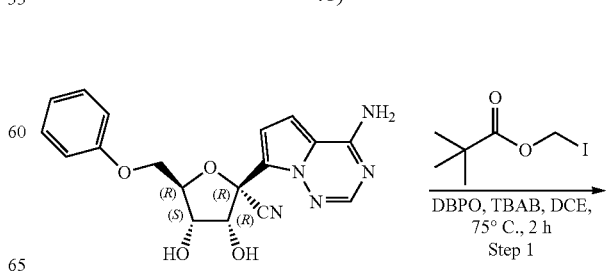

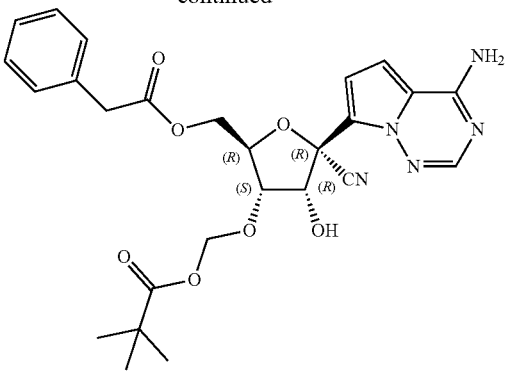

48

To a solution of [(2R,3S,4R,5R)-5-{4-aminopyrrolo[2,1-f][1,2,4]triazin-7-yl}-5-cyano-3,4-dihydroxyoxolan-2-yl] methyl 2-phenylacetate (12, 150 mg, 0.366 mmol) in DCE (10 mL) was added Tetrabutylammonium bromide (153.55 mg, 0.476 mmol), DBTO (118.60 mg, 0.476 mmol) and iodomethyl pivalate (221.67 mg, 0.916 mmol) under $N_2$ atmosphere, the resulting mixture was stirred at 75° C. for 2 h. The reaction was washed with DCM (5 mL×3). The combined organics were dried over sodium sulfate and concentrated in vacuo. The crude product was purified by prep-HPLC to afford 48 (12 mg, 6% yield) as a white solid. MS (ESI): m/z calcd. for $C_{26}H_{29}N_5O_7$ 523.21, found 524.1 [M+H]$^+$. $^1$H NMR (400 MHz, DMSO) δ 7.93 (br, s, 3H), 7.29-7.24 (m, 3H), 7.23-7.18 (m, 2H), 6.94 (d, J=4.4 Hz, 1H), 6.81 (d, J=4.4 Hz, 1H), 6.48 (d, J=6.4 Hz, 1H), 5.32 (d, J=6.4 Hz, 1H), 5.26 (d, J=6.4 Hz, 1H), 4.96-4.88 (t, J=5.6 Hz, 1H), 4.34-4.30 (m, 2H), 4.16-4.13 (m, 2H), 3.65 (s, 2H), 1.10 (s, 9H).

Example 25. Synthesis of (2R,3S,4R,5R)-2-(acetoxymethyl)-5-(4-aminopyrrolo[2,1-f][1,2,4]triazin-7-yl)-5-cyano-4-hydroxytetrahydrofuran-3-yl 3-methylbutanoate (Compound 49)

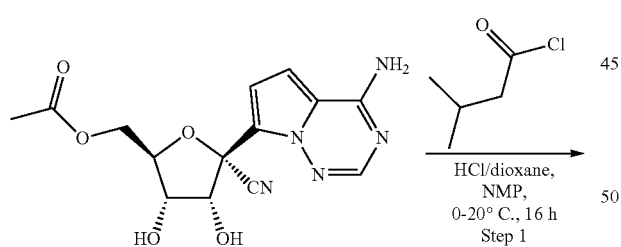

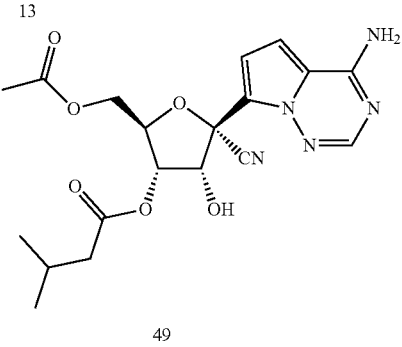

49

To a solution of 13 (100 mg, 0.30 mmol) in NMP (1.0 mL) was added HCl/dioxane (0.5 mL, 4 M). The mixture solution was stirred at 20° C. for 15 minutes. The reaction mixture was cooled at 0° C. and 3-methylbutanoyl chloride (0.29 mL, 2.4 mmol) was added at once. The reaction was stirred at 20° C. for 16 hours. The reaction was diluted with ACN (2.0 mL) and purified by prep-HPLC to obtain 49 (11.3 mg, 8.80% yield) as a white solid. MS (ESI): m/z calcd. for $C_{19}H_{23}N_5O_6$, 417.16, found 418.1 [M+H]$^+$. $^1$H NMR (400 MHz, DMSO-d$_6$) δ 7.93 (br s, 3H), 6.93 (d, J=4.8 Hz, 1H), 6.86 (d, J=4.8 Hz, 1H), 6.59 (d, J=6.0 Hz, 1H), 5.11 (m, 2H), 4.44 (dd, J=8.8, 4.0 Hz, 1H), 4.31 (dd, J=12.2, 3.6 Hz, 1H), 4.19 (dd, J=12.2, 5.2 Hz, 1H), 2.27 (d, J=7.2 Hz, 2H), 2.07 (dt, J=13.6, 6.8 Hz, 1H), 2.00 (s, 3H), 0.94 (dd, J=6.8, 0.8 Hz, 6H).

Example 26. Synthesis of (2R,3S,4R,5R)-2-(acetoxymethyl)-5-(4-aminopyrrolo[2,1-f][1,2,4]triazin-7-yl)-5-cyano-4-hydroxytetrahydrofuran-3-yl 2-cyclohexylacetate (Compound 50)

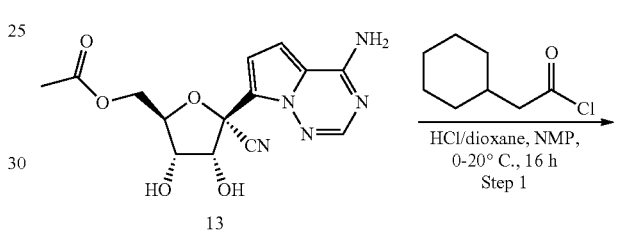

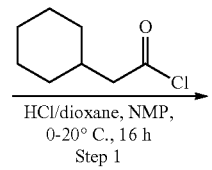

50

The title compound was prepared according to the procedure of Example 49, Step 1, using Compound 13 and 2-cyclohexylacetyl chloride. MS (ESI): mass calcd. for $C_{22}H_{27}N_5O_6$, 457.20, m/z found 458.1 [M+H]$^+$. $^1$H NMR (400 MHz, DMSO-d$_6$) δ 7.93 (br s, 3H), 6.93 (d, J=4.4 Hz, 1H), 6.86 (d, J=4.4 Hz, 1H), 6.62-6.53 (m, 1H), 5.12-5.07 (m, 2H), 4.43 (dd, J=8.4, 4.4 Hz, 1H), 4.31 (dd, J=12.0, 3.6 Hz, 1H), 4.19 (dd, J=12.0, 5.2 Hz, 1H), 2.26 (d, J=6.8 Hz, 2H), 2.00 (s, 3H), 1.81-1.58 (m, 6H), 1.28-1.10 (m, 3H), 1.01-0.90 (m, 2H).

Example 27. Synthesis of (2R,3S,4R,5R)-2-[(acetyloxy)methyl]-5-{4-aminopyrrolo[2,1-f][1,2,4]triazin-7-yl}-5-cyano-4-hydroxyoxolan-3-yl (2S)-2-amino-3-methylbutanoate (Compound 51)

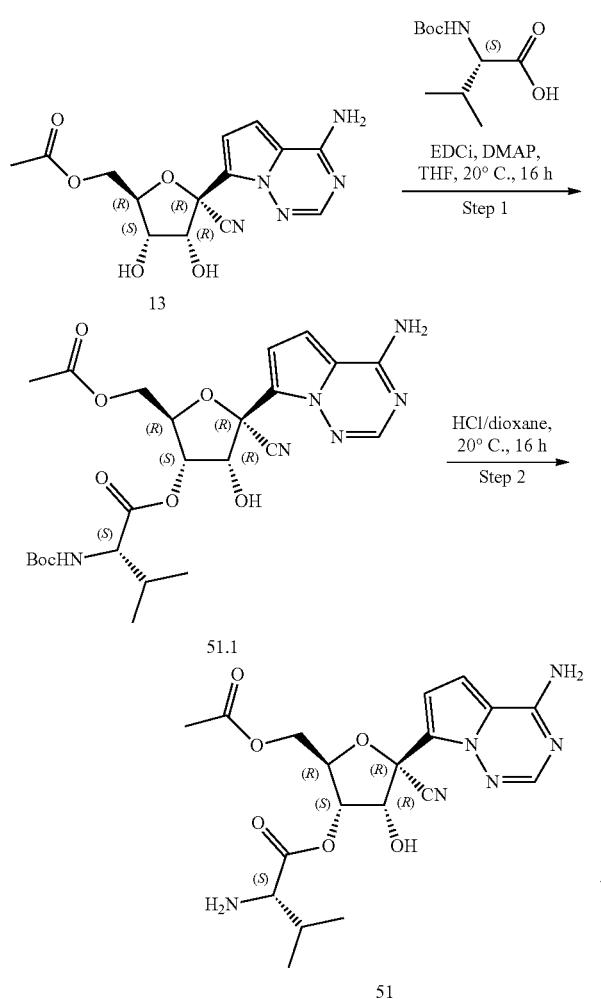

Step 1. Synthesis of (2R,3S,4R,5R)-2-[(acetyloxy)methyl]-5-{4-aminopyrrolo[2,1-f][1,2,4]triazin-7-yl}-5-cyano-4-hydroxyoxolan-3-yl (2S)-2-{[(tert-butoxy)carbonyl]amino}-3-methylbutanoate (51.1)

The compound 51.1 was prepared according to the procedure of Example 19, Step 1, using 13 and (2S)-2-{[(tert-butoxy)carbonyl]amino}-3-methylbutanoic acid. MS (ESI): mass calcd. for $C_{24}H_{32}N_6O_8$, 532.23 m/z found 533.2 $[M+H]^+$.

Step 2. Synthesis of (2R,3S,4R,5R)-2-[(acetyloxy)methyl]-5-{4-aminopyrrolo[2,1-f][1,2,4]triazin-7-yl}-5-cyano-4-hydroxyoxolan-3-yl (2S)-2-amino-3-methylbutanoate (51)

The title compound 51 was prepared according to the procedure of Example 19, Step 2, using 51.1. MS (ESI): mass calcd. for $C_{19}H_{24}N_6O_6$, 432.18, m/z found 433.3 $[M+H]^+$. $^1H$ NMR (400 MHz, DMSO) δ 7.90 (br, s, 3H), 6.94 (d, J=4.4 Hz, 1H), 6.88 (d, J=4.8 Hz, 1H), 6.61-6.55 (m, 1H), 5.20-5.09 (m, 2H), 4.43-4.40 (m, 1H), 4.31 (dd, J=12.0, 3.6 Hz, 1H), 4.20 (dd, J=12.0, 5.2 Hz, 1H), 3.23 (d, J=5.2 Hz, 1H), 2.05-2.02 (m, 1H), 2.00 (s, 3H), 0.92 (d, J=6.8 Hz, 3H), 0.86 (d, J=6.8 Hz, 3H).

Example 28. Synthesis of (2R,3S,4R,5R)-2-(acetoxymethyl)-5-(4-aminopyrrolo[2,1-f][1,2,4]triazin-7-yl)-5-cyano-4-hydroxytetrahydrofuran-3-yl 2-phenylacetate (Compound 52)

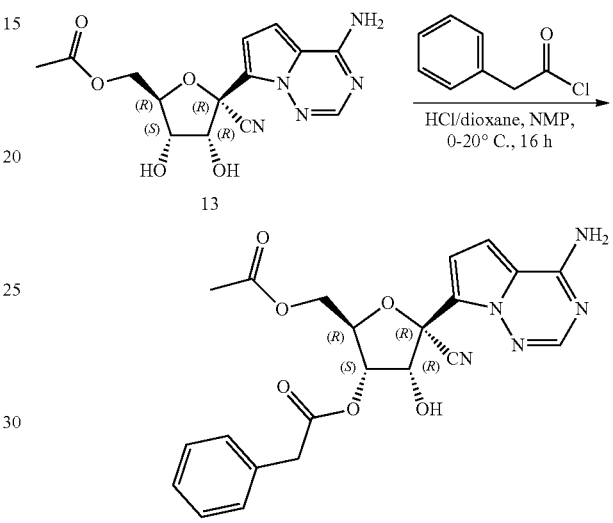

The title compound was prepared according to the procedure of Example 17, using 13 and 2-phenylacetyl chloride. MS (ESI): m/z calcd. for $C_{22}H_{21}N_5O_6$ 451.15, found 452.2 $[M+H]^+$. $^1H$ NMR (400 MHz, DMSO) δ 7.93 (br s, 3H), 7.35-7.20 (m, 5H), 6.93 (d, J=4.4 Hz, 1H), 6.87 (d, J=4.4 Hz, 1H), 6.66 (d, J=6.0 Hz, 1H), 5.12 (p, J=5.6 Hz, 2H), 4.46 (dd, J=9.2, 4.0 Hz, 1H), 4.31 (dd, J=12.0, 3.6 Hz, 1H), 4.17 (dd, J=12.0, 5.2 Hz, 1H), 3.77 (q, J=16.0 Hz, 2H), 1.98 (s, 3H).

Example 29. Synthesis of ((2R,3S,4R,5R)-3-acetoxy-5-(4-aminopyrrolo[2,1-f][1,2,4]triazin-7-yl)-5-cyano-4-hydroxytetrahydrofuran-2-yl)methyl acetate (Compound 53)

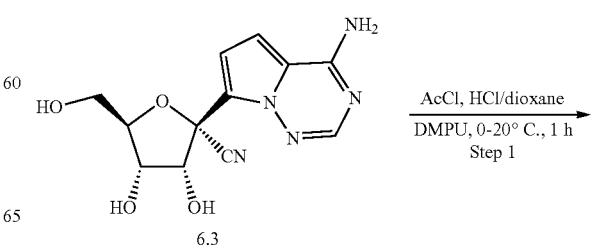

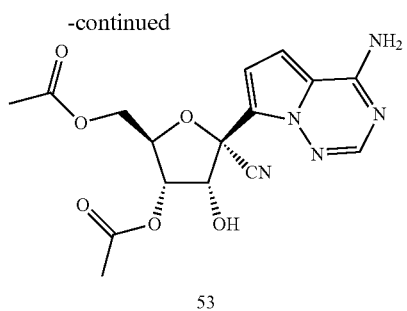

53

To a solution of 6.3 (2.00 g, 6.90 mmol) in DMPU (6 mL) was added HCl/dioxane (2.6 mL, 4 M). The mixture solution was stirred at 20° C. for 15 minutes. The reaction mixture was cooled at 0° C. and Acetyl chloride (0.98 mL, 13.8 mmol) was added at once. The reaction was stirred at 0° C. for 1 hour. The reaction was diluted with ACN (4.0 mL) and purified by prep-HPLC to obtain 53 (380 mg, 15.2% yield) as a white solid. MS (ESI): m/z calcd. for $C_1H_{17}N_5O_6$, 375.12, found 376.0 $[M+H]^+$. $^1$H NMR (400 MHz, DMSO-$d_6$) δ 7.94 (br s, 3H), 6.93 (dd, J=4.8, 2.0 Hz, 1H), 6.86 (d, J=4.8 Hz, 1H), 6.63-6.58 (m, 1H), 5.09-5.04 (m, 2H), 4.49-4.36 (m, 1H), 4.37-4.24 (m, 1H), 4.17 (dt, J=11.2, 5.6 Hz, 1H), 2.18-2.07 (m, 3H), 2.01 (d, J=8.0 Hz, 3H).

Example 30. Synthesis of (2R,3S,4R,5R)-2-(acetoxymethyl)-5-(4-aminopyrrolo[2,1-f][1,2,4]triazin-7-yl)-5-cyano-4-hydroxytetrahydrofuran-3-yl isobutyrate (Compound 54)

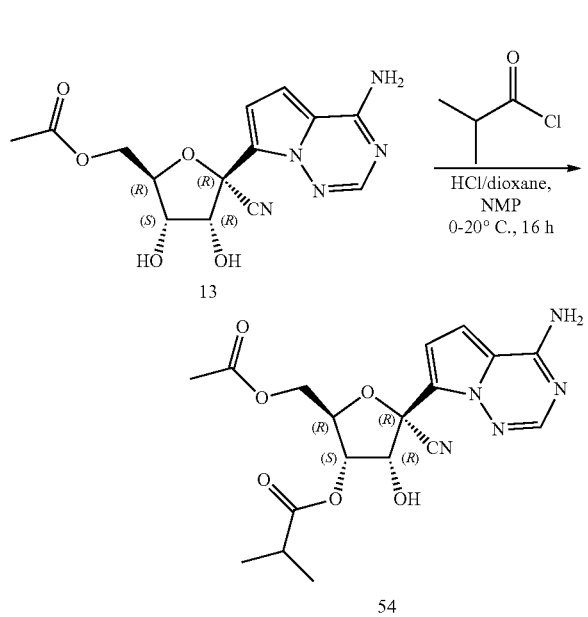

54

The title compound was prepared according to the procedure of Example 17, using 13 and isobutyryl chloride. MS (ESI): m/z calcd. for $C_{18}H_{21}N_5O$ 403.15, found 404.20 $[M+H]^+$. $^1$H NMR (400 MHz, DMSO) δ 7.93 (s, 3H), 6.93 (d, J=4.4 Hz, 1H), 6.87 (d, J=4.8 Hz, 1H), 6.54 (d, J=6.0 Hz, 1H), 5.18-5.08 (m, 2H), 4.50-4.41 (m, 1H), 4.31 (dd, J=12.4, 4.0 Hz, 1H), 4.20 (dd, J=12.0, 5.2 Hz, 1H), 2.63 (q, J=6.8 Hz, 1H), 2.00 (s, 3H), 1.15 (dd, J=7.2, 6.0 Hz, 6H).

Example 31. Synthesis of (2R,3S,4R,5R)-2-(acetoxymethyl)-5-(4-aminopyrrolo[2,1-f][1,2,4]triazin-7-yl)-5-cyano-4-hydroxytetrahydrofuran-3-yl propionate (Compound 55)

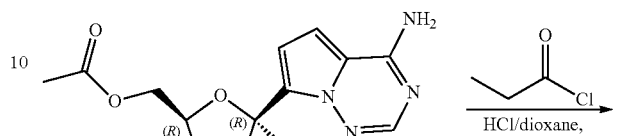

13

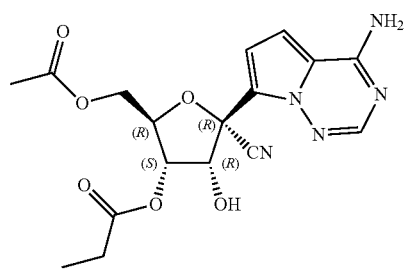

55

The title compound was prepared according to the procedure of Example 17, using 13 and propionyl chloride. MS (ESI): m/z calcd. for $C_{17}H_{19}N_5O_6$ 389.13, found 390.10 $[M+H]^+$. $^1$H NMR (400 MHz, DMSO) δ 7.93 (s, 3H), 6.93 (d, J=4.8 Hz, 1H), 6.86 (d, J=4.8 Hz, 1H), 6.58 (d, J=4.8 Hz, 1H), 5.10 (p, J=5.6 Hz, 2H), 4.45 (q, J=4.0 Hz, 1H), 4.32 (dd, J=12.0, 3.6 Hz, 1H), 4.18 (dd, J=12.0, 5.2 Hz, 1H), 2.40 (q, J=7.6 Hz, 2H), 2.00 (s, 3H), 1.08 (t, J=7.6 Hz, 3H).

Example 32. Synthesis of {[(2R,3S,4R,5R)-2-[(acetyloxy)methyl]-5-{4-aminopyrrolo[2,1-f][1,2,4]triazin-7-yl}-5-cyano-4-hydroxyoxolan-3-yl]oxy}methyl 2,2-dimethylpropanoate (Compound 56)

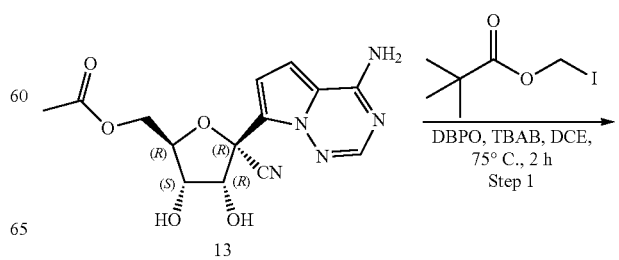

13

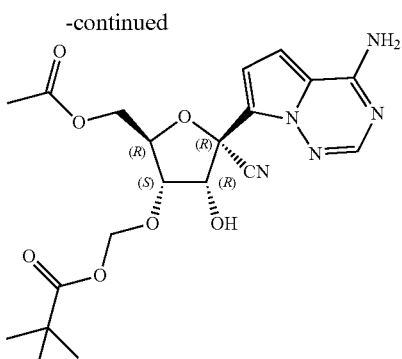

56

The compound 56 was prepared according to the procedure of Example 48, Step 1, using 13 and iodomethyl pivalate. MS (ESI): mass calcd. for $C_{20}H_{25}N_5O_7$, 447.18, m/z found 448.1 [M+H]⁺. ¹H NMR (400 MHz, DMSO) δ 7.92 (br, s, 3H), 6.92 (d, J=4.8 Hz, 1H), 6.83 (d, J=4.8 Hz, 1H), 6.49 (d, J=6.4 Hz, 1H), 5.35 (d, J=6.4 Hz, 1H), 5.28 (d, J=6.4 Hz, 1H), 5.02-4.93 (m, 1H), 4.39-4.25 (m, 2H), 4.19-4.06 (m, 2H), 2.00 (s, 3H), 1.11 (s, 9H).

Example 33. Synthesis of (2R,3S,4R,5R)-5-(4-aminopyrrolo[2,1-f][1,2,4]triazin-7-yl)-5-cyano-4-hydroxy-2-((isobutyryloxy)methyl)tetrahydrofuran-3-yl 3-methylbutanoate (Compound 57)

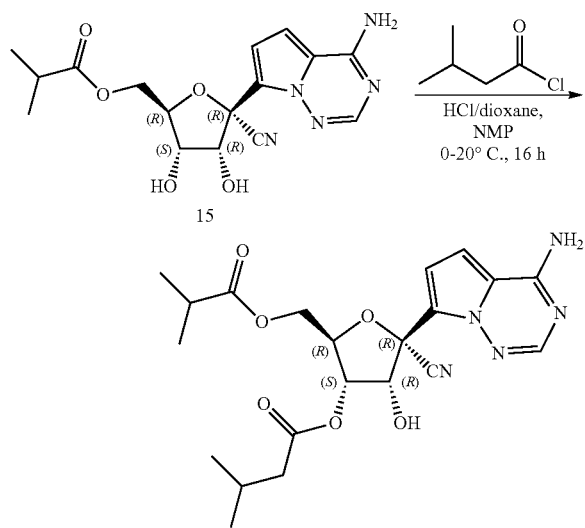

57

The title compound was prepared according to the procedure of Example 17, using 15 and 3-methylbutanoyl chloride. MS (ESI): m/z calcd. for $C_{21}H_{27}N_5O_6$ 445.20, found 446.20 [M+H]⁺. ¹H NMR (400 MHz, DMSO) δ 7.93 (s, 3H), 6.93 (d, J=4.8 Hz, 1H), 6.85 (d, J=4.8 Hz, 1H), 6.61 (d, J=6.4 Hz, 1H), 5.17-5.12 (m, 1H), 5.10-5.05 (m, 1H), 4.46 (q, J=4.4 Hz, 1H), 4.26 (qd, J=12.0, 4.0 Hz, 2H), 2.54 (q, J=6.8 Hz, 1H), 2.27 (d, J=7.2 Hz, 2H), 2.07 (dt J=13.6, 6.8 Hz, 1H), 1.04 (dd, J=6.8, 4.8 Hz, 6H), 0.94 (d, J=6.4 Hz, 6H).

Example 34. Synthesis of ((2R,3S,4R,5R)-5-(4-aminopyrrolo[2,1-f][1,2,4]triazin-7-yl)-5-cyano-3-(2-cyclohexylacetoxy)-4-hydroxytetrahydrofuran-2-yl)methyl isobutyrate (Compound 58)

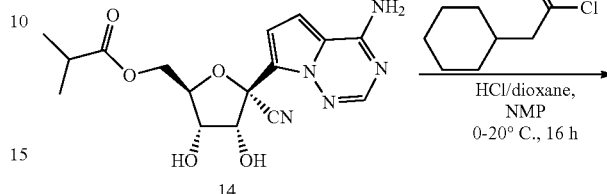

58

The title compound was prepared according to the procedure of Example 49, Step 1, using Compound 14 and 2-cyclohexylacetyl chloride. MS (ESI): mass calcd. for $C_{24}H_{31}N_5O_6$, 485.23, m/z found 486.2 [M+H]⁺. ¹H NMR (400 MHz, DMSO-d₆) δ 7.93 (br s, 3H), 6.93 (d, J=4.4 Hz, 1H), 6.85 (d, J=4.8 Hz, 1H), 6.61 (d, J=6.4 Hz, 1H), 5.16-5.11 (m, 1H), 5.07 (t, J=6.0 Hz, 1H), 4.45 (q, J=4.4 Hz, 1H), 4.25 (qd, J=12.0, 4.4 Hz, 2H), 2.57-2.51 (m, 1H), 2.28 (d, J=6.8 Hz, 2H), 1.82-1.58 (m, 6H), 1.23-0.90 (m, 11H).

Example 35. Synthesis of (2R,3S,4R,5R)-5-{4-aminopyrrolo[2,1-f][1,2,4]triazin-7-yl}-5-cyano-4-hydroxy-2-{[(2-methylpropanoyl)oxy]methyl}oxolan-3-yl (2S)-2-amino-3-methylbutanoate (Compound 59)

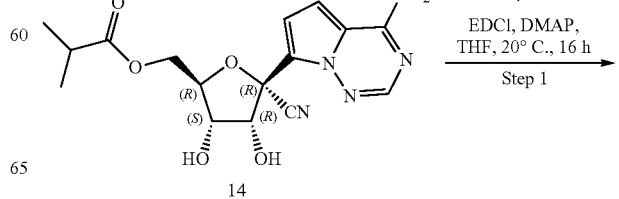

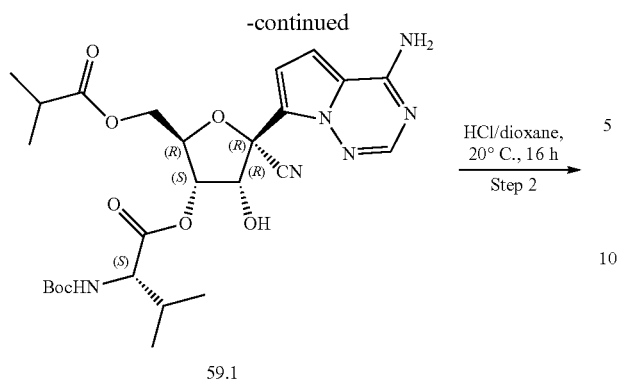

59.1

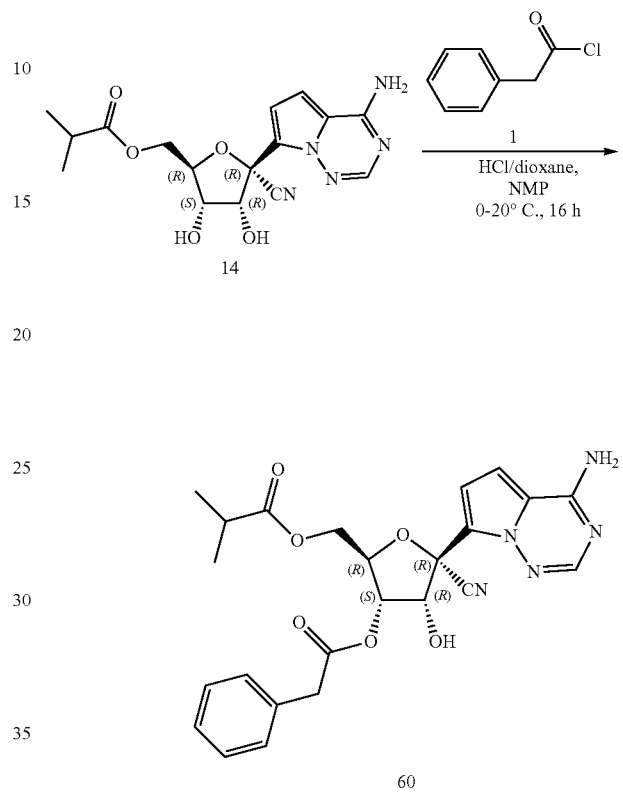

Step 1. Synthesis of (2R,3S,4R,5R)-5-{4-aminopyrrolo[2,1-f][1,2,4]triazin-7-yl}-5-cyano-4-hydroxy-2-{[(2-methylpropanoyl)oxy]methyl}oxolan-3-yl (2S)-2-{[(tert-butoxy)carbonyl]amino}-3-methylbutanoate (59.1)

The compound 59.1 was prepared according to the procedure of Example 19, Step 1, using 14 and (2S)-2-{[(tert-butoxy) carbonyl]amino}-3-methylbutanoic acid. MS (ESI): mass calcd. for $C_{26}H_{36}N_6O_8$, 560.26 m/z found 561.2 [M+H]$^+$.

Step 2: Synthesis of (2R,3S,4R,5R)-5-{4-aminopyrrolo[2,1-f][1,2,4]triazin-7-yl}-5-cyano-4-hydroxy-2-{[(2-methylpropanoyl)oxy]methyl}oxolan-3-yl (2S)-2-amino-3-methylbutanoate (59)

The title compound 59 was prepared according to the procedure of Example 19, Step 2, using 59.1. MS (ESI): mass calcd. for $C_{21}H_{28}N_6O_6$, 460.21, m/z found 461.3 [M+H]$^+$. $^1$H NMR (400 MHz, DMSO) δ 7.90 (br, s, 3H), 6.93 (d, J=4.8 Hz, 1H), 6.86 (d, J=4.4 Hz, 1H), 6.62-6.60 (m, 1H), 5.14-5.10 (m, 2H), 4.46-4.45 (m, 1H), 4.27 (d, J=4.0 Hz, 1H), 4.24 (d, J=4.8 Hz, 1H), 3.23 (d, J=5.2 Hz, 1H), 2.53-2.51 (m, 1H), 1.99-1.90 (m, 1H), 1.06-1.00 (m, 6H), 0.92 (d, J=6.8 Hz, 3H). 0.85 (d, J=6.8 Hz, 3H).

Example 36. Synthesis of ((2R,3S,4R,5R)-5-(4-aminopyrrolo[2,1-f][1,2,4]triazin-7-yl)-5-cyano-4-hydroxy-3-(2-phenylacetoxy)tetrahydrofuran-2-yl) methyl isobutyrate (Compound 60)

The title compound was prepared according to the procedure of Example 49, Step 1, using Compound 14 and 2-phenylacetyl chloride. MS (ESI): mass calcd. for $C_{24}H_{25}N_5O_6$, 479.18, m/z found 480.1 [M+H]$^+$. $^1$H NMR (400 MHz, DMSO-d$_6$) δ 7.93 (br s, 3H), 7.33-7.29 (m, 4H), 7.29-7.24 (m, 1H), 6.93 (d, J=4.8 Hz, 1H), 6.86 (d, J=4.8 Hz, 1H), 6.68 (d, J=6.4 Hz, 1H), 5.13 (dt, J=12.0, 5.6 Hz, 2H), 4.48 (q, J=4.4 Hz, 1H), 4.30-4.18 (m, 2H), 3.77 (q, J=15.8 Hz, 2H), 2.47-2.44 (m, 1H), 1.04-1.00 m, 6H).

Example 37. Synthesis of ((2R,3S,4R,5R)-3-acetoxy-5-(4-aminopyrrolo[2,1-f][1,2,4]triazin-7-yl)-5-cyano-4-hydroxytetrahydrofuran-2-yl)methyl isobutyrate (Compound 61)

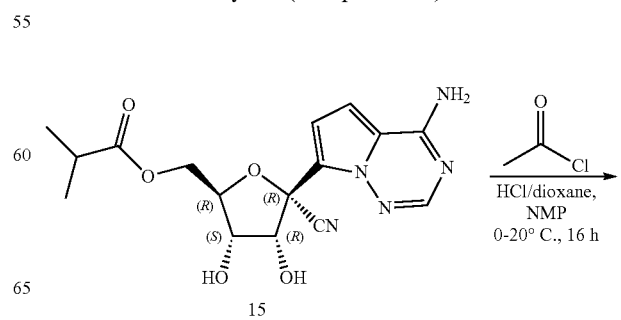

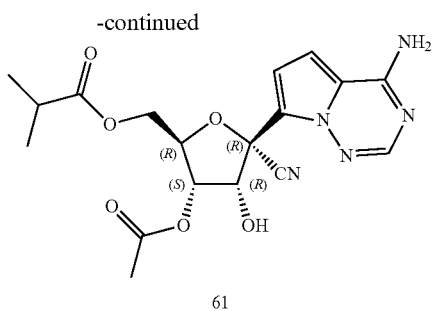

61

The title compound was prepared according to the procedure of Example 17, using 15 and acetyl chloride. MS (ESI): m/z calcd. for $C_{18}H_{21}N_5O_6$ 403.15, found 404.00 $[M+H]^+$. $^1$H NMR (400 MHz, DMSO) δ 7.93 (s, 3H), 6.93 (d, J=4.4 Hz, 1H), 6.85 (d, J=4.4 Hz, 1H), 6.63 (d, J=6.0 Hz, 1H), 5.07 (dt, J=19.2, 5.2 Hz, 2H), 4.48 (q, J=4.8 Hz, 1H), 4.33-4.27 (m, 1H), 4.25-4.16 (m, 1H), 2.53 (q, J=7.2 Hz, 1H), 2.09 (s, 3H), 1.05 (d, J=4.8 Hz, 3H), 1.03 (d, J=4.8 Hz, 3H).

Example 38. Synthesis of (2R,3S,4R,5R)-5-(4-aminopyrrolo[2,1-f][1,2,4]triazin-7-yl)-5-cyano-4-hydroxy-2-((isobutyryloxy)methyl)tetrahydrofuran-3-yl isobutyrate (Compound 62)

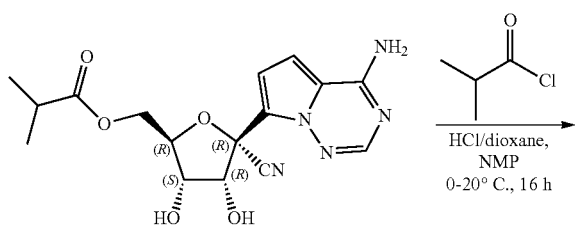

62

The title compound was prepared according to the procedure of Example 17, using 15 and isobutyryl chloride. MS (ESI): m/z calcd. for $C_{20}H_{25}N_5O_6$ 431.18, found 432.05 $[M+H]^+$. $^1$H NMR (400 MHz, DMSO) δ 7.92 (s, 3H), 6.93 (d, J=4.4 Hz, 1H), 6.85 (d, J=4.4 Hz, 1H), 6.57 (d, J=6.4 Hz, 1H), 5.20-5.06 (m, 2H), 4.46 (q, J=4.2 Hz, 1H), 4.25 (qd, J=12.0, 4.0 Hz, 2H), 2.67-2.58 (m, 1H), 2.54 (q, J=7.2 Hz, 1H), 1.15 (t, J=7.2 Hz, 6H), 1.04 (dd, J=6.8, 5.6 Hz, 6H).

Example 39. Synthesis of ((2R,3S,4R,5R)-5-(4-aminopyrrolo[2,1-f][1,2,4]triazin-7-yl)-5-cyano-4-hydroxy-3-(propionyloxy)tetrahydrofuran-2-yl)methyl isobutyrate (Compound 63)

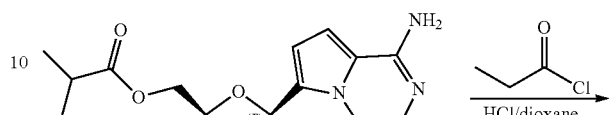

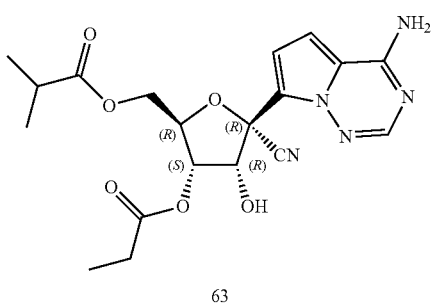

63

The title compound was prepared according to the procedure of Example 17, using 15 and propionyl chloride. MS (ESI): m/z calcd. for $C_{19}H_{23}N_5O_6$ 417.16, found 418.05 $[M+H]^+$. $^1$H NMR (400 MHz, DMSO) δ 7.93 (s, 3H), 6.93 (d, J=4.4 Hz, 1H), 6.85 (d, J=4.8 Hz, 1H), 6.59 (d, J=6.0 Hz, 1H), 5.16-5.11 (m, 1H), 5.09-5.04 (m, 1H), 4.47 (q, J=4.4 Hz, 1H), 4.26 (qd, J=12.0, 3.6 Hz, 2H), 2.54 (q, J=6.8 Hz, 1H), 2.40 (q, J=7.6 Hz, 2H), 1.10-1.02 (m, 9H).

Example 40. Synthesis of (((2R,3S,4R,5R)-5-(4-aminopyrrolo[2,1-f][1,2,4]triazin-7-yl)-5-cyano-4-hydroxy-2-((isobutyryloxy)methyl)tetrahydrofuran-3-yl)oxy)methyl pivalate (Compound 64)

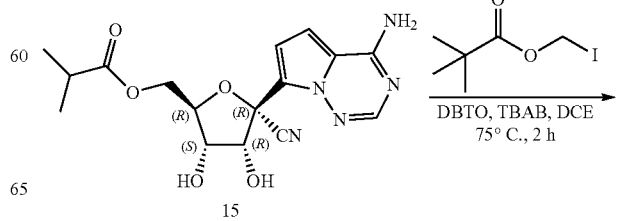

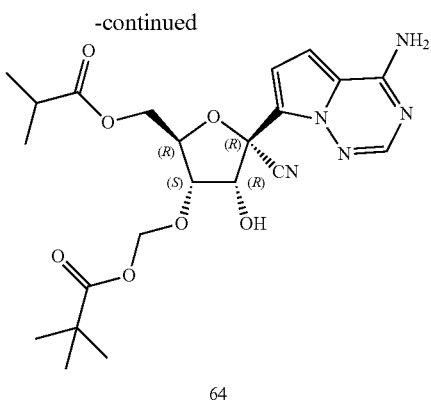

64

The title compound was prepared according to the procedure of Example 24, using 15 and iodomethyl pivalate. MS (ESI): m/z calcd. for $C_{22}H_{29}N_5O_6$ 475.21, found 476.30 [M+H]$^+$. $^1$H NMR (400 MHz, DMSO) δ 7.92 (s, 3H), 6.92 (d, J=4.4 Hz, 1H), 6.83 (d, J=4.4 Hz, 1H), 6.50 (d, J=6.4 Hz, 1H), 5.40-5.25 (m, 2H), 4.98 (dd, J=6.0, 5.2 Hz, 1H), 4.41-4.23 (m, 2H), 4.23-4.07 (m, 2H), 2.47 (q, J=7.2 Hz, 1H), 1.11 (s, 9H), 1.05 (q, J=3.6 Hz, 6H).

Example 41. Synthesis (2R,3S,4R,5R)-5-{4-aminopyrrolo[2,1-f][1,2,4]triazin-7-yl}-5-cyano-4-hydroxy-2-[(propanoyloxy)methyl]oxolan-3-yl 3-methylbutanoate (Compound 65)

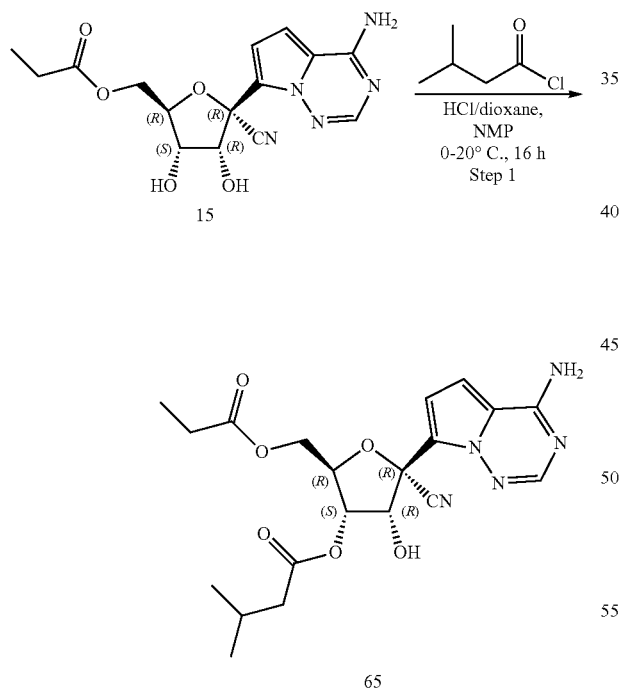

Step 1. Synthesis (2R,3S,4R,5R)-5-{4-aminopyrrolo[2,1-f][1,2,4]triazin-7-yl}-5-cyano-4-hydroxy-2-[(propanoyloxy)methyl]oxolan-3-yl 3-methylbutanoate (65)

To a solution of [(2R,3S,4R,5R)-5-{4-aminopyrrolo[2,1-f][1,2,4]triazin-7-yl}-5-cyano-3,4-dihydroxyoxolan-2-yl] methyl propanoate (15, 80 mg, 0.230 mmol) in NMP (3 mL) was added HCl in dioxane (4 M, 0.1 mL), The reaction was stirred at 25° C. for 15 minutes. Then 3-methylbutanoyl chloride (138.18 mg, 1.151 mmol) was added to the above solution at 0° C., the resulting mixture was stirred at 25° C. for 16 h. The reaction was quenched with water (1 mL) and purified by prep-HPLC to afford the title compound (38.0 mg, 37% yield) as a white solid. MS (ESI): m/z calcd. for $C_{20}H_{25}N_5O_6$ 431.18, found 432.1 [M+H]$^+$. $^1$H NMR (400 MHz, DMSO) δ 7.93 (br, s, 3H), 6.93 (d, J=4.4 Hz, 1H), 6.85 (d, J=4.8 Hz, 1H), 6.60 (d, J=6.4 Hz, 1H), 5.11-5.06 (m, 2H), 4.45 (dd, J=8.4, 4.8 Hz, 1H), 4.32 (dd, J=12.0, 3.6 Hz, 1H), 4.21 (dd, J=12.0, 5.2 Hz, 1H), 2.41-2.19 (m, 4H), 2.07-2.04 (m, 1H), 0.99 (t, J=7.6 Hz, 3H), 0.94 (dd, J=6.8, 0.8 Hz, 6H).

Example 42. Synthesis of [(2R,3S,4R,5R)-5-{4-aminopyrrolo[2,1-f][1,2,4]triazin-7-yl}-5-cyano-3-[(2-cyclohexylacetyl)oxy]-4-hydroxyoxolan-2-yl] methyl propanoate (Compound 66)

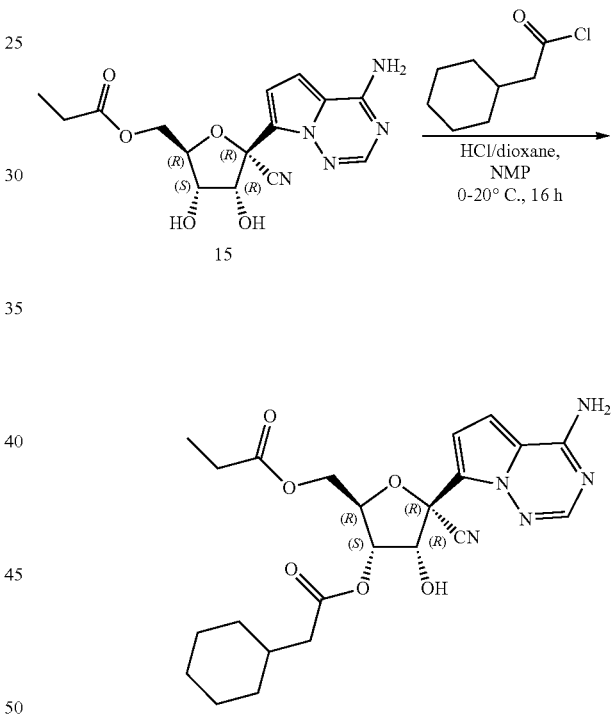

The title compound 66 was prepared according to the procedure of Example 65, Step 1, using 15 and 2-cyclohexylacetyl chloride. MS (ESI): mass calcd. for $C_{23}H_{29}N_5O_6$, 471.21, m/z found 472.2 [M+H]$^+$. $^1$H NMR (400 MHz, DMSO) δ 7.93-7.91 (br, s, 3H), 6.93 (d, J=4.4 Hz, 1H), 6.85 (d, J=4.8 Hz, 1H), 6.59 (d, J=6.0 Hz, 1H), 5.12-5.06 (m, 2H), 4.44-4.43 (m, 1H), 4.31 (dd, J=12.0, 4.0 Hz, 1H), 4.20 (dd, J=12.0, 5.2 Hz, 1H), 2.31-2.24 (m, 4H), 1.79-1.60 (m, 6H), 1.21-0.93 (m, 8H).

Example 43. Synthesis of (2R,3S,4R,5R)-5-{4-aminopyrrolo[2,1-f][1,2,4]triazin-7-yl}-5-cyano-4-hydroxy-2-[(propanoyloxy)methyl]oxolan-3-yl(2S)-2-amino-3-methylbutanoate (Compound 67)

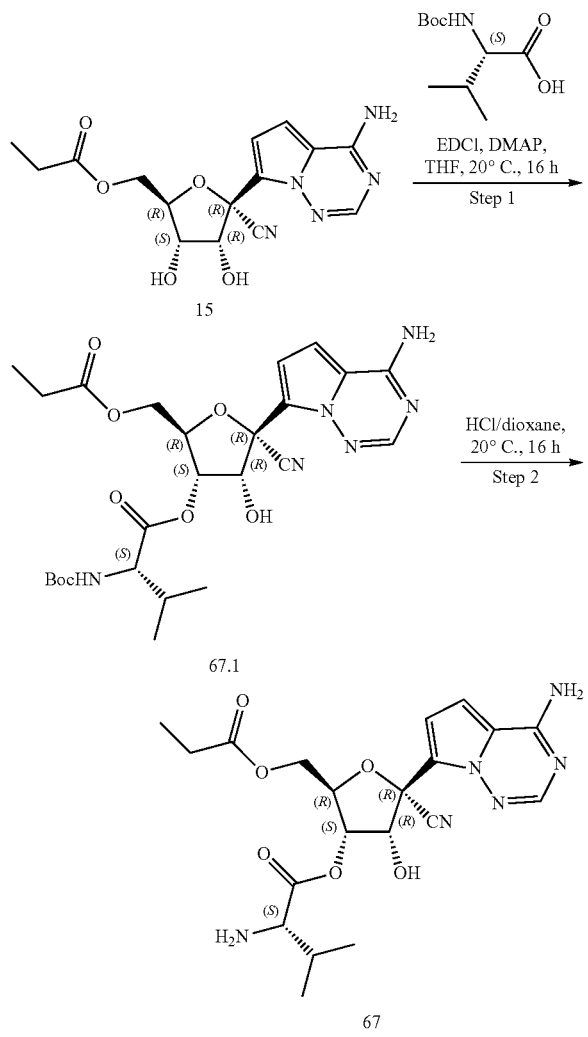

Step 1: Synthesis of (2R,3S,4R,5R)-5-{4-aminopyrrolo[2,1-f][1,2,4]triazin-7-yl}-5-cyano-4-hydroxy-2-[(propanoyloxy)methyl]oxolan-3-yl (2S)-2-{[(tert-butoxy)carbonyl]amino}-3-methylbutanoate (67.1)

The compound 67.1 was prepared according to the procedure of Example 19, Step 1, using 15 and (2S)-2-{[(tert-butoxy) carbonyl]amino}-3-methylbutanoic acid. MS (ESI): mass calcd. for $C_{25}H_{34}N_6O_8$, 546.24 m/z found 547.3 $[M+H]^+$.

Step 2: Synthesis of (2R,3S,4R,5R)-5-{4-aminopyrrolo[2,1-f][1,2,4]triazin-7-yl}-5-cyano-4-hydroxy-2-[(propanoyloxy)methyl]oxolan-3-yl (2S)-2-amino-3-methylbutanoate (67)

The title compound 67 was prepared according to the procedure of Example 19, Step 2, using 67.1. MS (ESI): mass calcd. for $C_{20}H_{26}N_6O_6$, 446.19, m/z found 447.3 $[M+H]^+$. $^1$H NMR (400 MHz, DMSO) δ 7.93 (br, s, 3H), 6.93 (d, J=4.8 Hz, 1H), 6.87 (d, J=4.8 Hz, 1H), 6.61-6.52 (m, 1H), 5.13-5.10 (m, 2H), 4.44-4.40 (m, 1H), 4.32 (dd, J=12.4, 4.0 Hz, 1H), 4.21 (dd, J=12.0, 5.2 Hz, 1H), 3.25 (d, J=5.2 Hz, 1H), 2.30-2.22 (m, 2H), 2.01-1.95 (m, 1H), 0.99 (t, J=7.6 Hz, 3H), 0.92 (d, J=6.8 Hz, 3H), 0.86 (d, J=6.8 Hz, 3H).

Example 44. Synthesis of [(2R,3S,4R,5R)-3-(acetyloxy)-5-{4-aminopyrrolo[2,1-f][1,2,4]triazin-7-yl}-5-cyano-4-hydroxyoxolan-2-yl]methyl propanoate (Compound 69)

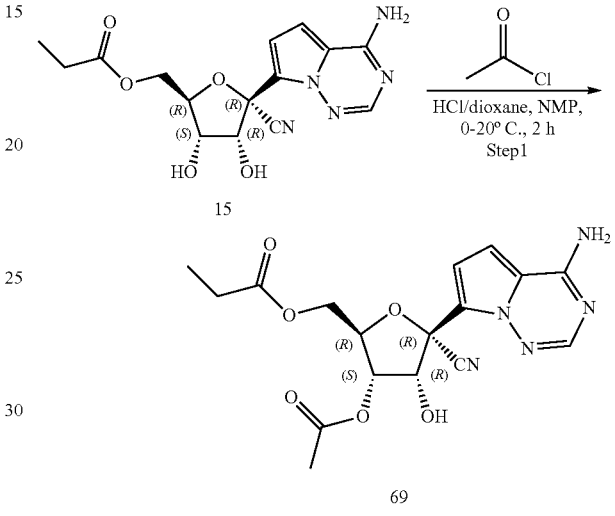

Step 1. Synthesis of [(2R,3S,4R,5R)-3-(acetyloxy)-5-{4-aminopyrrolo[2,1-f][1,2,4]triazin-7-yl}-5-cyano-4-hydroxyoxolan-2-yl]methyl propanoate (69)

The title compound 69 was prepared according to the procedure of Example 65, Step 1, using 15 and AcCl. MS (ESI): m/z calcd. for $C_{17}H_{19}N_5O_6$ 389.13, found 390.1 $[M+H]^+$. $^1$H NMR (400 MHz, DMSO) δ 7.93-7.90 (br, s, 3H), 6.93 (d, J=4.4 Hz, 1H), 6.85 (d, J=4.8 Hz, 1H), 6.61 (d, J=6.0 Hz, 1H), 5.07-5.05 (m, 2H), 4.46-4.45 (m, 1H), 4.33 (dd, J=12.4, 3.6 Hz, 1H), 4.20 (dd, J=12.4, 5.2 Hz, 1H), 2.30-2.28 (m, 2H), 2.09 (s, 3H), 0.99 (t, J=7.6 Hz, 3H).

Example 45. Synthesis of [(2R,3S,4R,5R)-5-{4-aminopyrrolo[2,1-f][1,2,4]triazin-7-yl}-5-cyano-4-hydroxy-3-[(2-methylpropanoyl)oxy]oxolan-2-yl]methyl propanoate (Compound 70)

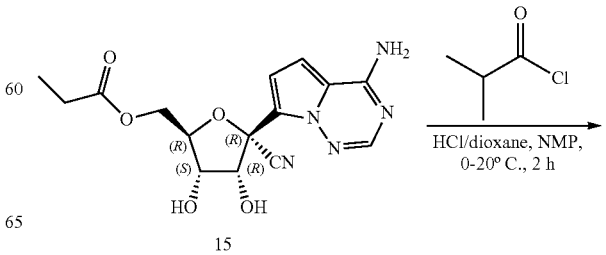

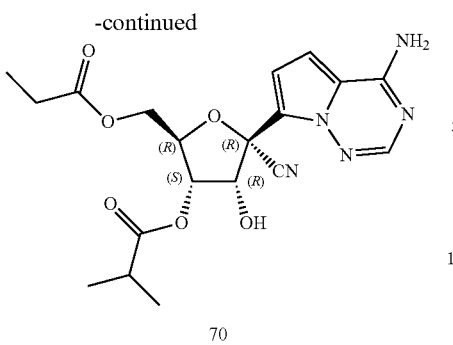

70

The title compound 70 was prepared according to the procedure of Example 65, Step 1, using 15 and isobutyryl chloride. MS (ESI): mass calcd. for C₁₉H₂₃N₅O₆, 417.16, m/z found 418.1 [M+H]⁺. ¹H NMR (400 MHz, DMSO) δ 7.92 (br, s, 3H), 6.93 (d, J=4.4 Hz, 1H), 6.86 (d, J=4.8 Hz, 1H), 6.55 (d, J=6.0 Hz, 1H), 5.20-5.06 (m, 2H), 4.45 (dd, J=8.8, 4.0 Hz, 1H), 4.31 (dd, J=12.0, 4.0 Hz, 1H), 4.21 (dd, J=12.0, 5.2 Hz, 1H), 2.70-2.56 (m, 1H), 2.29 (d, J=5.2 Hz, 2H), 1.15 (dd, J=6.8, 6.4 Hz, 6H), 0.99 (t, J=7.6 Hz, 3H).

Example 46. Synthesis of [(2R,3S,4R,5R)-3-(acetyloxy)-5-{4-aminopyrrolo[2,1-f][1,2,4]triazin-7-yl}-5-cyano-4-hydroxyoxolan-2-yl]methyl propanoate (Compound 71)

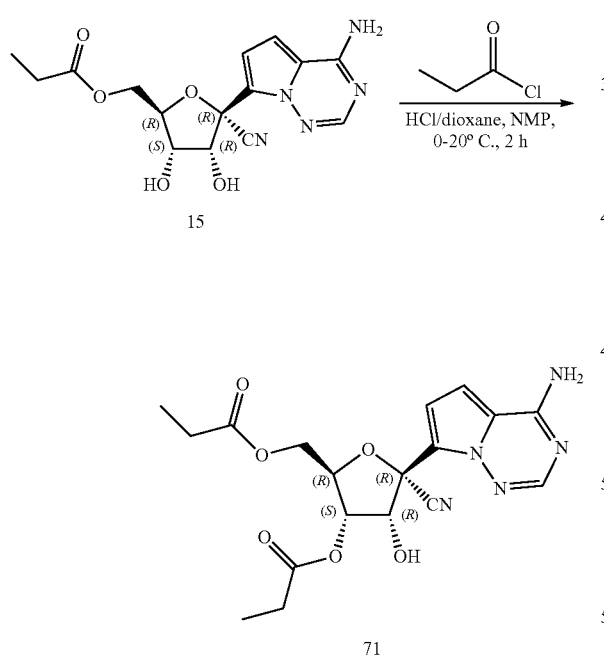

The title compound 71 was prepared according to the procedure of Example 65, Step 1, using 15 and propionyl chloride. MS (ESI): mass calcd. for C₁₈H₂₁N₅O₆, 403.15, m/z found 404.0 [M+H]⁺. ¹H NMR (400 MHz, DMSO) δ 7.93 (br, s, 3H), 6.93 (d, J=4.4 Hz, 1H), 6.85 (d, J=4.4 Hz, 1H), 6.59 (d, J=6.0 Hz, 1H), 5.10-5.05 (m, 2H), 4.46 (dd, J=8.4, 4.8 Hz, 1H), 4.33 (dd, J=12.0, 3.6 Hz, 1H), 4.20 (dd, J=12.0, 5.2 Hz, 1H), 2.40-2.38 (m, 2H), 2.35-2.24 (m, 2H), 1.08 (t, J=7.6 Hz, 3H), 0.99 (t, J=7.6 Hz, 3H).

Example 47. Synthesis of {[(2R,3S,4R,5R)-5-{4-aminopyrrolo[2,1-f][1,2,4]triazin-7-yl}-5-cyano-4-hydroxy-2-[(propanoyloxy)methyl]oxolan-3-yl]oxy}methyl 2,2-dimethylpropanoate (Compound 72)

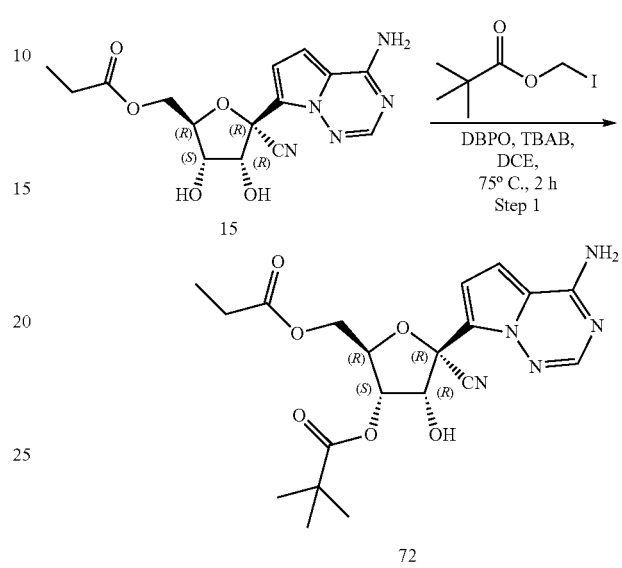

Step 1: Synthesis of {[(2R,3S,4R,5R)-5-{4-aminopyrrolo[2,1-f][1,2,4]triazin-7-yl}-5-cyano-4-hydroxy-2-[(propanoyloxy)methyl]oxolan-3-yl]oxy}methyl 2,2-dimethylpropanoate (72)

The compound 72 was prepared according to the procedure of Example 48, Step 1, using 15 and iodomethyl pivalate. MS (ESI): mass calcd. for C₂₁H₂₇N₅O₇, 461.19, m/z found 462.1 [M+H]⁺. ¹H NMR (400 MHz, DMSO) δ 7.92 (br, s, 3H), 6.92 (d, J=4.4 Hz, 1H), 6.83 (d, J=4.8 Hz, 1H), 6.49 (d, J=6.4 Hz, 1H), 5.35 (d, J=6.4 Hz, 1H), 5.28 (d, J=6.4 Hz, 1H), 4.97-4.96 (m, 1H), 4.39-4.28 (m, 2H), 4.19-4.08 (m, 2H), 2.28-2.26 (m, 2H), 1.11 (s, 9H), 1.00 (t, J=7.6 Hz, 3H).

Example 48. Synthesis of pentyl (7-((2R,3R,4S,5R)-2-cyano-3,4-dihydroxy-5-(hydroxymethyl)tetrahydrofuran-2-yl)pyrrolo[2,1-f][1,2,4]triazin-4-yl)carbamate (Compound 81)

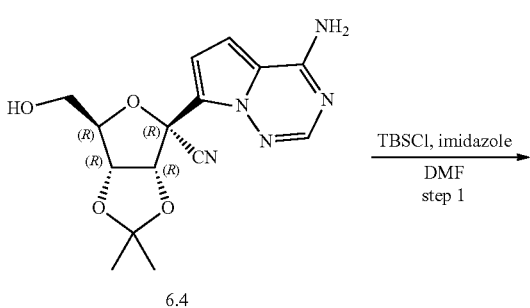

6.4

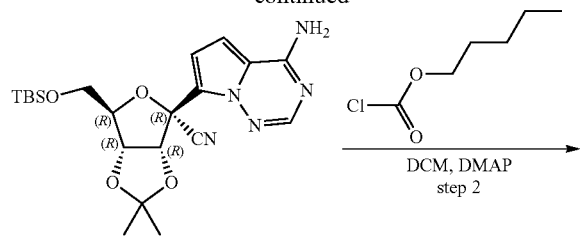

81.1

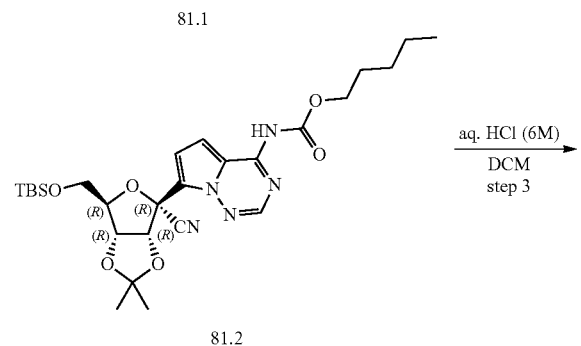

81.2

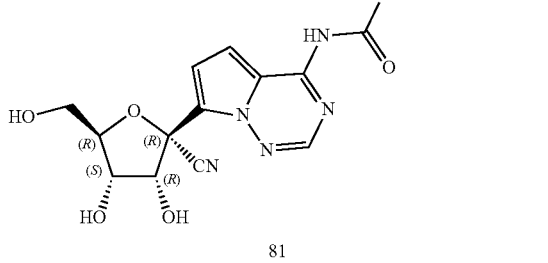

81

Step 1. Synthesis of (3aR,4R,6R,6aR)-4-(4-aminopyrrolo[2,1-f][1,2,4]triazin-7-yl)-6-(((tert-butyldimethylsilyl)oxy)methyl)-2,2-dimethyltetrahydrofuro[3,4-d][1,3]dioxole-4-carbonitrile (81.1)

To a mixture of 6.4 (4.00 g, 12.1 mmol) and imidazole (2.06 g, 30.2 mmol) in DMF (20 mL) was added TBSCl (2.19 g, 14.5 mmol) slowly at 0° C. The mixture was then stirred at 20° C., for 16 hours. TLC showed that the starting material was consumed completely. After completion, the mixture was quenched with water (300 mL) and extracted with Ethyl acetate (200 mL×3). The organic layer was then dried over sodium sulphate and concentrated in vacuo to afford a residue. The residue was purified by flash column chromatography (SiO$_2$, Ethyl acetate/Petroleum ether=0-30%) to obtain 81.1 as a colorless oil (4.8 g, 88.4% yield) which was confirmed by $^1$H NMR and LCMS. MS (ESI): mass calcd. for C$_{21}$H$_{31}$N$_5$O$_4$Si, 445.21, m/z found 446.25 [M+H]$^+$. $^1$H NMR (400 MHz, DMSO-d$_6$) δ 7.94 (s, 3H), 6.90 (d, J=4.4 Hz, 1H), 6.84 (d, J=4.4 Hz, 1H), 5.33 (d, J=6.4 Hz, 1H), 4.85 (dd, J=6.4, 2.8 Hz, 1H), 4.37 (dd, J=7.6, 4.8 Hz, 1H), 4.03 (q, J=7.2 Hz, 1H), 3.70 (dd, J=4.8, 1.2 Hz, 2H), 1.63 (s, 3H), 1.37 (s, 3H), 0.76 (s, 9H), −0.03 (s, 3H), −0.08 (s, 3H).

Step 2. Synthesis of pentyl (7-((3aR,4R,6R,6aR)-6-(((tert-butyldimethylsilyl)oxy)methyl)-4-cyano-2,2-dimethyltetrahydrofuro[3,4-d][1,3]dioxol-4-yl)pyrrolo[2,1-f][1,2,4]triazin-4-yl)carbamate (81.2)

A mixture 81.1 (200 mg, 0.45 mmol), DMAP (274.15 mg, 2.24 mmol) and DIEA (0.37 mL, 2.24 mmol) in DCM (2 mL) was added pentyl chloroformate (0.19 mL, 1.35 mmol) at 0° C. under N$_2$, then the reaction was stirred at 20° C. for 16 hours. The reaction mixture was poured into 50 mL of water and the organic layer was separated. The aqueous was extracted with DCM (50 mL) twice. The organic phase was washed with brine water (50 mL×3), then dried over anhydrous sodium sulfate, filtered and concentrated to remove the solvent. The residue was purified by flash column chromatography (Petroleum ether/ethyl acetate from 0% to 8%) to obtain 81.2 as a white solid (125 mg, 44.8% yield) MS (ESI): m/z calcd. for C$_{27}$H$_{41}$N$_5$O$_6$Si, 559.28, found 560.2[M+H]$^+$. $^1$H NMR (400 MHz, DMSO-d$_6$) δ 10.90 (s, 1H), 8.40 (s, 1H), 7.30 (d, J=4.8 Hz, 1H), 7.06 (d, J=4.8 Hz, 1H), 5.30 (d, J=6.2 Hz, 1H), 4.86 (dd, J=6.2, 2.4 Hz, 1H), 4.44 (d, J=2.4 Hz, 1H), 4.18 (t, J=6.8 Hz, 2H), 3.70 (d, J=4.4 Hz, 2H), 1.70-1.63 (m, 5H), 1.39-1.32 (m, 7H), 0.89 (t J=7.2 Hz, 3H), 0.73 (s, 9H), −0.08 (d, J=17.6 Hz, 6H).

Step 3. Synthesis of pentyl (7-((2R,3R,4S,5R)-2-cyano-3,4-dihydroxy-5-(hydroxymethyl)tetrahydrofuran-2-yl)pyrrolo[2,1-f][1,2,4]triazin-4-yl)carbamate To solution of 81.2 (65.0 mg, 0.12 mmol) in THF (1 mL) was added HCl (1 mL, 6M) at 0° C., then the reaction was stirred at 20° C. for 1 hour. The reaction was diluted with ACN (1.0 mL) and purified by prep-HPLC to obtain 81 (22.8 mg, 48.5% yield) as a white solid. MS (ESI): m/z calcd. for C$_{18}$H$_{23}$N$_5$O$_6$, 405.16, found 406.0 [M+H]$^+$. $^1$H NMR (400 MHz, DMSO-d$_6$) δ 10.97 (s, 1H), 8.32 (s, 1H), 7.25 (d, J=4.4 Hz, 1H), 7.08 (d, J=4.8 Hz, 1H), 6.21 (d, J=6.4 Hz, 1H), 5.24 (d, J=5.6 Hz, 1H), 4.91 (t, J=5.6 Hz, 1H), 4.70-4.55 (m, 1H), 4.16 (t, J=6.8 Hz, 2H), 4.07 (dd, J=9.2, 4.4 Hz, 1H), 3.95 (dd, J=10.8, 5.2 Hz, 1H), 3.69-3.60 (m, 1H), 3.56-3.47 (m, 1H), 1.67 (p, J=7.2 Hz, 2H), 1.41-1.30 (m, 4H), 0.90 (t, J=7.2 Hz, 3H).

Example 49. Synthesis of (2S)-2-amino-N-{7-[(2R,3R,4S,5R)-2-cyano-3,4-dihydroxy-5-(hydroxymethyl)oxolan-2-yl]pyrrolo[2,1-f][1,2,4]triazin-4-yl}-3-methylbutanamide (Compound 83)

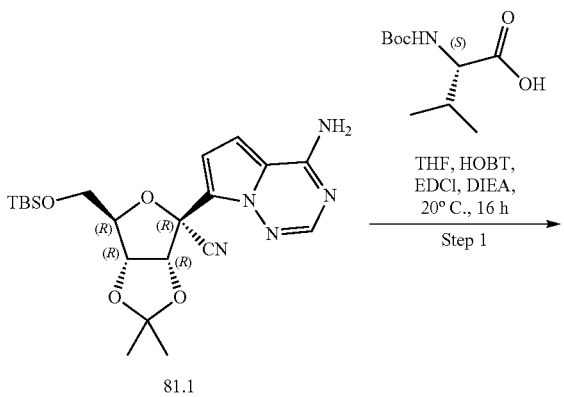

81.1

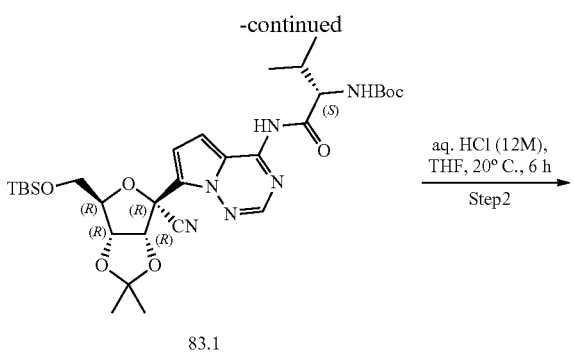

83.1 aq. HCl (12M),
THF, 20° C., 6 h
→
Step 2 added HCl (12M, 1 mL) at 0° C., the mixture was stirred at 25° C. for 6 h. The reaction was concentrated in vacuo and purified by prep-HPLC to afford the salt-forming compound. The compound was basified by NaHCO₃ (sat. aqueous, 1 mL) and purified by prep-HPLC to obtain 83 as a white solid (9.85 mg, 12% yield). MS (ESI): mass calcd. for C₁₇H₂₂N₆O₅, 390.17, m/z found 391.2 [M+H]⁺. ¹H NMR (400 MHz, DMSO) δ 8.21 (d, J=8.4 Hz, 1H), 7.97 (s, 1H), 7.56 (s, 1H), 7.23 (d, J=4.4 Hz, 1H), 7.13 (s, 1H), 6.89 (d, J=4.8 Hz, 1H), 6.12 (d, J=6.0 Hz, 1H), 5.20 (d, J=5.2 Hz, 1H), 4.90 (t, J=5.6 Hz, 1H), 4.64-4.60 (m, 2H), 4.05-4.01 (m, 1H), 3.94-3.90 (m, 1H), 3.74-3.59 (m, 1H), 3.57-3.47 (m, 1H), 2.18-2.05 (m, 1H), 0.96-0.85 (m, 6H).

Example 50. Synthesis of (S)-2-amino-N-(7-((2R, 3R,4S,5R)-2-cyano-3,4-dihydroxy-5-(hydroxymethyl)tetrahydrofuran-2-yl)pyrrolo[2,1-f][1,2,4]triazin-4-yl)-3-(4-fluorophenyl)propenamide (Compound 84)

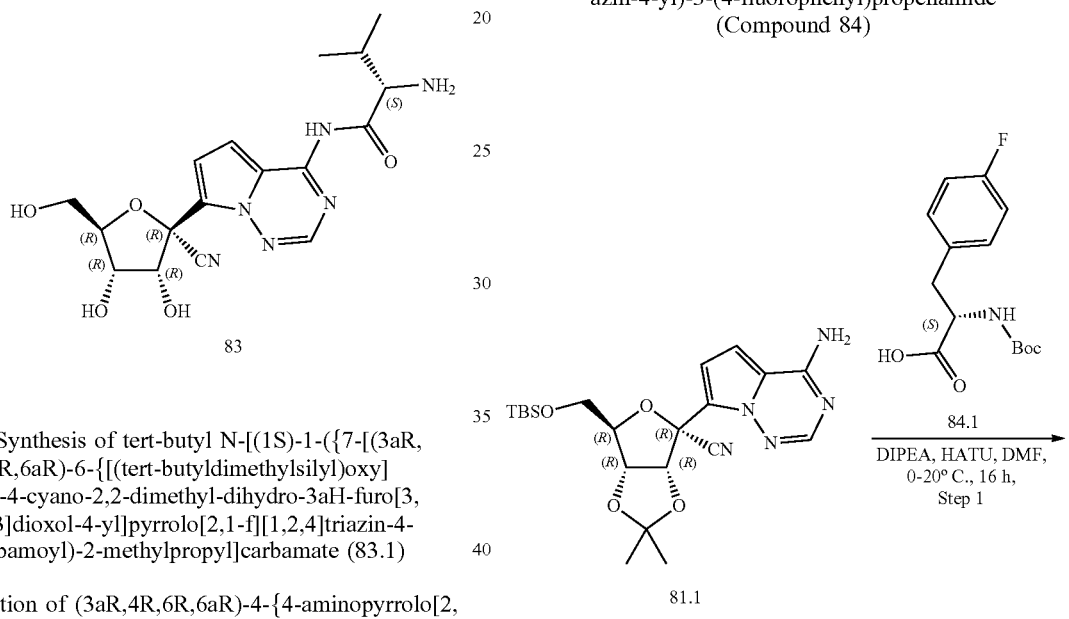

83

Step 1. Synthesis of tert-butyl N-[(1S)-1-({7-[(3aR, 4R,6R,6aR)-6-{[(tert-butyldimethylsilyl)oxy] methyl}-4-cyano-2,2-dimethyl-dihydro-3aH-furo[3, 4-d][1,3]dioxol-4-yl]pyrrolo[2,1-f][1,2,4]triazin-4-yl}carbamoyl)-2-methylpropyl]carbamate (83.1)

To a solution of (3aR,4R,6R,6aR)-4-{4-aminopyrrolo[2, 1-f][1,2,4]triazin-7-yl}-6-{[(tert-butyldimethylsilyl)oxy] methyl}-2,2-dimethyl-dihydro-3aH-furo[3,4-d][1,3]dioxole-4-carbonitrile (81.1, 200 mg, 0.4488 mmol) in THF (10 mL) was added (2S)-2-{[(tert-butoxy)carbonyl]amino}-3-methylbutanoic acid (146.08 mg, 0.6732 mmol), HOBT (90.96 mg, 0.6732 mmol), EDCI (129.05 mg, 0.6732 mmol) and DIEA (174.01 mg, 1.3464 mmol), the mixture was stirred at 25° C. for 16 h. The reaction was extracted with EA (5 mL×3). The combined organics were dried over sodium sulfate and concentrated in vacuo. The residue was purified by flash column chromatography (EA/PE from 2% to 20%) to obtain 83.1 as a white solid (190 mg, 59% yield). MS (ESI): mass calcd. for C₃₁H₄₈N₆O₇Si, 644.34, m/z found 645.3 [M+H]⁺.

Step 2. Synthesis of (2S)-2-amino-N-{7-[(2R,3R, 4S,5R)-2-cyano-3,4-dihydroxy-5-(hydroxymethyl) oxolan-2-yl]pyrrolo[2,1-f][1,2,4]triazin-4-yl}-3-methylbutanamide (83)

To a solution of tert-butyl N-[(1S)-1-({7-[(3aR,4R,6R, 6aR)-6-{[(tert-butyldimethylsilyl)oxy]methyl}-4-cyano-2, 2-dimethyl-dihydro-3aH-furo[3,4-d][1,3]dioxol-4-yl]pyrrolo[2,1-f][1,2,4]triazin-4-yl}carbamoyl)-2-methylpropyl] carbamate (83.1, 100 mg, 0.155 mmol) in THF (3 mL) was

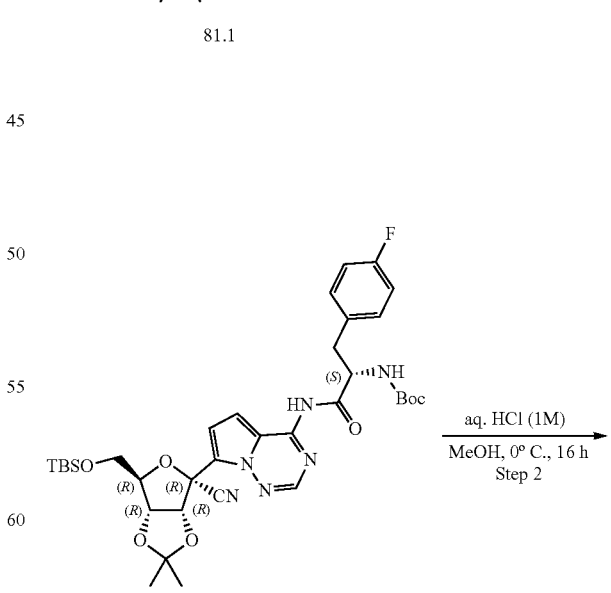

81.1

84.1
DIPEA, HATU, DMF,
0-20° C., 16 h,
Step 1
→

84.2 aq. HCl (1M)
MeOH, 0° C., 16 h
→
Step 2

-continued

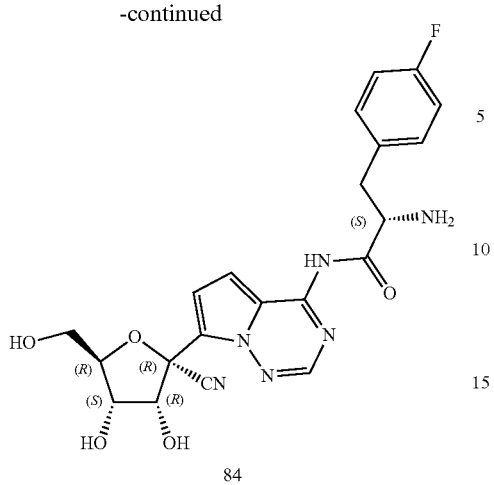

84

Step 1. Synthesis of tert-butyl((S)-1-((7-((3aR,4R, 6R,6aR)-6-(((tert-butyldimethylsilyl)oxy)methyl)-4-cyano-2,2-dimethyltetrahydrofuro[3,4-d][1,3]dioxol-4-yl)pyrrolo[2,1-f][1,2,4]triazin-4-yl)amino)-3-(4-fluorophenyl)-1-oxopropan-2-yl)carbamate (84.2)

To a solution of 81.1 (2.00 g, 4.5 mmol), 84.1 (1.28 g, 4.5 mmol) and DIPEA (0.87 g, 6.7 mmol) in dry DMF (20 mL) was added HATU (2.57 g, 6.7 mmol) at 0° C. The reaction mixture was stirred at 20° C. for 16 h. The reaction mixture was poured into ice water (40 mL) and extracted with EA (20 mL×2). The combined organic phase was washed with water (15 mL), followed by brine (15 mL×3), dried over anhydrous Na$_2$SO$_4$, filtered. The filtrate was concentrated to dryness. The residue was purified by FCC (Gradient: 5% EA in PE) to give 84.2 (2.47 g, 78% yield) as a white solid. MS (ESI): m/z calcd. for C$_{35}$H$_{47}$FN$_6$O$_7$Si 710.33, found 711.2 [M+H]$^+$. $^1$H NMR (400 MHz, DMSO) δ 11.17 (s, 1H), 8.51 (s, 1H), 7.42 (dd, J=8.0, 5.6 Hz, 2H), 7.33-7.20 (m, 2H), 7.15-7.07 (m, 3H), 5.31 (d, J=6.0 Hz, 1H), 4.87 (dd, J=6.0, 2.4 Hz, 1H), 4.49-4.44 (m, 1H), 3.71 (d, J=4.4 Hz, 1H), 3.12-3.00 (m, 1H), 2.86-2.75 (m, 1H), 1.66 (s, 3H), 1.38 (s, 3H), 1.32 (s, 9H), 0.73 (s, 9H), −0.07 (d, J=18.0 Hz, 6H).

Step 2. Synthesis of (S)-2-amino-N-(7-((2R,3R,4S, 5R)-2-cyano-3,4-dihydroxy-5-(hydroxymethyl)tetra-hydrofuran-2-yl)pyrrolo[2,1-f][1,2,4]triazin-4-yl)-3-(4-fluorophenyl)propanamide (84)

To a solution of 84.2 (50 mg, 0.07 mmol) in dry THF (0.5 mL) was added Conc. HCl (0.25 mL, 12 M) dropwise at 0° C. under nitrogen. The reaction mixture was stirred at 0° C. for 2 h. The reaction mixture was basified with aq. NaHCO$_3$ at 0° C. and adjust pH to 8. LC-MS showed peak shifting and the new peak has a same MS, which may be different salt form with different pH value. The organic solvent was removed with flowing nitrogen. The residue was diluted with ACN and purified by prep-HPLC to afford the title compound 84 (4.52 mg, 14% yield) as a white solid. MS (ESI): m/z calcd. for C$_{21}$H$_{21}$FN$_6$O$_5$ 456.16, found 457.1 [M+H]$^+$. $^1$H NMR (400 MHz, DMSO) δ 8.56 (d, J=8.4 Hz, 1H), 7.90 (s, 1H), 7.68 (s, 1H), 7.42-7.34 (m, 2H), 7.17 (s, 1H), 7.09-7.02 (m, 3H), 6.86 (d, J=4.4 Hz, 1H), 6.11 (d, J=6.0 Hz, 1H), 5.22 (d, J=4.0 Hz, 1H), 4.98-4.85 (m, 2H), 4.60 (t, J=5.6 Hz, 1H), 4.04 (dd, J=9.2, 4.4 Hz, 1H), 3.93 (dd, J=10.4, 5.2 Hz, 1H), 3.66-3.59 (m, 1H), 3.53-3.45 (m, 1H), 3.18 (dd, J=14.0, 4.0 Hz, 1H), 3.02 (dd, J=13.6, 11.2 Hz, 1H). $^{19}$F NMR (377 MHz, DMSO) δ −116.76.

Example 51. Synthesis of N-(7-((2R,3R,4S,5R)-2-cyano-3,4-dihydroxy-5-(hydroxymethyl)tetrahydro-furan-2-yl)pyrrolo[2,1-f][1,2,4]triazin-4-yl)benz-amide (Compound 85)

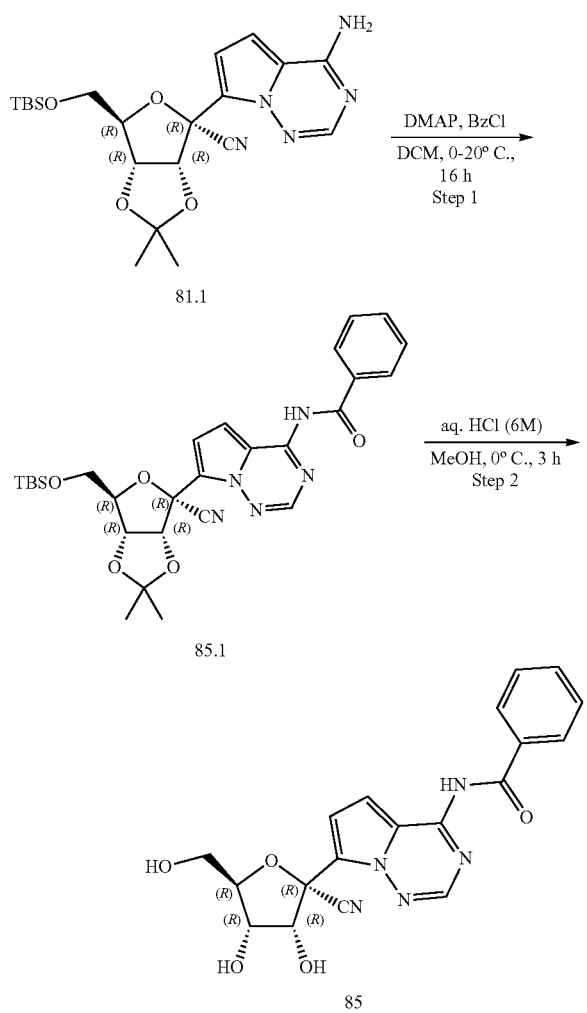

Step 1. Synthesis of N-(7-((3aR,4R,6R,6aR)-6-(((tert-butyldimethylsilyl)oxy)methyl)-4-cyano-2,2-dimethyltetrahydrofuro[3,4-d][1,3]dioxol-4-yl)pyr-rolo[2,1-f][1,2,4]triazin-4-yl)benzamide (85.1)

To a solution of 81.1 (2.00 g, 4.50 mmol) and DMAP (820 mg, 6.75 mmol) in dry DCM (20 mL) was added benzoyl chloride (950 mg, 6.75 mmol) dropwise at 0° C. The reaction mixture was stirred at 20° C. for 16 h. The mixture was washed with water (10 mL×2), followed by brine (10 mL), dried over anhydrous Na$_2$SO$_4$, filtered. The filtrate was concentrated to dryness. The residue was purified by FCC (Gradient: 5% EA in PE) to give 85.1 (1.99 g, 80% yield) as a white solid. MS (ESI): m/z calcd. for C$_{28}$H$_{35}$N$_5$O$_5$Si 549.24, found 550.4 [M+H]$^+$. $^1$H NMR (400 MHz, DMSO) δ 11.38 (s, 1H), 8.65-7.84 (m, 3H), 7.66 (t, J=6.8 Hz, 1H), 7.55 (t, J=7.6 Hz, 2H), 7.22-6.94 (m, 2H), 5.34 (d, J=6.4 Hz, 1H), 4.88 (dd, J=6.0, 2.8 Hz, 1H), 4.46 (d, J=2.0 Hz, 1H), 3.72 (d, J=4.8 Hz, 2H), 1.66 (s, 3H), 1.38 (s, 3H), 0.75 (s, 9H), −0.03 (s, 3H), −0.07 (s, 3H).

Step 2. Synthesis of N-(7-((2R,3R,4S,5R)-2-cyano-3,4-dihydroxy-5-(hydroxymethyl)tetrahydrofuran-2-yl)pyrrolo[2,1-f][1,2,4]triazin-4-yl)benzamide (85)

To a solution of 85.1 (0.10 g, 0.18 mmol) in MeOH (1.0 mL) was added aq. HCl (1.0 mL, 6 M) dropwise at 0° C. The reaction mixture was stirred at 0° C. for 3 h. The organic solvent was removed with flowing nitrogen. The residue was purified by prep-HPLC to afford the title compound 85 (23.55 mg, 33% yield) as a white solid. MS (ESI): m/z calcd. for $C_{19}H_{17}N_5O_5$ 395.12, found 396.0 [M+H]$^+$. $^1$H NMR (400 MHz, DMSO) δ 11.36 (s, 1H), 8.65-7.85 (m, 3H), 7.70-7.61 (m, 1H), 7.59-7.52 (m, 2H), 7.27-7.04 (m, 2H), 6.24 (d, J=6.4 Hz, 1H), 5.26 (d, J=5.6 Hz, 1H), 4.92 (t, J=5.6 Hz, 1H), 4.63 (t, J=5.6 Hz, 1H), 4.12-4.06 (m, 1H), 3.97 (dd, J=10.4, 5.2 Hz, 1H), 3.69-3.62 (m, 1H), 3.56-3.48 (m, 1H).

Example 52. Synthesis of ((2R,3S,4R,5R)-5-cyano-3,4-dihydroxy-5-(4-(((pentyloxy)carbonyl)amino)pyrrolo[2,1-f][1,2,4]triazin-7-yl)tetrahydrofuran-2-yl)methyl acetate (Compound 87)

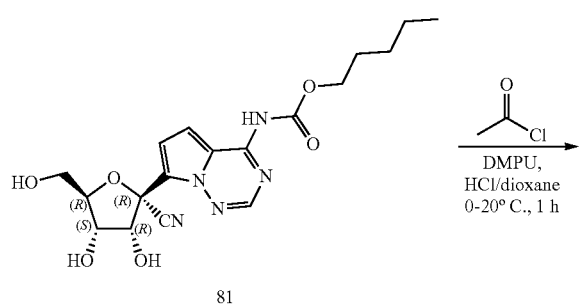

To a solution of pentyl 81 (80 mg, 0.19 mmol) in DMPU (1 mL) was added 4 M dioxane HCl (0.2 mL) dropwise at 0° C. The mixture was then stirred for 30 min and added acetyl chloride (0.2 mL) dropwise and stirred for another 30 min. After completion, the mixture was purified by prep-HPLC to afford 87 (30 mg, 33.6% yield) as a white solid. MS (ESI): m/z calcd. for $C_{20}H_{25}N_5O_7$, 447.18, found 448.25 [M+H]$^+$. $^1$H NMR (400 MHz, DMSO) δ 10.98 (s, 1H), 8.34 (s, 1H), 7.29 (d, J=4.4 Hz, 1H), 7.02 (d, J=4.8 Hz, 1H), 6.40 (d, J=6.0 Hz, 1H), 5.44 (d, J=6.0 Hz, 1H), 4.68 (t J=5.6 Hz, 1H), 4.32 (dd, J=12.0, 2.8 Hz, 1H), 4.28-4.23 (m, 1H), 4.20-4.11 (m, 3H), 3.93 (q, J=6.0 Hz, 1H), 2.01 (s, 3H), 1.67 (p, J=6.8 Hz, 2H), 1.41-1.28 (m, 4H), 0.90 (t J=6.8 Hz, 3H).

Example 53. Synthesis of ((2R,3S,4R,5R)-5-cyano-3,4-dihydroxy-5-(4-(((pentyloxy)carbonyl)amino)pyrrolo[2,1-f][1,2,4]triazin-7-yl)tetrahydrofuran-2-yl)methyl 2-cyclohexylacetate (Compound 88)

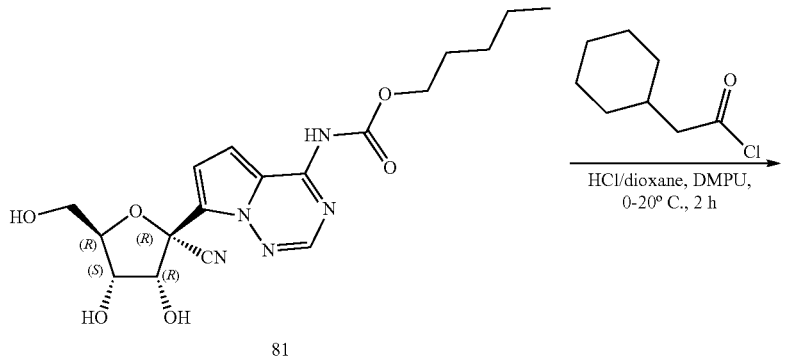

-continued

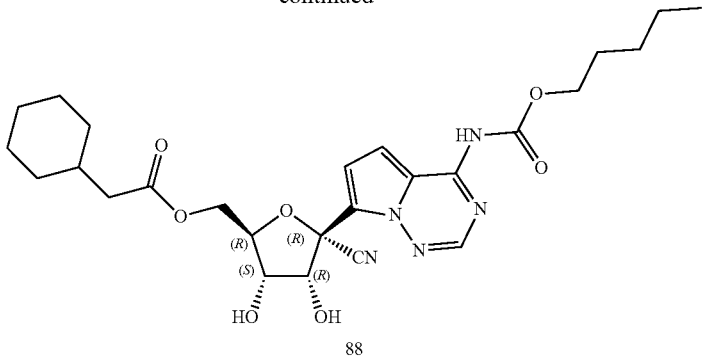

88

To a solution of 81 (60.0 mg, 0.16 mmol) in DMPU (1 mL) was added HCl/dioxane (0.2 mL, 4 M). The mixture solution was stirred at 20° C. for 15 minutes. The reaction mixture was cooled at 0° C. and 2-cyclohexylacetyl chloride (0.11 mL, 0.74 mmol) was added at once. The reaction was stirred at 0° C. for 2 hours. The reaction was diluted with ACN (2.0 mL) and purified by prep-HPLC to obtain 88 (28.8 mg, 36.6% yield) as a white solid. MS (ESI): m/z calcd. for $C_{26}H_{35}N_5O_7$, 529.25, found 530.2 [M+H]$^+$. $^1$H NMR (400 MHz, DMSO-d$_6$) δ 10.97 (s, 1H), 8.33 (s, 1H), 7.29 (d, J=4.0 Hz, 1H), 7.01 (d, J=4.8 Hz, 1H), 6.41 (d, J=6.0 Hz, 1H), 5.43 (d, J=6.0 Hz, 1H), 4.83-4.58 (m, 1H), 4.33-4.28 (m, 1H), 4.27-4.22 (m, 1H), 4.20-4.13 (m, 3H), 3.95 (dd, J=11.2, 6.0 Hz, 1H), 2.18-2.05 (m, 2H), 1.71-1.55 (m, 8H), 1.40-1.30 (m, 4H), 1.22-1.05 (m, 3H), 0.92-0.80 (m, 5H).

Example 54. Synthesis of ((2R,3S,4R,5R)-5-cyano-3,4-dihydroxy-5-(4-(((pentyloxy)carbonyl)amino)pyrrolo[2,1-f][1,2,4]triazin-7-yl)tetrahydrofuran-2-yl)methyl 2-phenylacetate (Compound 89)

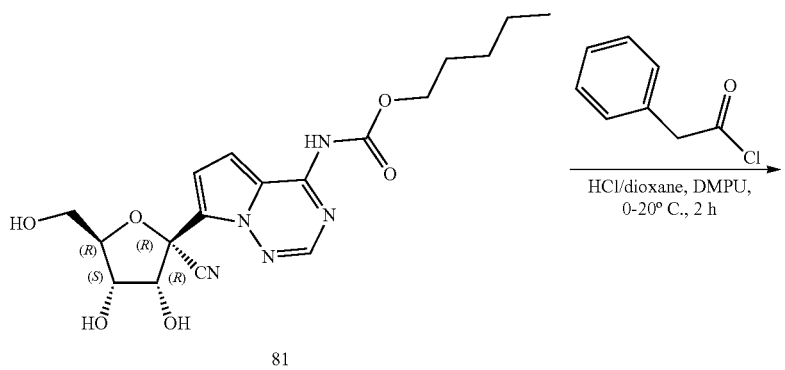

81

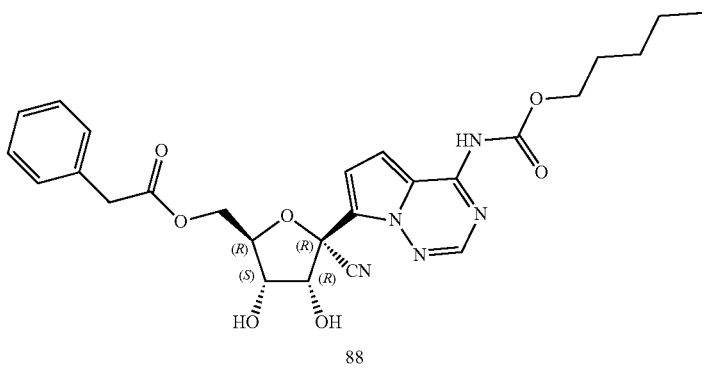

88

The title compound was prepared according to the procedure of Example 88, Step 1, using Compound 81 and 2-phenylacetyl chloride. MS (ESI): mass calcd. for $C_{26}H_{29}N_5O_7$, 523.21, m/z found 524.2 [M+H]$^+$. $^1$H NMR (400 MHz, DMSO-d$_6$) δ 10.99 (s, 1H), 8.33 (s, 1H), 7.33-7.19 (m, 6H), 6.97 (d, J=4.8 Hz, 1H), 6.40 (d, J=6.0 Hz, 1H), 5.45 (d, J=5.6 Hz, 1H), 4.64 (t J=5.6 Hz, 1H), 4.34 (dd, J=12.0, 2.4 Hz, 1H), 4.29-4.25 (m, 1H), 4.24-4.14 (m, 3H), 3.97-3.91 (m, 1H), 3.66 (s, 2H), 1.73-1.60 (m, 2H), 1.44-1.29 (m, 4H), 0.89 (t, J=7.2 Hz, 3H).

Example 55. Synthesis of ((2R,3S,4R,5R)-5-cyano-3,4-dihydroxy-5-(4-(((pentyloxy)carbonyl)amino) pyrrolo[2,1-f][1,2,4]triazin-7-yl)tetrahydrofuran-2-yl)methyl propionate (Compound 91)

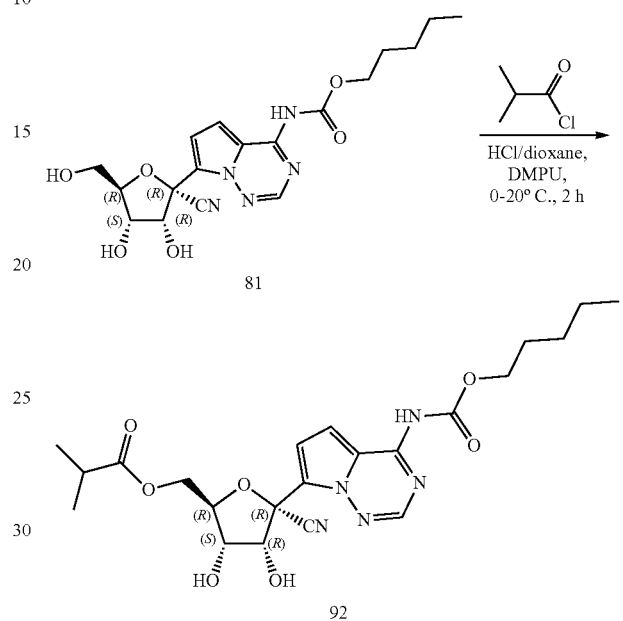

The title compound was prepared according to the procedure of Example 88, Step 1, using Compound 81 and propionyl chloride. MS (ESI): mass calcd. for $C_{21}H_{27}N_5O_7$, 461.19, m/z found 462.2 [M+H]$^+$. $^1$H NMR (400 MHz, DMSO-d$_6$) δ 10.98 (s, 1H), 8.33 (s, 1H), 7.28 (d, J=4.8 Hz, 1H), 7.00 (d, J=4.8 Hz, 1H), 6.41 (d, J=6.0 Hz, 1H), 5.43 (d, J=6.0 Hz, 1H), 4.86-4.46 (m, 1H), 4.33 (dd, J=12.0, 2.8 Hz, 1H), 4.28-4.22 (m, 1H), 4.19-4.13 (m, 3H), 3.94 (dd, J=11.6, 6.0 Hz, 1H), 2.35-2.24 (m, 2H), 1.71-1.63 (m, 2H), 1.46-1.26 (m, 4H), 0.99 (t, J=7.6 Hz, 3H), 0.90 (t, J=7.2 Hz, 3H).

Example 56. Synthesis of ((2R,3S,4R,5R)-5-cyano-3,4-dihydroxy-5-(4-(((pentyloxy)carbonyl)amino) pyrrolo[2,1-f][1,2,4]triazin-7-yl)tetrahydrofuran-2-yl)methyl isobutyrate (Compound 92)

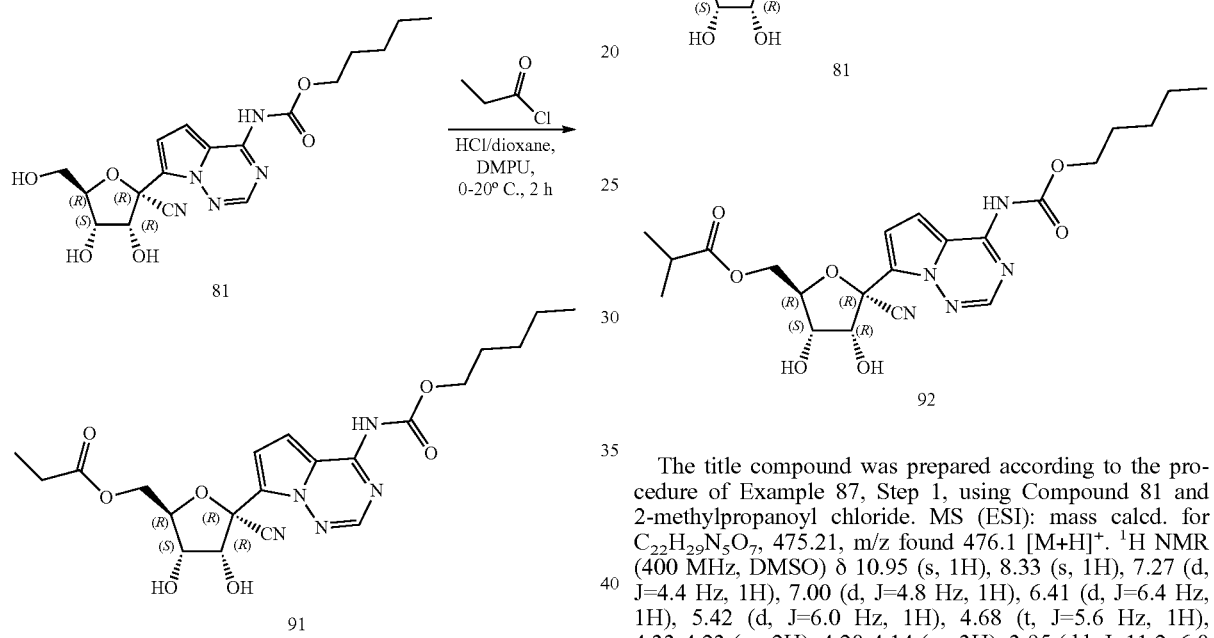

The title compound was prepared according to the procedure of Example 87, Step 1, using Compound 81 and 2-methylpropanoyl chloride. MS (ESI): mass calcd. for $C_{22}H_{29}N_5O_7$, 475.21, m/z found 476.1 [M+H]$^+$. $^1$H NMR (400 MHz, DMSO) δ 10.95 (s, 1H), 8.33 (s, 1H), 7.27 (d, J=4.4 Hz, 1H), 7.00 (d, J=4.8 Hz, 1H), 6.41 (d, J=6.4 Hz, 1H), 5.42 (d, J=6.0 Hz, 1H), 4.68 (t, J=5.6 Hz, 1H), 4.33-4.23 (m, 2H), 4.20-4.14 (m, 3H), 3.95 (dd, J=11.2, 6.0 Hz, 1H), 2.52 (s, 1H), 1.71-1.62 (m, 2H), 1.41-1.29 (m, 4H), 1.04 (m, 6H), 0.89 (t, J=7.2 Hz, 3H).

Example 57. Synthesis of ((2R,3S,4R,5R)-5-cyano-3,4-dihydroxy-5-(4-(((pentyloxy)carbonyl)amino) pyrrolo[2,1-f][1,2,4]triazin-7-yl)tetrahydrofuran-2-yl)methyl 3-methylbutanoate (Compound 93)

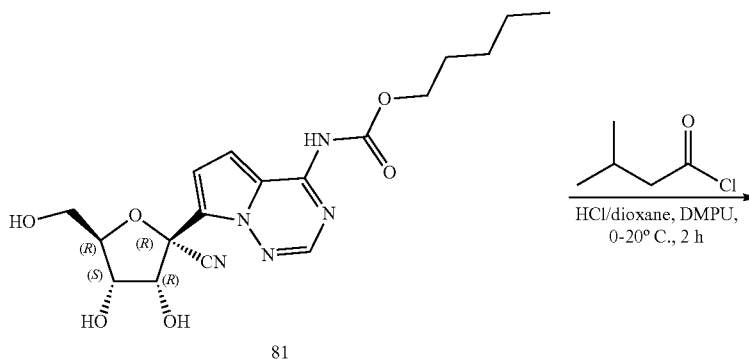

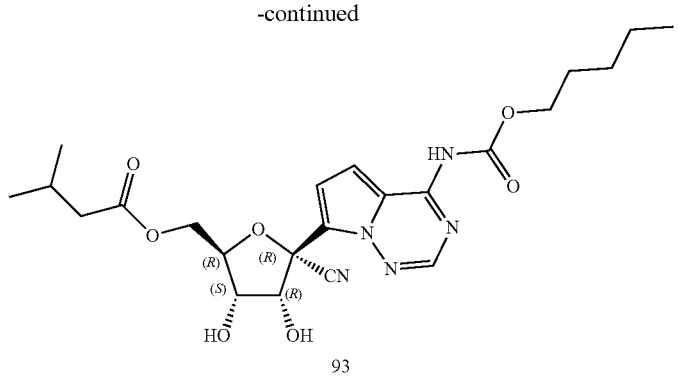

93

The title compound was prepared according to the procedure of Example 87, Step 1, using Compound 81 and 3-methylbutanoyl chloride. MS (ESI): mass calcd. for $C_{23}H_{31}N_5O_7$, 489.22, m/z found 490.3 [M+H]$^+$. $^1$H NMR (400 MHz, DMSO) δ 10.99 (s, 1H), 8.33 (s, 1H), 7.29 (d, J=4.8 Hz, 1H), 7.01 (d, J=4.8 Hz, 1H), 6.42 (d, J=6.0 Hz, 1H), 5.43 (d, J=5.2 Hz, 1H), 4.68 (t, J=5.6 Hz, 1H), 4.34-4.28 (m, 2H), 4.20-4.13 (m, 3H), 3.94 (dd, J=11.6, 6.0 Hz, 1H), 2.17-2.12 (m, 2H), 1.95-1.85 (m, 1H), 1.73-1.62 (m, 2H), 1.42-1.29 (m, 4H), 0.94-0.81 (m, 9H).

Example 58. Synthesis of ((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methyl 2-phenylacetate (Compound 97)

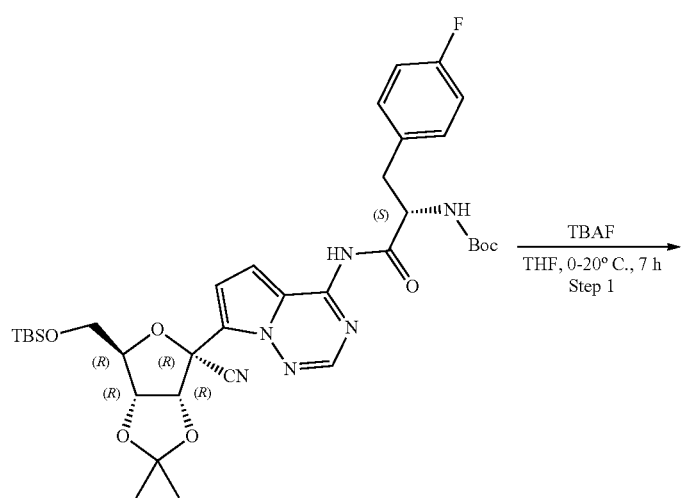

84.2

-continued
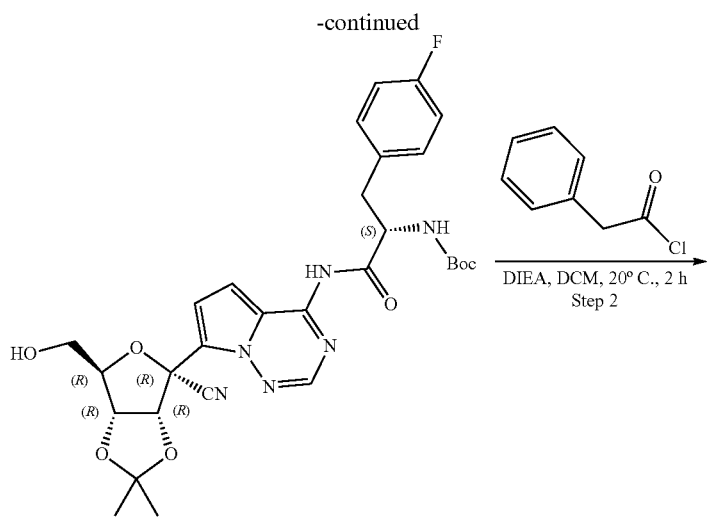
97.1
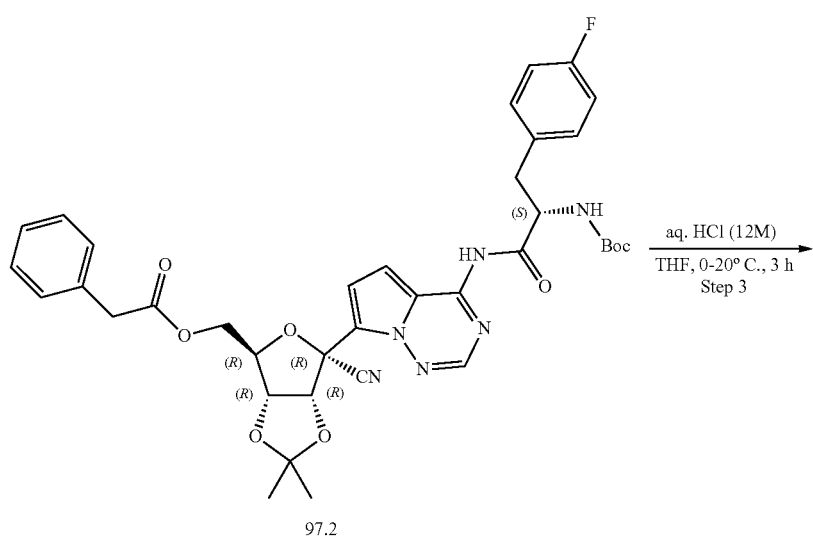
97.2
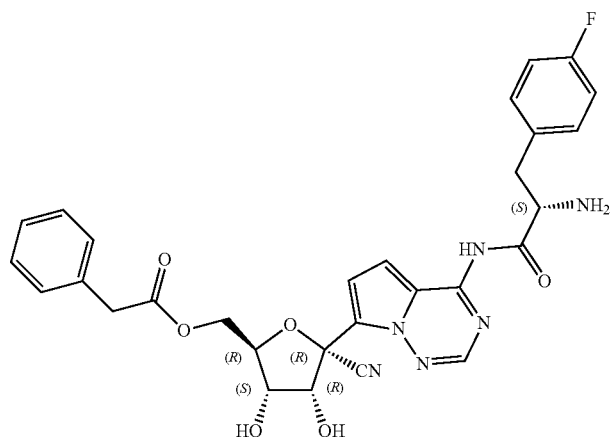
97

Step 1. Synthesis of tert-butyl((S)-1-((7-((3aR,4R, 6R,6aR)-4-cyano-6-(hydroxymethyl)-2,2-dimethyl-tetrahydrofuro[3,4-d][1,3]dioxol-4-yl)pyrrolo[2,1-f] [1,2,4]triazin-4-yl)amino)-3-(4-fluorophenyl)-1-oxopropan-2-yl)carbamate (97.1)

To a solution of 84.2 (1.40 g, 1.97 mmol) in dry THF (15 mL) was added TBAF (3.0 mL, 1 M in THF) dropwise at 0° C. The reaction mixture was stirred at 0° C. for 2 h and at 25° C. for another 5 h. The mixture was quenched with Sat. aq. $NH_4Cl$ (15 mL) and extracted with EA (10 mL×2). The combined organic phase was washed with brine (10 mL), dried over anhydrous $Na_2SO_4$, filtered. The filtrate was concentrated to dryness. The residue was purified by FCC (Gradient: 35% EA in PE) to 97.1 (820 mg, 70% yield) as a yellow solid. MS (ESI): m/z calcd. for $C_{29}H_{33}FN_6O_7$ 596.24, found 597.2 [M+H]$^+$. $^1$H NMR (400 MHz, DMSO) δ 11.20 (s, 1H), 8.51 (s, 1H), 7.43 (dd, J=8.4, 6.0 Hz, 2H), 7.33-7.06 (m, 5H), 5.36 (d, J=6.4 Hz, 1H), 5.02 (t J=5.6 Hz, 1H), 4.94-4.79 (m, 2H), 4.40-4.33 (m, 1H), 3.59-3.45 (m, 2H), 3.10 (dd, J=13.2, 3.2 Hz, 1H), 2.81 (dd, J=13.2, 11.2 Hz, 1H), 1.65 (s, 3H), 1.38 (s, 3H), 1.34-1.20 (m, 9H).

Step 2. Synthesis of ((3aR,4R,6R,6aR)-6-(4-((S)-2-((tert-butoxycarbonyl)amino)-3-(4-fluorophenyl) propanamido)pyrrolo[2,1-f][1,2,4]triazin-7-yl)-6-cyano-2,2-dimethyltetrahydrofuro[3,4-d][1,3]dioxol-4-yl)methyl 2-phenylacetate (97.2)

To a solution of 97.1 (200 mg, 0.335 mmol) and DIPEA (86.5 mg, 0.669 mmol) in dry DCM (1.5 mL) was added 2-phenylacetyl chloride (77.6 mg, 0.502 mmol) dropwise at 0° C. The reaction mixture was stirred at 20° C. for 2 h. The mixture was diluted with EA (5.0 mL) and washed with water (2.5 mL), followed by brine (2.5 mL), dried over anhydrous $Na_2SO_4$, filtered. The filtrate was concentrated to dryness. The residue was purified by FCC (Gradient: 30% EA in PE) to give 97.2 (122 mg, 85% yield) as a white solid. MS (ESI): m/z calcd. for $C_{37}H_{39}FN_6O_8$ 714.28, found 715.2 [M+H]+.

Step 3. Synthesis of ((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methyl 2-phenylacetate (97)

To a solution of 97.2 (50.0 mg, 0.07 mmol) in THF (0.4 mL) and water (0.2 mL) was added HCl/1,4-dioxane (0.3 mL, 4 M) dropwise at 0° C. The reaction mixture was stirred at 20° C. for 3 h. The reaction mixture was adjusted pH to 8 with Sat. aq. $NaHCO_3$ at 0° C. The organic solvent was removed with flowing nitrogen. The residue was purified by prep-HPLC to afford the title compound (4.41 mg, 11% yield) as a white solid. MS (ESI): m/z calcd. for $C_{29}H_{27}FN_6O_6$ 574.20, found 575.1 [M+H]$^+$. $^1$H NMR (400 MHz, DMSO) δ 8.58 (d, J=8.4 Hz, 1H), 7.92 (s, 1H), 7.69 (s, 1H), 7.39 (dd, J=8.4, 6.0 Hz, 2H), 7.32-7.13 (m, 6H), 7.11-7.01 (m, 3H), 6.78 (d, J=4.8 Hz, 1H), 6.33 (s, 1H), 5.43 (s, 1H), 4.98-4.89 (m, 1H), 4.63 (t, J=5.2 Hz, 1H), 4.33 (d, J=10.8 Hz, 1H), 4.25-4.15 (m, 2H), 3.96-3.87 (m, 1H), 3.66 (s, 2H), 3.22-3.15 (m, 1H), 3.07-2.98 (m, 1H). $^{19}$F NMR (377 MHz, DMSO) δ −116.75.

Example 59. Synthesis of ((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methyl 3-methylbutanoate (Compound 101)

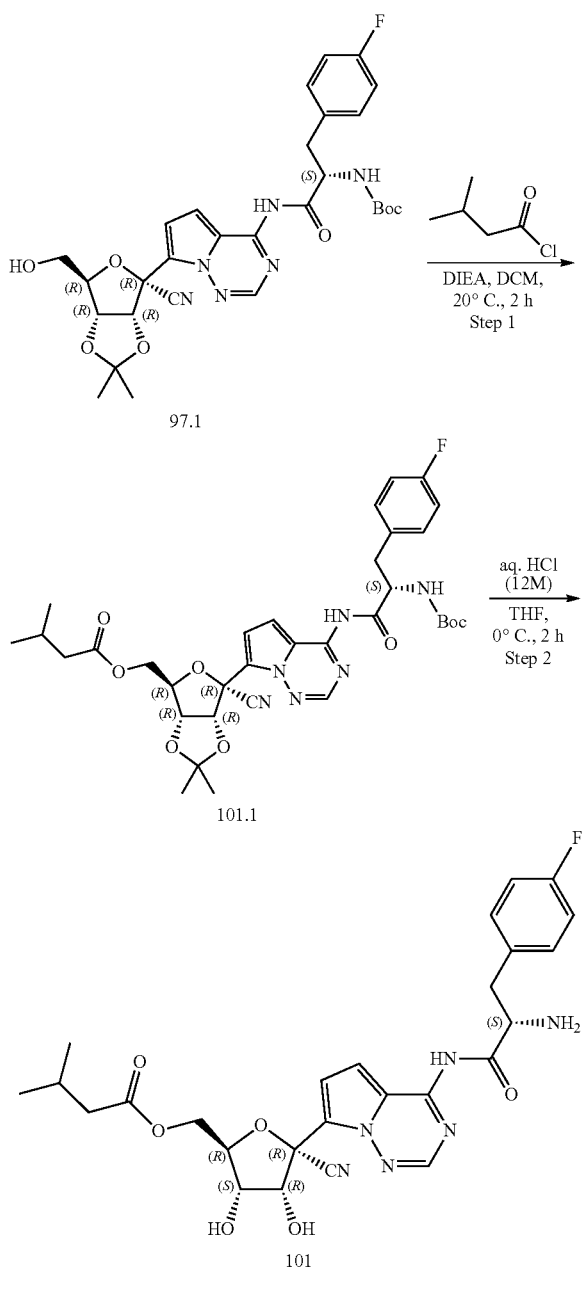

Step 1. Synthesis of ((3aR,4R,6R,6aR)-6-(4-((S)-2-((tert-butoxycarbonyl)amino)-3-(4-fluorophenyl) propanamido)pyrrolo[2,1-f][1,2,4]triazin-7-yl)-6-cyano-2,2-dimethyltetrahydrofuro[3,4-d][1,3]dioxol-4-yl)methyl 3-methylbutanoate (101.1)

To a solution of 97.1 (200 mg, 0.335 mmol) and DIPEA (64.9 mg, 0.502 mmol) in dry DCM (2.0 mL) was added 3-methylbutanoyl chloride (60.5 mg, 0.502 mmol) dropwise at 0° C. The reaction mixture was stirred at 25° C. for 16 h. The organic solvent was removed with flowing nitrogen. The residue was purified by prep-HPLC to give 101.1 (62.2 mg, crude) as a white solid. MS (ESI): m/z calcd. for $C_{34}H_{41}FN_6O_8$ 680.30, found 681.4 $[M+H]^+$.

Step 2. Synthesis of ((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methyl 3-methylbutanoate (101)

To a solution of 101.1 (62.2 mg, crude) in THF (0.6 mL) was added aq. HCl (0.3 mL, 12 M) dropwise at 0° C. The reaction mixture was stirred at 0° C. for 2 h. The organic solvent was removed with flowing nitrogen. The residue was purified by prep-HPLC to afford the title compound (4.32 mg, 8.5% yield) as a white solid. MS (ESI): m/z calcd. for $C_{26}H_{29}FN_6O_6$ 540.21, found 541.1 $[M+H]^+$. $^1$H NMR (400 MHz, DMSO) δ 11.04 (s, 1H), 8.69 (d, J=7.6 Hz, 1H), 7.91 (s, 1H), 7.47 (t, J=6.4 Hz, 2H), 7.15-6.99 (m, 3H), 6.89 (d, J=3.6 Hz, 1H), 6.09 (d, J=6.0 Hz, 1H), 5.48-5.30 (m, 1H), 5.19 (d, J=4.8 Hz, 1H), 4.93-4.81 (m, 1H), 4.65-4.53 (m, 1H), 4.08-3.99 (m, 1H), 3.97-3.90 (m, 1H), 3.65-3.59 (m, 1H), 3.51-3.48 (m, 1H), 3.18-3.13 (m, 1H), 3.05-2.97 (m, 1H), 2.41 (d, J=6.8 Hz, 2H), 2.11-2.00 (m, 1H), 0.93 (d, J=6.4 Hz, 6H). $^{19}$F NMR (377 MHz, DMSO) δ −116.44.

Example 60. Synthesis of ((2R,3S,4R,5R)-5-(4-benzamidopyrrolo[2,1-f][1,2,4]triazin-7-yl)-5-cyano-3,4-dihydroxytetrahydrofuran-2-yl)methyl acetate (Compound 103)

To a solution of 85 (80.0 mg, 0.20 mmol) in DMPU (0.5 mL) was added HCl/dioxane (0.1 mL, 4 M). The mixture solution was stirred at 0° C. for 15 minutes. Then acetyl chloride (47.6 mg, 0.61 mmol) was added at 0° C. The resulting mixture was stirred at 20° C. for another 2 hours. The reaction was diluted with ACN (2.0 mL) and purified by prep-HPLC to afford the title compound (21.1 mg, 23.8% yield) as a white solid. MS (ESI): m/z calcd. for $C_{21}H_{19}N_5O_6$ 437.13, found 438.2 $[M+H]^+$. $^1$H NMR (400 MHz, DMSO) δ 11.71 (s, 1H), 8.39 (s, 1H), 8.07 (s, 2H), 7.66 (t, J=6.8 Hz, 1H), 7.55 (t, J=7.6 Hz, 2H), 7.17 (d, J=4.4 Hz, 1H), 7.06 (s, 1H), 6.43 (d, J=6.0 Hz, 1H), 5.46 (d, J=5.6 Hz, 1H), 4.79-4.61 (m, 1H), 4.39-4.24 (m, 2H), 4.22-4.12 (m, 1H), 4.01-3.93 (m, 1H), 2.02 (s, 3H).

Example 61. Synthesis of ((2R,3S,4R,5R)-5-(4-benzamidopyrrolo[2,1-f][1,2,4]triazin-7-yl)-5-cyano-3,4-dihydroxytetrahydrofuran-2-yl)methyl 2-phenylacetate (Compound 105)

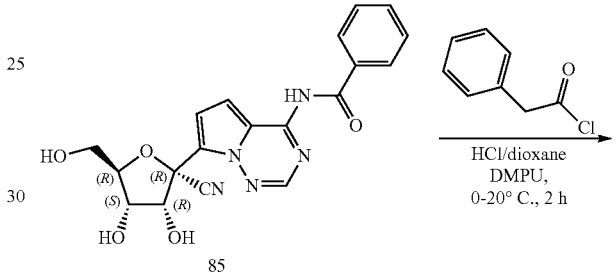

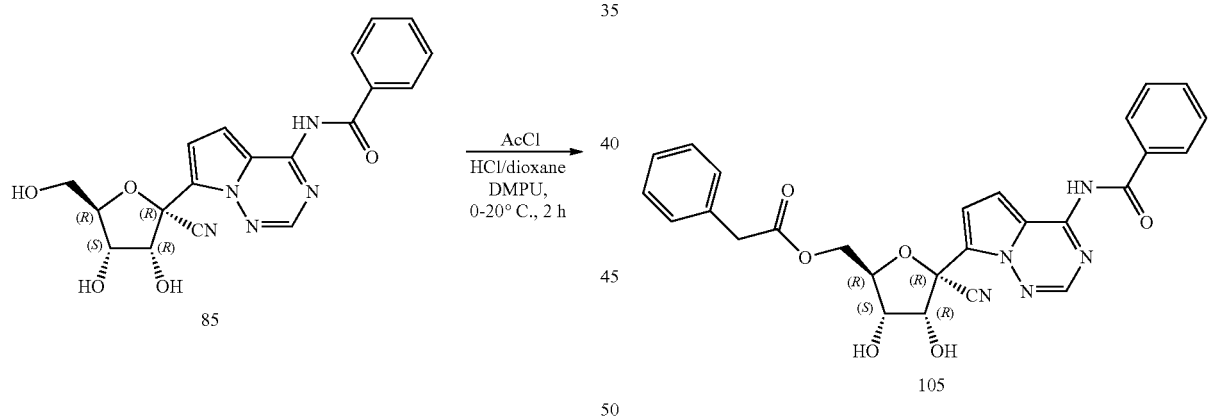

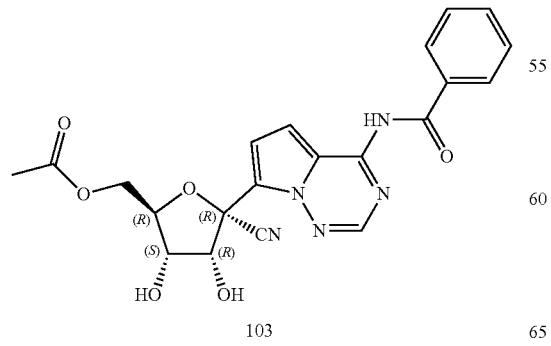

The title compound was prepared according to the procedure of Example 88, Step 1, using Compound 85 and 2-phenylacetyl chloride. MS (ESI): mass calcd. for $C_{27}H_{23}N_5O_6$, 513.16, m/z found 514.2 $[M+H]^+$. $^1$H NMR (400 MHz, DMSO-$d_6$) δ 11.88 (s, 1H), 8.36 (s, 1H), 8.07 (d, J=7.6 Hz, 2H), 7.64 (t, J=7.2 Hz, 1H), 7.55 (t, J=7.6 Hz, 2H), 7.36-7.19 (m, 5H), 7.16 (d, J=4.8 Hz, 1H), 7.02 (d, J=4.8 Hz, 1H), 6.42 (d, J=6.0 Hz, 1H), 5.46 (d, J=5.6 Hz, 1H), 4.66 (t, J=5.6 Hz, 1H), 4.36 (dd, J=12.0, 2.4 Hz, 1H), 4.32-4.26 (m, 1H), 4.22 (dd, J=12.0, 5.2 Hz, 1H), 3.99-3.94 (m, 1H), 3.68 (s, 2H).

Example 62. Synthesis of ((2R,3S,4R,5R)-5-(4-benzamidopyrrolo[2,1-f][1,2,4]triazin-7-yl)-5-cyano-3,4-dihydroxytetrahydrofuran-2-yl)methyl propionate (Compound 107)

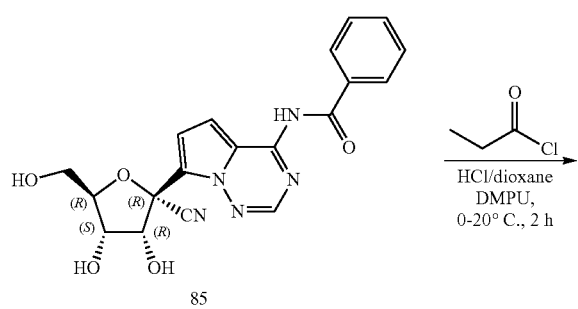

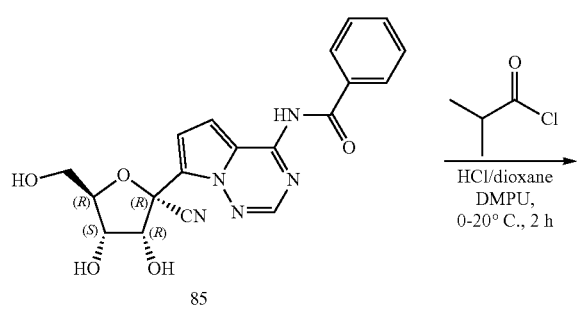

The title compound was prepared according to the procedure of Example 88, Step 1, using Compound 85 and propionyl chloride. MS (ESI): mass calcd. for $C_{22}H_{21}N_5O_6$, 451.15, m/z found 452.0 [M+H]⁺. ¹H NMR (400 MHz, DMSO-$d_6$) δ 11.81 (s, 1H), 8.37 (s, 1H), 8.06 (d, J=7.2 Hz, 2H), 7.65 (t J=7.6 Hz, 1H), 7.55 (t, J=7.6 Hz, 2H), 7.16 (d, J=4.8 Hz, 1H), 7.04 (d, J=4.8 Hz, 1H), 6.44 (d, J=6.0 Hz, 1H), 5.45 (d, J=6.0 Hz, 1H), 4.78-4.62 (m, 1H), 4.35 (dd, J=12.0, 2.8 Hz, 1H), 4.31-4.25 (m, 1H), 4.21-4.15 (m, 1H), 3.96 (dd, J=11.6, 6.0 Hz, 1H), 2.34-2.26 (m, 2H), 1.00 (t, J=7.6 Hz, 3H).

Example 63. Synthesis ((2R,3S,4R,5R)-5-(4-benzamidopyrrolo[2,1-f][1,2,4]triazin-7-yl)-5-cyano-3,4-dihydroxytetrahydrofuran-2-yl)methyl isobutyrate (Compound 108)

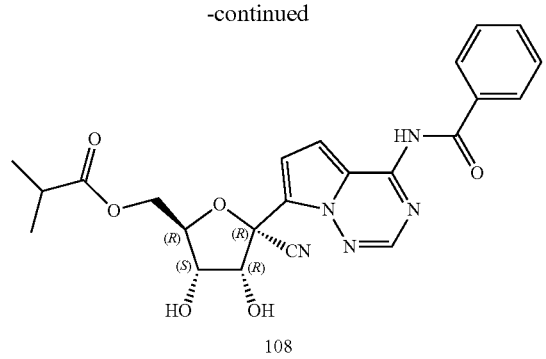

The title compound was prepared according to the procedure of Example 103, Step 1, using Compound 85 and 2-methylpropanoyl chloride. MS (ESI): mass calcd. for $C_{23}H_{23}N_5O_6$, 465.16, m/z found 466.1 [M+H]⁺. ¹H NMR (400 MHz, DMSO) δ 11.80 (s, 1H), 8.37 (s, 1H), 8.06 (d, J=7.2 Hz, 2H), 7.65 (t, J=7.2 Hz, 1H), 7.55 (t, J=7.6 Hz, 2H), 7.16 (d, J=4.0 Hz, 1H), 7.04 (d, J=4.4 Hz, 1H), 6.44 (d, J=6.0 Hz, 1H), 5.45 (d, J=5.6 Hz, 1H), 4.70 (t, J=5.2 Hz, 1H), 4.37-4.14 (m, 3H), 4.02-3.93 (m, 1H), 2.55-2.51 (m, 1H), 1.05 (dd, J=6.8, 2.4 Hz, 6H).

Example 64. Synthesis of ((2R,3S,4R,5R)-5-(4-benzamidopyrrolo[2,1-f][1,2,4]triazin-7-yl)-5-cyano-3,4-dihydroxytetrahydrofuran-2-yl)methyl 2-cyclohexylacetate (Compound 109)

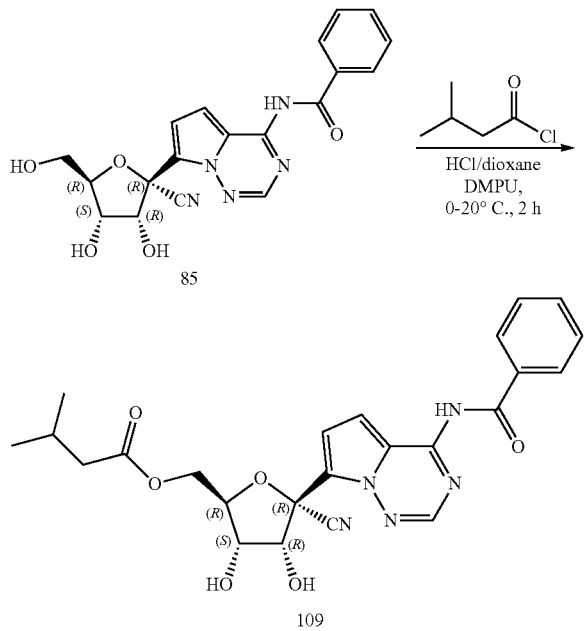

The title compound was prepared according to the procedure of Example 103, Step 1, using Compound 85 and 3-methylbutanoyl chloride. MS (ESI): mass calcd. for $C_{24}H_{25}N_5O_6$, 479.18, m/z found 480.1 [M+H]⁺. ¹H NMR (400 MHz, DMSO) δ 11.75 (s, 1H), 8.38 (s, 1H), 8.02 (d, J=7.2 Hz, 2H), 7.66 (t, J=7.6 Hz, 1H), 7.55 (t, J=7.6 Hz, 2H), 7.18 (d, J=4.8 Hz, 1H), 7.06 (d, J=4.4 Hz, 1H), 6.45 (d, J=6.0 Hz, 1H), 5.45 (d, J=6.0 Hz, 1H), 4.71 (s, 1H), 4.37-4.25 (m, 2H), 4.18 (dd, J=12.0, 5.2 Hz, 1H), 3.99-3.94 (m, 1H), 2.51 (s, 2H), 2.00-1.83 (m, 1H), 0.86 (dd, J=6.8, 3.2 Hz, 6H).

Example 65. Synthesis of ((2R,3S,4R,5R)-5-(4-((S)-2-amino-3-methylbutanamido)pyrrolo[2,1-f][1,2,4]triazin-7-yl)-5-cyano-3,4-dihydroxytetrahydrofuran-2-yl)methyl L-valinate (Compound 110)

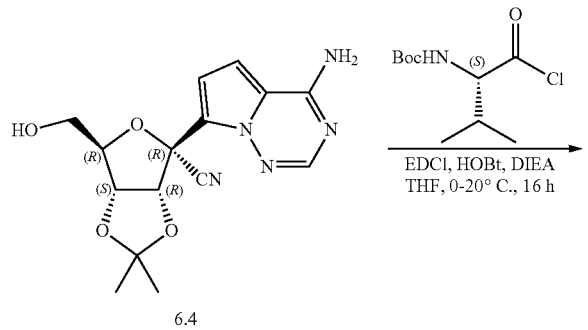

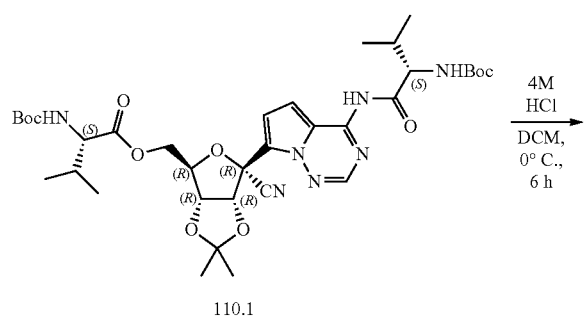

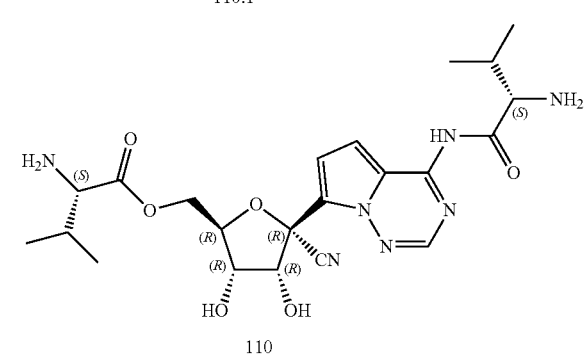

Step 1. Synthesis of ((3aR,4R,6R,6aR)-6-(4-((S)-2-((tert-butoxycarbonyl)amino)-3-methylbutanamido)pyrrolo[2,1-f][1,2,4]triazin-7-yl)-6-cyano-2,2-dimethyltetrahydrofuro[3,4-d][1,3]dioxol-4-yl)methyl (tert-butoxycarbonyl)-L-valinate (110.1)

To a solution of 6.4 (1.00 g, 3 mmol) in THF (15 mL) was added (2S)-2-{[(tert-butoxy)carbonyl]amino}-3-methylbutanoic acid (0.65 g, 3 mmol), HOBt (0.41 g, 3 mmol) and DIEA (0.58 g, 4.5 mmol) at 0° C., the mixture was then stirred at 0° C. for 5 min. Then added EDCI slowly into the mixture and stirred for 16 hours. After completion, the mixture was washed with water (50 mL) and extracted with ethyl acetate (50 mL×3). The organic layer was dried over sodium sulphate and concentrated in vacuo to afford a residue. The residue was purified with prep-HPLC to afford 110.1 (230 mg, 10.4% yield) as a white solid. MS (ESI): m/z calcd. for $C_{35}H_{51}N_7O_{10}$, 729.37, found 730.25 [M+H]$^+$. $^1$H NMR (400 MHz, DMSO) δ 11.02 (s, 1H), 8.47 (s, 1H), 7.20 (d, J=4.4 Hz, 1H), 7.17-6.70 (m, 3H), 5.42 (d, J=6.4 Hz, 1H), 4.92 (dd, J=6.4, 2.8 Hz, 1H), 4.63 (s, 1H), 4.42 (s, 1H), 4.25 (dd, J=12.0, 3.6 Hz, 1H), 4.14 (dd, J=12.0, 6.4 Hz, 1H), 3.71 (dd, J=46.0, 38.8 Hz, 1H), 2.09 (dd, J=13.2, 6.8 Hz, 1H), 1.79 (dd, J=13.6, 6.8 Hz, 1H), 1.66 (s, 3H), 1.45-1.23 (m, 21H), 0.94 (dd, J=14.4, 6.8 Hz, 6H), 0.76 (dd, J=15.2, 6.8 Hz, 6H).

Step 2. Synthesis of ((2R,3S,4R,5R)-5-(4-((S)-2-amino-3-methylbutanamido)pyrrolo[2,1-f][1,2,4]triazin-7-yl)-5-cyano-3,4-dihydroxytetrahydrofuran-2-yl)methyl L-valinate (110)

To a solution of 110.1 (100 mg, 0.13 mmol) in DCM (5 mL) was added 1 mL HCl/dioxane (5 mL) dropwise at 0° C. The mixture was then stirred at 0° C. for 2 hours. After completion, the mixture was dried through a nitrogen stream to afford a residue. The residue was purified with prep-HPLC to afford 110 (15 mg. 22.1% yield) as a white solid. MS (ESI): m/z calcd. for $C_{22}H_{31}N_7O_6$, 489.23, found 490.15 [M+H]$^+$. $^1$H NMR (400 MHz, DMSO) 8.23 (d, J=8.8 Hz, 1H), 7.98 (s, 1H), 7.56 (s, 1H), 7.25 (d, J=4.4 Hz, 1H), 7.13 (s, 1H), 6.83 (d, J=4.4 Hz, 1H), 6.36 (d, J=6.0 Hz, 1H), 5.40 (d, J=5.6 Hz, 1H), 4.72-4.61 (m, 2H), 4.37-4.22 (m, 3H), 3.94 (q, J=4.8 Hz, 1H), 3.30 (s, 1H), 2.23-2.13 (m, 1H), 1.92-1.80 (m, 1H), 0.96 (dd, J=6.8, 4.0 Hz, 6H), 0.83 (dd, J=16.4, 6.8 Hz, 6H).

Example 66. Synthesis of [(2R,3S,4R,5R)-5-{4-[(2S)-2-amino-3-methylbutanamido]pyrrolo[2,1-f][1,2,4]triazin-7-yl}-5-cyano-3,4-dihydroxyoxolan-2-yl]methyl 2-cyclohexylacetate (Compound 112)

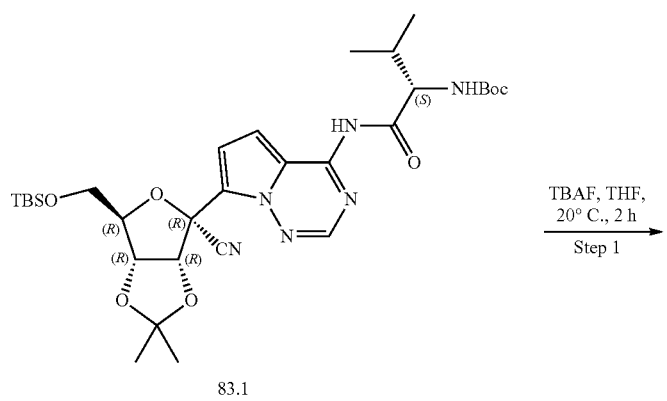

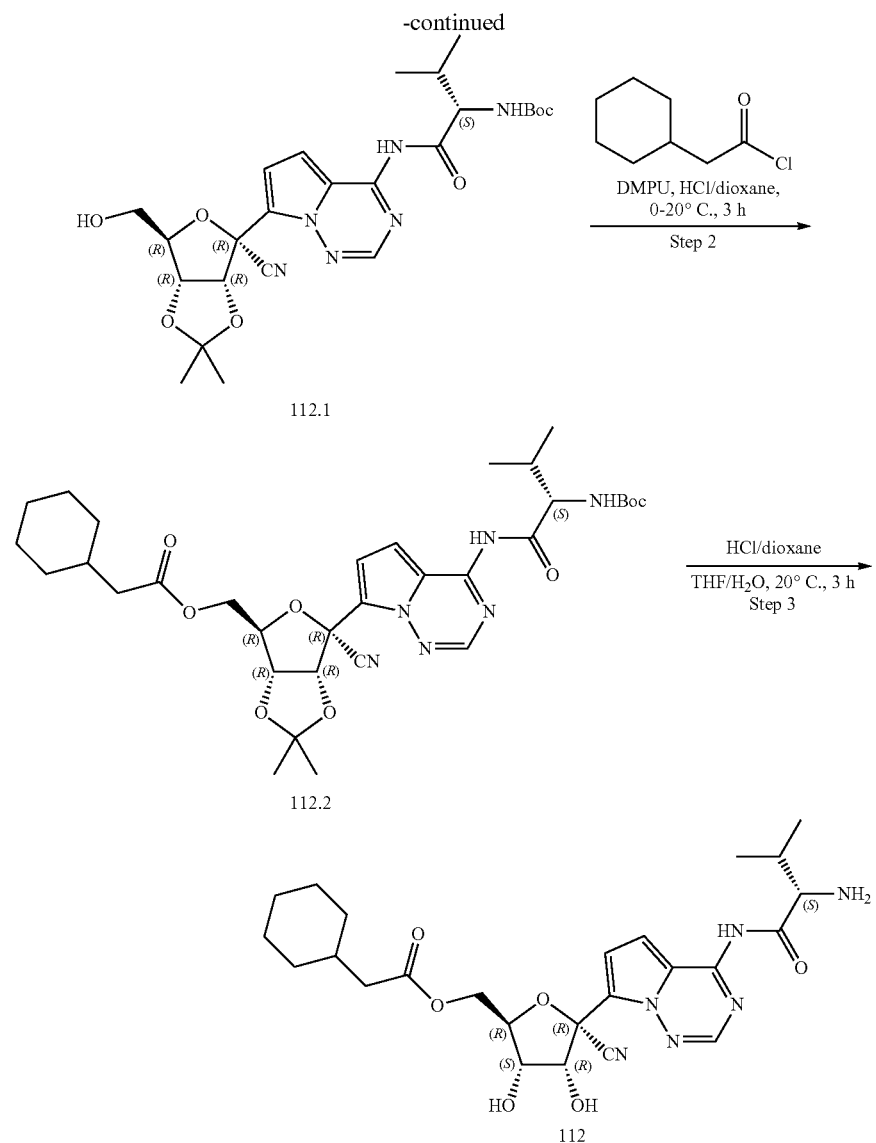

Step 1. Synthesis of tert-butyl((S)-1-((7-((3aR,4R, 6R,6aR)-4-cyano-6-(hydroxymethyl)-2,2-dimethyl-tetrahydrofuro[3,4-d][1,3]dioxol-4-yl)pyrrolo[2,1-f] [1,2,4]triazin-4-yl)amino)-3-methyl-1-oxobutan-2-yl)carbamate (112.1)

To a solution of tert-butyl N-[(1S)-1-({7-[(3aR,4R,6R, 6aR)-6-{[(tert-butyldimethylsilyl)oxy]methyl}-4-cyano-2, 2-dimethyl-dihydro-3aH-furo[3,4-d][1,3]dioxol-4-yl]pyr-rolo[2,1-f][1,2,4]triazin-4-yl}carbamoyl)-2-methylpropyl] carbamate (83.1, 450 mg, 0.697 mmol) in THF (5 mL) was added TBAF in THF (1M, 3.5 mL), the mixture was stirred at 25° C. for 2 h. The reaction was extracted with EA (5 mL×3). The combined organics were dried over sodium sulfate and concentrated in vacuo. The residue was purified by flash column chromatography (EA/PE from 2% to 50%) to obtain 112.1 as a white solid (320 mg, 82% yield). MS (ESI): mass calcd. for $C_{25}H_{34}N_6O_7$, 530.25, m/z found 531.2 [M+H]+.

Step 2. Synthesis of ((3aR,4R,6R,6aR)-6-(4-((S)-2-((tert-butoxycarbonyl)amino)-3-methylbutanamido) pyrrolo[2,1-f][1,2,4]triazin-7-yl)-6-cyano-2,2-dim-ethyltetrahydrofuro[3,4-d][1,3]dioxol-4-yl)methyl 2-cyclohexylacetate (112.2)

The compound 112.2 was prepared according to the procedure of Example 1, Step 4, using 112.1 and 2-cyclo-hexylacetyl chloride. MS (ESI): mass calcd. for $C_{33}H_{46}FN_6O_8$, 654.34, m/z found 655.3 [M+H]+.

Step 3. Synthesis of [(2R,3S,4R,5R)-5-{4-[(2S)-2-amino-3-methylbutanamido]pyrrolo[2,1-f][1,2,4] triazin-7-yl}-5-cyano-3,4-dihydroxyoxolan-2-yl] methyl 2-cyclohexylacetate (112)

To a solution of [(3aR,4R,6R,6aR)-6-{4-[(2S)-2-{[(tert-butoxy)carbonyl]amino}-3-methylbutanamido]pyrrolo[2,1-f][1,2,4]triazin-7-yl}-6-cyano-2,2-dimethyl-dihydro-3aH-furo[3,4-d][1,3]dioxol-4-yl]methyl 2-cyclohexylacetate (112.2, 80 mg, 0.122 mmol) in THF (2 mL) and water (1 mL) was added HCl in dioxane (4 M, 2 mL), the mixture was stirred at 25° C. for 6 h. The reaction was concentrated in vacuo and purified by prep-HPLC to afford the salt-forming compound. The compound was filtered, and the filter cake was washed with water (5 mL×3). Then the product was dried by lyophilization to give the title compound (26.02 mg, 41%) as a white solid. MS (ESI): mass calcd. for $C_{25}H_{34}N_6O_6$, 514.25, m/z found 515.2 [M+H]$^+$. $^1$H NMR (400 MHz, DMSO) δ 8.22 (d, J=8.8 Hz, 1H), 7.98 (s, 1H), 7.55 (s, 1H), 7.24 (d, J=4.4 Hz, 1H), 7.13 (s, 1H), 6.81 (d, J=4.4 Hz, 1H), 6.32 (d, J=6.0 Hz, 1H), 5.38 (d, J=6.0 Hz, 1H), 4.65-4.63 (m, 2H), 4.35-4.26 (m, 1H), 4.22-4.20 (m, 1H), 4.16 (dd, J=12.0, 5.2 Hz, 1H), 3.92-3.90 (m, 1H), 2.17-2.14 (m, 3H), 1.61-1.59 (m, 6H), 1.14-1.06 (m, 3H), 0.96 (dd, J=6.8, 4.0 Hz, 6H), 0.90-0.87 (m, 2H).

Example 67. Synthesis of (2R,3S,4R,5R)-5-{4-[(2S)-2-amino-3-methylbutanamido]pyrrolo[2,1-f][1,2,4]triazin-7-yl}-5-cyano-3,4-dihydroxyoxolan-2-yl] methyl 2-phenylacetate (Compound 113)

Step 1. Synthesis of [(3aR,4R,6R,6aR)-6-{4-[(2S)-2-{[(tert-butoxy)carbonyl]amino}-3-methylbutanamido]pyrrolo[2,1-f][1,2,4]triazin-7-yl}-6-cyano-2,2-dimethyl-dihydro-3aH-furo[3,4-d][1,3]dioxol-4-yl] methyl 2-phenylacetate (113.1)

The compound 113.1 was prepared according to the procedure of Example 1, Step 4, using 112.1 and 2-phenylacetyl chloride. MS (ESI): mass calcd. for $C_{33}H_{40}N_6O_8$, 648.29, m/z found 649.3 [M+H]$^+$.

Step 2. Synthesis of (2R,3R,4R,5R)-5-{4-[(2S)-2-amino-3-methylbutanamido]pyrrolo[2,1-f][1,2,4]triazin-7-yl}-5-cyano-3,4-dihydroxyoxolan-2-yl] methyl 2-phenylacetate (113)

The compound 113 was prepared according to the procedure of Example 112, Step 3, using 113.1. MS (ESI): mass calcd. for $C_{25}H_{23}N_4O_6$, 508.21, m/z found 509.1 [M+H]$^+$. $^1$H NMR (400 MHz, DMSO) δ 8.27 (d, J=8.8 Hz, 1H), 7.98 (s, 1H), 7.58 (s, 1H), 7.32-7.21 (m, 6H), 7.12 (s, 1H), 6.79

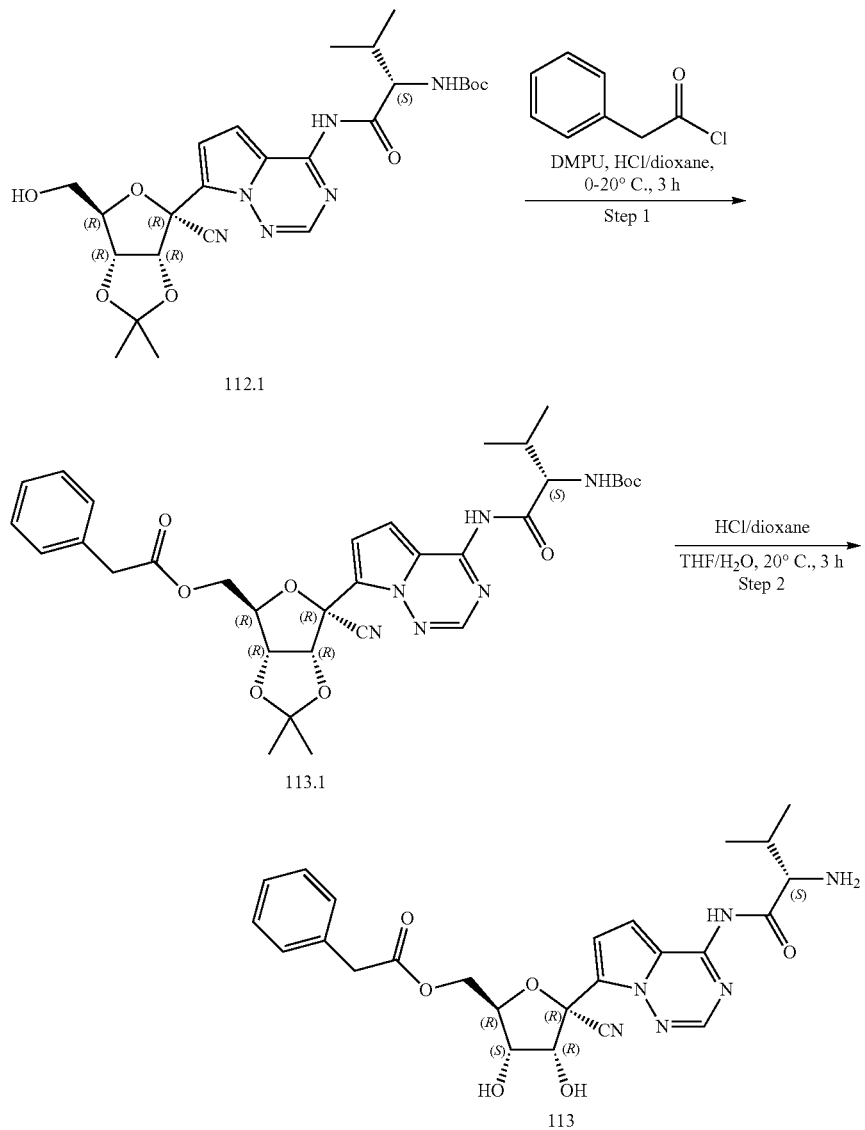

(d, J=4.4 Hz, 1H), 6.40 (d, J=5.2 Hz, 1H), 5.49 (d, J=5.2 Hz, 1H), 4.65 (t, J=8.0 Hz, 2H), 4.34 (dd, J=11.6, 2.4 Hz, 1H), 4.28-4.15 (m, 2H), 3.94-3.92 (m, 1H), 3.66 (s, 2H), 2.20-2.15 (in, 1H), 0.96 (dd, J=6.8, 4.4 Hz, 6H).

Example 68. Synthesis of [(2R,3S,4R,5R)-5-{4-[(2S)-2-amino-3-methylbutanamido]pyrrolo[2,1-f][1,2,4]triazin-7-yl}-5-cyano-3,4-dihydroxyoxolan-2-yl] methyl 2-methylpropanoate (Compound 116)

ylpropanoyl chloride. MS (ESI): mass calcd. for $C_{29}H_{40}N_6O_8$, 600.29, m/z found 601.3 [M+H]+.

Step 2: Synthesis of [(2R,3S,4R,5R)-5-{4-[(2S)-2-amino-3-methylbutanamido]pyrrolo[2,1-f][1,2,4]triazin-7-yl}-5-cyano-3,4-dihydroxyoxolan-2-yl] methyl 2-methylpropanoate (116)

The compound 116 was prepared according to the procedure of Example 112, Step 3, using 116.1. MS (ESI): mass

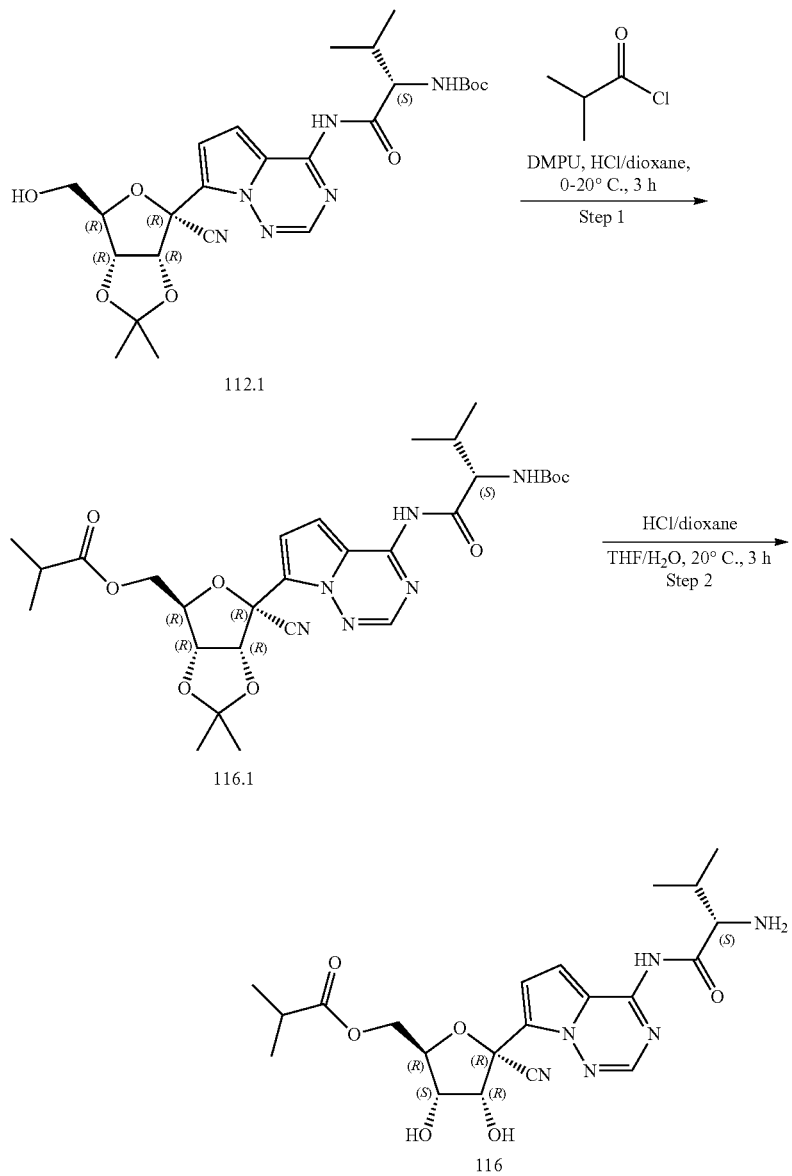

Step 1. Synthesis of [(3aR,4R,6R,6aR)-6-{4-[(2S)-2-{[(tert-butoxy)carbonyl]amino}-3-methylbutanamido]pyrrolo[2,1-f][1,2,4]triazin-7-yl}-6-cyano-2,2-dimethyl-dihydro-3aH-furo[3,4-d][1,3]dioxol-4-yl] methyl 2-methylpropanoate (116.1)

The compound 116.1 was prepared according to the procedure of Example 1, Step 4, using 112.1 and 2-methcalcd. for $C_{21}H_{28}N_6O_6$, 460.21, m/z found 461.3 [M+H]+.
$^1$H NMR (400 MHz, DMSO) δ 8.21 (d, J=8.8 Hz, 1H), 7.98 (s, 1H), 7.56 (s, 1H), 7.24 (d, J=4.4 Hz, 1H), 7.13 (s, 1H), 6.81 (d, J=4.8 Hz, 1H), 6.34-6.25 (m, 1H), 5.39-5.25 (m, 1H), 4.66-4.62 (m, 2H), 4.31 (dd, J=12.0, 2.4 Hz, 1H), 4.23-4.21 (m, 1H), 4.16 (dd, J=12.0, 5.2 Hz, 1H), 3.95 (d, J=5.2 Hz, 1H), 2.53-2.50 (m, 1H), 2.18-2.15 (m, 1H), 1.05 (dd, J=7.2, 2.8 Hz, 6H), 0.96 (dd, J=6.8, 3.2 Hz, 6H).

Example 69. Synthesis of [(2R,3S,4R,5R)-5-{4-[(2S)-2-amino-3-methylbutanamido]pyrrolo[2,1-f][1,2,4]triazin-7-yl}-5-cyano-3,4-dihydroxyoxolan-2-yl] methyl 3-methylbutanoate (Compound 117)

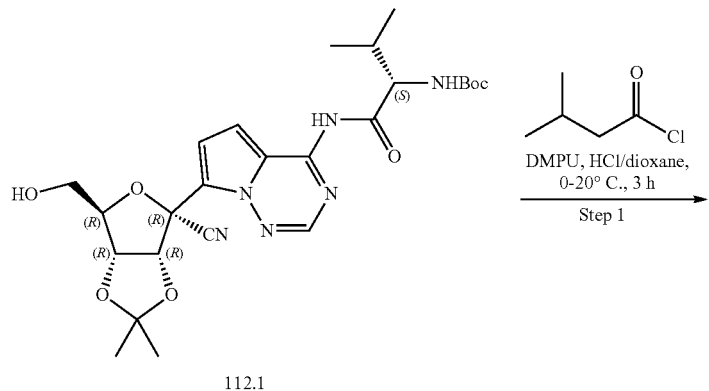

112.1

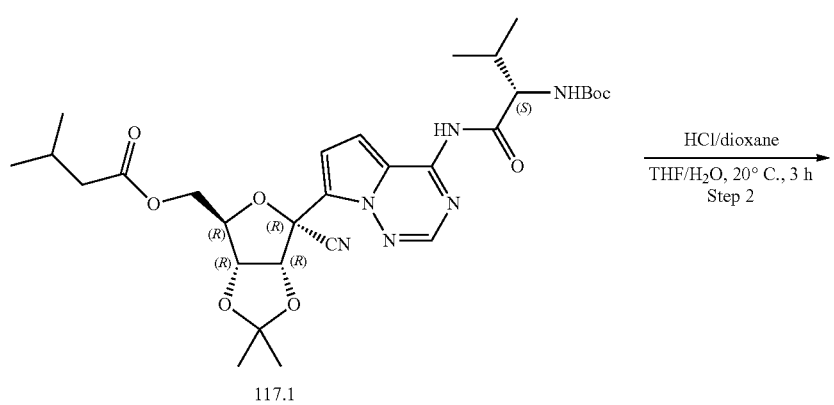

117.1

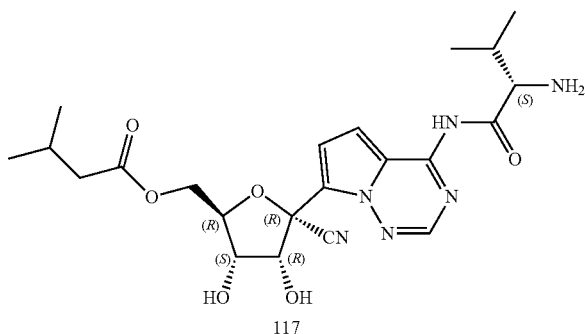

117

Step 1. Synthesis of [(3aR,4R,6R,6aR)-6-{4-[(2S)-2-{[(tert-butoxy)carbonyl]amino}-3-methylbutanamido]pyrrolo[2,1-f][1,2,4]triazin-7-yl}-6-cyano-2,2-dimethyl-dihydro-3aH-furo[3,4-d][1,3]dioxol-4-yl] methyl 3-methylbutanoate (117.1)

The compound 117.1 was prepared according to the procedure of Example 1, Step 4, using 117.1 and 3-methylbutanoyl chloride. MS (ESI): mass calcd. for $C_{30}H_{42}N_6O_8$, 614.31, m/z found 615.3 [M+H]+.

Step 2. Synthesis of [(2R,3S,4R,5R)-5-{4-[(2S)-2-amino-3-methylbutanamido]pyrrolo[2,1-f][1,2,4]triazin-7-yl}-5-cyano-3,4-dihydroxyoxolan-2-yl] methyl 3-methylbutanoate (117)

The compound 117 was prepared according to the procedure of Example 112, Step 1, using 117.1 and 3-methylbutanoyl chloride. MS (ESI): mass calcd. for $C_{22}H_{30}N_6O_6$, 474.22, m/z found 475.1 [M+H]+. $^1$H NMR (400 MHz, DMSO) δ 8.23 (d, J=8.4 Hz, 1H), 7.98 (s, 1H), 7.56 (s, 1H), 7.24 (d, J=4.4 Hz, 1H), 7.13 (s, 1H), 6.81 (d, J=4.8 Hz, 1H), 6.36 (d, J=6.0 Hz, 1H), 5.40 (d, J=6.0 Hz, 1H), 4.69-4.60 (m, 2H), 4.33 (dd, J=12.0, 2.4 Hz, 1H), 4.26-4.19 (m, 1H), 4.16 (dd, J=12.0, 5.6 Hz, 1H), 3.93-3.92 (m, 1H), 2.18-2.15 (m, 3H), 1.98-1.87 (m, 1H), 0.96 (dd, J=6.8, 3.6 Hz, 6H), 0.87 (dd, J=6.8, 2.4 Hz, 6H).

Example 70. Synthesis of (2R,3S,4R,5R)-5-{4-[(2S)-2-amino-3-methylbutanamido]pyrrolo[2,1-f][1,2,4]triazin-7-yl}-5-cyano-4-hydroxy-2-(hydroxymethyl)oxolan-3-yl (2S)-2-amino-3-methylbutanoate (Compound 129)

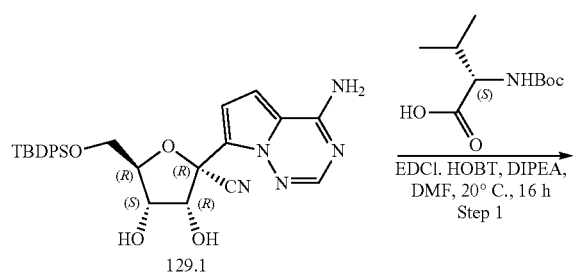

129.1

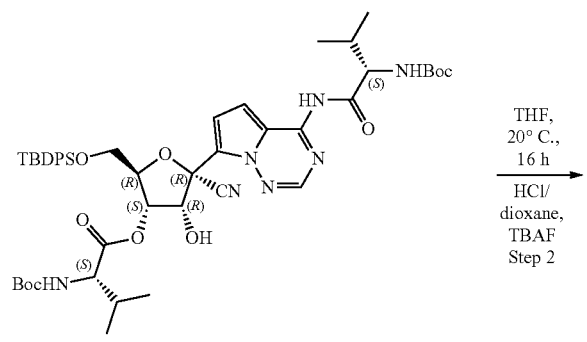

129.2

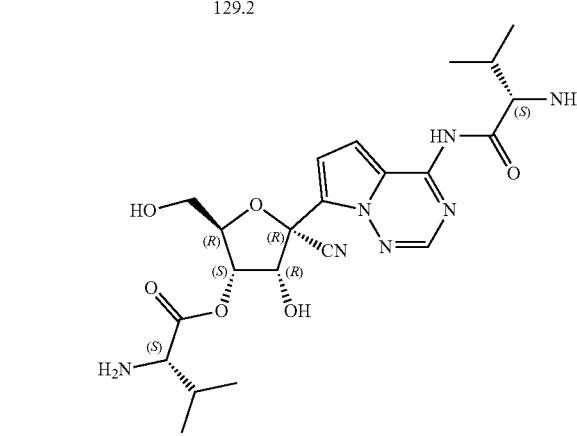

129

Step 1. Synthesis of (2R,3S,4R,5R)-5-{4-[(2S)-2-{[(tert-butoxy)carbonyl]amino}-3-methylbutanamido]pyrrolo[2,1-f][1,2,4]triazin-7-yl}-2-({1-[tert-butyl(hydroxy)phenylsilyl]phenyl}methyl)-5-cyano-4-hydroxyoxolan-3-yl (2S)-2-{[(tert-butoxy)carbonyl]amino}-3-methylbutanoate (129.1)

The compound 129.1 was prepared according to the procedure of Example 83., Step 1, using 129.1 and (2S)-2-cyclohexylpropanoic acid. MS (ESI): mass calcd. for $C_{48}H_{65}N_7O_{10}Si$, 927.46, m/z found 928.5 [M+H]$^+$.

Step 2. (2R,3S,4R,5R)-5-{4-[(2S)-2-amino-3-methylbutanamido]pyrrolo[2,1-f][1,2,4]triazin-7-yl}-5-cyano-4-hydroxy-2-(hydroxymethyl)oxolan-3-yl (2S)-2-amino-3-methylbutanoate (129)

To a solution of (2R,3S,4R,5R)-5-{4-[(2S)-2-{[(tert-butoxy)carbonyl]amino}-3-methylbutanamido]pyrrolo[2,1-f][1,2,4]triazin-7-yl}-2-{[(tert-butyldiphenylsilyl)oxy]methyl}-5-cyano-4-hydroxyoxolan-3-yl (2S)-2-{[(tert-butoxy)carbonyl]amino}-3-methylbutanoate (129.2, 100 mg, 0.107 mmol) in THF (2 mL) was added HCl in dioxane (4 M, 3 mL) and TBAF in THF (1 M, 4 mL), the mixture was stirred at 25° C. for 16 h. The reaction was concentrated in vacuo and purified by prep-HPLC to afford the salt-forming compound. The compound was basified by NaHCO$_3$ (sat. aqueous, 1 mL) and purified by prep-HPLC to obtain 129 as a white solid (11.58 mg, 22% yield). MS (ESI): mass calcd. for $C_{22}H_{31}N_7O_6$, 489.23, m/z found 490.3 [M+H]$^+$. $^1$H NMR (400 MHz, DMSO) δ 8.26 (d, J=8.0 Hz, 1H), 7.98 (s, 1H), 7.56 (s, 1H), 7.26 (d, J=4.4 Hz, 1H), 7.14 (s, 1H), 6.90 (d, J=4.4 Hz, 1H), 6.4-6.45 (m, 1H), 5.19 (dd, J=5.6, 3.6 Hz, 1H), 5.02-5.00 (m, 2H), 4.66 (t, J=8.0 Hz, 1H), 4.25-4.23 (m, 1H), 3.59-3.55 (m, 2H), 3.23 (d, J=5.2 Hz, 1H), 2.18-2.14 (m, 1H), 2.0-1.98 (m, 1H), 0.97-0.85 (m, 12H).

Example 71. Synthesis of [(2R,3R,4R,5R)-5-[2-amino-6-(methylamino)purin-9-yl]-4-fluoro-3-hydroxy-4-methyloxolan-2-yl]methyl (2S)-2-amino-3-methylbutanoate (Compound 176)

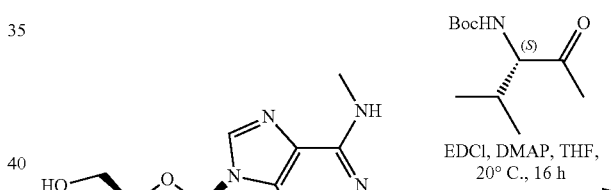

3.3

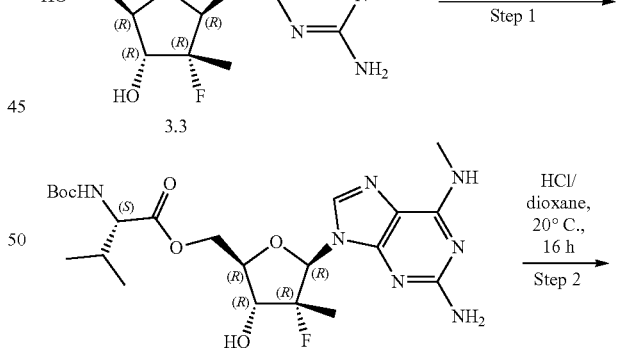

176.1

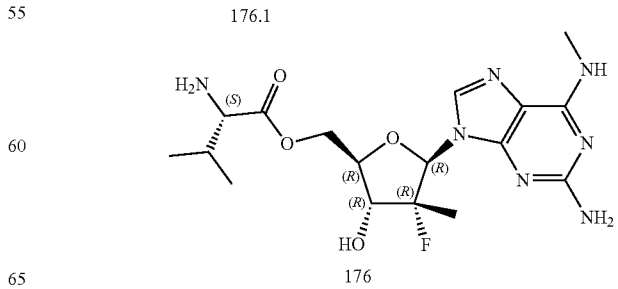

176

Step 1. Synthesis of ([(2R,3R,4R,5R)-5-[2-amino-6-(methylamino) purin-9-yl]-4-fluoro-3-hydroxy-4-methyloxolan-2-yl]methyl (2S)-2-{[(tert-butoxy)carbonyl]amino}-3-methylbutanoate methane (176.1)

The compound 176.1 was prepared according to the procedure of Example 19, Step 1, using 3.3 and (2S)-2-{[(tert-butoxy) carbonyl]amino}-3-methylbutanoic acid. MS (ESI): mass calcd. for $C_{22}H_{34}FN_7O_6$, 511.26 m/z found 512.3 $[M+H]^+$. $^1H$ NMR (400 MHz, DMSO) δ 7.81 (s, 1H), 7.30 (s, 1H), 7.19 (d, J=8.0 Hz, 1H), 6.03-6.00 (m, 3H), 5.80 (d, J=6.8 Hz, 1H), 4.50 (d, J=11.2 Hz, 1H), 4.37 (dd, J=12.0, 7.2 Hz, 1H), 4.06 (t, J=8.0 Hz, 1H), 3.86 (t, J=8.0 Hz, 1H), 3.30-3.25 (m, 1H), 2.87 (s, 3H), 2.02-1.98 (m, 1H), 1.36 (s, 9H), 1.09 (d, J=22.4 Hz, 3H), 0.86 (dd, J=6.8, 2.4 Hz, 6H).

Step 2. Synthesis of [(2R,3R,4R,5R)-5-[2-amino-6-(methylamino)purin-9-yl]-4-fluoro-3-hydroxy-4-methyloxolan-2-yl]methyl (2S)-2-amino-3-methylbutanoate (176)

The title compound 176 was prepared according to the procedure of Example 19, Step 2, using 176.1. MS (ESI): mass calcd. for $C_{17}H_{26}FN_7O_4$, 411.20, m/z found 412.1 $[M+H]^+$. $^1H$ NMR (400 MHz, DMSO) δ 7.83 (s, 1H), 7.34 (s, 1H), 6.12-5.97 (m, 3H), 5.82-5.80 (m, 1H), 4.52 (d, J=12.0 Hz, 1H), 4.34 (dd, J=12.4, 6.4 Hz, 2H), 4.10-4.05 (m, 1H), 3.18 ((d, J=5.2 Hz, 1H), 2.87 (s, 3H), 1.86-1.83 (m, 1H), 1.10 (d, J=22.4 Hz, 3H), 0.85 (dd, J=17.2, 6.8 Hz, 6H). $^{19}F$ NMR (376 MHz, DMSO) δ −159.87 (s, 1H).

Example 72. Synthesis of ((2R,3R,4R,5R)-5-(2-amino-6-(methylamino)-9H-purin-9-yl)-4-fluoro-3-hydroxy-4-methyltetrahydrofuran-2-yl)methyl propionate (Compound 180)

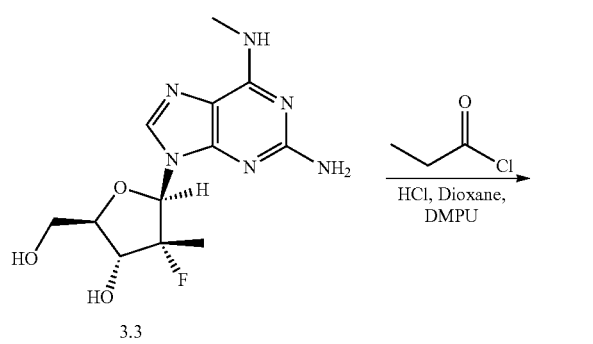

The title compound was prepared according to the procedure of Example 3, Step 3, using propanoyl chloride. MS (ESI): mass calcd. for $C_{15}H_{21}FN_6O_4$, 368.16, m/z found 369.2 $[M+H]^+$. $^1H$ NMR (400 MHz, DMSO-$d_6$) δ 7.81 (s, 1H), 7.32 (br s, 1H), 6.0-6.05 (m, 3H), 5.76 (br d, J=6.8 Hz, 1H), 4.29-4.47 (m, 4H), 4.04 (m, 1H), 2.87 (br s, 3H), 2.34-2.40 (m, 2H), 1.02-1.14 (m, 6H).

Example 73. Synthesis of (2R,3R,4R,5R)-5-(2-amino-6-(methylamino)-9H-purin-9-yl)-2-((2-cyclohexylacetoxy)methyl)-4-fluoro-4-methyltetrahydrofuran-3-yl 3-methylbutanoate (Compound 183)

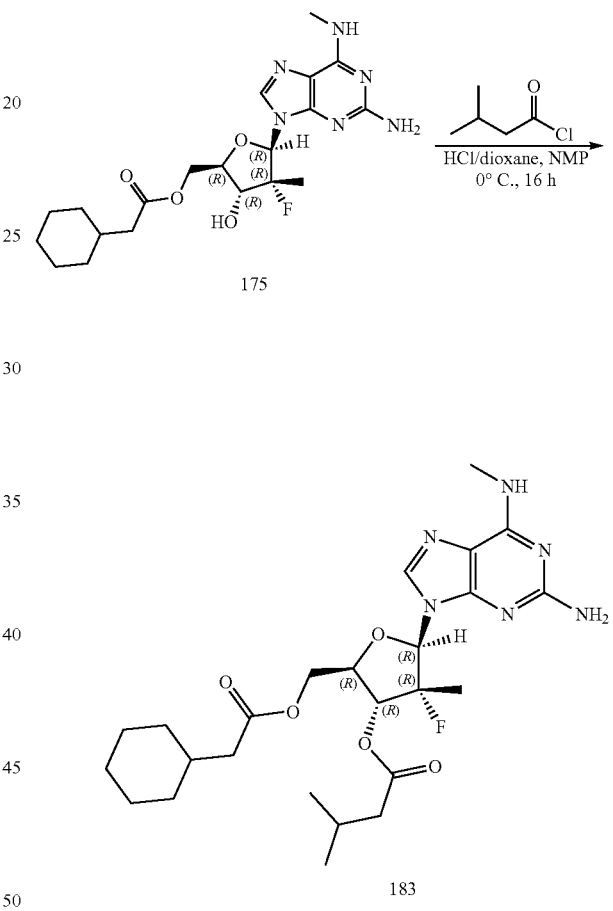

To a solution of 175 (100 mg, 0.22 mmol) in NMP was added 4 M HCl/dioxane (0.1 mL) dropwise at 0° C. The mixture was then stirred at 0° C. for 30 minutes. After that, 3-methylbutanoyl chloride was added into the mixture slowly. The reaction mixture was stirred at 20° C. for 16 hours. After completion, the mixture was purified by prep-HPLC to afford 183 (12 mg, 9.9% yield) as a white solid. MS (ESI): m/z calcd. for $C_{25}H_{37}FN_6O_5$, 520.28, found 521.20 $[M+H]^+$. $^1H$ NMR (400 MHz, DMSO) δ 7.88 (s, 1H), 7.39 (s, 1H), 6.13 (d, J=19.6 Hz, 1H), 5.95 (s, 3H), 4.45 (d, J=9.2 Hz, 1H), 4.33 (dd, J=15.2, 6.0 Hz, 2H), 2.87 (s, 3H), 2.37-2.31 (m, 2H), 2.21 (d, J=6.4 Hz, 2H), 2.03 (dt, J=13.6, 6.8 Hz, 1H), 1.62 (dd, J=21.2, 10.4 Hz, 6H), 1.24-1.09 (m, 6H), 0.93 (dt, J=17.2, 8.4 Hz, 8H). $^{19}F$ NMR (377 MHz, DMSO) δ −156.31 (s, 1F).

Example 74. Synthesis of (2R,3R,4R,5R)-5-(2-amino-6-(methylamino)-9H-purin-9-yl)-4-fluoro-4-methyl-2-((2-phenylacetoxy)methyl)tetrahydrofuran-3-yl 3-methylbutanoate (Compound 185)

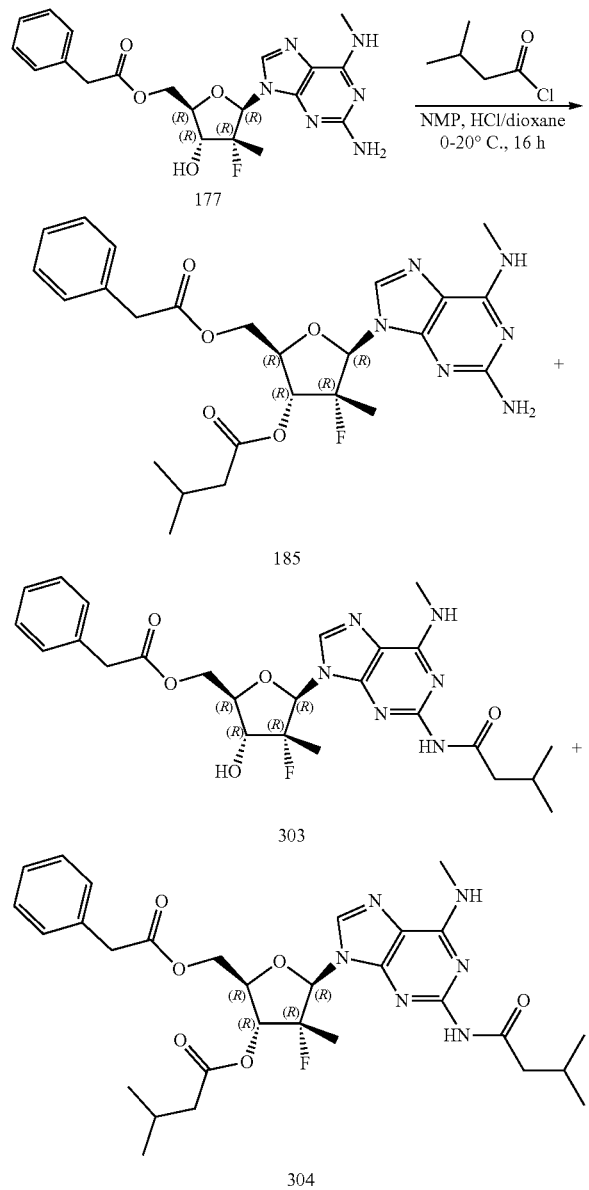

The title compound was prepared according to the procedure of Example 183, using 177 and 3-methylbutanoyl chloride. MS (ESI): m/z calcd. for $C_{25}H_{31}FN_6O_5$ 514.23, found 515.2 [M+H]$^+$. $^1$H NMR (400 MHz, DMSO) δ 7.86 (s, 1H), 7.48-7.13 (m, 6H), 6.13 (d, J=19.6 Hz, 1H), 6.04-5.74 (m, 3H), 4.51-4.43 (m, 1H), 4.41-4.28 (m, 2H), 3.72 (d, J=2.8 Hz, 2H), 2.87 (s, 3H), 2.34-2.30 (m, 2H), 2.06-1.97 (m, 1H), 1.14 (d, J=23.2 Hz, 3H), 0.94 (dd, J=6.8, 1.2 Hz, 6H). $^{19}$F NMR (377 MHz, DMSO) δ -156.01.

Example 75. Synthesis of (2R,3R,4R,5R)-2-(acetoxymethyl)-5-(2-amino-6-(methylamino)-9H-purin-9-yl)-4-fluoro-4-methyltetrahydrofuran-3-yl 3-methylbutanoate (Compound 186)

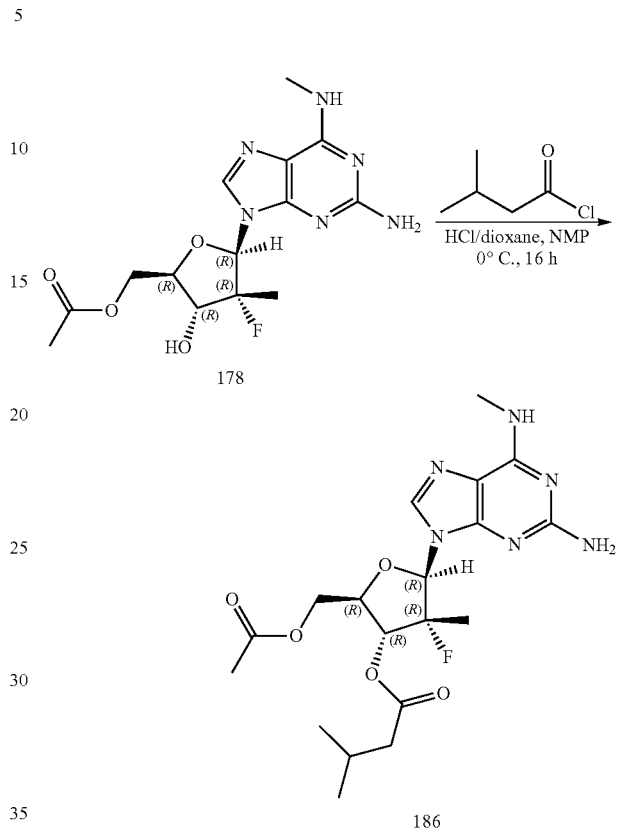

The title compound was prepared according to the procedure of Example 183, using 178 and 3-methylbutanoyl chloride. MS (ESI): m/z calcd. for $C_{19}H_{27}FN_6O_5$ 438.20, found 439.10 [M+H]$^+$. $^1$H NMR (400 MHz, DMSO) δ 8.05 (d, J=70.8 Hz, 3H), 7.17-7.09 (m, 1H), 6.97 (d, J=4.4 Hz, 1H), 6.84 (d, J=4.4 Hz, 1H), 6.34 (s, 1H), 5.40 (s, 1H), 4.68 (d, J=4.8 Hz, 1H), 4.38-4.18 (m, 3H), 3.98-3.83 (m, 2H), 1.96 (d, J=6.8 Hz, 1H), 1.34 (d, J=32.4 Hz, 9H), 0.82 (t, J=6.0 Hz, 6H). $^{19}$F NMR (377 MHz, DMSO) δ -156.17 (s, 1F).

Example 76. Synthesis of (2R,3R,4R,5R)-5-(2-amino-6-(methylamino)-9H-purin-9-yl)-4-fluoro-4-methyl-2-((propionyloxy)methyl)tetrahydrofuran-3-yl 3-methylbutanoate (Compound 188)

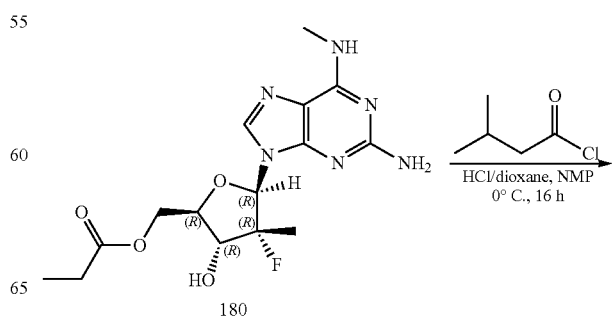

-continued

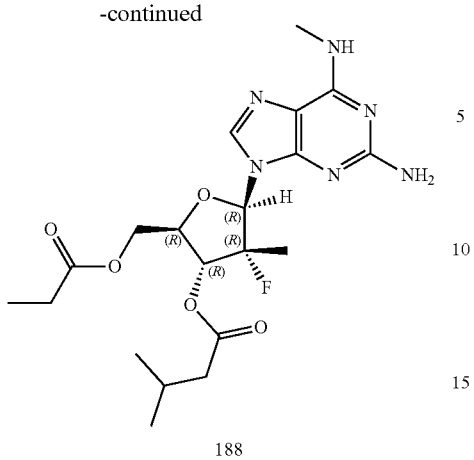

188

-continued

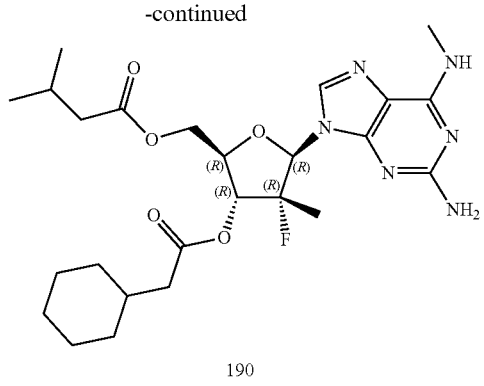

190

The title compound was prepared according to the procedure of Example 183, using 180 and 3-methylbutanoyl chloride. MS (ESI): m/z calcd. for $C_{20}H_{29}FN_6O_5$ 452.22, found 453.10 [M+H]⁺. ¹H NMR (400 MHz, DMSO) δ 7.89 (s, 1H), 7.39 (s, 1H), 6.13 (d, J=19.2 Hz, 1H), 5.90 (s, 3H), 4.46 (d, J=9.6 Hz, 1H), 4.39-4.27 (m, 2H), 2.87 (s, 3H), 2.39-2.30 (m, 4H), 2.10-1.97 (m, 1H), 1.15 (d, J=22.8 Hz, 3H), 1.03 (t, J=7.6 Hz, 3H), 0.94 (dd, J=6.8, 2.0 Hz, 6H). ¹⁹F NMR (377 MHz, DMSO) δ −156.26.

Example 77. Synthesis of ((2R,3R,4R,5R)-5-(2-amino-6-(methylamino)-9H-purin-9-yl)-3-(2-cyclohexylacetoxy)-4-fluoro-4-methyltetrahydrofuran-2-yl)methyl 3-methylbutanoate (Compound 190)

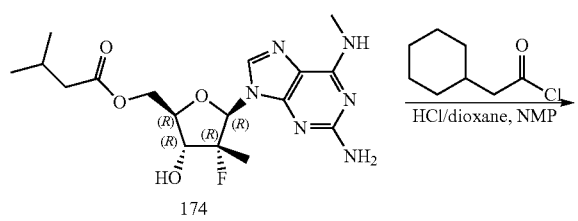

The title compound was prepared according to the procedure of Example 183, Step 1, using Compound 174 and 2-cyclohexylacetyl chloride. MS (ESI): mass calcd. for $C_{25}H_{37}FN_6O_5$, 520.28, m/z found 521.3 [M+H]⁺. ¹H NMR (400 MHz, DMSO-d₆) δ 7.88 (s, 1H), 7.39 (s, 1H), 6.13 (d, J=19.6 Hz, 1H), 6.02-5.74 (m, 3H), 4.44 (t, J=8.4 Hz, 1H), 4.37-4.23 (m, 2H), 2.87 (s, 3H), 2.33 (d, J=6.8 Hz, 2H), 2.22 (d, J=6.8 Hz, 2H), 1.98 (dt J=13.6, 6.8 Hz, 1H), 1.76-1.58 (m, 6H), 1.27-1.10 (m, 6H), 1.05-0.93 (m, 2H), 0.90 (dd, J=6.8, 2.4 Hz, 6H). ¹⁹F NMR (376 MHz, DMSO) δ −156.30.

Example 78. Synthesis of (2R,3R,4R,5R)-5-(2-amino-6-(methylamino)-9H-purin-9-yl)-2-((2-cyclohexylacetoxy)methyl)-4-fluoro-4-methyltetrahydrofuran-3-yl 2-cyclohexylacetate (Compound 191)

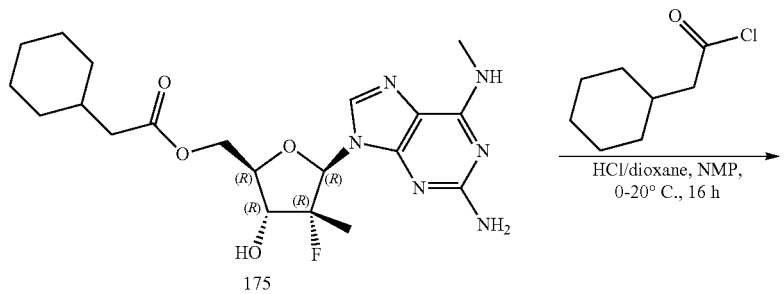

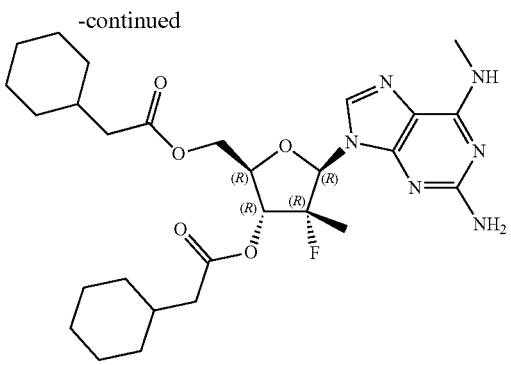

191

The title compound was prepared according to the procedure of Example 183, Step 1, using Compound 175 and 2-cyclohexylacetyl chloride. MS (ESI): mass calcd. for $C_{28}H_{41}FN_6O_5$, 560.31, m/z found 561.3 [M+H]$^+$. $^1$H NMR (400 MHz, DMSO-d$_6$) δ 7.88 (s, 1H), 7.39 (s, 1H), 6.13 (d, J=19.6 Hz, 1H), 6.05-5.80 (m, 3H), 4.47-4.41 (m, 1H), 4.35-4.27 (m, 2H), 2.87 (s, 3H), 2.33 (d, J=6.8 Hz, 2H), 2.21 (d, J=6.8 Hz, 2H), 1.74-1.61 (m, 11H), 1.26-1.10 (m, 10H), 1.02-0.86 (m, 4H). $^{19}$F NMR (376 MHz, DMSO) δ −156.30.

Example 79. Synthesis of ((2R,3R,4R,5R)-5-(2-amino-6-(methylamino)-9H-purin-9-yl)-3-(2-cyclohexylacetoxy)-4-fluoro-4-methyltetrahydrofuran-2-yl)methyl 2-phenylacetate (Compound 193)

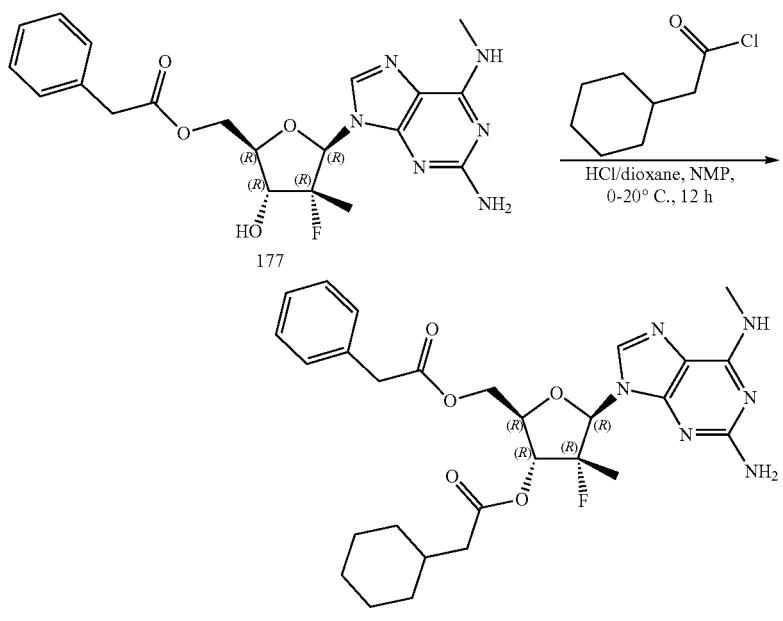

The title compound was prepared according to the procedure of Example 183, Step 1, using Compound 177 and 2-cyclohexylacetyl chloride. MS (ESI): mass calcd. for $C_{28}H_{35}FN_6O_5$, 554.27, m/z found 555.2 [M+H]$^+$. $^1$H NMR (400 MHz, DMSO-d$_6$) δ 7.86 (s, 1H), 7.51-7.12 ((m, 6H), 6.13 (d, J=19.6 Hz, 1H), 5.95-5.74 (m, 3H), 4.48 (dd, J=12.4, 2.8 Hz, 1H), 4.42-4.25 (m, 2H), 3.71 (d, J=2.8 Hz, 2H), 2.87 (s, 3H), 2.32 (d, J=6.8 Hz, 2H), 1.70-1.63 (m, 6H), 1.25-1.10 (m, 6H), 1.09-0.92 (m, 2H). $^{19}$F NMR (376 MHz, DMSO) δ −155.98.

Example 80. Synthesis of (2R,3R,4R,5R)-2-(acetoxymethyl)-5-(2-amino-6-(methylamino)-9H-purin-9-yl)-4-fluoro-4-methyltetrahydrofuran-3-yl 2-cyclohexylacetate (Compound 194)

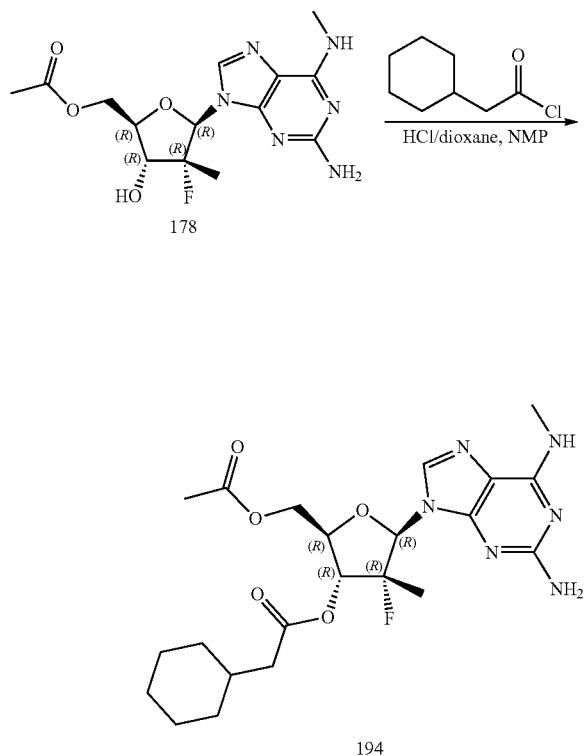

The title compound was prepared according to the procedure of Example 183, Step 1, using Compound 178 and 2-cyclohexylacetyl chloride. MS (ESI): mass calcd. for $C_{22}H_{31}FN_6O_5$, 478.23, m/z found 479.2 [M+H]$^+$. $^1$H NMR (400 MHz, DMSO-d$_6$) δ 7.90 (s, 1H), 7.38 (s, 1H), 6.13 (d, J=19.6 Hz, 1H), 5.80-5.60 (m, 3H), 4.46-4.42 (m, 1H), 4.35-4.27 (m, 2H), 2.87 (s, 3H), 2.33 (d, J=6.8 Hz, 2H), 2.04 (s, 3H), 1.70-1.60 (m, 6H), 1.24-1.10 (m, 6H), 1.03-0.94 (m, 2H). $^{19}$F NMR (376 MHz, DMSO) δ −156.14.

Example 81. Synthesis of ((2R,3R,4R,5R)-5-(2-amino-6-(methylamino)-9H-purin-9-yl)-3-(2-cyclohexylacetoxy)-4-fluoro-4-methyltetrahydrofuran-2-yl)methyl propionate (Compound 196)

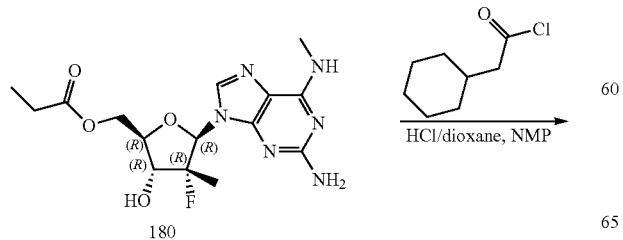

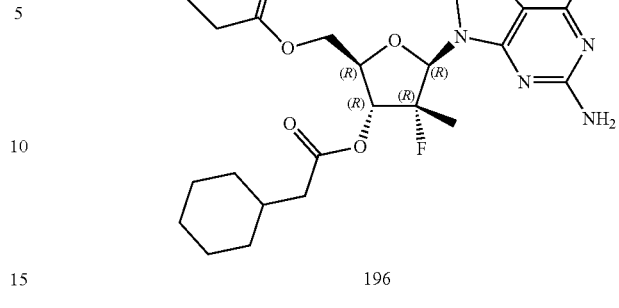

The title compound was prepared according to the procedure of Example 183, Step 1, using Compound 180 and 2-cyclohexylacetyl chloride. MS (ESI): mass calcd. for $C_{23}H_{33}FN_6O_5$, 492.25, m/z found 493.2 [M+H]$^+$. $^1$H NMR (400 MHz, DMSO-d$_6$) δ 7.89 (s, 1H), 7.39 (s, 1H), 6.13 (d, J=19.6 Hz, 1H), 6.05-5.80 (m, 3H), 4.48-4.43 (m, 1H), 4.39-4.26 (m, 2H), 2.87 (s, 3H), 2.39-2.30 (m, 4H), 1.75-1.58 (m, 6H), 1.28-1.10 (m, 6H), 1.06-0.93 (m, 5H). $^{19}$F NMR (376 MHz, DMSO) δ −156.23.

Example 82. Synthesis of [(2R,3R,4R,5R)-5-[2-amino-6-(methylamino) purin-9-yl]-4-fluoro-4-methyl-3-[(2-phenylacetyl)oxy]oxolan-2-yl]methyl 3-methylbutanoate (Compound 206) and [(2R,3R,4R,5R)-4-fluoro-3-hydroxy-4-methyl-5-[6-(methylamino)-2-(2-phenylacetamido)purin-9-yl]oxolan-2-yl]methyl 3-methylbutanoate (Compound 316)

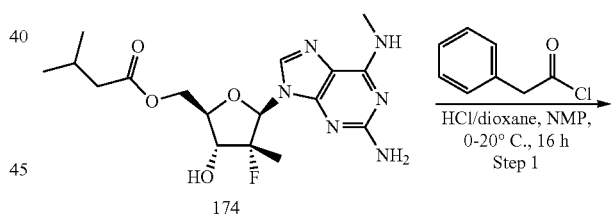

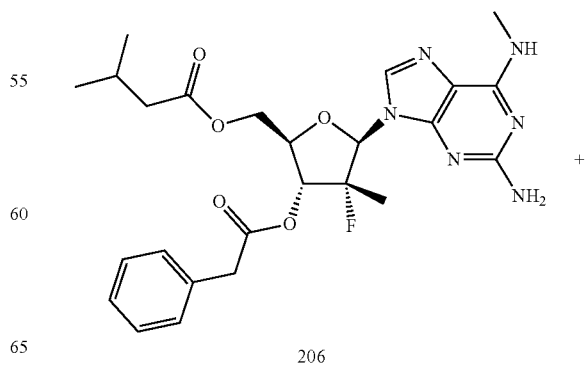

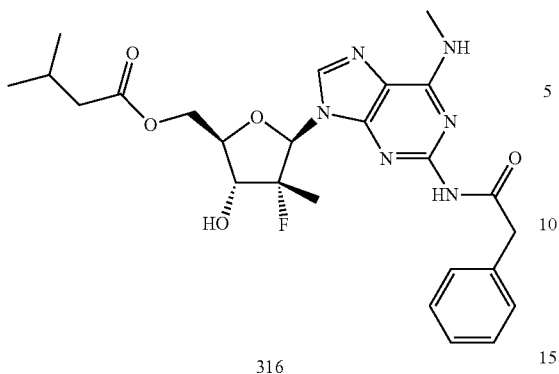

316

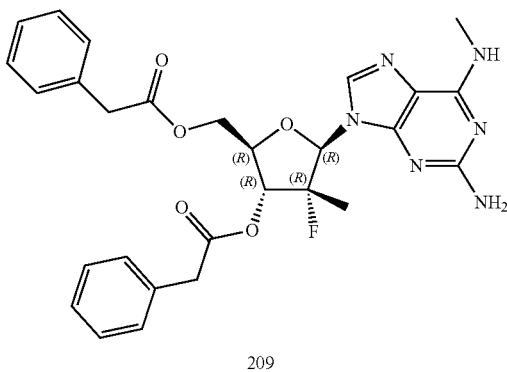

209

The title compounds 206 and 316 were prepared according to the procedure of Example 65, Step 1, using 174 and 2 2-phenylacetyl chloride.

For compound 206: MS (ESI): mass calcd. for $C_{25}H_{31}FN_6O_5$, 514.23, m/z found 515.2 [M+H]+. 1H NMR (400 MHz, DMSO) δ 7.87 (s, 1H), 7.40-7.25 (m, 6H), 6.13 (d, J=19.6 Hz, 1H), 5.92-5.90 (m, 3H), 4.44 (t, J=7.2 Hz, 1H), 4.35-4.29 (m, 2H), 3.83 (d, J=2.0 Hz, 2H), 2.86 (s, 3H), 2.18 (dd, J=7.2, 2.8 Hz, 2H), 1.96-1.92 (m, 1H), 1.12 (d, J=22.8 Hz, 3H), 0.88 (dd, J=6.8, 3.2 Hz, 6H). 19F NMR (376 MHz, DMSO) δ −156.22.

For compound 316: MS (ESI): mass calcd. for $C_{25}H_{31}FN_6O_5$, 514.23, m/z found 515.2 [M+H]+. 1H NMR (400 MHz) δ 10.25 (s, 1H), 8.13 (s, 1H), 7.85 (s, 1H), 7.33-7.21 (m, 5H), 6.13 (d, J=20.0 Hz, 1H), 5.66 (d, J=6.8 Hz, 1H), 4.78-4.70 (m, 1H), 4.47 (dd, J=12.4, 2.0 Hz, 1H), 4.33-4.30 (m, 1H), 4.04 (t, J=7.6 Hz, 1H), 3.83 (s, 2H), 2.94 (s, 3H), 2.20 (d, J=7.2 Hz, 2H), 1.97-1.94 (m, 1H), 1.12 (d, J=22.8 Hz, 3H), 0.89 (dd, J=6.8, 1.6 Hz, 6H). 19F NMR (376 MHz, DMSO) δ −158.53.

Example 83. Synthesis of (2R,3R,4R,5R)-5-(2-amino-6-(methylamino)-9H-purin-9-yl)-4-fluoro-4-methyl-2-((2-phenylacetoxy)methyl)tetrahydrofuran-3-yl 2-phenylacetate (Compound 209)

The title compound was prepared according to the procedure of Example 183, Step 1, using Compound 177 and 2-phenylacetyl chloride. MS (ESI): mass calcd. for $C_{28}H_{29}FN_6O_5$, 548.22, m/z found 549.1 [M+H]+. 1H NMR (400 MHz, DMSO-d6) δ 7.85 (s, 1H), 7.44-7.18 (m, 11H), 6.14 (d, J=19.6 Hz, 1H), 5.91 (s, 3H), 4.49-4.25 (m, 1H), 4.40-4.29 (m, 2H), 3.83 (d, J=2.0 Hz, 2H), 3.68 (d, J=4.8 Hz, 2H), 2.87 (s, 3H), 1.12 (d, J=22.8 Hz, 3H). 19F NMR (376 MHz, DMSO) δ −155.94.

Example 84. Synthesis of (2R,3R,4R,5R)-2-(acetoxymethyl)-5-(2-amino-6-(methylamino)-9H-purin-9-yl)-4-fluoro-4-methyltetrahydrofuran-3-yl 2-phenylacetate (Compound 210)

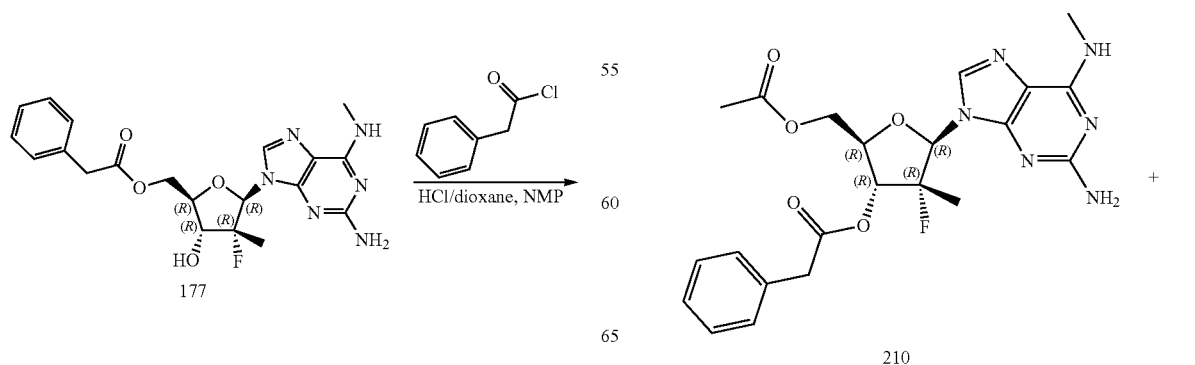

177

178

210

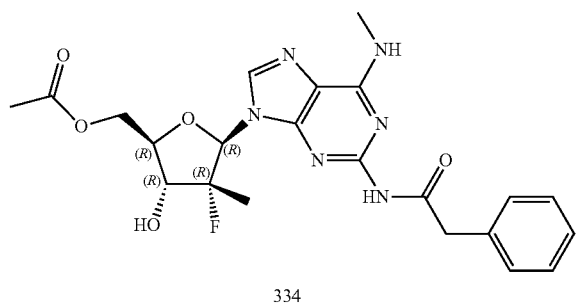

334

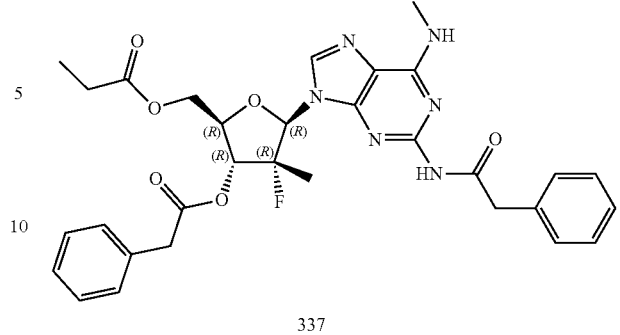

337

The title compound was prepared according to the procedure of Example 183, using 178 and 2-phenylacetyl chloride. MS (ESI): m/z calcd. for $C_{22}H_{25}FN_6O_5$ 472.19, found 473.1 [M+H]$^+$. $^1$H NMR (400 MHz, DMSO) δ 7.88 (s, 1H), 7.40-7.23 (m, 6H), 6.13 (d, J=19.6 Hz, 1H), 5.91 (s, 3H), 4.48-4.41 (m, 1H), 4.35-4.27 (m, 2H), 3.83 (d, J=1.6 Hz, 2H), 2.87 (s, 3H), 2.01 (s, 3H), 1.12 (d, J=22.8 Hz, 3H). $^{19}$F NMR (377 MHz, DMSO) δ −156.10.

Example 85. Synthesis of ((2R,3R,4R,5R)-5-(2-amino-6-(methylamino)-9H-purin-9-yl)-4-fluoro-4-methyl-3-(2-phenylacetoxy)tetrahydrofuran-2-yl) methyl propionate (Compound 212)

The title compound was prepared according to the procedure of Example 183, using 180 and 2-phenylacetyl chloride. MS (ESI): m/z calcd. for $C_{23}H_{27}FN_6O_5$ 486.20, found 487.2 [M+H]$^+$. $^1$H NMR (400 MHz, DMSO) δ 7.88 (s, 1H), 7.40-7.23 (m, 6H), 6.13 (d, J=19.2 Hz, 1H), 5.92 (s, 3H), 4.51-4.40 (m, 1H), 4.36-4.28 (m, 2H), 3.83 (d, J=2.8 Hz, 2H), 2.87 (s, 3H), 2.36-2.24 (m, 2H), 1.12 (d, J=23.2 Hz, 3H), 1.01 (t, J=7.2 Hz, 3H). $^{19}$F NMR (377 MHz, DMSO) δ −156.17.

Example 86. Synthesis of ((2R,3R,4R,5R)-3-acetoxy-5-(2-amino-6-(methylamino)-9H-purin-9-yl)-4-fluoro-4-methyltetrahydrofuran-2-yl)methyl 3-methylbutanoate (Compound 214)

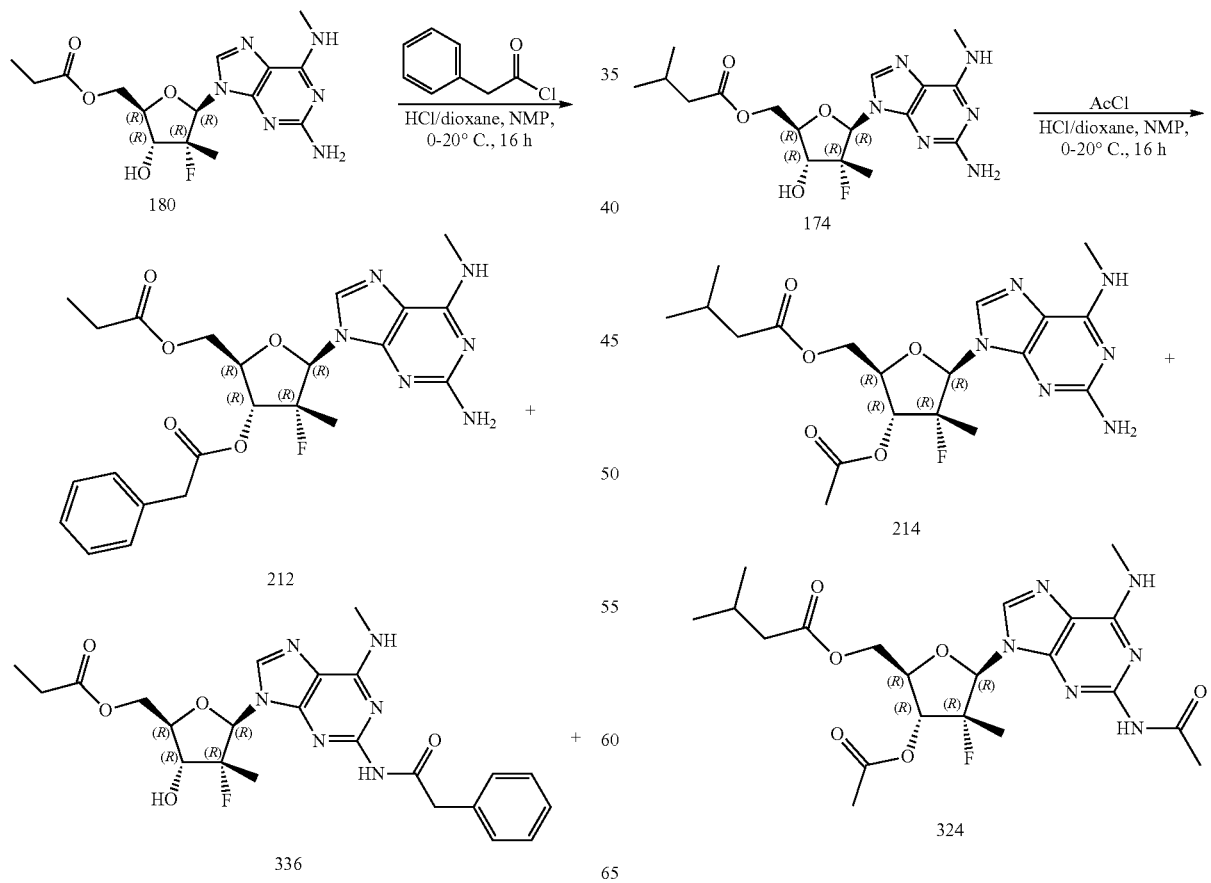

The title compound was prepared according to the procedure of Example 183, using 174 and acetyl chloride. MS (ESI): m/z calcd. for $C_{19}H_{27}FN_6O_5$ 438.20, found 439.2 [M+H]$^+$. $^1$H NMR (400 MHz, DMSO) δ 7.88 (s, 1H), 7.39 (s, 1H), 6.13 (d, J=19.2 Hz, 1H), 6.04-5.65 (m, 3H), 4.46 (dd, J=12.0, 2.8 Hz, 1H), 4.39-4.27 (m, 2H), 2.87 (s, 3H), 2.25-2.19 (m, 2H), 2.15 (s, 3H), 2.03-1.92 (m, 1H), 1.15 (d, J=23.2 Hz, 3H), 0.90 (dd, J=6.4, 2.4 Hz, 6H). $^{19}$F NMR (377 MHz, DMSO) δ −156.44.

Example 87. Synthesis of ((2R,3R,4R,5R)-3-acetoxy-5-(2-amino-6-(methylamino)-9H-purin-9-yl)-4-fluoro-4-methyltetrahydrofuran-2-yl)methyl 2-cyclohexylacetate (Compound 215)

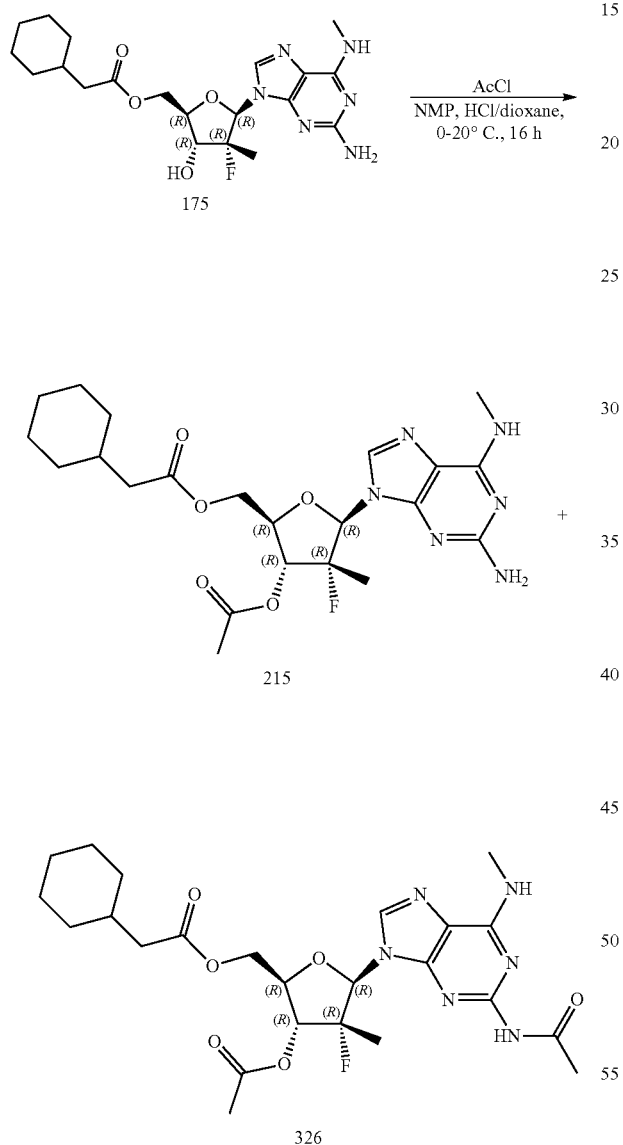

Example 88. Synthesis of ((2R,3R,4R,5R)-3-acetoxy-5-(2-amino-6-(methylamino)-9H-purin-9-yl)-4-fluoro-4-methyltetrahydrofuran-2-yl)methyl 2-phenylacetate (Compound 217)

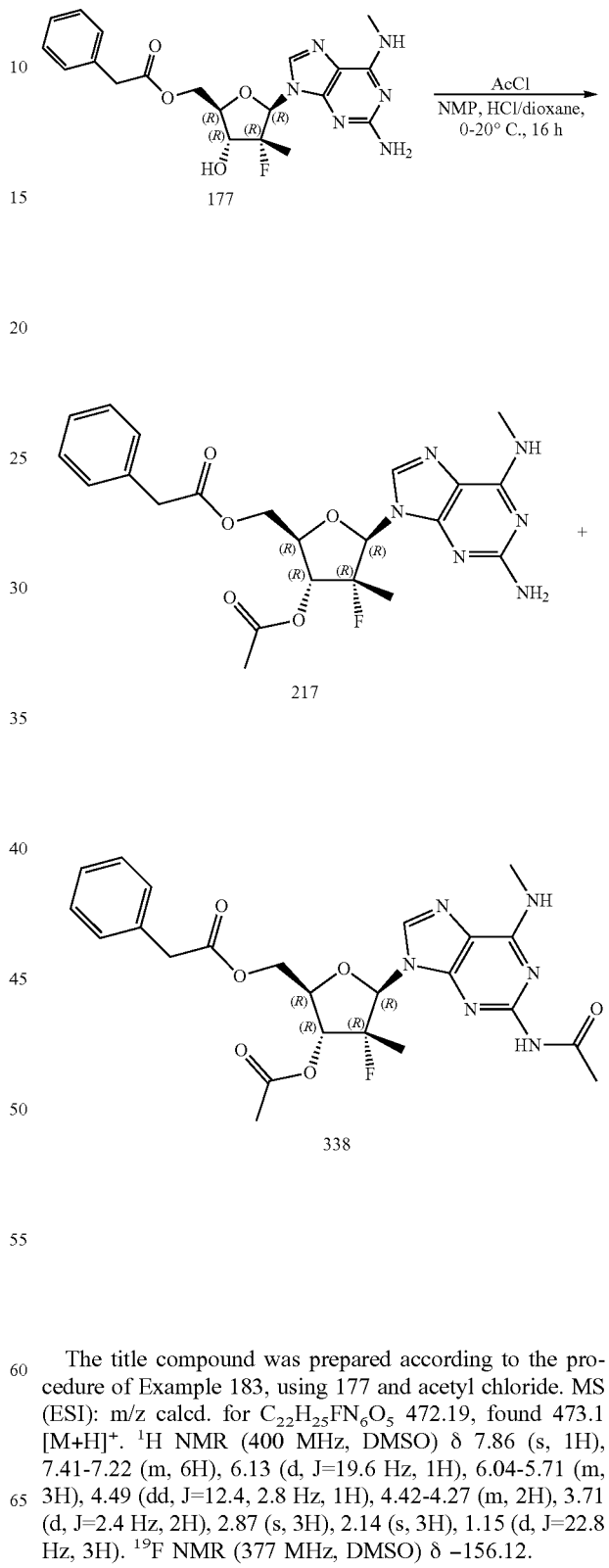

The title compound was prepared according to the procedure of Example 183, using 175 and acetyl chloride. MS (ESI): m/z calcd. for $C_{22}H_{31}FN_6O_5$ 478.23, found 479.2 [M+H]$^+$. $^1$H NMR (400 MHz, DMSO) δ 7.88 (s, 1H), 7.38 (s, 1H), 6.12 (d, J=19.6 Hz, 1H), 6.04-5.68 (m, 3H), 4.49-4.41 (m, 1H), 4.37-4.26 (m, 2H), 2.87 (s, 3H), 2.21 (d, J=6.8 Hz, 2H), 2.15 (s, 3H), 1.70-1.55 (m, 6H), 1.25-1.04 (m, 6H), 0.98-0.85 (m, 2H). $^{19}$F NMR (377 MHz, DMSO) δ −156.39.

The title compound was prepared according to the procedure of Example 183, using 177 and acetyl chloride. MS (ESI): m/z calcd. for $C_{22}H_{25}FN_6O_5$ 472.19, found 473.1 [M+H]$^+$. $^1$H NMR (400 MHz, DMSO) δ 7.86 (s, 1H), 7.41-7.22 (m, 6H), 6.13 (d, J=19.6 Hz, 1H), 6.04-5.71 (m, 3H), 4.49 (dd, J=12.4, 2.8 Hz, 1H), 4.42-4.27 (m, 2H), 3.71 (d, J=2.4 Hz, 2H), 2.87 (s, 3H), 2.14 (s, 3H), 1.15 (d, J=22.8 Hz, 3H). $^{19}$F NMR (377 MHz, DMSO) δ −156.12.

Example 89. Synthesis of ((2R,3R,4R,5R)-3-acetoxy-5-(2-amino-6-(methylamino)-9H-purin-9-yl)-4-fluoro-4-methyltetrahydrofuran-2-yl)methyl acetate (Compound 218)

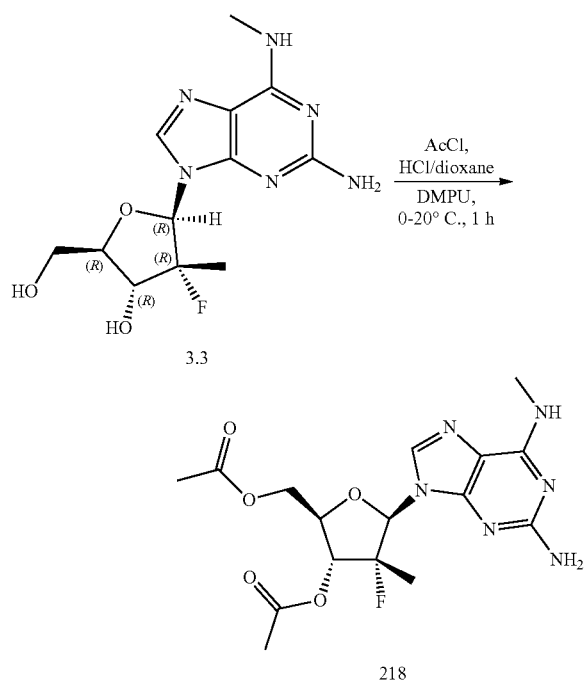

To a solution of 3.3 (500 mg, 1.6 mmol) in DMA (1 mL) was added HCl/dioxane (0.8 mL, 4 M). The mixture solution was stirred at 20° C. for 15 minutes. The reaction mixture was cooled at 0° C. and Acetyl chloride (0.91 mL, 12.8 mmol) was added at once. The reaction was stirred at 0° C. for 1 hour. The reaction was diluted with ACN (2.0 mL) and purified by prep-HPLC to obtain 218 (24.5 mg, 3.83% yield) as a white solid. MS (ESI): m/z calcd. for $C_{16}H_{21}FN_6O_5$, 396.16, found 397.0 [M+H]$^+$. $^1$H NMR (400 MHz, DMSO-d$_6$) δ 7.90 (s, 1H), 7.38 (s, 1H), 6.13 (d, J=19.6 Hz, 1H), 5.93-5.80 (m, 3H), 4.50-4.37 (m, 1H), 4.38-4.26 (m, 2H), 2.87 (s, 3H), 2.15 (s, 3H), 2.04 (s, 3H), 1.15 (d, J=22.8 Hz, 3H). $^{19}$F NMR (376 MHz, DMSO) δ −156.30.

Example 90. Synthesis of [(2R,3R,4R,5R)-3-(acetyloxy)-5-[2-amino-6-(methylamino)purin-9-yl]-4-fluoro-4-methyloxolan-2-yl]methyl 2-methylpropanoate (Compound 219) and [(2R,3R,4R,5R)-3-(acetyloxy)-5-[2-acetamido-6-(methylamino)purin-9-yl]-4-fluoro-4-methyloxolan-2-yl]methyl 2-methylpropanoate (Compound 323)

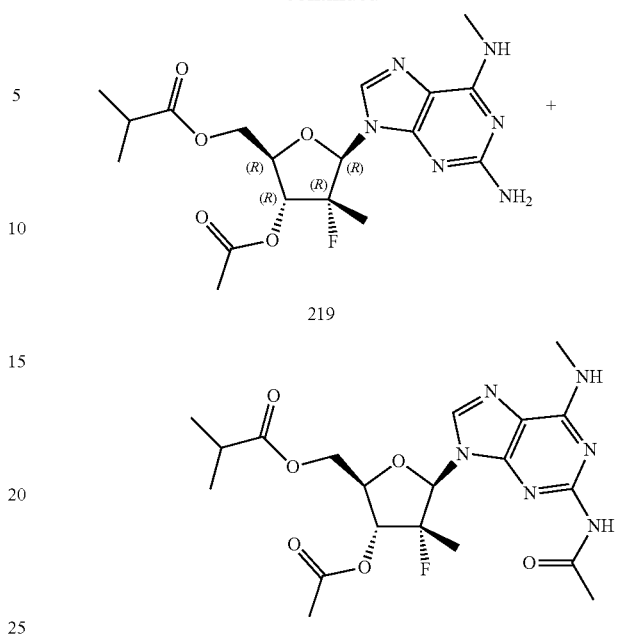

The title compound 219&323 was prepared according to the procedure of Example 65, Step 1, using 179 and acetyl chloride.

For compound 219: MS (ESI): mass calcd. for $C_{18}H_{25}FN_6O_5$, 424.19, m/z found 425.1 [M+H]$^+$. $^1$H NMR (400 MHz, DMSO) δ 7.89 (s, 1H), 7.40 (s, 1H), 6.13 (d, J=19.6 Hz, 1H), 5.90-5.86 (m, 3H), 4.45-4.44 (m, 1H), 4.37-4.31 (m, 2H), 2.87 (s, 3H), 2.58-2.52 (m, 1H), 2.15 (s, 3H), 1.20-1.07 (m, 9H). $^{19}$F NMR (376 MHz, DMSO) δ −156.51.

For compound 323: MS (ESI): mass calcd. for $C_{20}H_{27}FN_6O_6$, 466.20, m/z found 467.1 [M+H]$^+$. $^1$H NMR (400 MHz, DMSO) δ 9.94 (s, 1H), 8.18 (s, 1H), 7.91 (s, 1H), 6.23 (d, J=19.6 Hz, 1H), 6.11-6.08 (m, 1H), 4.47-4.37 (m, 2H), 4.36-4.29 (m, 1H), 2.94 (s, 3H), 2.55-2.51 (m, 1H), 2.20 (s, 3H), 2.14 (s, 3H), 1.17 (d, J=23.2 Hz, 3H), 1.08 (dd, J=7.2, 1.2 Hz, 6H). $^{19}$F NMR (376 MHz, DMSO) δ −155.42.

Example 91. Synthesis of ((2R,3R,4R,5R)-3-acetoxy-5-(2-amino-6-(methylamino)-9H-purin-9-yl)-4-fluoro-4-methyltetrahydrofuran-2-yl)methyl propionate (Compound 220)

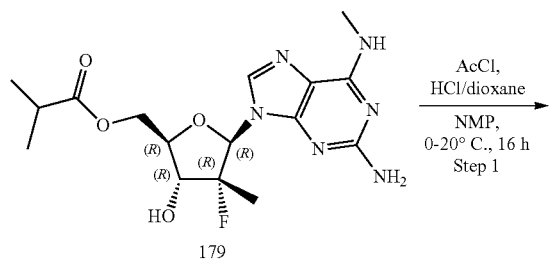

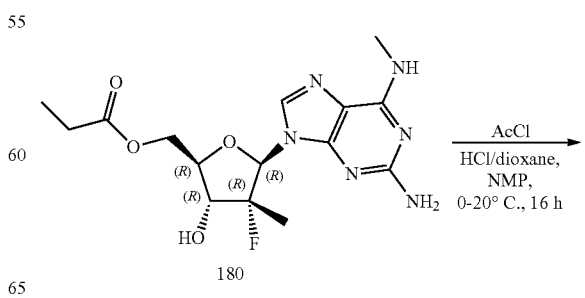

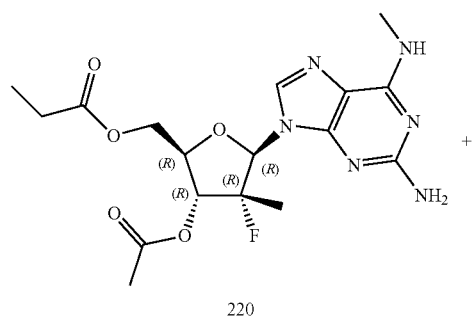

220

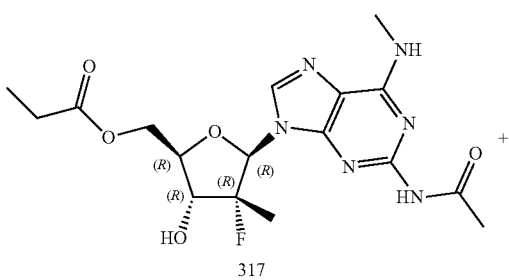

317

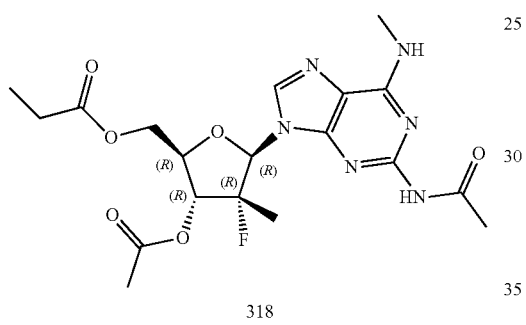

318

The title compound was prepared according to the procedure of Example 183, using 180 and acetyl chloride. MS (ESI): m/z calcd. for $C_{17}H_{23}FN_6O_5$ 410.17, found 411.1 [M+H]$^+$. $^1$H NMR (400 MHz, DMSO) δ 7.89 (s, 1H), 7.38 (s, 1H), 6.13 (d, J=19.2 Hz, 1H), 6.05-5.69 (m, 3H), 4.51-4.43 (m, 1H), 4.38-4.28 (m, 2H), 2.87 (s, 3H), 2.39-2.31 (m, 2H), 2.15 (s, 3H), 1.15 (d, J=22.8 Hz, 3H), 1.03 (t, J=7.2 Hz, 3H). $^{19}$F NMR (377 MHz, DMSO) δ −156.39.

Example 92. Synthesis of ((2R,3R,4R,5R)-5-(2-amino-6-(methylamino)-9H-purin-9-yl)-4-fluoro-3-(isobutyryloxy)-4-methyltetrahydrofuran-2-yl) methyl 3-methylbutanoate (Compound 222)

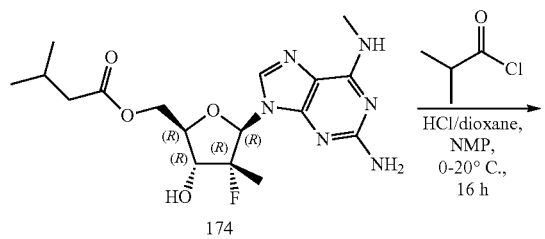

174

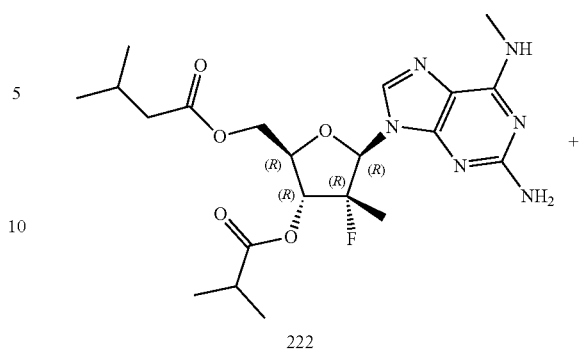

222

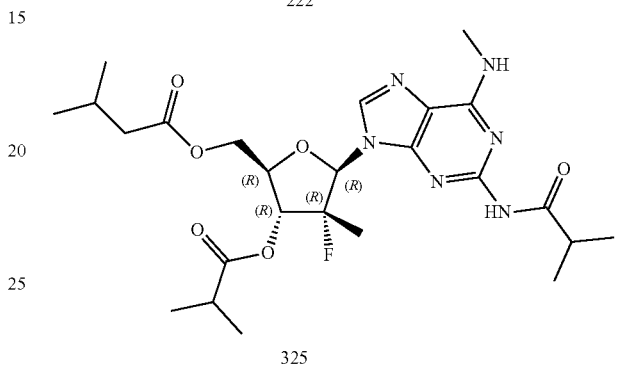

325

The title compound was prepared according to the procedure of Example 183, using 174 and 2-methylpropanoyl chloride. MS (ESI): m/z calcd. for $C_{21}H_{31}FN_6O_5$ 466.23, found 467.2 [M+H]$^+$. H NMR (400 MHz, DMSO) δ 7.88 (s, 1H), 7.39 (s, 1H), 6.13 (d, J=19.2 Hz, 1H), 6.05-5.70 (m, 3H), 4.49-4.39 (m, 1H), 4.37-4.28 (m, 2H), 2.87 (s, 3H), 2.72-2.64 (m, 1H), 2.22 (dd, J=6.8, 1.2 Hz, 2H), 2.03-1.92 (m, 1H), 1.18-1.09 (m, 9H), 0.89 (dd, J=6.8, 2.4 Hz, 6H). $^{19}$F NMR (377 MHz, DMSO) δ −156.75.

Example 93: Synthesis of (2R,3R,4R,5R)-5-[2-amino-6-(methylamino)purin-9-yl]-2-{[(2-cyclohexylacetyl)oxy]methyl}-4-fluoro-4-methyloxolan-3-yl 2-methylpropanoate (Compound 223) and [(2R,3R,4R,5R)-4-fluoro-3-hydroxy-4-methyl-5-[6-(methylamino)-2-(2-methylpropanamido)purin-9-yl]oxolan-2-yl]methyl 2-cyclohexylacetate (Compound 335)

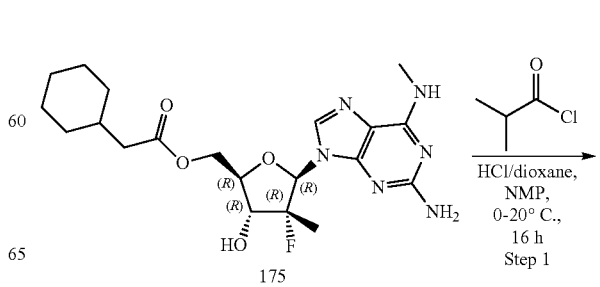

175

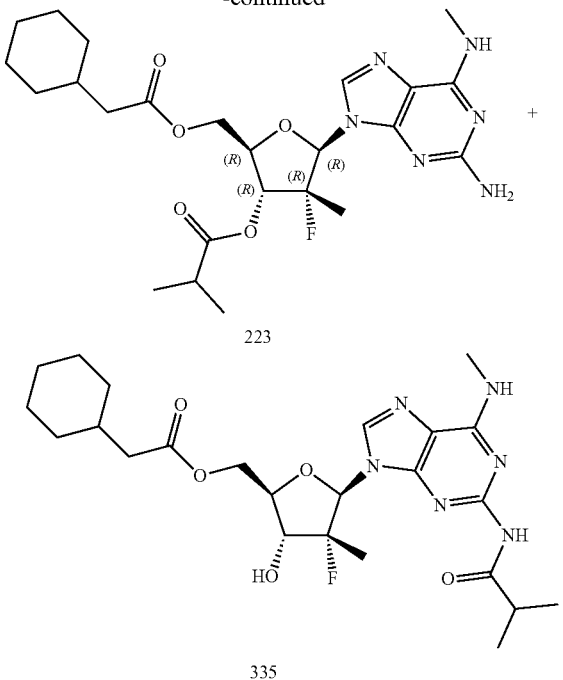

223

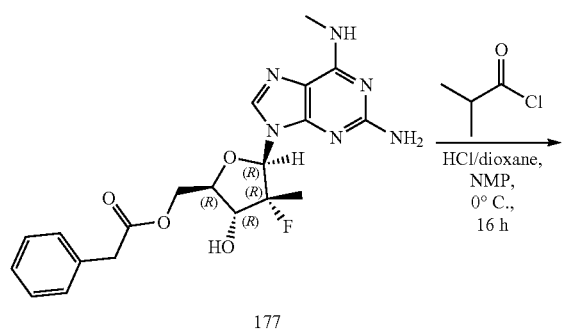

335

The title compounds 223 and 335 were prepared according to the procedure of Example 65, Step 1, using 175 and 2-methylpropanoyl chloride For compound 223: MS (ESI): mass calcd. for $C_{24}H_{35}FN_6O_5$, 506.27, m/z found 507.2 [M+H]+. $^1$H NMR (400 MHz, DMSO) δ 7.88 (s, 1H), 7.39 (s, 1H), 6.13 (d, J=19.6 Hz, 1H), 5.94-5.80 (m, 3H), 4.45-4.44 (m, 1H), 4.33-4.30 (m, 2H), 2.87 (s, 3H), 2.68-2.64 (m, 1H), 2.19 (dd, J=6.8, 2.0 Hz, 2H), 1.76-1.58 (m, 6H), 1.21-1.07 (m, 12H), 0.97-0.88 (m, 2H). $^{19}$F NMR (376 MHz, DMSO) δ −156.70.

For compound 335: MS (ESI): mass calcd. for $C_{24}H_{35}FN_6O_5$, 506.27, m/z found 507.2 [M+H]+. $^1$H NMR (400 MHz, DMSO) δ 9.93 (s, 1H), 8.12 (s, 1H), 7.80 (s, 1H), 6.13 (d, J=19.6 Hz, 1H), 5.64 (d, J=6.8 Hz, 1H), 4.80-4.78 (m, 1H), 4.44 (dd, J=12.4, 2.0 Hz, 1H), 4.3-4.30 (m, 1H), 4.04 (t, J=8.0 Hz, 1H), 2.94-2.90 (m, 4H), 2.17 (d, J=6.8 Hz, 2H), 1.62 (d, J=12.0 Hz, 6H), 1.23-1.06 (m, 12H), 0.95-0.86 (m, 2H). $^{19}$F NMR (376 MHz, DMSO) δ −158.73.

Example 94. Synthesis of (2R,3R,4R,5R)-5-(2-amino-6-(methylamino)-9H-purin-9-yl)-4-fluoro-4-methyl-2-((2-phenylacetoxy)methyl)tetrahydrofuran-3-yl isobutyrate (Compound 225)

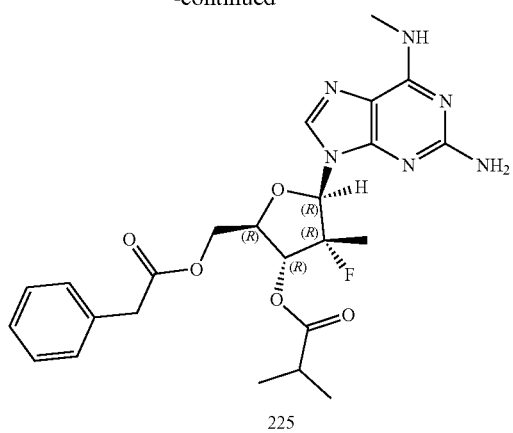

177

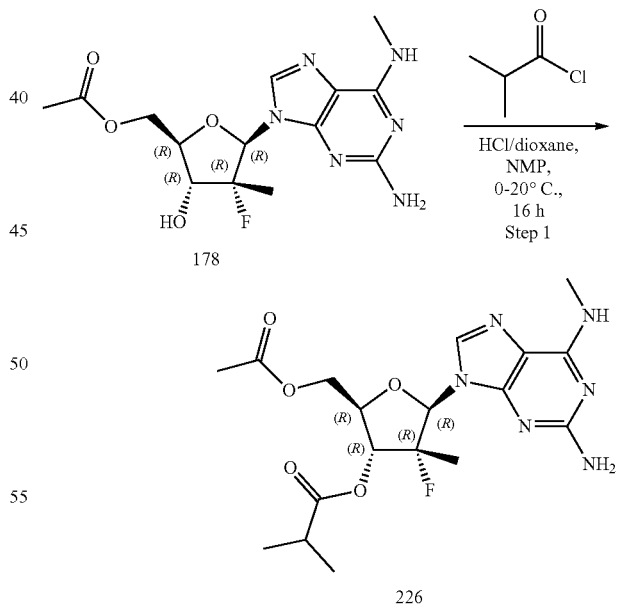

225

The title compound was prepared according to the procedure of Example 183, using 177 and isobutyryl chloride. MS (ESI): m/z calcd. for $C_{24}H_{29}FN_6O_5$ 500.22, found 501.15 [M+H]+. $^1$H NMR (400 MHz, DMSO) δ 7.88 (s, 1H), 7.38 (s, 1H), 7.38-7.17 (m, 5H), 6.16 (d, J=19.6 Hz, 1H), 5.95 (s, 3H), 4.66-4.23 (m, 3H), 3.82-3.66 (m, 2H), 2.90 (s, 3H), 2.75-2.63 (m, 1H), 1.30-1.08 (m, 9H). $^{19}$F NMR (377 MHz, DMSO) δ −156.45.

Example 95. Synthesis of (2R,3R,4R,5R)-2-[(acetyloxy)methyl]-5-[2-amino-6-(methylamino)purin-9-yl]-4-fluoro-4-methyloxolan-3-yl 2-methylpropanoate (Compound 226)

178

226

The title compound 226 was prepared according to the procedure of Example 65, Step 1, using 178 and isobutyryl chloride. For compound 226: MS (ESI): mass calcd. for $C_{18}H_{25}FN_6O_5$, 424.19, m/z found 425.1 [M+H]+. $^1$H NMR (400 MHz, DMSO) δ 7.90 (s, 1H), 7.38 (s, 1H), 6.13 (d, J=19.6 Hz, 1H), 5.94-5.90 (m, 3H), 4.44-4.40 (m, 1H), 4.38-4.25 (m, 2H), 2.87 (s, 3H), 2.68-2.63 (m, 1H), 2.02 (s, 3H), 1.18-1.09 (m, 9H). ¹⁹F NMR (376 MHz, DMSO) δ −156.59.

Example 96. Synthesis of ([(2R,3R,4R,5R)-5-[2-amino-6-(methylamino)purin-9-yl]-4-fluoro-4-methyl-3-[(2-methylpropanoyl)oxy]oxolan-2-yl] methylpropanoate (Compound 228) and [(2R,3R,4R,5R)-4-fluoro-3-hydroxy-4-methyl-5-[6-(methylamino)-2-(2-methylpropanamido)purin-9-yl] oxolan-2-yl]methylpropanoate (Compound 319)

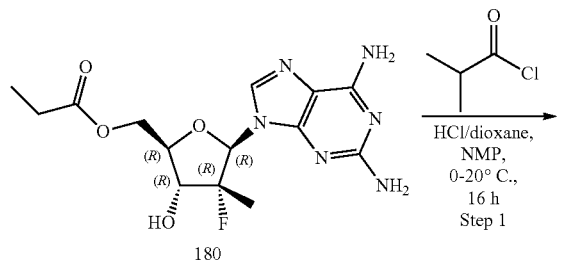

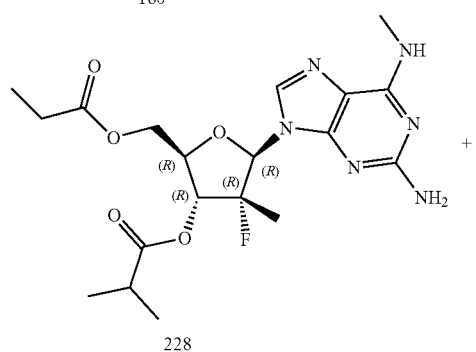

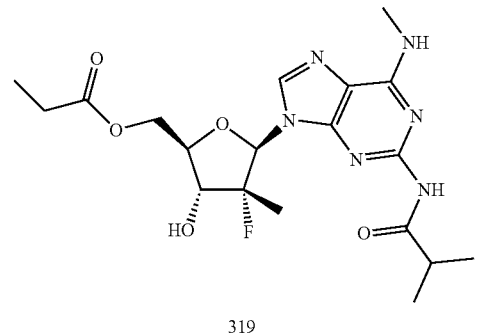

The title compounds 228 & 319 were prepared according to the procedure of Example 65, Step 1, using 180 and isobutyryl chloride.

For compound 228: MS (ESI): mass calcd. for $C_{19}H_{27}FN_6O_5$, 438.20, m/z found 439.2 [M+H]+. ¹H NMR (400 MHz, DMSO) δ 7.89 (s, 1H), 7.38 (s, 1H), 6.13 (d, J=19.6 Hz, 1H), 5.95-5.80 (m, 3H), 4.45-4.43 (m, 1H), 4.34-4.30 (m, 2H), 2.87 (s, 3H), 2.72-2.65 (m, 1H), 2.34-2.31 (m, 2H), 1.15-1.11 (m, 9H), 1.03 (t, J=7.6 Hz, 3H). ¹⁹F NMR (376 MHz, DMSO) δ −156.67.

For compound 319: MS (ESI): mass calcd. for $C_{19}H_{27}FN_6O_5$, 438.20, m/z found 439.2 [M+H]+. 1H NMR (400 MHz, DMSO) δ 9.94 (s, 1H), 8.12 (s, 1H), 7.80 (s, 1H), 6.13 (d, J=19.6 Hz, 1H), 5.63 (d, J=6.8 Hz, 1H), 4.85-4.80 (m, 1H), 4.39-4.35 (m, 2H), 4.06 (t, J=7.6 Hz, 1H), 2.94 (s, 3H), 2.51-2.49 (m, 1H), 2.33-2.28 (m, 2H), 1.16-1.06 (m, 9H), 1.00 (t, J=7.6 Hz, 3H). ¹⁹F NMR (376 MHz, DMSO) δ −158.71.

Example 97. Synthesis of [(2R,3R,4R,5R)-5-[2-amino-6-(methylamino)purin-9-yl]-4-fluoro-4-methyl-3-(propanoyloxy)oxolan-2-yl]methyl 3-methylbutanoate (Compound 230), [(2R,3R,4R,5R)-4-fluoro-3-hydroxy-4-methyl-5-[6-(methylamino)-2-propanamidopurin-9-yl]oxolan-2-yl] methyl 3-methylbutanoate (Compound 310), and [(2R,3R,4R,5R)-4-fluoro-4-methyl-5-[6-(methylamino)-2-propanamidopurin-9-yl]-3-(propanoyloxy) oxolan-2-yl]methyl 3-methylbutanoate (Compound 311)

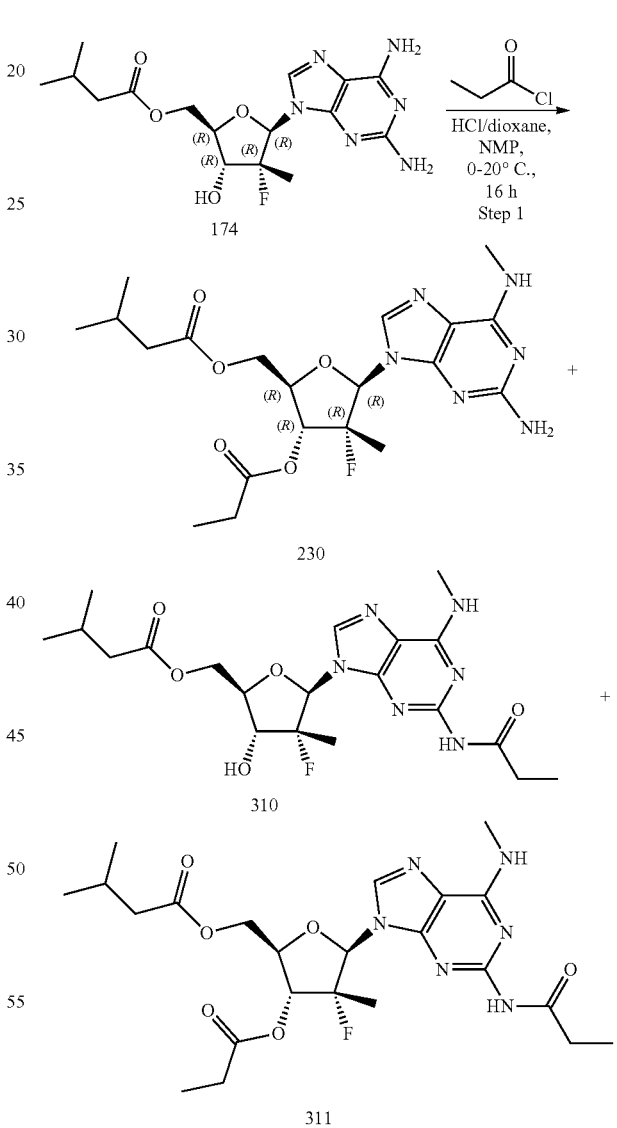

The title compounds 230, 310, and 311 were prepared according to the procedure of Example 65, Step 1, using 174 and propanoyl chloride.

For compound 230: MS (ESI): mass calcd. for $C_{20}H_{29}FN_6O_5$, 452.22, m/z found 453.2 [M+H]+. ¹H NMR (400 MHz, DMSO) δ 7.88 (s, 1H), 7.39 (s, 1H), 6.13 (d, J=19.6 Hz, 1H), 5.94-5.90 (m, 3H), 4.46 (dd, J=12.0, 2.4 Hz, 1H), 4.40-4.26 (m, 2H), 2.87 (s, 3H), 2.45 (d, J=7.2 Hz, 2H), 2.25-2.17 (m, 2H), 1.98-1.94 (m, 1H), 1.14 (d, J=22.8 Hz, 3H), 1.08 (t, J=7.6 Hz, 3H), 0.90 (dd, J=6.8, 2.8 Hz, 6H). $^{19}$F NMR (376 MHz, DMSO) δ −156.52.

For compound 310: MS (ESI): mass calcd. for $C_{20}H_{29}FN_6O_5$, 452.22, m/z found 453.2 [M+H]$^+$. $^1$H NMR (400 MHz, DMSO) δ 9.94 (s, 1H), 8.11 (s, 1H), 7.82 (s, 1H), 6.12 (d, J=20.0 Hz, 1H), 5.66 (d, J=7.2 Hz, 1H), 4.79-4.76 (m, 1H), 4.48 (dd, J=12.4, 2.0 Hz, 1H), 4.35-4.32 (m, 1H), 4.05 (t, J=8.0 Hz, 1H), 2.93 (s, 3H), 2.52-2.50 (m, 2H), 2.18 (d, J=6.8 Hz, 2H), 1.96-1.93 (m, 1H), 1.13 (d, J=22.8 Hz, 3H), 1.06 (t, J=7.6 Hz, 3H), 0.88 (dd, J=6.8, 1.6 Hz, 6H). $^{19}$F NMR (376 MHz, DMSO) δ −158.47.

For compound 311: MS (ESI): mass calcd. for $C_{23}H_{33}FN_6O_6$, 508.24, m/z found 509.2 [M+H]$^+$. $^1$H NMR (400 MHz, DMSO) δ 9.86 (s, 1H), 8.18 (s, 1H), 7.89 (s, 1H), 6.23 (d, J=20.0 Hz, 1H), 6.08 (d, J=15.6 Hz, 1H), 4.42-4.37 (m, 2H), 4.35-4.27 (m, 1H), 2.94 (s, 3H), 2.54-2.51 (m, 2H), 2.45-2.42 (m, 2H), 2.19 (d, J=7.2 Hz, 2H), 1.96-1.90 (m, 1H), 1.18 (d, J=23.6 Hz, 3H), 1.06-1.03 (m, 6H), 0.89 (dd, J=6.8, 2.0 Hz, 6H). $^{19}$F NMR (376 MHz, DMSO) δ −155.59.

Example 98. Synthesis of [(2R,3R,4R,5R)-5-[2-amino-6-(methylamino)purin-9-yl]-4-fluoro-4-methyl-3-(propanoyloxy)oxolan-2-yl]methyl cyclohexanecarboxylate (Compound 231) and [(2R,3R,4R,5R)-4-fluoro-3-hydroxy-4-methyl-5-[6-(methylamino)-2-propanamidopurin-9-yl]oxolan-2-yl]methyl cyclohexanecarboxylate (Compound 327)

The title compounds 231 and 327 were prepared according to the procedure of Example 65, Step 1, using 175 and propanoyl chloride For compound 231: MS (ESI): mass calcd. for $C_{23}H_{33}FN_6O_5$, 492.25, m/z found 493.2 [M+H]$^+$. $^1$H NMR (400 MHz, DMSO) δ 7.88 (s, 1H), 7.38 (s, 1H), 6.13 (d, J=19.6 Hz, 1H), 5.93-5.80 (m, 3H), 4.45 (d, J=8.0 Hz, 1H), 4.33-4.25 (m, 2H), 2.87 (s, 3H), 2.44 (d, J=7.6 Hz, 2H), 2.24-2.17 (m, 2H), 1.74-1.58 (m, 6H), 1.21-1.03 (m, 9H), 0.97-0.86 (m, 2H). $^{19}$F NMR (376 MHz, DMSO) δ −156.46.

For compound 327: MS (ESI): mass calcd. for $C_{23}H_{33}FN_6O_5$, 492.25, m/z found 493.2 [M+H]$^+$. $^1$H NMR (400 MHz, DMSO) δ 9.94 (s, 1H), 8.11 (s, 1H), 7.82 (s, 1H), 6.12 (d, J=19.8 Hz, 1H), 5.65 (d, J=6.8 Hz, 1H), 4.78-4.75 (m, 1H), 4.47 (dd, J=12.4, 2.0 Hz, 1H), 4.33 (dd, J=12.4, 7.2 Hz, 1H), 4.04 (t, J=7.8 Hz, 1H), 2.93 (s, 3H), 2.18 (d, J=6.8 Hz, 2H), 1.62-1.60 (m, 6H), 1.22-1.02 (m, 9H), 0.98-0.85 (m, 2H). $^{19}$F NMR (376 MHz, DMSO) δ −158.51.

Example 99. Synthesis of (2R,3R,4R,5R)-5-(2-amino-6-(methylamino)-9H-purin-9-yl)-4-fluoro-4-methyl-2-((2-phenylacetoxy)methyl)tetrahydrofuran-3-yl propionate (Compound 233)

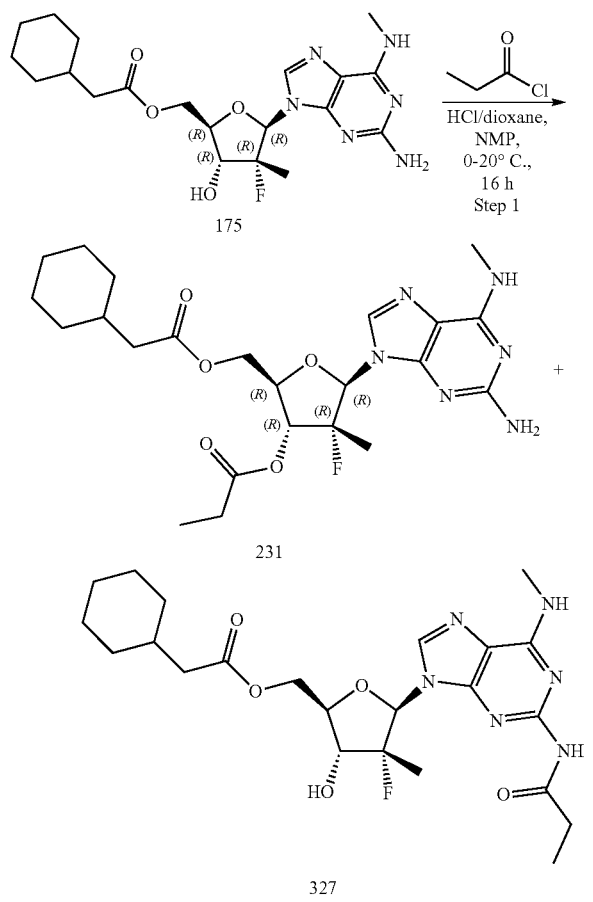

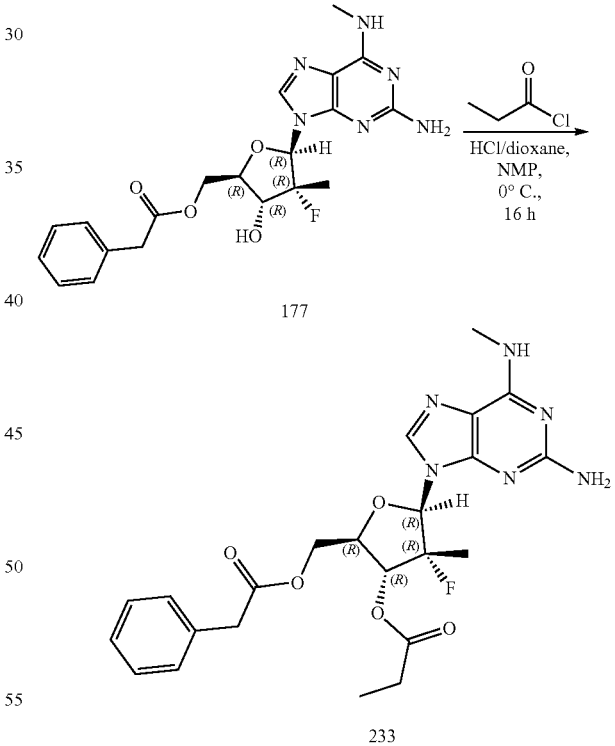

The title compound was prepared according to the procedure of Example 183, using 177 and propionyl chloride. MS (ESI): m/z calcd. for $C_{23}H_{27}FN_6O_5$ 486.20, found 487.15 [M+H]$^+$. $^1$H NMR (400 MHz, DMSO) δ 7.86 (s, 1H), 7.49-7.33 (m, 1H), 7.33-7.21 (m, 5H), 6.13 (d, J=19.6 Hz, 1H), 5.93 (s, 3H), 4.49 (dd, J=12.0, 2.8 Hz, 1H), 4.38 (dd, J=12.0, 6.0 Hz, 1H), 4.35-4.27 (m, 1H), 3.77-3.64 (m, 2H), 2.87 (s, 3H), 2.45 (q, J=7.2 Hz, 2H), 1.20-1.04 (m, 6H). $^{19}$F NMR (377 MHz, DMSO) δ −156.22.

Example 100. Synthesis of (2R,3R,4R,5R)-5-(2-amino-6-(methylamino)-9H-purin-9-yl)-4-fluoro-4-methyl-2-((propionyloxy)methyl)tetrahydrofuran-3-yl propionate (Compound 236)

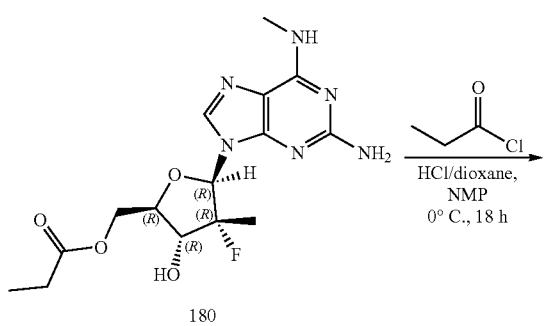

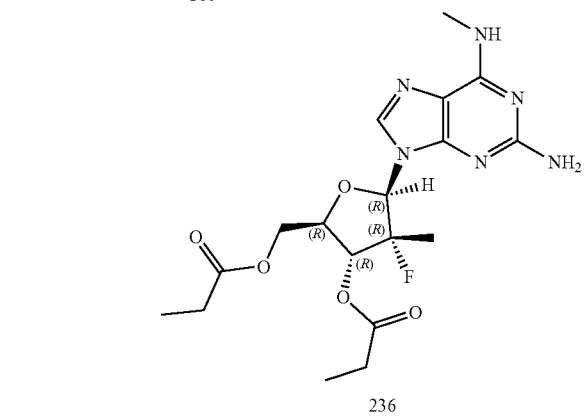

The title compound was prepared according to the procedure of Example 183, using 180 and propionyl chloride. MS (ESI): m/z calcd. for $C_{18}H_{25}FN_6O_5$ 424.19, found 425.10 [M+H]$^+$. $^1$H NMR (400 MHz, DMSO) δ 7.89 (s, 1H), 7.38 (s, 1H), 6.13 (d, J=19.6 Hz, 1H), 5.94 (s, 3H), 4.47 (d, J=9.2 Hz, 1H), 4.38-4.28 (m, 2H), 2.88 (s, 3H), 2.45 (q, J=7.6 Hz, 2H), 2.39-2.30 (m, 2H), 1.20-1.00 (m, 9H). $^{19}$F NMR (377 MHz, DMSO) δ −156.47.

Example 101. Synthesis of ((2R,3R,4R,5R)-5-(2-amino-6-(methylamino)-9H-purin-9-yl)-4-fluoro-3-hydroxy-4-methyltetrahydrofuran-2-yl)methyl (2-(octadecyloxy)ethyl) hydrogen phosphate (Compound 254)

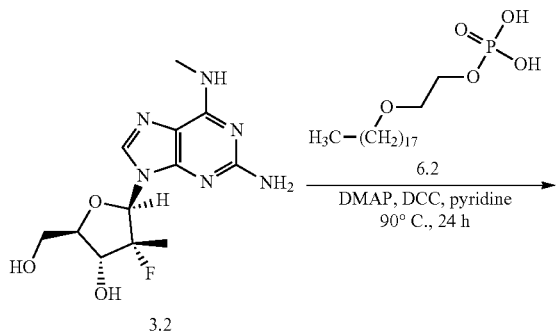

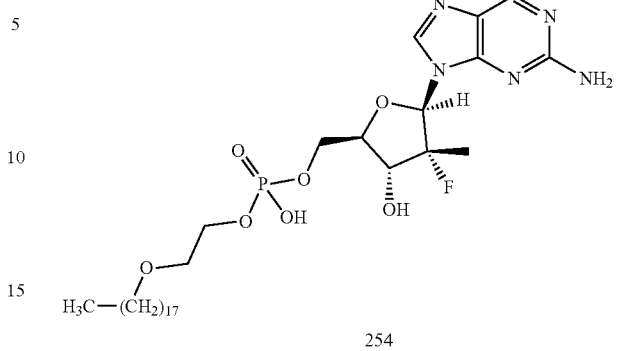

The title compound was prepared according to the procedure of Example 6, Step 3, utilizing alcohol 3.2. MS (ESI): mass calcd. for $C_{32}H_{58}FN_6O_7P$, 688.41, m/z found 687.4 [M−H]$^-$. $^1$H NMR (400 MHz, DMSO-d$_6$) δ 8.08 (s, 1H), 6.14 (d, J=18 Hz, 1H), 4.26-4.4 (m, 3H), 4.2 (m, 1H), 4.01 (m, 2H), 3.62 (m, 2H), 3.4 (m, 2H), 3.0-3.3 (m, 3H), 1.53 (m, 2H), 1.2-1.35 (br m, 30H), 1.19 (d, J=22 Hz, 3H), 0.92 (t, J=7 Hz, 3H).

Example 102. Synthesis of [(2R,3S,4R,5R)-5-{4-aminopyrrolo[2,1-f][1,2,4]triazin-7-yl}-5-cyano-3,4-dihydroxyoxolan-2-yl]methyl (2S)-3-methyl-2-(3-methylbutanamido)butanoate (Compound 255)

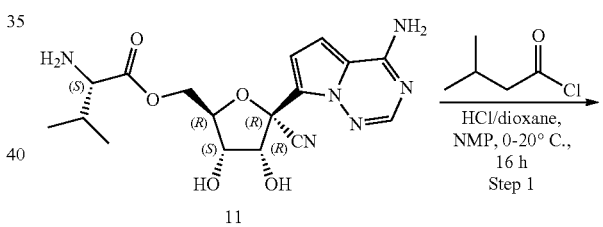

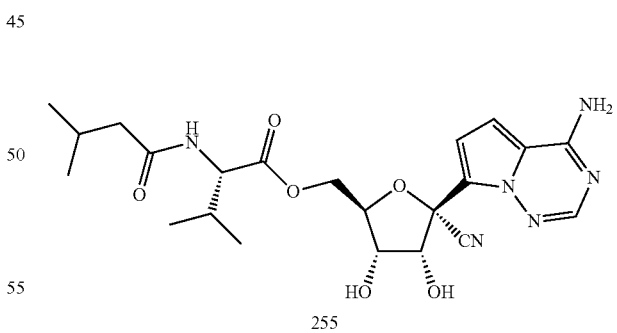

The title compound 255 was prepared according to the procedure of Example 65, Step 1, using 11 and 3-methylbutanoyl chloride. For compound 231: MS (ESI): mass calcd. for $C_{22}H_{30}FN_6O_6$, 474.22, m/z found 475.2 [M+H]$^+$. $^1$H NMR (400 MHz, DMSO) δ 8.03 (d, J=8.0 Hz, 1H), 7.92 (br, s, 3H), 6.92 (d, J=4.4 Hz, 1H), 6.83 (d, J=4.4 Hz, 1H), 6.36-6.34 (m, 1H), 5.40-5.35 (m, 1H), 4.68-4.64 (m, 1H), 4.35-4.18 (m, 4H), 3.91-3.87 (m, 1H), 2.06-1.97 (m, 4H), 0.91-0.87 (m, 6H), 0.85-0.81 (m, 6H).

Example 103. Synthesis of [({[(2R,3S,4R,5R)-5-{4-aminopyrrolo[2,1-f][1,2,4]triazin-7-yl}-5-cyano-3,4-dihydroxyoxolan-2-yl]methoxy}({[(2,2-dimethyl-propanoyl)oxy]methoxy})phosphoryl)oxy]methyl 2,2-dimethylpropanoate (Compound 256)
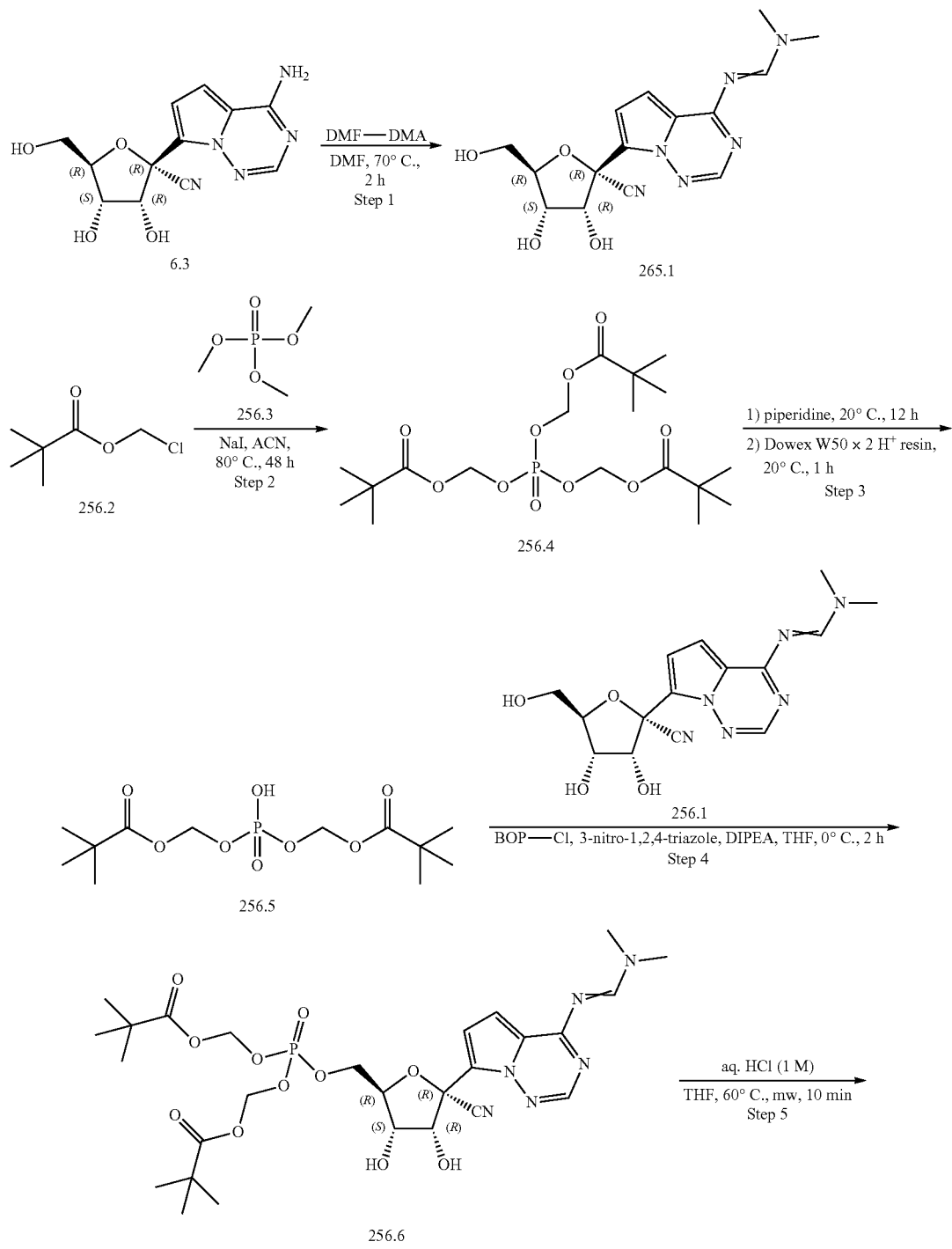

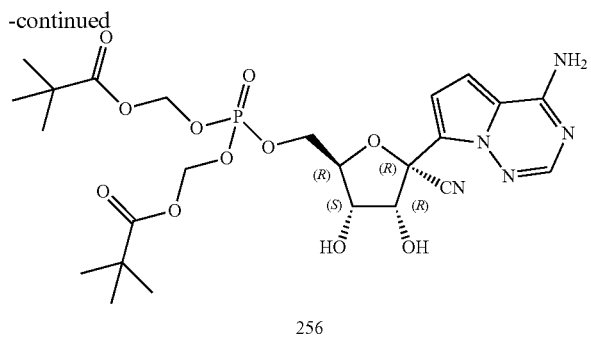

256

Step 1. Synthesis of N'-(7-((2R,3R,4S,5R)-2-cyano-3,4-dihydroxy-5-(hydroxymethyl)tetrahydrofuran-2-yl)pyrrolo[2,1-f][1,2,4]triazin-4-yl)-N,N-dimethylformimidamide (256.1)

To a solution of 6.3 (5.00 g, 17.2 mmol) in dry DMF (60 mL) was added DMF-DMA (2.46 g, 20.6 mmol). The reaction mixture was stirred at 70° C. for 2 h under nitrogen. The reaction mixture was diluted with EA (80 mL) and washed with water (150 mL×2), followed by brine (150 mL×2), dried over anhydrous $Na_2SO_4$, filtered. The filtrate was concentrated to dryness. The residue was slurried in MeOH (30 mL) for 1 h and filtered. The filter cake was washed with MeOH (5.0 mL), then dried in vacuo to give 256.1 (4.45 g, 74% yield) as a white solid. MS (ESI): m/z calcd. for $C_{15}H_{18}N_6O_4$ 346.14, found 347.1 [M+H]$^+$. $^1$H NMR (400 MHz, DMSO) δ 8.95 (s, 1H), 8.15 (s, 1H), 6.99 (d, J=4.4 Hz, 1H), 6.83 (d, J=4.4 Hz, 1H), 6.12 (d, J=6.4 Hz, 1H), 5.22 (d, J=5.2 Hz, 1H), 4.92 (t, J=5.6 Hz, 1H), 4.67 (dd, J=6.4, 5.6 Hz, 1H), 4.08 (dd, J=8.4, 4.4 Hz, 1H), 3.99 (q, J=5.2 Hz, 1H), 3.68-3.61 (m, 1H), 3.56-3.48 (m, 1H), 3.25 (s, 3H), 3.19 (s 3H).

Step 2. Synthesis of ((oxo-15-phosphanetriyl)tris(oxy))tris(methylene) tris(2,2-dimethylpropanoate) (256.4)

To a solution of 256.3 (5.00 g, 35.7 mmol) in dry ACN (30 mL) was sequentially added 256.2 (21.5 g, 0.143 mol) and sodium iodide (16.1 g, 0.107 mol). The reaction mixture was stirred at 80° C. for 72 h under nitrogen. TLC showed complete consumption of 256.3. The reaction mixture was diluted with $Et_2O$ (150 mL) and washed with water (80 mL×2), followed by Sat. aq. $Na_2S_2O_3$ (80 mL×2), dried over anhydrous $Na_2SO_4$, filtered. The filtrate was concentrated to dryness. The residue was purified by FCC (Gradient: 20% EA in PE) to give 256.4 (8.65 g, 55% yield) as a colorless oil. $^1$H NMR (400 MHz, CDCl$_3$) δ 5.66 (d, J=13.6 Hz, 6H), 1.24 (s, 27H). $^{31}$P NMR (162 MHz, CDCl$_3$) δ −5.22.

Step 3. Synthesis of ((hydroxyphosphoryl)bis(oxy))bis(methylene)bis(2,2-dimethylpropanoate) (256.5)

256.3 (8.65 g, 20 mmol) was dissolved in piperidine (50 mL) and stirred at 20° C. for 16 h under nitrogen. TLC showed complete consumption of 256.3. The reaction mixture was concentrated until constant weight. The residue was dissolved in water (180 mL) and treated with Dowex W50×2 H$^+$ form resin (150 g). The suspension was stirred at 20° C. for 1 h and filtered. The filtrate was concentrated to remove the solvent. The residue was lyophilized to give 256.4 (7.46 g, crude) as a white wax. $^1$H NMR (400 MHz, CDCl$_3$) δ 5.57 (d, J=12.4 Hz, 6H), 1.22 (s, 18H). $^{31}$P NMR (162 MHz, CDCl$_3$) δ −4.08.

Step 4. Synthesis of [({[(2R,3S,4R,5R)-5-cyano-5-(4-{[(dimethylamino)methylidene]amino}pyrrolo[2,1-f][1,2,4]triazin-7-yl)-3,4-dihydroxyoxolan-2-yl]methoxy}({[(2,2-dimethylpropanoyl)oxy]methoxy})phosphoryl)oxy]methyl 2,2-dimethylpropanoate (256.6)

To a solution of 256.1 (500 mg, 1.44 mmol) in dry THF (20 mL) was added a solution of triethylammonium bis(POM)phosphate in THF (prepared from 265.5 (565 mg, 1.73 mmol), THF (5.0 mL) and TEA (190 mg, 1.88 mmol)). The resulting mixture was cooled to 0° C. in an ice-batch and DIPEA (746 mg, 5.77 mmol) was added, followed by BOP-Cl (735 mg, 2.89 mmol) and 3-nitro-4,2,4-triazole (329 mg, 2.89 mmol). The reaction mixture was stirred at 0° C. for 2 h. The reaction mixture was diluted with DCM (150 mL) and washed with Sat. aq. NaHCO$_3$ (25 mL×2), followed by brine (25 mL). The aqueous phase was extracted with DCM (25 mL). The combined organic phase was dried over anhydrous $Na_2SO_4$, filtered. The filtrate was concentrated to dryness. The residue was purified by FCC (Gradient: 5% MeOH in DCM) to give 256.6 (71.1 mg, 7.5% yield) as a white solid. MS (ESI): m/z calcd. for $C_{27}H_{39}N_6O_{11}P$ 654.24, found 655.2 [M+H]$^+$. $^1$H NMR (400 MHz, DMSO) δ 8.94 (s, 1H), 8.14 (s, 1H), 6.92 (d, J=4.8 Hz, 1H), 6.81 (d, J=4.4 Hz, 1H), 6.37 (d, J=6.0 Hz, 1H), 5.57 (s, 2H), 5.54 (s, 2H), 5.44 (d, J=6.0 Hz, 1H), 4.73-4.69 (m, 1H), 4.32-4.23 (m, 2H), 4.20-4.14 (m, 1H), 3.96 (dd, J=11.2, 5.6 Hz, 1H), 3.25 (s, 3H), 3.18 (s, 3H), 1.14 (d, J=5.6 Hz, 18H). $^{31}$P NMR (162 MHz, DMSO) δ −3.93.

Step 5. Synthesis of [({[(2R,3S,4R,5R)-5-{4-aminopyrrolo[2,1-f][1,2,4]triazin-7-yl}-5-cyano-3,4-dihydroxyoxolan-2-yl]methoxy}({[(2,2-dimethylpropanoyl)oxy]methoxy})phosphoryl)oxy]methyl 2,2-dimethylpropanoate (Compound 256)

A solution of 256.6 (71.1 mg, 0.109 mmol) in dry THF (1.0 mL) was added aq. HCl (0.5 mL, 1 M). The reaction mixture was radiated at 60° C. in microwave reactor for 10 min under nitrogen. The organic solvent was removed with flowing nitrogen. The residue was purified by Prep-HPLC to afford the title compound 256 (30.6 mg, 47% yield) as a white solid. MS (ESI): m/z calcd. for $C_{24}H_{34}N_5O_{11}P$ 599.20, found 600.2 [M+H]$^+$. $^1$H NMR (400 MHz, DMSO) δ 7.92 (br s, 3H), 6.90 (d, J=4.4 Hz, 1H), 6.81 (d, J=4.4 Hz, 1H), 6.36 (d, J=6.0 Hz, 1H), 5.56 (dd, J=14.0, 1.2 Hz, 4H), 5.43

(d, J=5.6 Hz, 1H), 4.68 (t, J=5.6 Hz, 1H), 4.31-4.21 (m, 2H), 4.19-4.12 (m, 1H), 3.96-3.90 (m, 1H), 1.14 (d, J=5.2 Hz, 18H). $^{31}$P NMR (162 MHz, DMSO) δ −3.93.

Example 104. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-(tetrahydro-2H-pyran-4-yl)acetate (Compound 257)

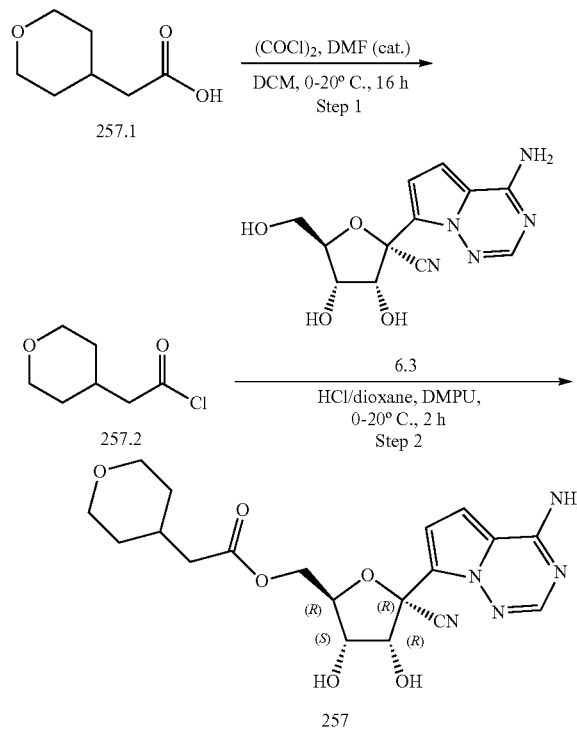

Step 1. Synthesis of 2-(tetrahydro-2H-pyran-4-yl)acetyl chloride (257.2)

To a solution of 257.1 (500 mg, 3.47 mmol) in dry DCM (7.0 mL) was added oxalyl chloride (660 mg, 5.20 mmol) dropwise at 0° C. The reaction mixture was stirred at 20° C. for 16 h. The reaction mixture was concentrated to dryness to give 257.2 (510 mg, crude) as a yellow oil, which was used directly in next step.

Step 2. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-(tetrahydro-2H-pyran-4-yl)acetate (257)

To a solution 6.3 (100 mg, 0.343 mmol) in DMPU (1.0 mL) was added HCl/1,4-dioxane (0.1 mL, 4 M) dropwise at 0° C. The reaction mixture was stirred at 0° C. for 15 min and then 257.2 (510 mg, crude) was added dropwise into the flask vessel. The reaction mixture was stirred at 20° C. for 2 h. The reaction mixture was purified by prep-HPLC to afford the title compound 257 (22.39 mg, 16% yield) as a white solid. MS (ESI): m/z calcd. for $C_{19}H_{23}N_5O_6$ 417.16, found 418.0 [M+H]$^+$. $^1$H NMR (400 MHz, DMSO) δ 7.92 (br s, 3H), 6.92 (d, J=4.8 Hz, 1H), 6.80 (d, J=4.4 Hz, 1H), 6.32 (d, J=6.0 Hz, 1H), 5.38 (d, J=5.6 Hz, 1H), 4.69 (t, J=5.6 Hz, 1H), 4.32 (dd, J=11.6, 2.4 Hz, 1H), 4.25-4.14 (m, 2H), 3.94 (dd, J=11.2, 6.0 Hz, 1H), 3.76 (dd, J=11.2, 2.8 Hz, 1H), 3.23 (t, J=11.6 Hz, 2H), 2.19 (dd, J=6.8, 2.4 Hz, 2H), 1.89-1.77 (m, 1H), 1.51 (d, J=11.6 Hz, 2H), 1.22-1.10 (m, 2H).

Example 105. Synthesis of [(2R,3S,4R,5R)-5-{4-aminopyrrolo[2,1-f][1,2,4]triazin-7-yl}-5-cyano-3,4-dihydroxyoxolan-2-yl]methyl 2-cyclopropylacetate (Compound 258)

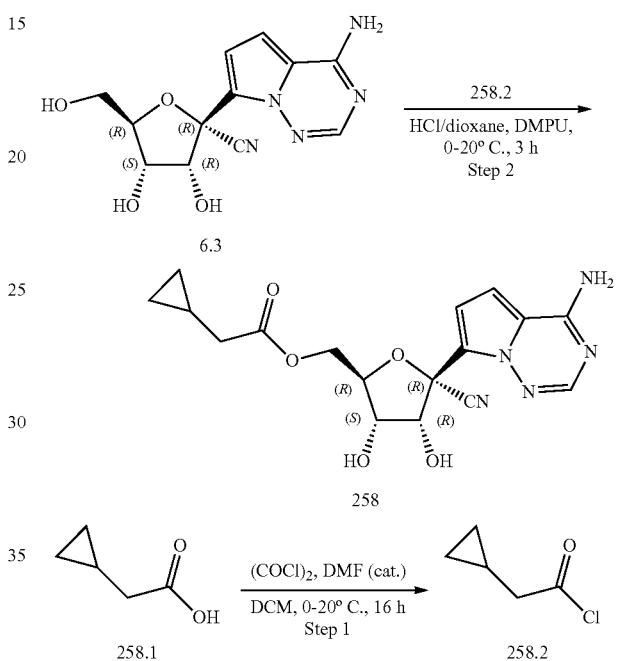

Step 1. Synthesis of 2-cyclopropylacetyl chloride (258.2)

To a solution of 2-cyclopropylacetic acid (258.1, 500 mg, 5.0 mmol) in DCM (3 mL) was added oxalyl chloride (0.48 mL, 5.64 mmol), followed by a few drops of DMF at 0° C. The resulting solution was stirred at 20° C. for 1 h The mixture was concentrated in vacuo. and the resulting acid chloride was used for next step without further purification.

Step 2. Synthesis of [(2R,3S,4R,5R)-5-{4-aminopyrrolo[2,1-f][1,2,4]triazin-7-yl}-5-cyano-3,4-dihydroxyoxolan-2-yl]methyl 2-cyclopropylacetate (258)

The compound 258 was prepared according to the procedure of Example 1, Step 4, using 6.3 and 258.2. MS (ESI): mass calcd. for $C_{17}H_{19}N_5O_5$, 373.14, m/z found 374.2 [M+H]$^+$. 1H NMR (400 MHz, DMSO) δ 7.92 (br, s, 3H), 6.90 (d, J=4.4 Hz, 1H), 6.80 (d, J=4.4 Hz, 1H), 6.31 (d, J=6.4 Hz, 1H), 5.38 (d, J=5.6 Hz, 1H), 4.68 (t, J=5.6 Hz, 1H), 4.34 (dd, J=12.0, 2.8 Hz, 1H), 4.26-4.20 (m, 1H), 4.16 (dd, J=12.0, 5.6 Hz, 1H), 3.95-3.91 (m, 1H), 2.25-2.18 (m, 2H), 0.95-0.84 (m, 1H), 0.4-0.40 (m, 2H), 0.13-0.06 (m, 2H).

Example 106. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-cyclopentylacetate (Compound 259)

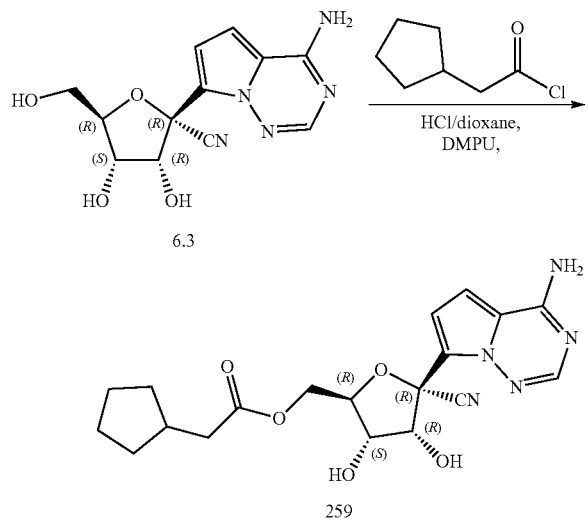

The title compound was prepared according to the procedure of Example 5, Step 4, using 6.3 and 2-cyclopentylacetyl chloride. MS (ESI): mass calcd. for $C_{19}H_{23}N_5O_5$, 401.17, m/z found 402.0 [M+H]$^+$. $^1$H NMR (400 MHz, DMSO-d$_6$) δ 7.92 (br s, 3H), 6.91 (d, J=4.4 Hz, 1H), 6.80 (d, J=4.4 Hz, 1H), 6.32 (d, J=6.0 Hz, 1H), 5.38 (d, J=6.0 Hz, 1H), 4.69 (t, J=5.6 Hz, 1H), 4.31 (dd, J=12.0, 2.8 Hz, 1H), 4.22 (dd, J=10.4, 4.4 Hz, 1H), 4.15 (dd, J=12.0, 5.6 Hz, 1H), 3.94 (dd, J=11.2, 6.0 Hz, 1H), 2.27 (dd, J=7.6, 2.0 Hz, 2H), 2.06 (dt, J=15.6, 8.0 Hz, 1H), 1.75-1.65 (m, 2H), 1.60-1.42 (m, 4H), 1.12-1.01 (m, 2H).

Example 107. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-(2,3-dihydro-1H-inden-2-yl)acetate (Compound 260)

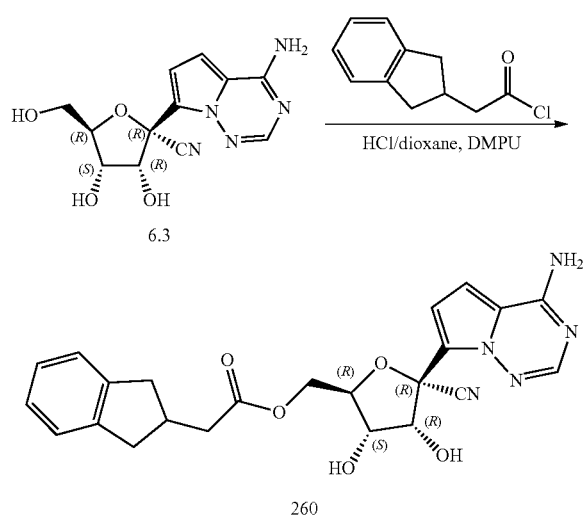

The title compound was prepared according to the procedure of Example 5, Step 4, using 6.3 and 2-(2,3-dihydro-1H-inden-2-yl)acetyl chloride (prepared according to *J. Am. Chem. Soc.* (2019), 141(9), 3849-3853). MS (ESI): mass calcd. for $C_{23}H_{23}N_5O_5$, 449.17, m/z found 450.0 [M+H]$^+$. $^1$H NMR (400 MHz, DMSO-d$_6$) δ 7.91 (br s, 3H), 7.19-7.08 (m, 4H), 6.90 (d, J=4.4 Hz, 1H), 6.81 (d, J=4.4 Hz, 1H), 6.32 (d, J=6.0 Hz, 1H), 5.40 (d, J=5.2 Hz, 1H), 4.71 (t, J=5.2 Hz, 1H), 4.34 (dd, J=11.2, 2.0 Hz, 1H), 4.27-4.17 (m, 2H), 3.99-3.93 (d, J=4.0 Hz, 1H), 3.05-2.96 (m, 2H), 2.69 (dt, J=14.8, 7.6 Hz, 1H), 2.60-2.52 (m, 2H), 2.47 (d, J=1.8 Hz, 2H).

Example 108. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-cycloheptylacetate (Compound 261)

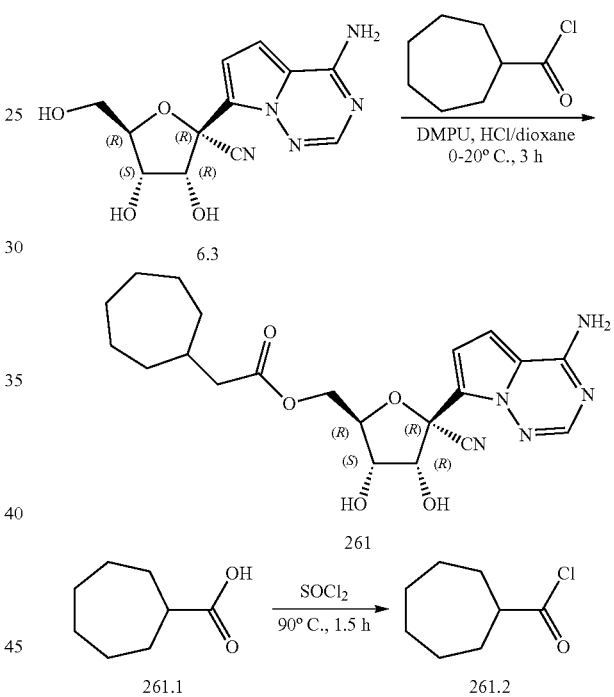

Step 1: Synthesis of cycloheptanecarbonyl chloride (261.2)

To a solution of 261.1 (500 mg, 3.2 mmol) in SOCl$_2$ (1.33 g, 11.2 mmol) was stirred at 90° C. for 1.5 hours. The crude (530 mg, 93.8% yield) was used in the next step without any purification.

Step 2: Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-cycloheptylacetate (261)

To a solution of 6.3 (100 mg, 0.34 mmol) in DMPU (1 mL) was added 0.3 mL 4 M HCl dioxane dropwise at 0° C., the mixture was then stirred for 30 minutes. Then added 261.2 (299 mg, 1.71 mmol) dropwise into the mixture and stirred for 3 hours. After completion, the mixture was diluted with water (2 mL) and purified by prep-HPLC to afford 261 as a white solid (90 mg, 60.4%). MS (ESI): m/z calcd. for $C_{21}H_{27}N_5O_5$, 429.20, found 430.25 [M+H]$^+$. $^1$H NMR (400 MHz, DMSO) δ 7.92 (s, 3H), 6.91 (d, J=4.4 Hz, 1H), 6.80 (d, J=4.8 Hz, 1H), 6.33 (d, J=5.6 Hz, 1H), 5.38 (s, 1H), 4.69 (d, J=4.8 Hz, 1H), 4.30 (dd, J=11.6, 2.4 Hz, 1H), 4.25-4.12 (m, 2H), 3.94 (t, J=5.6 Hz, 1H), 2.26-2.12 (m, 2H), 1.93-1.78 (m, 1H), 1.65-1.27 (m, 10H), 1.23-1.06 (m, 2H).

Example 109. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-(4,4-difluorocyclohexyl)acetate (Compound 262)

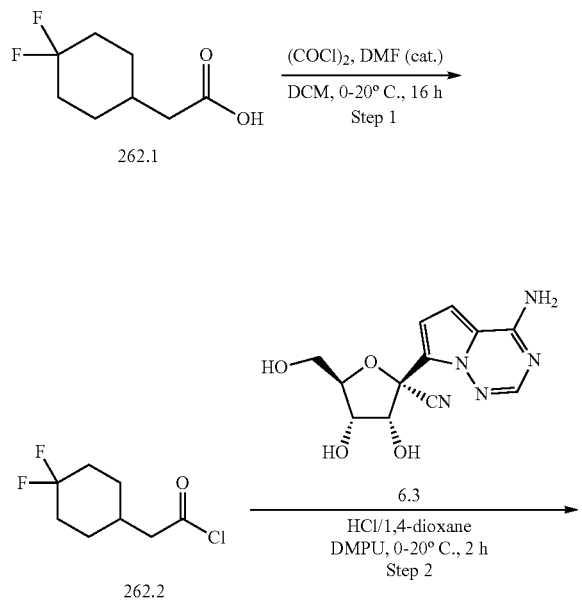

Step 1. Synthesis of 2-(4,4-difluorocyclohexyl)acetyl chloride (262.2)

To a solution of 262.1 (400 mg, 2.25 mmol) in dry DCM (4.5 mL) was added oxalyl chloride (427 mg, 3.37 mmol) dropwise at 0° C. The reaction mixture was stirred at 20° C. for 16 h. The reaction mixture was concentrated to dryness to give 262.2 (431 mg, crude) as a yellow oil, which was used directly in next step.

Step 2. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-(4,4-difluorocyclohexyl)acetate (262)

To a solution of 6.3 (100 mg, 0.343 mmol) in DMPU (1.0 mL) was added HCl/1,4-dioxane (0.1 mL, 4 M) dropwise at 0° C. The reaction mixture was stirred at 0° C. for 15 min and 262.2 (431 mg, crude) was added dropwise into the flask vessel. The reaction mixture was stirred at 20° C. for 2 h. The reaction mixture was purified by prep-HPLC to afford the title compound 262 (22.70 mg, 14% yield) as a white solid. MS (ESI): m/z calcd. for $C_{20}H_{23}F_2N_5O_5$ 451.17, found 452.1 [M+H]$^+$. $^1$H NMR (400 MHz, DMSO) δ 7.92 (br s, 3H), 6.91 (d, J=4.4 Hz, 1H), 6.80 (d, J=4.4 Hz, 1H), 6.31 (d, J=6.0 Hz, 1H), 5.38 (d, J=6.0 Hz, 1H), 4.70 (t, J=5.6 Hz, 1H), 4.32 (dd, J=11.2, 2.4 Hz, 1H), 4.25-4.15 (m, 2H), 3.94 (dd, J=11.2, 6.0 Hz, 1H), 2.30-2.19 (m, 2H), 1.99-1.87 (m, 2H), 1.84-1.65 (m, 5H), 1.23-1.11 (m, 2H). $^{19}$F NMR (377 MHz, DMSO) δ −89.81 (d, J=231.9 Hz, 1F), −99.51 (d, J=234.1 Hz, 1F).

Example 110. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-((3R,5R,7R)-adamantan-1-yl)acetate (Compound 263)

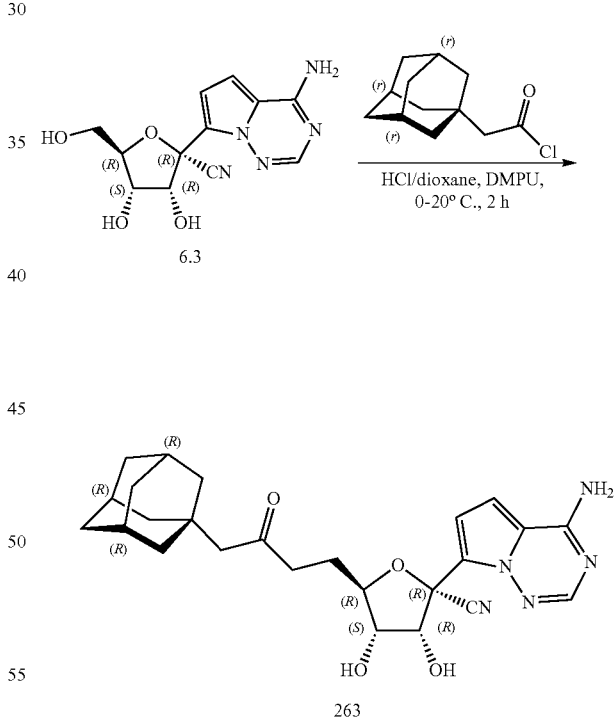

The title compound was prepared according to the procedure of Example 5, Step 4, using 6.3 and 2-(adamantan-1-yl)acetyl chloride. MS (ESI): m/z calcd. for $C_{24}H_{29}N_5O_5$ 467.22, found 468.1 [M+H]$^+$. $^1$H NMR (400 MHz, DMSO) δ 7.91 (br s, 3H), 6.91 (d, J=4.4 Hz, 1H), 6.81 (d, J=4.4 Hz, 1H), 6.30 (d, J=6.0 Hz, 1H), 5.37 (d, J=5.6 Hz, 1H), 4.72 (t, J=5.6 Hz, 1H), 4.29-4.13 (m, 3H), 3.95 (dd, J=10.8, 5.6 Hz, 1H), 2.00 (d, J=2.4 Hz, 2H), 1.86 (s, 3H), 1.65-1.47 (m, 12H).

Example 111. Synthesis of N-(7-((2R,3R,4S,5R)-2-cyano-3,4-dihydroxy-5-(hydroxymethyl)tetrahydrofuran-2-yl)pyrrolo[2,1-f][1,2,4]triazin-4-yl)pentanamide (Compound 264)

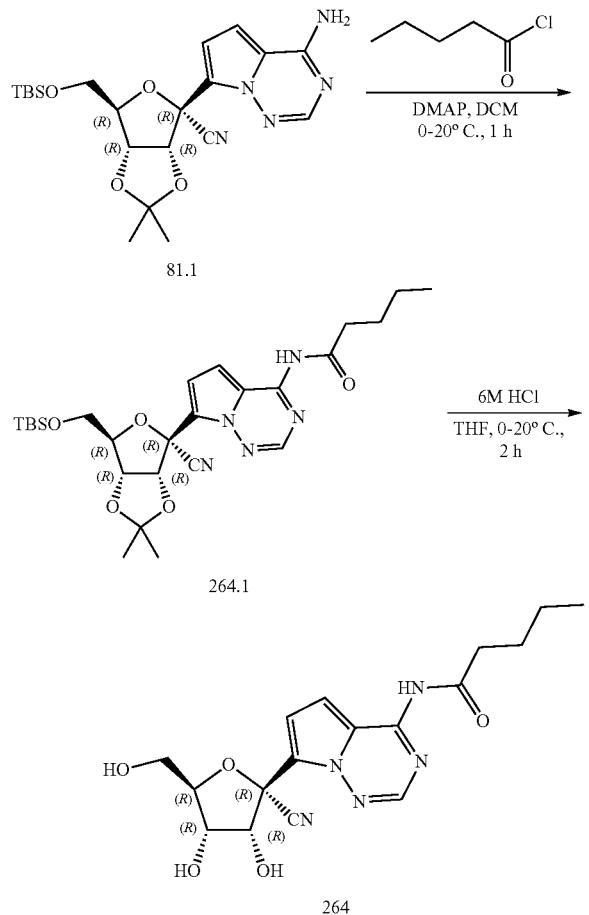

Step 1. Synthesis of N-(7-((3aR,4R,6R,6aR)-6-(((tert-butyldimethylsilyl)oxy)methyl)-4-cyano-2,2-dimethyltetrahydrofuro[3,4-d][1,3]dioxol-4-yl)pyrrolo[2,1-f][1,2,4]triazin-4-yl)pentanamide (264.1)

To a mixture of 81.1 (100 mg, 0.22 mmol) and DMAP (41 mg, 0.33 mmol) in DCM (1 mL) was added pentanoyl chloride (35 mg, 0.29 mmol) dropwise at 0° C. The mixture was then stirred at 20° C. for 1 hour. After completion, the reaction was quenched with water (10 mL) and extracted with ethyl acetate (10 mL×3). The organic layer was dried over sodium sulphate and concentrated in vacuo to afford a residue. The residue was purified by flash column chromatography to afford 264.1 (111 mg, 92.4% yield) as a white solid. MS (ESI): m/z calcd. for $C_{26}H_{39}N_5O_5Si$, 529.27, found 530.40 [M+H]$^+$. $^1$H NMR (400 MHz, DMSO) δ 10.99 (s, 1H), 8.52 (s, 1H), 7.36 (d, J=4.8 Hz, 1H), 7.18 (d, J=4.8 Hz, 1H), 5.40 (d, J=6.2 Hz, 1H), 4.95 (dd, J=6.2, 2.4 Hz, 1H), 4.57-4.52 (m, 1H), 3.80 (d, J=4.4 Hz, 2H), 2.80 (t, J=7.2 Hz, 2H), 1.74 (s, 3H), 1.73-1.65 (m, 2H), 1.49-1.39 (m, 5H), 1.00 (t, J=7.2 Hz, 3H), 0.84-0.80 (m, 9H), 0.02 (d, J=16.8 Hz, 6H).

Step 2. Synthesis of N-(7-((2R,3R,4S,5R)-2-cyano-3,4-dihydroxy-5-(hydroxymethyl)tetrahydrofuran-2-yl)pyrrolo[2,1-f][1,2,4]triazin-4-yl)pentanamide (264)

To a solution of 264.1 (80.0 mg, 0.15 mmol) in THF (2.0 mL) was added 6 M HCl (2.0 mL) dropwise at 0° C., the mixture was then stirred at 20° C. for 2 hours. After completion, the reaction mixture was purified by prep-HPLC to afford 264 (16 mg, 27.9% yield) as a white solid. MS (ESI): m/z calcd for $C_{17}H_{21}N_5O_5$, 375.15, found 376.15 [M+H]$^+$. $^1$H NMR (400 MHz, DMSO) δ 10.94 (s, 1H), 8.39 (s, 1H), 7.30 (d, J=4.8 Hz, 1H), 7.14 (d, J=4.8 Hz, 1H), 4.61 (d, J=4.8 Hz, 1H), 4.11-4.05 (m, 1H), 3.96-3.93 (m, 1H), 3.65 (dd, J=12.0, 3.2 Hz, 1H), 3.51 (dd, J=12.4, 4.4 Hz, 1H), 2.72 (t, J=7.2 Hz, 2H), 1.66-1.55 (m, 2H), 1.41-1.30 (m, 2H), 0.91 (t, J=7.6 Hz, 3H).

Example 112. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-cyclobutylacetate (Compound 265)

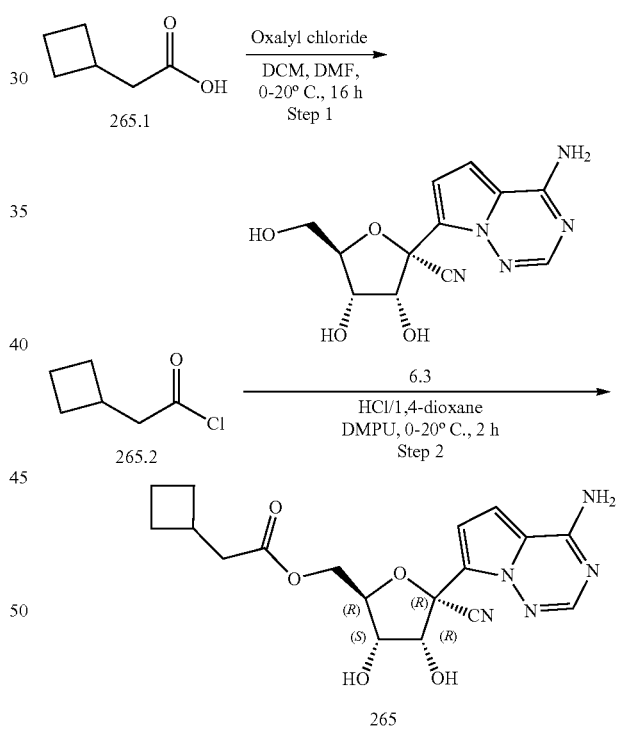

Step 1. Synthesis of 2-cyclobutylacetyl chloride (265.2)

To a solution of cyclobutylacetic acid (250 mg, 2.20 mmol) in dry DCM (4.5 mL) was added oxalyl chloride (418 mg, 3.30 mmol) dropwise at 0° C. The reaction mixture was stirred at 20° C. for 16 h. The reaction mixture was concentrated to dryness to give 265.2 (270 mg, crude) as a yellow oil, which was used directly in next step.

Step 2. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-cyclobutylacetate (Compound 265)

To a solution of 6.3 (100 mg, 0.343 mmol) in DMPU (1.0 mL) was added HCl/1,4-dioxane (0.1 mL, 4 M) dropwise at 0° C. The reaction mixture was stirred at 0° C. for 15 min and 265.2 (270 mg, crude) was added dropwise into the flask vessel. The reaction mixture was stirred at 20° C. for 2 h. The reaction mixture was purified by prep- to afford the title compound 265 (34.75 mg, 26% yield) as a white solid. MS (ESI): m/z calcd. for $C_{18}H_{21}N_5O_5$ 387.15, found 388.1 [M+H]$^+$. $^1$H NMR (400 MHz, DMSO) δ 7.92 (br s, 3H), 6.92 (d, J=4.4 Hz, 1H), 6.80 (d, J=4.4 Hz, 1H), 6.35 (s, 1H), 5.38 (s, 1H), 4.73-4.65 (m, 1H), 4.30 (dd, J=12.0, 2.8 Hz, 1H), 4.23-4.09 (m, 2H), 3.97-3.89 (m, 1H), 2.58-2.51 (m, 1H), 2.42-2.35 (m, 2H), 2.06-1.94 (m, 2H), 1.86-1.70 (m, 2H), 1.67-1.54 (m, 2H).

Example 113. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-((1r,4R)-4-aminocyclohexyl)acetate (Compound 266)

Step 1. Synthesis of ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl 2-((1r,4R)-4-((tert-butoxycarbonyl)amino)cyclohexyl)acetate (266.2)

To a solution of (3aR,4R,6R,6aR)-4-{4-aminopyrrolo[2,1-f][1,2,4]triazin-7-yl}-6-(hydroxymethyl)-2,2-dimethyl-dihydro-3aH-furo[3,4-d][1,3]dioxole-4-carbonitrile (6.3, 200 mg, 0.603 mol) in THF (20 mL) was added (4-{[tert-butyl(formyl)-$1^{3}$-oxidanyl]amino}cyclohexyl)acetic acid (202.71 mg, 0.784 mol), EDCI (347.13 mg, 1.810 mol) and DMAP (221.23 mg, 1.810 mmol), the mixture was stirred at 25° C. for 16 h. The reaction was washed with EtOAc (5 mL×3). The combined organics were dried over sodium sulfate and concentrated in vacuo. The crude product was purified by to afford 266.2 (250 mg, 65% yield) as a white solid. MS (ESI): m/z calcd. for $C_{28}H_{38}N_6O_7$ 570.23, found 571.2 [M+H]$^+$. $^1$H NMR (400 MHz, DMSO) δ 7.96 (br, s, 3H), 6.91 (d, J=4.4 Hz, 1H), 6.81 (d, J=4.8 Hz, 1H), 6.66 (d, J=8.0 Hz, 1H), 5.40 (d, J=6.4 Hz, 1H), 4.92 (dd, J=6.4, 2.8 Hz, 1H), 4.57 (dd, J=7.6, 4.8 Hz, 1H), 4.19 (dd, J=12.0, 4.4 Hz, 1H), 4.08 (dd, J=12.0, 5.6 Hz, 1H), 3.11-3.09 (m, 1H), 2.08 (dd, J=15.6, 6.8 Hz, 1H), 1.98 (dd, J=15.6, 7.2 Hz, 1H),

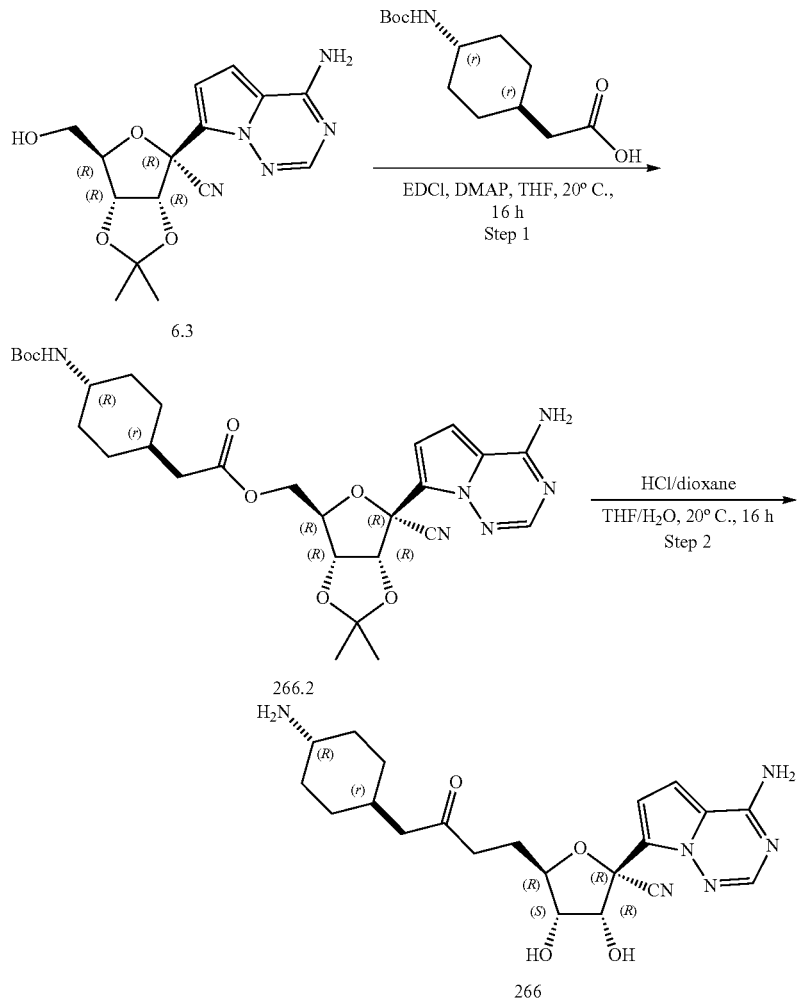

1.70 (d, J=10.8 Hz, 2H), 1.64 (s, 3H), 1.59 (d, J=12.0 Hz, 2H), 1.42-1.40 (m, 1H), 1.37 (s, 12H), 1.08-1.05 (m, 2H), 0.98-0.84 (m, 2H).

Step 2. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-((1r,4R)-4-aminocyclohexyl)acetate (Compound 266)

To a solution of [(3aR,4R,6R,6aR)-6-{4-aminopyrrolo[2,1-f][1,2,4]triazin-7-yl}-6-cyano-2,2-dimethyl-dihydro-3aH-furo[3,4-d][1,3]dioxol-4-yl]methyl 2-(4-{[(tert-butoxy)carbonyl]amino}cyclohexyl)acetate (266.2, 80 mg, 0.140 mmol) in THF (2 mL) and water (1 mL) was added HCl in dioxane (4M, 2 mL), the mixture was stirred at 25° C. for 4 h. The reaction concentrated in vacuo. The crude product was purified by to afford 266 (45.5 mg, 73% yield) as a white solid. MS (ESI): m/z calcd. for $C_{20}H_{26}N_6O_5$ 430.20, found 431.1 [M+H]$^+$. $^1$H NMR (400 MHz, DMSO) δ 7.85 (br, s, 3H), 6.94 (d, J=4.4 Hz, 1H), 6.80 (d, J=4.4 Hz, 1H), 6.47-6.45 (m, 1H), 5.51-5.47 (m, 1H), 4.68 (d, J=4.8 Hz, 1H), 4.31 (dd, J=11.6, 2.4 Hz, 1H), 4.25-4.08 (m, 2H), 3.93-3.90 (m, 1H), 2.82-2.80 (m, 1H), 2.20-2.18 (m, 2H), 1.87 (d, J=10.0 Hz, 2H), 1.70 (d, J=12.8 Hz, 2H), 1.65-1.49 (m, 1H), 1.25-1.20 (m, 2H), 1.00-0.90 (m, 2H).

Example 114. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-cyclohexylacetate (267)

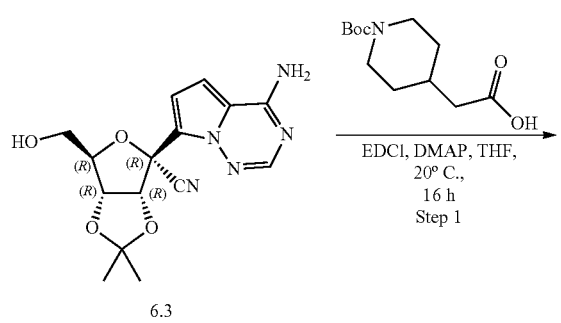

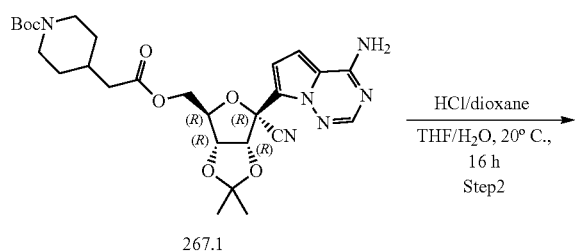

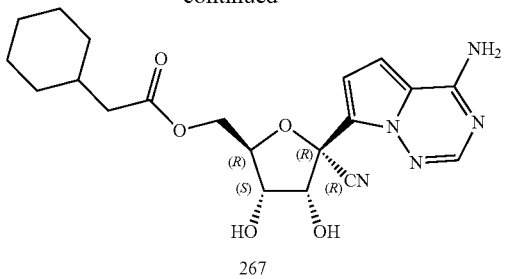

Step 1. Synthesis of tert-butyl 4-(2-(((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methoxy)-2-oxoethyl)piperidine-1-carboxylate (Compound 267.1)

The compound 267.1 was prepared according to the procedure of Example 266, Step 1, using 6.3 and 2-(1-(tert-butoxycarbonyl) piperidin-4-yl) acetic acid. MS (ESI): mass calcd. for $C_{27}H_{36}N_6O_7$, 556.26, m/z found 557.2 [M+H]$^+$. $^1$H NMR (400 MHz, DMSO) δ 7.96 (br s, 3H), 6.91 (d, J=4.4 Hz, 1H), 6.82 (d, J=4.8 Hz, 1H), 5.41 (d, J=6.4 Hz, 1H), 4.94 (dd, J=6.4, 2.8 Hz, 1H), 4.64-4.49 (m, 1H), 4.22 (dd, J=12.0, 4.0 Hz, 1H), 4.10 (dd, J=12.0, 6.4 Hz, 1H), 3.85 (d, J=11.2 Hz, 2H), 2.63-2.60 (m, 2H), 2.16 (dd, J=15.6, 7.2 Hz, 1H), 2.11-2.02 (m, 1H), 1.68-1.65 (m, 1H), 1.64 (s, 3H), 1.52 (d, J=10.8 Hz, 2H), 1.40 (s, 12H), 1.06-0.89 (m, 2H).

Step 2. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-cyclohexylacetate (Compound 267)

The title compound 267 was prepared according to the procedure of Example 266, Step 2, using 267.1. MS (ESI): mass calcd. for $C_{19}H_{24}N_6O_5$, 416.18, m/z found 417.2 [M+H]$^+$. $^1$H NMR (400 MHz, DMSO) δ 7.92-7.90 (br, s, 3H), 6.93 (d, J=4.8 Hz, 1H), 6.81 (d, J=4.4 Hz, 1H), 6.49-6.40 (m, 1H), 5.50-5.40 (m, 1H), 4.70 (d, J=4.8 Hz, 1H), 4.32 (dd, J=11.2, 2.0 Hz, 1H), 4.27-4.15 (m, 2H), 3.93 (t, J=5.2 Hz, 1H), 3.10-3.05 (m, 2H), 2.72-2.68 (m, 2H), 2.26 (d, J=7.2 Hz, 2H), 1.87-1.80 (m, 1H), 1.70 (d, J=12.0 Hz, 2H), 1.25-1.20 (m, 2H).

Example 115. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-(1-(methylsulfonyl)piperidin-4-yl)acetate (Compound 268)

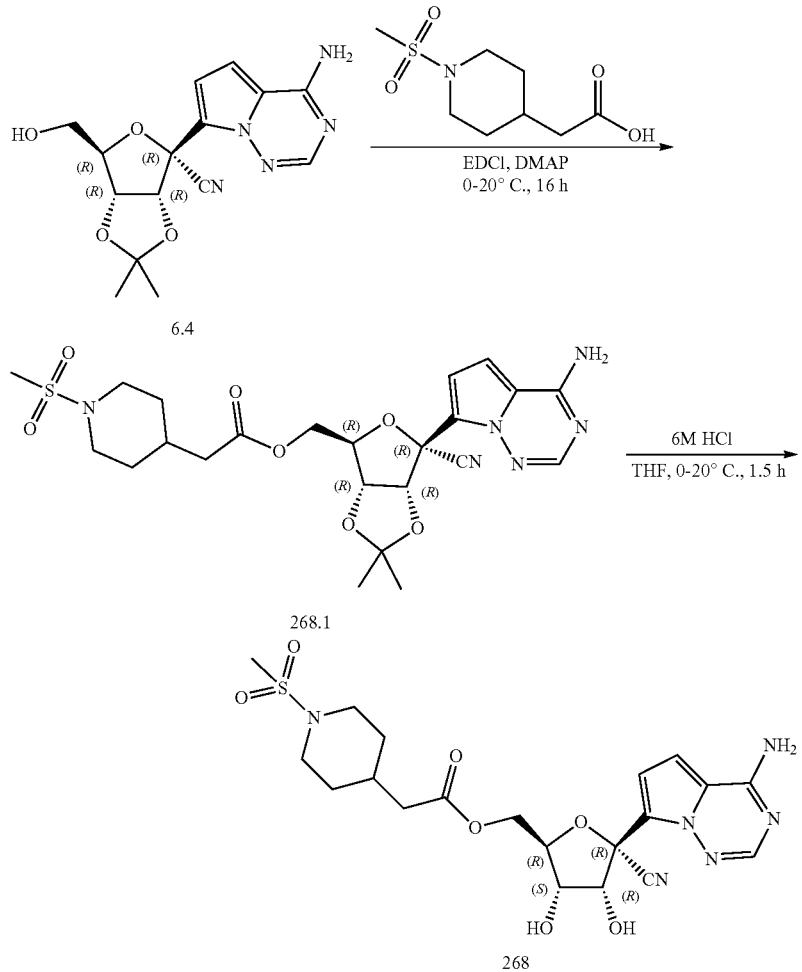

Step 1. Synthesis of ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl 2-(1-(methylsulfonyl)piperidin-4-yl)acetate (268.1)

To a mixture of 6.4 (300 mg, 0.90 mmol), (1-methanesulfonylpiperidin-4-yl)acetic acid (200 mg, 0.90 mmol) and EDCI (520 mg, 2.71 mmol) in THF was added DMAP (331 mmol, 2.71 mmol) slowly at 0° C., the mixture was then stirred for 16 hours. After completion, the reaction mixture was quenched with water (20 mL) and extracted with ethyl acetate (20 mL×3). The organic layer was dried over sodium sulphate and concentrated in vacuo to afford a residue. The residue was purified by prep-HPLC to afford 268.1 (302 mg, 61.3% yield) as a white solid. MS (ESI): m/z calcd. for $C_{23}H_{30}N_6O_7S$, 534.19, found 535.30 [M+H]$^+$. $^1$H NMR (400 MHz, DMSO) δ 7.97 (s, 3H), 6.91 (d, J=4.4 Hz, 1H), 6.83 (d, J=4.4 Hz, 1H), 5.42 (d, J=6.4 Hz, 1H), 4.95 (dd, J=6.4, 2.8 Hz, 1H), 4.60-4.55 (m, 1H), 4.23 (dd, J=12.0, 4.0 Hz, 1H), 4.10 (dd, J=12.0, 5.6 Hz, 1H), 3.47 (d, J=11.6 Hz, 2H), 2.82 (s, 3H), 2.61 (dd, J=16.8, 7.6 Hz, 2H), 2.22 (dd, J=15.6, 6.8 Hz, 1H), 2.16-2.06 (m, 1H), 1.65 (d, J=10.4 Hz, 6H), 1.38 (s, 3H), 1.22-1.09 (m, 2H).

Step 2. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-(1-(methylsulfonyl)piperidin-4-yl)acetate (268)

To a solution of 268.1 (200 mg, 0.37 mmol) in THF (2.0 mL) was added 6 M HCl (2.0 mL) dropwise at 0° C., the mixture was then stirred at 20° C. for 2 hours. The mixture was quenched with water (2 mL) and dried with a stream of nitrogen to remove the solvent away. The residue was purified by prep-HPLC to afford 268 (130 mg, 69.5% yield) as a white solid. MS (ESI): m/z calcd. for $C_{20}H_{26}N_6O_7S$, 494.16, found 495.20 [M+H]$^+$. $^1$H NMR (400 MHz, DMSO) δ 8.28-7.87 (m, 3H), 6.96 (d, J=4.4 Hz, 1H), 6.83 (d, J=4.8 Hz, 1H), 6.33 (s, 1H), 5.41 (s, 1H), 4.69 (d, J=4.8 Hz, 1H), 4.33 (dd, J=11.6, 2.4 Hz, 1H), 4.26-4.15 (m, 2H), 3.98-3.90 (m, 1H), 3.50 (s, 2H), 2.83 (s, 3H), 2.65 (dt, J=12.0, 2.0 Hz, 2H), 2.28 (dd, J=6.8, 2.4 Hz, 2H), 1.80-1.66 (m, 3H), 1.27-1.12 (m, 2H).

Example 116. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-cyclohexyl-2-methylpropanoate (Compound 269)

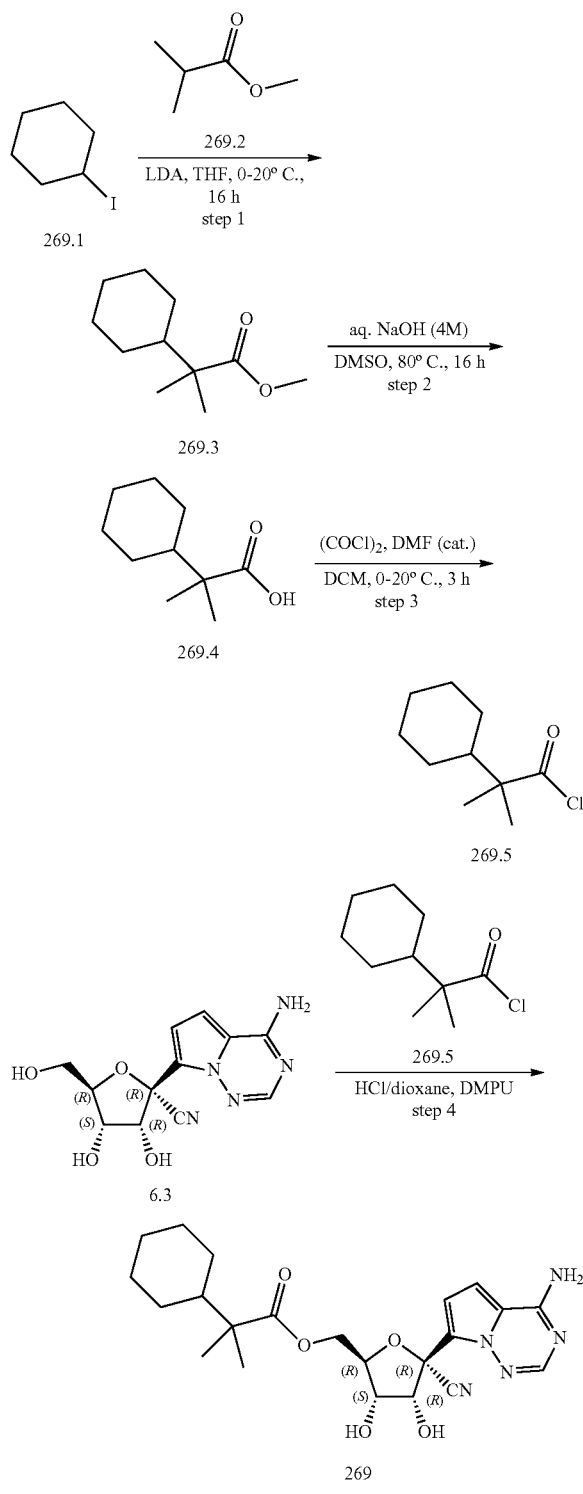

Step 1: Synthesis of methyl 2-cyclohexyl-2-methylpropanoate (269.3)

A solution of LDA (5.40 mL, 2M) in THF (30 mL) was added methyl 269.2 (1.00 g, 9.80 mmol) at 0° C. under $N_2$, then the reaction was stirred at 0° C. for 30 minutes. Then the mixtures was added 269.1 (1.4 mL, 10.7 mmol) at 0° C., and the reaction was stirred at 20° C. for 16 hours. The reaction was quenched by HCl (50 mL, 1M) and extracted with MTBE (50 mL×3). The combined organics were dried over sodium sulfate and concentrated. The residue was purified by flash column chromatography (EA/PE from 0% to 0%) to obtain 269.3 as a yellow oil (500 mg, 26.5% yield). $^1$H NMR (400 MHz, CDCl$_3$) δ 3.65 (s, 3H), 1.80-1.71 (m, 2H), 1.68-1.62 (m, 1H), 1.58-1.52 (m, 3H), 1.29-1.23 (m, 2H), 1.09 (s, 6H), 1.04-0.95 (m, 2H), 0.90-0.85 (m, 1H).

Step 2: Synthesis of 2-cyclohexyl-2-methylpropanoic acid (269.4)

To a solution of 269.3 (500 mg, 2.7 mmol) in DMSO (5 mL) was added NaOH (5 mL, 4 M), then the reaction was stirred at 80° C. for 16 hours. The mixture was poured into ice-water (50 mL) and acidified with aq. HCl (50 mL, 1 M, pH=2~3) and a white solid was formed in the aqueous layer, then filtered to obtain 269.4 as a white solid (120 mg, 24.7% yield). $^1$H NMR (400 MHz, CDCl$_3$) δ 1.79-1.75 (m, 2H), 1.71-1.55 (m, 4H), 1.34-1.19 (m, 2H), 1.12 (s, 6H), 1.09-0.96 (mi, 2H).

Step 3: Synthesis of 2-cyclohexyl-2-methylpropanoyl chloride (269.5)

To a round bottom flask equipped with a gas bubbler was added 269.4 (120 mg, 0.70 mmol) and DCM (1 mL). Oxalyl chloride (0.12 mL, 1.41 mmol) was added followed by a few drops of DMF at 20° C. The resulting solution was stirred at 20° C. until gas evolution ceased (~1 h). The mixture was concentrated 3 times from DCM to obtain 269.5 (100 mg, crude) and the resulting acid chloride was used without further purification for the coupling above.

Step 4: Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-cyclohexyl-2-methylpropanoate (269.5)

The title compound was prepared according to the procedure of Example 5, Step 4, using 6.3 and 269.5. MS (ESI): mass calcd. for $C_{22}H_{29}N_5O_5$, 443.22, m/z found 444.1 [M+H]$^+$. $^1$H NMR (400 MHz, DMSO-d$_6$) δ 7.92 (br s, 3H), 6.91 (d, J=4.4 Hz, 1H), 6.81 (d, J=4.4 Hz, 1H), 6.35 (d, J=5.6 Hz, 1H), 5.38 (s, 1H), 4.71 (d, J=4.4 Hz, 1H), 4.31-4.12 (m, 3H), 3.97 (s, 1H), 1.67-1.51 (m, 3H), 1.48-1.37 (m, 3H), 1.14-0.96 (m, 9H), 0.93-0.80 (m, 2H).

Example 117. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-(4-(trifluoromethyl)cyclohexyl)acetate (Compound 270) and (2R,3S,4R,5R)-5-(4-aminopyrrolo[2,1-f][1,2,4]triazin-7-yl)-5-cyano-4-hydroxy-2-((2-(4-(trifluoromethyl)cyclohexyl)acetoxy)methyl)tetrahydrofuran-3-yl 2-(4-(trifluoromethyl)cyclohexyl)acetate (Compound 271)

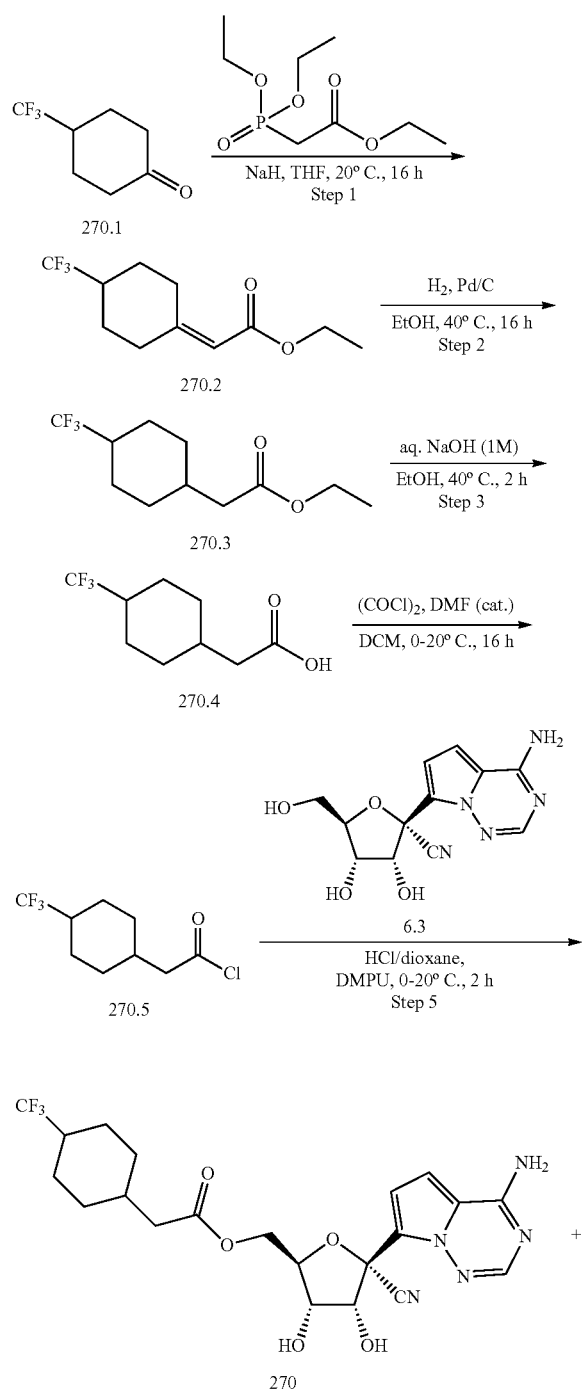

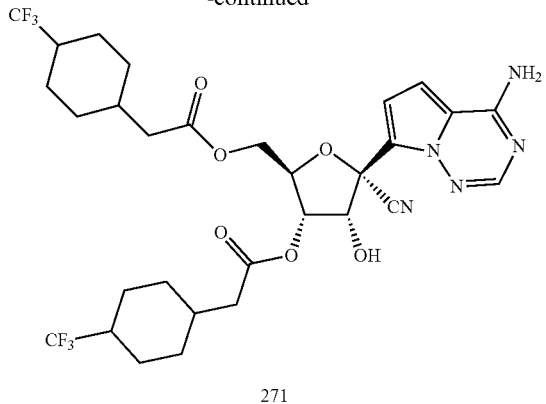

Step 1. Synthesis of ethyl 2-(4-(trifluoromethyl)cyclohexylidene)acetate (270.2)

To a solution of ethyl 2-(diethoxyphosphoryl)acetate (810 mg, 3.61 mmol) in dry THF (10 mL) was added sodium hydride (150 mg, 60%, 3.76 mmol). The reaction mixture was stirred at 20° C. for 1 h, then a solution of 270.1 (500 mg, 3.01 mmol) in dry THF (5.0 mL) was added dropwise to the solution. The reaction mixture was stirred at 20° C. for 16 h. The reaction mixture was quenched with water (30 mL) and extracted with EA (10 mL×3). The combined organic phase was washed with brine (10 mL), dried over anhydrous $Na_2SO_4$, filtered. The filtrate was concentrated to dryness. The residue was purified by FCC (Gradient: 5% EA in PE) to give 270.2 (561 mg, 79% yield) as a colorless oil. MS (ESI): m/z calcd. for $C_{11}H_{15}F_3O_2$ 236.10, found 237.0 $[M+H]^+$. $^1$H NMR (400 MHz, $CDCl_3$) δ 5.68 (s, 1H), 4.15 (q, J=7.2 Hz, 2H), 3.94 (d, J=14.4 Hz, 1H), 2.39 (d, J=13.6 Hz, 1H), 2.32-2.15 (m, 2H), 2.13-2.05 (m, 2H), 1.92 (td, J=14.0, 4.4 Hz, 1H), 1.53-1.40 (m, 2H), 1.28 (t J=7.2 Hz, 3H). $^{19}$F NMR (377 MHz) δ −194.12.

Step 2. Synthesis of ethyl 2-(4-(trifluoromethyl)cyclohexyl)acetate (270.3)

To a solution of 270.2 (561 mg, 2.37 mmol) in EtOH (10 mL) was added Pd/C (56 mg, 10% w.t %). The reaction mixture was degassed with $H_2$ for three times and stirred at 40° C. for 16 h under $H_2$. TLC detected complete consumption of 270.2. The reaction mixture was filtered, and the filtrate was concentrated to dryness to give 270.3 (514 mg, 910% yield) as a colorless oil. $^1$H NMR (400 MHz, $CDCl_3$) δ 4.18-4.09 (m, 2H), 2.36-2.18 (m, 2H), 2.12-1.53 (m, 8H), 1.41-1.29 (m, 1H), 1.28-1.23 (m, 3H), 1.07-0.95 (m, 1H). $^{19}$F NMR (377 MHz, $CDCl_3$) δ −73.82.

Step 3. Synthesis of 2-(4-(trifluoromethyl)cyclohexyl)acetic acid (270.4)

To a solution of 270.3 (514 mg, 2.16 mmol) in EtOH (8.0 mL) was added a solution of sodium hydroxide (173 mg, 4.31 mmol) in $H_2O$ (4.0 mL). The reaction mixture was stirred at 40° C. for 2 h under nitrogen. TLC showed complete consumption of 270.3. The reaction mixture was diluted with water (10 mL). The aqueous solution was acidified with HCl (1 M) and extracted with EA (5.0 mL×3). The combined organic phase was washed with brine (5.0 mL), dried over anhydrous Na₂SO₄, filtered. The filtrate was concentrated to dryness give 270.4 (462 mg, 97% yield) as a white solid. ¹H NMR (400 MHz CDCl₃) δ 5.92 (br, 1H), 2.33 (dd, J=52.4, 7.6 Hz, 2H), 2.25-1.52 (m, 8H), 1.42-1.25 (m, 1H), 1.10-0.98 (m, 1H). ¹⁹F NMR (377 MHz) δ −194.49.

Step 4. Synthesis of 2-(4-(trifluoromethyl)cyclohexyl)acetyl chloride (270.5)

To a solution of 270.4 (462 mg, 2.20 mmol) in dry DCM (10 mL) was added oxalyl chloride (418 mg, 3.30 mmol) dropwise at 0° C. The reaction mixture was stirred at 20° C. for 16 h. The reaction mixture was concentrated to dryness to give 270.5 (481 mg, crude), which was used directly in next step.

Step 5. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-(4-(trifluoromethyl)cyclohexyl)acetate (270) and (2R,3S,4R,5R)-5-(4-aminopyrrolo[2,1-f][1,2,4]triazin-7-yl)-5-cyano-4-hydroxy-2-((2-(4-(trifluoromethyl)cyclohexyl)acetoxy)methyl)tetrahydrofuran-3-yl 2-(4-(trifluoromethyl)cyclohexyl)acetate (271)

To a solution of 6.3 (100 mg, 0.343 mmol) in DMPU (1.0 mL) was added HCl/1,4-dioxane (0.1 mL, 4 M) dropwise at 0° C. The reaction mixture was stirred at 0° C. for 15 min and 270.5 (481 mg, crude) was added dropwise into the flask vessel. The reaction mixture was stirred at 20° C. for 2 h. The reaction mixture was purified by prep-HPLC to afford the title compound 270 (60.50 mg, 36% yield) and 271 (49.18 mg, 21% yield) such as a white solid.

Compound 270: MS (ESI): m/z calcd. for C₂₁H₂₄F₃N₅O₅ 483.17, found 484.3 [M+H]⁺. ¹H NMR (400 MHz, DMSO) δ 7.92 (br s, 3H), 6.91 (dd, J=4.4, 1.6 Hz, 1H), 6.80 (d, J=4.4 Hz, 1H), 6.32 (d, J=6.0 Hz, 1H), 5.38 (d, J=6.0 Hz, 1H), 4.69 (q, J=5.2 Hz, 1H), 4.35-4.25 (m, 1H), 4.25-4.13 (m, 2H), 3.98-3.89 (m, 1H), 2.35-2.09 (m, 3H), 2.08-1.37 (m, 7H), 1.26-1.13 (m, 1H), 1.04-0.90 (m, 1H). ¹⁹F NMR (377 MHz, DMSO) δ −70.74, −72.30.

Compound 271: MS (ESI): m/z calcd. for C₃₀H₃₅F₆N₅O₆ 675.25, found 676.2 [M+H]⁺. ¹H NMR (400 MHz, DMSO) δ 7.92 (br s, 3H), 6.93 (dd, J=4.4, 1.6 Hz, 1H), 6.86 (d, J=4.8 Hz, 1H), 6.66-6.59 (m, 1H), 5.17-5.04 (m, 2H), 4.46 (dd, J=8.4, 4.0 Hz, 1H), 4.33-4.21 (m, 2H), 2.43 (d, J=7.2 Hz, 1H), 2.33-2.27 (m, 2H), 2.23-1.98 (m, 3H), 1.90-1.36 (m, 13H), 1.31-1.24 (m, 1H), 1.21-0.85 (m, 6H). ¹⁹F NMR (377 MHz, DMSO) δ −70.83, −72.35.

Example 118. Synthesis of ((2R,3R,4R,5R)-5-(2-amino-6-(methylamino)-9H-purin-9-yl)-3,4-dihydroxy-4-methyltetrahydrofuran-2-yl)methyl isobutyrate ((2R,3S,4R,5R)-5-(4-aminopyrrolo[2,1-f][1,2,4]triazin-7-yl)-5-cyano-3,4-dihydroxytetrahydrofuran-2-yl)methyl 2-(4,4-dimethylcyclohexyl)acetate (Compound 272)

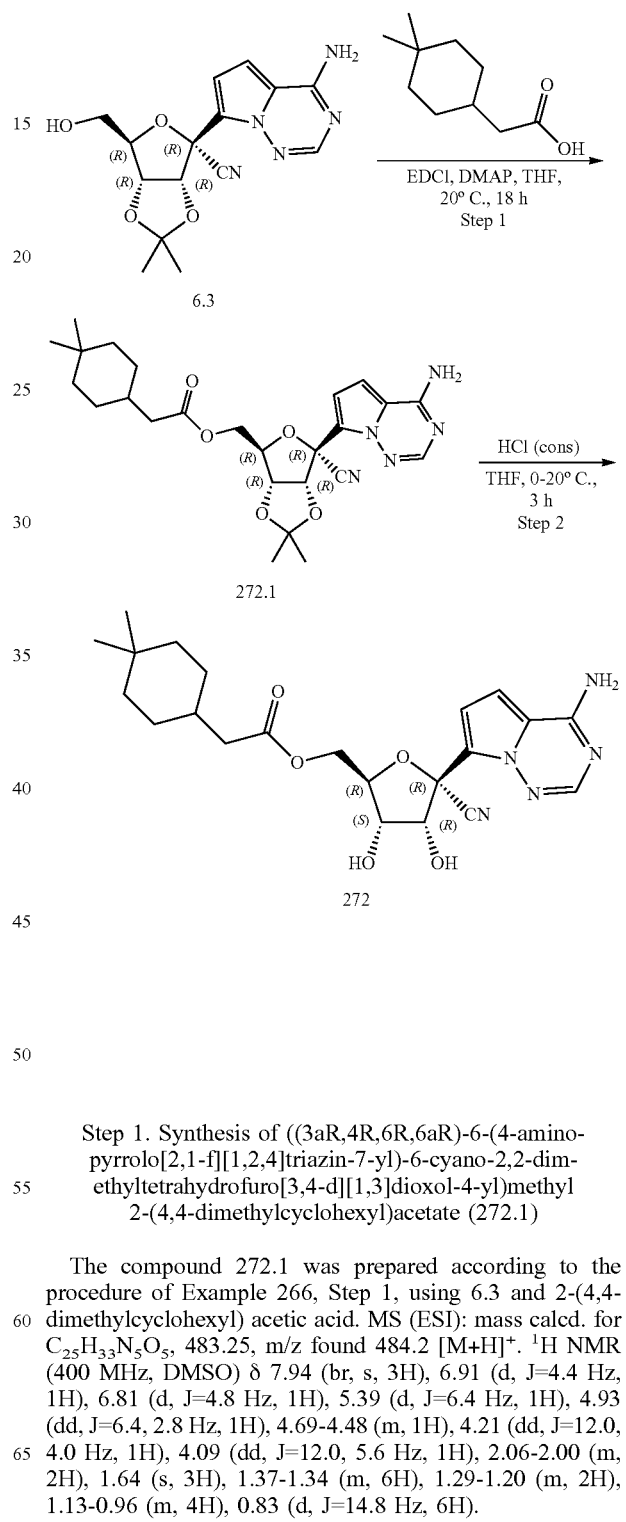

Step 1. Synthesis of ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl 2-(4,4-dimethylcyclohexyl)acetate (272.1)

The compound 272.1 was prepared according to the procedure of Example 266, Step 1, using 6.3 and 2-(4,4-dimethylcyclohexyl) acetic acid. MS (ESI): mass calcd. for C₂₅H₃₃N₅O₅, 483.25, m/z found 484.2 [M+H]⁺. ¹H NMR (400 MHz, DMSO) δ 7.94 (br, s, 3H), 6.91 (d, J=4.4 Hz, 1H), 6.81 (d, J=4.8 Hz, 1H), 5.39 (d, J=6.4 Hz, 1H), 4.93 (dd, J=6.4, 2.8 Hz, 1H), 4.69-4.48 (m, 1H), 4.21 (dd, J=12.0, 4.0 Hz, 1H), 4.09 (dd, J=12.0, 5.6 Hz, 1H), 2.06-2.00 (m, 2H), 1.64 (s, 3H), 1.37-1.34 (m, 6H), 1.29-1.20 (m, 2H), 1.13-0.96 (m, 4H), 0.83 (d, J=14.8 Hz, 6H).

Step 2. Synthesis of ((2R,3R,4R,5R)-5-(2-amino-6-(methylamino)-9H-purin-9-yl)-3,4-dihydroxy-4-methyltetrahydrofuran-2-yl)methyl isobutyrate ((2R,3S,4R,5R)-5-(4-aminopyrrolo[2,1-f][1,2,4]triazin-7-yl)-5-cyano-3,4-dihydroxytetrahydrofuran-2-yl)methyl 2-(4,4-dimethylcyclohexyl)acetate (272)

To a solution of [(3aR,4R,6R,6aR)-6-{4-aminopyrrolo[2,1-f][1,2,4]triazin-7-yl}-6-cyano-2,2-dimethyl-dihydro-3aH-furo[3,4-d][1,3]dioxol-4-yl]methyl 2-(4,4-dimethylcyclohexyl)acetate (272.1, 100 mg, 0.206 mmol) in THF (3 mL) was added HCl (12M, 1 mL) at 0° C., the mixture was stirred at 25° C. for 3 h. The reaction was concentrated in vacuo. The crude product was purified by prep-HPLC to afford 272 (83.32 mg, 91% yield) as a white solid. MS (ESI): mass calcd. for $C_{22}H_{29}N_5O_5$, 443.22, m/z found 444.3 [M+H]$^+$. $^1$H NMR (400 MHz, DMSO) δ 7.92-7.90 (br, s, 3H), 6.91 (d, J=4.4 Hz, 1H), 6.80 (d, J=4.8 Hz, 1H), 6.31 (d, J=6.0 Hz, 1H), 5.37 (d, J=5.2 Hz, 1H), 4.68 (t, J=5.2 Hz, 1H), 4.30 (dd, J=11.2, 2.4 Hz, 1H), 4.25-4.19 (m, 1H), 4.16 (dd, J=11.2, 5.6 Hz, 1H), 3.93-3.90 (m, 1H), 2.19 (dd, J=7.2, 2.0 Hz, 2H), 1.53-1.48 (m, 3H), 1.27-1.20 (m, 2H), 1.18-1.05 (m, 4H), 0.84 (d, J=10.8 Hz, 6H).

Example 119. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-(1-methylcyclohexyl)acetate (Compound 273)

Step 1: Synthesis of ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl 2-(1-methylcyclohexyl)acetate (273.1)

To a solution of 6.4 (300 mg, 0.91 mol) in THF (10 mL) was added (1-methylcyclohexyl)acetic acid (183.90 mg, 1.18 mol), EDCI (520.75 mg, 2.72 mol) and DMAP (331.87 mg, 2.72 mmol), then the mixture was stirred at 25° C. for 16 hours. The mixture was diluted with water (50 mL) and extracted with EtOAc (50 mL×3). The organic phase was washed with brine water (50 mL×3), then dried over anhydrous sodium sulfate, filtered and concentrated to remove the solvent. The residue was purified by flash column chromatography (EA/PE from 0% to 15%) to obtain 273.1 as a white solid (450 mg, 52.9% yield). MS (ESI): mass calcd. for $C_{24}H_{31}N_5O_5$, 469.23, m/z found 470.1 [M+H]$^+$.

Step 2: Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-(1-methylcyclohexyl)acetate (273)

To a solution of 273.1 (100 mg, 0.213 mol) in THF (1 mL) was added HCl (1 mL, 12M) at 0° C., the mixture was stirred at 0° C. for 1.5 h, and then the reaction was stirred at 20° C. for 0.5 h. The reaction was diluted with ACN (2.0 mL) and purified by prep-HPLC to obtain 273 (34.0 mg, 37.0% yield) as a white solid. MS (ESI): m/z calcd. for $C_{21}H_{27}N_5O_5$, 429.20, found 430.1 [M+H]$^+$. $^1$H NMR (400 MHz, DMSO-$d_6$) δ 7.92 (br s, 1H), 6.91 (d, J=4.4 Hz, 1H), 6.81 (d, J=4.4 Hz, 1H), 6.31 (d, J=6.0 Hz, 1H), 5.37 (d, J=6.0 Hz, 1H), 4.70 (t, J=5.6 Hz, 1H), 4.34-4.11 (m, 3H), 3.94 (d, J=5.6 Hz, 1H), 2.19 (d, J=2.4 Hz, 2H), 1.40-1.30 (m, 8H), 1.25-1.18 (m, 2H), 0.91 (s, 3H).

Example 120. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-(4-phenyltetrahydro-2H-pyran-4-yl)acetate (Compound 274)

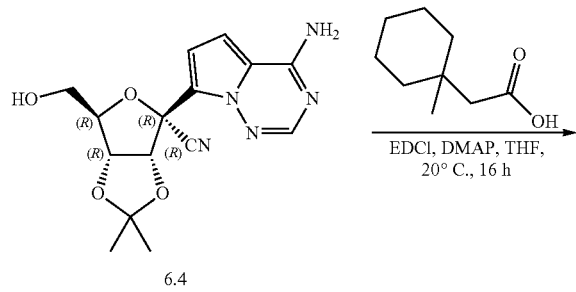

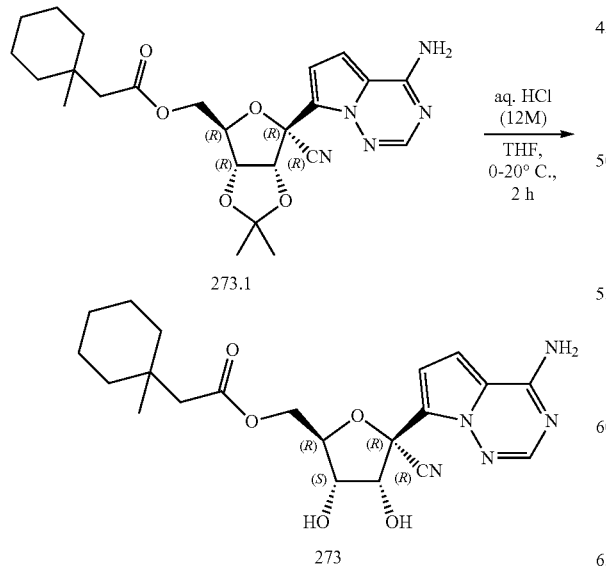

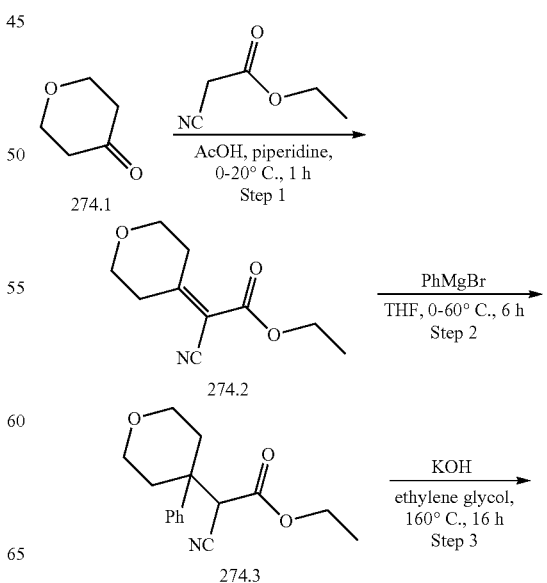

-continued

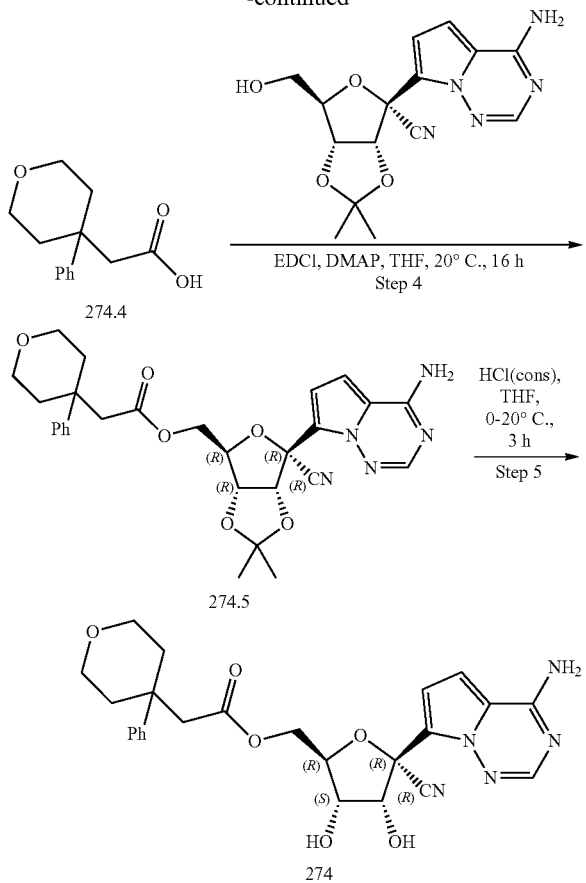

Step 1. Synthesis of ethyl 2-cyano-2-(tetrahydro-4H-pyran-4-ylidene)acetate (274.2)

To a mixture of oxan-4-one (274.1, 5 g, 0.049 mol) and ethyl cyanoacetate (5.64 g, 0.049 mol) was added acetic acid (0.30 g, 0.0045 mmol) and piperidine (0.425 g, 0.0045 mol) at 0° C., then acetic acid (0.30 g, 0.0045 mmol) and piperidine (0.425 g, 0.0045 mol) was added to the above solution at 25° C., the resulting mixture was stirred at 25° C. for 0.5 h. The reaction was quenched by NaHCO$_3$ (sat. aqueous, 10 mL) and extracted with EtOAc (10 mL×3). The combined organics were dried over sodium sulfate and concentrated in vacuo to obtain 274.2 as a light-yellow solid (10 g, 92% yield). $^1$H NMR (400 MHz, CDCl$_3$) δ 4.43-4.24 (m, 2H), 3.87 (t, J=5.6 Hz, 2H), 3.80 (t J=5.6 Hz, 2H), 3.19 (t, J=5.6 Hz, 2H), 2.80 (t, J=5.2 Hz, 2H), 1.38 (t J=3.2 Hz, 2H, 3H).

Step 2. Synthesis of ethyl 2-cyano-2-(4-phenyltetrahydro-2H-pyran-4-yl)acetate (274.3)

To a solution of ethyl 2-cyano-2-(oxan-4-ylidene)acetate (274.2, 3 g, 0.015 mol) in dry THF (30 ml) and the mixture was added PhMgBr (1M in THF, 30.8 mL) dropwise at 0° C., the solution was heated to 60° C. for 6 h. The reaction was quenched by NH$_4$Cl (sat. aqueous, 10 mL) and extracted with EA (10 mL×3). The combined organics were dried over sodium sulfate and concentrated. The residue was purified by flash column chromatography (EA/PE from 22% to 20%) to obtain 107.3 as a light-yellow solid (1.5 g, 48% yield). $^1$H NMR (400 MHz, CDCl$_3$) δ 7.44-7.30 (m, 5H), 3.94-3.90 (m, 2H), 3.85-3.82 (m, 2H), 3.65 (s, 1H), 3.59-3.41 (m, 2H), 2.69-2.43 (m, 2H), 2.21-2.09 (m, 2H), 1.00 (t, J=7.2 Hz, 3H).

Step 3. Synthesis of 2-(4-phenyltetrahydro-2H-pyran-4-yl) acetic acid (274.4)

To a solution of ethyl 2-cyano-2-(4-phenyloxan-4-yl) acetate (274.3, 250 mg, 0.914 mmol) in ethylene glycol (5 mL) was added KOH (102.65 mg, 1.83 mmol), the resulting mixture was stirred at 160° C. for 16 h. and concentrated in vacuo. The reaction was washed with ethyl ether (5 mL×3) and dried in vacuum. The crude product was purified by prep-HPLC to afford 274.4 (160 mg, 75% yield) as a white solid. $^1$H NMR (400 MHz, MeOD) δ 7.44-7.31 (m, 4H), 7.22 (t, J=7.2 Hz, 1H), 3.81-3.79 (m, 2H), 3.59-3.57 (m, 2H), 2.63 (s, 2H), 2.40-2.24 (m, 2H), 2.18-2.03 (m, 2H).

Step 4. Synthesis of ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl 2-(4-phenyltetrahydro-2H-pyran-4-yl)acetate (274.5)

To a solution of (3aR,4R,6R,6aR)-4-{4-aminopyrrolo[2,1-f][1,2,4]triazin-7-yl}-6-(hydroxymethyl)-2,2-dimethyl-dihy (200 mg, 0.603 mmol) in THF (15 mL) was added (4-phenyloxan-4-yl)acetic acid (274.4, 132.79 mg, 0.603 mmol), EDCI (347.13 mg, 1.810 mmol) and DMAP (221.23 mg, 1.810 mmol), the mixture was stirred at 25° C. for 16 h. The reaction was washed with EA (5 mL×3) and dried in vacuum. The crude product was purified by prep-HPLC to afford 274.5 (200 mg, 59% yield) as a white solid. MS (ESI): m/z calcd. for C$_{28}$H$_{31}$N$_5$O$_6$ 533.23, found 534.2 [M+H]$^+$. $^1$H NMR (400 MHz, DMSO) δ 7.96 (br, s, 3H), 7.31-7.22 (m, 4H), 7.21-7.13 (m, 1H), 6.92 (d, J=4.4 Hz, 1H), 6.77 (d, J=4.8 Hz, 1H), 5.24 (d, J=6.4 Hz, 1H), 4.58 (dd, J=6.4, 2.8 Hz, 1H), 4.34-4.30 (m, 1H), 3.95 (dd, J=12.0, 4.0 Hz, 1H), 3.82 (dd, J=12.0, 5.6 Hz, 1H), 3.62-3.60 (m, 2H), 3.49-3.36 (m, 2H), 2.54-2.50 (m, 2H), 2.07-2.05 (m, 2H), 1.94-1.79 (m, 2H), 1.62 (s, 3H), 1.36 (s, 3H).

Step 5. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-(4-phenyltetrahydro-2H-pyran-4-yl)acetate (274)

To a solution of [(3aR,4R,6R,6aR)-6-{4-aminopyrrolo[2,1-f][1,2,4]triazin-7-yl}-6-cyano-2,2-dimethyl-dihydro-3aH-furo[3,4-d][1,3]dioxol-4-yl]methyl 2-(4-phenyloxan-4-yl) acetate (274.5, 150 mg, 0.281 mmol) in THF (3 mL) was added HCl (12 M, 1 mL) at 0° C., the mixture was stirred at 25° C. for 4 h. The reaction was dried in vacuum. The crude product was purified by prep-HPLC to afford the title compound 274 (112.15 mg, 81% yield) as a white solid. MS (ESI): m/z calcd. for C$_{25}$H$_{27}$N$_5$O$_6$ 493.20, found 494.3 [M+H]. $^1$H NMR (400 MHz, DMSO) δ 7.93-7.90 (br, s, 3H), 7.30-7.21 (m, 4H), 7.16 (t, J=6.8 Hz, 1H), 6.94 (d, J=4.4 Hz, 1H), 6.75 (d, J=4.4 Hz, 1H), 6.27-6.20 (m, 1H), 5.28-5.20 (m, 1H), 4.63-4.60 (m, 1H), 4.08-4.00 (m, 2H), 3.89 (dd, J=12.4, 6.0 Hz, 1H), 3.72 (t, J=5.6 Hz, 1H), 3.69-3.60 (m, 2H), 3.40-3.35 (m, 2H), 2.63 (s, 2H), 2.15-2.03 (m, 2H), 2.02-1.88 (m, 2H).

Example 121. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl (R)-2-cyclohexylpropanoate (Compound 275)

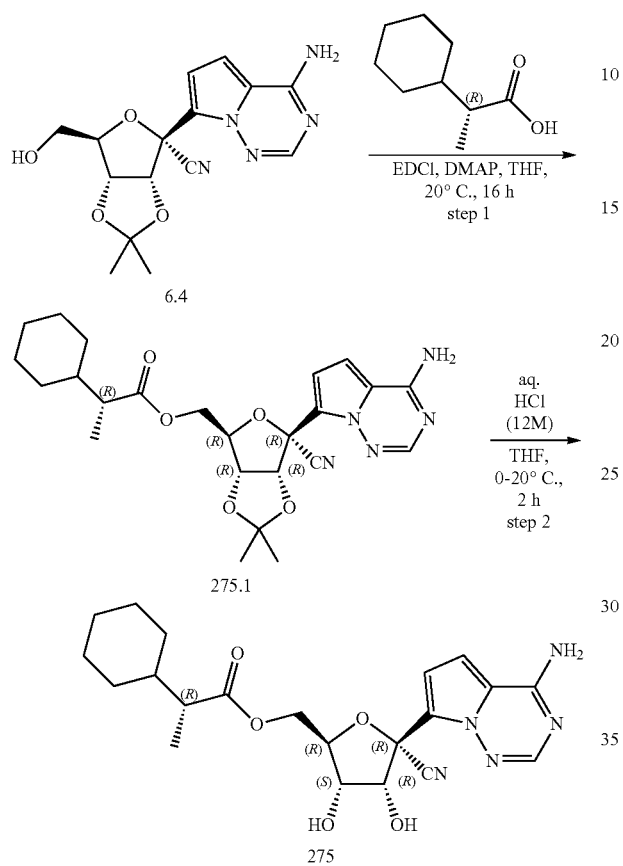

Step 1. Synthesis of ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl (R)-2-cyclohexylpropanoate (275.1)

The title compound was prepared according to the procedure of Example 273, Step 1, using 6.4 and (R)-2-cyclohexylpropanoic acid. MS (ESI): mass calcd. for $C_{24}H_{31}N_5O_5$, 469.23, m/z found 470.2 [M+H]$^+$. $^1$H NMR (400 MHz, DMSO-d$_6$) δ 7.96 (br s, 3H), 6.91 (d, J=4.8 Hz, 1H), 6.84 (d, J=4.8 Hz, 1H), 5.43 (d, J=6.4 Hz, 1H), 4.92 (dd, J=6.4, 3.2 Hz, 1H), 4.55 (d, J=3.2 Hz, 1H), 4.22 (dd, J=12.0, 4.4 Hz, 1H), 4.11 (dd, J=12.0, 6.0 Hz, 1H), 2.16 (t, J=7.2 Hz, 1H), 1.67-1.51 (m, 7H), 1.47-1.30 (m, 5H), 1.18-0.99 (m, 3H), 0.94 (d, J=7.2 Hz, 3H), 0.90-0.80 (m, 2H).

Step 2. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl (R)-2-cyclohexylpropanoate (275)

The title compound was prepared according to the procedure of Example 273, Step 2, using 275.1. MS (ESI): mass calcd. for $C_{21}H_{27}N_5O_5$, 429.20, m/z found 430.1 [M+H]$^+$.

$^1$H NMR (400 MHz, DMSO-d$_6$) δ 7.92 (br s, 3H), 6.91 (d, J=4.4 Hz, 1H), 6.81 (d, J=4.4 Hz, 1H), 6.32 (d, J=6.0 Hz, 1H), 5.38 (d, J=5.6 Hz, 1H), 4.69 (t, J=5.2 Hz, 1H), 4.35-4.10 (m, 3H), 3.96 (d, J=5.2 Hz, 1H), 2.19 (t, J=7.2 Hz, 1H), 1.60 (d, J=17.6 Hz, 4H), 1.44 (dd, J=24.4, 10.8 Hz, 2H), 1.20-1.02 (m, 3H), 0.98 (d, J=7.2 Hz, 3H), 0.94-0.79 (m, 2H).

Example 122. Synthesis ((2R,3S,4R,5R)-5-cyano-3,4-dihydroxy-5-(4-pentanamidopyrrolo[2,1-f][1,2,4]triazin-7-yl)tetrahydrofuran-2-yl)methyl isobutyrate (Compound 276)

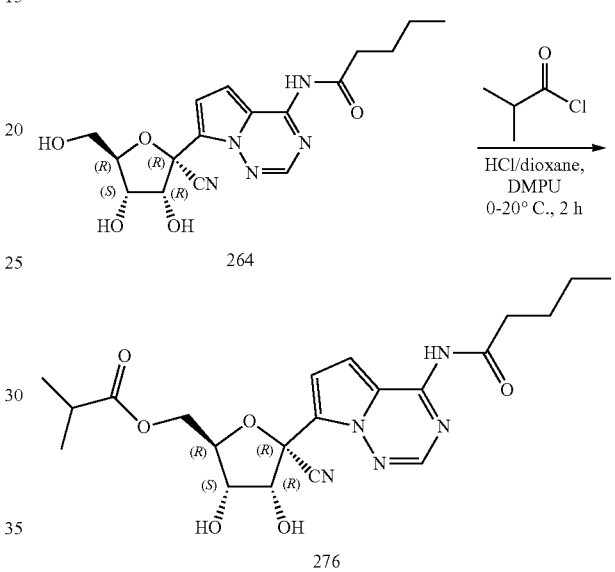

The title compound was prepared according to the procedure of Example 288, Step 1, using Compound 264 and 2-methylpropanoyl chloride. MS (ESI): mass calcd. for $C_{21}H_{27}N_5O_6$, 445.20, m/z found 446.1 [M+H]$^+$. $^1$H NMR (400 MHz, DMSO) δ 10.88 (s, 1H), 8.39 (s, 1H), 7.27 (d, J=4.4 Hz, 1H), 7.04 (d, J=4.8 Hz, 1H), 6.42 (d, J=6.0 Hz, 1H), 5.43 (d, J=6.0 Hz, 1H), 4.68 (t, J=5.6 Hz, 1H), 4.33-4.23 (m, 2H), 4.17 (dd, J=11.6, 4.4 Hz, 1H), 3.95 (dd, J=11.2, 6.0 Hz, 1H), 2.70 (m, 2H), 2.53 (s, 1H), 1.66-1.53 (m, 2H), 1.40-1.28 (m, 2H), 1.03 (dd, J=7.2, 3.6 Hz, 6H), 0.90 (t, J=7.6 Hz, 3H).

Example 123. Synthesis of ((2R,3S,4R,5R)-5-cyano-3,4-dihydroxy-5-(4-pentanamidopyrrolo[2,1-f][1,2,4]triazin-7-yl)tetrahydrofuran-2-yl)methyl 2-phenylacetate (Compound 277)

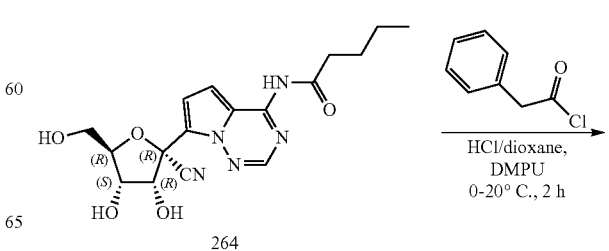

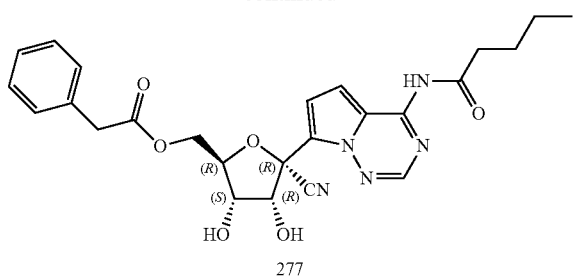

277

The title compound was prepared according to the procedure of Example 5, Step 4, using 264 and 2-phenylacetyl chloride. MS (ESI): mass calcd. for $C_{25}H_{27}N_5O_6$, 493.20, m/z found 494.1 [M+H]$^+$. $^1$H NMR (400 MHz, DMSO-d$_6$) δ 10.89 (s, 1H), 8.39 (s, 1H), 7.32-7.20 (m, 6H), 7.02 (d, J=4.8 Hz, 1H), 6.43 (d, J=6.0 Hz, 1H), 5.47 (d, J=5.6 Hz, 1H), 4.64 (t, J=5.2 Hz, 1H), 4.37-4.33 (m, 1H), 4.31-4.25 (m, 1H), 4.23-4.18 (m, 1H), 3.94 (dd, J=11.2, 6.0 Hz, 1H), 2.72 (t, J=7.2 Hz, 2H), 1.66-1.56 (m, 2H), 1.40-1.31 (m, 2H), 0.91 (t, J=7.2 Hz, 3H).

Example 124. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-((1r,4R)-4-methylcyclohexyl)acetate (Compound 278)

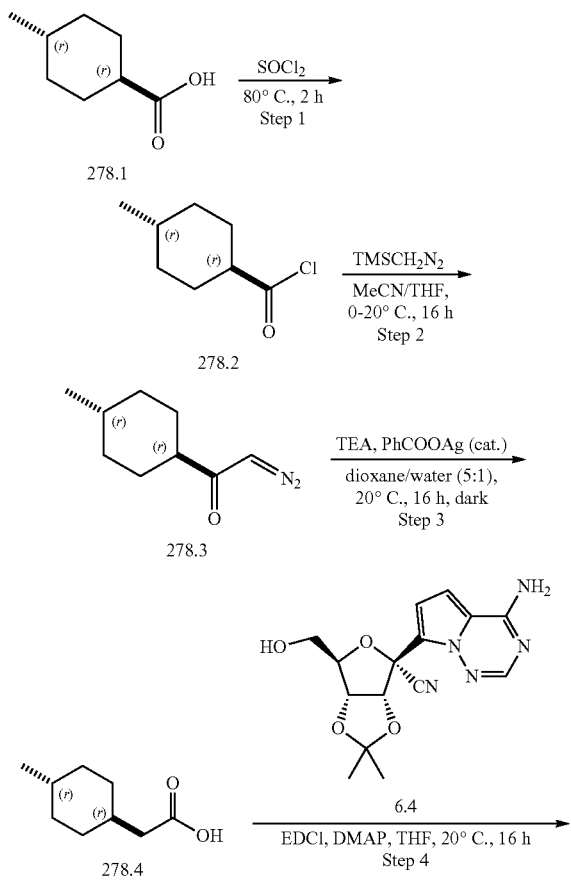

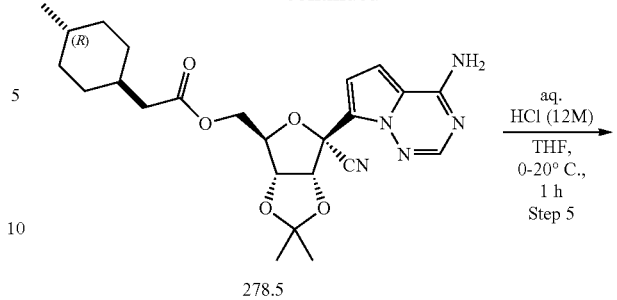

278.5

278

Step 1. Synthesis of (1r,4r)-4-methylcyclohexane-1-carbonyl chloride (278.2)

A solution of 4-methylcyclohexane-1-carboxylic acid (500 mg, 3.52 mmol) in SOCl$_2$ (2.5 mL) was stirred at 80° C. for 2 h. The reaction mixture was concentrated to dryness to give 278.2 (533 mg, crude) as a yellow oil, which was used directly in next step.

Step 2. Synthesis of 2-diazo-1-((1r,4r)-4-methylcyclohexyl)ethan-1-one (278.3)

To a solution of 278.2 (533 mg, crude) in THF (10 mL) and ACN (10 mL) was added TMSCHN$_2$ (7.0 mL, 14.0 mmol, 2 M in hexane) dropwise at 0° C. The reaction mixture was stirred at 20° C. for 16 h. The reaction mixture was concentrated to remove the solvent. The residue was diluted with EA (10 mL) and washed with water (5.0 mL×2), followed by brine (5.0 mL), dried over anhydrous Na$_2$SO$_4$, filtered. The filtrate was concentrated to dryness. The residue was purified by FCC (Gradient: 10% EA in PE) to give 278.3 (354 mg, 60% yield) as a yellow oil. MS (ESI): mass calcd. for $C_9H_{14}N_2O$, 166.11, m/z found 167.0 [M+H]$^+$. $^1$H NMR (400 MHz, CDCl$_3$) δ 5.25 (s, 1H), 2.15 (s, 1H), 1.88-1.73 (m, 4H), 1.48-1.28 (m, 3H), 0.99-0.86 (m, 5H).

Step 3. Synthesis of 2-((1r,4r)-4-methylcyclohexyl)acetic acid (278.4)

To a solution of 278.3 (354 mg, 2.13 mmol) in 1,4-dioxane (60 mL) and water (12 mL) was added silver benzoate (48.8 mg, 0.21 mmol) and TEA (860 mg, 8.52 mmol) under nitrogen. The reaction mixture was sonicated at 20° C. for 1 h while protected from light and then stirred at 20° C. for another 16 h in the dark. TLC showed complete consumption of 278.3. The reaction mixture was filtered, and the filtrate was concentrated to remove solvent. The residue was diluted with water (10 mL) and adjusted pH to 2-3 with HCl (1 M), extracted with EA (5.0 mL×3). The combined organic phase was washed with brine (5.0 mL)

and dried over anhydrous Na$_2$SO$_4$, filtered. The filtrate was concentrated to dryness to give 278.4 (342 mg, crude) as a yellow solid. $^1$H NMR (400 MHz, DMSO) δ 12.06 (s, 1H), 2.06 (d, J=6.8 Hz, 2H), 1.73-1.47 (m, 5H), 1.31-1.20 (m, 1H), 0.99-0.82 (m, 7H).

Step 4. Synthesis of ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl 2-((1r,4R)-4-methylcyclohexyl)acetate (278.5)

A solution of 278.4 (150 mg, 0.96 mmol), EDCI (552 mg, 2.9 mmol) and DMAP (352 mg, 2.9 mmol) in dry THF (15 mL) was stirred at 20° C. for 30 min and then 6.4 (255 mg, 0.77 mmol) was added. The reaction mixture was stirred at 20° C. for 16 h. The mixture was quenched with water (15 mL) and extracted with EA (5.0 mL×2). The combined organic phase was washed with brine (5.0 mL), dried over anhydrous Na$_2$SO$_4$, filtered. The filtrate was concentrated to dryness. The residue was purified by FCC (Gradient: 25% EA in PE) to give 278.5 (309 mg, 69% yield) as a white solid. MS (ESI): mass calcd. for C$_{24}$H$_{31}$N$_5$O$_5$, 469.23, m/z found 470.2 [M+H]$^+$. $^1$H NMR (400 MHz, DMSO) δ 7.92 (br s, 3H), 6.90 (d, J=4.4 Hz, 1H), 6.81 (d, J=4.4 Hz, 1H), 5.39 (d, J=6.0 Hz, 1H), 4.93 (dd, J=6.4, 2.8 Hz, 1H), 4.61-4.54 (m, 1H), 4.20 (dd, J=12.0, 4.0 Hz, 1H), 4.09 (dd, J=12.0, 5.6 Hz, 1H), 2.10-1.93 (m, 2H), 1.64 (s, 3H), 1.61-1.50 (m, 4H), 1.42-1.31 (m, 4H), 1.22-1.18 (m, 1H), 0.92-0.71 (m, 7H).

Step 5. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-((1r,4R)-4-methylcyclohexyl)acetate (278)

To a solution of 278.5 (120 mg, 0.26 mmol) in dry THF (1.2 mL) was added Conc. HCl (0.6 mL) dropwise at 0° C. The reaction mixture was stirred at 20° C. for 30 min. LC-MS showed complete consumption of 278.5. The organic solvent was removed with flowing nitrogen and the residue was diluted with ACN. The solution was purified by prep-HPLC to afford the title compound (61.23 mg, 55% yield) as a white solid. MS (ESI): mass calcd. for C$_{21}$H$_{27}$N$_5$O$_5$, 429.20, m/z found 430.2 [M+H]$^+$. $^1$H NMR (400 MHz, DMSO) δ 7.92 (br s, 3H), 6.91 (d, J=4.4 Hz, 1H), 6.80 (d, J=4.4 Hz, 1H), 6.31 (d, J=6.0 Hz, 1H), 5.37 (d, J=6.0 Hz, 1H), 4.69 (t, J=5.6 Hz, 1H), 4.30 (dd, J=12.0, 2.4 Hz, 1H), 4.24-4.12 (m, 2H), 3.94 (dd, J=11.2, 5.6 Hz, 1H), 2.19-2.08 (m, 2H), 1.65-1.47 (m, 5H), 1.28-1.15 (m, 1H), 0.97-0.77 (m, 7H).

Example 125. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-(spiro[4.5]decan-8-yl)acetate (Compound 279)

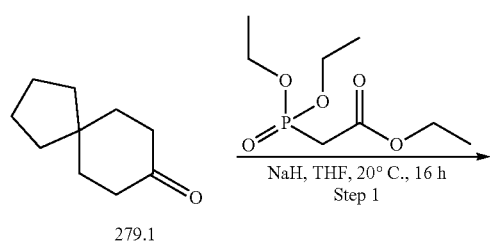

Step 1. Synthesis of ethyl 2-(spiro[4.5]decan-8-ylidene)acetate (279.2)

To a solution of ethyl 2-(diethoxyphosphoryl)acetate (884 mg, 3.94 mmol) in dry THF (5.0 mL) was added sodium hydride (158 mg, 60%, 3.94 mmol) in an ice bath. The reaction mixture was stirred at 20° C. for 1 h and then a solution of 279.1 (500 mg, 3.28 mmol) in dry THF (1.0 mL) was added dropwise. The reaction mixture was stirred at 20° C. for 16 h. The reaction mixture was quenched with water (10 mL) and extracted with EA (5.0 mL×3). The combined organic phase was washed with brine (5.0 mL), dried over anhydrous Na$_2$SO$_4$, filtered. The filtrate was concentrated to dryness. The residue was purified by FCC (Gradient: 5% EA in PE) to give 279.2 (610 mg, 84% yield) as a colorless oil.

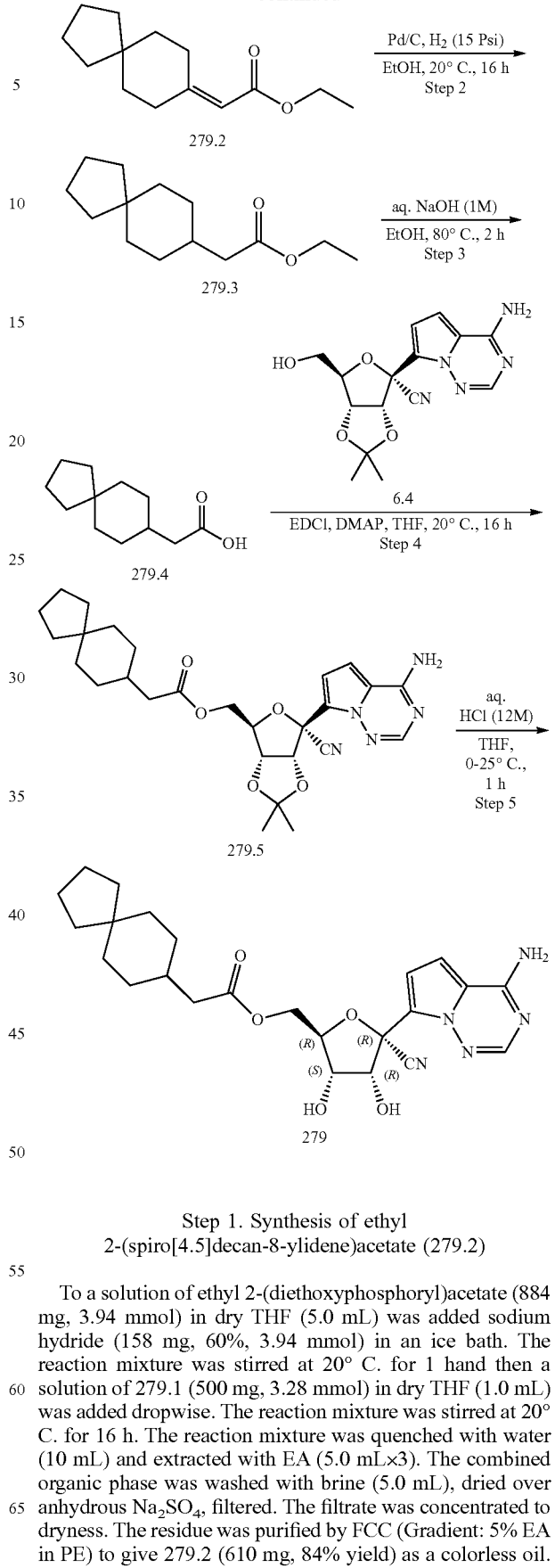

MS (ESI): m/z calcd. for $C_{14}H_{22}O_2$ 222.16, found 223.3 [M+H]$^+$. $^1$H NMR (400 MHz, CDCl$_3$) δ 5.61 (s, 1H), 4.14 (q, J=7.2 Hz, 2H), 2.87-2.81 (m, 2H), 2.23-2.17 (m, 2H), 1.66-1.58 (m, 4H), 1.54 (s, 2H), 1.51-1.41 (m, 6H), 1.27 (t, J=7.2 Hz, 3H).

Step 2. Synthesis of ethyl 2-(spiro[4.5]decan-8-yl)acetate (279.3)

To a solution of 279.2 (610 mg, 2.74 mmol) in EtOH (10 mL) was added Pd/C (61.0 mg, 10% w.t %). The reaction mixture was degassed with H$_2$ for three times and stirred at 20° C. for 16 h under H$_2$. TLC detected complete consumption of 279.2. The reaction mixture was filtered, the filtrate was concentrated to dryness to give 279.3 (613 mg, 99% yield) as a colorless oil. $^1$H NMR (400 MHz, CDCl$_3$) δ 4.12 (q, J=7.2 Hz, 2H), 2.18 (d, J=7.2 Hz, 1H), 1.79-1.68 (m, 1H), 1.63-1.54 (m, 3H), 1.48-1.41 (m, 1H), 1.40-1.22 (m, 5H), 1.15-1.03. (m, 1H).

Step 3. Synthesis of 2-(spiro[4.5]decan-8-yl)acetic acid (279.4)

To a solution of 279.3 (613 mg, 2.73 mmol) in EtOH (6.0 mL) was added a solution of sodium hydroxide (219 mg, 5.47 mmol) in water (6.0 mL). The reaction mixture was stirred at 80° C. for 2 h under nitrogen. TLC showed complete consumption of 279.3. The reaction mixture was concentrated to remove the organic solvent. The residue was diluted with water (10 mL) and extracted with EA (5.0 mL). The aqueous phase was acidified with HCl (1 M) and extracted with EA (5.0 mL×2). The combined organic phase was washed with brine (5.0 mL) and then concentrated to give 279.4 (562 mg, crude) as a white solid. $^1$H NMR (400 MHz, DMSO) δ 11.95 (s, 1H), 2.08 (d, J=6.8 Hz, 2H), 1.65-1.47 (m, 7H), 1.44-1.27 (m, 6H), 1.26-1.15 (m, 2H), 1.09-0.97 (m, 2H).

Step 4. Synthesis of ((3aR,4R,6R,6aR)-6-(4-amino-pyrrolo[2,1-f][1,2,4]triazin-7-yl)-6-cyano-2,2-dimethyltetrahydrofuro[3,4-d][1,3]dioxol-4-yl)methyl 2-(spiro[4.5]decan-8-yl)acetate (279.5)

A solution of 279.4 (200 mg, 1.0 mmol), EDCI (586 mg, 3.1 mmol) and DMAP (373 mg, 3.1 mmol) in dry THF (20 mL) was stirred at 20° C. for 30 min and then 6.4 (321 mg, 0.97 mmol) was added. The reaction mixture was stirred at 20° C. for 16 h. The mixture was quenched with water (15 mL) and extracted with EA (5.0 mL×2). The combined organic phase was washed with brine (5.0 mL), dried over anhydrous Na$_2$SO$_4$, filtered. The filtrate was concentrated to dryness. The residue was purified by FCC (Gradient: 25% EA in PE) to give 279.5 (450 mg, 87% yield) as a colorless oil. MS (ESI): m/z calcd. for $C_{27}H_{35}N_5O_5$ 509.26, found 510.4 [M+H]$^+$. $^1$H NMR (400 MHz, DMSO) δ 7.91 (br s, 3H), 6.90 (d, J=4.4 Hz, 1H), 6.80 (d, J=4.4 Hz, 1H), 5.39 (d, J=6.4 Hz, 1H), 4.93 (dd, J=6.4, 2.8 Hz, 1H), 4.61-4.54 (m, 1H), 4.21 (dd, J=12.0, 4.0 Hz, 1H), 4.09 (dd, J=12.0, 5.6 Hz, 1H), 2.12-1.99 (m, 2H), 1.64 (s, 3H), 1.56-1.47 (m, 4H), 1.45-1.22 (m, 12H), 1.16-1.05 (m, 2H), 1.01-0.87 (m, 2H).

Step 5. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-(spiro[4.5]decan-8-yl)acetate (279)

To a solution of 279.5 (100 mg, 0.20 mmol) in dry THF (1.0 mL) was added Conc. HCl (0.5 mL) dropwise at 0° C.

The reaction mixture was stirred at 20° C. for 30 min. LC-MS showed complete consumption of 279.5. The organic solvent was removed with flowing nitrogen and the residue was diluted with ACN. The solution was purified by prep-HPLC to afford the title compound (33.12 mg, 36% yield) as a white solid. MS (ESI): m/z calcd. for $C_{24}H_{31}N_5O_5$ 469.23, found 470.3 [M+H]$^+$. $^1$H NMR (400 MHz, DMSO) δ 7.92 (br s, 3H), 6.91 (d, J=4.4 Hz, 1H), 6.80 (d, J=4.4 Hz, 1H), 6.32 (d, J=6.0 Hz, 1H), 5.37 (d, J=5.2 Hz, 1H), 4.68 (t, J=5.2 Hz, 1H), 4.30 (dd, J=11.6, 2.4 Hz, 1H), 4.24-4.13 (m, 2H), 3.93 (dd, J=11.2, 6.0 Hz, 1H), 2.20-2.12 (m, 2H), 1.63-1.44 (m, 7H), 1.40-1.25 (m, 6H), 1.21-1.11 (m, 2H), 1.06-0.94 (m, 2H).

Example 126. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-(1,1-dioxidotetrahydro-2H-thiopyran-4-yl)acetate (Compound 280)

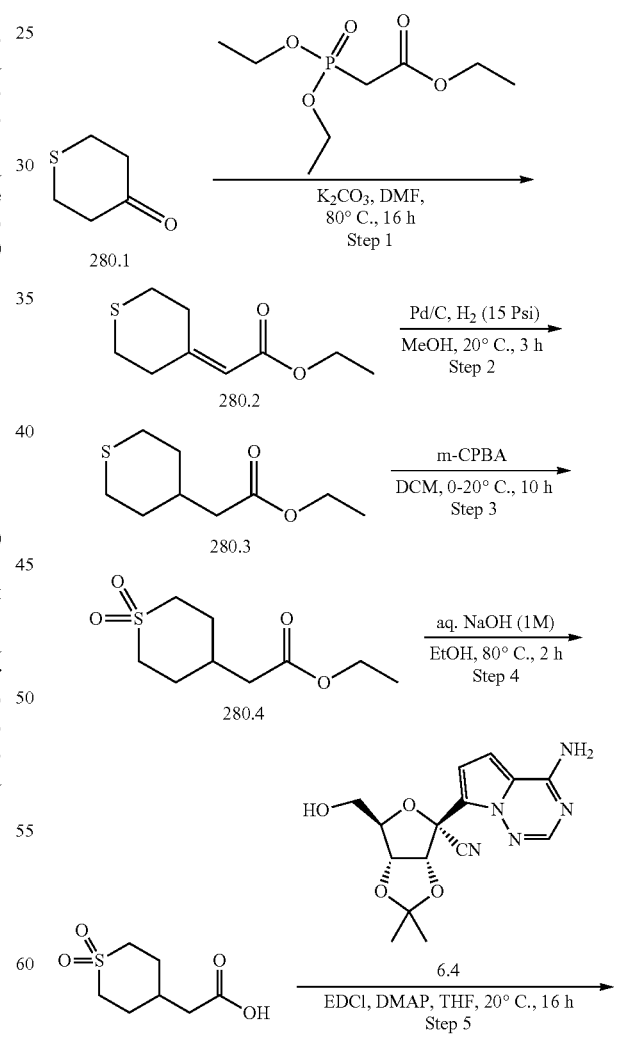

-continued

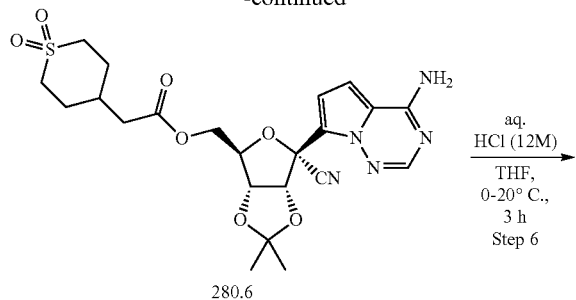

280.6

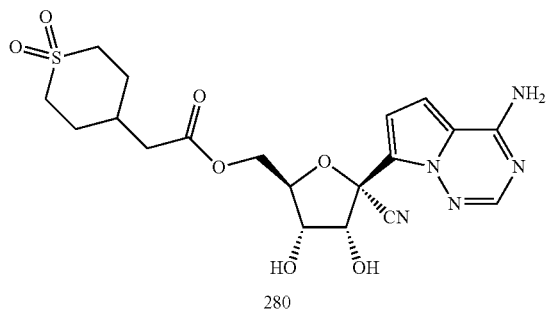

280

Step 1. Synthesis of ethyl 2-(tetrahydro-4H-thiopyran-4-ylidene)acetate (280.2)

To a solution of ethyl 2-(diethoxyphosphoryl)acetate (2.12 g, 9.40 mmol) and 280.1 (1.00 g, 8.6 mmol) in dry DMF (10 mL) was added potassium carbonate (1.78 g, 12.9 mmol). The reaction mixture was stirred at 80° C. for 16 h under nitrogen. The reaction mixture was diluted with water (50 mL) and extracted with EA (15 mL×3). The combined organic phase was washed with brine (20 mL×3), dried over anhydrous $Na_2SO_4$, filtered. The filtrate was concentrated to dryness. The residue was purified by FCC (Gradient: 5% EA in PE) to give 280.2 (1.39 g, 87% yield) as a white solid. MS (ESI): mass calcd. for $C_9H_{14}O_2S$, 186.07, m/z found 187.0 [M+H]+. 1H NMR (400 MHz, $CDCl_3$) δ 5.67 (s, 1H), 4.15 (q, J=7.2 Hz, 2H), 3.22-3.17 (m, 2H), 2.80-2.73 (m, 4H), 2.56-2.51 (m, 2H), 1.28 (t, J=7.2 Hz, 4H).

Step 2. Synthesis of ethyl 2-(tetrahydro-2H-thiopyran-4-yl)acetate (280.3)

To a solution of 280.2 (1.00 g, 5.37 mmol) and nickel (II) chloride hexahydrate (1.28 g, 5.37 mmol) in dry THF (10 mL) was added sodium borohydride (1.02 g, 26.8 mmol) in four portions at 0° C. The reaction mixture was stirred at 0° C. for 6 h and at 20° C. for 10 h. TLC showed about half consumption of 280.2. The reaction mixture was quenched with EA (10 mL) and Sat. aq. $NH_4Cl$ (20 mL). Filtered, the aqueous phase was extracted with EA (10 mL). The combined organic phase was washed with brine (10 mL), dried over anhydrous $Na_2SO_4$, filtered. The filtrate was concentrated to dryness. The residue was purified by FCC (Gradient: 5% EA in PE) to give 280.3 (329 mg, 33% yield) as a colorless oil. 1H NMR (400 MHz, $CDCl_3$) δ 4.13 (q, J=7.2 Hz, 2H), 2.75-2.66 (m, 2H), 2.63-2.55 (m, 2H), 2.21 (d, J=7.2 Hz, 2H), 2.06-1.97 (m, 2H), 1.90-1.78 (m, 1H), 1.46-1.35 (m, 2H), 1.26 (t, J=7.2 Hz, 3H).

Step 3. Synthesis of ethyl 2-(1,1-dioxidotetrahydro-2H-thiopyran-4-yl)acetate (280.4)

To a solution of 280.3 (329 mg, 1.75 mmol) in dry DCM (10 mL) was added m-CPBA (754 mg, 4.37 mmol) portionwise at 0° C. The reaction mixture was stirred at 0° C. for 6 h and at 20° C. for another 4 h. TLC showed complete consumption of 280.3. The mixture was diluted with DCM (10 mL) and washed with Sat. aq. $Na_2S_2O_3$ (10 mL), followed by Sat. aq. $NaHCO_3$ (10 mL), water (10 mL) and brine (5.0 mL). The organic phase was dried over anhydrous $Na_2SO_4$, filtered. The filtrate was concentrated to dryness. The residue was concentrated to dryness to give 280.4 (693 mg, crude) as a yellow oil. 1H NMR (400 MHz, DMSO) δ 4.06 (q, J=7.2 Hz, 2H), 3.15 (td, J=13.2, 3.2 Hz, 2H), 3.03-2.94 (m, 2H), 2.34-2.23 (m, 2H), 2.09-1.92 (m, 3H), 1.73-1.57 (m, 2H), 1.18 (t, J=7.2 Hz, 3H).

Step 4. Synthesis of 2-(1,1-dioxidotetrahydro-2H-thiopyran-4-yl)acetic acid (280.5)

To a solution of 280.4 (693 mg, 3.15 mmol) in EtOH (6.0 mL) was added a solution of sodium hydroxide (251 mg, 6.29 mmol) in water (6.0 mL). The reaction mixture was stirred at 80° C. for 2 h under nitrogen. TLC showed complete consumption of 280.4. The reaction mixture was concentrated to remove the organic solvent. The residue was diluted with water (10 mL) and extracted with EA (5.0 mL). The aqueous phase was acidified with HCl (1 M) and extracted with EA (5.0 mL×5). The combined organic phase washed with brine (5.0 mL) and then concentrated to give 280.5 (501 mg, crude) as a yellow oil.

Step 5. Synthesis of ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl 2-(1,1-dioxidotetrahydro-2H-thiopyran-4-yl)acetate (280.6)

A solution of 280.5 (155 mg, 0.81 mmol), EDCI (464 mg, 2.42 mmol) and DMAP (296 mg, 2.42 mmol) in dry THF (12 mL) was stirred at 20° C. for 30 min and then 6.4 (240 mg, 0.73 mmol) was added. the reaction mixture was stirred at 20° C. for 16 h. The mixture was quenched with water (15 mL) and extracted with EA (5.0 mL×2). The combined organic phase was washed with brine (5.0 mL), dried over anhydrous $Na_2SO_4$, filtered. The filtrate was concentrated to dryness. The residue was purified by FCC (Gradient: 50% EA in PE) to give 280.6 (208 mg, crude with DMAP) as a colorless oil. MS (ESI): mass calcd. for $C_{22}H_{27}N_5O_7S$, 505.16, m/z found 506.3 [M+H]+.

Step 6. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-(1,1-dioxidotetrahydro-2H-thiopyran-4-yl)acetate (280)

To a solution of 280.6 (208 mg, 0.41 mmol) in dry THF (2.0 mL) was added Conc. HCl (1.0 mL) dropwise at 0° C. The reaction mixture was stirred at 20° C. for 30 min. The organic solvent was removed with flowing nitrogen and the residue was diluted with ACN. The solution was purified by prep-HPLC to afford the title compound (64.73 mg, 33% yield) as a white solid. MS (ESI): mass calcd. for $C_{19}H_{23}N_5O_7S$, 465.13, m/z found 466.2 [M+H]+. 1H NMR (400 MHz, DMSO) δ 7.92 (br s, 3H), 6.92 (d, J=4.4 Hz, 1H), 6.81 (d, J=4.4 Hz, 1H), 6.31 (d, J=6.4 Hz, 1H), 5.39 (d, J=5.6 Hz, 1H), 4.70 (t, J=5.6 Hz, 1H), 4.33 (dd, J=11.4, 2.0 Hz, 1H), 4.25-4.14 (m, 2H), 3.94 (dd, J=11.2, 5.6 Hz, 1H), 3.12 (td, J=13.6, 3.2 Hz, 2H), 3.00-2.91 (m, 2H), 2.39-2.27 (m, 2H), 2.06-1.91 (m, 3H), 1.70-1.58 (m, 2H).

Example 127: Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl (S)-2-cyclohexylpropanoate (Compound 281)

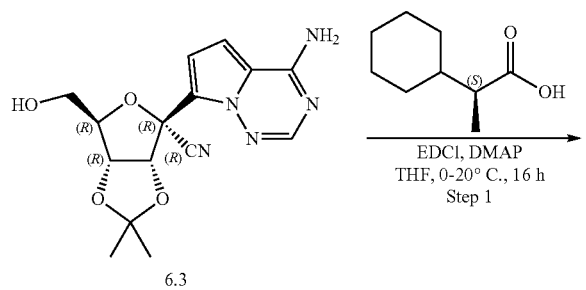

Step 1. Synthesis of ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl (S)-2-cyclohexylpropanoate (281.1)

The compound 281.1 was prepared according to the procedure of Example 266, Step 1, using 6.3 and (S)-2-cyclohexylpropanoic acid. MS (ESI): mass calcd. for $C_{24}H_{31}N_5O_5$, 469.23, m/z found 470.2 [M+H]+. 1H NMR (400 MHz, DMSO) δ 7.92-7.90 (br, s, 3H), 6.91 (d, J=4.4 Hz, 1H), 6.81 (d, J=4.4 Hz, 1H), 6.32 (d, J=6.0 Hz, 1H), 5.37 (d, J=5.6 Hz, 1H), 4.71 (t, J=5.6 Hz, 1H), 4.39-4.13 (m, 3H), 4.08-3.83 (m, 1H), 2.24-2.17 (m, 1H), 1.64-1.36 (m, 6H), 1.20-1.00 (m, 3H), 0.98 (d, J=7.2 Hz, 3H), 0.95-0.83 (m, 2H).

Step 2: Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl (S)-2-cyclohexylpropanoate (Compound 281)

The title compound 281 was prepared according to the procedure of Example 272, Step 2, using 281.1. MS (ESI): mass calcd. for $C_{21}H_{27}N_5O_5$, 429.20, m/z found 430.2 [M+H]+. 1H NMR (400 MHz, DMSO) δ 7.92-7.90 (br, s, 3H), 6.91 (d, J=4.4 Hz, 1H), 6.81 (d, J=4.4 Hz, 1H), 6.32 (d, J=6.0 Hz, 1H), 5.37 (d, J=5.6 Hz, 1H), 4.71 (t, J=5.6 Hz, 1H), 4.39-4.13 (m, 3H), 4.08-3.83 (m, 1H), 2.24-2.17 (m, 1H), 1.64-1.36 (m, 6H), 1.20-1.00 (m, 3H), 0.98 (d, J=7.2 Hz, 3H), 0.95-0.83 (m, 2H).

Example 128. Synthesis of ((2R,3S,4R,5R)-5-cyano-3,4-dihydroxy-5-(4-pentanamidopyrrolo[2,1-f][1,2,4]triazin-7-yl)tetrahydrofuran-2-yl)methyl propionate (Compound 282)

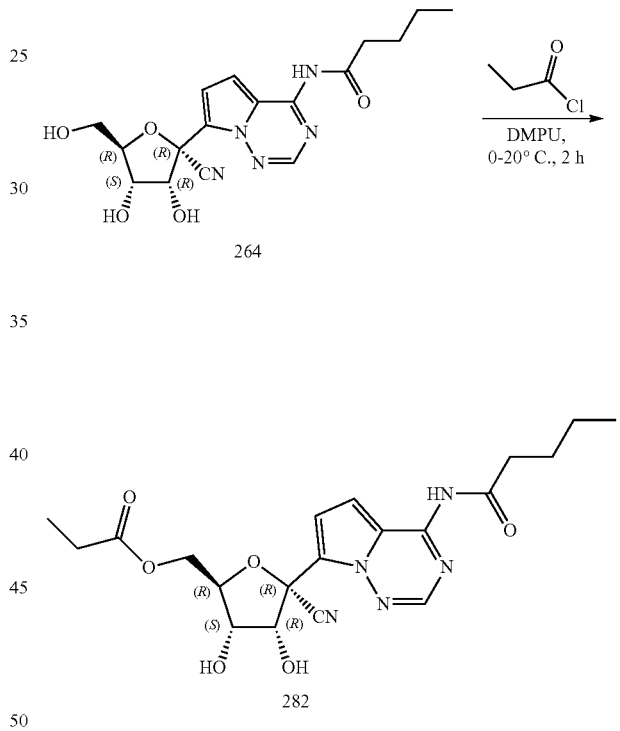

The title compound was prepared according to the procedure of Example 5, Step 4, using 264 and propionyl chloride. MS (ESI): mass calcd. for $C_{20}H_{25}N_5O_6$, 431.18, m/z found 432.2 [M+H]+. 1H NMR (400 MHz, DMSO-$d_6$) δ 10.90 (s, 1H), 8.39 (s, 1H), 7.27 (d, J=4.8 Hz, 1H), 7.04 (d, J=4.8 Hz, 1H), 6.44 (d, J=6.0 Hz, 1H), 5.45 (d, J=6.0 Hz, 1H), 4.67 (t, J=5.2 Hz, 1H), 4.38-4.31 (m, 1H), 4.29-4.24 (m, 1H), 4.19-4.13 (m, 1H), 3.94 (dd, J=11.6, 6.0 Hz, 1H), 2.71 (t, J=7.6 Hz, 2H), 2.34-2.27 (m, 2H), 1.67-1.54 (m, 2H), 1.40-1.30 (m, 2H), 0.99 (t, J=7.6 Hz, 3H), 0.91 (t, J=7.2 Hz, 3H).

Example 129. Synthesis ((2R,3S,4R,5R)-5-cyano-3, 4-dihydroxy-5-(4-pentanamidopyrrolo[2,1-f][1,2,4]triazin-7-yl)tetrahydrofuran-2-yl)methyl 3-methylbutanoate (Compound 283)

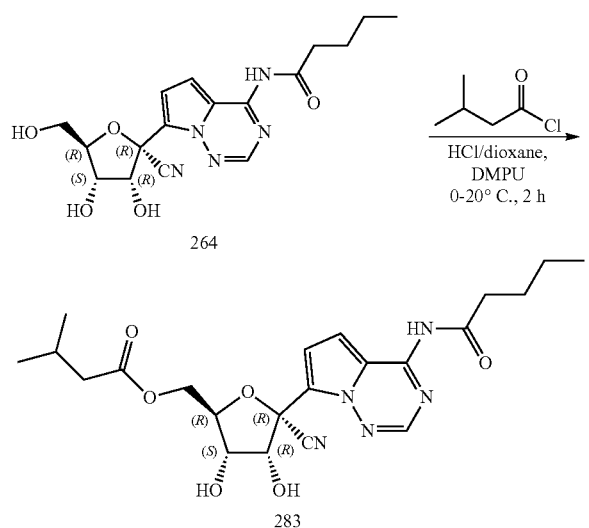

The title compound was prepared according to the procedure of Example 288, Step 1, using Compound 264 and 3-methylbutanoyl chloride. MS (ESI): mass calcd. for $C_{22}H_{29}N_5O_6$, 459.21, m/z found 460.3 [M+H]$^+$. $^1$H NMR (400 MHz, DMSO) δ 10.89 (s, 1H), 8.39 (s, 1H), 7.29 (d, J=4.8 Hz, 1H), 7.05 (d, J=4.8 Hz, 1H), 6.43 (d, J=6.0 Hz, 1H), 5.44 (d, J=6.0 Hz, 1H), 4.70-4.65 (m, 1H), 4.35-4.23 (m, 2H), 4.17 (dd, J=12.0, 5.2 Hz, 1H), 3.94 (dd, J=11.6, 6.4 Hz, 1H), 2.75-2.67 (m, 2H), 2.20-2.08 (m, 2H), 1.91 (m, 1H), 1.66-1.54 (m, 2H), 1.40-1.28 (m, 2H), 0.95-0.81 (m, 9H).

Example 130. Synthesis ((2R,3S,4R,5R)-5-cyano-3, 4-dihydroxy-5-(4-pentanamidopyrrolo[2,1-f][1,2,4]triazin-7-yl)tetrahydrofuran-2-yl)methyl 2-cyclohexylacetate (Compound 284)

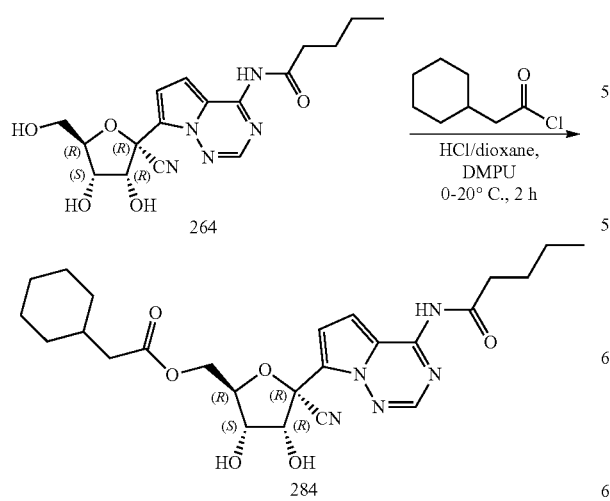

The title compound was prepared according to the procedure of Example 288, Step 1, using Compound 264 and 2-cyclohexylacetyl chloride. MS (ESI): mass calcd. for $C_{25}H_{33}N_5O_6$, 499.24, m/z found 500.1 [M+H]$^+$. $^1$H NMR (400 MHz, DMSO) δ 10.85 (s, 1H), 8.39 (s, 1H), 7.29 (d, J=4.8 Hz, 1H), 7.05 (d, J=4.8 Hz, 1H), 6.55 (s, 1H), 5.55 (s, 1H), 4.68 (d, J=4.8 Hz, 1H), 4.34-4.22 (m, 2H), 4.16 (dd, J=12.0, 5.2 Hz, 1H), 3.99-3.90 (m, 1H), 2.72 (t, J=7.6 Hz, 2H), 2.19-2.05 (m, 2H), 1.65-1.53 (m, 8H), 1.42-1.29 (m, 2H), 1.21-1.04 (m, 3H), 0.94-0.80 (m, 5H).

Example 131. Synthesis of ((2R,3S,4R,5R)-5-(4-benzamidopyrrolo[2,1-f][1,2,4]triazin-7-yl)-5-cyano-3,4-dihydroxytetrahydrofuran-2-yl)methyl 2-cyclohexylacetate (Compound 285)

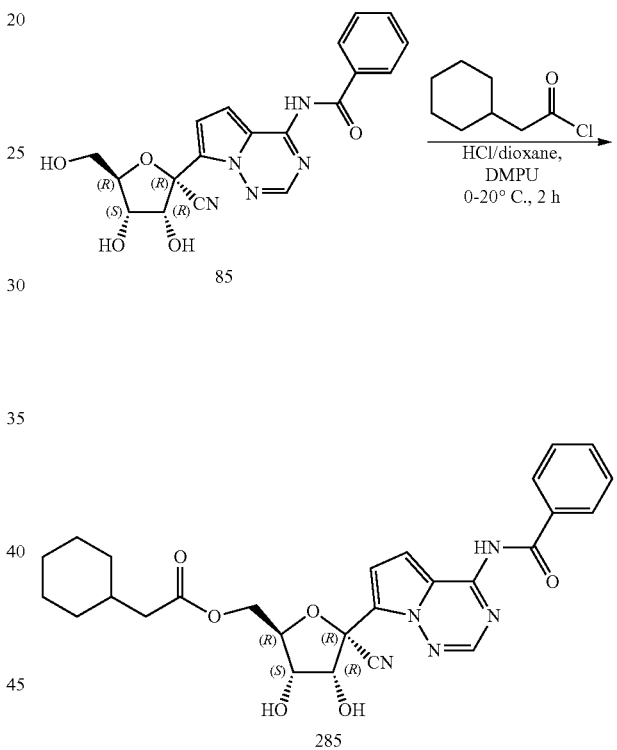

The title compound was prepared according to the procedure of Example 103, Step 1, using Compound 85 and 2-cyclohexylacetyl chloride. MS (ESI): mass calcd. for $C_{27}H_{29}N_5O_6$, 519.21, m/z found 520.1 [M+H]$^+$. $^1$H NMR (400 MHz, DMSO) δ 11.89 (s, 1H), 8.34 (s, 1H), 8.06 (d, J=8.0 Hz, 2H), 7.64 (t, J=7.6 Hz, 1H), 7.54 (t, J=7.6 Hz, 2H), 7.15 (d, J=3.2 Hz, 1H), 7.03 (d, J=4.8 Hz, 1H), 6.45 (s, 1H), 5.47 (s, 1H), 4.70 (s, 1H), 4.35-4.24 (m, 2H), 4.17 (dd, J=12.0, 5.2 Hz, 1H), 3.97 (t, J=5.6 Hz, 1H), 2.20-2.04 (m, 2H), 1.60 (d, J=11.2 Hz, 6H), 1.24-0.99 (m, 3H), 0.96-0.79 (m, 2H).

Example 132. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-(1-aminocyclohexyl)acetate

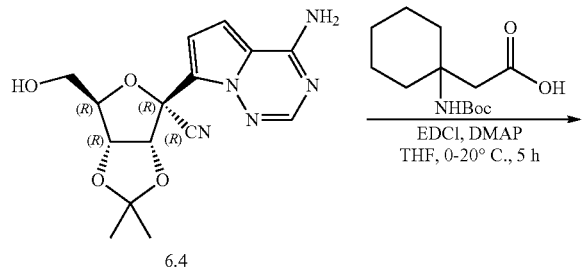

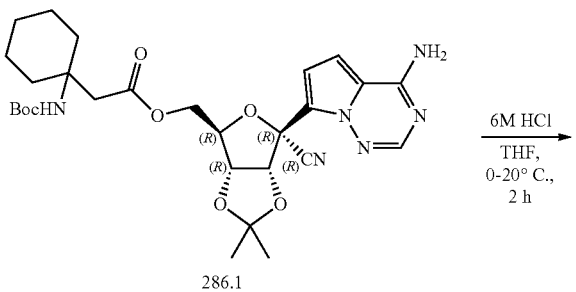

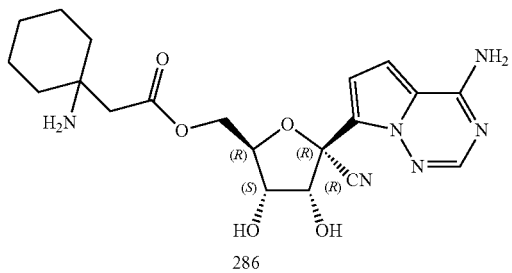

Step 1. Synthesis of ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl 2-(1-((tert-butoxycarbonyl)amino)cyclohexyl)acetate (286.1)

To a mixture of 6.4 (300 mg, 0.90 mmol), (1-{[(tert-butoxy)carbonyl]amino}cyclohexyl)acetic acid (233 mg, 0.90 mmol) and EDCI (520 mg, 2.71 mmol) in THF was added DMAP (331 mg, 2.71 mmol) at 0° C. slowly. The mixture was then stirred at 20° C. for about 5 hours. After completion, the reaction mixture was quenched with water (10 mL) and extracted with ethyl acetate (10 mL×3). The organic layer was dried over sodium sulphate and concentrated in vacuo to afford a residue. The residue was purified by prep-HPLC to afford 286.1 (410 mg, 78.5% yield) as a white solid. MS (ESI): m/z calcd. for $C_{28}H_{38}N_6O_7$, 570.28, found 571.35 [M+H]$^+$. $^1$H NMR (400 MHz, DMSO) δ 7.96 (s, 3H), 6.91 (d, J=4.4 Hz, 1H), 6.83 (d, J=4.4 Hz, 1H), 6.24 (s, 1H), 5.43 (d, J=6.4 Hz, 1H), 4.96 (dd, J=6.4, 3.2 Hz, 1H), 4.54 (dd, J=8.4, 5.2 Hz, 1H), 4.18 (dd, J=12.0, 4.4 Hz, 1H), 4.07 (dd, J=12.0, 6.0 Hz, 1H), 1.95 (d, J=10.0 Hz, 2H), 1.64 (s, 3H), 1.55-1.00 (m, 22H).

Step 2. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-(1-aminocyclohexyl)acetate (286)

To a solution of 286.1 (200 mg, 0.37 mmol) in THF (2.0 mL) was added 6 M HCl (2.0 mL) dropwise at 0° C., the mixture was then stirred at 20° C. for 2 hours. The mixture was quenched with water (2 mL) and dried with a stream of nitrogen to remove the solvent away. The residue was purified by prep-HPLC to afford 286 (113 mg, 74.6% yield) as a white solid. MS (ESI): m/z calcd. for $C_{20}H_{26}N_6O_5$, 430.20, found 431.10 [M+H]$^+$. $^1$H NMR (400 MHz, DMSO) δ 7.93 (s, 5H), 6.93 (d, J=4.4 Hz, 1H), 6.84 (d, J=4.4 Hz, 1H), 6.35 (d, J=4.8 Hz, 1H), 5.46 (s, 1H), 4.74 (s, 1H), 4.41-4.32 (m, 1H), 4.30-4.20 (m, 2H), 3.97 (t, J=5.2 Hz, 1H), 2.68 (s, 2H), 1.71-1.20 (m, 10H).

Example 133. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-(1-methoxycyclohexyl)acetate (Compound 287)

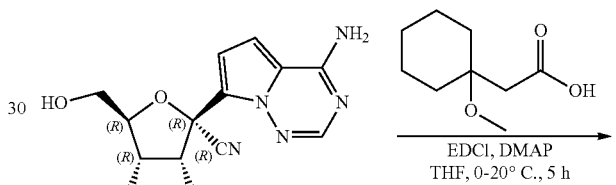

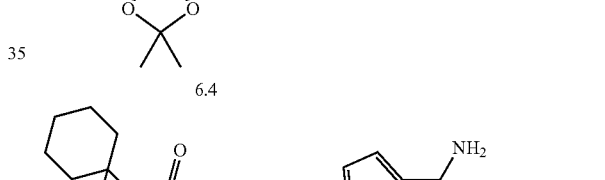

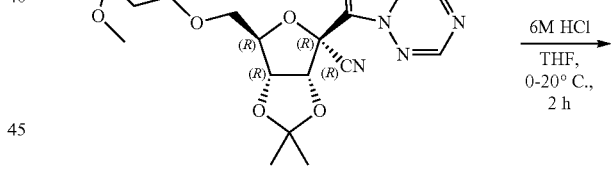

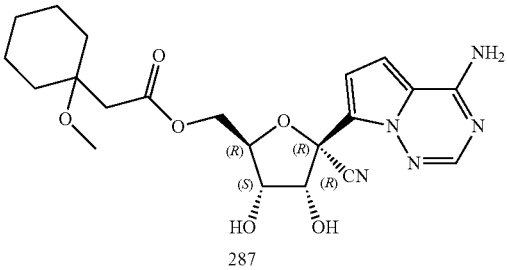

Step 1. Synthesis of ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl 2-(1-methoxycyclohexyl)acetate (287.1)

To a mixture of 6.4 (200 mg, 0.60 mmol) and (1-methoxycyclohexyl)acetic acid (103.9 mg, 0.60 mmol) and EDCI (347 mg, 1.81 mmol) in THF (4 mL) was added DMAP (221 mg, 1.81 mmol) at 0° C. slowly. The mixture was then stirred at 20° C. for about 5 hours. After completion, the reaction mixture was quenched with water (20 mL) and extracted with ethyl acetate (20 mL×3). The organic layer was dried over sodium sulphate and concentrated in vacuo to afford a residue. The residue was purified by prep-HPLC to afford 287.1 (220 mg, 74.3% yield) as a white solid. MS (ESI): m/z calcd. for $C_{24}H_{31}N_5O_6$, 485.23, found 486.30 $[M+H]^+$. $^1H$ NMR (400 MHz, DMSO) δ 7.96 (s, 3H), 6.91 (d, J=4.4 Hz, 1H), 6.85 (d, J=4.4 Hz, 1H), 5.42 (d, J=6.4 Hz, 1H), 4.93 (dd, J=6.4, 2.8 Hz, 1H), 4.55 (dd, J=7.6, 5.2 Hz, 1H), 4.14 (ddd, J=18.0, 12.0, 5.2 Hz, 2H), 3.04 (s, 3H), 2.37 (s, 2H), 1.65 (d, J=11.2 Hz, 5H), 1.47-1.28 (m, 10H), 1.14 (d, J=9.6 Hz, 1H).

Step 2. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-(1-methoxycyclohexyl)acetate (287)

To a solution of 287.1 (150 mg, 0.3 mmol) in THF (1.5 mL) was added 6 M HCl (1.5 mL) dropwise at 0° C., the mixture was then stirred at 20° C. for 2 hours. LCMS (ENB214167-097-M2) showed that the starting material was consumed completely. The mixture was quenched with water (2 mL) and dried with a stream of nitrogen to remove the solvent away. The residue was purified by prep-HPLC to afford 287 (113 mg, 74.8% yield) as a white solid. MS (ESI): m/z calcd. for $C_{21}H_{27}N_5O_6$, 445.20, found 446.25 $[M+H]^+$. $^1H$ NMR (400 MHz, DMSO) δ 7.92 (s, 3H), 6.91 (d, J=4.4 Hz, 1H), 6.81 (d, J=4.8 Hz, 1H), 6.30 (d, J=6.4 Hz, 1H), 5.38 (d, J=5.6 Hz, 1H), 4.71 (t, J=5.2 Hz, 1H), 4.31-4.18 (m, 2H), 4.18-4.08 (m, 1H), 3.96 (q, J=5.2 Hz, 1H), 3.06 (s, 3H), 2.43 (s, 2H), 1.74-1.61 (m, 2H), 1.48-1.31 (m, 7H), 1.20-1.09 (m, 1H).

Example 134. Synthesis ((2R,3S,4R,5R)-5-cyano-3,4-dihydroxy-5-(4-pentanamidopyrrolo[2,1-f][1,2,4]triazin-7-yl)tetrahydrofuran-2-yl)methyl acetate (Compound 288)

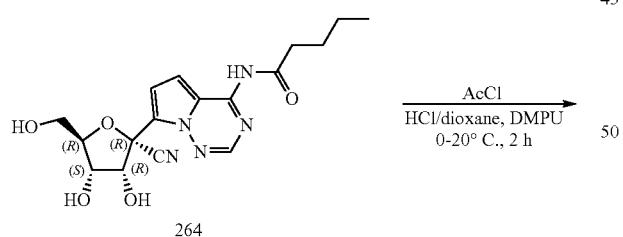

264

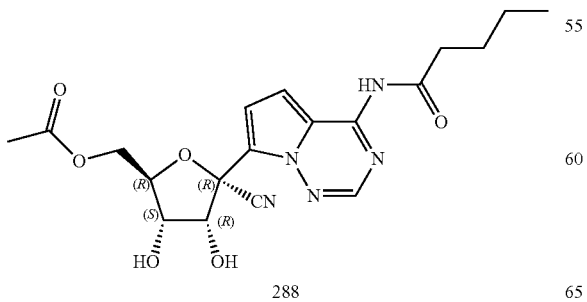

288

To a solution of 264 (80.0 mg, 0.21 mmol) in DMPU (0.5 mL) was added HCl/dioxane (0.1 mL, 4 M). The mixture solution was stirred at 0° C. for 15 minutes. Then acetyl chloride (50.2 mg, 0.64 mmol) was added at 0° C. The resulting mixture was stirred at 20° C. for another 2 hours. The reaction was diluted with ACN (2.0 mL) and purified by prep-HPLC to afford the title compound (19.5 mg, 21.5% yield) as a white solid. MS (ESI): m/z calcd. for $C_{19}H_{23}N_5O_6$ 417.16, found 418.1 $[M+H]^+$. $^1H$ NMR (400 MHz, DMSO) δ 10.89 (s, 1H), 8.40 (s, 1H), 7.29 (d, J=4.8 Hz, 1H), 7.05 (d, J=4.8 Hz, 1H), 6.42 (d, J=6.0 Hz, 1H), 5.44 (d, J=6.0 Hz, 1H), 4.71-4.61 (m, 1H), 4.35-4.23 (m, 2H), 4.15 (dd, J=12.0, 5.6 Hz, 1H), 3.93 (dd, J=12.0, 5.2 Hz, 1H), 2.73-2.66 (m, 2H), 2.01 (s, 3H), 1.65-1.55 (m, 2H), 1.41-1.29 (m, 2H), 0.91 (t, J=7.2 Hz, 3H).

Example 135. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 1-phenylcyclopropane-1-carboxylate (Compound 289)

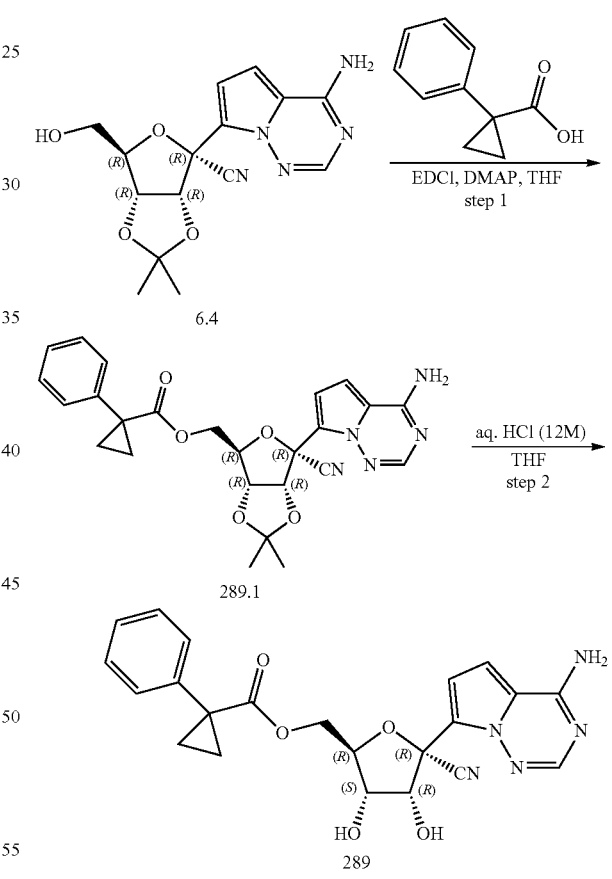

Step 1. Synthesis of ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl 1-phenylcyclopropane-1-carboxylate (289.1)

The title compound was prepared according to the procedure of Example 273, Step 1, using 6.4 and 1-phenylcyclopropane-1-carboxylic acid. MS (ESI): mass calcd. for $C_{25}H_{25}N_5O_5$, 475.19, m/z found 476.1 $[M+H]^+$.

Step 2. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 1-phenylcyclopropane-1-carboxylate (289)

The title compound was prepared according to the procedure of Example 273, Step 2, using 289.1. MS (ESI): mass calcd. for $C_{22}H_{21}N_5O_5$, 435.15, m/z found 436.0 [M+H]$^+$. $^1$H NMR (400 MHz, DMSO-d$_6$) δ 7.93 (br s, 3H), 7.33-7.19 (m, 5H), 6.92 (d, J=4.4 Hz, 1H), 6.64 (d, J=4.4 Hz, 1H), 6.21 (d, J=6.0 Hz, 1H), 5.36 (d, J=5.2 Hz, 1H), 4.41 (t, J=5.2 Hz, 1H), 4.30-4.23 (m, 1H), 4.20-4.10 (m, 2H), 3.87-3.80 (m, 1H), 1.50-1.41 (m, 2H), 1.23-1.12 (m, 2H).

Example 136. Synthesis of (2R,3S,4R,5R)-5-(4-aminopyrrolo[2,1-f][1,2,4]triazin-7-yl)-5-cyano-4-hydroxy-2-(hydroxymethyl)tetrahydrofuran-3-yl benzoate (Compound 290)

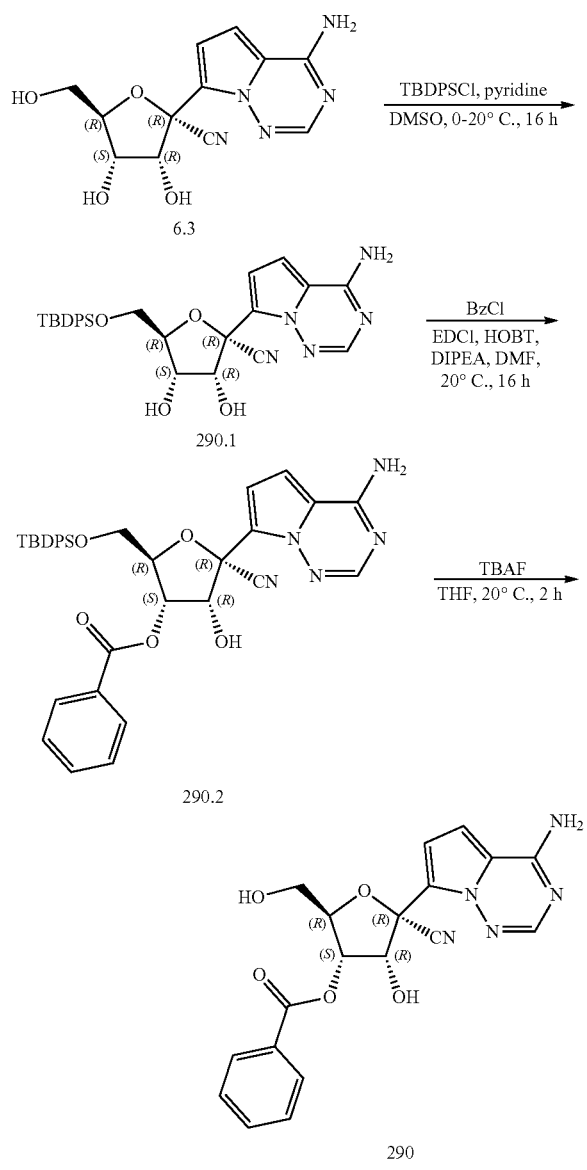

Step 1. Synthesis of (2R,3R,4S,5R)-2-(4-aminopyrrolo[2,1-f][1,2,4]triazin-7-yl)-5-(((tert-butyldiphenylsilyl)oxy)methyl)-3,4-dihydroxytetrahydrofuran-2-carbonitrile (290.1)

To a solution of 6.3 (1.00 g, 3.4 mmol) and pyridine (540 mg, 6.8 mmol) in dry DMSO (10 mL) was added TBDPSCl (1.03 g, 3.7 mmol) dropwise. The reaction mixture was stirred at 20° C. for 16 hours. The reaction mixture was poured into cold water (25 mL) and white solid precipitated. Filter, the filter cake was collected and dried to obtain 290.1 (1.90 g, 94.1% yield) as a white solid. MS (ESI): m/z calcd. for $C_{28}H_{31}N_5O_4Si$, 529.21, found 530.2 [M+H]$^+$. $^1$H NMR (400 MHz, MeOD) δ 7.79 (s, 1H), 7.63-7.55 (m, 4H), 7.41-7.35 (m, 3H), 7.30 (dd, J=13.2, 7.2 Hz, 4H), 6.86-6.81 (m, 2H), 4.37 (t, J=5.2 Hz, 1H), 4.34-4.27 (m, 1H), 3.93 (dd, J=11.6, 2.8 Hz, 1H), 3.83 (dd, J=11.6, 3.6 Hz, 1H), 1.00-0.92 (m, 9H).

Step 2. Synthesis of (2R,3S,4R,5R)-5-(4-aminopyrrolo[2,1-f][1,2,4]triazin-7-yl)-2-(((tert-butyldiphenylsilyl)oxy)methyl)-5-cyano-4-hydroxytetrahydrofuran-3-yl benzoate (290.2)

A solution of benzoic acid (184 mg, 1.51 mmol), HOBT (612 mg, 4.53 mmol), EDCI (869 mg 4.53 mmol) and DIPEA (586 mg, 4.53 mmol) in dry DMF (8.0 mL) was stirred at 25° C. for 1 h. Then 290.1 (800 mg, 1.51 mmol) was added into the flask vessel. The reaction mixture was stirred at 25° C. for 16 h. The reaction mixture was quenched with water (10 mL) and extracted with EA (5.0 mL×2). The combined organic phase was washed with brine (5.0 mL), dried over anhydrous Na$_2$SO$_4$, filtered. The filtrate was concentrated to dryness. The residue was purified by FCC (Gradient: 15% EA in PE) to give 290.2 (582 mg, 93% purity, 57% yield) as a white solid. MS (ESI): m/z calcd. for $C_{35}H_{35}N_5O_5Si$, 633.24, found 634.1 [M+H]$^+$. $^1$H NMR (400 MHz, DMSO) δ 8.13 (d, J=7.2 Hz, 2H), 7.91 (br s, 3H), 7.73-7.67 (m, 1H), 7.60-7.51 (m, 4H), 7.48-7.35 (m, 4H), 7.29 (t, J=7.2 Hz, 2H), 7.21 (t, J=7.6 Hz, 2H), 6.86 (dd, J=16.0, 4.4 Hz, 2H), 6.73 (d, J=6.4 Hz, 1H), 5.70 (dd, J=5.2, 3.2 Hz, 1H), 5.20 (t, J=6.0 Hz, 1H), 4.55 (dd, J=6.0, 3.2 Hz, 1H), 3.89-4.77 (m, 2H), 0.94 (s, 9H).

Step 3. Synthesis of (2R,3S,4R,5R)-5-(4-aminopyrrolo[2,1-f][1,2,4]triazin-7-yl)-5-cyano-4-hydroxy-2-(hydroxymethyl)tetrahydrofuran-3-yl benzoate (290)

A mixture of 290.2 (80.0 mg, 0.126 mmol) in THF (1.0 mL) was added TBAF (0.2 mL, 1M) dropwise. The reaction mixture was stirred at 20° C. for 2 h. The reaction was diluted with ACN (2.0 mL) and purified by prep-HPLC to obtain 290 (12.0 mg, 24% yield) as a white solid. MS (ESI): m/z calcd. for $C_{19}H_{17}N_5O_5$, 395.12, found 396.0 [M+H]$^+$. $^1$H NMR (400 MHz, DMSO-d$_6$) δ 8.16-8.09 (m, 2H), 7.96 (br s, 3H), 7.69 (t, J=7.2 Hz, 1H), 7.56 (t, J=7.6 Hz, 2H), 6.93 (q, J=4.8 Hz, 2H), 6.56 (d, J=6.4 Hz, 1H), 5.53 (dd, J=5.6, 2.8 Hz, 1H), 5.12 (q, J=6.0 Hz, 2H), 4.44 (q, J=3.6 Hz, 1H), 3.73-3.51 (m, 2H).

Example 137. Synthesis of ((2R,3R,4R,5R)-5-(2-amino-6-(2-cyclohexyl-N-methylacetamido)-9H-purin-9-yl)-4-fluoro-3-hydroxy-4-methyltetrahydrofuran-2-yl)methyl 2-cyclohexylacetate (Compound 291)

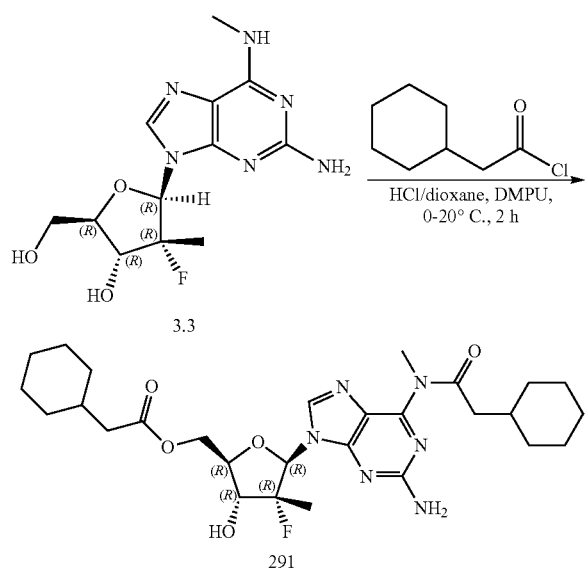

To a solution of 3.3 (1.00 g, 3.2 mmol) in DMPU (4 mL) was added HCl in dioxane (4 M, 1.6 mL), The solution was stirred at 20° C. for 15 min. The reaction mixture was cooled at 0° C. and 2-cyclohexylacetyl chloride (0.59 mL, 3.8 mmol) was added at once. The reaction was stirred for 2 hours at 0° C. The reaction was diluted with ACN (4.0 mL) and purified by prep-HPLC to obtain 291 (27.8 mg, 1.55% yield) as a white solid. MS (ESI): m/z calcd. for $C_{25}H_{41}FN_6O_5$, 560.31, found 561.3 [M+H]$^+$. (H NMR (400 MHz, DMSO-$d_6$) δ 8.18 (s, 1H), 6.82 (s, 2H), 6.14 (d, J=19.2 Hz, 1H), 5.84 (s, 1H), 4.56-4.25 (m, 3H), 4.16-4.03 (m, 1H), 2.42-2.32 (m, 2H), 2.23 (d, J=6.8 Hz, 2H), 1.58 (dd, J=28.8, 10.8 Hz, 13H), 1.25-0.73 (m, 15H). $^{19}$F NMR (376 MHz, DMSO) δ −159.44 (s, 1H).

Example 138. Synthesis of ((2R,3R,4R,5R)-5-(2-(2-cyclohexylacetamido)-6-(methylamino)-9H-purin-9-yl)-4-fluoro-3-hydroxy-4-methyltetrahydrofuran-2-yl)methyl 2-cyclohexylacetate (Compound 292)

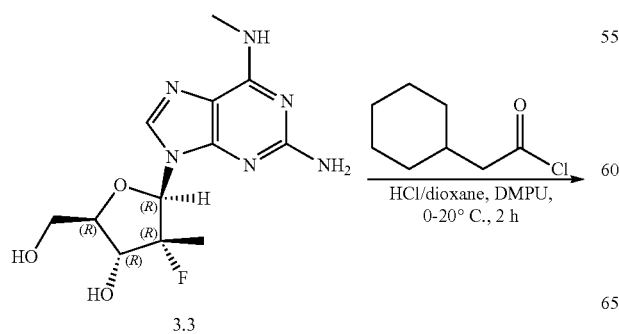

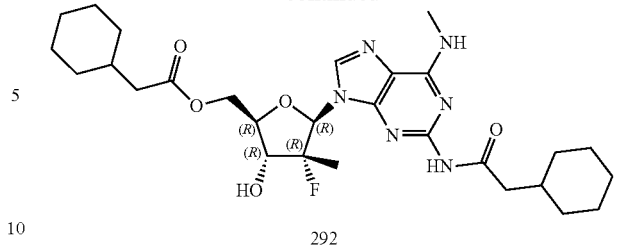

To a solution of 3.3 (1.00 g, 3.2 mmol) in DMPU (4 mL) was added HCl in dioxane (4 M, 1.6 mL), The solution was stirred at 20° C. for 15 min. The reaction mixture was cooled at 0° C. and 2-cyclohexylacetyl chloride (0.59 mL, 3.8 mmol) was added at once. The reaction was stirred for 2 hours at 0° C. The reaction was diluted with ACN (4.0 mL) and purified by prep-HPLC to obtain 292 (28.0 mg, 1.52% yield) as a white solid. MS (ESI): m/z calcd. for $C_{25}H_{41}FN_6O_5$, 560.31, found 561.3 [M+H]$^+$. $^1$H NMR (400 MHz, DMSO-$d_6$) δ 9.93 (s, 1H), 8.12 (s, 1H), 7.83 (d, J=17.6 Hz, 1H), 6.12 (d, J=20.0 Hz, 1H), 5.64 (s, 1H), 4.86 (s, 1H), 4.47 (dd, J=12.4, 2.0 Hz, 1H), 4.33 (dd, J=12.4, 7.6 Hz, 1H), 4.03 (t, J=8.0 Hz, 1H), 2.93 (s, 3H), 2.38 (s, 1H), 2.17 (d, J=6.8 Hz, 2H), 1.84-1.54 (m, 13H), 1.30-1.05 (m, 10H), 0.93 (dt, J=16.4, 10.8 Hz, 4H). $^{19}$F NMR (376 MHz, DMSO) δ −159.44.

Example 139. Synthesis of ((2R,3R,4R,5R)-4-fluoro-4-methyl-5-(6-(methylamino)-2-propionamido-9H-purin-9-yl)-3-(propionyloxy)tetrahydrofuran-2-yl)methyl isobutyrate (Compound 293)

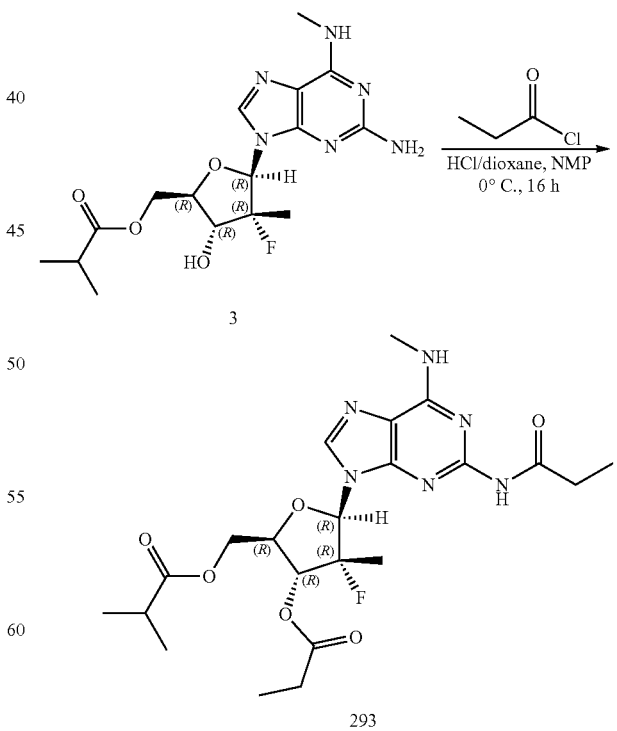

To a solution of 3 (50 mg, 0.13 mmol) in NMP (0.5 mL) was added 4 M HCl/dioxane (0.05 mL) dropwise, the mixture was then stirred at 0° C. for 20 minutes. Propanoyl chloride (0.05 mL) was added dropwise to the mixture at 0° C., the mixture was then stirred at 20° C. for 16 hours. After completion, the mixture was purified by prep-HPLC to afford 293 (20 mg, 30.9% yield) as a white solid. MS (ESI): m/z calcd. for $C_{22}H_{31}FN_6O_6$, 494.23, found 495.20 [M+H]$^+$. $^1$H NMR (400 MHz, DMSO) δ 9.88 (s, 1H), 8.18 (s, 1H), 7.89 (s, 1H), 6.17 (dd, J=55.6, 17.6 Hz, 2H), 4.53-4.21 (m, 3H), 2.94 (s, 3H), 2.59-2.52 (m, 2H), 2.48-2.31 (m, 3H), 1.24-0.94 (m, 15H). $^{19}$F NMR (377 MHz, DMSO) δ −155.61.

Example 140. Synthesis of (2R,3R,4R,5R)-4-fluoro-5-(2-isobutyramido-6-(methylamino)-9H-purin-9-yl)-2-((isobutyryloxy)methyl)-4-methyltetrahydrofuran-3-yl isobutyrate (Compound 294)

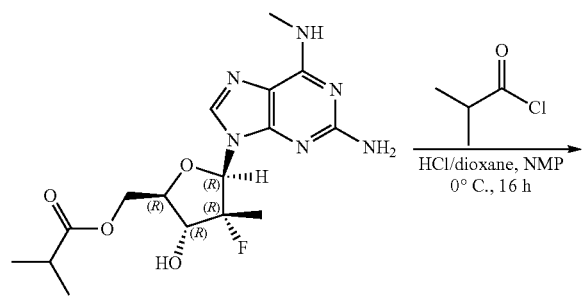

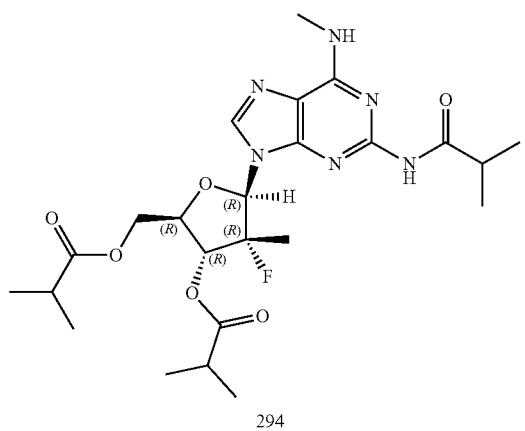

294

The title compound was prepared according to the procedure of Example 293, using 3 and isobutyryl chloride. MS (ESI): m/z calcd. for $C_{24}H_{35}FN_6O_6$ 522.26, found 523.25 [M+H]$^+$. $^1$H NMR (400 MHz, DMSO) δ 9.90 (s, 1H), 8.18 (s, 1H), 7.87 (s, 1H), 6.24 (d, J=19.6 Hz, 2H), 4.51-4.27 (m, 3H), 2.94 (s, 4H), 2.71-2.63 (m, 1H), 2.57-2.52 (m, 1H), 1.25-1.03 (m, 21H). $^{19}$F NMR (377 MHz, DMSO) δ −156.16.

Example 141. Synthesis of (2R,3R,4R,5R)-4-fluoro-2-((isobutyryloxy)methyl)-4-methyl-5-(6-(methylamino)-2-(3-methylbutanamido)-9H-purin-9-yl)tetrahydrofuran-3-yl 3-methylbutanoate (Compound 295)

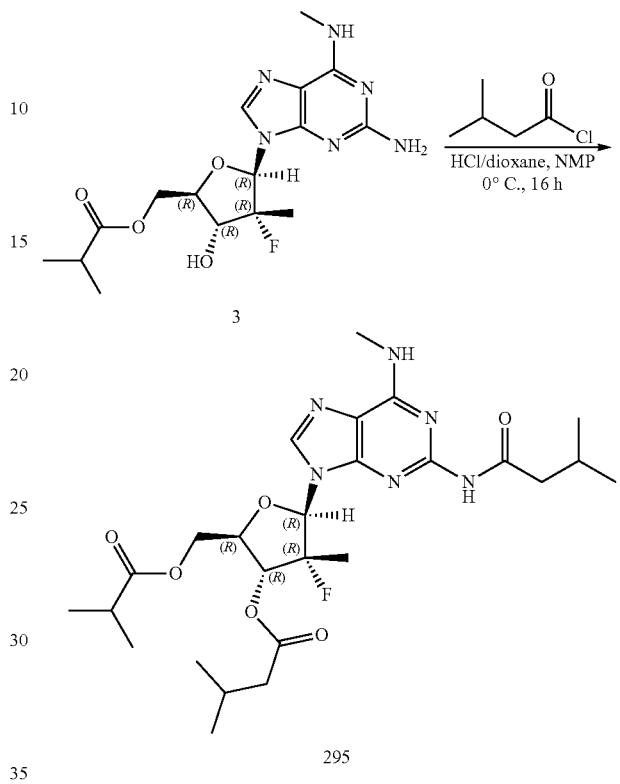

The title compound was prepared according to the procedure of Example 293, using 3 and 3-methylbutanoyl chloride. MS (ESI): m/z calcd. for $C_{26}H_{39}FN_6O_6$ 550.29, found 551.25 [M+H]$^+$. $^1$H NMR (400 MHz, DMSO) δ 9.91 (s, 1H), 8.17 (s, 1H), 7.87 (s, 1H), 6.23 (d, J=19.6 Hz, 2H), 4.56-4.25 (m, 3H), 2.95 (s, 3H), 2.57-2.51 (m, 1H), 2.32 (dd, J=17.6, 6.8 Hz, 4H), 2.04 (t, J=15.6, 6.8 Hz, 2H), 1.18 (d, J=23.2 Hz, 3H), 1.07 (d, J=7.2 Hz, 6H), 0.99-0.88 (m, 12H). $^{19}$F NMR (377 MHz, DMSO) δ −155.59.

Example 142. Synthesis of ((2R,3R,4R,5R)-5-(2-(2-cyclohexylacetamido)-6-(methylamino)-9H-purin-9-yl)-3-(2-cyclohexylacetoxy)-4-fluoro-4-methyltetrahydrofuran-2-yl)methyl isobutyrate (Compound 296)

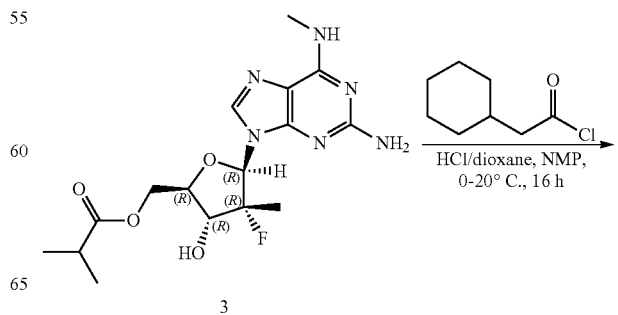

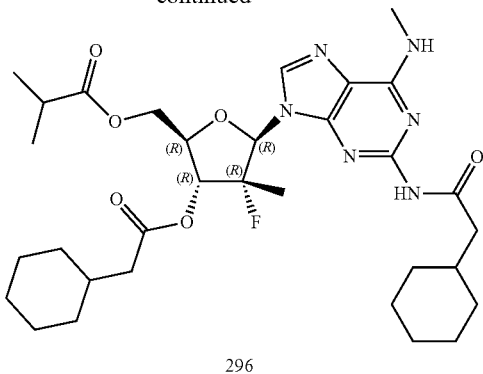

296

To a solution of 3 (100 mg, 0.26 mmol) in NMP (1 mL) was added HCl in dioxane (4 M, 0.3 mL), the solution was stirred at 20° C. for 15 minutes. The reaction mixture was cooled at 0° C. and 2-cyclohexylacetyl chloride (0.2 mL, 1.3 mmol) was added at once. The reaction was stirred at 20° C. for 16 hours. The reaction was diluted with ACN (2 mL) and purified by prep-HPLC to obtain 296 (25.5 mg, 14.7% yield) as a white solid. MS (ESI): m/z calcd. for $C_{32}H_{47}FN_6O_6$, 630.35, found 631.4 [M+H]+. 1H NMR (400 MHz, DMSO-$d_6$) δ 9.91 (s, 1H), 8.16 (s, 1H), 7.86 (s, 1H), 6.23 (d, J=19.6 Hz, 2H), 4.48-4.39 (m, 2H), 4.34-4.27 (m, 1H), 2.94 (s, 3H), 2.56-2.52 (m, 1H), 2.36-2.27 (m, 4H), 1.76-1.60 (m, 11H), 1.25-0.92 (m, 20H).

Example 143. Synthesis of ((2R,3R,4R,5R)-4-fluoro-3-hydroxy-4-methyl-5-(6-(methylamino)-2-(2-phenylacetamido)-9H-purin-9-yl)tetrahydrofuran-2-yl)methyl isobutyrate (Compound 297)

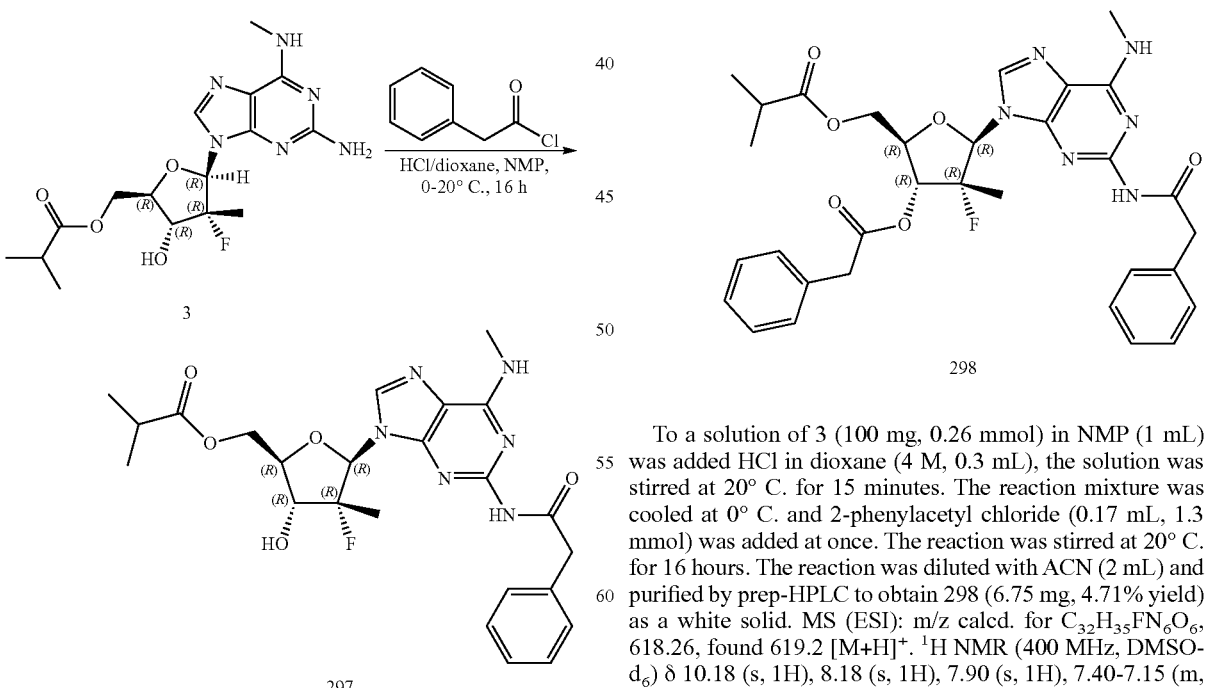

To a solution of 3 (100 mg, 0.26 mmol) in NMP (1 mL) was added HCl in dioxane (4 M, 0.3 mL), the solution was stirred at 20° C. for 15 minutes. The reaction mixture was cooled at 0° C. and 2-phenylacetyl chloride (0.17 mL, 1.3 mmol) was added at once. The reaction was stirred at 20° C. for 16 hours. The reaction was diluted with ACN (2 mL) and purified by prep-HPLC to obtain 297 (8.72 mg, 6.65% yield) as a white solid. MS (ESI): m/z calcd. for $C_{24}H_{29}FN_6O_5$, 500.22, found 501.3 [M+H]+. 1H NMR (400 MHz, DMSO-$d_6$) δ 10.24 (s, 1H), 8.13 (s, 1H), 7.85 (s, 1H), 7.35-7.28 (m, 4H), 7.25-7.19 (m, 1H), 6.12 (d, J=20.0 Hz, 1H), 5.65 (d, J=6.0 Hz, 1H), 4.81 (s, 1H), 4.46 (dd, J=12.4, 2.0 Hz, 1H), 4.32 (dd, J=12.4, 7.6 Hz, 1H), 4.04 (t, J=8.0 Hz, 1H), 3.82 (s, 2H), 2.93 (s, 2H), 2.57-2.52 ((m, 1H), 1.10 (t, J=15.6 Hz, 10H). 19F NMR (376 MHz, DMSO) δ −158.63.

Example 144. Synthesis of ((2R,3R,4R,5R)-4-fluoro-4-methyl-5-(6-(methylamino)-2-(2-phenylacetamido)-9H-purin-9-yl)-3-(2-phenylacetoxy)tetrahydrofuran-2-yl)methyl isobutyrate (Compound 298)

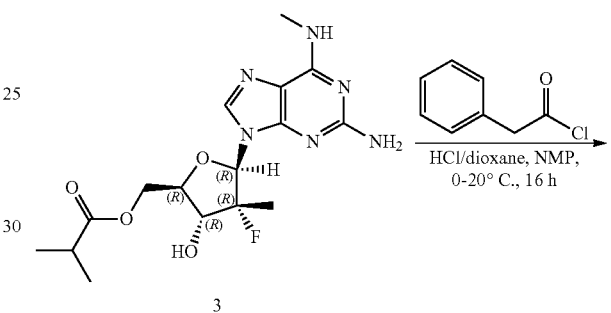

To a solution of 3 (100 mg, 0.26 mmol) in NMP (1 mL) was added HCl in dioxane (4 M, 0.3 mL), the solution was stirred at 20° C. for 15 minutes. The reaction mixture was cooled at 0° C. and 2-phenylacetyl chloride (0.17 mL, 1.3 mmol) was added at once. The reaction was stirred at 20° C. for 16 hours. The reaction was diluted with ACN (2 mL) and purified by prep-HPLC to obtain 298 (6.75 mg, 4.71% yield) as a white solid. MS (ESI): m/z calcd. for $C_{32}H_{35}FN_6O_6$, 618.26, found 619.2 [M+H]+. 1H NMR (400 MHz, DMSO-$d_6$) δ 10.18 (s, 1H), 8.18 (s, 1H), 7.90 (s, 1H), 7.40-7.15 (m, 10H), 6.23 (d, J=19.6 Hz, 2H), 4.46-4.29 (m, 3H), 3.89-3.71 (m, 4H), 2.92 (s, 3H), 1.23 (s, 1H), 1.13 (d, J=23.2 Hz, 3H), 1.06 (dd, J=7.2, 2.0 Hz, 6H). 19F NMR (376 MHz, DMSO) δ −155.52.

Example 145. Synthesis of ((2R,3R,4R,5R)-4-fluoro-3-hydroxy-4-methyl-5-(6-(methylamino)-2-(2-phenylacetamido)-9H-purin-9-yl)tetrahydrofuran-2-yl)methyl 2-cyclohexylacetate (Compound 299)

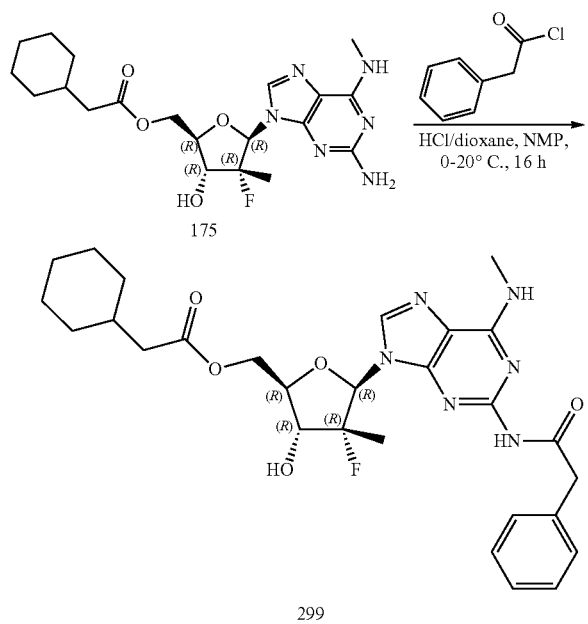

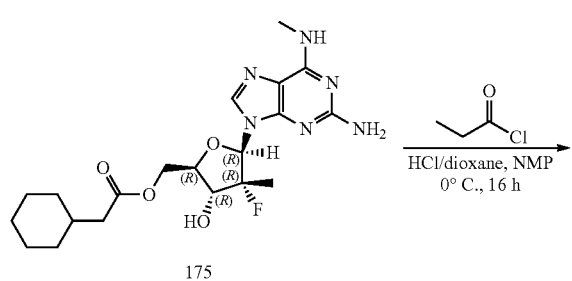

To a solution of 175 (100 mg, 0.22 mmol) in NMP (1 mL) was added HCl in dioxane (4 M, 0.2 mL), the solution was stirred at 20° C. for 15 minutes. The reaction mixture was cooled at 0° C. and 2-phenylacetyl chloride (0.21 mL, 1.6 mmol) was added at once. The reaction was stirred at 20° C. for 16 hours. The reaction was diluted with ACN (2 mL) and purified by prep-HPLC to obtain 299 (9.27 mg, 7.29% yield) as a white solid. MS (ESI): m/z calcd. for $C_{25}H_{35}FN_6O_5$, 554.27, found 555.2 [M+H]$^+$. $^1$H NMR (400 MHz, DMSO-d$_6$) δ 10.24 (s, 1H), 8.12 (s, 1H), 7.84 (s, 1H), 7.35-7.28 (m, 4H), 7.25-7.20 (m, 1H), 6.12 (d, J=20.0 Hz, 1H), 5.64 (d, J=7.2 Hz, 1H), 4.77 (s, 1H), 4.46 (dd, J=12.4, 2.0 Hz, 1H), 4.30 (dd, J=12.4, 7.2 Hz, 1H), 4.02 (t, J=7.6 Hz, 1H), 3.82 (s, 2H), 2.93 (s, 3H), 2.17 (d, J=6.8 Hz, 2H), 1.62 (d, J=12.8 Hz, 6H), 1.15 (dd, J=29.6, 17.6 Hz, 6H), 0.89 (dd, J=18.8, 8.8 Hz, 2H).

Example 146. Synthesis of (2R,3R,4R,5R)-2-((2-cyclohexylacetoxy)methyl)-4-fluoro-4-methyl-5-(6-(methylamino)-2-propionamido-9H-purin-9-yl)tetrahydrofuran-3-yl propionate (Compound 300)

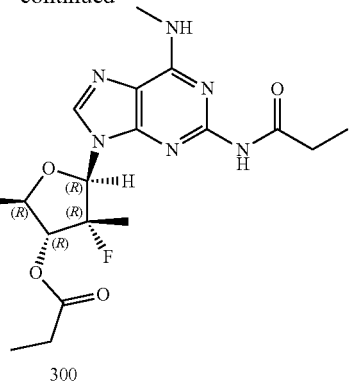

The title compound was prepared according to the procedure of Example 293, using 175 and propionyl chloride. MS (ESI): m/z calcd. for $C_{26}H_{37}FN_6O_6$ 548.28, found 549.35 [M+H]$^+$. $^1$H NMR (400 MHz, DMSO) δ 9.85 (s, 1H), 8.17 (s, 1H), 7.89 (s, 1H), 6.23 (d, J=19.6 Hz, 1H), 6.08 (d, J=14.8 Hz, 1H), 4.48-4.25 (m, 3H), 2.94 (s, 3H), 2.54 (Q, J=7.6 Hz, 2H), 2.45 (q, J=7.6 Hz, 2H), 2.17 (d, J=6.8 Hz, 2H), 1.69-1.54 (m, 6H), 1.24-1.02 (m, 12H), 0.97-0.82 (m, 2H). $^{19}$F NMR (377 MHz, DMSO) δ −155.53.

Example 147. Synthesis of (2R,3R,4R,5R)-2-((2-cyclohexylacetoxy)methyl)-4-fluoro-5-(2-isobutyramido-6-(methylamino)-9H-purin-9-yl)-4-methyl-tetrahydrofuran-3-yl isobutyrate (Compound 301)

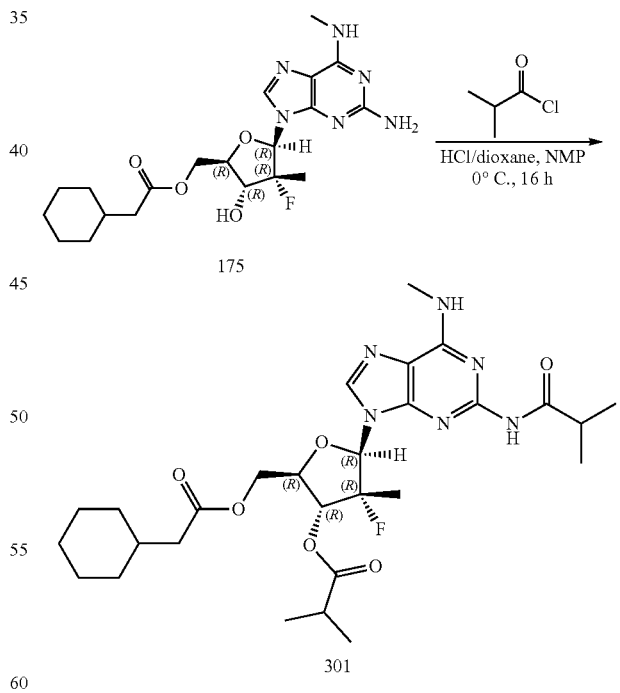

The title compound was prepared according to the procedure of Example 293, using 175 and isobutyryl chloride. MS (ESI): m/z calcd. for $C_{28}H_{41}FN_6O_6$ 576.31, found 577.25 [M+H]$^+$. $^1$H NMR (400 MHz, DMSO) δ 9.88 (s, 1H), 8.17 (s, 1H), 7.87 (s, 1H), 6.23 (d, J=19.6 Hz, 2H), 4.48-4.27 (m, 3H), 2.94 (s, 4H), 2.71-2.63 (m, 1H), 2.16 (d, J=6.4 Hz, 2H), 1.71-1.51 (m, 6H), 1.26-1.03 (m, 18H), 0.96-0.83 (m, 2H). $^{19}$F NMR (377 MHz, DMSO) δ −156.04.

Example 148. Synthesis of (2R,3R,4R,5R)-4-fluoro-4-methyl-5-(6-(methylamino)-2-propionamido-9H-purin-9-yl)-2-((2-phenylacetoxy)methyl)tetrahydrofuran-3-yl propionate (Compound 302)

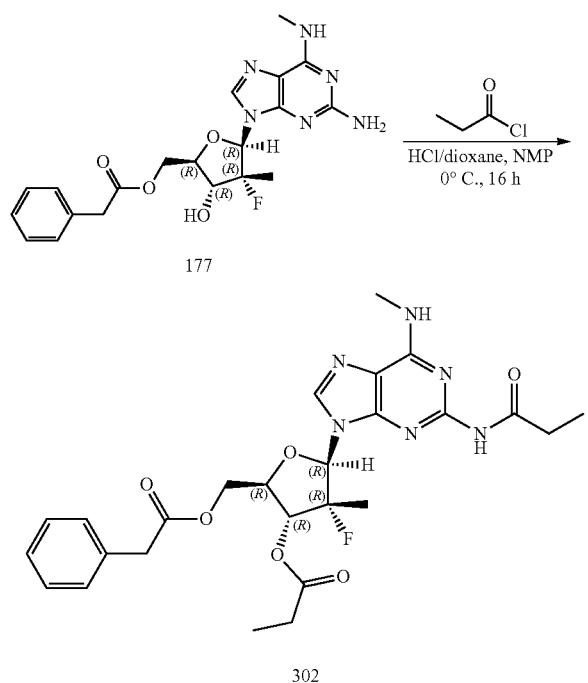

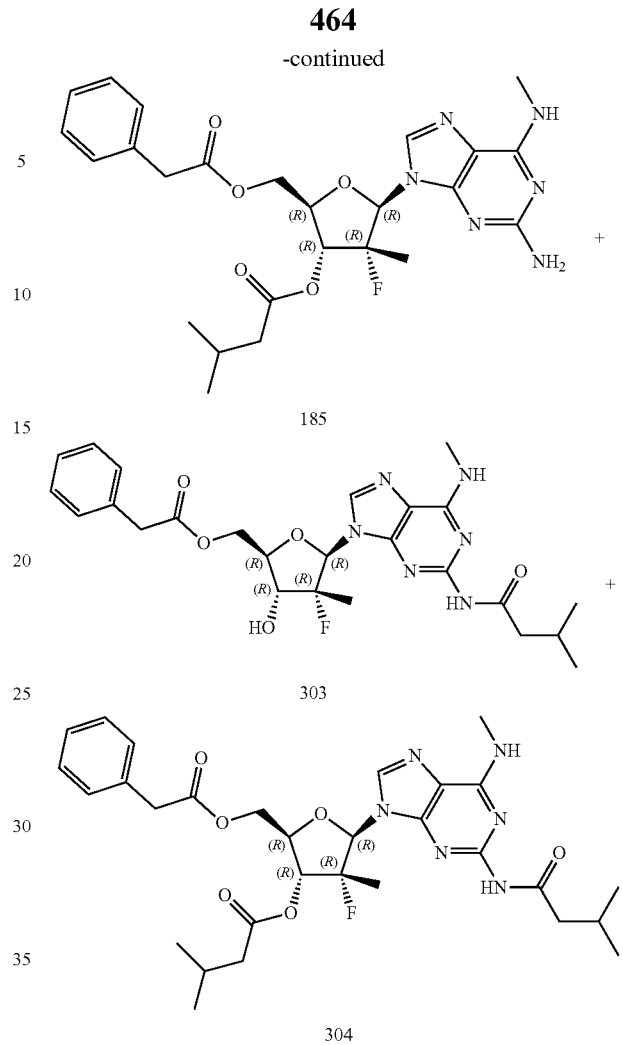

The title compound was prepared according to the procedure of Example 293, using 177 and propionyl chloride. MS (ESI): m/z calcd. for $C_{26}H_{31}FN_6O_6$ 542.23, found 543.15 [M+H]$^+$. $^1$H NMR (400 MHz, DMSO) δ 9.88 (s, 1H), 8.16 (s, 1H), 7.88 (s, 1H), 7.35-7.19 (m, 5H), 6.24 (d, J=19.6 Hz, 1H), 6.18-5.99 (m, 1H), 4.51-4.41 (m, 2H), 4.37-4.30 (m, 1H), 3.74-3.63 (m, 2H), 2.94 (s, 3H), 2.57-2.52 (m, 2H), 2.44 (q, J=7.2 Hz, 2H), 1.18 (d, J=23.2 Hz, 3H), 1.10-1.00 (m, 6H). $^{19}$F NMR (377 MHz, DMSO) δ −155.41.

Example 149. Synthesis of ((2R,3R,4R,5R)-4-fluoro-3-hydroxy-4-methyl-5-(6-(methylamino)-2-(3-methylbutanamido)-9H-purin-9-yl)tetrahydrofuran-2-yl)methyl 2-phenylacetate (Compound 303)

The title compound was prepared from Example 185. MS (ESI): m/z calcd. for $C_{25}H_{31}FN_6O_5$ 514.23, found 515.2 [M+H]$^+$. $^1$H NMR (400 MHz, DMSO) δ 9.94 (s, 1H), 8.12 (s, 1H), 7.81 (s, 1H), 7.32-7.21 (m, 5H), 6.13 (d, J=20.0 Hz, 1H), 5.63 (s, 1H), 4.88 (s, 1H), 4.50-4.36 (m, 2H), 4.05 (t J=8.0 Hz, 1H), 3.68 (s, 2H), 2.94 (s, 3H), 2.43-2.34 (m, 2H), 2.12-2.01 (m, 1H), 1.13 (d, J=22.4 Hz, 3H), 0.91 (d, J=6.4 Hz, 6H). $^{19}$F NMR (377 MHz, DMSO) δ −158.33.

Example 150. Synthesis of (2R,3R,4R,5R)-4-fluoro-4-methyl-5-(6-(methylamino)-2-(3-methylbutanamido)-9H-purin-9-yl)-2-((2-phenylacetoxy)methyl)tetrahydrofuran-3-yl 3-methylbutanoate (Compound 304)

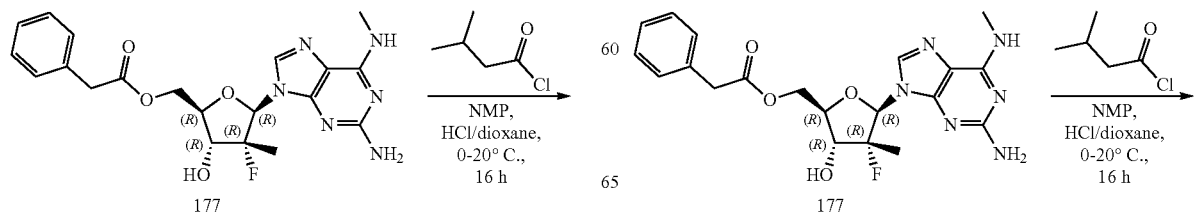

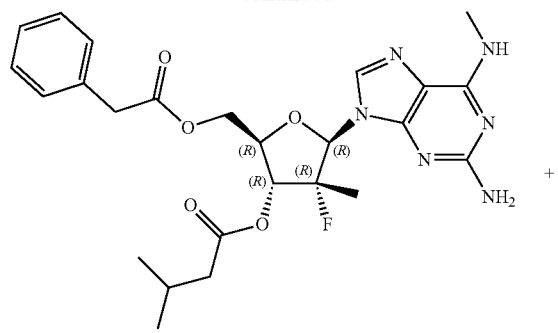

185

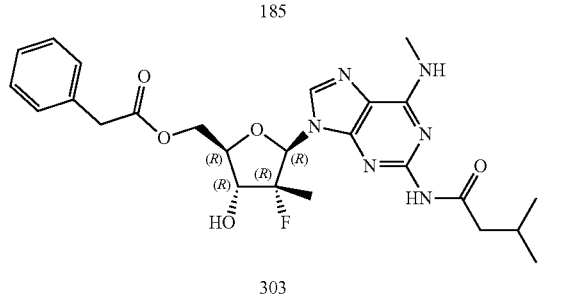

303

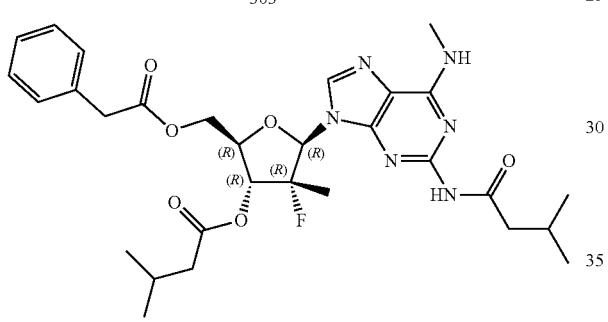

304

The title compound was prepared from Example 185. MS (ESI): m/z calcd. for $C_{30}H_{39}FN_6O_6$ 598.29, found 599.3 [M+H]$^+$. $^1$H NMR (400 MHz, DMSO) δ 9.91 (s, 1H), 8.16 (s, 1H), 7.85 (s, 1H), 7.32-7.21 (m, 5H), 6.44-6.16 (m, 2H), 4.53-4.43 (m, 2H), 4.35-4.29 (m, 1H), 3.67 (s, 2H), 2.94 (s, 3H), 2.35-2.27 (m, 4H), 2.07-1.96 (m, 2H), 1.17 (d, J=23.2 Hz, 3H), 0.94 (d, J=6.4 Hz, 6H), 0.90 (d, J=6.8 Hz, 6H). $^{19}$F NMR (377 MHz, DMSO) δ −155.42.

Example 151. Synthesis of ((2R,3R,4R,5R)-5-(2-(2-cyclohexylacetamido)-6-(methylamino)-9H-purin-9-yl)-4-fluoro-3-hydroxy-4-methyltetrahydrofuran-2-yl)methyl 2-phenylacetate (Compound 305)

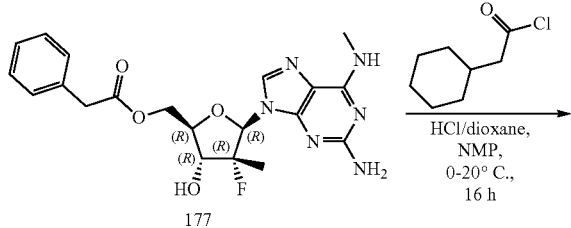

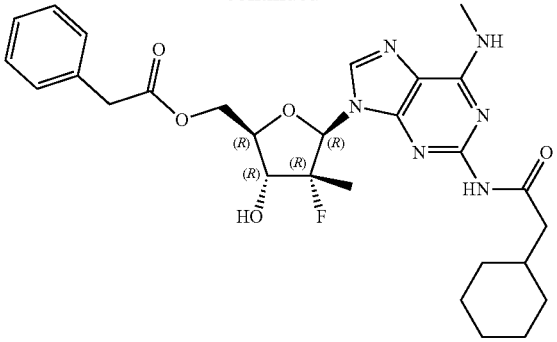

305

To a solution of 177 (100 mg, 0.23 mmol) in NMP (1 mL) was added HCl in dioxane (4 M, 0.5 mL), the solution was stirred at 20° C. for 15 minutes. The reaction mixture was cooled at 0° C. and 2-cyclohexylacetyl chloride (0.36 mL, 2.32 mmol) was added at once. The reaction was stirred at 20° C. for 16 hours. The reaction was diluted with ACN (2 mL) and purified by prep-HPLC to obtain 305 (8.40 mg 6.50% yield) as a white solid. MS (ESI): m/z calcd. for $C_2H_{35}FN_6O_5$, 554.27, found 555.3 [M+H]$^+$. $^1$H NMR (400 MHz, DMSO-d$_6$) δ 9.93 (s, 1H), 8.12 (s, 1H), 7.80 (s, 1H), 7.36-7.17 (m, 5H), 6.13 (d, J=20.0 Hz, 1H), 5.62 (s, 1H), 4.85 (s, 1H), 4.48 (dd, J=12.4, 2.0 Hz, 1H), 4.39 (dd, J=12.4, 7.2 Hz, 1H), 4.05 (t, J=7.6 Hz, 1H), 3.68 (s, 2H), 2.93 (s, 3H), 2.36 (s, 2H), 1.79-1.57 (m, 6H), 1.24-1.08 (m, 6H), 0.98-0.90 (m, 2H).

Example 152. Synthesis of ((2R,3R,4R,5R)-5-(2-(2-cyclohexylacetamido)-6-(methylamino)-9H-purin-9-yl)-3-(2-cyclohexylacetoxy)-4-fluoro-4-methyltetrahydrofuran-2-yl)methyl 2-phenylacetate (Compound 306)

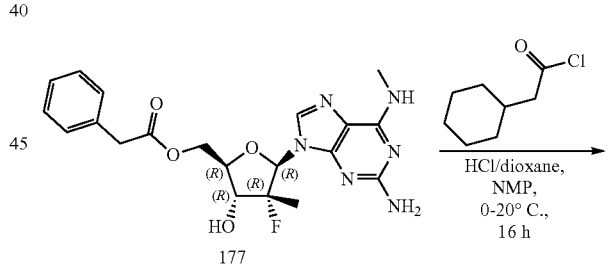

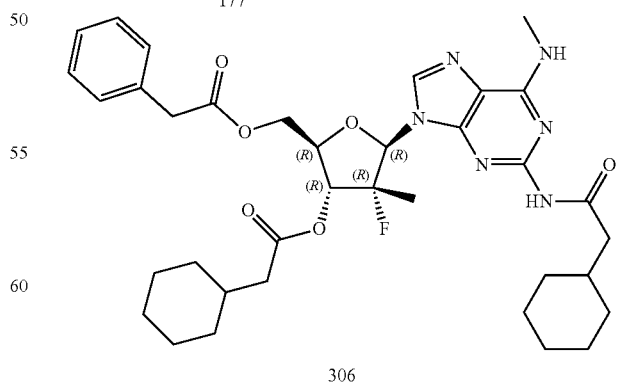

306

To a solution of 177 (100 mg, 0.23 mmol) in NMP (1 mL) was added HCl in dioxane (4 M, 0.5 mL), the solution was stirred at 20° C. for 15 minutes. The reaction mixture was cooled at 0° C. and 2-cyclohexylacetyl chloride (0.36 mL, 2.32 mmol) was added at once. The reaction was stirred at 20° C. for 16 hours. The reaction was diluted with ACN (2 mL) and purified by prep-HPLC to obtain 306 (12.0 mg 7.62% yield) as a white solid. MS (ESI): m/z calcd. for $C_{36}H_{47}FN_6O_6$, 678.35, found 679.43 [M+H]$^+$. $^1$H NMR (400 MHz, DMSO-d$_6$) δ 9.91 (s, 1H), 8.15 (s, 1H), 7.85 (s, 1H), 7.40-7.09 (m, 5H), 6.23 (d, J=20.0 Hz, 2H), 4.47 (d, J=5.2 Hz, 2H), 4.31 (dt, J=9.6, 5.2 Hz, 1H), 3.67 (s, 2H), 2.94 (s, 3H), 2.28 (d, J=6.8 Hz, 2H), 1.75-1.57 (m, 12H), 0.99-0.83 (m, 11H), 1.01-0.86 (m, 4H). $^{19}$F NMR (376 MHz, DMSO) δ −155.45.

Example 153. Synthesis of ((2R,3R,4R,5R)-4-fluoro-3-hydroxy-4-methyl-5-(6-(methylamino)-2-(2-phenylacetamido)-9H-purin-9-yl)tetrahydrofuran-2-yl)methyl 2-phenylacetate (Compound 307)

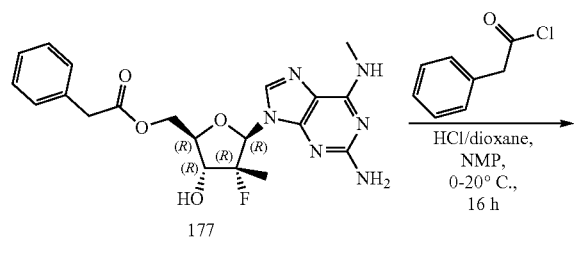

Example 154. Synthesis of (2R,3R,4R,5R)-4-fluoro-4-methyl-5-(6-(methylamino)-2-(2-phenylacetamido)-9H-purin-9-yl)-2-((2-phenylacetoxy)methyl)tetrahydrofuran-3-yl 2-phenylacetate (Compound 308)

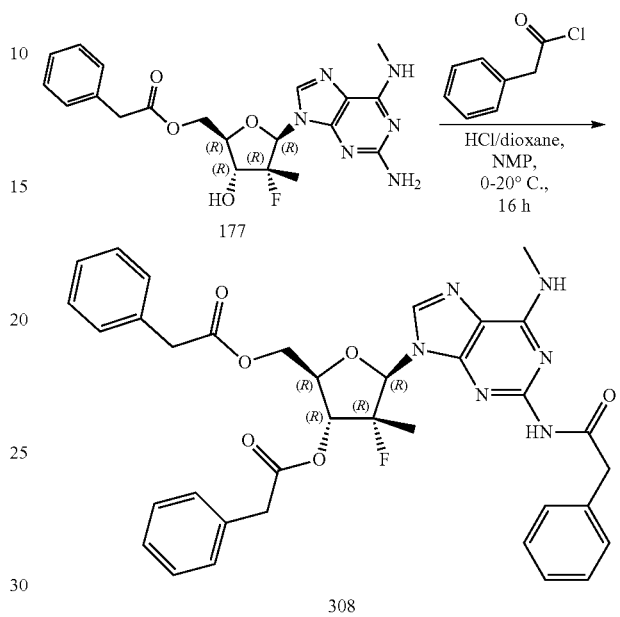

To a solution of 177 (100 mg, 0.23 mmol) in NMP (1 mL) was added HCl in dioxane (4 M, 0.5 mL), the solution was stirred at 20° C. for 15 minutes. The reaction mixture was cooled at 0° C. and 2-phenylacetyl chloride (0.25 mL, 1.85 mmol) was added at once. The reaction was stirred at 20° C. for 16 hours. The reaction was diluted with ACN (2 mL) and purified by prep-HPLC to obtain 308 (22.1 mg, 13.9% yield) as a white solid. MS (ESI): m/z calcd. for $C_{36}H_{35}FN_6O_6$, 666.26, found 667.2 [M+H]$^+$. $^1$H NMR (400 MHz, DMSO-d$_6$) δ 10.18 (s, 1H), 8.16 (s, 1H), 7.89 (s, 1H), 7.33-7.17 (m, 15H), 6.24 (m, 2H), 4.49-4.39 (m, 2H), 4.34 (dt, J=9.6, 4.8 Hz, 1H), 3.86-3.74 (m, 4H), 3.69-3.61 (m, 2H), 2.93 (s, 3H), 1.14 (d, J=23.2 Hz, 3H).

Example 155. Synthesis of (2R,3R,4R,5R)-4-fluoro-4-methyl-5-(6-(methylamino)-2-propionamido-9H-purin-9-yl)-2-((propionyloxy)methyl)tetrahydrofuran-3-yl propionate (Compound 309)

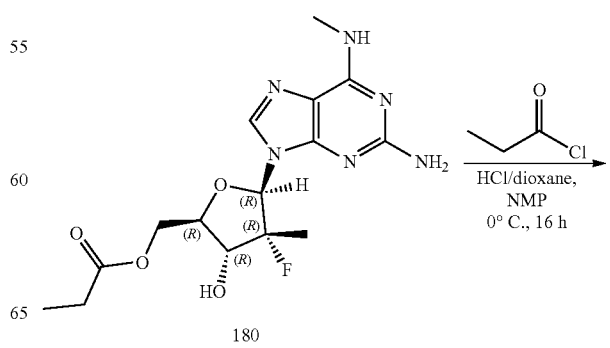

To a solution of 177 (100 mg, 0.23 mmol) in NMP (1 mL) was added HCl in dioxane (4 M, 0.5 mL), the solution was stirred at 20° C. for 15 minutes. The reaction mixture was cooled at 0° C. and 2-phenylacetyl chloride (0.25 mL, 1.85 mmol) was added at once. The reaction was stirred at 20° C. for 16 hours. The reaction was diluted with ACN (2 mL) and purified by prep-HPLC to obtain 307 (13.6 mg, 10.3% yield) as a white solid. MS (ESI): m/z calcd. for $C_{25}H_{29}FN_6O_5$, 548.22, found 549.1 [M+H]$^+$. $^1$H NMR (400 MHz, DMSO-d$_6$) δ 10.24 (s, 1H), 8.13 (s, 1H), 7.84 (s, 1H), 7.35-7.17 (m, 10H), 6.13 (d, J=20.0 Hz, 1H), 5.64 (s, 1H), 4.85 (s, 1H), 4.52-4.43 (m, 1H), 4.37 (dd, J=12.4, 7.6 Hz, 1H), 4.04 (t, J=7.6 Hz, 1H), 3.81 (s, 2H), 3.68 (s, 2H), 2.93 (s, 3H), 1.11 (d, J=22.8 Hz, 3H).

-continued

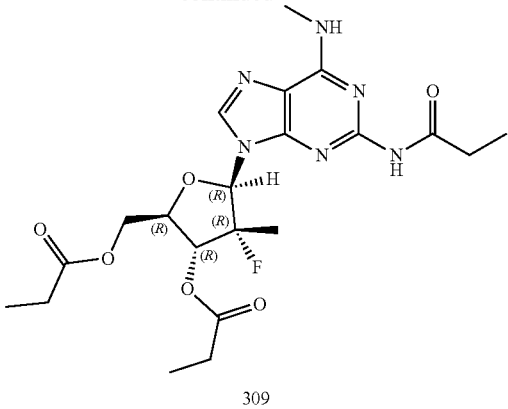

309

The title compound was prepared according to the procedure of Example 293, using 180 and propionyl chloride. MS (ESI): m/z calcd. for $C_{21}H_{29}FN_6O_6$ 480.21, found 481.10 [M+H]+. 1H NMR (400 MHz, DMSO) δ 9.87 (s, 1H), 8.19 (s, 1H), 7.89 (s, 1H), 6.23 (d, J=19.6 Hz, 1H), 6.09 (d, J=15.2 Hz, 1H), 4.51-4.24 (m, 3H), 2.95 (s, 3H), 2.59-2.51 (m, 2H), 2.45 (q, J=7.2 Hz, 2H), 2.32 (q, J=7.2 Hz, 2H), 1.26-0.96 (m, 12H). 19F NMR (377 MHz, DMSO) δ −155.56.

Example 156. Synthesis of (2R,3R,4R,5R)-5-(2-amino-6-(methylamino)-9H-purin-9-yl)-4-fluoro-4-methyl-2-(((3-methylbutanoyl)oxy)methyl)tetrahydrofuran-3-yl 3-methylbutanoate (Compound 312)

The title compound was prepared according to the procedure of Example 183, using 174 and 3-methylbutanoyl chloride. MS (ESI): m/z calcd. for $C_{22}H_{33}FN_6O_5$ 480.25, found 481.25 [M+H]+. 1H NMR (400 MHz, DMSO) δ 7.89 (s, 1H), 7.39 (s, 1H), 6.13 (d, J=19.6 Hz, 1H), 6.04-5.76 (m, 3H), 4.50-4.40 (m, 1H), 4.40-4.26 (m, 2H), 2.87 (s, 3H), 2.33 (dd, J=7.6, 1.2 Hz, 2H), 2.26-2.19 (m, 2H), 2.08-1.92 (m, 2H), 1.14 (d, J=22.8 Hz, 3H), 0.99-0.85 (m, 12H). 19F NMR (377 MHz, DMSO) δ −156.35.

Example 157. Synthesis of (2R,3R,4R,5R)-4-fluoro-4-methyl-5-(6-(methylamino)-2-(3-methylbutanamido)-9H-purin-9-yl)-2-(((3-methylbutanoyl)oxy)methyl)tetrahydrofuran-3-yl 3-methylbutanoate (Compound 313)

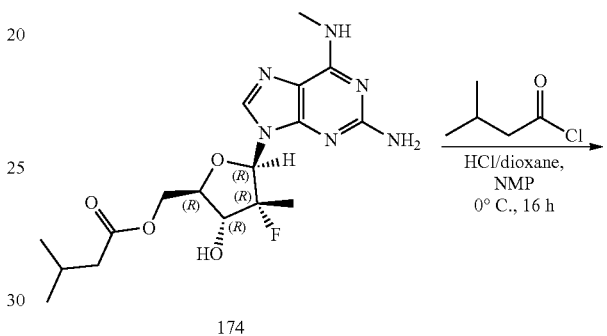

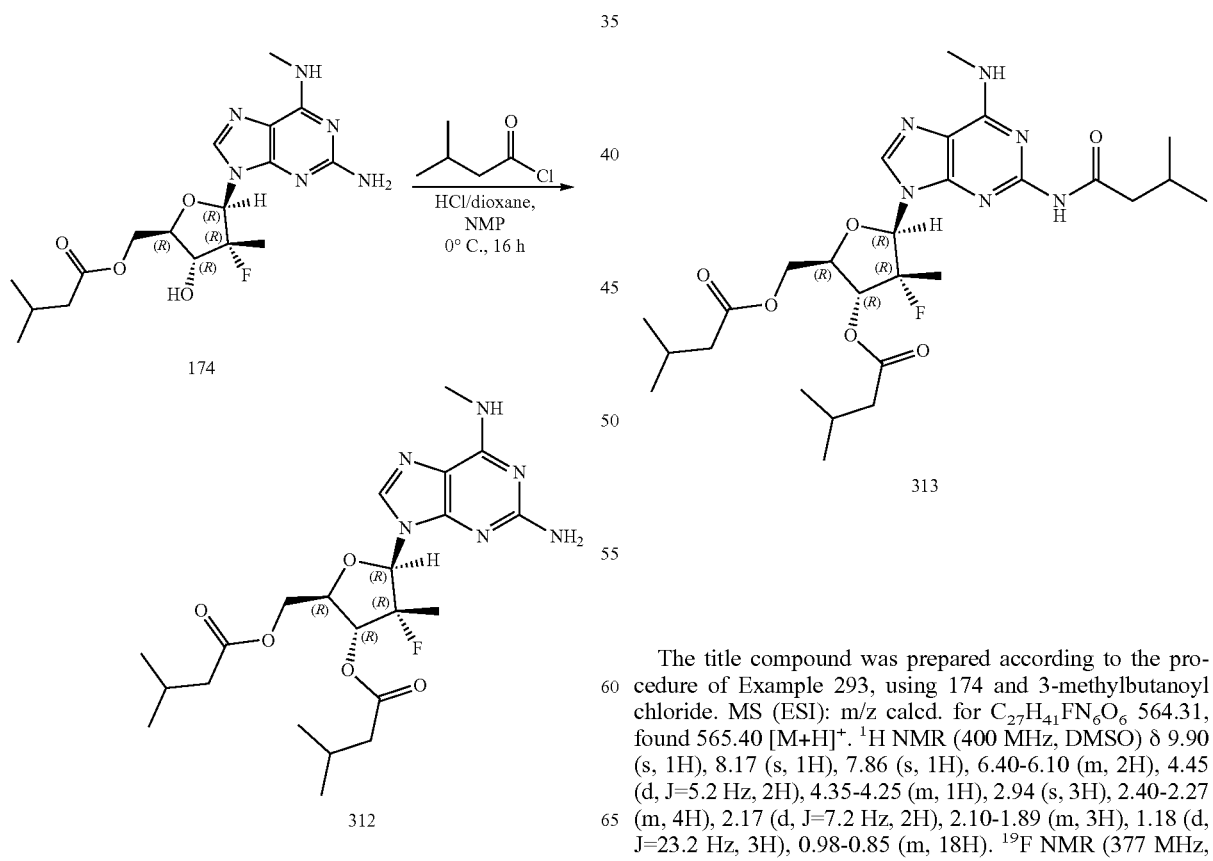

The title compound was prepared according to the procedure of Example 293, using 174 and 3-methylbutanoyl chloride. MS (ESI): m/z calcd. for $C_{27}H_{41}FN_6O_6$ 564.31, found 565.40 [M+H]+. 1H NMR (400 MHz, DMSO) δ 9.90 (s, 1H), 8.17 (s, 1H), 7.86 (s, 1H), 6.40-6.10 (m, 2H), 4.45 (d, J=5.2 Hz, 2H), 4.35-4.25 (m, 1H), 2.94 (s, 3H), 2.40-2.27 (m, 4H), 2.17 (d, J=7.2 Hz, 2H), 2.10-1.89 (m, 3H), 1.18 (d, J=23.2 Hz, 3H), 0.98-0.85 (m, 18H). 19F NMR (377 MHz, DMSO) δ −155.56.

Example 158. Synthesis of ((2R,3R,4R,5R)-5-(2-(2-cyclohexylacetamido)-6-(methylamino)-9H-purin-9-yl)-4-fluoro-3-hydroxy-4-methyltetrahydrofuran-2-yl)methyl 3-methylbutanoate (Compound 314)

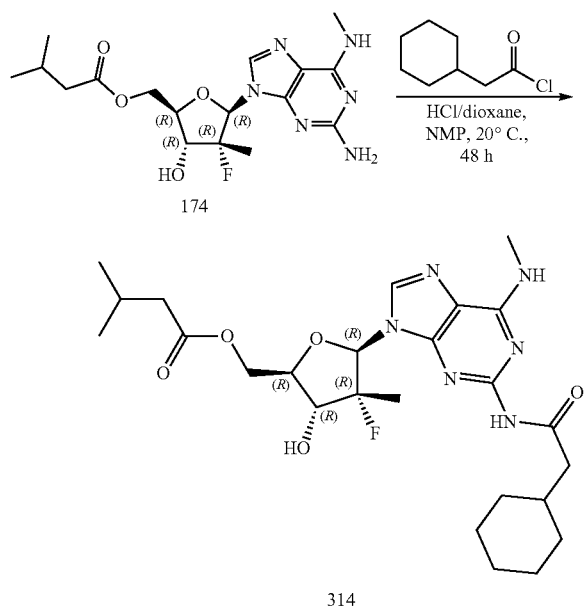

To a solution of 174 (100 mg, 0.25 mmol) in NMP (1 mL) was added HCl in dioxane (4 M, 0.5 mL), the solution was stirred at 20° C. for 15 minutes. The reaction mixture was cooled at 0° C. and 2-cyclohexylacetyl chloride (0.39 mL, 2.52 mmol) was added at once. The reaction was stirred at 20° C. for 48 hours. The reaction was diluted with ACN (2 mL) and purified by prep-HPLC to obtain 314 (7.30 mg 5.55% yield) as a white solid. MS (ESI): m/z calcd. for $C_{25}H_{37}FN_6O_5$, 520.28, found 521.3 $[M+H]^+$. $^1H$ NMR (400 MHz, DMSO-$d_6$) δ 9.93 (s, 1H), 8.12 (s, 1H), 7.81 (s, 1H), 6.12 (d, J=20.0 Hz, 1H), 5.62 (s, 1H), 4.82 (s, 1H), 4.55-4.41 (m, 1H), 4.35 (dd, J=12.4, 7.6 Hz, 1H), 4.04 (t, J=8.0 Hz, 1H), 2.93 (s, 3H), 2.38-2.33 (m, 2H), 2.18 (d, J=7.2 Hz, 2H), 1.96-1.91 (m, 1H), 1.84-1.59 (m, 6H), 1.23-1.10 (m, 6H), 1.00-0.91 (m, 2H), 0.88 (dd, J=6.8, 1.2 Hz, 6H).

Example 159. Synthesis of ((2R,3R,4R,5R)-5-(2-(2-cyclohexylacetamido)-6-(methylamino)-9H-purin-9-yl)-3-(2-cyclohexylacetoxy)-4-fluoro-4-methyltetrahydrofuran-2-yl)methyl 3-methylbutanoate (Compound 315)

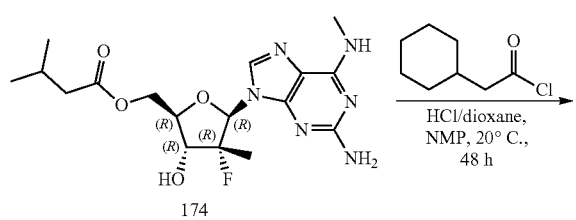

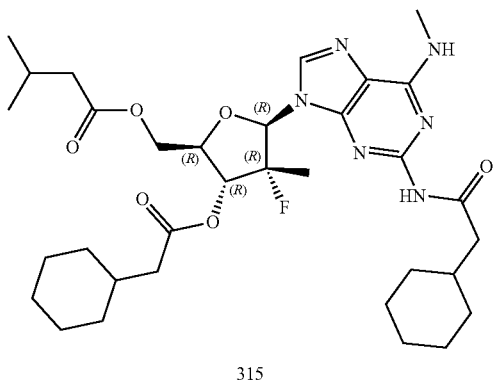

To a solution of 174 (100 mg, 0.25 mmol) in NMP (1 mL) was added HCl in dioxane (4 M, 0.5 mL), the solution was stirred at 20° C. for 15 minutes. The reaction mixture was cooled at 0° C. and 2-cyclohexylacetyl chloride (0.39 mL, 2.52 mmol) was added at once. The reaction was stirred at 20° C. for 48 hours. The reaction was diluted with ACN (2 mL) and purified by prep-HPLC to obtain 315 (35.4 mg 21.4% yield) as a white solid. MS (ESI): m/z calcd. for $C_{33}H_{49}FN_6O_6$, 644.37, found 645.4 $[M+H]^+$. $^1H$ NMR (400 MHz, DMSO-$d_6$) δ 9.90 (s, 1H), 8.16 (s, 1H), 7.85 (s, 1H), 6.22 (d, J=19.6 Hz, 2H), 4.51-4.37 (m, 2H), 4.35-4.26 (m, 1H), 2.94 (s, 3H), 2.30 (d, J=6.8 Hz, 2H), 2.17 (d, J=7.2 Hz, 2H), 1.95 (dt, J=14.0, 6.8 Hz, 1H), 1.77-1.57 (m, 12H), 1.20-1.14 (m, 10H), 1.05-0.91 (m, 4H), 0.88 (dd, J=6.8, 0.8 Hz, 6H).

Example 160. Synthesis of ((2R,3R,4R,5R)-5-(2-acetamido-6-(methylamino)-9H-purin-9-yl)-4-fluoro-3-hydroxy-4-methyltetrahydrofuran-2-yl)methyl propionate (Compound 317)

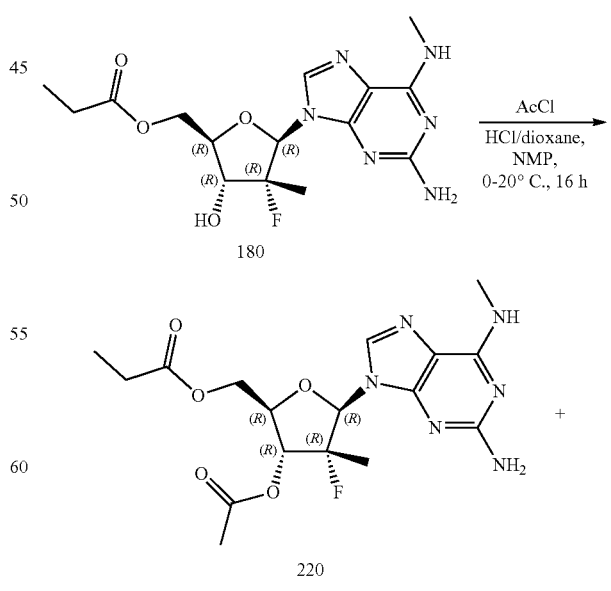

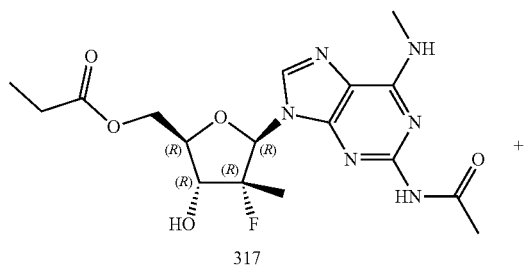

317

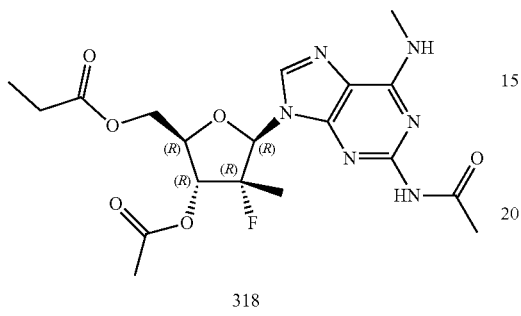

318

The title compound was prepared from Example 220. MS (ESI): m/z calcd. for $C_{17}H_{23}FN_6O_5$ 410.17, found 411.1 [M+H]$^+$. (H NMR (400 MHz, DMSO) δ 10.01 (s, 1H), 8.12 (s, 1H), 7.84 (s, 1H), 6.12 (d, J=19.6 Hz, 1H), 5.70-5.60 (m, 1H), 4.91-4.70 (br, 1H), 4.49-4.43 (m, 1H), 4.39-4.32 (m, 1H), 4.07-4.01 (m, 1H), 2.93 (s, 3H), 2.35-2.29 (m, 2H), 2.19 (s, 3H), 1.13 (d, J=22.8 Hz, 3H), 1.01 (t, J=7.6 Hz, 3H). $^{19}$F NMR (377 MHz, DMSO) δ -158.46.

Example 161. Synthesis of ((2R,3R,4R,5R)-5-(2-acetamido-6-(methylamino)-9H-purin-9-yl)-3-acetoxy-4-fluoro-4-methyltetrahydrofuran-2-yl)methyl propionate (Compound 318)

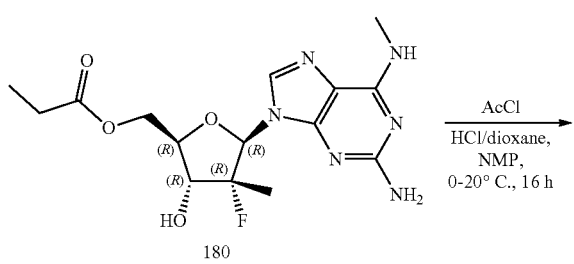

317

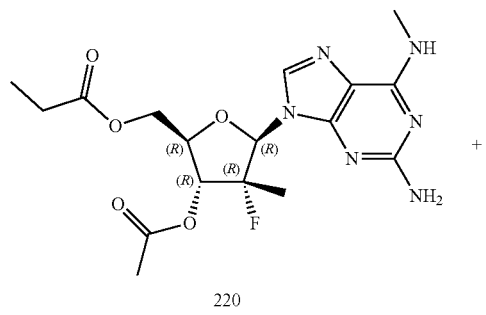

220

318

The title compound was prepared from Example 220. MS (ESI): m/z calcd. for $C_{19}H_{25}FN_6O_6$ 452.18, found 453.1 [M+H]$^+$. (H NMR (400 MHz, DMSO) δ 9.93 (s, 1H), 8.18 (s, 1H), 7.90 (s, 1H), 6.23 (d, J=20.0 Hz, 1H), 6.17-5.98 (m, 1H), 4.47-4.38 (m, 2H), 4.35-4.29 (m, 1H), 2.93 (s, 3H), 2.35-2.28 (m, 2H), 2.20 (s, 3H), 2.14 (s, 3H), 1.17 (d, J=23.2 Hz, 3H), 1.01 (t, J=7.6 Hz, 3H). $^{19}$F NMR (377 MHz, DMSO) δ -155.35.

Example 162. Synthesis of (2R,3R,4R,5R)-4-fluoro-4-methyl-5-(6-(methylamino)-2-(3-methylbutanamido)-9H-purin-9-yl)-2-((propionyloxy)methyl)tetrahydrofuran-3-yl 3-methylbutanoate (Compound 320)

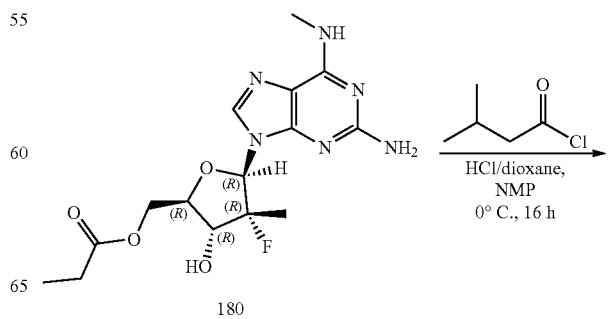

180

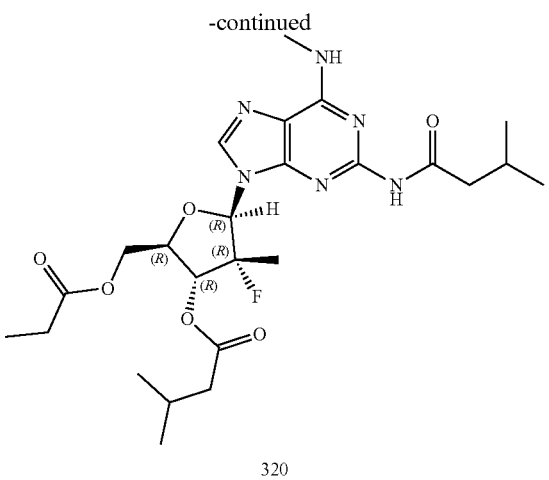

320

The title compound was prepared according to the procedure of Example 293, using 180 and 3-methylbutanoyl chloride. MS (ESI): m/z calcd. for $C_{25}H_{37}FN_6O_6$ 536.28, found 537.15 [M+H]$^+$. $^1$H NMR (400 MHz, DMSO) δ 9.90 (s, 1H), 8.18 (s, 1H), 7.86 (s, 1H), 6.23 (d, J=19.6 Hz, 2H), 4.44 (d, J=4.8 Hz, 2H), 4.36-4.27 (m, 1H), 2.94 (s, 3H), 2.39-2.25 (m, 6H), 2.11-1.96 (m, 2H), 1.18 (d, J=23.2 Hz, 3H), 1.00 (t, J=7.2 Hz, 3H), 0.95 (dd, J=6.8, 1.6 Hz, 6H), 0.91 (dd, J=6.4, 0.4 Hz, 6H). $^{19}$F NMR (377 MHz, DMSO) δ −155.51.

Example 163. Synthesis of ((2R,3R,4R,5R)-5-(2-(2-cyclohexylacetamido)-6-(methylamino)-9H-purin-9-yl)-4-fluoro-3-hydroxy-4-methyltetrahydrofuran-2-yl)methyl propionate (Compound 321)

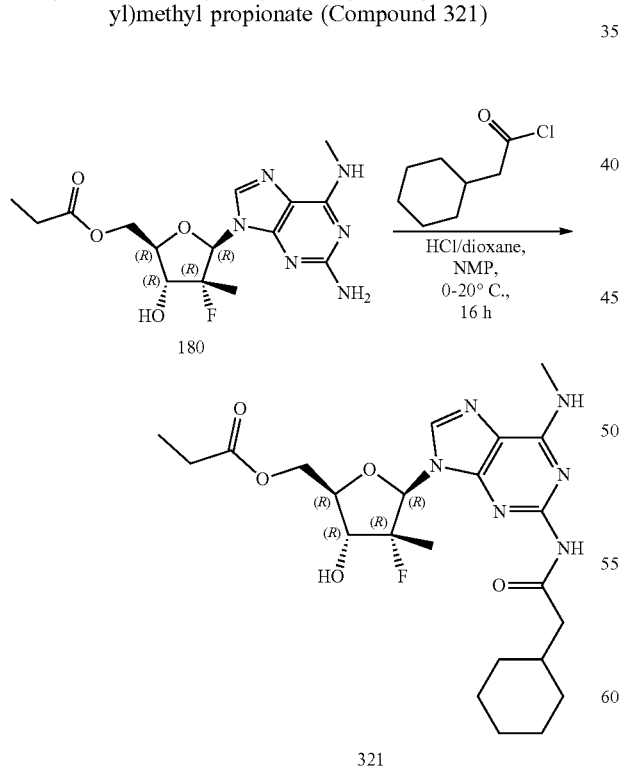

321

To a solution of 180 (100 mg, 0.27 mmol) in NMP (1 mL) was added HCl in dioxane (4 M, 0.5 mL), the solution was stirred at 20° C. for 15 minutes. The reaction mixture was cooled at 0° C. and 2-cyclohexylacetyl chloride (0.33 mL, 2.17 mmol) was added at once. The reaction was stirred at 20° C. for 16 hours. The reaction was diluted with ACN (2 mL) and purified by prep-HPLC to obtain 321 (12.0 mg 8.99% yield) as a white solid. MS (ESI): m/z calcd. for $C_{23}H_{33}FN_6O_5$, 492.25, found 493.2 [M+H]$^+$. $^1$H NMR (400 MHz, DMSO-d$_6$) δ 9.92 (s, 1H), 8.12 (s, 1H), 7.81 (s, 1H), 6.12 (d, J=20.0 Hz, 1H), 5.63 (d, J=6.4 Hz, 1H), 4.82 (s, 1H), 4.45 (dd, J=12.4, 2.0 Hz, 1H), 4.36 (dd, J=12.4, 7.2 Hz, 1H), 4.05 (t, J=7.6 Hz, 1H), 2.93 (s, 3H), 2.32 (d, J=7.6 Hz, 2H), 1.81-1.59 (m, 7H), 1.32-1.07 (m, 7H), 1.03-0.92 (m, 5H).

Example 164. Synthesis of ((2R,3R,4R,5R)-5-(2-(2-cyclohexylacetamido)-6-(methylamino)-9H-purin-9-yl)-3-(2-cyclohexylacetoxy)-4-fluoro-4-methyltetrahydrofuran-2-yl)methyl propionate (Compound 322)

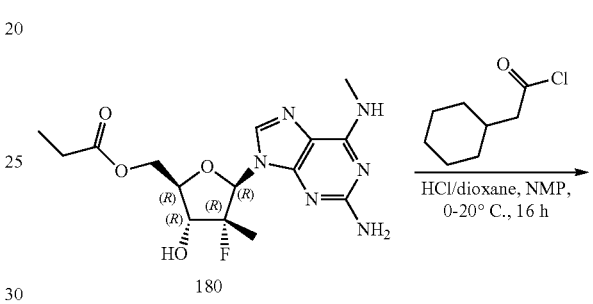

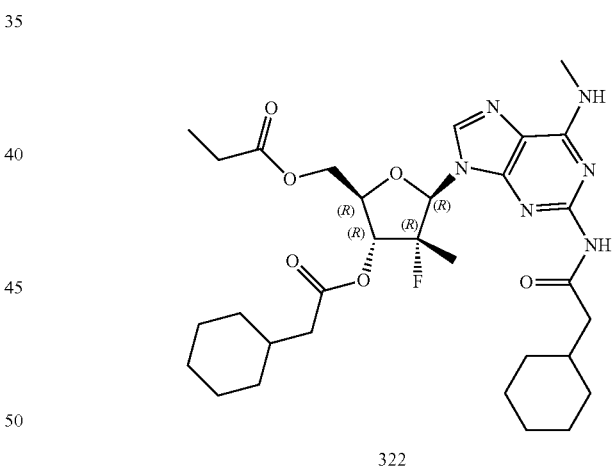

322

To a solution of 180 (100 mg, 0.27 mmol) in NMP (1 mL) was added HCl in dioxane (4 M, 0.5 mL), the solution was stirred at 20° C. for 15 minutes. The reaction mixture was cooled at 0° C. and 2-cyclohexylacetyl chloride (0.33 mL, 2.17 mmol) was added at once. The reaction was stirred at 20° C. for 16 hours. The reaction was diluted with ACN (2 mL) and purified by prep-HPLC to obtain 322 (31.8 mg, 19.0% yield) as a white solid. MS (ESI): m/z calcd. for $C_{31}H_{45}FN_6O_6$, 616.34, found 617.3 [M+H]$^+$. $^1$H NMR (400 MHz, DMSO-d$_6$) δ 9.90 (s, 1H), 8.17 (s, 1H), 7.85 (s, 1H), 6.35-6.20 (m, 2H), 4.47-4.40 (m, 2H), 4.31 (dt, J=9.6, 5.2 Hz, 1H), 2.94 (s, 3H), 2.35-2.26 (m, 5H), 1.80-1.58 (m, 12H), 1.30-1.09 (m, 10H), 1.02-0.92 (m, 7H). $^{19}$F NMR (376 MHz, DMSO) δ −155.52.

Example 165. Synthesis of ((2R,3R,4R,5R)-5-(2-acetamido-6-(methylamino)-9H-purin-9-yl)-3-acetoxy-4-fluoro-4-methyltetrahydrofuran-2-yl)methyl 3-methylbutanoate (Compound 324)

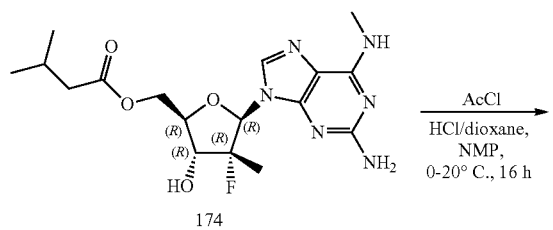
174

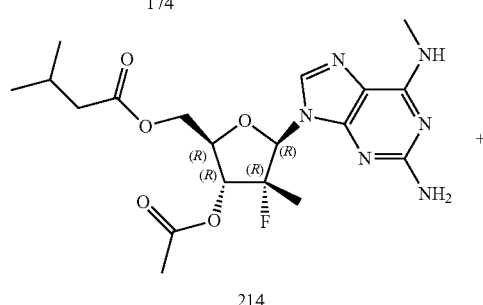
214

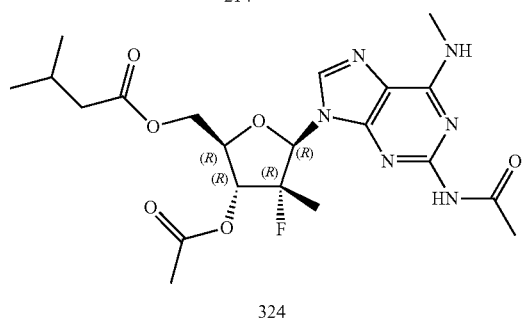
324

The title compound was prepared from Example 214. MS (ESI): m/z calcd. for $C_{21}H_{29}FN_6O_6$ 480.21, found 481.2 [M+H]$^+$. $^1$H NMR (400 MHz, DMSO) δ 9.92 (s, 1H), 8.17 (s, 1H), 7.90 (s, 1H), 6.23 (d, J=20.0 Hz, 1H), 6.17-5.99 (m, 1H), 4.48-4.38 (m, 2H), 4.34-4.28 (m, 1H), 2.94 (s, 3H), 2.22-2.13 (m, 8H), 2.00-1.92 (m, 1H), 1.17 (d, J=22.8 Hz, 3H), 0.89 (dd, J=6.4, 1.2 Hz, 6H). $^{19}$F NMR (377 MHz, DMSO) δ −155.37.

Example 166. Synthesis of ((2R,3R,4R,5R)-4-fluoro-5-(2-isobutyramido-6-(methylamino)-9H-purin-9-yl)-3-(isobutyryloxy)-4-methyltetrahydrofuran-2-yl)methyl 3-methylbutanoate (Compound 325)

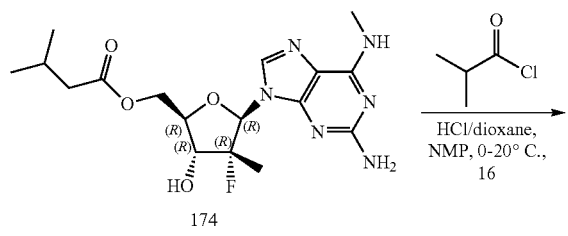
174

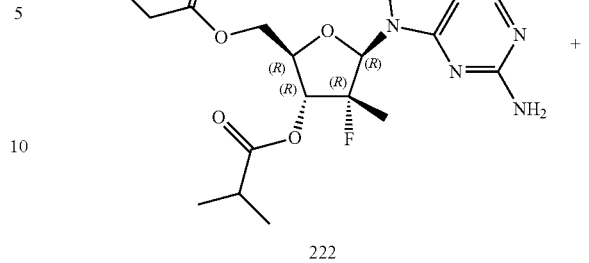
222

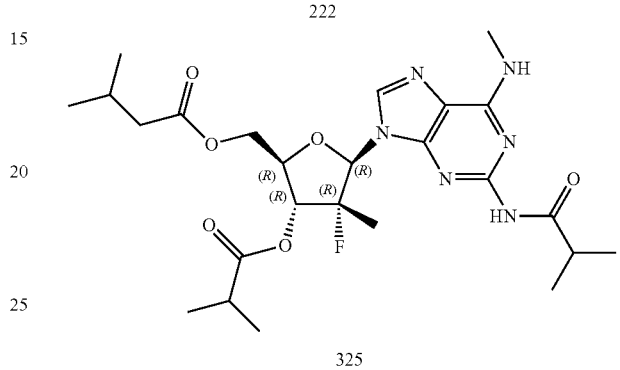
325

The title compound was prepared from Example 222. MS (ESI): m/z calcd. for $C_{25}H_{37}FN_6O_6$ 536.28, found 537.3 [M+H]$^+$. $^1$H NMR (400 MHz, DMSO) δ 9.89 (s, 1H), 8.17 (s, 1H), 7.86 (s, 1H), 6.34-5.96 (m, 2H), 4.47-4.36 (m, 2H), 4.35-4.29 (m, 1H), 2.94 (s, 3H), 2.71-2.63 (m, 1H), 2.18 (d, J=7.2 Hz, 2H), 2.01-1.90 (m, 1H), 1.21-1.12 (m, 9H), 1.06 (dd, J=6.8, 4.0 Hz, 6H), 0.88 (dd, J=6.8, 2.0 Hz, 6H). $^{19}$F NMR (377 MHz, DMSO) δ −156.11.

Example 167. Synthesis of ((2R,3R,4R,5R)-5-(2-acetamido-6-(methylamino)-9H-purin-9-yl)-3-acetoxy-4-fluoro-4-methyltetrahydrofuran-2-yl)methyl 2-cyclohexylacetate (Compound 326)

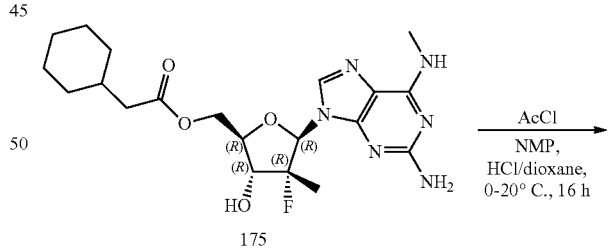
175

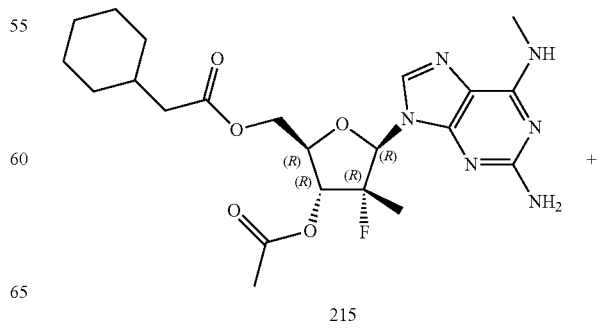
215

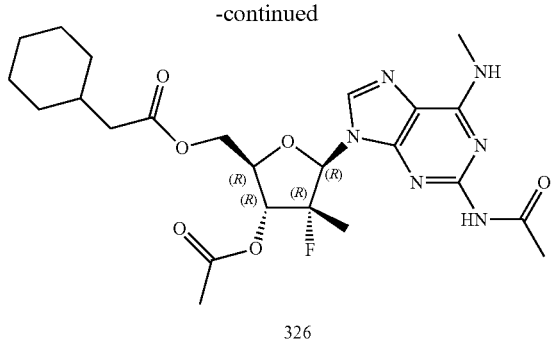

326

The title compound was prepared from Example 215. MS (ESI): m/z calcd. for $C_{24}H_{33}FN_6O_6$ 520.24, found 521.2 [M+H]$^+$. $^1$H NMR (400 MHz, DMSO) δ 9.90 (s, 1H), 8.17 (s, 1H), 7.91 (s, 1H), 6.23 (d, J=19.6 Hz, 1H), 6.08 (d, J=18.4 Hz, 1H), 4.47-4.35 (m, 2H), 4.33-4.27 (m, 1H), 2.94 (s, 3H), 2.26-2.08 (m, 8H), 1.68-1.53 (m, 6H), 1.25-1.03 (m, 6H), 0.96-0.83 (m, 2H). $^{19}$F NMR (377 MHz, DMSO) δ -155.31.

Example 168. Synthesis of ((2R,3R,4R,5R)-5-(2-acetamido-6-(methylamino)-9H-purin-9-yl)-4-fluoro-3-hydroxy-4-methyltetrahydrofuran-2-yl) methyl acetate (Compound 328)

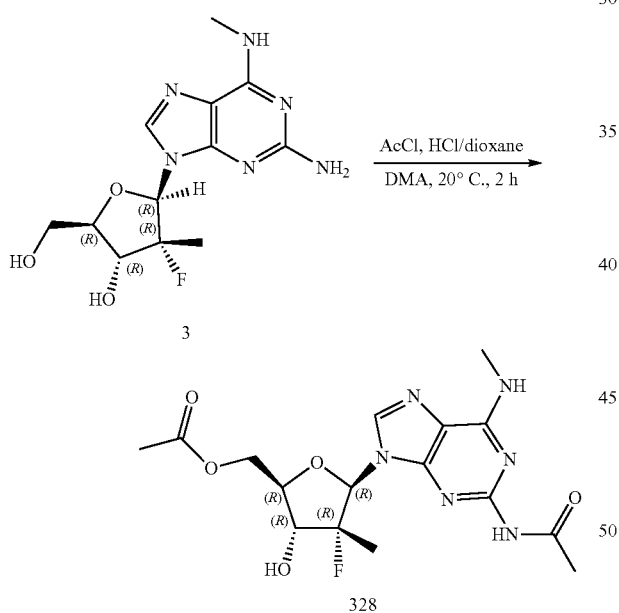

To a solution of 3 (700 mg, 2.24 mmol) in DMA (3 mL) was added HCl/dioxane (1.1 mL, 4 M). The mixture solution was stirred at 20° C. for 15 minutes. The reaction mixture was cooled at 0° C. and Acetyl chloride (1.27 mL, 17.9 mmol) was added at once. The reaction was stirred at 0° C. for 1 hour. The reaction was diluted with ACN (4.0 mL) and purified by prep-HPLC to obtain 328 (12.6 mg, 1.35% yield) as a white solid. MS (ESI): m/z calcd. for $C_{16}H_{21}FN_6O_5$, 396.16, found 397.1 [M+H]$^+$. $^1$H NMR (400 MHz, DMSO-d$_6$) δ 10.01 (s, 1H), 8.13 (s, 1H), 7.83 (d, J=10.4 Hz, 1H), 6.12 (d, J=20.0 Hz, 1H), 5.65 (d, J=7.2 Hz, 1H), 4.82 (s, 1H), 4.45 (dd, J=12.4, 2.0 Hz, 1H), 4.34 (dd, J=12.4, 7.6 Hz, 1H), 4.05 (t, J=7.6 Hz, 1H), 2.93 (s, 3H), 2.19 (s, 3H), 2.01 (s, 3H), 1.17-1.09 (m, 3H). $^{19}$F NMR (376 MHz, DMSO) δ -158.32 (s, 1H).

Example 169. Synthesis of (2R,3R,4R,5R)-2-(acetoxymethyl)-5-(2-amino-6-(methylamino)-9H-purin-9-yl)-4-fluoro-4-methyltetrahydrofuran-3-yl propionate (Compound 329), ((2R,3R,4R,5R)-4-fluoro-3-hydroxy-4-methyl-5-(6-(methylamino)-2-propionamido-9H-purin-9-yl)tetrahydrofuran-2-yl) methyl acetate (Compound 330), and (2R,3R,4R, 5R)-2-(acetoxymethyl)-4-fluoro-4-methyl-5-(6-(methylamino)-2-propionamido-9H-purin-9-yl) tetrahydrofuran-3-yl propionate (Compound 331)

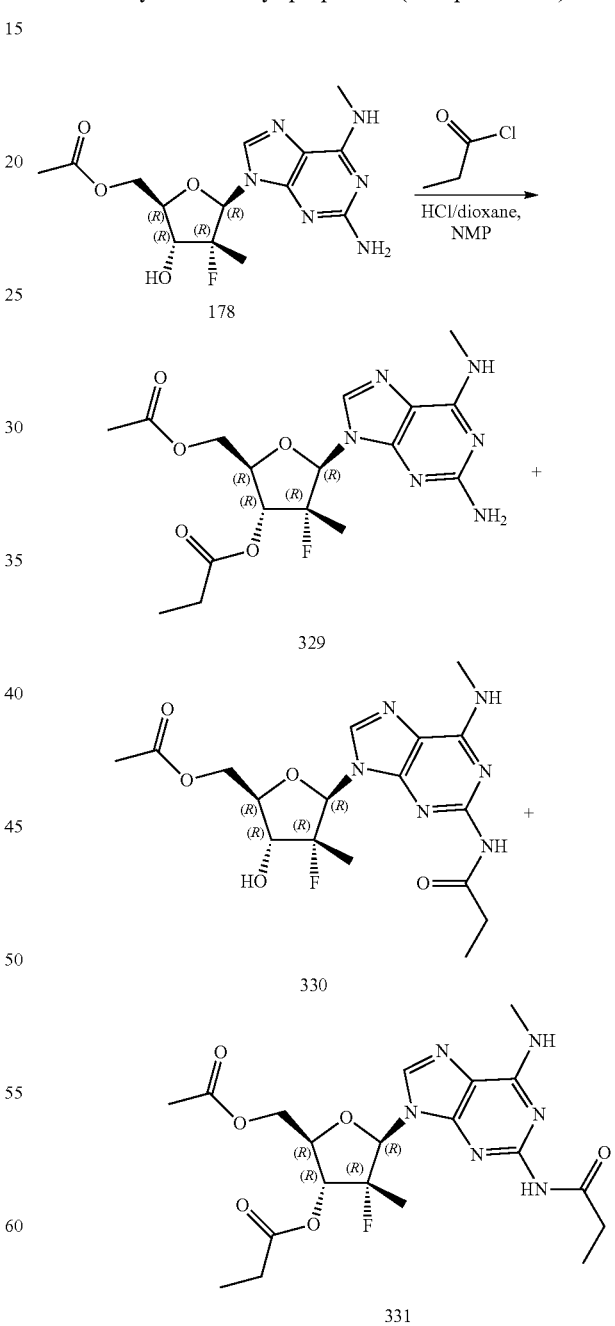

The title compound 329& 330& 331 was prepared according to the procedure of Example 65, Step 1, using 178 and propionyl chloride For compound 329: MS (ESI): mass calcd. for $C_{17}H_{23}FN_6O_5$, 410.17, m/z found 411.1 [M+H]$^+$. $^1$H NMR (400 MHz, DMSO) δ 7.90 (s, 1H), 7.38 (s, 1H), 6.13 (d, J=19.6 Hz, 1H), 5.97 (d, J=29.2 Hz, 3H), 4.53-4.39 (m, 1H), 4.38-4.25 (m, 2H), 2.88 (s, 3H), 2.48-2.43 (m, 2H), 2.06-2.00 (m, 3H), 1.15 (d, J=22.8 Hz, 6H), 1.08 (t J=7.6 Hz, 3H). $^{19}$F NMR (376 MHz, DMSO) δ −156.37.

For compound 330: MS (ESI): mass calcd. for $C_{17}H_{23}FN_6O_5$, 410.17, m/z found 411.1 [M+H]$^+$. $^1$H NMR (400 MHz, DMSO) δ 9.94 (s, 1H), 8.12 (s, 1H), 7.81 (s, 1H), 6.12 (d, J=20.0 Hz, 1H), 5.65 (d, J=6.4 Hz, 1H), 4.78 (s, 1H), 4.44 (dd, J=12.4, 2.0 Hz, 1H), 4.35 (dd, J=12.4, 7.2 Hz, 1H), 4.06 (d, J=7.6 Hz, 1H), 2.93 (s, 3H), 2.52 (s, 2H), 2.01 (s, 3H), 1.16-1.03 (m, 6H).

For compound 331: MS (ESI): mass calcd. for $C_{20}H_{27}FN_6O_6$, 466.20, m/z found 467.1 [M+H]+$^{19}$F NMR (376 MHz, DMSO) δ −155.50.

Example 170. Synthesis of (2R,3R,4R,5R)-2-(acetoxymethyl)-4-fluoro-4-methyl-5-(6-(methylamino)-2-(3-methylbutanamido)-9H-purin-9-yl)tetrahydrofuran-3-yl 3-methylbutanoate (Compound 332)

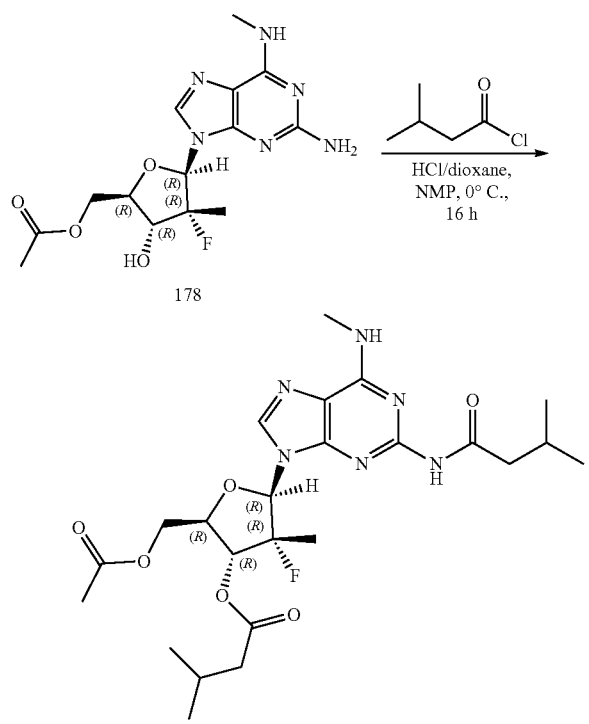

332

The title compound was prepared according to the procedure of Example 293, using 178 and 3-methylbutanoyl chloride. MS (ESI): m/z calcd. for $C_{24}H_{35}FN_6O_6$ 522.26, found 523.15 [M+H]$^+$. $^1$H NMR (400 MHz, DMSO) δ 9.90 (s, 1H), 8.18 (s, 1H), 7.86 (s, 1H), 6.23 (d, J=19.6 Hz, 2H), 4.49-4.38 (m, 2H), 4.36-4.28 (m, 1H), 2.94 (s, 3H), 2.40-2.26 (m, 4H), 2.11-1.96 (m, 5H), 1.18 (d, J=23.2 Hz, 3H), 0.98-0.83 (m, 12H). $^{19}$F NMR (377 MHz, DMSO) δ −155.47.

Example 171. Synthesis of (2R,3R,4R,5R)-2-(acetoxymethyl)-5-(2-(2-cyclohexylacetamido)-6-(methylamino)-9H-purin-9-yl)-4-fluoro-4-methyltetrahydrofuran-3-yl 2-cyclohexylacetate (Compound 333)

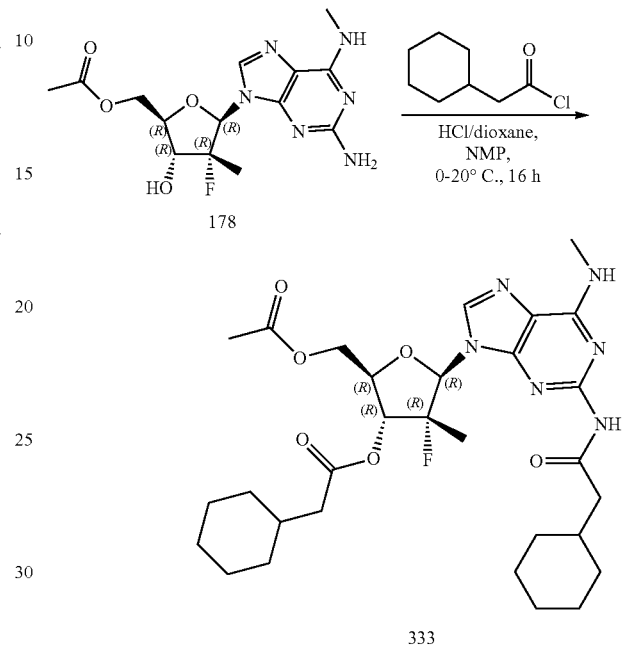

333

To a solution of 178 (100 mg, 0.28 mmol) in NMP (1 mL) was added HCl in dioxane (4 M, 0.5 mL), the solution was stirred at 20° C. for 15 minutes. The reaction mixture was cooled at 0° C. and 2-cyclohexylacetyl chloride (0.35 mL, 2.25 mmol) was added at once. The reaction was stirred at 20° C. for 16 hours. The reaction was diluted with ACN (2 mL) and purified by prep-HPLC to obtain 333 (35.5 mg 20.6% yield) as a white solid. MS (ESI): m/z calcd. for $C_{30}H_{43}FN_6O_6$, 602.32, found 603.4 [M+H]$^+$. $^1$H NMR (400 MHz, DMSO-d$_6$) δ 9.90 (s, 1H), 8.17 (s, 1H), 7.85 (s, 1H), 6.25-6.19 (m, 2H), 4.41 (d, J=5.2 Hz, 2H), 4.33-4.28 (m, 1H), 2.94 (s, 3H), 2.38-2.26 (m, 4H), 2.00 (s, 3H), 1.74-1.60 (m, 11H), 1.32-1.05 (m, 10H), 1.05-0.87 (m, 4H). $^{19}$F NMR (376 MHz, DMSO) δ −155.48.

Example 172. Synthesis of ((2R,3R,4R,5R)-4-fluoro-3-hydroxy-4-methyl-5-(6-(methylamino)-2-(2-phenylacetamido)-9H-purin-9-yl)tetrahydrofuran-2-yl)methyl acetate (Compound 334)

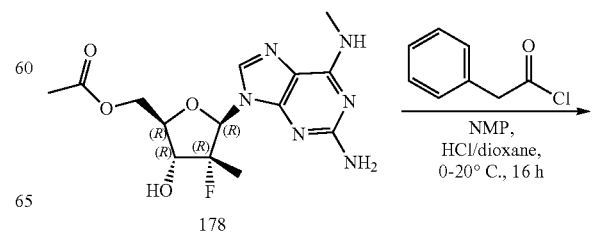

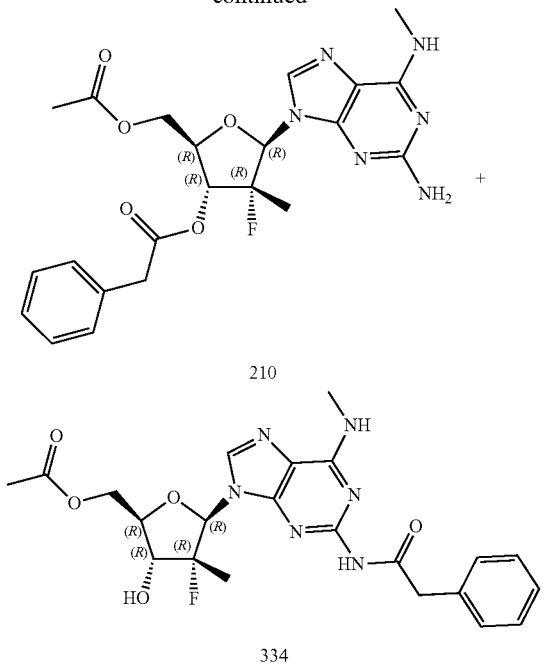

210

334

The title compound was prepared from Example 210. MS (ESI): m/z calcd. for $C_{22}H_{25}FN_6O_5$ 472.19, found 473.1 [M+H]$^+$. $^1$H NMR (400 MHz, DMSO) δ 10.23 (s, 1H), 8.13 (s, 1H), 7.84 (s, 1H), 7.35-7.28 (m, 4H), 7.25-7.20 (m, 1H), 6.12 (d, J=20.0 Hz, 1H), 5.64 (s, 1H), 4.80 (s, 1H), 4.45-4.38 (m, 1H), 4.35-4.29 (m, 1H), 4.07-4.01 (m, 1H), 3.82 (s, 2H), 2.93 (s, 3H), 2.01 (s, 3H), 1.11 (d, J=22.4 Hz, 3H). $^{19}$F NMR (377 MHz, DMSO) δ −158.02.

Example 173. Synthesis of ((2R,3R,4R,5R)-4-fluoro-3-hydroxy-4-methyl-5-(6-(methylamino)-2-(2-phenylacetamido)-9H-purin-9-yl)tetrahydrofuran-2-yl)methyl propionate (Compound 336)

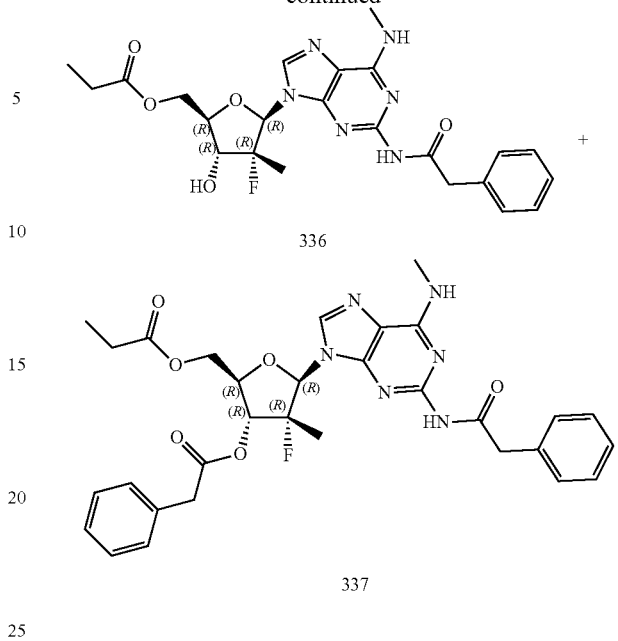

336

337

The title compound was prepared from Example 212. MS (ESI): m/z calcd. for $C_{23}H_{27}FN_6O_5$ 486.20, found 487.2 [M+H]$^+$. $^1$H NMR (400 MHz, DMSO) δ 10.23 (s, 1H), 8.13 (s, 1H), 7.84 (s, 1H), 7.35-7.20 (m, 5H), 6.12 (d, J=20.0 Hz, 1H), 5.64 (d, J=6.0 Hz, 1H), 4.79 (s, 1H), 4.47-4.30 (m, 2H), 4.07-4.00 (m, 1H), 3.82 (s, 2H), 2.93 (s, 3H), 2.32 (q, J=7.6 Hz, 2H), 1.11 (d, J=22.4 Hz, 3H), 1.01 (t, J=7.6 Hz, 3H). $^{19}$F NMR (377 MHz, DMSO) δ −158.58.

Example 174. Synthesis of ((2R,3R,4R,5R)-4-fluoro-4-methyl-5-(6-(methylamino)-2-(2-phenylacetamido)-9H-purin-9-yl)-3-(2-phenylacetoxy)tetrahydrofuran-2-yl)methyl propionate (Compound 337)

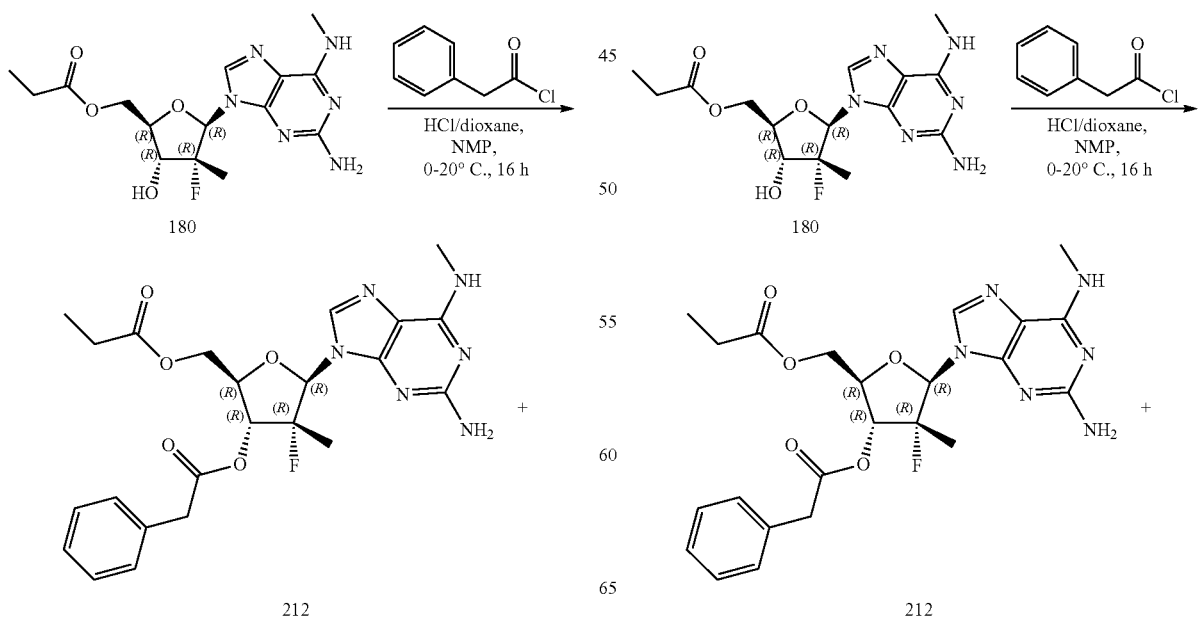

180                                              180

212                                              212

485

-continued

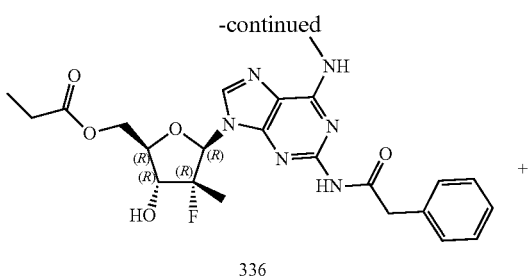
336

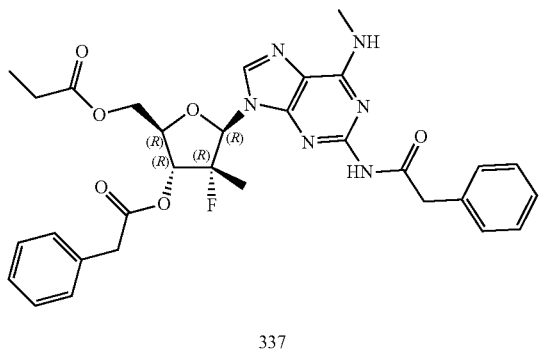
337

The title compound was prepared from Example 212. MS (ESI): m/z calcd. for C₃₁H₃₃FN₆O₆ 604.24, found 605.2 [M+H]⁺. ¹H NMR (400 MHz, DMSO) δ 10.17 (s, 1H), 8.18 (s, 1H), 7.89 (s, 1H), 7.36-7.18 (m, 10H), 6.23 (d, J=19.6 Hz, 2H), 4.42-4.30 (m, 3H), 3.82 (s, 4H), 2.92 (s, 3H), 2.28 (q, J=7.6 Hz, 2H), 1.14 (d, J=23.2 Hz, 3H), 0.99 (t, J=7.6 Hz, 3H). ¹⁹F NMR (377 MHz, DMSO) δ −155.42.

Example 175. Synthesis of ((2R,3R,4R,5R)-5-(2-acetamido-6-(methylamino)-9H-purin-9-yl)-3-acetoxy-4-fluoro-4-methyltetrahydrofuran-2-yl)methyl 2-phenylacetate (Compound 338)

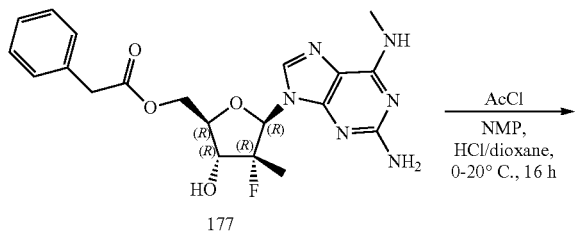

486

-continued

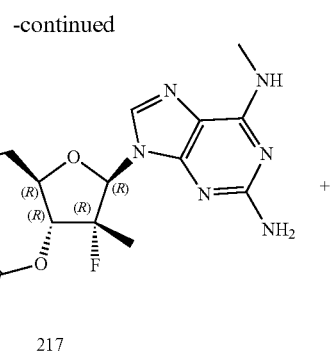
217

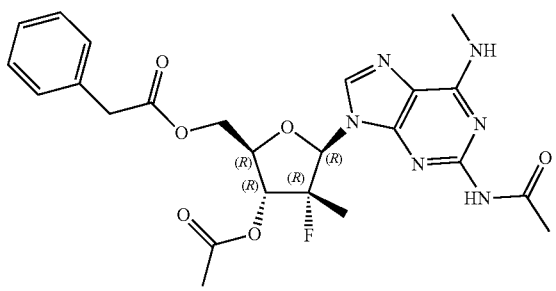
338

The title compound was prepared from Compound 217. MS (ESI): m/z calcd. for C₂₄H₂₇FN₆O₆ 514.20, found 515.1 [M+H]⁺. ¹H NMR (400 MHz, DMSO) δ 9.93 (s, 1H), 8.16 (s, 1H), 7.89 (s, 1H), 7.33-7.22 (m, 5H), 6.24 (d, J=20.0 Hz, 1H), 6.11 (s, 1H), 4.50-4.41 (m, 2H), 4.35-4.29 (m, 1H), 3.68 (s, 2H), 2.93 (s, 3H), 2.19 (s, 3H), 2.13 (s, 3H), 1.17 (d, J=23.2 Hz, 3H). ¹⁹F NMR (377 MHz, DMSO) δ −155.20.

Example 176. Synthesis of ((2R,3S,4R,5R)-5-cyano-3,4-dihydroxy-5-(4-(((pentyloxy)carbonyl)amino)pyrrolo[2,1-f][1,2,4]triazin-7-yl)tetrahydrofuran-2-yl)methyl L-valinate (Compound 86)

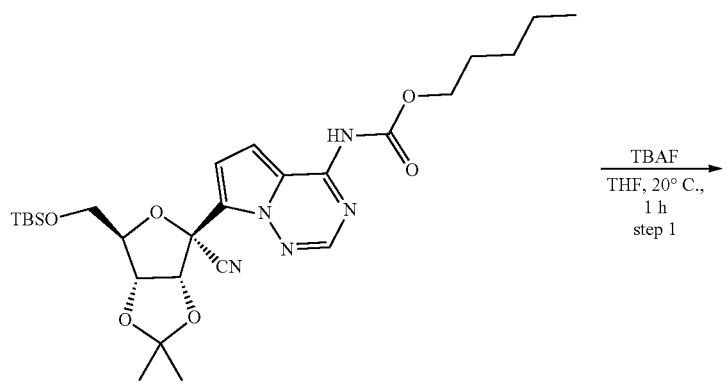
81.1

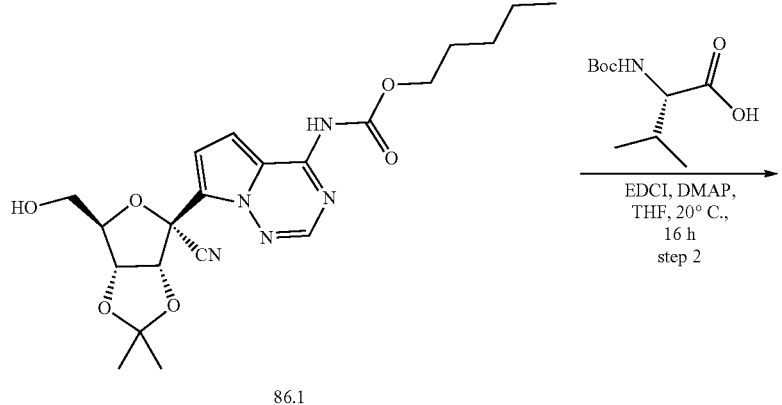

86.1

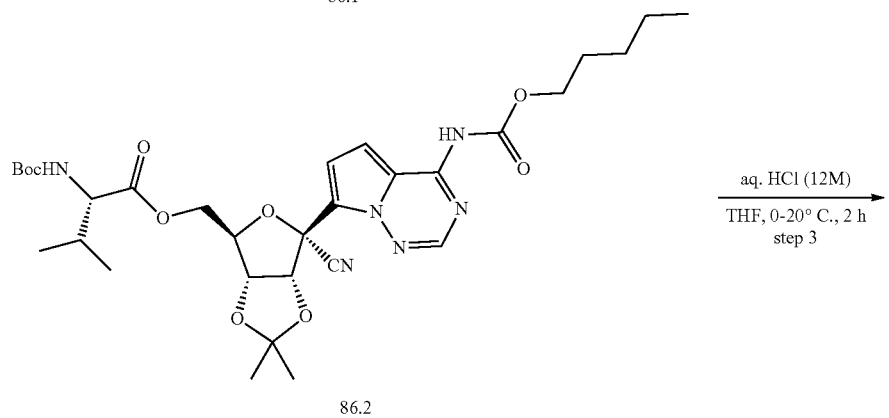

86.2

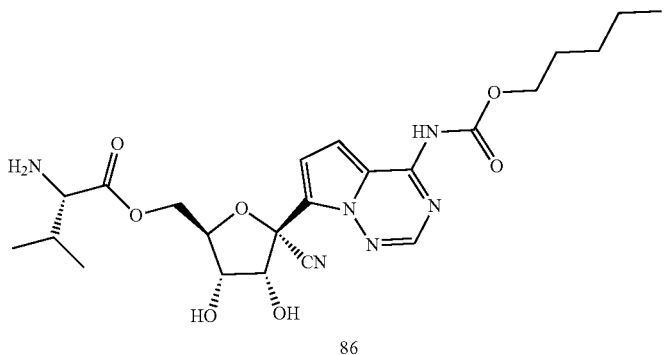

86

Step 1. Synthesis of pentyl (7-((3aR,4R,6R,6aR)-4-cyano-6-(hydroxymethyl)-2,2-dimethyltetrahydrofuro[3,4-d][1,3]dioxol-4-yl)pyrrolo[2,1-f][1,2,4]triazin-4-yl)carbamate (86.1)

The title compound 86.1 was prepared according to the procedure of Example 58, Step 1, using 81.1. MS (ESI): mass calcd. for $C_{21}H_{27}N_5O_6$, 445.20 m/z found 446.2 [M+H]+. $^1$H NMR (400 MHz, DMSO) δ 10.97 (s, 1H), 8.39 (s, 1H), 7.30 (d, J=4.4 Hz, 1H), 7.11 (d, J=4.8 Hz, 1H), 5.35 (d, J=6.4 Hz, 1H), 5.03 (t, J=5.6 Hz, 1H), 4.90 (dd, J=6.4, 2.8 Hz, 1H), 4.36 (dd, J=8.0, 5.2 Hz, 1H), 4.18 (t, J=6.8 Hz, 2H), 3.59-3.45 (m, 2H), 1.72-1.63 (m, 5H), 1.35 (dd, J=14.0, 10.8 Hz, 7H), 0.90 (t, J=7.2 Hz, 3H).

Step 2. Synthesis of ((3aR,4R,6R,6aR)-6-cyano-2,2-dimethyl-6-(4-(((pentyloxy)carbonyl)amino)pyrrolo[2,1-f][1,2,4]triazin-7-yl)tetrahydrofuro[3,4-d][1,3]dioxol-4-yl)methyl (tert-butoxycarbonyl)-L-valinate (86.2)

The title compound 86.2 was prepared according to the procedure of Example 19, Step 1, using 86.1 and (tert-butoxycarbonyl)-L-valine. MS (ESI): mass calcd. for $C_{31}H_{44}N_6O_9$, 644.32, m/z found 645.5 [M+H]+. $^1$H NMR (400 MHz, DMSO) δ 10.93 (s, 1H), 8.42 (s, 1H), 7.32 (d, J=4.8 Hz, 1H), 7.14 (d, J=8.0 Hz, 1H), 7.06 (d, J=4.8 Hz, 1H), 5.42 (d, J=6.4 Hz, 1H), 4.93 (dd, J=6.4, 2.8 Hz, 1H), 4.61 (s, 1H), 4.29-4.10 (m, 4H), 3.76 (s, 1H), 1.82 (dd, J=13.2, 6.8 Hz, 1H), 1.76-1.60 (m, 5H), 1.41-1.22 (m, 16H), 0.90 (t J=7.2 Hz, 3H), 0.77 (dd, J=13.2, 6.8 Hz, 6H).

489

Step 3. Synthesis of ((2R,3S,4R,5R)-5-cyano-3,4-dihydroxy-5-(4-(((pentyloxy)carbonyl)amino)pyrrolo[2,1-f][1,2,4]triazin-7-yl)tetrahydrofuran-2-yl)methyl L-valinate (86)

The title compound 86 was prepared according to the procedure of Example 19, Step 2, using 86.2. MS (ESI): mass calcd. for $C_{23}H_{32}N_6O_7$, 504.23 m/z found 505.2 $[M+H]^+$. $^1H$ NMR (400 MHz, DMSO) δ 8.35 (s, 1H), 7.31 (d, J=4.8 Hz, 1H), 7.04 (d, J=4.8 Hz, 1H), 6.45 (s, 1H), 5.46 (s, 1H), 4.69 (s, 1H), 4.33-4.25 (m, 3H), 4.18 (t, J=6.8 Hz, 2H), 3.95 (s, 1H), 3.21 (d, J=5.2 Hz, 1H), 1.84-1.75 (m, 1H), 1.71-1.64 (m, 2H), 1.41-1.31 (m, 4H), 0.90 (t, J=7.2 Hz, 3H), 0.82 (d, J=6.8 Hz, 3H), 0.78 (d, J=6.8 Hz, 3H).

Example 177. ((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methyl L-valinate (Compound 94)

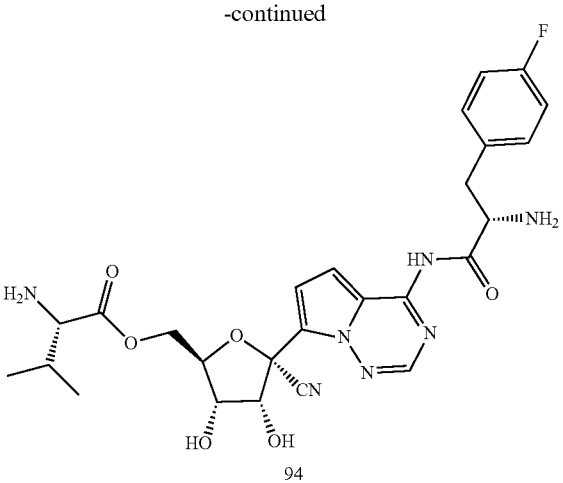

Step 1. Synthesis of ((3aR,4R,6R,6aR)-6-(4-((S)-2-((tert-butoxycarbonyl)amino)-3-(4-fluorophenyl)propanamido)pyrrolo[2,1-f][1,2,4]triazin-7-yl)-6-cyano-2,2-dimethyltetrahydrofuro[3,4-d][1,3]dioxol-4-yl)methyl (tert-butoxycarbonyl)-L-valinate (94.1)

A solution of (tert-butoxycarbonyl)-L-valine (37 mg, 0.17 mmol), EDCI (48 mg, 0.25 mmol), HOBT (34 mg, 0.25 mmol) and DIEA (65 mg, 0.50 mmol) in dry DMF (1.0 mL) was stirred at 20° C. for 1 h. Then 97.1 (100 mg, 0.17 mmol) was added into the flask vessel. The reaction mixture was stirred at 20° C. for 16 h. The reaction mixture was purified by prep-HPLC (0.1% FA) to give 94.1 (71 mg, 53% yield) as a white solid. MS (ESI): mass calcd. for $C_{39}H_{50}FN_7O_{10}$, 795.36, m/z found 796.3 $[M+H]^+$. $^1H$ NMR (400 MHz, DMSO) δ 11.21 (s, 1H), 8.52 (s, 1H), 7.42 (dd, J=7.2, 5.2 Hz, 2H), 7.33-7.20 (m, 2H), 7.16-7.07 (m, 4H), 5.43 (d, J=6.4 Hz, 1H), 4.96-4.77 (m, 2H), 4.67-4.60 (m, 1H), 4.30-4.11 (m, 2H), 3.76 (t, J=7.2 Hz, 1H), 3.13-3.01 (m, 1H), 2.81 (dd, J=13.2, 11.2 Hz, 1H), 1.86-1.75 (m, 1H), 1.66 (s, 3H), 1.38 (s, 3H), 1.36-1.22 (m, 18H), 0.77 (dd, J=14.4, 6.8 Hz, 6H). $^{19}F$ NMR (377 MHz, DMSO) δ −116.72 (s, 1F).

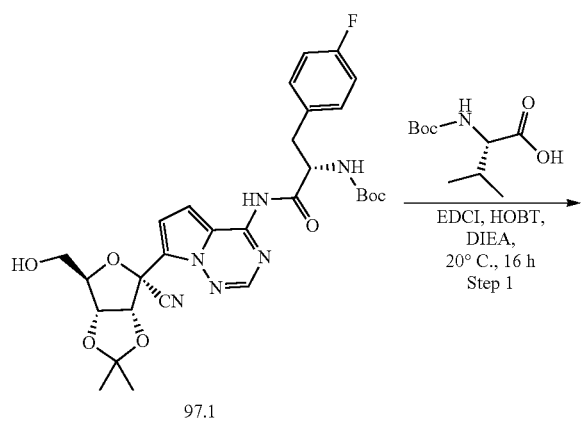

Step 2. Synthesis of ((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methyl L-valinate (94)

To a solution of 94.1 (71 mg, 0.089 mmol) in THF (0.8 mL) was added conc. HCl (0.4 mL, 12 M) dropwise at 0° C. The reaction mixture was stirred at 0° C. for 2 h. The organic solvent was removed with flowing nitrogen. The residue was purified by prep-HPLC (0.1% FA) to give a crude product. The crude product was dissolved with THF and adjusted pH to 8 with Sat. aq. NaHCO₃. The organic solvent was removed with flowing nitrogen and the residue was purified by prep-HPLC (0.10% FA) to afford Compound 94 (8.69 mg, 18% yield) as a white solid. MS (ESI): mass calcd. for $C_{26}H_{30}FN_7O_6$, 555.22, m/z found 556.2 $[M+H]^+$. $^1H$ NMR (400 MHz, DMSO) δ 8.58 (d, J=8.0 Hz, 1H), 7.91 (s, 1H), 7.39 (dd, J=8.4, 5.6 Hz, 2H), 7.09-7.02 (m, 3H), 6.81 (d, J=4.4 Hz, 1H), 6.36 (s, 1H), 5.39 (s, 1H), 4.97-4.89 (m, 1H), 4.64 (d, J=4.8 Hz, 1H), 4.32-4.18 (m, 3H), 3.92 (t, J=5.2 Hz, 1H), 3.20-3.12 (m, 2H), 3.02 (dd, J=13.6, 11.6 Hz, 2H), 1.82-1.71 (m, 1H), 0.79 (dd, J=20.8, 6.4 Hz, 6H). $^{19}$F NMR (377 MHz, DMSO) δ −116.75 (s, 1F).

Example 178. Synthesis of ((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methyl acetate (Compound 95)

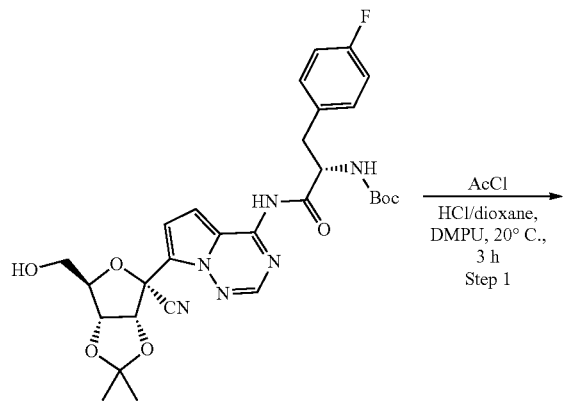

97.1

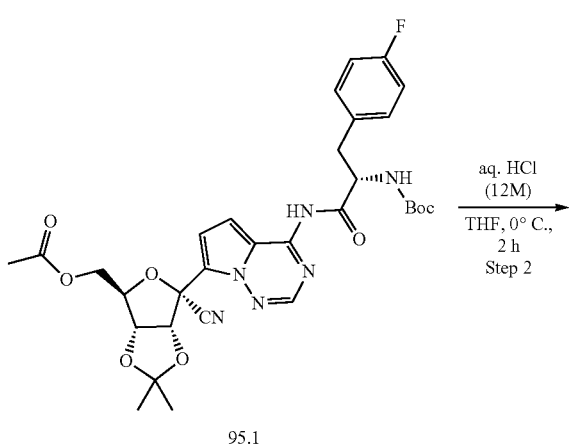

95.1

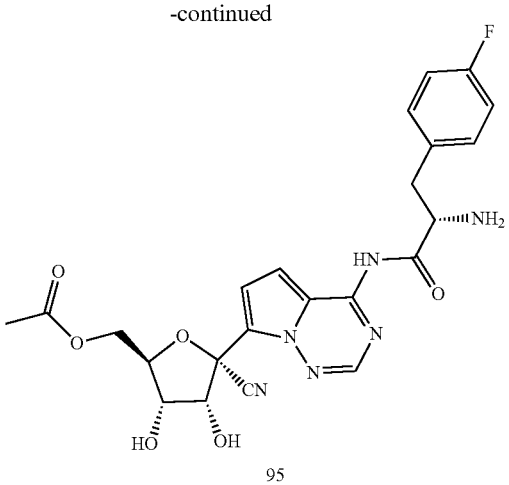

95

Step 1. Synthesis of ((3aR,4R,6R,6aR)-6-(4-((S)-2-((tert-butoxycarbonyl)amino)-3-(4-fluorophenyl)propanamido)pyrrolo[2,1-f][1,2,4]triazin-7-yl)-6-cyano-2,2-dimethyltetrahydrofuro[3,4-d][1,3]dioxol-4-yl)methyl acetate (95.1)

To a solution of 97.1 (100 mg, 0.17 mmol) in DMPU (1.0 mL) was added HCl/1,4-dioxane (0.1 mL, 4 M) at 0° C. under nitrogen. The reaction mixture was stirred at 0° C. for 30 min and then acetyl chloride (105 mg, 1.33 mmol) was added dropwise. The reaction mixture was stirred at 20° C. for 3 h. The reaction mixture was purified by prep-HPLC (0.10% FA) to give 95.1 (58 mg, 54% yield) as a white solid. MS (ESI): mass calcd. for $C_{31}H_{35}FN_6O_8$, 638.25, m/z found 639.2 [M+H]$^+$.

Step 2. Synthesis of ((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methyl acetate (95)

To a solution of 95.1 (58 mg, 0.09 mmol) in THF (0.6 mL) was added conc. HCl (0.3 mL, 12 M) dropwise at 0° C. The reaction mixture was stirred at 0° C. for 2 h. The organic solvent was removed with flowing nitrogen. The residue was purified by prep-HPLC (0.1% FA) to give a crude product. The crude product was dissolved with THF and adjusted pH to 8 with Sat. aq. NaHCO$_3$. The organic solvent was removed with flowing nitrogen and the residue was purified by prep-HPLC (0.10% FA) to afford Compound 95 (9.32 mg, 21% yield) as a white solid. MS (ESI): m/z calcd. for $C_{23}H_{23}FN_6O_6$ 498.17, found 499.1 [M+H]$^+$. $^1$H NMR (400 MHz, DMSO) δ 8.56 (d, J=8.4 Hz, 1H), 7.91 (s, 1H), 7.69 (s, 1H), 7.39 (dd, J=8.4, 5.6 Hz, 2H), 7.18 (s, 1H), 7.10-7.03 (m, 3H), 6.80 (d, J=4.8 Hz, 1H), 6.31 (d, J=6.0 Hz, 1H), 5.38 (d, J=6.0 Hz, 1H), 4.97-4.89 (m, 1H), 4.66 (t, J=5.6 Hz, 1H), 4.30 (dd, J=11.6, 2.4 Hz, 1H), 4.23-4.17 (m, 1H), 4.12 (dd, J=12.0, 6.0 Hz, 1H), 3.91 (dd, J=11.6, 6.4 Hz, 1H), 3.18 (dd, J=14.0, 3.6 Hz, 1H), 3.07-2.98 (dd, J=13.6, 11.2 Hz, 1H), 1.99 (s, 3H). $^{19}$F NMR (377 MHz, DMSO) δ−116.75 (s, 1F).

Example 179. ((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methyl 2-cyclohexylacetate (Compound 96)
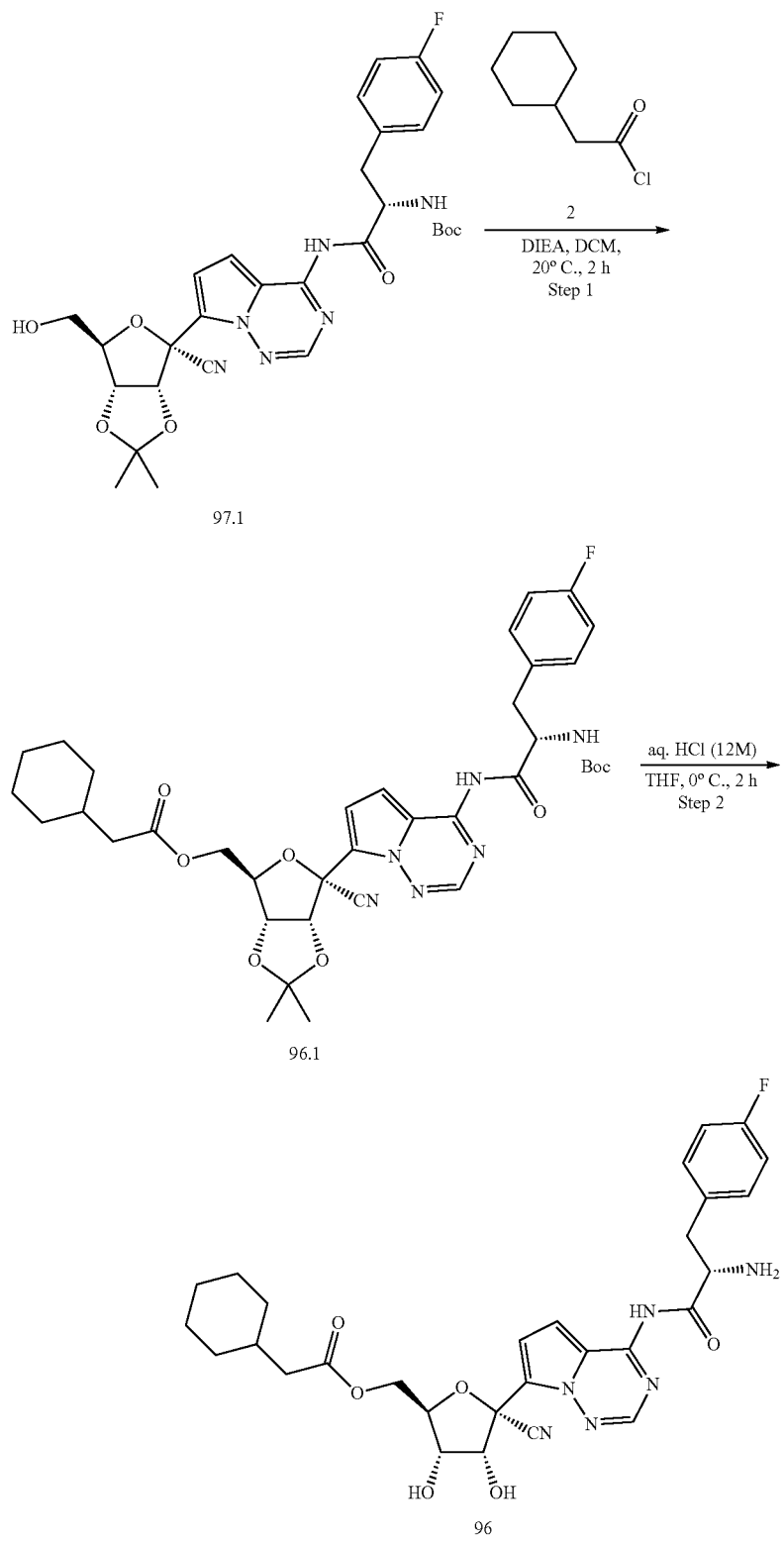

Step 1. Synthesis of ((3aR,4R,6R,6aR)-6-(4-((S)-2-((tert-butoxycarbonyl)amino)-3-(4-fluorophenyl)propanamido)pyrrolo[2,1-f][1,2,4]triazin-7-yl)-6-cyano-2,2-dimethyltetrahydrofuro[3,4-d][1,3]dioxol-4-yl)methyl 2-cyclohexylacetate (96.1)

The title compound was prepared according to the procedure of Example 58, Step 2, using 97.1 and 2-cyclohexylacetyl chloride. MS (ESI): mass calcd. for $C_{37}H_{45}FN_6O_8$, 720.33, m/z found 721.2 [M+H]$^+$.

Step 2. Synthesis of ((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methyl 2-cyclohexylacetate (96)

The title compound was prepared according to the procedure of Example 178, Step 2, using 96.1. MS (ESI): mass calcd. for $C_{29}H_{33}FN_6O_6$, 580.24, m/z found 581.2 [M+H]$^+$. $^1$H NMR (400 MHz, DMSO) δ 8.55 (d, J=8.4 Hz, 1H), 7.91 (s, 1H), 7.67 (s, 1H), 7.39 (dd, J=8.4, 5.6 Hz, 2H), 7.17 (s, 1H), 7.09-7.02 (m, 3H), 6.79 (d, J=4.4 Hz, 1H), 6.30 (d, J=6.0 Hz, 1H), 5.36 (d, J=6.0 Hz, 1H), 4.97-4.90 (m, 1H), 4.66-4.61 (m, 1H), 4.29 (dd, J=11.6, 2.4 Hz, 1H), 4.23-4.12 (m, 2H), 3.91 (dd, J=11.2, 6.4 Hz, 1H), 3.17 (dd, J=14.0, 3.6 Hz, 1H), 3.03 (dd, J=13.6, 11.2 Hz, 1H), 2.16 (d, J=6.4 Hz, 2H), 1.67-1.52 (m, 6H), 1.24-0.99 (m, 3H), 0.90 (dd, J=22.8, 12.0 Hz, 2H). $^{19}$F NMR (377 MHz, DMSO) δ −116.77 (s, 1F).

Example 180. ((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methyl propionate (Compound 99)

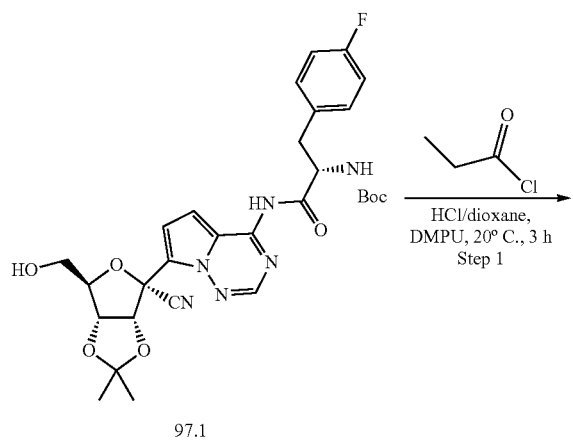

97.1

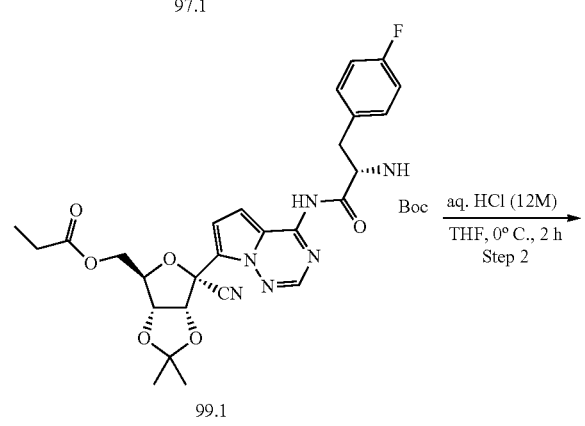

99.1

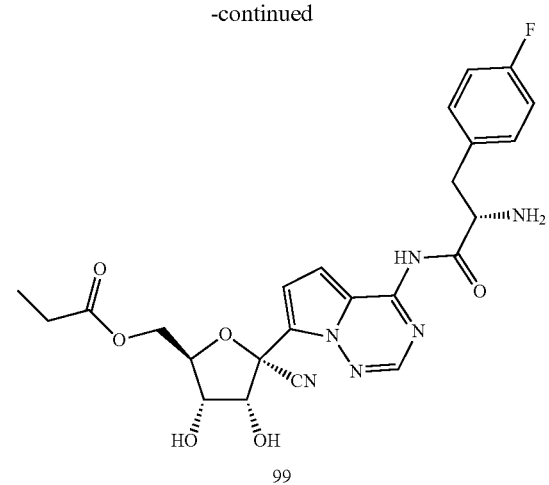

99

Step 1. Synthesis of ((3aR,4R,6R,6aR)-6-(4-((S)-2-((tert-butoxycarbonyl)amino)-3-(4-fluorophenyl)propanamido)pyrrolo[2,1-f][1,2,4]triazin-7-yl)-6-cyano-2,2-dimethyltetrahydrofuro[3,4-d][1,3]dioxol-4-yl)methyl propionate (95.1)

The title compound was prepared according to the procedure of Example 178, Step 1, using 97.1 and propionyl chloride. MS (ESI): mass calcd. for $C_{32}H_{37}FN_6O_8$, 652.27, m/z found 653.4 [M+H]$^+$. $^1$H NMR (400 MHz, DMSO) δ 11.32 (s, 1H), 8.50 (s, 1H), 7.49-7.36 (dd, J=7.6, 6.0 Hz, 1H), 7.32-7.05 (m, 5H), 5.41 (d, J=6.0 Hz, 1H), 4.98 (dd, J=6.0, 2.4 Hz, 1H), 4.91-4.76 (m, 1H), 4.68-4.62 (m, 1H), 4.23 (dd, J=12.0, 4.0 Hz, 1H), 4.10 (dd, J=12.0, 5.6 Hz, 1H), 3.09 (dd, J=14.4, 3.2 Hz, 1H), 2.87-2.74 (m, 1H), 2.27-2.03 (m, 2H), 1.66 (s, 3H), 1.39 (s, 3H), 1.37-1.13 (m, 11H), 0.90 (t, J=7.6 Hz, 3H). $^{19}$F NMR (377 MHz, DMSO) δ −116.75 (s, 1F).

Step 2. Synthesis of ((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methyl propionate (99)

The title compound was prepared according to the procedure of Example 178, Step 2, using 99.1. MS (ESI): mass calcd. for $C_{24}H_{25}FN_6O_6$, 512.18, m/z found 513.1 [M+H]$^+$. $^1$H NMR (400 MHz, DMSO) δ 8.55 (d, J=8.4 Hz, 1H), 7.91 (s, 1H), 7.39 (dd, J=7.2, 6.0 Hz, 2H), 7.10-7.01 (m, 3H), 6.79 (d, J=4.4 Hz, 1H), 6.32 (d, J=5.2 Hz, 1H), 5.39 (d, J=4.4 Hz, 1H), 4.97-4.88 (m, 1H), 4.65 (t, J=4.8 Hz, 1H), 4.35-4.28 (m, 1H), 4.23-4.18 (m, 1H), 4.13 (dd, J=12.0, 5.2 Hz, 1H), 3.95-3.89 (m, 1H), 3.21-3.14 (m, 1H), 3.07-2.98 (m, 1H), 2.34-2.21 (m, 2H), 0.97 (t, J=7.6 Hz, 3H). $^{19}$F NMR (377 MHz, DMSO) δ −116.75 (s, 1F).

Example 181. ((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methyl isobutyrate (Compound 100)

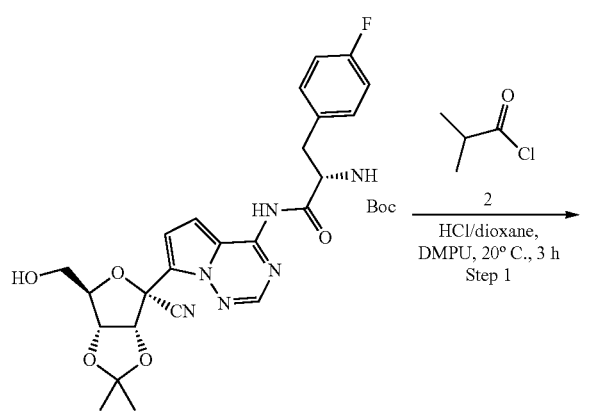

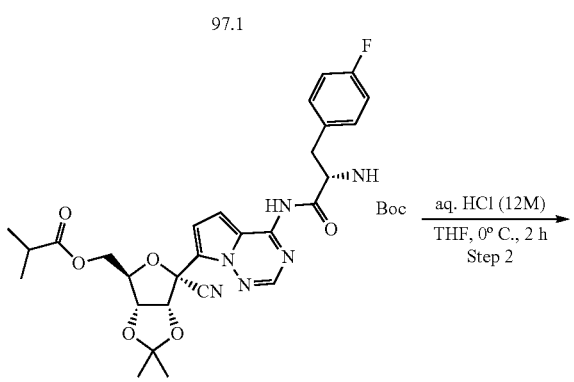

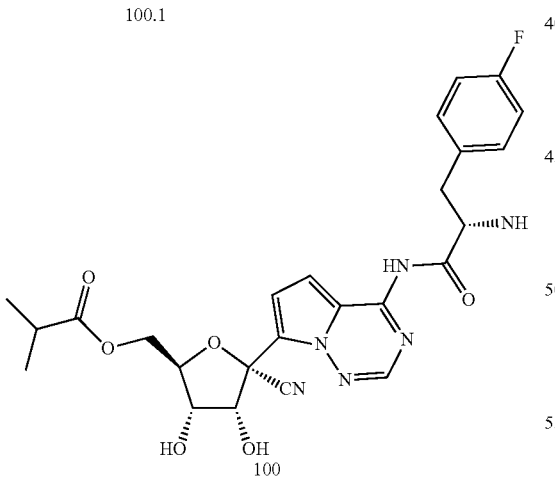

Step 1. Synthesis of ((3aR,4R,6R,6aR)-6-(4-((S)-2-((tert-butoxycarbonyl)amino)-3-(4-fluorophenyl)propanamido)pyrrolo[2,1-f][1,2,4]triazin-7-yl)-6-cyano-2,2-dimethyltetrahydrofuro[3,4-d][1,3]dioxol-4-yl)methyl isobutyrate (100.1)

The title compound was prepared according to the procedure of Example 178, Step 1, using 97.1 and isobutyryl chloride. MS (ESI): mass calcd. for $C_{33}H_{39}FN_6O_8$, 666.28, m/z found 667.2 [M+H]$^+$. $^1$H NMR (400 MHz, DMSO) δ 11.20 (s, 1H), 8.52 (s, 1H), 7.42 (dd, J=8.0, 6.0 Hz, 2H), 7.30 (d, J=8.0 Hz, 1H), 7.23 (d, J=4.4 Hz, 1H), 7.15-7.06 (m, 3H), 5.40 (d, J=6.0 Hz, 1H), 4.98 (dd, J=6.4, 2.8 Hz, 1H), 4.85 (br, 1H), 4.68-4.62 (m, 1H), 4.22 (dd, J=12.0, 4.0 Hz, 1H), 4.10 (dd, J=12.0, 5.6 Hz, 1H), 3.08 (dd, J=13.6, 3.6 Hz, 1H), 2.81 (dd, J=13.2, 10.8 Hz, 1H), 2.43-2.34 (m, 1H), 1.66 (s, 3H), 1.39 (s, 3H), 1.34-1.21 (m, 9H), 0.96 (dd, J=18.0, 7.2 Hz, 6H).

Step 2. Synthesis of ((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methyl isobutyrate (100)

The title compound was prepared according to the procedure of Example 178, Step 2, using 100.1. MS (ESI): mass calcd. for $C_{25}H_{27}FN_6O_6$, 526.20, m/z found 527.1 [M+H]$^+$. $^1$H NMR (400 MHz, DMSO) δ 8.58 (d, J=8.4 Hz, 1H), 8.49 (s, 1H), 7.91 (s, 1H), 7.69 (s, 1H), 7.39 (dd, J=8.4, 6.0 Hz, 2H), 7.16 (s, 1H), 7.09-7.03 (m, 3H), 6.79 (d, J=4.4 Hz, 1H), 6.39 (d, J=4.4 Hz, 1H), 5.43 (d, J=4.0 Hz, 1H), 4.96-4.88 (m, 1H), 4.65 (t, J=5.2 Hz, 1H), 4.29 (dd, J=12.0, 2.8 Hz, 1H), 4.24-4.19 (m, 1H), 4.13 (dd, J=12.0, 4.8 Hz, 1H), 3.97-3.91 (m, 1H), 3.17 (dd, J=13.6, 3.6 Hz, 1H), 3.06-2.98 (m, 1H), 2.48-2.42 (m, 1H), 1.00 (dd, J=11.6, 7.2 Hz, 6H). $^{19}$F NMR (377 MHz, DMSO) δ −116.79 (s, 1F).

Example 182. Synthesis of ((2R,3S,4R,5R)-5-(4-benzamidopyrrolo[2,1-f][1,2,4]triazin-7-yl)-5-cyano-3,4-dihydroxytetrahydrofuran-2-yl)methyl L-valinate (Compound 102)

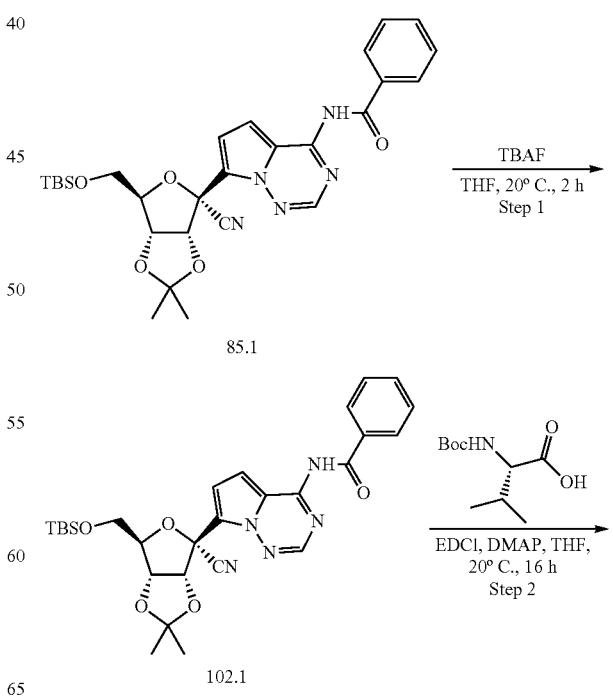

-continued

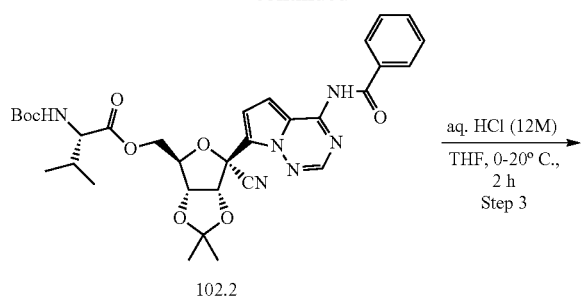

102.2 aq. HCl (12M)
―――――――――→
THF, 0-20° C.,
2 h
Step 3

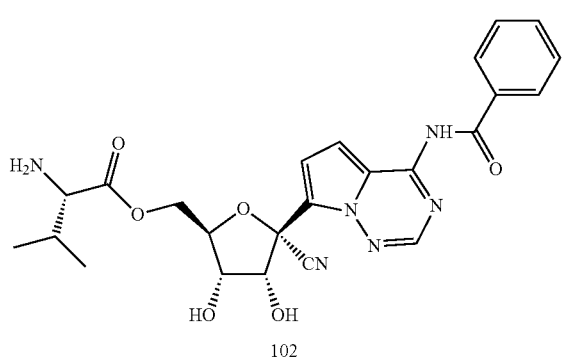

102

Step 1. Synthesis of N-(7-((3aR,4R,6R,6aR)-4-cyano-6-(hydroxymethyl)-2,2-dimethyltetrahydrofuro[3,4-d][1,3]dioxol-4-yl)pyrrolo[2,1-f][1,2,4]triazin-4-yl)benzamide (102.1)

The compound 102.1 was prepared according to the procedure of Example 58, Step 1, using 85.1. MS (ESI): mass calcd. for $C_{22}H_{21}N_5O_5$, 435.15, m/z found 436.1 $[M+H]^+$.

Step 2. ((3aR,4R,6R,6aR)-6-(4-benzamidopyrrolo[2,1-f][1,2,4]triazin-7-yl)-6-cyano-2,2-dimethyltetrahydrofuro[3,4-d][1,3]dioxol-4-yl)methyl (tert-butoxycarbonyl)-L-valinate (102.2)

The compound 102.2 was prepared according to the procedure of Example 266, Step 1, using 102.1 and (tert-butoxycarbonyl)-L-valine. MS (ESI): mass calcd. for $C_{32}H_{38}N_6O_8$, 634.69, m/z found 635.2 $[M+H]^+$.

Step 3. Synthesis of ((2R,3S,4R,5R)-5-(4-benzamidopyrrolo[2,1-f][1,2,4]triazin-7-yl)-5-cyano-3,4-dihydroxytetrahydrofuran-2-yl)methyl L-valinate (Compound 102)

The compound 102 was prepared according to the procedure of Example 112, Step 3, using 102.2. MS (ESI): mass calcd. for $C_{24}H_{26}N_6O_6$, 494.51, m/z found 495.1 $[M+H]^+$. $^1$H NMR (400 MHz, DMSO) δ 8.39 (s, 1H), 8.06 (d, J=7.2 Hz, 2H), 7.67 (t, J=7.2 Hz, 1H), 7.56 (t, J=7.6 Hz, 2H), 7.18 (d, J=4.8 Hz, 1H), 7.09 (d, J=4.0 Hz, 1H), 6.52 (d, J=6.0 Hz, 1H), 5.54 (d, J=5.6 Hz, 1H), 4.74 (t, J=5.2 Hz, 1H), 4.42 (d, J=4.4 Hz, 2H), 4.34-4.32 (m, 1H), 4.03-3.95 (m, 1H), 3.80 (d, J=4.0 Hz, 1H), 2.05-2.03 (m, 1H), 0.90 (t, J=6.8 Hz, 6H).

Example 183. Synthesis of ((2R,3S,4R,5R)-5-(4-((S)-2-amino-3-methylbutanamido)pyrrolo[2,1-f][1,2,4]triazin-7-yl)-5-cyano-3,4-dihydroxytetrahydrofuran-2-yl)methyl propionate (Compound 115)

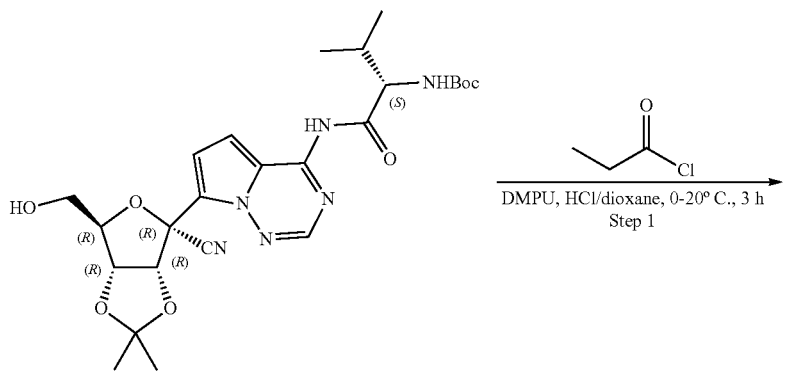

112.1

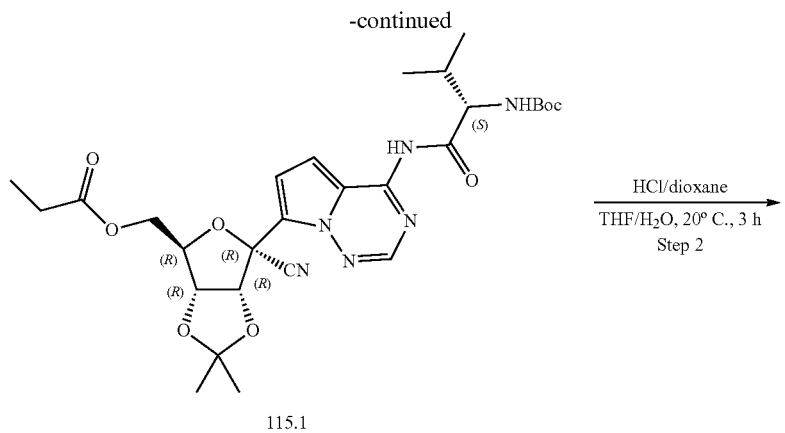

115.1

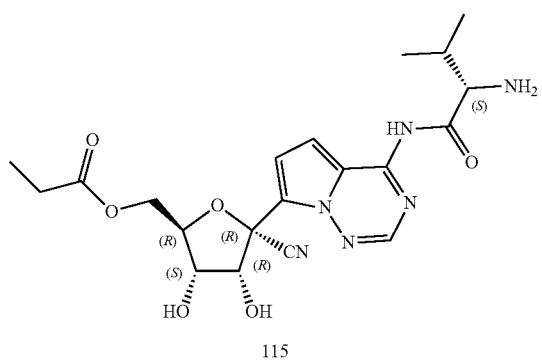

115

Step 1. Synthesis of ((3aR,4R,6R,6aR)-6-(4-((S)-2-((tert-butoxycarbonyl)amino)-3-methylbutanamido)pyrrolo[2,1-f][1,2,4]triazin-7-yl)-6-cyano-2,2-dimethyltetrahydrofuro[3,4-d][1,3]dioxol-4-yl)methyl propionate (115.1)

The compound 115.1 was prepared according to the procedure of Example 1, Step 4, using 112.1 and propionyl chloride. MS (ESI): mass calcd. for $C_{28}H_{38}N_6O_8$, 586.65, m/z found 587.3 $[M+H]^+$.

Step 2. Synthesis of ((2R,3S,4R,5R)-5-(4-((S)-2-amino-3-methylbutanamido)pyrrolo[2,1-f][1,2,4]triazin-7-yl)-5-cyano-3,4-dihydroxytetrahydrofuran-2-yl)methyl propionate (Compound 115)

The compound 115 was prepared according to the procedure of Example 66, Step 3, using 112.2. MS (ESI): mass calcd. for $C_{20}H_{26}N_6O_6$, 446.46, m/z found 447.1 $[M+H]^+$. $^1$H NMR (400 MHz, DMSO) δ 8.22 (d, J=8.4 Hz, 1H), 7.98 (s, 1H), 7.56 (s, 1H), 7.24 (d, J=4.4 Hz, 1H), 7.12 (s, 1H), 6.80 (d, J=4.8 Hz, 1H), 6.34 (d, J=6.0 Hz, 1H), 5.40 (d, J=6.0 Hz, 1H), 4.70-4.61 (m, 2H), 4.33 (dd, J=12.0, 2.4 Hz, 1H), 4.24-4.20 (m, 1H), 4.15 (dd, J=12.0, 5.6 Hz, 1H), 3.93-3.90 (m, 1H), 2.33-2.27 (m, 2H), 2.23-2.14 (m, 1H), 1.00 (t, J=7.6 Hz, 3H), 0.96 (dd, J=6.8, 3.6 Hz, 6H).

Example 184. Synthesis of (2R,3S,4R,5R)-5-(4-benzamidopyrrolo[2,1-f][1,2,4]triazin-7-yl)-5-cyano-4-hydroxy-2-(hydroxymethyl)tetrahydrofuran-3-yl L-valinate (Compound 128)

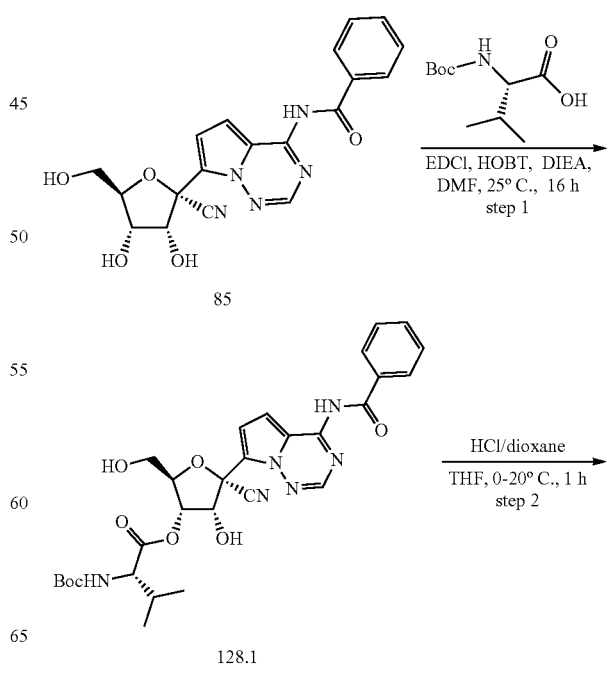

128.1

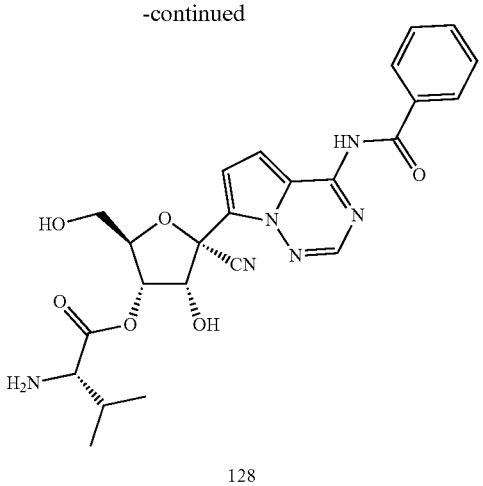

128

Step 1. Synthesis of (2R,3S,4R,5R)-5-(4-benzamidopyrrolo[2,1-f][1,2,4]triazin-7-yl)-5-cyano-4-hydroxy-2-(hydroxymethyl)tetrahydrofuran-3-yl (tert-butoxycarbonyl)-L-valinate (128.1)

To a mixture of (2S)-2-{[tert-butyl(formyl)-$1^{3}$-oxidanyl]amino}-3-methylbutanoic acid 85 (55.2 mg, 0.253 mmol), EDCI (72.7 mg, 0.379 mmol) and 1-Hydroxybenzotrizole (51.3 mg, 0.379 mmol) in DMF (1 mL) under nitrogen. The DIEA (98.1 mg, 0.379 mmol) was added in mixture, the reaction mixture was stirred for 30 min and N-{7-[(2R,3R,4S,5R)-2-cyano-3,4-dihydroxy-5-(hydroxymethyl)oxolan-2-yl]pyrrolo[2,1-f][1,2,4]triazin-4-yl}benzamide (100 mg, 0.253 mmol) was added dropwise. The reaction mixture stirred at 25° C. for 16 h. The residue was quenched with water and extracted with EtOAc. The organic phase was washed with brine, dried over $Na_2SO_4$ and evaporated in vacuo to give the crude product. The crude product was purified by prep-HPLC to afford product 128.1 (41.7 mg, 23.8% yield) as a white solid. MS (ESI): m/z calcd. for $C_{29}H_{34}N_6O_8$, 594.6, found 595.4 [M+H]$^+$. $^1$H NMR (400 MHz, DMSO) δ 11.41 (s, 1H), 8.46 (s, 1H), 8.05 (s, 2H), 7.66 (t J=7.2 Hz, 1H), 7.56 (t, J=7.6 Hz, 2H), 7.18 (s, 2H), 7.08 (d, J=8.8 Hz, 1H), 6.64 (d, J=6.8 Hz, 1H), 5.20-5.16 (m, 1H), 5.08 (t, J=5.6 Hz, 1H), 4.99 (s, 1H), 4.27 (s, 1H), 4.15-4.07 (m, 1H), 3.66-3.53 (m, 2H), 1.41 (s, 9H), 0.91 (dd, J=12.4, 6.8 Hz, 6H).

Step 2. Synthesis of (2R,3S,4R,5R)-5-(4-benzamidopyrrolo[2,1-f][1,2,4]triazin-7-yl)-5-cyano-4-hydroxy-2-(hydroxymethyl)tetrahydrofuran-3-yl L-valinate (Compound 128)

To a solution of compound 128.1 (40 mg, 0.0672 mmol) in THF (1 mL), then HCl/1,4-dioxane (0.5 mL, 4M) was added in mixture at 0° C. The mixture was stirred at 20° C. for 2 h. The residue was quenched with water and extracted with EtOAc. The organic phase was washed with brine, dried over $Na_2SO_4$ and evaporated in vacuo to give the crude product. The crude product was purified by prep-HPLC to afford product 128 (4.52 mg, 12.8% yield) as a white solid. MS (ESI): m/z calcd. for $C_{24}H_{26}N_6O_6$, 494.5, found 495.1 [M+H]$^+$. $^1$H NMR (400 MHz, DMSO) δ 8.39 (s, 1H), 8.22 (s, 1H), 8.06 (d, J=8.0 Hz, 2H), 7.65 (t, J=7.2 Hz, 1H), 7.55 (t, J=7.6 Hz, 2H), 7.15 (d, J=12.8 Hz, 2H), 6.62 (s, 1H), 5.21 (dd, J=5.6, 3.6 Hz, 1H), 5.09 (s, 1H), 5.01 (d, J=5.2 Hz, 1H), 4.29 (d, J=3.6 Hz, 1H), 3.62-3.54 (m, 2H), 3.25 (d, J=5.2 Hz, 1H), 2.09-1.98 (m, 1H), 0.94 (d, J=6.8 Hz, 3H), 0.88 (d, J=6.8 Hz, 3H).

Example 185. Synthesis of (2R,3S,4R,5R)-5-(4-((S)-2-amino-3-(4-fluorophenyl)propanamido)pyrrolo[2,1-f][1,2,4]triazin-7-yl)-5-cyano-4-hydroxy-2-(hydroxymethyl)tetrahydrofuran-3-yl 2-cyclohexylacetate (Compound 137)

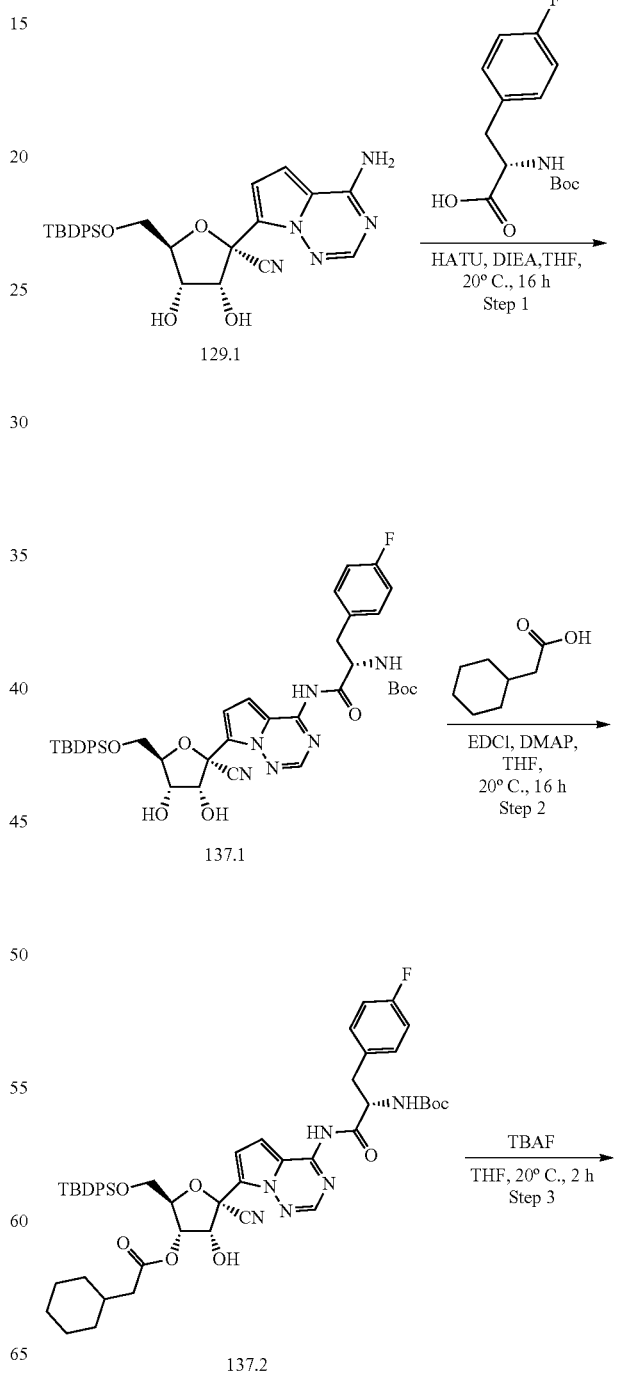

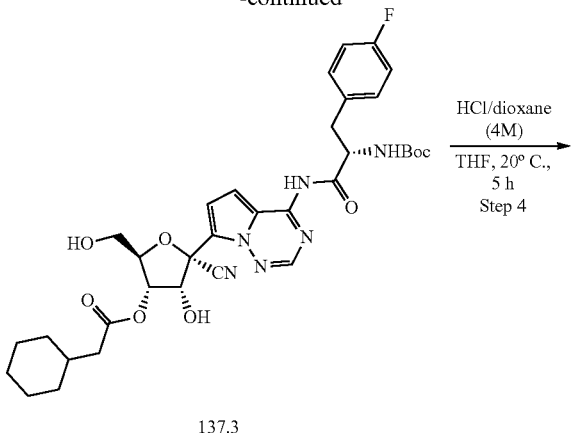

137.3

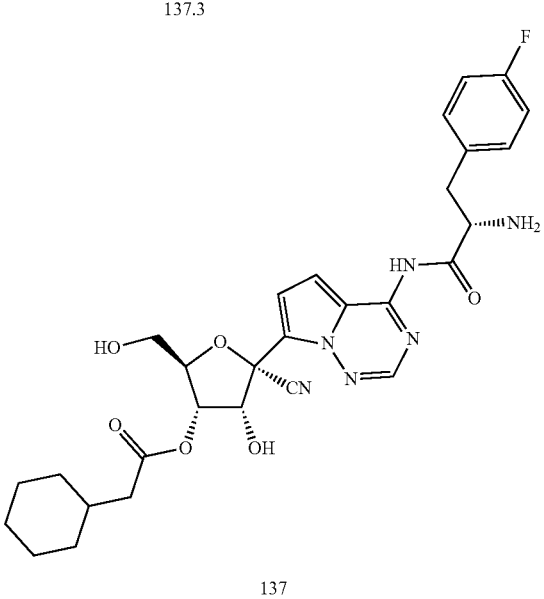

137

Step 1. Synthesis of tert-butyl ((S)-1-((7-((2R,3R,4S,5R)-5-(((tert-butyldiphenylsilyl)oxy)methyl)-2-cyano-3,4-dihydroxytetrahydrofuran-2-yl)pyrrolo[2,1-f][1,2,4]triazin-4-yl)amino)-3-(4-fluorophenyl)-1-oxopropan-2-yl)carbamate (137.1)

To a solution of (S)-2-((tert-butoxycarbonyl)amino)-3-(4-fluorophenyl)propanoic acid (1.71 g, 0.006 mmol) in THF (20 mL) was added HATU (3.42 g, 0.009 mmol), the solution was stirred at 25° C. for 1 h. To the above solution was added 129.1 (1.6 g, 0.003 mmol) and DIEA (2.34 mg, 0.018 mmol), and the mixture was stirred at 25° C. for 16 h. The reaction was washed with EtOAc (10 mL×3). The combined organics were dried over sodium sulfate and concentrated in vacuo. The crude product was purified by flash column chromatography eluting with EA in PE from 0% to 50% to obtain 137.1 (0.85 g, 0.001 mol, 33% yield) as a white solid. MS (ESI): m/z calcd. for $C_{42}H_{47}FN_6O_7Si$ 794.96, found 795.2 [M+H]$^+$. $^1$H NMR (400 MHz, DMSO) δ 11.15 (s, 1H), 8.45 (s, 1H), 7.55 (dd, J=18.0, 7.2 Hz, 4H), 7.48-7.40 (m, 4H), 7.33-7.07 (m, 4H), 7.18-7.03 (m, 4H), 6.41 (d, J=6.0 Hz, 1H), 5.33 (d, J=5.6 Hz, 1H), 4.86-4.80 (m, 1H), 4.79-4.68 (m, 1H), 4.21-4.18 (m, 2H), 3.86 (d, J=10.0 Hz, 1H), 3.74 (dd, J=11.6, 3.6 Hz, 1H), 3.10 (d, J=10.0 Hz, 1H), 2.90-2.76 (m, 1H), 1.32 (s, 9H), 0.90 (s, 9H).

Step 2. Synthesis of (2R,3S,4R,5R)-5-(4-((S)-2-((tert-butoxycarbonyl)amino)-3-(4-fluorophenyl)propanamido)pyrrolo[2,1-f][1,2,4]triazin-7-yl)-2-(((tert-butyldiphenylsilyl)oxy)methyl)-5-cyano-4-hydroxytetrahydrofuran-3-yl 2-cyclohexylacetate (137.2)

The compound 137.2 was prepared according to the procedure of Example 19, Step 1, using 137.1 and 2-cyclohexylacetic acid. MS (ESI): mass calcd. for $C_{50}H_{59}FN_6O_8Si$, 919.14, m/z found 919.4 [M+H]$^+$.

Step 3. Synthesis of (2R,3S,4R,5R)-5-(4-((S)-2-((tert-butoxycarbonyl)amino)-3-(4-fluorophenyl)propanamido)pyrrolo[2,1-f][1,2,4]triazin-7-yl)-5-cyano-4-hydroxy-2-(hydroxymethyl)tetrahydrofuran-3-yl 2-cyclohexylacetate (137.3)

The compound 137.3 was prepared according to the procedure of Example 97, Step 1, using 137.2. MS (ESI): mass calcd. for $C_{34}H_{41}FN_6O_8Si$, 680.73, m/z found 681.3 [M+H]$^+$. $^1$H NMR (400 MHz, DMSO) δ 11.29 (s, 1H), 8.46 (s, 1H), 7.50-7.37 (m, 2H), 7.24-7.22 (m, 2H), 7.16-7.09 (m, 3H), 6.60 (d, J=5.6 Hz, 1H), 5.24-5.16 (m, 1H), 5.06-5.05 (m, 1H), 4.98 (t, J=5.6 Hz, 1H), 4.85-4.80 (m, 1H), 4.29 (d, J=3.6 Hz, 1H), 3.58-3.56 (m, 2H), 3.12 (d, J=10.4 Hz, 1H), 2.81 (t, J=12.4 Hz, 1H), 2.27 (d, J=6.8 Hz, 2H), 1.81-1.72 (m, 3H), 1.64-1.58 (m, 3H), 1.32 (s, 9H), 1.17-1.10 (m, 3H), 1.03-0.91 (m, 2H).

Step 4. Synthesis of (2R,3S,4R,5R)-5-(4-((S)-2-amino-3-(4-fluorophenyl)propanamido)pyrrolo[2,1-f][1,2,4]triazin-7-yl)-5-cyano-4-hydroxy-2-(hydroxymethyl)tetrahydrofuran-3-yl 2-cyclohexylacetate (Compound 137)

The compound 137 was prepared according to the procedure of Example 19, Step 2, using 137.3. MS (ESI): mass calcd. for $C_{29}H_{33}FN_6O_6$, 580.62, m/z found 581.2 [M+H]$^+$. $^1$H NMR (400 MHz, DMSO) δ 8.60 (d, J=8.4 Hz, 1H), 7.92 (s, 1H), 7.68 (s, 1H), 7.38 (dd, J=8.4, 5.6 Hz, 2H), 7.19 (s, 1H), 7.06 (dd, J=10.0, 7.6 Hz, 3H), 6.87 (d, J=4.4 Hz, 1H), 6.43 (d, J=6.6 Hz, 1H), 5.20-5.12 (m, 1H), 5.00 (t, J=5.6 Hz, 1H), 4.95-4.92 (m, 2H), 4.29-4.20 (m, 1H), 3.64-3.45 (m, 2H), 3.22-3.15 (m, 1H), 3.09-2.97 (m, 1H), 2.25 (d, J=6.8 Hz, 2H), 1.90-1.69 (m, 3H), 1.65-1.58 (m, 3H), 1.29-1.05 (m, 3H), 0.99-0.93 (m, 2H). $^{19F}$ NMR (377 MHz, DMSO) δ −116.77 (s, 1H).

Example 186. Synthesis of (2R,3S,4R,5R)-5-(4-((S)-2-amino-3-methylbutanamido)pyrrolo[2,1-f][1,2,4]triazin-7-yl)-5-cyano-4-hydroxy-2-(hydroxymethyl)tetrahydrofuran-3-yl 2-cyclohexylacetate (Compound 139)

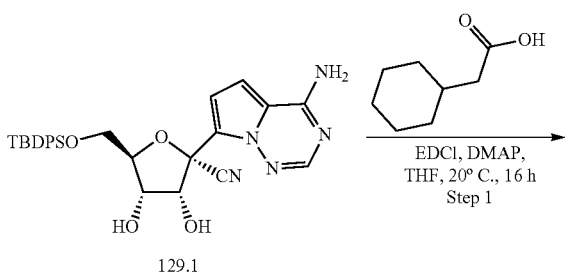

129.1

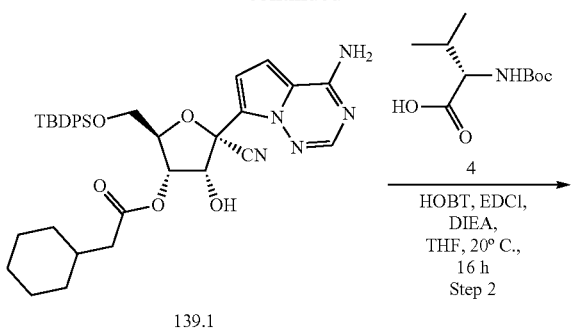

139.1

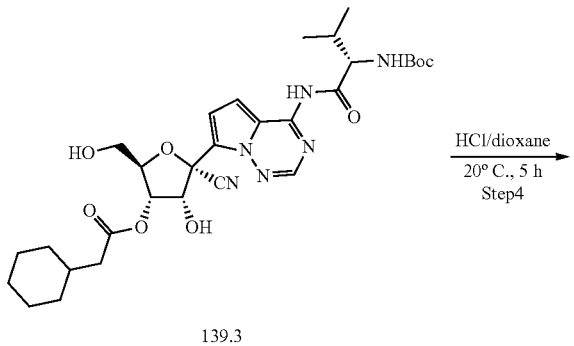

139.2

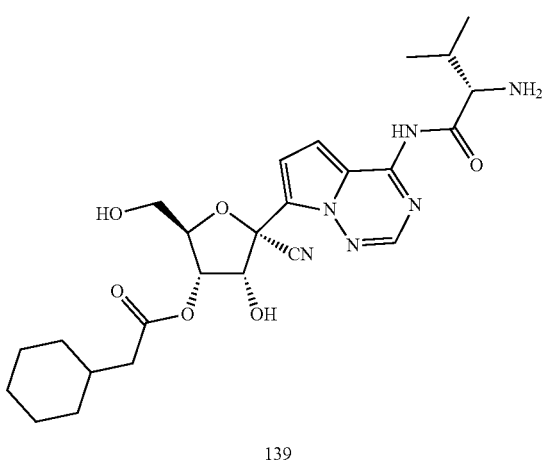

139.3

139

Step 1. Synthesis of (2R,3S,4R,5R)-5-(4-aminopyrrolo[2,1-f][1,2,4]triazin-7-yl)-2-(((tert-butyldiphenylsilyl)oxy)methyl)-5-cyano-4-hydroxytetrahydrofuran-3-yl 2-cyclohexylacetate (139.1)

The compound 139.1 was prepared according to the procedure of Example 19, Step 1, using 129.1 and 2-cyclohexylacetic acid. MS (ESI): mass calcd. for $C_{36}H_{43}N_5O_5Si$, 653.86, m/z found 654.3 [M+H]$^+$. $^1$H NMR (400 MHz, DMSO) δ 7.89-7.80 (m, 3H), 7.53 (d, J=6.8 Hz, 2H), 7.49-7.31 (m, 6H), 7.24 (t, J=7.6 Hz, 2H), 6.85 (d, J=4.4 Hz, 1H), 6.80 (d, J=4.4 Hz, 1H), 6.63 (d, J=6.4 Hz, 1H), 5.36 (t, J=4.8 Hz, 1H), 5.05 (t, J=6.0 Hz, 1H), 4.36 (d, J=3.6 Hz, 1H), 3.77-3.75 (m, 2H), 2.26 (d, J=6.8 Hz, 2H), 1.87-1.53 (m, 6H), 1.32-0.95 (m, 5H), 0.92 (s, 9H).

Step 2. Synthesis of (2R,3S,4R,5R)-5-(4-((S)-2-((tert-butoxycarbonyl)amino)-3-methylbutanamido)pyrrolo[2,1-f][1,2,4]triazin-7-yl)-2-(((tert-butyldiphenylsilyl)oxy)methyl)-5-cyano-4-hydroxytetrahydrofuran-3-yl 2-cyclohexylacetate (139.2)

The compound 139.2 was prepared according to the procedure of Example 129, Step 1, using 139.1 and (tert-butoxycarbonyl)-L-valine. MS (ESI): mass calcd. for $C_{46}H_{60}N_6O_8Si$, 853.11, m/z found 853.4 [M+H]$^+$.

Step 3. Synthesis of (2R,3S,4R,5R)-5-(4-((S)-2-((tert-butoxycarbonyl)amino)-3-methylbutanamido)pyrrolo[2,1-f][1,2,4]triazin-7-yl)-5-cyano-4-hydroxy-2-(hydroxymethyl)tetrahydrofuran-3-yl 2-cyclohexylacetate (139.3)

The compound 139.3 was prepared according to the procedure of Example 97, Step 1, using 139.2. MS (ESI): mass calcd. for $C_{30}H_{42}N_6O_8$, 614.70, m/z found 615.2 [M+H]$^+$.

Step 4. Synthesis of (2R,3S,4R,5R)-5-(4-((S)-2-amino-3-methylbutanamido)pyrrolo[2,1-f][1,2,4]triazin-7-yl)-5-cyano-4-hydroxy-2-(hydroxymethyl)tetrahydrofuran-3-yl 2-cyclohexylacetate (Compound 139)

The compound 139 was prepared according to the procedure of Example 19, Step 2, using 139.3. MS (ESI): mass calcd. for $C_{25}H_{34}N_6O_6$, 514.58, m/z found 515.2 [M+H]$^+$. $^1$H NMR (400 MHz, DMSO) δ 8.26 (d, J=8.4 Hz, 1H), 7.99 (s, 1H), 7.57 (s, 1H), 7.25 (d, J=4.4 Hz, 1H), 7.14 (s, 1H), 6.89 (d, J=4.8 Hz, 1H), 6.46 (d, J=6.4 Hz, 1H), 5.17 (dd, J=5.2, 3.6 Hz, 1H), 5.03 (t J=5.6 Hz, 1H), 4.97 (t, J=6.4 Hz, 1H), 4.66 (t, J=8.0 Hz, 1H), 4.25-4.24 (m, 1H), 3.68-3.46 (m, 2H), 2.26 (d, J=7.2 Hz, 2H), 2.18-2.15 (m, 1H), 1.90-1.53 (m, 7H), 1.22-1.10 (m, 4H), 0.95 (dd, J=6.8, 4.4 Hz, 6H).

Example 187. Synthesis of (2R,3S,4R,5R)-5-cyano-4-hydroxy-2-(hydroxymethyl)-5-(4-(((pentyloxy)carbonyl)amino)pyrrolo[2,1-f][1,2,4]triazin-7-yl)tetrahydrofuran-3-yl 2-phenylacetate (Compound 141)
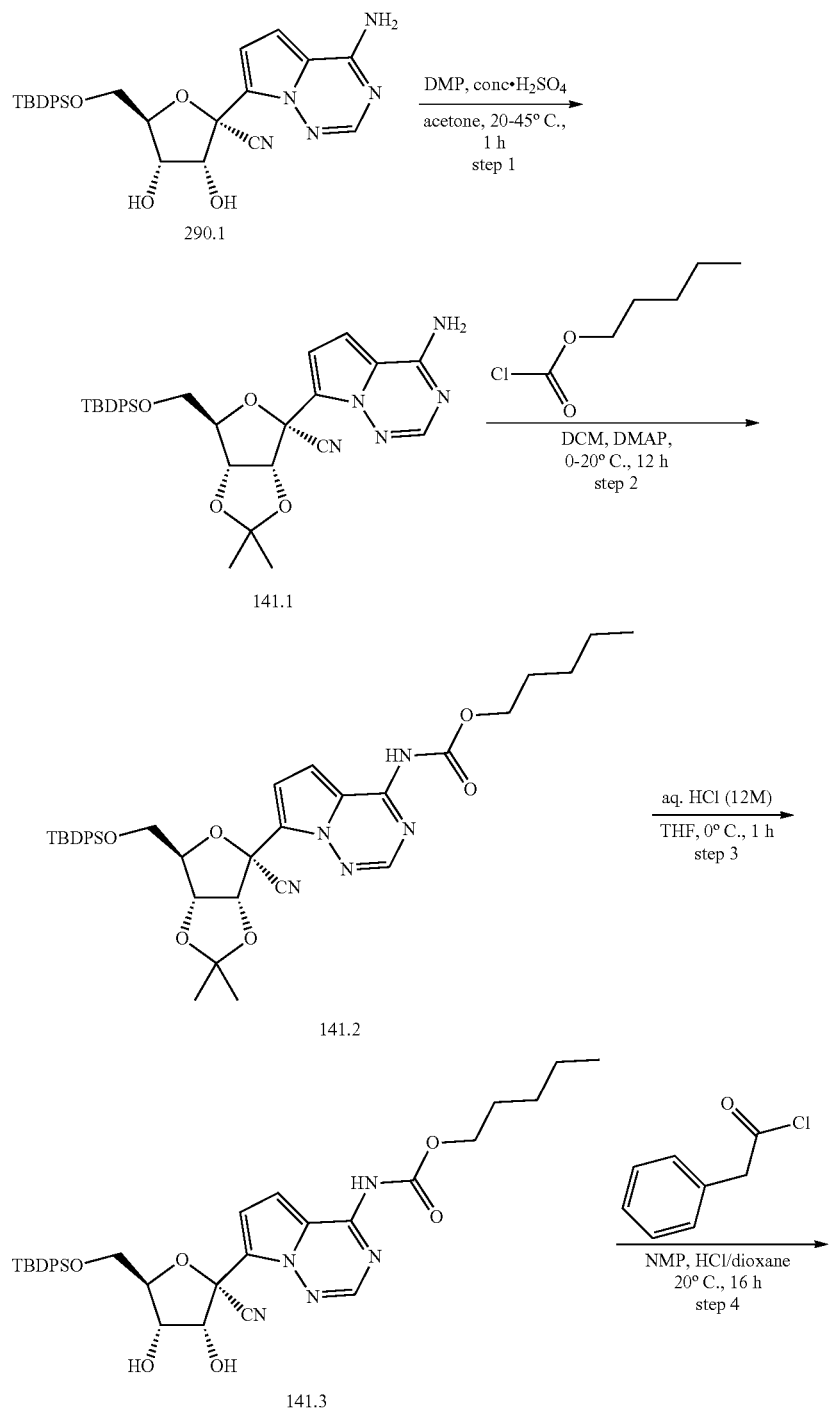

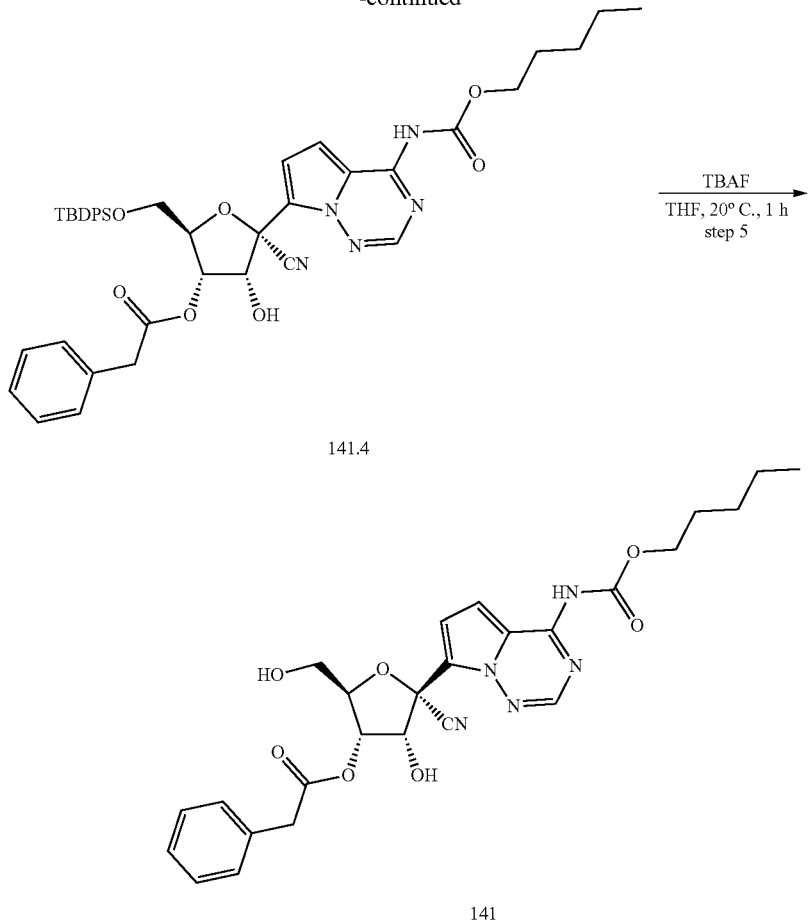

141.4

141

Step 1. Synthesis of (3aR,4R,6R,6aR)-4-(4-amino-pyrrolo[2,1-f][1,2,4]triazin-7-yl)-6-(((tert-butyldi-phenylsilyl)oxy)methyl)-2,2-dimethyltetrahydrofuro[3,4-d][1,3]dioxole-4-carbonitrile (141.1)

The title compound 141.1 was prepared according to the procedure of Example 6, Step 2, using 290.1. MS (ESI): mass calcd. for $C_{31}H_{35}N_5O_4Si$, 569.25 m/z found 570.2 [M+H]$^+$. $^1$H NMR (400 MHz, DMSO) δ 7.89 (br s, 3H), 7.52 (t, J=8.4 Hz, 4H), 7.43 (t, J=7.6 Hz, 2H), 7.34 (t, J=7.6 Hz, 4H), 6.88 (dd, J=10.8, 4.4 Hz, 2H), 5.36 (d, J=6.4 Hz, 1H), 4.91 (dd, J=6.4, 2.8 Hz, 1H), 4.45 (d, J=3.2 Hz, 1H), 3.77 (d, J=4.8 Hz, 2H), 1.64 (s, 3H), 1.36 (s, 3H), 0.92 (s, 9H).

Step 2. Synthesis of pentyl (7-((3aR,4R,6R,6aR)-6-(((tert-butyldiphenylsilyl)oxy)methyl)-4-cyano-2,2-dimethyltetrahydrofuro[3,4-d][1,3]dioxol-4-yl)pyr-rolo[2,1-f][1,2,4]triazin-4-yl)carbamate (141.2)

The title compound 141.2 was prepared according to the procedure of Example 48, Step 2, using 141.1 and pentyl carbonochloridate. MS (ESI): mass calcd. for $C_{37}H_{45}N_5O_6Si$, 683.31, m/z found 684.2 [M+H]$^+$. $^1$H NMR (400 MHz, DMSO) δ 10.92 (s, 1H), 8.35 (s, 1H), 7.54-7.48 (m, 4H), 7.45-7.40 (m, 2H), 7.36-7.32 (m, 4H), 7.30-7.28 (m, 1H), 7.08 (d, J=4.4 Hz, 1H), 5.34 (d, J=6.0 Hz, 1H), 4.91 (dd, J=6.2, 2.8 Hz, 1H), 4.50 (d, J=2.8 Hz, 1H), 4.19 (t, J=6.8 Hz, 2H), 3.76 (t, J=8.0 Hz, 2H), 1.72-1.60 (m, 5H), 1.40-1.34 (m, 7H), 0.92-0.88 (m, 12H).

Step 3. Synthesis of pentyl (7-((2R,3R,4S,5R)-5-(((tert-butyldiphenylsilyl)oxy)methyl)-2-cyano-3,4-dihydroxytetrahydrofuran-2-yl)pyrrolo[2,1-f][1,2,4]triazin-4-yl)carbamate (141.3)

To a solution of pentyl 141.2 (500 mg, 0.73 mmol) in THF (5 mL) was added HCl (2 mL, 12 M) at 0° C., then the reaction was stirred at 20° C. for 1 h. The mixture was adjusted to pH 8 with aqueous NaHCO$_3$ and extracted with EtOAc (50 mL×3). The organic phase was washed with brine water (50 mL×3), then dried over anhydrous sodium sulfate, filtered and concentrated to remove the solvent. The residue was purified by flash column chromatography (Petroleum ether/Ethyl acetate from 0% to 30%) to obtain 141.3 as a light yellow solid (250 mg, 50.5% yield). MS (ESI): mass calcd. for $C_{34}H_{41}N_5O_6Si$, 643.28 m/z found 644.2 [M+H]$^+$. $^1$H NMR (400 MHz, DMSO) δ 10.86 (s, 1H), 8.35 (s, 1H), 7.57 (d, J=7.2 Hz, 2H), 7.52 (d, J=7.2 Hz, 2H), 7.43 (q, J=7.2 Hz, 2H), 7.38-7.28 (m, 4H), 7.23 (d, J=4.8 Hz, 1H), 7.00 (d, J=4.8 Hz, 1H), 6.38 (d, J=6.4 Hz, 1H), 5.32 (d, J=5.2 Hz, 1H), 4.82-4.64 (m, 1H), 4.18 (t, J=5.6 Hz, 4H), 3.84 (d, J=10.0 Hz, 1H), 3.72 (dd, J=11.6, 3.2 Hz, 1H), 1.72-1.62 (m, 2H), 1.40-1.32 (m, 4H), 0.94-0.99 (m, 12H).

Step 4. Synthesis of (2R,3S,4R,5R)-2-(((tert-butyl-diphenylsilyl)oxy)methyl)-5-cyano-4-hydroxy-5-(4-(((pentyloxy)carbonyl)amino)pyrrolo[2,1-f][1,2,4]triazin-7-yl)tetrahydrofuran-3-yl 2-phenylacetate (141.4)

The title compound 141.4 was prepared according to the procedure of Example 17, Step 2, using 141.3 and 2-phenylacetyl chloride. MS (ESI): mass calcd. for $C_{42}H_{47}N_5O_7Si$, 761.32 m/z found 762.2 [M+H]$^+$. $^1$H NMR (400 MHz, DMSO) δ 10.91 (s, 1H), 8.33 (s, 1H), 7.49 (d, J=7.6 Hz, 2H), 7.46-7.26 (m, 11H), 7.21 (t, J=7.6 Hz, 3H), 6.99 (d, J=4.0 Hz, 1H), 6.80 (d, J=6.4 Hz, 1H), 5.54-5.34 (m, 1H), 5.07 (t, J=6.0 Hz, 1H), 4.42 (d, J=3.2 Hz, 1H), 4.17 (t, J=6.4 Hz, 2H), 3.83-3.72 (m, 4H), 1.76-1.60 (m, 2H), 1.40-1.30 (m, 4H), 0.94-0.85 (m, 12H).

Step 5. Synthesis of (2R,3S,4R,5R)-5-cyano-4-hydroxy-2-(hydroxymethyl)-5-(4-(((pentyloxy)carbonyl)amino)pyrrolo[2,1-f][1,2,4]triazin-7-yl)tetrahydrofuran-3-yl 2-phenylacetate (141)

The title compound 141 was prepared according to the procedure of Example 58, Step 1, using 141.4. MS (ESI): mass calcd. for $C_{26}H_{29}N_5O_7$, 523.21 m/z found 524.2 [M+H]$^+$. $^1$H NMR (400 MHz, DMSO) δ 10.97 (s, 1H), 8.36 (s, 1H), 7.38-7.22 (m, 6H), 7.09 (d, J=4.4 Hz, 1H), 6.64 (d, J=6.4 Hz, 1H), 5.28-5.14 (m, 1H), 5.05 (t, J=5.6 Hz, 1H), 4.98 (t, J=6.0 Hz, 1H), 4.32-4.27 (m, 1H), 4.17 (t, J=6.8 Hz, 2H), 3.86-3.71 (m, 2H), 3.64-3.50 (m, 2H), 1.69-1.63 (m, 2H), 1.36-1.31 (m, 4H), 0.90 (t, J=7.2 Hz, 3H).

Example 188. Synthesis of (2R,3S,4R,5R)-5-(4-benzamidopyrrolo[2,1-f][1,2,4]triazin-7-yl)-5-cyano-4-hydroxy-2-(hydroxymethyl)tetrahydrofuran-3-yl 2-phenylacetate (Compound 143)

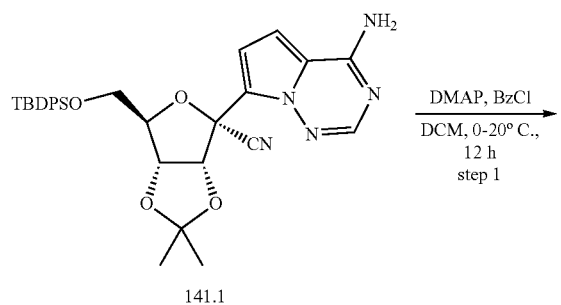

141.1

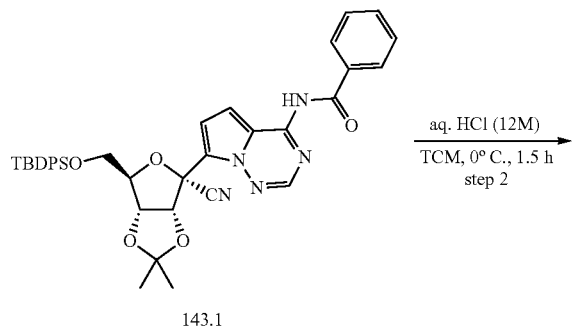

143.1

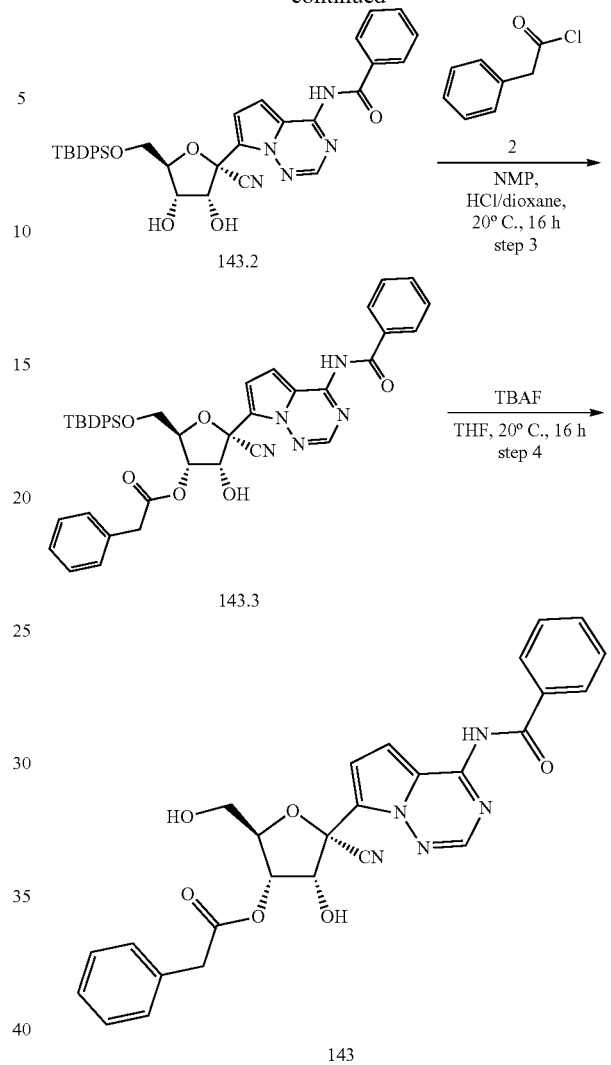

Step 1. Synthesis of N-(7-((3aR,4R,6R,6aR)-6-(((tert-butyldiphenylsilyl)oxy)methyl)-4-cyano-2,2-dimethyltetrahydrofuro[3,4-d][1,3]dioxol-4-yl)pyrrolo[2,1-f][1,2,4]triazin-4-yl)benzamide (143.1)

The title compound 143.1 was prepared according to the procedure of Example 51, Step 1, using 141.1 and benzoyl chloride. MS (ESI): mass calcd. for $C_{38}H_{39}N_5O_5Si$, 673.27 m/z found 674.2 [M+H]$^+$. $^1$H NMR (400 MHz, DMSO) 11.40 (s, 1H), 8.20-7.90 (m, 3H), 7.71-7.32 (m, 15H), 7.15 (s, 2H), 5.37 (d, J=6.4 Hz, 1H), 4.93 (dd, J=6.4, 2.8 Hz, 1H), 4.51 (d, J=2.8 Hz, 1H), 1.66 (s, 3H), 1.37 (s, 3H), 0.92 (s, 9H).

Step 2. Synthesis of N-(7-((2R,3R,4S,5R)-5-(((tert-butyldiphenylsilyl)oxy)methyl)-2-cyano-3,4-dihydroxytetrahydrofuran-2-yl)pyrrolo[2,1-f][1,2,4]triazin-4-yl)benzamide (143.2)

The title compound 143.2 was prepared according to the procedure of Example 187, Step 3, using 143.1. MS (ESI): mass calcd. for $C_{35}H_{35}N_5O_5Si$, 633.24, m/z found 634.1 [M+H]$^+$. $^1$H NMR (400 MHz, DMSO) δ 11.35 (s, 1H), 8.46

(s, 1H), 7.99 (d, J=7.6 Hz, 2H), 7.67 (t, J=7.2 Hz, 1H), 7.63-7.49 (m, 6H), 7.46-7.29 (m, 6H), 7.08 (d, J=4.4 Hz, 2H), 6.39 (d, J=6.0 Hz, 1H), 5.34 (d, J=5.2 Hz, 1H), 4.71-4.76 (m, 1H), 4.26-4.12 (m, 2H), 3.88-3.85 (m, 1H), 3.77-3.73 (m, 1H), 0.92 (s, 9H).

Step 3. Synthesis of (2R,3S,4R,5R)-5-(4-benzamidopyrrolo[2,1-f][1,2,4]triazin-7-yl)-2-(((tert-butyldiphenylsilyl)oxy)methyl)-5-cyano-4-hydroxytetrahydrofuran-3-yl 2-phenylacetate (143.3)

The title compound 143.3 was prepared according to the procedure of Example 17, Step 2, using 141.2 and 2-phenylacetyl chloride. MS (ESI): mass calcd. for $C_{43}H_{41}N_5O_6Si$, 751.28 m/z found 752.2 [M+H]$^+$. $^1$H NMR (400 MHz, DMSO) δ 11.40 (s, 1H), 8.42-8.01 (m, 2H), 7.76-6.95 (m, 20H), 6.82 (d, J=6.8 Hz, 1H), 5.45-5.42 (m, 1H), 5.08 (s, 1H), 4.43 (d, J=3.6 Hz, 1H), 3.78 (d, J=3.2 Hz, 3H), 1.36-1.17 (m, 2H), 0.90 (s, 9H).

Step 4. Synthesis of (2R,3S,4R,5R)-5-(4-benzamidopyrrolo[2,1-f][1,2,4]triazin-7-yl)-5-cyano-4-hydroxy-2-(hydroxymethyl)tetrahydrofuran-3-yl 2-phenylacetate (143)

The title compound 143 was prepared according to the procedure of Example 58, Step 1, using 143.3. MS (ESI): mass calcd. for $C_{27}H_{23}N_5O_6$, 513.16 m/z found 514.2 [M+H]$^+$. $^1$H NMR (400 MHz, DMSO) δ 11.91 (s, 1H), 8.33 (s, 1H), 8.06 (d, J=7.6 Hz, 2H), 7.63 (t, J=7.2 Hz, 1H), 7.54 (t, J=7.6 Hz, 2H), 7.37-7.23 (m, 5H), 7.13-7.09 (m, 2H), 6.66 (d, J=6.4 Hz, 1H), 5.27-5.17 (m, 1H), 5.11-5.06 (m, 1H), 5.00 (t, J=6.0 Hz, 1H), 4.28-4.34 (m, 1H), 3.87-3.67 (m, 2H), 3.64-3.51 (m, 2H).

Example 189. Synthesis of (2R,3S,4R,5R)-5-(4-((S)-2-amino-3-methylbutanamido)pyrrolo[2,1-f][1,2,4]triazin-7-yl)-5-cyano-4-hydroxy-2-(hydroxymethyl)tetrahydrofuran-3-yl 2-phenylacetate (Compound 144)

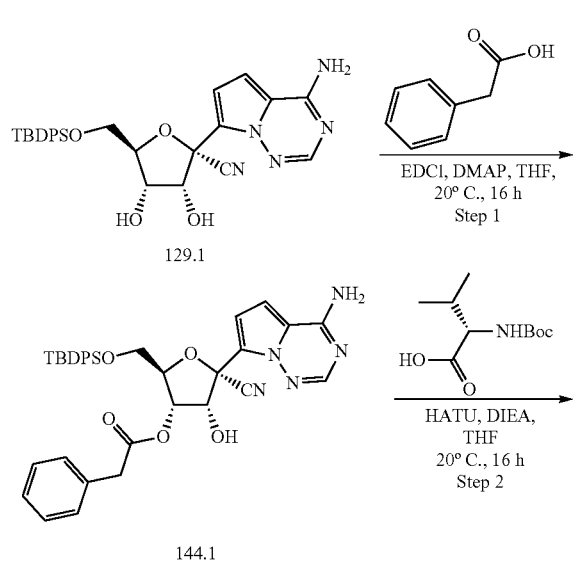

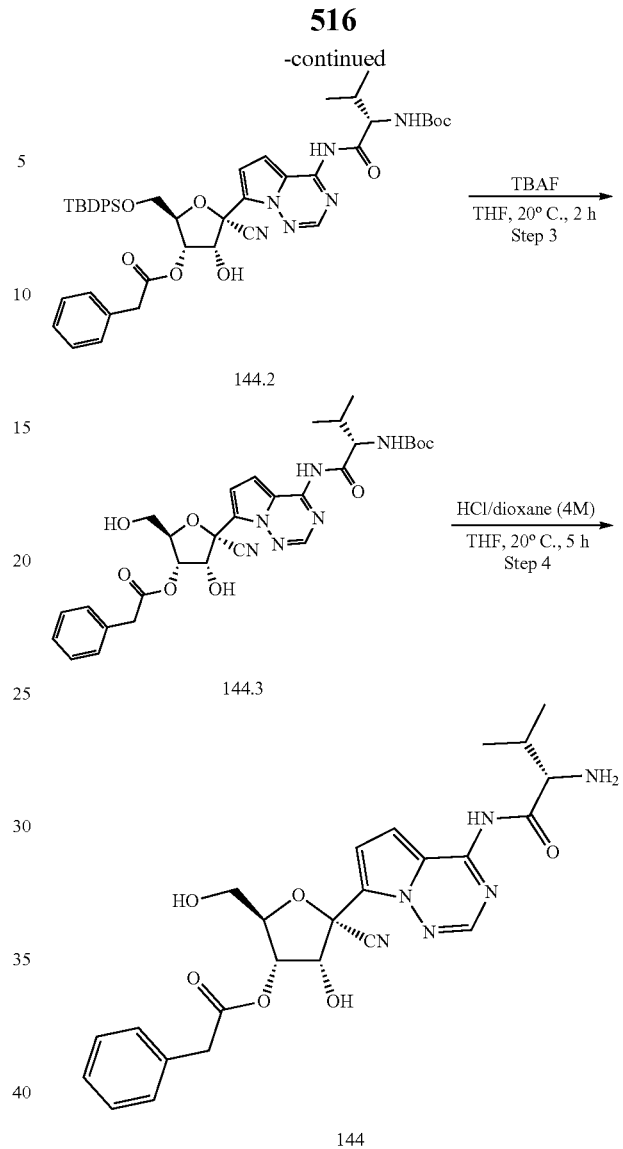

Step 1. Synthesis of (2R,3S,4R,5R)-5-(4-aminopyrrolo[2,1-f][1,2,4]triazin-7-yl)-2-(((tert-butyldiphenylsilyl)oxy)methyl)-5-cyano-4-hydroxytetrahydrofuran-3-yl 2-phenylacetate (144.1)

The compound 144.1 was prepared according to the procedure of Example 19, Step 1, using 129.1 and 2-phenylacetic acid. MS (ESI): mass calcd. for $C_{36}H_{37}N_5O_5Si$, 647.81, m/z found 648.2. [M+H]$^+$.

Step 2. Synthesis of (2R,3S,4R,5R)-5-(4-((S)-2-((tert-butoxycarbonyl)amino)-3-methylbutanamido)pyrrolo[2,1-f][1,2,4]triazin-7-yl)-2-(((tert-butyldiphenylsilyl)oxy)methyl)-5-cyano-4-hydroxytetrahydrofuran-3-yl 2-phenylacetate (144.2)

Compound 144.2 was prepared according to the procedure of Example 129, Step 1, using 139.1 and (tert-butoxycarbonyl)-L-valine. MS (ESI): mass calcd. for $C_{46}H_{54}N_6O_8Si$, 847.06, m/z found 847.3 [M+H]$^+$.

Step 3. Synthesis of (2R,3S,4R,5R)-5-(4-((S)-2-((tert-butoxycarbonyl)amino)-3-methylbutanamido)pyrrolo[2,1-f][1,2,4]triazin-7-yl)-5-cyano-4-hydroxy-2-(hydroxymethyl)tetrahydrofuran-3-yl 2-phenylacetate (144.3)

Compound 144.3 was prepared according to the procedure of Example 97, Step 1, using 144.2. MS (ESI): mass calcd. for $C_{30}H_{36}N_6O_8$, 608.65, m/z found 609.2 $[M+H]^+$.

Step 4. Synthesis of (2R,3S,4R,5R)-5-(4-((S)-2-amino-3-methylbutanamido)pyrrolo[2,1-f][1,2,4]triazin-7-yl)-5-cyano-4-hydroxy-2-(hydroxymethyl)tetrahydrofuran-3-yl 2-phenylacetate (Compound 144)

Compound 144 was prepared according to the procedure of Example 19, Step 2, using 144.3. MS (ESI): mass calcd. for $C_{25}H_{28}N_6O_6$, 508.54, m/z found 509.2 $[M+H]^+$. 1H NMR (400 MHz, DMSO) δ 8.27 (d, J=8.8 Hz, 1H), 7.99 (s, 1H), 7.57 (s, 1H), 7.37-7.26 (m, 5H), 7.25 (d, J=4.8 Hz, 1H), 7.15 (s, 1H), 6.90 (d, J=4.8 Hz, 1H), 6.54 (d, J=6.4 Hz, 1H), 5.25-5.16 (m, 1H), 5.04 (t J=5.6 Hz, 1H), 5.00 (t, J=6.0 Hz, 1H), 4.66 (t, J=8.4 Hz, 1H), 4.27-4.25 (m, 1H), 3.76 (d, J=11.2 Hz, 2H), 3.57-3.52 (m, 2H), 2.18-2.15 (m, 1H), 0.95 (dd, J=6.4, 4.4 Hz, 6H).

Example 190. Synthesis of ((2R,3S,4R,5R)-5-(4-((S)-2-amino-3-methylbutanamido)pyrrolo[2,1-f][1,2,4]triazin-7-yl)-5-cyano-3,4-dihydroxytetrahydrofuran-2-yl)methyl acetate (Compound 339)

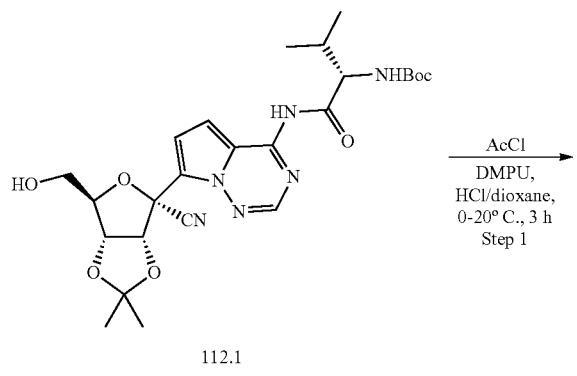

Step 1. Synthesis of ((3aR,4R,6R,6aR)-6-(4-((S)-2-((tert-butoxycarbonyl)amino)-3-methylbutanamido)pyrrolo[2,1-f][1,2,4]triazin-7-yl)-6-cyano-2,2-dimethyltetrahydrofuro[3,4-d][1,3]dioxol-4-yl)methyl acetate (339.1)

The compound 339.1 was prepared according to the procedure of Example 1, Step 4, using 112.1 and AcCl. MS (ESI): mass calcd. for $C_{27}H_{36}N_6O_8$, 572.62, m/z found 573.2 $[M+H]^+$.

Step 2. Synthesis of Synthesis of ((2R,3S,4R,5R)-5-(4-((S)-2-amino-3-methylbutanamido)pyrrolo[2,1-f][1,2,4]triazin-7-yl)-5-cyano-3,4-dihydroxytetrahydrofuran-2-yl)methyl acetate (Compound 339)

The compound 339 was prepared according to the procedure of Example 112, Step 3, using 112.1. MS (ESI): mass calcd. for $C_{19}H_{26}N_6O_6$, 432.44, m/z found 433.1 $[M+H]^+$. 1H NMR (400 MHz, DMSO) δ 8.21 (d, J=8.4 Hz, 1H), 7.98 (s, 1H), 7.55 (s, 1H), 7.24 (d, J=4.4 Hz, 1H), 7.13 (s, 1H), 6.81 (d, J=4.8 Hz, 1H), 6.32 (d, J=6.0 Hz, 1H), 5.39 (d, J=6.0 Hz, 1H), 4.73-4.61 (m, 2H), 4.32 (dd, J=12.0, 2.4 Hz, 1H), 4.22-4.20 (m, 1H), 4.14 (dd, J=12.0, 6.0 Hz, 1H), 3.92-3.90 (m, 1H), 2.18-2.15 (m, 1H), 2.01 (s, 3H), 0.96 (dd, J=6.8, 3.6 Hz, 6H).

Example 191. Synthesis of (2R,3S,4R,5R)-5-cyano-4-hydroxy-2-(hydroxymethyl)-5-(4-pentanamidopyrrolo[2,1-f][1,2,4]triazin-7-yl)tetrahydrofuran-3-yl 2-phenylacetate (Compound 340)

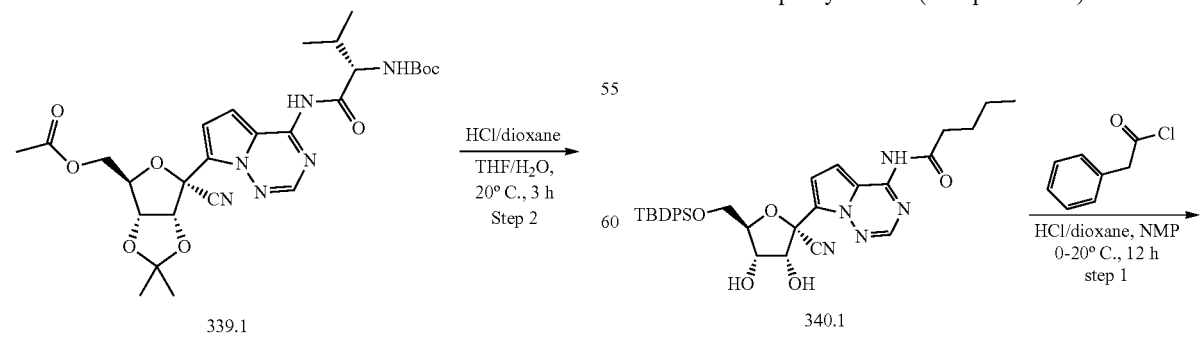

519
-continued

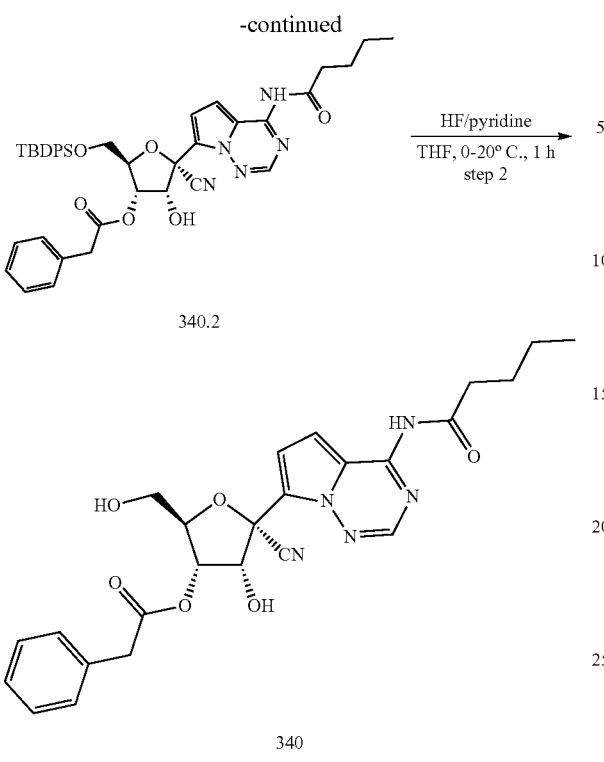

340.2

340

Step 1. Synthesis of (2R,3S,4R,5R)-2-(((tert-butyl-diphenylsilyl)oxy)methyl)-5-cyano-4-hydroxy-5-(4-pentanamidopyrrolo[2,1-f][1,2,4]triazin-7-yl)tetrahydrofuran-3-yl 2-phenylacetate (340.2.)

The title compound was prepared according to the procedure of Example 17, Step 2, using 340.1 and 2-phenylacetyl chloride. MS (ESI): m/z calcd. for $C_{41}H_{45}N_5O_6Si$, 731.1, found 732.2 [M+H]$^+$. $^1$H NMR (400 MHz, DMSO) δ 10.89 (s, 1H), 8.37 (s, 1H), 7.49 (d, J=7.6 Hz, 2H), 7.42 (d, J=7.2 Hz, 3H), 7.37-7.27 (m, 7H), 7.23-7.19 (m, 3H), 7.03 (d, J=4.8 Hz, 1H), 6.80 (d, J=6.8 Hz, 1H), 5.46-5.37 (m, 1H), 5.07 (t, J=6.0 Hz, 1H), 4.42 (d, J=3.2 Hz, 1H), 3.77 (s, 3H), 2.72 (t, J=7.2 Hz, 2H), 1.67-1.54 (m, 2H), 1.35 (dd, J=14.8, 7.2 Hz, 2H), 1.23 (s, 2H), 0.93-0.85 (m, 12H).

Step 2. Synthesis of (2R,3S,4R,5R)-5-cyano-4-hydroxy-2-(hydroxymethyl)-5-(4-pentanamidopyrrolo[2,1-f][1,2,4]triazin-7-yl)tetrahydrofuran-3-yl 2-phenylacetate (Compound 340)

To a solution of compound 340.2 (40 mg, 0.0547 mmol) in THF (1 mL) was added HF/pyridine (27.1 mg, 0.274 mmol) at 0° C. The reaction mixture was stirred for 1 h at 20° C. The residue was quenched with water and extracted with EtOAc. The organic phase was washed with brine, dried over Na$_2$SO$_4$ and evaporated in vacuo to give the crude product. The crude product was purified by prep-HPLC to afford product 340 (4.89 mg, 15.9% yield) as a white solid. MS (ESI): m/z calcd. for $C_{25}H_{27}N_5O_6$, 493.5, found 494.1 [M+H]. $^1$H NMR (400 MHz, DMSO) δ 10.91 (s, 1H), 8.42 (s, 1H), 7.36-7.24 (m, 6H), 7.13 (d, J=4.8 Hz, 1H), 6.65 (d, J=6.4 Hz, 1H), 5.24-5.17 (m, 1H), 4.98 (s, 2H), 4.30 (d, J=4.0 Hz, 1H), 3.82-3.72 (m, 2H), 3.62-3.52 (m, 2H), 2.72 (t, J=7.6 Hz, 2H), 1.66-1.54 (m, 2H), 1.42-1.30 (m, 2H), 0.91 (t, J=7.6 Hz, 3H).

Example 192. Synthesis of ((2R,3S,4R,5R)-5-cyano-3,4-dihydroxy-5-(4-pentanamidopyrrolo[2,1-f][1,2,4]triazin-7-yl)tetrahydrofuran-2-yl)methyl L-valinate (Compound 341)

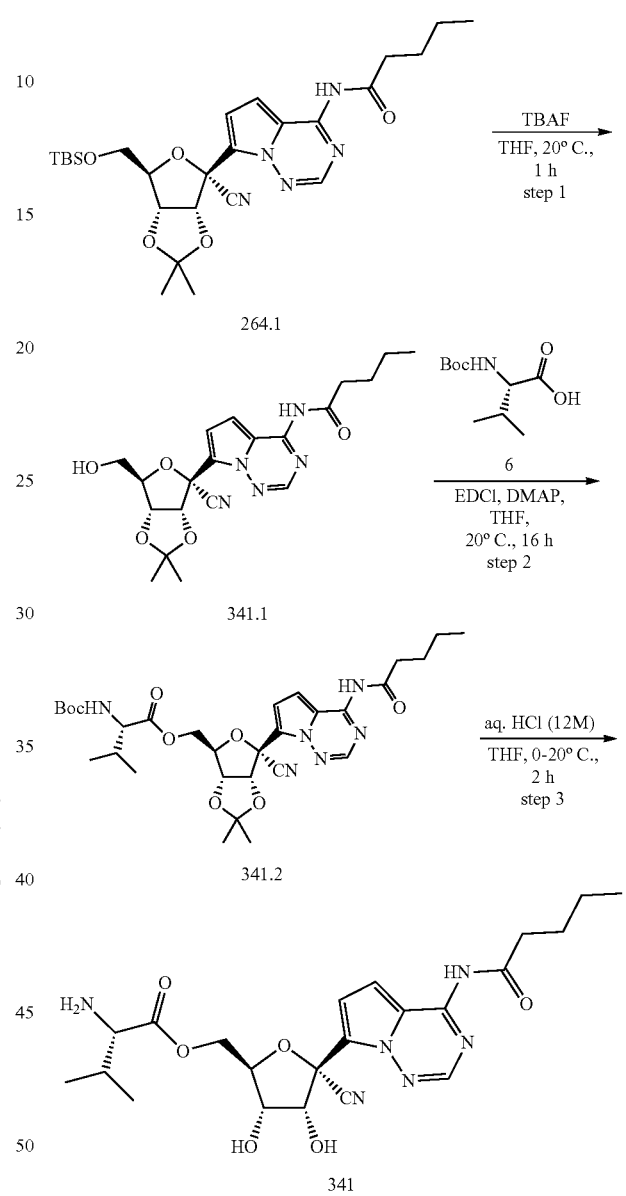

264.1

341.1

341.2

341

Step 1. Synthesis of N-(7-((3aR,4R,6R,6aR)-4-cyano-6-(hydroxymethyl)-2,2-dimethyltetrahydrofuro[3,4-d][1,3]dioxol-4-yl)pyrrolo[2,1-f][1,2,4]triazin-4-yl)pentanamide (341.1)

The title compound 341.1 was prepared according to the procedure of Example 58, Step 1, using 264.1. MS (ESI): mass calcd. for $C_{20}H_{25}N_5O_5$, 415.19 m/z found 416.2 [M+H]$^+$. $^1$H NMR (400 MHz, DMSO) δ 10.92 (s, 1H), 8.43 (s, 1H), 7.27 (d, J=4.8 Hz, 1H), 7.14 (d, J=4.8 Hz, 1H), 5.35 (d, J=6.4 Hz, 1H), 5.03 (t, J=5.6 Hz, 1H), 4.90 (dd, J=6.4, 2.8 Hz, 1H), 4.36 (dd, J=8.0, 5.2 Hz, 1H), 3.61-3.45 (m, 2H), 2.72 (dd, J=9.2, 5.2 Hz, 2H), 1.66-1.57 (m, 5H), 1.39-1.33 (m, 5H), 0.91 (t, J=7.2 Hz, 3H).

Step 2. Synthesis of ((3aR,4R,6R,6aR)-6-cyano-2,2-dimethyl-6-(4-pentanamidopyrrolo[2,1-f][1,2,4]triazin-7-yl)tetrahydrofuro[3,4-d][1,3]dioxol-4-yl)methyl (tert-butoxycarbonyl)-L-valinate (341.2)

The title compound 341.2 was prepared according to the procedure of Example 19, Step 1, using 341.1 and (tert-butoxycarbonyl)-L-valine. MS (ESI): mass calcd. for $C_{30}H_{42}N_6O_8$, 614.31, m/z found 615.3 [M+H]$^+$. $^1$H NMR (400 MHz, DMSO) δ 10.93 (s, 1H), 8.44 (s, 1H), 7.28 (d, J=4.8 Hz, 1H), 7.15 (d, J=8.1 Hz, 1H), 7.08 (d, J=4.8 Hz, 1H), 5.42 (d, J=6.4 Hz, 1H), 4.93 (dd, J=6.4, 2.8 Hz, 1H), 4.62 (s, 1H), 4.24 (dd, J=12.0, 4.0 Hz, 1H), 4.14 (dd, J=12.0, 6.4 Hz, 1H), 3.82-3.69 (m, 1H), 2.72 (t, J=7.2 Hz, 2H), 1.82 (d, J=6.8 Hz, 1H), 1.65 (d, J=6.0 Hz, 3H), 1.60 (dd, J=15.2, 7.6 Hz, 2H), 1.40-1.33 (m, 14H), 0.91 (t, J=7.2 Hz, 3H), 0.77 (dd, J=13.6, 6.8 Hz, 6H).

Step 3. Synthesis of ((2R,3S,4R,5R)-5-cyano-3,4-dihydroxy-5-(4-pentanamidopyrrolo[2,1-f][1,2,4]triazin-7-yl)tetrahydrofuran-2-yl)methyl L-valinate (341)

The title compound 341 was prepared according to the procedure of Example 19, Step 2, using 341.2. MS (ESI): mass calcd. for $C_{22}H_{30}N_6O_6$, 474.22 m/z found 475.2 [M+H]$^+$. $^1$H NMR (400 MHz, DMSO) δ 10.92 (s, 1H), 8.39 (s, 1H), 7.29 (d, J=4.8 Hz, 1H), 7.07 (d, J=4.8 Hz, 1H), 6.47 (d, J=6.0 Hz, 1H), 5.47 (s, 1H), 4.69 (t, J=5.2 Hz, 1H), 4.36-4.26 (m, 3H), 3.97-3.92 (m, 1H), 3.30 (s, 1H), 2.72 (t, J=7.2 Hz, 2H), 1.88-1.79 (m, 1H), 1.67-1.55 (m, 2H), 1.40-1.30 (m, 2H), 0.91 (t J=7.2 Hz, 3H), 0.82 (dd, J=14.4, 6.8 Hz, 6H).

Example 193. Synthesis of (2R,3S,4R,5R)-5-(4-benzamidopyrrolo[2,1-f][1,2,4]triazin-7-yl)-5-cyano-4-hydroxy-2-(hydroxymethyl)tetrahydrofuran-3-yl 2-cyclohexylacetate (Compound 342)

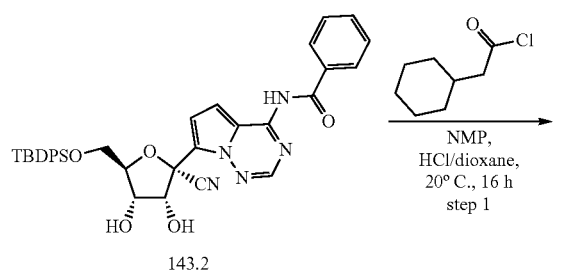

143.2

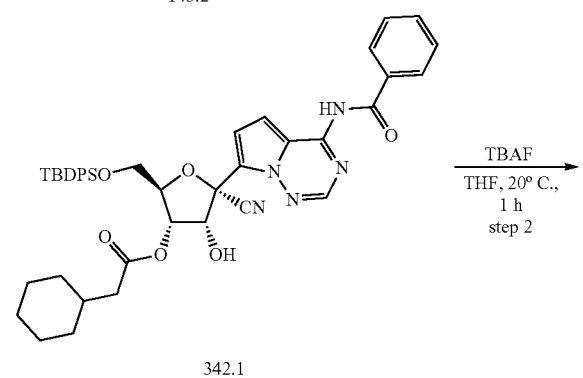

342.1

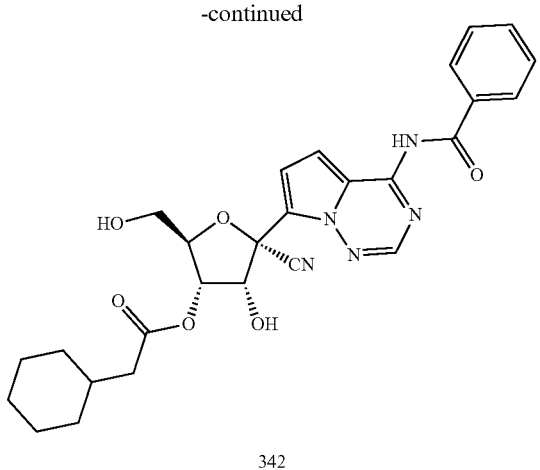

342

Step 1. Synthesis of (2R,3S,4R,5R)-5-(4-benzamidopyrrolo[2,1-f][1,2,4]triazin-7-yl)-2-(((tert-butyldiphenylsilyl)oxy)methyl)-5-cyano-4-hydroxytetrahydrofuran-3-yl 2-cyclohexylacetate (342.1)

The title compound 342.1 was prepared according to the procedure of Example 17, Step 2, using 143.2 and 2-cyclohexylacetyl chloride. MS (ESI): mass calcd. for $C_{43}H_{47}N_5O_6Si$, 757.33 m/z found 758.3 [M+H]$^+$. $^1$H NMR (400 MHz, DMSO) δ 11.40 (s, 1H), 8.42 (s, 1H), 8.04 (s, 2H), 7.70-7.62 (m, 1H), 7.58-7.51 (m, 4H), 7.47-7.44 (m, 3H), 7.41-7.33 (m, 3H), 7.24 (t, J=7.6 Hz, 2H), 7.13 (d, J=4.4 Hz, 1H), 7.04 (s, 1H), 6.75 (d, J=6.4 Hz, 1H), 5.47-5.35 (m, 1H), 5.06 (t, J=6.0 Hz, 1H), 4.42 (d, J=3.6 Hz, 1H), 3.79 (d, J=2.8 Hz, 2H), 2.28 (d, J=6.8 Hz, 2H), 1.85-1.70 (m, 3H), 1.68-1.56 (m, 3H), 1.28-1.20 (m, 5H), 0.92 (s, 9H).

Step 2. Synthesis of (2R,3S,4R,5R)-5-(4-benzamidopyrrolo[2,1-f][1,2,4]triazin-7-yl)-5-cyano-4-hydroxy-2-(hydroxymethyl)tetrahydrofuran-3-yl 2-cyclohexylacetate (342)

The title compound 342 was prepared according to the procedure of Example 19, Step 2, using 342.1. MS (ESI): mass calcd. for $C_{27}H_{29}N_5O_6$, 519.21, m/z found 520.0 [M+H]$^+$. $^1$H NMR (400 MHz, DMSO) δ 11.85 (s, 1H), 8.37 (s, 1H), 8.06 (d, J=7.6 Hz, 2H), 7.65 (t, J=7.2 Hz, 1H), 7.55 (t, J=7.6 Hz, 2H), 7.16-7.06 (m, 2H), 6.59 (d, J=6.8 Hz, 1H), 5.25-5.16 (m, 1H), 5.07 (t, J=5.6 Hz, 1H), 4.97 (t, J=6.0 Hz, 1H), 4.34-4.22 (m, 1H), 3.64-3.51 (m, 2H), 2.27 (d, J=6.8 Hz, 2H), 1.82-1.72 (m, 3H), 1.69-1.56 (m, 3H), 1.32-1.07 (m, 3H), 1.05-0.90 (m, 2H).

Example 194. Synthesis of (2R,3R,4R,5R)-4-acetoxy-5-(4-aminopyrrolo[2,1-f][1,2,4]triazin-7-yl)-5-cyano-2-((2-phenylacetoxy)methyl)tetrahydrofuran-3-yl L-valinate (Compound 343)

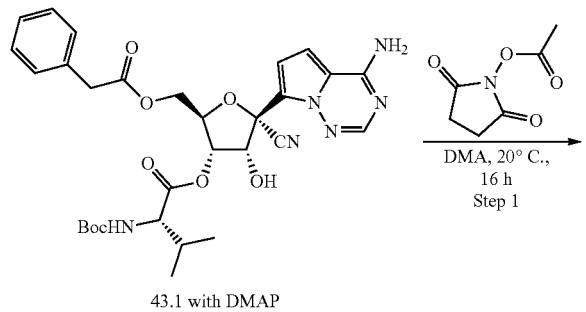

43.1 with DMAP

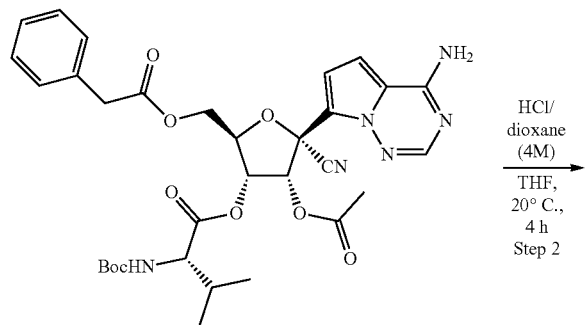

343.1

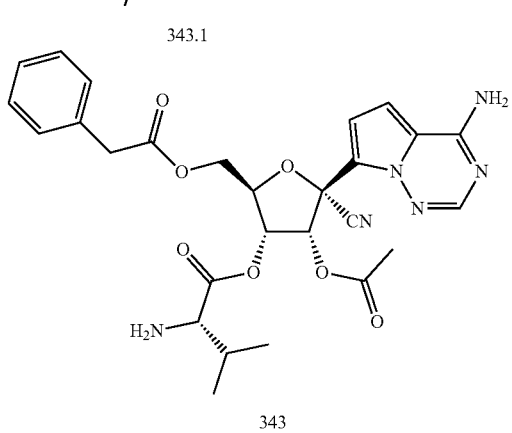

343

Step 1. Synthesis of (2R,3R,4R,5R)-4-acetoxy-5-(4-aminopyrrolo[2,1-f][1,2,4]triazin-7-yl)-5-cyano-2-((2-phenylacetoxy)methyl)tetrahydrofuran-3-yl (tert-butoxycarbonyl)-L-valinate (343.1)

To a solution of 43.1 (containing DMAP, 80 mg, 0.131 mmol) in DMF (3 mL) was added 2,5-dioxopyrrolidin-1-yl acetate (61.94 mg, 0.394 mmol), the mixture was stirred at 20° C. for 16 h. The reaction was washed with EtOAc (5 mL×3). The combined organics were dried over sodium sulfate and concentrated in vacuo. The crude product was purified by prep-HPLC to afford 343 (40 mg, 42% yield) as a white solid. MS (ESI): m/z calcd. for $C_{32}H_{38}N_6O_9$ 650.69, found 651.2 [M+H]$^+$.

Step 2. Synthesis of Synthesis of (2R,3R,4R,5R)-4-acetoxy-5-(4-aminopyrrolo[2,1-f][1,2,4]triazin-7-yl)-5-cyano-2-((2-phenylacetoxy)methyl)tetrahydrofuran-3-yl L-valinate (Compound 343)

The compound 343 was prepared according to the procedure of Example 19, Step 2, using 343.1. MS (ESI): mass calcd. for $C_{27}H_{30}N_6O_7$, 550.57, m/z found 551.2 [M+H]$^+$. $^1$H NMR (400 MHz, DMSO) δ 8.02 (d, J=22.0 Hz, 2H), 7.94 (s, 1H), 7.49-7.13 (m, 5H), 6.94 (d, J=4.4 Hz, 1H), 6.79 (d, J=4.8 Hz, 1H), 6.09 (d, J=6.0 Hz, 1H), 5.45 (dd, J=5.6, 3.6 Hz, 1H), 4.61-4.58 (m, 1H), 4.40 (dd, J=12.4, 3.6 Hz, 1H), 4.30 (dd, J=12.0, 4.8 Hz, 1H), 3.66 (d, J=4.4 Hz, 2H), 3.21 (d, J=5.6 Hz, 1H), 2.11 (s, 3H), 1.95-1.92 (m, 1H), 0.90 (dd, J=14.4, 6.8 Hz, 6H).

Example 195. Synthesis of (2R,3S,4R,5R)-5-(4-acetamidopyrrolo[2,1-f][1,2,4]triazin-7-yl)-5-cyano-4-hydroxy-2-((2-phenylacetoxy)methyl)tetrahydrofuran-3-yl L-valinate (Compound 344)

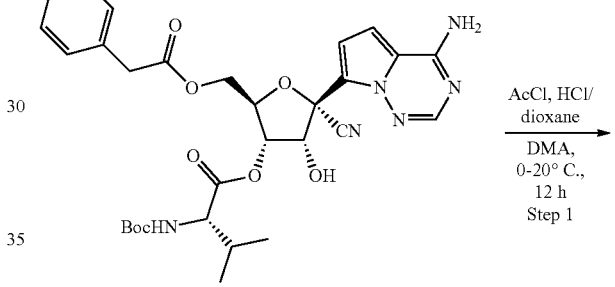

43

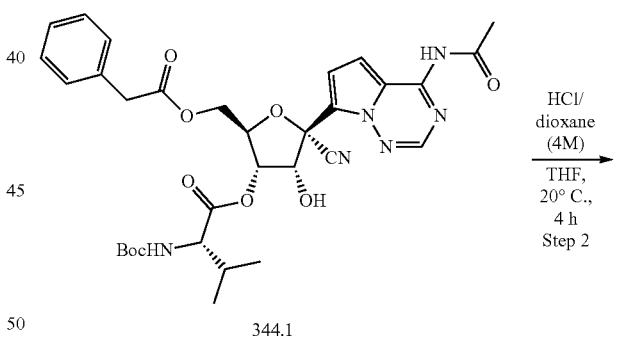

344.1

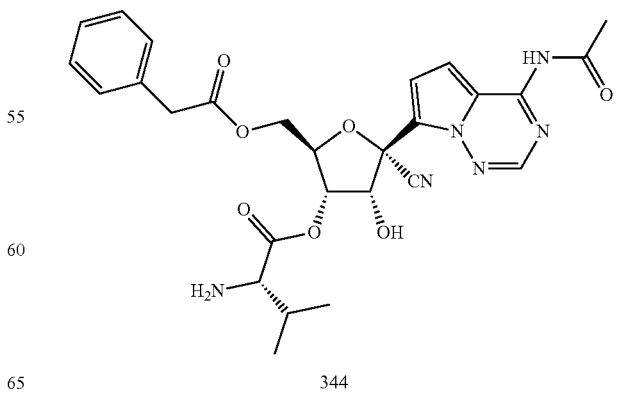

344

Step 1. Synthesis of (2R,3S,4R,5R)-5-(4-acetamidopyrrolo[2,1-f][1,2,4]triazin-7-yl)-5-cyano-4-hydroxy-2-((2-phenylacetoxy)methyl)tetrahydrofuran-3-yl (tert-butoxycarbonyl)-L-valinate (344.1)

To a solution of 43.1 (60 mg, 0.098 mmol) in DMA (2 mL) was added HCl in dioxane (4 M, 0.1 mL), The reaction was stirred at 20° C. for 15 min. Then acetyl chloride (387.00 mg, 4.93 mmol) was added to the above solution at 0° C., The resulting mixture was stirred at 20° C. for 16 h. The crude product was purified by prep-HPLC to afford 344 (30 mg, 42% yield) as a white solid. MS (ESI): m/z calcd. for $C_{32}H_{38}N_6O_9$ 650.69, found 651.2 $[M+H]^+$.

Step 2. Synthesis of (2R,3S,4R,5R)-5-(4-acetamidopyrrolo[2,1-f][1,2,4]triazin-7-yl)-5-cyano-4-hydroxy-2-((2-phenylacetoxy)methyl)tetrahydrofuran-3-yl L-valinate (Compound 344)

The compound 344 was prepared according to the procedure of Example 19, Step 2, using 344.1. MS (ESI): mass calcd. for $C_{27}H_{30}N_6O_7$, 550.57, m/z found 551.2 $[M+H]^+$.
$^1$H NMR (400 MHz, DMSO) δ 11.00 (s, 1H), 8.39 (s, 1H), 7.33 (d, J=4.8 Hz, 1H), 7.29-7.23 (m, 3H), 7.20-7.18 (m, 2H), 7.07 (d, J=4.8 Hz, 1H), 6.69 (d, J=6.4 Hz, 1H), 5.15 (t, J=5.2 Hz, 1H), 5.04 (t J=5.6 Hz, 1H), 4.52-4.49 (m, 1H), 4.32 (dd, J=12.4, 3.6 Hz, 1H), 4.26 (dd, J=12.4, 4.8 Hz, 1H), 3.66 (s, 2H), 3.25 (d, J=5.2 Hz, 1H), 2.40 (s, 3H), 2.01-1.97 (m, 1H), 0.90 (dd, J=20.0, 6.8 Hz, 6H).

Example 196. Synthesis of (2R,3S,4R,5R)-5-(4-((S)-2-amino-3-(4-fluorophenyl)propanamido)pyrrolo[2,1-f][1,2,4]triazin-7-yl)-5-cyano-4-hydroxy-2-(hydroxymethyl)tetrahydrofuran-3-yl 2-(1-aminocyclohexyl)acetate (Compound 345)

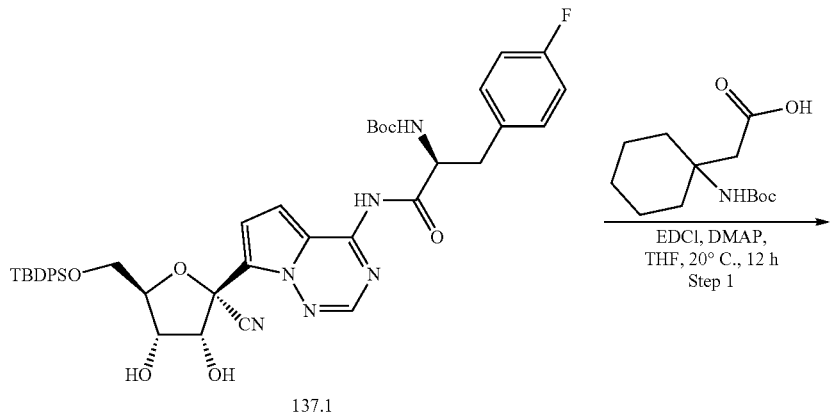

137.1

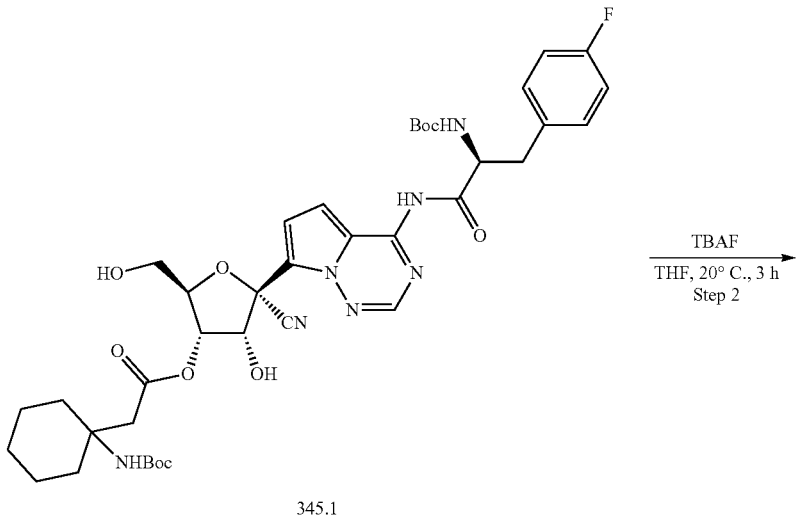

345.1

-continued

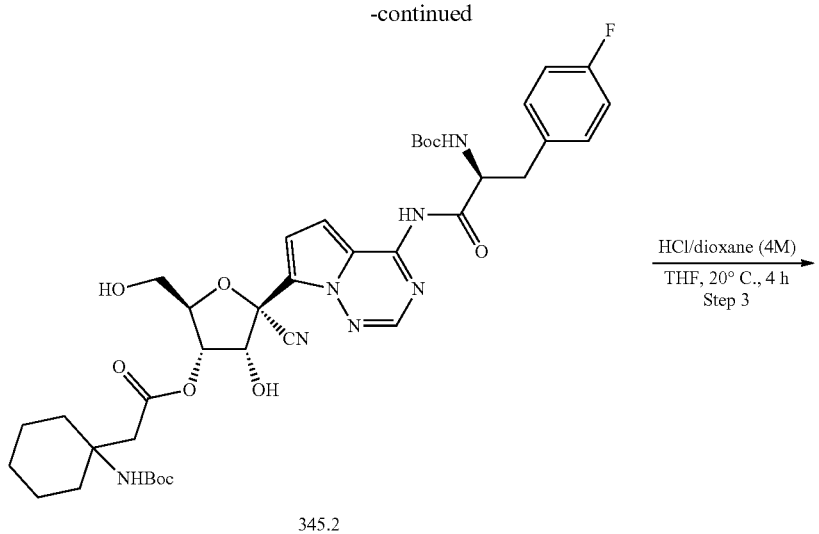

345.2

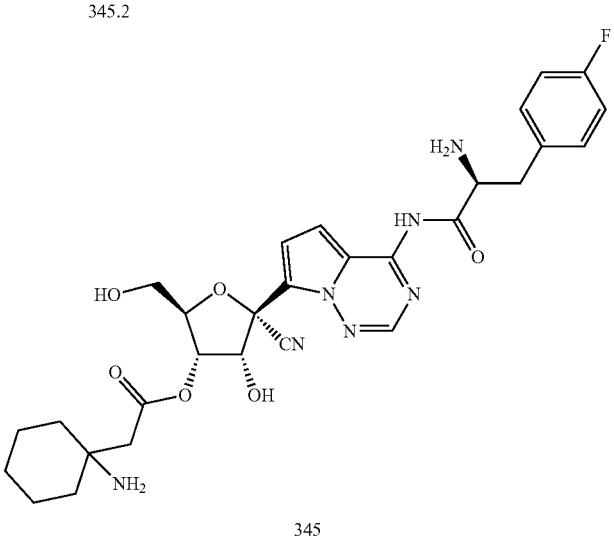

345

Step 1. Synthesis of (2R,3S,4R,5R)-5-(4-((S)-2-((tert-butoxycarbonyl)amino)-3-(4-fluorophenyl)propanamido)pyrrolo[2,1-f][1,2,4]triazin-7-yl)-2-((((tert-butyldiphenylsilyl)oxy)methyl)-5-cyano-4-hydroxytetrahydrofuran-3-yl 2-(1-((tert-butoxycarbonyl)amino)cyclohexyl)acetate (345.1)

The compound 345.1 was prepared according to the procedure of Example 19, Step 1, using 137.1 and 2-(1-((tert-butoxycarbonyl)amino)cyclohexyl)acetic acid. MS (ESI): mass calcd. for $C_{55}H_{68}FN_7O_{10}Si$, 1034.27, m/z found 1034.5 $[M+H]^+$.

Step 2. Synthesis of (2R,3S,4R,5R)-5-(4-((S)-2-((tert-butoxycarbonyl)amino)-3-(4-fluorophenyl)propanamido)pyrrolo[2,1-f][1,2,4]triazin-7-yl)-5-cyano-4-hydroxy-2-(hydroxymethyl)tetrahydrofuran-3-yl 2-(1-((tert-butoxycarbonyl)amino)cyclohexyl)acetate (345.2)

Compound 345.2 was prepared according to the procedure of Example 97, Step 1, using 345.1. MS (ESI): mass calcd. for $C_{39}H_{50}FN_7O_{10}$, 795.87, m/z found 796.2 $[M+H]^+$. $^1H$ NMR (400 MHz, DMSO) δ 11.22 (s, 1H), 8.48 (s, 1H), 7.45-7.40 (m, 2H), 7.27-7.22 (m, 2H), 7.17-7.10 (m, 3H), 6.58 (d, J=6.4 Hz, 1H), 6.27-6.25 (m, 1H), 5.06-5.02 (m, 2H), 4.94 (t, J=6.0 Hz, 1H), 4.87-4.85 (m, 1H), 4.37-4.27 (m, 1H), 3.71-3.51 (m, 2H), 3.11-3.09 (m, 1H), 2.86-2.77 (m, 1H), 2.70-2.66 (m, 2H), 1.45-1.22 (m, 28H).

Step 3. Synthesis of (2R,3S,4R,5R)-5-(4-((S)-2-amino-3-(4-fluorophenyl)propanamido)pyrrolo[2,1-f][1,2,4]triazin-7-yl)-5-cyano-4-hydroxy-2-(hydroxymethyl)tetrahydrofuran-3-yl 2-(1-aminocyclohexyl)acetate (Compound 345)

Compound 345 was prepared according to the procedure of Example 19, Step 2, using 345.2. MS (ESI): mass calcd. for $C_{29}H_{34}FN_7O_6$, 595.63, m/z found 596.2 $[M+H]^+$. $^1H$ NMR (400 MHz, DMSO) δ 8.60 (d, J=8.0 Hz, 1H), 8.32 (s, 1H), 7.93 (s, 1H), 7.69 (s, 1H), 7.38 (dd, J=8.4, 5.6 Hz, 2H), 7.18 (s, 1H), 7.06 (dd, J=10.4, 7.2 Hz, 3H), 6.87 (d, J=4.4 Hz, 1H), 5.33-5.22 (m, 1H), 4.97-4.95 (m, 1H), 4.90 (d, J=5.6 Hz, 1H), 4.28-4.27 (m, 1H), 3.56-3.50 (m, 2H), 3.23-3.16 (m, 1H), 3.06-2.98 (m, 1H), 2.42 (d, J=12.8 Hz, 2H), 1.59-1.30 (m, 10H). $^{19}F$ NMR (376 MHz, DMSO) δ −116.76 (s, 1F).

Example 197. Synthesis of (2R,3S,4R,5R)-5-(4-butyramidopyrrolo[2,1-f][1,2,4]triazin-7-yl)-5-cyano-4-hydroxy-2-((2-phenylacetoxy)methyl)tetrahydrofuran-3-yl L-valinate (Compound 346)

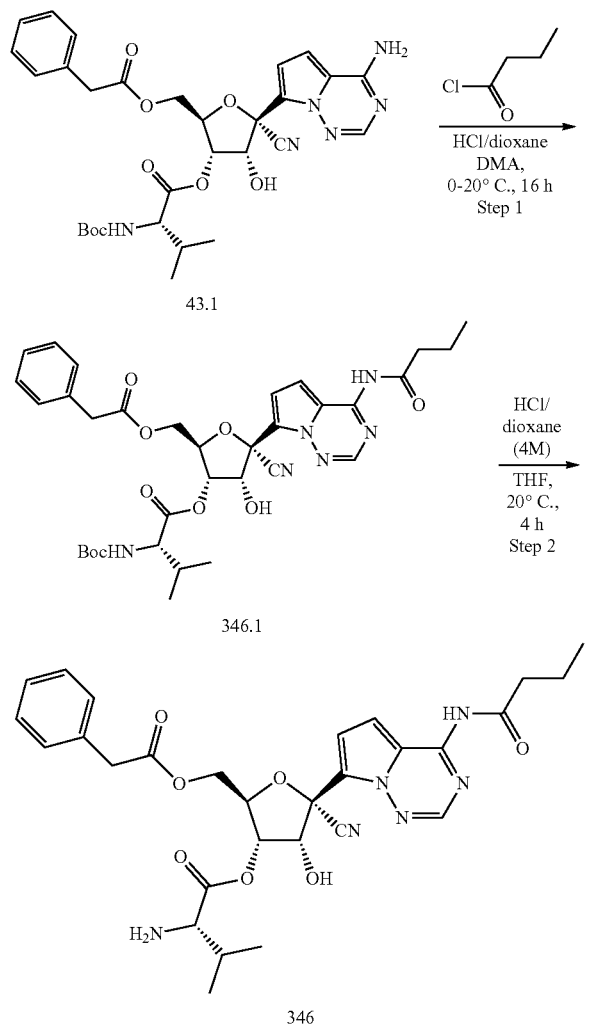

Step 1. Synthesis of (2R,3S,4R,5R)-5-(4-butyramidopyrrolo[2,1-f][1,2,4]triazin-7-yl)-5-cyano-4-hydroxy-2-((2-phenylacetoxy)methyl)tetrahydrofuran-3-yl (tert-butoxycarbonyl)-L-valinate (346.1)

The compound 346.1 was prepared according to the procedure of Example 195, Step 1, using 43.1 and butyryl chloride. MS (ESI): mass calcd. for $C_{34}H_{42}N_6O_9$, 678.74, m/z found 679.3 $[M+H]^+$.

Step 2. Synthesis of (2R,3S,4R,5R)-5-(4-butyramidopyrrolo[2,1-f][1,2,4]triazin-7-yl)-5-cyano-4-hydroxy-2-((2-phenylacetoxy)methyl)tetrahydrofuran-3-yl L-valinate (Compound 346)

Compound 346 was prepared according to the procedure of Example 19, Step 2, using 346.1. MS (ESI): mass calcd. for $C_{29}H_{34}N_6O_7$, 578.63, m/z found 579.3 $[M+H]^+$. 1H NMR (400 MHz, DMSO) δ 10.94 (s, 1H), 8.40 (s, 1H), 7.32-7.18 (m, 6H), 7.07 (d, J=4.8 Hz, 1H), 6.69 (d, J=6.0 Hz, 1H), 5.20-5.09 (m, 1H), 5.05 (t, J=4.8 Hz, 1H), 4.50 (dd, J=8.0, 4.4 Hz, 1H), 4.32 (dd, J=12.4, 3.6 Hz, 1H), 4.26 (dd, J=12.4, 4.8 Hz, 1H), 3.66 (s, 2H), 3.25 (d, J=5.2 Hz, 1H), 2.71 (t, J=7.2 Hz, 2H), 2.07-1.97 (m, 1H), 1.65-1.60 (m, 2H), 0.94 (dd, J=14.0, 6.8 Hz, 6H), 0.86 (t, J=6.0 Hz, 3H).

Example 198. Synthesis of (2R,3S,4R,5R)-5-cyano-4-hydroxy-5-(4-isobutyramidopyrrolo[2,1-f][1,2,4]triazin-7-yl)-2-((2-phenylacetoxy)methyl)tetrahydrofuran-3-yl L-valinate (Compound 347)

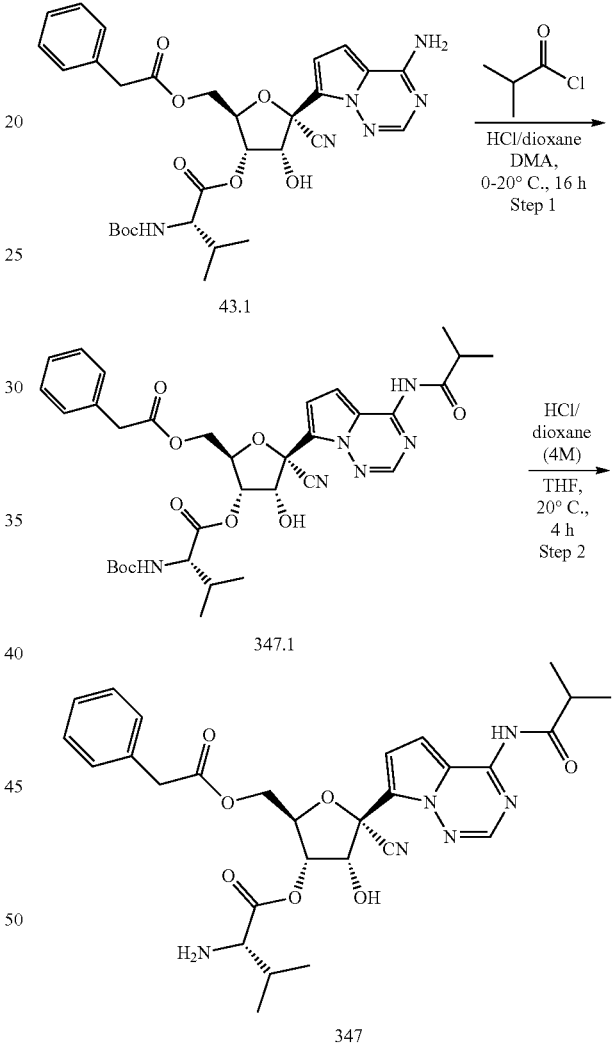

Step 1. Synthesis of (2R,3S,4R,5R)-5-cyano-4-hydroxy-5-(4-isobutyramidopyrrolo[2,1-f][1,2,4]triazin-7-yl)-2-((2-phenylacetoxy)methyl)tetrahydrofuran-3-yl (tert-butoxycarbonyl)-L-valinate (347.1)

Compound 347.1 was prepared according to the procedure of Example 195, Step 1, using 43.1 and isobutyryl chloride. MS (ESI): mass calcd. for $C_{34}H_{42}N_6O_9$, 678.74, m/z found 679.3 $[M+H]^+$.

Step 2. Synthesis of (2R,3S,4R,5R)-5-cyano-4-hydroxy-5-(4-isobutyramidopyrrolo[2,1-f][1,2,4]triazin-7-yl)-2-((2-phenylacetoxy)methyl)tetrahydrofuran-3-yl L-valinate (Compound 347)

Compound 347 was prepared according to the procedure of Example 19, Step 2, using 347.1. MS (ESI): mass calcd. for $C_{29}H_{34}NO_7$, 578.63, m/z found 579.2 [M+H]$^+$. $^1$H NMR (400 MHz, DMSO) δ 10.91 (s, 1H), 8.41 (s, 1H), 7.28-7.18 (m, 6H), 7.08 (d, J=4.8 Hz, 1H), 6.70-6.68 (m, 1H), 5.19-5.12 (m, 1H), 5.04 (d, J=5.6 Hz, 1H), 4.51 (dd, J=8.0, 4.0 Hz, 1H), 4.33 (dd, J=12.4, 3.6 Hz, 1H), 4.26 (dd, J=12.4, 4.8 Hz, 1H), 3.66 (s, 2H), 3.28 (d, J=5.2 Hz, 1H), 3.11-3.07 (m, 1H), 2.09-1.98 (m, 1H), 1.16 (d, J=6.8 Hz, 6H), 0.95-0.85 (m, 6H).

Example 199. Synthesis of (2R,3S,4R,5R)-5-(4-acetamidopyrrolo[2,1-f][1,2,4]triazin-7-yl)-5-cyano-2-((2-cyclohexylacetoxy)methyl)-4-hydroxytetrahydrofuran-3-yl L-valinate (Compound 348)

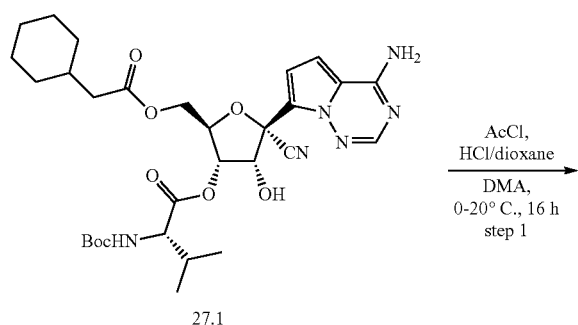

27.1

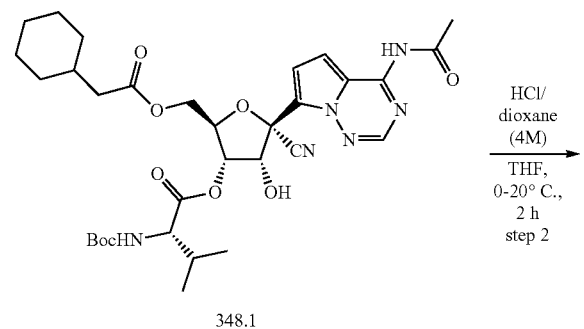

348.1

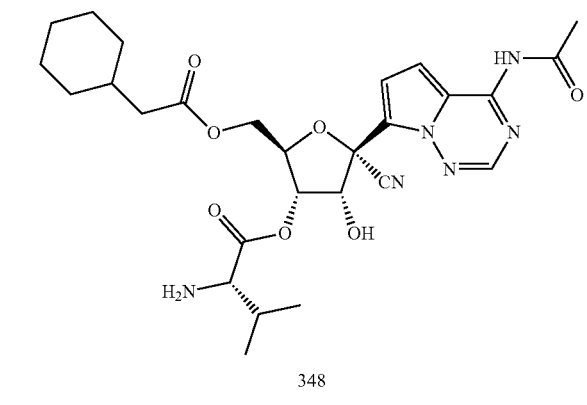

348

Step 1. Synthesis of (2R,3S,4R,5R)-5-(4-acetamidopyrrolo[2,1-f][1,2,4]triazin-7-yl)-5-cyano-2-((2-cyclohexylacetoxy)methyl)-4-hydroxytetrahydrofuran-3-yl (tert-butoxycarbonyl)-L-valinate (348.1)

To a solution 27.1 (200 mg, 0.325 mmol) in DMA (1.0 mL) was added HCl solution in 1-4 dioxane (0.2 mL, 4 M) and the mixture was stirred at 20° C. for 15 minutes. Then the reaction mixture was cooled at 0° C. and acetyl chloride (0.46 mL, 6.5 mmol) was added at once. The reaction was stirred at 20° C. for 12 h. The reaction was diluted with ACN (1 mL) and purified by prep-HPLC (column: Gemini-C18 150×21.2 mm, 5 μm; mobile phase: ACN-H$_2$O (0.1% FA); gradient: 40%-70%) to obtain 348.1 (40 mg, 17.8% yield) as a white solid. MS (ESI): mass calcd. for $C_{32}H_{44}N_6O_9$, 656.30 m/z found 657.2 [M+H]$^+$. $^1$H NMR (400 MHz, DMSO) δ 10.99 (s, 1H), 8.40 (s, 1H), 7.33 (d, J=4.8 Hz, 1H), 7.11 (t, J=8.0 Hz, 2H), 6.76 (d, J=6.4 Hz, 1H), 5.13 (t, J=5.2 Hz, 1H), 5.10-5.03 (m, 1H), 4.46 (d, J=3.6 Hz, 1H), 4.29 (dd, J=12.4, 3.2 Hz, 1H), 4.18 (dd, J=12.4, 4.8 Hz, 1H), 4.06 (dd, J=8.0, 6.0 Hz, 1H), 2.40 (s, 3H), 2.26-2.16 (m, 1H), 2.15-2.06 (m, 2H), 1.56 (s, 6H), 1.40 (s, 9H), 1.11 (d, J=10.4 Hz, 3H), 0.94-0.80 (m, 8H).

Step 2. Synthesis of (2R,3S,4R,5R)-5-(4-acetamidopyrrolo[2,1-f][1,2,4]triazin-7-yl)-5-cyano-2-((2-cyclohexylacetoxy)methyl)-4-hydroxytetrahydrofuran-3-yl L-valinate (348)

To a solution of 348.1 (40 mg, 0.061 mmol) in THF (1.0 mL) was added HCl in dioxane (2.0 mL, 4 M) at 0° C., then the reaction was stirred at 20° C. for 2 h. After completion, the mixture was concentrated in vacuo to afford a residue, the residue was purified by prep-HPLC (mobile phase: ACN-H$_2$O (0.1% FA), 20%-45%) to afford 348 (14.61 mg, 38.9% yield) as a white solid. MS (ESI): mass calcd. for $C_{27}H_{36}N_6O_7$, 556.26, m/z found 557.2 [M+H]$^+$. $^1$H NMR (400 MHz, DMSO) δ 11.00 (s, 1H), 8.40 (s, 1H), 7.34 (d, J=4.8 Hz, 1H), 7.10 (d, J=4.8 Hz, 1H), 6.72 (d, J=6.0 Hz, 1H), 5.17-5.12 (m, 1H), 5.10-5.06 (m, 1H), 4.49 (d, J=4.0 Hz, 1H), 4.31-4.26 (m, 1H), 4.24-4.19 (m, 1H), 3.24 (d, J=5.2 Hz, 1H), 2.40 (s, 3H), 2.16-2.09 (m, 2H), 2.03-1.96 (m, 1H), 1.60-1.50 (m, 6H), 1.18-1.05 (m, 3H), 0.92 (d, J=6.8 Hz, 3H), 0.87-0.82 ((m, 5H).

Example 200. Synthesis of (2R,3S,4R,5R)-5-cyano-2-((2-cyclohexylacetoxy)methyl)-4-hydroxy-5-(4-isobutyramidopyrrolo[2,1-f][1,2,4]triazin-7-yl)tetrahydrofuran-3-yl L-valinate (Compound 349)

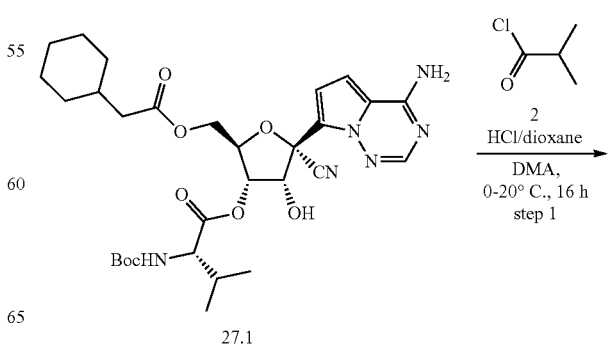

27.1

533
-continued

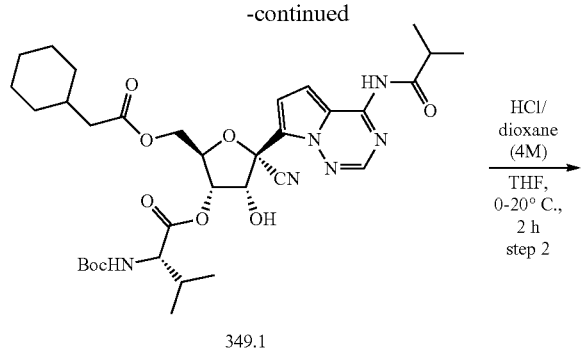

349.1

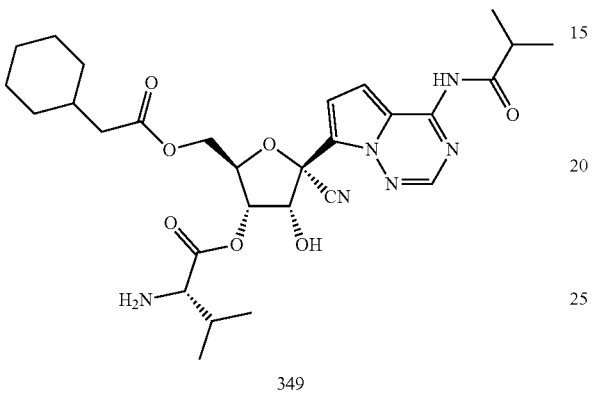

349

Step 1. Synthesis of (2R,3S,4R,5R)-5-cyano-2-((2-cyclohexylacetoxy)methyl)-4-hydroxy-5-(4-isobutyramidopyrrolo[2,1-f][1,2,4]triazin-7-yl)tetrahydrofuran-3-yl (tert-butoxycarbonyl)-L-valinate (349.1)

The title compound 349.1 was prepared according to the procedure of Example 199, Step 1, using 27.1 and isobutyryl chloride. MS (ESI): mass calcd. for $C_{34}H_{48}N_6O_9$, 684.35 m/z found 685.3 [M+H]$^+$. $^1$H NMR (400 MHz, DMSO) δ 10.91 (s, 1H), 8.41 (s, 1H), 7.28 (d, J=4.8 Hz, 1H), 7.17-7.04 (m, 2H), 6.77 (d, J=6.4 Hz, 1H), 5.18-5.12 (m, 1H), 5.11-5.07 (m, 1H), 4.53-4.41 (m, 1H), 4.29 (dd, J=12.4, 3.6 Hz, 1H), 4.18 (dd, J=12.4, 4.8 Hz, 1H), 4.07 (dd, J=8.0, 5.6 Hz, 1H), 3.12 (dt, J=13.6, 6.8 Hz, 1H), 2.27-2.16 (m, 1H), 2.15-2.06 (m, 2H), 1.62-1.50 (m, 6H), 1.41-1.36 (m, 9H), 1.17-1.04 (m, 9H), 0.95-0.77 (m, 8H).

Step 2. Synthesis of (2R,3S,4R,5R)-5-cyano-2-((2-cyclohexylacetoxy)methyl)-4-hydroxy-5-(4-isobutyramidopyrrolo[2,1-f][1,2,4]triazin-7-yl)tetrahydrofuran-3-yl L-valinate (349)

The title compound 349 was prepared according to the procedure of Example 199, Step 2, using 349.1. MS (ESI): mass calcd. for $C_{29}H_{40}N_6O_7$, 584.30, m/z found 585.3 [M+H]$^+$. $^1$H NMR (400 MHz, DMSO) δ 10.90 (s, 1H), 8.41 (s, 1H), 7.28 (d, J=4.8 Hz, 1H), 7.11 (d, J=4.8 Hz, 1H), 6.72 (d, J=6.0 Hz, 1H), 5.18-5.12 (m, 1H), 5.11-5.07 (m, 1H), 4.50 (q, J=4.0 Hz, 1H), 4.28 (dd, J=12.4, 3.6 Hz, 1H), 4.21 (dd, J=12.4, 4.8 Hz, 1H), 3.24 (d, J=5.2 Hz, 1H), 3.16-3.08 (m, 1H), 2.18-2.10 (m, 2H), 2.03-1.95 (m, 1H), 1.61-1.50 (m, 6H), 1.18-1.05 (m, 9H), 0.96-0.80 (m, 8H).

534
Example 201. Synthesis of (2R,3S,4R,5R)-5-(4-butyramidopyrrolo[2,1-f][1,2,4]triazin-7-yl)-5-cyano-2-((2-cyclohexylacetoxy)methyl)-4-hydroxytetrahydrofuran-3-yl L-valinate (Compound 350)

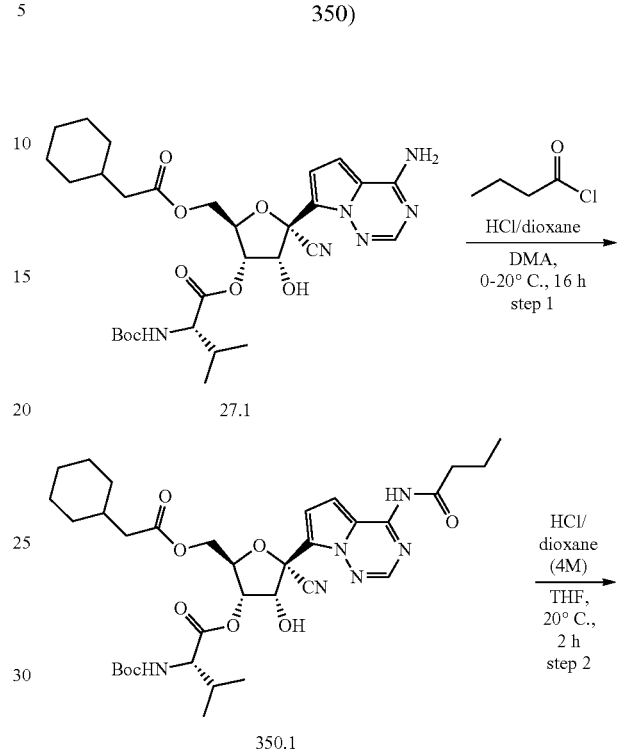

27.1

350.1

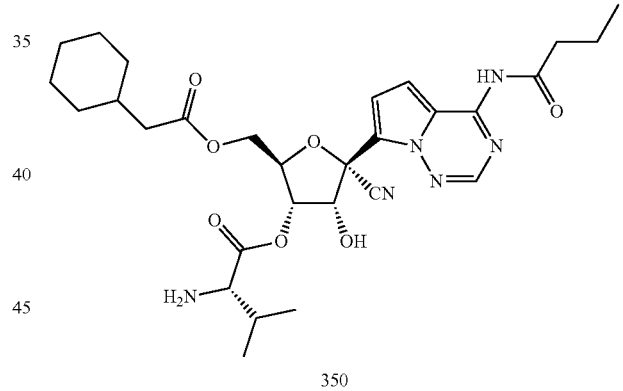

350

Step 1. Synthesis of (2R,3S,4R,5R)-5-(4-butyramidopyrrolo[2,1-f][1,2,4]triazin-7-yl)-5-cyano-2-((2-cyclohexylacetoxy)methyl)-4-hydroxytetrahydrofuran-3-yl (tert-butoxycarbonyl)-L-valinate (350.1)

The title compound 350.1 was prepared according to the procedure of Example 199, Step 1, using 27.1 and butyryl chloride. MS (ESI): mass calcd. for $C_{34}H_{48}N_6O_9$, 684.35 m/z found 685.3 [M+H]+. $^1$H NMR (400 MHz, DMSO) δ 10.94 (s, 1H), 8.40 (s, 1H), 7.32 (d, J=4.8 Hz, 1H), 7.11 (t, J=7.6 Hz, 2H), 6.76 (d, J=6.4 Hz, 1H), 5.13 (t, J=5.2 Hz, 1H), 5.10-5.04 (m, 1H), 4.46 (d, J=4.0 Hz, 1H), 4.29 (dd, J=12.4, 3.2 Hz, 1H), 4.22-4.14 (m, 1H), 4.12-4.04 (m, 1H), 2.70 (t, J=7.2 Hz, 2H), 2.26-2.06 (m, 3H), 1.69-1.52 (m, 8H), 1.40 (s, 9H), 1.15-0.81 (m, 14H).

Step 2. Synthesis of (2R,3S,4R,5R)-5-(4-butyramidopyrrolo[2,1-f][1,2,4]triazin-7-yl)-5-cyano-2-((2-cyclohexylacetoxy)methyl)-4-hydroxytetrahydrofuran-3-yl L-valinate (350)

The title compound 350 was prepared according to the procedure of Example 199, Step 2, using 350.1. MS (ESI): mass calcd. for $C_{29}H_{40}N_6O_7$, 584.30, m/z found 585.2 [M+H]$^+$. $^1$H NMR (400 MHz, DMSO) δ 10.94 (s, 1H), 8.40 (s, 1H), 7.32 (d, J=4.8 Hz, 1H), 7.08 (d, J=4.8 Hz, 1H), 6.75-6.70 (m, 1H), 5.16-5.11 (m, 1H), 5.10-5.06 (m, 1H), 4.51-4.47 (m, 1H), 4.31-4.16 (m, 2H), 3.24 (d, J=5.2 Hz, 1H), 2.73-2.66 (m, 2H), 2.19-2.07 (m, 2H), 2.04-1.95 (m, 1H), 1.69-1.51 (m, 8H), 1.19-0.99 (m, 3H), 0.97-0.90 (m, 6H), 0.88-0.82 (m, 5H).

Example 202. Synthesis of (2R,3R,4R,5R)-2-(4-aminopyrrolo[2,1-f][1,2,4]triazin-7-yl)-2-cyano-5-((2-phenylacetoxy)methyl)tetrahydrofuran-3,4-diyl (2S,2'S)-bis(2-amino-3-methylbutanoate) (Compound 351)

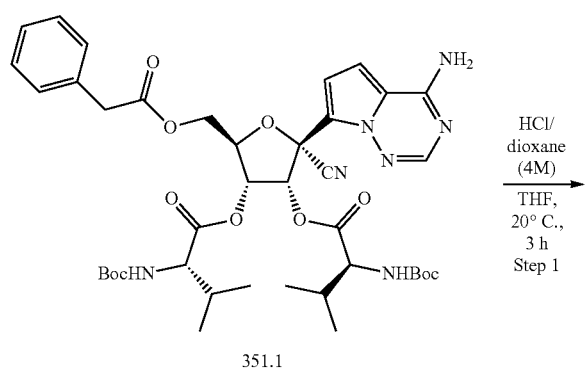

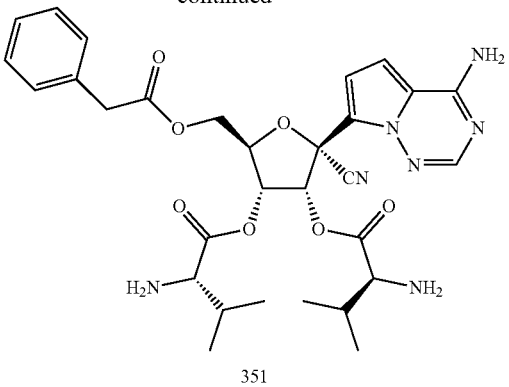

Step 1. Synthesis of (2R,3R,4R,5R)-2-(4-aminopyrrolo[2,1-f][1,2,4]triazin-7-yl)-2-cyano-5-((2-phenylacetoxy)methyl)tetrahydrofuran-3,4-diyl (2S,2'S)-bis(2-amino-3-methylbutanoate) (Compound 351)

The compound 351 was prepared according to the procedure of Example 19, Step 2, using 351.1. MS (ESI): mass calcd. for $C_{30}H_{37}N_7O_7$, 607.67, m/z found 608.2 [M+H]$^+$. $^1$H NMR (400 MHz, DMSO) δ 8.02 (d, J=24.0 Hz, 2H), 7.95 (s, 1H), 7.25-7.20 (m, 5H), 6.95 (d, J=4.4 Hz, 1H), 6.81 (d, J=4.8 Hz, 1H), 6.13 (d, J=6.0 Hz, 1H), 5.46 (dd, J=5.6, 4.0 Hz, 1H), 4.57-4.55 (m, 1H), 4.42 (dd, J=12.4, 3.2 Hz, 1H), 4.31 (dd, J=12.4, 4.8 Hz, 1H), 3.67 (d, J=2.8 Hz, 2H), 3.30 (d, J=5.2 Hz, 1H), 3.27 (d, J=4.8 Hz, 1H), 2.04-2.00 (m, 1H), 1.93-1.90 (m, 1H), 0.90 (dd, J=13.2, 6.8 Hz, 6H), 0.85 (d, J=6.8 Hz, 6H).

Example 203. Synthesis of ((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methyl 2-(1-aminocyclohexyl)acetate (Compound 352)

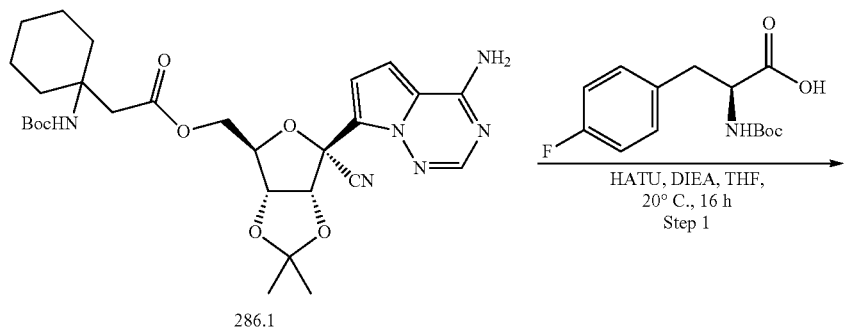

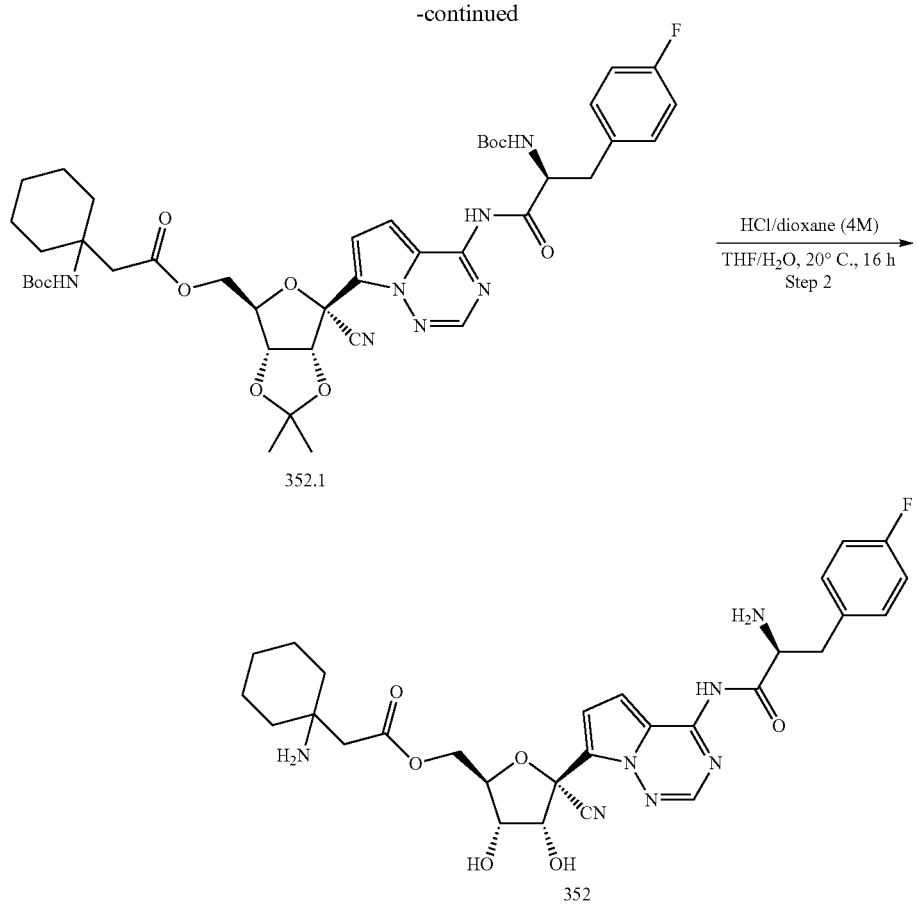

352.1

352

Step 1. Synthesis of ((3aR,4R,6R,6aR)-6-(4-((S)-2-((tert-butoxycarbonyl)amino)-3-(4-fluorophenyl)propanamido)pyrrolo[2,1-f][1,2,4]triazin-7-yl)-6-cyano-2,2-dimethyltetrahydrofuro[3,4-d][1,3]dioxol-4-yl)methyl 2-(1-((tert-butoxycarbonyl)amino)cyclohexyl)acetate (Compound 352.1)

The compound 352.1 was prepared according to the procedure of Example 185, Step 1, using 286.1 and (S)-2-((tert-butoxycarbonyl)amino)-3-(4-fluorophenyl)propanoic acid. MS (ESI): mass calcd. for $C_{42}H_{54}FN_7O_{10}$, 835.93, m/z found 836.2 [M+H]$^+$.

Step 2. Synthesis of Synthesis of ((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methyl 2-(1-aminocyclohexyl)acetate (Compound 352)

The compound 352 was prepared according to the procedure of Example 49, Step 2, using 352.1. MS (ESI): mass calcd. for $C_{29}H_{34}FN_7O_6$, 595.63, m/z found 596.3 [M+H]$^+$. $^1$H NMR (400 MHz, DMSO) δ 8.57 (d, J=8.4 Hz, 1H), 7.91 (s, 1H), 7.69 (s, 1H), 7.39 (dd, J=8.4, 5.6 Hz, 2H), 7.17 (s, 1H), 7.09-7.03 (m, 3H), 6.81 (d, J=4.4 Hz, 1H), 6.33-6.30 (m, 1H), 5.50-5.45 (m, 1H), 4.93 (dd, J=13.2, 5.6 Hz, 1H), 4.66 (d, J=4.4 Hz, 1H), 4.30 (d, J=10.8 Hz, 1H), 4.24-4.16 (m, 2H), 3.94-3.90 (m, 1H), 3.17 (d, J=10.4 Hz, 1H), 3.01 (d, J=13.6 Hz, 1H), 2.40 (s, 2H), 1.43-1.31 (m, 10H). $^{19}$F NMR (376 MHz, DMSO) δ −116.76 (s, 1F).

Example 204. Synthesis of ((2R,3S,4R,5R)-5-(4-acetamidopyrrolo[2,1-f][1,2,4]triazin-7-yl)-5-cyano-4-hydroxy-3-(propionyloxy)tetrahydrofuran-2-yl)methyl L-valinate (Compound 353)

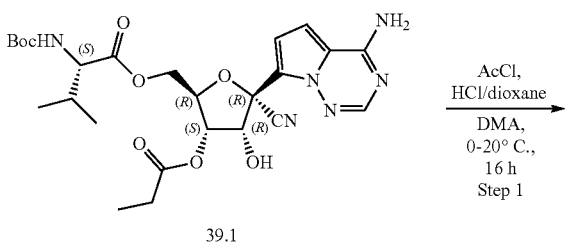

39.1

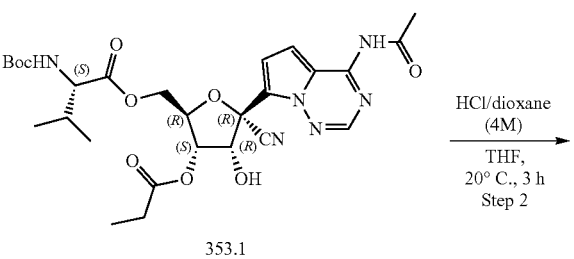

353.1

539
-continued

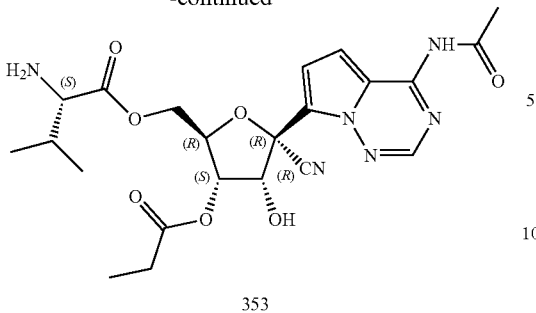

353

Step 1. Synthesis of ((2R,3S,4R,5R)-5-(4-acetami-dopyrrolo[2,1-f][1,2,4]triazin-7-yl)-5-cyano-4-hy-droxy-3-(propionyloxy)tetrahydrofuran-2-yl)methyl (tert-butoxycarbonyl)-L-valinate (353.1)

Compound 353.1 was prepared according to the procedure of Example 195, Step 1, using 39.1 and AcCl. MS (ESI): mass calcd. for $C_{27}H_{36}N_6O_9$, 588.62, m/z found 589.2 [M+H]$^+$.

540

Step 2. Synthesis of ((2R,3S,4R,5R)-5-(4-acetami-dopyrrolo[2,1-f][1,2,4]triazin-7-yl)-5-cyano-4-hy-droxy-3-(propionyloxy)tetrahydrofuran-2-yl)methyl L-valinate (Compound 353)

Compound 353 was prepared according to the procedure of Example 19, Step 2, using 347.1. MS (ESI): mass calcd. for $C_{22}H_{25}N_6O_7$, 488.50, m/z found 489.1 [M+H]$^+$. $^1$H NMR (400 MHz, DMSO) δ 10.97 (s, 1H), 8.40 (s, 1H), 7.32 (d, J=4.4 Hz, 1H), 7.10 (d, J=4.8 Hz, 1H), 6.71 (d, J=6.0 Hz, 1H), 5.15 (t, J=5.2 Hz, 1H), 5.05 (t, J=6.0 Hz, 1H), 4.53-4.50 (m, 1H), 4.29-4.24 (m, 2H), 3.09 (d, J=5.2 Hz, 1H), 2.41-2.38 (m, 5H), 1.78-1.73 (m, 1H), 1.09 (t, J=7.2 Hz, 3H), 0.77 (dd, J=22.4, 6.8 Hz, 6H).

Example 205. Synthesis of ((2R,3S,4R,5R)-5-(4-butyramidopyrrolo[2,1-f][1,2,4]triazin-7-yl)-5-cyano-3,4-dihydroxytetrahydrofuran-2-yl)methyl 2-(1-aminocyclohexyl)acetate (Compound 354)

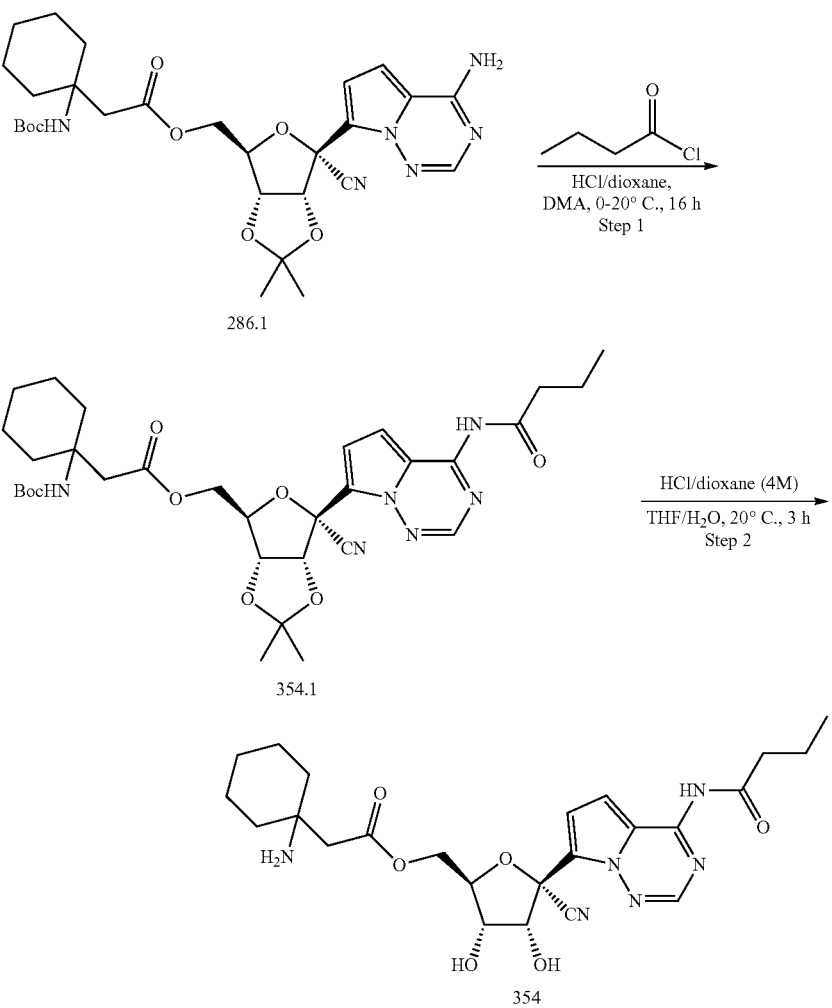

Step 1. Synthesis of ((3aR,4R,6R,6aR)-6-(4-butyramidopyrrolo[2,1-f][1,2,4]triazin-7-yl)-6-cyano-2,2-dimethyltetrahydrofuro[3,4-d][1,3]dioxol-4-yl)methyl 2-(1-((tert-butoxycarbonyl)amino)cyclohexyl)acetate (354.1)

Compound 354.1 was prepared according to the procedure of Example 195, Step 1, using 286.1 and butyryl chloride. MS (ESI): mass calcd. for $C_{32}H_{44}N_6O_8$, 640.74, m/z found 641.2 $[M+H]^+$.

Step 2. Synthesis of ((2R,3S,4R,5R)-5-(4-butyramidopyrrolo[2,1-f][1,2,4]triazin-7-yl)-5-cyano-3,4-dihydroxytetrahydrofuran-2-yl)methyl 2-(1-aminocyclohexyl)acetate (Compound 354)

Compound 354 was prepared according to the procedure of Example 49, Step 2, using 354.1. MS (ESI): mass calcd. for $C_{24}H_{32}N_6O_6$, 500.56, m/z found 501.1 $[M+H]^+$. $^1$H NMR (400 MHz, DMSO) δ 8.40 (s, 1H), 7.30 (d, J=4.8 Hz, 1H), 7.07 (d, J=4.8 Hz, 1H), 6.46 (d, J=6.0 Hz, 1H), 5.49-5.48 (m, 1H), 4.71 (t, J=4.4 Hz, 1H), 4.38-4.28 (m, 2H), 4.23 (dd, J=11.6, 5.6 Hz, 1H), 3.96 (t, J=5.6 Hz, 1H), 2.70 (t, J=7.2 Hz, 2H), 2.55 (s, 2H), 1.68-1.61 (m, 2H), 1.54-1.31 (m, 10H), 0.94 (t, J=7.2 Hz, 3H).

Example 206. Synthesis of (2R,3S,4R,5R)-5-(4-(((acetoxymethoxy)carbonyl)amino)pyrrolo[2,1-f][1,2,4]triazin-7-yl)-5-cyano-4-hydroxy-2-((2-phenylacetoxy)methyl)tetrahydrofuran-3-yl L-valinate (Compound 355)

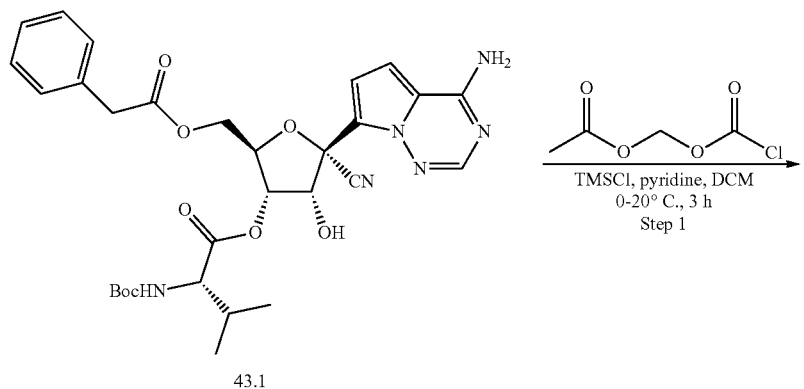

43.1

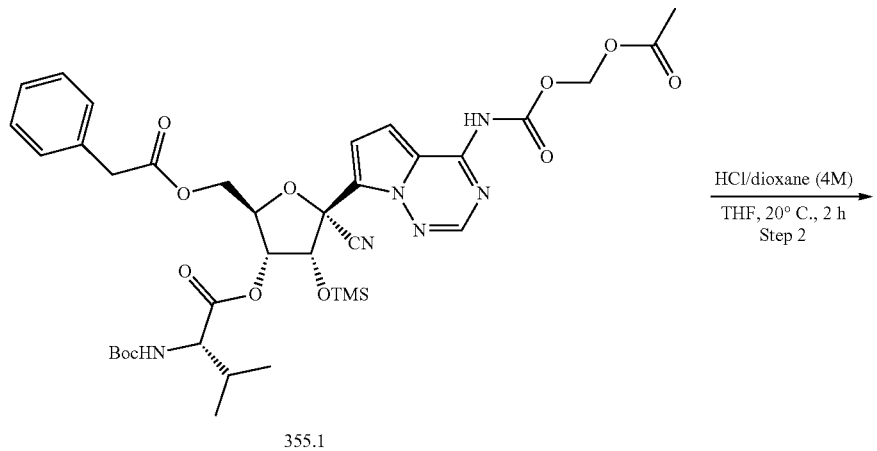

355.1

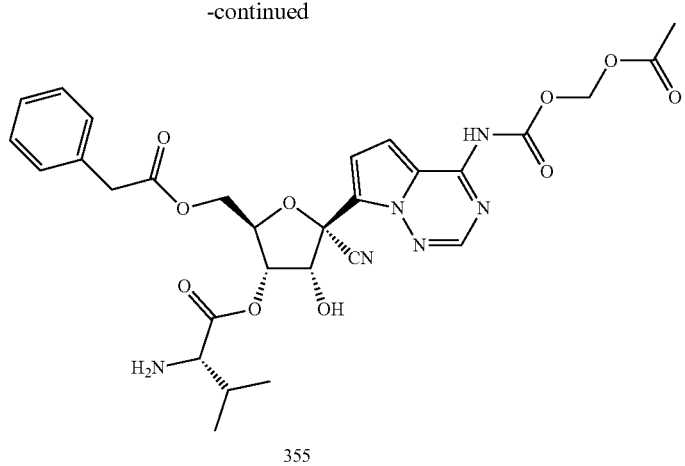

355

Step 1. Synthesis of (2R,3R,4R,5R)-5-(4-(((acetoxymethoxy)carbonyl)amino)pyrrolo[2,1-f][1,2,4]triazin-7-yl)-5-cyano-2-((2-phenylacetoxy)methyl)-4-((trimethylsilyl)oxy)tetrahydrofuran-3-yl (tert-butoxycarbonyl)-L-valinate (355.1)

To a solution of 43.1 (80 mg, 0.131 mmol) in DCM (5 mL) was added TMSCl (42.83 mg, 0.394 mmol) at 0° C. and stirred at 20° C. for 2 h. To the above solution was added [(chlorocarbonyl)oxy]methyl acetate (60.13 mg, 0.394 mmol) at 0° C. and stirred at 0° C. for 2 h. The reaction was washed with DCM (5 mL×3). The combined organics were dried over sodium sulfate and concentrated in vacuo. The crude product was purified by prep-HPLC to afford 355.1 (25 mg, 21% yield) as a white solid. MS (ESI): m/z calcd. for $C_{37}H_{48}N_6O_{12}Si$ 796.91, found 797.3 [M+H]$^+$. $^1$H NMR (400 MHz, DMSO) δ 11.52 (s, 1H), 8.29 (s, 1H), 7.30-7.21 (m, 6H), 7.14 (d, J=8.4 Hz, 1H), 6.99-6.95 (m, 1H), 5.79 (s, 2H), 5.26 (d, J=5.2 Hz, 1H), 5.16 (t, J=5.2 Hz, 1H), 4.60-4.48 (m, 1H), 4.40 (dd, J=12.4, 3.2 Hz, 1H), 4.30 (dd, J=12.0, 5.2 Hz, 1H), 4.04 (dd, J=8.0, 6.0 Hz, 1H), 3.69 (s, 2H), 2.20-2.12 (m, 1H), 2.11 (s, 3H), 1.38 (s, 9H), 0.88 (t, J=6.8 Hz, 6H), 0.00 (s, 9H).

Step 2. Synthesis of (2R,3S,4R,5R)-5-(4-(((acetoxymethoxy)carbonyl)amino)pyrrolo[2,1-f][1,2,4]triazin-7-yl)-5-cyano-4-hydroxy-2-((2-phenylacetoxy)methyl)tetrahydrofuran-3-yl L-valinate (Compound 355)

The compound 355 was prepared according to the procedure of Example 19, Step 2, using 355.1. MS (ESI): mass calcd. for $C_{29}H_{32}N_6O_{10}$, 624.61, m/z found 625.1 [M+H]$^+$. $^1$H NMR (400 MHz, DMSO) δ 8.35 (s, 1H), 7.24-7.18 (m, 6H), 7.02 (d, J=4.4 Hz, 1H), 6.69 (d, J=6.0 Hz, 1H), 5.81 (s, 2H), 5.15 (t, J=4.8 Hz, 1H), 5.04-5.02 (m, 1H), 4.50-4.49 (m, 1H), 4.33 (dd, J=12.4, 3.2 Hz, 1H), 4.26 (dd, J=12.4, 4.8 Hz, 1H), 3.66 (s, 2H), 3.25 (d, J=5.2 Hz, 1H), 2.12 (s, 3H), 2.06-1.97 (m, 1H), 0.89 (dd, J=26.4, 6.4 Hz, 6H).

Example 207. (2R,3R,4R,5R)-2-(4-aminopyrrolo[2,1-f][1,2,4]triazin-7-yl)-2-cyano-5-((2-cyclohexylacetoxy)methyl)tetrahydrofuran-3,4-diyl (2S,2'S)-bis(2-amino-3-methylbutanoate) (Compound 356.1)

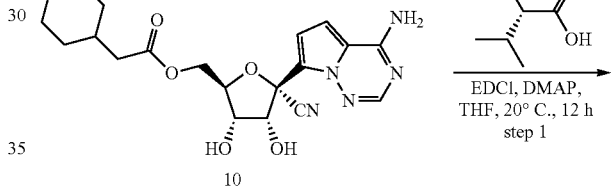

10

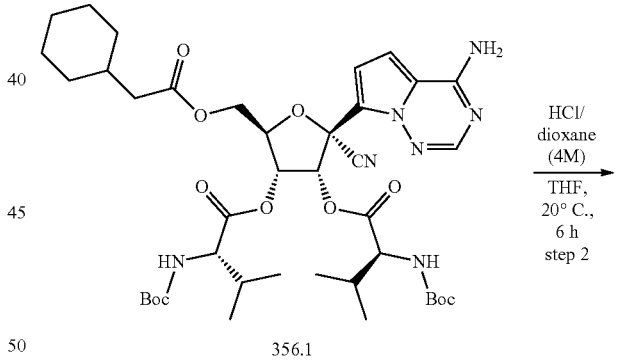

356.1

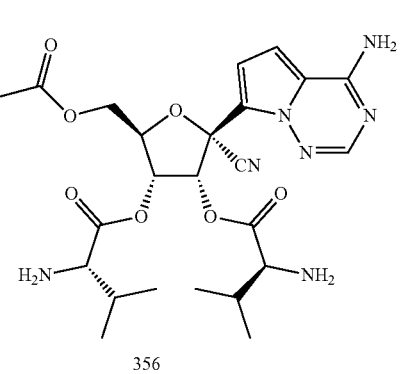

356

Step 1. Synthesis of (2R,3R,4R,5R)-2-(4-aminopyrrolo[2,1-f][1,2,4]triazin-7-yl)-2-cyano-5-((2-cyclohexylacetoxy)methyl)tetrahydrofuran-3,4-diyl (2S,2'S)-bis(2-((tert-butoxycarbonyl)amino)-3-methylbutanoate) (356.1)

To a solution of compound 10 (6.0 g, 14.4 mmol) in THF (200 mL) was added (tert-butoxycarbonyl)-L-valine (3.14 g, 14.4 mmol), EDCI (8.28 g, 43.2 mmol) and DMAP (5.28 g, 43.2 mmol), the mixture was stirred at 25° C. for 16 h. The organic phase was washed with brine water (100 mL×3), then dried over anhydrous sodium sulfate, filtered and concentrated to remove the solvent. the residue was purified by prep-HPLC [Gradient: 70%-95% ACN in water (0.1% FA)] to obtain 356.1 (3.0 g, 26% yield) as a white solid. MS (ESI): mass calcd. for C₄₀H₅₉N₇O₁, 813.43 m/z found 814.7 [M+H]⁺. ¹H NMR (400 MHz, DMSO) δ 7.95 (br s, 3H), 7.22 (d, J=8.4 Hz, 1H), 7.17 (d, J=8.4 Hz, 1H), 6.93 (d, J=4.4 Hz, 1H), 6.82 (d, J=4.4 Hz, 1H), 6.04 (d, J=6.0 Hz, 1H), 5.46 (dd, J=5.2, 3.2 Hz, 1H), 4.52 (d, J=3.2 Hz, 1H), 4.44-4.33 (m, 1H), 4.30-4.23 (m, 1H), 4.12-4.07 (m, 1H), 4.06-3.98 (m, 1H), 2.35-2.25 (m, 1H), 2.20-2.05 (m, 3H), 1.56 (s, 6H), 1.39 (d, J=5.2 Hz, 16H), 1.25-0.99 (m, 5H), 0.98-0.75 (m, 14H).

Step 2. Synthesis of (2R,3R,4R,5R)-2-(4-aminopyrrolo[2,1-f][1,2,4]triazin-7-yl)-2-cyano-5-((2-cyclohexylacetoxy)methyl)tetrahydrofuran-3,4-diyl (2S,2'S)-bis(2-amino-3-methylbutanoate) (356)

The title compound 356 was prepared according to the procedure of Example 199, Step 2, using 356.1. MS (ESI): mass calcd. for C₃₀H₄₃N₇O₇, 613.32, m/z found 614.3 [M+H]⁺. ¹H NMR (400 MHz, DMSO) δ 8.11-7.90 (m, 3H), 6.95 (d, J=4.8 Hz, 1H), 6.85 (d, J=4.8 Hz, 1H), 6.18 (d, J=6.0 Hz, 1H), 5.51-5.40 (m, 1H), 4.57 (dd, J=7.6, 4.0 Hz, 1H), 4.40-4.35 (m, 1H), 4.32-4.25 (m, 1H), 3.38 (d, J=4.8 Hz, 1H), 3.34 (d, J=4.8 Hz, 1H), 2.21-1.92 (m, 4H), 1.65-1.50 (m, 6H), 1.20-1.00 (m, 3H), 0.98-0.80 (m, 14H).

Example 208. Synthesis of ((2R,3S,4R,5R)-5-(4-butyramidopyrrolo[2,1-f][1,2,4]triazin-7-yl)-5-cyano-4-hydroxy-3-(propionyloxy)tetrahydrofuran-2-yl)methyl L-valinate (Compound 357)

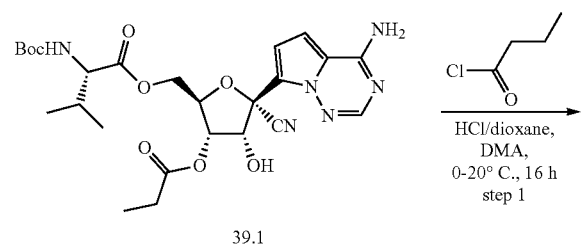

39.1

HCl/dioxane, DMA, 0-20° C., 16 h
step 1

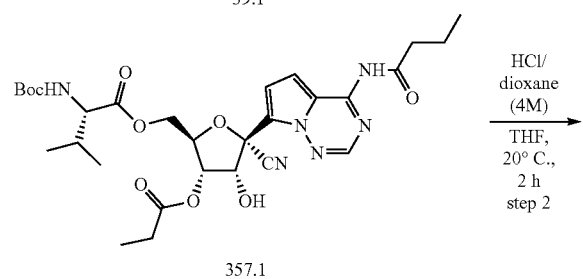

357.1

HCl/dioxane (4M)
THF, 20° C., 2 h
step 2

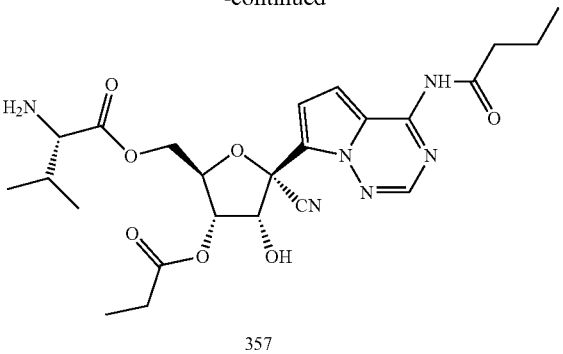

357

Step 1. Synthesis of ((2R,3S,4R,5R)-5-(4-butyramidopyrrolo[2,1-f][1,2,4]triazin-7-yl)-5-cyano-4-hydroxy-3-(propionyloxy)tetrahydrofuran-2-yl)methyl (tert-butoxycarbonyl)-L-valinate (357.1)

The title compound 357.1 was prepared according to the procedure of Example 199, Step 1, using 39.1 and butyryl chloride. MS (ESI): mass calcd. for C₂₉H₄₀N₆O₉, 616.29 m/z found 617.2 [M+H]⁺. ¹H NMR (400 MHz, DMSO) δ 10.92 (s, 1H), 8.40 (s, 1H), 7.30 (d, J=4.8 Hz, 1H), 7.17 (d, J=8.0 Hz, 1H), 7.10 (d, J=4.8 Hz, 1H), 6.71 (d, J=6.4 Hz, 1H), 5.12 (d, J=5.2 Hz, 1H), 5.05 (d, J=6.0 Hz, 1H), 4.56-4.50 (m, 1H), 4.32-4.24 (m, 2H), 3.88-3.80 (m, 1H), 2.70 (t, J=7.2 Hz, 2H), 2.41 (q, J=7.6 Hz, 2H), 1.99-1.83 (m, 1H), 1.67-1.59 (m, 2H), 1.36 (s, 8H), 1.20 (s, 1H), 1.08 (t, J=7.6 Hz, 3H), 0.94 (t, J=7.6 Hz, 3H), 0.80-0.74 (m, 6H).

Step 2. Synthesis of ((2R,3S,4R,5R)-5-(4-butyramidopyrrolo[2,1-f][1,2,4]triazin-7-yl)-5-cyano-4-hydroxy-3-(propionyloxy)tetrahydrofuran-2-yl)methyl L-valinate (357)

The title compound 357 was prepared according to the procedure of Example 199, Step 2, using 357.1. MS (ESI): mass calcd. for C₂₄H₃₂N₆O₇, 516.23 m/z found 517.2 [M+H]⁺. ¹H NMR (400 MHz, DMSO) δ 10.93 (s, 1H), 8.40 (s, 1H), 7.31 (d, J=4.8 Hz, 1H), 7.10 (d, J=4.8 Hz, 1H), 6.71 (d, J=6.4 Hz, 1H), 5.15 (t, J=5.2 Hz, 1H), 5.06 (t, J=6.0 Hz, 1H), 4.53 (q, J=4.4 Hz, 1H), 4.33-4.24 (m, 2H), 3.09 (d, J=5.2 Hz, 1H), 2.70 (t, J=7.2 Hz, 2H), 2.44-2.38 (m, 2H), 1.78-1.73 (m, 2H), 1.69-1.60 (m, 2H), 1.08 (t, J=7.6 Hz, 3H), 0.94 (t, J=7.2 Hz, 3H), 0.79 (d, J=6.8 Hz, 3H), 0.74 (d, J=6.8 Hz, 3H).

Example 209. Synthesis of (2R,3S,4R,5R)-5-(4-
(((acetoxymethoxy)carbonyl)amino)pyrrolo[2,1-f][1,
2,4]triazin-7-yl)-5-cyano-2-((2-cyclohexylacetoxy)
methyl)-4-hydroxytetrahydrofuran-3-yl L-valinate
(Compound 358)

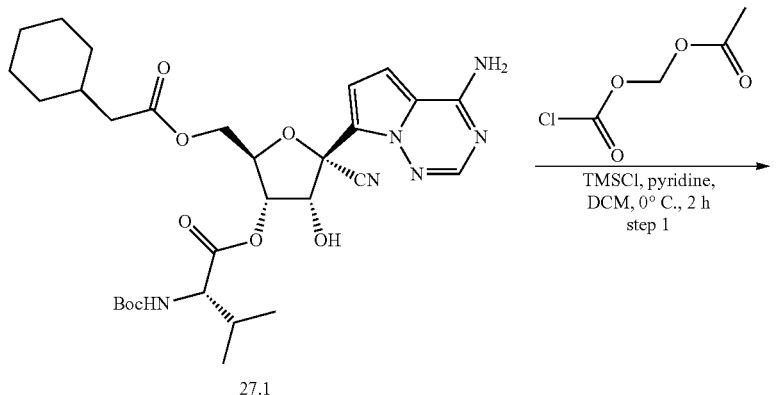

27.1

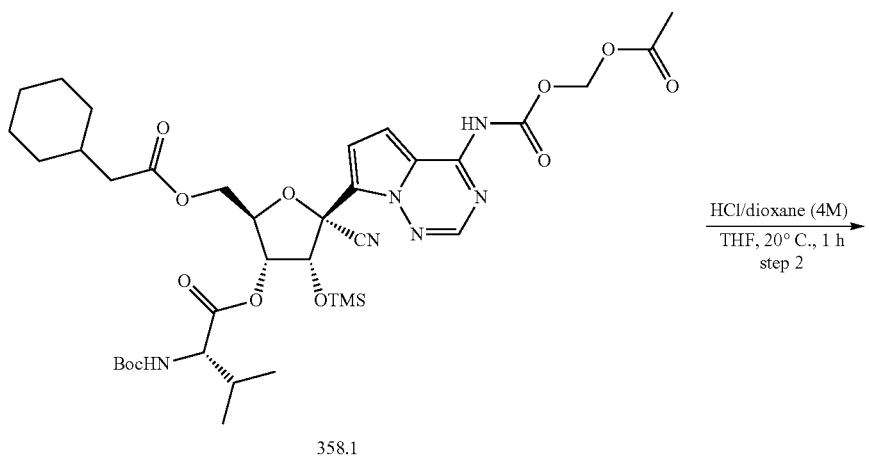

358.1

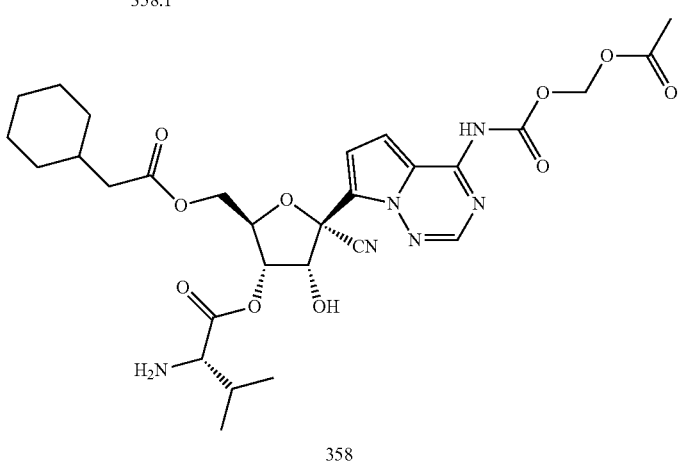

358

Step 1. Synthesis of (2R,3R,4R,5R)-5-(4-(((acetox-ymethoxy)carbonyl)amino)pyrrolo[2,1-f][1,2,4]tri-azin-7-yl)-5-cyano-2-((2-cyclohexylacetoxy)methyl)-4-((trimethylsilyl)oxy)tetrahydrofuran-3-yl (tert-butoxycarbonyl)-L-valinate (358.1)

To a solution of 27.1 (80.0 mg, 0.13 mmol) and pyridine (0.13 mL, 1.56 mmol) in DCM (1.0 mL) was added TMSCl (42.4 mg, 0.39 mmol) at 0° C., the mixture was stirred at 20° C. for 1 h. And then the reaction was added [(chlorocarbonyl)oxy]methyl acetate (29.8 mg, 0.195 mmol) at 0° C., the mixture was stirred at 0° C. for 1 h. Then the reaction was diluted with water (50 mL) and extracted with DCM (50 mL×3). The organic phase was washed with brine water (50 mL×3), then dried over anhydrous sodium sulfate, filtered and concentrated to remove the solvent. The residue was diluted with ACN (2 mL) and purified by prep-HPLC (mobile phase: ACN-H₂O (0.1% FA), 50%-80%) to obtain 358.1 (25.0 mg, 22.8% yield) as a white solid. MS (ESI): mass calcd. for C$_{37}$H$_{54}$N$_6$O$_{12}$Si, 802.36 m/z found 803.3 [M+H]⁺. ¹H NMR (400 MHz, DMSO) δ 11.45 (s, 1H), 8.32 (s, 1H), 7.27 (s, 1H), 7.17-7.11 (m, 1H), 7.05 (s, 1H), 5.79 (s, 2H), 5.28 (d, J=5.2 Hz, 1H), 5.16 (t J=5.2 Hz, 1H), 4.49 (dd, J=8.8, 5.2 Hz, 1H), 4.34 (dd, J=12.0, 3.2 Hz, 1H), 4.26 (dd, J=12.4, 5.2 Hz, 1H), 4.04 (dd, J=8.4, 6.0 Hz, 1H), 2.22-2.15 (m, 2H), 2.11 (s, 3H), 1.60 (d, J=13.2 Hz, 6H), 1.38 (s, 9H), 1.26-0.81 (m, 12H), 0.00 (s, 9H).

Step 2. Synthesis of (2R,3S,4R,5R)-5-(4-(((acetoxymethoxy)carbonyl)amino)pyrrolo[2,1-f][1,2,4]triazin-7-yl)-5-cyano-2-((2-cyclohexylacetoxy)methyl)-4-hydroxytetrahydrofuran-3-yl L-valinate (358)

The title compound 358 was prepared according to the procedure of Example 199, Step 2, using 358.1. MS (ESI): mass calcd. for C$_{29}$H$_{38}$N$_6$O$_{10}$, 630.26 m/z found 631.2 [M+H]⁺. ¹H NMR (400 MHz, DMSO) δ 8.34 (s, 1H), 7.28-7.25 (m, 1H), 7.08-7.02 (m, 1H), 6.70 (d, J=6.4 Hz, 1H), 5.80 (s, 2H), 5.17-5.13 (m, 1H), 5.11-5.07 (m, 1H), 4.51-4.46 (m, 1H), 4.31-4.26 (m, 1H), 4.24-4.19 (m, 1H), 3.25 (d, J=5.2 Hz, 1H), 2.17-2.09 (m, 5H), 2.04-1.97 (m, 1H), 1.65-1.50 (m, 7H), 1.20-1.05 (m, 3H), 0.95-0.84 (m, 7H).

Example 210. Synthesis of ((2R,3S,4R,5R)-5-(4-acetamidopyrrolo[2,1-f][1,2,4]triazin-7-yl)-5-cyano-3,4-dihydroxytetrahydrofuran-2-yl)methyl 2-(1-aminocyclohexyl)acetate (Compound 359)

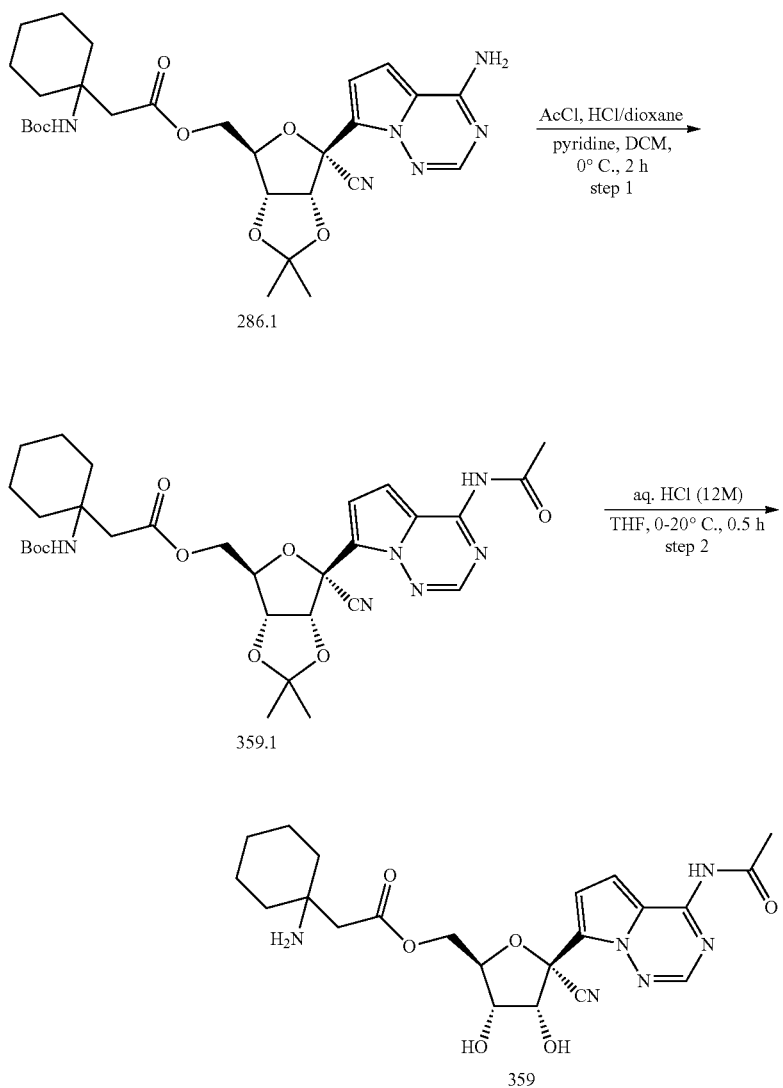

Step 1. Synthesis of ((3aR,4R,6R,6aR)-6-(4-acet-amidopyrrolo[2,1-f][1,2,4]triazin-7-yl)-6-cyano-2,2-dimethyltetrahydrofuro[3,4-d][1,3]dioxol-4-yl)methyl 2-(1-((tert-butoxycarbonyl)amino)cyclohexyl)acetate (359.1)

To a solution of 286.1 (250 mg, 0.438 mmol) and pyridine (416 mg, 5.26 mmol) in DCM (1.0 mL) was added acetyl chloride (68.8 mg, 0.88 mmol) at 0° C., then the reaction was stirred at 0° C. for 2 h. After completion, the mixture was concentrated in vacuo to afford a residue, the residue was purified by prep-HPLC (mobile phase: ACN-H$_2$O (0.1% FA), 40%-70%) to afford 359.1 (180 mg, 63.7% yield) as a white solid. MS (ESI): mass calcd. for C$_{30}$H$_{40}$N$_6$O$_8$, 612.29 m/z found 613.2 [M+H]$^+$. $^1$H NMR (400 MHz, DMSO) δ 10.99 (s, 1H), 8.43 (s, 1H), 7.31 (d, J=4.8 Hz, 1H), 7.07 (d, J=4.8 Hz, 1H), 6.26 (s, 1H), 5.41 (d, J=6.2 Hz, 1H), 4.96 (dd, J=6.4, 2.8 Hz, 1H), 4.62 (s, 1H), 4.21-4.15 (m, 1H), 4.10-4.05 (m, 1H), 2.48 (s, 2H), 2.39 (s, 3H), 1.96-1.88 (m, 2H), 1.65 (s, 3H), 1.43-1.15 (m, 20H).

Step 2. Synthesis of ((2R,3S,4R,5R)-5-(4-acetamidopyrrolo[2,1-f][1,2,4]triazin-7-yl)-5-cyano-3,4-dihydroxytetrahydrofuran-2-yl)methyl 2-(1-aminocyclohexyl)acetate (359)

To a solution of 359.1 (100 mg, 0.163 mmol) in THF (1.0 mL) was added HCl (0.8 mL, 4 M) at 0° C., then the reaction was stirred at 0° C. for 0.5 h. After completion, the mixture was concentrated in vacuo to afford a residue, the residue was purified by Prep-HPLC [Gradient: 5-35% ACN in water (0.1% FA)] to obtain 359 (39.5 mg, 49.0% yield) as a white solid. MS (ESI): mass calcd. for C$_{22}$H$_{28}$N$_6$O$_6$, 472.21 m/z found 473.1 [M+H]$^+$. $^1$H NMR (400 MHz, DMSO) δ 8.41-8.38 (m, 1H), 7.32 (d, J=4.8 Hz, 1H), 7.07 (d, J=4.8 Hz, 1H), 6.60-6.40 (m, 1H), 4.71 (d, J=4.8 Hz, 1H), 4.35-4.25 (m, 2H), 4.23-4.18 (m, 1H), 3.96 (t, J=5.6 Hz, 1H), 2.44 (s, 2H), 2.39 (s, 3H), 1.53-1.29 (m, 10H).

Example 211. Synthesis of (2R,3S,4R,5R)-5-cyano-4-hydroxy-2-((2-phenylacetoxy)methyl)-5-(4-((((pivaloyloxy)methoxy)carbonyl)amino)pyrrolo[2,1-f][1,2,4]triazin-7-yl)tetrahydrofuran-3-yl L-valinate (Compound 360)

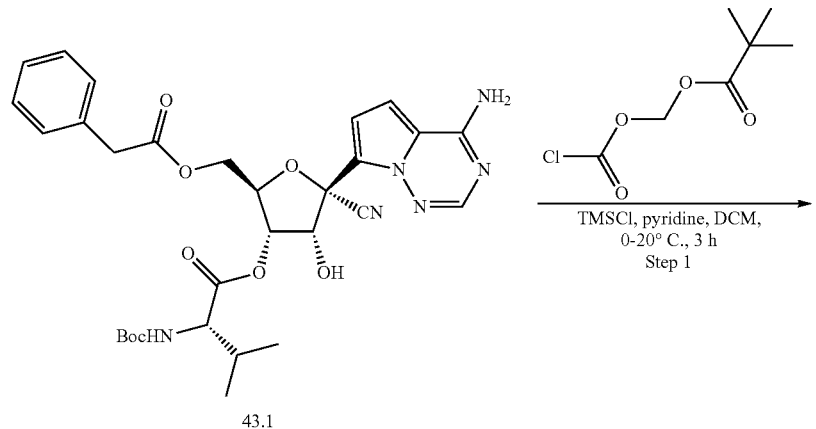

43.1

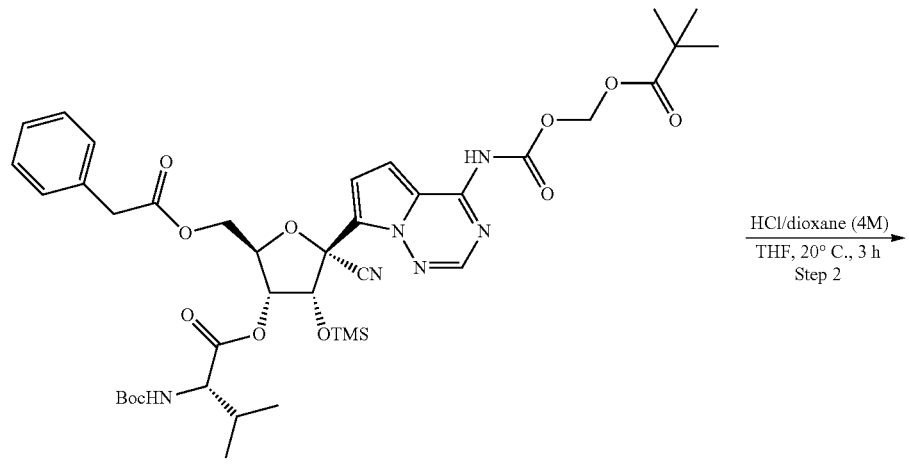

360.1

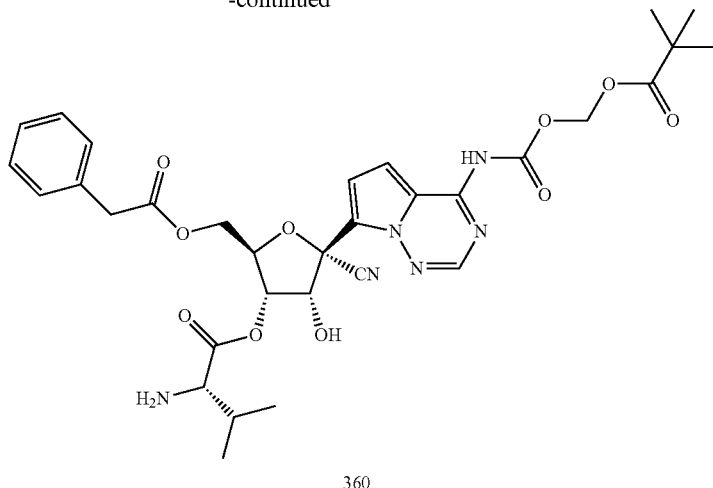

360

Step 1. Synthesis of (2R,3R,4R,5R)-5-cyano-2-((2-phenylacetoxy)methyl)-5-(4-((((pivaloyloxy)methoxy)carbonyl)amino)pyrrolo[2,1-f][1,2,4]triazin-7-yl)-4-((trimethylsilyl)oxy)tetrahydrofuran-3-yl (tert-butoxycarbonyl)-L-valinate (360.1)

The compound 360.1 was prepared according to the procedure of Example 206, Step 1, using 43.1 and ((chlorocarbonyl)oxy)methyl pivalate. MS (ESI): mass calcd. for $C_{40}H_{54}N_6O_{12}Si$, 838.99, m/z found 839.3 [M+H]$^+$.

Step 2. Synthesis of (2R,3S,4R,5R)-5-cyano-4-hydroxy-2-((2-phenylacetoxy)methyl)-5-(4-((((pivaloyloxy)methoxy)carbonyl)amino)pyrrolo[2,1-f][1,2,4]triazin-7-yl)tetrahydrofuran-3-yl L-valinate (Compound 360)

The compound 360 was prepared according to the procedure of Example 19, Step 2, using 360.1. MS (ESI): mass calcd. for $C_{32}H_3N_6O_{10}$, 666.69, m/z found 667.2 [M+H]$^+$. $^1$H NMR (400 MHz, DMSO) δ 8.39 (s, 1H), 7.33-7.17 (m, 6H), 7.06 (d, J=4.4 Hz, 1H), 6.76 (d, J=6.4 Hz, 1H), 5.85 (s, 2H), 5.25-5.15 (m, 1H), 5.05 (t, J=6.0 Hz, 1H), 4.53 (d, J=4.0 Hz, 1H), 4.34-4.24 (m, 2H), 3.66 (s, 2H), 3.50-3.47 (m, 1H) 2.10-2.09 (m, 1H), 1.18 (s, 9H), 0.93 (dd, J=16.0, 6.8 Hz, 6H).

Example 212. Synthesis of (2R,3S,4R,5R)-5-cyano-2-((2-cyclohexylacetoxy)methyl)-4-hydroxy-5-(4-((((pivaloyloxy)methoxy)carbonyl)amino)pyrrolo[2,1-f][1,2,4]triazin-7-yl)tetrahydrofuran-3-yl L-valinate (Compound 361)

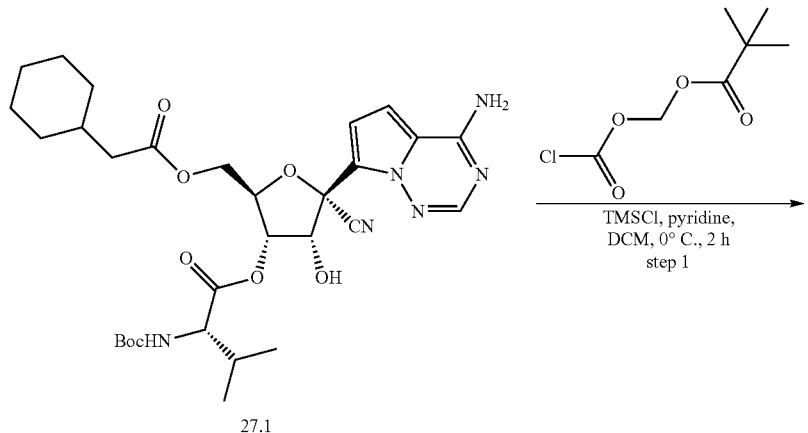

27.1

-continued

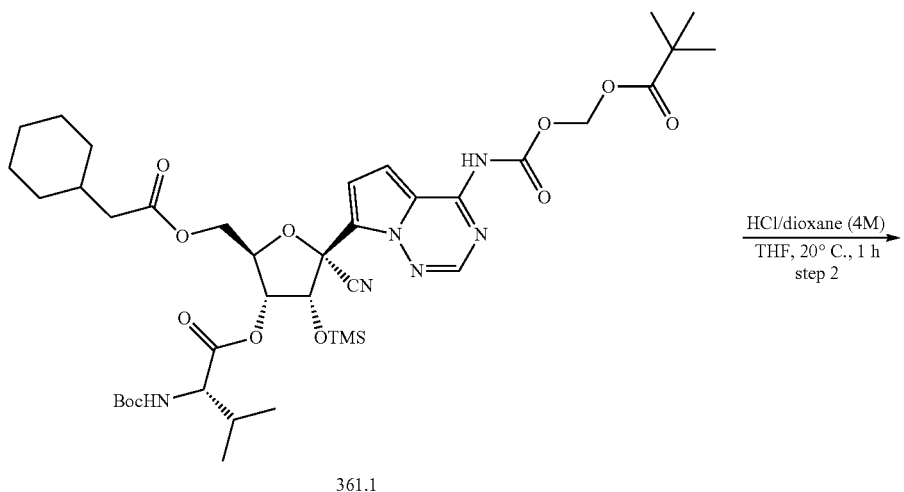

361.1

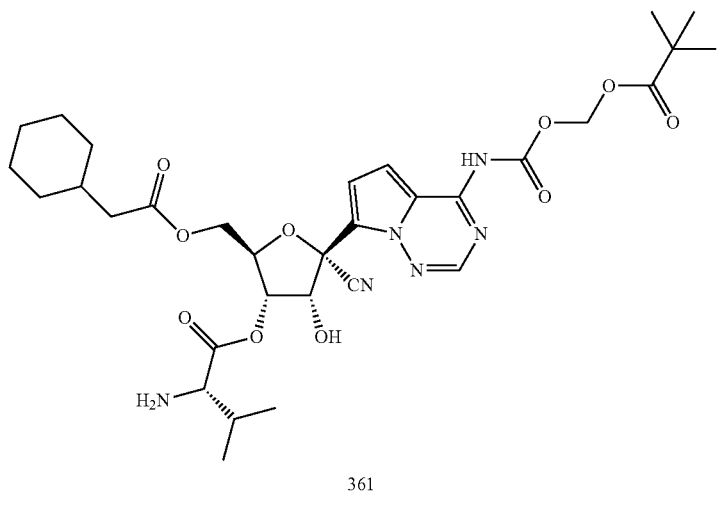

361

Step 1. Synthesis of (2R,3R,4R,5R)-5-cyano-2-((2-cyclohexylacetoxy)methyl)-5-(4-(((((pivaloyloxy)methoxy)carbonyl)amino)pyrrolo[2,1-f][1,2,4]triazin-7-yl)-4-((trimethylsilyl)oxy)tetrahydrofuran-3-yl (tert-butoxycarbonyl)-L-valinate (358.1)

The title compound 361.1 was prepared according to the procedure of Example 209, Step 1, using 27.1 and ((chlorocarbonyl)oxy)methyl pivalate. MS (ESI): mass calcd. for $C_{40}H_{60}N_6O_{12}Si$, 844.40 m/z found 845.3 [M+H]$^+$. $^1$H NMR (400 MHz, DMSO) δ 11.31 (s, 1H), 8.41 (s, 1H), 7.36 (s, 1H), 7.15 (d, J=8.4 Hz, 1H), 7.09 (s, 1H), 5.84 (s, 2H), 5.25 (s, 1H), 5.15 (t, J=5.2 Hz, 1H), 4.50 (d, J=4.0 Hz, 1H), 4.34 (d, J=9.6 Hz, 1H), 4.25 (dd, J=12.4, 5.2 Hz, 1H), 4.06-4.01 (m, 1H), 2.18-2.08 (m, 3H), 1.59 (d, J=12.0 Hz, 6H), 1.38 (s, 9H), 1.17 (s, 11H), 0.94-0.83 (m, 9H), 0.02 (s, 9H).

Step 2. Synthesis of (2R,3S,4R,5R)-5-cyano-2-((2-cyclohexylacetoxy)methyl)-4-hydroxy-5-(4-(((((pivaloyloxy)methoxy)carbonyl)amino)pyrrolo[2,1-f][1,2,4]triazin-7-yl)tetrahydrofuran-3-yl L-valinate (361)

The title compound 361 was prepared according to the procedure of Example 209, Step 2, using 361.1. MS (ESI): mass calcd. for $C_{32}H_{44}N_6O_{10}$, 672.31 m/z found 673.2 [M+H]$^+$. $^1$H NMR (400 MHz, DMSO) δ 8.34 (s, 1H), 7.26 (s, 1H), 7.06 (d, J=4.8 Hz, 1H), 6.70 (d, J=6.0 Hz, 1H), 5.83 (s, 2H), 5.18-5.12 (m, 1H), 5.10-5.06 (m, 1H), 4.53-4.45 (m, 1H), 4.30-4.26 (m, 1H), 4.24-4.19 (m, 1H), 3.25 (d, J=5.2 Hz, 1H), 2.20-2.06 (m, 2H), 2.03-1.96 (m, 1H), 1.62-1.50 (m, 6H), 1.17 (s, 9H), 1.12-0.98 (m, 3H), 0.96-0.80 (m, 8H).

Example 213. Synthesis of ((2R,3S,4R,5R)-5-cyano-4-hydroxy-5-(4-isobutyramidopyrrolo[2,1-f][1,2,4]triazin-7-yl)-3-(propionyloxy)tetrahydrofuran-2-yl)methyl L-valinate (Compound 362)

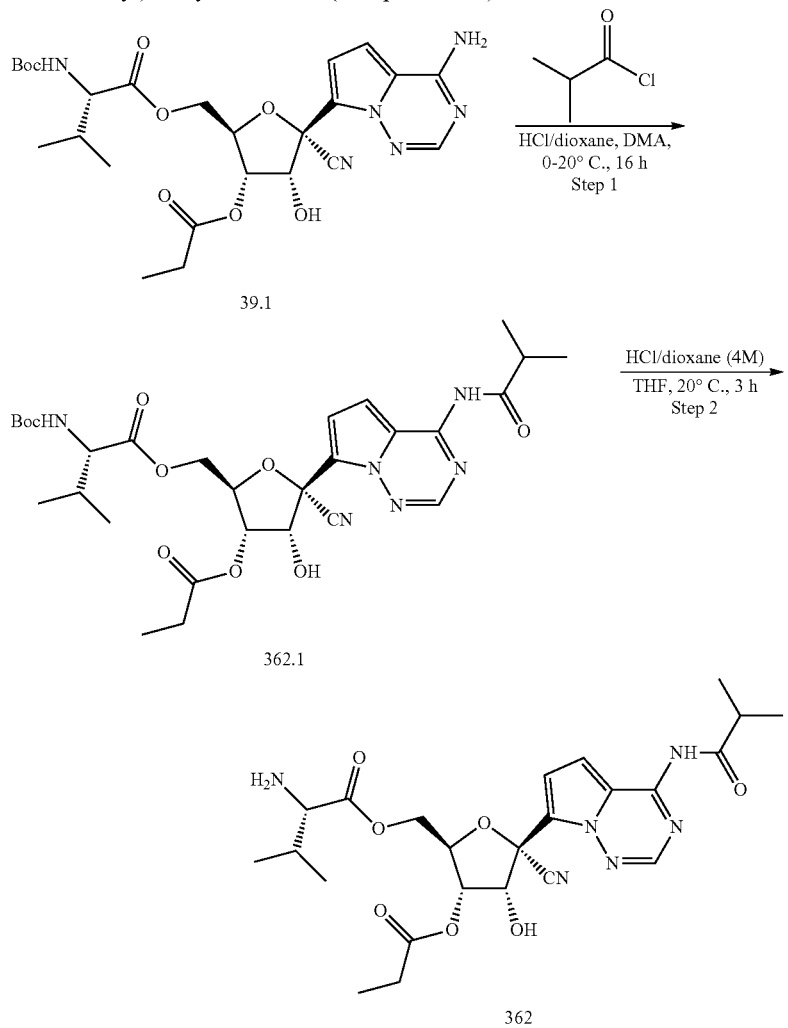

Step 1. Synthesis of ((2R,3S,4R,5R)-5-cyano-4-hydroxy-5-(4-isobutyramidopyrrolo[2,1-f][1,2,4]triazin-7-yl)-3-(propionyloxy)tetrahydrofuran-2-yl)methyl (tert-butoxycarbonyl)-L-valinate (362.1)

Compound 362.1 was prepared according to the procedure of Example 195, Step 1, using 39.1 and isobutyryl chloride. MS (ESI): mass calcd. for $C_{29}H_{40}N_6O_9$, 616.67, m/z found 617.2 [M+H]$^+$.

Step 2. Synthesis of Synthesis of ((2R,3S,4R,5R)-5-cyano-4-hydroxy-5-(4-isobutyramidopyrrolo[2,1-f][1,2,4]triazin-7-yl)-3-(propionyloxy)tetrahydrofuran-2-yl)methyl L-valinate (Compound 362)

Compound 362 was prepared according to the procedure of Example 19, Step 2, using 362.1. MS (ESI): mass calcd. for $C_{24}H_{32}NO_7$, 516.56, m/z found 517.1 [M+H]$^+$. 1H NMR (400 MHz, DMSO) δ 10.90 (s, 1H), 8.41 (s, 1H), 7.27 (d, J=4.8 Hz, 1H), 7.11 (d, J=4.8 Hz, 1H), 6.71 (d, J=6.4 Hz, 1H), 5.15 (t, J=5.2 Hz, 1H), 5.06 (t, J=6.0 Hz, 1H), 4.58-4.50 (m, 1H), 4.33-4.25 (m, 2H), 3.12-3.08 (m, 2H), 2.44-2.38 (m, 2H), 1.77-1.75 (m, 1H), 1.15 (d, J=6.8 Hz, 6H), 1.08 (t, J=7.6 Hz, 3H), 0.77 (dd, J=16.0, 9.2 Hz, 6H).

Example 214. Synthesis of ((2R,3S,4R,5R)-5-(4-(((acetoxymethoxy)carbonyl)amino)pyrrolo[2,1-f][1,2,4]triazin-7-yl)-5-cyano-3,4-dihydroxytetrahydrofuran-2-yl)methyl 2-(1-aminocyclohexyl)acetate (Compound 363)

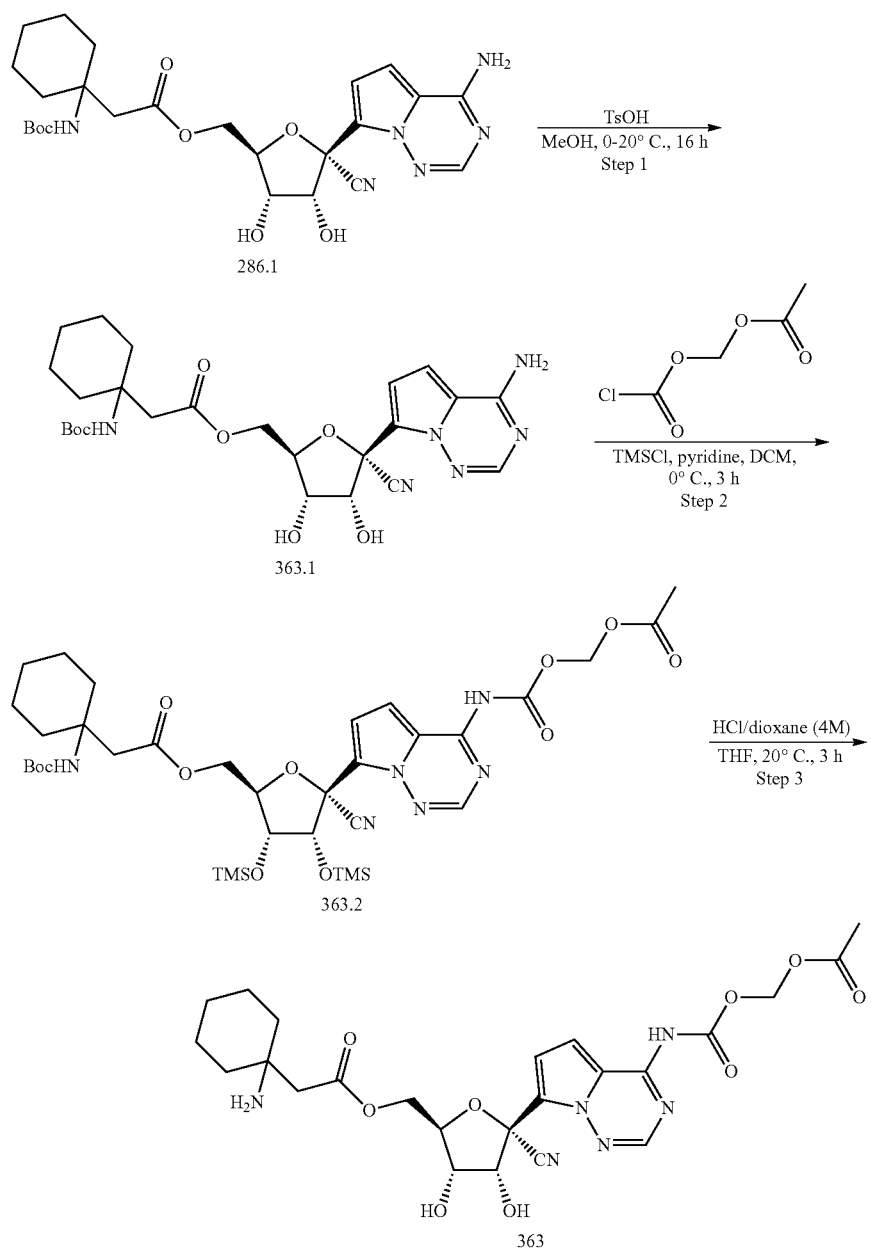

Step 1. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl 2-(1-((tert-butoxycarbonyl)amino)cyclohexyl)acetate (363.1)

Compound 363.1 was prepared according to the procedure of Example 17, Step 1, using 363.1. MS (ESI): mass calcd. for $C_{25}H_{34}N_6O_7$, 530.58, m/z found 531.2 [M+H]$^+$.

Step 2. Synthesis of (2R,3R,4R,5R)-5-cyano-2-((2-phenylacetoxy)methyl)-5-(4-((((pivaloyloxy)methoxy)carbonyl)amino)pyrrolo[2,1-f][1,2,4]triazin-7-yl)-4-((trimethylsilyl)oxy)tetrahydrofuran-3-yl (tert-butoxycarbonyl)-L-valinate (360.1)

Compound 363.2 was prepared according to the procedure of Example 206, Step 1, using 363.1 and ((chlorocarbonyl)oxy)methyl acetate. MS (ESI): mass calcd. for $C_{35}H_{54}N_6O_{11}Si_2$, 791.02, m/z found 791.3 [M+H]$^+$.

Step 3. Synthesis of ((2R,3S,4R,5R)-5-(4-(((acetoxymethoxy)carbonyl)amino)pyrrolo[2,1-f][1,2,4]triazin-7-yl)-5-cyano-3,4-dihydroxytetrahydrofuran-2-yl)methyl 2-(1-aminocyclohexyl)acetate (Compound 363)

Compound 363 was prepared according to the procedure of Example 19, Step 2, using 363.2. MS (ESI): mass calcd. for $C_{24}H_{30}N_6O_9$, 546.54, m/z found 547.1 [M+H]$^+$. $^1$H NMR (400 MHz, DMSO) δ 8.28 (s, 1H), 8.23 (s, 1H), 7.16 (d, J=4.4 Hz, 1H), 6.99 (d, J=4.8 Hz, 1H), 6.43-6.40 (m, 1H), 5.78 (s, 2H), 4.72 (d, J=4.4 Hz, 1H), 4.36-4.24 (m, 2H), 4.20 (dd, J=11.6, 5.8 Hz, 1H), 3.96 (t J=5.8 Hz, 1H), 2.44 (s, 2H), 2.11 (s, 3H), 1.61-1.22 (m, 10H).

Example 215. Synthesis of ((2R,3S,4R,5R)-5-(4-(((acetoxymethoxy)carbonyl)amino)pyrrolo[2,1-f][1,2,4]triazin-7-yl)-5-cyano-4-hydroxy-3-(propionyloxy)tetrahydrofuran-2-yl)methyl L-valinate (Compound 364)

Step 1. Synthesis of ((2R,3R,4R,5R)-5-(4-(((acetoxymethoxy)carbonyl)amino)pyrrolo[2,1-f][1,2,4]triazin-7-yl)-5-cyano-3-(propionyloxy)-4-((trimethylsilyl)oxy)tetrahydrofuran-2-yl)methyl (tert-butoxycarbonyl)-L-valinate (364.1)

The title compound 364.1 was prepared according to the procedure of Example 209, Step 1, using 39.1 and ((chlorocarbonyl)oxy)methyl acetate. MS (ESI): mass calcd. for $C_{32}H_{46}N_6O_{12}Si$, 734.29 m/z found 735.3 [M+H]$^+$. $^1$H NMR (400 MHz, DMSO) δ 12.55-10.65 (m, 1H), 8.32 (s, 1H), 7.27 (s, 1H), 7.18 (d, J=8.0 Hz, 1H), 7.07 (s, 1H), 5.79 (s, 2H), 5.27 (d, J=4.4 Hz, 1H), 5.15 (t, J=5.2 Hz, 1H), 4.54 (d, J=4.0 Hz, 1H), 4.36 (s, 2H), 3.90 (t, J=6.8 Hz, 1H), 2.45-2.35 (m, 2H), 2.11 (s, 3H), 2.02-1.94 (m, 1H), 1.37 (s, 9H), 1.07 (t J=7.6 Hz, 3H), 0.81 (d, J=6.8 Hz, 6H), −0.01 (d, J=4.4 Hz, 9H).

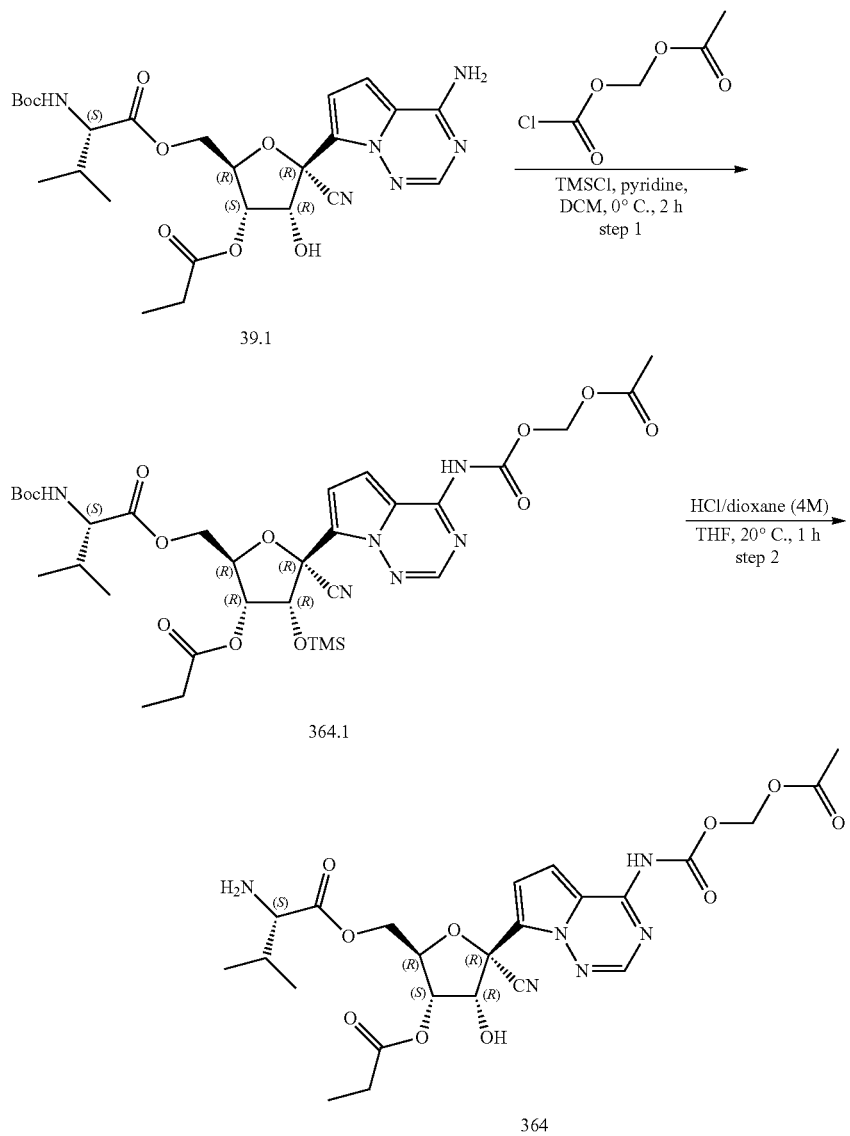

Step 2. Synthesis of ((2R,3S,4R,5R)-5-(4-(((acetoxymethoxy)carbonyl)amino)pyrrolo[2,1-f][1,2,4]triazin-7-yl)-5-cyano-4-hydroxy-3-(propionyloxy)tetrahydrofuran-2-yl)methyl L-valinate (364)

The title compound 364 was prepared according to the procedure of Example 209, Step 2, using 364.1. MS (ESI): mass calcd. for $C_{24}H_{30}N_6O_{10}$, 562.20 m/z found 563.2 [M+H]$^+$. $^1$H NMR (400 MHz, DMSO) δ 8.36 (s, 1H), 7.30-7.26 (m, 1H), 7.07 (d, J=4.4 Hz, 1H), 6.70 (d, J=6.4 Hz, 1H), 5.80 (s, 2H), 5.16 (t, J=5.2 Hz, 1H), 5.06 (t, J=6.0 Hz, 1H), 4.55-4.50 (m, 1H), 4.34-4.24 (m, 2H), 3.14 (d, J=5.2 Hz, 1H), 2.41 (q, J=7.6 Hz, 2H), 2.12 (s, 3H), 1.82-1.72 (m, 1H), 1.08 (t, J=7.6 Hz, 3H), 0.80 (d, J=6.8 Hz, 3H), 0.75 (d, J=6.8 Hz, 3H).

Example 216. Synthesis of ((2R,3S,4R,5R)-5-cyano-4-hydroxy-5-(4-((((pivaloyloxy)methoxy)carbonyl)amino)pyrrolo[2,1-f][1,2,4]triazin-7-yl)-3-(propionyloxy)tetrahydrofuran-2-yl)methyl L-valinate (Compound 365)

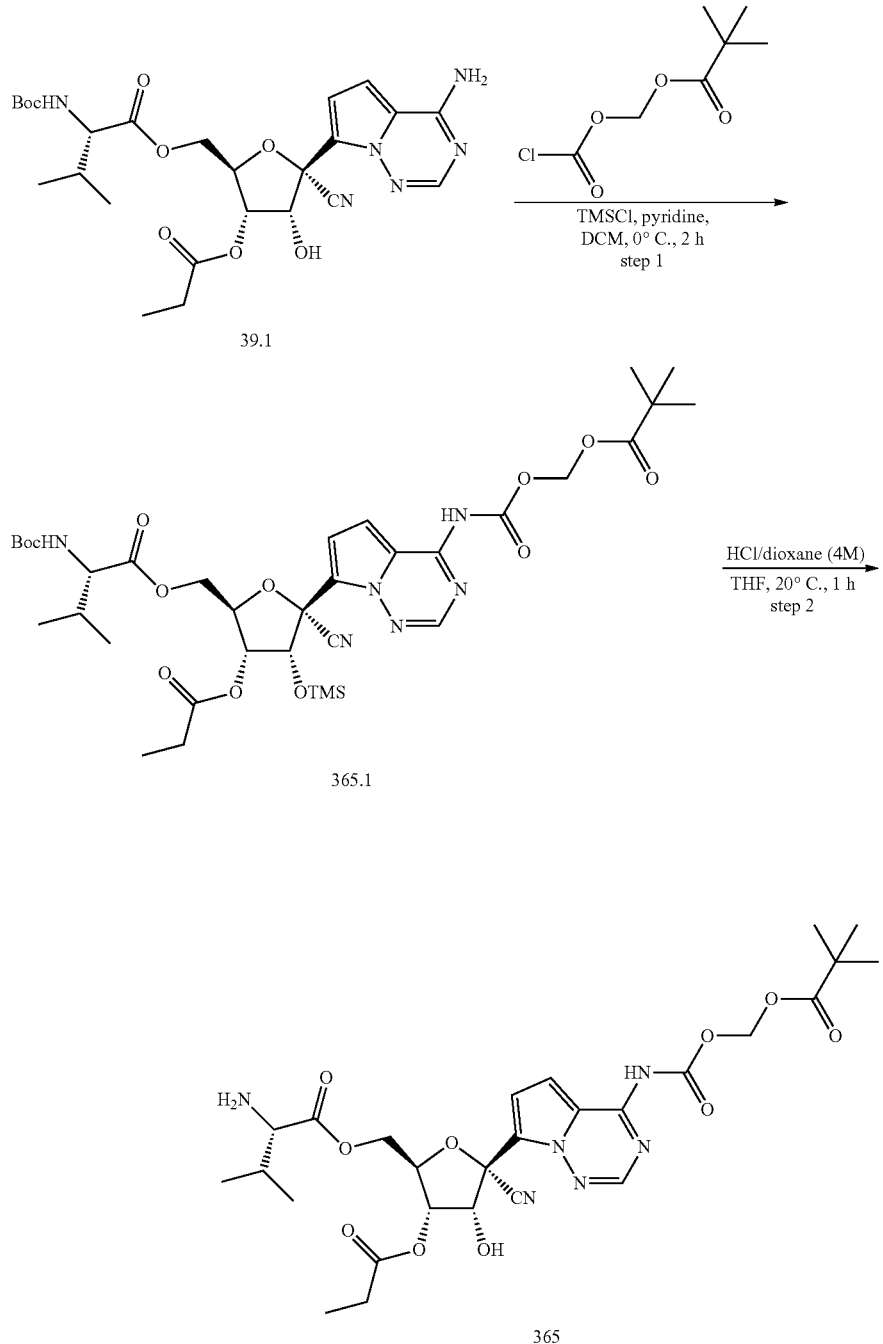

Step 1. Synthesis of ((2R,3R,4R,5R)-5-cyano-5-(4-((((pivaloyloxy)methoxy)carbonyl)amino)pyrrolo[2,1-f][1,2,4]triazin-7-yl)-3-(propionyloxy)-4-((trimethylsilyl)oxy)tetrahydrofuran-2-yl)methyl (tert-butoxycarbonyl)-L-valinate (365.1)

The title compound 365.1 was prepared according to the procedure of Example 209, Step 1, using 39.1 and ((chlorocarbonyl)oxy)methyl pivalate. MS (ESI): mass calcd. for $C_{35}H_{52}N_6O_{12}Si$, 776.34 m/z found 777.3 [M+H]$^+$. $^1$H NMR (400 MHz, DMSO) δ 11.39 (s, 1H), 8.36 (s, 1H), 7.31 (s, 1H), 7.18 (d, J=8.0 Hz, 1H), 7.09 (s, 1H), 5.83 (s, 2H), 5.25 (d, J=4.8 Hz, 1H), 5.14 (t, J=5.2 Hz, 1H), 4.54 (dd, J=9.2, 4.8 Hz, 1H), 4.38-4.34 (m, 2H), 3.98-3.83 (m, 1H), 2.45-2.31 (m, 2H), 2.03-1.90 (m, 1H), 1.40-1.25 (m, 9H), 1.17 (s, 9H), 1.06 (t, J=7.6 Hz, 3H), 0.81 (d, J=6.8 Hz, 6H), 0.00 (s, 9H).

Step 2. Synthesis of ((2R,3S,4R,5R)-5-cyano-4-hydroxy-5-(4-((((pivaloyloxy)methoxy)carbonyl)amino)pyrrolo[2,1-f][1,2,4]triazin-7-yl)-3-(propionyloxy)tetrahydrofuran-2-yl)methyl L-valinate (365)

The title compound 365 was prepared according to the procedure of Example 209, Step 2, using 365.1. MS (ESI): mass calcd. for $C_{27}H_{36}N_6O_{10}$, 604.25 m/z found 605.2 [M+H]$^+$. $^1$H NMR (400 MHz, DMSO) δ 8.35 (s, 1H), 7.27 (d, J=4.4 Hz, 1H), 7.07 (d, J=4.8 Hz, 1H), 6.70 (d, J=6.4 Hz, 1H), 5.83 (s, 2H), 5.15 (t, J=5.2 Hz, 1H), 5.06 (t, J=6.0 Hz, 1H), 4.55-4.49 (m, 1H), 4.34-4.24 (m, 2H), 3.13 (d, J=5.2 Hz, 1H), 2.44-2.36 (m, 2H), 1.81-1.70 (m, 1H), 1.17 (s, 9H), 1.12-1.06 (m, 3H), 0.83-0.78 (m, 3H), 0.77-0.72 (m, 3H).

Example 217. Synthesis of (((((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methoxy)carbonyl)oxy)methyl acetate (Compound 366)

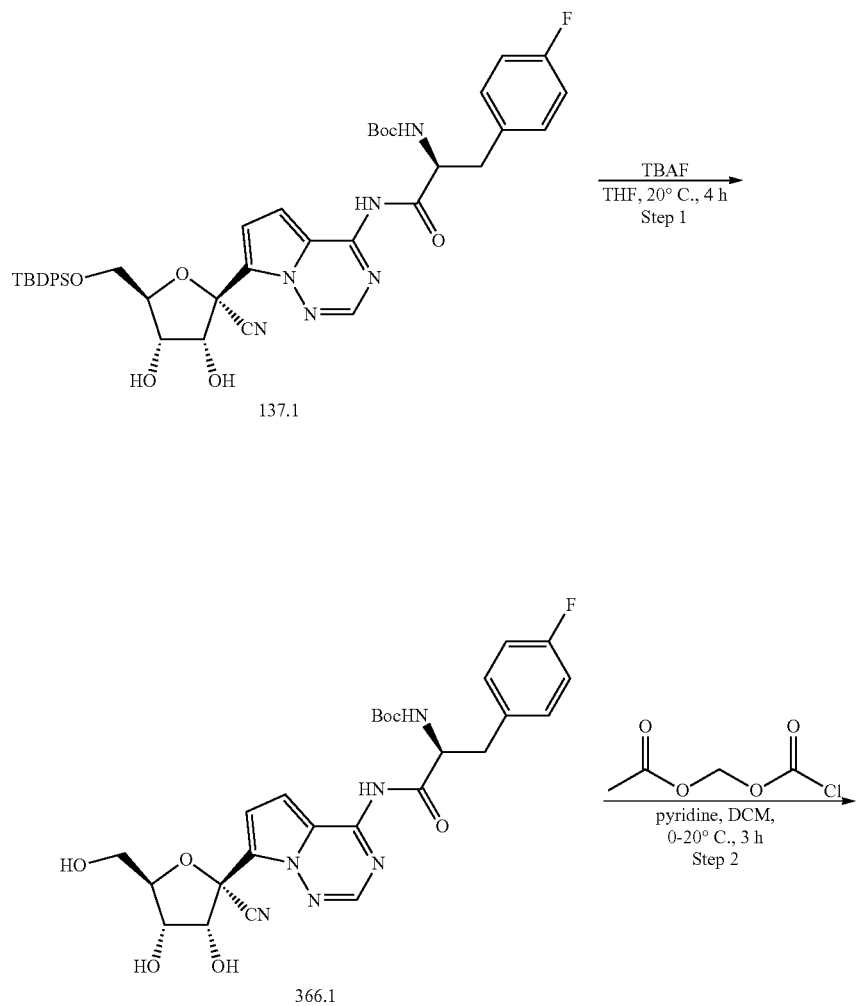

-continued

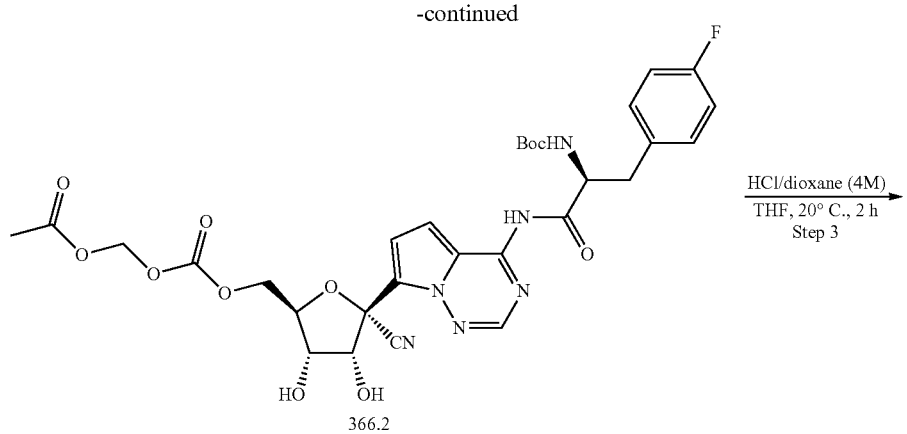
366.2

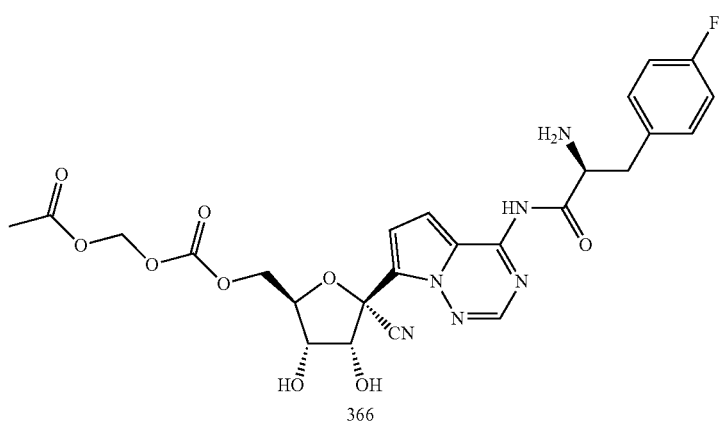
366

Step 1. Synthesis of tert-butyl ((S)-1-((7-((2R,3R,4S,5R)-2-cyano-3,4-dihydroxy-5-(hydroxymethyl)tetrahydrofuran-2-yl)pyrrolo[2,1-f][1,2,4]triazin-4-yl)amino)-3-(4-fluorophenyl)-1-oxopropan-2-yl)carbamate (366.1)

Compound 366.1 was prepared according to the procedure of Example 97, Step 1, using 137.1. MS (ESI): mass calcd. for $C_{26}H_{29}FN_6O_7$, 556.55, m/z found 557.1 $[M+H]^+$.

Step 2. Synthesis of (((((2R,3S,4R,5R)-5-(4-((S)-2-((tert-butoxycarbonyl)amino)-3-(4-fluorophenyl)propanamido)pyrrolo[2,1-f][1,2,4]triazin-7-yl)-5-cyano-3,4-dihydroxytetrahydrofuran-2-yl)methoxy)carbonyl)oxy)methyl acetate (366.2)

To a solution of 366.1 (50 mg, 0.089 mmol) in DCM (2 mL) was added pyridine (142.06 mg, 1.796 mmol) and [(chlorocarbonyl)oxy]methyl acetate (20.55 mg, 0.134 mmol) at 0° C., the mixture was stirred at 25° C. for 4 h. The reaction was washed with DCM (5 mL×3). The combined organics were dried over sodium sulfate and concentrated in vacuo. The crude product was purified by prep-HPLC to afford 366.2 (6 mg, 9% yield) as a white solid. MS (ESI): mass calcd. for $C_{30}H_{33}FN_6O_{11}$, 672.62, m/z found 673.2 $[M+H]^+$. $^1$H NMR (400 MHz, DMSO) δ 11.23 (s, 1H), 8.44 (s, 1H), 7.42 (t, J=5.6 Hz, 2H), 7.19-7.15 (m, 2H), 7.12 (t, J=8.4 Hz, 2H), 7.03-7.01 (m, 1H), 6.51 (d, J=5.2 Hz, 1H), 5.67 (s, 2H), 5.55-5.50 (m, 1H), 4.83-4.80 (m, 1H), 4.69 (t, J=4.4 Hz, 1H), 4.49 (d, J=9.2 Hz, 1H), 4.33-4.27 (m, 2H), 3.96-3.92 (m, 1H), 3.11 (d, J=11.4 Hz, 1H), 2.86-2.77 (m, 1H), 1.32 (s, 9H).

Step 3. Synthesis of (((((2R,3S,4R,5R)-5-(4-((S)-2-amino-3-(4-fluorophenyl)propanamido)pyrrolo[2,1-f][1,2,4]triazin-7-yl)-5-cyano-3,4-dihydroxytetrahydrofuran-2-yl)methoxy)carbonyl)oxy)methyl acetate (Compound 366)

Compound 366 was prepared according to the procedure of Example 19, Step 2, using 366.2. MS (ESI): mass calcd. for $C_{25}H_{25}FN_6O_9$, 572.51, m/z found 573.2 $[M+H]^+$. $^1$H NMR (400 MHz, DMSO) δ 8.59 (d, J=8.0 Hz, 1H), 7.90 (s, 1H), 7.69 (s, 1H), 7.38 (dd, J=8.0, 6.0 Hz, 2H), 7.17 (s, 1H), 7.06-7.03 (m, 3H), 6.77 (d, J=4.4 Hz, 1H), 6.38 (d, J=6.0 Hz, 1H), 5.67 (s, 2H), 5.50 (d, J=5.6 Hz, 1H), 4.93-4.90 (m, 1H), 4.65 (t, J=5.2 Hz, 1H), 4.44-4.42 (m, 1H), 4.35-4.20 (m, 2H), 3.93-3.92 (m, 1H), 3.18 (dd, J=14.0, 3.6 Hz, 1H), 3.07-2.98 (m, 1H), 2.08 (s, 3H). $^{19}$F NMR (377 MHz, DMSO) δ −116.75 (s, 1F).

Example 218. Synthesis of (((7-((2R,3R,4S,5R)-5-((2-(1-aminocyclohexyl)acetoxy)methyl)-2-cyano-3,4-dihydroxytetrahydrofuran-2-yl)pyrrolo[2,1-f][1,2,4]triazin-4-yl)carbamoyl)oxy)methyl pivalate (Compound 367)

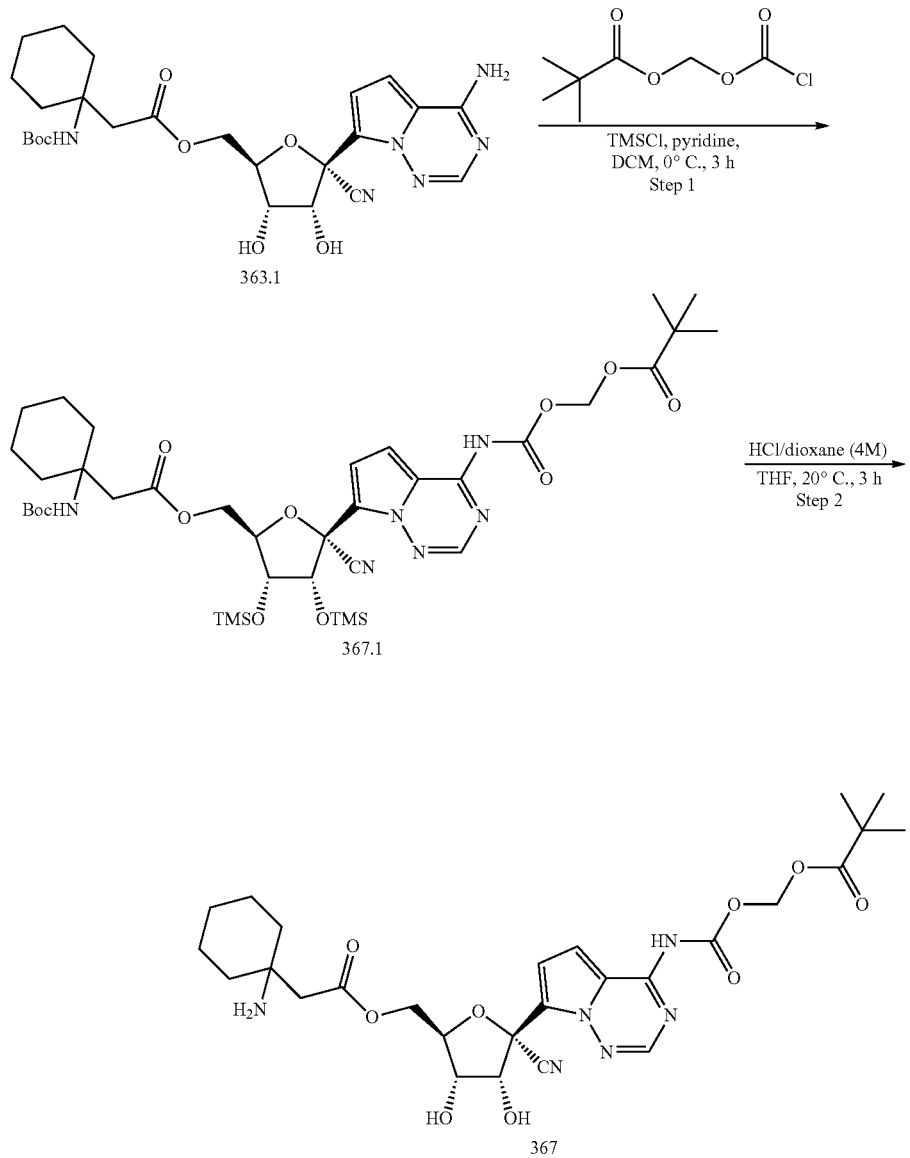

Step 1. Synthesis of (((7-((2R,3R,4R,5R)-5-((2-(1-((tert-butoxycarbonyl)amino)cyclohexyl)acetoxy)methyl)-2-cyano-3,4-bis((trimethylsilyl)oxy)tetrahydrofuran-2-yl)pyrrolo[2,1-f][1,2,4]triazin-4-yl)carbamoyl)oxy)methyl pivalate (367.1)

Compound 367.1 was prepared according to the procedure of Example 206, Step 1, using 363.1 and ((chlorocarbonyl)oxy)methyl pivalate. MS (ESI): mass calcd. for $C_{38}H_{60}N_6O_{11}Si_2$, 833.10, m/z found 833.3 [M+H]$^+$.

Step 2. Synthesis of Synthesis of (((7-((2R,3R,4S,5R)-5-((2-(1-aminocyclohexyl)acetoxy)methyl)-2-cyano-3,4-dihydroxytetrahydrofuran-2-yl)pyrrolo[2,1-f][1,2,4]triazin-4-yl)carbamoyl)oxy)methyl pivalate (Compound 367)

The title compound 367 was prepared according to the procedure of Example 19, Step 2, using 367.1. MS (ESI): mass calcd. for $C_{27}H_{36}N_6O_9$, 588.62, m/z found 589.2 [M+H]$^+$. $^1$H NMR (400 MHz, DMSO) δ 8.27 (s, 1H), 7.12 (d, J=4.4 Hz, 1H), 6.97 (d, J=4.8 Hz, 1H), 6.43-6.40 (m, 1H), 5.80 (s, 2H), 4.71 (d, J=4.4 Hz, 1H), 4.35-4.14 (m, 3H), 3.96 (t, J=5.2 Hz, 1H), 2.40 (s, 2H), 1.66-1.21 (m, 10H), 1.17 (s, 9H).
Example 219. Synthesis (2R,3S,4R,5R)-2-((2-(1-aminocyclohexyl)acetoxy)methyl)-5-(4-aminopyrrolo[2,1-f][1,2,4]triazin-7-yl)-5-cyano-4-hydroxytetrahydrofuran-3-yl 2-cyclohexylacetate (Compound 368)
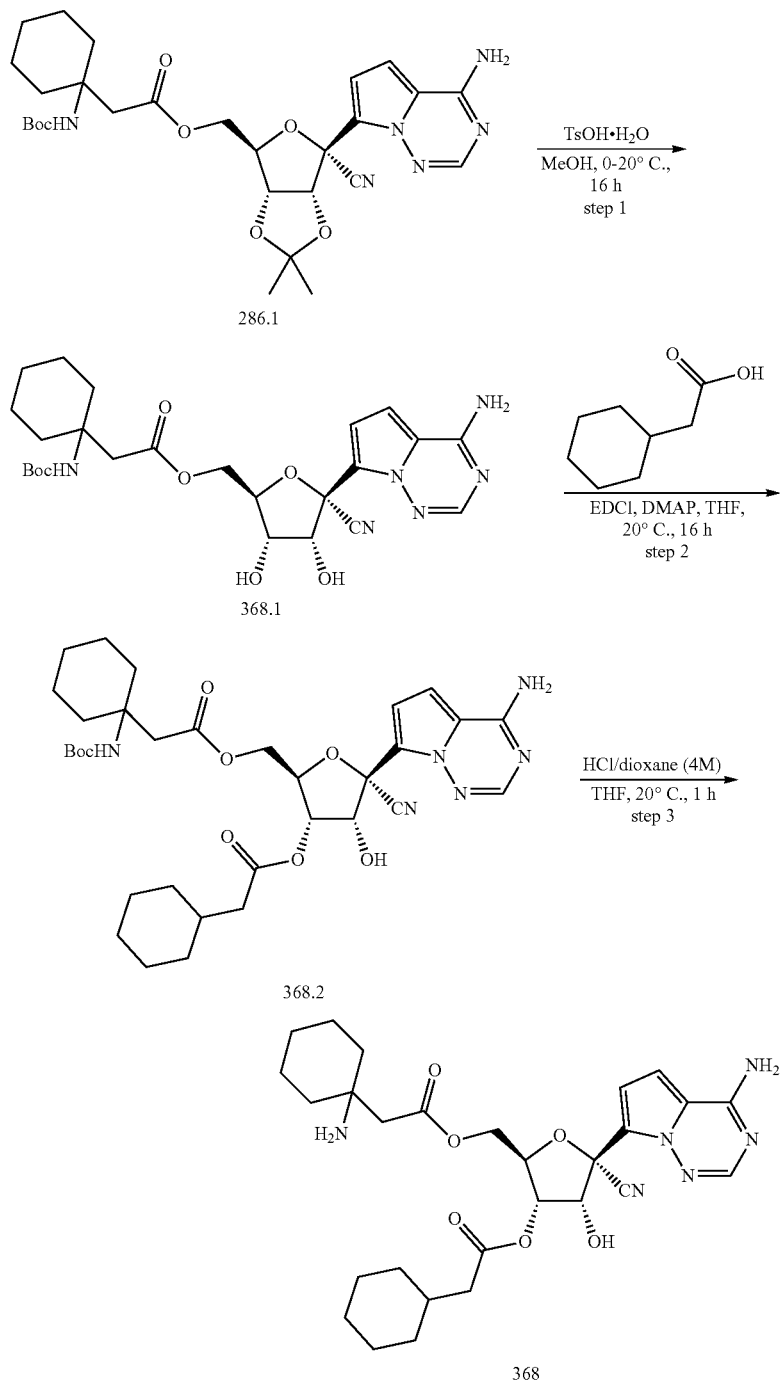

Step 1. Synthesis of ((2R,3S,4R,5R)-5-(4-aminopyr-rolo[2,1-f][1,2,4]triazin-7-yl)-5-cyano-3,4-dihydroxytetrahydrofuran-2-yl)methyl 2-(1-((tert-butoxycarbonyl)amino)cyclohexyl)acetate (368.1)

The title compound 368.1 was prepared according to the procedure of Example 17, Step 1, using 288.1 and TsOH·H$_2$O. MS (ESI): mass calcd. for C$_{25}$H$_{34}$N$_6$O$_7$, 530.25 m/z found 531.2 [M+H]$^+$. $^1$H NMR (400 MHz, DMSO) δ 7.92 (br s, 3H), 6.91 (d, J=4.8 Hz, 1H), 6.81 (d, J=4.8 Hz, 1H), 6.32-6.26 (m, 2H), 5.35 (d, J=6.0 Hz, 1H), 4.71 (t, J=5.6 Hz, 1H), 4.29-4.21 (m, 2H), 4.16-4.10 (m, 1H), 3.96-3.90 (m, 1H), 2.60 (s, 2H), 2.02-1.96 (m, 2H), 1.49-1.16 (m, 17H).

Step 2. Synthesis of (2R,3S,4R,5R)-5-(4-aminopyr-rolo[2,1-f][1,2,4]triazin-7-yl)-2-((2-(1-((tert- butoxycarbonyl)amino)cyclohexyl)acetoxy)methyl)-5-cyano-4-hydroxytetrahydrofuran-3-yl 2-cyclohexylacetate (368.2)

To a solution of 368.1 (250 mg, 0.471 mmol) in THF (10 mL) was added cyclohexylacetic acid (70.4 mg, 0.494 mmol), EDCI (271 mg, 1.414 mmol) and DMAP (172.7 mg, 1.414 mmol), the mixture was stirred at 25° C. for 16 h. After completion, the mixture was concentrated in vacuo to afford a residue. Then the reaction residue was diluted with water (50 mL) and extracted with EtOAc (50 mL×3). The organic layer was dried over sodium sulphate and concentrated under reduce pressure to afford a crude. The residue was purified by Prep-HPLC [Gradient: 40-70% ACN in water (0.1% FA)] to obtain 368.2 (65 mg, 20% yield) as a white solid. MS (ESI): mass calcd. for C$_{33}$H$_{46}$N$_6$O$_8$, 654.34 m/z found 655.3 [M+H]$^+$. $^1$H NMR (400 MHz, DMSO) δ 7.92 (br s, 3H), 6.93 (d, J=4.4 Hz, 1H), 6.86 (d, J=4.4 Hz, 1H), 6.59 (d, J=5.6 Hz, 1H), 6.27 (s, 1H), 5.11 (d, J=4.4 Hz, 2H), 4.44 (d, J=3.6 Hz, 1H), 4.26 (dd, J=12.0, 3.6 Hz, 1H), 4.19 (dd, J=12.0, 5.6 Hz, 1H), 2.62-2.54 (m, 2H), 2.26 (d, J=6.8 Hz, 2H), 1.95 (s, 2H), 1.77 (dd, J=11.6, 8.0 Hz, 3H), 1.62 (t, J=14.8 Hz, 3H), 1.40-1.06 (m, 20H), 1.01-0.88 (m, 2H).

Step 3. Synthesis of (2R,3S,4R,5R)-2-((2-(1-aminocyclohexyl)acetoxy)methyl)-5-(4-aminopyrrolo[2,1-f][1,2,4]triazin-7-yl)-5-cyano-4-hydroxytetrahydrofuran-3-yl 2-cyclohexylacetate (368)

The title compound 368 was prepared according to the procedure of Example 209, Step 2, using 368.2. MS (ESI): mass calcd. for C$_{28}$H$_{38}$N$_6$O$_6$, 554.29 m/z found 555.3 [M+H]$^+$. $^1$H NMR (400 MHz, DMSO) δ 7.92 (br s, 3H), 6.93 (d, J=4.4 Hz, 1H), 6.87 (d, J=4.8 Hz, 1H), 6.68-6.56 (m, 1H), 5.21-5.01 (m, 2H), 4.50-4.41 (m, 1H), 4.32-4.22 (m, 2H), 2.39-2.37 (m, 2H), 2.26 (d, J=6.8 Hz, 2H), 1.78-1.46 (m, 8H), 1.46-1.06 (m, 11H), 1.03-0.89 (m, 2H).

Example 220. Synthesis of (2R,3S,4R,5R)-5-(4-(((acetoxymethoxy)carbonyl)amino)pyrrolo[2,1-f][1,2,4]triazin-7-yl)-5-cyano-4-hydroxy-2-(hydroxymethyl)tetrahydrofuran-3-yl 2-cyclohexylacetate (Compound 369)

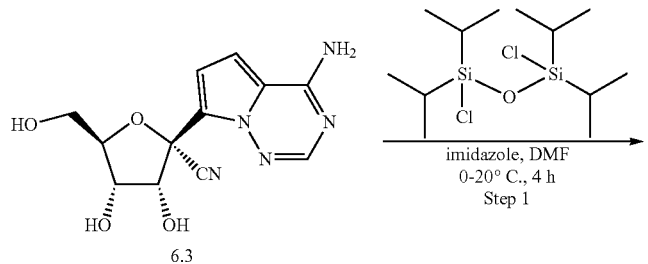

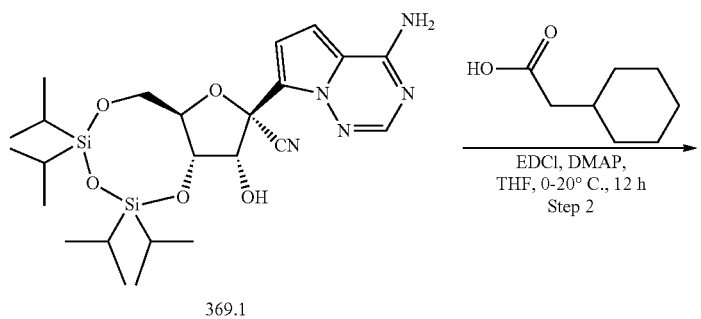

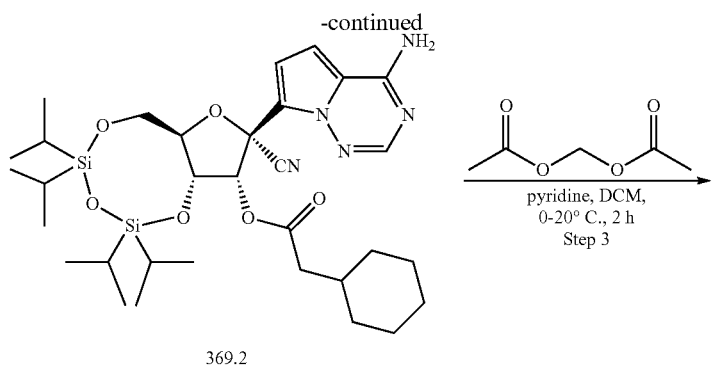

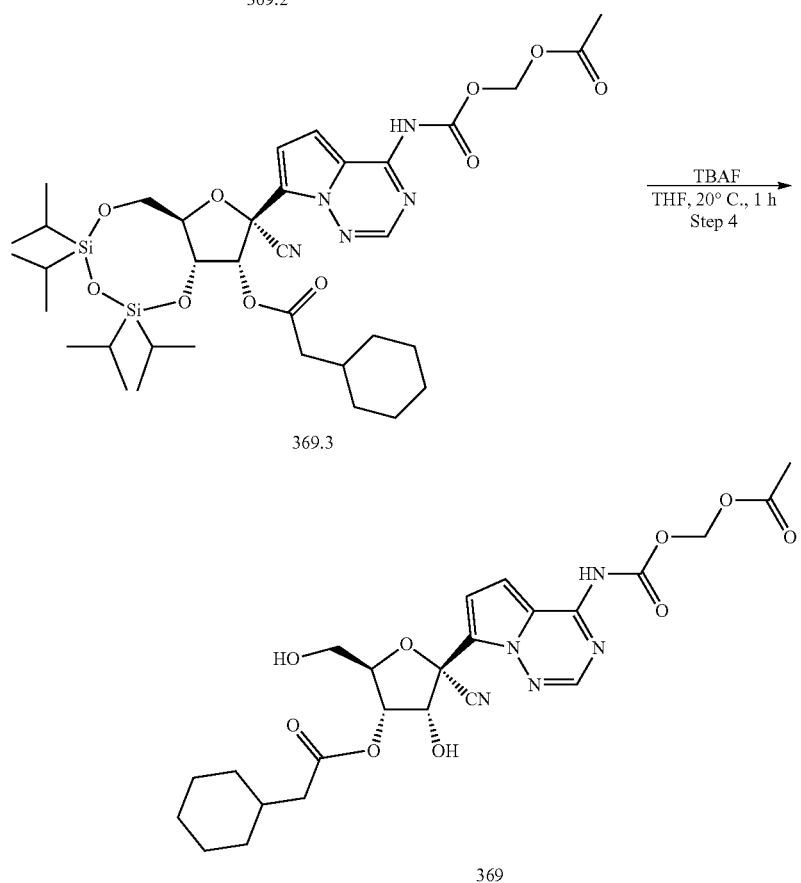

Step 1. Synthesis of (6aR,8R,9R,9aS)-8-(4-amino-pyrrolo[2,1-f][1,2,4]triazin-7-yl)-9-hydroxy-2,2,4,4-tetraisopropyltetrahydro-6H-furo[3,2-f][1,3,5,2,4]trioxadisilocine-8-carbonitrile (369.1)

To a solution of 6.3 (4 g, 0.013 mol) and imidazole (5.6 g, 0.082 mol) in DMF (40 mL) was added chloro[(chloro-diisopropylsilyl)oxy]diisopropylsilane (5.19 g, 0.016 mmol) at 0° C., the mixture was stirred at 25° C. for 4 h. The reaction was extracted with EA (10 mL×3). The combined organics were dried over sodium sulfate and concentrated in vacuo. The residue was purified by flash column chromatography (EA/PE from 0% to 30%) to obtain 369.1 as a white solid (5.00 g, 65% yield). MS (ESI): mass calcd. for $C_{24}H_{39}N_5O_5Si_2$, 533.78, m/z found 534.2 [M+H]$^+$.

Step 2. Synthesis of (6aR,8R,9R,9aR)-8-(4-amino-pyrrolo[2,1-f][1,2,4]triazin-7-yl)-8-cyano-2,2,4,4-tetraisopropyltetrahydro-6H-furo[3,2-f][1,3,5,2,4]trioxadisilocin-9-yl 2-cyclohexylacetate (369.2)

The compound 369.2 was prepared according to the procedure of Example 19, Step 1, using 369.1 and 2-cyclohexylacetic acid. MS (ESI): mass calcd. for $C_{32}H_{51}N_5O_6Si_2$, 657.96, m/z found 658.3 [M+H]$^+$ 0.1H NMR (400 MHz, DMSO) δ 8.01 (d, J=18.8 Hz, 2H), 7.89 (s, 1H), 6.93 (d, J=4.4 Hz, 1H), 6.82 (d, J=4.4 Hz, 1H), 5.87 (d, J=5.2 Hz, 1H), 4.54 (dd, J=8.8, 5.2 Hz, 1H), 4.14 (t, J=10.4 Hz, 2H), 4.01-3.91 (m, 1H), 2.35 (d, J=6.4 Hz, 2H), 1.88-1.72 (m, 3H), 1.62-1.60 (m, 3H), 1.23-1.09 (m, 3H), 1.08-0.84 (m, 30H).

Step 3. Synthesis of (6aR,8R,9R,9aR)-8-(4-(((acetoxymethoxy)carbonyl)amino)pyrrolo[2,1-f][1,2,4]triazin-7-yl)-8-cyano-2,2,4,4-tetraisopropyltetrahydro-6H-furo[3,2-f][1,3,5,2,4]trioxadisilocin-9-yl 2-cyclohexylacetate (369.3)

The compound 369.3 was prepared according to the procedure of Example 206, Step 1, using 369.2 and ((chlorocarbonyl)oxy)methyl acetate. MS (ESI): mass calcd. for $C_{36}H_{55}N_5O_{10}Si_2$, 774.03, m/z found 774.3 [M+H]$^+$.

Step 4. Synthesis of (2R,3S,4R,5R)-5-(4-(((acetoxymethoxy)carbonyl)amino)pyrrolo[2,1-f][1,2,4]triazin-7-yl)-5-cyano-4-hydroxy-2-(hydroxymethyl)tetrahydrofuran-3-yl 2-cyclohexylacetate (Compound 369)

The compound 369 was prepared according to the procedure of Example 97, Step 1, using 369.3. MS (ESI): mass calcd. for $C_{24}H_{29}N_5O_9$, 531.52, m/z found 532.2 [M+H]$^+$.
$^1$H NMR (400 MHz, DMSO) δ 11.28 (s, 1H), 8.43 (s, 1H), 7.31-7.30 (m, 1H), 7.11-7.10 (m, 1H), 6.58 (d, J=6.8 Hz, 1H), 5.81 (s, 2H), 5.26-5.14 (m, 1H), 5.04 (t, J=5.6 Hz, 1H), 4.95 (t J=6.0 Hz, 1H), 4.28-4.26 (m, 1H), 3.75-3.43 (m, 2H), 2.27 (d, J=6.8 Hz, 2H), 2.12 (s, 3H), 1.85-1.58 (m, 6H), 1.28-1.09 (m, 3H), 0.96-0.90 (m, 2H).

Example 221. Synthesis of ((((7-((2R,3R,4S,5R)-2-cyano-4-(2-cyclohexylacetoxy)-3-hydroxy-5-(hydroxymethyl)tetrahydrofuran-2-yl)pyrrolo[2,1-f][1,2,4]triazin-4-yl)carbamoyl)oxy)methyl pivalate (Compound 370)

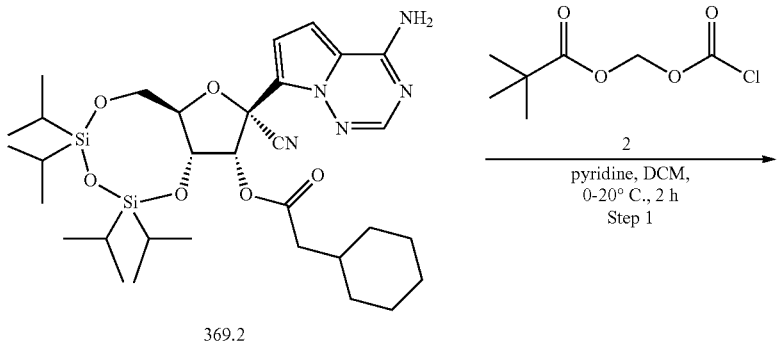

369.2

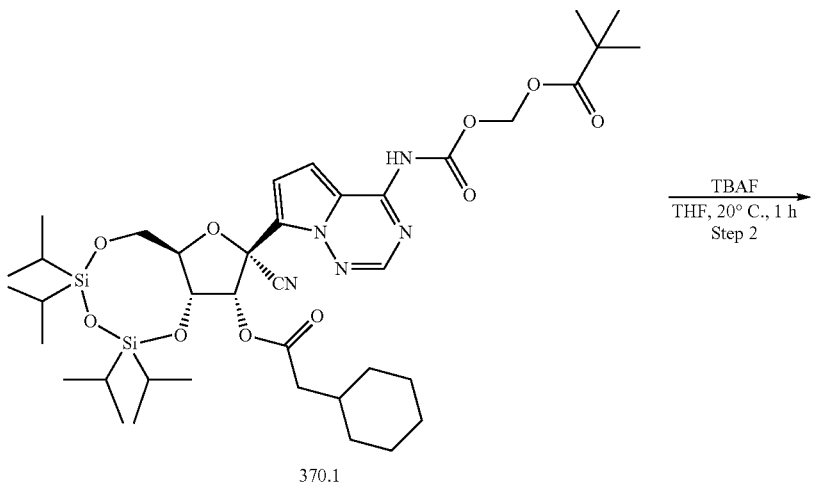

370.1

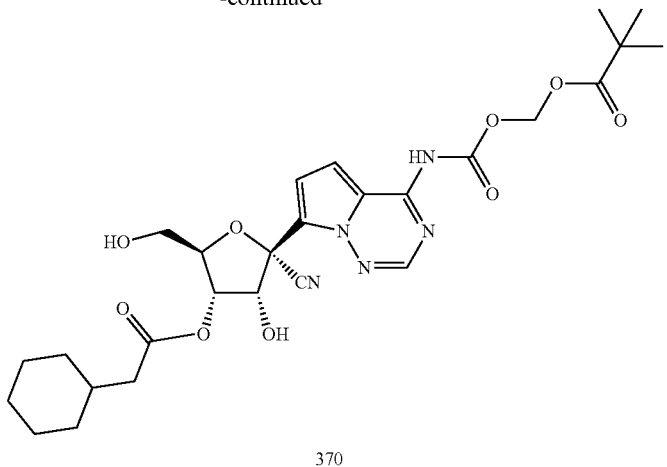

370

Step 1. Synthesis of (((7-((6aR,8R,9R,9aR)-8-cyano-9-(2-cyclohexylacetoxy)-2,2,4,4-tetraisopropyltetrahydro-6H-furo[3,2-f][1,3,5,2,4]trioxadisilocin-8-yl)pyrrolo[2,1-f][1,2,4]triazin-4-yl)carbamoyl)oxy)methyl pivalate (370.1)

The compound 370.1 was prepared according to the procedure of Example 206, Step 1, using 369.2 and ((chlorocarbonyl)oxy)methyl pivalate. MS (ESI): mass calcd. for $C_{39}H_{61}N_5O_{10}Si_2$, 816.11, m/z found 816.3[M+H]$^+$.

Step 2. Synthesis of (((7-((2R,3R,4S,5R)-2-cyano-4-(2-cyclohexylacetoxy)-3-hydroxy-5-(hydroxymethyl)tetrahydrofuran-2-yl)pyrrolo[2,1-f][1,2,4]triazin-4-yl)carbamoyl)oxy)methyl pivalate (Compound 370)

The title compound 370 was prepared according to the procedure of Example 97, Step 1, using 370.1. MS (ESI): mass calcd. for $C_{27}H_{35}N_5O_9$, 573.60, m/z found 574.3 [M+H] 1H NMR (400 MHz, DMSO) δ 11.28 (s, 1H), 8.42 (s, 1H), 7.30-7.28 (s, 1H), 7.11-7.09 (s, 1H), 6.58 (d, J=6.4 Hz, 1H), 5.84 (s, 2H), 5.31-5.13 (m, 1H), 5.03 (t, J=5.6 Hz, 1H), 4.94 (t, J=6.0 Hz, 1H), 4.28 (d, J=3.6 Hz, 1H), 3.69-3.46 (m, 2H), 2.26 (d, J=6.8 Hz, 2H), 1.88-1.70 (m, 3H), 1.62-1.58 (m, 3H), 1.25-1.10 (m, 12H), 1.02-0.91 (m, 2H).

Example 222. Synthesis ((2R,3S,4R,5R)-5-(4-aminopyrrolo[2,1-f][1,2,4]triazin-7-yl)-5-cyano-3-(2-cyclohexylacetoxy)-4-hydroxytetrahydrofuran-2-yl)methyl (S)-2-amino-3,3-dimethylbutanoate (Compound 371)

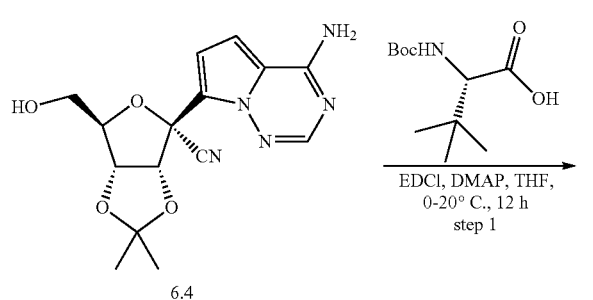

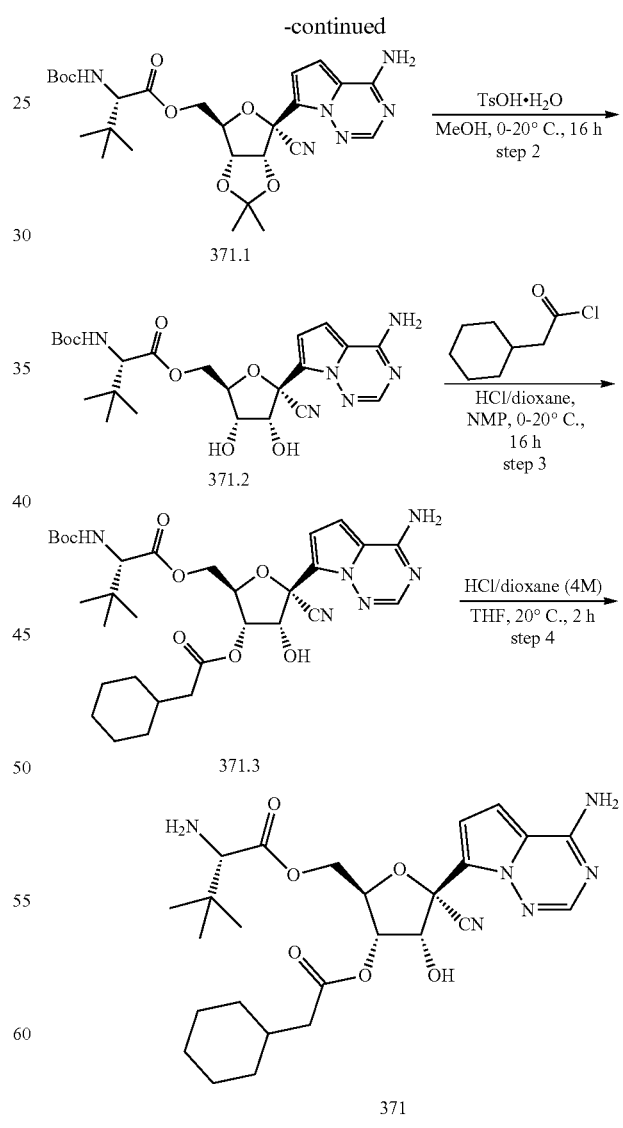

Step 1. Synthesis of ((3aR,4R,6R,6aR)-6-(4-amino-pyrrolo[2,1-f][1,2,4]triazin-7-yl)-6-cyano-2,2-dimethyltetrahydrofuro[3,4-d][1,3]dioxol-4-yl)methyl (S)-2-((tert-butoxycarbonyl)amino)-3,3-dimethylbutanoate (371.1)

To a solution of 6.4 (1.50 g, 4.53 mmol) in THF (80 mL) was added (2S)-2-{[(tert-butoxy)carbonyl]amino}-3,3-dimethylbutanoic acid (1.35 g, 5.85 mmol), EDCI (2.59 g, 13.5 mmol) and DMAP (1.65 g, 13.5 mmol), the mixture was stirred at 25° C. for 16 h. After completion, the mixture was concentrated in vacuo to afford a residue. Then the reaction residue was diluted with water (100 mL) and extracted with EtOAc (100 mL×3). The organic layer was dried over sodium sulphate and concentrated under reduce pressure to afford a crude. The residue was purified by Prep-HPLC [Gradient: 5-40% ACN in water (0.1% FA)] to obtain 371.1 (1.80 g, 69% yield) as a white solid. MS (ESI): mass calcd. for $C_{26}H_{36}N_6O_7$, 544.26 m/z found 545.3 [M+H]$^+$. $^1$H NMR (400 MHz, DMSO) δ 7.95 (br s, 3H), 7.09 (d, J=8.4 Hz, 1H), 6.90 (d, J=4.4 Hz, 1H), 6.85 (d, J=4.4 Hz, 1H), 5.44 (d, J=6.4 Hz, 1H), 4.94 (dd, J=6.4, 3.2 Hz, 1H), 4.52 (s, 1H), 4.27-4.20 (m, 1H), 4.17-4.11 (m, 1H), 3.82 (d, J=8.4 Hz, 1H), 1.64 (s, 3H), 1.40-1.26 (m, 1H), 0.87 (s, 9H).

Step 2. ((2R,3S,4R,5R)-5-(4-aminopyrrolo[2,1-f][1,2,4]triazin-7-yl)-5-cyano-3,4-dihydroxytetrahydrofuran-2-yl)methyl (S)-2-((tert-butoxycarbonyl)amino)-3,3-dimethylbutanoate (371.2)

The title compound 371.2 was prepared according to the procedure of Example 17, Step 1, using 371.1 and TsOH·H$_2$O. MS (ESI): mass calcd. for $C_{23}H_{32}N_6O_7$, 504.23 m/z found 505.2 [M+H]$^+$. $^1$H NMR (400 MHz, DMSO) δ 7.92 (br s, 3H), 7.05 (d, J=8.4 Hz, 1H), 6.92 (d, J=4.4 Hz, 1H), 6.83 (d, J=4.4 Hz, 1H), 6.33 (d, J=6.0 Hz, 1H), 5.39 (d, J=6.0 Hz, 1H), 4.70 (t, J=5.6 Hz, 1H), 4.40-4.14 (m, 3H), 3.96-3.80 (m, 2H), 1.43-1.29 (m, 9H), 0.89 (s, 9H).

Step 3. Synthesis of ((2R,3S,4R,5R)-5-(4-aminopyrrolo[2,1-f][1,2,4]triazin-7-yl)-5-cyano-3-(2-cyclohexylacetoxy)-4-hydroxytetrahydrofuran-2-yl) methyl (S)-2-((tert-butoxycarbonyl)amino)-3,3-dimethylbutanoate (371.3)

The title compound 371.3 was prepared according to the procedure of Example 17, Step 2, using 371.2 and 2-cyclohexylacetyl chloride. MS (ESI): mass calcd. for $C_{31}H_{44}N_6O_8$, 628.32 m/z found 629.3 [M+H]$^+$. $^1$H NMR (400 MHz, DMSO) δ 7.93 (br s, 3H), 7.07 (d, J=8.4 Hz, 1H), 6.93 (d, J=4.8 Hz, 1H), 6.88 (d, J=4.8 Hz, 1H), 6.66-6.59 (m, 1H), 5.09 (d, J=5.2 Hz, 2H), 4.46 (d, J=4.0 Hz, 1H), 4.33-4.25 (m, 2H), 3.84 (d, J=8.4 Hz, 1H), 2.25 (d, J=6.4 Hz, 2H), 1.80-1.68 (m, 3H), 1.66-1.55 (m, 3H), 1.37 (s, 7H), 1.29-1.04 (m, 5H), 1.02-0.91 (m, 2H), 0.85 (s, 9H).

Step 4. Synthesis of ((2R,3S,4R,5R)-5-(4-aminopyrrolo[2,1-f][1,2,4]triazin-7-yl)-5-cyano-3-(2-cyclohexylacetoxy)-4-hydroxytetrahydrofuran-2-yl) methyl (S)-2-amino-3,3-dimethylbutanoate (371)

The title compound 371 was prepared according to the procedure of Example 209, Step 2, using 371.3. MS (ESI): mass calcd. for $C_{28}H_{38}N_6O_6$, 528.27 m/z found 529.3 [M+H]$^+$. $^1$H NMR (400 MHz, DMSO) δ 7.92 (br s, 3H), 6.93 (d, J=4.4 Hz, 1H), 6.87 (d, J=4.8 Hz, 1H), 6.62 (d, J=6.0 Hz, 1H), 5.13-5.07 (m, 2H), 4.49-4.44 (m, 1H), 4.37-4.17 (m, 2H), 2.96 (s, 1H), 2.25 (d, J=6.4 Hz, 2H), 1.81-1.55 (m, 6H), 1.31-1.07 (m, 3H), 1.00-0.89 (m, 2H), 0.86-0.78 (m, 9H).

Example 223. Synthesis of ((2R,3S,4R,5R)-5-(4-aminopyrrolo[2,1-f][1,2,4]triazin-7-yl)-5-cyano-3-(2-cyclohexylacetoxy)-4-hydroxytetrahydrofuran-2-yl)methyl L-phenylalaninate (Compound 372)

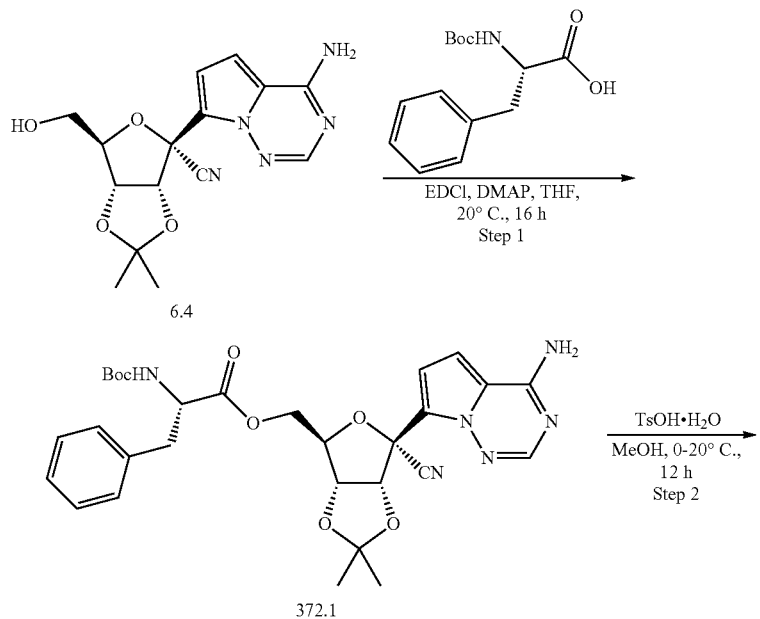

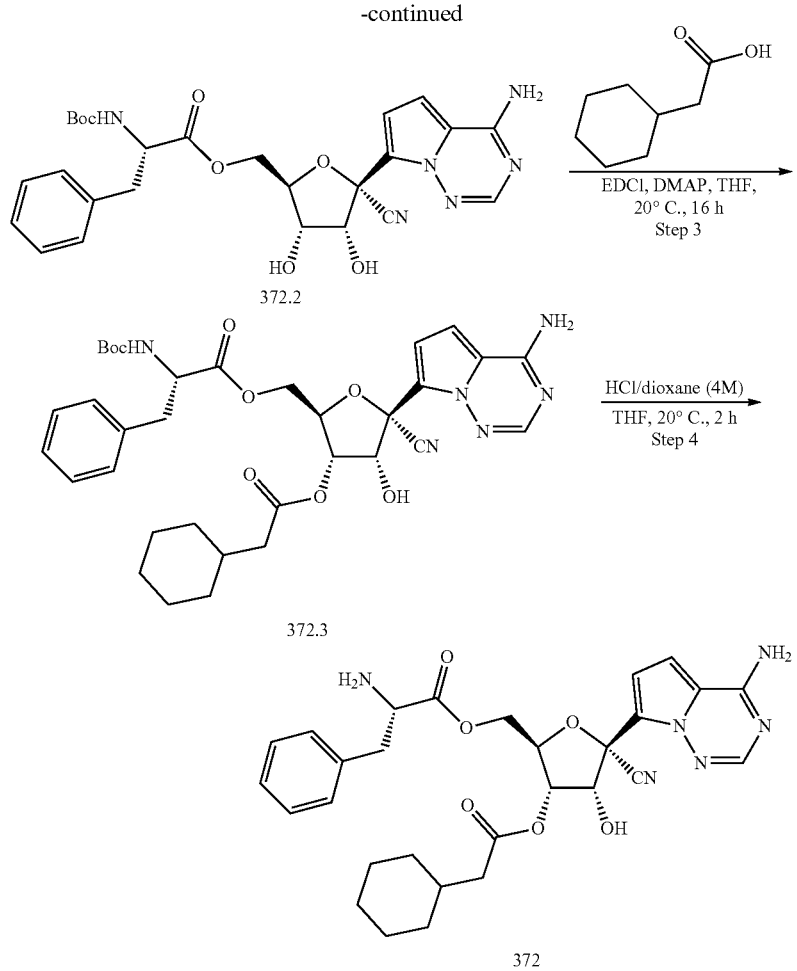
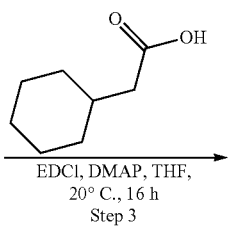

Step 1. Synthesis of ((3aR,4R,6R,6aR)-6-(4-amino-pyrrolo[2,1-f][1,2,4]triazin-7-yl)-6-cyano-2,2-dimethyltetrahydrofuro[3,4-d][1,3]dioxol-4-yl)methyl (tert-butoxycarbonyl)-L-phenylalaninate (372.1)

The title compound 372.1 was prepared according to the procedure of Example 19, Step 1, using 6.4 and (tert-butoxycarbonyl)-L-phenylalanine. MS (ESI): mass calcd. for $C_{29}H_{34}N_6O_7$, 578.63, m/z found 579.2 $[M+H]^+$.

Step 2. Synthesis of ((2R,3S,4R,5R)-5-(4-aminopyr-rolo[2,1-f][1,2,4]triazin-7-yl)-5-cyano-3,4-dihydroxytetrahydrofuran-2-yl)methyl (tert-butoxycarbonyl)-L-phenylalaninate (372.2)

The title compound 372.2 was prepared according to the procedure of Example 17, Step 1, using 372.2. MS (ESI): mass calcd. for $C_{26}H_{30}N_6O_7$, 538.56, m/z found 539.2 $[M+H]^+$.

Step 3. Synthesis of ((2R,3S,4R,5R)-5-(4-aminopyr-rolo[2,1-f][1,2,4]triazin-7-yl)-5-cyano-3-(2-cyclo-hexylacetoxy)-4-hydroxytetrahydrofuran-2-yl) methyl (tert-butoxycarbonyl)-L-phenylalaninate (372.3)

The title compound 372.3 was prepared according to the procedure of Example 19, Step 1, using 372.2 and 2-cyclohexylacetic acid. MS (ESI): mass calcd. for $C_{34}H_{42}N_6O_8$, 662.74, m/z found 663.4 $[M+H]^+$.

Step 4. Synthesis of ((2R,3S,4R,5R)-5-(4-aminopyr-rolo[2,1-f][1,2,4]triazin-7-yl)-5-cyano-3-(2-cyclo-hexylacetoxy)-4-hydroxytetrahydrofuran-2-yl) methyl L-phenylalaninate (Compound 372)

Compound 372 was prepared according to the procedure of Example 19, Step 2, using 372.3. MS (ESI): mass calcd. for $C_{29}H_{34}N_6O_6$, 562.63, m/z found 563.2 $[M+H]^+$. $^1H$ NMR (400 MHz, DMSO) δ 7.92 (brs, 3H), 7.22-7.09 (m, 5H), 6.93 (d, J=4.4 Hz, 1H), 6.87 (d, J=4.8 Hz, 1H), 6.59 (d, J=6.0 Hz, 1H), 5.08-5.05 (m, 2H), 4.44 (dd, J=8.0, 4.0 Hz, 1H), 4.22-4.17 (m, 2H), 3.55 (t, J=6.4 Hz, 1H), 2.75-2.69 (m, 2H), 2.27 (d, J=6.8 Hz, 2H), 1.83-1.59 (m, 6H), 1.25-1.07 (m, 3H), 1.00-0.89 (m, 2H).

Example 224. Synthesis of ((2R,3S,4R,5R)-5-(4-acetamidopyrrolo[2,1-f][1,2,4]triazin-7-yl)-5-cyano-3-(2-cyclohexylacetoxy)-4-hydroxytetrahydrofuran-2-yl)methyl (S)-2-amino-3,3-dimethylbutanoate (Compound 373)

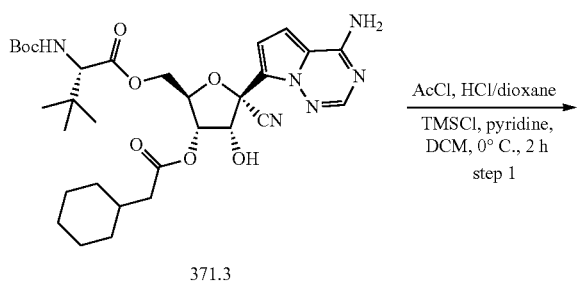

371.3

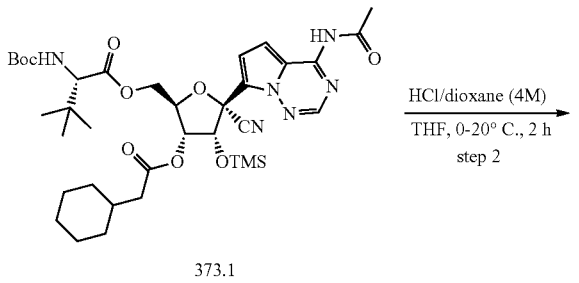

373.1

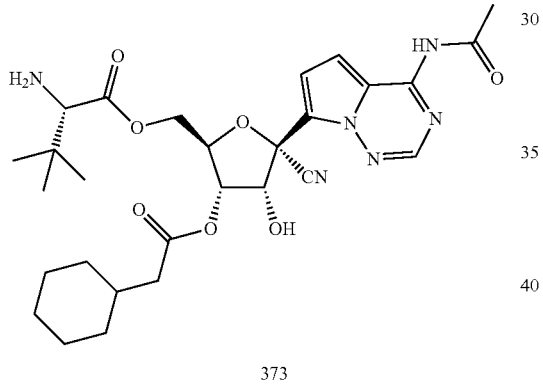

373

Step 1. Synthesis of ((2R,3R,4R,5R)-5-(4-acetamidopyrrolo[2,1-f][1,2,4]triazin-7-yl)-5-cyano-3-(2-cyclohexylacetoxy)-4-((trimethylsilyl)oxy)tetrahydrofuran-2-yl)methyl (S)-2-((tert-butoxycarbonyl)amino)-3,3-dimethylbutanoate (373.1)

The title compound 373.1 was prepared according to the procedure of Example 209, Step 1, using 371.3 and acetyl chloride. MS (ESI): mass calcd. for $C_{36}H_{54}N_6O_9Si$, 742.37 m/z found 743.3 $[M+H]^+$. $^1$H NMR (400 MHz, DMSO) δ 10.99 (s, 1H), 8.38 (s, 1H), 7.35 (d, J=4.8 Hz, 1H), 7.19-7.06 (m, 2H), 5.31 (d, J=5.2 Hz, 1H), 5.18 (t, J=5.2 Hz, 1H), 4.54 (dd, J=9.2, 4.8 Hz, 1H), 4.36 (s, 2H), 3.88 (d, J=8.4 Hz, 1H), 2.39 (s, 3H), 2.29-2.21 (m, 2H), 1.80-1.67 (m, 3H), 1.70-1.54 (m, 3H), 1.45-1.30 (m, 9H), 1.23-1.05 (m, 3H), 1.04-0.92 (m, 2H), 0.87 (s, 9H), −0.03 (s, 9H).

Step 2. Synthesis of ((2R,3S,4R,5R)-5-(4-acetamidopyrrolo[2,1-f][1,2,4]triazin-7-yl)-5-cyano-3-(2-cyclohexylacetoxy)-4-hydroxytetrahydrofuran-2-yl)methyl (S)-2-amino-3,3-dimethylbutanoate (373)

The title compound 373 was prepared according to the procedure of Example 209, Step 2, using 373.1. MS (ESI): mass calcd. for $C_{28}H_{38}N_6O_7$, 570.28 m/z found 571.3 $[M+H]^+$. $^1$H NMR (400 MHz, DMSO) δ 10.99 (s, 1H), 8.40 (s, 1H), 7.32 (d, J=4.8 Hz, 1H), 7.11 (d, J=4.8 Hz, 1H), 6.80-6.68 (m, 1H), 5.17-5.11 (m, 1H), 5.09-5.04 (m, 1H), 4.54-4.48 (m, 1H), 4.33-4.22 (m, 2H), 2.98-2.96 (m, 1H), 2.40 (s, 3H), 2.28-2.25 (m, 2H), 1.80-1.69 (m, 3H), 1.67-1.56 (m, 3H), 1.27-1.08 (m, 3H), 1.00-0.89 (m, 2H), 0.85-0.79 (m, 9H).

Example 225. Synthesis of (((7-((2R,3R,4S,5R)-5-(((L-phenylalanyl)oxy)methyl)-2-cyano-4-(2-cyclohexylacetoxy)-3-hydroxytetrahydrofuran-2-yl)pyrrolo[2,1-f][1,2,4]triazin-4-yl)carbamoyl)oxy)methyl pivalate (Compound 374)

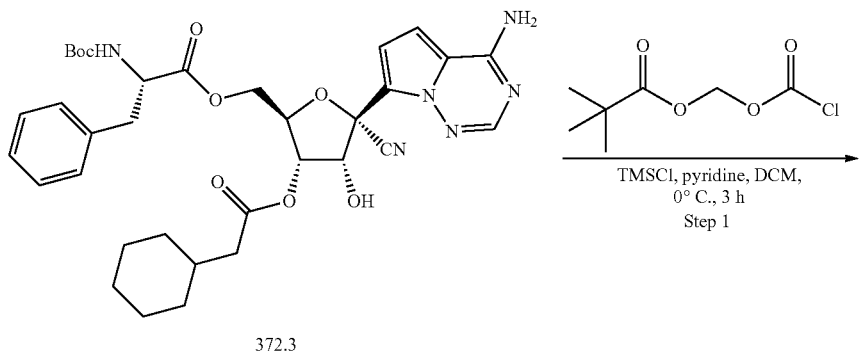

372.3

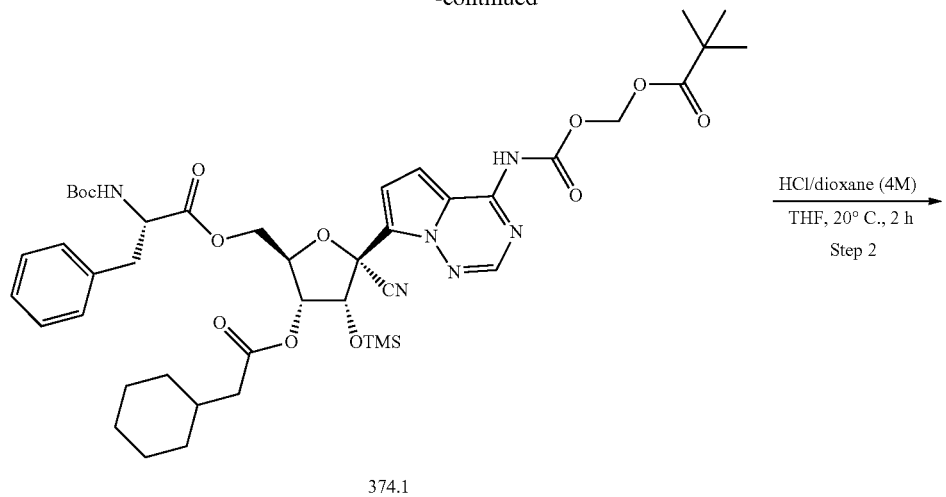

374.1

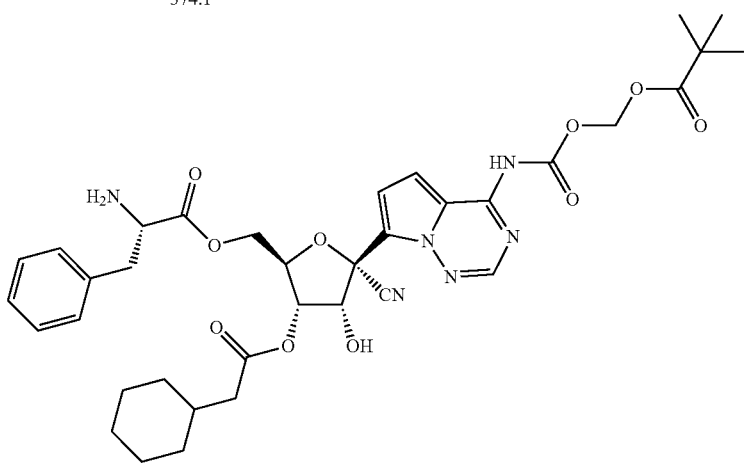

374

Step 1. Synthesis of ((((7-((2R,3R,4R,5R)-5-(((((tert-butoxycarbonyl)-L-phenylalanyl)oxy)methyl)-2-cyano-4-(2-cyclohexylacetoxy)-3-((trimethylsilyl)oxy)tetrahydrofuran-2-yl)pyrrolo[2,1-f][1,2,4]triazin-4-yl)carbamoyl)oxy)methyl pivalate (374.1)

The title compound 374.1 was prepared according to the procedure of Example 206, Step 1, using 372.3 and ((chlorocarbonyl)oxy)methyl pivalate. MS (ESI): mass calcd. for $C_{44}H_{60}N_6O_{12}Si$, 893.08, m/z found 893.4 [M+H]$^+$.

Step 2. Synthesis of ((((7-((2R,3R,4S,5R)-5-(((L-phenylalanyl)oxy)methyl)-2-cyano-4-(2-cyclohexylacetoxy)-3-hydroxytetrahydrofuran-2-yl)pyrrolo[2,1-f][1,2,4]triazin-4-yl)carbamoyl)oxy)methyl pivalate (Compound 374)

Compound 374.1 was prepared according to the procedure of Example 19, Step 2, using 374.1. MS (ESI): mass calcd. for $C_{36}H_{44}N_6O_{10}$, 720.78, m/z found 721.3 [M+H]$^+$. $^1$H NMR (400 MHz, DMSO) δ 8.35 (s, 1H), 7.27 (d, J=4.0 Hz, 1H), 7.18-7.06 (m, 6H), 6.69 (d, J=6.0 Hz, 1H), 5.83 (s, 2H), 5.15-4.97 (m, 2H), 4.48-4.46 (m, 1H), 4.25-4.17 (m, 2H), 3.55 (t, J=6.8 Hz, 1H), 2.82-2.70 (m, 2H), 2.27 (d, J=6.8 Hz, 2H), 1.87-1.57 (m, 7H), 1.26-1.17 (m, 11H), 0.99-0.90 (m, 2H).

Example 226. Synthesis of ((2R,3S,4R,5R)-5-cyano-3,4-dihydroxy-5-(4-((((pivaloyloxy)methoxy)carbonyl)amino)pyrrolo[2,1-f][1,2,4]triazin-7-yl)tetrahydrofuran-2-yl)methyl 2-cyclohexyl-2-methylpropanoate (Compound 375)

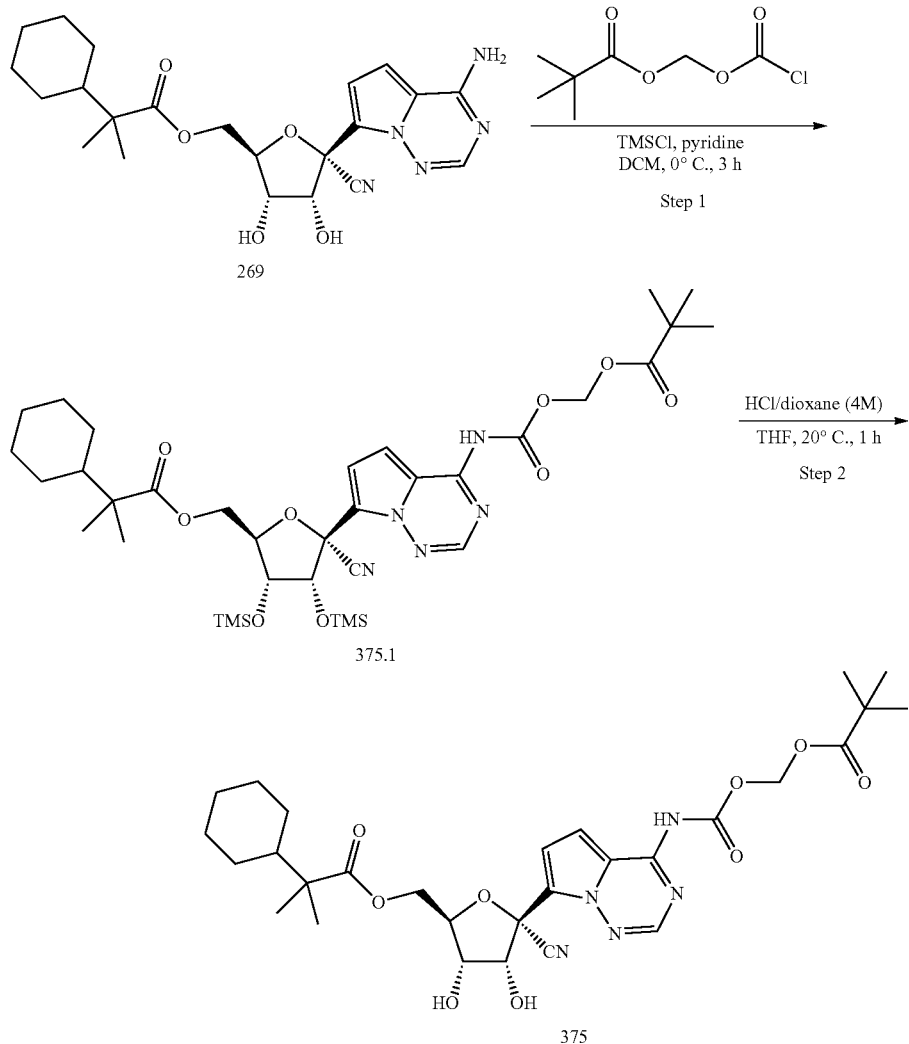

Step 1. Synthesis of (((7-((2R,3R,4R,5R)-2-cyano-5-(((2-cyclohexyl-2-methylpropanoyl)oxy)methyl)-3,4-bis((trimethylsilyl)oxy)tetrahydrofuran-2-yl)pyrrolo[2,1-f][1,2,4]triazin-4-yl)carbamoyl)oxy)methyl pivalate (375.1

The title compound 375.1 was prepared according to the procedure of Example 206, Step 1, using 269 and ((chlorocarbonyl)oxy)methyl pivalate. MS (ESI): mass calcd. for $C_{35}H_{55}N_5O_9Si_2$, 746.02, m/z found 746.4 [M+H]$^+$.

Step 2. Synthesis of ((2R,3S,4R,5R)-5-cyano-3,4-dihydroxy-5-(4-((((pivaloyloxy)methoxy)carbonyl)amino)pyrrolo[2,1-f][1,2,4]triazin-7-yl)tetrahydrofuran-2-yl)methyl 2-cyclohexyl-2-methylpropanoate (Compound 375)

The title compound 375 was prepared according to the procedure of Example 19, Step 2, using 375.1. MS (ESI): mass calcd. for $C_{29}H_{39}N_5O_9$, 601.66, m/z found 602.3 [M+H]$^+$. $^1$H NMR (400 MHz, DMSO) δ 11.27 (s, 1H), 8.40 (s, 1H), 7.31-7.30 (m, 1H), 7.05-7.04 (m, 1H), 6.45 (d, J=6.0 Hz, 1H), 5.84 (s, 2H), 5.43 (d, J=6.0 Hz, 1H), 4.71 (t, J=5.6 Hz, 1H), 4.34-4.25 (m, 1H), 4.19 (d, J=3.6 Hz, 2H), 3.99-3.96 (m, 1H), 1.67-1.47 (m, 3H), 1.45-1.29 (m, 3H), 1.17 (s, 9H), 1.05-0.78 (m, 11H).

Example 227. Synthesis of ((2R,3S,4R,5R)-5-(4-((butoxycarbonyl)amino)pyrrolo[2,1-f][1,2,4]triazin-7-yl)-5-cyano-3,4-dihydroxytetrahydrofuran-2-yl)methyl 2-cyclohexyl-2-methylpropanoate (Compound 379)

The title compound was prepared according to the procedure of Example 57, using 2-cyclohexyl-2-methylpropanoyl chloride. MS (ESI): mass calcd. for $C_{27}H_{37}N_5O_7$, 543.27, m/z found 544.2 [M+H]$^+$.

Example 228. Synthesis of (2R,3S,4R,5R)-5-cyano-4-hydroxy-5-(4-((((5-methyl-2-oxo-1,3-dioxol-4-yl)methoxy)carbonyl)amino)pyrrolo[2,1-f][1,2,4]triazin-7-yl)-2-((2-phenylacetoxy)methyl)tetrahydrofuran-3-yl L-valinate (Compound 383)
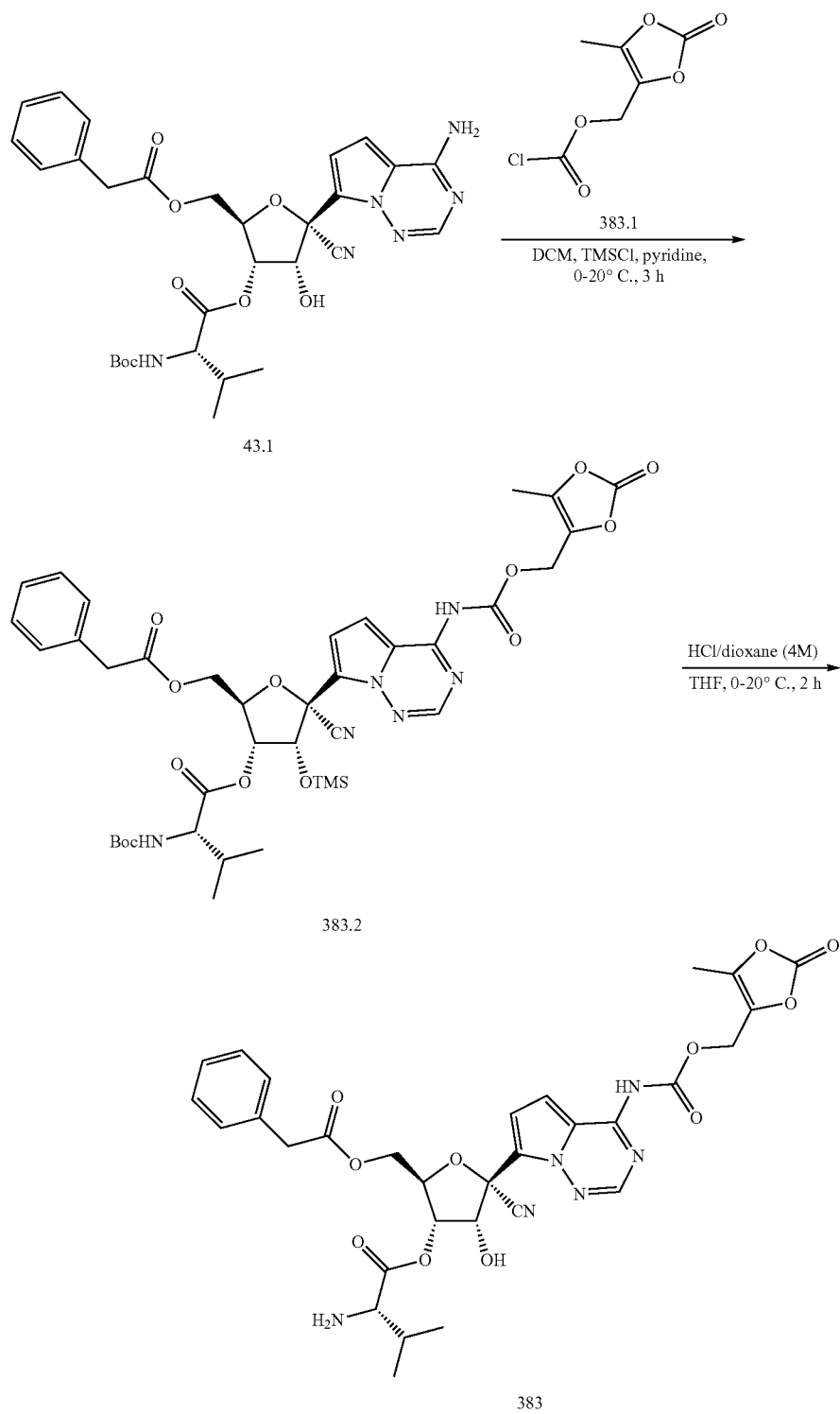

The title compound was prepared according to the procedure of Example 206, using (5-methyl-2-oxo-1,3-dioxol-4-yl)methyl carbonochloridate in Step 1. MS (ESI): mass calcd. for $C_{31}H_{32}N_6O_1$, 664.21, m/z found 665.2 [M+H]$^+$.
Example 229. Synthesis of (2R,3S,4R,5R)-5-cyano-2-((2-cyclohexylacetoxy)methyl)-4-hydroxy-5-(4-(((((5-methyl-2-oxo-1,3-dioxol-4-yl)methoxy)carbonyl)amino)pyrrolo[2,1-f][1,2,4]triazin-7-yl)tetrahydrofuran-3-yl L-valinate (Compound 385)
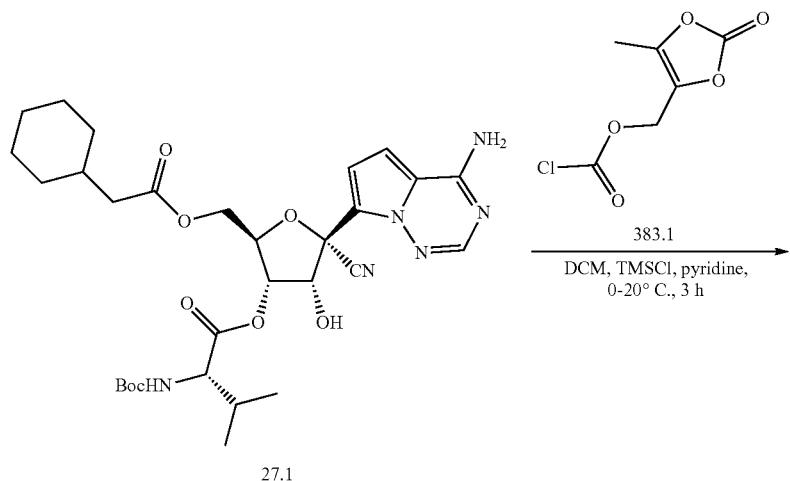
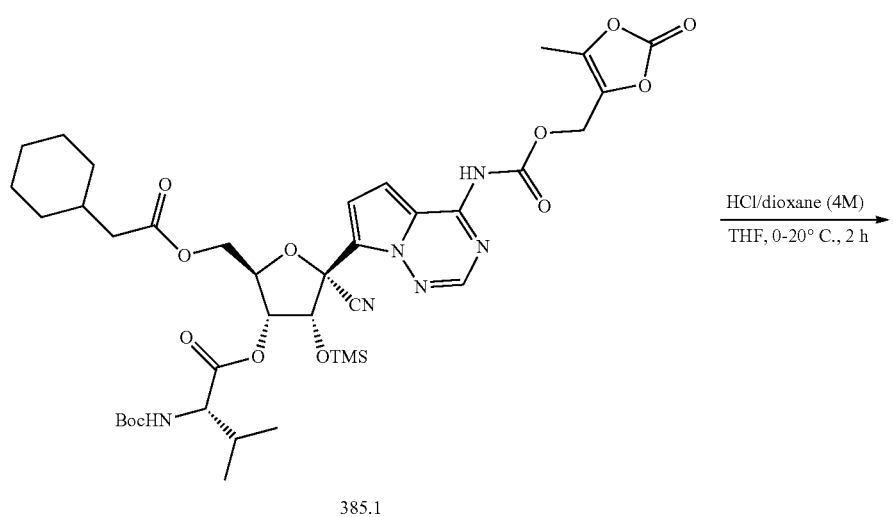

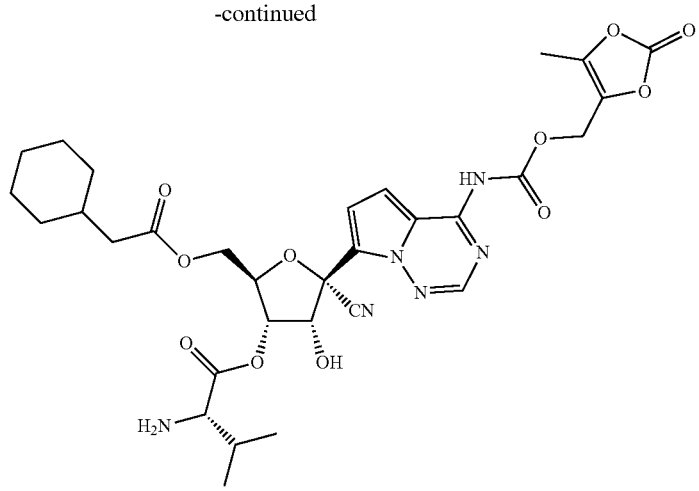

385

The title compound was prepared according to the procedure of Example 209, using (5-methyl-2-oxo-1,3-dioxol-4-yl)methyl carbonochloridate in Step 1. MS (ESI): mass calcd. for $C_{31}H_{38}N_6O_{11}$, 670.26, m/z found 671.2 [M+H]+.

Example 230. Synthesis of (2R,3S,4R,5R)-5-cyano-2-((2-cyclohexylacetoxy)methyl)-4-hydroxy-5-(4-((((5-methyl-2-oxo-1,3-dioxol-4-yl)methoxy)carbonyl)amino)pyrrolo[2,1-f][1,2,4]triazin-7-yl)tetrahydrofuran-3-yl L-valinate (Compound 392)

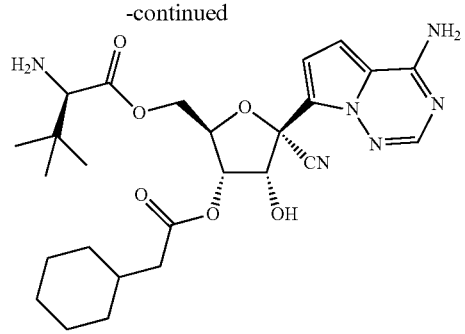

392

The title compound was prepared according to the procedure of Example 18, using Compound 411.2 in Step 1. MS (ESI): mass calcd. for $C_{26}H_{36}N_6O_6$, 528.27, m/z found 529.3 [M+H]+. $^1$H NMR (400 MHz, DMSO) δ 7.93 (br s, 3H), 6.92 (d, J=4.4 Hz, 1H), 6.86 (d, J=4.8 Hz, 1H), 6.58 (d, J=6.0 Hz, 1H), 5.19-5.14 (m, 1H), 5.11 (t, J=6.0 Hz, 1H), 4.45 (dd, J=8.8, 4.4 Hz, 1H), 4.32-4.18 (m, 2H), 2.96 (s, 1H), 2.26 (d, J=6.8 Hz, 2H), 1.78-1.70 (m, 3H), 1.69-1.54 (m, 3H), 1.29-1.08 (m, 3H), 1.28-1.10 (m, 2H), 0.85-0.74 (m, 9H).

Example 231. Synthesis of ((2R,3S,4R,5R)-5-cyano-3,4-dihydroxy-5-(4-((((pivaloyloxy)methoxy)carbonyl)amino)pyrrolo[2,1-f][1,2,4]triazin-7-yl)tetrahydrofuran-2-yl)methyl (S)-2-amino-3,3-dimethylbutanoate (Compound 395)

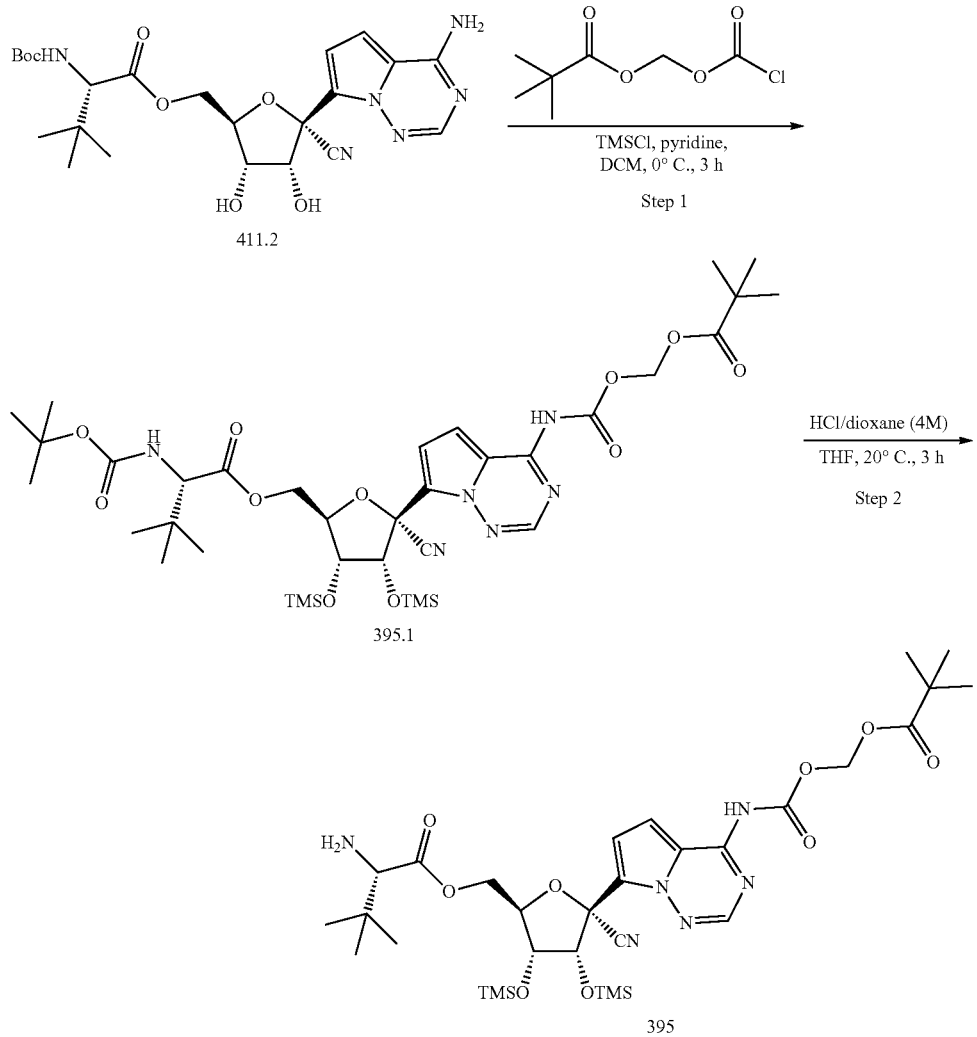

The title compound was prepared according to the procedure of Example 218, using Compound 411.2 in Step 1. MS (ESI): mass calcd. for $C_{25}H_{34}N_6O_9$, 562.24, m/z found 563.2 [M+H]$^+$. $^1$H NMR (400 MHz, DMSO) δ 8.37 (s, 1H), 7.29 (d, J=4.4 Hz, 1H), 7.07 (d, J=4.8 Hz, 1H), 6.45 (d, J=6.0 Hz, 1H), 5.84 (s, 2H), 5.46 (d, J=5.6 Hz, 1H), 4.72-4.67 (m, 1H), 4.31-4.23 (m, 3H), 3.94 (d, J=4.4 Hz, 1H), 3.07 (s, 1H), 1.17 (s, 9H), 0.84 (s, 9H).

Example 232. Synthesis of (2R,3S,4R,5R)-5-(4-aminopyrrolo[2,1-f][1,2,4]triazin-7-yl)-5-cyano-2-((2-cyclohexylacetoxy)methyl)-4-hydroxytetrahydrofuran-3-yl (S)-2-amino-3,3-dimethylbutanoate (Compound 397)

The title compound was prepared according to the procedure of Example 16, using (R)-Boc-tert-leucine in Step 1. MS (ESI): mass calcd. for $C_{26}H_{36}N_6O_6$, 528.27, m/z found 529.2 [M+H]$^+$. $^1$H NMR (400 MHz, DMSO) δ 7.98-7.93 (m, 3H), 6.94 (d, J=4.4 Hz, 1H), 6.86 (d, J=4.4 Hz, 1H), 6.63-6.60 (m, 1H), 5.22-4.98 (m, 2H), 4.46 (dd, J=8.4, 4.4 Hz, 1H), 4.30 (dd, J=12.4, 3.6 Hz, 1H), 4.25-4.15 (m, 1H), 3.08 (s, 1H), 2.15 (dd, J=6.8, 3.6 Hz, 2H), 1.58-1.57 (m, 6H), 1.11-1.08 (m, 3H), 1.00-0.77 (m, 11H).

Example 233. Synthesis of (2R,3S,4R,5R)-5-(4-(((acetoxymethoxy)carbonyl)amino)pyrrolo[2,1-f][1,2,4]triazin-7-yl)-5-cyano-4-hydroxy-2-((2-phenylacetoxy)methyl)tetrahydrofuran-3-yl (S)-2-amino-3,3-dimethylbutanoate (Compound 399)
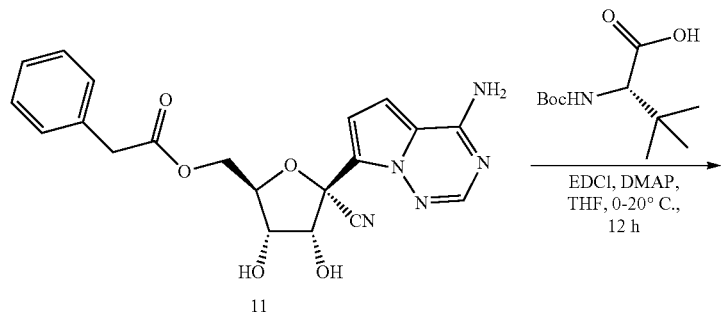
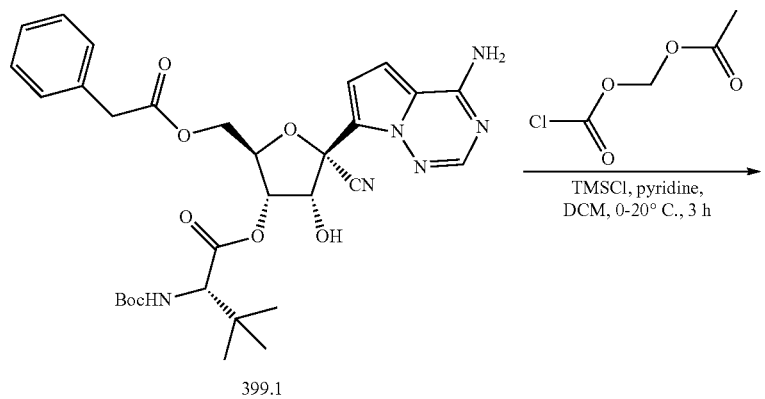
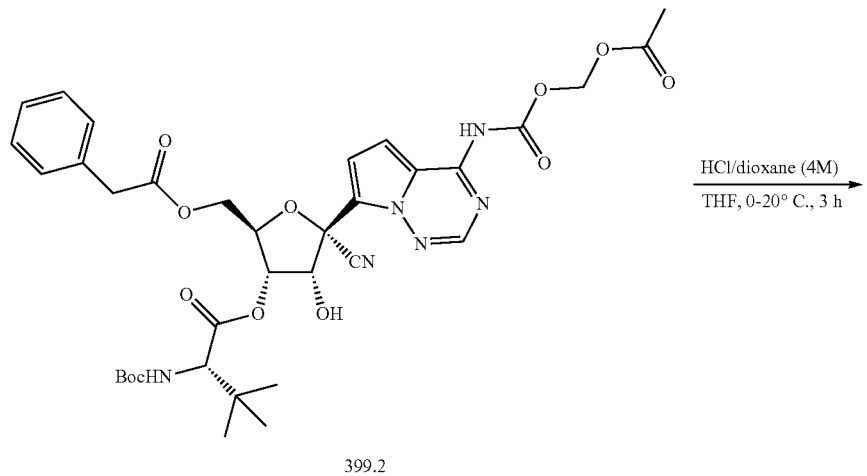

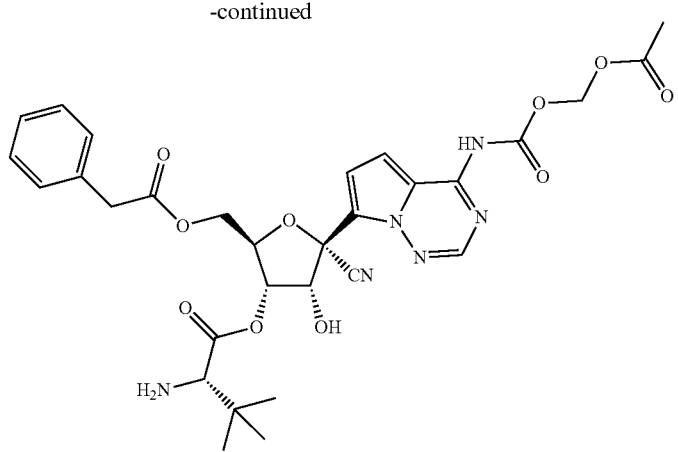

399

Step 1. Synthesis of (2R,3S,4R,5R)-5-(4-aminopyr-rolo[2,1-f][1,2,4]triazin-7-yl)-5-cyano-4-hydroxy-2-((2-phenylacetoxy)methyl)tetrahydrofuran-3-yl (S)-2-((tert-butoxycarbonyl)amino)-3,3-dimethylbutanoate (399.1)

The title compound was prepared according to the procedure of Example 212, using Compound 11 and (R)-Boc-tert-leucine.

Step 2. Synthesis of (2R,3S,4R,5R)-5-(4-(((acetoxymethoxy)carbonyl)amino)pyrrolo[2,1-f][1,2,4]triazin-7-yl)-5-cyano-4-hydroxy-2-((2-phenylacetoxy)methyl)tetrahydrofuran-3-yl (S)-2-((tert-butoxycarbonyl)amino)-3,3-dimethylbutanoate (399.2)

The title compound was prepared from Compound 399.1 according to the procedure of Example 206, Step 1.

Step 3. Synthesis of (2R,3S,4R,5R)-5-(4-(((acetoxymethoxy)carbonyl)amino)pyrrolo[2,1-f][1,2,4]triazin-7-yl)-5-cyano-4-hydroxy-2-((2-phenylacetoxy)methyl)tetrahydrofuran-3-yl (S)-2-amino-3,3-dimethylbutanoate (Compound 399)

The title compound was prepared according to the procedure of Example 206, Step 2. MS (ESI): mass calcd. for $C_{30}H_{34}N_6O_{10}$, 638.23, m/z found 639.3 [M+H]$^+$. $^1$H NMR (400 MHz, DMSO) δ 8.38 (s, 1H), 7.42-7.14 (m, 6H), 7.04 (d, J=4.4 Hz, 1H), 6.70 (d, J=6.4 Hz, 1H), 5.81 (s, 2H), 5.20-5.10 (m, 1H), 5.04 (t, J=6.0 Hz, 1H), 4.51 (dd, J=8.0, 4.4 Hz, 1H), 4.33 (dd, J=12.4, 3.6 Hz, 1H), 4.25 (dd, J=12.4, 5.2 Hz, 1H), 3.66 (s, 2H), 3.11 (s, 1H), 2.12 (s, 3H), 0.93 (s, 9H).

Example 234. Synthesis of (2R,3S,4R,5R)-5-cyano-4-hydroxy-5-(4-isobutyramidopyrrolo[2,1-f][1,2,4]triazin-7-yl)-2-((2-phenylacetoxy)methyl)tetrahydrofuran-3-yl (S)-2-amino-3,3-dimethylbutanoate (Compound 401)

The title compound was prepared according to the procedure of Example 198, utilizing Compound 399.1 in Step 2. MS (ESI): mass calcd. for $C_{30}H_{36}N_6O_7$, 592.26, m/z found 593.3 [M+H]$^+$. $^1$H NMR (400 MHz, DMSO) δ 10.92 (s, 1H), 8.41 (s, 1H), 7.32-7.15 (m, 6H), 7.08 (d, J=4.8 Hz, 1H), 6.71 (d, J=6.4 Hz, 1H), 5.17-5.08 (m, 1H), 5.05 (t, J=6.0 Hz, 1H), 4.52 (dd, J=8.0, 4.4 Hz, 1H), 4.33 (dd, J=12.0, 3.6 Hz, 1H), 4.25 (dd, J=12.4, 4.8 Hz, 1H), 3.66 (s, 2H), 3.18-3.11 (m, 1H), 3.09 (s, 1H), 1.16 (d, J=6.8 Hz, 6H), 0.93 (s, 9H).

Example 235. Synthesis of (2R,3S,4R,5R)-5-cyano-4-hydroxy-5-(4-isobutyramidopyrrolo[2,1-f][1,2,4]triazin-7-yl)-2-((2-phenylacetoxy)methyl)tetrahydrofuran-3-yl (S)-2-amino-3,3-dimethylbutanoate (Compound 402)

The title compound was prepared according to the procedure of Example 224, utilizing ((chlorocarbonyl)oxy)methyl acetate in place of acetyl chloride in Step 1. MS (ESI): mass calcd. for $C_{30}H_{40}N_6O_{10}$, 644.28, m/z found 645.3 [M+H]$^+$. $^1$H NMR (400 MHz, DMSO) δ 8.37 (s, 1H), 7.29 (d, J=4.8 Hz, 1H), 7.09 (d, J=4.8 Hz, 1H), 6.73 (d, J=6.4 Hz, 1H), 5.81 (s, 2H), 5.22-5.09 (m, 1H), 5.06 (t, J=6.0 Hz, 1H), 4.51 (dd, J=8.4, 4.4 Hz, 1H), 4.33-4.22 (m, 2H), 3.00-2.94 (m, 1H), 2.35-2.24 (m, 2H), 2.12 (s, 3H), 1.83-1.68 (m, 3H), 1.67-1.56 (m, 3H), 1.27-1.08 (m, 3H), 1.01-0.92 (m, 2H), 0.86-0.75 (m, 9H).

Example 236. Synthesis of (2R,3S,4R,5R)-5-cyano-4-hydroxy-5-(4-isobutyramidopyrrolo[2,1-f][1,2,4]triazin-7-yl)-2-((2-phenylacetoxy)methyl)tetrahydrofuran-3-yl (S)-2-amino-3,3-dimethylbutanoate (Compound 409)
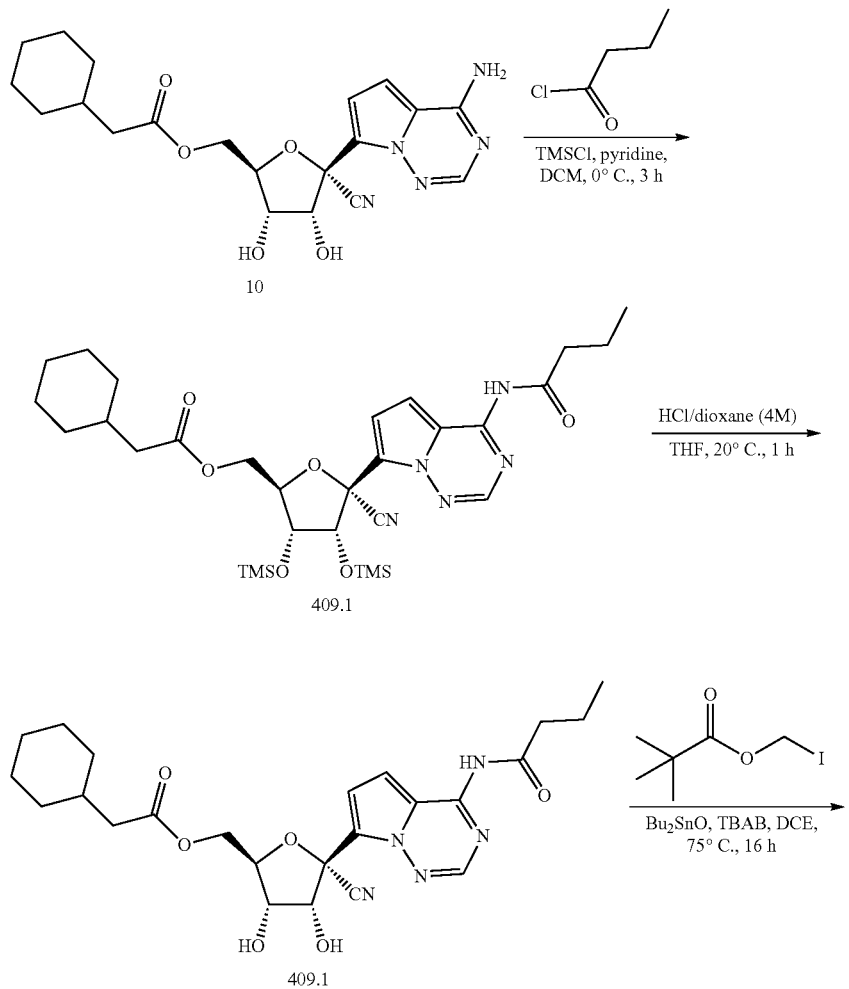

Step 1: Synthesis of ((2R,3R,4R,5R)-5-(4-butyramidopyrrolo[2,1-f][1,2,4]triazin-7-yl)-5-cyano-3,4-bis((trimethylsilyl)oxy)tetrahydrofuran-2-yl)methyl 2-cyclohexylacetate (409.1)

The compound 409.1 was prepared according to the procedure of Example 206, Step 1, using 10 and butyryl chloride. MS (ESI): mass calcd. for $C_{30}H_{47}N_5O_6Si_2$, 629.31, m/z found 630.2 [M+H]$^+$. $^1$H NMR (400 MHz, DMSO) δ 10.93 (s, 1H), 8.38 (s, 1H), 7.33 (d, J=4.8 Hz, 1H), 7.04 (d, J=4.8 Hz, 1H), 4.93 (d, J=4.0 Hz, 1H), 4.41 (dd, J=12.4, 3.2 Hz, 1H), 4.28 (dt, J=7.2, 3.6 Hz, 1H), 4.18-4.09 (m, 2H), 2.69 (t, J=7.2 Hz, 2H), 2.15 (d, J=6.8 Hz, 2H), 1.70-1.54 (m, 8H), 1.17-1.01 (m, 3H), 0.91 (dt J=12.8, 7.2 Hz, 5H), 0.17-0.04 (m, 18H).

Step 2: Synthesis of ((2R,3S,4R,5R)-5-(4-butyramidopyrrolo[2,1-f][1,2,4]triazin-7-yl)-5-cyano-3,4-dihydroxytetrahydrofuran-2-yl)methyl 2-cyclohexylacetate (409.2)

Compound 409.2 was prepared according to the procedure of Example 209, Step 2, using 409.1. MS (ESI): mass calcd. for $C_{24}H_{31}N_5O_6$, 485.23 m/z found 486.2 [M+H]$^+$.

Step 3. Synthesis of (((2R,3S,4R,5R)-5-(4-butyramidopyrrolo[2,1-f][1,2,4]triazin-7-yl)-5-cyano-2-((2-cyclohexylacetoxy)methyl)-4-hydroxytetrahydrofuran-3-yl)oxy)methyl pivalate (409)

The title compound was prepared according to the procedure of Example 24, Step 1, using 409.2 and iodomethyl pivalate. MS (ESI): mass calcd. for $C_{30}H_{41}N_5O_8$, 599.30 m/z found 600.3 [M+H]$^+$. $^1$H NMR (400 MHz, DMSO) δ 10.94 (s, 1H), 8.38 (s, 1H), 7.29 (d, J=4.8 Hz, 1H), 7.07 (d, J=4.8 Hz, 1H), 6.65 (d, J=6.4 Hz, 1H), 5.36 (d, J=6.4 Hz, 1H), 5.29 (d, J=6.4 Hz, 1H), 4.96 (t, J=5.6 Hz, 1H), 4.39-4.37 (m, 1H), 4.29 (dd, J=12.4, 3.2 Hz, 1H), 4.18-4.08 (m, 2H), 2.69 (t, J=7.2 Hz, 2H), 2.10 (dd, J=6.8, 2.8 Hz, 2H), 1.69-1.52 (m, 9H), 1.12-1.10 (s, 11H), 0.94 (t, J=7.6 Hz, 3H), 0.85-0.80 (m, 2H).

Example 237. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl (S)-2-amino-3,3-dimethylbutanoate (Compound 410)

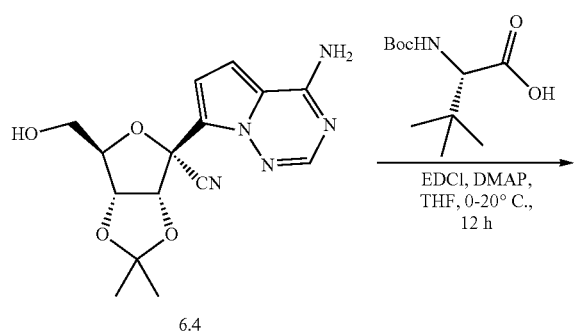

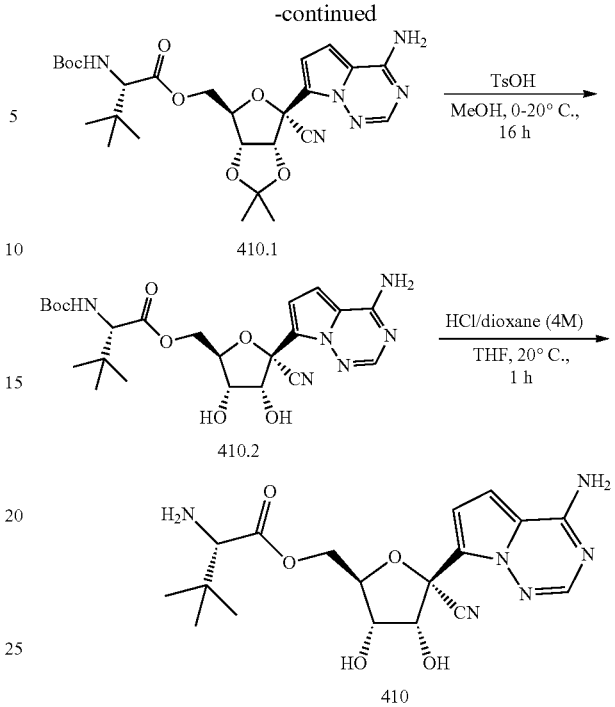

The title compound was prepared according to the procedure of Example 132, using (R)-Boc-tert-leucine in Step 1. MS (ESI): mass calcd. for $C_{18}H_{24}N_6O_5$, 404.18, m/z found 405.2 [M+H]$^+$. $^1$H NMR (400 MHz, DMSO) δ 7.92 (br s, 3H), 6.91 (d, J=4.4 Hz, 1H), 6.83 (d, J=4.4 Hz, 1H), 6.40-6.30 (m, 1H), 5.45-5.35 (m, 1H), 4.71 (s, 1H), 4.30-4.19 (m, 3H), 3.96-3.92 (m, 1H), 3.01 (s, 1H), 0.84 (s, 9H).

Example 238. Synthesis of ((2R,3S,4R,5R)-5-(4-aminopyrrolo[2,1-f][1,2,4]triazin-7-yl)-5-cyano-3,4-dihydroxytetrahydrofuran-2-yl)methyl (R)-2-amino-3,3-dimethylbutanoate (Compound 411)

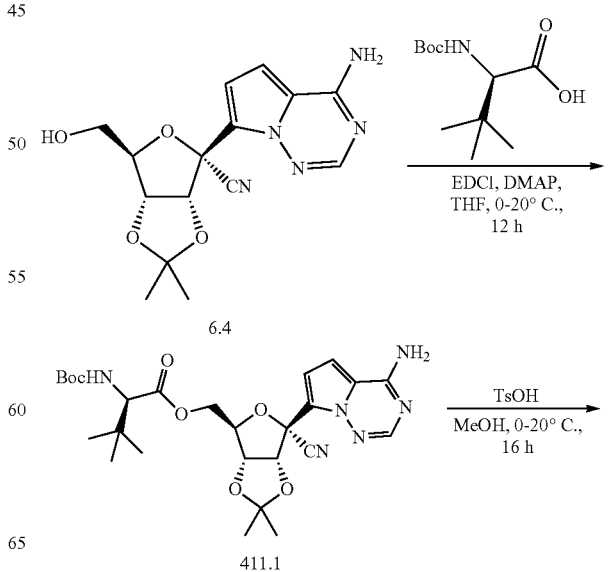

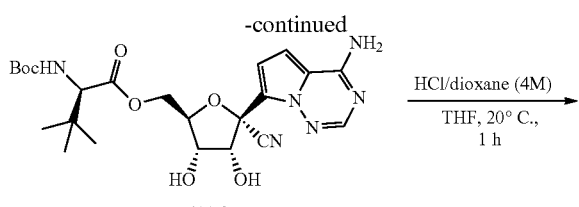

The title compound was prepared according to the procedure of Example 132, using (S)-Boc-tert-leucine in Step 1. MS (ESI): mass calcd. for $C_{18}H_{24}N_6O_5$, 404.18, m/z found 405.2 [M+H]⁺. ¹H NMR (400 MHz, DMSO) δ 7.92 (br s, 3H), 6.91 (d, J=4.4 Hz, 1H), 6.82 (d, J=4.4 Hz, 1H), 6.50-6.20 (m, 1H), 5.50-5.25 (m, 1H), 4.72 (d, J=5.2 Hz, 1H), 4.30-4.18 (m, 1H), 3.99-3.94 (m, 1H), 3.07-3.00 (m, 1H), 0.85 (s, 9H).

Example 239. Synthesis of (2R,3R,4R,5R)-2-(4-aminopyrrolo[2,1-f][1,2,4]triazin-7-yl)-2-cyano-5-(((2-cyclohexyl-2-methylpropanoyl)oxy)methyl)tetrahydrofuran-3,4-diyl diacetate (Compound 412)

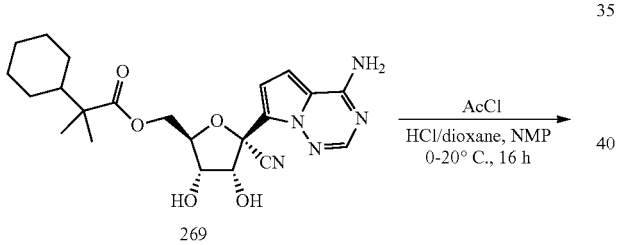

To a solution of 269 (600 mg, 1.35 mmol) in NMP (3 mL), 4M HCl solution in 1-4 dixane (0.7 mL, 4 M) was added and stirred at 20° C. for 15 minutes. The reaction mixture was cooled at 0° C. and a cetyl chloride (2.89 mL, 40.6 mmol) was added at once. The reaction was stirred at 20° C. for 16 h. The reaction was diluted with ACN (1 mL) and purified by prep-HPLC (column: Gemini-C18 150×21.2 mm, 5 um; mobile phase: ACN-H₂O (0.1% FA); gradient: 20%-65%) to obtain 413 (48.25 mg, 6.60 yield) as a white solid. MS (ESI): mass calcd. for $C_{26}H_{33}N_5O_7$, 527.24 m/z found 528.2 [M+H]⁺. ¹H NMR (400 MHz, DMSO) δ 8.14-7.82 (m, 3H), 6.94 (d, J=4.8 Hz, 1H), 6.76 (d, J=4.8 Hz, 1H), 6.04 (d, J=6.0 Hz, 1H), 5.42-5.39 (m, 1H), 4.64 (q, J=3.6 Hz, 1H), 4.31-4.20 (m, 2H), 2.12 (d, J=1.6 Hz, 6H), 1.61-1.49 (m, 3H), 1.46-1.34 (m, 3H), 1.15-0.93 (m, 9H), 0.90-0.78 (m, 2H).

Example 240. Synthesis of ((2R,3S,4R,5R)-5-(4-aminopyrrolo[2,1-f][1,2,4]triazin-7-yl)-5-cyano-3-(2-cyclohexylacetoxy)-4-hydroxytetrahydrofuran-2-yl)methyl (S)-2-acetamido-3,3-dimethylbutanoate (Compound 413)

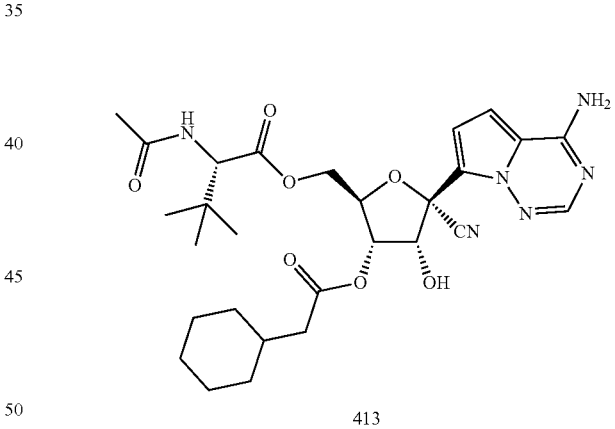

The title compound 413 was prepared according to the procedure of Example 17, Step 2, using 371. MS (ESI): mass calcd. for $C_{25}H_{38}N_6O_7$, 570.28, m/z found 571.2 [M+H]⁺. ¹H NMR (400 MHz, DMSO) δ 8.07 (d, J=8.4 Hz, 1H), 7.92 (br s, 3H), 6.92 (d, J=4.4 Hz, 1H), 6.88 (d, J=4.8 Hz, 1H), 6.65-6.60 (m, 1H), 5.13-5.01 (m, 2H), 4.48-4.45 (m, 1H), 4.30 (d, J=4.4 Hz, 2H), 4.15 (d, J=8.4 Hz, 1H), 2.25 (d, J=6.8 Hz, 2H), 1.89 (s, 3H), 1.83-1.57 (m, 6H), 1.27-1.09 (m, 3H), 0.98-0.93 (m, 2H), 0.86 (s, 9H)

Example 241. Synthesis of ((2R,3S,4R,5R)-5-cyano-5-(4-(2-cyclohexylacetamido)pyrrolo[2,1-f][1,2,4]triazin-7-yl)-3,4-dihydroxytetrahydrofuran-2-yl)methyl (S)-2-amino-3,3-dimethylbutanoate (Compound 414)

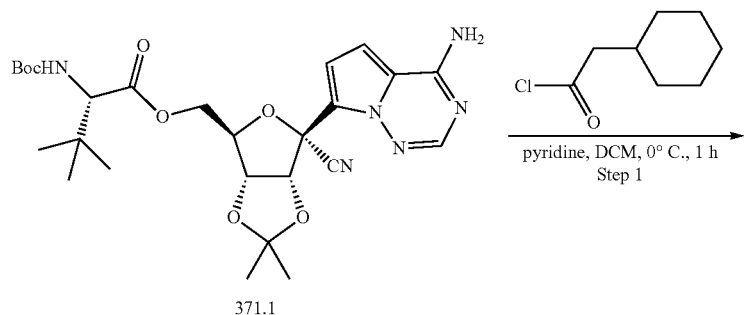

371.1

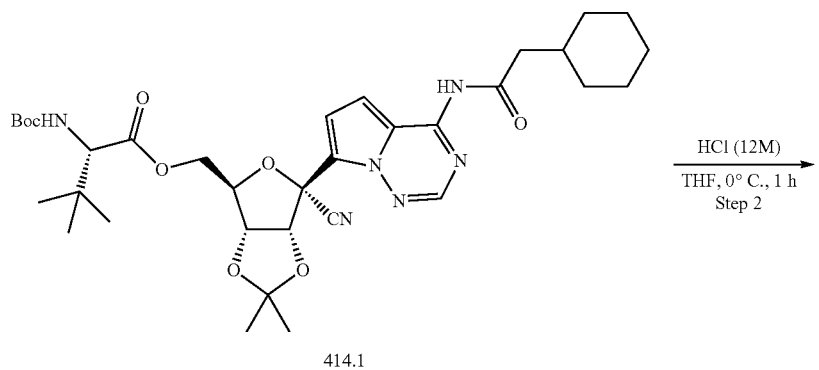

414.1

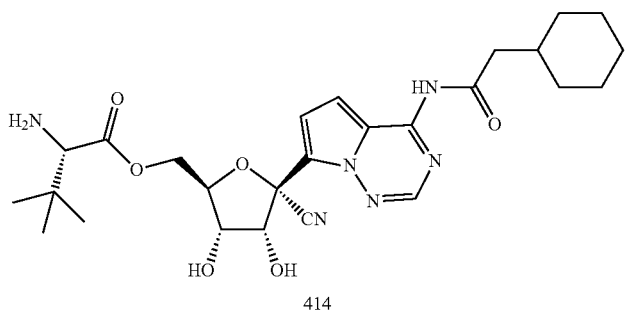

414

Step 1. Synthesis of ((3aR,4R,6R,6aR)-6-cyano-6-(4-(2-cyclohexylacetamido)pyrrolo[2,1-f][1,2,4]triazin-7-yl)-2,2-dimethyltetrahydrofuro[3,4-d][1,3]dioxol-4-yl)methyl (S)-2-((tert-butoxycarbonyl)amino)-3,3-dimethylbutanoate (414.1)

The title compound 414.1 was prepared according to the procedure of Example 210, Step 1, using 371.7 and 2-cyclohexylacetyl chloride. MS (ESI): mass calcd. for $C_{34}H_{48}N_6O_8$, 668.35 m/z found 669.4 [M+H]$^+$. $^1$H NMR (400 MHz, DMSO) δ 10.91 (s, 1H), 8.43 (s, 1H), 7.24 (d, J=4.8 Hz, 1H), 7.14-7.08 (m, 2H), 5.44 (d, J=6.4 Hz, 1H), 4.94 (dd, J=6.4, 2.8 Hz, 1H), 4.61-4.55 (m, 1H), 4.24 (dd, J=12.0, 4.4 Hz, 1H), 4.13 (dd, J=12.0, 6.8 Hz, 1H), 3.80 (d, J=8.4 Hz, 1H), 2.57 (d, J=6.8 Hz, 2H), 1.88-1.78 (m, 1H), 1.76-1.67 (m, 3H), 1.66-1.57 (m, 5H), 1.38-1.32 (m, 11H), 1.30-1.21 (m, 4H), 1.05-0.95 (m, 2H), 0.86 (s, 9H).

Step 2. Synthesis of ((2R,3S,4R,5R)-5-cyano-5-(4-(2-cyclohexylacetamido)pyrrolo[2,1-f][1,2,4]triazin-7-yl)-3,4-dihydroxytetrahydrofuran-2-yl)methyl (S)-2-amino-3,3-dimethylbutanoate (414)

The title compound 416 was prepared according to the procedure of Example 210, Step 2, using 414.1. MS (ESI): mass calcd. for $C_{26}H_{36}N_6O_6$, 528.27 m/z found 529.2 [M+H]$^+$. $^1$H NMR (400 MHz, DMSO) δ 10.88 (s, 1H), 8.39 (s, 1H), 7.26 (d, J=4.8 Hz, 1H), 7.09 (d, J=4.4 Hz, 1H), 6.46 (d, J=5.6 Hz, 1H), 5.50-5.40 (m, 1H), 4.69 (t, J=4.8 Hz, 1H), 4.32-4.19 (m, 3H), 3.97-3.90 (m, 1H), 2.99 (s, 1H), 2.57 (d, J=6.8 Hz, 2H), 1.88-1.78 (m, 1H), 1.77-1.57 (m, 5H), 1.31-1.09 (m, 3H), 1.06-0.94 (m, 2H), 0.90-0.80 (m, 9H).

Example 242. Synthesis of ((2R,3S,4R,5R)-5-cyano-4-hydroxy-5-(4-((((pivaloyloxy)methoxy)carbonyl)amino)pyrrolo[2,1-f][1,2,4]triazin-7-yl)-3-(propionyloxy)tetrahydrofuran-2-yl)methyl (S)-2-amino-3,3-dimethylbutanoate (Compound 415)
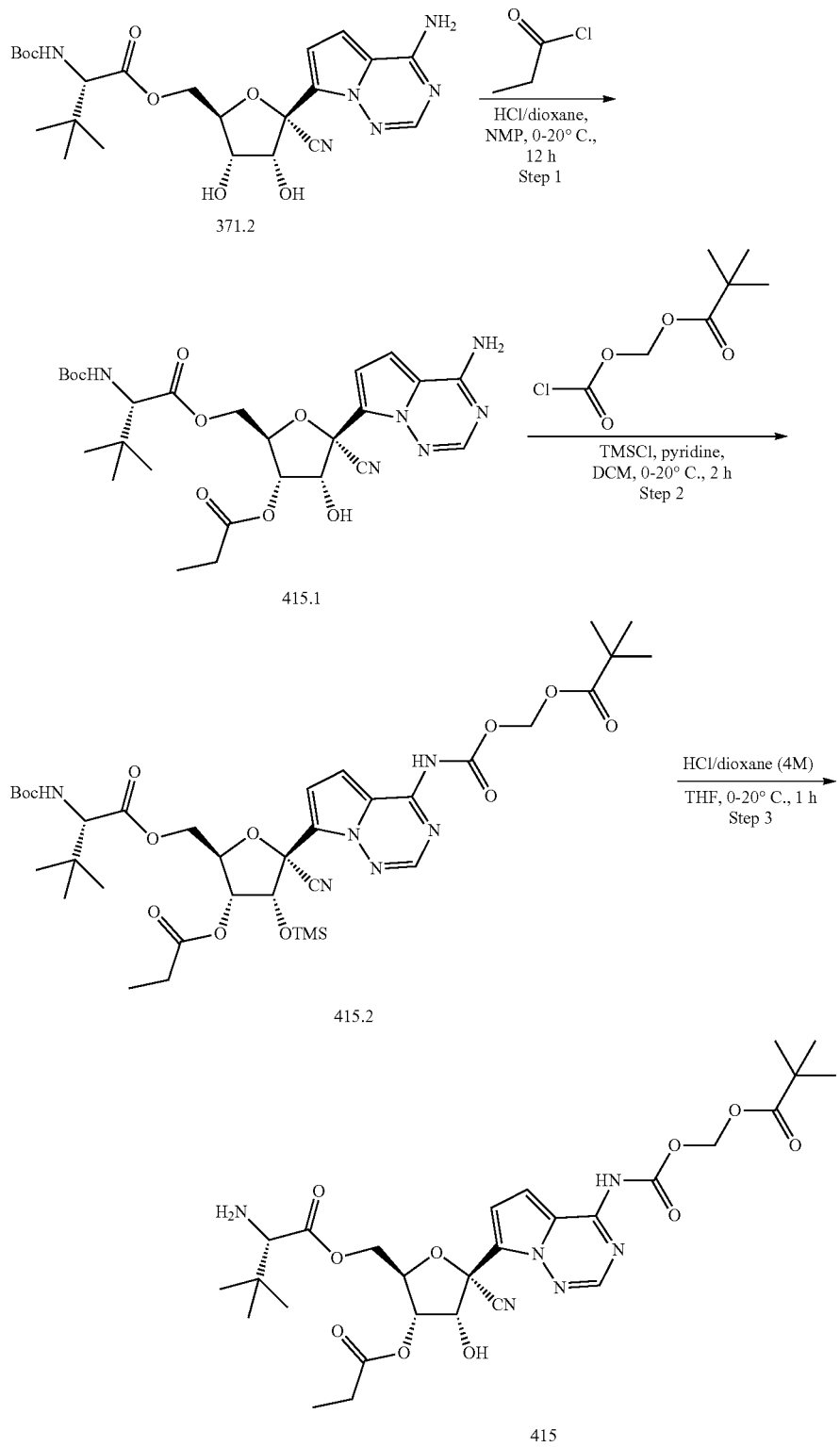

Step 1. Synthesis of ((2R,3S,4R,5R)-5-(4-aminopyrrolo[2,1-f][1,2,4]triazin-7-yl)-5-cyano-4-hydroxy-3-(propionyloxy)tetrahydrofuran-2-yl)methyl (S)-2-((tert-butoxycarbonyl)amino)-3,3-dimethylbutanoate (415.1)

The title compound 415.1 was prepared according to the procedure of Example 17, Step 2, using 371.2 and propionyl chloride. MS (ESI): mass calcd. for $C_{26}H_{36}N_6O_8$, 560.26 m/z found 561.2 [M+H]$^+$. $^1$H NMR (400 MHz, DMSO) δ 7.92 (br s, 3H), 7.07 (d, J=8.4 Hz, 1H), 6.92 (d, J=4.8 Hz, 1H), 6.87 (d, J=4.8 Hz, 1H), 6.60 (d, J=6.0 Hz, 1H), 5.13-5.08 (m, 2H), 4.50-4.42 (m, 1H), 4.30 (d, J=4.4 Hz, 2H), 3.84 (d, J=8.4 Hz, 1H), 2.40 (q, J=7.6 Hz, 2H), 1.42-1.20 (m, 9H), 1.07 (t, J=7.6 Hz, 3H), 0.86 (s, 9H).

Step 2. ((2R,3R,4R,5R)-5-cyano-5-(4-((((pivaloyloxy)methoxy)carbonyl)amino)pyrrolo[2,1-f][1,2,4]triazin-7-yl)-3-(propionyloxy)-4-((trimethylsilyl)oxy)tetrahydrofuran-2-yl)methyl (S)-2-((tert-butoxycarbonyl)amino)-3,3-dimethylbutanoate (415.2)

The title compound 415.2 was prepared according to the procedure of Example 209, Step 1, using 417.1 and ((chlorocarbonyl)oxy)methyl pivalate. MS (ESI): mass calcd. for $C_{36}H_{54}N_6O_{12}Si$, 790.36 m/z found 791.3 [M+H]$^+$.

Step 3. Synthesis of ((2R,3S,4R,5R)-5-cyano-4-hydroxy-5-(4-((((pivaloyloxy)methoxy)carbonyl)amino)pyrrolo[2,1-f][1,2,4]triazin-7-yl)-3-(propionyloxy)tetrahydrofuran-2-yl)methyl (S)-2-amino-3,3-dimethylbutanoate (415)

The title compound 415 was prepared according to the procedure of Example 209, Step 2, using 415.2. MS (ESI): mass calcd. for $C_{28}H_{38}N_6O_{10}$, 618.26 m/z found 619.3 [M+H]$^+$. $^1$H NMR (400 MHz, DMSO) δ 8.30 (s, 1H), 7.20-7.18 (m, 1H), 7.05-7.02 (m, 1H), 6.68 (d, J=6.4 Hz, 1H), 5.81 (s, 2H), 5.16 (t, J=5.2 Hz, 1H), 5.07 (t J=5.6 Hz, 1H), 4.51-4.48 (m, 1H), 4.32-4.21 (m, 2H), 2.96 (s, 1H), 2.40 (q, J=7.6 Hz, 2H), 1.17 (s, 9H), 1.08 (t, J=7.6 Hz, 3H), 0.81 (s, 9H).

Compounds 11, 13, 17-26, 28-32, 41, 42, 44-48, 53, 57, 60, 62, 63, 65, 68, 70, 71, 96, 174, 175, 177, 178, 183, 187, 195, 207, 211, 227, and 235 were prepared in a similar manner to the preceding Example procedures, and MS (ESI) data are shown in Table 1.

Example I: Oral Composition of a Compounds of Formula (I), (Ia), (Ib), (Ic), (Id), (Ie), (if), (Ig), (II), (III), (IV), (V), (VIa), (VIb), and (VIc), or a Pharmaceutically Acceptable Salt, Solvate, or Stereoisomer Thereof To prepare a pharmaceutical composition for oral delivery, 400 mg of compound described herein, or a pharmaceutically acceptable salt, solvate, or stereoisomer thereof and the following ingredients are mixed intimately and pressed into single scored tablets.

| Tablet Formulation | |
| --- | --- |
| Ingredient | Quantity per tablet (mg) |
| compound | 400 |
| cornstarch | 50 |
| croscarmellose sodium | 25 |
| lactose | 120 |
| magnesium stearate | 5 |

The following ingredients are mixed intimately and loaded into a hard-shell gelatin capsule.

| Capsule Formulation | |
| --- | --- |
| Ingredient | Quantity per capsule (mg) |
| compound | 200 |
| lactose spray dried | 148 |
| magnesium stearate | 2 |

Example II: Evaluation of Cellular Permeability in Caco-2 Cell Monolayers

The bidirectional permeability of compounds across the Caco-2 cell monolayer was assessed. The Caco-2 model is a widely used in vitro model for small intestinal absorption and potential for efflux.

Cell culture. Caco-2 cells were grown in DMEM supplemented with 10% fetal bovine serum (FBS), 1% Penicillin-Streptomycin and 1% MEM NEAA. The cells were incubated at 37° C., 5% $CO_2$/95% air and saturated humidity. After reaching 80-90% confluency, the cells were gently detached with trypsin. Cells at passage 39 were seeded on the 24-well BD insert system at the density of 8×10$^4$ cells/cm$^2$ and cultured for 19 days with medium changed every 2-3 days. Measure the transepithelial electrical resistance (TEER) value of each well. The wells can be used only when their TEER values are greater than 600 Ohms/cm$^2$.

Transport assay. After removing the cell culture medium from the 24-well insert plate, the cells were rinsed with warm transport buffer. Appropriate dosing and receiving solutions were applied to the donor and receiver chambers to initiate the transport assay in apical to basolateral (A to B) or basolateral to apical (B to A) directions (500 and 1300 μL for apical and basolateral wells, respectively). Duplicate wells in each direction were used for the test compound and control compound. The plate was incubated in $CO_2$ incubator at 37° C., with 5% $CO_2$/95% air and saturated humidity without shaking. The sample after 10-minute incubation was used as the $T_0$ sample, and the sample after 90-minute incubation was used as the $T_{90}$ sample. To and $T_{90}$ samples were collected from the donor and receiver side of each well at the designed timepoint, mixed with the transport buffer and acetonitrile/MeOH (1:1, v/v) and the internal standard for LC/MS/MS analysis. All samples were vortexed and centrifuged at 4000 rpm at 4° C. for 15 minutes, diluted with pure water and stored at 4° C. before bioanalysis by LC/MS/MS.

Sample analysis. The concentrations of test compounds and control compounds in Caco-2 cells were quantitatively determined by LC/MS/MS method after protein precipitation.

Calculations. The apparent permeability ($P_{app}$, cm/s), efflux ratio (ER) and recovery parameters were calculated for Caco-2 drug transport assay using the following equations:

$$P_{app} = \frac{V_R}{\text{Area} \times \text{Time}} \times \frac{[\text{drug}]_{recevier}}{[\text{drug}]_{initial,donor}} = \frac{V_R}{\text{Area} \times \text{Time}} \times \frac{C_R}{C_0}$$

$$ER = \frac{P_{app}(B \text{ to } A)}{P_{app}(A \text{ to } B)}$$

where $V_R$ is the solution volume in the receiver chamber (0.4 mL on the apical side, 1.2 mL on the basolateral side); Area is the surface area for the insert membrane, i.e., 0.3 cm² for the area of the monolayer; Time is incubation time, expressed in seconds, i.e., 5400 s (90 min) for the current experiment; Co is the initial concentration of test compound or peak area ratio of control compounds in the donor chamber (μM); $V_D$ is the volume in the donor chambers (0.4 mL on the apical side, 1.2 mL on the basolateral side); $C_D$ and $C_R$ are the final concentrations of test compounds or peak area ratio of control compounds in donor and receiver chambers, respectively.

Data for representative compounds is shown in Table 2. Compounds with $P_{app}$<1.0 are classified as low permeability, $P_{app}$ between 1-10 are classified as medium permeability, and $P_{app} \geq 10$ are classified as high permeability. An efflux ratio (ER)>2 indicates the compounds are potential substrates for intestinal cell efflux transporters.

TABLE 2

Bidirectional Caco-2 permeability assay results.

| Compound No. | $P_{app}$, A-B (×10⁻⁶ cm s⁻¹) | Papp, B-A, (×10⁻⁶ cm s⁻¹) | ER |
|---|---|---|---|
| 3 | 1.8 | 3.5 | 2.0 |
| 8 | 0.2 | 0.5 | 2.4 |
| 9 | 3.0 | 4.7 | 1.6 |
| 10 | 3.0 | 4.7 | 1.6 |
| 11 | 0.4 | 0.1 | 0.4 |
| 12 | 3.0 | 8.9 | 3.0 |
| 13 | 0.2 | 0.6 | 2.7 |
| 14 | 2.3 | 2.2 | 1.0 |
| 15 | 2.9 | 7 | 3.4 |
| 17 | 15 | 21 | 1.4 |
| 18 | 16 | 8.8 | 0.6 |
| 20 | 10 | 9.8 | 1.0 |
| 22 | 7.0 | 10 | 1.5 |
| 23 | 6.3 | 8.1 | 1.3 |
| 24 | 8.1 | 3.6 | 0.44 |
| 25 | 56 | 42 | 0.7 |
| 27 | 0.10 | 9.9 | 100 |
| 29 | 2.0 | 2.1 | 1.1 |
| 30 | 7.3 | 7.1 | 1.0 |
| 31 | 5.6 | 5.6 | 1.0 |
| 32 | 6.9 | 5.5 | 0.8 |
| 34 | 1.6 | 4.8 | 3.0 |
| 36 | 1.1 | 10.3 | 9.8 |
| 37 | 0.37 | 0.12 | 0.33 |
| 38 | 0.22 | 3.3 | 15 |
| 39 | 0.23 | 2.3 | 10 |
| 41 | 19 | 31 | 1.6 |
| 43 | 0.74 | 0.22 | 0.30 |
| 44 | 9.8 | 25 | 2.5 |
| 45 | 0.8 | 3.4 | 4.3 |
| 46 | 2.7 | 4.8 | 1.8 |
| 47 | 2.0 | 5.1 | 2.5 |
| 48 | 6.9 | 1.9 | 0.27 |
| 49 | 3.9 | 2.7 | 0.70 |
| 50 | 1.9 | 0.76 | 0.39 |
| 52 | 1.4 | 0.89 | 0.65 |
| 54 | 2.6 | 2.4 | 0.94 |
| 56 | 4.7 | 4.0 | 0.84 |
| 58 | 4.1 | 2.1 | 0.5 |
| 60 | 2.8 | 1.7 | 0.58 |
| 62 | 3.0 | 2.4 | 0.80 |
| 64 | 5.9 | 7.1 | 1.2 |
| 66 | 2.7 | 0.36 | 0.13 |
| 67 | 0.30 | 0.10 | 0.33 |
| 68 | 3.3 | 9.3 | 2.8 |
| 70 | 1.8 | 1.6 | 0.82 |
| 71 | 0.94 | 2.3 | 2.4 |
| 72 | 5.8 | 3.2 | 0.55 |
| 81 | 1.0 | 14.7 | 14 |
| 83 | 0.07 | 0.2 | 3.0 |
| 84 | 0.0 | 0.0 | |
| 85 | 0.37 | 11 | 31 |
| 86 | 0.33 | 11 | 35 |
| 87 | 5.5 | 14 | 2.7 |
| 88 | 2.1 | 1.6 | 0.78 |
| 89 | 2.1 | 6.6 | 3.2 |
| 91 | 1.9 | 4.1 | 2.1 |
| 92 | 2.7 | 4.6 | 1.7 |
| 93 | 2.8 | 1.5 | 0.54 |
| 94 | 0.07 | 0.64 | 9.1 |
| 96 | 0.45 | 5.2 | 12 |
| 97 | 3.8 | 6.6 | 1.8 |
| 100 | 0.03 | 2.7 | 92 |
| 101 | 0.07 | 13 | 175 |
| 102 | 0.02 | 6.7 | 280 |
| 103 | 1.5 | 12 | 8.0 |
| 105 | 0.77 | 1.4 | 1.8 |
| 107 | 2.1 | 7.5 | 3.6 |
| 108 | 1.5 | 2.0 | 1.4 |
| 109 | 1.4 | 1.3 | 0.9 |
| 110 | 0.02 | 0.33 | 15 |
| 112 | 0.14 | 6.1 | 44 |
| 113 | 0.01 | 4.8 | 320 |
| 115 | 0.04 | 1.7 | 47 |
| 116 | 0.15 | 1.2 | 7.9 |
| 117 | 0.22 | 3.3 | 15 |
| 128 | 0.30 | 6.4 | 22 |
| 129 | 0.03 | 0.02 | 0.7 |
| 137 | 0.60 | 2.7 | 4.5 |
| 139 | 0.18 | 6.1 | 34 |
| 141 | 0.14 | 0.04 | 0.33 |
| 143 | 0.67 | 0.12 | 0.18 |
| 144 | 0.03 | 1.8 | 53 |
| 178 | 6.7 | 4.4 | 0.7 |
| 180 | 4.6 | 7.6 | 1.6 |
| 186 | 19 | 7.2 | 0.38 |
| 187 | 11 | 2.4 | 0.22 |
| 194 | 12 | 2.1 | 0.18 |
| 195 | 6.3 | 1.1 | 0.18 |
| 210 | 15 | 5.8 | 0.38 |
| 211 | 6.2 | 4.8 | 0.8 |
| 215 | 9.3 | 1.6 | 0.18 |
| 217 | 14 | 6.1 | 0.45 |
| 220 | 20 | 13 | 0.64 |
| 223 | 20 | 6.9 | 0.34 |
| 227 | 8.5 | 3.2 | 0.40 |
| 235 | 11 | 4.5 | 0.4 |
| 254 | 2.2 | 1.7 | 0.8 |
| 255 | 2.1 | 5.3 | 2.5 |
| 257 | 0.03 | 1.4 | 46 |
| 258 | 0.09 | 0.30 | 3.5 |
| 259 | 2.0 | 0.6 | 0.30 |
| 261 | 0.79 | 1.1 | 1.4 |
| 262 | 0.91 | 4.4 | 4.8 |
| 263 | 13 | 19 | 1.5 |
| 264 | 0.03 | 0.53 | 20 |
| 265 | 0.29 | 0.36 | 1.2 |
| 266 | 0.19 | 0.38 | 2 |
| 267 | 0.42 | 0.27 | 0.65 |
| 268 | 0.04 | 1.8 | 45 |
| 269 | 15 | 20 | 1.3 |
| 270 | 1.9 | 6.9 | 3.7 |
| 271 | 0.06 | 0.52 | 8.7 |
| 272 | 1.2 | 0.64 | 0.52 |
| 273 | 3.7 | 3.2 | 0.85 |
| 274 | 0.85 | 12 | 14 |
| 275 | 11 | 16 | 1.6 |

TABLE 2-continued

Bidirectional Caco-2 permeability assay results.

| Compound No. | $P_{app}$, A-B ($\times 10^{-6}$ cm s$^{-1}$) | Papp, B-A, ($\times 10^{-6}$ cm s$^{-1}$) | ER |
|---|---|---|---|
| 276 | 0.36 | 2.9 | 8.0 |
| 277 | 0.47 | 5.4 | 12 |
| 278 | 2.2 | 4.9 | 2.2 |
| 279 | 1.4 | 0.90 | 0.64 |
| 280 | 0.38 | 0.91 | 2.4 |
| 281 | 13 | 29 | 2.3 |
| 282 | 0.72 | 4.1 | 5.6 |
| 283 | 3.0 | 1.0 | 0.34 |
| 284 | 1.7 | 0.95 | 0.56 |
| 285 | 1.1 | 0.90 | 0.83 |
| 286 | 0.01 | 0.40 | 67 |
| 287 | 5.2 | 13 | 2.4 |
| 288 | 0.91 | 6.9 | 7.7 |
| 289 | 6.4 | 25 | 3.8 |
| 291 | 11 | 17 | 1.6 |
| 292 | 2.0 | 1.0 | 0.5 |
| 312 | 23 | 6.5 | 0.28 |
| 329 | 16 | 18 | 1.1 |
| 330 | 0.54 | 7.0 | 13 |
| 331 | 7.9 | 16 | 2.1 |
| 332 | 11 | 2.6 | 0.22 |
| 334 | 0.76 | 19 | 25 |
| 340 | 0.64 | 0.23 | 0.35 |
| 341 | 0.13 | 2.3 | 18 |
| 342 | 1.1 | 0.39 | 0.34 |
| 343 | 1.2 | 6.5 | 5.6 |
| 344 | 0.80 | 9.7 | 12 |
| 345 | 0.09 | 3.9 | 43 |
| 346 | 1.6 | 9.0 | 5.7 |
| 347 | 7.0 | 17 | 2.4 |
| 348 | 0.43 | 13 | 30 |
| 349 | 1.9 | 10 | 5.6 |
| 350 | 1.9 | 6.9 | 4.3 |
| 351 | 0.17 | 0.92 | 5.5 |
| 352 | 0.25 | 1.4 | 5.7 |
| 354 | 10 | 3.0 | 0.29 |
| 355 | 1.5 | 0.49 | 0.33 |
| 356 | 0.60 | 3.6 | 6.0 |
| 357 | 3.1 | 6.0 | 1.9 |
| 358 | 0.30 | 0.10 | 0.33 |
| 360 | 0.49 | 0.16 | 0.33 |
| 361 | 0.15 | 0.05 | 0.33 |
| 362 | 4.6 | 6.7 | 1.5 |
| 363 | 0.07 | 0.02 | 0.33 |
| 364 | 1.8 | 2.0 | 1.1 |
| 365 | 1.5 | 4.1 | 2.8 |
| 366 | 2.7 | 1.1 | 0.39 |
| 367 | 2.8 | 1.6 | 0.57 |
| 368 | 1.4 | 18 | 13 |
| 370 | 0.30 | 0.23 | 0.77 |
| 371 | 15 | 21 | 1.3 |
| 372 | 0.73 | 0.83 | 1.1 |
| 373 | 24 | 29 | 1.2 |
| 374 | 0.004 | 0.08 | 19 |
| 375 | 0.02 | 0.02 | 1.1 |
| 379 | 1.6 | 2.5 | 1.6 |
| 383 | <1 | <1 | — |
| 385 | <1 | <1 | — |
| 392 | 5.6 | 16.4 | 3.0 |
| 395 | 0.01 | 0.24 | 19.2 |
| 397 | 2.8 | 7.3 | 2.6 |
| 399 | 0.00 | 0.00 | — |
| 401 | 3.8 | 15.3 | 4.1 |
| 402 | 0.00 | 0.09 | — |
| 409 | 0.46 | 0.10 | 0.22 |
| 410 | 0.47 | 1.49 | 3.2 |
| 411 | 0.12 | 2.50 | 20.7 |
| 412 | 5.1 | 0.9 | 0.2 |
| 413 | 4.3 | 13.8 | 3.2 |

Example III: Evaluation of Oral Bioavailability in Sprague-Dawley Rats

The single dose pharmacokinetics of Example Compounds were evaluated in fasted male Sprague-Dawley rats following oral gavage. Compounds were be dosed as solutions or acceptable suspensions in vehicles generally-regarded as safe for in vivo studies. Groups of three rats per compound were utilized, and blood samples were collected at 0.25, 0.5, 1, 2, 4, 8 and 24 h post-dose, stored on ice prior to plasma preparation by centrifugation at 4° C. at 6000 rpm for 5 min. Plasma samples were stored at −80° C. Concentrations of Example Compounds and corresponding nucleosides resulting from metabolic processing were determined using ultra-high performance liquid chromatography-triple-quadrupole mass spectrometry, with an internal standard. Pharmacokinetic parameters were derived from the resulting plasma concentration/time graphs, and include the following: plasma half-life ($t_{1/2}$) time to maximum plasma concentration ($T_{max}$), maximum plasma concentration ($C_{max}$), area under the curve of the plasma concentration/time graph ($AUC_{last}$, through last timepoint obtained, and $AUC_{Inf}$, including the extrapolated area), and mean residence time ($MRT_{Inf}$). The resulting $AUC_{Inf}$ for the resulting nucleosides were be compared with that resulting from intravenous bolus administration of the corresponding nucleosides in three rats, and an oral bioavailability (F, %) was be calculated as $$F = \frac{AUCinf, PO}{AUCinf, IV} \times \frac{Dose\ (IV)}{Dose\ (PO)} \times \frac{FW(\text{prodrug})}{FW(\text{nucleoside})}$$

Rat pharmacokinetic parameters for representative compounds are shown in Table 3. Bioavailabilities were calculated using the following $AUC_{inf}$ values following 3 mg/kg IV dosing of parent nucleosides: Compounds 6-15, 18, 20, 25, 29-32, 41, and 44-47 used 2110 ng*h/mL; Compounds 3, 180, 221, and 254 used 2069 ng*h/mL.

TABLE 3

Pharmacokinetic parameters following oral dosing of 10 mg/kg in Sprague-Dawley rats. $C_{max}$ and $AUC_{inf}$ derived for parent nucleosides, and formula weight-corrected bioavailabilities of Compounds are shown.

| Compound Number | $C_{max}$ (ng/mL) | $AUC_{inf}$ (ng * h/mL) | F (%) |
|---|---|---|---|
| 3 | 1460 | 3303 | 62 |
| 6 | 206 | 1540 | 50 |
| 7 | 89 | 1068 | 41 |
| 8 | 58 | 262 | 8 |
| 9 | 758 | 1876 | 34 |
| 10 | 890 | 2448 | 50 |
| 11 | 507 | 1388 | 30 |
| 12 | 539 | 1352 | 27 |
| 13 | 449 | 1395 | 23 |
| 14 | 495 | 1167 | 21 |
| 15 | 517 | 1122 | 19 |
| 18 | 731 | 1312 | 32 |
| 20 | 892 | 1741 | 42 |
| 25 | 946 | 1612 | 39 |
| 27 | 859 | 2640 | 66 |
| 29 | 1190 | 2646 | 59 |
| 30 | 1000 | 1714 | 41 |
| 31 | 850 | 1707 | 39 |
| 32 | 779 | 1236 | 32 |
| 34 | 573 | 2420 | 66 |
| 41 | 1850 | 2609 | 63 |
| 44 | 475 | 1241 | 29 |
| 45 | 1277 | 2597 | 57 |

TABLE 3-continued

Pharmacokinetic parameters following oral dosing of 10 mg/kg in Sprague-Dawley rats. $C_{max}$ and $AUC_{inf}$ derived for parent nucleosides, and formula weight-corrected bioavailabilities of Compounds are shown.

| Compound Number | $C_{max}$ (ng/mL) | $AUC_{inf}$ (ng * h/mL) | F (%) |
|---|---|---|---|
| 46 | 1507 | 2882 | 67 |
| 47 | 1530 | 2806 | 64 |
| 89 | 1657 | 2390 | 61 |
| 112 | 8 | 19 | 0.5 |
| 180 | 905 | 2156 | 37 |
| 211 | 2297 | 2751 | 64 |
| 227 | 2190 | 2734 | 57 |
| 254 | 57 | 385 | 12 |
| 262 | 867 | 2680 | 59 |
| 274 | 11 | 34.7 | 1 |
| 279 | 594 | 2260 | 52 |
| 284 | 1317 | 2330 | 57 |
| 289 | 606 | 2020 | 43 |

What is claimed is:

1. A compound of Formula (V), or a pharmaceutically acceptable salt, solvate, or stereoisomer thereof:

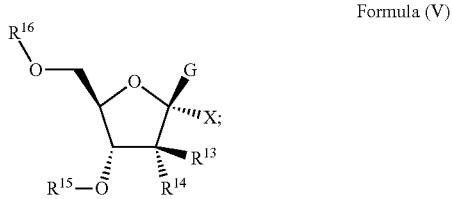

Formula (V)

wherein:
X is hydrogen or —CN;
G is

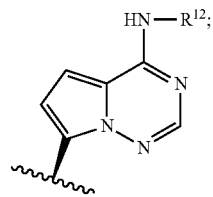

$R^{12}$ is —C(=O)$R^{22}$, —C(=O)O$R^{22}$, or $C_1$-$C_6$alkyl optionally substituted with one or more $R^{12a}$;
each $R^{12a}$ is independently halogen, —CN, —OH, —O$R^a$, —N$R^cR^d$, cycloalkyl, or heterocycloalkyl;
or two $R^{12a}$ on the same atom are taken together to form an oxo;
$R^{22}$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkyl, alkylene, cycloalkyl, heterocycloalkyl, aryl, and heteroaryl is optionally and independently substituted with one or more $R^{22a}$;
each $R^{22a}$ is independently halogen, —CN, —NO$_2$, —OH, —O$R^a$, —OC(=O)$R^a$, —OC(=O)O$R^b$, —OC(=O)N$R^cR^d$, —S(=O)$R^a$, —S(=O)$_2$$R^a$, —S(=O)$_2$N$R^cR^d$, —N$R^cR^d$, —C(=O)$R^a$, —C(=O)O$R^b$, —C(=O)N$R^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;
or two $R^{22a}$ on the same atom are taken together to form an oxo;
or two $R^{22a}$ are taken together to form a cycloalkyl or heterocycloalkyl; each optionally and independently substituted with one or more R;
$R^{13}$ is hydrogen or $C_1$-$C_6$alkyl;
$R^{14}$ is —OH or fluoro;
$R^{15}$ is hydrogen, —C(=O)$R^{25}$, —C(=O)O$R^{25}$, —CH$_2$—O—C(=O)$R^{25}$, or —CH$_2$—O—C(=O)O$R^{25}$;
$R^{25}$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkyl, alkylene, cycloalkyl, heterocycloalkyl, aryl, and heteroaryl is optionally and independently substituted with one or more R 25a;
each $R^{25a}$ is independently halogen, —CN, —NO$_2$, —OH, —O$R^a$, —OC(=O)$R^a$, —OC(=O)O$R^b$, —OC(=O)N$R^cR^d$, —S(=O)$R^a$, —S(=O)$_2$$R^a$, —S(=O)$_2$N$R^cR^d$, —N$R^cR^d$, —C(=O)$R^a$, —C(=O)O$R^b$, —C(=O)N$R^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;
or two $R^{25a}$ on the same atom are taken together to form an oxo;
or two $R^{25a}$ are taken together to form a cycloalkyl or heterocycloalkyl; each optionally and independently substituted with one or more R;
$R^{16}$ is —C(=O)$R^{26}$, —C(=O)O$R^{26}$, —CH$_2$—O—C(=O)$R^{26}$, —CH$_2$—O—C(=O)O$R^{26}$, or $C_1$-$C_6$alkyl optionally substituted with one or more $R^{16a}$;
each $R^{16a}$ is independently halogen, —CN, —OH, —O$R^a$, —N$R^cR^d$, cycloalkyl, or heterocycloalkyl;
or two $R^{16a}$ on the same atom are taken together to form an oxo;
$R^{26}$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkyl, alkylene, cycloalkyl, heterocycloalkyl, aryl, and heteroaryl is optionally and independently substituted with one or more $R^{26a}$;
each $R^{26a}$ is independently halogen, —CN, —NO$_2$, —OH, —O$R^a$, —OC(=O)$R^a$, —OC(=O)O$R^b$, —OC(=O)N$R^cR^d$, —S(=O)$R^a$, —S(=O)$_2$$R^a$, —S(=O)$_2$N$R^cR^d$, —N$R^cR^d$, —C(=O)$R^a$, —C(=O)O$R^b$, —C(=O)N$R^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, cycloalkyl, heterocycloalkyl, aryl, and heteroaryl is optionally and independently substituted with one or more R;

or two R²⁶ᵃ on the same atom are taken together to form an oxo;

or two R²⁶ᵃ are taken together to form a cycloalkyl or heterocycloalkyl; each optionally and independently substituted with one or more R;

each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl), wherein the alkyl, alkenyl, alkynyl, cycloalkyl, heterocycloalkyl, aryl, and heteroaryl is independently optionally substituted with one or more R;

each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl), wherein the alkyl, alkenyl, alkynyl, cycloalkyl, heterocycloalkyl, aryl, and heteroaryl is independently optionally substituted with one or more R;

$R^c$ and $R^d$ are each independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl), wherein the alkyl, alkenyl, alkynyl, cycloalkyl, heterocycloalkyl, aryl, and heteroaryl is independently optionally substituted with one or more R;

or $R^c$ and $R^d$ are taken together with the atom to which they are attached to form a heterocycloalkyl optionally substituted with one or more R; and each R is independently halogen, —CN, —OH, —OCH₃, —S(=O)CH₃, —S(=O)₂CH₃, —S(=O)₂NH₂, —S(=O)₂NHCH₃, —S(=O)₂N(CH₃)₂, —NH₂, —NHCH₃, —N(CH₃)₂, —C(=O)CH₃, —C(=O)OH, —C(=O)OCH₃, $C_1$-$C_6$alkyl, $C_1$-$C_6$haloalkyl, $C_1$-$C_6$hydroxyalkyl, $C_1$-$C_6$aminoalkyl, and $C_1$-$C_6$heteroalkyl;

or two R on the same atom are taken together to form an oxo.

2. The compound of claim 1, or a pharmaceutically acceptable salt, solvate, or stereoisomer thereof, wherein X is —CN; $R^{13}$ is hydrogen; and $R^{14}$ is —OH.

3. The compound of claim 1, or a pharmaceutically acceptable salt, solvate, or stereoisomer thereof, wherein $R^{12}$ is —C(=O)R²² or —C(=O)OR²².

4. The compound of claim 3, or a pharmaceutically acceptable salt, solvate, or stereoisomer thereof, wherein $R^{22}$ is $C_1$-$C_6$alkyl optionally and independently substituted with one or more $R^{22a}$.

5. The compound of claim 4, or a pharmaceutically acceptable salt, solvate, or stereoisomer thereof, wherein each $R^{22a}$ is independently halogen, —OH, —OR^a, —NR^cR^d, $C_1$-$C_6$alkyl, or $C_1$-$C_6$haloalkyl.

6. The compound of claim 1, or a pharmaceutically acceptable salt, solvate, or stereoisomer thereof, wherein $R^{15}$ is hydrogen, —C(=O)R²⁵, or —C(=O)OR²⁵.

7. The compound of claim 6, or a pharmaceutically acceptable salt, solvate, or stereoisomer thereof, wherein $R^{25}$ is $C_1$-$C_6$alkyl or $C_1$-$C_6$aminoalkyl; wherein the alkyl is optionally and independently substituted with one or more $R^{25a}$.

8. The compound of claim 6, or a pharmaceutically acceptable salt, solvate, or stereoisomer thereof, wherein $R^{25}$ is $C_1$-$C_6$alkylene(cycloalkyl) or $C_1$-$C_6$alkylene(aryl); wherein the alkylene, cycloalkyl, and aryl is optionally and independently substituted with one or more $R^{25a}$.

9. The compound of claim 6, or a pharmaceutically acceptable salt, solvate, or stereoisomer thereof, wherein each $R^{25a}$ is independently halogen, —OH, —OR^a, —NR^cR^d, $C_1$-$C_6$alkyl, or $C_1$-$C_6$haloalkyl.

10. The compound of claim 1, or a pharmaceutically acceptable salt, solvate, or stereoisomer thereof, wherein $R^{16}$ is —C(=O)R²⁶ or —C(=O)OR²⁶.

11. The compound of claim 10, or a pharmaceutically acceptable salt, solvate, or stereoisomer thereof, wherein $R^{26}$ is alkyl optionally and independently substituted with one or more $R^{26a}$.

12. The compound of claim 10, or a pharmaceutically acceptable salt, solvate, or stereoisomer thereof, wherein $R^{26}$ is $C_1$-$C_6$alkylene(cycloalkyl) or $C_1$-$C_6$alkylene(aryl); wherein the alkylene, cycloalkyl, and aryl is optionally and independently substituted with one or more $R^{26a}$.

13. The compound of claim 10, or a pharmaceutically acceptable salt, solvate, or stereoisomer thereof, wherein each $R^{26a}$ is independently halogen, —OH, —OR^a, —NR^cR^d, $C_1$-$C_6$alkyl, or $C_1$-$C_6$haloalkyl.

14. The compound of claim 1, wherein the compound is selected from the group consisting of:

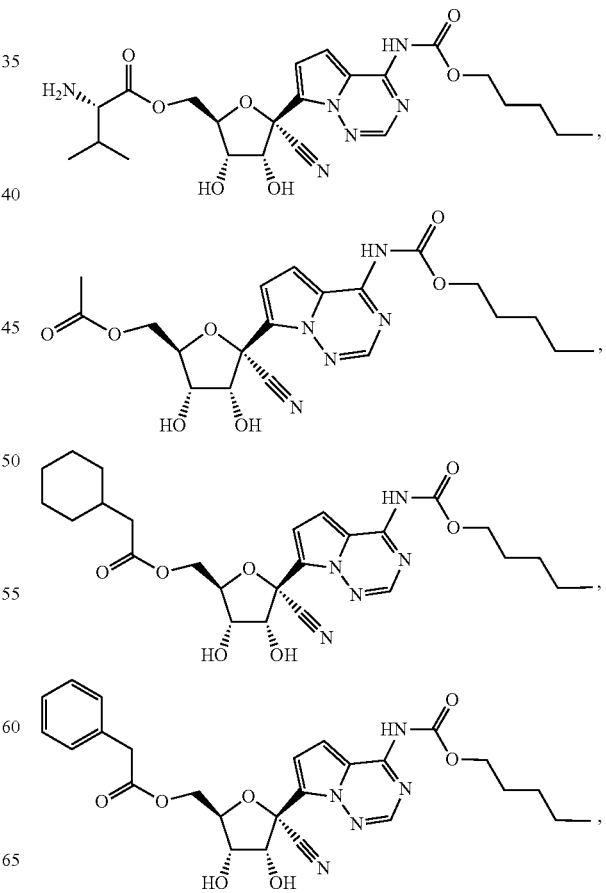

623
-continued
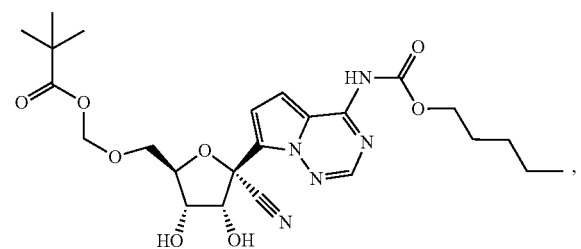
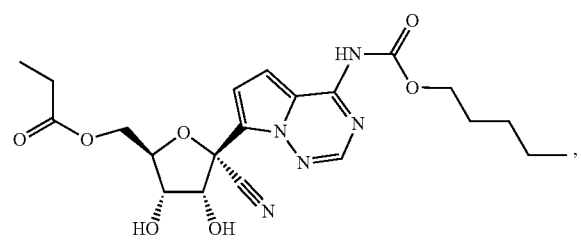
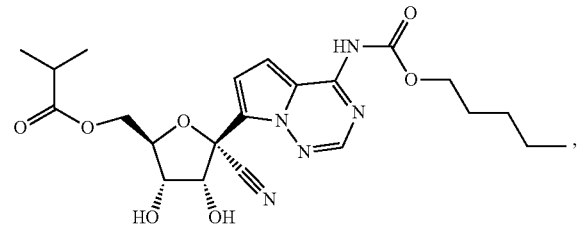
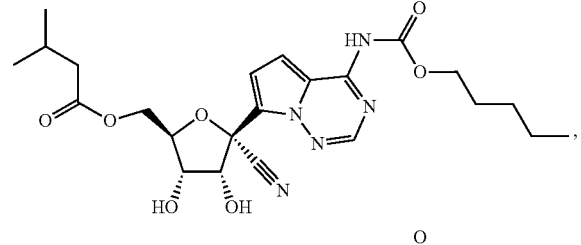
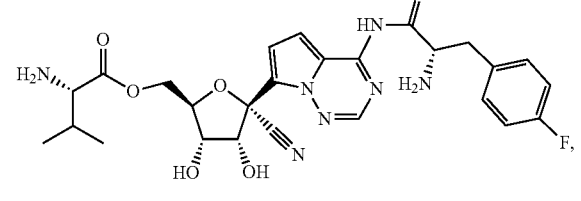
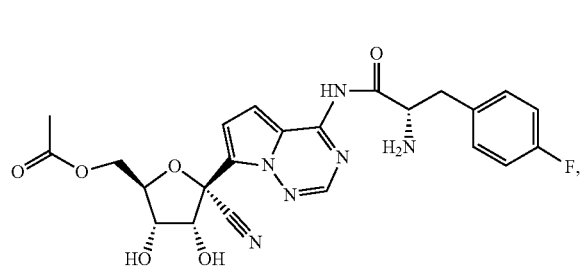
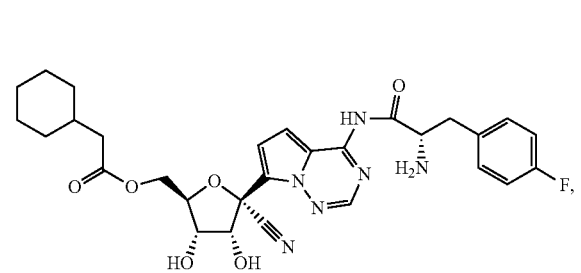
624
-continued
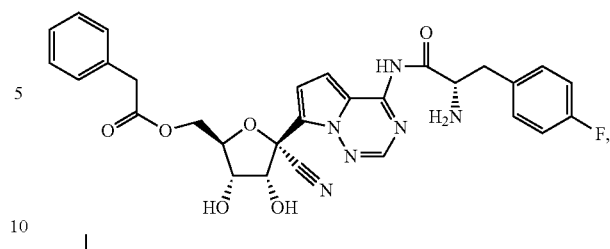
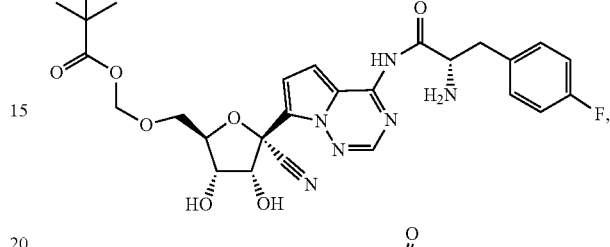
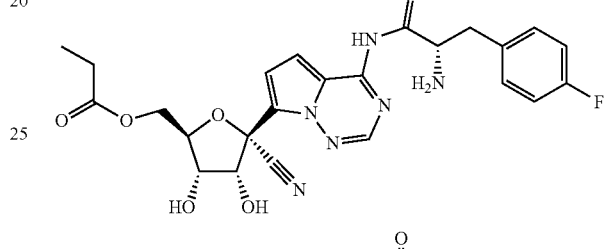
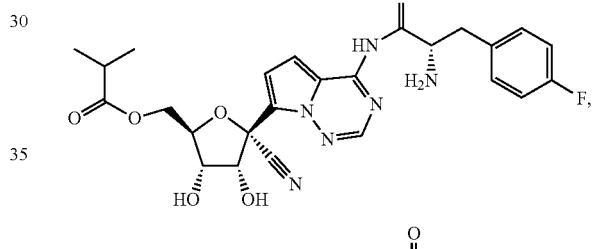
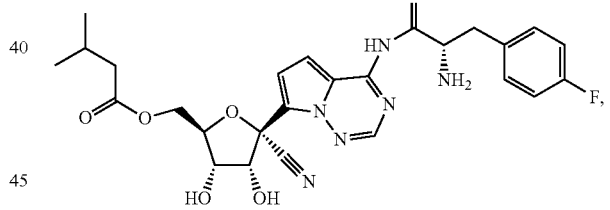
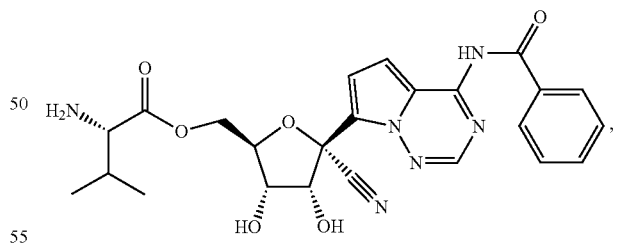
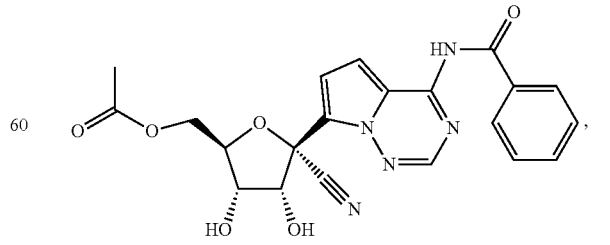

625
-continued
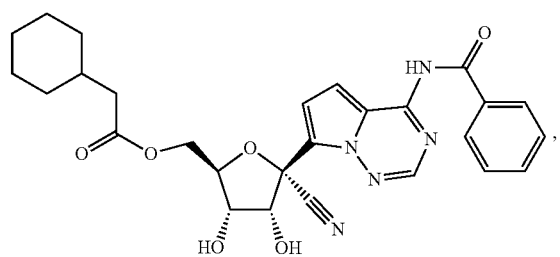
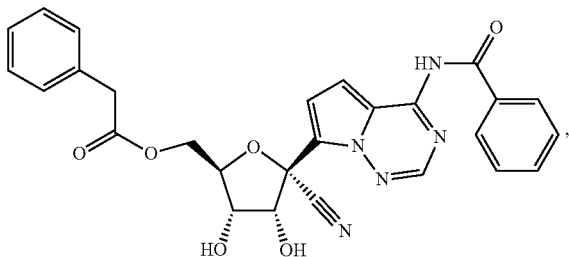
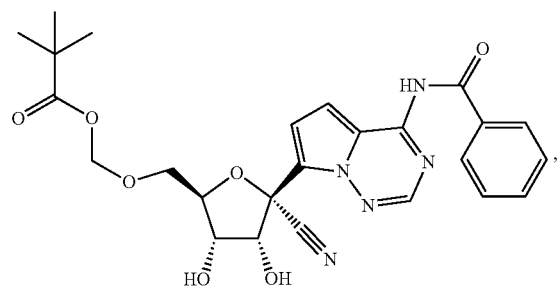
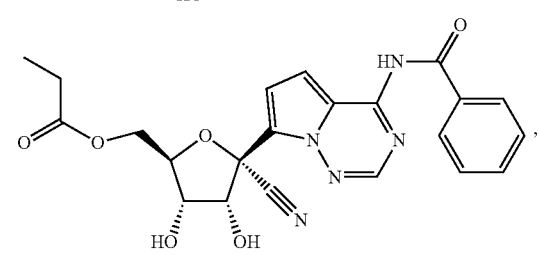
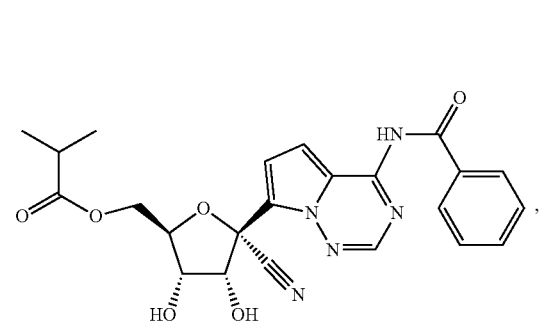
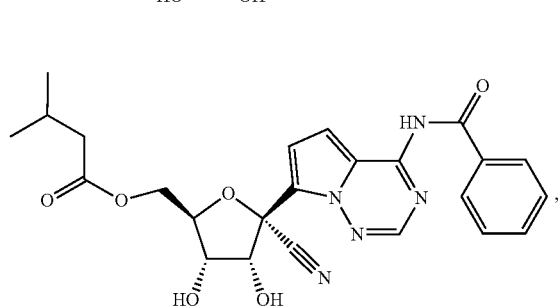
626
-continued
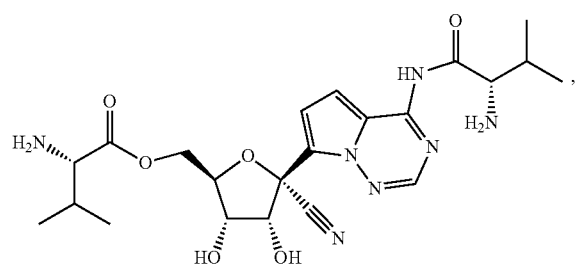
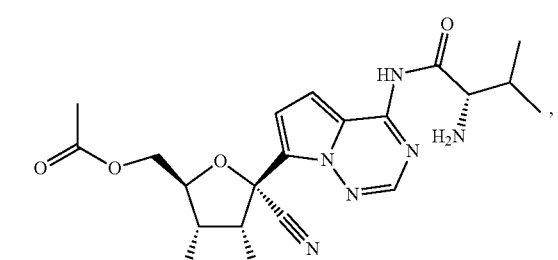
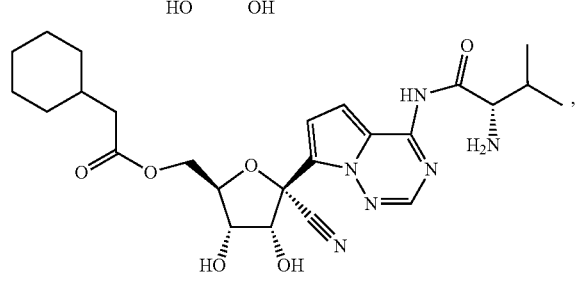
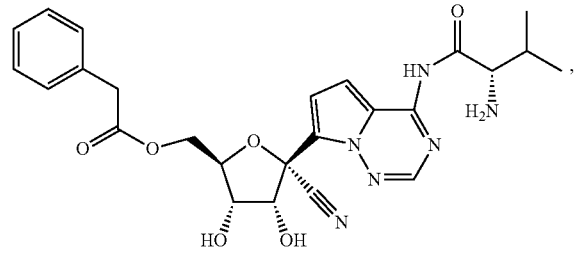
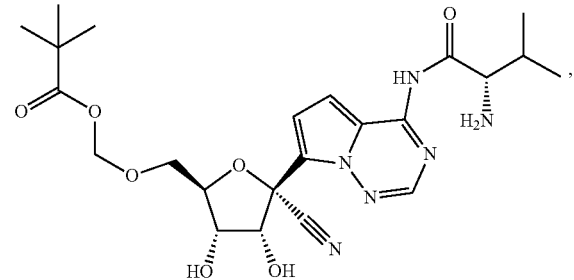
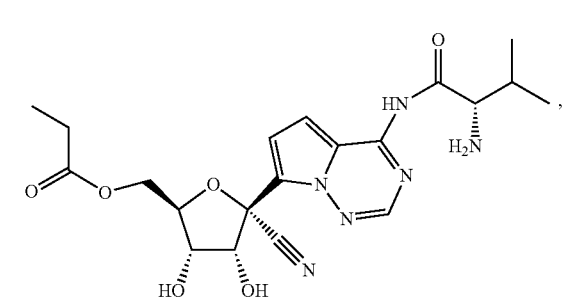

627
-continued
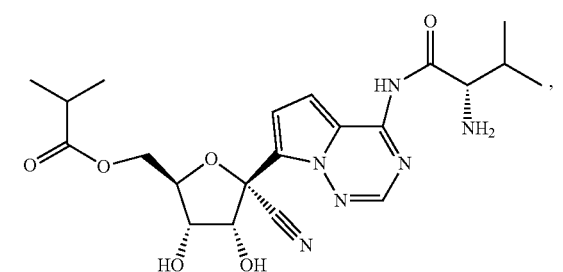
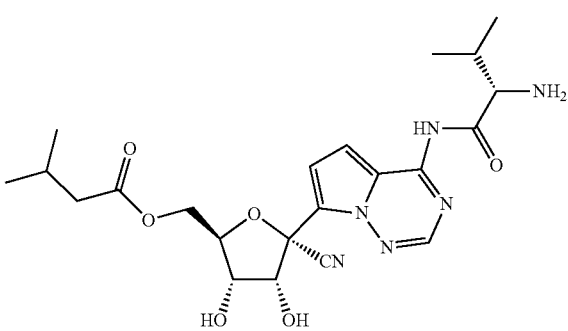
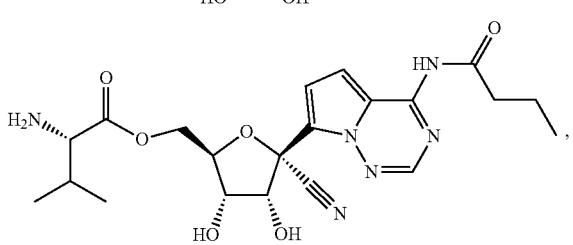
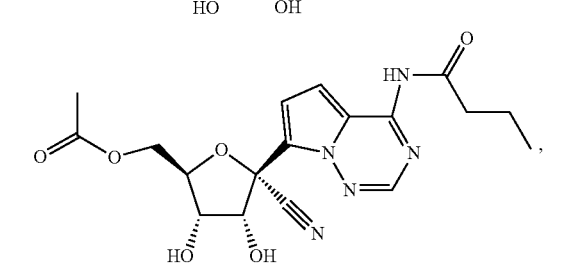
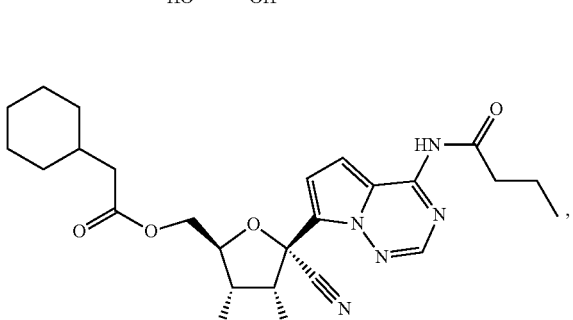
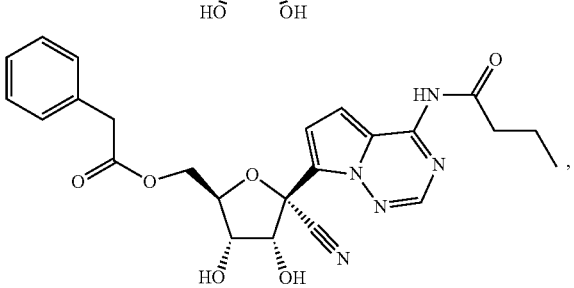
628
-continued
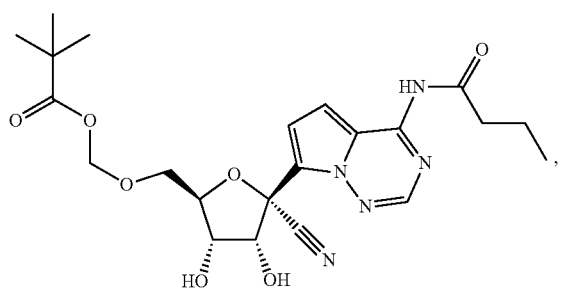
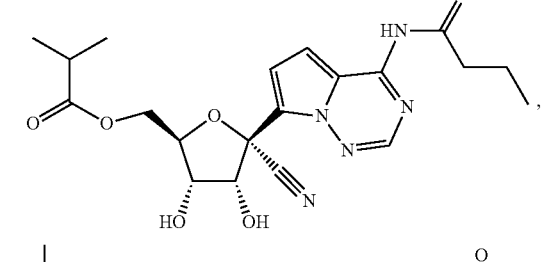
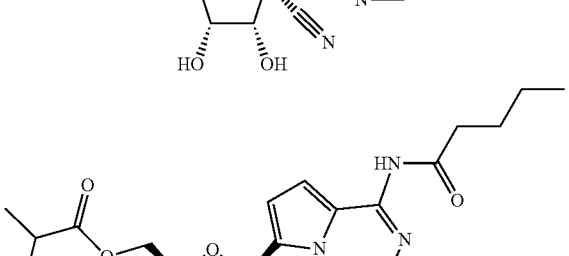
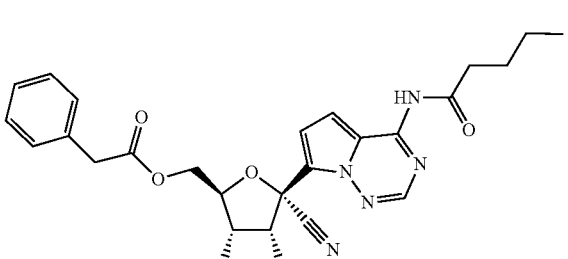

629
-continued
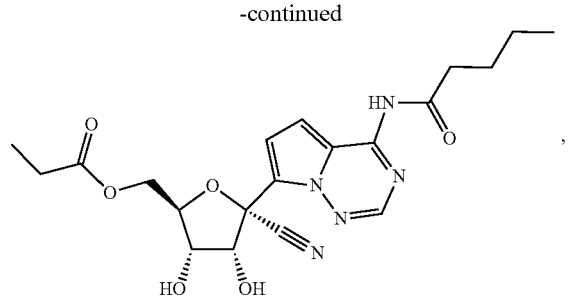
,
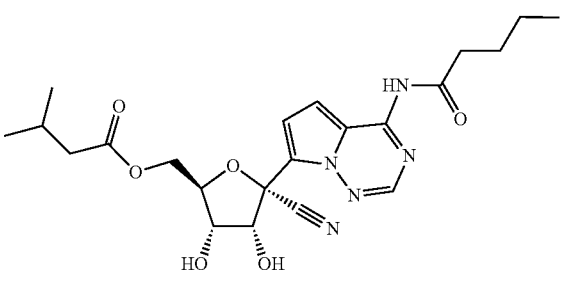
,
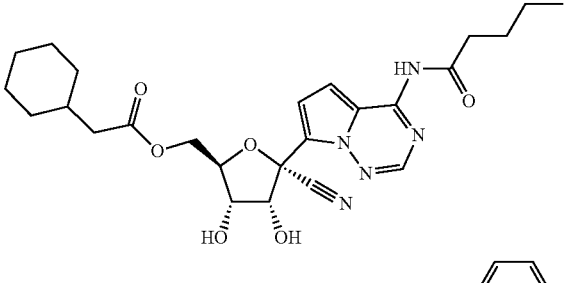
,
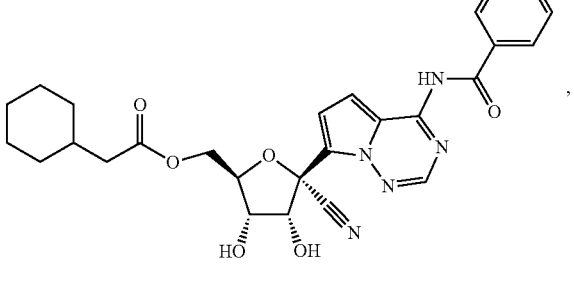
,
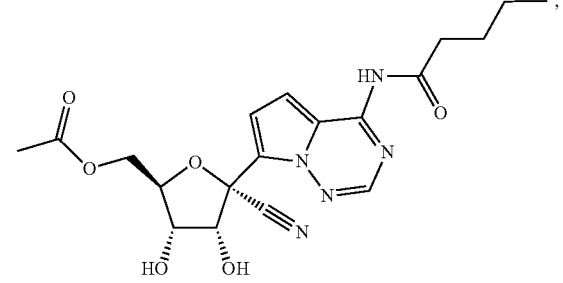
,
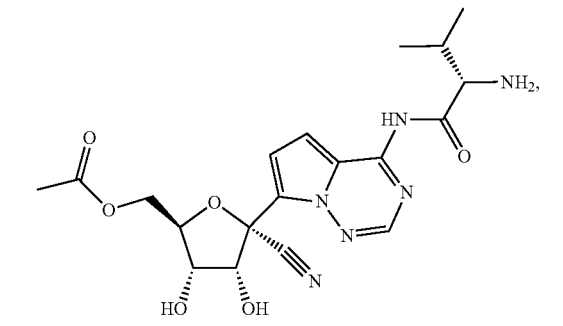
630
-continued
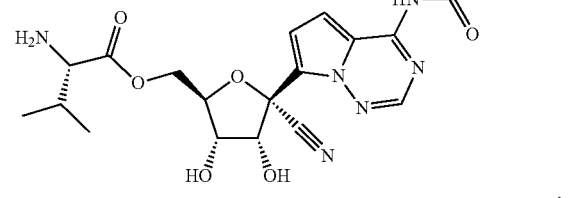
,
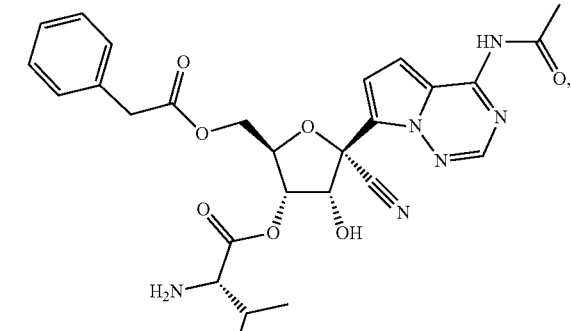
,
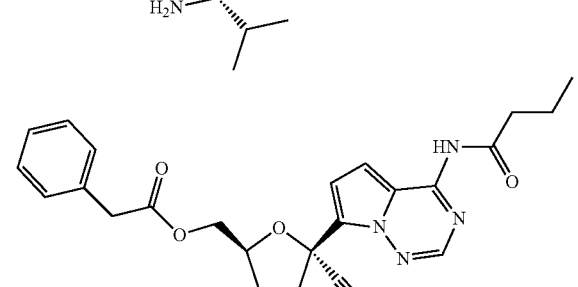
,
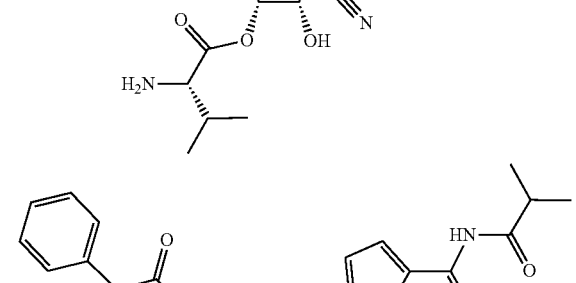
,
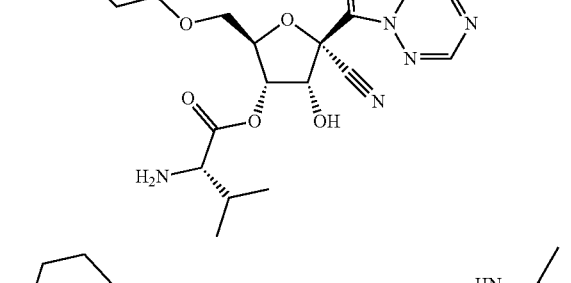
,
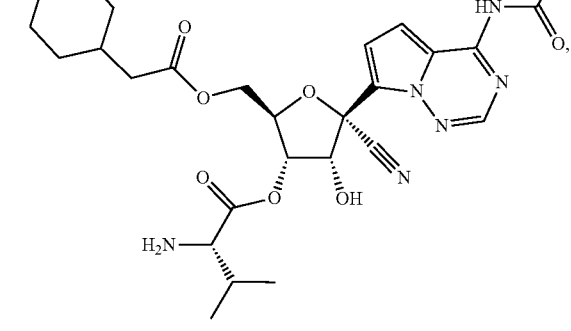

631
-continued
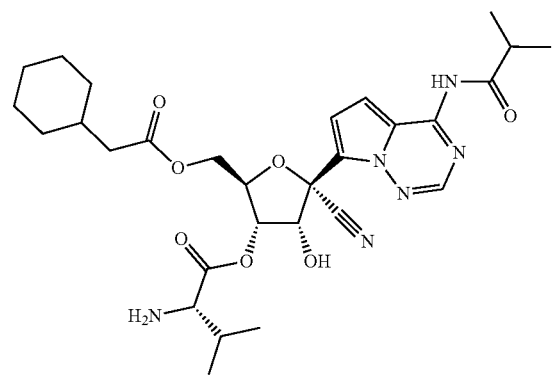
,
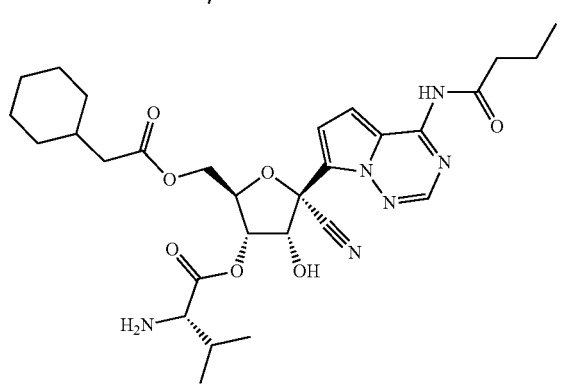
,
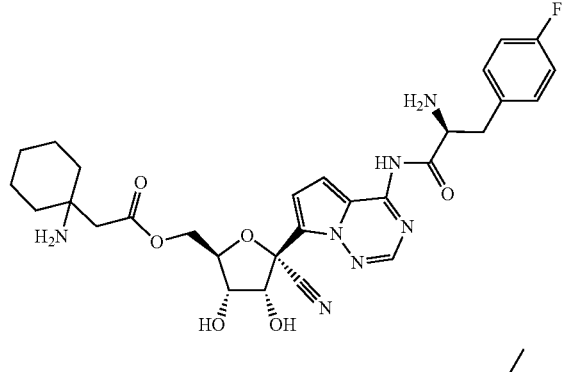
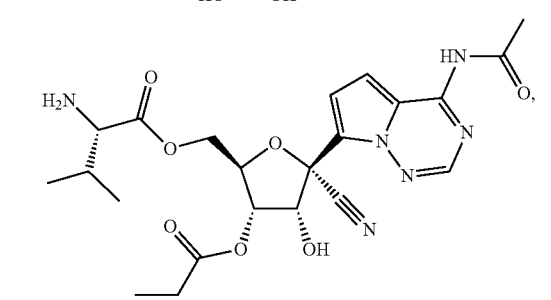
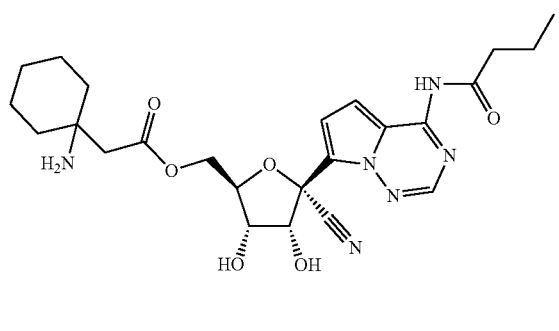
632
-continued
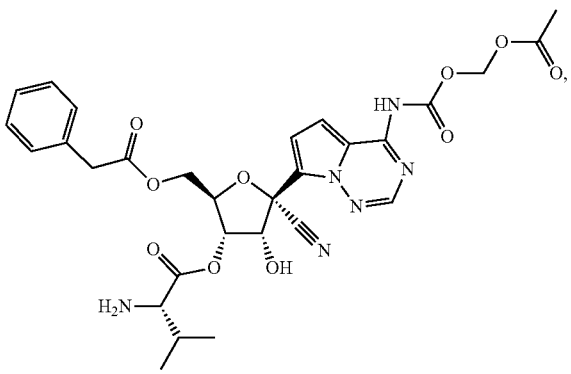
,
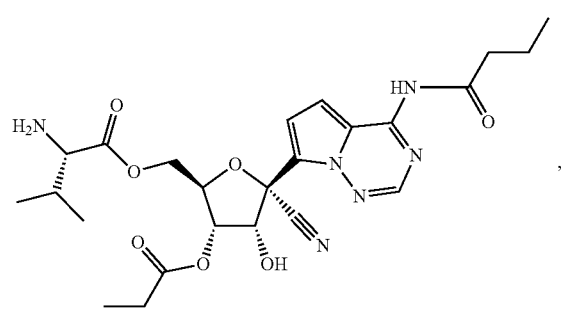
,
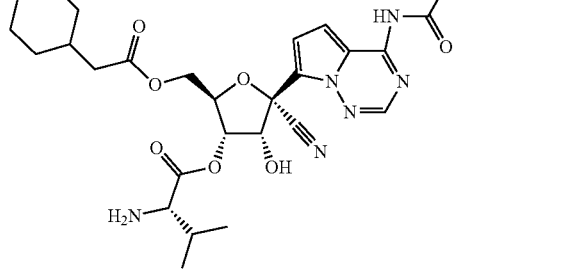
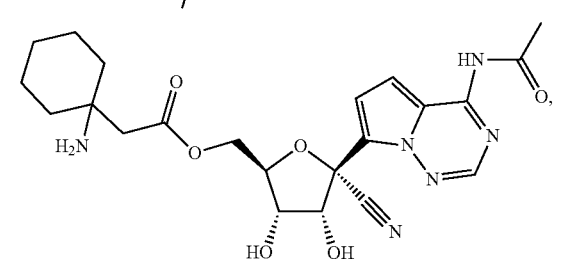
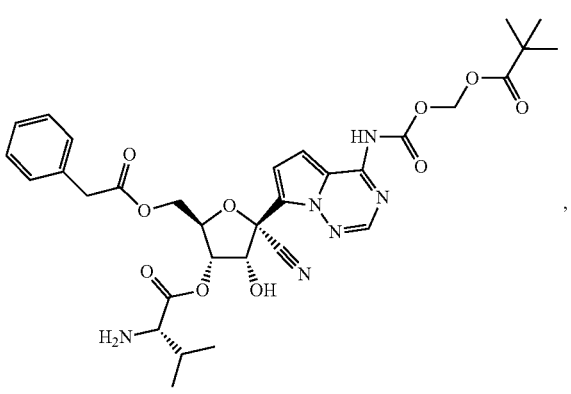
,

633
-continued
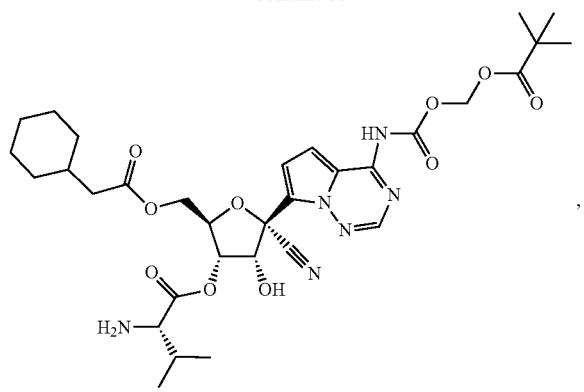
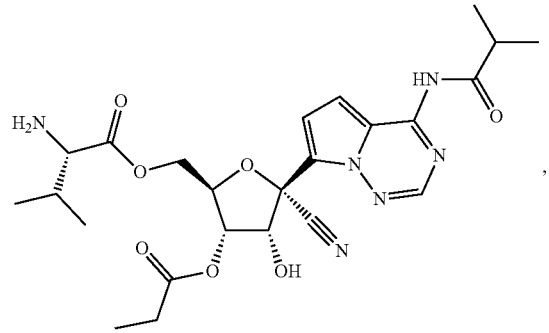
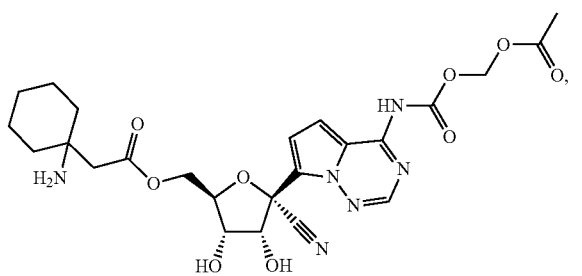
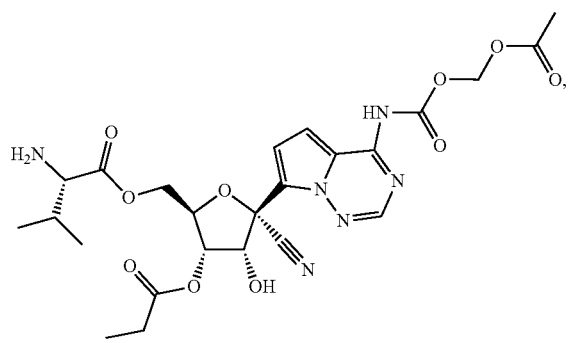
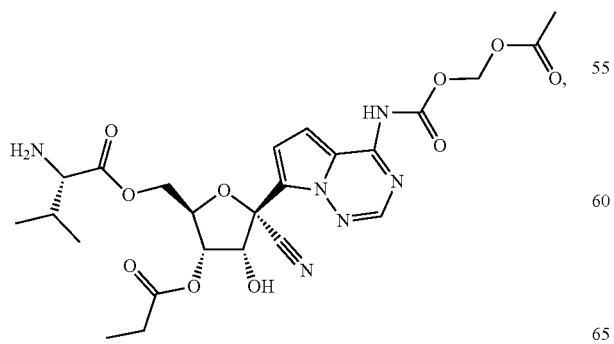
634
-continued
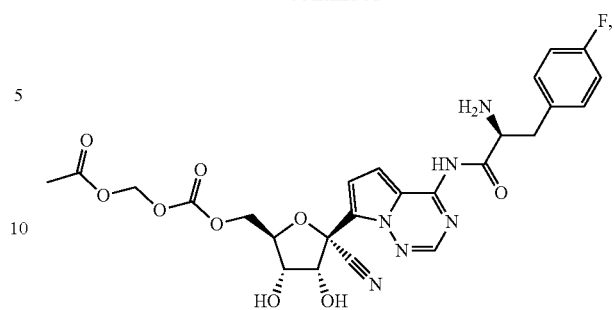
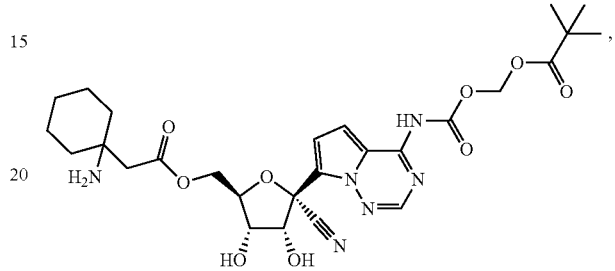
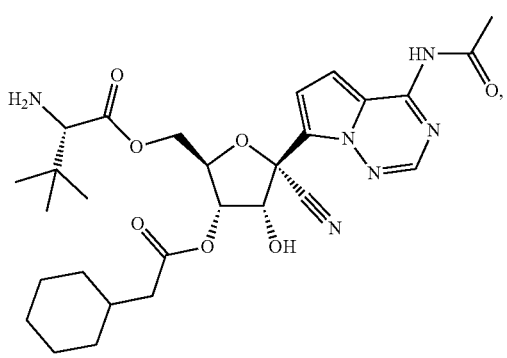
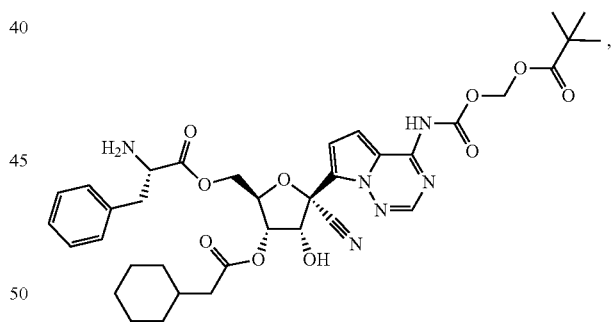
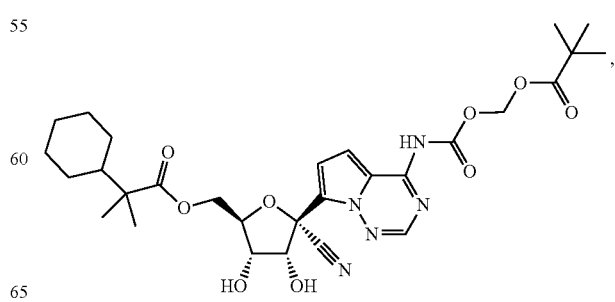

635
-continued
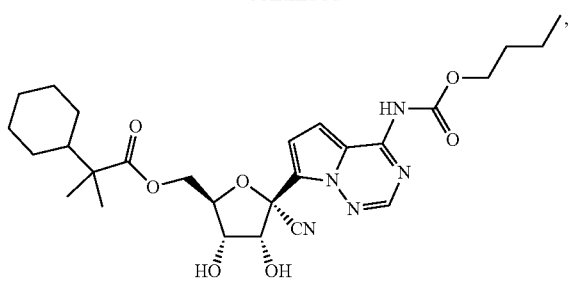
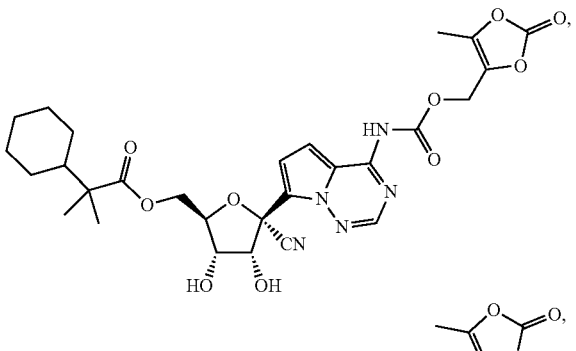
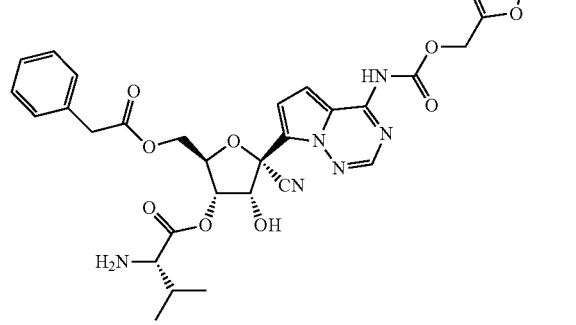
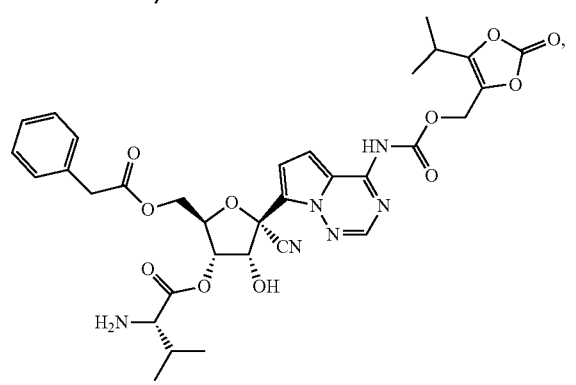
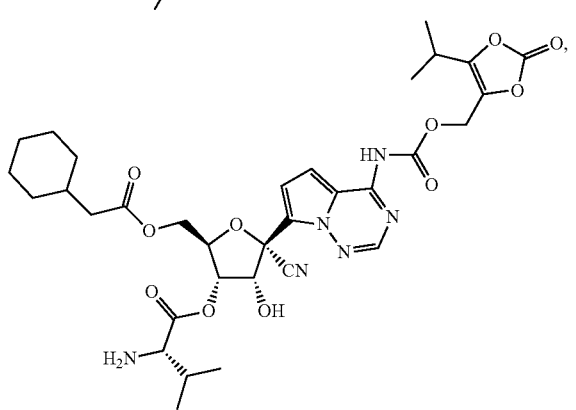
636
-continued
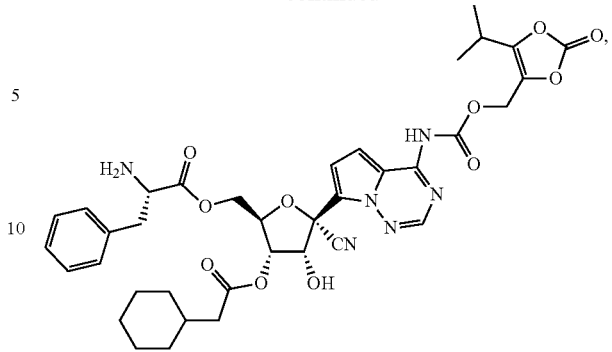
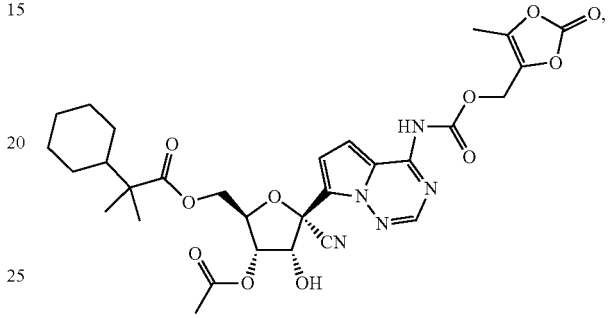
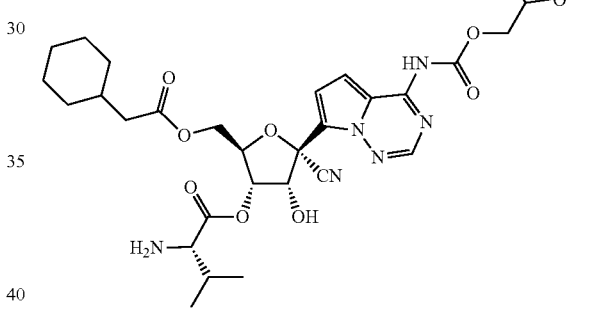
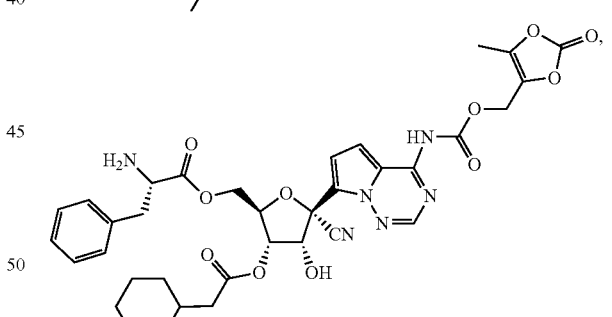
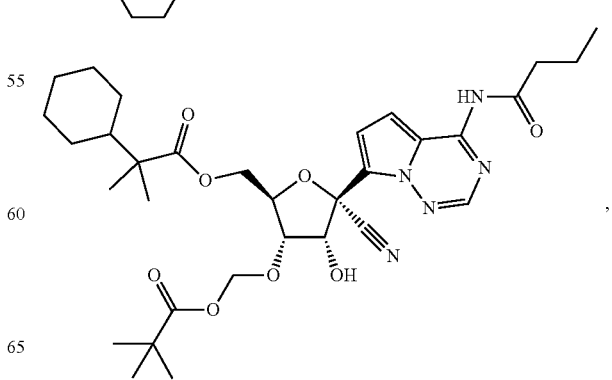

637
-continued
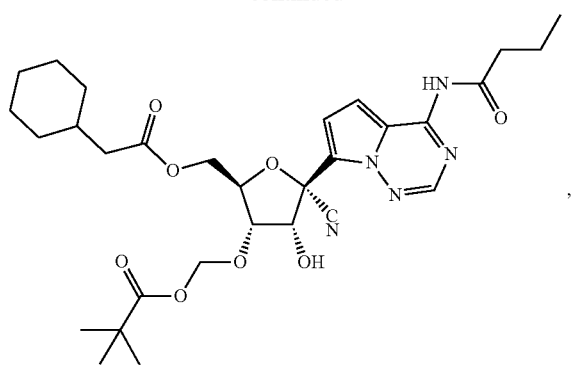
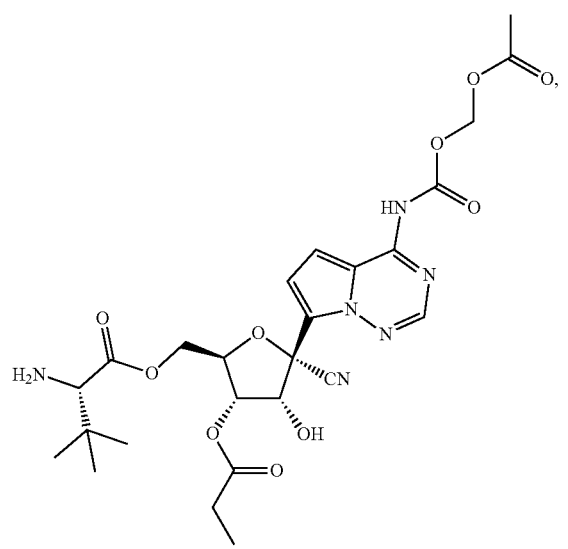
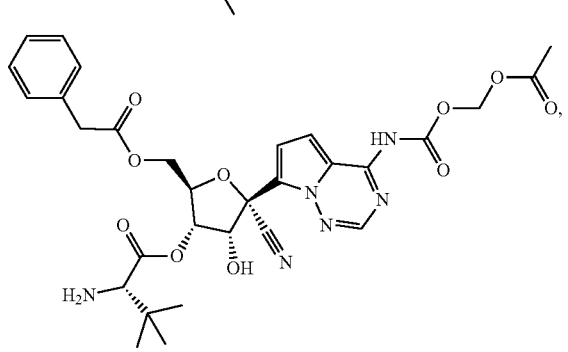
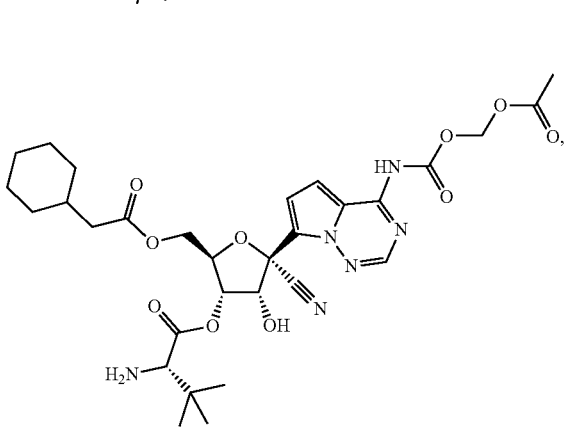
638
-continued
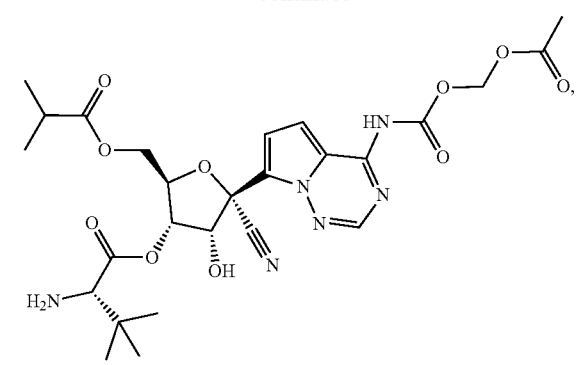
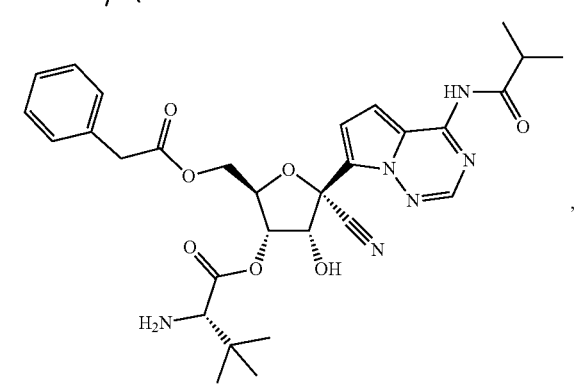
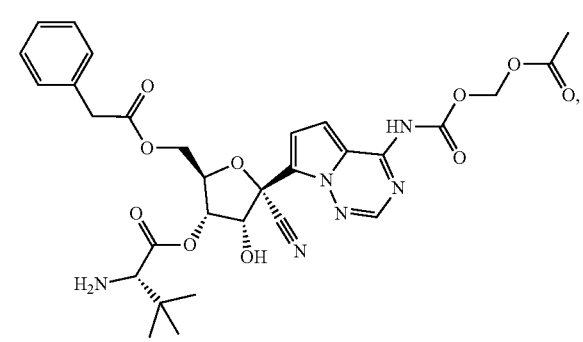
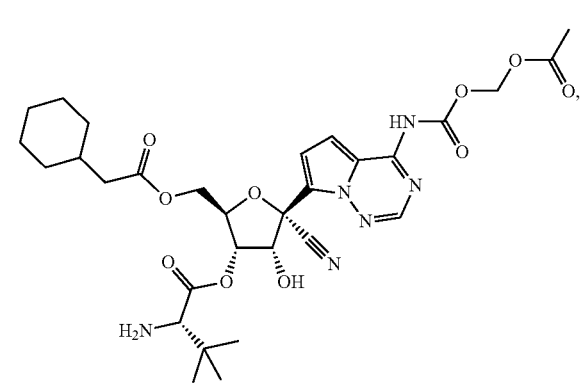

639
-continued
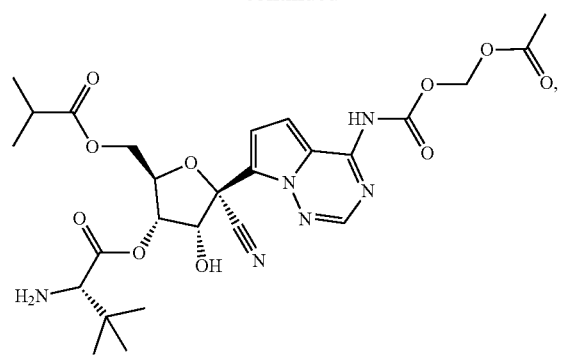
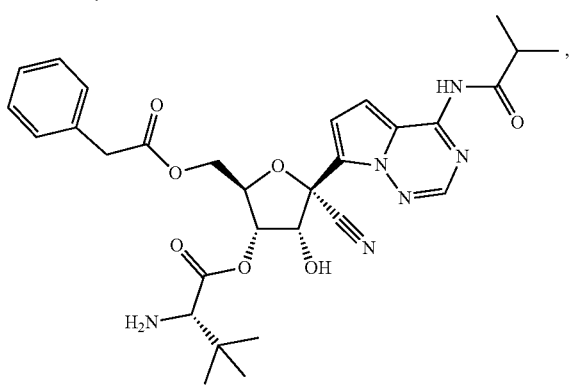
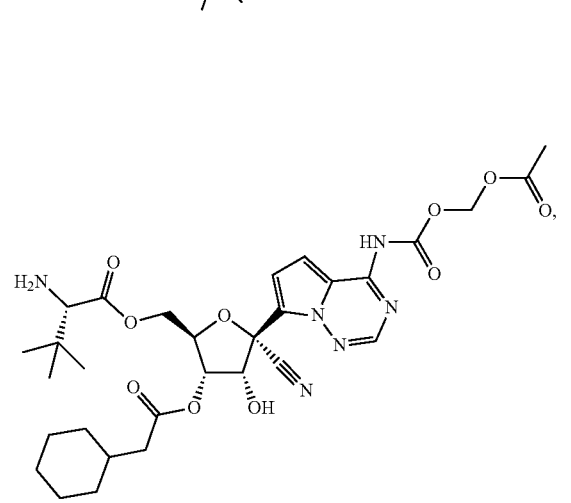
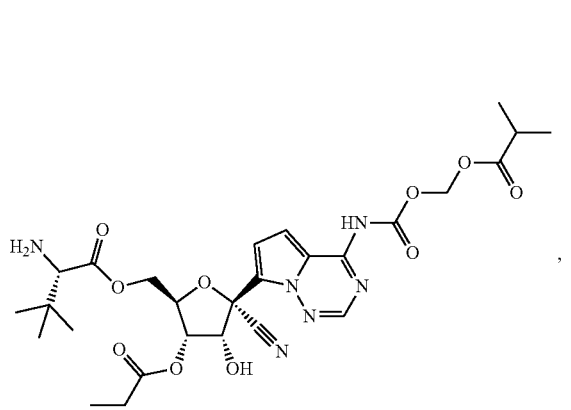
640
-continued
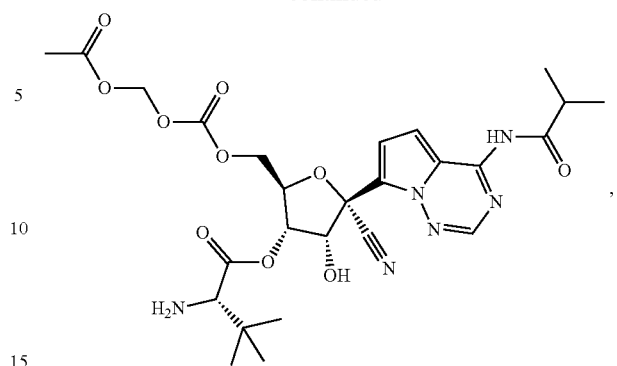
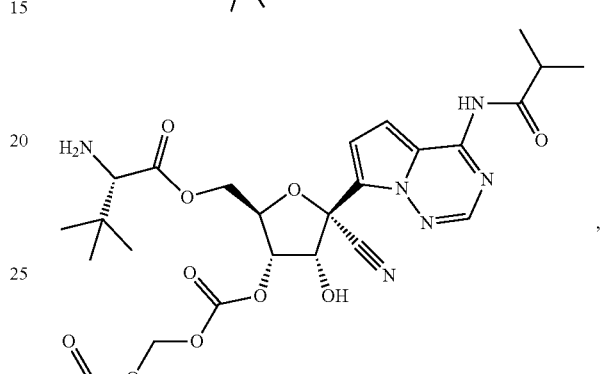
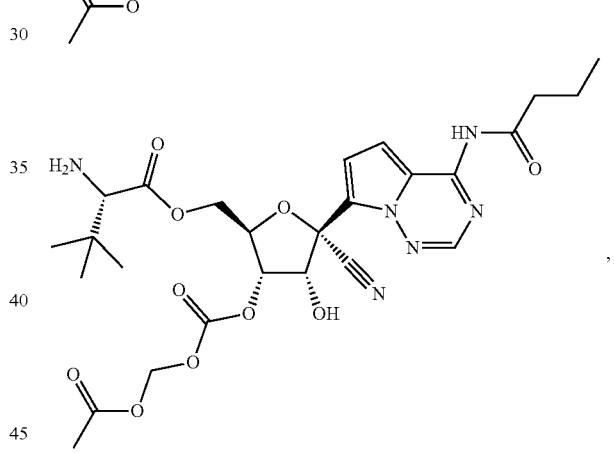
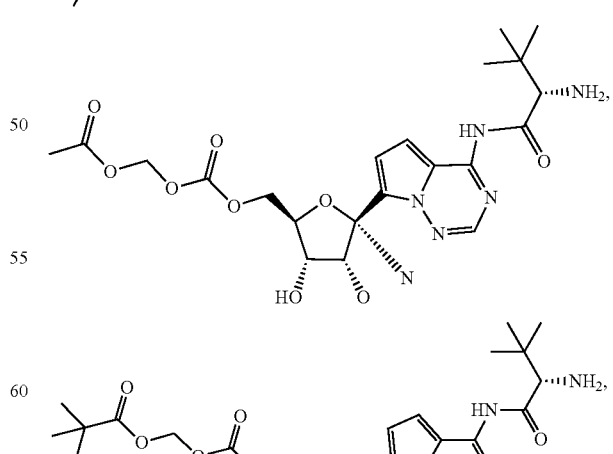
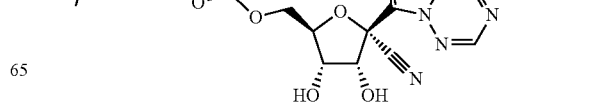

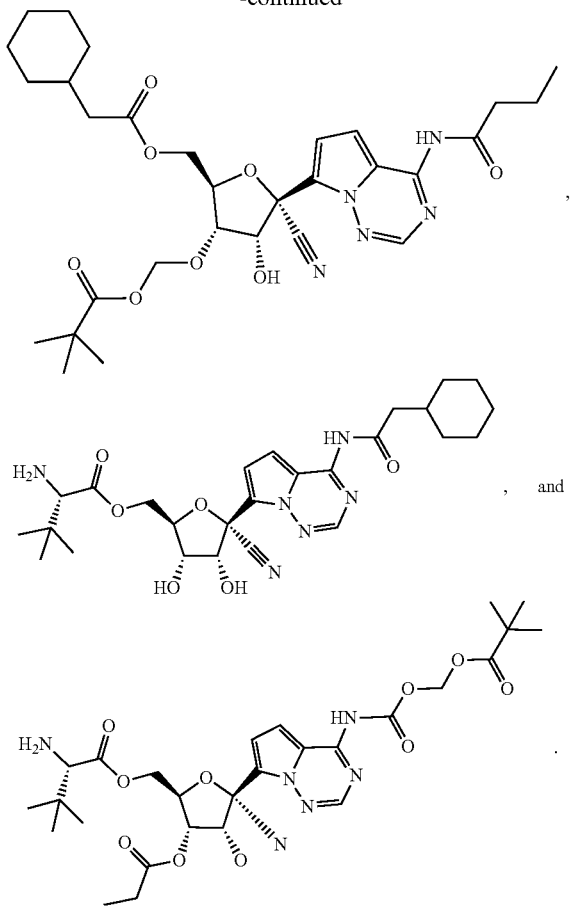

or a pharmaceutically acceptable salt, solvate, or stereoisomer thereof.

15. A pharmaceutical composition comprising the compound of claim 1, or a pharmaceutically acceptable salt, solvate, or stereoisomer thereof, and at least one pharmaceutically acceptable carrier.

16. A method of treating a viral infection, comprising administering to a subject in need thereof a therapeutically effective amount of the compound of claim 1, or a pharmaceutically acceptable salt, solvate, or stereoisomer thereof.

17. The method of claim 16, further comprising administering at least one antiviral agent.

18. The method of claim 16, wherein the viral infection is caused by a virus selected from the group consisting of coronavirus disease 2019 (SARS-COV-2), Yellow Fever, Eastern Equine Encephalitis virus, Human Immunodeficiency virus (HIV), "African Swine Fever Viruses," Arbovirus, Adenoviridae, Arenaviridae, Arterivirus, Astroviridae, Baculoviridae, Bimaviridae, Bimaviridae, Bunyaviridae, Caliciviridae, Caulimoviridae, Circoviridae, Coronaviridae, Cystoviridae, Ebolavirus, Deltaviridae, Filviridae, Filoviridae, Flaviviridae, Iridoviridae, Mononegavirus, Myoviridae, Papiloma virus, Papovaviridae, Paramyxoviridae, Prions, Parvoviridae, Phycodnaviridae, Poxviridae, Potyviridae, Reoviridae, Retroviridae, Rhabdoviridae, Tectiviridae, Togaviridae, pox, papilloma, corona, influenza, sendai virus (SeV), sindbis virus (SINV), vaccinia viruses, West Nile, Hanta, viruses which cause the common cold, and any combination thereof.

19. The method of claim 16, wherein the viral infection is caused by coronavirus disease 2019 (SARS-COV-2) or an Ebolavirus.

* * * * *